United States Patent
Zhu et al.

(10) Patent No.: US 7,342,016 B2
(45) Date of Patent: Mar. 11, 2008

(54) FARNESYL PROTEIN TRANSFERASE INHIBITORS AS ANTITUMOR AGENTS

(75) Inventors: Hugh Y. Zhu, Scotch Plains, NJ (US); F. George Njoroge, Warren, NJ (US); Alan B. Cooper, West Caldwell, NJ (US); Timothy J. Guzi, Chatham, NJ (US); Dinanath F. Rane, Morganville, NJ (US); Keith P. Minor, Sayerville, NJ (US); Ronald J. Doll, Convent Station, NJ (US); Viyyoor M. Girijavallabhan, Parsippany, NJ (US); Bama Santhanam, Bridgewater, NJ (US); Patrick A. Pinto, Morris Plains, NJ (US); Bancha Vibulbhan, Kenilworth, NJ (US); Kartik M. Keertikar, East Windsor, NJ (US); Carmen S. Alvarez, Roselle Park, NJ (US); John J. Baldwin, Gwynedd Valley, PA (US); Ge Li, Shanghai (CN); Chia-Yu Huang, Plainsboro, NJ (US); Ray A. James, Plainsboro, NJ (US); James J-S Wang, Westfield, NJ (US); Jagdish A. Desai, Monroe Township, NJ (US)

(73) Assignees: Schering Corporation, Kenilworth, NJ (US); Pharmacopeia, Inc., Cranbury, NJ (US)

( * ) Notice: Subject to any disclaimer, the term of this patent is extended or adjusted under 35 U.S.C. 154(b) by 477 days.

(21) Appl. No.: 10/325,896

(22) Filed: Dec. 19, 2002

(65) Prior Publication Data

US 2004/0122018 A1 Jun. 24, 2004

Related U.S. Application Data

(63) Continuation-in-part of application No. 10/085,896, filed on Feb. 27, 2002, now abandoned, which is a continuation-in-part of application No. 09/940,811, filed on Aug. 28, 2001, now abandoned.

(60) Provisional application No. 60/229,183, filed on Aug. 30, 2000.

(51) Int. Cl.
*A61K 31/497* (2006.01)
*A61K 31/44* (2006.01)
*C07D 401/14* (2006.01)
*C07D 221/06* (2006.01)

(52) U.S. Cl. .................. 514/253.04; 514/290; 544/361; 546/93

(58) Field of Classification Search ................ 514/253; 544/61, 361
See application file for complete search history.

(56) References Cited

U.S. PATENT DOCUMENTS

| | | | |
|---|---|---|---|
| 5,089,496 A * | 2/1992 | Piwinski et al. | 514/253.03 |
| 5,151,423 A | 9/1992 | Piwinski et al. | |
| 5,393,890 A | 2/1995 | Syoji et al. | |
| 5,416,087 A | 5/1995 | Wong et al. | |
| 5,696,121 A * | 12/1997 | Bishop et al. | 514/253.03 |
| 5,714,609 A | 2/1998 | Doll et al. | |
| 5,719,148 A | 2/1998 | Bishop et al. | |
| 5,721,236 A | 2/1998 | Bishop et al. | |
| 5,728,703 A | 3/1998 | Bishop et al. | |
| 5,861,395 A * | 1/1999 | Taveras et al. | 514/232.8 |
| 5,874,442 A | 2/1999 | Doll et al. | |
| 5,925,648 A | 7/1999 | Cooper et al. | |
| 6,071,907 A | 6/2000 | Njoroge et al. | |
| 6,075,025 A * | 6/2000 | Bishop et al. | 514/253.03 |
| 2005/0059672 A1* | 3/2005 | Zhu et al. | 514/253.03 |

FOREIGN PATENT DOCUMENTS

EP 0270818 A1 10/1987

(Continued)

OTHER PUBLICATIONS

Kaminski et al. "Identification of Novel Farnesyl Protein Transferase Inhibtiors using three-dimensional database searching methods," J. Med. Chem 1997, 40, pp. 4103-4112.*

(Continued)

*Primary Examiner*—James O. Wilson
*Assistant Examiner*—Ebenezer Sackey
(74) *Attorney, Agent, or Firm*—Henry C. Jeanette

(57) ABSTRACT

Disclosed are novel tricyclic compounds represented by the formula (1.0):

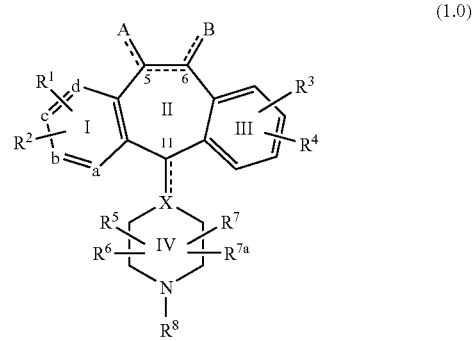

and a pharmaceutically acceptable salt or solvate thereof. The compounds are useful for inhibiting farnesyl protein transferase. Also disclosed are pharmaceutical compositions comprising compounds of formula 1.0. Also disclosed are methods of treating cancer using the compounds of formula 1.0.

49 Claims, No Drawings

FOREIGN PATENT DOCUMENTS

| | | |
|---|---|---|
| EP | 0 988 300 B1 | 8/2002 |
| WO | WO94/24107 | 10/1994 |
| WO | WO95/10516 | 4/1995 |
| WO | WO96/30363 | 10/1996 |
| WO | WO97/02348 | 1/1997 |
| WO | WO98/11092 | 3/1998 |
| WO | WO98/57948 | 12/1998 |
| WO | WO98/57949 | 12/1998 |
| WO | WO98/57960 | 12/1998 |
| WO | WO 00/37458 | 6/2000 |
| WO | WO 00/37459 | 6/2000 |
| WO | WO 01/56552 A2 | 8/2001 |
| WO | WO 02/18368 | 3/2002 |

OTHER PUBLICATIONS

PCT International Search Report dated Feb. 5, 2002 for corresponding PCT Application No. PCT/US01/26792.

PCT International Search Report dated Aug. 4, 2003 for corresponding PCT Application No. PCT/US03/05479.

Mallams, A.K. et al., Inhibitors of Farnesyl Protein Transferase, 4-Amido, 4-Carbamoyl, and 4-Carboxamido Derivatives of 1-(8-Chloro-6,11-dihydro-5H-benzo[5,6]-cycloheptal[1,2-b]pyridine-11-yl)piperazine and 1-(3-Bromo-8-chloro-6,11 dihydro-5H-benzo[5,6]cycloheptal[1,2-b]pyridine-11-yl)piperazine, *Journal of Medicinal Chemistry* 41(6):877-893 (1998).

Njoroge, F.G. et al., Potent, Selective, and Orally Bioavailable Tricyclic Pyridyl Acetamide N-Oxide Inhibitors of Farnesyl Protein Transferase with Enhanced in Vivo Antitumor Activity, *J. Med. Chem.* 41(10):1561-1567 (1998).

Schering-Plough Discontinues Phase III Clinical Study of Sarasar(TM) (Lonafarnib) in Non-Small-Cell Lung Cancer, Schering-Plough Press Release, Feb. 5, 2004.

\* cited by examiner

FARNESYL PROTEIN TRANSFERASE INHIBITORS AS ANTITUMOR AGENTS

REFERENCE TO RELATED APPLICATIONS

This application is a continuation-in-part of application Ser. No. 10/085,896 filed Feb. 27, 2002 now abandoned (the disclosure of which is incorporated herein by reference thereto), which in turn is a continuation-in-part of application Ser. No. 08/940,811 filed Aug. 28, 2001 now abandoned (the disclosure of which is incorporated herein by reference thereto), which in turn claims the benefit of Provisional Application Ser. No. 60/229,183 filed Aug. 30, 2000.

BACKGROUND

WO 95/10516, published Apr. 20, 1995 and WO 97/23478, published Jul. 3, 1997 disclose tricyclic compounds useful for inhibiting farnesyl protein transferase.

WO 98/54966 published Dec. 10, 1998 discloses methods of treating cancer by administering at least two therapeutic agents selected from a group consisting of a compound which is an antineoplastic agent and a compound which is an inhibitor of prenyl-protein transferase (e.g., a farnesyl protein transferase inhibitor).

Farnesyl Protein Transferase (FPT) Inhibitors are known in the art, see for example U.S. Pat. No. 5,874,442 issued Feb. 23, 1999. Methods of treating proliferative diseases (e.g., cancers) by administering an FPT inhibitor in conjunction with an antineoplastic agent and/or radiation therapy are also known, see for example U.S. Pat. No. 6,096,757 issued Aug. 1, 2000.

Shih et al., "The farnesyl protein transferase inhibitor SCH66336 synergizes with taxanes in vitro and enhances their antitumor activity in vivo", Cancer Chemother Pharmacol (2000) 46: 387-393 discloses a study of the combination of SCH 66336 with paclitaxel, and SCH 66336 with docetaxel on certain cancer cell lines.

WO 01/45740 published Jun. 28, 2001 discloses a method of treating cancer (breast cancer) comprising administering a selective estrogen receptor modulator (SERM) and at least one farnesyl transferase inhibitor (FTI). FTI-277 is the exemplified FTI.

The WEB site http://www.osip.com/press/pr/07-25-01 discloses a press release of OSI Pharmaceuticals. The press release announces the initiation of a Phase III clinical trial evaluating the use of the epidermal growth factor inhibitor Tarceva (™) (OSI-774) in combination with Carboplatin (Paraplatin®) and Paclitaxel (Taxol®) for the treatment of Non Small Cell Lung Cancer.

The WEB site http://cancertrials.nci.nih.gov/types/lung/iressa12100.html in a disclosure posted Dec. 14, 2000 discloses the following list of open clinical trials for advanced (stage IIIB and IV) non-small cell lung cancer, from NCI's clinical trials database:

(1) phase III Randomized Study of ZD 1839 (IRESSA, an epidermal growth factor inhibitor) combined with gemcitabine and cisplatin in chemotherapy-naïve patients with Stage IIIB or IV non-small cell lung cancer; and (2) phase III Randomized Study of ZD 1839 (IRESSA, an epidermal growth factor inhibitor) combined with paclitaxel and carboplatin in chemotherapy-naïve patients with Stage IIIB or IV non-small cell lung cancer.

WO 01/56552 published Aug. 9, 2001 discloses the use of an FPT inhibitor for the preparation of a pharmaceutical composition for treating advanced breast cancer. The FPT inhibitor may be used in combination with one or more other treatments for advanced breast cancer especially endocrine therapy such as an antiestrogen agent such as an estrogen receptor antagonist (e.g., tamoxifen) or a selective estrogen receptor modulator or an aromatase inhibitor. Other anti-cancer agents which may be employed include, amongst others, platinum coordination compounds (such as cisplatin or carboplatin), taxanes (such as paclitaxel or docetaxel), anti-tumor nucleoside derivatives (such as gemcitabine), and HER2 antibodies (such as trastzumab).

WO 01/62234 published Aug. 30, 2001 discloses a method of treatment and dosing regimen for treating mammalian tumors by the discontinuous administration of a farnesyl transferase inhibitor over an abbreviated one to five day dosing schedule. Disclosed is a regimen wherein the farnesyl protein transferase inhibitor is administered over a one to five day period followed by at least two weeks without treatment. It is disclosed that in previous studies farnesyl protein transferase inhibitors have been shown to inhibit the growth of mammalian tumors when administered as a twice daily dosing schedule. It is further disclosed that the administration of a farnesyl protein transferase inhibitor in a single dose daily for one to five days produced a marked suppression of tumor growth lasting one to at least 21 days. It is also disclosed that the FTI may be used in combination with one or more other anti-cancer agents such as, platinum coordination compounds (e.g., cisplatin or carboplatin), taxane compounds (e.g., paclitaxel or docetaxel), anti-tumor nucleoside derivatives (e.g., gemcitabine), HER2 antibodies (e.g., trastzumab), and estrogen receptor antagonists or selective estrogen receptor modulators (e.g., tamoxifen).

WO 01/64199 published Sep. 7, 2001 discloses a combination of particular FPT inhibitors with taxane compounds (e.g., paclitaxel or docetaxel) useful in the treatment of cancer.

In view of the current interest in inhibitors of farnesyl protein transferase, a welcome contribution to the art would be compounds useful for the inhibition of farnesyl protein transferase. Such a contribution is provided by this invention.

SUMMARY OF THE INVENTION

This invention provides compounds useful for the inhibition of farnesyl protein transferase (FPT). The FPT inhibitor compounds of this invention are represented by the formula:

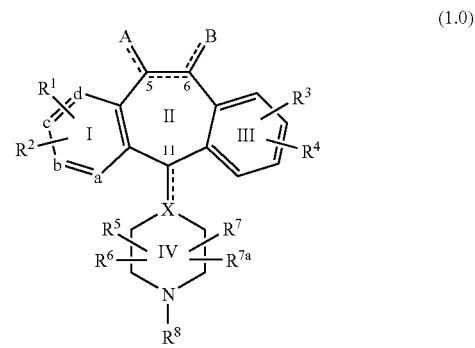

(1.0)

or a pharmaceutically acceptable salt or solvate thereof, wherein:

one of a, b, c and d represents N or $N^+O^-$, and the remaining a, b, c, and d groups represent carbon, wherein each carbon has an $R^1$ or $R^2$ group bound to said carbon; or each of a, b, c, and d is carbon, wherein each carbon has an $R^1$ or $R^2$ group bound to said carbon;

the dotted line (---) represents optional bonds;

X represents N or CH when the optional bond (to C11) is absent, and represents C when the optional bond (to C11) is present;

when the optional bond is present between carbon atom 5 (i.e., C-5) and carbon atom 6 (i.e., C-6) (i.e., there is a double bond between C-5 and C-6) then there is only one A substituent bound to C-5 and there is only one B substituent bound to C-6, and A or B is other than H;

when the optional bond is not present between carbon atom 5 and carbon atom 6 (i.e., there is a single bond between C-5 and C-6) then there are two A substituents bound to C-5, wherein each A substituent is independently selected, and two B substituents bound to C-6, wherein each B substituent is independently selected, and wherein at least one of the two A substituents or one of the two B substituents is H, and wherein at least one of the two A substituents or one of the two B substituents is other than H, (i.e., when there is a single bond between C-5 and C-6 one of the four substituents (A, A, B, and B) is H and one is other than H);

A and B are independently selected from the group consisting of:
(1) —H;
(2) —$R^9$;
(3) —$R^9$—C(O)—$R^9$;
(4) —$R^9$—$CO_2$—$R^{9a}$;
(5) —$(CH_2)_pR^{26}$;
(6) —$C(O)N(R^9)_2$, wherein each $R^9$ is the same or different;
(7) —$C(O)NHR^9$;
(8) —$C(O)NH$—$CH_2$—$C(O)$—$NH_2$;
(9) —$C(O)NHR^{26}$;
(10) —$(CH_2)_pC(R^9)$—O—$R^{9a}$;
(11) —$(CH_2)_p(R^9)_2$, wherein each $R^9$ is the same or different;
(12) —$(CH_2)_pC(O)R^9$;
(13) —$(CH_2)_pC(O)R^{27a}$;
(14) —$(CH_2)_pC(O)N(R^9)_2$, wherein each $R^9$ is the same or different;
(15) —$(CH_2)_pC(O)NH(R^9)$;
(16) —$(CH_2)_pC(O)N(R^{26})_2$, wherein each $R^{26}$ is the same or different;
(17) —$(CH_2)_pN(R^9)$—$R^{9a}$, (e.g. —$CH_2$—N(CH2-pyridine)—$CH_2$-imidazole);
(18) —$(CH_2)_pN(R^{26})_2$, wherein $R^{26}$ is the same or different (e.g., —$(CH_2)p$—NH—$CH_2$—$CH_3$);
(19) —$(CH_2)_pNHC(O)R^{50}$;
(20) —$(CH_2)_pNHC(O)_2R^{50}$;
(21) —$(CH_2)_pN(C(O)R^{27a})_2$ wherein each $R^{27a}$, is the same or different;
(22) —$(CH_2)_pNR^{51}C(O)R^{27}$;
(23) —$(CH_2)_pNR^{51}C(O)R^{27}$ wherein $R^{51}$ is not H, and $R^{51}$ and $R^{27}$ taken together with the atoms to which they are bound form a 5 or 6 membered heterocycloalkyl ring consisting;
(24) —$(CH_2)_pNR^{51}C(O)NR^{27}$;
(25) —$(CH_2)_pNR^{51}C(O)NR^{27}$ wherein $R^{51}$ is not H, and $R^{51}$ and $R^{27}$ taken together with the atoms to which they are bound form a 5 or 6 membered heterocycloalkyl ring;

(26) —$(CH_2)_pNR^{51}C(O)N(R^{27a})_2$, wherein each $R^{27a}$, is the same or different;
(27) —$(CH_2)_pNHSO_2N(R^{51})_2$, wherein each $R^{51}$ is the same or different;
(28) —$(CH_2)_pNHCO_2R^{50}$;
(29) —$(CH_2)_pNC(O)NHR^{51}$;
(30) —$(CH_2)_pCO_2R^{51}$;
(31) —$NHR^9$;

(32)

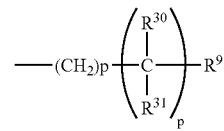

wherein $R^{30}$ and $R^{31}$ are the same or different, and each p is independently selected; provided that for each

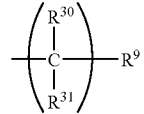

group when one of $R^{30}$ or $R^{31}$ is selected from the group consisting of: —OH, =O, —$OR^{9a}$, —$NH_2$, —$NHR^{9a}$, —$N(R^{9a})_2$, —$N_3$, —$NHR^{9b}$, and —$N(R^{9a})R^{9b}$, then the remaining $R^{30}$ or $R^{31}$ is selected from the group consisting of: H, alkyl, aryl (e.g., phenyl), and arylalkyl (e.g., benzyl);

(33)

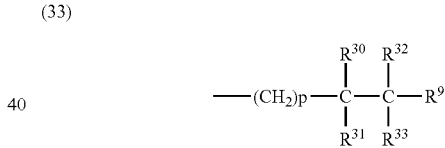

wherein $R^{30}$, $R^{31}$, $R^{32}$ and $R^{33}$ are the same or different; provided that when one of $R^{30}$ or $R^{31}$ is selected from the group consisting of: —OH, =O, —$OR^{9a}$, —$NH_2$, —$NHR^{9a}$, —$N(R^{9a})_2$, —$N_3$, —$NHR^{9b}$, and —$N(R^{9a})R^{9b}$, then the remaining $R^{30}$ or $R^{31}$ is selected from the group consisting of: H, alkyl, aryl (e.g., phenyl), and arylalkyl (e.g., benzyl); and provided that when one of $R^{32}$ or $R^{33}$ is selected from the group consisting of: —OH, =O, —$OR^{9a}$, —$NH_2$, —$NHR^{9a}$, —$N(R^{9a})_2$, —$N_3$, —$NHR^{9b}$, and —$N(R^{9a})R^{9b}$, then the remaining $R^{32}$ or $R^{33}$ is selected from the group consisting of: H, alkyl, aryl (e.g., phenyl), and arylalkyl (e.g., benzyl);
(34) -alkenyl-$CO_2R^{9a}$;
(35) -alkenyl-$C(O)R^{9a}$;
(36) -alkenyl-$CO_2R^{51}$;
(37) -alkenyl-C(O)—$R^{27a}$;
(38) $(CH_2)_p$-alkenyl-$CO_2$—$R^{51}$;
(37) -$(CH_2)_pC$=$NOR^{51}$; and
(39) —$(CH_2)_p$-phthalimid;
p is 0, 1, 2, 3 or 4;
each $R^1$ and $R^2$ is independently selected from the group consisting of:
(1) H;
(2) Halo;

(3) —$CF_3$,
(4) —$OR^{10}$;
(5) —$COR^{10}$,
(6) —$SR^{10}$;
(7) —$S(O)_tR^{15}$ wherein t is 0, 1 or 2;
(8) —$N(R^{10})_2$;
(9) —$NO_2$;
(10) —$OC(O)R^{10}$;
(11) —$CO_2R^{10}$;
(12) —$OCO_2R^{15}$;
(13) —CN;
(14) —$NR^{10}COOR^{15}$;
(15) —$SR^{15}C(O)OR^{15}$;
(16) —$SR^{15}N(R^{13})_2$ provided that $R^{15}$ in —$SR^{15}N(R^{13})_2$ is not —$CH_2$ and wherein each $R^{13}$ is independently selected from the group consisting of: H and —$C(O)OR^{15}$;
(17) benzotriazol-1-yloxy;
(18) tetrazol-5-ylthio;
(19) substituted tetrazol-5-ylthio;
(20) alkynyl;
(21) alkenyl; and
(22) alkyl, said alkyl or alkenyl group optionally being substituted with halogen, —$OR^{10}$ or —$CO_2R^{10}$;

$R^3$ and $R^4$ are the same or different and each independently represent H, and any of the substituents of $R^1$ and $R^2$;

$R^5$, $R^6$, $R^7$ and $R^{7a}$ each independently represent: H, —$CF_3$, —$COR^{10}$, alkyl or aryl, said alkyl or aryl optionally being substituted with —$S(O)_tR^{15}$, —$NR^{10}COOR^{15}$, —$C(O)R^{10}$, or —$CO_2R^{10}$, or $R^5$ is combined with $R^6$ to represent =O or =S;

$R^8$ is selected from the group consisting of:

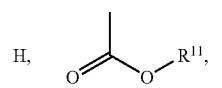
(2.0)

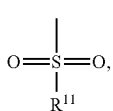
(3.0)

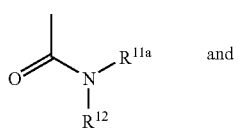
and
(4.0)

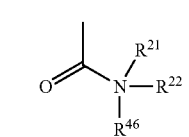
(5.0)

$R^9$ is selected from the group consisting of:
(1) unsubstituted heteroaryl;
(2) substituted heteroaryl;
(3) arylalkoxy;
(4) substituted arylalkoxy;
(5) heterocycloalkyl;
(6) substituted heterocycloalkyl;
(7) heterocycloalkylalkyl;
(8) substituted heterocycloalkylalkyl;
(9) unsubstituted heteroarylalkyl;
(10) substituted heteroarylalkyl;
(11) unsubstituted heteroarylalkenyl;
(12) substituted heteroarylalkenyl;
(13) unsubstituted heteroarylalkynyl; and
(14) substituted heteroarylalkynyl;

wherein said substituted $R^9$ groups are substituted with one or more (e.g. 1, 2 or 3) substituents selected from the group consisting of:
(1) —OH, provided that when there is more than one —OH group then each —OH group is bound to a different carbon atom (i.e., only one —OH group can be bound to a carbon atom);
(2) —$CO_2R^{14}$;
(3) —$CH_2OR^{14}$,
(4) halogen (e.g. Br, Cl or F),
(5) alkyl (e.g. methyl, ethyl, propyl, butyl or t-butyl);
(6) amino;
(7) trityl;
(8) heterocycloalkyl;
(9) cycloalkyl, (e.g., cyclopropyl or cyclohexyl);
(10) arylalkyl;
(11) heteroaryl;
(12) heteroarylalkyl and (13)

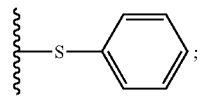

wherein $R^{14}$ is independently selected from: H; alkyl; aryl, arylalkyl, heteroaryl and heteroarylalkyl;

$R^{9a}$ is selected from the group consisting of: alky and arylalkyl;

$R^{9b}$ is selected from the group consisting of:
(1) —$C(O)R^{9a}$;
(2) —$SO_2R^{9a}$;
(3) —$C(O)NHR^{9a}$;
(4) —$C(O)OR^{9a}$; and
(5) —$C(O)N(R^{9c})_2$;

Each $R^{9c}$ is independently selected from the group consisting of: H, alkyl and arylalkyl;

$R^{10}$ is selected from the group consisting of: H; alkyl; aryl and arylalkyl;

$R^{11}$ is selected from the group consisting of:
(1) alkyl;
(2) substituted alkyl;
(3) unsubstituted aryl;
(4) substituted aryl;
(5) unsubstituted cycloalkyl;
(6) substituted cycloalkyl;
(7) unsubstituted heteroaryl;
(8) substituted heteroaryl;
(9) heterocycloalkyl; and
(10) substituted heterocycloalkyl;

wherein said substituted alkyl, substituted cycloalkyl, and substituted heterocycloalkyl $R^{11}$ groups are substituted with one or more (e.g. 1, 2 or 3) substituents, provided that selected from the group consisting of:
(1) —OH, provided that when there is more than one —OH group then each —OH group is bound to a different carbon atom (i.e., only one —OH group can be bound to a carbon atom);

(2) fluoro; and
(3) alkyl; and wherein said substituted aryl and substituted heteroaryl $R^{11}$ groups are substituted with one or more (e.g. 1, 2 or 3) substituents independently selected from the group consisting of:
  (1) —OH, provided that when there is more than one —OH group then each —OH group is bound to a different carbon atom (i.e., only one —OH group can be bound to a carbon atom);
  (2) halogen (e.g. Br, Cl or F); and
  (3) alkyl;

$R^{11a}$ is selected from the group consisting of:
  (1) H;
  (2) OH;
  (3) alkyl;
  (4) substituted alkyl;
  (5) aryl;
  (6) substituted aryl;
  (7) unsubstituted cycloalkyl:
  (8) substituted cycloalkyl;
  (9) unsubstituted heteroaryl;
  (10) substituted heteroaryl;
  (11) heterocycloalkyl;
  (12) substituted heterocycloalkyl; and
  (13) —$OR^{9a}$;

wherein said substituted alkyl, substituted cycloalkyl, and substituted heterocycloalkyl $R^{11a}$ groups are substituted with one or more (e.g. 1, 2 or 3) substituents independently selected from the group consisting of:
  (1) —OH, provided that when there is more than one —OH group then each —OH group is bound to a different carbon atom (i.e., only one —OH group can be bound to a carbon atom);
  (2) —CN;
  (3) —$CF_3$;
  (4) fluoro;
  (5) alkyl;
  (6) cycloalkyl;
  (7) heterocycloalkyl;
  (8) arylalkyl;
  (9) heteroarylalkyl;
  (10) alkenyl and
  (11) heteroalkenyl; and wherein said substituted aryl and substituted heteroaryl $R^{11a}$ groups have one or more (e.g. 1, 2 or 3) substituents independently selected from the group consisting of:
  (1) —OH, provided that when there is more than one —OH group then each —OH group is bound to a different carbon atom (i.e., only one —OH group can be bound to a carbon atom);
  (2) —CN;
  (3) —$CF_3$;
  (4) halogen (e.g Br, Cl or F);
  (5) alkyl;
  (6) cycloalkyl;
  (7) heterocycloalkyl;
  (8) arylalkyl;
  (9) heteroarylalkyl;
  (10) alkenyl; and
  (11) heteroalkenyl;

$R^{12}$ is selected from the group consisting of: H, alkyl, piperidine Ring V, cycloalkyl, and -alkyl-(piperidine Ring V);

$R^{15}$ is selected from the group consisting of: alkyl and aryl;

$R^{21}$, $R^{22}$ and $R^{46}$ are independently selected from the group consisting of:
  (1) —H;
  (2) alkyl (e.g., methyl, ethyl, propyl, butyl or t-butyl);
  (3) unsubstituted aryl, (e.g. phenyl);
  (4) substituted aryl substituted with one or more substituents independently selected from the group consisting of: alkyl, halogen, $CF_3$ and OH;
  (5) unsubstituted cycloalkyl, (e.g. cyclohexyl);
  (6) substituted cycloalkyl substituted with one or more substituents independently selected from the group consisting of: alkyl, halogen, $CF_3$ and OH;
  (7) heteroaryl of the formula,

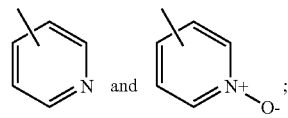

(8) heterocycloalkyl of the formula:

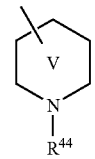

(i.e., piperidine Ring V) wherein $R^{44}$ is selected from the group consisting of:
    (a) —H,
    (b) alkyl, (e.g., methyl, ethyl, propyl, butyl or t-butyl);
    (c) alkylcarbonyl (e.g., $CH_3C(O)$—);
    (d) alkyloxy carbonyl (e.g., —$C(O)O$-t-$C_4H_9$, —$C(O)OC_2H_5$, and —$C(O)OCH_3$);
    (e) haloalkyl (e.g., trifluoromethyl); and
    (f) —$C(O)NH(R^{51})$;
  (9) —$NH_2$ provided that only one of $R^{21}$, $R^{22}$, and $R^{46}$ group can be —$NH_2$, and provided that when one of $R^{21}$, $R^{22}$, and $R^{46}$ is —$NH_2$ then the remaining groups are not —OH;
  (10) —OH provided that only one of $R^{21}$, $R^{22}$, and $R^{46}$ group can be —OH, and provided that when one of $R^{21}$, $R^{22}$, and $R^{46}$ is —OH then the remaining groups are not —$NH_2$; and
  (11) alkyl substituted with one or more substituents (e.g., 1-3, or 1-2, and preferably 1) selected from the group consisting of: —OH and —$NH_2$, and provided that there is only one —OH or one —$NH_2$ group on a substituted carbon; or
  (12) $R^{21}$ and $R^{22}$ taken together with the carbon to which they are bound form a cyclic ring selected from the group consisting of:
    (a) unsubstituted cycloalkyl (e.g., cyclopropyl, cyclobutyl, cyclopentyl, and cyclohexyl);
    (b) cycloalkyl substituted with one or more substituents independently selected from the group consisting of: alkyl, halogen, $CF_3$ and OH;
    (c) unsubstituted cycloalkenyl

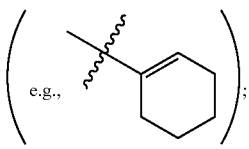

(d) cycloalkenyl substituted with one or more substituents independently selected from the group consisting of: alkyl, halogen, $CF_3$ and OH;
(e) heterocycloalkyl, e.g., a piperidyl ring of the formula:

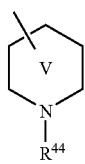

wherein $R^{44}$ is selected from the group consisting of:
(1) —H,
(2) alkyl, (e.g., methyl, ethyl, propyl, butyl or t-butyl);
(3) alkylcarbonyl (e.g., $CH_3C(O)$—);
(4) alkyloxy carbonyl (e.g., —$C(O)O$-t-$C_4H_9$, —$C(O)OC_2H_5$, and —$C(O)OCH_3$);
(5) haloalkyl (e.g., trifluoromethyl); and
(6) —$C(O)NH(R^{51})$;
(f) unsubstituted aryl (e.g., phenyl);
(g) aryl substituted with one or more substituents independently selected from the group consisting of: alkyl (e.g., methyl), halogen (e.g., Cl, Br and F), —CN, —$CF_3$, OH and alkoxy (e.g., methoxy); and
(i) heteroaryl selected from the group consisting of:

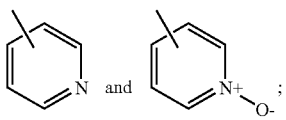

$R^{26}$ is selected from the group consisting of:
(1) —H;
(2) alkyl (e.g. methyl, ethyl, propyl, butyl or t-butyl);
(3) alkoxy (e.g. methoxy, ethoxy, propoxy);
(4) —$CH_2$—CN;
(5) $R^9$;
(6) —$CH_2CO_2H$;
(7) —C(O)alkyl; and
(8) $CH_2CO_2$alkyl;
$R^{27}$ is selected from the group consisting of:
(1) —H;
(2) —OH;
(3) alkyl (e.g. methyl, ethyl, propyl, or butyl); and
(4) alkoxy;
$R^{27a}$ is selected from the group consisting of:
(1) alkyl (e.g. methyl, ethyl, propyl, or butyl); and
(2) alkoxy;
$R^{30}$, $R^{31}$, $R^{32}$ and $R^{33}$ are independently selected from the group consisting of:

(1) —H;
(2) —OH;
(3) =O;
(4) alkyl;
(5) aryl (e.g. phenyl);
(6) arylalkyl (e.g. benzyl);
(7) —$OR^{9a}$;
(8) —$NH_2$;
(9) —$NHR^{9a}$;
(10) —$N(R^{9a})_2$ wherein each $R^{9a}$ is independently selected;
(11) —$N_3$;
(12) —$NHR^{9b}$; and
(13) —$N(R^{9a})R^{9b}$;
$R^{50}$ is selected from the group consisting of:
(1) alkyl;
(2) unsubstituted heteroaryl;
(3) substituted heteroary; and
(4) amino;
wherein said substituents on said substituted $R^{50}$ groups are independently selected from the group consisting of: alkyl (e.g., methyl, ethyl, propyl, and butyl); halogen (e.g., Br, Cl, and F); and —OH;
$R^{51}$ is selected from the group consisting of: H, and alkyl (e.g., methyl, ethyl, propyl, butyl and t-butyl); and
provided that a ring carbon atom adjacent to a ring heteroatom in a substituted heterocycloalkyl moiety is not substituted with a heteroatom or a halo atom; and
provided that a ring carbon atom, that is not adjacent to a ring heteroatom, in a substituted heterocycloalkyl moiety, is not substituted with more than one heteroatom; and
provided that a ring carbon atom, that is not adjacent to a ring heteroatom, in a substituted heterocycloalkyl moiety, is not substituted with a heteroatom and a halo atom; and
provided that a ring carbon in a substituted cycloalkyl moiety is not substituted with more than one heteroatom; and
provided that a carbon atom in a substituted alkyl moiety is not substituted with more than one heteroatom; and
provided that the same carbon atom in a substituted alkyl moiety is not substituted with both heteroatoms and halo atoms.

This invention also provides pharmaceutical compositions comprising an effective amount of a compound of formula 1.0 and a pharmaceutically acceptable carrier.

This invention also provides a method of inhibiting farnesyl protein transferase in a patient in need of such treatment comprising administering to said patient an effective amount of at least one (usually one) compound of formula 1.0.

This invention also provides methods of treating (or inhibiting) tumors (i.e., cancers) in a patient in need of such treatment comprising administering to said patient an effective amount of at least one (usually one) compound of formula 1.0.

This invention also provides methods of treating (or inhibiting) tumors (i.e., cancers) in a patient in need of such treatment comprising administering to said patient an effective amount of at least one (usually one) compound of formula 1.0 in combination with at least one chemotherapeutic agent (also know in the art as antineoplastic agent or anticancer agent).

This invention also provides methods of treating (or inhibiting) tumors (i.e., cancers) in a patient in need of such treatment comprising administering to said patient an effective amount of at least one (usually one) compound of formula 1.0 in combination with at least one chemotherapeutic agent (also know in the art as antineoplastic agent or anticancer agent) and/or radiation.

This invention also provides methods of treating (or inhibiting) tumors (i.e., cancers) in a patient in need of such treatment comprising administering to said patient an effective amount of at least one (usually one) compound of formula 1.0 in combination with at least one signal transduction inhibitor.

In the methods of this invention the compounds of formula 1.0 can be administered concurrently or sequentially (i.e., consecutively) with the chemotherapeutic agents or the signal transduction inhibitor.

DETAILED DESCRIPTION OF THE INVENTION

As described herein, unless otherwise indicated, the use of a drug or compound in a specified period (e.g., once a week, or once every three weeks, etc.,) is per treatment cycle.

As used herein, the following terms have the following meanings unless otherwise described:
AD HPLC is a HPLC column from Chiral Technologies;
AUC-represents "Area Under the Curve";
BOC-represents tert-butyloxycarbonyl;
CBZ-represents —C(O)OCH$_2$C$_6$H$_5$ (i.e., benzyloxycarbonyl);
CH$_2$Cl$_2$-represents dichloromethane;
CIMS-represents chemical ionization mass spectrum;
Cmpd-represents Compound;
DBU-represents 1,8-Diazabicyclo[5.4.0]undec-7-ene;
DEAD-represents diethylazodicarboxylate;
DEC-represents EDCI which represents 1-(3-dimethylaminopropyl)-3-ethylcarbodiimide hydrochloride;
DMF-represents N,N-dimethylformamide;
DPPA-represents diphenylphosphoryl azide
Et-represents ethyl;
Et$_3$N-represents TEA which represents triethylamine;
EtOAc-represents ethyl acetate;
EtOH-represents ethanol;
FAB-represents FABMS which represents fast atom bombardment mass spectroscopy;
HOBT-represents 1-hydroxybenzotriazole hydrate;
HRMS-represents high resolution mass spectroscopy;
IPA-represents isopropanol;
i-PrOH-represents isopropanol;
Me-represents methyl;
MeOH-represents methanol;
MH$^+$-represents the molecular ion plus hydrogen of the molecule in the mass spectrum;
MS-represents mass spectroscopy;
NMM-represents N-methylmorpholine;
OD HPLC is a HPLC column from Chiral Technologies;
PPh$_3$-represents triphenyl phosphine;
Ph-represents phenyl;
Pr-represents propyl;
SEM-represents 2,2-(Trimethylsilyl)ethoxymethyl;
TBDMS-represents tert-butyldimethylsilyl;
t-BUTYL-represents —C—(CH$_3$)$_3$;
TFA-represents trifluoroacetic acid;
THF-represents tetrahydrofuran;
Tr-represents trityl;
Tf-represents SO$_2$CF$_3$;
at least one-represents one or more-(e.g. 1-6), more preferrably 1-4 with 1, 2 or 3 being most preferred;
alkenyl-represents straight and branched carbon chains having at least one carbon to carbon double bond and containing from 2-12 carbon atoms, preferably from 2 to 6 carbon atoms and most preferably from 3 to 6 carbon atoms;
alkoxy-represents an alkyl moiety, alkyl as defined below, covalently bonded to an adjacent structural element through an oxygen atom, for example, methoxy, ethoxy, propoxy, butoxy and the like;
alkyl-represents straight and branched carbon chains and contains from one to twenty carbon atoms, preferably one to six carbon atoms, more preferably one to four carbon atoms; even more preferably one to two carbon atoms;
alkylcarbonyl-represents an alkyl group, as defined above, covalently bonded to a carbonyl moiety (—CO—), for example, —COCH$_3$;
alkyloxycarbonyl-represents an alkyl group, as defined above, covalently bonded to a carbonyl moiety (—CO—) through an oxygen atom, for example, —C(O)—OC$_2$H$_5$;
alkynyl-represents straight and branched carbon chains having at least one carbon to carbon triple bond and containing from 2-12 carbon atoms, preferably from 2 to 6 carbon atoms and most preferably from 2 to 4 carbon atoms;
amino-represents an —NH$_2$ moiety;
antineoplastic agent-represents a chemotherapeutic agent effective against cancer;
aryl-represents a carbocyclic group containing from 6 to 15 carbon atoms in the unsubstituted carbocyclic group and having at least one aromatic ring (e.g., aryl is a phenyl ring), with all available substitutable carbon atoms of the carbocyclic group being intended as possible points of attachment of said aryl group, said aryl group being unsubstituted or substituted, said substituted aryl group having one or more (e.g., 1 to 3) substituents independently selected from the group consisting of: halo, alkyl, hydroxy, alkoxy, phenoxy, CF$_3$, —C(O)N(R$^{18}$)$_2$, —SO$_2$R$^{18}$, —SO$_2$N(R$^{18}$)$_2$, amino, alkylamino, dialkylamino, —COOR$^{23}$ and —NO$_2$ (preferably said substitutents are independently selected from the group consisting of: alkyl (e.g., C$_1$-C$_6$ alkyl), halogen (e.g., Cl and Br), —CF$_3$ and —OH), wherein each R$^{18}$ is independently selected from the group consisting of: H, alkyl, aryl, arylalkyl, heteroaryl and cycloalkyl, and wherein R is selected from the group consisting of: alkyl and aryl;
arylalkyl-represents an alkyl group, as defined above, substituted with an aryl group, as defined above;
arylheteroalkyl-represents a heteroalkyl group, as defined below, substituted with an aryl group, as defined above;
aryloxy-represents an aryl moiety, as defined above, covalently bonded to an adjacent structural element through an oxygen atom, for example, —O-phenyl (i.e., phenoxy);
compound-with reference to the antineoplastic agents, includes the agents that are antibodies;
concurrently-represents (1) simultaneously in time (e.g., at the same time), or (2) at different times during the course of a common treatment schedule;
consecutively-means one following the other;
cycloalkenyl-represents unsaturated carbocyclic rings of from 3 to 20 carbon atoms in the unsubstituted ring, preferably 3 to 7 carbon atoms, said cycloalkenyl ring comprising at least one (usually one) double bond, and said cycloalkenyl ring being unsubstituted or substituted, said substituted cycloalkenyl ring having one or more (e.g., 1, 2 or 3) substituents independently selected from the group consisting of: alkyl (e.g., methyl and ethyl), halogen, —CF$_3$ and —OH;

cycloalkyl—represents saturated carbocyclic rings of from 3 to 20 carbon atoms in the unsubstituted ring, preferably 3 to 7 carbon atoms, said cycloalkyl ring being unsubstituted or substituted, said substituted cycloalkyl ring having one or more (e.g., 1, 2 or 3) substituents independently selected from the group consisting of: alkyl (e.g., methyl and ethyl), halogen, —CF$_3$ and —OH; for example, 1-substituted cycloalkyl rings, such as, for example,

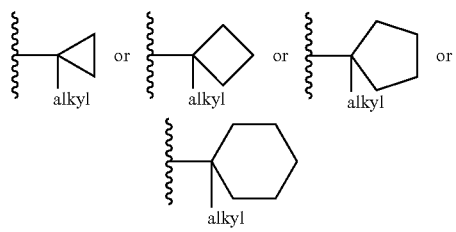

wherein said alkyl is generally a C$_1$-C$_6$ alkyl group, usually a C$_1$-C$_2$ alkyl group, and preferably a methyl group; thus, examples of cycloalkyl rings substituted at the 1-position with methyl include but are not limited to:

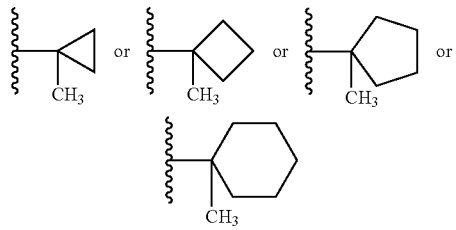

cycloalkylalkyl—represents an alkyl group, as defined above, substituted with a cycloalkyl group, as defined above;

different—as used in the phrase "different antineoplastic agents" means that the agents are not the same compound or structure; preferably, "different" as used in the phrase "different antineoplastic agents" means not from the same class of antineoplastic agents; for example, one antineoplastic agent is a taxane, and another antineoplastic agent is a platinum coordinator compound;

effective amount—represents a therapeutically effective amount; for example, the amount of the compound (or drug), or radiation, that results in: (a) the reduction, alleviation or disappearance of one or more symptoms caused by the cancer, (b) the reduction of tumor size, (c) the elimination of the tumor, and/or (d) long-term disease stabilization (growth arrest) of the tumor; for example, in the treatment of lung cancer (e.g., non small cell lung cancer) a therapeutically effective amount is that amount that alleviates or eliminates cough, shortness of breath and/or pain; also, for example, a therapeutically effective amount of the FPT inhibitor is that amount which results in the reduction of farnesylation; the reduction in farnesylation may be determined by the analysis of pharmacodynamic markers such as Prelamin A and HDJ-2 (DNAJ-2) using techniques well known in the art;

halo (or halogen)—represents fluoro, chloro, bromo or iodo;

haloalkyl—represents an alkyl group, as defined above, substituted with a halo group;

heteroatom—represents a O, N or S atom;

heteroalkenyl—represents straight and branched carbon chains having at least one carbon to carbon double bond and containing from two to twenty carbon atoms, preferably two to six carbon atoms interrupted by 1 to 3 heteroatoms selected from the group consisting of: —O—, —S—and —N—, provided that when there is more than one heteroatom, the heteroatoms are not adjacent to one another;

heteroalkyl—represents straight and branched carbon chains containing from one to twenty carbon atoms, preferably one to six carbon atoms interrupted by 1 to 3 heteroatoms selected from the group consisting of: —O—, —S—and —N—, provided that when there is more than one heteroatom, the heteroatoms are not adjacent to one another;

heteroalkynyl—represents straight and branched carbon chains having at least one carbon to carbon triple bond and containing from two to twenty carbon atoms, preferably two to six carbon atoms interrupted by 1 to 3 heteroatoms selected from the group consisiting of: —O—, —S— and —N-provided that when there is more than one heteroatom, the heteroatoms are not adjacent to one another;

heteroaryl—represents unsubstituted or substituted cyclic groups, having at least one heteroatom selected from the group consisting of: O, S or N (provided that any O and S atoms are not adjacent to one another), said heteroaryl group comprises O and S atoms, said heteroatom interrupting a carbocyclic ring structure and having a sufficient number of delocalized pi electrons to provide aromatic character, with the unsubstituted heteroaryl group preferably containing from 2 to 14 carbon atoms, wherein said substituted heteroaryl group is substitued with one or more (e.g., 1, 2 or 3) of the same or different R$^{34}$ (as defined for formula 1.1) groups, examples of heteroaryl groups include but are not limited to: e.g., 2- or 3-furyl, 2- or 3-thienyl, 2-, 4- or 5-thiazolyl, 2-, 4- or 5-imidazolyl, 2-, 4- or 5-pyrimidinyl, 2-pyrazinyl, 3- or 4-pyridazinyl, 3-, 5- or 6-[1,2,4-triazinyl], 3- or 5-[1,2,4-thiadizolyl], 2-, 3-, 4-, 5-, 6- or 7-benzofuranyl, 2-, 3-, 4-, 5-, 6- or 7-indolyl, 3-, 4- or 5-pyrazolyl, 2-, 4- or 5-oxazolyl, triazolyl, 2-, 3- or 4-pyridyl, or 2-, 3- or 4-pyridyl N-oxide, wherein pyridyl N-oxide can be represented as:

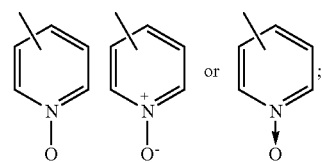

heteroarylalkenyl—represents an alkenyl group, as defined above, substituted with a heteroaryl group, as defined below;

heteroarylalkyl—represents an alkyl group, as defined above, substituted with a heteroaryl group, as defined above;

heterocycloalkylalkyl—represents an alkyl group, as defined above, substituted with a heterocycloalkyl group, as defined below;

heterocycloalkyl—represents a saturated carbocylic ring containing from 3 to 15 carbon atoms, preferably from 4 to 6 carbon atoms, which carbocyclic ring is interrupted by 1 to 3 hetero groups selected from the group consisting of: —O—, —S— or —NR$^{24}$ wherein R$^{24}$ is selected from the group consisting of: H, alkyl, aryl, and —C(O)N(R$^{18}$)$_2$ wherein R$^{18}$ is as above defined, examples of heterocycloalkyl groups include but are not limited to: 2- or 3-tetrahydrofuranyl, 2- or 3-tetrahydrothienyl, 2-, 3- or 4-piperidinyl, 2- or 3-pyrrolidinyl, 1-, 2-, 3-, or 4-piperizinyl, 2- or 4-dioxanyl, morpholinyl, and

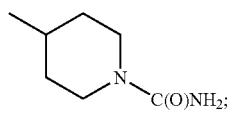

heterocycloalkylalkyl—represents an alkyl group, as defined above, substituted with a heterocycloalkyl group, as above;

"in association with"—means, in reference to the combination therapies of the invention, that the agents or components are adminstered concurrently or sequentially;

patient—represents a mammal, such as a human;

sequentially—represents (1) administration of one component of the method ((a) compound of the invention, or (b) chemotherapeutic agent, signal transduction inhibitor and/or radiation therapy) followed by administration of the other component or components; after adminsitration of one component, the next component can be administered substantially immediately after the first component, or the next component can be administered after an effective time period after the first component; the effective time period is the amount of time given for realization of maximum benefit from the administration of the first component.

The positions in the tricyclic ring system are:

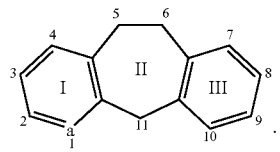

A "+" or a "−" in Ring II in the compounds below indicates the "(+)-isomer" or "(−)-isomer", respectively.

As well known in the art, a bond drawn from a particular atom wherein no moiety is depicted at the terminal end of the bond indicates a methyl group bound through that bond to the atom. For example:

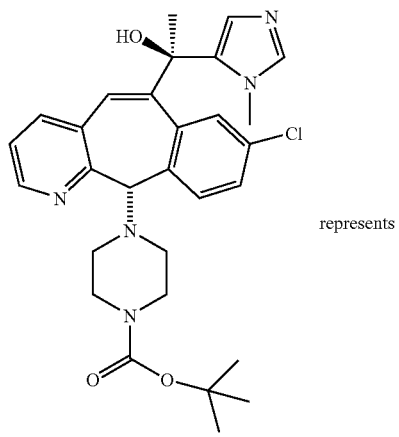
represents

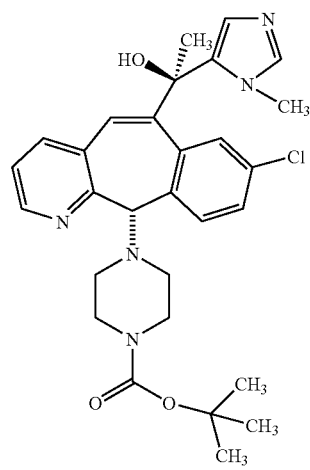

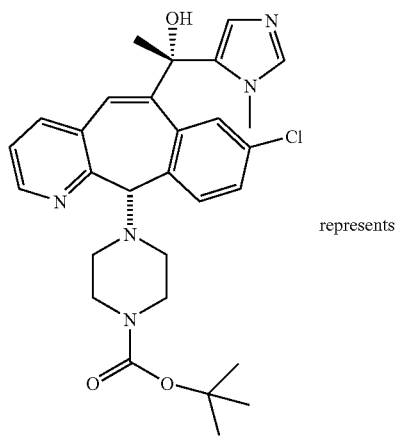
represents

-continued
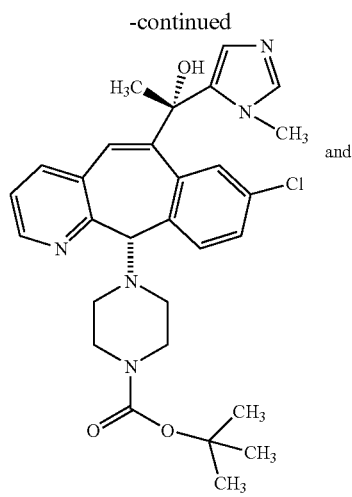
and
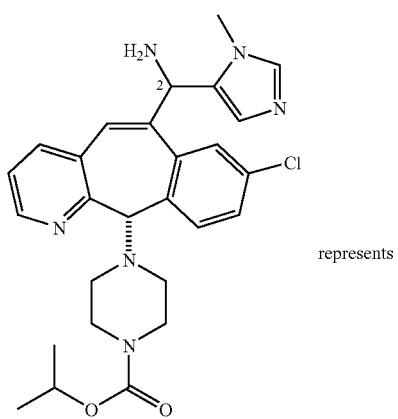
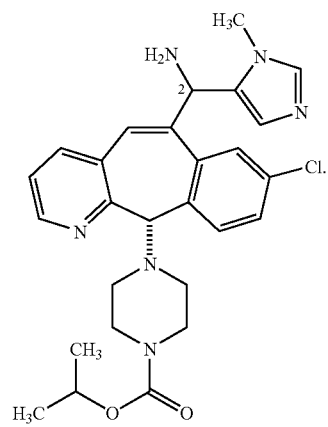
Those skilled in the art will appreciate that the numbers "1" and "2" in a formula, e.g.,
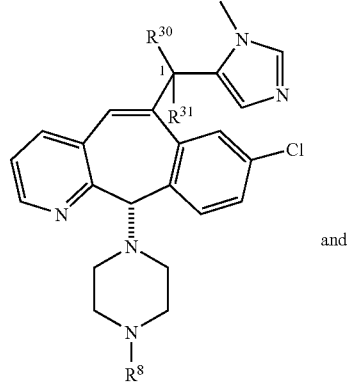
and
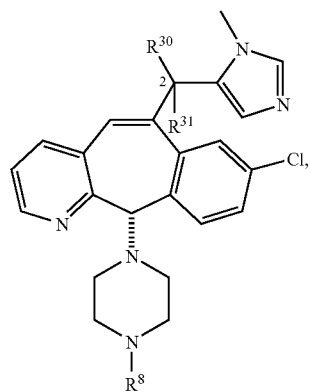
represent Isomers 1 and 2, respectively. One of the isomers is
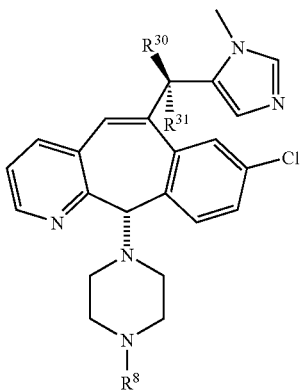
represents and one of the isomers is:

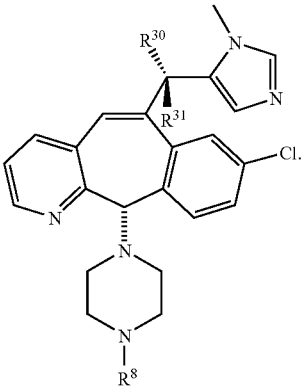

For example, for the isomers

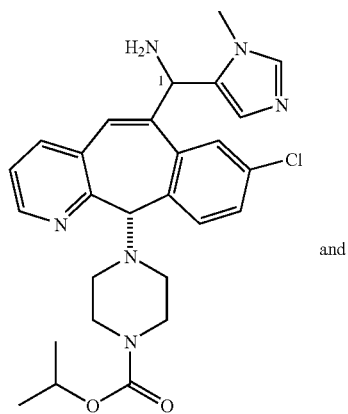

and

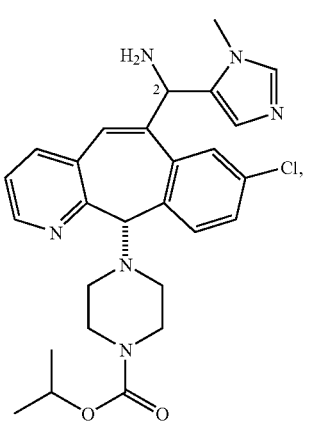

one isomers is

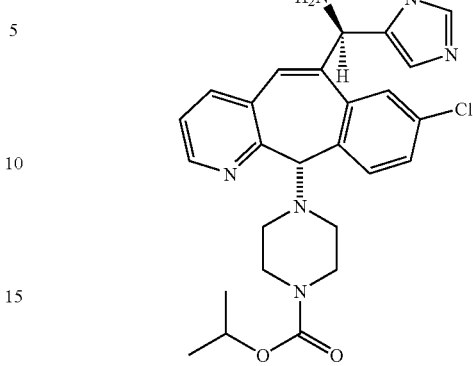

and one isomer is:

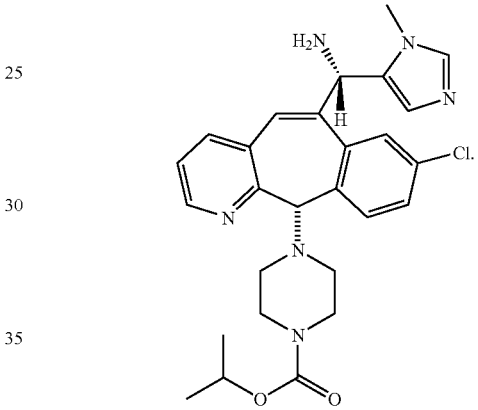

For the compounds of this invention, Isomer 1 means that the compound is the first isomer to be obtained from the separation column being used to separate the diastereomer mixture (e.g., the first isomer obtained by HPLC) or is a derivative of that first isomer. Isomer 2 means that the compound is the second isomer to be obtained from the separation column being used to separate the diastereomer mixture (e.g., the second isomer obtained by HPLC) or is a derivative of that second isomer.

Those skilled in the art will appreciate that the compounds of formula 1.0 are also represented by compounds of formula 1.1:

(1.1)

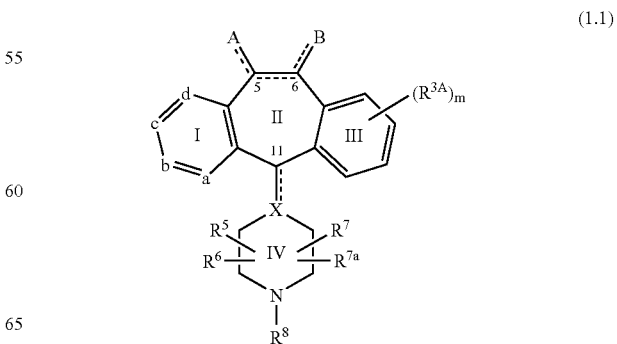

or a pharmaceutically acceptable salt or solvate thereof, wherein:
(A) one of a, b, c and d represents N or $N^+O^-$, and the remaining a, b, c, and d groups represent $CR^1$ (i.e., carbon with an $R^1$ group) wherein each $R^1$ group on each carbon is the same or different; or
(B) each a, b, c, and d group represents $CR^1$ (i.e., carbon with an $R^1$ group) wherein each $R^1$ group on each carbon is the same or different;
(C) the dotted lines (---) represent optional bonds;
(D) X represents N or CH when the optional bond (to C11) is absent, and represents C when the optional bond (to C11) is present;
(E) when the optional bond is present between carbon atom 5 (i.e., C-5) and carbon atom 6 (i.e., C-6) (i.e., there is a double bond between C-5 and C-6) then there is only one A substituent bound to C-5 and there is only one B substituent bound to C-6, and A or B is other than H;
(F) when the optional bond is not present between carbon atoms 5 and 6 (i.e., there is a single bond between C-5 and C-6) then:
 (1) there are two A substituents bound to C-5 wherein each A substituent is independently selected; and
 (2) there are two B substituents bound to C-6 wherein each B substituent is independently selected; and
 (3) at least one of the two A substituents or one of the two B substituents is H; and
 (4) at least one of the two A substituents or one of the two B substituents is other than H; (i.e., when there is a single bond between C-5 and C-6 one of the four substituents;
(G) A and B is independently selected from the group consisting of:
 (1) —H;
 (2) —$R^9$;
 (3) —$R^9$—C(O)—$R^9$;
 (4) —$R^9$—$CO_2$—$R^{9a}$;
 (5) —$(CH_2)_pR^{26}$;
 (6) —$C(O)N(R^9)_2$, wherein each $R^9$ is the same or different;
 (7) —$C(O)NHR^9$;
 (8) —C(O)NH—$CH_2$—C(O)—$NH_2$;
 (9) —$C(O)NHR^{26}$;
 (10) —$(CH_2)_pC(R^9)$—O—$R^{9a}$;
 (11) —$(CH_2)_{p-1}CH(R^9)_2$, provided that p is not 0, and wherein each $R^9$ is the same or different;
 (12) —$(CH_2)_pC(O)R^9$;
 (13) —$(CH_2)_pC(O)R^{27a}$;
 (14) —$(CH_2)_pC(O)N(R^9)_2$, wherein each $R^9$ is the same or different;
 (15) —$(CH_2)_pC(O)NH(R^9)$;
 (16) —$(CH_2)_pC(O)N(R^{26})_2$, wherein each $R^{26}$ is the same or different;
 (17) —$(CH_2)_pN(R^9)$—$R^{9a}$ (e.g. —$CH_2$—N($CH_2$-pyridine)-$CH_2$-imidazole);
 (18) —$(CH_2)_pN(R^{26})_2$, wherein each $R^{26}$ is the same or different (e.g., —$(CH_2)_p$—N H—$CH_2$—$CH_3$);
 (19) —$(CH_2)_pNHC(O)R^{50}$;
 (20) —$(CH_2)_pNHC(O)_2R^{50}$;
 (21) —$(CH_2)_pN(C(O)R^{27a})_2$ wherein each $R^{27a}$ is the same or different;
 (22) —$(CH_2)_pNR^{51}C(O)R^{27}$,
 (23) —$(CH_2)_pNR^{51}C(O)R^{27}$ wherein $R^{51}$ is not H, and $R^{51}$ and $R^{27}$ taken together with the atoms to which they are bound form a 5 or 6 membered heterocycloalkyl ring;
 (24) —$(CH_2)_pNR^{51}C(O)NR^{27}$,
 (25) —$(CH_2)_pNR^{51}C(O)NR^{27}$ wherein $R^{51}$ is not H, and $R^{51}$ and $R^{27}$ taken together with the atoms to which they are bound form a 5 or 6 membered heterocycloalkyl ring;
 (26) —$(CH_2)_pNR^{51}C(O)N(R^{27a})_2$, wherein each $R^{27a}$ is the same or different;
 (27) —$(CH_2)_pNHSO_2N(R^{51})_2$, wherein each $R^{51}$ is the same or different;
 (28) —$(CH_2)_pNHCO_2R^5$;
 (29) —$(CH_2)_pNC(O)NHR^{51}$;
 (30) —$(CH_2)_pCO_2R^{51}$;
 (31) —$NHR^9$;

(32)

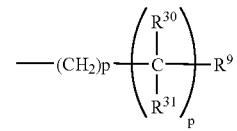

wherein $R^{30}$ and $R^{31}$ are the same or different, and each p is independently selected; provided that for each

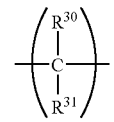

group when one of $R^{30}$ or $R^{31}$ is selected from the group consisting of: —OH, =O, —$OR^9$, —$NH_2$, —$NHR^{9a}$, —$N(R^{9a})_2$, —$N_3$, —$NHR^{9b}$, and —$N(R^{9a})R^{9b}$, then the remaining $R^{30}$ or $R^{31}$ is selected from the group consisting of: H, alkyl, aryl (e.g., phenyl), and arylalkyl (e.g., benzyl);

(33)

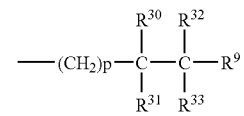

wherein $R^{30}$, $R^{31}$, $R^{32}$ and $R^{33}$ are the same or different; provided that when one of $R^{30}$ or $R^{31}$ is selected from the group consisting of: —OH, =O, —$OR^{9a}$, —$NH_2$, —$NHR^{9a}$, —$N(R^9)_2$, —$N_3$, —$NHR^{9b}$, and —$N(R^{9a})R^{9b}$, then the remaining $R^{30}$ or $R^3$ is selected from the group consisting of: H, alkyl, aryl (e.g., phenyl), and arylalkyl (e.g., benzyl); and provided that when one of $R^{32}$ or $R^{33}$ is selected from the group consisting of: —OH, =O, —$OR^{9a}$, —$NH_2$, —$NHR^{9a}$, —$N(R^{9a})_2$, —$N_3$, —$NHR^{9b}$, and —$N(R^{9a})R^{9b}$, then the remaining $R^{32}$ or $R^{33}$ is selected from the group consisting of: H, alkyl, aryl (e.g., phenyl), and arylalkyl (e.g., benzyl);
 (34) -alkenyl-$CO_2R^{9a}$;
 (35) -alkenyl-$C(O)R^{9a}$;
 (36) -alkenyl-$CO_2R^{51}$;
 (37) -alkenyl-C(O)—$R^{27a}$;
 (38) $(CH_2)_p$-alkenyl-$CO_2$—$R^{51}$;
 (39) —$(CH_2)_pC$=$NOR^{51}$; and

(40) —(CH$_2$)$_p$-Phthalimid;

(H) p is 0, 1, 2, 3 or 4;

(I) R$^1$ is selected from the group consisting of:
(1) H;
(2) halo;
(3) —CF$_3$;
(4) —OR
(5) COR$^{10}$;
(6) —SR$^{10}$;
(7) —S(O)$_t$R$^{15}$;
(8) —N(R$^{10}$)$_2$;
(9) —NO$_2$;
(10) —OC(O)R$^{10}$;
(11) CO$_2$R$^{10}$;
(12) —OCO$_2$R$^{15}$;
(13) —CN;
(14) —NR$^{10}$COOR$^{15}$;
(15) —SR$^5$C(O)OR$^{15}$;
(16) —SR$^{15}$N(R$^{13}$)$_2$ wherein each R$^{13}$ is independently selected from the group consisting of: H and —C(O)OR$^{15}$, and provided that R$^{15}$ in —SR$^{15}$N(R$^{13}$)$_2$ is not —CH$_2$;
(17) benzotriazol-1-yloxy;
(18) tetrazol-5-ylthio;
(19) substituted tetrazol-5-ylthio;
(20) alkynyl;
(21) alkenyl;
(22) alkyl;
(23) alkyl substituted with one or more (e.g., 1, 2 or 3) substitutents independently selected from the group consisting of: halogen, —OR and —CO$_2$R$^{10}$;
(24) alkenyl substituted with one or more (e.g., 1, 2 or 3) substitutents independently selected from the group consisting of: halogen, —OR and —CO$_2$R$^{10}$;

(J) Each R$^{3,4}$ is independently selected from the group consisting of:
(1) halo;
(2) —CF$_3$;
(3) —OR$^{10}$;
(4) COR$^{10}$;
(5) —SR$^{10}$;
(6) —S(O)$_t$R$^{15}$;
(7) —N(R$^{10}$)$_2$;
(8) —NO$_2$;
(9) —OC(O)R$^{10}$;
(10) CO$_2$R$^{10}$;
(11) —OCO$_2$R$^{15}$;
(12) —CN;
(13) —NR$^{10}$COOR$^{15}$;
(14) —SR C(O)OR$^{15}$;
(15) —SR$^{15}$N(R$^{13}$)$_2$ wherein each R$^{13}$ is independently selected from the group consisting of: H and —C(O)OR$^{15}$, and provided that R$^{15}$ in —SR$^{15}$N(R$^{13}$)$_2$ is not —CH$_2$;
(16) benzotriazol-1-yloxy;
(17) tetrazol-5-ylthio;
(18) substituted tetrazol-5-ylthio;
(19) alkynyl;
(20) alkenyl;
(21) alkyl;
(22) alkyl substituted with one or more (e.g., 1, 2 or 3) substitutents independently selected from the group consisting of: halogen, —OR$^{10}$ and —CO$_2$R$^{10}$; and
(23) alkenyl substituted with one or more (e.g., 1, 2 or 3) substitutents independently selected from the group consisting of: halogen, —OR$^{10}$ and —CO$_2$R$^{10}$;

(K) m is 0, 1 or 2;

(L) t is 0, 1 or 2

(M) R$^5$, R$^6$, R$^7$ and R$^{7a}$ are each independently selected from the group consisting of:
(1) H;
(2) —CF$_3$;
(3) —COR$^{10}$;
(4) alkyl;
(5) unsubstituted aryl;
(6) alkyl substituted with one or more (e.g., 1, 2 or 3) groups selected from the group consisting of: —S(O)$_t$R$^{15}$, —NR COOR$^{10}$, —C(O)R$^{15}$, and —CO$_2$R$^{10}$; and
(7) aryl substituted with one or more (e.g., 1, 2, or 3) groups selected from the group consisting of: —S(O)$_t$R$^{15}$, —NR$^{10}$COOR$^{15}$, —C(O)R$^{10}$, and —CO$_2$R$^{10}$; or (N) R together with R represents =O or =S;

(O) R$^8$ is selected from the group consisting of:

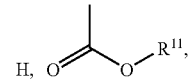

(2.0)

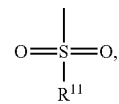

(3.0)

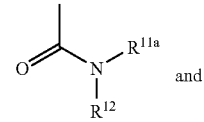

and (4.0)

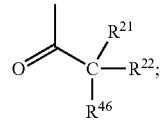

(5.0)

(P) R$^9$ is selected from the group consisting of:
(1) unsubstituted heteroaryl;
(2) substituted heteroaryl;
(3) unsubstituted arylalkoxy;
(4) substituted arylalkoxy;
(5) heterocycloalkyl;
(6) substituted heterocycloalkyl;
(7) heterocycloalkylalkyl;
(8) substituted heterocycloalkylalkyl;
(9) unsubstituted heteroarylalkyl;
(10) substituted heteroarylalkyl;
(11) unsubstituted heteroarylalkenyl;
(12) substituted heteroarylalkenyl;
(13) unsubstituted heteroarylalkynyl and
(14) substituted heteroarylalkynyl;

wherein said substituted R$^9$ groups are substituted with one or more (e.g. 1, 2 or 3) substituents independently selected from the group consisting of:
(1) —OH, provided that when there is more than one —OH group then each —OH group is bound to a different carbon atom (i.e., only one —OH group can be bound to a carbon atom);
(2) —CO$_2$R$^{14}$;
(3) —CH$_2$OR$^{14}$,
(4) halogen (e.g. Br, Cl or F), (5) alkyl (e.g. methyl, ethyl, propyl, butyl or t-butyl);
(6) amino;
(7) trityl;
(8) heterocycloalkyl;
(9) cycloalkyl, (e.g. cyclopropyl or cyclohexyl);
(10) arylalkyl;
(11) heteroaryl;
(12) heteroarylalkyl and (13)

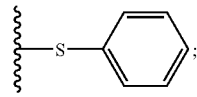

;

wherein $R^{14}$ is independently selected from the group consisting of: H; alkyl; aryl, arylalkyl, heteroaryl and heteroarylalkyl;
  (Q) $R^{9a}$ is selected from the group consisting of: alky and arylalkyl;
  (R) $R^{9b}$ is selected from the group consisting of:
    (1) —C(O)$R^{9a}$;
    (2) —SO$_2$$R^{9a}$;
    (3) —C(O)NH$R^{9a}$;
    (4) —C(O)O$R^{9a}$; and
    (5) —C(O)N($R^{9c}$)$_2$;
  (S) Each $R^{9c}$ is independently selected from the group consisting of: H, alkyl and arylalkyl;
  (T) $R^{10}$ is selected from the group consisting of: H; alkyl; aryl and arylalkyl;
  (U) $R^{11}$ is selected from the group consisting of:
    (1) alkyl;
    (2) substituted alkyl;
    (3) unsubstituted aryl;
    (4) substituted aryl;
    (5) unsubstituted cycloalkyl;
    (6) substituted cycloalkyl;
    (7) unsubstituted heteroaryl;
    (8) substituted heteroaryl;
    (9) heterocycloalkyl; and
    (10) substituted heterocycloalkyl;
wherein said substituted alkyl, substituted cycloalkyl, and substituted heterocycloalkyl $R^{11}$ groups are substituted with one or more (e.g. 1, 2 or 3) substituents selected from the group consisting of:
    (1) —OH, provided that when there is more than one —OH group then each —OH group is bound to a different carbon atom (i.e., only one —OH group can be bound to a carbon atom);
    (2) fluoro; and
    (3) alkyl; and
wherein said substituted aryl and substituted heteroaryl $R^{11}$ groups are substituted with one or more (e.g. 1, 2 or 3) substituents selected from the group consisting of:
    (1) —OH, provided that when there is more than one —OH group then each —OH group is bound to a different carbon atom (i.e., only one —OH group can be bound to a carbon atom);
    (2) halogen (e.g. Br, Cl or F); and
    (3) alkyl;
  (V) $R^{11a}$ is selected from the group consisting of:
    (1) H;
    (2) OH;
    (3) alkyl;
    (4) substituted alkyl;
    (5) unsubstituted aryl;
    (6) substituted aryl;
    (7) unsubstituted cycloalkyl;
    (8) substituted cycloalkyl;
    (9) unsubstituted heteroaryl;
    (10) substituted heteroaryl;
    (11) heterocycloalkyl;
    (12) substituted heterocycloalkyl; and
    (13) O$R^{9a}$;
wherein said substituted alkyl, substituted cycloalkyl, and substituted heterocycloalkyl $R^{11a}$ groups are substituted with one or more (e.g. 1, 2 or 3) substituents selected from the group consisting of:
    (1) —OH, provided that when there is more than one —OH group then each —OH group is bound to a different carbon atom (i.e., only one —OH group can be bound to a carbon atom);
    (2) —CN;
    (3) —CF$_3$;
    (4) fluoro;
    (5) alkyl;
    (6) cycloalkyl;
    (7) heterocycloalkyl;
    (8) arylalkyl;
    (9) heteroarylalkyl;
    (10) alkenyl and
    (11) heteroalkenyl; and
wherein said substituted aryl and substituted heteroaryl $R^{11a}$ groups are substituted with one or more (e.g. 1, 2 or 3) substituents selected from the group consisting of:
    (1) —OH, provided that when there is more than one —OH group then each —OH group is bound to a different carbon atom (i.e., only one —OH group can be bound to a carbon atom);
    (2) —CN;
    (3) —CF$_3$;
    (4) halogen (e.g Br, Cl or F);
    (5) alkyl;
    (6) cycloalkyl;
    (7) heterocycloalkyl;
    (8) arylalkyl;
    (9) heteroarylalkyl;
    (10) alkenyl and
    (11) heteroalkenyl;
  (W) $R^{12}$ is selected from the group consisting of: H, alkyl, piperidine Ring V, cycloalkyl, and -alkyl-(piperidine Ring V);
  (X) $R^{15}$ is selected from the group consisting of: alkyl and aryl;
  (Y) $R^{21}$, $R^{22}$ and $R^{46}$ are independently selected from the group consisting of:
    (1) H;
    (2) alkyl (e.g., methyl, ethyl, propyl, butyl or t-butyl);
    (3) unsubstituted aryl (e.g. phenyl);
    (4) substituted aryl substituted with one or more substituents independently selected from the group consisting of: alkyl, halogen, CF$_3$ and OH;
    (5) unsubstituted cycloalkyl, (e.g. cyclohexyl);
    (6) substituted cycloalkyl substituted with one or more substituents independently selected from: alkyl, halogen, CF$_3$ or OH;

(7) heteroaryl of the formula,

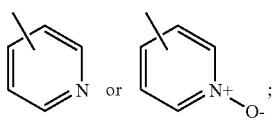

(8) piperidine Ring V:

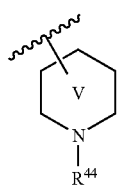

wherein $R^{44}$ is selected from the group consisting of:
  (a) H,
  (b) alkyl, (e.g., methyl, ethyl, propyl, butyl or t-butyl),
  (c) alkylcarbonyl (e.g., $CH_3C(O)$—);
  (d) alkyloxy carbonyl (e.g., —$C(O)O$-t-$C_4H_9$, —$C(O)OC_2H_5$, and —$C(O)OCH_3$);
  (e) haloalkyl (e.g., trifluoromethyl) and
  (f) —$C(O)NH(R^{51})$;
(9) —$NH_2$ provided that only one of $R^{21}$, $R^{22}$, and $R^{46}$ group can be —$NH_2$, and provided that when one of $R^{21}$, $R^{22}$, and $R^{46}$ is —$NH_2$ then the remaining groups are not —OH;
(10) —OH provided that only one of $R^{21}$, $R^{22}$, and $R^{46}$ group can be —OH, and provided that when one of $R^{21}$, $R^{22}$, and $R^{46}$ is —OH then the remaining groups are not —$NH_2$; and
(11) alkyl substituted with one or more substituents (e.g., 1-3, or 1-2, and preferably 1) selected from the group consisting of: —OH and —$NH_2$, and provided that there is only one —OH or one —$NH_2$ group on a substituted carbon; or
(12) $R^{21}$ and $R^{22}$ taken together with the carbon to which they are bound form a cyclic ring selected from the group consisting of:
  (a) unsubstituted cycloalkyl (e.g., cyclopropyl, cyclobutyl, cyclopentyl, and cyclohexyl);
  (b) cycloalkyl substituted with one or more substituents independently selected from the group consisting of: alkyl, halogen, $CF_3$ and OH;
  (c) unsubstituted cycloalkenyl

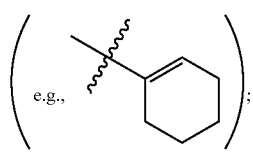

(d) cycloalkenyl substituted with one or more substituents independently selected from the group consisting of: alkyl, halogen, $CF_3$ and OH;
  (e) heterocycloalkyl, e.g., a piperidyl ring of the formula:

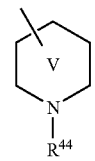

wherein $R^{44}$ is selected from the group consisting of:
  (1) —H,
  (2) alkyl, (e.g., methyl, ethyl, propyl, butyl or t-butyl);
  (3) alkylcarbonyl (e.g., $CH_3C(O)$—);
  (4) alkyloxy carbonyl (e.g., —$C(O)O$-t-$C_4H_9$, —$C(O)OC_2H_5$, and-$C(O)OCH_3$);
  (5) haloalkyl (e.g., trifluoromethyl); and
  (6) —$C(O)NH(R^{51})$;
  (f) unsubstituted aryl (e.g., phenyl);
  (g) aryl substituted with one or more substituents independently selected from the group consisting of: alkyl (e.g., methyl), halogen (e.g., Cl, Br and F), —CN, —$CF_3$, OH and alkoxy (e.g., methoxy); and
  (i) heteroaryl selected from the group consisting of:

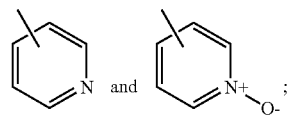

(Z) $R^{26}$ is selected from the group consisting of:
  (1) H;
  (2) alkyl (e.g. methyl, ethyl, propyl, butyl or t-butyl);
  (3) alkoxy (e.g. methoxy, ethoxy, propoxy);
  (4) —$CH_2$—CN;
  (5) $R^9$;
  (6) —$CH_2CO_2H$;
  (7) —C(O)alkyl and
  (8) $CH_2CO_2$alkyl;
(AA) $R^{27}$ is selected from the group consisting of:
  (1) H;
  (2) —OH;
  (3) alkyl (e.g. methyl, ethyl, propyl, or butyl), and
  (4) alkoxy;
(AB) $R^{27}$, is selected from the group consisting of:
  (1) alkyl (e.g. methyl, ethyl, propyl, or butyl); and
  (2) alkoxy;
(AC) $R^{30}$, $R^{31}$, $R^{32}$ and $R^{33}$ are independently selected from the group consisting of:
  (1) —H;
  (2) —OH;
  (3) =O;
  (4) alkyl;
  (5) aryl (e.g. phenyl);
  (6) arylalkyl (e.g. benzyl);
  (7) —$OR^{9a}$;
  (8) —$NH_2$;
  (9) —$NHR^{9a}$;
  (10) —$N(R^{9a})_2$ wherein each $R^{9a}$ is independently selected;
  (11) —$N_3$;
  (12) —$NHR^{9b}$; and
  (13) —$N(R^{9a})R^{9b}$;

(AD) $R^{50}$ is selected from the group consisting of:
  (1) alkyl;
  (2) unsubstituted heteroaryl;
  (3) substituted heteroaryl; and
  (4) amino;

wherein said substituents on said substituted heteroaryl group are independently selected from one or more (e.g., 1, 2 or 3) substitutents selected from the group consisting of: alkyl (e.g. methyl, ethyl, propyl, or butyl); halogen (e.g., Br, Cl, or F); and —OH;

(AE) $R^{51}$ is selected from the group consisting of: —H and alkyl (e.g., methyl, ethyl, propyl, butyl and t-butyl); and
  (AF) provided that a ring carbon atom adjacent to a ring heteroatom in a substituted heterocycloalkyl moiety is not substituted with a heteroatom or a halo atom; and
  (AG) provided that a ring carbon atom, that is not adjacent to a ring heteroatom, in a substituted heterocycloalkyl moiety, is not substituted with more than one heteroatom; and
  (AH) provided that a ring carbon atom, that is not adjacent to a ring heteroatom, in a substituted heterocycloalkyl moiety, is not substituted with a heteroatom and a halo atom; and
  (AI) provided that a ring carbon in a substituted cycloalkyl moiety is not substituted with more than one heteroatom; and
  (AJ) provided that a carbon atom in a substituted alkyl moiety is not substituted with more than one heteroatom; and
  (AK) provided that the same carbon atom in a substituted alkyl moiety is not substituted with both heteroatoms and halo atoms.

When there is a single bond between C-5 and C-6, then there are two A substituents bound to C-5 and there are two B substituents bound to C-6

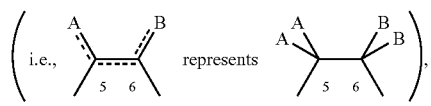

and each A and each B are independently selected, and at least one of the two A substituents or one of the two B substituents is H, and at least one of the two A substituents or one of the two B substituants is other than H (i.e., when there is a single bond between C-5 and C-6 one of the four substituents (A, A, B, and B) is H and one is other than H).

The substituted $R^9$ groups can be substituted on any portion of the group that has substitutable carbon atoms. For example, a group that has a ring moiety (e.g., a heterocycloalkyl or heteroaryl ring) bound to a hydrocarbon moiety (e.g., alkyl, alkenyl or alkynyl) can be substituted on the ring moiety and/or the hydrocarbon moiety. Thus, for example, substitued heteroarylalkyl can be substituted on the heteroaryl moiety and/or the alkyl moiety.

Piperidine Ring V includes the rings:

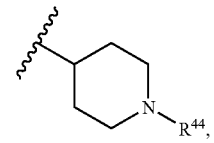
Va

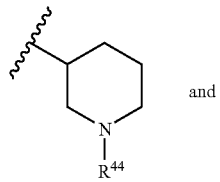
and
Vb

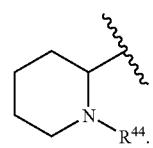
Vc

Examples of Ring V include, but are not limited to:

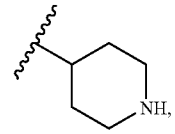
V1

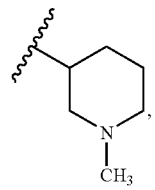
V2

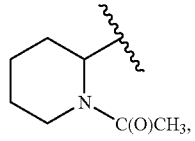
V3

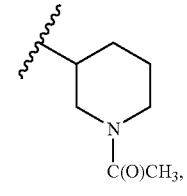
V4

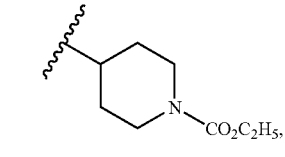
V5

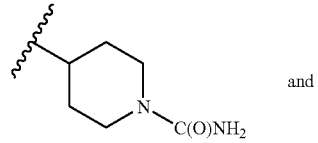
and
V6

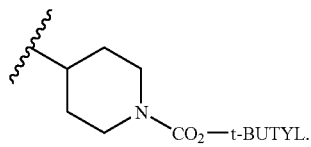

One embodiment of this invention is directed to compounds of formula 1.1 wherein the C-5 to C-6 double bond is present, A is H, and B is the group:

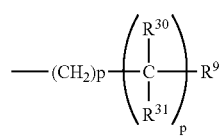

wherein p of the $-(CH_2)_p-$ moiety of said B group is 0, and wherein p of the

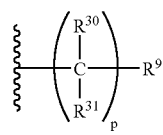

moiety of said B group is 1, and all other substitutents are as defined for formula 1.1. Preferably $R^9$ is unsubstituted heteroaryl (e.g., imidazolyl) or substituted heteroaryl (e.g., substituted imidazolyl). Most preferably $R^9$ is a substituted heteroaryl, more preferably substituted imidazolyl, even more preferably an N-alkylimidazolyl, and still more preferably

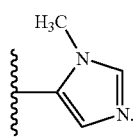

Preferably $R^{30}$ is selected from the group consisting of: —OH, —NH$_2$, —OR$^{9a}$ (wherein $R^{9a}$ is $C_1$ to $C_3$ alkyl), N$_3$, and —NHR$^{9b}$, and $R^{31}$ is selected from the group consisting of: H and alkyl (e.g., methyl). Most preferably (1) $R^{30}$ is —OH and $R^{31}$ is H; (2) $R^{30}$ is —NH$_2$ and $R^{31}$ is H; (3) $R^{30}$ is —OR$^{9a}$ (wherein $R^{9a}$ is $C_1$ to $C_3$ alkyl), and $R^{31}$ is H or alkyl (e.g., $C_1$-$C_6$, $C_1$-$C_4$, $C_1$-$C_2$, said alkyl group preferably being methyl), and preferably H; (4) $R^{30}$ is N$_3$, and $R^{31}$ is H or alkyl (e.g., $C_1$-$C_6$, $C_1$-$C_4$, $C_1$-$C_2$, said alkyl group preferably being methyl), and preferably H; or (5) $R^{30}$ is —NHR$^{9b}$ (wherein $R^{9b}$ is as defined for formula 1.1), and $R^{31}$ is H or alkyl (e.g., $C_1$-$C_6$, $C_1$-$C_4$, $C_1$-$C_2$, said alkyl group preferably being methyl), and preferably H. More preferably $R^{30}$ is —NH$_2$ or —NHR$^{9b}$, and $R^{31}$ is H. Still more preferably $R^{30}$ is —NH$_2$ and $R^{31}$ is H. Preferably X is N. Preferably a is N. Preferably b is CR$^1$ wherein $R^1$ is H. Preferably c is CR$^1$ wherein $R^1$ is H or halo (e.g., Br or Cl), and most preferably H. Preferably d is is CR$^1$ wherein $R^1$ is H. Preferably $R^5$, $R^6$, $R^7$, and $R^{7a}$ are H. Preferably m is 1 and $R^{3A}$ is halo (e.g., Br or Cl), and most preferably Cl. When m is 1, $R^{3A}$ is preferably at the C-8 position, i.e., preferably $R^{3A}$ is 8-halo and most preferably 8-Cl. $R^8$ is preferably 2.0, 3.0, 4.0 or 5.0. When $R^8$ is 2.0, $R^{11}$ is preferably alkyl (e.g., $C_1$ to $C_4$), most preferably t-butyl or isopropyl, and more preferably isopropyl. Preferably $R^8$ is 2.0. Preferably the compounds of this embodiment have the stereochemistry shown in formulas 1.5A, 1.6A or 1.7A.

One embodiment of this invention is directed to compounds of formula 1.1 having the formula:

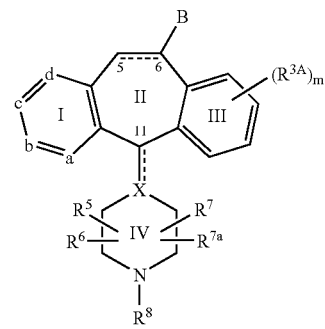

wherein:
(1) a, b, c, d, $R^{3A}$, $R^5$, $R^6$, $R^7$, $R^{7a}$, $R^8$ and X are as defined for formula 1.1;
(2) B is the group:

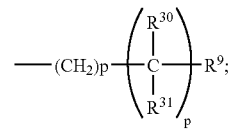

(3) in said B group:
(a) p of the $-(CH_2)_p-$ moiety is 0;
(b) p of the

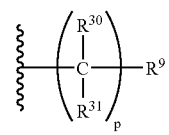

moiety is 1 to 3, preferably 1 to 2, most preferably 1;
(c) when p is 1 for the moiety

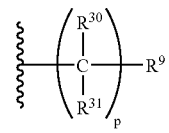

then $R^{30}$ is selected from the group consisting of: —OH, or —NH$_2$ (preferably —OH), and $R^{31}$ is alkyl, most preferably $C_1$-$C_6$ alkyl, more preferably $C_1$-$C_4$ alkyl, still more preferably $C_1$-$C_2$ alkyl, and even more preferably methyl;

(d) when p is 2 or 3 for the moiety

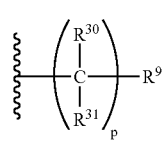

then: (1) for one —$CR^{30}R^{31}$— moiety, $R^{30}$ is selected from the group consisting of: —OH or —$NH_2$, and $R^{31}$ is alkyl, most preferably $C_1$-$C_6$ alkyl, more preferably $C_1$-$C_4$ alkyl, still more preferably $C_1$-$C_2$ alkyl, and even more preferably methyl; and (2) for the remaining —$CR^{30}R^{31}$— moieties $R^{30}$ and $R^{31}$ are hydrogen; and (e) $R^9$ is unsubstituted heteroaryl (e.g., imidazolyl) or substituted heteroaryl, preferably substituted heteroaryl, most preferably heteroaryl substituted with alkyl (e.g., methyl), more preferably substituted imidazolyl, still more preferably imidazolyl substituted with alkyl, even more preferably imidazolyl substituted with methyl, yet more preferably imidazolyl substituted on a ring nitrogen with methyl, provided that when said heteroaryl group contains nitrogen in the ring, then said heteroaryl group is not bound by a ring nitrogen to the adjacent —$CR^{30}R^{31}$— moiety when $R^{30}$ is —OH or —$NH_2$.

Another embodiment of this invention is directed to compounds of formula 1.1 having the formula:

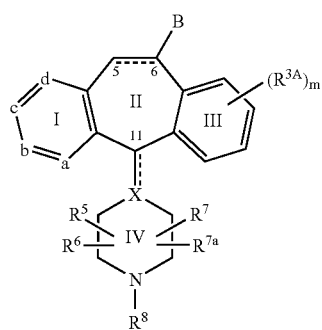

(1.3)

wherein:
(1) $R^8$ and X are as defined for formula 1.0;
(2) B is the group:

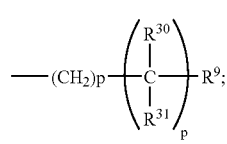

(3) in said B group:
(a) p of the —$(CH_2)_p$— moiety is 0;
(b) p of the

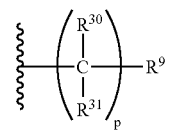

moiety is 1 to 3, preferably 1 to 2, most preferably 1;
(c) when p is 1 for the moiety

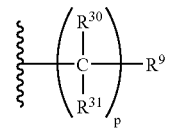

then $R^{30}$ is selected from the group consisting of: —OH or —$NH_2$, and $R^{31}$ is alkyl, most preferably $C_1$-$C_6$ alkyl, more preferably $C_1$-$C_4$ alkyl, still more preferably $C_1$-$C_2$ alkyl, and even more preferably methyl;

(d) when p is 2 or 3 for the moiety

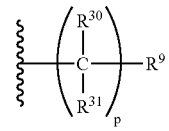

then: (1) for one —$CR^{30}R^{31}$— moiety, $R^{30}$ is selected from the group consisting of: —OH or —$NH_2$, and $R^{31}$ is alkyl, most preferably $C_1$-$C_6$ alkyl, more preferably $C_1$-$C_4$ alkyl, still more preferably $C_1$-$C_2$ alkyl, and even more preferably methyl; and (2) for the remaining —$CR^{30}R^{31}$— moieties $R^{30}$ and $R^{31}$ are hydrogen; and (e) $R^9$ is unsubstituted heteroaryl (e.g., imidazolyl) or substituted heteroaryl, preferably substituted heteroaryl, most preferably heteroaryl substituted with alkyl (e.g., methyl), more preferably substituted imidazolyl, still more preferably imidazolyl substituted with alkyl, even more preferably imidazolyl substituted with methyl, yet more preferably imidazolyl substituted on a ring nitrogen with methyl, provided that when said heteroaryl group contains nitrogen in the ring, then said heteroaryl group is not bound by a ring nitrogen to the adjacent —$CR^{30}R^{31}$— moiety when $R^{30}$ is —OH or —$NH_2$;

(4) a is N;
(5) b, c and d are $CR^1$ groups wherein all of said $R^1$ substituents are H, or one $R^1$ substituent is halo (e.g., Br, Cl or F) and the remaining two $R^1$ substituents are hydrogen;
(6) m is 1, and $R^{3A}$ is halo (e.g., Br or Cl), or m is 2 and each $R^{3A}$ is the same or different halo (e.g., Br or Cl); and
(7) $R^5$, $R^6$, $R^7$, and $R^{7a}$ are H.

Another embodiment of this invention is directed to compounds of formula 1.1 having the formula:

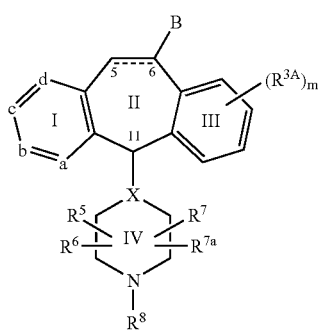

(1.4)

wherein:
(1) $R^8$ is as defined for formula 1.0;
(2) B is the group:

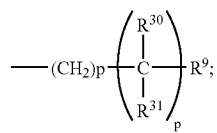

(3) in said B group:
(a) p of the —$(CH_2)_p$— moiety is 0;
(b) p of the

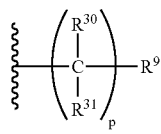

moiety is 1 to 3, preferably 1 to 2, most preferably 1;
(c) when p is 1 for the moiety

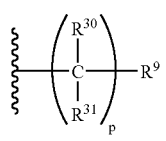

then $R^{30}$ is selected from the group consisting of: —OH or —$NH_2$, and $R^{31}$ is alkyl, most preferably $C_1$-$C_6$ alkyl, more preferably $C_1$-$C_4$ alkyl, still more preferably $C_1$-$C_2$ alkyl, and even more preferably methyl;
(d) when p is 2 or 3 for the moiety

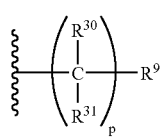

then: (1) for one —$CR^{30}R^{31}$— moiety, $R^{30}$ is selected from the group consisting of: —OH or —$NH_2$, and $R^{31}$ is alkyl, most preferably $C_1$-$C_6$ alkyl, more preferably $C_1$-$C_4$ alkyl, still more preferably $C_1$-$C_2$ alkyl, and even more preferably methyl; and (2) for the remaining —$CR^{30}R^{31}$— moieties $R^{30}$ and $R^{31}$ are hydrogen; and
(e) $R^9$ is unsubstituted heteroaryl (e.g., imidazolyl) or substituted heteroaryl, preferably substituted heteroaryl, most preferably heteroaryl substituted with alkyl (e.g., methyl), more preferably substituted imidazolyl, still more preferably imidazolyl substituted with alkyl, even more preferably imidazolyl substituted with methyl, yet more preferably imidazolyl substituted on a ring nitrogen with methyl, provided that when said heteroaryl group contains nitrogen in the ring, then said heteroaryl group is not bound by a ring nitrogen to the adjacent —$CR^{30}R^{31}$— moiety when $R^{30}$ is —OH or —$NH_2$;
(4) a is N;
(5) b, c and d are $CR^1$ groups wherein all of said $R^1$ substituents are H, or one $R^1$ substituent is halo (e.g., Br, Cl or F) and the remaining two $R^1$ substituents are hydrogen;
(6) m is 1, and $R^{3A}$ is halo (e.g., Br or Cl), or m is 2 and each $R^{3A}$ is the same or different halo (e.g., Br or Cl);
(7) X is N or CH; and
(8) $R^5$, $R^6$, $R^7$, and $R^{7a}$ are H.

Another embodiment of this invention is directed to compounds of formula 1.1 having the formula:

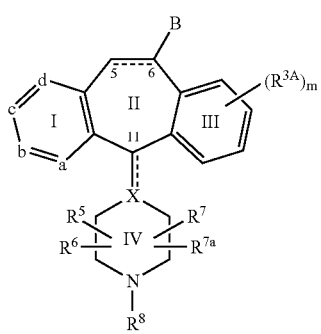

(1.4A)

wherein:
(1) a, b, c, d, $R^{3A}$, $R^5$, $R^6$, $R^7$, $R^{7a}$, $R^8$ and X are as defined for formula 1.1;
(2) B is the group:

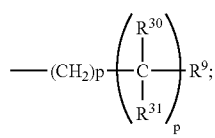

(3) in said B group:
(a) p of the —$(CH_2)_p$— moiety is 0;
(b) p of the

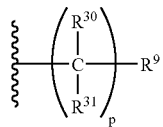

moiety is 1 to 3, preferably 1 to 2, most preferably 1;
(c) when p is 1 for the moiety

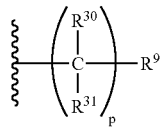

then
(i) $R^{30}$ is —OH, and $R^{31}$ is H; or
(ii) $R^{30}$ is —NH$_2$, and $R^{31}$ is H; or
(iii) $R^{30}$ is selected from the group consisting of:
  (1) —OR$^{9a}$ wherein R$^{9a}$ is $C_1$ to $C_3$ alkyl, preferably $C_1$-$C_2$ alkyl, and more preferably methyl, e.g., —OR$^{9a}$ is —OCH$_3$;
  (2) —N$_3$;
  (3) —NHR$^{9b}$ wherein R$^{9b}$ is as defined for formula 1.1; and
  (4) —N(R$^{9a}$)R$^{9b}$ wherein R$^{9a}$ and R$^{9b}$ is as defined for formula 1.1; and
$R^{31}$ is selected from the group consisting of: H and alkyl (e.g., $C_1$-$C_6$ alkyl, $C_1$-$C_4$ alkyl, $C_1$-$C_2$ alkyl, and methyl);
(d) when p is 2 or 3 for the moiety

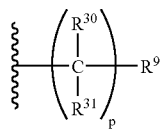

then:
(i) for one —CR$^{30}$R$^{31}$— moiety
  (1) $R^{30}$ is —OH, and $R^{31}$ is H; or
  (2) $R^{30}$ is —NH$_2$, and $R^{31}$ is H; or
  (3) $R^{30}$ is selected from the group consisting of:
    (a) —OR$^{9a}$ wherein R$^{9a}$ is $C_1$ to $C_3$ alkyl, preferably $C_1$-$C_2$ alkyl, and more preferably methyl, e.g., —OR$^{9a}$ is —OCH$_3$;
    (b) —N$_3$;
    (c) —NHR$^{9b}$ wherein R$^{9b}$ is as defined for formula 1.1; and
    (d) —N(R$^{9a}$)R$^{9b}$ wherein R$^{9a}$ and R$^{9b}$ is as defined for formula 1.1; and
$R^{31}$ is selected from the group consisting of: H and alkyl (e.g., $C_1$-$C_6$ alkyl, $C_1$-$C_2$ alkyl, and methyl); and
(ii) for the remaining —CR$^{30}$R$^{31}$— moieties $R^{30}$ and $R^3$ are hydrogen; and
(e) $R^9$ is unsubstituted heteroaryl (e.g., imidazolyl) or substituted heteroaryl, preferably substituted heteroaryl, most preferably heteroaryl substituted with alkyl (e.g., methyl), more preferably substituted imidazolyl, still more preferably imidazolyl substituted with alkyl, even more preferably imidazolyl substituted with methyl, yet more preferably imidazolyl substituted on a ring nitrogen with methyl, provided that when said heteroaryl group contains nitrogen in the ring, then said heteroaryl group is not bound by a ring nitrogen to the adjacent —CR$^{30}$R$^{31}$— moiety when $R^{30}$ is selected from the group consisting of: —OH, —NH$_2$, —OR$^{9a}$, —N$_3$, and —NHR$^{9b}$.

Another embodiment of this invention is directed to compounds of formula 1.1 having the formula:

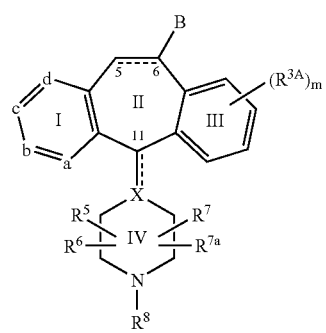

(1.4B)

wherein:
(1) $R^8$ and X are as defined for formula 1.0;
(2) B is the group:

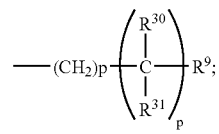

(3) in said B group:
  (a) p of the —(CH$_2$)$_p$— moiety is 0;
  (b) p of the

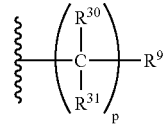

moiety is 1 to 3, preferably 1 to 2, most preferably 1;
(c) when p is 1 for the moiety

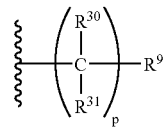

then
(i) $R^{30}$ is —OH, and $R^{31}$ is H; or
(ii) $R^{30}$ is —NH$_2$, and $R^{31}$ is H; or
(iii) $R^{30}$ is selected from the group consisting of:
  (1) —OR$^{9a}$ wherein R$^{9a}$ is $C_1$ to $C_3$ alkyl, preferably $C_1$-$C_2$ alkyl, and more preferably methyl, e.g., —OR$^{9a}$ is —OCH$_3$;
  (2) —N$_3$;

(3) —NHR$^{9b}$ wherein R$^{9b}$ is as defined for formula 1.1; and
(4) —N(R$^{9a}$)R$^{9b}$ wherein R$^{9a}$ and R$^{9b}$ is as defined for formula 1.1; and
R$^{31}$ is selected from the group consisting of: H and alkyl (e.g., C$_1$-C$_6$ alkyl, C$_1$-C$_4$ alkyl, C$_1$-C$_2$ alkyl, and methyl);
(d) when p is 2 or 3 for the moiety

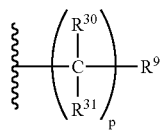

then:
(i) for one —CR$^{30}$R$^{31}$— moiety
 (1) R$^{30}$ is —OH, and R$^{31}$ is H; or
 (2) R$^{30}$ is —NH$_2$, and R$^{31}$ is H; or
 (3) R$^{30}$ is selected from the group consisting of:
  (a) —OR$^{9a}$ wherein R$^{9a}$ is C$_1$ to C$_3$ alkyl, preferably C$_1$-C$_2$ alkyl, and more preferably methyl, e.g., —OR$^{9a}$ is —OCH$_3$;
  (b) —N$_3$;
  (c) —NHR$^{9b}$ wherein R$^{9b}$ is as defined for formula 1.1; and
  (d) —N(R$^{9a}$)R$^{9b}$ wherein R$^{9a}$ and R$^{9b}$ is as defined for formula 1.1; and
R$^{31}$ is selected from the group consisting of: H and alkyl (e.g., C$_1$-C$_6$ alkyl, C$_1$-C$_2$ alkyl, and methyl); and
(ii) for the remaining —CR$^{30}$R$^{31}$— moieties R$^{30}$ and R$^{31}$ are hydrogen; and
(e) R$^9$ is unsubstituted heteroaryl (e.g., imidazolyl) or substituted heteroaryl, preferably substituted heteroaryl, most preferably heteroaryl substituted with alkyl (e.g., methyl), more preferably substituted imidazolyl, still more preferably imidazolyl substituted with alkyl, even more preferably imidazolyl substituted with methyl, yet more preferably imidazolyl substituted on a ring nitrogen with methyl, provided that when said heteroaryl group contains nitrogen in the ring, then said heteroaryl group is not bound by a ring nitrogen to the adjacent —CR$^{30}$R$^{31}$— moiety when R$^{30}$ is selected from the group consisting of: —OH, —NH$_2$, —OR$^{9a}$, —N$_3$, and —NHR$^{9b}$;
(4) a is N;
(5) b, c and d are CR$^1$ groups wherein all of said R$^1$ substituents are H, or one R$^1$ substituent is halo (e.g., Br, Cl or F) and the remaining two R$^1$ substituents are hydrogen;
(6) m is 1, and R$^{3A}$ is halo (e.g., Br or Cl), or m is 2 and each R$^{3A}$ is the same or different halo (e.g., Br or Cl); and
(7) R$^5$, R$^6$, R$^7$, and R$^{7a}$ are H.

Another embodiment of this invention is directed to compounds of formula 1.1 having the formula:

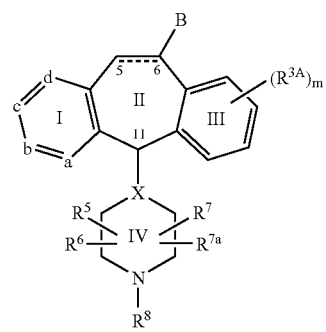

(1.4C)

wherein:
(1) R$^8$ is as defined for formula 1.0;
(2) B is the group:

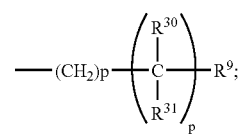

(3) in said B group:
 (a) p of the —(CH$_2$)$_p$— moiety is 0;
 (b) p of the

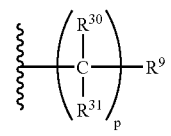

moiety is 1 to 3, preferably 1 to 2, most preferably 1;
(c) when p is 1 for the moiety

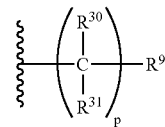

then
(i) R$^{30}$ is —OH, and R$^{31}$ is H; or
(ii) R$^{30}$ is —NH$_2$, and R$^{31}$ is H; or
(iii) R$^{30}$ is selected from the group consisting of:
 (1) —OR$^{9a}$ wherein R$^{9a}$ is C$_1$ to C$_3$ alkyl, preferably C$_1$-C$_2$ alkyl, and more preferably methyl, e.g., —OR$^{9a}$ is —OCH$_3$;
 (2) —N$_3$;
 (3) —NHR$^{9b}$ wherein R$^{9b}$ is as defined for formula 1.1; and
 (4) —N(R$^{9a}$)R$^{9b}$ wherein R$^{9a}$ and R$^{9b}$ is as defined for formula 1.1; and
R$^{31}$ is selected from the group consisting of: H and alkyl (e.g., C$_1$-C$_6$ alkyl, C$_1$-C$_4$ alkyl, C$_1$-C$_2$ alkyl, and methyl);

(d) when p is 2 or 3 for the moiety

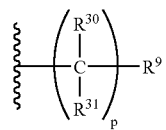

then:
(i) for one —CR$^{30}$R$^{31}$— moiety
 (1) R$^{30}$ is —OH, and R$^{31}$ is H; or
 (2) R$^{30}$ is —NH$_2$, and R$^{31}$ is H; or
 (3) R$^{30}$ is selected from the group consisting of:
  (a) —OR$^{9a}$ wherein R$^{9a}$ is C$_1$ to C$_3$ alkyl, preferably C$_1$-C$_2$ alkyl, and more preferably methyl, e.g., —OR$^{9a}$ is —OCH$_3$;
  (b) —N$_3$;
  (c) —NHR$^{9b}$ wherein R$^{9b}$ is as defined for formula 1.1; and
  (d) —N(R$^{9a}$)R$^{9b}$ wherein R$^{9a}$ and R$^{9b}$ is as defined for formula 1.1; and
 R$^{31}$ is selected from the group consisting of: H and alkyl (e.g., C$_1$-C$_6$ alkyl, C$_1$-C$_2$ alkyl, and methyl); and
(ii) for the remaining —CR$^{30}$R$^{31}$— moieties R$^{30}$ and R$^{31}$ are hydrogen; and
(e) R$^9$ is unsubstituted heteroaryl (e.g., imidazolyl) or substituted heteroaryl, preferably substituted heteroaryl, most preferably heteroaryl substituted with alkyl (e.g., methyl), more preferably substituted imidazolyl, still more preferably imidazolyl substituted with alkyl, even more preferably imidazolyl substituted with methyl, yet more preferably imidazolyl substituted on a ring nitrogen with methyl, provided that when said heteroaryl group contains nitrogen in the ring, then said heteroaryl group is not bound by a ring nitrogen to the adjacent —CR$^{30}$R$^{31}$— moiety when R$^{30}$ is selected from the group consisting of: —OH, —NH$_2$, —OR$^{9a}$, —N$_3$, and —NHR$^{9b}$;
(4) a is N;
(5) b, c and d are CR$^1$ groups wherein all of said R$^1$ substituents are H, or one R$^1$ substituent is halo (e.g., Br, Cl or F) and the remaining two R$^1$ substituents are hydrogen;
(6) m is 1, and R$^{3A}$ is halo (e.g., Br or Cl), or m is 2 and each R$^{3A}$ is the same or different halo (e.g., Br or Cl);
(7) X is N or CH; and
(8) R$^5$, R$^6$, R$^7$, and R$^{7a}$ are H.

Another embodiment of this invention is directed to compounds of formula 1.1 having the formula:

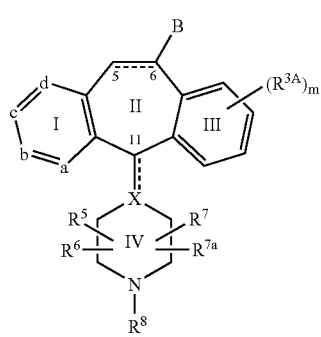

(1.4D)

wherein:
(1) a, b, c, d, R$^{3A}$, R$^5$, R$^6$, R$^7$, R$^8$ R and X are as defined for formula 1.1;
(2) B is the group:

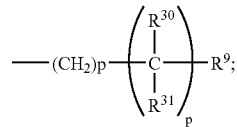

(3) in said B group:
(a) p of the —(CH$_2$)$_p$— moiety is 0;
(b) p of the

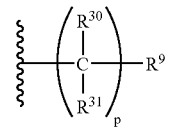

moiety is 1;
(c)
 (i) R$^{30}$ is —OH, and R$^{31}$ is H; or
 (ii) R$^{30}$ is —NH$_2$, and R$^{31}$ is H; or
 (iii) R$^{30}$ is selected from the group consisting of:
  (1) —OR$^{9a}$ wherein R$^{9a}$ is C$_1$ to C$_3$ alkyl, preferably C$_1$-C$_2$ alkyl, and more preferably methyl (e.g., —OR$^{9a}$ is —OCH$_3$);
  (2) —N$_3$;
  (3) —NHR$^{9b}$ wherein R$^{9b}$ is as defined for formula 1.1; and
  (4) —N(R$^{9a}$)R$^{9b}$ wherein R$^{9a}$ and R$^{9b}$ is as defined for formula 1.1; and
 R$^{31}$ is selected from the group consisting of: H and alkyl (e.g., C$_1$-C$_6$ alkyl, C$_1$-C$_4$ alkyl, C$_1$-C$_2$ alkyl, and methyl); and
(d) R$^9$ is unsubstituted heteroaryl (e.g., imidazolyl) or substituted heteroaryl, preferably substituted heteroaryl, most preferably heteroaryl substituted with alkyl (e.g., methyl), more preferably substituted imidazolyl, still more preferably imidazolyl substituted with alkyl, even more preferably imidazolyl substituted with methyl, yet more preferably imidazolyl substituted on a ring nitrogen with methyl, provided that when said heteroaryl group contains nitrogen in the ring, then said heteroaryl group is not bound by a ring nitrogen to the adjacent —CR$^{30}$R$^{31}$— moiety when R$^{30}$ is selected from the group consisting of: —OH, —NH$_2$, —OR$^{9a}$, —N$_3$, and —NHR$^{9b}$.

Another embodiment of this invention is directed to compounds of formula 1.4E having the formula:

(1.4E)

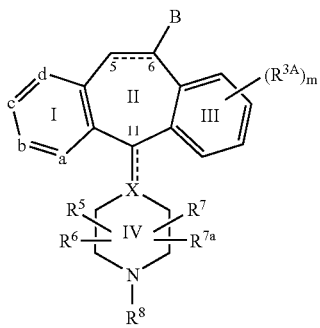

wherein:
(1) $R^8$ and X are as defined for formula 1.0;
(2) B is the group:

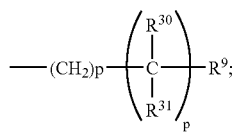

(3) in said B group:
 (a) p of the —$(CH_2)_p$— moiety is 0;
 (b) p of the

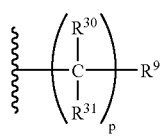

moiety is 1;
(c)
 (i) $R^{30}$ is —OH, and $R^{31}$ is H; or
 (ii) $R^{30}$ is —$NH_2$, and $R^{31}$ is H; or
 (iii) $R^{30}$ is selected from the group consisting of:
  (1) —$OR^{9a}$ wherein $R^{9a}$ is $C_1$ to $C_3$ alkyl, preferably $C_1$-$C_2$ alkyl, and more preferably methyl (e.g., —$OR^{9a}$ is —$OCH_3$);
  (2) —$N_3$;
  (3) —$NHR^{9b}$ wherein $R^{9b}$ is as defined for formula 1.1; and
  (4) —$N(R^{9a})R^{9b}$ wherein $R^{9a}$ and $R^{9b}$ is as defined for formula 1.1; and
 $R^{31}$ is selected from the group consisting of: H and alkyl (e.g., $C_1$-$C_6$ alkyl, $C_1$-$C_4$ alkyl, $C_1$-$C_2$ alkyl, and methyl); and
(e) $R^9$ is unsubstituted heteroaryl (e.g., imidazolyl) or substituted heteroaryl, preferably substituted heteroaryl, most preferably heteroaryl substituted with alkyl (e.g., methyl), more preferably substituted imidazolyl, still more preferably imidazolyl substituted with alkyl, even more preferably imidazolyl substituted with methyl, yet more preferably imidazolyl substituted on a ring nitrogen with methyl, provided that when said heteroaryl group contains nitrogen in the ring, then said heteroaryl group is not bound by a ring nitrogen to the adjacent —$CR^{30}R^{31}$— moiety when $R^{30}$ is selected from the group consisting of: —OH, —$NH_2$, —$OR^{9a}$, —$N_3$, and —$NHR^{9b}$;
(4) a is N;
(5) b, c and d are $CR^1$ groups wherein all of said $R^1$ substituents are H, or one $R^1$ substituent is halo (e.g., Br, Cl or F) and the remaining two $R^1$ substituents are hydrogen;
(6) m is 1, and $R^{3A}$ is halo (e.g., Br or Cl), or m is 2 and each $R^{3A}$ is the same or different halo (e.g., Br or Cl); and
(7) $R^5$, $R^6$, $R^7$, and $R^{7a}$ are H.

Another embodiment of this invention is directed to compounds of formula 1.1 having the formula:

(1.4F)

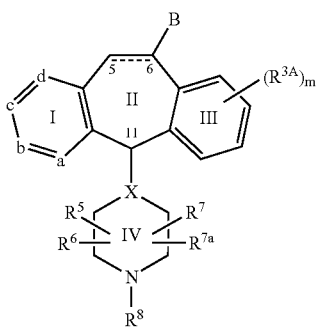

wherein:
(1) $R^8$ is as defined for formula 1.0;
(2) B is the group:

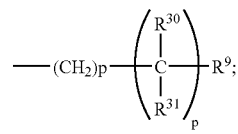

(3) in said B group:
 (a) p of the —$(CH_2)_p$— moiety is 0;
 (b) p of the

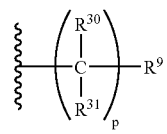

moiety is 1;
(c)
 (i) $R^{30}$ is —OH, and $R^{31}$ is H; or
 (ii) $R^{30}$ is —$NH_2$, and $R^{31}$ is H; or
 (iii) $R^{30}$ is selected from the group consisting of:
  (1) —$OR^{9a}$ wherein $R^{9a}$ is $C_1$ to $C_3$ alkyl, preferably $C_1$-$C_2$ alkyl, and more preferably methyl (e.g., —$OR^{9a}$ is —$OCH_3$);
  (2) —$N_3$;
  (3) —$NHR^{9b}$ wherein $R^{9b}$ is as defined for formula 1.1; and
  (4) —$N(R^{9a})R^{9b}$ wherein $R^{9a}$ and $R^{9b}$ is as defined for formula 1.1; and $R^{31}$ is selected from the group consisting of: H and alkyl (e.g., $C_1$-$C_6$ alkyl, $C_1$-$C_4$ alkyl, $C_1$-$C_2$ alkyl, and methyl); and (e) $R^9$ is unsubstituted heteroaryl (e.g., imidazolyl) or substituted heteroaryl, preferably substituted heteroaryl, most preferably heteroaryl substituted with alkyl (e.g., methyl), more preferably substituted imidazolyl, still more preferably imidazolyl substituted with alkyl, even more preferably imidazolyl substituted with methyl, yet more preferably imidazolyl substituted on a ring nitrogen with methyl, provided that when said heteroaryl group contains nitrogen in the ring, then said heteroaryl group is not bound by a ring nitrogen to the adjacent —$CR^{30}R^{31}$— moiety when $R^{30}$ is selected from the group consisting of: —OH, —$NH_2$, —$OR^{9a}$, —$N_3$, and —$NHR^{9b}$;

(4) a is N;

(5) b, c and d are $CR^1$ groups wherein all of said $R^1$ substituents are H, or one $R^1$ substituent is halo (e.g., Br, Cl or F) and the remaining two $R^1$ substituents are hydrogen;

(6) m is 1, and $R^{3A}$ is halo (e.g., Br or Cl), or m is 2 and each $R^{3A}$ is the same or different halo (e.g., Br or Cl);

(7) X is N or CH; and (8) $R^5$, $R^6$, $R^7$, and $R^{7a}$ are H.

Another embodiment of this invention is directed to compounds of formulas 1.2, 1.3, 1.4, 1.4A, 1.4B, 1.4C, 1.4D, 1.4 E, and 1.4F wherein X is CH.

Another embodiment of this invention is directed to compounds of formulas 1.2, 1.3, 1.4, 1.4A, 1.4B, 1.4C, 1.4D, 1.4 E, and 1.4F wherein X is CH, and the optional bond between C5 and C6 is present (i.e., there is a double bond between C5 and C6).

Another embodiment of this invention is directed to compounds of formulas 1.2, 1.3, 1.4, 1.4A, 1.4B, 1.4C, 1.4D, 1.4 E, and 1.4F wherein X is N.

Another embodiment of this invention is directed to compounds of formulas 1.2, 1.3, 1.4, 1.4A, 1.4B, 1.4C, 1.4D, 1.4 E, and 1.4F wherein X is N, and the optional bond between C5 and C6 is present (i.e., there is a double bond between C5 and C6).

Another embodiment of this invention is directed to a compound of formula 1.4 wherein p is 1 for the moiety

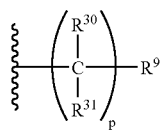

and $R^{30}$ is —$NH_2$.

Another embodiment of this invention is directed to a compound of formula 1.4 wherein p is 1 for the moiety

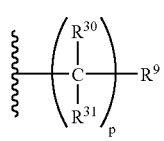

$R^{30}$ is —$NH_2$, and X is N.

Another embodiment of this invention is directed to a compound of formula 1.4D wherein p is 1 for the moiety

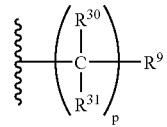

$R^{30}$ is —$NH_2$, $R^{31}$ is —$CH_3$, X is N, and the optional bond between C5 and C6 is present (i.e., there is a double bond between C5 and C6).

Another embodiment of this invention is directed to a compound of formula 1.4A, or a compound of formula 1.4B, or a compound of formula 1.4C wherein $R^{30}$ is —OH, and $R^{31}$ is H.

Another embodiment of this invention is directed to a compound of formula 1.4A, or a compound of formula 1.4B, or a compound of formula 1.4C wherein $R^{30}$ is —OH, $R^{31}$ is H, and X is N.

Another embodiment of this invention is directed to a compound of formula 1.4A, or a compound of formula 1.4B, or a compound of formula 1.4C wherein $R^{30}$ is —OH, $R^{31}$ is H, X is N, and the optional bond between C5 and C6 is present (i.e., there is a double bond between C5 and C6).

Another embodiment of this invention is directed to a compound of formula 1.4A, or a compound of formula 1.4B, or a compound of formula 1.4C wherein $R^{30}$ is —$NH_2$, and $R^{31}$ is H.

Another embodiment of this invention is directed to a compound of formula 1.4A, or a compound of formula 1.4B, or a compound of formula 1.4C wherein $R^{30}$ is —$NH_2$, and $R^{31}$ is H, and X is N.

Another embodiment of this invention is directed to a compound of formula 1.4A, or a compound of formula 1.4B, or a compound of formula 1.4C wherein $R^{30}$ is —$NH_2$, and $R^{31}$ is H, X is N, and the optional bond between C5 and C6 is present (i.e., there is a double bond between C5 and C6).

Another embodiment of this invention is directed to a compound of formula 1.4A, or a compound of formula 1.4B, or a compound of formula 1.4C wherein $R^{30}$ is selected from the group consisting of:

(1) —$OR^{9a}$ wherein $R^{9a}$ is $C_1$ to $C_3$ alkyl, preferably $C_1$-$C_2$ alkyl, and more preferably methyl (e.g., —$OR^{9a}$ is —$OCH_3$);

(2) —$N_3$;

(3) —$NHR^{9b}$ wherein $R^{9b}$ is as defined for formula 1.1; and (4) —$NR^{9a}R^{9b}$ wherein $R^{9a}$ and $R^{9b}$ is as defined for formula 1.1; and $R^{31}$ is selected from the group consisting of: H and alkyl (e.g., $C_1$-$C_6$ alkyl, $C_1$-$C_4$ alkyl, $C_1$-$C_2$ alkyl, and methyl).

Another embodiment of this invention is directed to a compound of formula 1.4A, or a compound of formula 1.4B, or a compound of formula 1.4C wherein $R^{30}$ is selected from the group consisting of:

(1) —$OR^{9a}$ wherein $R^{9a}$ is $C_1$ to $C_3$ alkyl, preferably $C_1$-$C_2$ alkyl, and more preferably methyl (e.g., —$OR^{9a}$ is —$OCH_3$);

(2) —$N_3$;

(3) —$NHR^{9b}$ wherein $R^{9b}$ is as defined for formula 1.1; and (4) —$NR^{9a}R^{9b}$ wherein $R^{9a}$ and $R^{9b}$ is as defined for formula 1.1; and $R^{31}$ is selected from the group consisting of: H and alkyl (e.g., $C_1$-$C_6$ alkyl, $C_1$-$C_4$ alkyl, $C_1$-$C_2$ alkyl, and methyl), and X is N.

Another embodiment of this invention is directed to a compound of formula 1.4A, or a compound of formula 1.4B, or a compound of formula 1.4C wherein $R^{30}$ is selected from the group consisting of:
(1) —$OR^{9a}$ wherein $R^{9a}$ is $C_1$ to $C_3$ alkyl, preferably $C_1$-$C_2$ alkyl, and more preferably methyl (e.g., —$OR^{9a}$ is —$OCH_3$);
(2) —$N_3$;
(3) —$NHR^{9b}$ wherein $R^{9b}$ is as defined for formula 1.1; and
(4) —$NR^{9a} R^{9b}$ wherein $R^{9a}$ and $R^{9b}$ is as defined for formula 1.1; and $R^{31}$ is selected from the group consisting of: H and alkyl (e.g., $C_1$-$C_6$ alkyl, $C_1$-$C_4$ alkyl, $C_1$-$C_2$ alkyl, and methyl), and X is N, and the optional bond between C5 and C6 is present (i.e., there is a double bond between C5 and C6).

Another embodiment of this invention is directed to a compound of formula 1.4D wherein $R^{30}$ is —OH, and $R^{31}$ is H.

Another embodiment of this invention is directed to a compound of formula 1.4D wherein $R^{30}$ is —OH, $R^{31}$ is H, and X is N.

Another embodiment of this invention is directed to a compound of formula 1.4D wherein $R^{30}$ is —OH, $R^{31}$ is H, X is N, and the optional bond between C5 and C6 is present (i.e., there is a double bond between C5 and C6).

Another embodiment of this invention is directed to a compound of formula 1.4D wherein $R^{30}$ is —$NH_2$, and $R^{31}$ is H.

Another embodiment of this invention is directed to a compound of formula 1.4D wherein $R^{30}$ is —$NH_2$, and $R^{31}$ is H, and X is N.

Another embodiment of this invention is directed to a compound of formula 1.4D wherein $R^{30}$ is —$NH_2$, and $R^{31}$ is H, X is N, and the optional bond between C5 and C6 is present (i.e., there is a double bond between C5 and C6).

Another embodiment of this invention is directed to a compound of formula 1.4D wherein $R^{30}$ is selected from the group consisting of:
(1) —$OR^{9a}$ wherein $R^{9a}$ is $C_1$ to $C_3$ alkyl, preferably $C_1$-$C_2$ alkyl, and more preferably methyl (e.g., —$OR^{9a}$ is —$OCH_3$);
(2) —$N_3$;
(3) —$NHR^{9b}$ wherein $R^{9b}$ is as defined for formula 1.1; and
(4) —$NR^{9a} R^{9b}$ wherein $R^{9a}$ and $R^{9b}$ is as defined for formula 1.1; and $R^{31}$ is selected from the group consisting of: H and alkyl (e.g., $C_1$-$C_6$ alkyl, $C_1$-$C_4$ alkyl, $C_1$-$C_2$ alkyl, and methyl).

Another embodiment of this invention is directed to a compound of formula 1.4D wherein $R^{30}$ is selected from the group consisting of:
(1) —$OR^{9a}$ wherein $R^{9a}$ is $C_1$ to $C_3$ alkyl, preferably $C_1$-$C_2$ alkyl, and more preferably methyl (e.g., —$OR^{9a}$ is —$OCH_3$);
(2) —$N_3$;
(3) —$NHR^{9b}$ wherein $R^{9b}$ is as defined for formula 1.1; and
(4) —$NR^{9a}R^{9b}$ wherein $R^{9a}$ and $R^{9b}$ is as defined for formula 1.1; and $R^{31}$ is selected from the group consisting of: H and alkyl (e.g., $C_1$-$C_6$ alkyl, $C_1$-$C_4$ alkyl, $C_1$-$C_2$ alkyl, and methyl), and X is N.

Another embodiment of this invention is directed to a compound of formula 1.4D wherein $R^{30}$ is selected from the group consisting of:
(1) —$OR^{9a}$ wherein $R^{9a}$ is $C_1$ to $C_3$ alkyl, preferably $C_1$-$C_2$ alkyl, and more preferably methyl (e.g., —$OR^{9a}$ is —$OCH_3$);
(2) —$N_3$;
(3) —$NHR^{9b}$ wherein $R^{9b}$ is as defined for formula 1.1; and
(4) —$NR^{9a} R^{9b}$ wherein $R^{9a}$ and $R^{9b}$ is as defined for formula 1.1; and $R^{31}$ is selected from the group consisting of: H and alkyl (e.g., $C_1$-$C_6$ alkyl, $C_1$-$C_4$ alkyl, $C_1$-$C_2$ alkyl, and methyl), and X is N, and the optional bond between C5 and C6 is present (i.e., there is a double bond between C5 and C6).

Another embodiment of this invention is directed to a compound of formula 1.4E wherein $R^{30}$ is —OH, and $R^{31}$ is H.

Another embodiment of this invention is directed to a compound of formula 1.4E wherein $R^{30}$ is —OH, $R^{31}$ is H, and X is N.

Another embodiment of this invention is directed to a compound of formula 1.4E wherein $R^{30}$ is —OH, $R^{31}$ is H, X is N, and the optional bond between C5 and C6 is present (i.e., there is a double bond between C5 and C6).

Another embodiment of this invention is directed to a compound of formula 1.4E wherein $R^{30}$ is —$NH_2$, and $R^{31}$ is H.

Another embodiment of this invention is directed to a compound of formula 1.4E wherein $R^{30}$ is —$NH_2$, and $R^{31}$ is H, and X is N.

Another embodiment of this invention is directed to a compound of formula 1.4E wherein $R^{30}$ is —$NH_2$, and $R^{31}$ is H, X is N, and the optional bond between C5 and C6 is present (i.e., there is a double bond between C5 and C6).

Another embodiment of this invention is directed to a compound of formula 1.4E wherein $R^{30}$ is selected from the group consisting of:
(1) —$OR^{9a}$ wherein $R^{9a}$ is $C_1$ to $C_3$ alkyl, preferably $C_1$-$C_2$ alkyl, and more preferably methyl (e.g., —$OR^{9a}$ is —$OCH_3$);
(2) —$N_3$;
(3) —$NHR^{9b}$ wherein $R^{9b}$ is as defined for formula 1.1; and
(4) —$NR^{9a}R^{9b}$ wherein $R^{9a}$ and $R^{9b}$ is as defined for formula 1.1; and $R^{31}$ is selected from the group consisting of: H and alkyl (e.g., $C_1$-$C_6$ alkyl, $C_1$-$C_4$ alkyl, $C_1$-$C_2$ alkyl, and methyl).

Another embodiment of this invention is directed to a compound of formula 1.4E wherein $R^{30}$ is selected from the group consisting of:
(1) —$OR^{9a}$ wherein $R^{9a}$ is $C_1$ to $C_3$ alkyl, preferably $C_1$-$C_2$ alkyl, and more preferably methyl (e.g., —$OR^{9a}$ is —$OCH_3$);
(2) —$N_3$;
(3) —$NHR^{9b}$ wherein $R^{9b}$ is as defined for formula 1.1; and
(4) —$NR^{9a} R^{9b}$ wherein $R^{9a}$ and $R^{9b}$ is as defined for formula 1.1; and $R^{31}$ is selected from the group consisting of: H and alkyl (e.g., $C_1$-$C_6$ alkyl, $C_1$-$C_4$ alkyl, $C_1$-$C_2$ alkyl, and methyl), and X is N.

Another embodiment of this invention is directed to a compound of formula 1.4E wherein $R^{30}$ is selected from the group consisting of:
(1) —$OR^{9a}$ wherein $R^{9a}$ is $C_1$ to $C_3$ alkyl, preferably $C_1$-$C_2$ alkyl, and more preferably methyl (e.g., —$OR^{9a}$ is —$OCH_3$);
(2) —$N_3$;
(3) —$NHR^{9b}$ wherein $R^{9b}$ is as defined for formula 1.1; and (4) —$NR^{9a}R^{9b}$ wherein $R^{9a}$ and $R^{9b}$ is as defined for formula 1.1; and $R^{31}$ is selected from the group consisting of: H and alkyl (e.g., $C_1$-$C_6$ alkyl, $C_1$-$C_4$ alkyl, $C_1$-$C_2$ alkyl, and methyl), and X is N, and the optional bond between C5 and C6 is present (i.e., there is a double bond between C5 and C6).

Another embodiment of this invention is directed to a compound of formula 1.4F wherein $R^{30}$ is —OH, and $R^{31}$ is H.

Another embodiment of this invention is directed to a compound of formula 1.4F wherein $R^{30}$ is —OH, $R^{31}$ is H, and X is N.

Another embodiment of this invention is directed to a compound of formula 1.4F wherein $R^{30}$ is —OH, $R^{31}$ is H, X is N, and the optional bond between C5 and C6 is present (i.e., there is a double bond between C5 and C6).

Another embodiment of this invention is directed to a compound of formula 1.4F wherein $R^{30}$ is —$NH_2$, and $R^{31}$ is H.

Another embodiment of this invention is directed to a compound of formula 1.4F wherein $R^{30}$ is —$NH_2$, and $R^{31}$ is H, and X is N.

Another embodiment of this invention is directed to a compound of formula 1.4F wherein $R^{30}$ is —$NH_2$, and $R^{31}$ is H, X is N, and the optional bond between C5 and C6 is present (i.e., there is a double bond between C5 and C6).

Another embodiment of this invention is directed to a compound of formula 1.4F wherein $R^{30}$ is selected from the group consisting of:
(1) —$OR^{9a}$ wherein $R^{9a}$ is $C_1$ to $C_3$ alkyl, preferably $C_1$-$C_2$ alkyl, and more preferably methyl (e.g., —$OR^{9a}$ is —$OCH_3$);
(2) —$N_3$;
(3) —$NHR^{9b}$ wherein $R^{9b}$ is as defined for formula 1.1; and
(4) —$NR^{9a}R^{9b}$ wherein $R^{9a}$ and $R^{9b}$ is as defined for formula 1.1; and $R^{31}$ is selected from the group consisting of: H and alkyl (e.g., $C_1$-$C_6$ alkyl, $C_1$-$C_4$ alkyl, $C_1$-$C_2$ alkyl, and methyl).

Another embodiment of this invention is directed to a compound of formula 1.4F wherein $R^{30}$ is selected from the group consisting of:
(1) —$OR^{9a}$ wherein $R^{9a}$ is $C_1$ to $C_3$ alkyl, preferably $C_1$-$C_2$ alkyl, and more preferably methyl (e.g., —$OR^{9a}$ is —$OCH_3$);
(2) —$N_3$;
(3) —$NHR^{9b}$ wherein $R^{9b}$ is as defined for formula 1.1; and
(4) —$NR^{9a}R^{9b}$ wherein $R^{9a}$ and $R^{9b}$ is as defined for formula 1.1; and $R^{31}$ is selected from the group consisting of: H and alkyl (e.g., $C_1$-$C_6$ alkyl, $C_1$-$C_4$ alkyl, $C_1$-$C_2$ alkyl, and methyl), and X is N.

Another embodiment of this invention is directed to a compound of formula 1.4F wherein $R^{30}$ is selected from the group consisting of:
(1) —$OR^{9a}$ wherein $R^{9a}$ is $C_1$ to $C_3$ alkyl, preferably $C_1$-$C_2$ alkyl, and more preferably methyl (e.g., —$OR^{9a}$ is —$OCH_3$);
(2) —$N_3$;
(3) —$NHR^{9b}$ wherein $R^{9b}$ is as defined for formula 1.1; and
(4) —$NR^{9a}R^{9b}$ wherein $R^{9a}$ and $R^{9b}$ is as defined for formula 1.1; and $R^{31}$ is selected from the group consisting of: H and alkyl (e.g., $C_1$-$C_6$ alkyl, $C_1$-$C_4$ alkyl, $C_1$-$C_2$ alkyl, and methyl), and X is N, and the optional bond between C5 and C6 is present (i.e., there is a double bond between C5 and C6).

Another embodiment of this invention is directed to compounds of formula 1.4D, 1.4E or 1.4F wherein $R^{30}$ is —$OR^{9a}$ and $R^{31}$ is H.

Another embodiment of this invention is directed to compounds of formula 1.4D, 1.4E or 1.4F wherein $R^{30}$ is —$OR^{9a}$, $R^{31}$ is H, and X is N.

Another embodiment of this invention is directed to compounds of formula 1.4D, 1.4E or 1.4F wherein $R^{30}$ is —$OR^{9a}$, $R^{31}$ is H, X is N, and the optional bond between C5 and C6 is present (i.e., there is a double bond between C5 and C6).

Another embodiment of this invention is directed to compounds of formula 1.4D, 1.4E or 1.4F wherein $R^{30}$ is —$N_3$ and $R^{31}$ is H.

Another embodiment of this invention is directed to compounds of formula 1.4D, 1.4E or 1.4F wherein $R^{30}$ is —$N_3$, $R^{31}$ is H, and X is N.

Another embodiment of this invention is directed to compounds of formula 1.4D, 1.4E or 1.4F wherein $R^{30}$ is —$N_3$, $R^{31}$ is H, X is N, and the optional bond between C5 and C6 is present (i.e., there is a double bond between C5 and C6).

Another embodiment of this invention is directed to compounds of formula 1.4D, 1.4E or 1.4F wherein $R^{30}$ is —$NHR^{9b}$ and $R^{31}$ is H.

Another embodiment of this invention is directed to compounds of formula 1.4D, 1.4E or 1.4F wherein $R^{30}$ is —$NHR^{9b}$, $R^{31}$ is H, and X is N.

Another embodiment of this invention is directed to compounds of formula 1.4D, 1.4E or 1.4F wherein $R^{30}$ is —$NHR^{9b}$, $R^{31}$ is H, X is N, and the optional bond between C5 and C6 is present (i.e., there is a double bond between C5 and C6).

Another embodiment of this invention is directed to compounds of formula 1.4D, 1.4E or 1.4F wherein $R^{30}$ is —$NR^{9a}R^{9b}$ and $R^{31}$ is H.

Another embodiment of this invention is directed to compounds of formula 1.4D, 1.4E or 1.4F wherein $R^{30}$ is —$NR^{9a}R^{9b}$, $R^{31}$ is H, and X is N.

Another embodiment of this invention is directed to compounds of formula 1.4D, 1.4E or 1.4F wherein $R^{30}$ is —$NR^{9a}R^{9b}$, $R^{31}$ is H, X is N, and the optional bond between C5 and C6 is present (i.e., there is a double bond between C5 and C6).

Another embodiment of this invention is directed to compounds of formula 1.4D, 1.4E or 1.4F wherein $R^{30}$ is —$OR^{9a}$ and $R^{31}$ is alkyl (e.g., methyl).

Another embodiment of this invention is directed to compounds of formula 1.4D, 1.4E or 1.4F wherein $R^{30}$ is —$OR^{9a}$, $R^{31}$ is alkyl (e.g., methyl), and X is N.

Another embodiment of this invention is directed to compounds of formula 1.4D, 1.4E or 1.4F wherein $R^{30}$ is —$OR^{9a}$, $R^{31}$ is alkyl (e.g., methyl), X is N, and the optional bond between C5 and C6 is present (i.e., there is a double bond between C5 and C6).

Another embodiment of this invention is directed to compounds of formula 1.4D, 1.4E or 1.4F wherein $R^{30}$ is —$N_3$ and $R^{31}$ is alkyl (e.g., methyl).

Another embodiment of this invention is directed to compounds of formula 1.4D, 1.4E or 1.4F wherein $R^{30}$ is —$N_3$, $R^{31}$ is alkyl (e.g., methyl), and X is N.

Another embodiment of this invention is directed to compounds of formula 1.4D, 1.4E or 1.4F wherein $R^{30}$ is —$N_3$, $R^{31}$ is alkyl (e.g., methyl), X is N, and the optional bond between C5 and C6 is present (i.e., there is a double bond between C5 and C6).

Another embodiment of this invention is directed to compounds of formula 1.4D, 1.4E or 1.4F wherein $R^{30}$ is —$NHR^{9b}$ and $R^{31}$ is alkyl (e.g., methyl).

Another embodiment of this invention is directed to compounds of formula 1.4D, 1.4E or 1.4F wherein $R^{30}$ is —$NHR^{9b}$, $R^{31}$ is alkyl (e.g., methyl), and X is N.

Another embodiment of this invention is directed to compounds of formula 1.4D, 1.4E or 1.4F wherein $R^{30}$ is —$NHR^{9b}$, $R^{31}$ is alkyl (e.g., methyl), X is N, and the optional bond between C5 and C6 is present (i.e., there is a double bond between C5 and C6).

Another embodiment of this invention is directed to compounds of formula 1.4D, 1.4E or 1.4F wherein $R^{30}$ is —$NR^{9a}R^{9b}$ and $R^{31}$ is alkyl (e.g., methyl).

Another embodiment of this invention is directed to compounds of formula 1.4D, 1.4E or 1.4F wherein $R^{30}$ is —$NR^{9a}R^{9b}$, $R^{31}$ is alkyl (e.g., methyl), and X is N.

Another embodiment of this invention is directed to compounds of formula 1.4D, 1.4E or 1.4F wherein $R^{30}$ is —$NR^{9a}R^{9b}$, $R^{31}$ is alkyl (e.g., methyl), X is N, and the optional bond between C5 and C6 is present (i.e., there is a double bond between C5 and C6).

Another embodiment of this invention is directed to compounds of formulas 1.4D, 1.4E and 1.4F, wherein for the $R^{30}$ substituent —$NHR^{9b}$, 9b is preferably —$C(O)R^{9a}$, and more preferably —$C(O)R^{9a}$ wherein $R^{9a}$ is alkyl.

Another embodiment of this invention is directed to compounds of formulas 1.4D, 1.4E and 1.4F, wherein for the $R^{30}$ substituent —$NHR^{9b}$, 9b is preferably —$C(O)R^{9a}$, and more preferably —$C(O)R^{9a}$ wherein $R^{9a}$ is alkyl; and $R^{31}$ is H.

Another embodiment of this invention is directed to any of the embodiments directed to formulas 1.4D, 1.4E and 1.4F wherein $R^8$ is formula 2.0 wherein $R^{11}$ is as defined for formula 1.0.

Another embodiment of this invention is directed to any of the embodiments directed to formulas 1.4D, 1.4E and 1.4F wherein $R^8$ is formula 3.0 wherein $R^{11}$ is as defined for formula 1.0.

Another embodiment of this invention is directed to any of the embodiments directed to formulas 1.4D, 1.4E and 1.4F wherein $R^8$ is 4.0 wherein $R^{11a}$ and $R^{12}$ are as defined for formula 1.0.

Another embodiment of this invention is directed to any of the embodiments directed to formulas 1.4D, 1.4E and 1.4F wherein $R^8$ is 5.0 wherein $R^{21}$, $R^{22}$, and $R^{46}$ are as defined for formula 1.0.

Another embodiment of this invention is directed to any of the embodiments directed to formulas 1.4D, 1.4E and 1.4F, wherein $R^8$ is formula 2.0 wherein $R^{11}$ is alkyl (e.g., isopropyl or t-butyl).

Another embodiment of this invention is directed to any of the embodiments directed to formulas 1.4D, 1.4E and 1.4F, wherein $R^8$ is formula 2.0 wherein $R^{11}$ is alkyl (e.g., isopropyl or t-butyl, and preferably isopropyl), $R^{30}$ is —$NH_2$ and $R^{31}$ is H.

Another embodiment of this invention is directed to compounds of formulas 1.4D, 1.4E and 1.4F, wherein for the $R^{30}$ substituent —$NHR^{9b}$, 9b is preferably —$C(O)R^{9a}$, and more preferably —$C(O)R^{9a}$ wherein $R^{9a}$ is alkyl, and $R^8$ is formula 2.0 wherein $R^{11}$ is alkyl (e.g., isopropyl or t-butyl).

Another embodiment of this invention is directed to compounds of formulas 1.4D, 1.4E and 1.4F, wherein for the $R^{30}$ substituent —$NHR^{9b}$, 9b is preferably —$C(O)R^{9a}$, and more preferably —$C(O)R^{9a}$ wherein $R^{9a}$ is alkyl, and $R^{31}$ is H, and $R^8$ is formula 2.0 wherein $R^{11}$ is alkyl (e.g., isopropyl or t-butyl).

Another embodiment of this invention is directed to any of the embodiments directed to formulas 1.4D, 1.4E and 1.4F wherein substituent a in Ring I is N, and substituents b, c, and d in Ring I are $CR^1$ groups, and all of said $R^1$ substituents are H.

Another embodiment of this invention is directed to any of the embodiments directed to formulas 1.4D, 1.4E and 1.4F wherein substituent a in Ring I is N, and substituents b, c, and d in Ring I are $CR^1$ groups, and said $R^1$ substituent at C-3 is halo and said $R^1$ substituents at C-2 and C-4 are hydrogen.

Another embodiment of this invention is directed to any of the embodiments directed to formulas 1.4D, 1.4E and 1.4F wherein m is 1 and $R^{34}$ is halo.

Another embodiment of this invention is directed to any of the embodiments directed to formulas 1.4D, 1.4E and 1.4F wherein m is 1 and $R^{34}$ is Cl.

Another embodiment of this invention is directed to any of the embodiments directed to formulas 1.4D, 1.4E and 1.4F wherein m is 1 and $R^{34}$ is halo at the C-8 position.

Another embodiment of this invention is directed to any of the embodiments directed to formulas 1.4D, 1.4E and 1.4F wherein m is 1 and $R^{34}$ is Cl at the C-8 position.

Another embodiment of this invention is directed to any of the embodiments directed to formulas 1.4D, 1.4E and 1.4F wherein m is 2, and each $R^{34}$ is the same or different halo, and said halo substitution is at the C-7 and C-8 position or the C-8 and C-10 position.

Another embodiment of this invention is directed to any of the embodiments directed to formulas 1.4D, 1.4E and 1.4F wherein $R^9$ is unsubstituted heteroaryl or substituted heteroaryl.

Another embodiment of this invention is directed to any of the embodiments directed to formulas 1.4D, 1.4E and 1.4F wherein $R^9$ is substituted heteroaryl.

Another embodiment of this invention is directed to any of the embodiments directed to formulas 1.4D, 1.4E and 1.4F wherein $R^9$ is substituted heteroaryl wherein said heteroaryl is mono substituted.

Another embodiment of this invention is directed to any of the embodiments directed to formulas 1.4D, 1.4E and 1.4F wherein $R^9$ is unsubstituted imidazolyl or substituted imidazolyl.

Another embodiment of this invention is directed to any of the embodiments directed to formulas 1.4D, 1.4E and 1.4F wherein $R^9$ is substituted imidazolyl.

Another embodiment of this invention is directed to any of the embodiments directed to formulas 1.4D, 1.4E and 1.4F wherein $R^9$ is substituted imidazolyl wherein said imidazolyl is mono substituted and the substituent is alkyl (e.g., $C_1$ to $C_3$ alkyl, or $C_1$ to $C_2$ alkyl), and preferably said substituent is methyl.

Another embodiment of this invention is directed to any of the embodiments directed to formulas 1.4D, 1.4E and 1.4F wherein $R^9$ is.

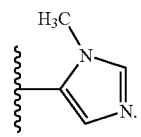

In another embodiment, $R^8$ is 2.0 in formula 1.2 wherein $R^{11}$ is as defined for formula 1.0.

In another embodiment, $R^8$ is 3.0 in formula 1.2 wherein $R^{11}$ is as defined for formula 1.0.

In another embodiment, $R^8$ is 4.0 in formula 1.2 wherein $R^{11a}$ and $R^{12}$ are as defined for formula 1.0.

In another embodiment, $R^8$ is 5.0 in formula 1.2 wherein $R^{21}$, $R^{22}$, and $R^{46}$ are as defined for formula 1.0.

In another embodiment, $R^8$ is 2.0 in formula 1.3 wherein $R^{11}$ is as defined for formula 1.0.

In another embodiment, $R^8$ is 3.0 in formula 1.3 wherein $R^{11}$ is as defined for formula 1.0.

In another embodiment, $R^8$ is 4.0 in formula 1.3 wherein $R^{11a}$ and $R^{12}$ are as defined for formula 1.0.

In another embodiment, $R^8$ is 5.0 in formula 1.3 wherein $R^{21}$, $R^{22}$, and $R^{46}$ are as defined for formula 1.0.

In another embodiment, $R^8$ is 2.0 in formula 1.4 wherein $R^{11}$ is as defined for formula 1.0.

In another embodiment, $R^8$ is 3.0 in formula 1.4 wherein $R^{11}$ is as defined for formula 1.0.

In another embodiment, $R^8$ is 4.0 in formula 1.4 wherein $R^{11a}$ and $R^{12}$ are as defined for formula 1.0.

In another embodiment, $R^8$ is 5.0 in formula 1.4 wherein $R^{21}$, $R^{22}$, and $R^{46}$ are as defined for formula 1.0.

Preferably, in formulas 1.3 and 1.4, all $R^1$ substituents are H, or $R^1$ at C-3 is halo and $R^1$ at C-2 and C-4 is hydrogen, most preferably all $R^1$ substituents are hydrogen.

Preferably, in formulas 1.3 and 1.4, when m is 1 then $R^{3A}$ is preferably Cl at the C-8 position.

In formulas 1.3 and 1.4, when m is 2, then the substitution is 7,8-dihalo, or 8,10-dihalo.

Preferably, in formulas 1.3 and 1.4, the optional double bond between C5 and C6 is present, i.e., preferably there is a double bond between C5 and C6.

Preferably, in formulas 1.2 and 1.3 X is N.

Preferably, in formula 1.4 X is N.

Another embodiment of this invention is directed to compounds of formula 1.4 having the formula:

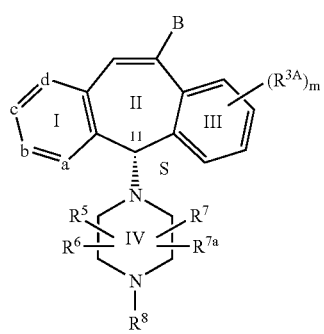

(1.5)

wherein all substituents are as defined for formula 1.4. Preferably $R^8$ is 2.0, most preferably 2.0 wherein $R^{11}$ is alkyl, more preferably 2.0 wherein $R^{11}$ is t-butyl or isopropyl, and even more preferably 2.0 wherein $R^{11}$ is isopropyl.

Another embodiment of the invention is directed to compounds of formula 1.5 having the formula:

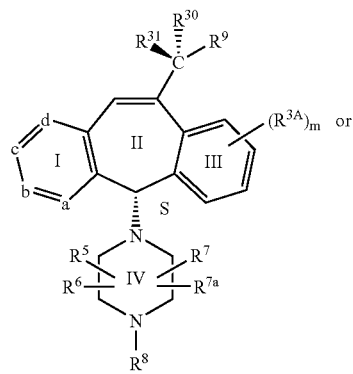

(1.6)

wherein all substituents are as defined for formula 1.4. Preferably $R^8$ is 2.0, most preferably 2.0 wherein $R^{11}$ is alkyl, more preferably 2.0 wherein $R^{11}$ is t-butyl or isopropyl, and even more preferably 2.0 wherein $R^{11}$ is isopropyl.

Thus, one embodiment of the invention is directed to compounds of formula 1.5 having the formula:

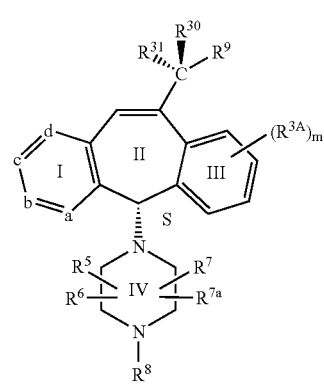

(1.7)

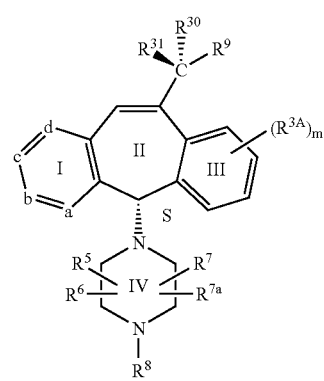

(1.6)

wherein all substituents are as defined for formula 1.4. Preferably $R^8$ is 2.0, most preferably 2.0 wherein $R^{11}$ is alkyl, more preferably 2.0 wherein $R^{11}$ is t-butyl or isopropyl, and even more preferably 2.0 wherein $R^{11}$ is isopropyl.

Another embodiment of the invention is directed to compounds of formula 1.5 having the formula:

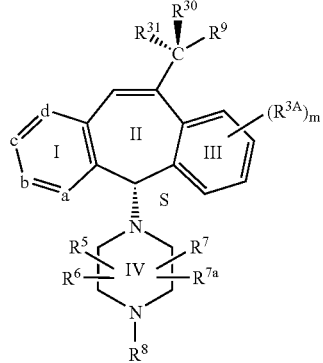
(1.7)

wherein all substituents are as defined for formula 1.4. Preferably $R^8$ is 2.0, most preferably 2.0 wherein $R^{11}$ is alkyl, more preferably 2.0 wherein $R^{11}$ is t-butyl or isopropyl, and even more preferably 2.0 wherein $R^{11}$ is isopropyl.

In formulas 1.2, 1.3, 1.4, 1.5, 1.6, and 1.7, $R^9$ is preferably:

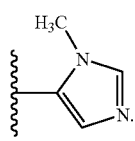

Another embodiment of this invention is directed to compounds of formula 1.4D, 1.4E or 1.4F having the formula:

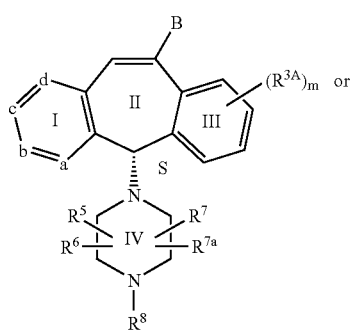
(1.5A)

wherein all substituents are as defined for formulas 1.4D, 1.4E or 1.4F. Compounds of formula 1.5A include compounds wherein $R^8$ is 2.0, and include compounds wherein $R^8$ is 2.0 wherein $R^{11}$ is alkyl (e.g., $C_1$ to $C_4$, such as, isopropy or t-butyl). Preferably $R^8$ is 2.0, $R^{11}$ is isopropyl, $R^{30}$ is —NH$_2$, and $R^{31}$ is H.

Another embodiment of the invention is directed to compounds of formula 1.5A having the formula:

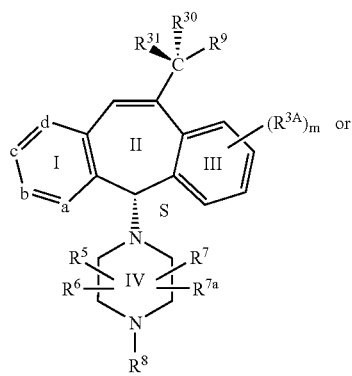
(1.6A)

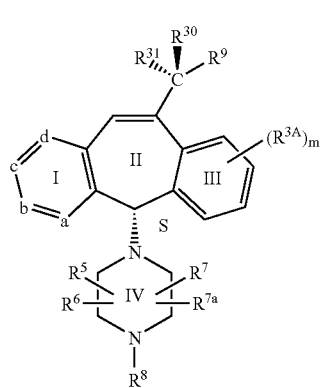
(1.7A)

wherein all substituents are as defined for formulas 1.4D, 1.4E or 1.4F. Compounds of formula 1.5A include compounds wherein $R^8$ is 2.0, and include compounds wherein $R^8$ is 2.0 wherein $R^{11}$ is alkyl (e.g., $C_1$ to $C_4$, such as, isopropy or t-butyl). Preferably $R^8$ is 2.0, $R^{11}$ is isopropyl, $R^{30}$ is —NH$_2$, and $R^{31}$ is H.

Thus, one embodiment of the invention is directed to compounds of formula 1.5A having the formula:

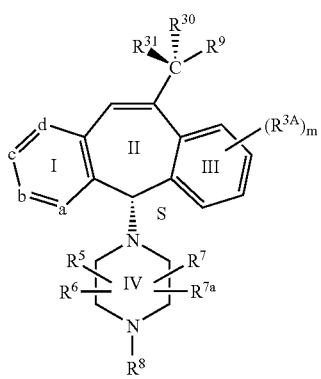
(1.6A)

wherein all substituents are as defined for formulas 1.4D, 1.4E or 1.4F. Compounds of formula 1.5A include compounds wherein $R^8$ is 2.0, and include compounds wherein $R^8$ is 2.0 wherein $R^{11}$ is alkyl (e.g., $C_1$ to $C_4$, such as, isopropy or t-butyl). Preferably $R^8$ is 2.0, $R^{11}$ is isopropyl, $R^{30}$ is —NH$_2$, and $R^{31}$ is H.

Another embodiment of the invention is directed to compounds of formula 1.5A having the formula:

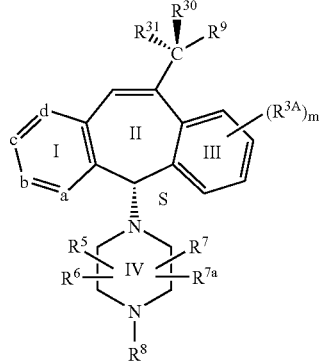
(1.7A)

wherein all substituents are as defined for formulas 1.4D, 1.4E or 1.4F. Compounds of formula 1.5A include compounds wherein $R^8$ is 2.0, and include compounds wherein $R^8$ is 2.0 wherein $R^{11}$ is alkyl (e.g., $C_1$ to $C_4$, such as, isopropy or t-butyl). Preferably $R^8$ is 2.0, $R^{11}$ is isopropyl, $R^{30}$ is —$NH_2$, and $R^{31}$ is H.

In formulas 1.4D, 1.4E, 1.4F, 1.5A, 1.6A, and 1.7A, $R^9$ is preferably:

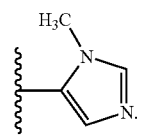

The compounds of formula 1.0 include the R isomer:

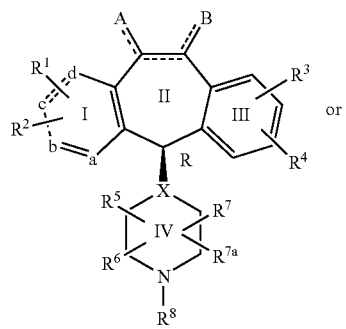
(1.0A)

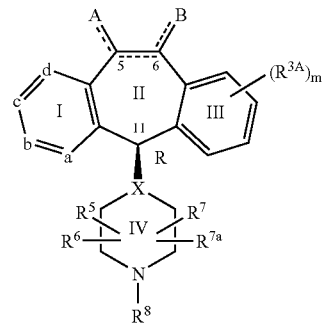
(1.1A)

wherein:
X is N or CH;
a is N or C(N or $CR^1$ in 1.1A); and
the optional bond between C-5 and C-6 is present and B is H, or the optional bond between C-5 and C-6 is absent and each B is H.

The compounds of formula 1.0 also include the S isomer:

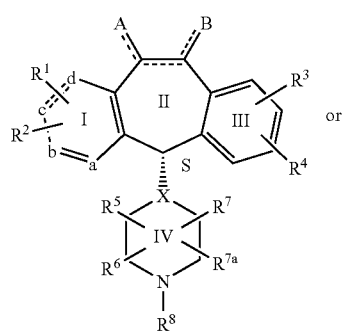
(1.0B)

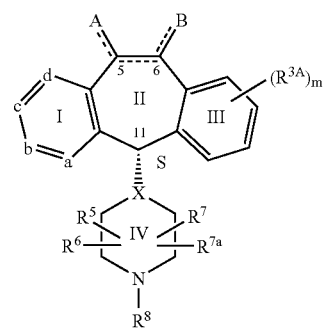
(1.1B)

wherein:
X is N or CH (preferably N);
a is N or C (a is N or $CR^1$ in 1.1B); and
the optional bond between C-5 and C-6 is present and A is H, or the optional bond between C-5 and C-6 is absent and each A is H (preferably the optional bond between C-5 and C-6 is present).

In one embodiment of the compounds of formula 1.0, $R^1$, $R^2$, $R^3$, and $R^4$ are independently selected from the group consisting of: H and halo, more preferably H, Br, F and Cl, and even more preferably H and Cl. Representative compounds of formula 1.0 include dihalo (e.g., 3,8-dihalo) and monohalo (e.g., 8-halo) substituted compounds, such as, for example: (a) 3-bromo-8-chloro, (b) 3,8-dichloro, (c) 3-bromo, (d) 3-chloro, (e) 3-fluoro, (f) 8-chloro or (g) 8-bromo.

In one embodiment of the compounds of formula 1.1, each $R^1$ is independently selected from the group consisting of: H and halo, most preferably H, Br, F and Cl, and more preferably H and Cl. Each $R^3$ is independently selected from the group consisting of: H and halo, most preferably H, Br, F and Cl, and more preferably H and Cl. Representative compounds of formula 1.1 include dihalo (e.g., 3,8-dihalo) and monohalo (e.g., 3-halo or 8-halo) substituted compounds, such as, for example: (a) 3-bromo-8-chloro, (b) 3,8-dichloro, (c) 3-bromo, (d) 3-chloro, (e) 3-fluoro, (f) 8-chloro or (g) 8-bromo.

In one embodiment of the invention, substituent a in compounds of formula 1.0 is preferably C or N, with N being preferred, and substituent a in compounds of formula 1.1 is $CR^1$ or N, with N being preferred.

In one embodiment of the invention, $R^8$ in compounds of formula 1.0 is selected from the group consisting of:

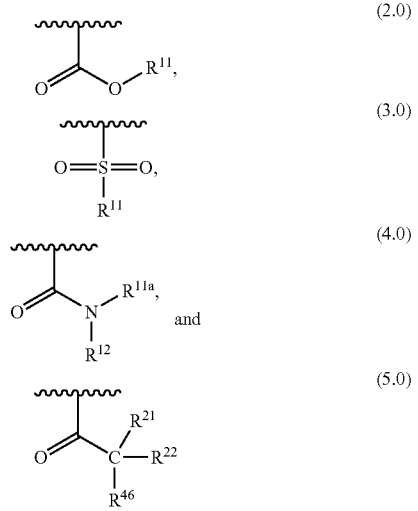

In one embodiment of the invention, $R^8$ in compounds of formula 1.0 is 2.0 or 4.0; and preferably $R^8$ is 2.0.

In one embodiment of the invention, for compounds of formula 1.0, $R^{11a}$ is selected from the group consisting of: alkyl, substituted alkyl, unsubstituted aryl, substituted aryl, heteroaryl, substituted heteroaryl, unsubstituted cyloalkyl and substituted cycloalkyl, wherein:
  (1) said substituted aryl and substituted heteroaryl $R^{11a}$ groups are substituted with one or more (e.g. 1, 2 or 3) substituents independently selected from the group consisting of: halo (preferably F or Cl), cyano, —$CF_3$, and alkyl;
  (2) said substituted cycloalkyl $R^{11a}$ groups are substituted with one or more (e.g., 1, 2 or 3) substituents independently selected from the group consisting of: fluoro, cyano, —$CF_3$, and alkyl; and
  (3) said substituted alkyl $R^{11a}$ groups are substituted with one or more (e.g., 1, 2 or 3) substituents selected from the group consisting of: fluoro, cyano and $CF_3$.

In one embodiment of the invention, for compounds of formula 1.0, $R^{11a}$ is selected from the group consisting of: alkyl, unsubstituted aryl, substituted aryl, unsubstituted cyloalkyl, and substituted cycloalkyl, wherein:
  (1) said substituted aryl is substituted with one or more (e.g., 1, 2 or 3) substituents independently selected from the group consisting of: halo, (preferably F or Cl), —CN and $CF_3$; and
  (2) said substituted cycloalkyl is substituted with one or more (e.g., 1, 2 or 3) substituents independently selected from the group consisting of: fluoro, —CN and $CF_3$.

In one embodiment of the invention, for compounds 1.0, $R^{11a}$ is selected from the group consisting of: methyl, t-butyl, phenyl, cyanophenyl, chlorophenyl, fluorophenyl, and cyclohexyl. In another embodiment, $R^{11a}$ is selected from the group consisting of: t-butyl, cyanophenyl, chlorophenyl, fluorophenyl and cyclohexyl. In another embodiment, $R^{11a}$ is cyanophenyl (e.g., p-cyanophenyl).

In one embodiment of the invention, for compounds of formula 1.0, $R^{11}$ is selected from the group consisting of alkyl, unsubstituted cycloalkyl, and substituted cycloalkyl, wherein said substituted cycloalkyl group is substituted with 1, 2 or 3 substituents independently selected from the group consisting of: fluoro and alkyl (preferably methyl or t-butyl). Examples of $R^{11}$ groups include: methyl, ethyl, propyl, isopropyl, t-butyl, cyclohexyl or substituted cyclohexyl. In one embodiment of the invention, $R^{11}$ is selected from the group consisting of: methyl, isopropyl, t-butyl, cyclohexyl and fluorocyclohexyl (preferably p-fluorocyclohexyl). In one embodiment of the invention, $R^{11}$ is selected from the group consisting of: methyl, isopropyl, t-butyl, and cyclohexyl. In one embodiment of the invention $R^{11}$ is t-butyl or cyclohexyl. In one embodiment of the invention $R^{11}$ is t-butyl for 2.0, and $R^{11}$ is methyl for 3.0. In one embodiment of this invention $R^{11}$ is isopropyl.

In one embodiment of the invention, for compounds of formula 1.0, $R^{12}$ is selected from the group consisting of: H and methyl. In one embodiment of the invention, $R^{12}$ is H.

In one embodiment of the invention, for compounds of formula 1.0, $R^5$, $R^6$, $R^7$ and $R^{7a}$ are H.

In one embodiment of the invention, for compounds of formula 1.0, $R^9$ is selected from the group consisting of:
  (1) unsubstituted heteroaryl;
  (2) substituted heteroaryl;
  (3) arylalkoxy;
  (4) substituted arylalkoxy;
  (5) heterocycloalkyl;
  (6) substituted heterocycloalkyl;
  (7) heterocycloalkylalkyl;
  (8) substituted heterocycloalkylalkyl;
  (9) heteroarylalkyl;
  (10) substituted heteroarylalkyl;
  (11) heteroarylalkenyl and
  (12) substituted heteroarylalkenyl;

wherein said substituted $R^9$ groups are substituted with one or more substituents (e.g., 1, 2, or 3) independently selected from the group consisting of:
  (1) —OH;
  (2) —$CO_2R^{14}$, wherein $R^{14}$ is selected from the group consisting of: H and alkyl (e.g., methyl and ethyl), preferably alkyl, most preferably methyl or ethyl;

(3) alkyl substituted with one or more —OH groups (e.g., 1, 2, or 3, preferably 1), for example, —$(CH_2)_qOH$ wherein, q is 1-4, with q=1 being preferred;
(4) halo (e.g., Br, F, I, or Cl);
(5) alkyl, usually $C_1$-$C_6$ alkyl, preferably $C_1$-$C_4$ alkyl (e.g., methyl, ethyl, propyl, isopropyl, t-butyl or butyl, preferably isopropyl, or t-butyl);
(6) amino;
(7) trityl;
(8) heterocycloalkyl;
(9) arylalkyl (e.g. benzyl);
(10) heteroaryl (e.g. pyridyl) and
(11) heteroarylalkyl;

In one embodiment of the invention, for the compounds of formula 1.0, $R^9$ is selected from the group consisting of:
(1) heterocycloalkyl;
(2) substituted heterocycloalkyl;
(3) heterocycloalkylalkyl;
(4) substituted heterocycloalkylalkyl;
(5) unsubstituted heteroarylalkyl;
(6) substituted heteroarylalkyl;
(7) unsubstituted heteroarylalkenyl and
(8) substituted heteroarylalkenyl;

wherein said substituted $R^9$ groups are substituted with one or more substituents (e.g., 1, 2, or 3) independently selected from the group consisting of:
(1) —OH;
(2) —$CO_2R^{14}$ wherein $R^{14}$ is selected from the group consisting of: H and alkyl (e.g., methyl or ethyl), preferably alkyl, and most preferably methyl and ethyl;
(3) alkyl, substituted with one or more —OH groups (e.g., 1, 2, or 3, preferably 1), for example —$(CH_2)qOH$ wherein, q is 1-4, with q=1 being preferred.
(4) halo (e.g., Br or Cl);
(5) alkyl, usually $C_1$-$C_6$ alkyl, preferably $C_1$-$C_4$ alkyl (e.g. methyl, ethyl, propyl, isopropyl, butyl or t-butyl, most preferably t-butyl);
(6) amino;
(7) trityl;
(8) heterocycloalkyl,
(9) arylalkyl;
(10) heteroaryl and
(11) heteroaryalkyl;

In one embodiment of the invention, for formula 1.0, $R^9$ is selected from the group consisting of:
(1) heterocycloalkyl;
(2) substituted heterocycloalkyl;
(3) heterocycloalkylalkyl;
(4) substituted heterocycloalkylalkyl;
(5) unsubstituted heteroarylalkyl;
(6) substituted heteroarylalkyl;
(7) unsubstituted heteroarylalkenyl and
(8) substituted heteroarylalkenyl;

wherein said substituted $R^9$ groups are substituted with one or more substituents (e.g., 1, 2, or 3) independently selected from the group consisting of:
(1) halo (e.g., Br, or Cl);
(2) alkyl, usually $C_1$-$C_6$ alkyl, preferably $C_1$-$C_4$ alkyl (e.g. methyl, ethyl, propyl, isopropyl, butyl or t-butyl, most preferably t-butyl);
(3) alkyl, substituted with one or more (i.e. 1, 2, or 3, preferably 1) —OH groups, (e.g. —$(CH_2)_qOH$ wherein q is 1-4, with q=1 being preferred).
(4) amino;
(5) trityl;
(6) arylalkyl, and
(7) heteroarylalkyl.

In one embodiment of the invention, $R^9$ is selected from the group consisting of:
(1) heterocycloalkylalkyl;
(2) substituted heterocycloalkylalkyl;
(3) unsubstituted heteroarylalkyl and
(4) substituted heteroarylalkyl;

wherein said substituted $R^9$ groups are substituted with one or more substituents (e.g., 1, 2, or 3) independently selected from the group consisting of:
(1) halo (e.g., Br, or Cl);
(2) alkyl usually $C_1$-$C_6$ alkyl, preferably $C_1$-$C_4$ alkyl (e.g. methyl, ethyl, propyl, isopropyl, butyl and t-butyl, most preferably t-butyl);
(3) amino; and
(4) trityl.

In one embodiment of the invention, for formula 1.0, $R^9$ is selected from the group consisting of:
(1) heterocycloalkylalkyl;
(2) substituted heterocycloalkylalkyl;
(3) unsubstituted heteroarylalkyl and
(4) substituted heteroarylalkyl;

wherein said substituted $R^9$ groups are substituted with one or more substituents (e.g., 1, 2, or 3) independently selected from the group consisting of:
(1) halo (e.g., Br, or Cl); and
(2) alkyl, usually $C_1$-$C_6$ alkyl, preferably $C_1$-$C_4$ alkyl (e.g. methyl, ethyl, propyl, isopropyl, butyl or t-butyl, most preferably t-butyl).

In one embodiment of the invention, for formula 1.0, $R^9$ is selected from the group consisting of:
(1) piperidinyl;
(2) piperizinyl;
(3) —$(CH_2)_p$-piperidinyl;
(4) —$(CH_2)_p$-piperizinyl;
(5) —$(CH_2)_p$-morpholinyl and
(6) —$(CH_2)_p$-imidazolyl;

wherein p is 0 to 1, and wherein the ring moiety of each $R^9$ group is optionally substituted with one, two or three substituents independently selected from the group consisting of:
(1) halo (e.g., Br, or Cl); and
(2) alkyl, usually $C_1$-$C_6$ alkyl, preferably $C_1$-$C_4$ alkyl (e.g. methyl, ethyl, propyl, isopropyl, butyl or t-butyl, most preferably t-butyl).

In one embodiment of the invention, for formula 1.0, $R^9$ is selected from the group consisting of:
(1) -piperizinyl;
(2) —$(CH_2)_p$-piperidinyl;
(3) —$(CH_2)_p$-imidazolyl; and
(4) —$(CH_2)_p$-morpholinyl, wherein p is 1 to 4, and the ring moiety of each $R^9$ group is optionally substituted with one, two or three substituents independently selected from the group consisting of: methyl, ethyl, and isopropyl.

In one embodiment of the invention, for formula 1.0, $R^9$ is selected from the group consisting of: —$(CH_2)$-imidazolyl, wherein said imidazolyl ring is optionally substituted with 1, 2, or 3 substituants, preferably 1, independently selected from the group consisting of: methyl or ethyl.

In one embodiment of the invention, for formula 1.0, $R^9$ is —$(CH_2)$-(2-methyl)-imidazolyl.

In one embodiment of the invention, for formula 1.0, at least one of $R^{21}$, $R^{22}$ and $R^{46}$ is other than H or alkyl. In one embodiment of the invention, $R^{21}$ and $R^{22}$ is H and $R^{46}$ is other than H or alkyl. In one embodiment of the invention, $R^{21}$ and $R^{22}$ is H and $R^{46}$ is selected from the group consisting of: heteroaryl and heterocycloalkyl.

In one embodiment of the invention, for formula 1.0, said heteroaryl groups for said $R^{21}$, $R^{22}$ or $R^{46}$ are independently selected from the group consisting of: 3-pyridyl, 4-pyridyl, 3-pyridyl-N-Oxide and 4-pyridyl-N-Oxide. In one embodiment of the invention, said heteroaryl groups for said $R^{21}$, $R^{22}$ or $R^{46}$ are independently selected from the group consisting of: 4-pyridyl and 4-pyridyl-N-Oxide. In one embodiment of the invention, said heteroaryl group for said $R^{21}$, $R^{22}$ or $R^{46}$ is 4-pyridyl-N-Oxide.

In one embodiment of the invention, for formula 1.0, said heterocycloalkyl groups for $R^{21}$, $R^{22}$, or $R^{46}$ are selected from piperidines of Ring V:

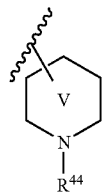

wherein $R^{44}$ is —C(O)NHR$^{51}$. In one embodiment of the invention, $R^{51}$ is —C(O)NH$_2$. In one embodiment of the invention, piperidine Ring V is:

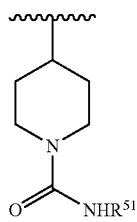

and in one embodiment of the invention Ring V is:

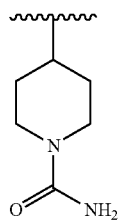

Thus, in one embodiment of the invention, for formula 1.0, $R^{21}$, $R^{22}$ and $R^{46}$ are independently selected from the group consisting of:

(1) H;
(2) aryl (most preferably phenyl);
(3) heteroaryl and
(4) heterocycloalkyl (i.e., Piperidine Ring V)

wherein at least one of $R^{21}$, $R^{22}$, or $R^{46}$ is other than H, and in one embodiment of the invention $R^{21}$ and $R^{22}$ are H and $R^{46}$ is other than H, and in one embodiment of the invention $R^{21}$ and $R^{22}$ are H and $R^{46}$ is selected from the group consisting of: heteroaryl and heterocycloalkyl, and in one embodiment of the invention $R^{21}$ and $R^{22}$ are H and $R^{46}$ is Piperidine Ring V; wherein the definitions of heteroaryl and Piperidine Ring V are as described above.

In one embodiment of the invention, for formula 1.0, A and B are independently selected from the group consisting of:

(1) —H;
(2) —R$^9$;
(3) —R$^9$—C(O)—R$^9$;
(4) —R$^9$—CO$_2$—R$^{9a}$;
(5) —C(O)NHR$^9$;
(6) —C(O)NH—CH$_2$—C(O)—NH$_2$;
(7) —C(O)NHR$^{26}$;
(8) —(CH$_2$)$_p$(R$^9$)$_2$ wherein each R$^9$ is the same or different;
(9) —(CH$_2$)$_p$C(O)R$^9$;
(10) —(CH$_2$)$_p$C(O)R$^{27a}$;
(11) —(CH$_2$)$_p$C(O)N(R$^9$)$_2$, wherein each R$^9$ is the same or different;
(12) —(CH$_2$)$_p$C(O)NH(R$^9$);
(13) —(CH$_2$)$_p$NHC(O)R$^{50}$;
(14) —(CH$_2$)$_p$NHC(O)$_2$R$^{50}$;
(15) —(CH$_2$)$_p$N(C(O)R$^{27a}$)$_2$ wherein each R$^{27}$, is the same or different;
(16) —(CH$_2$)$_p$NR$^{51}$C(O)R$^{27}$;
(17) —(CH$_2$)$_p$NR$^{51}$C(O)R$^{27}$ wherein R$^{51}$ is not H, and R$^{51}$ and R$^{27}$, taken together with the atoms to which they are bound, form a 5 or 6 memebered heterocycloalkyl ring;
(18) —(CH$_2$)$_p$NR$^{51}$C(O)NR$^{27}$;
(19) —(CH$_2$)$_p$NR$^{51}$C(O)NR$^{27}$ wherein R$^{51}$ is not H, and R$^{51}$ and R$^{27}$, taken together with the atoms to which they are bound, form a 5 or 6 membered heterocycloalkyl ring;
(20) —(CH$_2$)$_p$NR$^{51}$C(O)N(R$^{27a}$)$_2$, wherein each R$^{27a}$ is the same or different;
(21) —(CH$_2$)$_p$NHSO$_2$N(R$^{51}$)$_2$, wherein each R$^{51}$ is the same or different;
(22) —(CH$_2$)$_p$NHCO$_2$R$^{50}$;
(23) —(CH$_2$)$_p$CO$_2$R$^{51}$;
(24) —NHR$^9$;

(25)
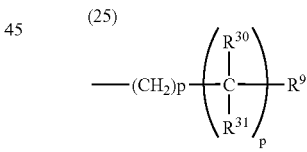

wherein $R^{30}$ and $R^{31}$ are the same or different and

(26)
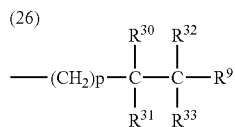

wherein $R^{30}$, $R^{31}$, $R^{32}$ and $R^{33}$ are the same or different.

In one embodiment of the invention, for formula 1.0, A and B are independently selected from the group consisting of:

(1) —H;
(2) —R$^9$;

(3) —R$^9$—C(O)—R$^9$;
(4) —R$^9$—CO$_2$—R$^{9a}$;
(5) —C(O)NHR$^9$;
(6) —(CH$_2$)$_p$(R$^9$)$_2$, wherein each R$^9$ is the same or different;
(7) —(CH$_2$)$_p$C(O)R$^9$;
(8) —(CH$_2$)$_p$C(O)N(R$^9$)$_2$, wherein each R$^9$ is the same or different;
(9) —(CH$_2$)$_p$C(O)NH(R$^9$);
(10) —(CH$_2$)$_p$NR$^{50}$C(O)R$^{27}$;
(11) —(CH$_2$)$_p$NR$^{51}$C(O)R$^{27}$ wherein R$^{51}$ is not H, and R$^{51}$ and R$^{27}$, taken together with the atoms to which they are bound, form a 5 or 6 membered heterocycloalkyl ring;
(12) —(CH$_2$)$_p$NR$^{51}$C(O)NR$^{27}$;
(13) —(CH$_2$)$_p$NR$^{51}$C(O)NR$^{27}$ wherein R$^5$ is not H, and R$^{51}$ and R$^{27}$, taken together with the atoms to which they are bound, form a 5 or 6 membered heterocycloalkyl ring;
(14) —NHR$^9$; and

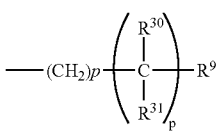

(15)

wherein R$^{30}$ and R$^{31}$ are the same or different.

Examples of A and B include but are not limited to:

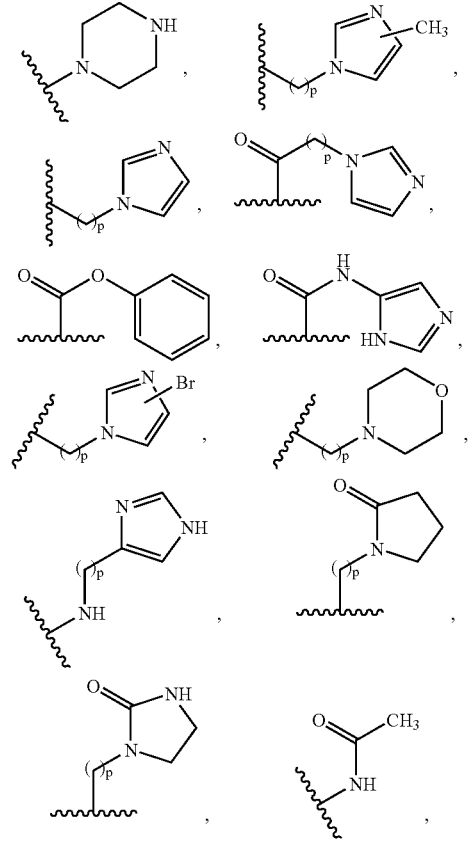

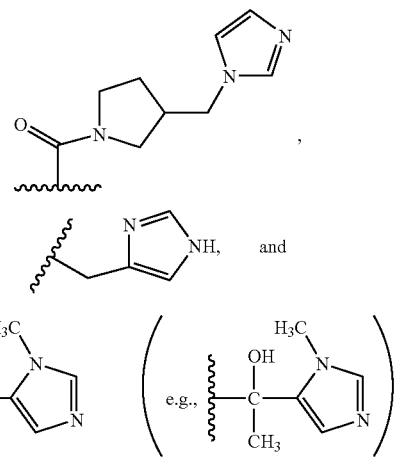

wherein p is 0, 1, 2, 3 or 4.

Examples of A and B also include but are not limited to:

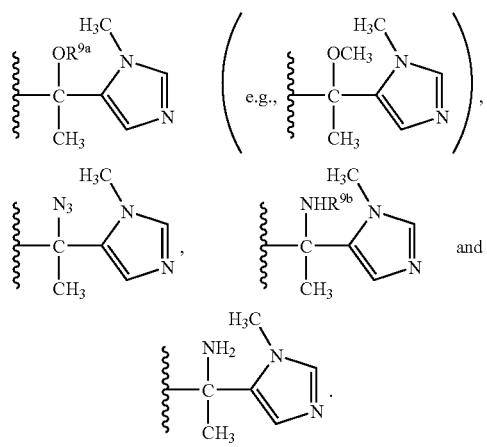

Examples of A and B also include but are not limited to:

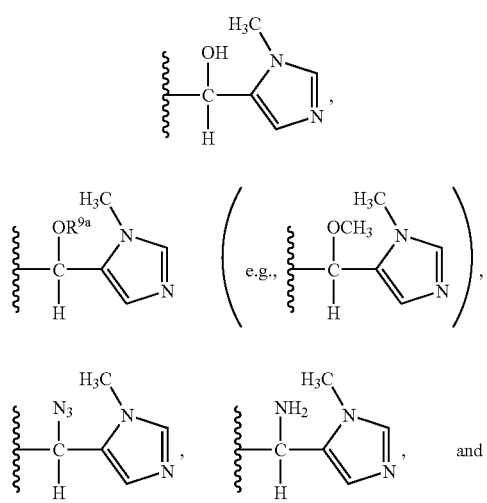

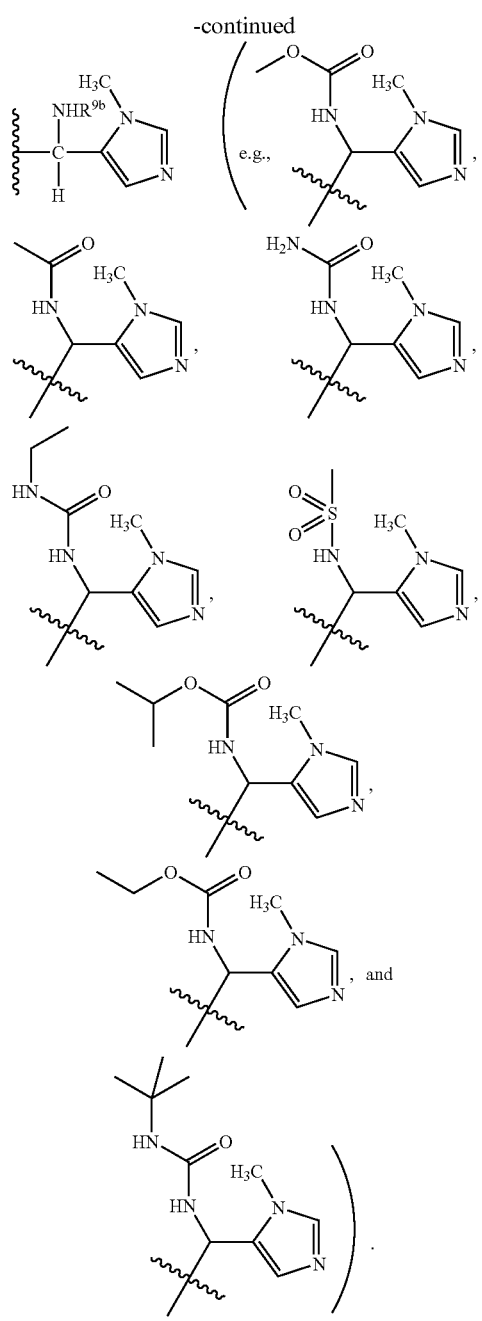
Thus, examples of B include but are not limited to:
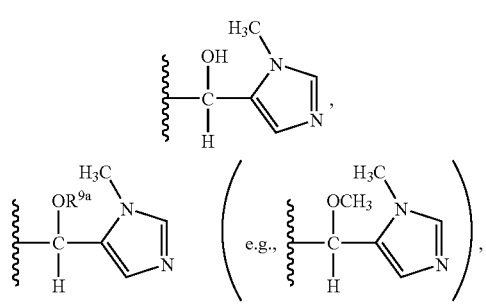
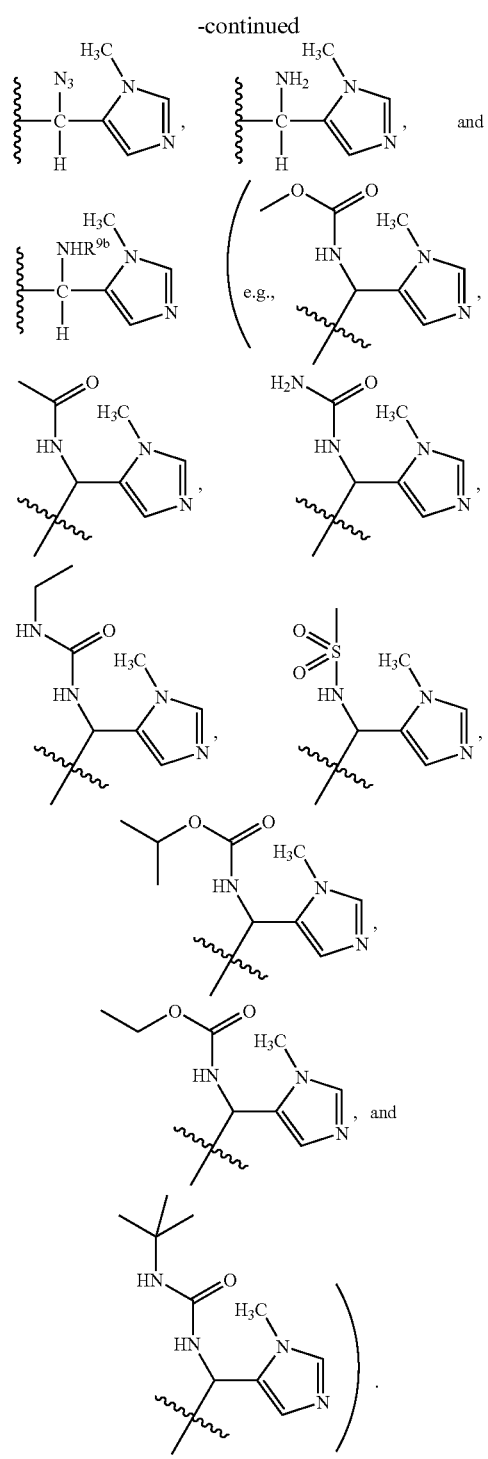
Preferred examples of B include:
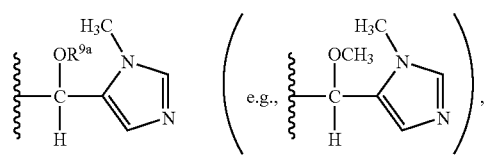

-continued
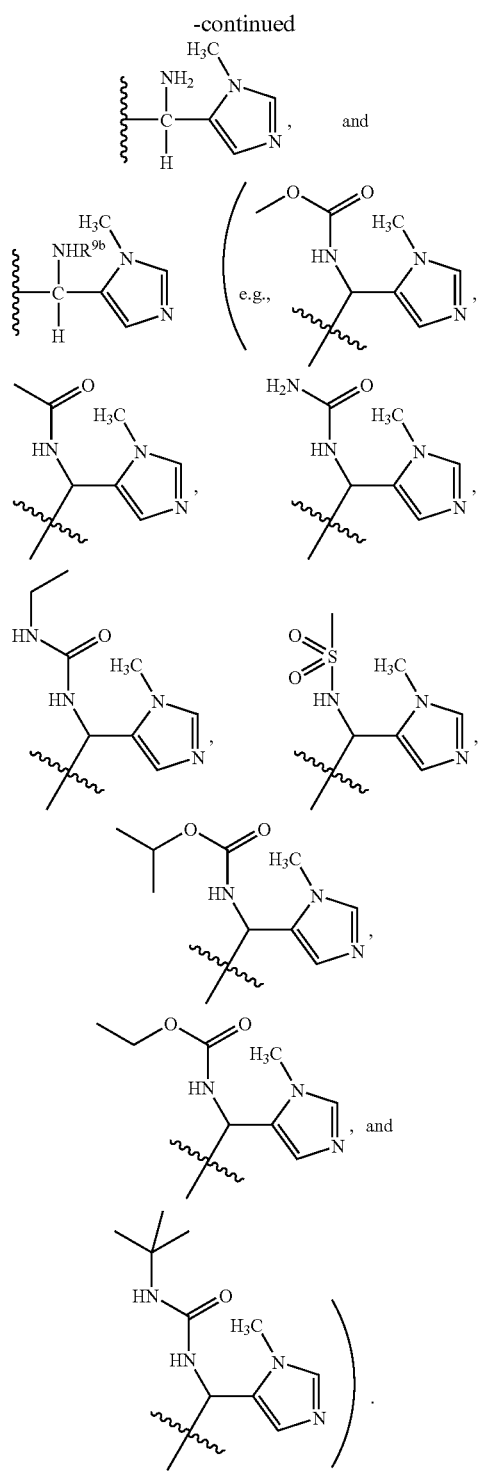
More preferred examples of B include:
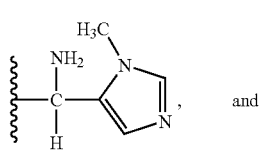
-continued
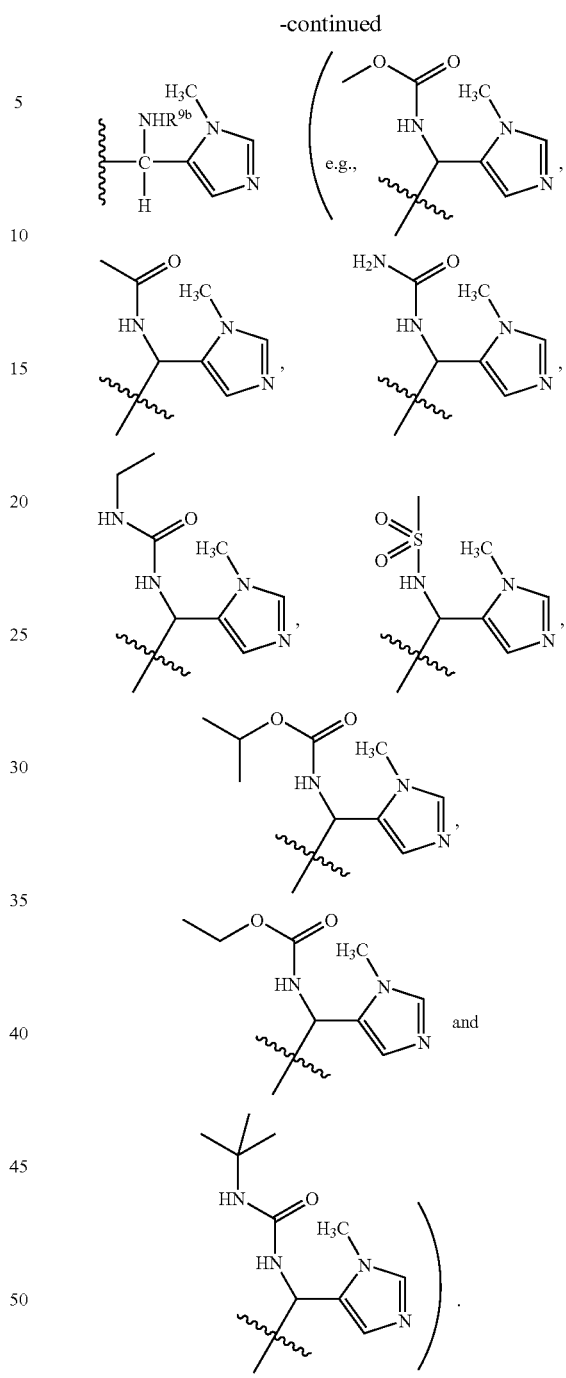
A most preferred example of B is:
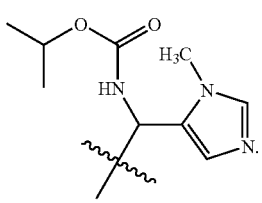

Examples of R[8] groups include, but are not limited to:
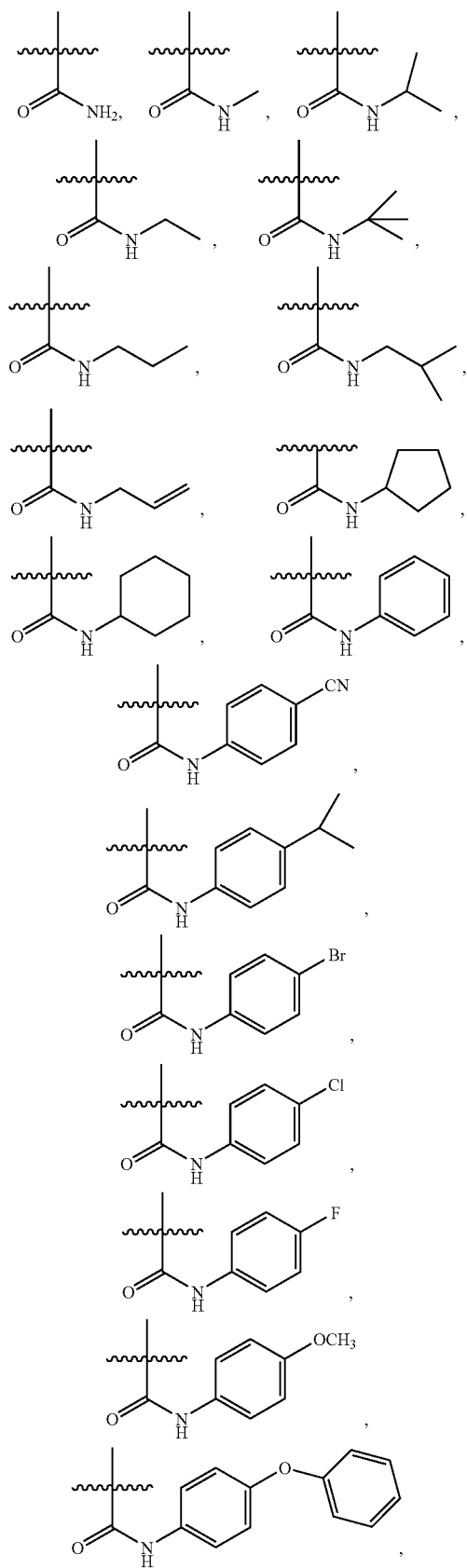
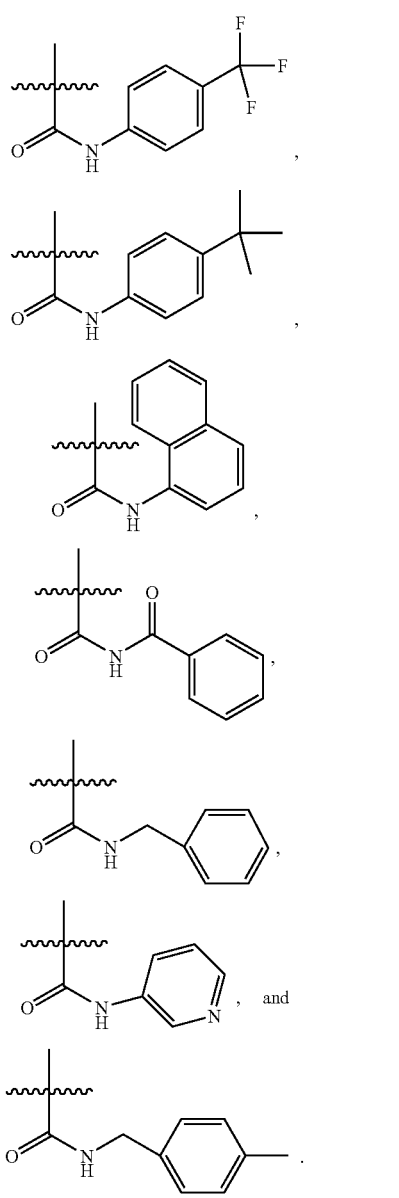
Examples of R[8] also include, but are not limited to:
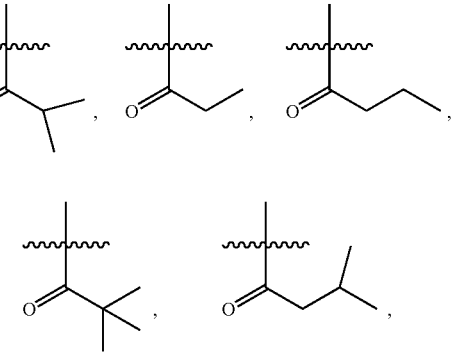

-continued
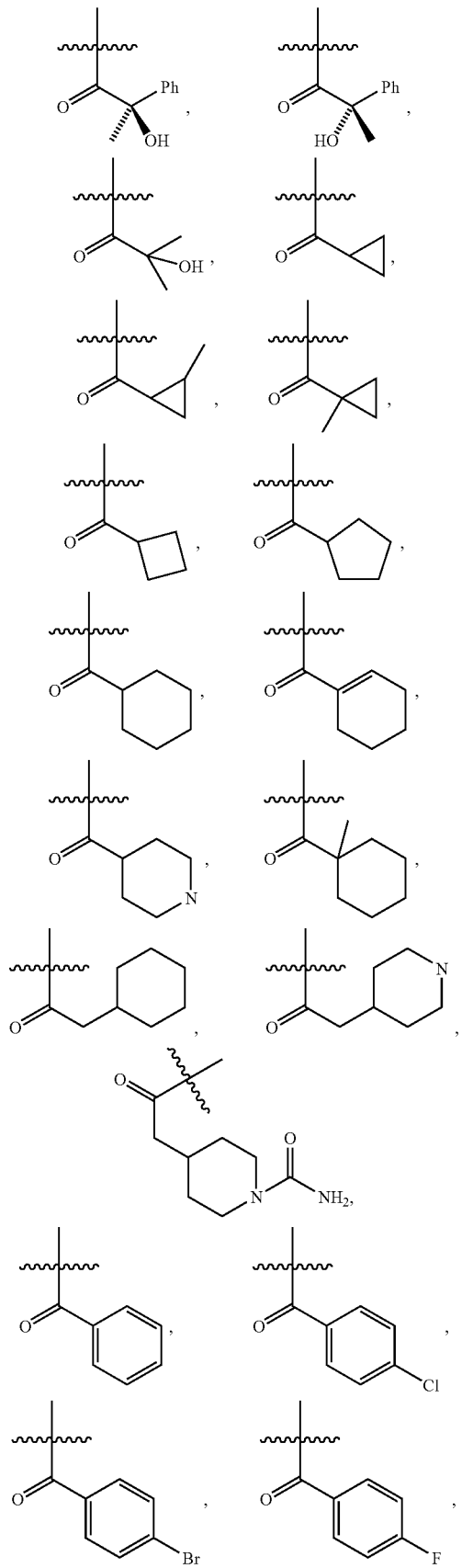
-continued
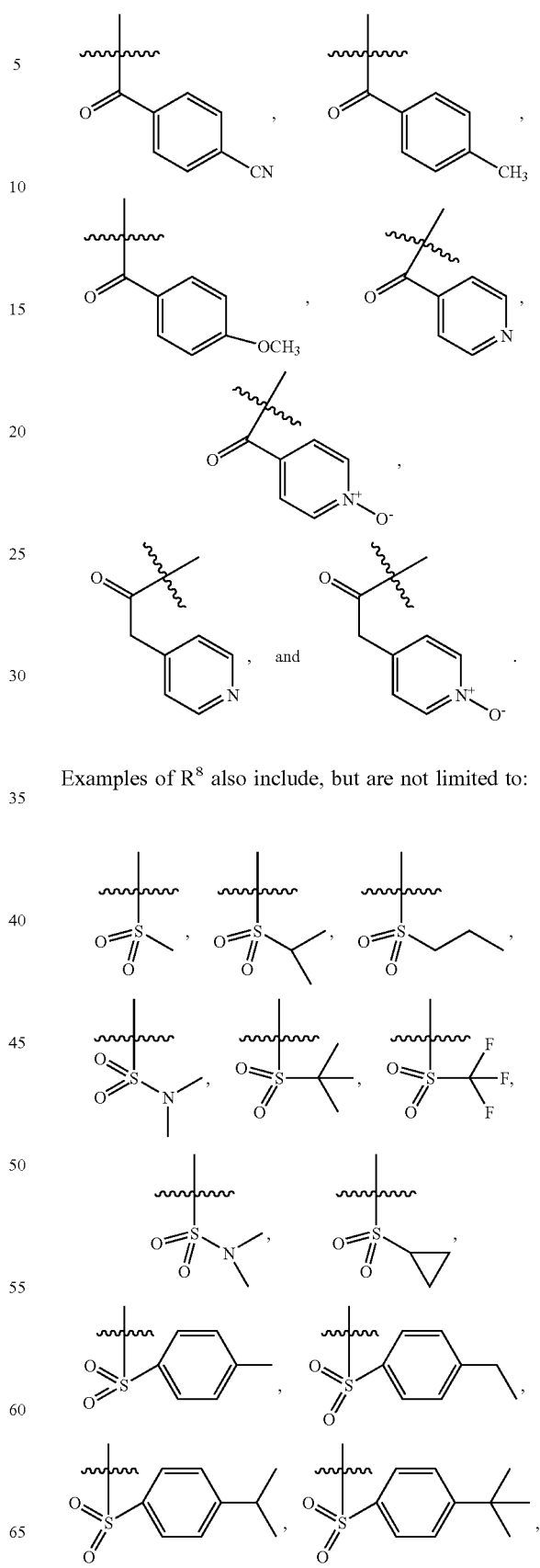
Examples of $R^8$ also include, but are not limited to:

-continued

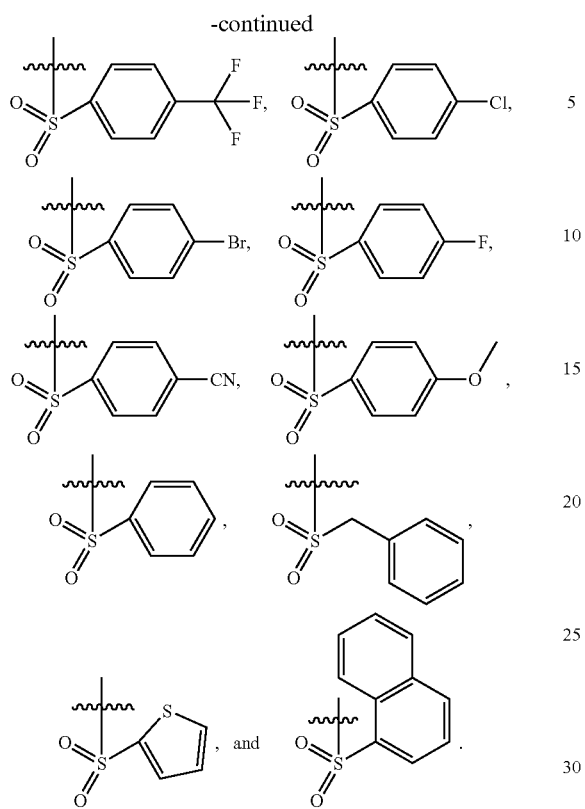

Examples of R⁸ also include, but are not limited to:

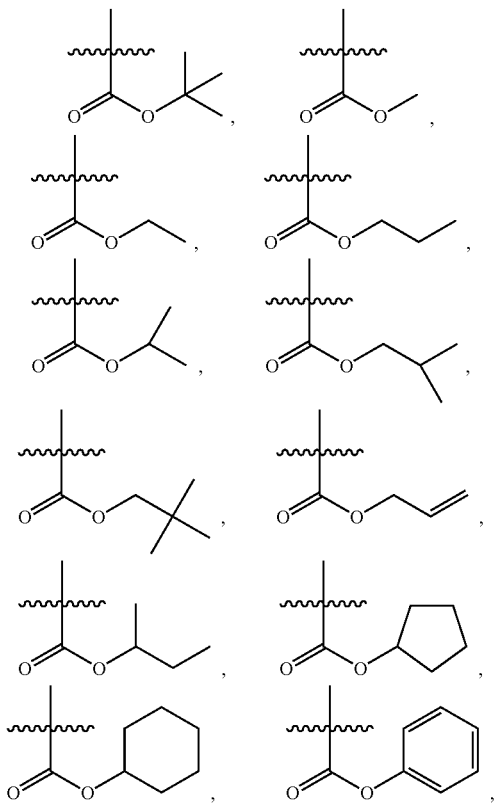

-continued

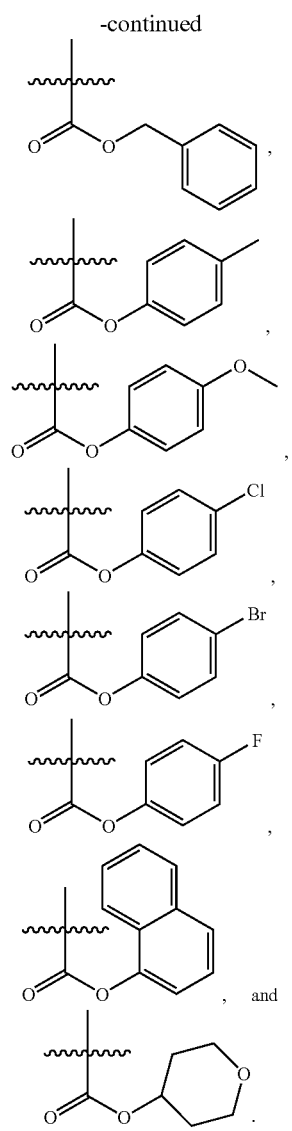

In one embodiment of the invention, for formula 1.0, when the optional bond between C-5 and C-6 is present (i.e., there is a double bond between C-5 and C-6), then one of A or B is H and the other is $R^9$, and $R^9$ is selected from the group consisting of:
(1) heteroaryl;
(2) substituted heteroaryl;
(3) arylalkyl;
(4) substituted arylalkyl;
(5) arylalkoxy;
(6) substituted arylalkoxy;
(7) heterocycloalkyl;
(8) substituted heterocycloalkyl;
(9) heterocycloalkylalkyl;
(10) substituted heterocycloalkylalkyl;
(11) unsubstituted heteroarylalkyl;
(12) substituted heteroarylalkyl;
(13) alkenyl;
(14) substituted alkenyl;
(15) unsubstituted heteroarylalkenyl; and
(16) substituted heteroarylalkenyl, wherein said substituted $R^9$ groups are substituted with one or more (e.g. 1, 2 or 3) substituents independently selected from the group consisting of:
(1) —OH;
(2) —CO$_2$R$^{14}$;
(3) —CH$_2$OR$^{14}$,
(4) halo,
(5) alkyl (e.g. methyl, ethyl, propyl, butyl or t-butyl);
(6) amino;
(7) trityl;
(8) heterocycloalkyl;
(9) arylalkyl;
(10) heteroaryl and
(11) heteroarylalkyl, wherein $R^{14}$ is independently selected from the group consisting of: H; and alkyl, preferably methyl and ethyl.

In one embodiment of the invention, for formula 1.0, when there is a double bond between C-5 and C-6, A is H and B is $R^9$. In one embodiment of the invention, for formula 1.0, when there is a double bond between C-5 and C-6, A is H and B is $R^9$ wherein $R^9$ is selected from the group consisting of:
(1) arylalkyl;
(2) substituted arylalkyl;
(3) arylalkoxy;
(4) substituted arylalkoxy;
(5) heterocycloalkyl;
(6) substituted heterocycloalkyl;
(7) heterocycloalkylalkyl;
(8) substituted heterocycloalkylalkyl;
(9) unsubstituted heteroarylalkyl;
(10) substituted heteroarylalkyl;
(11) alkenyl;
(12) substituted alkenyl;
(13) unsubstituted heteroarylalkenyl; and
(14) substituted heteroarylalkenyl, wherein said substituted $R^9$ groups are substituted with one or more (e.g. 1, 2 or 3) substituents independently selected from the group consisting of:
(1) —OH;
(2) halo, (preferably Br);
(3) alkyl (e.g. methyl, ethyl, propyl, butyl, or t-butyl);
(4) amino; and
(5) trityl.

In one embodiment of the invention, for formula 1.0, when there is a double bond between C-5 and C-6, A is H and B is $R^9$ wherein $R^9$ is selected from the group consisting of:
(1) heterocycloalkylalkyl;
(2) substituted heterocycloalkylalkyl;
(3) unsubstituted heteroarylalkyl; and
(4) substituted heteroarylalkyl;

wherein said substituents for said substituted $R^9$ groups are the same or different alkyl groups (e.g., $C_1$-$C_4$ alkyl).

In one embodiment of the invention, for formula 1.0, when there is a double bond between C-5 and C-6, A is H and B is $R^9$ wherein $R^9$ is selected from the group consisting of:
(1) unsubstituted heteroaryl($C_1$-$C_3$)alkyl; and
(2) substituted heteroaryl ($C_1$-$C_3$)alkyl;

wherein the substituents for said substituted $R^9$ group are as defined above.

In one embodiment of the invention, for formula 1.0, when there is a double bond between C-5 and C-6, A is H and B is $R^9$ wherein $R^9$ is selected from the grooup consisting of:
(1) unsubstituted heteroaryl($C_1$-$C_3$)alkyl, with unsubstituted heteroaryl-CH$_2$— being preferred; and
(2) substituted heteroaryl($C_1$-$C_3$)alkyl, with substituted heteroaryl-CH$_2$— being preferred;

wherein the substituents for said substituted $R^9$ groups are selected from one or more (e.g. 1, 2 or 3, with one being preferred) of the same or different alkyl groups (e.g., —CH$_3$, —C$_2$H$_5$, —C$_3$H$_4$, with —CH$_3$ being preferred).

In one embodiment of the invention, for formula 1.0, when there is a double bond between C-5 and C-6, A is H and B is $R^9$ wherein $R^9$ is selected from the group consisting of:
(1) —CH$_2$-imidazolyl;
(2) substituted imidazolyl-CH$_2$—;
(3) —(CH$_2$)$_2$-imidazolyl;
(4) substituted imidazolyl-(CH$_2$)$_2$—;
(5) —(CH$_2$)$_3$-imidazolyl;
(6) substituted imidazolyl-(CH$_2$)$_3$—;
(7) —CH$_2$-piperazinyl and
(8) —CH$_2$-morpholinyl;

wherein the substituents for said substituted $R^9$ groups are selected from one or more (e.g. 1, 2 or 3, with one being preferred) of the same or different alkyl groups (e.g., —CH$_3$, —C$_2$H$_5$, —C$_3$H$_4$, with —CH$_3$ being preferred). Preferably, the substituted imidazolyl groups are selected from the group consisting of:

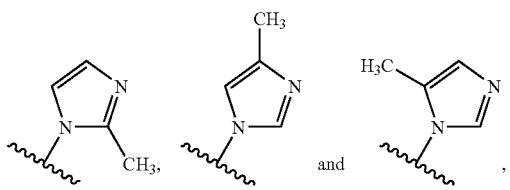

with the substituted imidazolyl:

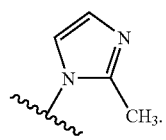

being most preferred.

In one embodiment of the invention, for formula 1.0, when there is a double bond between C-5 and C-6, A is H and B is $R^9$ wherein $R^9$ is substituted imidazolyl-CH$_2$—, with

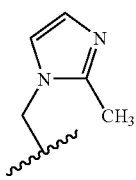

being preferred.

In one embodiment of the invention, for formula 1.0, when B is H and A is $R^9$, and there is a double bond between C-5 and C-6, the $R^9$ groups for A are those described above for B.

In one embodiment of the invention, for formula 1.0, when the optional bond between C-5 and C-6 is not present (i.e, there is a single bond between C-5 and C-6), each A and each B are independently selected and the definitions of A and B are the same as those described above when the optional bond is present, provided that when there is a single bond between C-5 and C-6 then one of the two A substituents or one of the two B substituents is H (i.e., when there is a single bond between C-5 and C-6 one of the four substituents (A, A, B, and B) has to be H).

In one embodiment of the invention, for compounds of formula 1.0, there is a double bond between C-5 and C-6.

Compounds of formula 1.0, having C-11 R- and S-stereochemistry include:

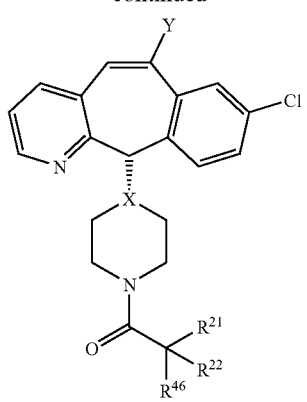

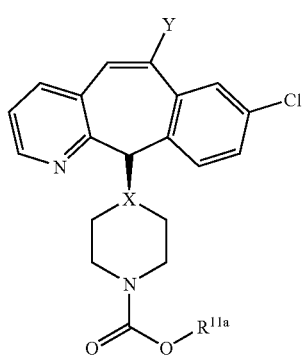

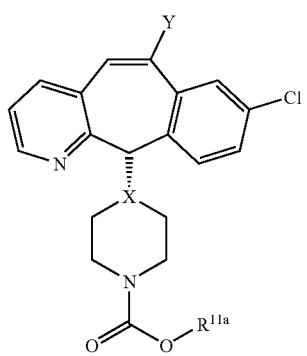

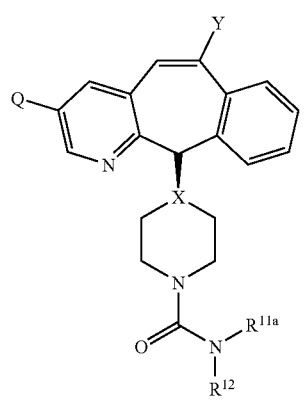

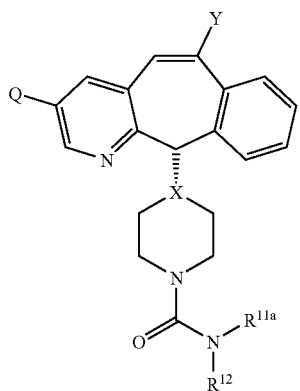
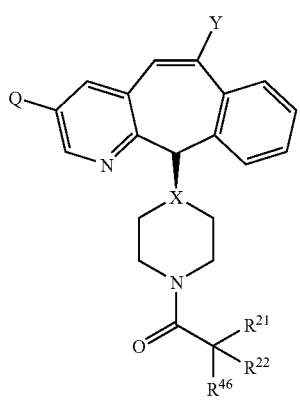
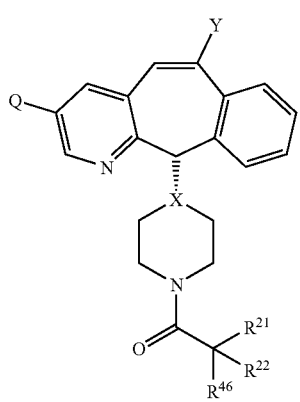
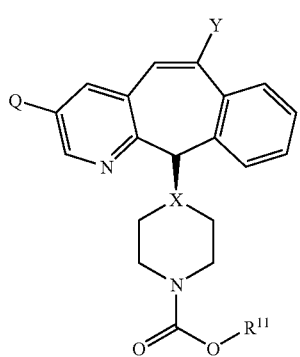
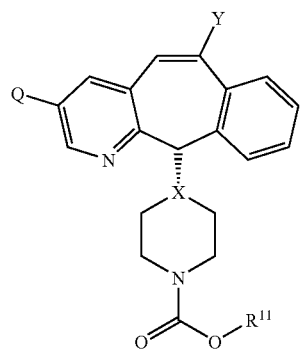
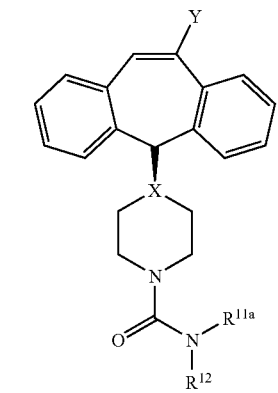
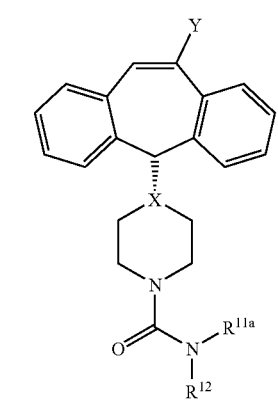
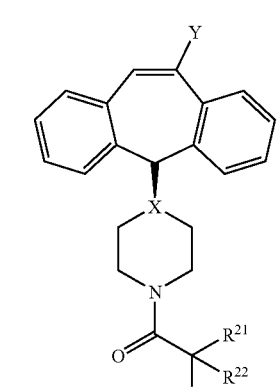

-continued
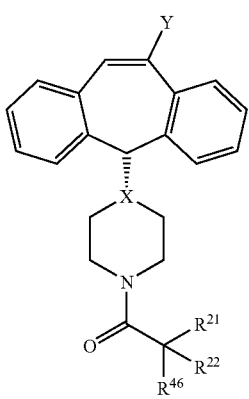
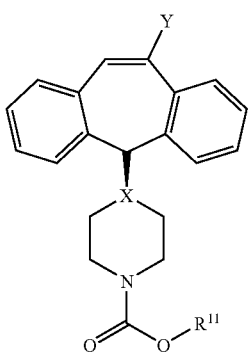
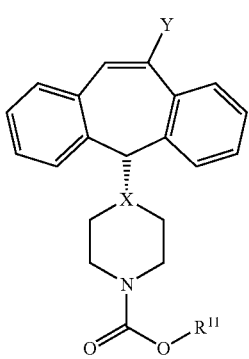
wherein:
X is N or C;
Q is Br or Cl; and
Y is alkyl, arylalkyl, or heteroarylalkyl.
Representative compounds of this invention include but are not limited to:
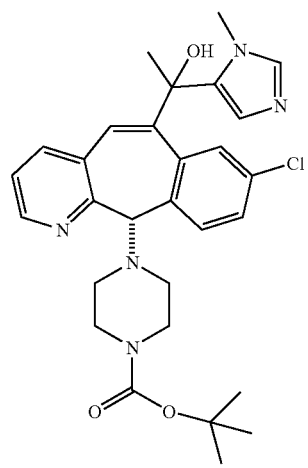
795.1
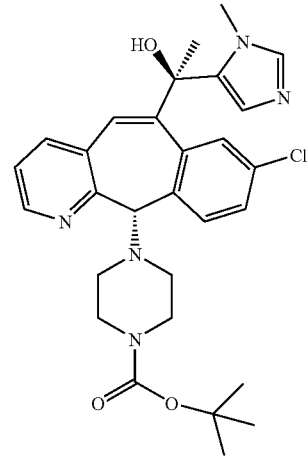
888a
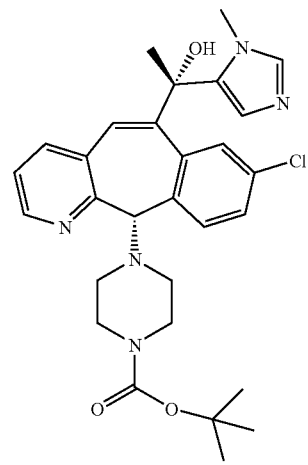
888b 85
-continued
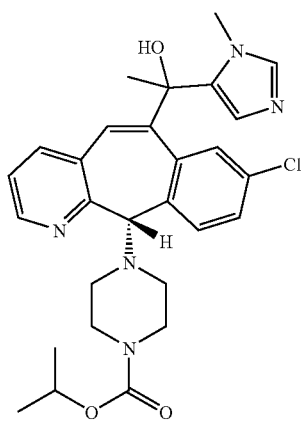
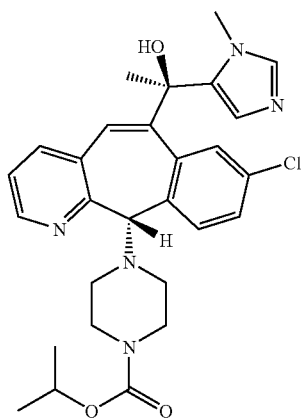

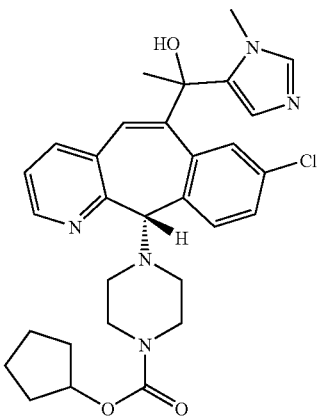
86
-continued
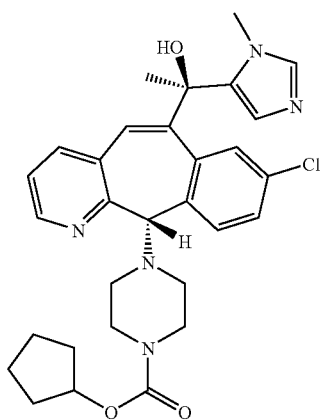
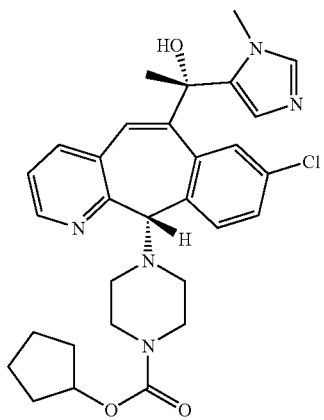
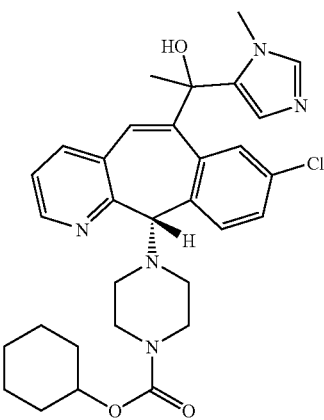
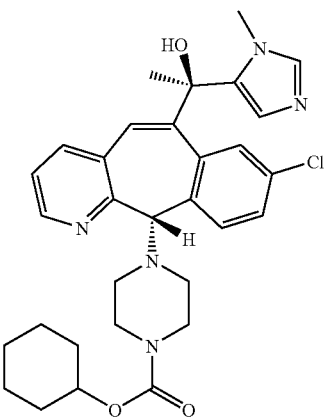

87
-continued
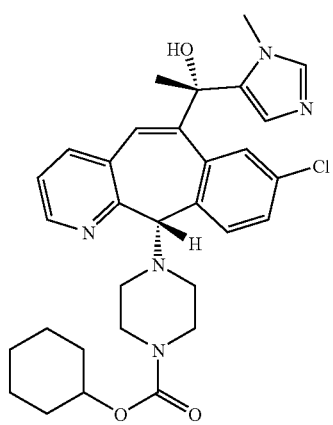
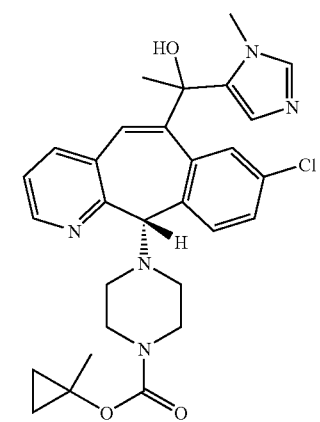
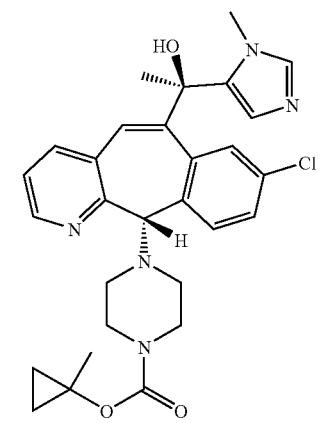
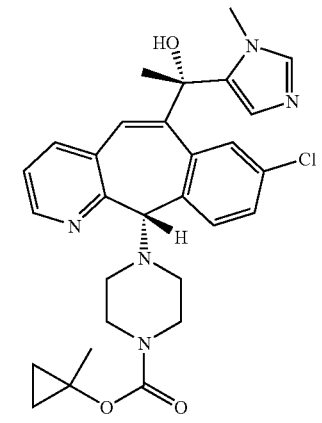
88
-continued
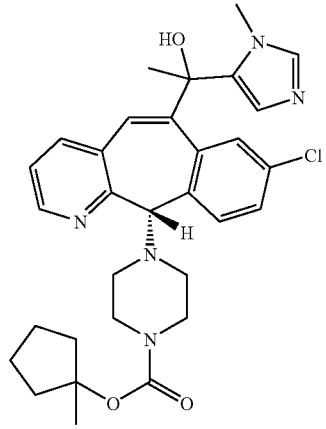
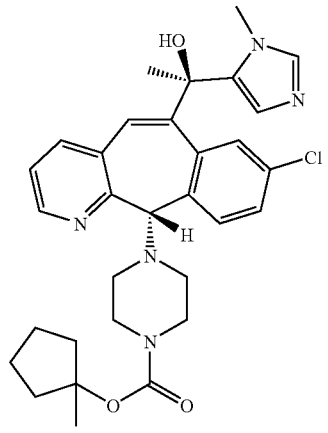
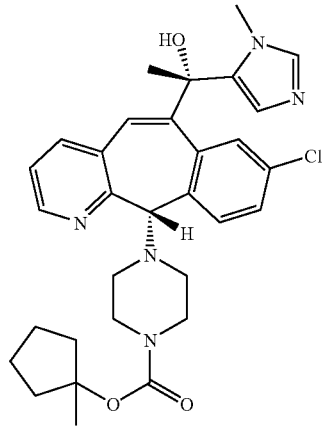
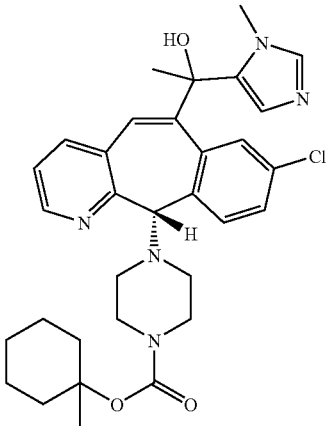

-continued
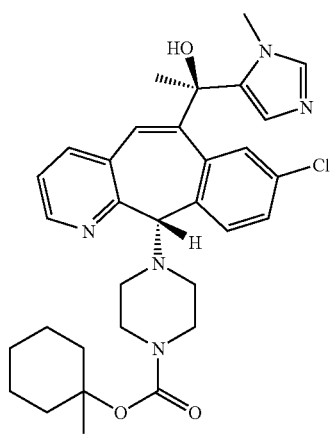
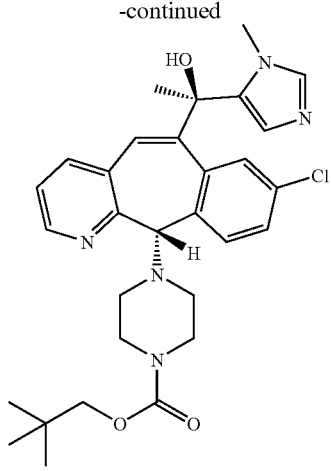
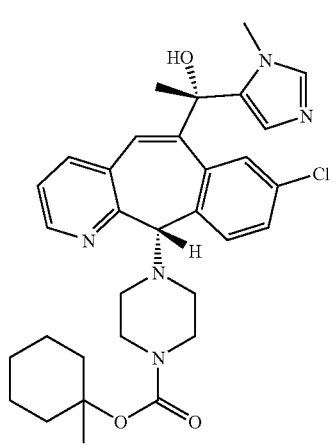
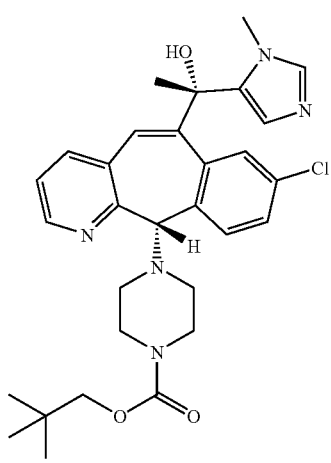
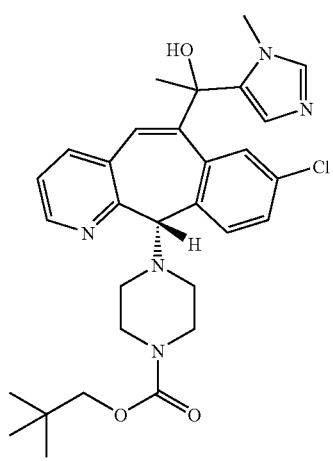
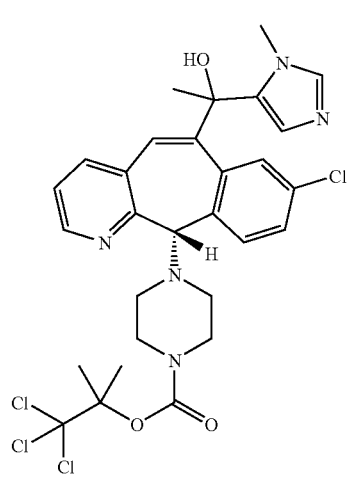

-continued
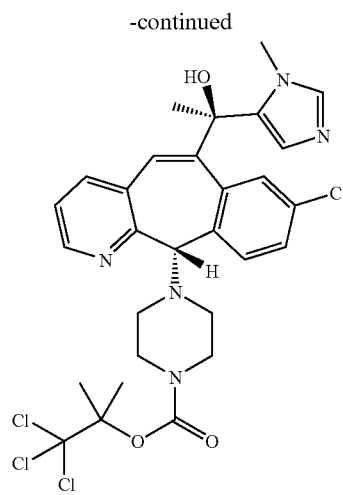
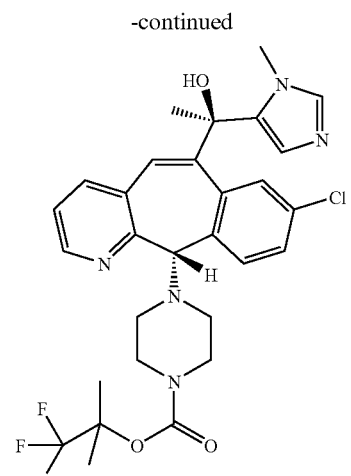
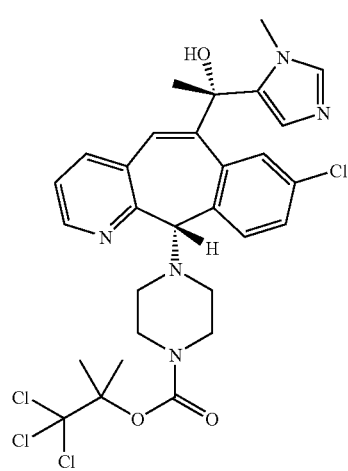
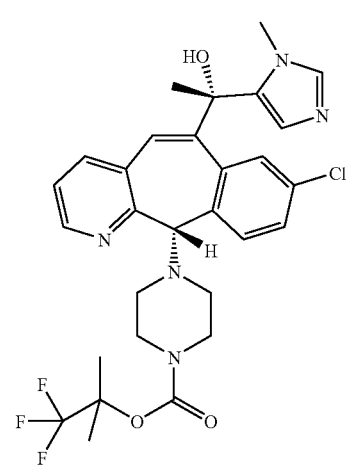
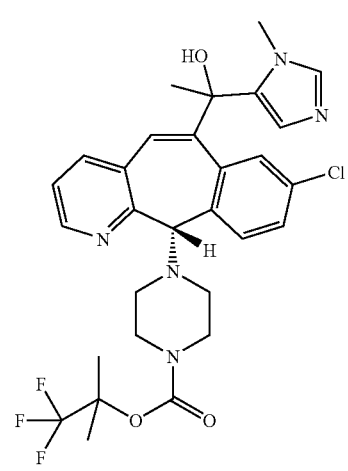
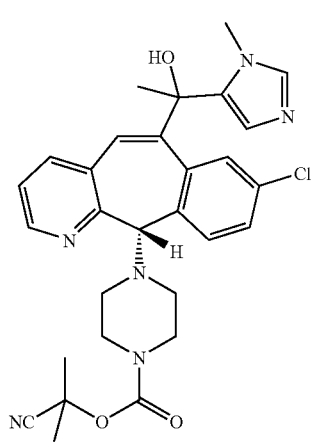

-continued
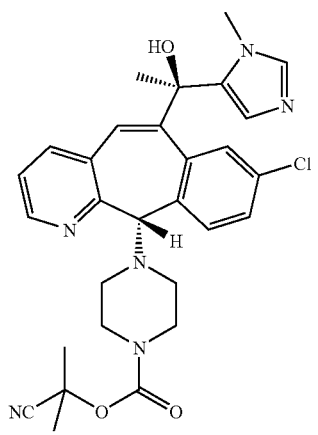
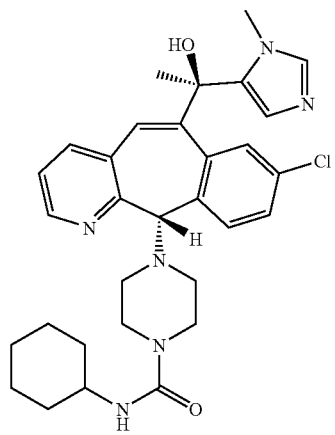
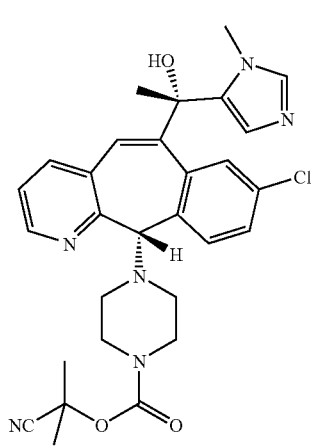
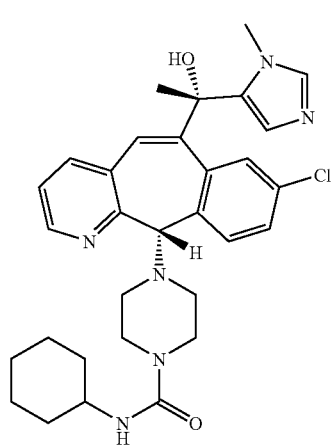
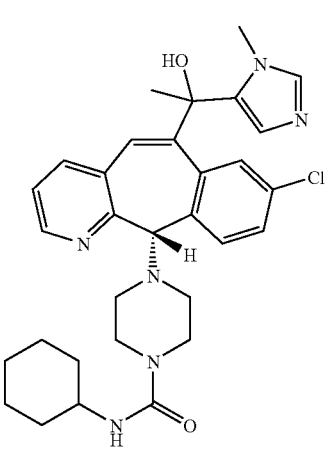
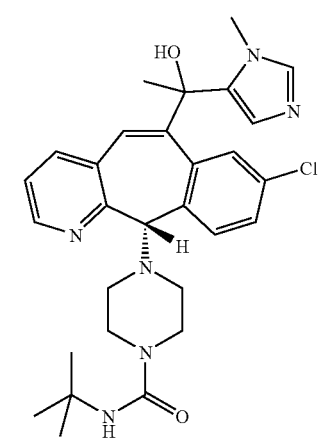

-continued
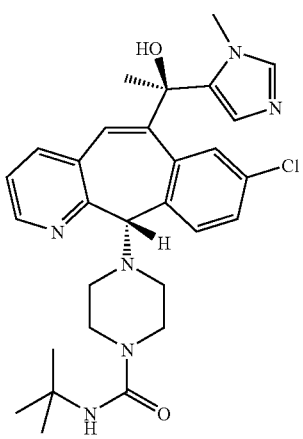
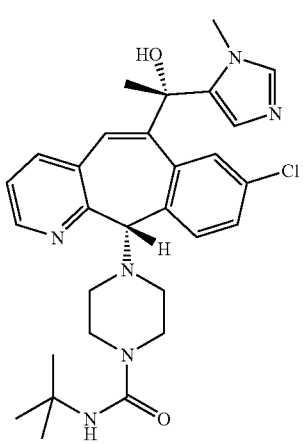
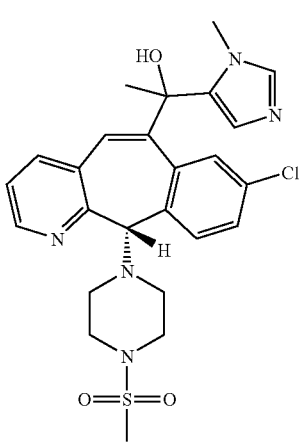
-continued
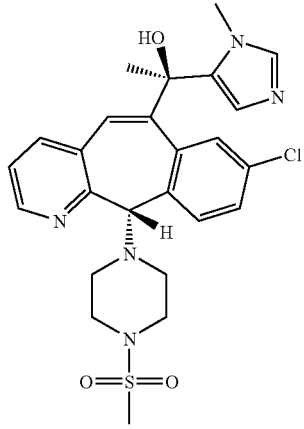
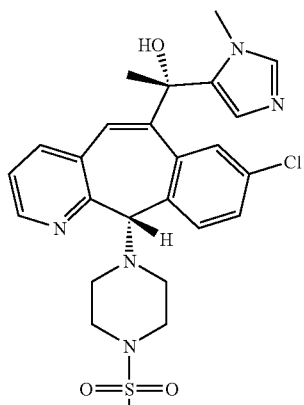
(139)
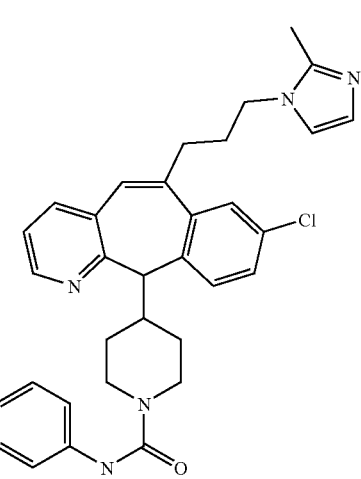

(628)
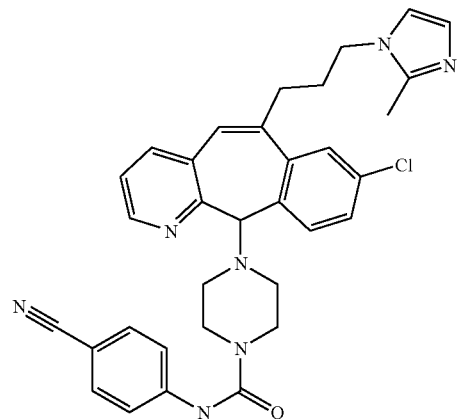
(699)
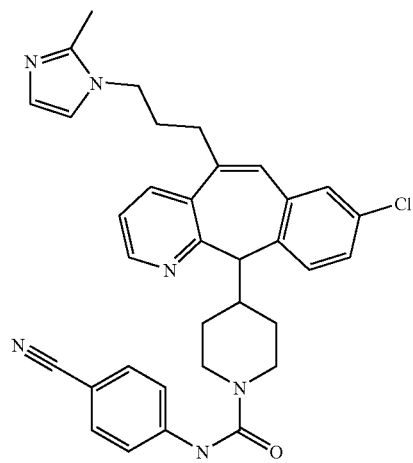
(326)
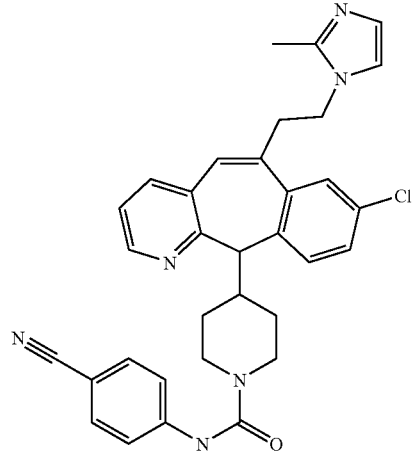
(644)
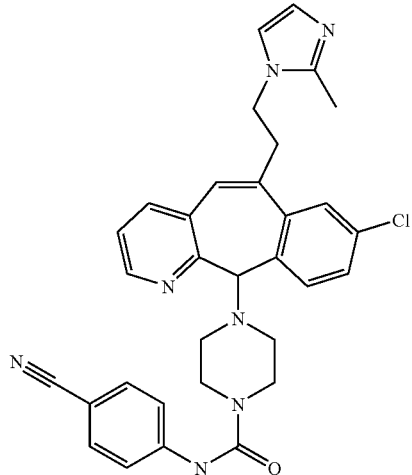
(332)
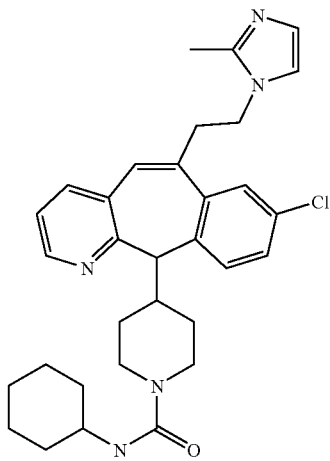
(362a)
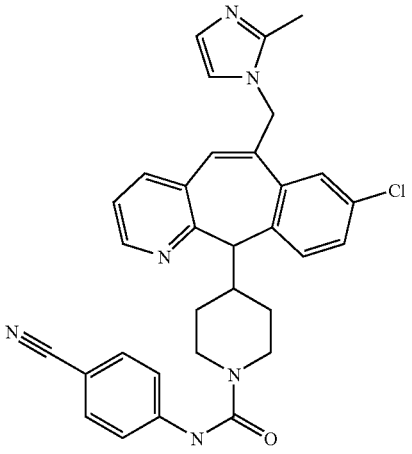

-continued
(372)
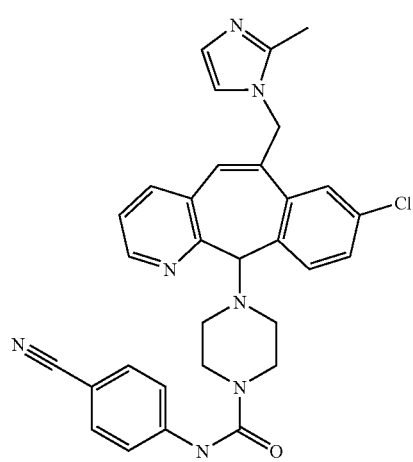
(230)
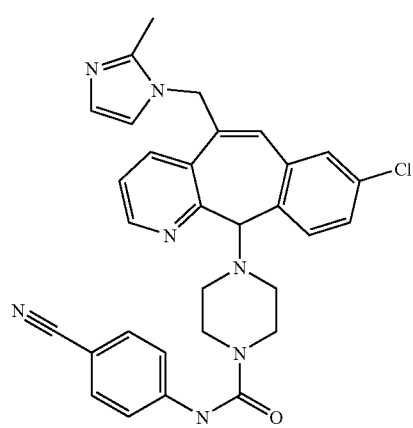
(378)
-continued
(690)
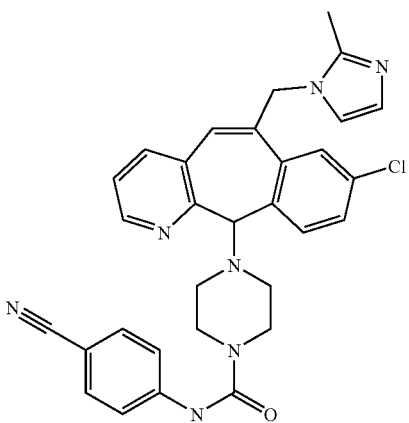
(784)
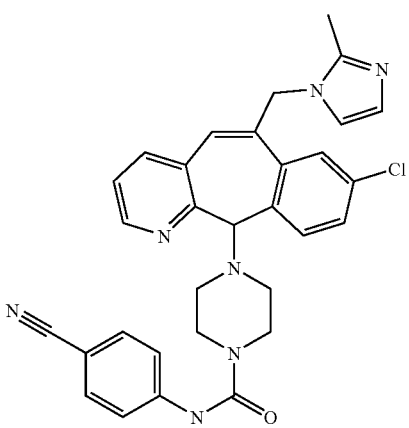
(684)
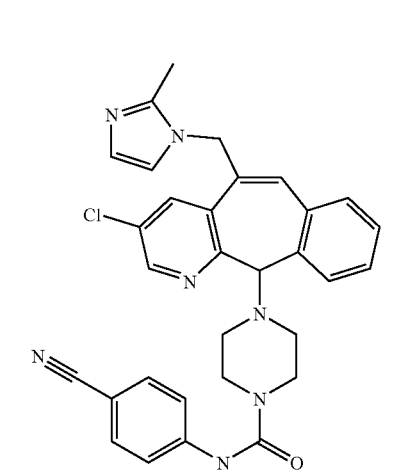

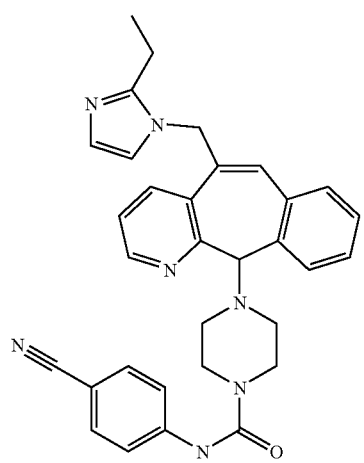
(688)
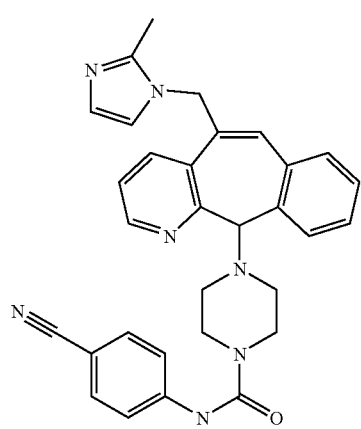
(686)
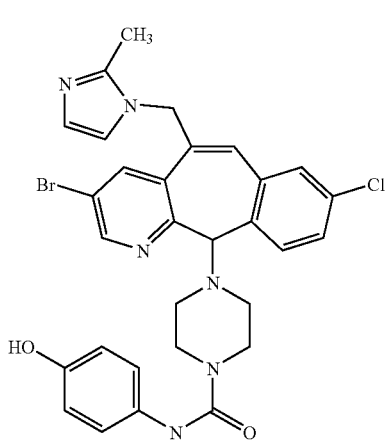
(683.2)
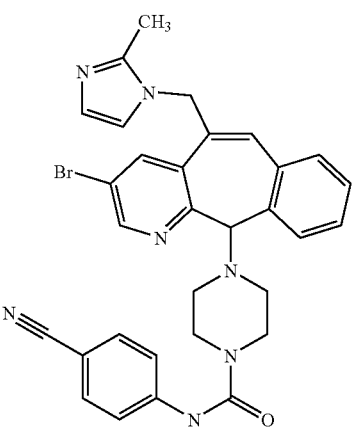
(877)
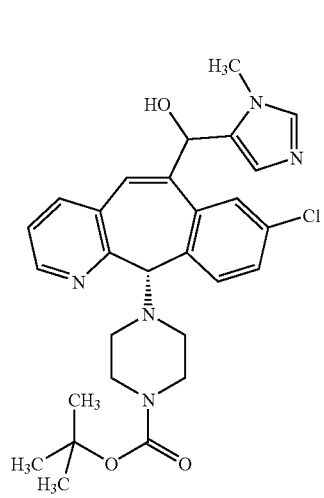
(790)
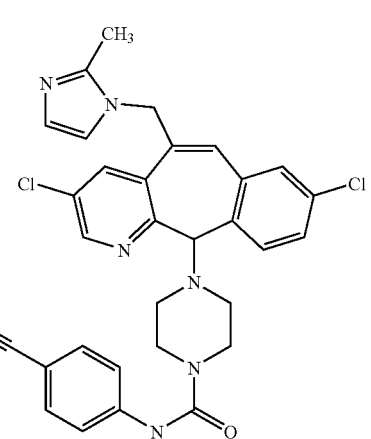
(816)

103
-continued
(788)
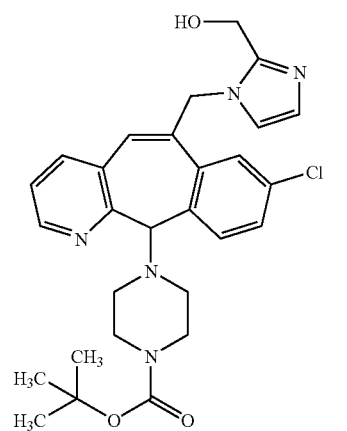
(793)
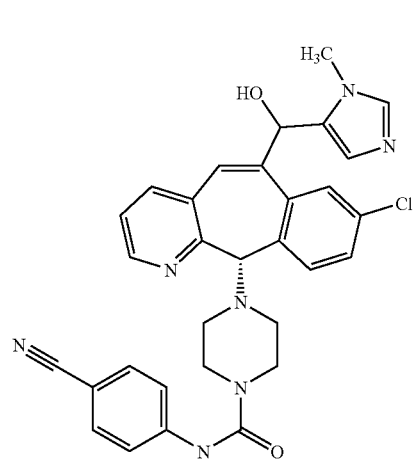
(778)
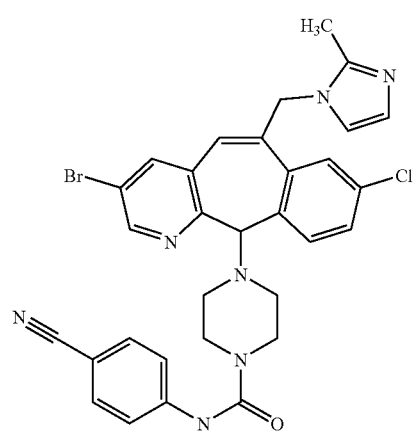
104
-continued
(375.1)
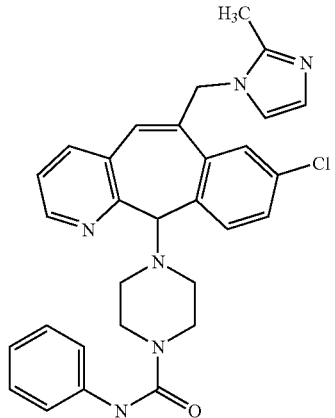
(372)
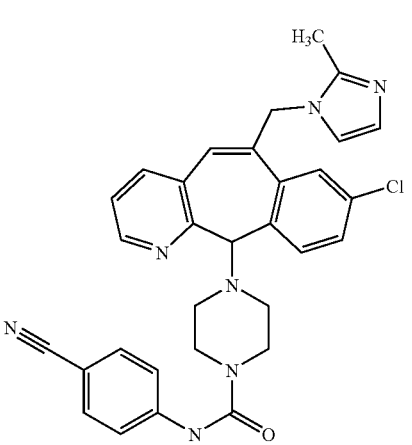
372.1
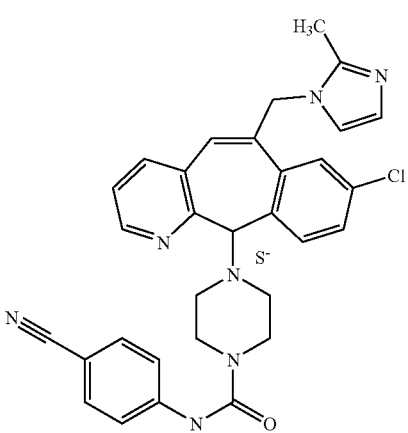

105
372.1
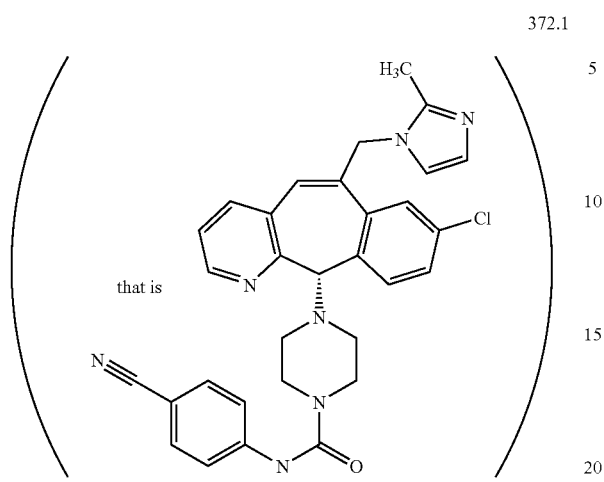
that is
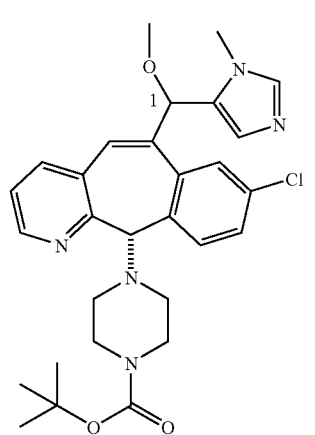
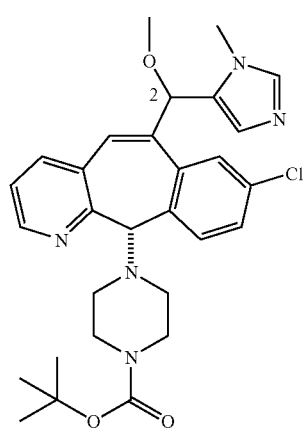
106
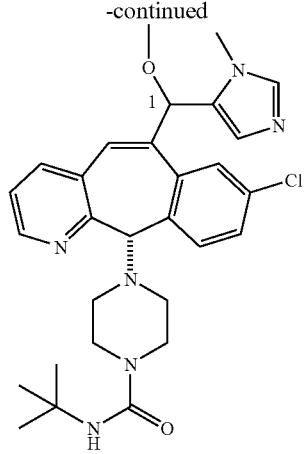
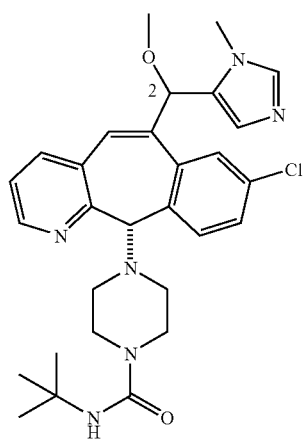
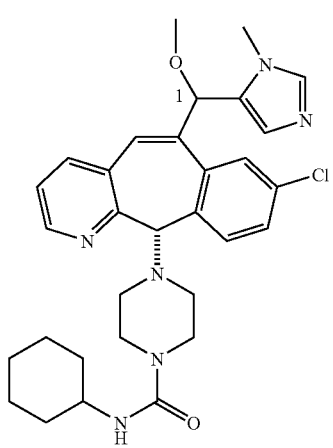

107
-continued
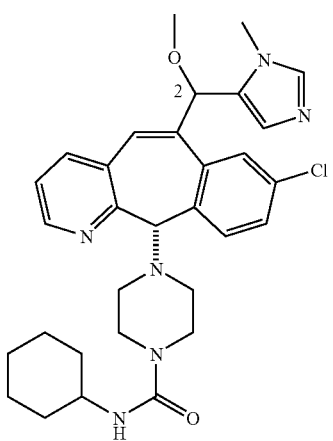
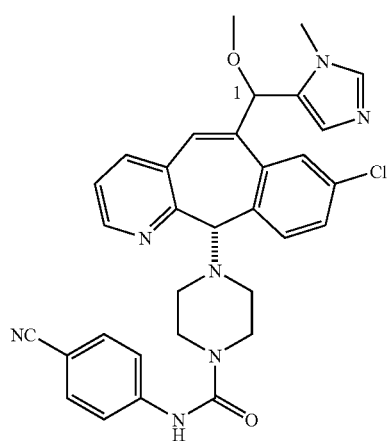
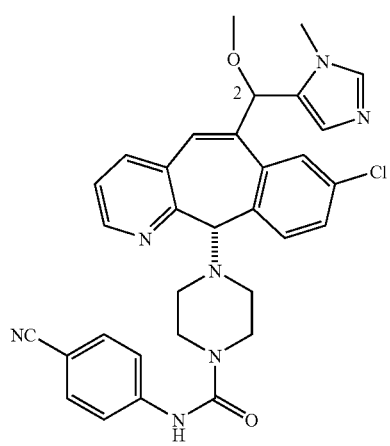
108
-continued
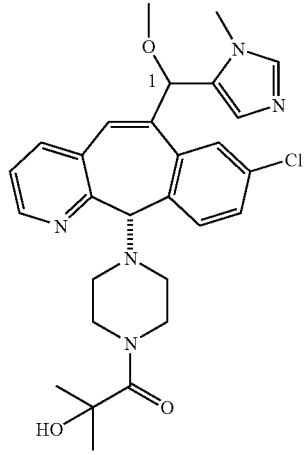
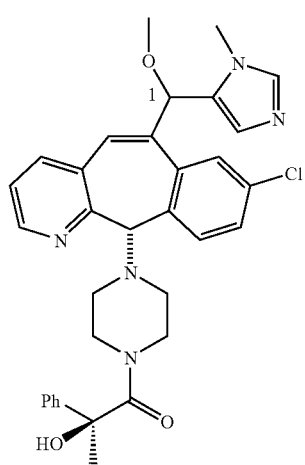
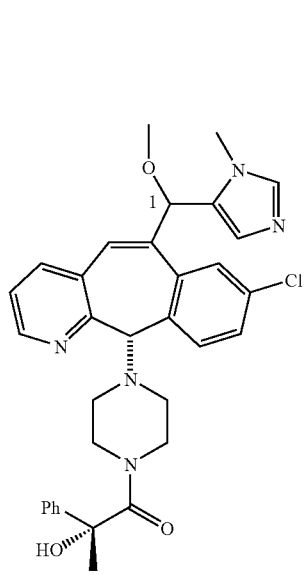

109
-continued
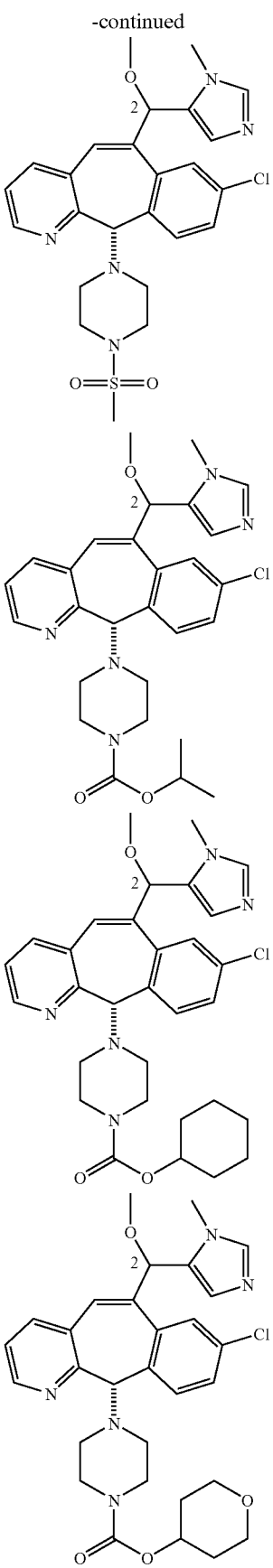
110
-continued
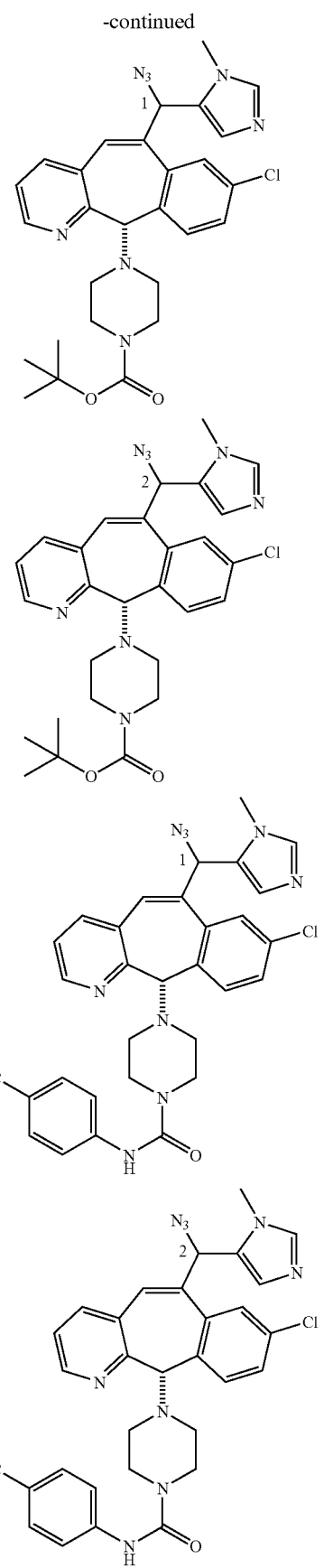

111
-continued
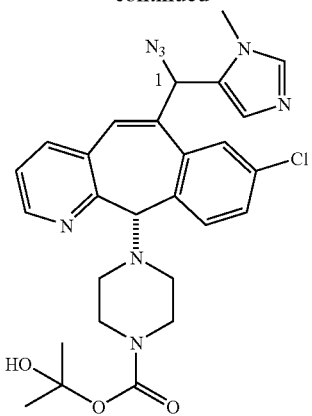
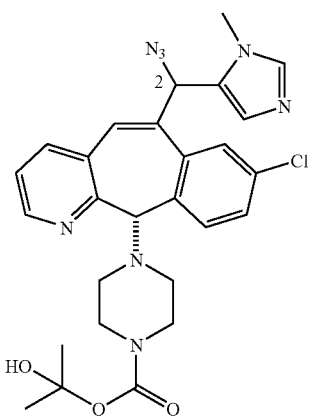
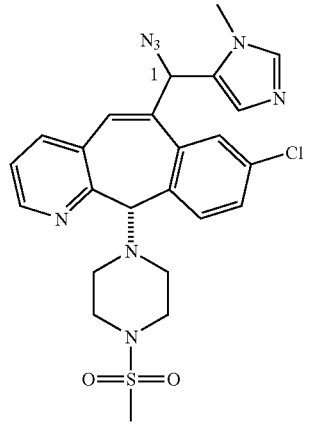
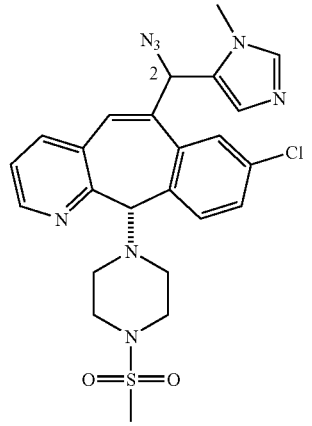
112
-continued
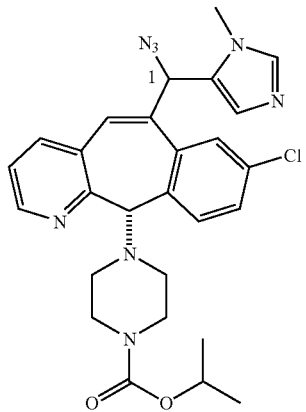
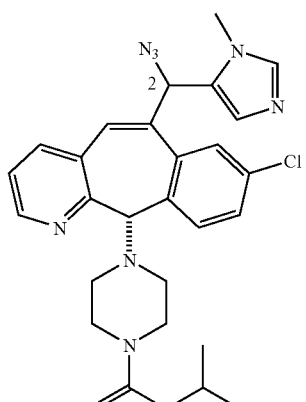
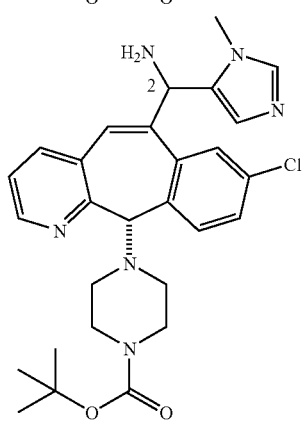
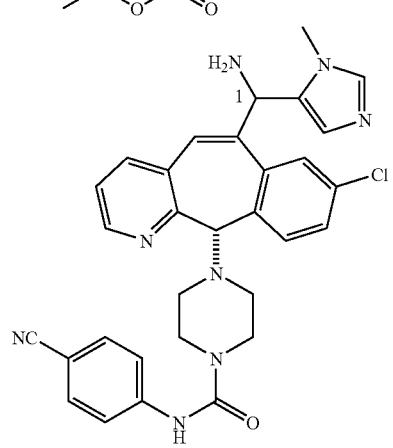

113
-continued
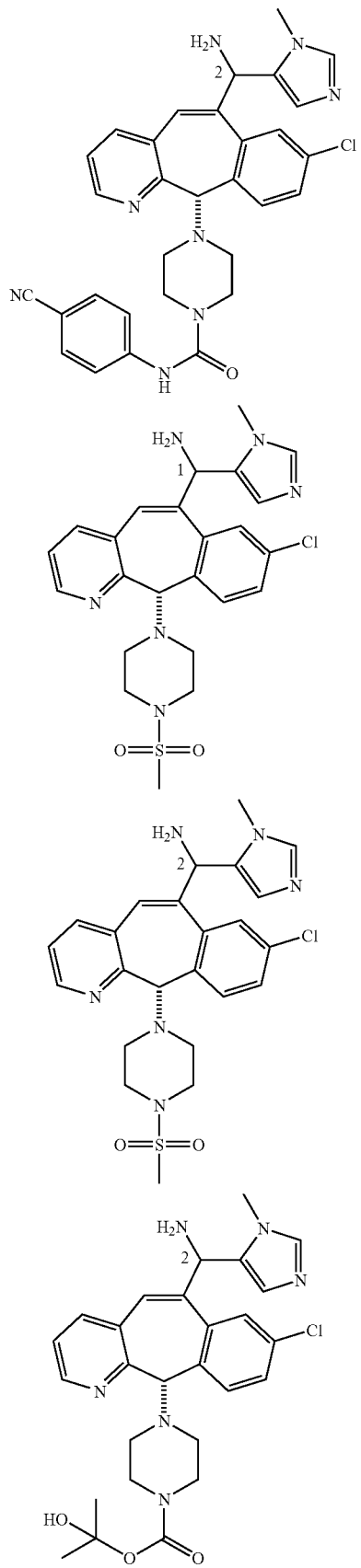
114
-continued
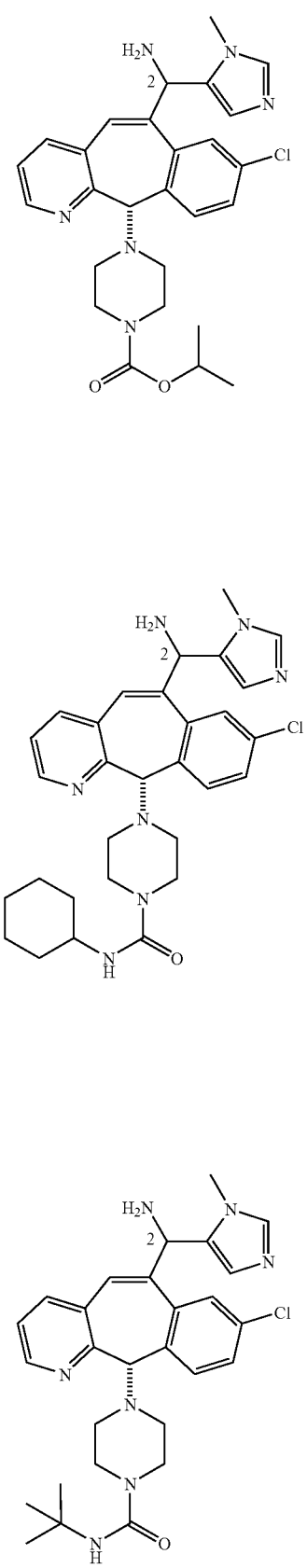

115                                     116
-continued                              -continued
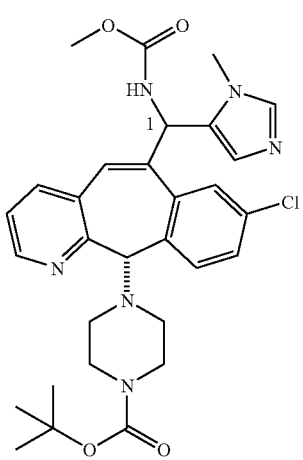
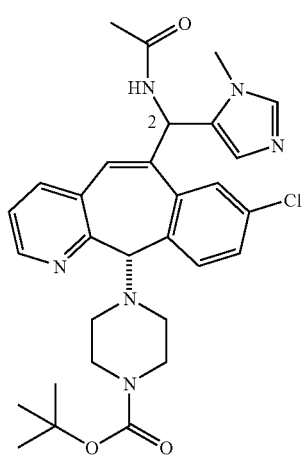

-continued
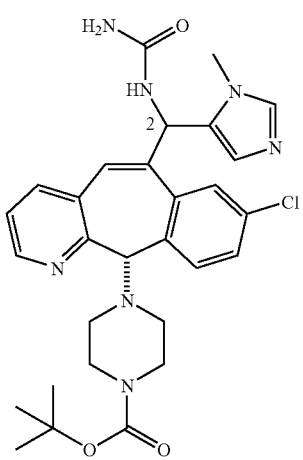
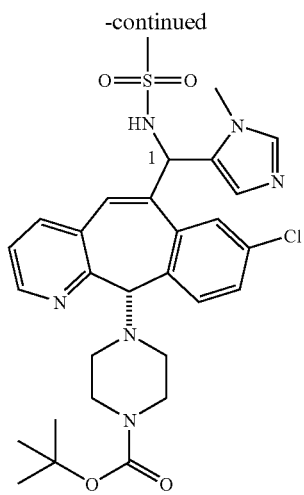
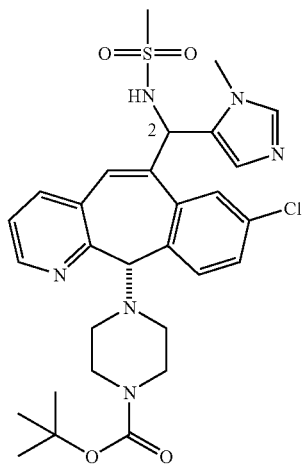
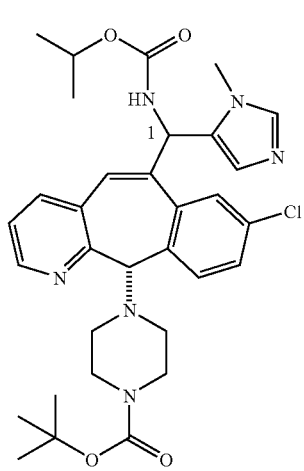

119
-continued
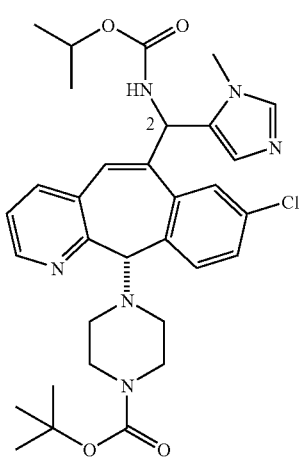
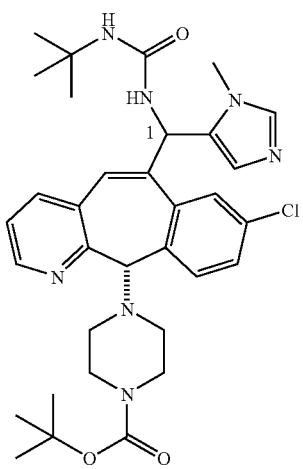
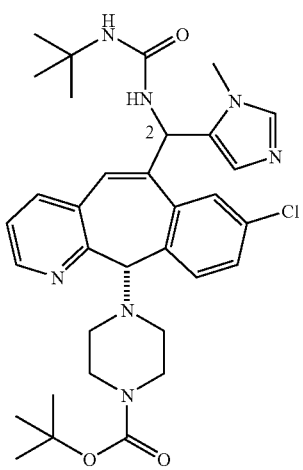
120
-continued
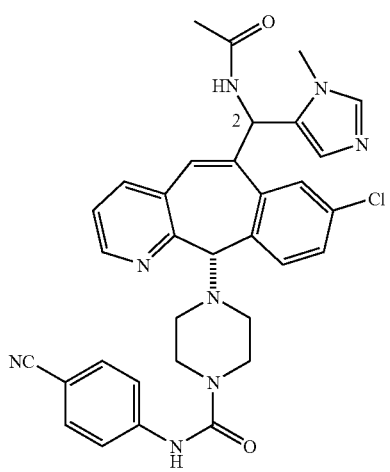
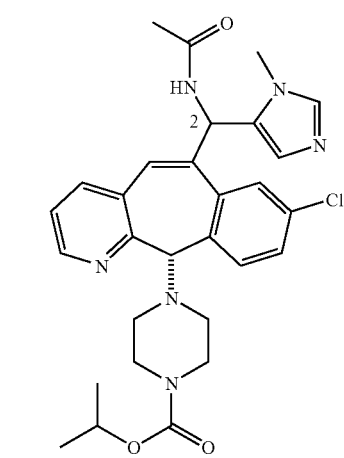
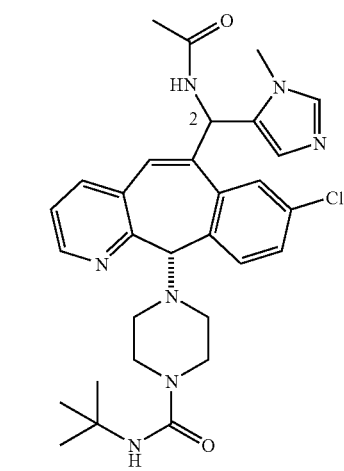

121 122

-continued

123
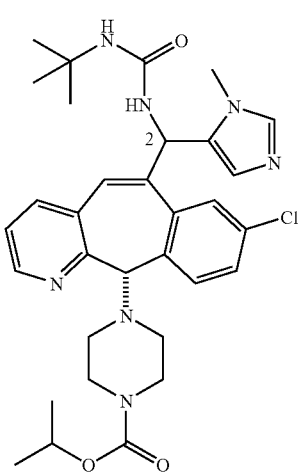
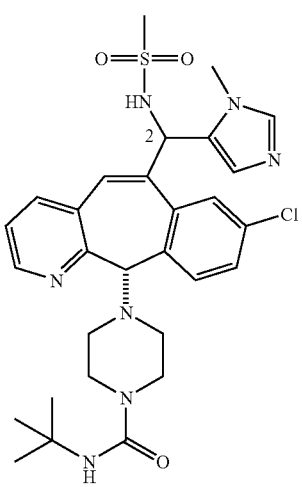
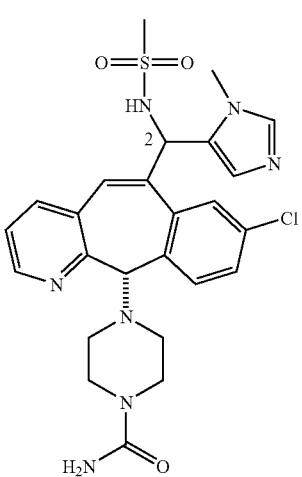
124
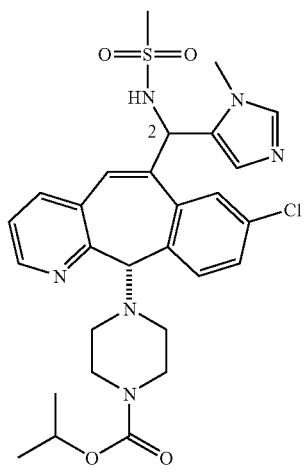
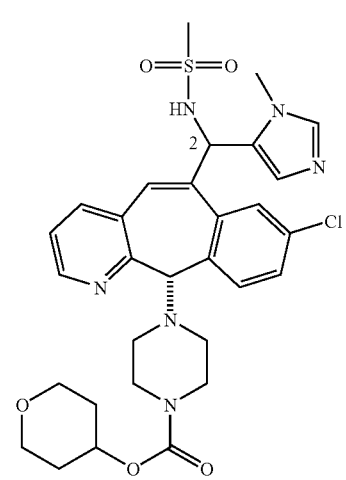
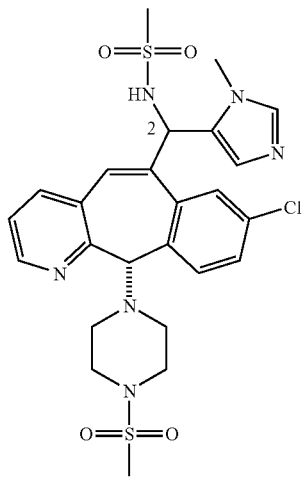

-continued
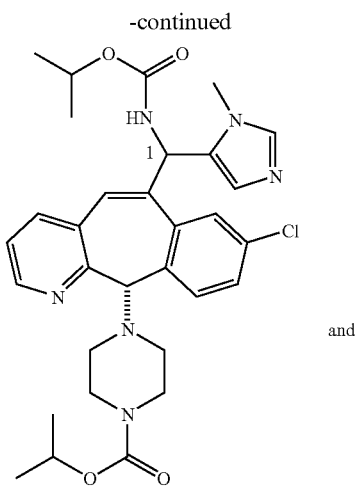
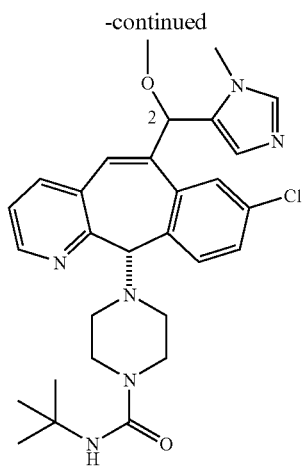
and
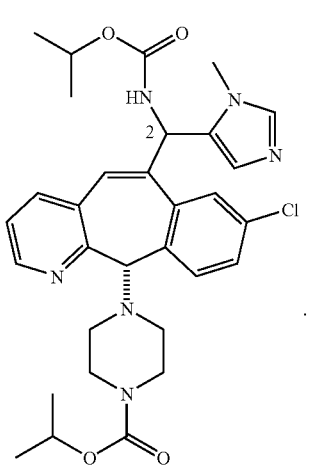
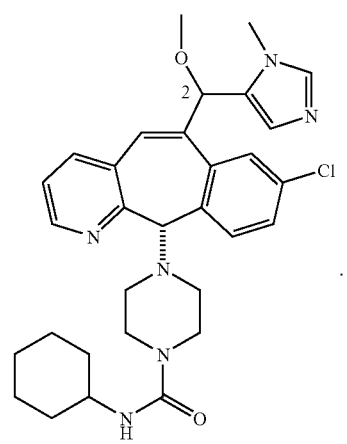
Preferred compounds of the invention are:
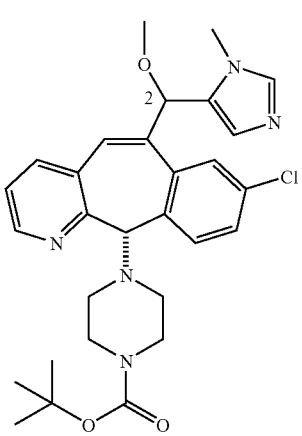
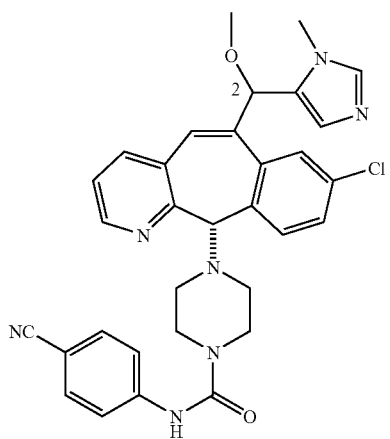

127
-continued
128
-continued
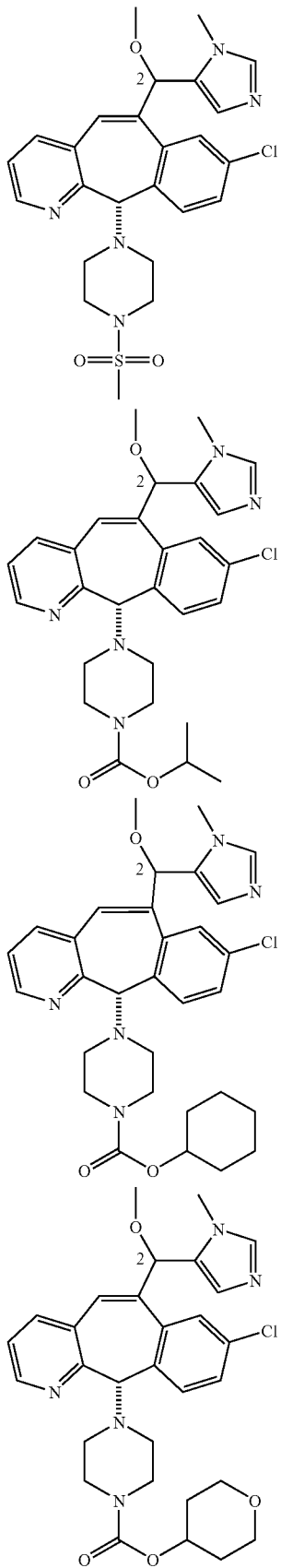
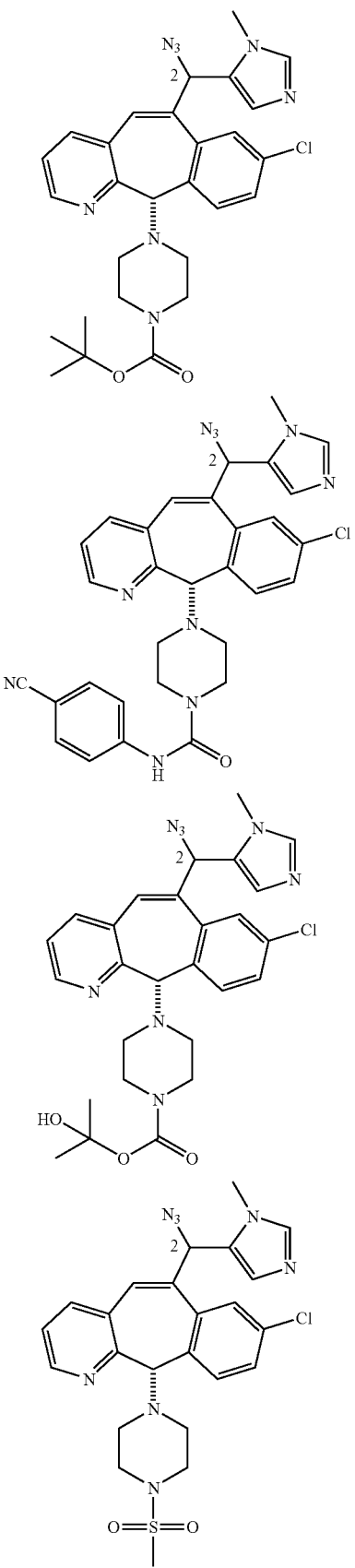

-continued
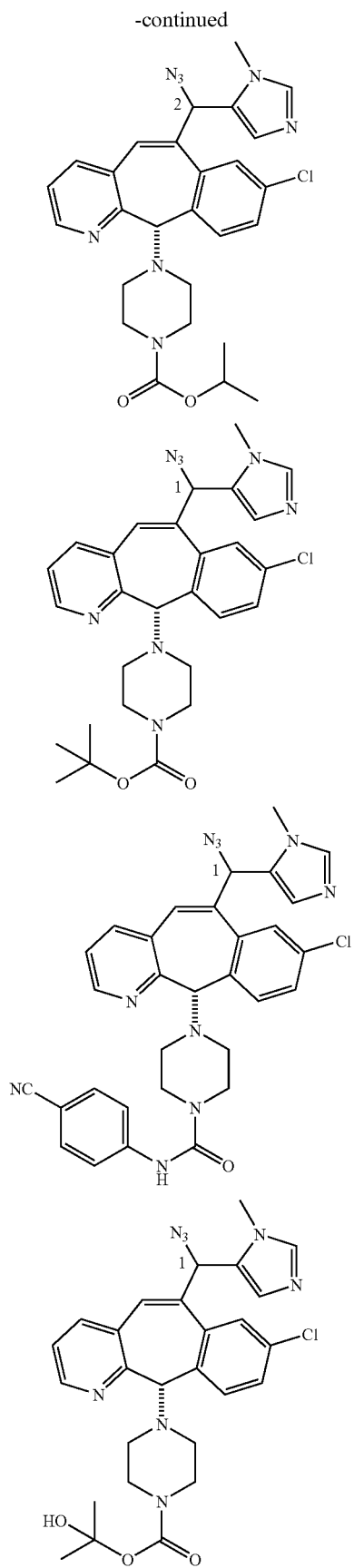
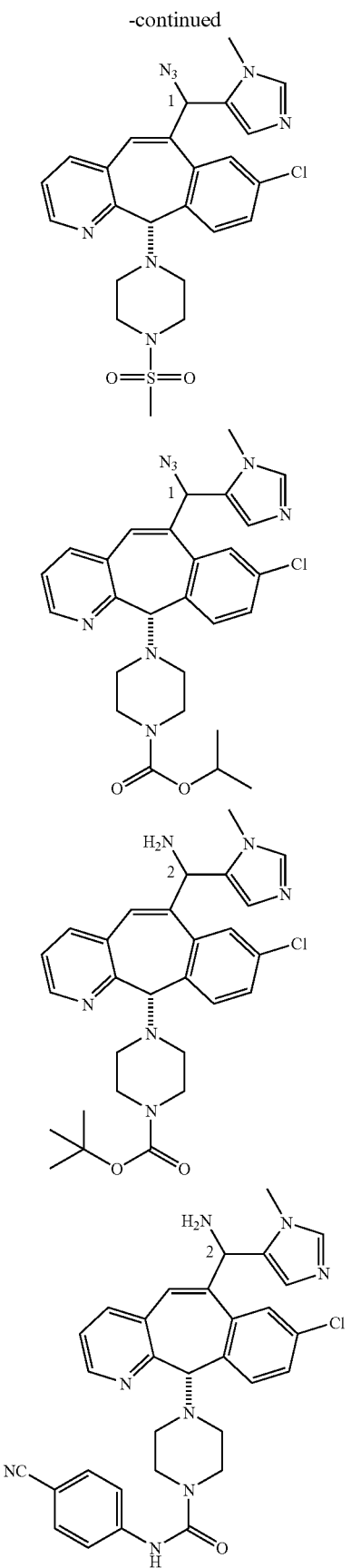

131
-continued
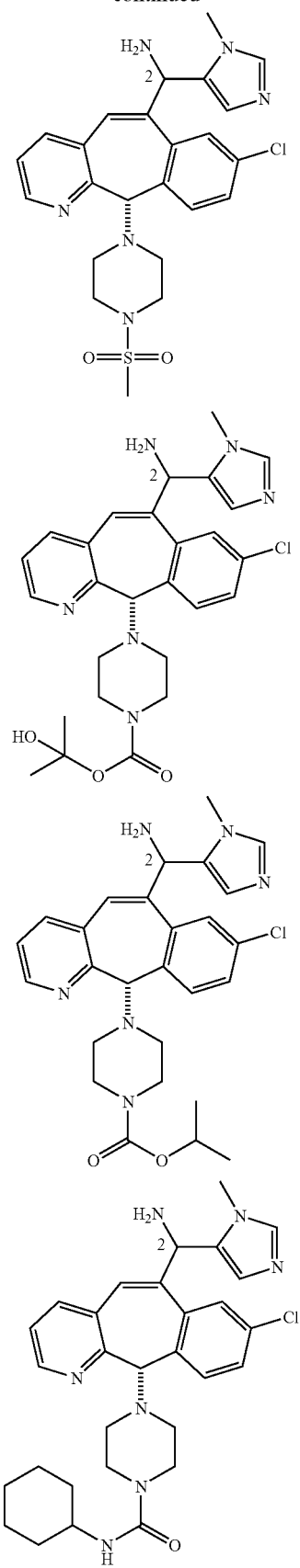
132
-continued
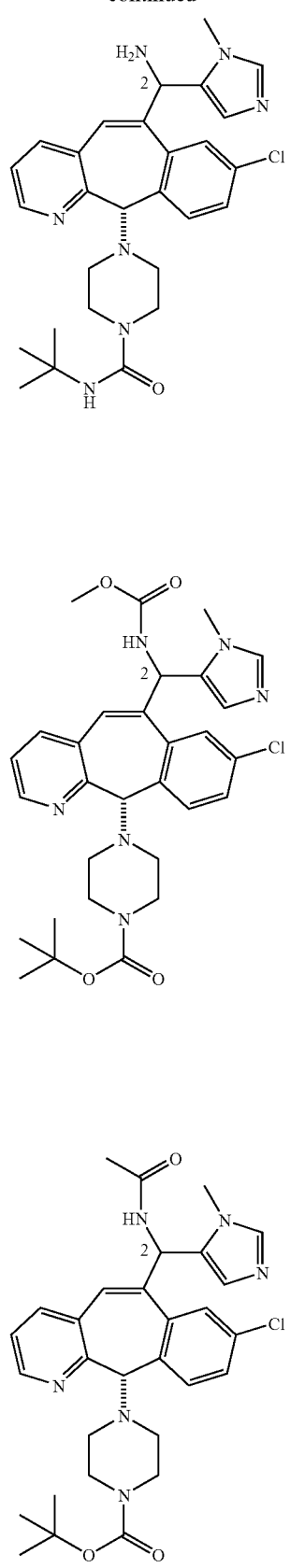

133
-continued
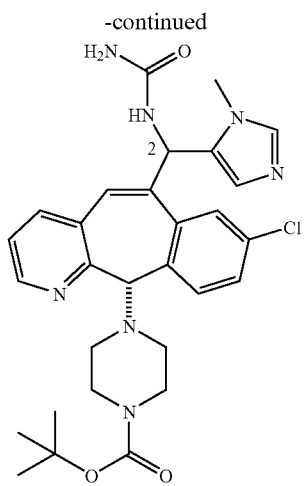
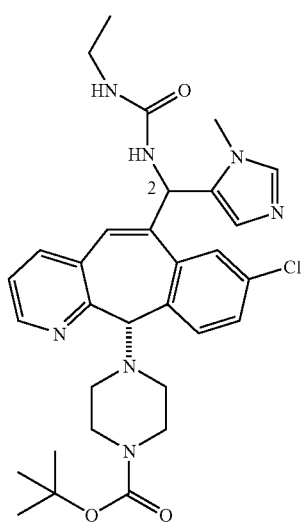
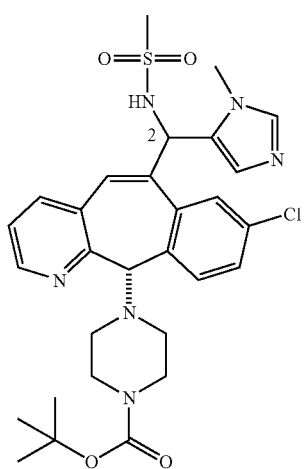
134
-continued
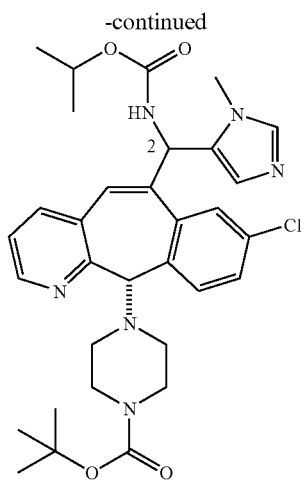
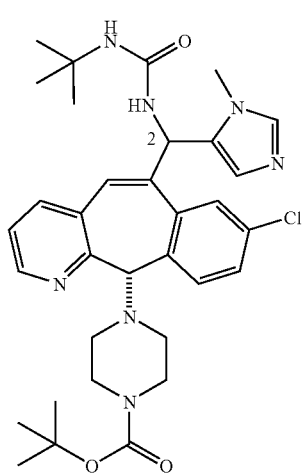
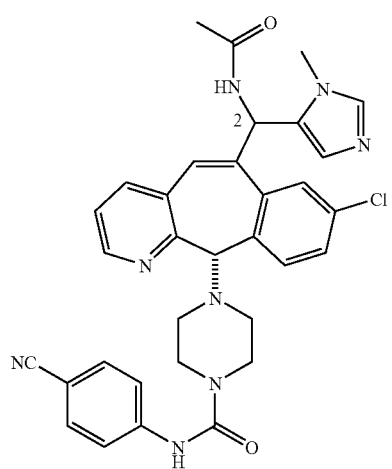

135
-continued
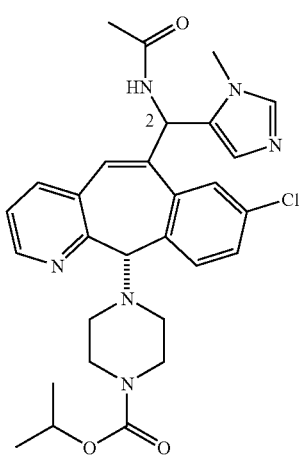
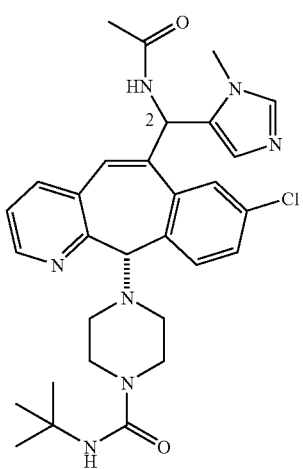
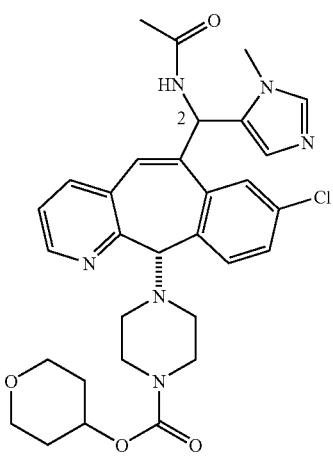
136
-continued
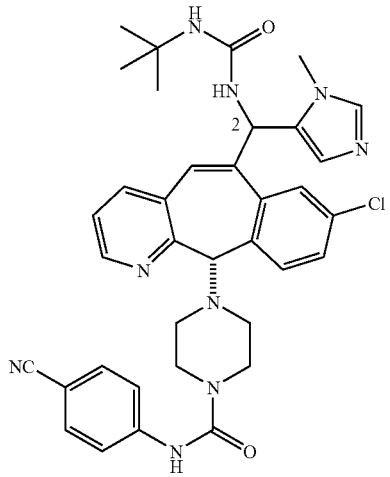
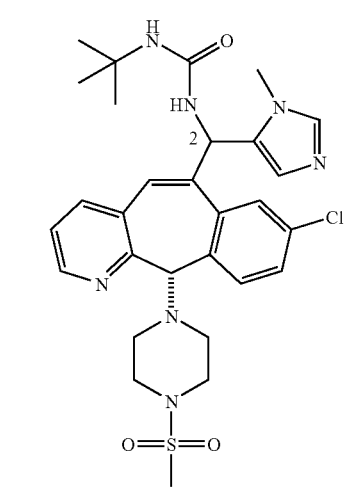
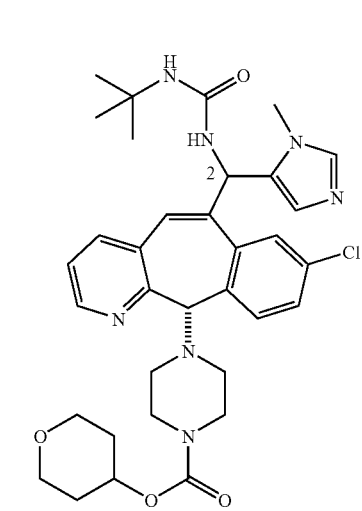

137
-continued
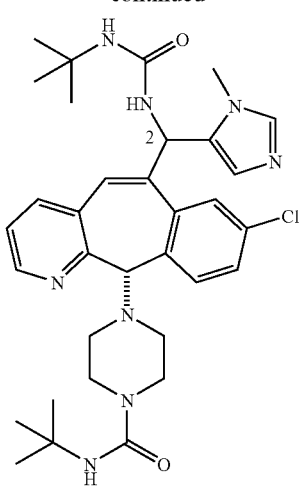
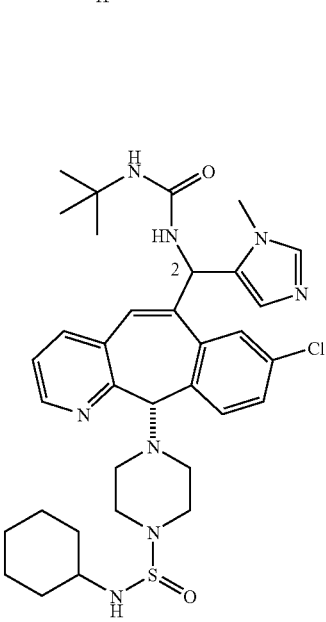
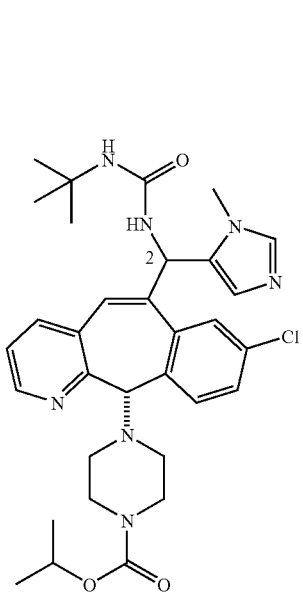
138
-continued
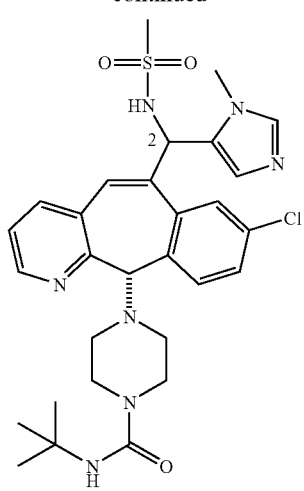
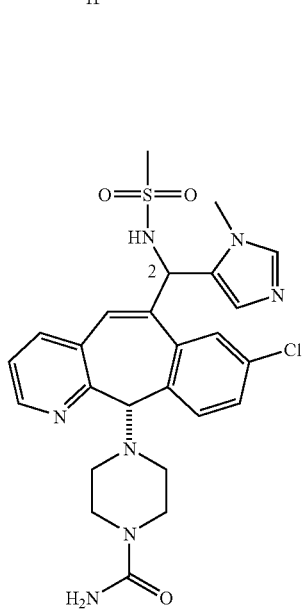
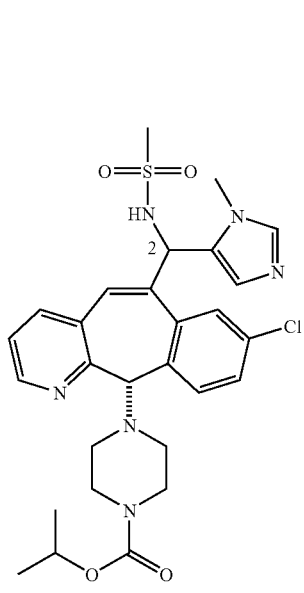

-continued
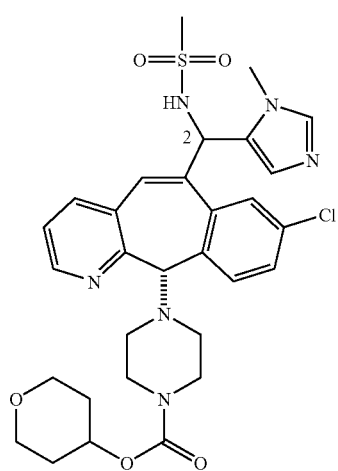
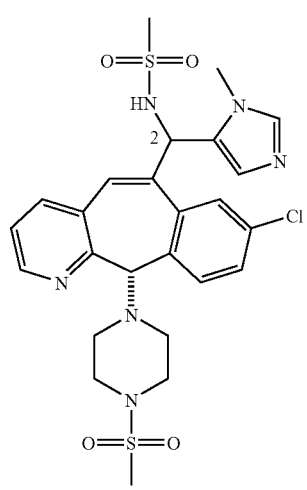
and
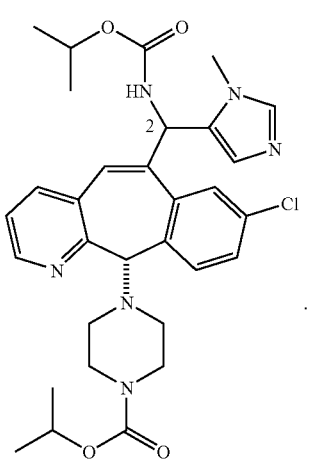
More preferred compounds of the invention are:
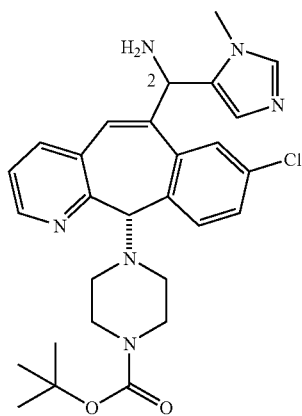
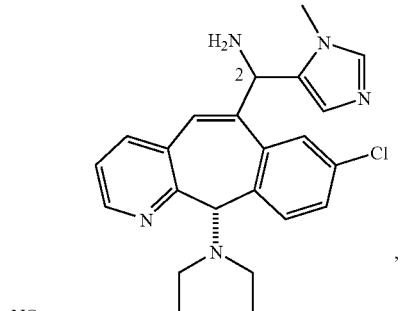
,
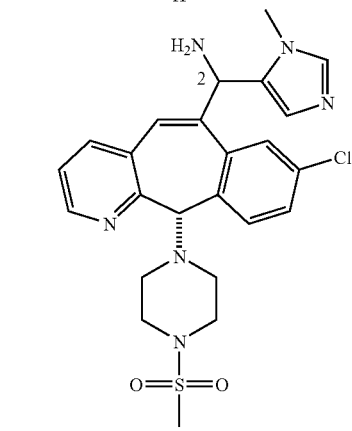
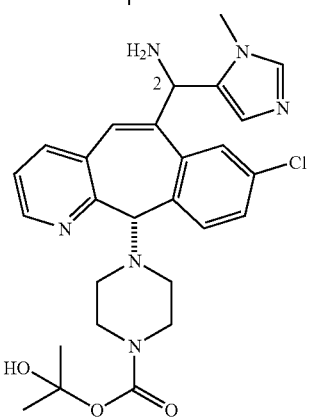

141
-continued
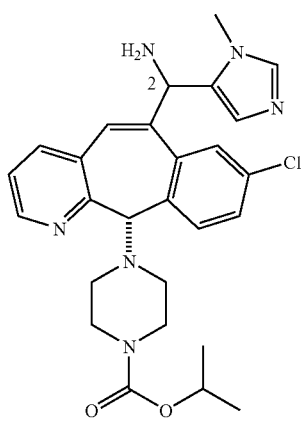
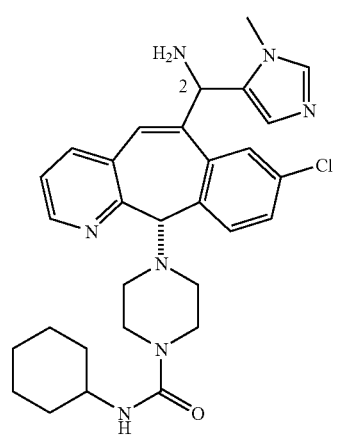
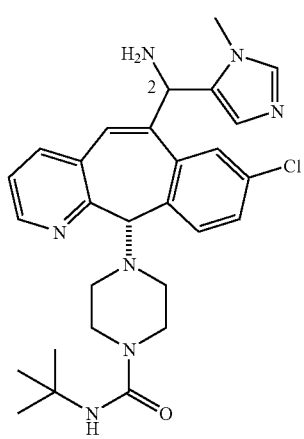
142
-continued
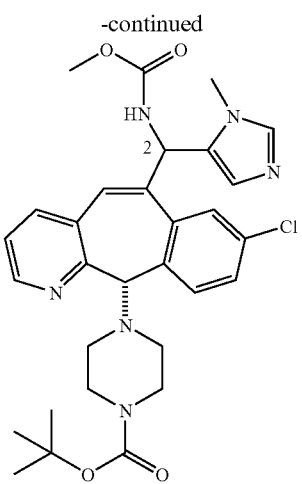
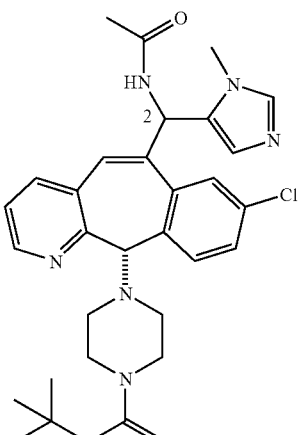
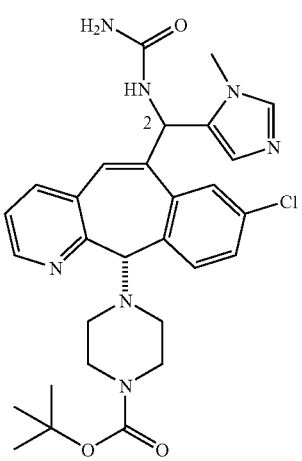

143
-continued
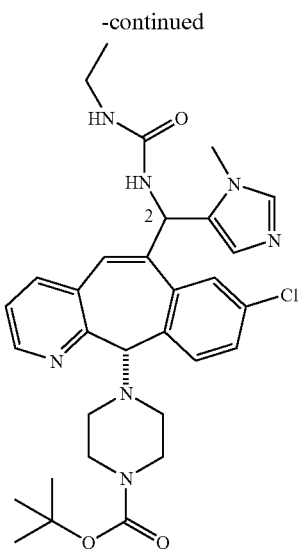
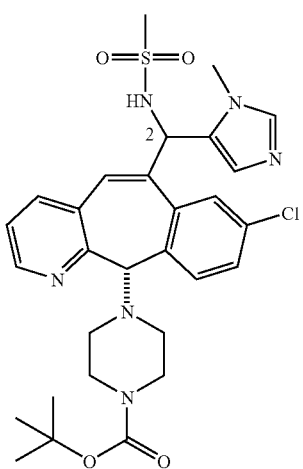
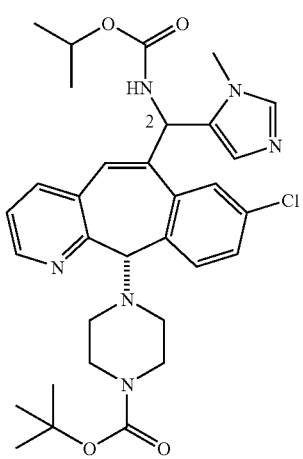
144
-continued
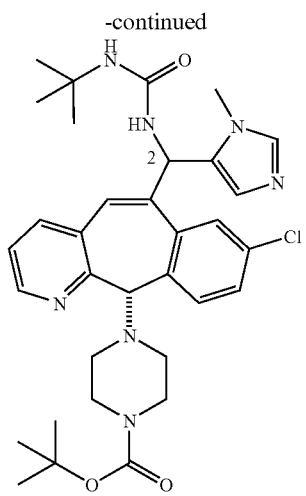
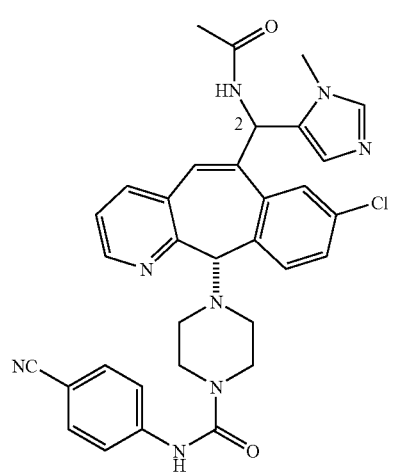
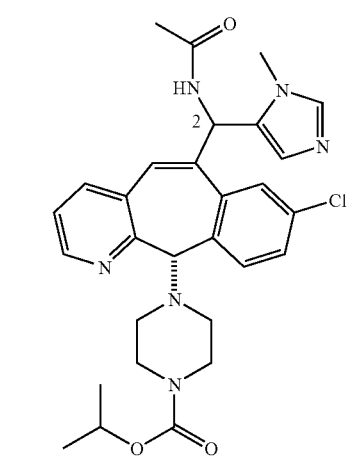

145
-continued
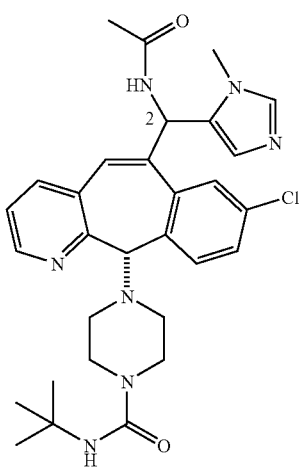
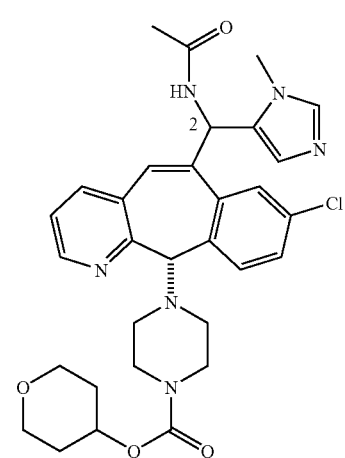
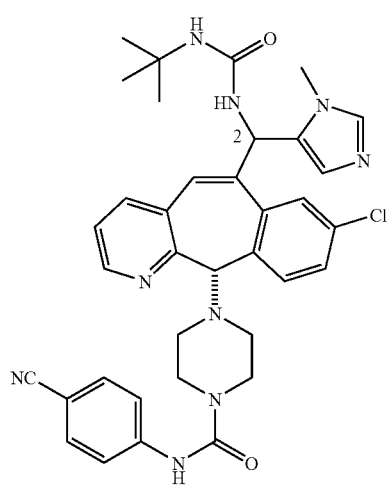
146
-continued
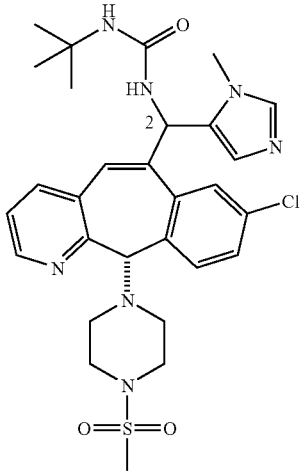
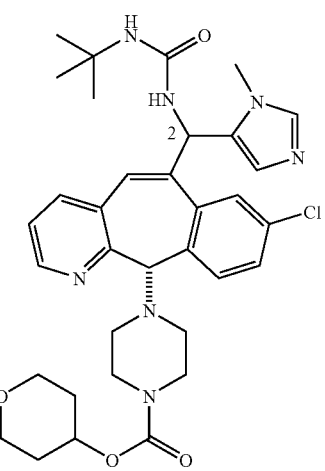
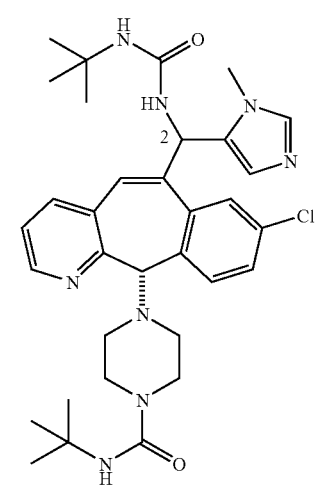

147
-continued
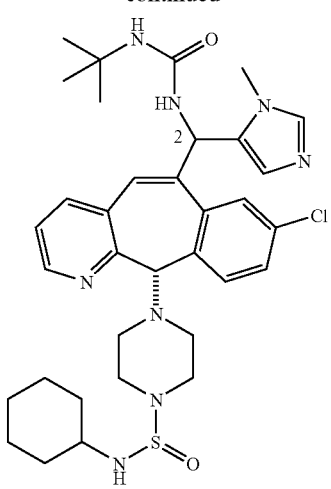
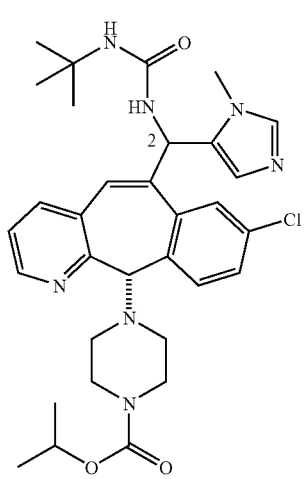
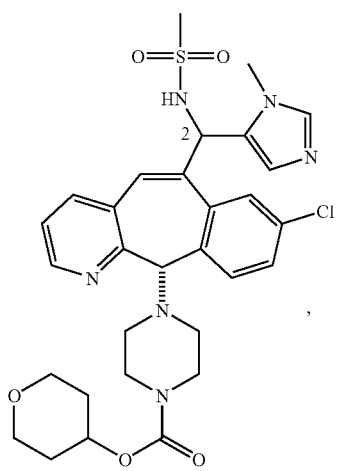
148
-continued
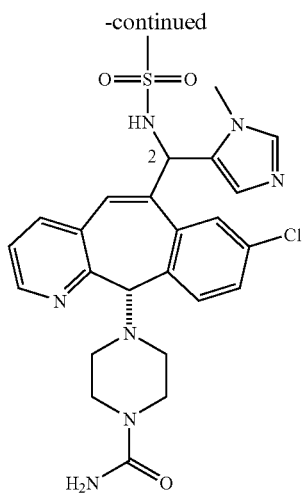
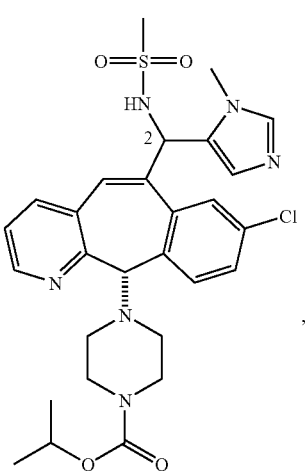
, -continued
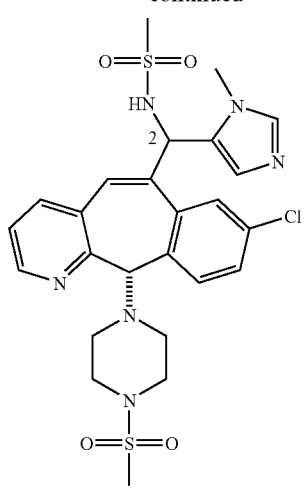
, and
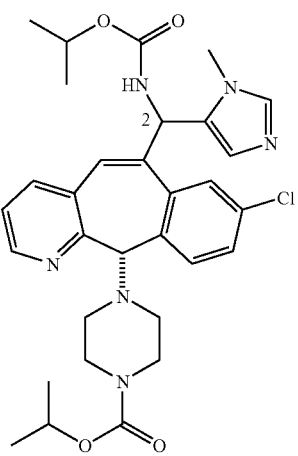
Most preferred compounds of the invention are:
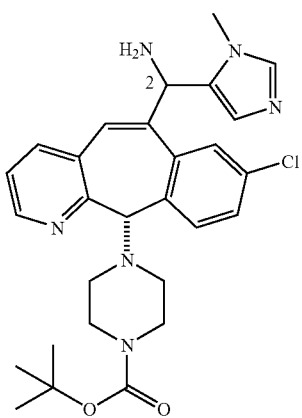
-continued
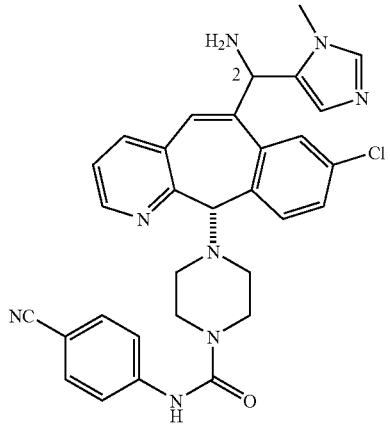
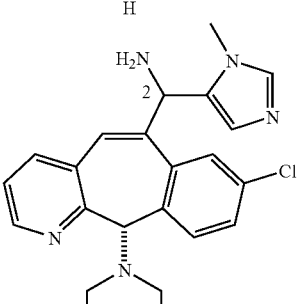
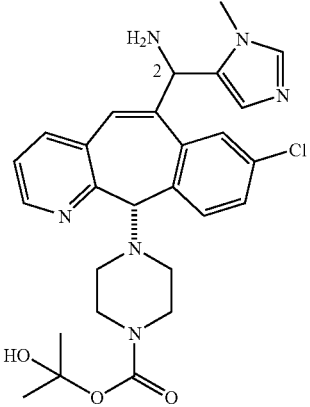
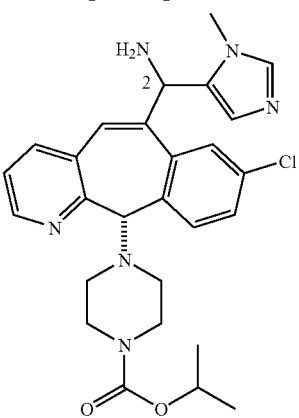

151
-continued
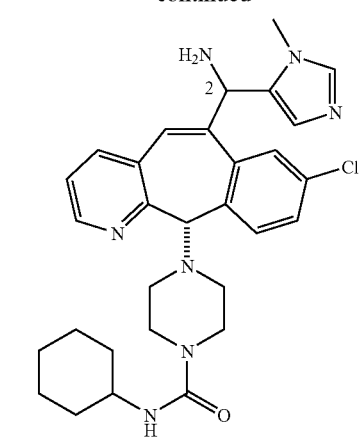
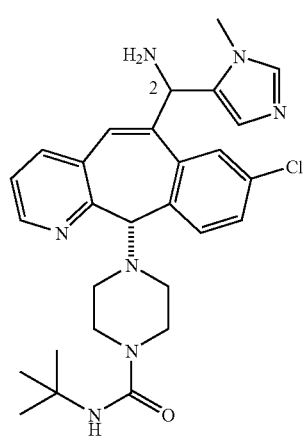
and
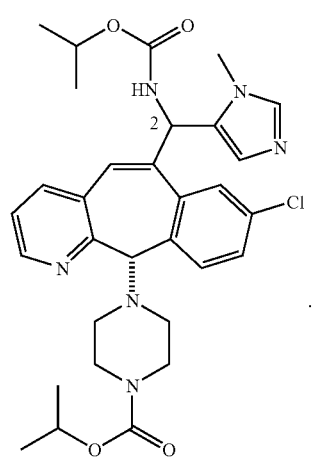
152
Compounds of the formula:
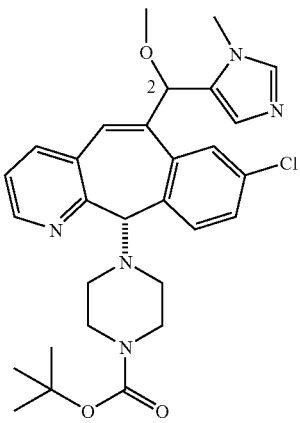
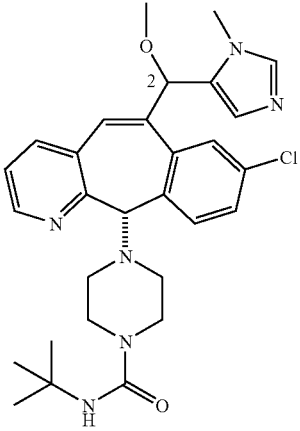
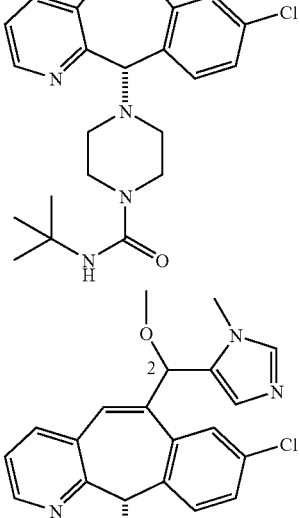

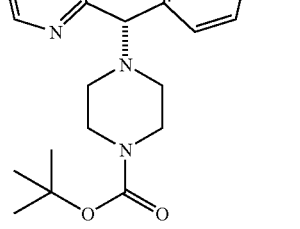

153
-continued
154
-continued
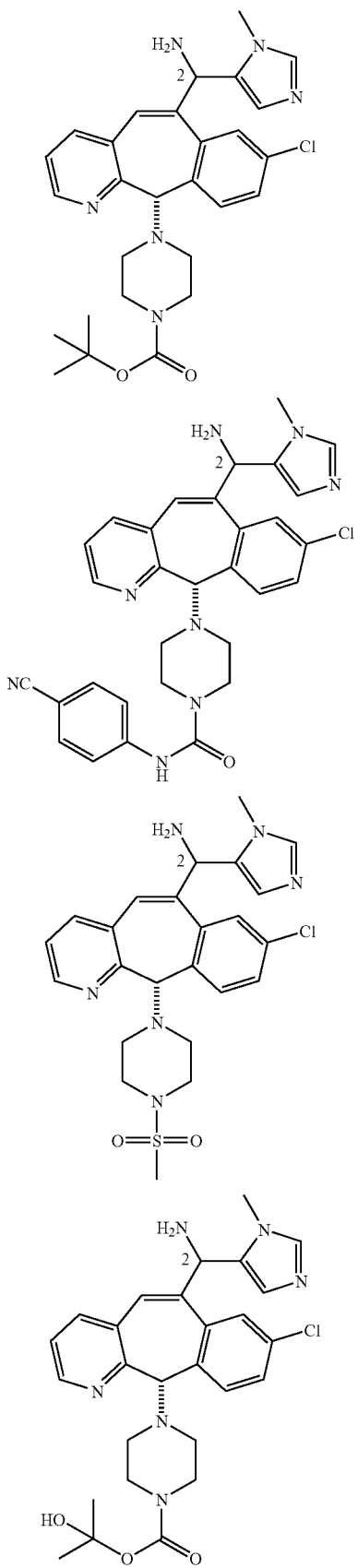
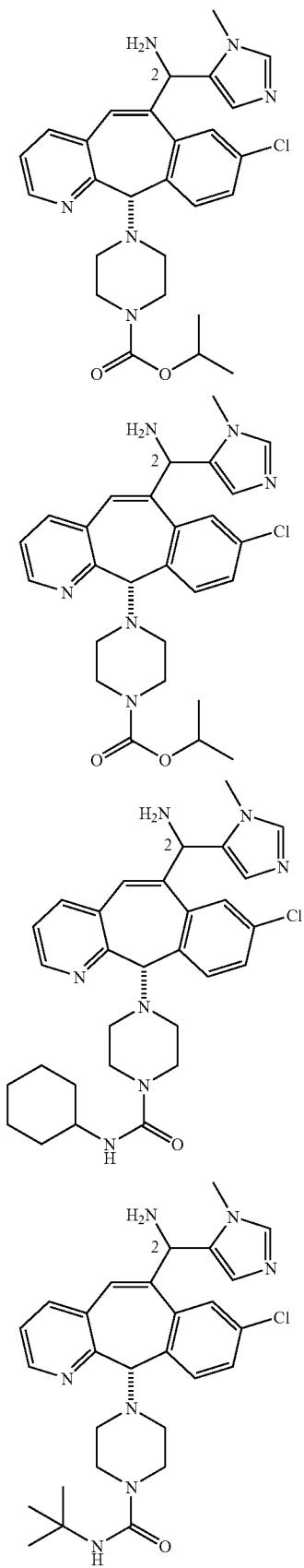

155
-continued
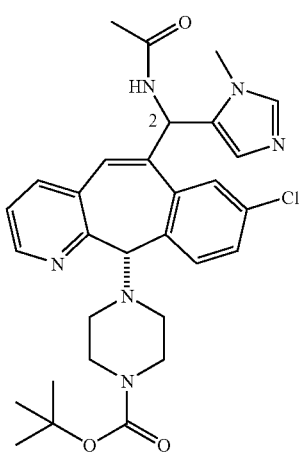
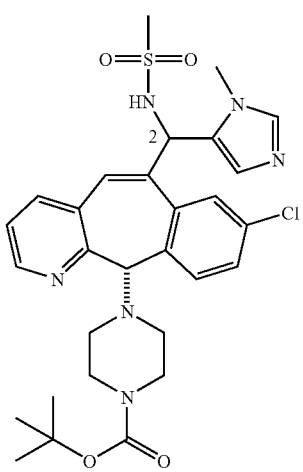
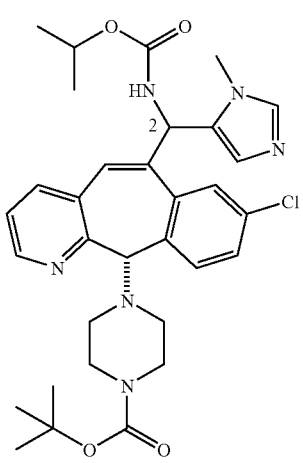
156
-continued
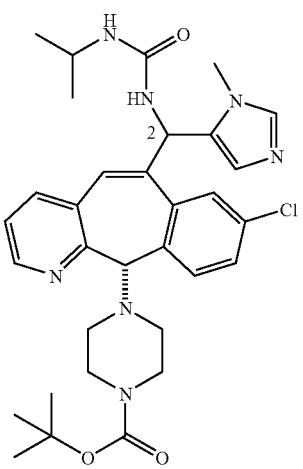
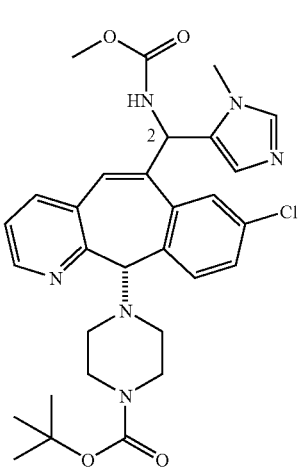
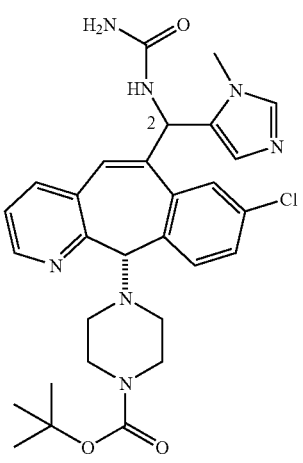

-continued
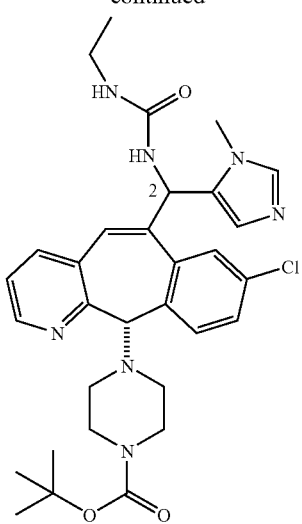
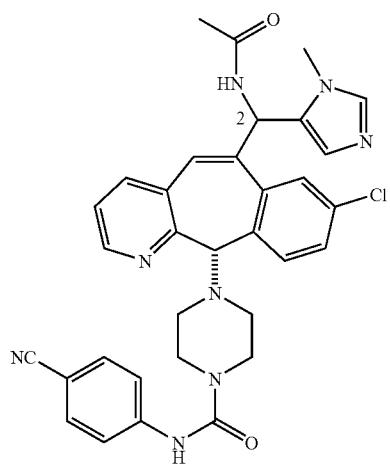
-continued
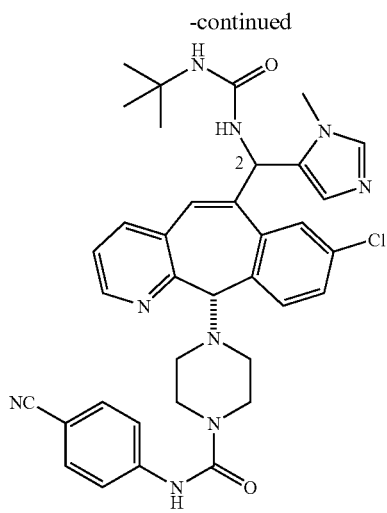
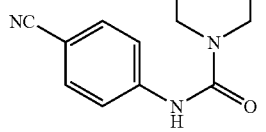 and
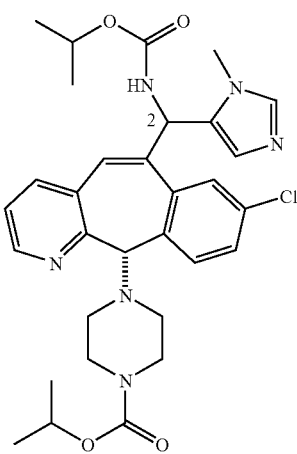
had an FPT IC$_{50}$ within the range of <0.5 nM to 7.9 nM, and a Soft Agar IC$_{50}$ within the range of <0.5 nM to 18 nM.
Compounds of the formula:
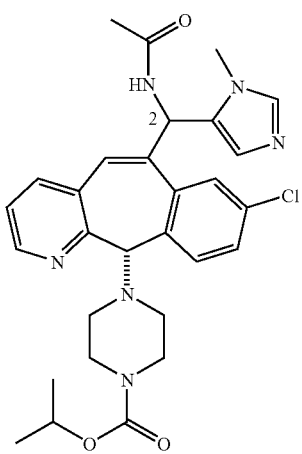
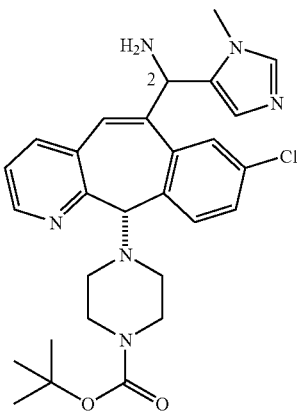

-continued
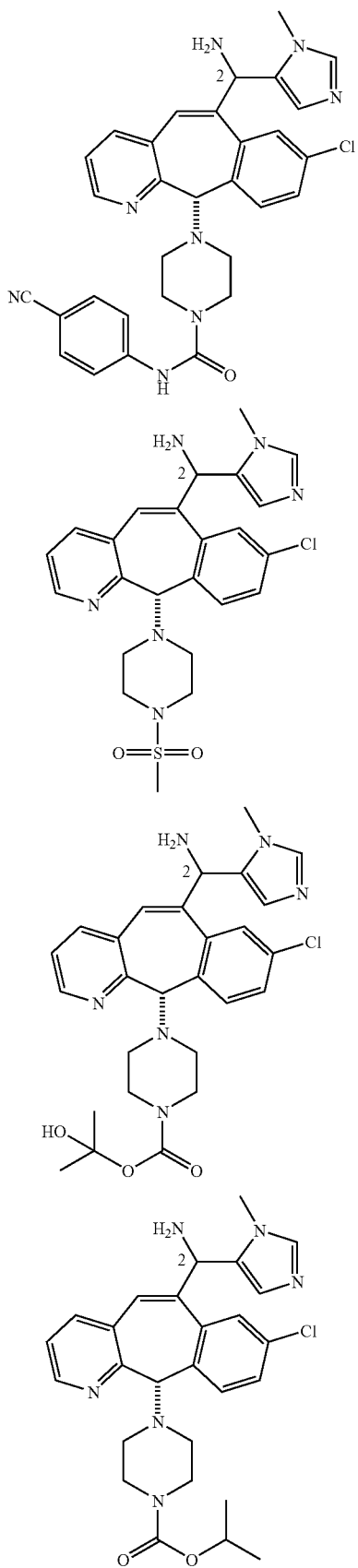
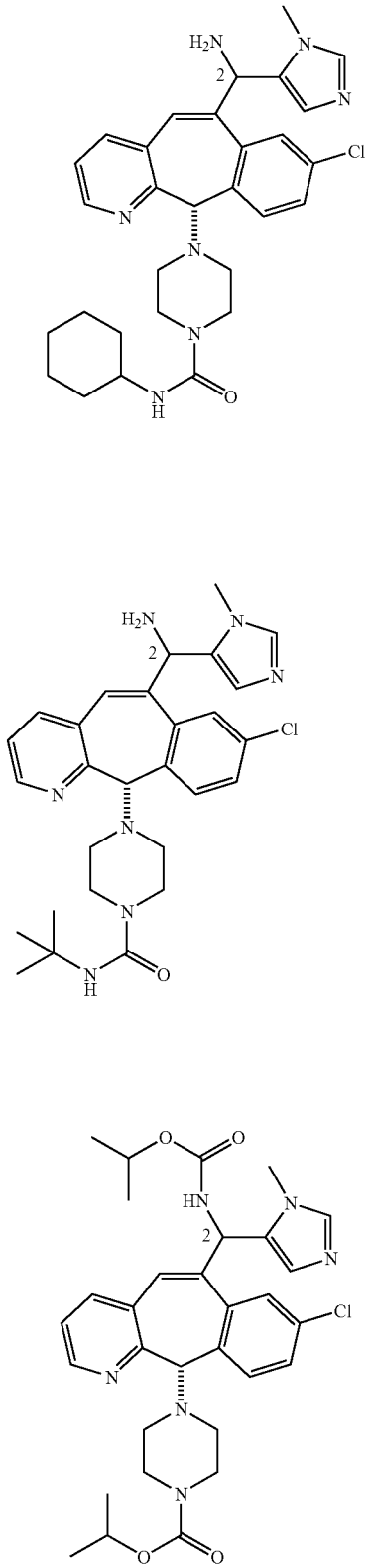
had an FPT IC$_{50}$ within the range of 0.18 nM to 1.2 nM, and a Soft Agar IC$_{50}$ within the range of <0.5 nM to 1 nM.
Another embodiment of this invention is directed to compounds selected from the group consisting of:

161
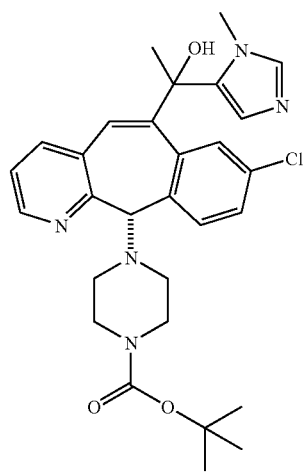
888a
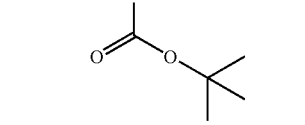
888b
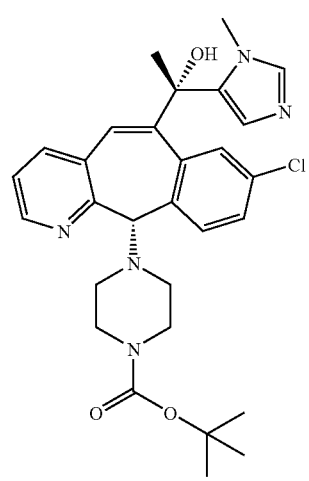
162
795.1
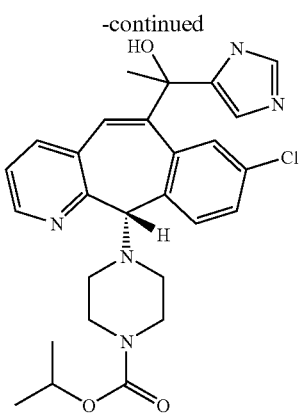
-continued
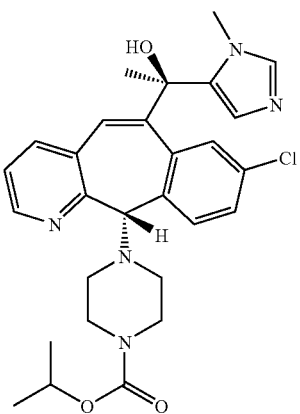
and
Another embodiment of this invention is directed to compounds selected from the group consisting of:

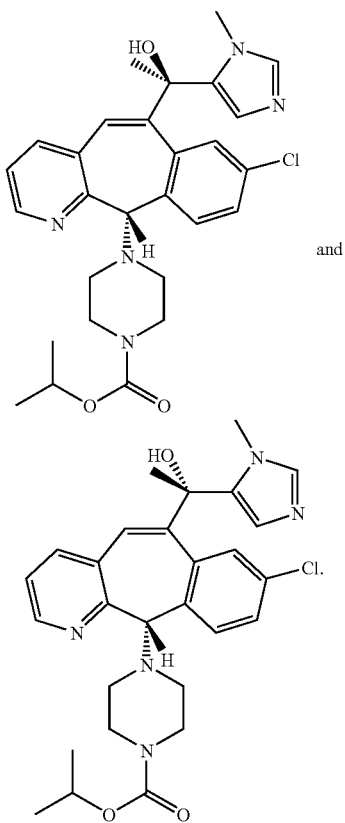

and

Lines drawn into the ring systems indicate that the indicated bond may be attached to any of the substitutable ring carbon atoms.

Certain compounds of the invention may exist in different isomeric (e.g., enantiomers, diastereoisomers, atropisomers) forms. The invention contemplates all such isomers both in pure form and in admixture, including racemic mixtures. Enol forms are also included.

Certain tricyclic compounds will be acidic in nature, e.g. those compounds which possess a carboxyl or phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic tricyclic compounds also form pharmaceutically acceptable salts, e.g., acid addition salts. For example, the pyrido-nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous NaOH, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purposes of the invention.

The compounds of formula 1.0 can exist in unsolvated as well as solvated forms, including hydrated forms, e.g., hemi-hydrate. In general, the solvated forms, with pharmaceutically acceptable solvents such as water, ethanol and the like are equivalent to the unsolvated forms for purposes of the invention.

The compounds of this invention: (i) potently inhibit farnesyl protein transferase, but not geranylgeranyl protein transferase I, in vitro; (ii) block the phenotypic change induced by a form of transforming Ras which is a farnesyl acceptor but not by a form of transforming Ras engineered to be a geranylgeranyl acceptor; (iii) block intracellular processing of Ras which is a farnesyl acceptor but not of Ras engineered to be a geranylgeranyl acceptor; and (iv) block abnormal cell growth in culture induced by transforming Ras.

The compounds of this invention inhibit farnesyl protein transferase and the farnesylation of the oncogene protein Ras. Thus, this invention further provides a method of inhibiting farnesyl protein transferase, (e.g., ras farnesyl protein transferase) in mammals, especially humans, by the administration of an effective amount (e.g., a therapeutically effective amount) of one or more (e.g., one) compounds of this invention. The administration of the compounds of this invention to patients, to inhibit farnesyl protein transferase, is useful in the treatment of the cancers described below.

This invention provides a method for inhibiting or treating the abnormal growth of cells, including transformed cells, by administering an effective amount (e.g., a therapeutically effective amount) of one or more (e.g., one) compounds of this invention. Abnormal growth of cells refers to cell growth independent of normal regulatory mechanisms (e.g., loss of contact inhibition). This includes the abnormal growth of: (1) tumor cells (tumors) expressing an activated Ras oncogene; (2) tumor cells in which the Ras protein is activated as a result of oncogenic mutation in another gene; and (3) benign and malignant cells of other proliferative diseases in which aberrant Ras activation occurs.

This invention also provides a method for inhibiting or treating tumor (i.e., cancer) growth by administering an effective amount (e.g., a therapeutically effective amount) of one or more (e.g., one) compounds of this invention to a mammal (e.g., a human) in need of such treatment. In particular, this invention provides a method for inhibiting or treating the growth of tumors expressing an activated Ras oncogene by the administration of an effective amount (e.g., a therapeutically effective amount) of the above described compounds.

The present invention also provides a method of treating proliferative diseases, especially cancers (i.e, tumors), comprising administering an effective amount (e.g., a therapeutically effective amount) of one or more (e.g., one) compounds of the invention, described herein, to a mammal (e.g., a human) in need of such treatment in combination with an effective amount of at least one anti-cancer agent (i.e., a chemotherapeutic agent) and/or radiation.

The present invention also provides a method of treating proliferative diseases, especially cancers (i.e., tumors), comprising administering an effective amount (e.g., a therapeutically effective amount) of one or more (e.g., one) compounds of the invention to a mammal (e.g., a human) in need of such treatment in combination with an effective amount of at least one signal transduction inhibitor.

Examples of proliferative diseases (tumors, i.e., cancers) which may be inhibited or treated include, but are not limited to:
- (A) lung cancer (e.g., lung adenocarcinoma and non small cell lung cancer);
- (B) pancreatic cancers (e.g., pancreatic carcinoma such as, for example, exocrine pancreatic carcinoma);
- (C) colon cancers (e.g., colorectal carcinomas, such as, for example, colon adenocarcinoma and colon adenoma);
- (D) myeloid leukemias (for example, acute myelogenous leukemia (AML), CML, and CMML);
- (E) thyroid follicular cancer;
- (F) myelodysplastic syndrome (MDS);
- (G) bladder carcinoma;
- (H) epidermal carcinoma;
- (I) melanoma;
- (J) breast cancer;
- (K) prostate cancer;
- (L) head and neck cancers (e.g., squamous cell cancer of the head and neck);
- (M) ovarian cancer;
- (N) gliomas;
- (O) cancers of mesenchymal origin (e.g., fibrosarcomas and rhabdomyosarcomas);
- (P) sarcomas;
- (Q) tetracarcinomas;
- (R) nuroblastomas;
- (S) kidney carcinomas;
- (T) hepatomas;
- (U) non-Hodgkin's lymphoma;
- (V) multiple myeloma; and
- (W) anaplastic thyroid carcinoma.

For example, embodiments of this invention include methods of treating cancer wherein said cancer is selected from the group consisting of: pancreatic cancers, lung cancers, myeloid leukemias, thyroid follicular tumors, myelodysplastic syndrome, head and neck cancers, melanomas, breast cancers, prostate cancers, ovarian cancers, bladder cancers, gliomas, epidermal cancers, colon cancers, non-Hodgkin's lymphomas, and multiple myelomas comprising administering to said patient an effective amount of a compound of claim 1

Also for example, embodiments of this invention include methods of treating cancer wherein said cancers are selected from the group consisting of: lung cancer (e.g., non-small cell lung cancer), head and neck cancer (e.g., squamous cell cancer of the head and neck), bladder cancer, breast cancer, prostate cancer, and myeloid leukemias (e.g., CML and AML), non-Hodgkin's lymphoma and multiple myeloma.

This invention also provides a method of treating cancer in a patient in need of such treatment comprising administering a therapeutically effective amount of one or more (e.g., one) compounds of the invention and therapeutically effective amounts of at least two different antineoplastic agents selected from: (1) taxanes, (2) platinum coordinator compounds, (3) epidermal growth factor (EGF) inhibitors that are antibodies, (4) EGF inhibitors that are small molecules, (5) vascular endolithial growth factor (VEGF) inhibitors that are antibodies, (6) VEGF kinase inhibitors that are small molecules, (7) estrogen receptor antagonists or selective estrogen receptor modulators (SERMs), (8) anti-tumor nucleoside derivatives, (9) epothilones, (10) topoisomerase inhibitors, (11) vinca alkaloids, (12) antibodies that are inhibitors of αvβ3 integrins, (13) small molecules that are inhibitors of αvβ3 integrins, (14) folate antagonists, (15) ribonucleotide reductase inhibitors, (16) anthracyclines, (17) biologics; (18) thalidomide (or related imid), and (19) Gleevec.

This invention also provides a method of treating cancer in a patient in need of such treatment comprising administering therapeutically effective amounts of one or more (e.g., one) compounds of the invention and an antineoplastic agent selected from: (1) EGF inhibitors that are antibodies, (2) EGF inhibitors that are small molecules, (3) VEGF inhibitors that are antibodies, and (4) VEGF inhibitors that are small molecules. Radiation therapy can also be used in conjunction with the above combination therapy, i.e., the above method using a combination of compounds of the invention and antineoplastic agent can also comprise the administration of a therapeutically effect amount of radiation.

This invention also provides a method of treating leukemias (e.g., acute myeloid leukemia (AML), and chronic myeloid leukemia (CML)) in a patient in need of such treatment comprising administering therapeutically effective amounts of one or more (e.g., one) compounds of the invention and: (1) Gleevec and interferon to treat CML; (2) Gleevec and pegylated interferon to treat CML; (3) an anti-tumor nucleoside derivative (e.g., Ara-C) to treat AML; or (4) an anti-tumor nucleoside derivative (e.g., Ara-C) in combination with an anthracycline to treat AML.

This invention also provides a method of treating non-Hodgkin's lymphoma in a patient in need of such treatment comprising administering therapeutically effective amounts of one or more (e.g., one) compounds of the invention and: (1) a biologic (e.g., Rituxan); (2) a biologic (e.g., Rituxan) and an anti-tumor nucleoside derivative (e.g., Fludarabine); or (3) Genasense (antisense to BCL-2).

This invention also provides a method of treating multiple myeloma in a patient in need of such treatment comprising administering therapeutically effective amounts of one or more (e.g., one) compounds of the invention and: (1) a proteosome inhibitor (e.g., PS-341 from Millenium); or (2) Thalidomide (or related imid).

This invention also provides a method of treating cancer comprising administering to a patient in need of such treatment therapeutically effective amounts of:
- (a) an FPT inhibitor of formula 1.0;
- (b) at least two different antineoplastic agents selected from the group consisting of:
  - (1) taxanes;
  - (2) platinum coordinator compounds;
  - (3) EGF inhibitors that are antibodies;
  - (4) EGF inhibitors that are small molecules;
  - (5) VEGF inhibitors that are antibodies;
  - (6) VEGF kinase inhibitors that are small molecules;
  - (7) estrogen receptor antagonists or selective estrogen receptor modulators;
  - (8) anti-tumor nucleoside derivatives;
  - (9) epothilones;
  - (10) topoisomerase inhibitors;
  - (11) vinca alkaloids;
  - (12) antibodies that are inhibitors of αVβ3 integrins;
  - (13) small molecule inhibitors of αVβ3 integrins
  - (14) folate antagonists;
  - (15) ribonucleotide reductase inhibitors;
  - (16) anthracyclines;
  - (17) biologics;
  - (18) Thalidomide (or related Imid); and
  - (19) Gleevec.

This invention also provides a method of treating cancer comprising administering to a patient in need of such treatment therapeutically effective amounts of:
(a) an FPT inhibitor of formula 1.0;
(b) at least two different antineoplastic agents selected from the group consisting of
    (1) taxanes;
    (2) platinum coordinator compounds;
    (3) EGF inhibitors that are antibodies;
    (4) EGF inhibitors that are small molecules;
    (5) VEGF inhibitors that are antibodies;
    (6) VEGF kinase inhibitors that are small molecules;
    (7) estrogen receptor antagonists or selective estrogen receptor modulators;
    (8) antitumor nucleoside derivatives;
    (9) epothilones;
    (10) topoisomerase inhibitors;
    (11) vinca alkaloids;
    (12) antibodies that are inhibitors of αVβ3 integrins; or
    (13) small molecule inhibitors of αvβ3 integrins
    (14) folate antagonists;
    (15) ribonucleotide reductase inhibitors;
    (16) anthracyclines;
    (17) biologics; and
    (18) Thalidomide (or related Imid).

This invention also provides a method of treating cancer comprising administering to a patient in need of such treatment therapeutically effective amounts of:
(a) an FPT inhibitor of formula 1.0;
(b) at least two different antineoplastic agents selected from the group consisting of:
    (1) taxanes;
    (2) platinum coordinator compounds;
    (3) EGF inhibitors that are antibodies;
    (4) EGF inhibitors that are small molecules;
    (5) VEGF inhibitors that are antibodies;
    (6) VEGF kinase inhibitors that are small molecules;
    (7) estrogen receptor antagonists or selective estrogen receptor modulators;
    (8) anti-tumor nucleoside derivatives;
    (9) epothilones;
    (10) topoisomerase inhibitors;
    (11) vinca alkaloids;
    (12) antibodies that are inhibitors of αVβ3 integrins; or
    (13) small molecule inhibitors of αVβ3 integrins
    (14) folate antagonists;
    (15) ribonucleotide reductase inhibitors;
    (16) anthracyclines; and
    (17) biologics.

This invention also provides a method of treating cancer comprising administering to a patient in need of such treatment therapeutically effective amounts of:
(a) an FPT inhibitor of formula 1.0;
(b) at least two different antineoplastic agents selected from the group consisting of:
    (1) taxanes;
    (2) platinum coordinator compounds;
    (3) EGF inhibitors that are antibodies;
    (4) EGF inhibitors that are small molecules;
    (5) VEGF inhibitors that are antibodies;
    (6) VEGF kinase inhibitors that are small molecules;
    (7) estrogen receptor antagonists or selective estrogen receptor modulators;
    (8) anti-tumor nucleoside derivatives;
    (9) epothilones;
    (10) topoisomerase inhibitors;
    (11) vinca alkaloids;
    (12) antibodies that are inhibitors of αVβ3 integrins; and
    (13) small molecule inhibitors of αVβ3 integrins.

This invention also provides a method of treating non small cell lung cancer comprising administering to a patient in need of such treatment therapeutically effective amounts of:
(a) an FPT inhibitor of formula 1.0;
(b) at least two different antineoplastic agents selected from the group consisting of:
    (1) taxanes;
    (2) platinum coordinator compounds;
    (3) EGF inhibitors that are antibodies;
    (4) EGF inhibitors that are small molecules;
    (5) VEGF inhibitors that are antibodies;
    (6) VEGF kinase inhibitors that are small molecules;
    (7) estrogen receptor antagonists or selective estrogen receptor modulators;
    (8) anti-tumor nucleoside derivatives;
    (9) epothilones;
    (10) topoisomerase inhibitors;
    (11) vinca alkaloids;
    (12) antibodies that are inhibitors of αVβ3 integrins; and
    (13) small molecule inhibitors of αVβ3 integrins.

This invention also provides a method of treating non small cell lung cancer comprising administering to a patient in need of such treatment therapeutically effective amounts of:
(a) an FPT inhibitor of formula 1.0;
(b) at least two different antineoplastic agents selected from the group consisting of:
    (1) taxanes;
    (2) platinum coordinator compounds;
    (3) anti-tumor nucleoside derivatives;
    (4) topoisomerase inhibitors; and
    (5) vinca alkaloids.

This invention also provides a method of treating non small cell lung cancer in a patient in need of such treatment comprising administering therapeutically effective amounts of:
(a) an FPT inhibitor of formula 1.0;
(b) carboplatin; and
(c) paclitaxel.

This invention also provides a method of treating non small cell lung cancer in a patient in need of such treatment comprising administering therapeutically effective amounts of:
(a) an FPT inhibitor of formula 1.0;
(b) cisplatin; and
(c) gemcitabine.

This invention also provides a method of treating non small cell lung cancer in a patient in need of such treatment comprising administering therapeutically effective amounts of:
(a) an FPT inhibitor of formula 1.0;
(b) carboplatin; and
(c) gemcitabine.

This invention also provides a method of treating non small cell lung cancer in a patient in need of such treatment comprising administering therapeutically effective amounts of:
(a) an FPT inhibitor of formula 1.0;
(b) Carboplatin; and
(c) Docetaxel.

This invention also provides a method of treating cancer in a patient in need of such treatment comprising administering therapeutically effective amounts of:
(a) an FPT inhibitor of formula 1.0;
(b) an antineoplastic agent selected from the group consisting of:
(1) EGF inhibitors that are antibodies;
(2) EGF inhibitors that are small molecules;
(3) VEGF inhibitors that are antibodies; and
(4) VEGF kinase inhibitors that are small molecules.

This invention also provides a method of treating squamous cell cancer of the head and neck, in a patient in need of such treatment comprising administering therapeutically effective amounts of:
(a) an FPT inhibitor of formula 1.0; and
(b) one or more antineoplastic agents selected from the group consisting of:
(1) taxanes; and
(2) platinum coordinator compounds.

This invention also provides a method of treating squamous cell cancer of the head and neck, in a patient in need of such treatment comprising administering therapeutically effective amounts of:
(a) an FPT inhibitor of formula 1.0;
(b) at least two different antineoplastic agents selected from the group consisting of:
(1) taxanes:
(2) platinum coordinator compounds; and
(3) anti-tumor nucleoside derivatives (e.g., 5-Fluorouracil).

This invention also provides a method of treating CML in a patient in need of such treatment comprising administering therapeutically effective amounts of:
(a) an FPT inhibitor of formula 1.0;
(b) Gleevec; and
(c) interferon (e.g., Intron-A).

This invention also provides a method of treating CML in a patient in need of such treatment comprising administering therapeutically effective amounts of:
(a) an FPT inhibitor of formula 1.0;
(b) Gleevec; and
(c) pegylated interferon (e.g., Peg-Intron, and Pegasys).

This invention also provides a method of treating AML in a patient in need of such treatment comprising administering therapeutically effective amounts of:
(a) an FPT inhibitor of formula 1.0;
(b) an anti-tumor nucleoside derivative (e.g., Cytarabine (i.e., Ara-C)).

This invention also provides a method of treating AML in a patient in need of such treatment comprising administering therapeutically effective amounts of:
(a) an FPT inhibitor of formula 1.0;
(b) an anti-tumor nucleoside derivative (e.g., Cytarabine (i.e., Ara-C)); and
(c) an anthracycline.

This invention also provides a method of treating non-Hodgkin's lymphoma in a patient in need of such treatment comprising administering therapeutically effective amounts of:
(a) an FPT inhibitor of formula 1.0;
(b) Rituximab (Rituxan).

This invention also provides a method of treating non-Hodgkin's lymphoma in a patient in need of such treatment comprising administering therapeutically effective amounts of:
(a) an FPT inhibitor of formula 1.0;
(b) Rituximab (Rituxan); and
(c) an anti-tumor nucleoside derivative (e.g., Fludarabine (i.e., F-ara-A).

This invention also provides a method of treating non-Hodgkin's lymphoma in a patient in need of such treatment comprising administering therapeutically effective amounts of:
(a) an FPT inhibitor of formula 1.0;
(b) Genasense (antisense to BCL-2).

This invention also provides a method of treating multiple myeloma in a patient in need of such treatment comprising administering therapeutically effective amounts of:
(a) an FPT inhibitor of formula 1.0;
(b) a proteosome inhibitor (e.g., PS-341 (Millenium)).

This invention also provides a method of treating multiple myeloma in a patient in need of such treatment comprising administering therapeutically effective amounts of:
(a) an FPT inhibitor of formula 1.0;
(b) Thalidomide or related imid.

This invention also provides a method of treating multiple myeloma in a patient in need of such treatment comprising administering therapeutically effective amounts of:
(a) an FPT inhibitor of formula 1.0;
(b) Thalidomide.

This invention is also directed to the methods of treating cancer described herein, particularly those described above, wherein in addition to the administration of the FPT inhibitor and antineoplastic agents radiation therapy is also administered prior to, during, or after the treatment cycle.

It is believed that this invention also provides a method for inhibiting or treating proliferative diseases, both benign and malignant, wherein Ras proteins are aberrantly activated as a result of oncogenic mutation in other genes—i.e., the Ras gene itself is not activated by mutation to an oncogenic form—with said inhibition or treatment being accomplished by the administration of an effective amount (e.g. a therapeutically effective amount) of one or more (e.g., one) compounds of the invention to a mammal (e.g., a human) in need of such treatment. For example, the benign proliferative disorder neurofibromatosis, or tumors in which Ras is activated due to mutation or overexpression of tyrosine kinase oncogenes (e.g., neu, src, abl, lck, and fyn), may be inhibited or treated by the tricyclic compounds described herein.

The compounds of the invention useful in the methods of this invention inhibit or treat the abnormal growth of cells. Without wishing to be bound by theory, it is believed that these compounds may function through the inhibition of G-protein function, such as Ras p21, by blocking G-protein isoprenylation, thus making them useful in the treatment of proliferative diseases such as tumor growth and cancer. Without wishing to be bound by theory, it is believed that these compounds inhibit ras farnesyl protein transferase, and thus show antiproliferative activity against ras transformed cells.

The method of treating proliferative diseases (cancers, i.e., tumors), according to this invention, includes a method for treating (inhibiting) the abnormal growth of cells, including transformed cells, in a, by administering, concurrently or sequentially, an effective amount of a compound of this invention and an effective amount of a chemotherapeutic agent and/or radiation.

In preferred embodiments, the methods of the present invention include methods for treating or inhibiting tumor growth in a patient in need of such treatment by administering, concurrently or sequentially, (1) an effective amount of a compound of this invention and (2) an effective amount of at least one antineoplastic agent, microtubule affecting agent and/or radiation therapy. For example, one embodiment of these methods is directed to a method of treating cancers selected from the group consisting of: lung cancer, prostate cancer and myeloid leukemias.

The methods of treating proliferative diseases, according to this invention, also include a method for treating (inhibiting) proliferative diseases, both benign and malignant, wherein ras proteins are aberrantly activated as a result of oncogenic mutation in other genes—i.e., the ras gene itself is not activated by mutation to an oncogenic form. This method comprises administering, concurrently or sequentially, an effective amount of a compound of this invention and an effective amount of an antineoplastic agent and/or radiation therapy to a patient in need of such treatment. Examples of such proliferative diseases which may be treated include: the benign proliferative disorder neurofibromatosis, or tumors in which ras is activated due to mutation or overexpression of tyrosine kinase oncogenes (e.g., neu, src, abl, lck, lyn, fyn).

For radiation therapy, γ-radiation is preferred.

The methods of treating proliferative diseases (cancers, i.e., tumors), according to this invention, also include a method for treating (inhibiting) the abnormal growth of cells, including transformed cells, in a patient in need of such treatment, by administering, concurrently or sequentially, an effective amount of a compound of this invention and an effective amount of at least one signal transduction inhibitor.

Typical signal transduction inhibitors include but are not limited to:
(i) Bcr/abl kinase inhibitors such as, for example, STI 571 (Gleevec);
(ii) Epidermal growth factor (EGF) receptor inhibitor such as, for example, Kinase inhibitors (Iressa, OSI-774) and antibodies (Imclone: C225 [Goldstein et al. (1995), Clin Cancer Res. 1:1311-1318], and Abgenix: ABX-EGF) and
(iii) HER-2/neu receptor inhibitors such as, for example, Herceptin® (trastuzumab).

Embodiments of the methods of treatment of this invention are directed to the use of a combination of drugs (compounds) for the treatment of cancer, i.e., this invention is directed to a combination therapy for the treatment of cancer. Those skilled in the art will appreciate that the drugs are generally administered individually as a pharmaceutical composition. The use of a pharmaceutical composition comprising more than one drug is within the scope of this invention.

The antineoplastic agents are usually administered in the dosage forms that are readily available to the skilled clinician, and are generally administered in their normally prescribed amounts (as for example, the amounts described in the Physician's Desk Reference, 56$^{th}$ Edition, 2002 (published by Medical Economics company, Inc. Montvale, N. J. 07645-1742 the disclosure of which is incorporated herein by reference thereto), or the amounts described in the manufacture's literature for the use of the agent).

For example, the FPT inhibitor can be administered orally (e.g., as a capsule), and the antineoplastic agents can be administered intravenously, usually as an IV solution. The use of a pharmaceutical composition comprising more than one drug is within the scope of this invention.

The FPT inhibitor and the antineoplastic agents are administered in therapeutically effective dosages to obtain clinically acceptable results, e.g., reduction or elimination of symptoms or of the tumor. Thus, the FPT inhibitor and antineoplastic agents can be administered concurrently or consecutively in a treatment protocol. The administration of the antineoplastic agents can be made according to treatment protocols already known in the art.

The FPT inhibitor and antineoplastic agents are administered in a treatment protocol that usually lasts one to seven weeks, and is repeated typically from 6 to 12 times. Generally the treatment protocol lasts one to four weeks. Treatment protocols of one to three weeks may also be used. A treatment protocol of one to two weeks may also be used. During this treatment protocol or cycle the FPT inhibitor is administered daily while the antineoplastic agents are administered one or more times a week. Generally, the FPT inhibitor can be administered daily (i.e., once per day), preferably twice per day, and the antineoplastic agent is administered once a week or once every three weeks. For example, the taxanes (e.g., Paclitaxel (e.g., Taxol®) or Docetaxel (e.g., Taxotere®)) can be administered once a week or once every three weeks.

However, those skilled in the art will appreciate that treatment protocols can be varied according to the needs of the patient. Thus, the combination of compounds (drugs) used in the methods of this invention can be administered in variations of the protocols described above. For example, the FPT inhibitor can be administered discontinuously rather than continuously during the treatment cycle. Thus, for example, during the treatment cycle the FPT inhibitor can be administered daily for a week and then discontinued for a week, with this administration repeating during the treatment cycle. Or the FPT inhibitor can be administered daily for two weeks and discontinued for a week, with this administration repeating during the treatment cycle. Thus, the FPT inhibitor can be administered daily for one or more weeks during the cycle and discontinued for one or more weeks during the cycle, with this pattern of administration repeating during the treatment cycle. This discontinuous treatment can also be based upon numbers of days rather than a full week. For example, daily dosing for 1 to 6 days, no dosing for 1 to 6 days with this pattern repeating during the treatment protocol. The number of days (or weeks) wherein the FPT inhibitor is not dosed does not have to equal the number of days (or weeks) wherein the FPT inhibitor is dosed. Usually, if a discontinuous dosing protocol is used, the number of days or weeks that the FPT inhibitor is dosed is at least equal or greater than the number of days or weeks that the FPT inhibitor is not dosed.

The antineoplastic agent could be given by bolus or continuous infusion. The antineoplastic agent could be given daily to once every week, or once every two weeks, or once every three weeks, or once every four weeks during the treatment cycle. If administered daily during a treatment cycle, this daily dosing can be discontinuous over the number of weeks of the treatment cycle. For example, dosed for a week (or a number of days), no dosing for a week (or a number of days, with the pattern repeating during the treatment cycle.

The FPT inhibitor can be administered orally, preferably as a solid dosage form, more preferably a capsule, and while the total therapeutically effective daily dose can be administered in one to four, or one to two divided doses per day, generally, the therapeutically effective dose is given once or twice a day, preferably twice a day. The FPT inhibitor can be administered in an amount of about 50 to about 400 mg once per day, and can be administered in an amount of about 50 to about 300 mg once per day. The FPT inhibitor is generally administered in an amount of about 50 to about 350 mg twice a day, usually 50 mg to about 200 mg twice a day, preferably, about 75 mg to about 125 mg administered twice a day, and most preferably about 100 mg administered twice a day.

If the patient is responding, or is stable, after completion of the therapy cycle, the therapy cycle can be repeated according to the judgment of the skilled clinician. Upon completion of the therapy cycles the patient can be continued on the FPT inhibitor at the same dose that was administered in the treatment protocol, or, if the dose was less than 200 mg twice a day, the dose can be raised to 200 mg twice a day. This maintenance dose can be continued until the patient progresses or can no longer tolerate the dose (in which case the dose can be reduced and the patient can be continued on the reduced dose).

The antineoplastic agents used with the FPT inhibitor are administered in their normally prescribed dosages during the treatment cycle (i.e., the antineoplastic agents are administered according to the standard of practice for the administration of these drugs). For example: (a) about 30 to about 300 mg/m$^2$ for the taxanes; (b) about 30 to about 100 mg/m$^2$ for Cisplatin; (c) AUC of about 2 to about 8 for Carboplatin; (d) about 2 to about 4 mg/m$^2$ for EGF inhibitors that are antibodies; (e) about 50 to about 500 mg/m$^2$ for EGF inhibitors that are small molecules; (f) about 1 to about 10 mg/m$^2$ for VEGF kinase inhibitors that are antibodies; (g) about 50 to about 2400 mg/m$^2$ for VEGF inhibitors that are small molecules; (h) about 1 to about 20 mg for SERMs; (i) about 500 to about 1250 mg/m$^2$ for the anti-tumor nucleosides 5-Fluorouracil, Gemcitabine and Capecitabine; (j) for the anti-tumor nucleoside Cytarabine (Ara-C) 100-200 mg/m$^2$/day for 7 to 10 days every 3 to 4 weeks, and high doses for refractory leukemia and lymphoma, i.e., 1 to 3 gm/m$^2$ for one hour every 12 hours for 4-8 doses every 3 to four weeks; (k) for the anti-tumor nucleoside Fludarabine (F-ara-A) 10-25 mg/m$^2$/day every 3 to 4 weeks; (l) for the anti-tumor nucleoside Decitabine 30 to 75 mg/m$^2$ for three days every 6 weeks for a maximum of 8 cycles; (m) for the anti-tumor nucleoside Chlorodeoxyadenosine (CdA, 2-CdA) 0.05-0.1 mg/kg/day as continuous infusion for up to 7 days every 3 to 4 weeks; (n) about 1 to about 100 mg/m$^2$ for epothilones; (o) about 1 to about 350 mg/m$^2$ for topoisomerase inhibitors; (p) about 1 to about 50 mg/m$^2$ for vinca alkaloids; (q) for the folate antagonist Methotrexate (MTX) 20-60 mg/m$^2$ by oral, IV or IM every 3 to 4 weeks, the intermediate dose regimen is 80-250 mg/m$^2$ IV over 60 minutes every 3 to 4 weeks, and the high dose regimen is 250-1000 mg/m$^2$ IV given with leucovorin every 3 to 4 weeks; (r) for the folate antagonist Premetrexed (Alimta) 300-600 mg/m$^2$ (10 minutes IV infusion day 1) every 3 weeks; (s) for the ribonucleotide reductase inhibitor Hydroxyurea (HU) 20-50 mg/kg/day (as needed to bring blood cell counts down); (t) the platinum coordinator compound Oxaliplatin (Eloxatin) 50-100 mg/m$^2$ every 3 to 4 weeks (preferably used for solid tumors such as non-small cell lung cancer, colorectal cancer and ovarian cancer); (u) for the anthracycline daunorubicin 10-50 mg/m$^2$/day IV for 3-5 days every 3 to 4 weeks; (v) for the anthracycline Doxorubicin (Adriamycin) 50-100 mg/m$^2$ IV continuous infusion over 1-4 days every 3 to 4 weeks, or 10-40 mg/m$^2$ IV weekly; (w) for the anthracycline Idarubicin 10-30 mg/m$^2$ daily for 1-3 days as a slow IV infusion over 10-20 minutes every 3 to 4 weeks; (x) for the biologic interferon (Intron-A, Roferon) 5 to 20 million IU three times per week; (y) for the biologic pegylated interferon (Peg-intron, Pegasys) 3 to 4 micrograms/kg/day chronic sub cutaneous (until relapse or loss of activity); and (z) for the biologic Rituximab (Rituxan) (antibody used for non-Hodgkin's lymphoma) 200-400 mg/m$^2$ IV weekly over 4-8 weeks for 6 months.

Gleevec can be used orally in an amount of about 200 to about 800 mg/day.

Thalidomide (and related imids) can be used orally in amounts of about 200 to about 800 mg/day, and can be contiuously dosed or used until releapse or toxicity. See for example Mitsiades et al., "Apoptotic signaling induced by immunomodulatory thalidomide analogs in human multiple myeloma cells; therapeutic implications", Blood, 99 (12): 4525-30, Jun. 15, 2002, the disclosure of which is incorporated herein by reference thereto.

For example, Paclitaxel (e.g., Taxol® can be administered once per week in an amount of about 50 to about 100 mg/m$^2$ with about 60 to about 80 mg/m$^2$ being preferred. In another example Paclitaxel (e.g., Taxol® can be administered once every three weeks in an amount of about 150 to about 250 mg/m$^2$ with about 175 to about 225 mg/m$^2$ being preferred.

In another example, Docetaxel (e.g., Taxotere®) can be administered once per week in an amount of about 10 to about 45 mg/m$^2$. In another example Docetaxel (e.g., Taxotere®) can be administered once every three weeks in an amount of about 50 to about 100 mg/m$^2$.

In another example Cisplatin can be administered once per week in an amount of about 20 to about 40 mg/m$^2$. In another example Cisplatin can be administered once every three weeks in an amount of about 60 to about 100 mg/m$^2$.

In another example Carboplatin can be administered once per week in an amount to provide an AUC of about 2 to about 3. In another example Carboplatin can be administered once every three weeks in an amount to provide an AUC of about 5 to about 8.

Thus, in one example (e.g., treating non small cell lung cancer):
(1) the FPT inhibitor is administered in an amount of about 50 mg to about 200 mg twice a day, preferably, about 75 mg to about 125 mg administered twice a day, and most preferably about 100 mg administered twice a day;
(2) Paclitaxel (e.g., Taxol®) is administered once per week in an amount of about 50 to about 100 mg/m$^2$ with about 60 to about 80 mg/m$^2$ being preferred; and
(3) Carboplatin is administered once per week in an amount to provide an AUC of about 2 to about 3.

In another example (e.g., treating non small cell lung cancer):
(1) the FPT inhibitor is administered in an amount of about 50 mg to about 200 mg twice a day, preferably, about 75 mg to about 125 mg administered twice a day, and most preferably about 100 mg administered twice a day;
(2) Paclitaxel (e.g., Taxol®) is administered once per week in an amount of about 50 to about 100 mg/m$^2$ with about 60 to about 80 mg/m$^2$ being preferred; and
(3) Cisplatin is administered once per week in an amount of about 20 to about 40 mg/m$^2$.

In another example (e.g., treating non small cell lung cancer):
(1) the FPT inhibitor is administered in an amount of about 50 mg to about 200 mg twice a day, preferably, about 75 mg to about 125 mg administered twice a day, and most preferably about 100 mg administered twice a day;
(2) Docetaxel (e.g., Taxotere®) is administered once per week in an amount of about 10 to about 45 mg/m$^2$; and
(3) Carboplatin is administered once per week in an amount to provide an AUC of about 2 to about 3.

In another example (e.g., treating non small cell lung cancer):
(1) the FPT inhibitor is administered in an amount of about 50 mg to about 200 mg twice a day, preferably, about 75 mg to about 125 mg administered twice a day, and most preferably about 100 mg administered twice a day;
(2) Docetaxel (e.g., Taxotere®) is administered once per week in an amount of about 10 to about 45 mg/m2; and
(3) Cisplatin is administered once per week in an amount of about 20 to about 40 mg/m$^2$.

Thus, in one example (e.g., treating non small cell lung cancer):
(1) the FPT inhibitor is administered in an amount of about 50 mg to about 200 mg twice a day, preferably, about 75 mg to about 125 mg administered twice a day, and most preferably about 100 mg administered twice a day;
(2) Paclitaxel (e.g., Taxol®) is administered once every three weeks in an amount of about 150 to about 250 mg/m$^2$, with about 175 to about 225 mg/m$^2$ being preferred, and with 175 mg/m$^2$ being most preferred; and
(3) Carboplatin is administered once every three weeks in an amount to provide an AUC of about 5 to about 8, and preferably 6.

In a preferred example of treating non small cell lung cancer:
(1) the FPT inhibitor is administered in an amount of 100 mg administered twice a day;
(2) Paclitaxel (e.g., Taxol®) is administered once every three weeks in an amount of 175 mg/m$^2$; and
(3) Carboplatin is administered once every three weeks in an amount to provide an AUC of 6.

In another example (e.g., treating non small cell lung cancer):
(1) the FPT inhibitor is administered in an amount of about 50 mg to about 200 mg twice a day, preferably, about 75 mg to about 125 mg administered twice a day, and most preferably about 100 mg administered twice a day;
(2) Paclitaxel (e.g., Taxol®) is administered once every three weeks in an amount of about 150 to about 250 mg/m$^2$, with about 175 to about 225 mg/m$^2$ being preferred; and
(3) Cisplatin is administered once every three weeks in an amount of about 60 to about 100 mg/m$^2$.

In another example (e.g., treating non small cell lung cancer):
(1) the FPT inhibitor is administered in an amount of about 50 mg to about 200 mg twice a day, preferably, about 75 mg to about 125 mg administered twice a day, and most preferably about 100 mg administered twice a day;
(2) Docetaxel (e.g., Taxotere®) is administered once every three weeks in an amount of about 50 to about 100 mg/m$^2$; and
(3) Carboplatin is administered once every three weeks in an amount to provide an AUC of about 5 to about 8.

In another example (e.g., treating non small cell lung cancer):
(1) the FPT inhibitor is administered in an amount of about 50 mg to about 200 mg twice a day, preferably, about 75 mg to about 125 mg administered twice a day, and most preferably about 100 mg administered twice a day;
(2) Docetaxel (e.g., Taxotere®) is administered once every three weeks in an amount of about 50 to about 100 mg/m$^2$; and
(3) Cisplatin is administered once every three weeks in an amount of about 60 to about 100 mg/m$^2$.

In a preferred example for treating non small cell lung cancer using the FPT inhibitor, Docetaxel and Carboplatin:
(1) the FPT inhibitor is administered in an amount of about 50 mg to about 200 mg twice a day, preferably, about 75 mg to about 125 mg administered twice a day, and most preferably about 100 mg administered twice a day;
(2) Docetaxel (e.g., Taxotere®) is administered once every three weeks in an amount of about 75 mg/m$^2$; and
(3) Carboplatin is administered once every three weeks in an amount to provide an AUC of about 6.

In the above examples the Docetaxel (e.g., Taxotere®) and Cisplatin, the Docetaxel (e.g., Taxotere®) and Carboplatin, the Paclitaxel (e.g., Taxol®) and Carboplatin, or the Paclitaxel (e.g., Taxol®) and Cisplatin are preferably administered on the same day.

In another example (e.g., CML):
(1) the FPT inhibitor is administered in an amount of about 100 mg to about 200 mg administered twice a day;
(2) Gleevec is administered in an amount of about 400 to about 800 mg/day orally; and
(3) interferon (Intron-A) is administered in an amount of about 5 to about 20 million IU three times per week.

In another example (e.g., CML):
(1) the FPT inhibitor is administered in an amount of about 100 mg to about 200 mg administered twice a day;
(2) Gleevec is administered in an amount of about 400 to about 800 mg/day orally; and
(3) pegylated interferon (Peg-Intron or Pegasys) is administered in an amount of about 3 to about 6 micrograms/kg/day.

In another example (e.g., non-Hodgkin's lymphoma):
(1) the FPT inhibitor is administered in an amount of about 50 mg to about 200 mg twice a day, preferably, about 75 mg to about 125 mg administered twice a day, and most preferably about 100 mg administered twice a day; and
(2) Genasense (antisense to BCL-2) is administered as a continuous IV infusion at a dose of about 2 to about 5 mg/kg/day (e.g., 3 mg/kg/day) for 5 to 7 days every 3 to 4 weeks.

In another example (e.g., multiple myeloma):
(1) the FPT inhibitor is administered in an amount of about 50 mg to about 200 mg twice a day, preferably, about 75 mg to about 125 mg administered twice a day, and most preferably about 100 mg administered twice a day; and
(2) the proteosome inhibitor (e.g., PS-341-Millenium) is administered in an amount of about 1.5 mg/m$^2$ twice weekly for two consecutive weeks with a one week rest period.

In another example (e.g., multiple myeloma):
(1) the FPT inhibitor is administered in an amount of about 50 mg to about 200 mg twice a day, preferably, about 75 mg to about 125 mg administered twice a day, and most preferably about 100 mg administered twice a day; and
(2) the Thalidomide (or related imid) is administered orally in an amount of about 200 to about 800 mg/day, with dosing being continuous until relapse or toxicity.

In the above examples the Taxotere and cisplatin, the Taxotere and carboplatin, the Taxol and carboplatin, or the Taxol and cisplatin are preferably administered on the same day.

Antineoplastic agents that can be used in combination with the FPT inhibitor are:
(1) taxanes such as paclitaxel (TAXOL®) and/or docetaxel (Taxotere®);
(2) platinum coordinator compounds, such as, for example, carboplatin, cisplatin and oxaliplatin;
(3) EGF inhibitors that are antibodies, such as: HER2 antibodies (such as, for example trastuzumab (Herceptin®), Genentech, Inc.), Cetuximab (Erbitux, IMC-C225, ImClone Systems), EMD 72000 (Merck KGaA), anti-EFGR monoclonal antibody ABX (Abgenix), TheraCIM-h-R3 (Center of Molecular Immunology), monoclonal antibody 425 (Merck KGaA), monoclonal antibody ICR-62 (ICR, Sufton, England); Herzyme (Elan Pharmaceutical Technologies and Ribozyme Pharmaceuticals), PKI 166 (Novartis), EKB 569 (Wyeth-Ayerst), GW 572016 (GlaxoSmithKline), Cl 1033 (Pfizer Global Research and Development), trastuzmab-maytansinoid conjugate (Genentech, Inc.), mitumomab (Imclone Systems and Merck KGaA) and Melvax II (Imclone Systems and Merck KgaA);
(4) EGF inhibitors that are small molecules, such as, Tarceva (TM) (OSI-774, OSI Pharmaceuticals, Inc.), and Iressa (ZD 1839, Astra Zeneca);
(5) VEGF inhibitors that are antibodies such as: bevacizumab (Genentech, Inc.), and IMC-1C11 (ImClone Systems), DC 101 (a KDR VEGF Receptor 2 from ImClone Systems);
(6) VEGF kinase inhibitors that are small molecules such as SU 5416 and SU 6688 (both from Sugen, Inc.);
(7) estrogen receptor antagonists or selective estrogen receptor modulators (SERMs), such as tamoxifen, idoxifene, raloxifene, trans-2,3-dihydroraloxifene, levormeloxifene, droloxifene, MDL 103,323, and acolbifene (Schering Corp.);
(8) anti-tumor nucleoside derivatives such as 5-fluorouracil, gemcitabine or capecitabine;
(9) epothilones such as BMS-247550 (Bristol-Myers Squibb), and EP0906 (Novartis Pharmaceuticals);
(10) topoisomerase inhibitors such as topotecan (Glaxo SmithKline), and Camptosar (Pharmacia);
(11) vinca alkaloids, such as, navelbine (Anvar and Fabre, France), vincristine and vinblastine; and
(12) antibodies that are inhibitors of $\alpha V\beta 3$ integrins, such as, LM-609 (see, Clinical Cancer Research, Vol. 6, page 3056-3061, August 2000, the disclosure of which is incorporated herein by reference thereto).

Preferred antineoplastic agents are selected from: paclitaxel, docetaxel, carboplatin, cisplatin, gemcitabine, tamoxifen, Herceptin, Cetuximab, Tarceva, Iressa, bevacizumab, navelbine, IMC-1C11, SU5416 or SU6688. Most preferred antineoplastic agents are selected from: paclitaxel, docetaxel, carboplatin, cisplatin, navelbine, gemcitabine, or Herceptin.

In general when more than one antineoplastic agent is used in the methods of this invention, the antineoplastic agents are administered on the same day either concurrently or consecutively in their standard dosage form. For example, the antineoplastic agents are usually administered intravenously, preferably by an IV drip using IV solutions well known in the art (e.g., isotonic saline (0.9% NaCl) or dextrose solution (e.g., 5% dextrose)).

When two or more antineoplastic agents are used, the antineoplastic agents are generally administered on the same day; however, those skilled in the art will appreciate that the antineoplastic agents can be administered on different days and in different weeks. The skilled clinician can administer the antineoplastic agents according to their recommended dosage schedule from the manufacturer of the agent and can adjust the schedule according to the needs of the patient, e.g., based on the patient's response to the treatment. For example, when gemcitabine is used in combination with a platinum coordinator compound, such as, for example, cisplatin, to treat lung cancer, both the gemcitabine and the cisplatin are given on the same day on day one of the treatment cycle, and then gemcitabine is given alone on day 8 and given alone again on day 15

Thus, one embodiment of this invention is directed to a method of treating cancer comprising administering to a patient in need of such treatment therapeutically effective amounts of the FPT inhibitor, a taxane, and a platinum coordination compound.

Another embodiment of this invention is directed to a method of treating cancer comprising administering to a patient in need of such treatment therapeutically effective amounts of the FPT inhibitor, a taxane, and a platinum coordination compound, wherein said FPT inhibitor is administered every day, said taxane is administered once per week per cycle, and said platinum coordinator compound is administered once per week per cycle. Preferably the treatment is for one to four weeks per cycle.

Another embodiment of this invention is directed to a method of treating cancer comprising administering to a patient in need of such treatment therapeutically effective amounts of the FPT inhibitor, a taxane, and a platinum coordination compound, wherein said FPT inhibitor is administered every day, said taxane is administered once every three weeks per cycle, and said platinum coordinator compound is administered once every three weeks per cycle. Preferably the treatment is for one to three weeks per cycle.

Another embodiment of this invention is directed to a method of treating cancer comprising administering to a patient in need of such treatment therapeutically effective amounts of the FPT inhibitor, paclitaxel, and carboplatin. Preferably, said FPT inhibitor is administered every day, said paclitaxel is administered once per week per cycle, and said carboplatin is administered once per week per cycle. Preferably the treatment is for one to four weeks per cycle.

Another embodiment of this invention is directed to a method of treating cancer comprising administering to a patient in need of such treatment therapeutically effective amounts of the FPT inhibitor, paclitaxel, and carboplatin. Preferably, said FPT inhibitor is administered every day, said paclitaxel is administered once every three weeks per cycle, and said carboplatin is administered once every three weeks per cycle. Preferably the treatment is for one to three weeks per cycle.

Preferably, non small cell lung cancer is treated in the methods described in the above embodiments.

Another embodiment of this invention is directed to a method for treating non small cell lung cancer in a patient in need of such treatment comprising administering daily a therapeutically effective amount of the FPT inhibitor, administering a therapeutically effective amount of carboplatin once a week per cycle, and administering a therapeutically effective amount of paclitaxel once a week per cycle, wherein the treatment is given for one to four weeks per cycle. Preferably said FPT inhibitor is administered twice per day. Preferably said carboplatin and said paclitaxel are administered on the same day, and more preferably said carboplatin and said paclitaxel are administered consecutively, and most preferably said carboplatin is administered after said paclitaxel.

Another embodiment of this invention is directed to a method for treating non small cell lung cancer in a patient in need of such treatment comprising administering daily a therapeutically effective amount of the FPT inhibitor, administering a therapeutically effective amount of carboplatin once every three weeks per cycle, and administering a therapeutically effective amount of paclitaxel once every three weeks per cycle, wherein the treatment is given for one to three weeks. Preferably said FPT inhibitor is administered twice per day. Preferably said carboplatin and said paclitaxel are administered on the same day, and more preferably said carboplatin and said paclitaxel are administered consecutively, and most preferably said carboplatin is administered after said paclitaxel.

Another embodiment of this invention is directed to a method for treating non small cell lung cancer in a patient in need of such treatment comprising administering about 50 to about 200 mg of the FPT inhibitor twice a day, administering carboplatin once per week per cycle in an amount to provide an AUC of about 2 to about 8 (preferably about 2 to about 3), and administering once per week per cycle about 60 to about 300 mg/m$^2$ (preferably about 50 to 100 mg/m$^2$, more preferably about 60 to about 80 mg/m$^2$) of paclitaxel, wherein the treatment is given for one to four weeks per cycle. In a more preferred embodiment said FPT inhibitor is administered in amount of about 75 to about 125 mg twice a day, with about 100 mg twice a day being preferred. Preferably said carboplatin and said paclitaxel are administered on the same day, and more preferably said carboplatin and said paclitaxel are administered consecutively, and most preferably said carboplatin is administered after said paclitaxel.

In a preferred embodiment, this invention is directed to a method for treating non small cell lung cancer in a patient in need of such treatment comprising administering about 50 to about 200 mg of the FPT inhibitor twice a day, administering carboplatin once every three weeks per cycle in an amount to provide an AUC of about 2 to about 8 (preferably about 5 to about 8, most preferably 6), and administering once every three weeks per cycle about 150 to about 250 mg/m$^2$ (preferably about 175 to about 225 mg/m$^2$, most preferably 175 mg/m$^2$) of paclitaxel, wherein the treatment is given for one to three weeks. In a more preferred embodiment said FPT inhibitor is administered in an amount of about 75 to about 125 mg twice a day, with about 100 mg twice a day being preferred. Preferably said carboplatin and said paclitaxel are administered on the same day, and more preferably said carboplatin and said paclitaxel are administered consecutively, and most preferably said carboplatin is administered after said paclitaxel.

Other embodiments of this invention are directed to methods of treating cancer as described in the above embodiments except that in place of paclitaxel and carboplatin the taxanes and platinum coordinator compounds used together in the methods are: (1) docetaxel (Taxotere®) and cisplatin; (2) paclitaxel and cisplatin; and (3) docetaxel and carboplatin. In the methods of this invention cisplatin is preferably used in amounts of about 30 to about 100 mg/m$^2$. In the methods of this invention docetaxel is preferably used in amounts of about 30 to about 100 mg/m$^2$.

In another embodiment this invention is directed to a method of treating cancer comprising administering to a patient in need of such treatment therapeutically effective amounts of the FPT inhibitor, a taxane, and an EGF inhibitor that is an antibody. Preferably the taxane used is paclitaxel, and preferably the EGF inhibitor is a HER2 antibody (more preferably Herceptin) or Cetuximab, and most preferably Herceptin is used. The length of treatment, and the amounts and administration of the FPT inhibitor and the taxane are as described in the embodiments above. The EGF inhibitor that is an antibody is administered once a week per cycle, and is preferably administered on the same day as the taxane, and more preferably is administered consecutively with the taxane. For example, Herceptin is administered in a loading dose of about 3 to about 5 mg/m$^2$ (preferably about 4 mg/m$^2$), and then is administered in a maintenance dose of about 2 mg/m$^2$ once per week per cycle for the remainder of the treatment cycle (usually the cycle is 1 to 4 weeks). Preferably the cancer treated is breast cancer.

In another embodiment this invention is directed to a method of treating cancer comprising administering to a patient in need of such treatment therapeutically effective amounts of:
(1) the FPT inhibitor;
(2) a taxane; and
(3) an antineoplastic agent selected from:
  (a) an EGF inhibitor that is a small molecule;
  (b) a VEGF inhibitor that is an antibody; or
  (c) a VEGF kinase inhibitor that is a small molecule.

Preferably, the taxane paclitaxel or docetaxel is used. Preferably the antineoplastic agent is selected from: tarceva, Iressa, bevacizumab, SU5416 or SU6688. The length of treatment, and the amounts and administration of the FPT inhibitor and the taxane are as described in the embodiments above. The VEGF kinase inhibitor that is an antibody is usually given once per week per cycle. The EGF and VEGF inhibitors that are small molecules are usually given daily per cycle. Preferably, the VEGF inhibitor that is an antibody is given on the same day as the taxane, and more preferably is administered concurrently with the taxane. When the EGF inhibitor that is a small molecule or the VEGF inhibitor that is a small molecule is administered on the same day as the taxane, the administration is preferably concurrently with the taxane. The EGF or VEGF kinase inhibitor is generally administered in an amount of about 10 to about 500 mg/m$^2$. Preferably the cancer treated is non small cell lung cancer.

In another embodiment this invention is directed to a method of treating cancer comprising administering to a patient in need of such treatment therapeutically effective amounts of the FPT inhibitor, an anti-tumor nucleoside derivative, and a platinum coordination compound.

Another embodiment of this invention is directed to a method of treating cancer comprising administering to a patient in need of such treatment therapeutically effective amounts of the FPT inhibitor, an anti-tumor nucleoside derivative, and a platinum coordination compound, wherein said FPT inhibitor is administered every day, said anti-tumor nucleoside derivative is administered once per week per cycle, and said platinum coordinator compound is administered once per week per cycle. Although the treatment can be for one to four weeks per cycle, the treatment is preferably for one to seven weeks per cycle.

Another embodiment of this invention is directed to a method of treating cancer comprising administering to a patient in need of such treatment therapeutically effective amounts of the FPT inhibitor, an anti-tumor nucleoside derivative, and a platinum coordination compound, wherein said FPT inhibitor is administered every day, said an anti-tumor nucleoside derivative is administered once per week per cycle, and said platinum coordinator compound is administered once every three weeks per cycle. Although the treatment can be for one to four weeks per cycle, the treatment is preferably for one to seven weeks per cycle.

Another embodiment of this invention is directed to a method of treating cancer comprising administering to a patient in need of such treatment therapeutically effective amounts of the FPT inhibitor, gemcitabine, and cisplatin. Preferably, said FPT inhibitor is administered every day, said gemcitabine is administered once per week per cycle, and said cisplatin is administered once per week per cycle. Preferably the treatment is for one to seven weeks per cycle.

Another embodiment of this invention is directed to a method of treating cancer comprising administering to a patient in need of such treatment therapeutically effective amounts of the FPT inhibitor, gemcitabine, and cisplatin. Preferably, said FPT inhibitor is administered every day, said gemcitabine is administered once per week per cycle, and said cisplatin is administered once every three weeks per cycle. Preferably the treatment is for one to seven weeks.

Another embodiment of this invention is directed to a method of treating cancer comprising administering to a patient in need of such treatment therapeutically effective amounts of the FPT inhibitor, gemcitabine, and carboplatin. Preferably, said FPT inhibitor is administered every day, said gemcitabine is administered once per week per cycle, and said carboplatin is administered once per week per cycle. Preferably the treatment is for one to seven weeks per cycle.

Another embodiment of this invention is directed to a method of treating cancer comprising administering to a patient in need of such treatment therapeutically effective amounts of the FPT inhibitor, gemcitabine, and carboplatin. Preferably, said FPT inhibitor is administered every day, said gemcitabine is administered once per week per cycle, and said carboplatin is administered once every three weeks per cycle. Preferably the treatment is for one to seven weeks per cycle.

Preferably, non small cell lung cancer is treated in the methods using gemcitabine in the embodiments described above.

In the above embodiments using gemcitabine, the FPT inhibitor and the platinum coordinator compound are administered as described above for the embodiments using taxanes. Gemcitabine is administered in an amount of about 500 to about 1250 mg/m$^2$. The gemcitabine is preferably administered on the same day as the platinum coordinator compound, and more preferably consecutively with the platinum coordinator compound, and most preferably the gemcitabine is administered after the platinum coordinator compound.

Another embodiment of this invention is directed to a method of treating cancer in a patient in need of such treatment comprising administering to said patient the FPT inhibitor and an antineoplastic agent selected from: (1) EGF inhibitors that are antibodies, (2) EGF inhibitors that are small molecules, (3) VEGF inhibitors that are antibodies, and (4) VEGF kinase inhibitors that are small molecules all as described above. The treatment is for one to seven weeks per cycle, and generally for one to four weeks per cycle. The FPT inhibitor is administered in the same manner as described above for the other embodiments of this invention. The small molecule antineoplastic agents are usually administered daily, and the antibody antineoplastic agents are usually administered once per week per cycle. The antineoplastic agents are preferably selected from: Herceptin, Cetuximab, Tarceva, Iressa, bevacizumab, IMC-1C11, SU5416 or SU6688. Preferably non small cell lung cancer is treated.

In the embodiments of this invention wherein a platinum coordinator compound is used as well as at least one other antineoplastic agent, and these drugs are administered consecutively, the platinum coordinator compound is generally administered after the other antineoplastic agents have been administered.

Other embodiments of this invention include the administration of a therapeutically effective amount of radiation to the patient in addition to the administration of the FPT inhibitor and antineoplastic agents in the embodiments described above. Radiation is administered according to techniques and protocols well know to those skilled in the art.

Another embodiment of this invention is directed to a pharmaceutical composition comprising at least two different antineoplastic agents and a pharmaceutically acceptable carrier for intravenous administration. Preferably the pharmaceutically acceptable carrier is an isotonic saline solution (0.9% NaCl) or a dextrose solution (e.g., 5% dextrose).

Another embodiment of this invention is directed to a pharmaceutical composition comprising the FPT inhibitor and at least two different antineoplastic agents and a pharmaceutically acceptable carrier for intravenous administration. Preferably the pharmaceutically acceptable carrier is an isotonic saline solution (0.9% NaCl) or a dextrose solution (e.g., 5% dextrose).

Another embodiment of this invention is directed to a pharmaceutical composition comprising the FPT inhibitor and at least one antineoplastic agent and a pharmaceutically acceptable carrier for intravenous administration. Preferably the pharmaceutically acceptable carrier is an isotonic saline solution (0.9% NaCl) or a dextrose solution (e.g., 5% dextrose).

In the method of treating embodiments, and in the pharmaceutical composition embodiments, the FPT inhibitor is preferably a compound selected from the compounds of formulas 1.4, 1.4D, 1.4E 1.4F, 1.5, 1.5A, 1.6, 1.6A, 1.7, and 1.7A.

Those skilled in the art will appreciate that the compounds (drugs) used in the methods of this invention are available to the skilled clinician in pharmaceutical compositions (dosage forms) from the manufacture and are used in those compositions. So, the recitation of the compound or class of compounds in the above described methods can be replaced with a recitation of a pharmaceutical composition comprising the particular compound or class of compounds. For example, the embodiment directed to a method of treating cancer comprising administering to a patient in need of such treatment therapeutically effective amounts of the FPT inhibitor, a taxane, and a platinum coordination compound, includes within its scope a method of treating cancer comprising administering to a patient in need of such treatment therapeutically effective amounts of a pharmaceutical composition comprising the FPT inhibitor (1.0), a pharmaceutical composition comprising a taxane, and a pharmaceutical composition comprising a platinum coordination compound.

The actual dosage employed may be varied depending upon the requirements of the patient and the severity of the condition being treated. Determination of the proper dosage for a particular situation is within the skill of the art.

The amount and frequency of administration of the FPT inhibitor and the antineoplastic agents will be regulated according to the judgment of the attending clinician (physician) considering such factors as age, condition and size of the patient as well as severity of the cancer being treated.

The antineoplastic agent can be administered according to therapeutic protocols well known in the art. It will be apparent to those skilled in the art that the administration of the antineoplastic agent can be varied depending on the cancer being treated and the known effects of the antineoplastic agent on that disease. Also, in accordance with the knowledge of the skilled clinician, the therapeutic protocols (e.g., dosage amounts and times of administration) can be varied in view of the observed effects of the administered therapeutic agents on the patient, and in view of the observed responses of the cancer to the administered therapeutic agents.

The initial administration can be made according to established protocols known in the art, and then, based upon the observed effects, the dosage, modes of administration and times of administration can be modified by the skilled clinician.

The particular choice of antineoplastic agent will depend upon the diagnosis of the attending physicians and their judgement of the condition of the patient and the appropriate treatment protocol.

The determination of the order of administration, and the number of repetitions of administration of the antineoplastic agent during a treatment protocol, is well within the knowledge of the skilled physician after evaluation of the cancer being treated and the condition of the patient.

Thus, in accordance with experience and knowledge, the practicing physician can modify each protocol for the administration of an antineoplastic agent according to the individual patient's needs, as the treatment proceeds. All such modifications are within the scope of the present invention.

The attending clinician, in judging whether treatment is effective at the dosage administered, will consider the general well-being of the patient as well as more definite signs such as relief of cancer-related symptoms (e.g., pain, cough (for lung cancer), and shortness of breath (for lung cancer)), inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

Chemotherapeutic Agents

Classes of compounds that can be used as chemotherapeutic agents (antineoplastic agent/microtubule affecting agents) include but are not limited to: alkylating agents, antimetabolites, natural products and their derivatives, hormones and steroids (including synthetic analogs), and synthetics. Examples of compounds within these classes are given below.

Alkylating agents (including nitrogen mustards, ethylenimine derivatives, alkyl sulfonates, nitrosoureas and triazenes): Uracil mustard, Chlormethine, Cyclophosphamide (Cytoxan®), Ifosfamide, Melphalan, Chlorambucil, Pipobroman, Triethylene-melamine, Triethylenethiophosphoramine;, Busulfan, Carmustine, Lomustine, Streptozocin, Dacarbazine, and Temozolomide.

Antimetabolites (including folic acid antagonists, pyrimidine analogs, purine analogs and adenosine deaminase inhibitors): Methotrexate, 5-Fluorouracil, Floxuridine, Cytarabine, 6-Mercaptopurine, 6-Thioguanine, Fludarabine phosphate, Pentostatine, and Gemcitabine.

Natural products and their derivatives (including vinca alkaloids, antitumor antibiotics, enzymes, lymphokines and epipodophyllotoxins): Vinblastine, Vincristine, Vindesine, Bleomycin, Dactinomycin, Daunorubicin, Doxorubicin, Epirubicin, Idarubicin, paclitaxel (paclitaxel is commercially available as Taxol® and is described in more detail below in the subsection entitled "Microtubule Affecting Agents"), paclitaxel derivatives (e.g. taxotere), Mithramycin, Deoxyco-formycin, Mitomycin-C, L-Asparaginase, Interferons (especially IFN-a), Etoposide, and Teniposide.

Hormones and steroids (including synthetic analogs): 17α-Ethinylestradiol, Diethylstilbestrol, Testosterone, Prednisone, Fluoxymesterone, Dromostanolone propionate, Testolactone, Megestrolacetate, Tamoxifen, Methylprednisolone, Methyl-testosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, Zoladex.

Synthetics (including inorganic complexes such as platinum coordination complexes): Cisplatin, Carboplatin, Hydroxyurea, Amsacrine, Procarbazine, Mitotane, Mitoxantrone, Levamisole, and Hexamethylmelamine.

Other chemotherapeutics include Navelbene, CPT-11, Anastrazole, Letrazole, Capecitabinbe, Reloxafine, and Droloxafine.

Particularly preferred are the antineoplastic agents selected from Cyclophasphamide, 5-Fluorouracil, Temozolomide, Vincristine, Cisplatin, Carboplatin, and Gemcitabine. Most preferably, the antineoplastic agent is selected from Gemcitabine, Cisplatin and Carboplatin.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR), e.g., 1996 edition (Medical Economics Company, Montvale, N. J. 07645-1742, USA); the disclosure of which is incorporated herein by reference thereto.

Microtubule Affecting Agents

As used herein, a microtubule affecting agent (e.g., paclitaxel, a paclitaxel derivative or a paclitaxel-like compound) is a compound that interferes with cellular mitosis, i.e., having an anti-mitotic effect, by affecting microtubule formation and/or action. Such agents can be, for instance, microtubule stabilizing agents or agents which disrupt microtubule formation.

Microtubule affecting agents useful in the invention are well known to those of skill in the art and include, but are not limited to allocolchicine (NSC 406042), Halichondrin B (NSC 609395), colchicine (NSC 757), colchicine derivatives (e.g., NSC 33410), dolastatin 10 (NSC 376128), maytansine (NSC 153858), rhizoxin (NSC 332598), paclitaxel (Taxol®, NSC 125973), paclitaxel derivatives (e.g., Taxotere, NSC 608832), thiocolchicine (NSC 361792), trityl cysteine (NSC 83265), vinblastine sulfate (NSC 49842), vincristine sulfate (NSC 67574), epothilone A, epothilone, and discodermolide (see Service, (1996) Science, 274:2009) estramustine, nocodazole, MAP4, and the like. Examples of such agents are also described in the scientific and patent literature, see, e.g., Bulinski (1997) J. Cell Sci. 110:3055-3064; Panda (1997) Proc. Natl. Acad. Sci. USA 94:10560-10564; Muhlradt (1997) Cancer Res. 57:3344-3346; Nicolaou (1997) Nature 387:268-272; Vasquez (1997) Mol. Biol. Cell. 8:973-985; Panda (1996) J. Biol. Chem. 271:29807-29812.

Particularly preferred agents are compounds with paclitaxel-like activity. These include, but are not limited to paclitaxel and paclitaxel derivatives (paclitaxel-like compounds) and analogues. Paclitaxel and its derivatives (e.g. Taxol and Taxotere) are available commercially. In addition, methods of making paclitaxel and paclitaxel derivatives and analogues are well known to those of skill in the art (see, e.g., U.S. Pat. Nos. 5,569,729; 5,565,478; 5,530,020; 5,527,924; 5,508,447; 5,489,589; 5,488,116; 5,484,809; 5,478,854; 5,478,736; 5,475,120; 5,468,769; 5,461,169; 5,440,057; 5,422,364; 5,411,984; 5,405,972; and 5,296,506).

More specifically, the term "paclitaxel" as used herein refers to the drug commercially available as Taxol® (NSC number: 125973). Taxol® inhibits eukaryotic cell replication by enhancing polymerization of tubulin moieties into stabilized microtubule bundles that are unable to reorganize into the proper structures for mitosis. Of the many available chemotherapeutic drugs, paclitaxel has generated interest because of its efficacy in clinical trials against drug-refractory tumors, including ovarian and mammary gland tumors (Hawkins (1992) Oncology, 6: 17-23, Horwitz (1992) Trends Pharmacol. Sci. 13: 134-146, Rowinsky (1990) J. Natl. Canc. Inst. 82: 1247-1259).

Additional microtubule affecting agents can be assessed using one of many such assays known in the art, e.g., a semiautomated assay which measures the tubulin-polymerizing activity of paclitaxel analogs in combination with a cellular assay to measure the potential of these compounds to block cells in mitosis (see Lopes (1997) Cancer Chemother. Pharmacol. 41:3747).

Generally, activity of a test compound is determined by contacting a cell with that compound and determining whether or not the cell cycle is disrupted, in particular, through the inhibition of a mitotic event. Such inhibition may be mediated by disruption of the mitotic apparatus, e.g., disruption of normal spindle formation. Cells in which mitosis is interrupted may be characterized by altered morphology (e.g., microtubule compaction, increased chromosome number, etc.).

Compounds with possible tubulin polymerization activity can be screened in vitro. For example, the compounds are screened against cultured WR21 cells (derived from line 69-2 wap-ras mice) for inhibition of proliferation and/or for altered cellular morphology, in particular for microtubule compaction. In vivo screening of positive-testing compounds can then be performed using nude mice bearing the WR21 tumor cells. Detailed protocols for this screening method are described by Porter (1995) Lab. Anim. Sci., 45 (2):145-150.

Other methods of screening compounds for desired activity are well known to those of skill in the art. Typically such assays involve assays for inhibition of microtubule assembly and/or disassembly. Assays for microtubule assembly are described, for example, by Gaskin et al. (1974) J. Molec. Biol., 89: 737-758. U.S. Pat. No. 5,569,720 also provides in vitro and in vivo assays for compounds with paclitaxel-like activity.

Methods for the safe and effective administration of the above-mentioned microtubule affecting agents are known to those skilled in the art. In addition their administration is described in the standard literature. For example, the administration of many of the chemotherapeutic agents is described in the "Physicians' Desk Reference" (cited above).

General Preparative Schemes

The following processes may be employed to produce compounds of the invention.

Pyridyl Tricyclic Compounds

One skilled in the art will appreciate that the compounds of the invention represented by Formula 1, wherein one of a, b, c or d is N or $N^+$—$O^-$ can be prepared according to the following schemes:

Scheme 1:

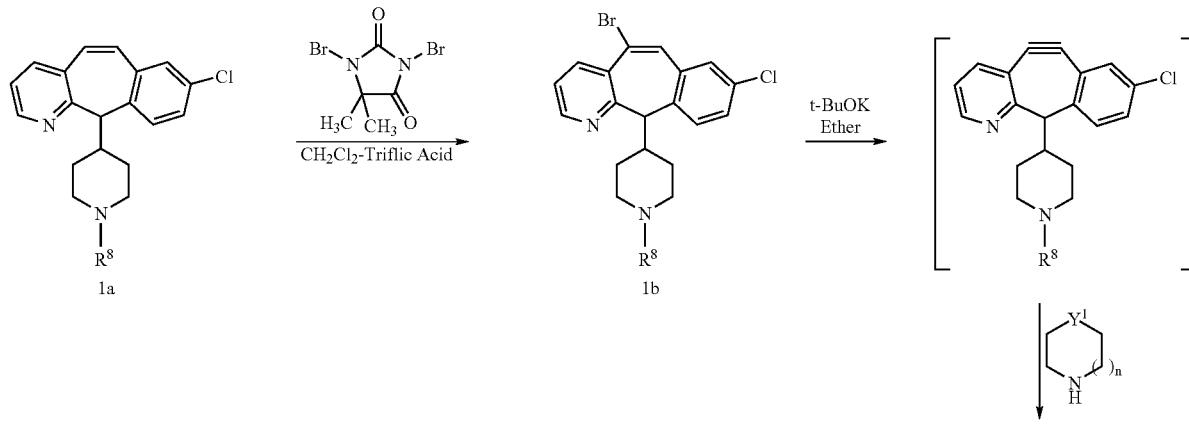

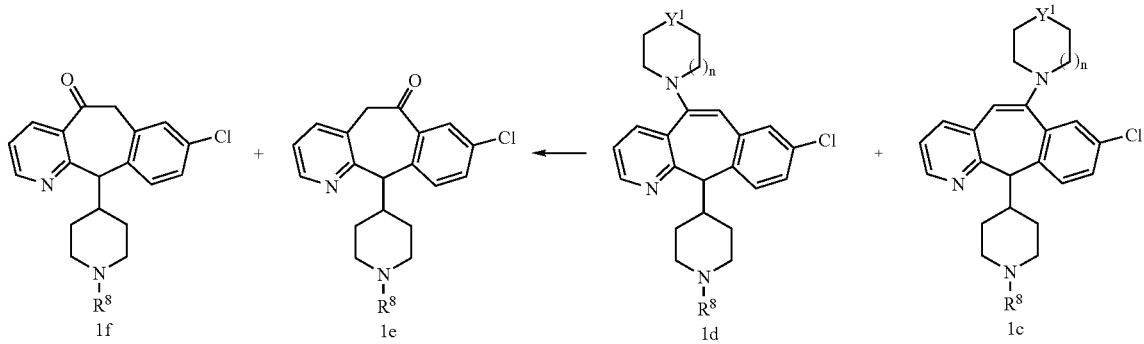

The synthesis of 5-bromo tricyclic compound 1b begins with bridgehead olefin 1a (*J. Med Chem* (1998), 41, 1561-1567) which is treated with dibromo dimethylhydantoin in triflic acid media. Further treatment of the vinylbromide with potassium t-butoxide in the presence of the appropriate secondary amine gives the 5 and 6-substituted enamine adducts. $Y^1$ represents —$CH_2$—, —O— or —NH—. When $Y^1$ is NH (piperazine case), acylations, sulfonylations and amide formation can be carried out using standard procedures. Treatment of these amine adducts with HCl(aq) at the appropriate temperatures results in the formation of the 5 and 6 azaketones, 1f and 1e respectively.

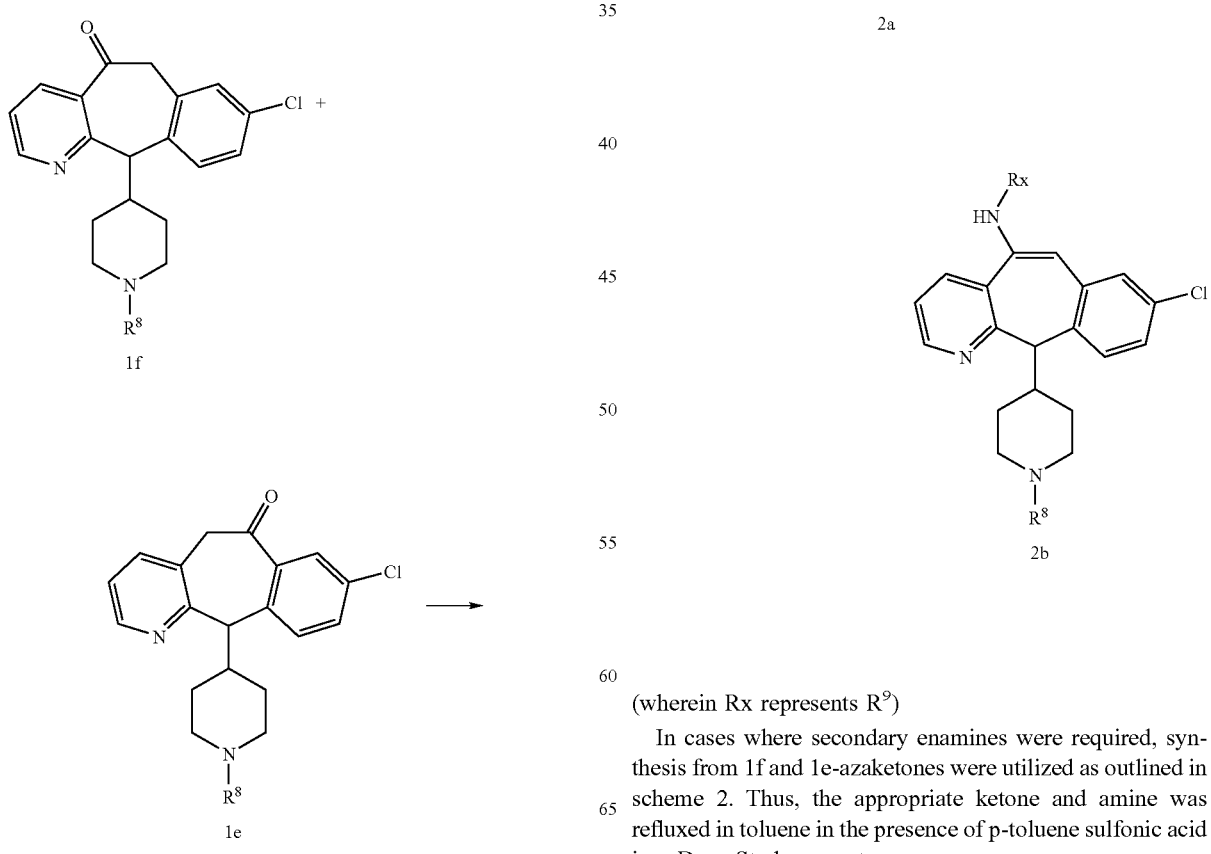

(wherein Rx represents $R^9$)

In cases where secondary enamines were required, synthesis from 1f and 1e-azaketones were utilized as outlined in scheme 2. Thus, the appropriate ketone and amine was refluxed in toluene in the presence of p-toluene sulfonic acid in a Dean Stark apparatus.

Scheme 3:

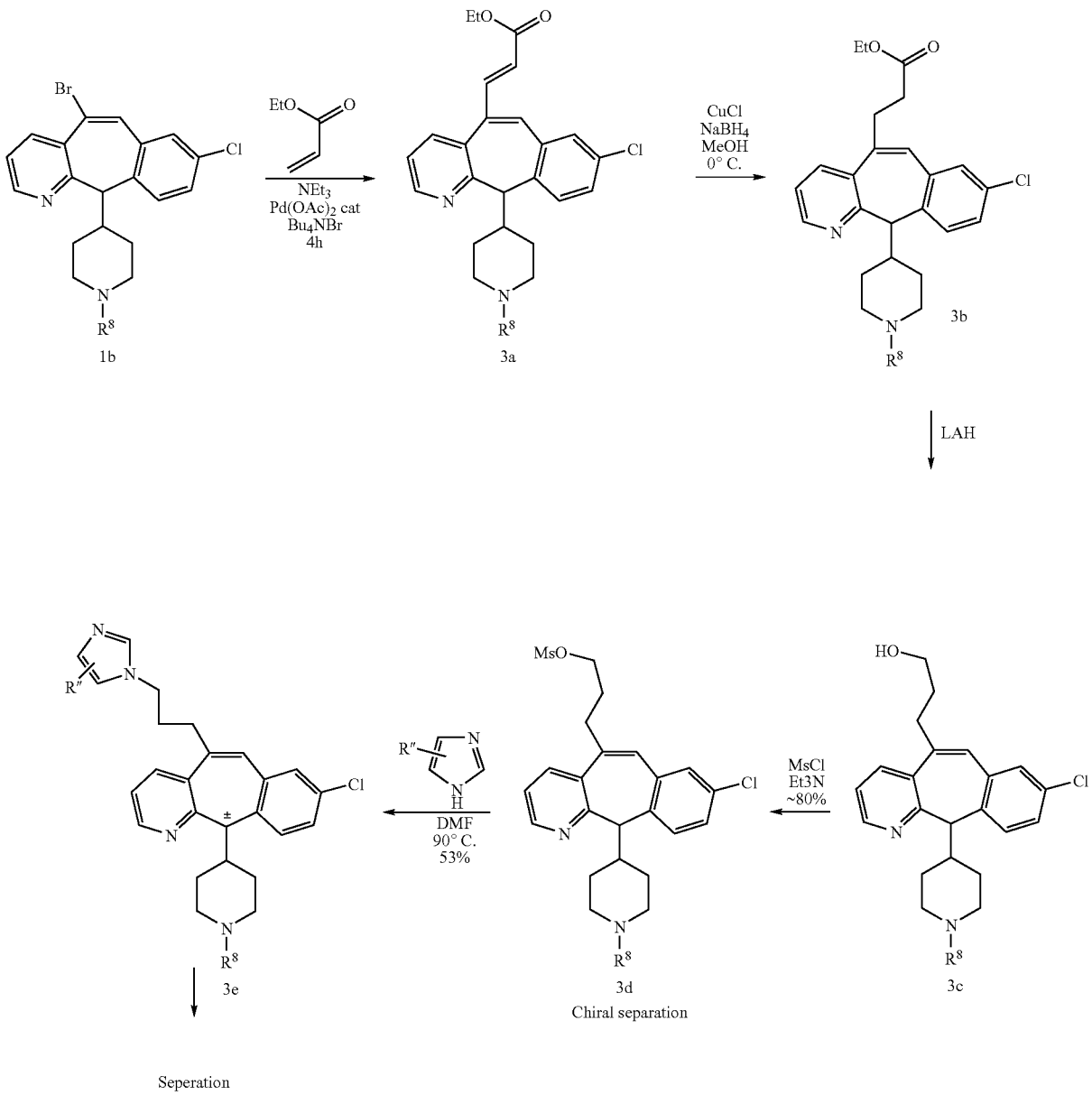

(wherein R" represents H or alkyl (e.g., methly and ethyl).

Synthesis of 3-carbon spaced analogs can be prepared as outlined in Scheme 3. Thus, subjecting tricyclic vinyl bromide 1b to a Heck type reaction using ethyl acrylate and catalyzed by $Pd^0$ gives the α-β un-saturated ester 3a. Reduction of the conjugated double bond was carried out using copper chloride-sodium borohydride reducing reagent. The ester was further reduced to alcohol using lithium aluminum hydride. Treatment of the alcohol with methanesulfonyl chloride in an appropriate aprotic solvent, followed by displacement with an appropriate sodium salt resulted in the desired imidazole targets. In most cases, separation of isomers were effected at this point. Where the $R^8$ group of 3e was a BOC group, deprotection using HCl-dioxane gave the hydrochloride salts of amines. Using standard chemistry, these amines were converted to ureas, carbamates, sulfonamides and amides.

Those skilled in the art will recognize that when a metal hydride, such as NaH, is used in the conversion of 3d to 3e in Scheme 3, reduction of the C5-C6 double bond can take place. This is exemplified in Preparative Example 59 Step B.

Scheme 4: PREPARATION OF 6-SUBSTITUTED CARBON ANALOGUES

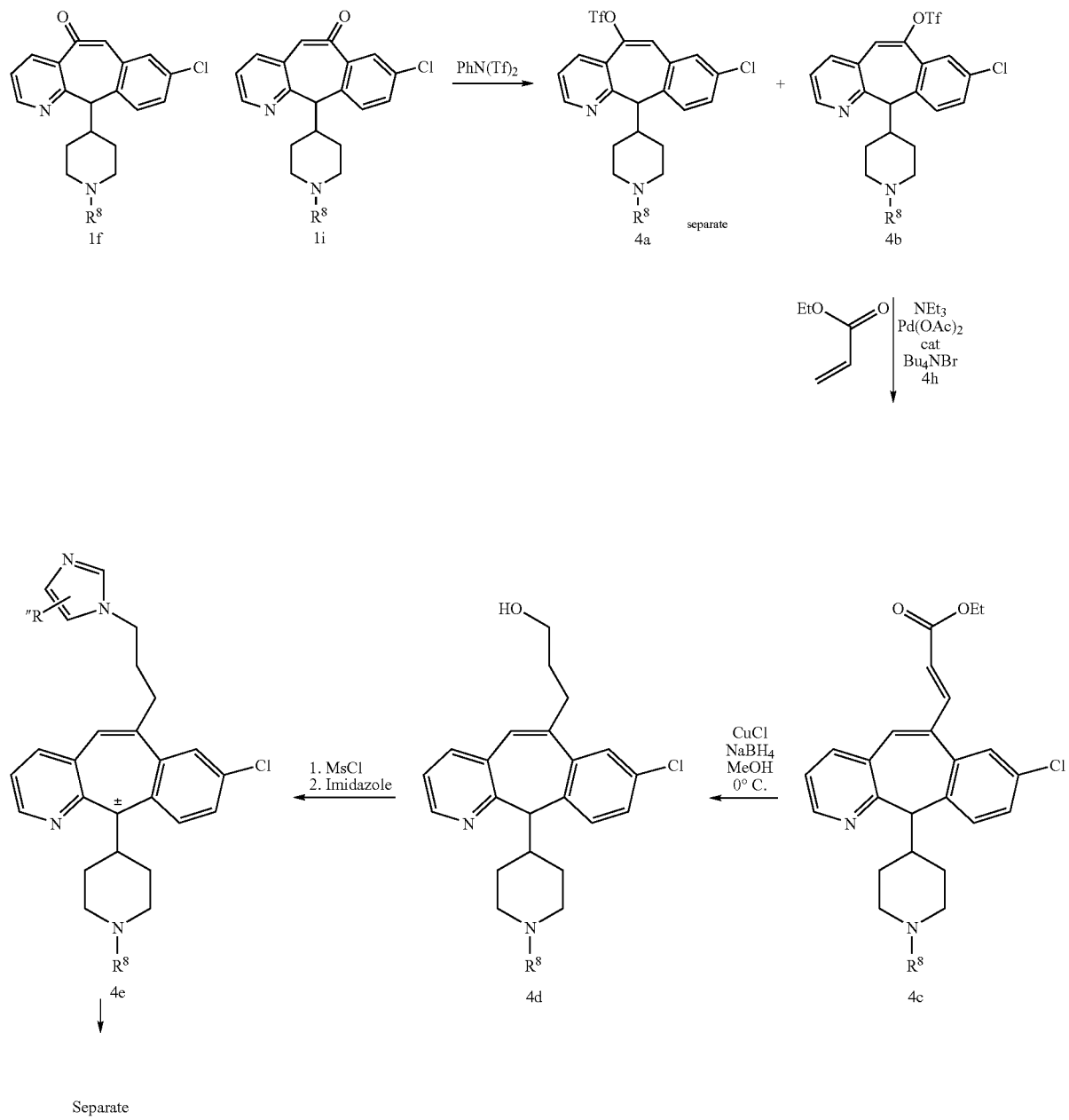

(wherein R" represents H or alkyl (e.g., methly and ethyl).

Preparation of 6-substituted 3-carbon spaced imidazole compounds was carried out as outlined in scheme 4. A mixture of ketones 1f and 1i were treated with N-phenytrifluoromethane sulfonimide to give a seperable mixture of 5 and 6-tricyclic triflate compounds. The 6-trilate adduct was converted to the desired 3-carbon spaced analogs using similar protocol as described for the 5-bromo tricyclic compounds outlined in scheme 3.

Scheme 5: SYNTHESIS OF 2-CARBON SPACER ANALOGUES

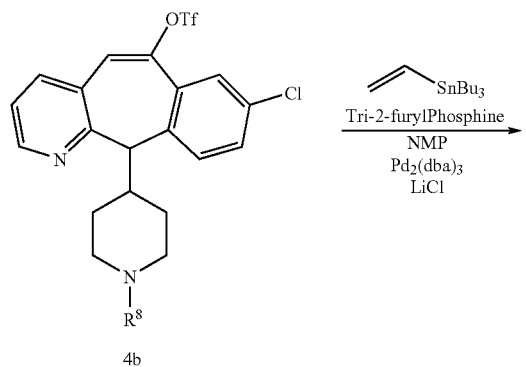

4b

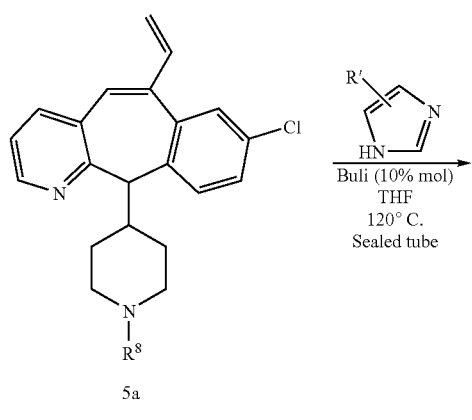

5a

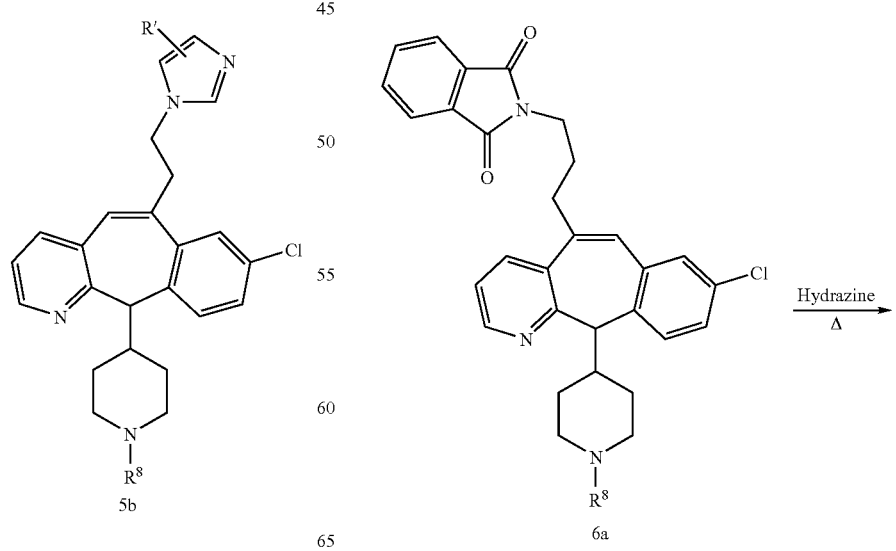

5b (wherein R' represents H or alkyl (e.g., methly and ethyl)).

Two carbon spaced analogs were prepared as outlined in scheme 5. Thus, triflate 4b was subjected to Stille chemistry, by reacting with tributylvinyl stannate catalyzed by an appropriate Pd⁰ to afford the tricyclic vinyl compound 5b. The 2-carbon spaced compounds were obtained by treating the tricylic compound with the appropriate imidazole that had been previously treated with Buli-THF in a sealed tube and refluxed at 120° C. Further funtionalization was carried out as previously described Suberane compounds were prepared in a similar way Scheme 6:

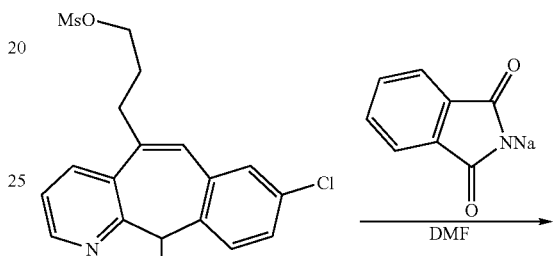

3d

6a

Lactams 7a can be prepared from amine 6b by reacting with bromo butanonyl acid chloride as outlined in Scheme 7.

Scheme 8: PREPARATION OF CYCLIC UREAS

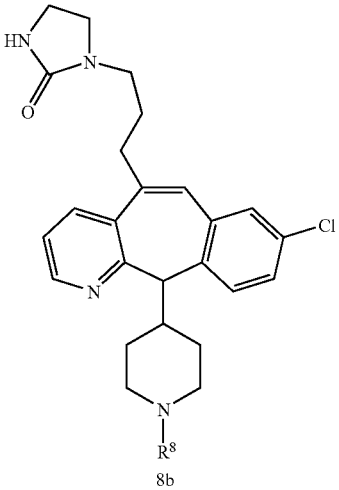

Scheme 6 illustrates a method of making amine 6b through phthalimido displacement of a mesylate followed by hydazine hydrolysis of the phthalimido moiety. Amine 6b can be converted to targets that have acyl, sufonyl, carbamoyl and urea functionalities.

Scheme 7

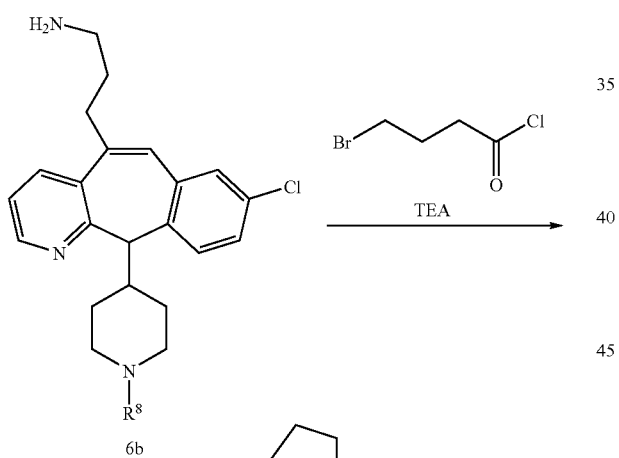

Cyclic urea can be prepared from the mesylate shown above by treating with the salt of the cyclic urea 8a as outlined in scheme 8.

Scheme 9: PREPARATION OF 5-SUBSTITUTED PROPANOIC ACID DERIVATES:

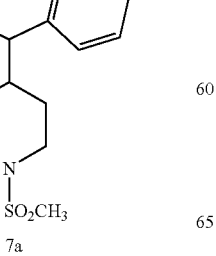

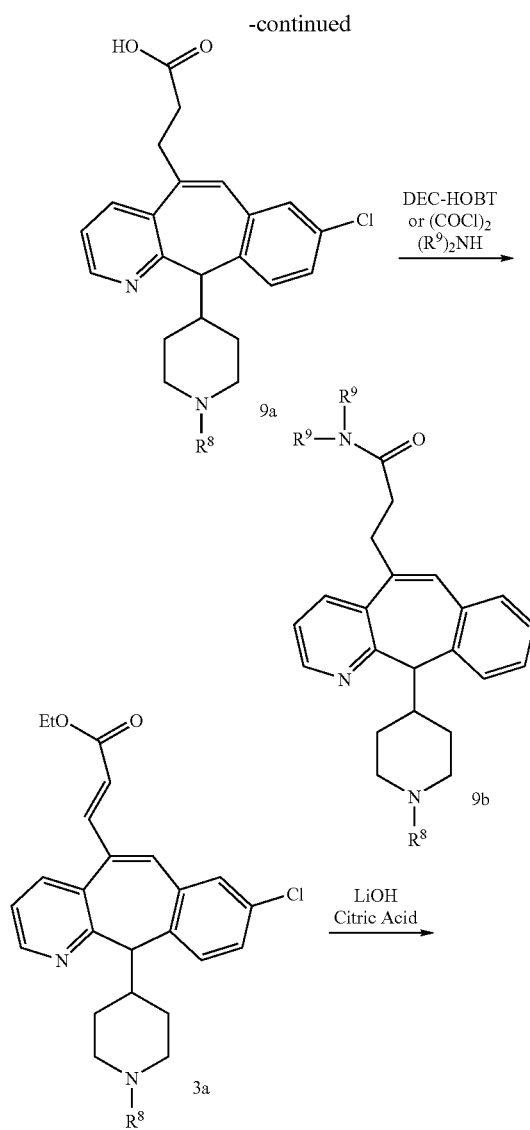
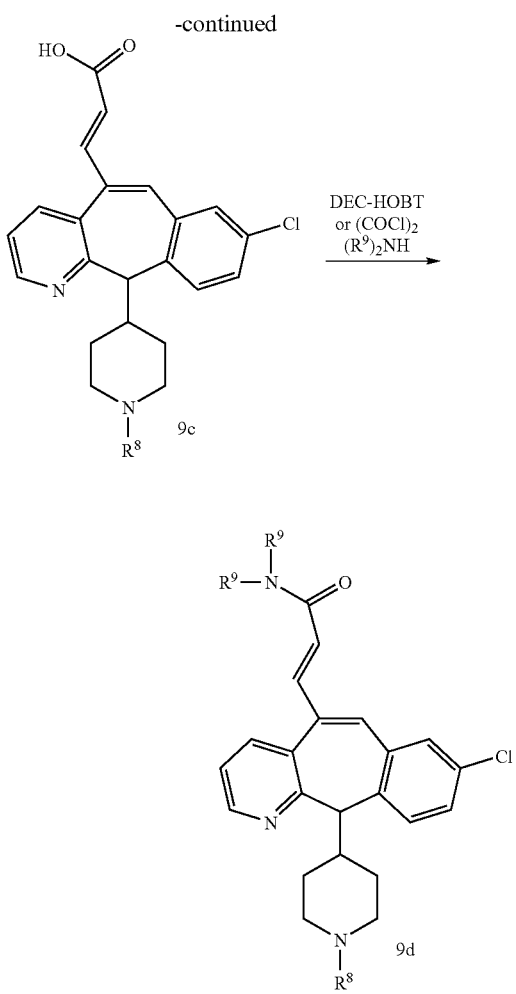
Amides from 3-carbon spaced carboxylic acid 9a and 9c can be prepared as outlined in Scheme 9 using either DEC-HOBT mediated protocol or from the appropriate acid chloride.
Scheme 10:
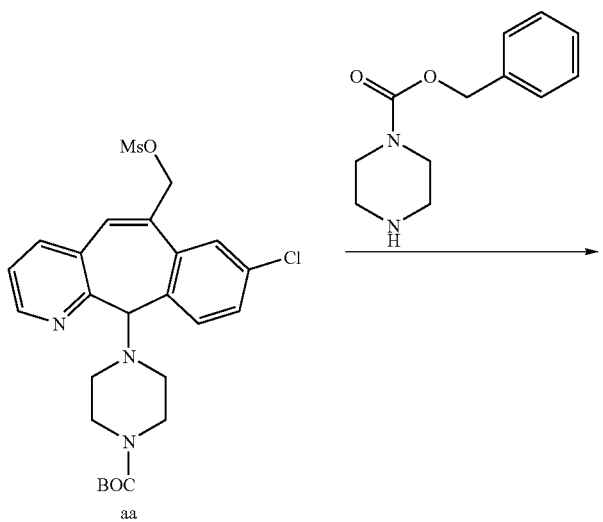

-continued

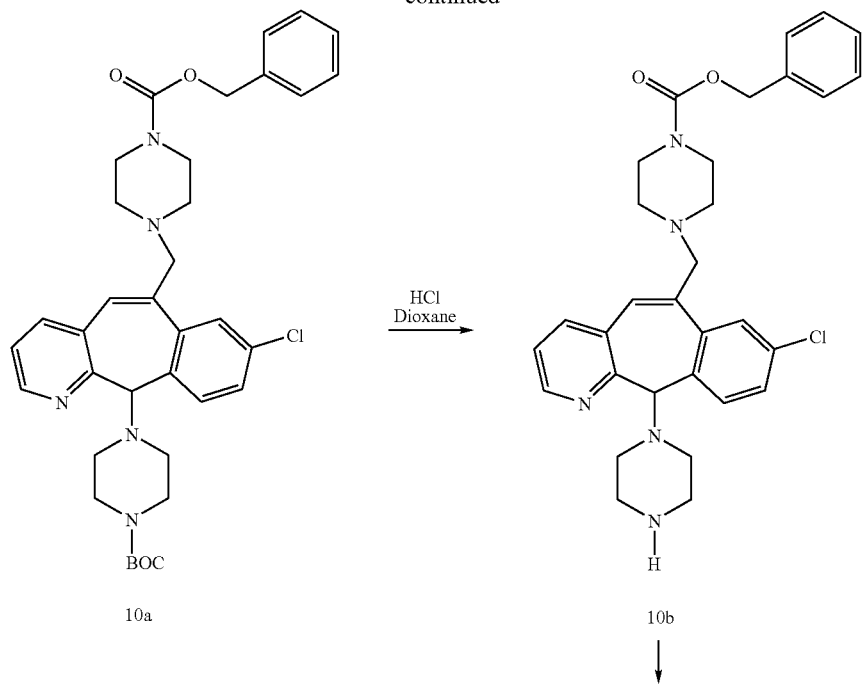

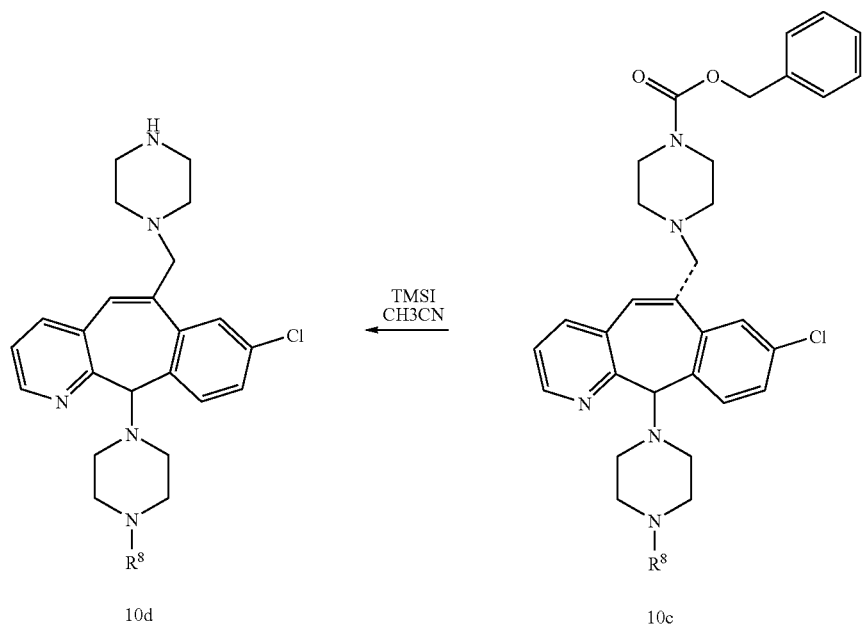

Preparation of piperazine compounds off the bridgehead starts from mesylate aa which is reacted with CBZ-protected piperazine. The BOC group is then removed and the resulting amine 10c is functionalized appropriately. Removal of CBZ group off the piperazine is effected with TMSI.

Mesylate aa is prepared by first carbonylating compound H from Scheme 14 using Pd⁰, triphenyl phosphine, carbon monoxide, DBU, in methanol to give the carboethoxy product. The carboethoxy product is then reduced with lithium aluminum hydride to give the resulting alcohol. This alcohol is converted to the mesylate aa using mesyl chloride and triethylamine.

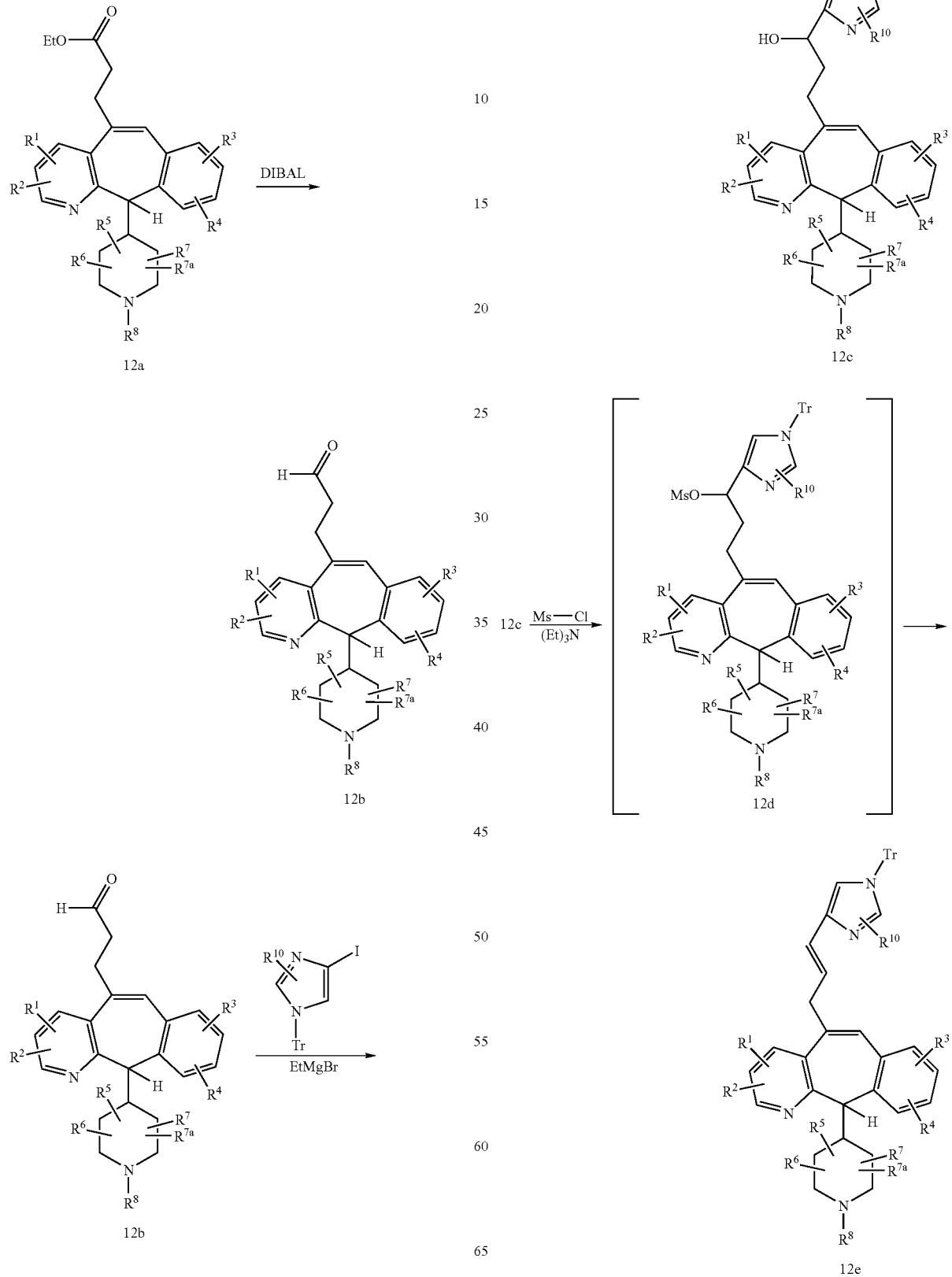

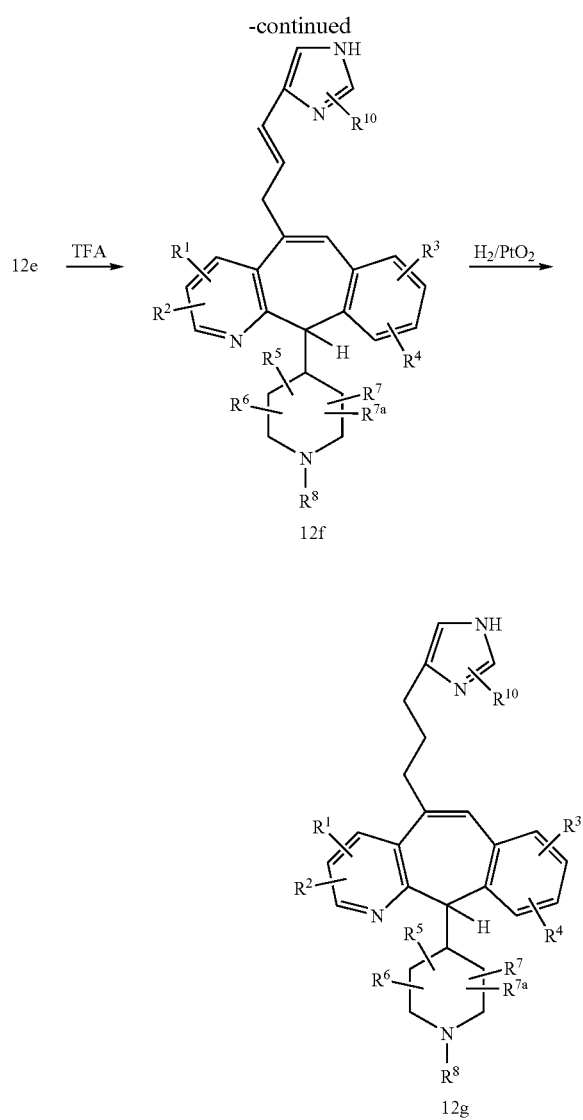

12f

12g

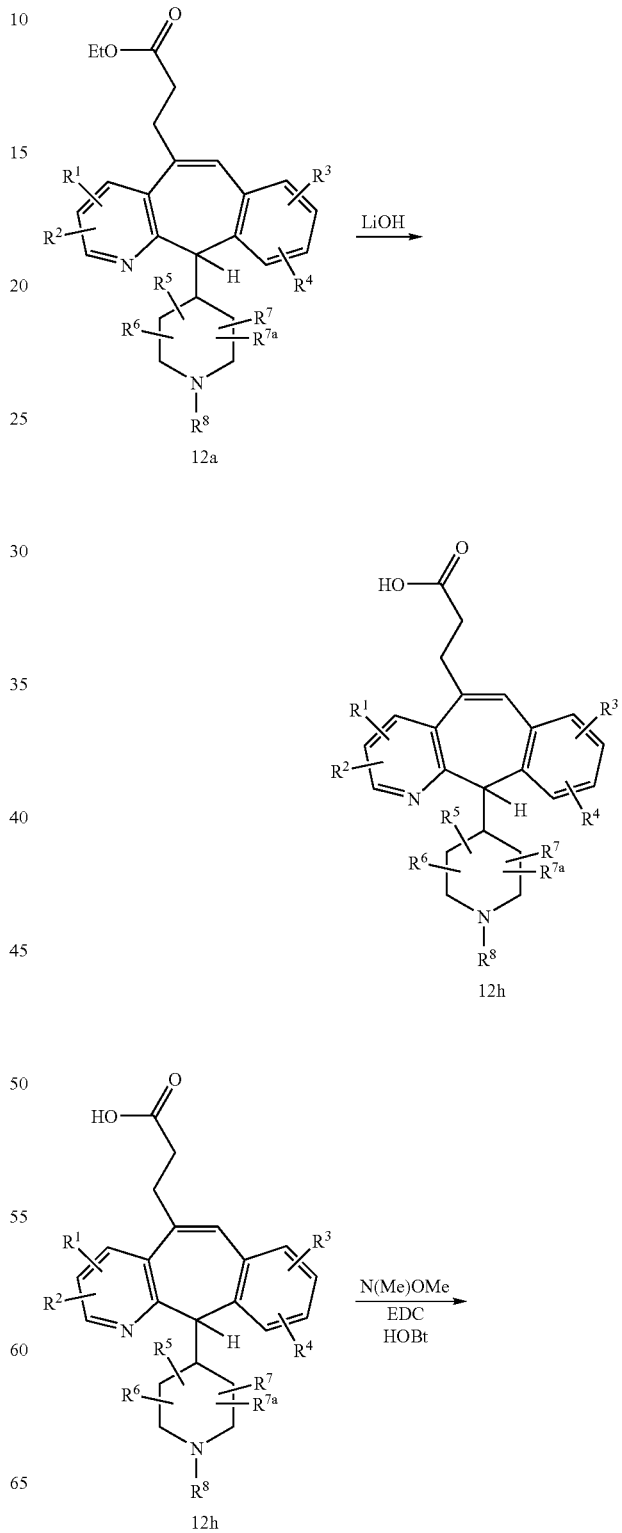

Scheme 12:

12a

12h

12h followed by reaction with an appropriately substituted and tritylated imidazole iodide in the presence of ethylmagnesium bromide in solvents such as dichloromethane at ambient temperature yields the adduct 12c (shown in Scheme 12 below).

Compound 12a is reduced with DIBAL in an inert solvent such as toluene or tetrahydrofuran to give 12b after acidic workup. Treatment of 12b with an appropriately substituted and tritylated imidazole iodide in the presence of ethylmagnesium bromide in solvents such as dichloromethane at ambient temperature yields the adduct 12c. Elimination of the hydroxyl group by converting the hydroxyl group to an appropriate leaving group such as a mesylate, tosylate, or halide, using methanesulfonyl chloride, p-toluenesulfonyl chloride, or thionyl chloride, followed by elimination using an appropriate base such as triethylamine gives 12e. Removal of the trityl group with acid such as trifluoroacetic acid or hydrochloric acid gives the double bond compound 12f which is then hydrogenated using an appropriate catalyst such as platinum oxide under from 1 to 55 psi of hydrogen in an appropriate solvent such as ethanol gave the desired product 12 g.

Alternatively the ester 12a can be saponified with an appropriate base such as lithium hydroxide to obtain the acid 12 h. Converting the acid 12 h to the "Weinreb amide"

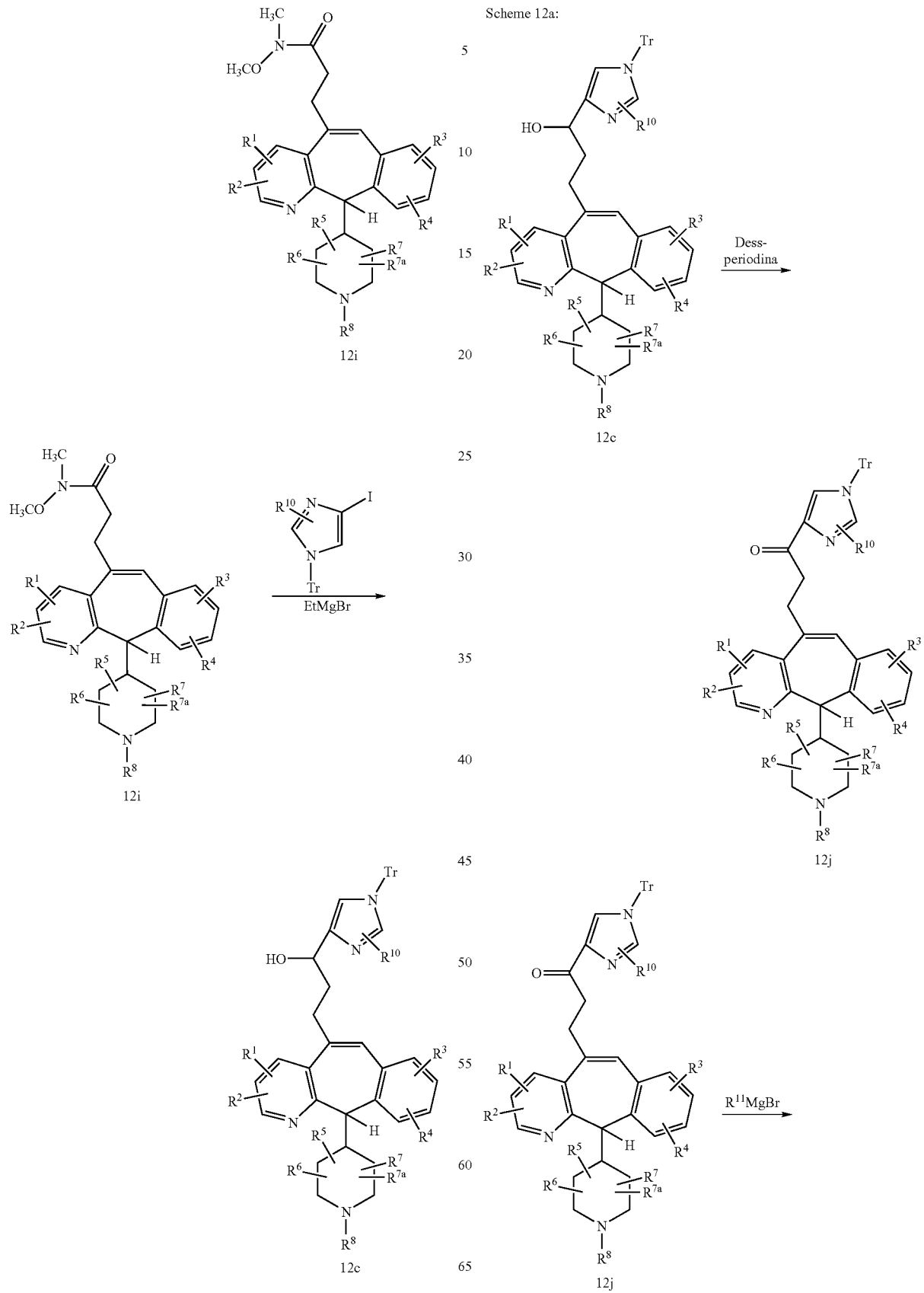

-continued

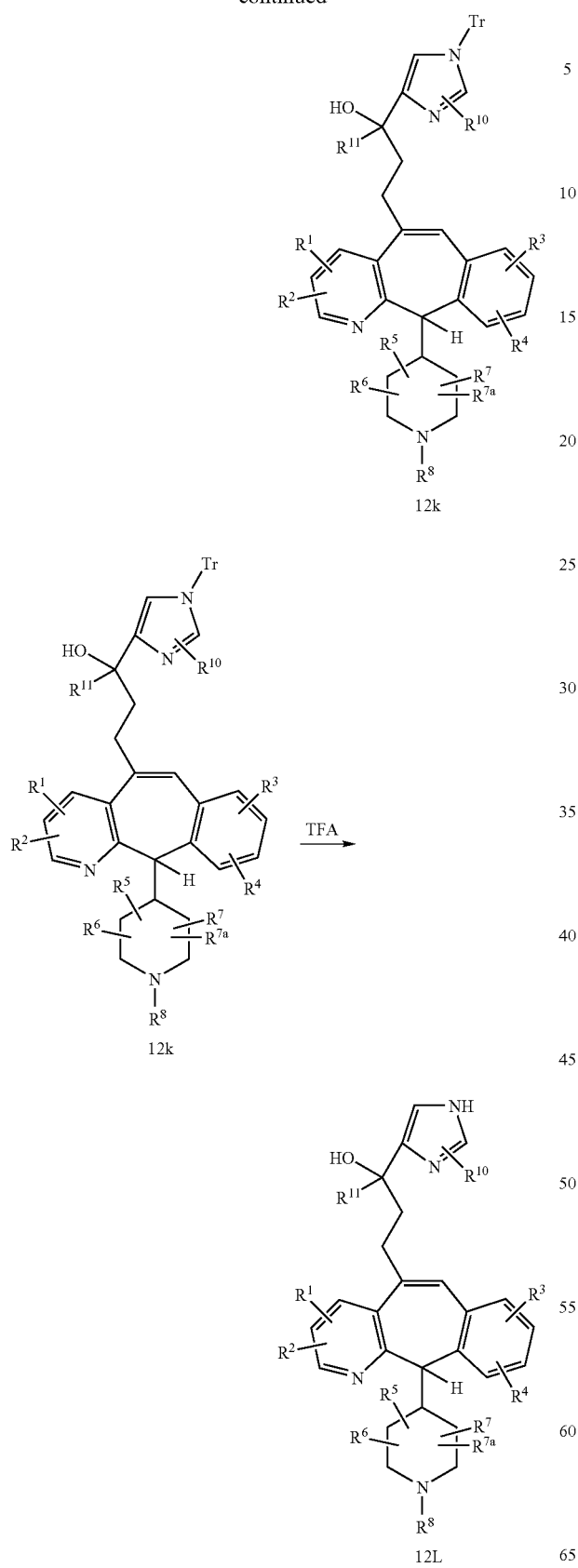

Compounds of type 12L were prepared as shown above. Oxidation of the hydroxyl compound 12c can be accomplished with the Dess Martin periodinane to obtain 12j. Reaction with a grignard reagent gave 12 k. The trityl group is removed under standard conditions mentioned above to give the desired compound 12L.

Scheme 13:
C-Substituted Imidazole Single Methylene Bridgehead Compounds

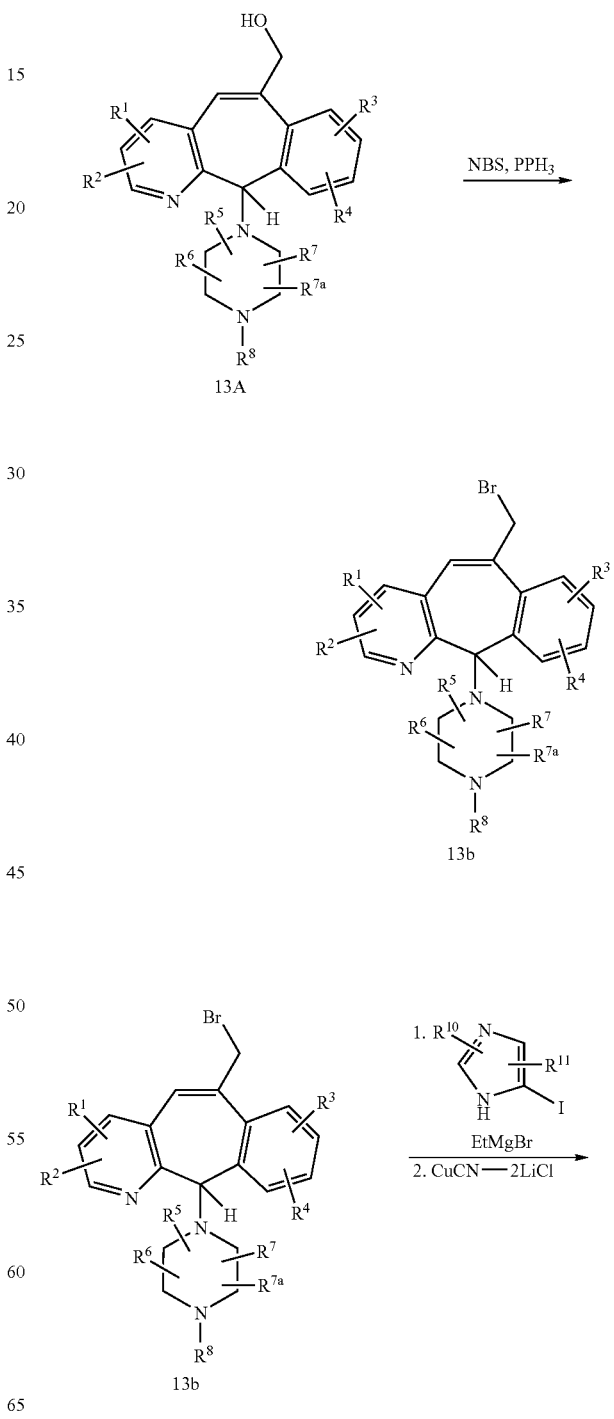

-continued

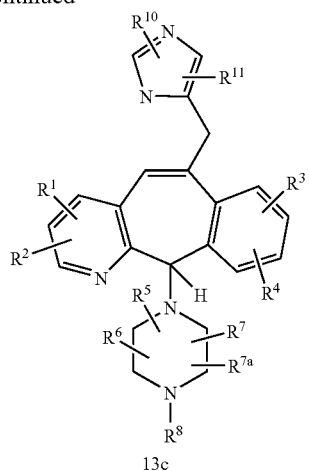

13c

Single methylene bridgehead C-Imidazole derivatives (13c) were prepared as shown above. Compound 13a was first converted to bromide 13b. Treatment of compound 13b with C-imidazole cuprates (prepared from corresponding iodo imidazole) yielded the adduct 13c.

Scheme 14: Preparation of One-methylene Piperazines

Ketone A is brominated with brominating reagents such as NBS, with a small amount of an activator such as benzoyl peroxide, in solvents such as dichloromethane at elevated temperature, such as 80-100° C. to give dibromo compound B.

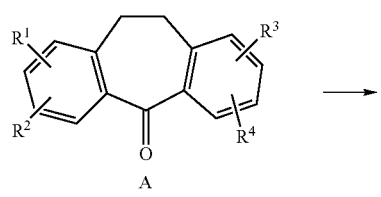

A

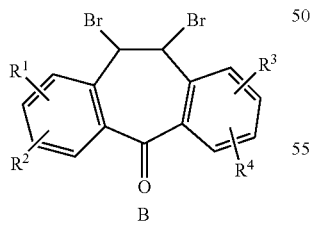

B

Dibromo compound B is reacted with a base such as DBU in a solvent such as dichloromethane at temperatures from 0° C. to room temperature to give vinylbromides C and D. These vinylbromides are separated by chromatography such as silica gel flash chromatography using solvents mixtures such as ethyl acetate and hexane. Alternatively, vinylbromides C and D can be separated by crystallization from solvents such as dichloromethane.

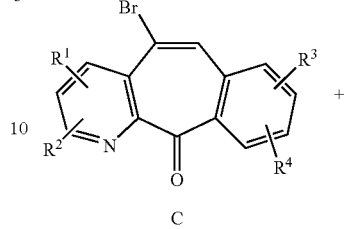

C

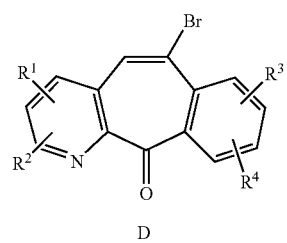

D

The ketone groups of separated vinylbromides C and D are reduced to the corresponding alcohols E and F with a reducing agent such as NaBH$_4$ in solvents such as methanol or ethanol at temperatures of 0° C. to room temperature.

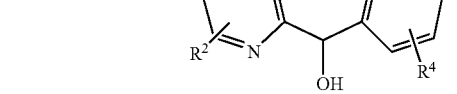

E

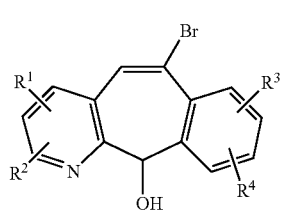

F

The resulting alcohols functions of E and F are converted to a leaving group, such as a halide, with reagents such as SOCl$_2$ in solvents such as dichloromethane containing a base such as 2,6-lutidine and running the reaction at 0° C. to room temperature. The resulting intermediate halides are reacted, without purification, with piperazine or a protected piperazine, such as BOC-piperazine in a solvent such as dichloromethane at room temperature giving intermediates G and H.

G

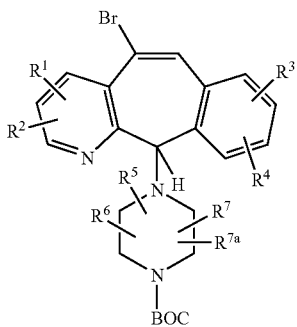

H

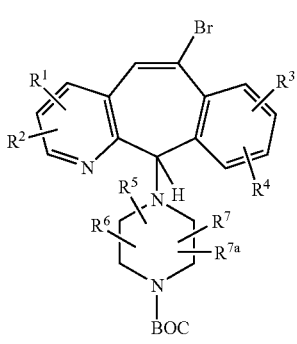

The vinylhalide intermediates are carbonylated with CO gas under a pressure of about 100 psi and a temperature of 80° C. to 100° C. using a palladium catalyst such as $PdCl_2$ and triphenyl phosphine in toluene and containing DBU and an alcohol such as methanol. If methanol is used, methyl esters I and J are obtained.

I

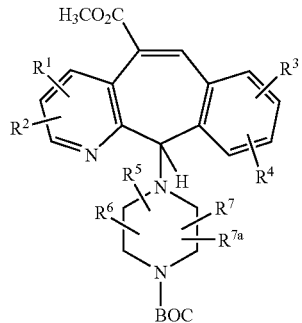

J

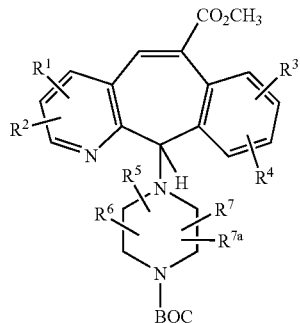

The ester functions are of I and J are reduced to hydroxymethyl functions of K and L. This can be done directly by first removing the protecting BOC group with TFA or HCl-dioxane and then reducing with a reducing agent such as DIBAL-H, followed by reintroduction of the BOC group with di-tert-butyl dicarbonate. Alternatively, the ester function is hydrolyzed with LiOH and water followed by neutralization with citric acid. The resulting carboxylic acids are then converted into a function that is easily reduced, such as a mixed anhydride or an acyl imidazole. This is done by reacting the resulting carbocylic acids with a chloroformate to form the mixed anhydride or with carbonyldiimidazole to form the acyl imidazole (Synlett. (1995), 839). The resulting activated carboxylic acids are reduced with $NaBH_4$ in solvents such as methanol, ethanol or aqueous THF.

K

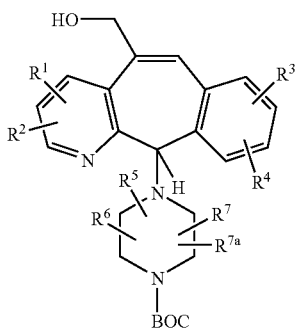

L

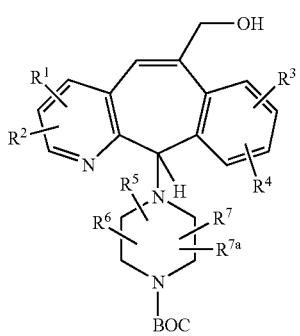

The hydroxy functions of K and L are converted into leaving groups such as a methanesulfonate or an arylsulfonate such as a tosylate, by reacting with the appropriate sulfonyl chloride in dichloromethane containing a base such as triethylamine. The sulfonate leaving groups can be displaced by nucleophiles such amines. The nucloephile (Nuc in structures O and P below) can also be basic heterocycles such as imidazole or a substituted imidazole. In the case of an imidazole, the anion of the imidazole is first formed with NaH in DMF and then reacted with the above sulfonate. Displacement of the sulfonates with a nucleophile gives O and P, which can be converted to the compounds of this invention 1.0, by first removing the BOC protecting group and then forming the desired amide, urea, carbamate or sulfonamide on the resulting amine by methods well known in the art.

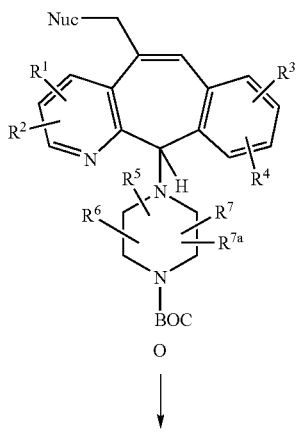

Formula (1.0)

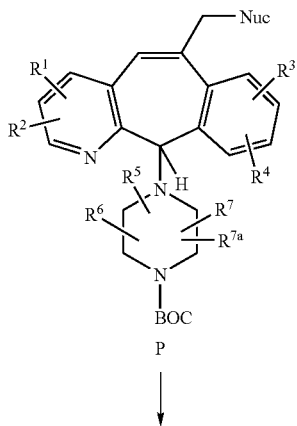

Formula (1.0)

Scheme 15:
Preparation of one-methylene piperidenes

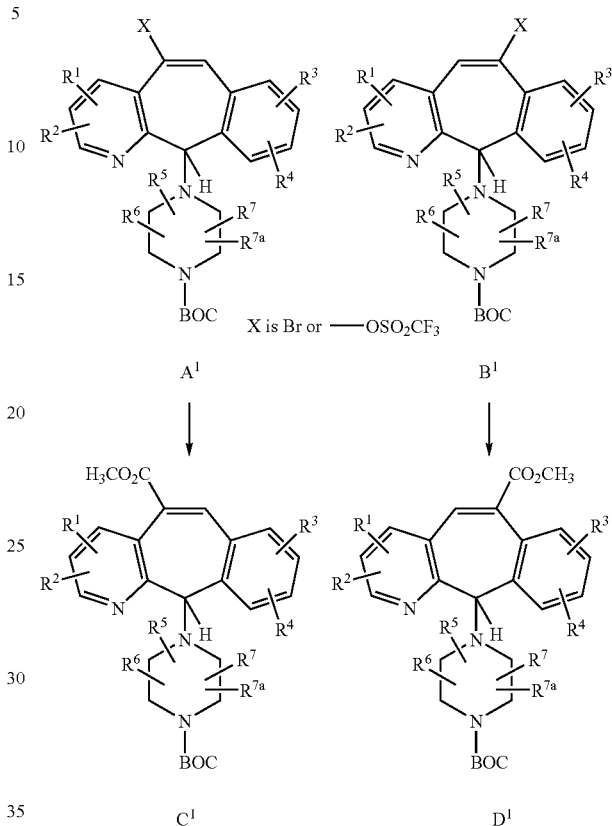

The vinylhalide or vinyltriflate intermediates $A^1$ and $B^1$ (Scheme 10) are carbonylated with CO gas under a pressure of about 100 ps; and a temperature of 80° C. to 100° C. using a palladium catalyst such as $PdCl_2$ and triphenyl phosphine in toluene and containing DBU and an alcohol such as methanol. If methanol is used, methyl esters $C^1$ and $D^1$ are obtained. Intermediates $C^1$ and $D^1$ are reacted as are intermediates $I^1$ and $J^1$ (see Scheme 15a below) following essentially the same procedure as in Scheme 14 to yield compounds of Formula 1.0 of this invention.

Scheme 15a:

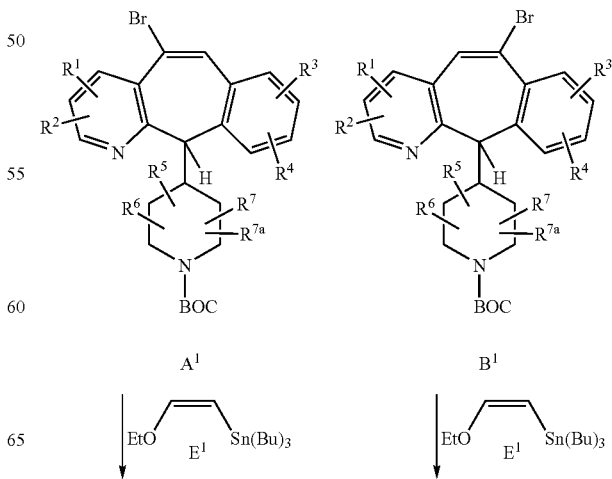

-continued

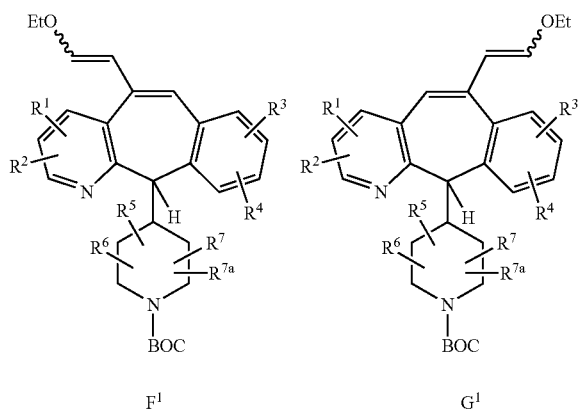

F¹   G¹

Alternatively, Intermediates A¹ and B¹ can be reacted with tin vinylether E¹, in the presence of PdCl$_2$, as described in Tetrahedron, (1991), 47, 1877, to yield vinylethers F¹ and G¹ (Scheme 15a). Allowing F¹ and G¹ to stand until aldehyde is visible by NMR (at least two weeks) and then reacting with Hg(OAc)$_2$, KI followed by NaBH$_4$, as described in J. Chem. Soc., Perkin Trans., (1984), 1069 and Tet. Lett., (1988), 6331, yields mixtures H¹, I¹ and J¹, and K¹. Intermediates H¹ and J¹ are separated and reacted, as are intermediates K¹ and L¹, following essentially the same procedure as in Scheme 14 to yield compounds of Formula 1.0, of this invention.

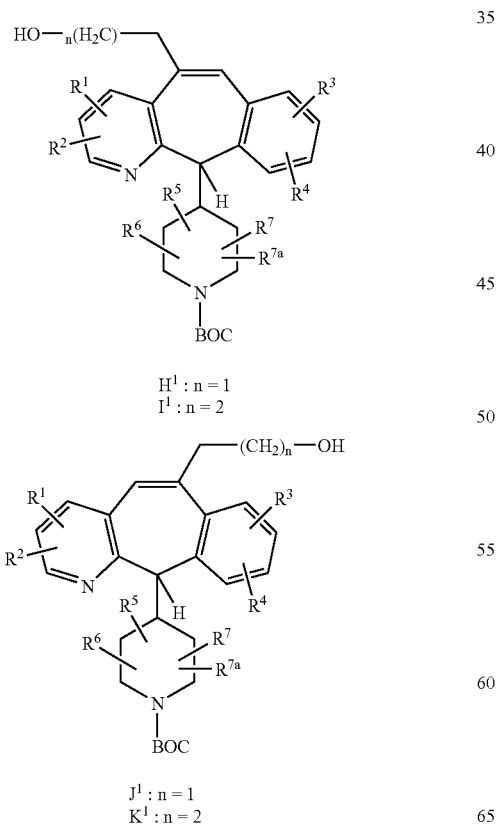

H¹ : n = 1
I¹ : n = 2

J¹ : n = 1
K¹ : n = 2

Those skilled in the art will appreciate that Schemes 11, 12, 12a, 13, 14, 15 and 15a using reactants having the moieties

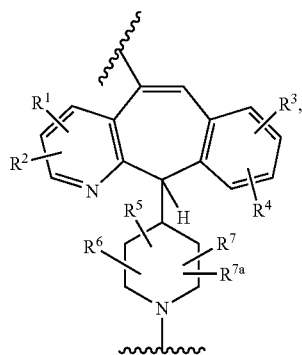

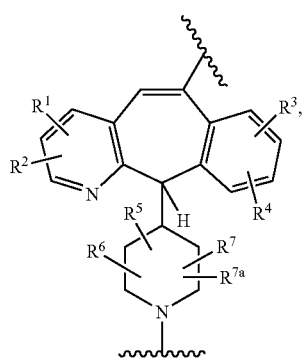

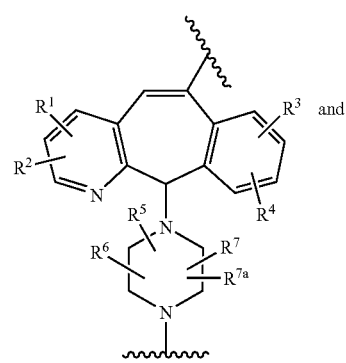 and

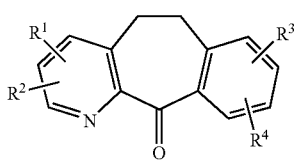

(related to formula 1.0), for example, are also representative of reactants having the moieties:

217                                                             218
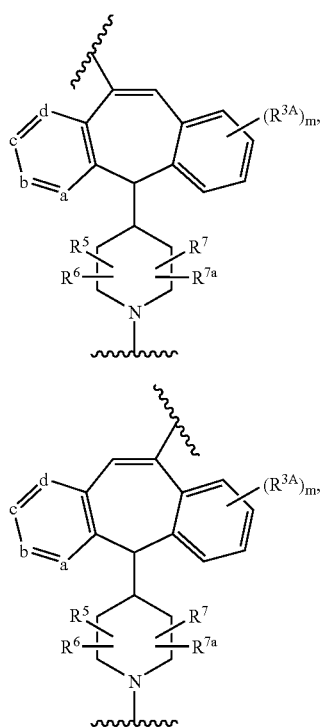
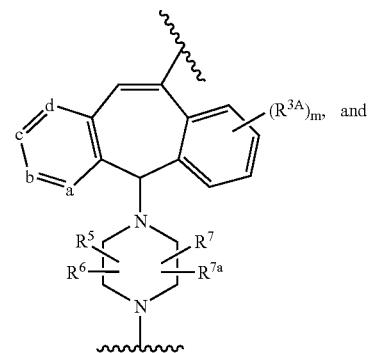
-continued
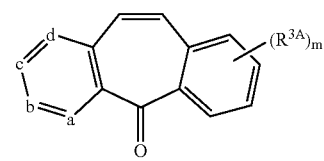
(related to compounds of formula 1.1).
Scheme 16:
Branching on the methylene chain
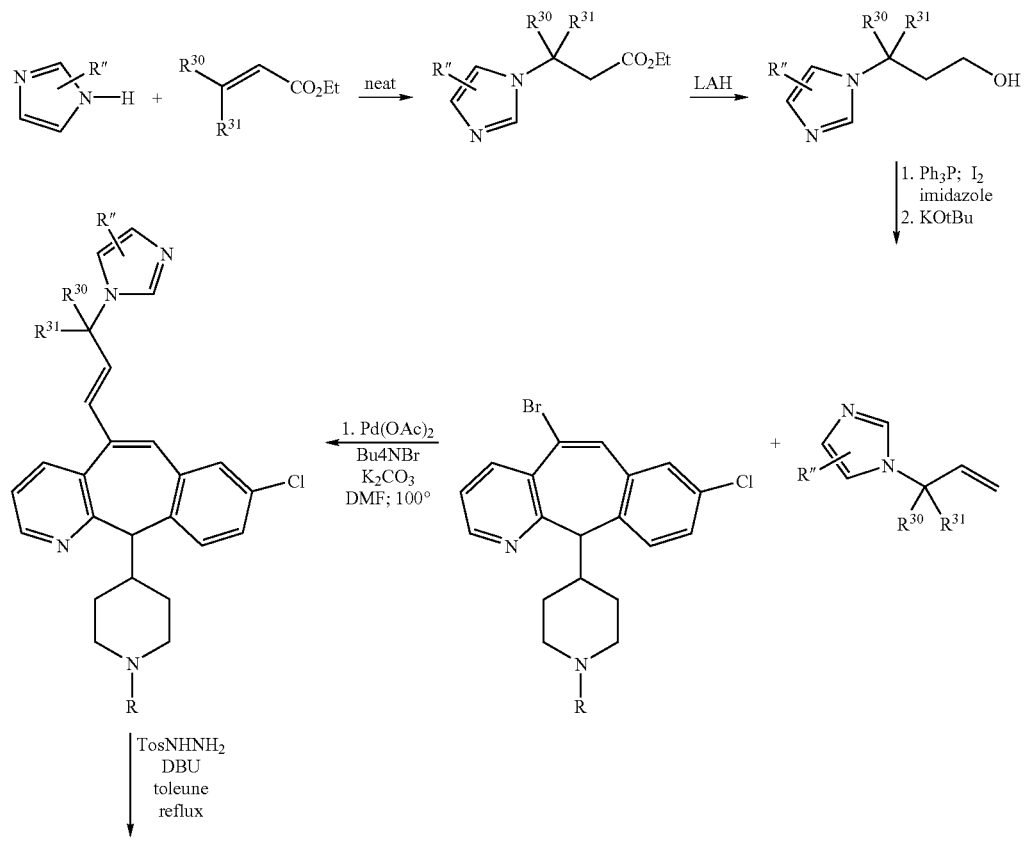

-continued

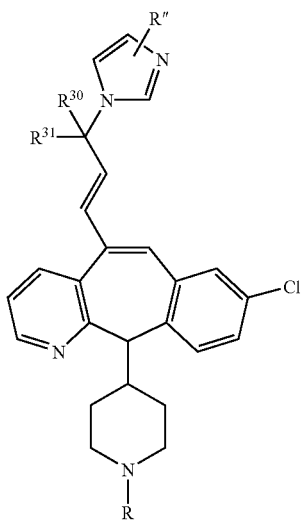

(wherein R represents $R^8$, and $R^{11}$ represents $R^{10}$)

In Scheme 16, compounds with substitution along the chain can be synthesized starting with a substituted ethyl acrylate derivative. Addition of imidazole across the olefin followed by reduction gives the terminal alkene, which can be added to the appropriately substituted vinyl bromide under Heck reaction conditions. Selective reduction of the di-substituted olefin gives the saturated derivative.

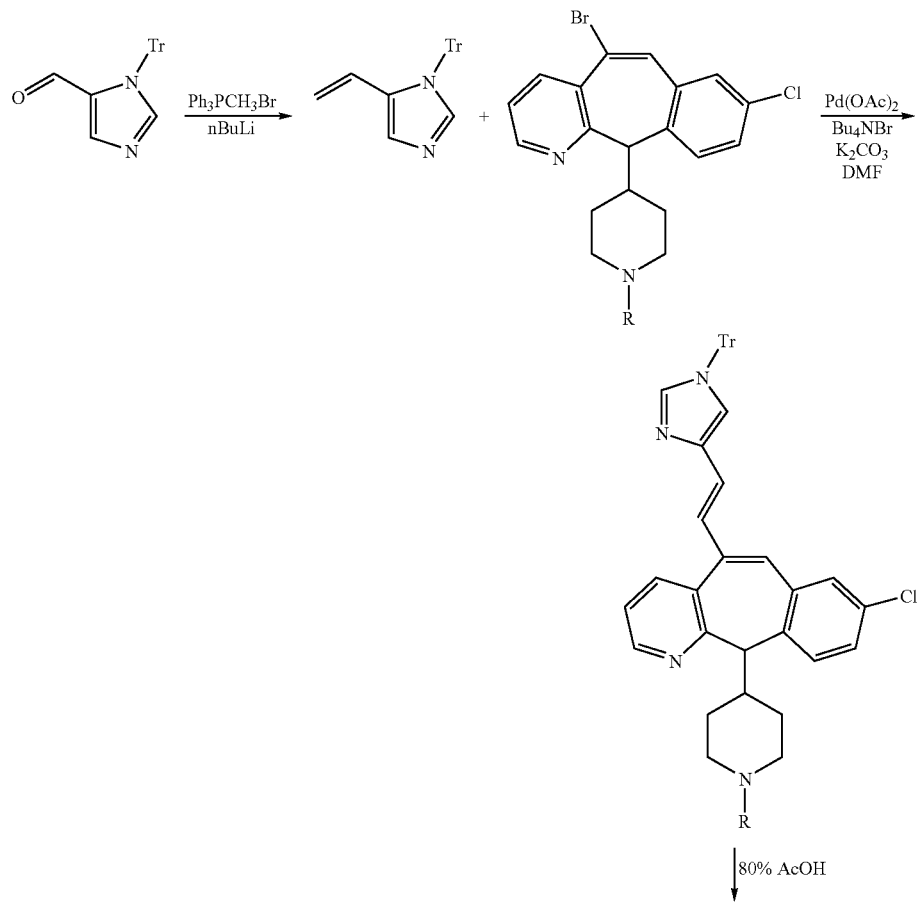

Scheme 17:
C-linked imidazoles

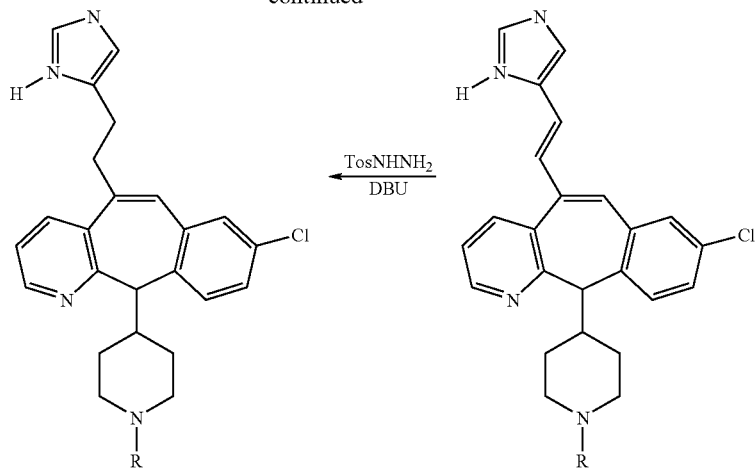

(wherein R represents R[8])

In Scheme 17, the synthesis of the C-linked imidazoles proceeds through the Heck reaction of the appropriately substituted vinyl imidazole with the appropriate vinyl bromide. Selective reduction of the resulting di-substituted olefin gives the target compound. A similar procedure can be carried out with differentially N-substituted imidazoles to give N-alkyl imidazole derivatives.

Suberyl Compounds

One skilled in the art will appreciate that the compounds of the invention represented by Formula 1.0, wherein a, b, c and d are C (or a, b, c, and d are CR[1] in formula 1.1) can be prepared according to Scheme 18:

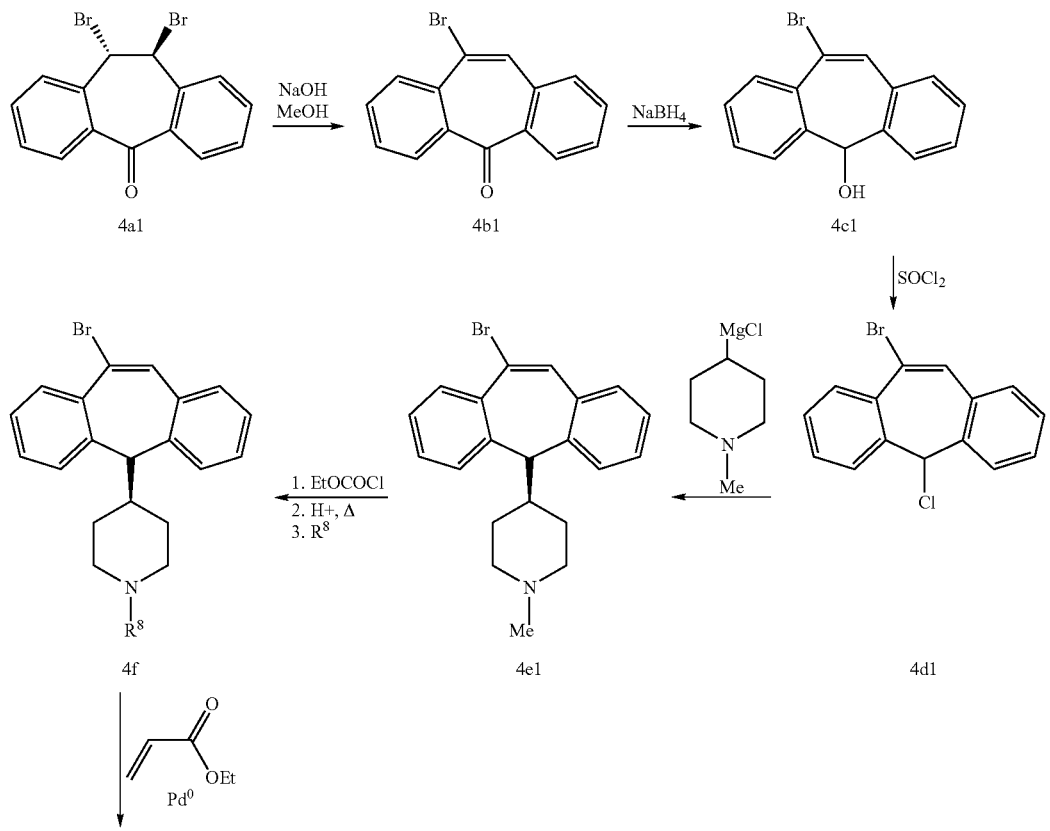

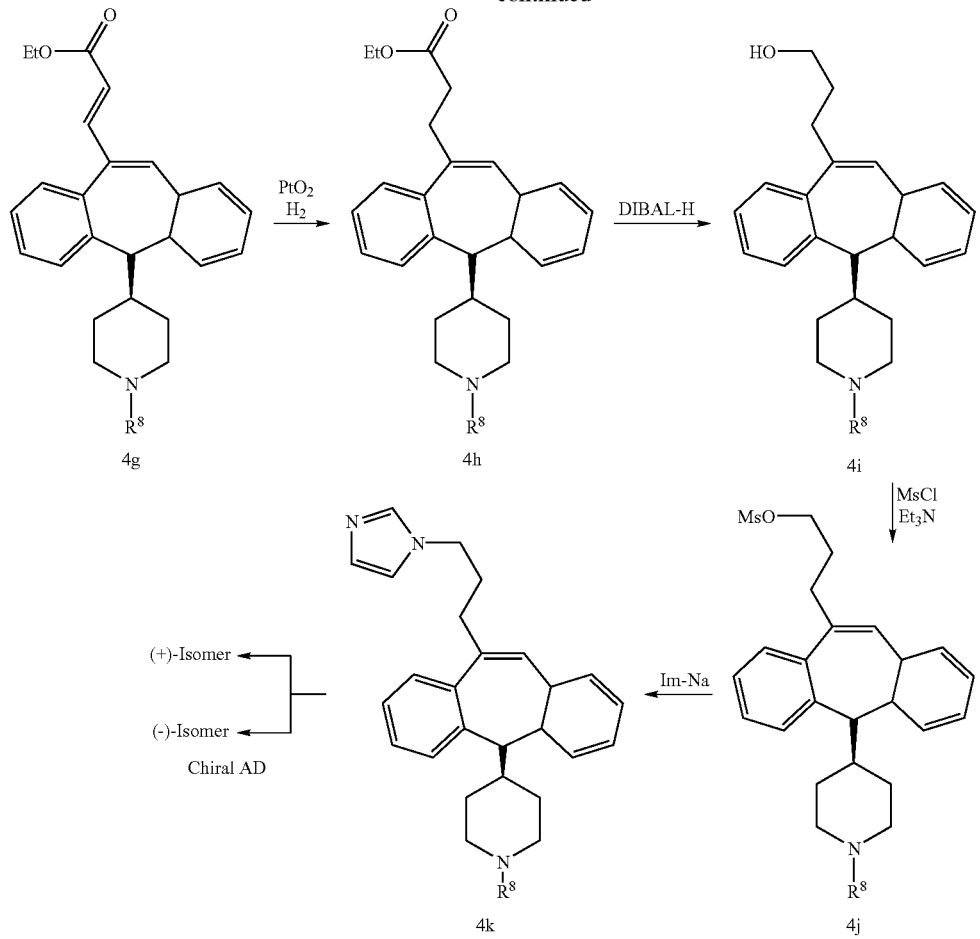

Tricyclic vinyl bromide azaketone 4b was prepared as described by Rupard et. al. (*J. Med. Chem.* 1989, 32, 2261-2268). Reduction of ketone to alcohol 4c was carried out with NaBH₄. The alcohol was converted to chloride 4d and then treated with N-methylpiperidine Grignard reagent to give piperidine derivative 4e. Demethylation was effected with ethyl chloroformate followed by acid hydrolysis and subsequent derivitization (i.e sulfonylation, acylation and carbomylation etc.). Preparation of compounds with 3-carbon substituted imidazole moieties on the suberane trycyclic bridgehead was carried out in a similar way as described in scheme 3.

Scheme 19:

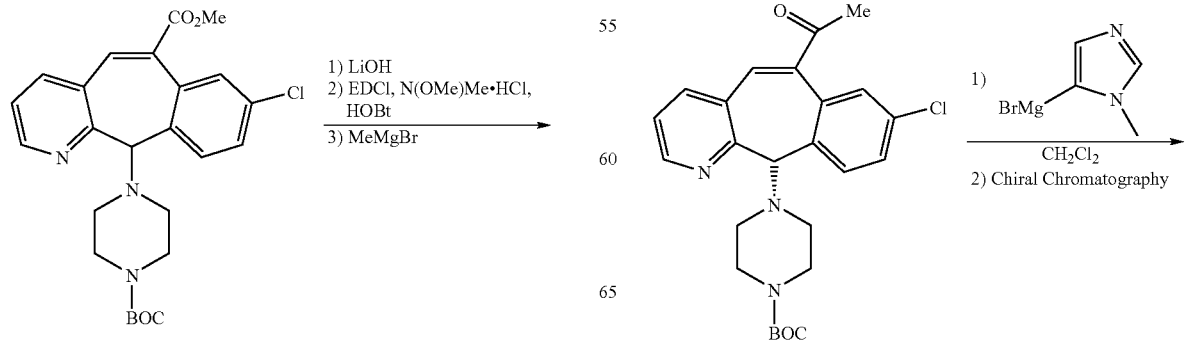

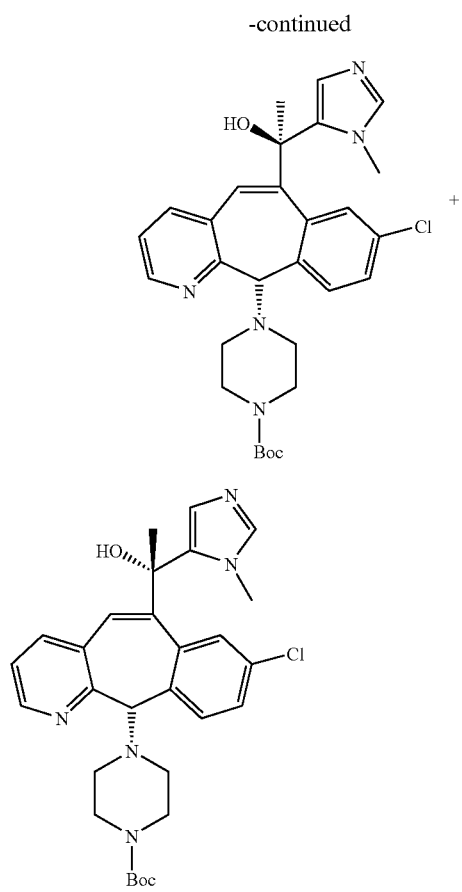
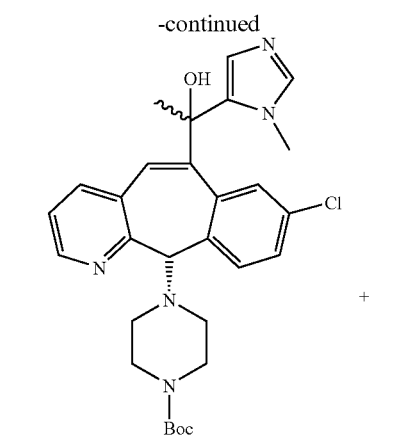
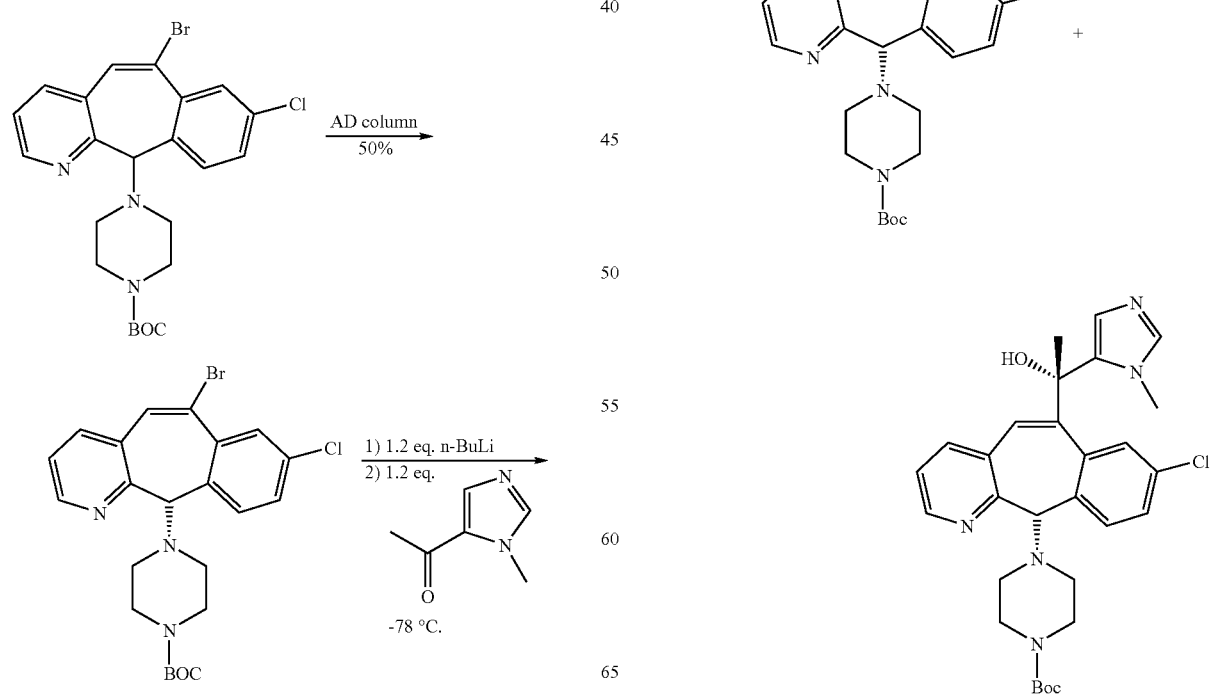
Scheme 20:

Scheme 21:
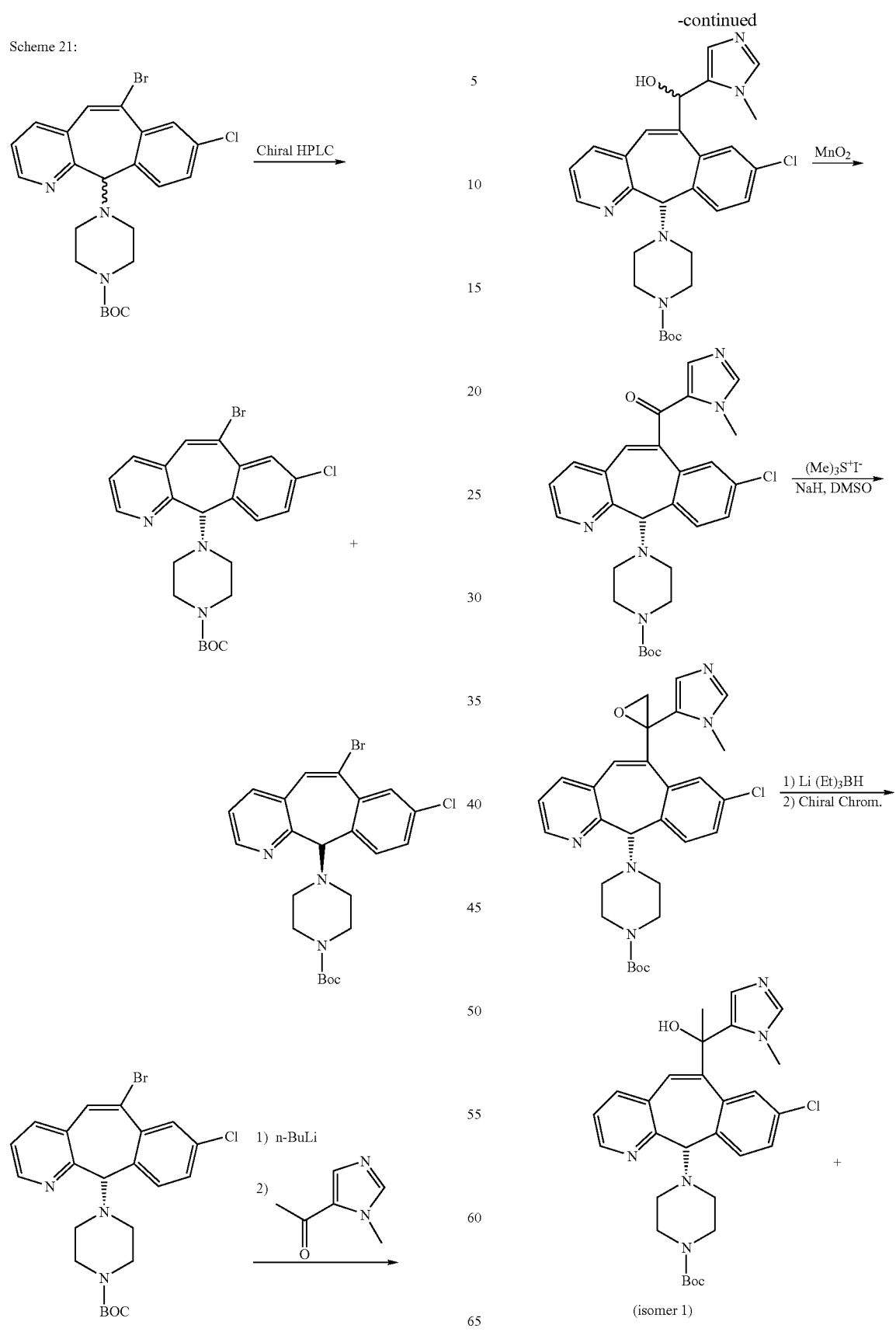

229
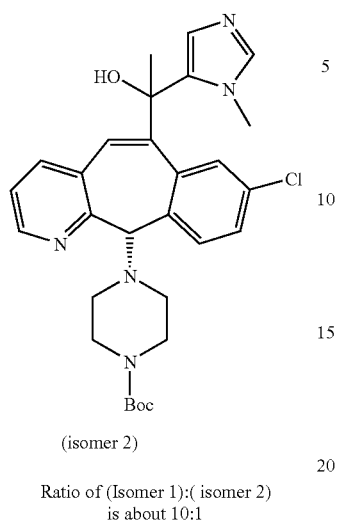
(isomer 2)
Ratio of (Isomer 1):(isomer 2) is about 10:1
Preparation of substituted 5-acetyl-imidazoles
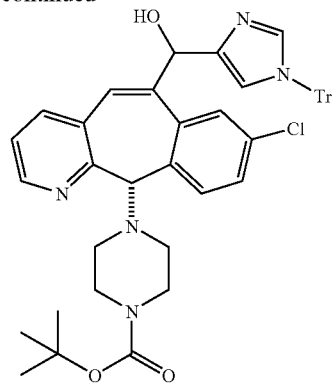
Scheme 22:
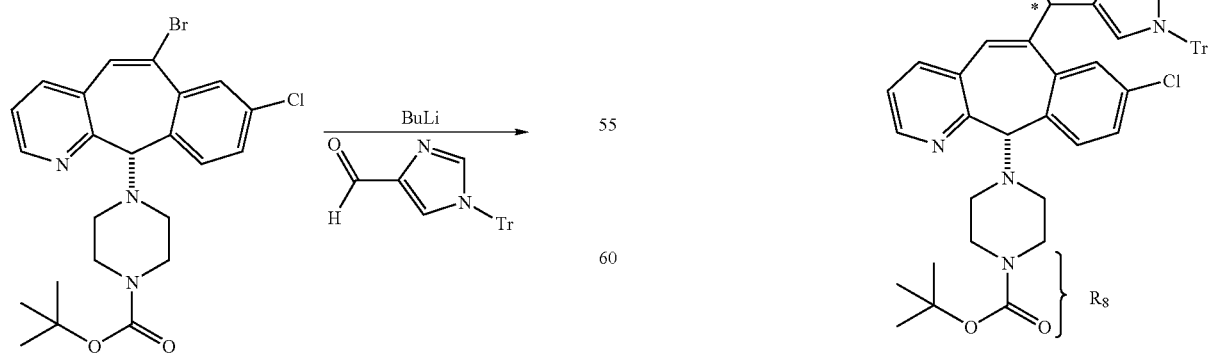
230
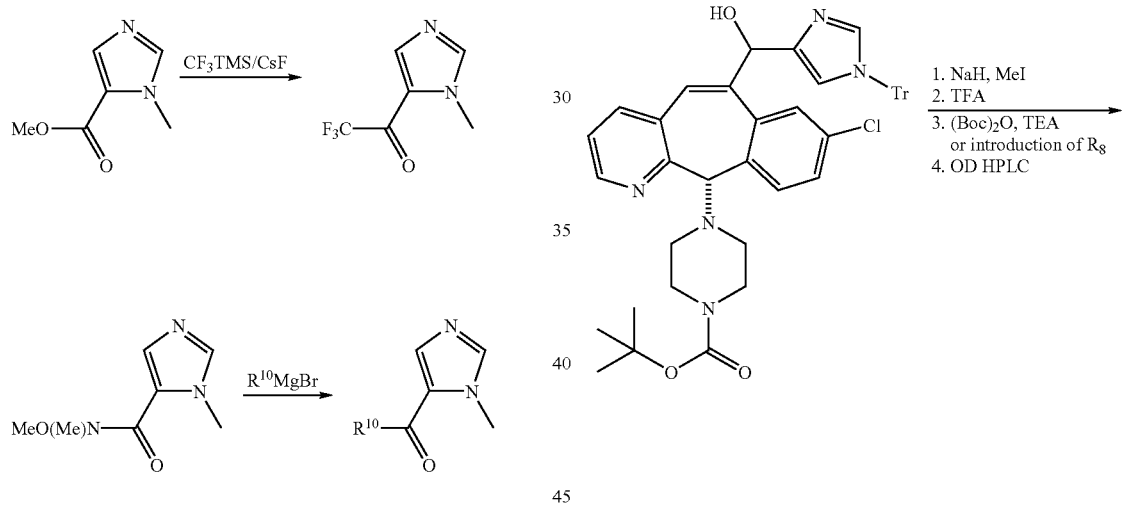
\* Chiral center, formula represents Isomer 1 or Isomer 2

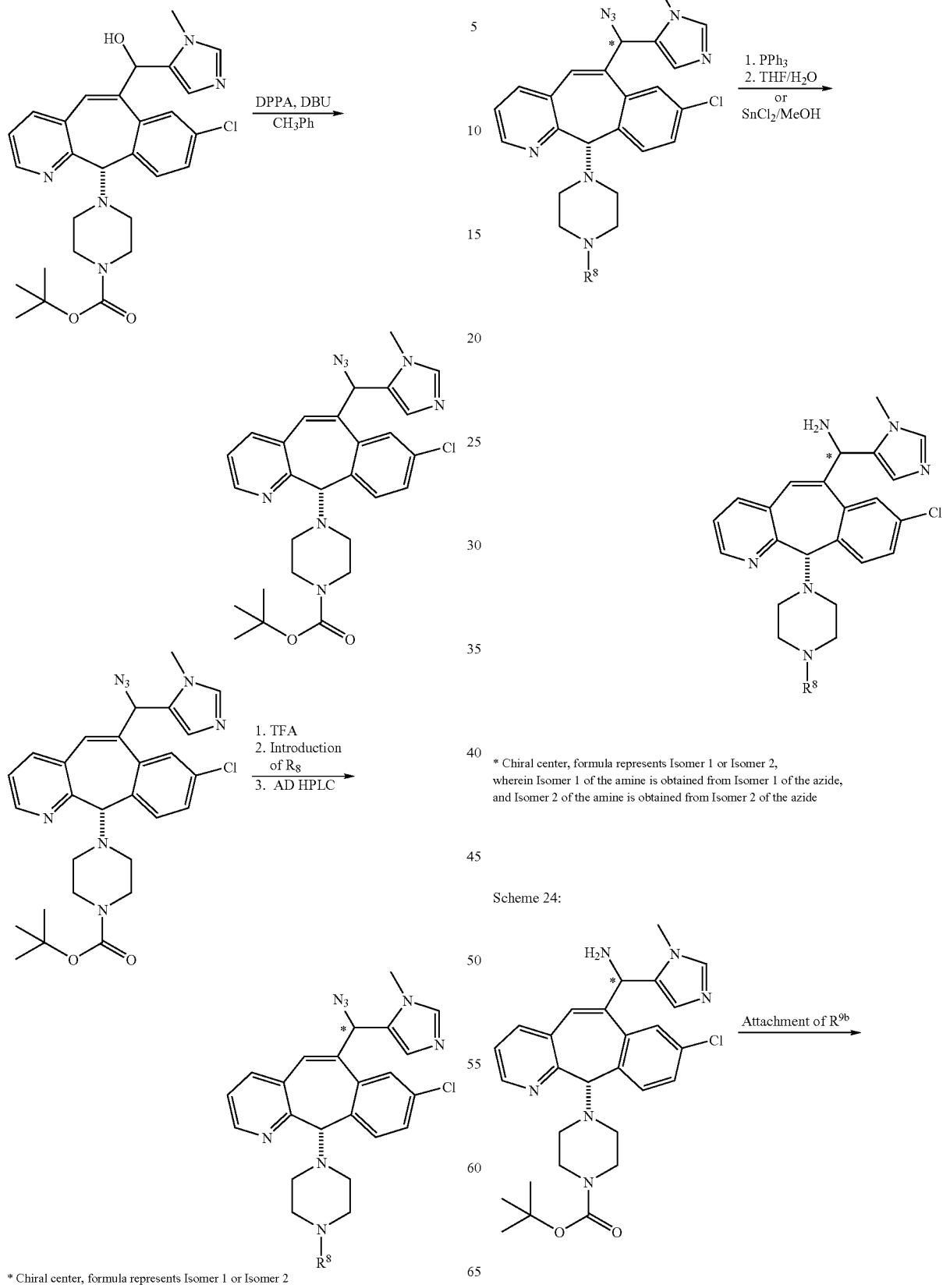

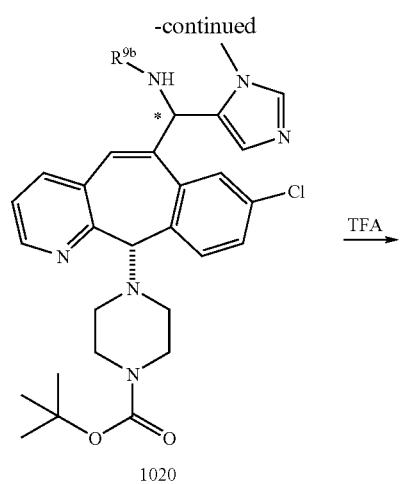

1020

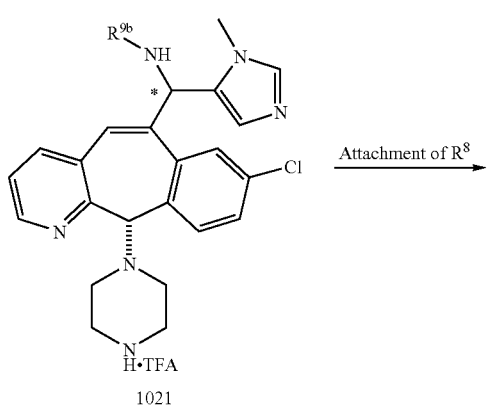

1021

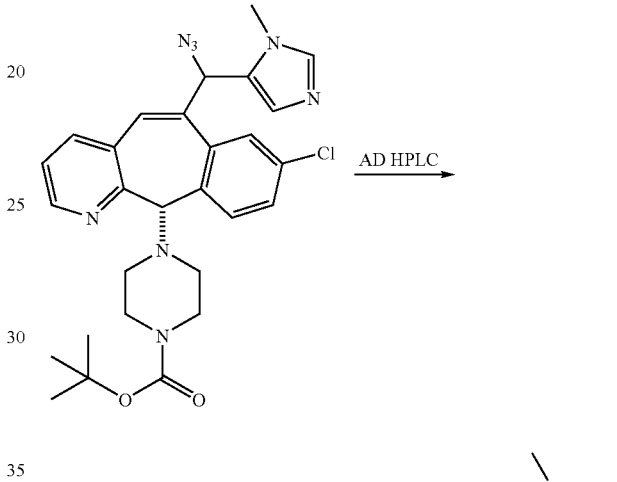

1022

* Chiral center, formula represents Isomer 1 or Isomer 2, wherein Isomer 1 of 1022 is obtained from Isomer 1 of the starting amine, and Isomer 2 of 1022 is obtained from Isomer 2 of the starting amine Each isomer (Isomer 1 and Isomer 2) of the starting amine was reacted with an acid chloride or anhydride to obtain an amide group, with an isocyarate to obtain a urea, with an chlorocarbonate to obtain a carbamate, with a sulfonylchloride to obtain a sulfonamide in an appropriate solvent such as dichloromethane and an equal equivalent of base such as triethylamine to obtain the desired product compound 1020. Compound 1020 can then be treated with trifluoroacetic acid to obtain compound 1021. Compound 1021 can then be reacted with an acid chloride or anhydride to obtain an amide group, with an isocyanate to obtain a urea, with an chlorocarbonate to obtain a carbamate, with a sulfonylchloride to obtain a sulfonamide in an appropriate solvent such as dichloromethane and an equal equivalent of base such as triethylamine to obtain the desired product compound 1022.

Scheme 25:

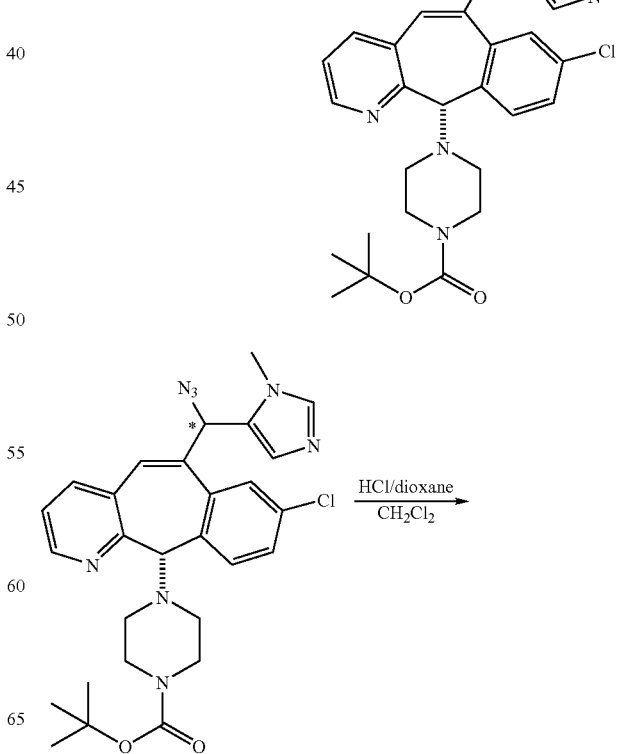

-continued
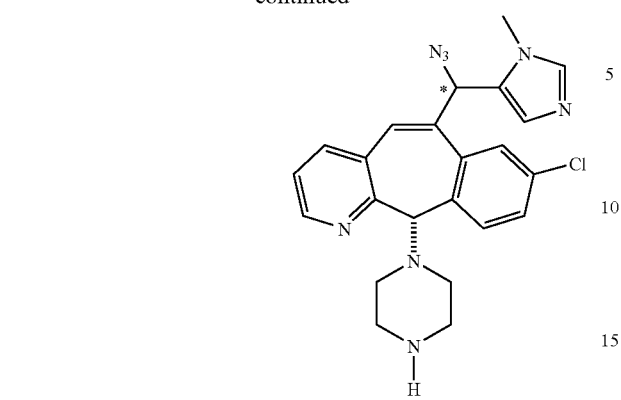
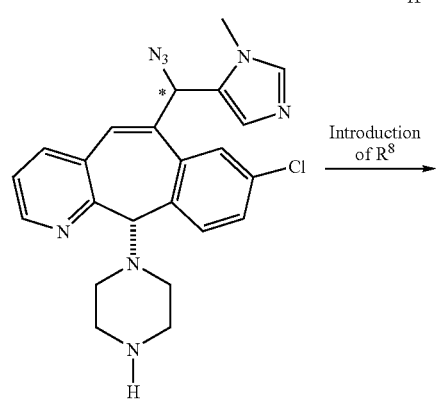
* Chiral center, formula represents Isomer 1 or Isomer 2
Scheme 26:
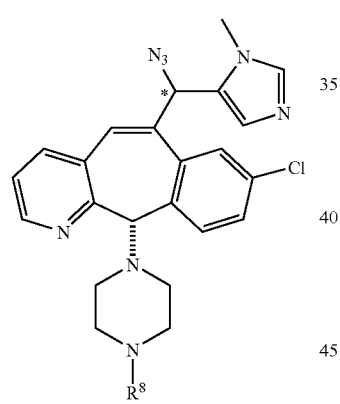
-continued
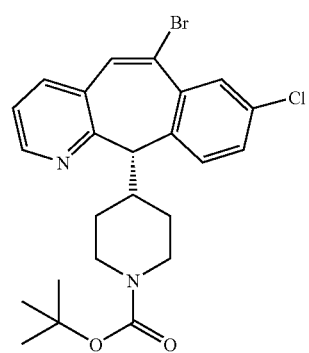
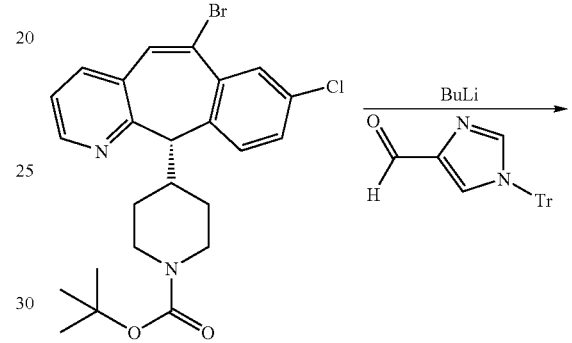
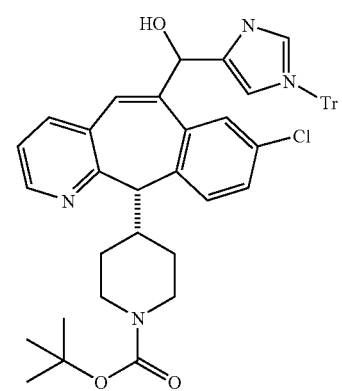
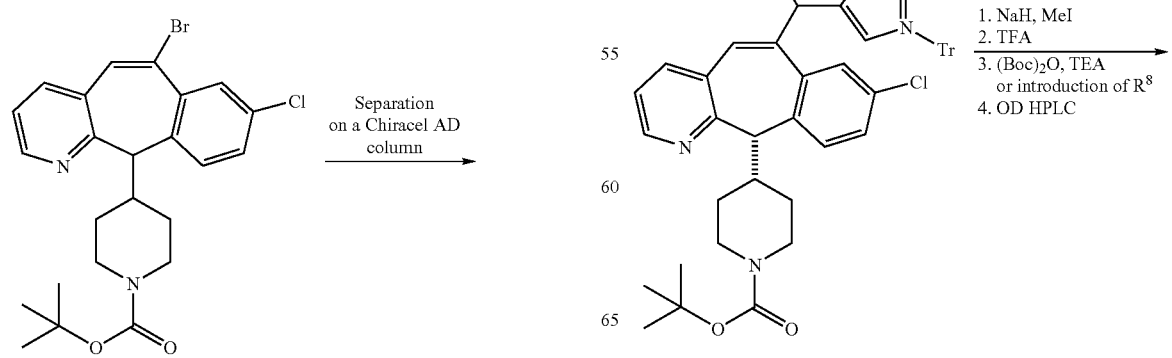

237
-continued
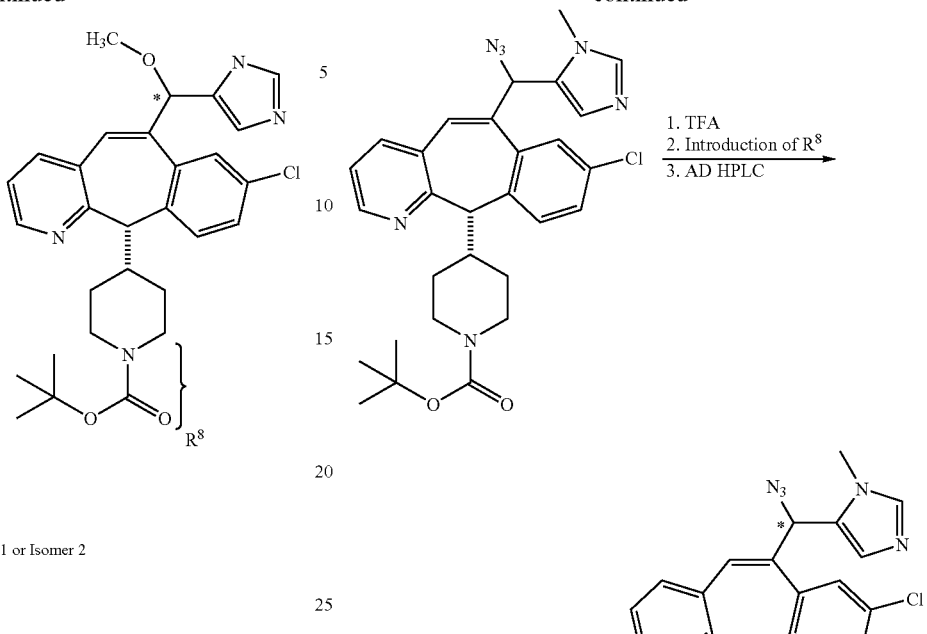
* Chiral center, formula represents Isomer 1 or Isomer 2
Scheme 27:
238
-continued
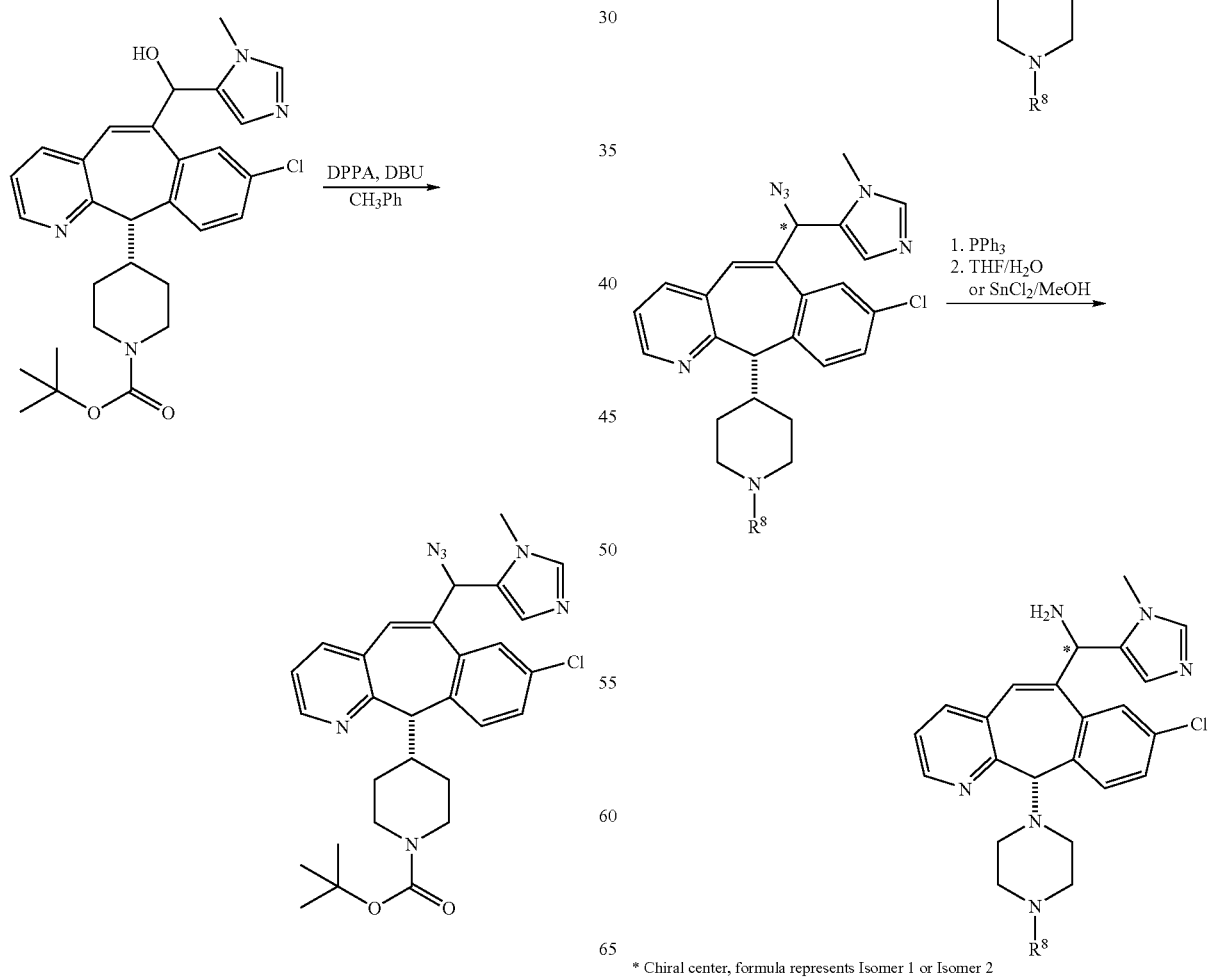
* Chiral center, formula represents Isomer 1 or Isomer 2

Scheme 28:
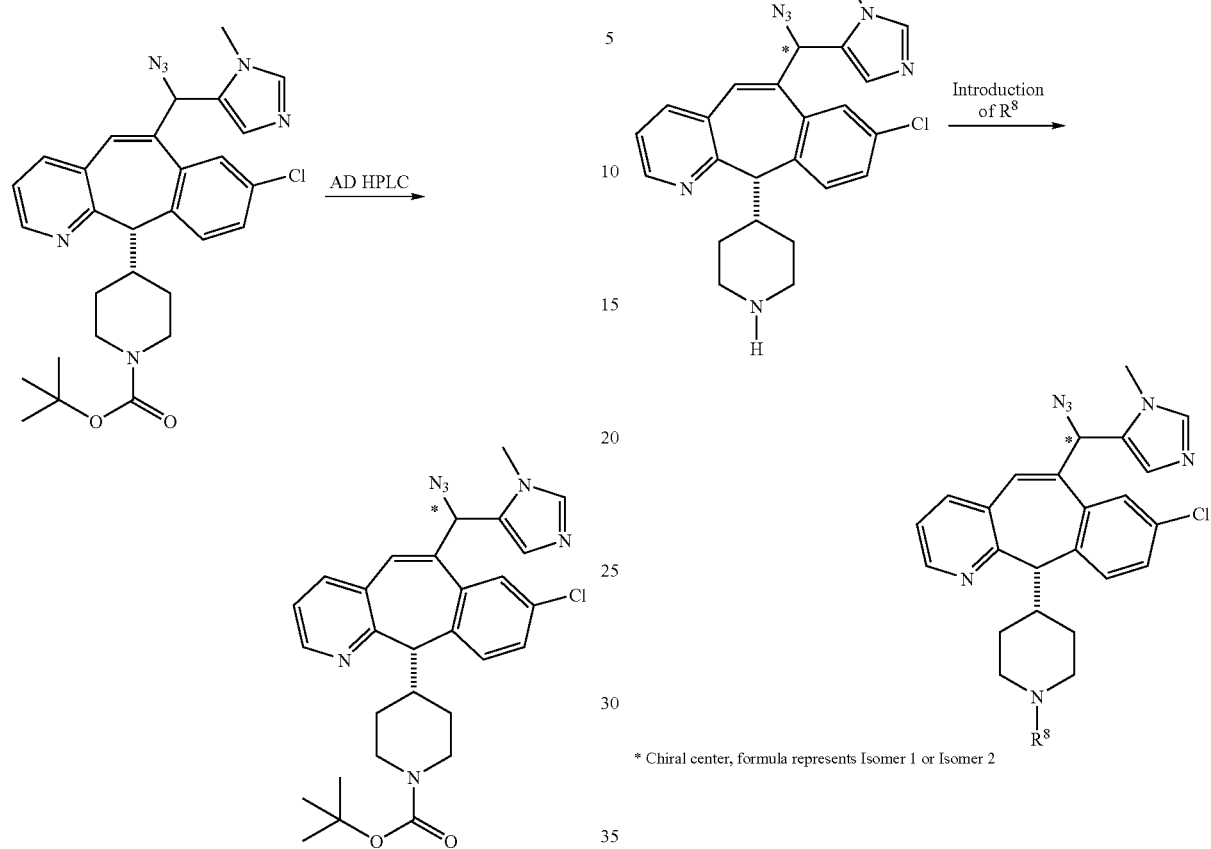
*Chiral center, formula represents Isomer 1 or Isomer 2
Scheme 29:
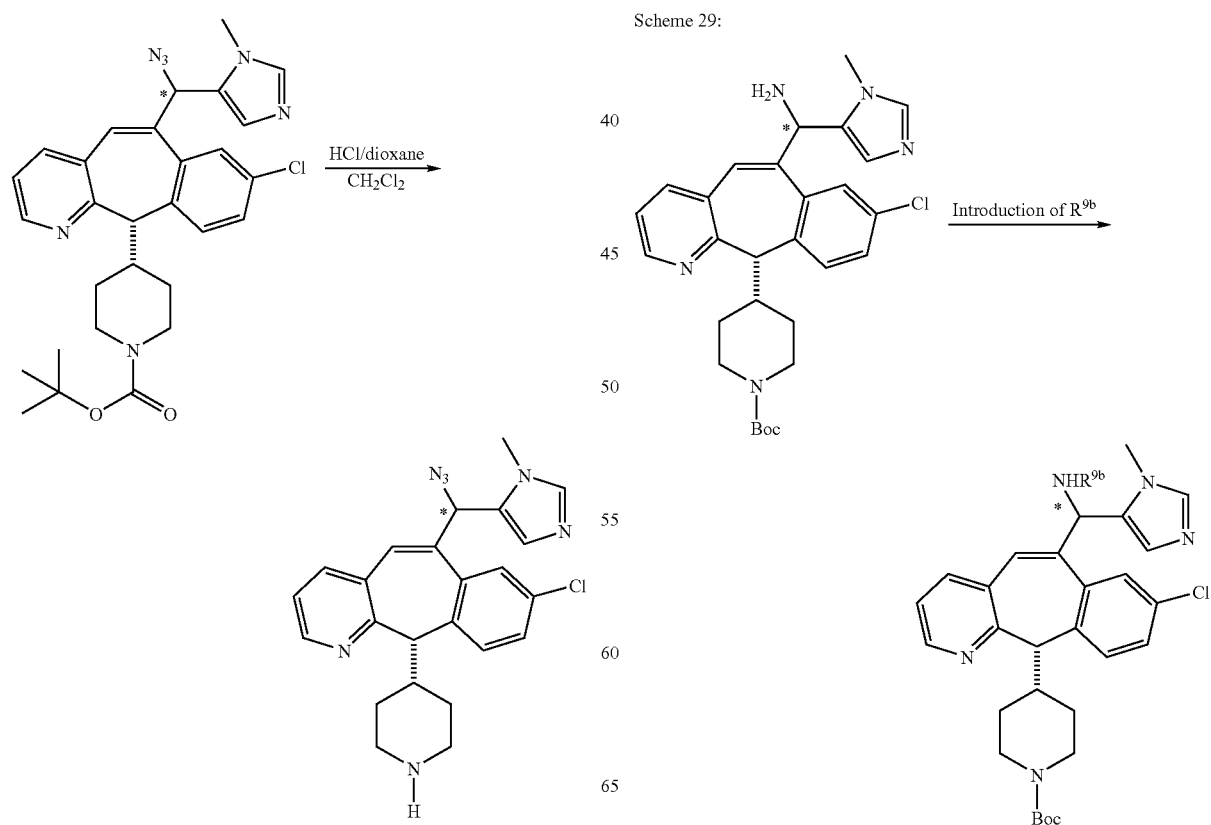

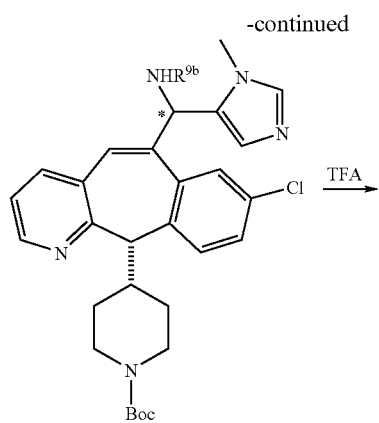

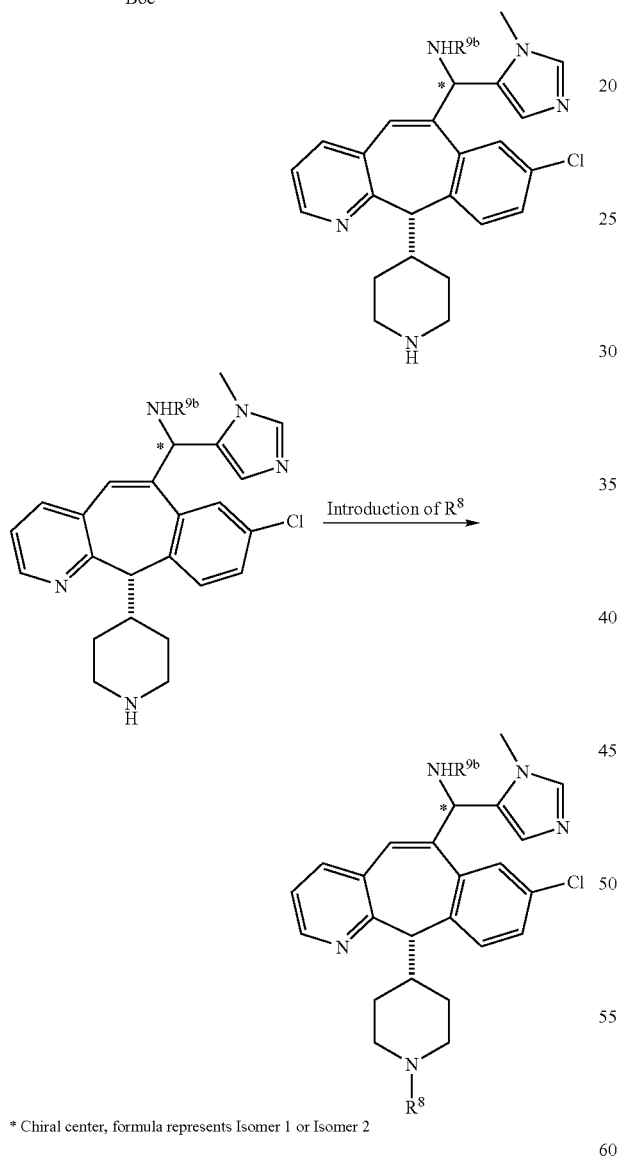

* Chiral center, formula represents Isomer 1 or Isomer 2

In order to obtain a compound with an $R^{9b}$ group, the amine (starting reactant), was reacted with an acid chloride or anhydride to obtain an amide group, with an isocyanate to obtain a urea, with an chloroformate to obtain a carbamate, or with a sulfonylchloride to obtain a sulfonamide, in an appropriate solvent, such as dichloromethane, and an equal equivalent of a base, such as triethylamine, to obtain a compound with the desired $R^{9b}$ substitutent. The $R^{9b}$ substituted compound can then be treated with trifluoroacetic acid to remove the BOC group to give the piperidine compound with an unsubstituted nitrogen. To introduce the desired $R^8$ group the piperidine compound with the unsubstituted nitrogen can be reacted with an acid chloride or anhydride to obtain an amide group, with an isocyanate to obtain a urea, with an chloroformate to obtain a carbamate, or with a sulfonylchloride to obtain a sulfonamide, in an appropriate solvent, such as dichloromethane, and an equal equivalent of a base, such as triethylamine, to obtain the compound with the desired $R^8$ substituent.

Scheme 30

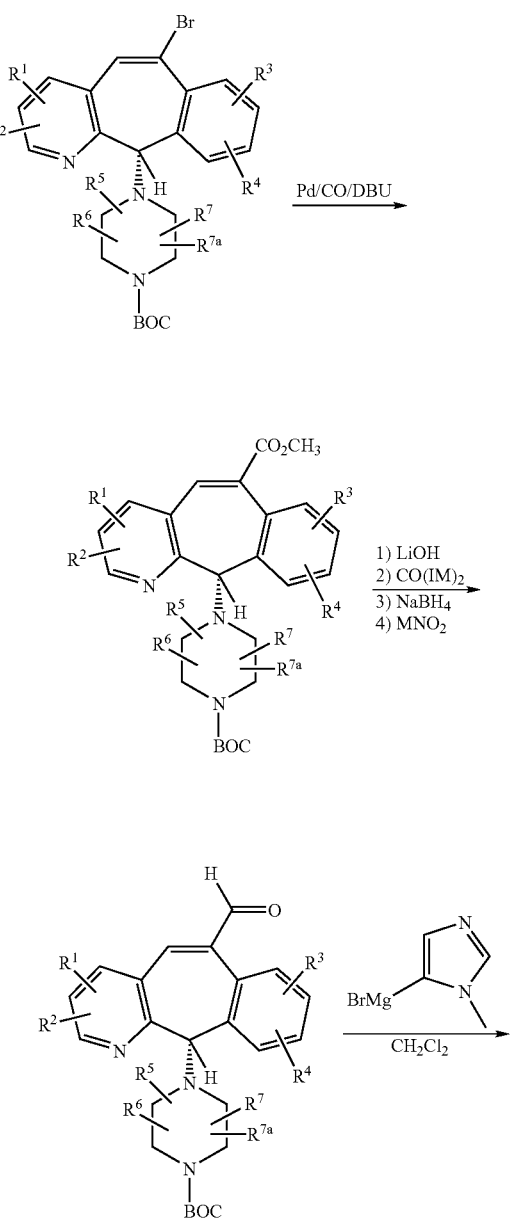

-continued
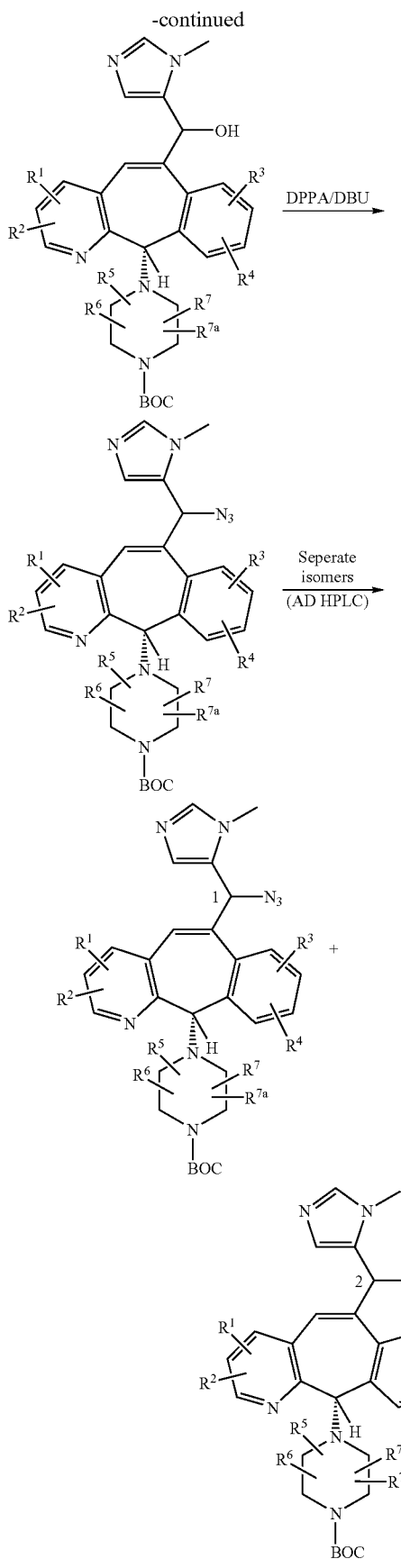
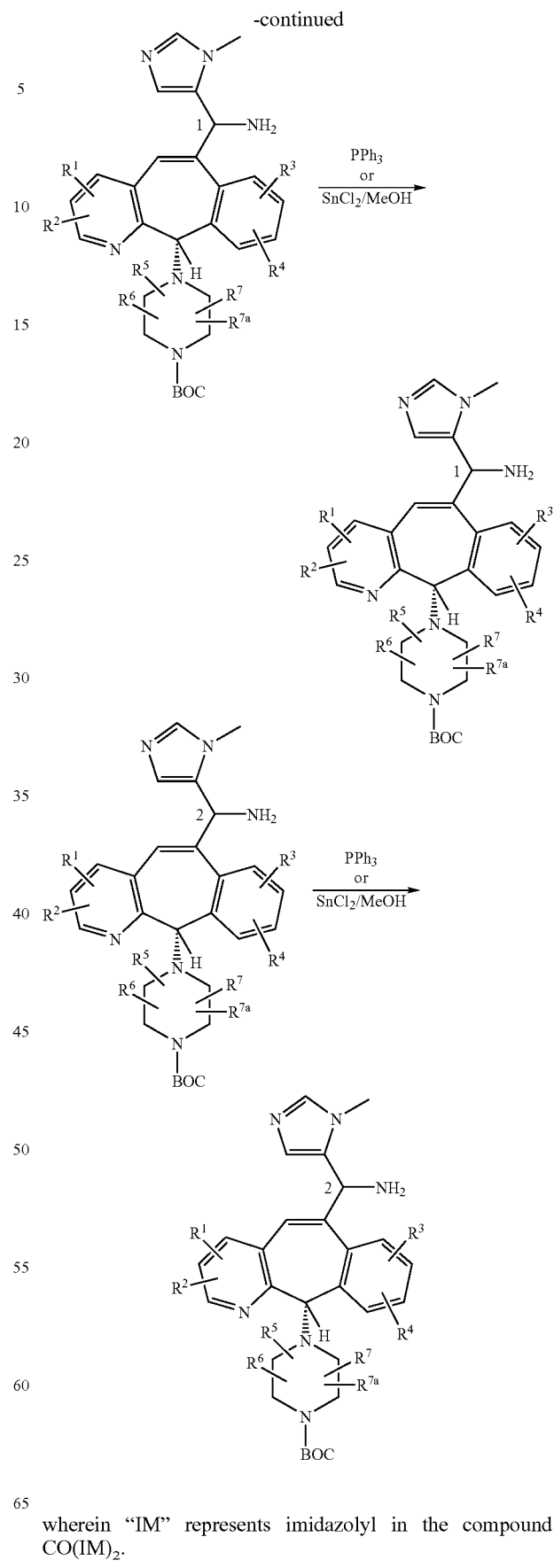
wherein "IM" represents imidazolyl in the compound CO(IM)$_2$.

Scheme 31
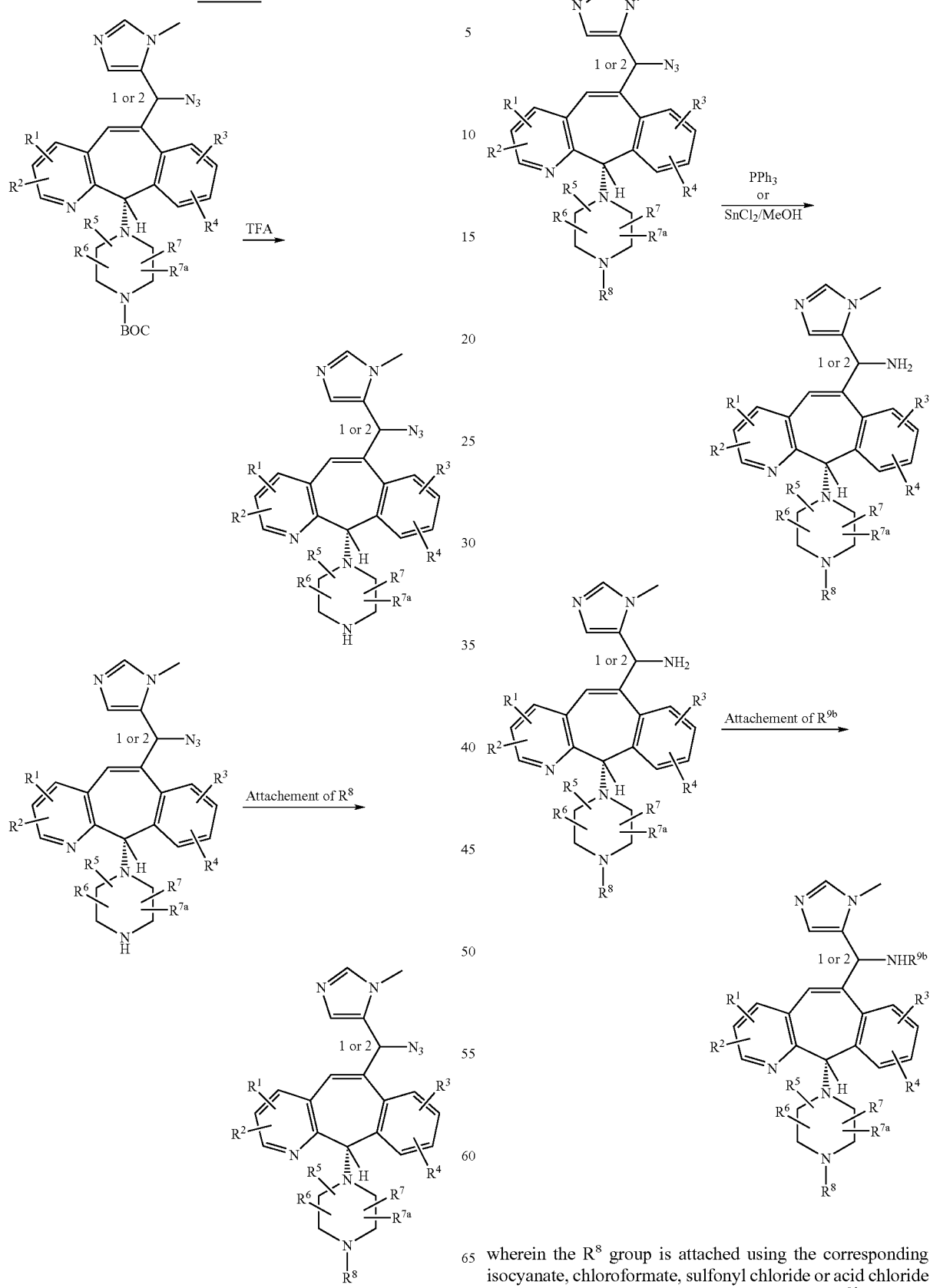
wherein the $R^8$ group is attached using the corresponding isocyanate, chloroformate, sulfonyl chloride or acid chloride of the group to be attached, and wherein the $R^{9b}$ group is

PREPARATIVE EXAMPLE 1

Step A

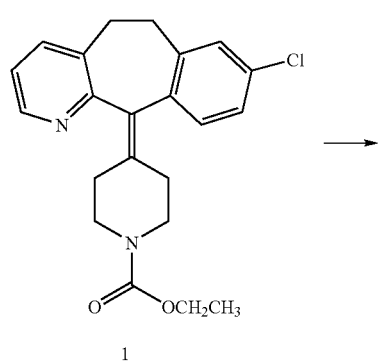
1

Loratadine® (448 g, 1.17 mol) was refluxed in 2 L of 70% aqueous HCl (1.4 L conc. HCl in 600 ml H$_2$O) for 12 h. The reaction mixture was then cooled and poured into ice. It was then basified with 950 mL of 50% NaOH followed by extraction with CH$_2$Cl$_2$ (1×4 L, and 2×2.5 L). The organic phase was washed with brine, dried over Na$_2$SO$_4$ and MgSO$_4$ and then filtered. All the volatiles were then removed to give 368 g of the title compound (2). MH$^+$=311

Step B

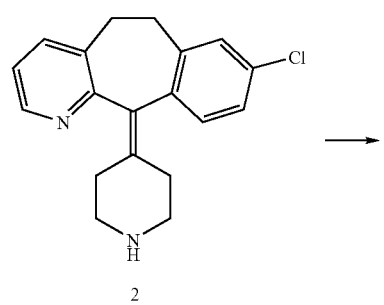
2

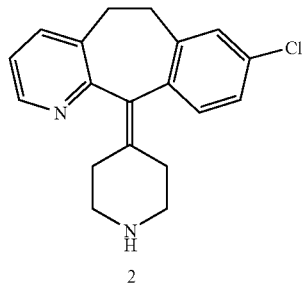
2

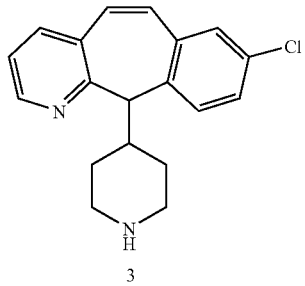
3

To the title compound from Preparative Example 1, Step A (363 g, 1.17 mol) was added trifuromethane sulfonic acid (1.8 Kg) under N$_2$. The reaction mixture was refluxed at 170° C. The progress of the reaction was monitored by $^1$H NMR. After 4 days the reaction was only 63% complete. After 8 days the reaction was found to be 80% complete according to $^1$H NMR; thus another 130 mL of CF$_3$SO$_3$H were added and refluxing continued for another 24 h. It was then poured into ice and basified with 800 mL of NaOH (50%) and extracted twice with CH$_2$Cl$_2$ (1×8 L then 1×7 L). The organic phase was combined, washed with H$_2$O and filtered through celite. It was then dried over MgSO$_4$ and Na$_2$SO$_4$ and again filtered through celite. The filtrate was concentrated to give a black brown semi-solid that was pre adsorbed on 600 g of silica gel and then chromatographed on 2.3 Kg of silica gel eluting first with 5% CH$_3$OH—CH$_2$Cl$_2$ (saturated with ammonia) and then with 10% CH$_3$OH—CH$_2$Cl$_2$ (saturated with ammonia) to give 102 g of the title compound (3) as a solid. mp=73-75; MS (FAB) m/z 483 (MH$^+$).

Step C

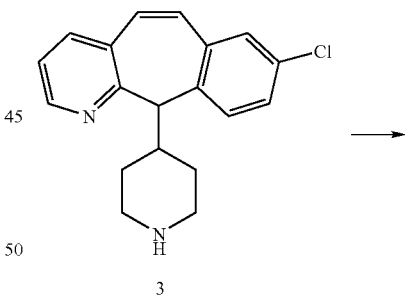
3

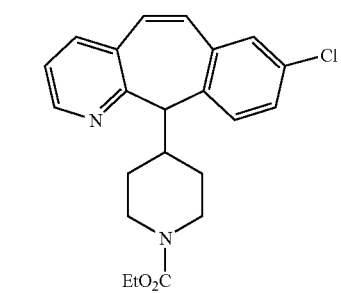
4

To a solution of the title compound of Preparative Example 1, Step B (145 g) in 1 L of $CH_2Cl_2$ at 0° C. was added ethylchloroformate (55 mL), dropwise. The reaction mixture was stirred at room temperature overnight. It was further diluted with 1 L $CH_2Cl_2$ and stirred with 2 L of dilute $NaHCO_3$, pH~7-8. The organic layer was separated and dried over $MgSO_4$ and $Na_2SO_4$, filtered and concentrated to afford 174 g of a brown black gum. The crude compound was purified by silica gel column chromatography, eluting with 20-60% ethyl acetate-hexane to afford the title compound (4). MS (FAB) m/z 383 ($MH^+$).

Step D

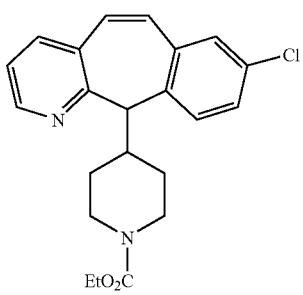

4

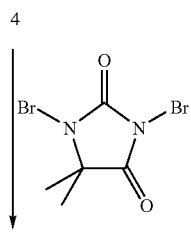

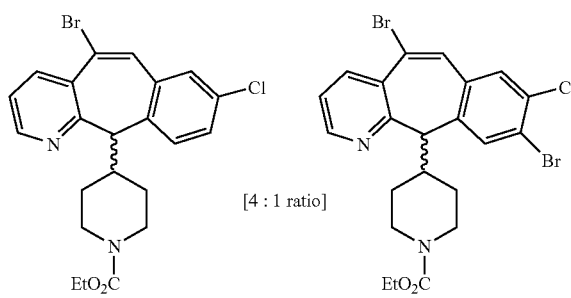

[4 : 1 ratio]

6                5

The title compound of Preparative Example 1, Step C (251 g, 0.65 mol) was dissolved in 1.65 L of $CH_2Cl_2$ and dibromo dimethylhydantoin, (132 g, 0.462 mol) was then added. The solution was stirred until the system was homogeneous. The solution was cooled to 0° C. under $N_2$ atmosphere and 174 mL of $CF_3SO_3H$ were added over 37 min. while keeping temperatures between ⁻1 to 1° C. The reaction mixture was stirred for 3 h, cooled to ⁻10° C. and basified with 50% NaOH (170 mL), keeping the temperature below 1° C. The aqueous phase was extracted with $CH_2Cl_2$ and then dried over $MgSO_4$, dried and concentrated to give 354 g of yellow foam that was chromatographed on silica gel eluting with 10-50% of ethyl acetate-hexanes gradient to give 50 g of compound (5) (14% yield) and 147 grams of the desired title compound (6) (49% yield). Compound (6) MS m/z (rel intens) 462 ($MH^+$); Compound (5) MS m/z (rel intens) 542 ($MH^+$).

Step E

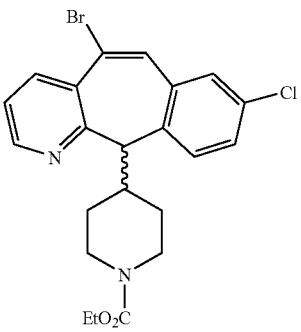

6

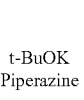 t-BuOK
Piperazine

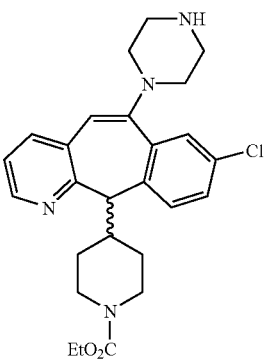    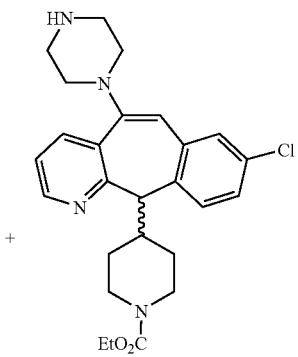

7                8

To a solution of piperazine 0.186 g (2.2 mmol, 5 equiv.) in 5 mL of THF was added 0.20 g (0.4 mmol) of compound 6 (from Preparative Example 1, Step D. The reactants stirred at room temperature until everything was in solution. To this mixture was added potassium t-butoxide (0.243 g, 2.1 mmol, 5 equivalents) in one portion. The reaction mixture was stirred at room temperature for 2 h. All of the THF was removed by rotary evaporation and the resulting crude product was purified by flash chromatography eluting with 3-4% (10% $CH_3OH$: saturated with $NH_4OH$)—$CH_2Cl_2$ to give a mixture of title compounds (7) and (8). FAB m/z 467 ($MH^+$).

Step F

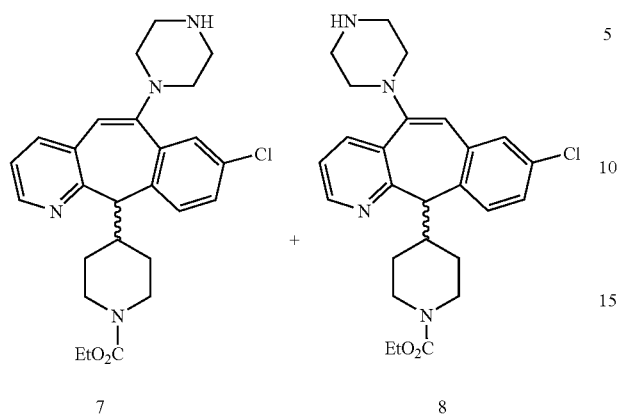

The mixture of compounds from Preparative Example 1, Step E (43.6 g) in 100 mL of conc. HCl was stirred at room temperature for 16 h. The reaction mixture was pored into ice and with conc. NH₄OH and then extracted with CH₂Cl₂ to give a mixture of compounds (9) and (10). MS (FAB) m/z 399 (MH⁺).

PREPARATIVE EXAMPLE 2

Step A

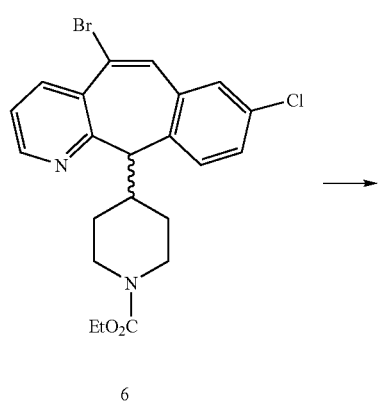

-continued

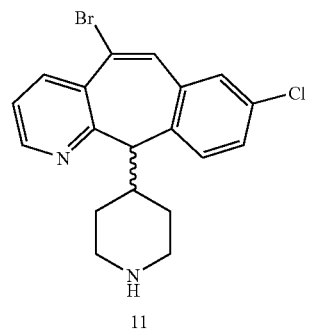

Compound 6 from Preparative Example 1, Step D (10 g, 21.7 mmol) was hydrolyzed in the same manner as described in Preparative Example 1, Step A, to give the title compound (11). MH+=389.

Step B

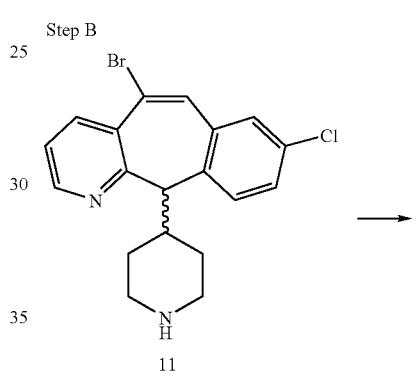

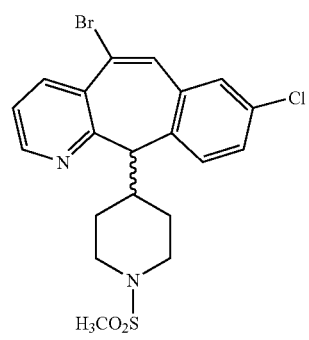

To the amine product from Preparative Example 2, Step A (20 g, 0.5 mol) and triethylamine (10.4 g, 14.4 mL, 1.02 mol) dissolved in anhydrous dichloromethane (100 mL) was added methanesulfonyl chloride (8.8 g, 6 mL, 0.77 mol). After stirring at room temperature overnight, the solution was diluted with dichloromethane, washed with saturated NaHCO₃ and dried over anhydrous magnesium sulfate. Filtration and concentration in vacuo afforded the crude product that was purified by flash chromatography on a silica gel column, eluting with 1% CH₃OH (saturated with ammonia)—CH₂Cl₂ to give the title compound (12). MS (FAB) m/z 469 (MH⁺).

Step C

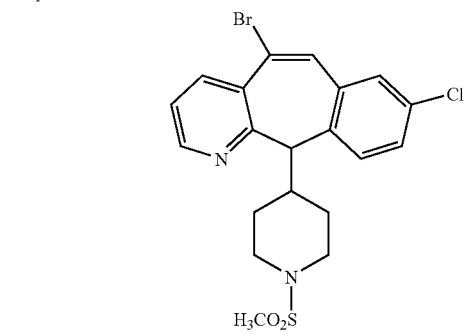

12

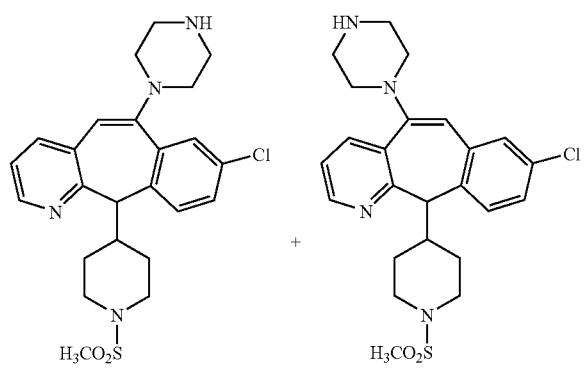

13  +  14

Product from Preparative Example 2, Step B (21.25 g, 45.3 mmol) was treated in the same manner as described in Preparative Example 1, Step E, to give 22.2 g of a mixture of compounds (13) and (14). MS (473) (MH⁺).

Step D

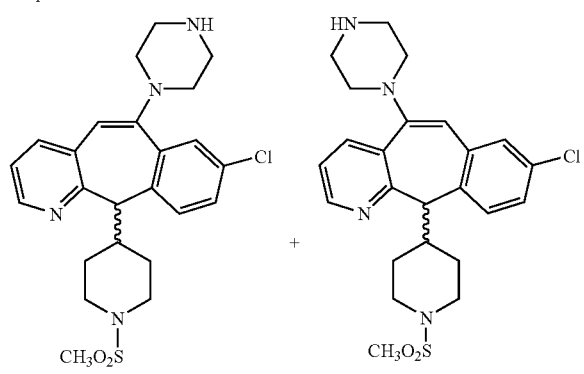

13  +  14

-continued

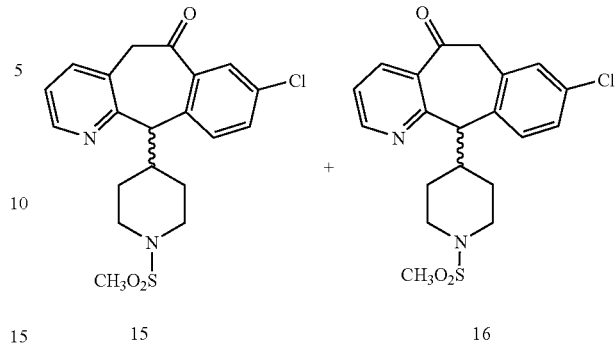

15  +  16

The product from Preparative Example 2, Step C (22.5 g) was dissolved in 150 mL of conc. HCl and stirred for 16 h. The reaction mixture was poured into ice, basified with conc. NH$_4$OH and then extracted with CH$_2$Cl$_2$ to give a mixture of compounds (15) and (16). MS (FAB) m/z 405 (MH⁺).

PREPARATIVE EXAMPLE 2A

Step A

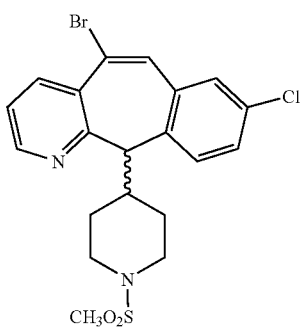

12

17  +  18

Separation of compound of Preparative Example 2 Step B by HPLC using a Chiralpack AD column eluting with 40-50% isopropanol:60-50% hexane-0.2% diethylamine gave enantiomeric amines (17) and (18).

Compound 17: mp=118-119; $[\alpha]_D^{22}$=+136.9° (9.00 mg/2 mL, MeOH); MS (FAB) m/z 469 (MH⁺).

Compound 18: mp=119-120; $[\alpha]_D^{22}$=−178.2° (9.90 mg/2 mL, MeOH); MS (FAB) m/z 469 (MH$^+$).

Step B

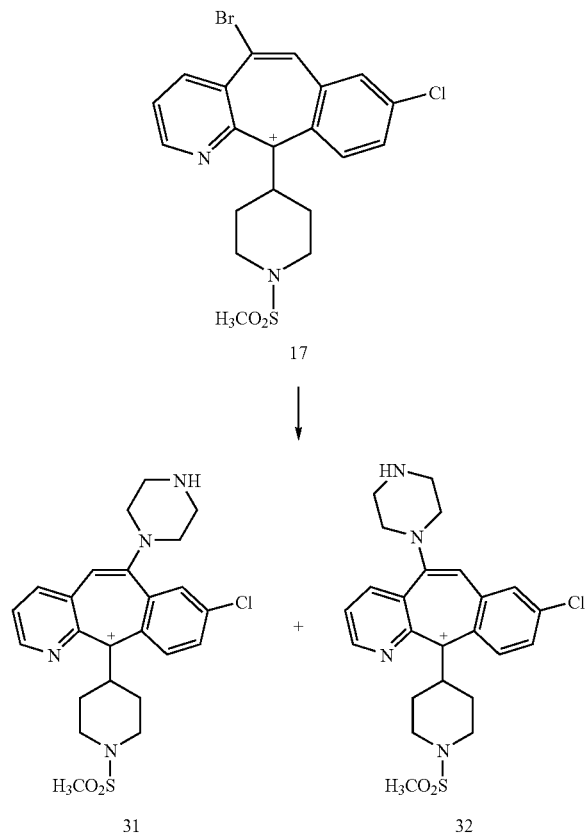

Product 17 from Preparative Example 2A, Step A (21.25 g, 45.3 mmol) was treated in the same manner as described in Preparative Example 1, Step E, to give 22.2 g of a mixture of compounds (31) and (32). MS (473) (MH$^+$).

PREPARATIVE EXAMPLE 3

Step A

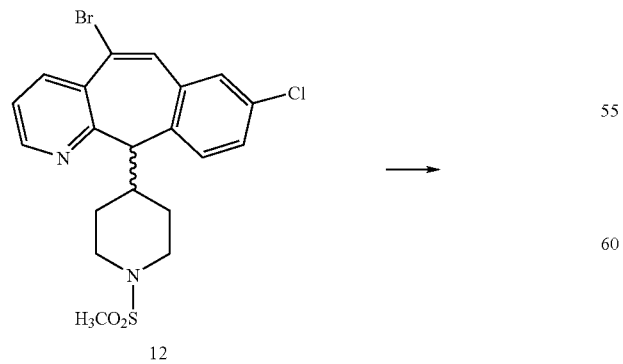

-continued

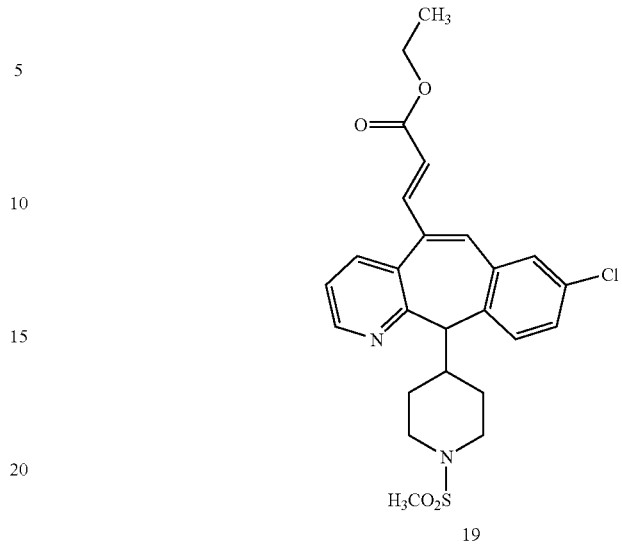

To a solution of the title compound from Preparative Example 2, Step B (2.0 g, 4.3 mmole) in DMF (50 ml) under nitrogen atmosphere, was added triethyl amine (17 ml), ethyl arcrylate (2.5 ml), potassium carbonate (3 g, 21.4 mmole), tetrabutylamonium bromide (2.8 g, 8.6 mmole) and palladium (II) acetate (0.1255 g, 0.56 mmol). The resulting mixture was heated to 100° C., and stirred for 4 h then it was cooled to room temperature and the solvent was removed. To the residue was added CH$_2$Cl$_2$ and water and the mixture was then extracted with CH$_2$Cl$_2$. The organic layer was dried over magnesium sulfate, filtered and concentrated to dryness. The crude product was purified using pre-adsorbed flash silica column chromatography eluting with 30-50% ethyl acetate-hexane gradient to give the title compound (19). MS 487 (MH$^+$).

Step B

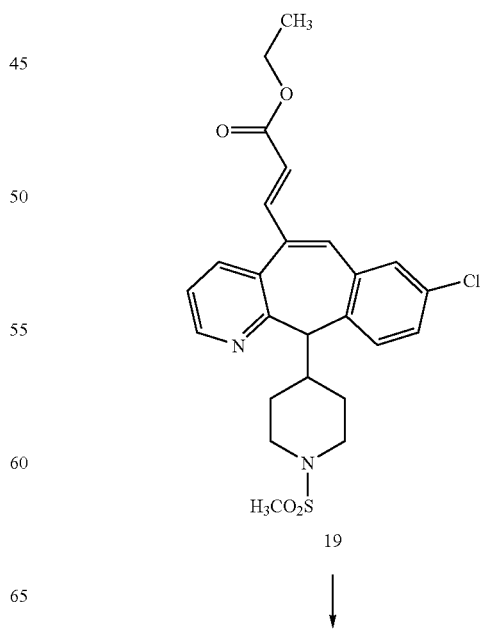

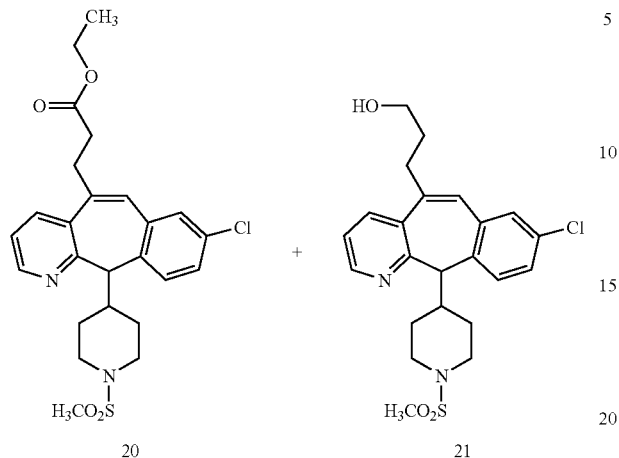

To a solution of the title compound from Preparative Example 3, Step A (6.4 g, 13 mmole) in ethanol (500 ml), was added copper chloride (0.96 g, 9.7 mmole). The reaction was cooled to 0° C. Portionwise, added sodium borohydride (4.97 g, 131 mmole). The reaction stirred overnight at room temperature. Another portion of sodium borohydride (2.46 g, 65 mmole) was added and the reaction stirred for 2 more hours, then the solvent was removed. To the residue was added saturated sodium bicarbonate and the mixture was extracted with $CH_2Cl_2$. The organic layer was dried over sodium sulfate, filtered and concentrated to dryness to afford a mixture of the reduced ester (20) and the alcohol (21) title compounds. This crude mixture was taken on to the next step without purification.

Step C

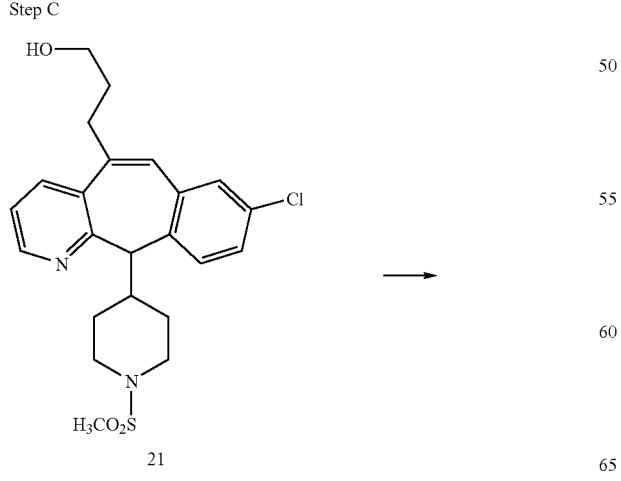

To a solution of the products from Preparative Example 3, Step B (5.74 g) in $CH_2Cl_2$ (100 ml) was added triethyl amine (2.4 ml). Slowly, methane sulfonyl chloride (0.8 ml) was added and the mixture stirred over night at room temperature. To the reaction was added saturated sodium bicarbonate and then it was extracted with $CH_2Cl_2$. The organic layer was dried over magnesium sulfate, filtered and concentrated to dryness. The crude product mixture was separated on a Biotage® column, eluting with 30% ethyl acetate-$CH_2Cl_2$, to afford the desired title compound (22). MS 525 ($MH^+$). (recovered unreacted ester (20))

PREPARATIVE EXAMPLE 4

Step A

To a solution of title compound (11) from Preparative Example 2, Step A (20 g, 51.32 mmole) in CH₃OH/H₂O (400 ml, 50:1) was added di-tert-butyl dicarbonate (16.8 g, 77.0 mmole). The pH was adjusted to 9 and the mixture was stirred for 4 h. The solvent was removed, then water was added. The mixture was extracted with CH₂Cl₂. The organic layer was dried over magnesium sulfate, filtered and concentrated to dryness affording the title compound (23). MS 491 (MH+).

Step B

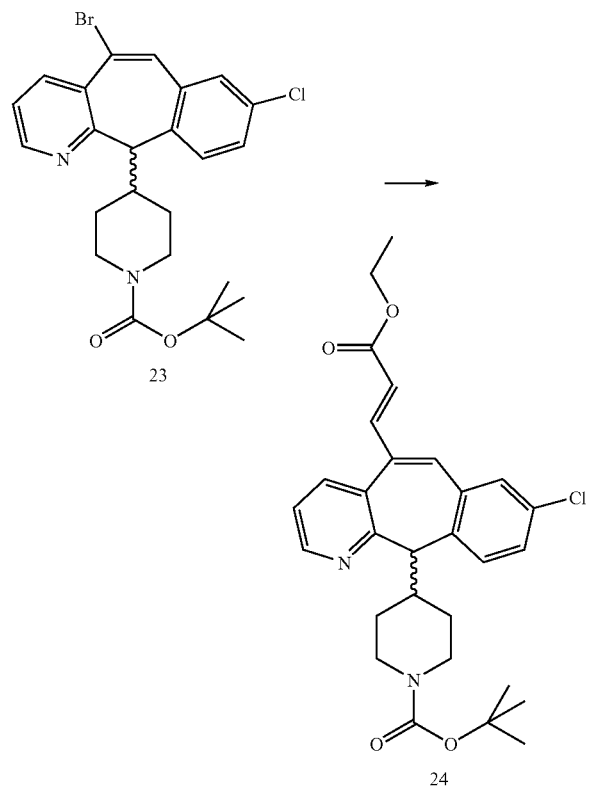

Following a similar procedure as in Preparative Example 3, Step A, the title compound (24) was prepared. MS 509 (MH+).

Step C

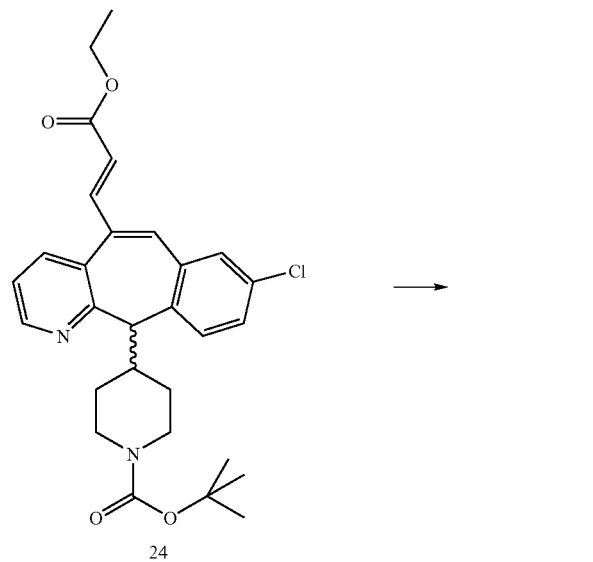

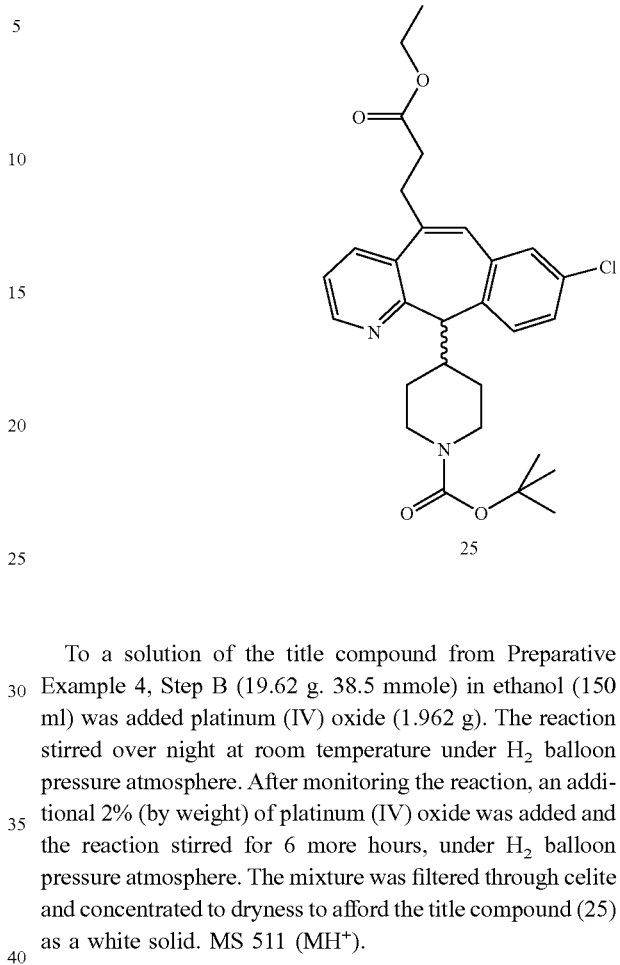

To a solution of the title compound from Preparative Example 4, Step B (19.62 g. 38.5 mmole) in ethanol (150 ml) was added platinum (IV) oxide (1.962 g). The reaction stirred over night at room temperature under H₂ balloon pressure atmosphere. After monitoring the reaction, an additional 2% (by weight) of platinum (IV) oxide was added and the reaction stirred for 6 more hours, under H₂ balloon pressure atmosphere. The mixture was filtered through celite and concentrated to dryness to afford the title compound (25) as a white solid. MS 511 (MH⁺).

Step D

-continued

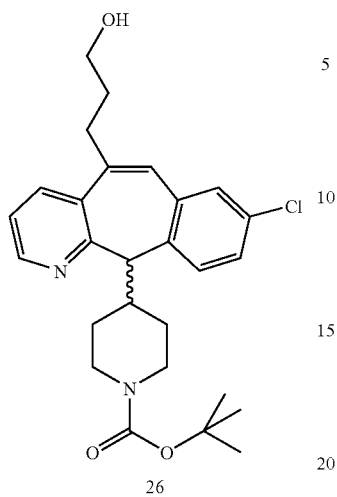
26

Dissolved product from Preparative Example 4, Step C (2.0 g, 3.9 mmole) in THF (30 ml) and cooled to 0° C. in an ice bath. To the reaction was added diisobutylaluminum hydride (7.8 ml, 7.8 mmole). The reaction was allowed to stir and come to room temperature over night. The reaction did not go to completion. The mixture was cooled in an ice bath (0° C.) and fresh diisobutylaluminum hydride/toluene (7.8 ml) was added. After the reaction stirred for 4 more hours, it was still not complete. The reaction mixture was cooled to 0° C., and an additional 3.9 ml of diisobutylaluminum hydride as added. The reaction stirred for 3 more hours. The crude reaction mixture was then extracted with ethyl acetate: 10% citric acid, and 1.0 N NaOH. The organic layer was dried over magnesium sulfate, filtered and concentrated to dryness to afford the desired title compound (26). MS 471 (MH$^+$).

Step E

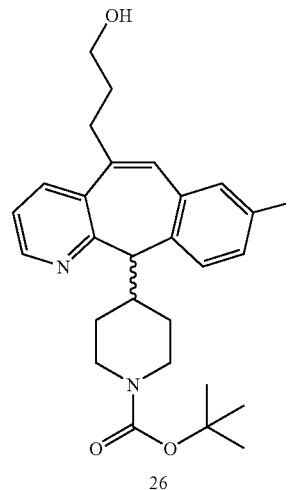
26

-continued

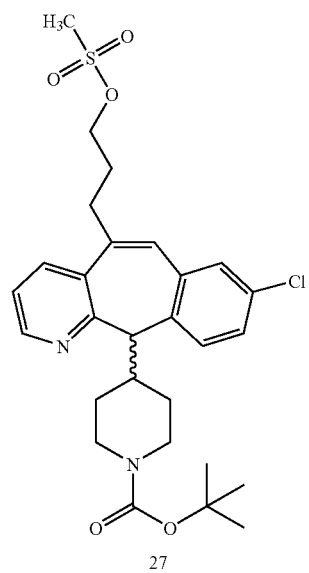
27

Following a similar procedure described in Preparative Example 3, Step C, the title compound (27) was prepared. MS 549 (MH$^+$).

Step F

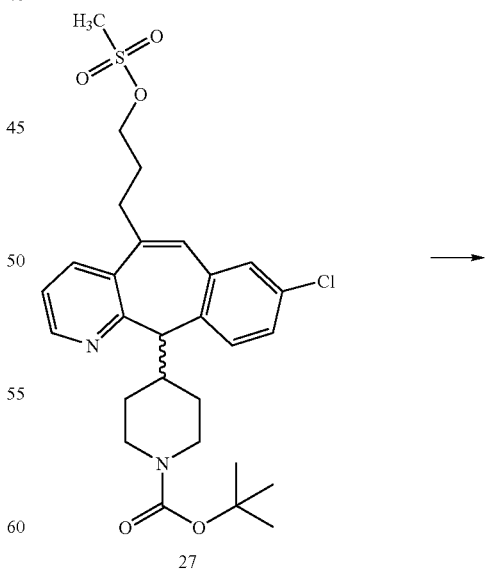
27

-continued

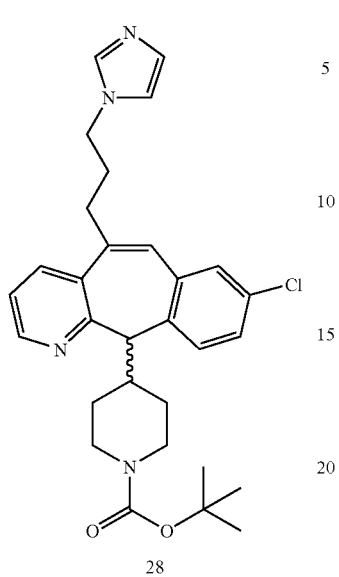
28

To a solution of the title compound from Preparative Example 4, Step E (1.6 g, 3.01 mmole) in DMF (50 ml) was added imidazolylsodium (Aldrich) (0.407 g, 4.52 mmole). The reaction mixture was heated to 90° C. for 2 h. The reaction was cooled and the DMF was removed. Saturated sodium bicarbonate was added and the mixture was extracted with $CH_2Cl_2$. The organic layer was dried over magnesium sulfate, filtered and concentrated to dryness. The crude product was purified by column chromatography eluting with 2% $CH_3OH$: saturated with ammonia-$CH_2Cl_2$, to afford the title compound (28). MS 519 ($MH^+$).

Step G

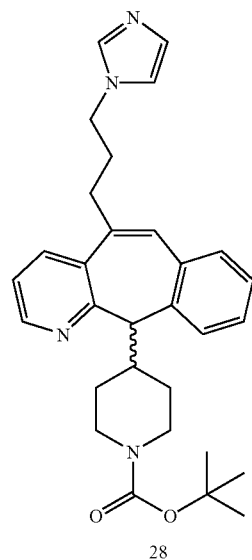
28

-continued

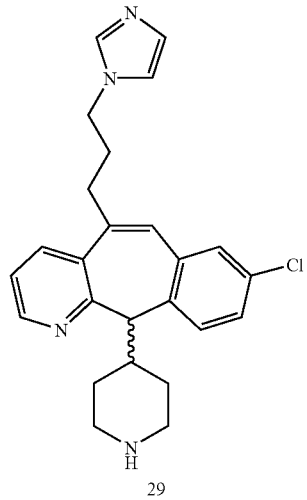
29

Dissolved the product from Preparative Example 4, Step F (0.55 g, 1.08 mmole) in 4 N dioxane/HCl (20 ml). The reaction mixture was stirred for 3 h at room temperature and then concentrated to dryness to afford the title compound (29) as a light yellow solid. HRMS 419 ($MH^+$).

PREPARATIVE EXAMPLE 5

Step A

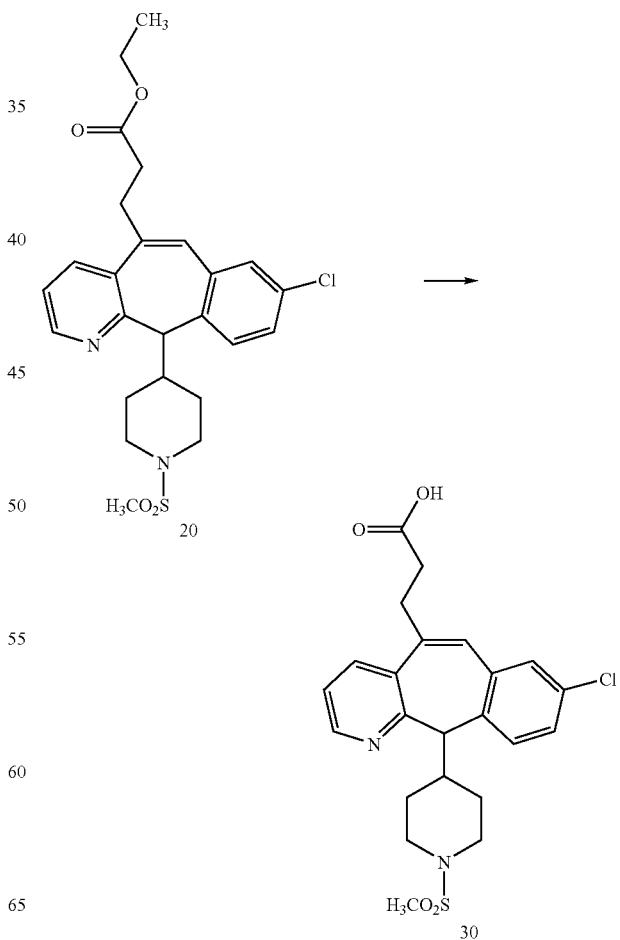

Compound (20) from Preparative Example 3, Step B (0.67 g, 1.37 mmole) was dissolved in THF (5 ml). To the mixture was added 1N NaOH (6.9 ml) and the resulting solution stirred over night at room temperature. The reaction mixture was concentrated, acidified with 10% citric acid (w/v) and extracted with $CH_2Cl_2$. The organic layer was drived over magnesium sulfate, filtered and concentrated to dryness to afford the title compound (30) as a yellow solid. mp 122.7-123.4° C.; MS 461 ($MH^+$).

EXAMPLE 1

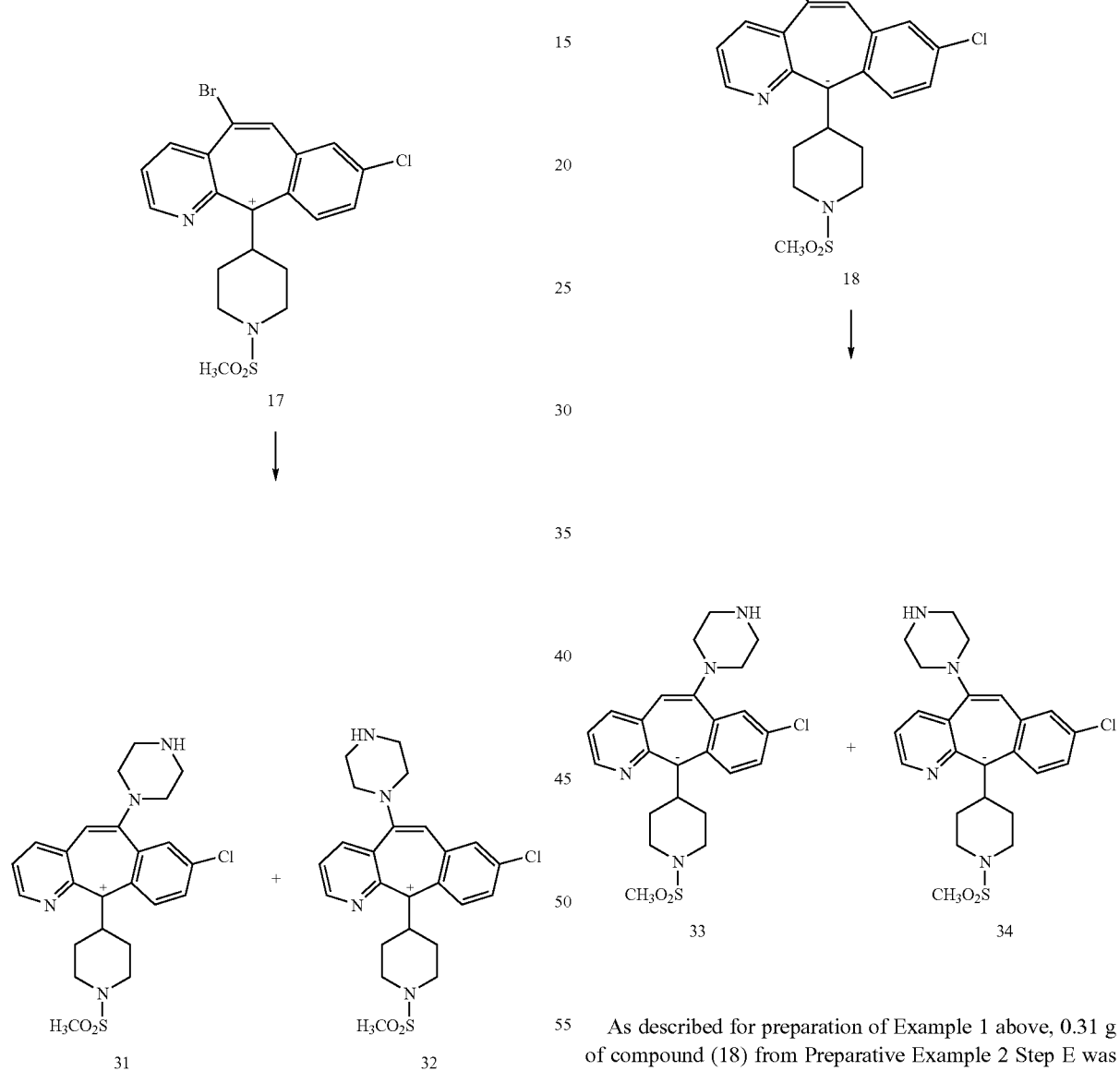

Compound (17) from Preparative Example 2, Step E 0.31 g (0.66 mmol) was treated in the same manner as described in Preparative Example 1, Step E to give a mixture of compounds (31) and (32) that were further separated on a HPLC Chiralpack AD column eluting with 30% isopropanol—70% hexane—0.2% diethylamine to give 0.04 g of target compound (31) and 0.07 g of target compound (32).

Compound 31: mp=174-175; $[\alpha]_D^{22}=+96.0°$ (3.6 mg/2 mL, $CH_2Cl_2$); MS (FAB) m/z 473 ($MH^+$).

Compound 32: mp=173-174; $[\alpha]_D^{22}=+21.7°$ (8.4 mg/2 mL, $CH_2Cl_2$); MS (FAB) m/z 473 ($MH^+$).

EXAMPLE 2

As described for preparation of Example 1 above, 0.31 g of compound (18) from Preparative Example 2 Step E was converted to a mixture of compounds (33) and (34) that were subsequently separated on a Chiralpack AD column HPLC eluting with and 30% isopropanol—70% hexane—0.2% diethylamine as eluent to give 0.12 g of target compound (33) and 0.04 g of target compound (34).

Compound 33: mp=178-179; $[\alpha]_D^{22}=-30.5°$ (9.5 mg/2 mL, $CH_2Cl_2$); MS (FAB) m/z 473 ($MH^+$).

Compound 34: mp=172-173; $[\alpha]_D^{22}=-84°$ (3.5 mg/2 mL, $CH_2Cl_2$); MS (FAB) m/z 473 ($MH^+$).

EXAMPLE 3

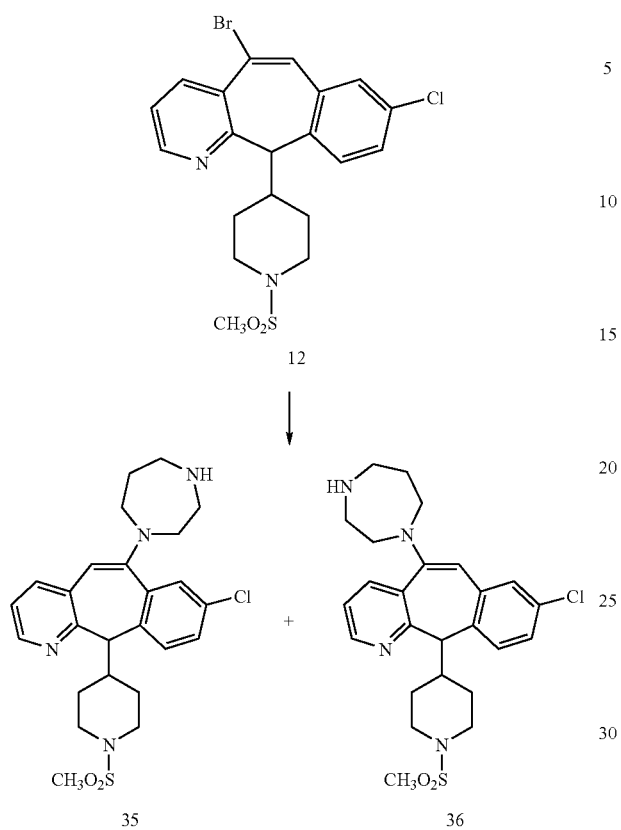

Product from Preparative Example 2, Step B (0.4 g, 0.86 mmol) was treated in the same manner as described in Preparative Example 1 Step E, substituting homopiperazine (Aldrich), to give of a mixture of compounds 35 and 36 that were further separated by flash chromatography, eluting with 10% CH₃OH: saturated with NH₃/CH₂Cl₂ as eluent to give 0.13 g of target compound (35) and 0.17 g of target compound (36).

Compound (35): mp=116-117; MS (FAB) m/z 487 (MH⁺).
Compound (36): mp=111-112; MS (FAB) m/z 487 (MH⁺).

EXAMPLE 4

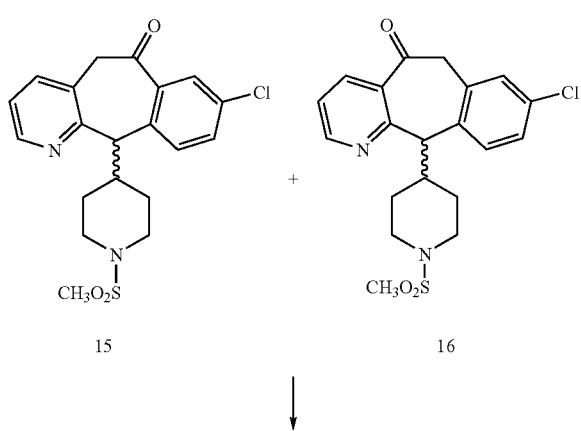

-continued

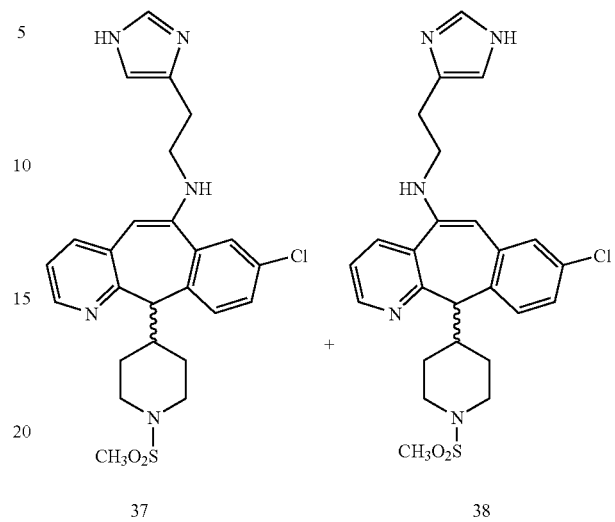

The ketones of Preparative Example 2, Step D (0.50 g, 1.23 mmol), Histamine® (0.21 g, 1.8 mmol) and p-toluene sulfonic acid (monohydrate) were dissolved in anhydrous toluene (40 mL) and refluxed in a Dean Stark trap apparatus for 24 h. The reaction mixture was then cooled, diluted with ethyl acetate and extracted with NaHCO₃. The organic layer was then dried over MgSO₄ and concentrated to dryness. Purification by flash chromatography on silica gel, eluting with 3% CH₃OH(saturated with NH₃)—CH₂Cl₂, afforded 0.17 g (28% yield) 5-substituted histamine adduct (38) as the first eluting product and 0.08 g (13% yield) of the 6-substituted histamine adduct (37) as the second eluting product.

Compound (37): mp=124-125; MS (FAB) m/z 498 (MH⁺).
Compound (38): mp=119-120; MS (FAB) m/z 498 (MH⁺).

EXAMPLES (5) AND (6)

By using the same procedure as above and substituting the appropriate amines, compounds of the formula:

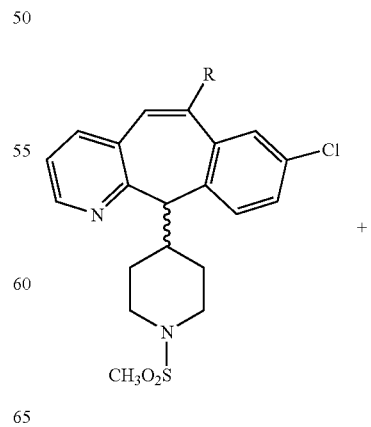

-continued

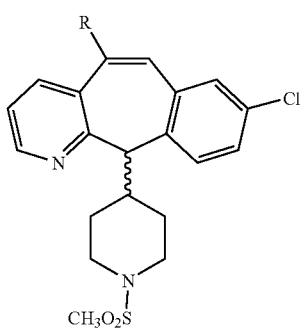

were prepared wherein R is as defined in Table 1 below. In the "Compound #" column, one compound # represents the C5 substituted compound and the other compound # represents the C6 substituted compound.

TABLE 1

| Ex | R = | Compound # |
|----|-----|------------|
| 5  | (imidazolyl-ethyl-NH-) | (39) AND (40). |
| 6  | (pyridin-3-yl-methyl-NH-) | (41) AND (42). |

EXAMPLE 7

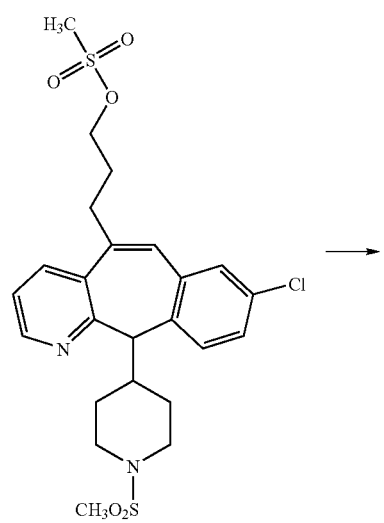

22

-continued

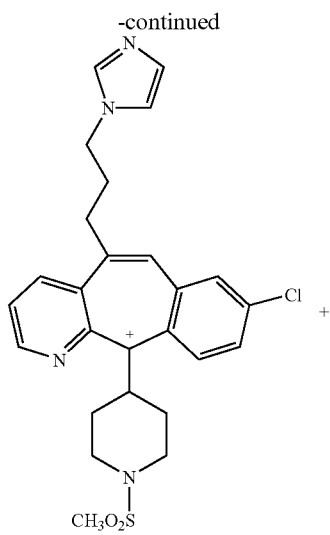

43

44

To a solution of the title compound (22) from Preparative Example 3, Step C (1.0 g, 2.03 mmole) in DMF (20 ml) was added imidazolylsodium (0.257 g, 2.85 mmole). The reaction mixture was heated to 90° C. for 2 h. Cooled the reaction and removed DMF. Added saturated sodium bicarbonate and extracted with CH$_2$Cl$_2$. Dried organic layer over magnesium sulfate, filtered and concentrated to dryness. Crude product was purified by Biotage column chromatography eluting with 3% CH$_3$OH: (saturated with ammonia)-CH$_2$Cl$_2$, to afford the title compound as an enantiomeric mixture. The mixture was separated into pure enantiomers on Prep HPLC Chiral AD column eluting with 35-40% Isopropanol-Hexane: 0.2% Diethyl amine, to give the title compounds (43) and (44). MS 497 (MH$^+$)

EXAMPLE 8

Step A

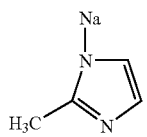
45

2-methylimidazole was dissolved in DMF (10 ml). To this was added one equivalent of NaH and the reaction was allowed to stir at room temperature for 1 h.

Step B

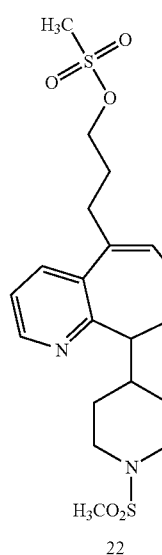

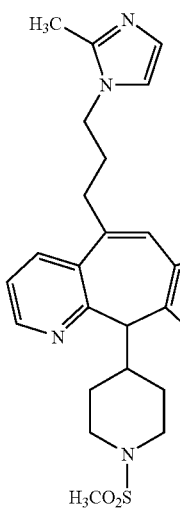
46

Following a similar procedure as described in Example 7, substituting 2-methyl imidazoyl sodium (45) for imidazoyl sodium, the racemic mixture of the title compound (46) was prepared. MS 511 (MH$^+$).

EXAMPLE 9

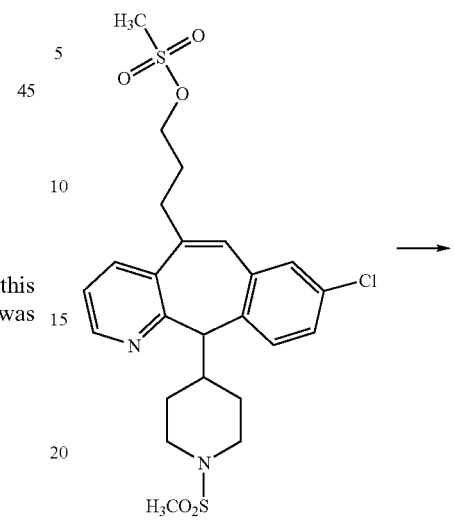

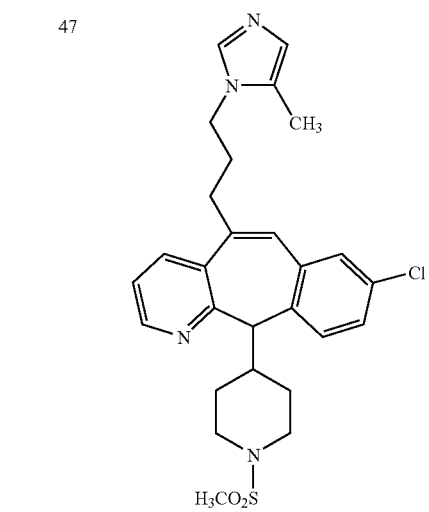

Compound (22) was reacted in the same the same manner as Example 8, substituting 4-methylimidazole in Step A, affording a mixture of 4 and 5-methyl substituted imidazole derivatives (47) and (48).

EXAMPLE 10

Step A

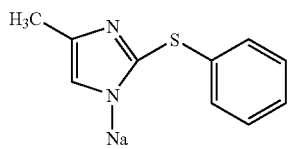

49

To SEM protected methylimidazole (30 g, 0.141 mole) prepared according to literature procedure, Whitten, J. P., J. Org. Chem. 1986, 51, 1891-1894, in THF (250 ml) at −78° C. was added 2.5 M n-butyl lithium (74 ml, 0.184 mole) over 1 h. The solution was stirred for 1 h at −78° C., then a solution of diphenyl disulfide (34.27 g, 0.155 mole) in THF (125 ml) was added over ½h. The mixture was stirred and warmed to room temperature over night. The solvents were removed and then the residue was diluted with ethyl acetate (250 ml) and washed with 1.0 M NaOH (5×50 ml) and then brine (50 ml). The organic layer was dried over $Na_2SO_4$, filtered and concentrated. The crude product (45.28 g, 0.141 mole) was dissolved in ethanol (100 ml) and 5 M aqueous HCl (100 ml) and stirred for 12 h. at 60° C. The solvent was removed and the residue was dissolved in distilled $H_2O$. 5M aqueous NaOH was added until pH=8, then the mixture was extracted with ethyl acetate. Combined organic layers and washed with brine, dried over $Na_2SO_4$, filtered and concentrated. Purified by flash chromatography eluting with 70% Hexanes:Acetone to afford the product as a white solid. The amine was further reacted with NaH (1 equivalent) in DMF for 1 h. affording the title compound (49).

Step B

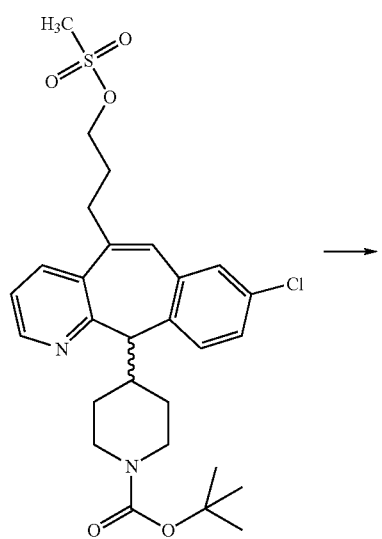

27

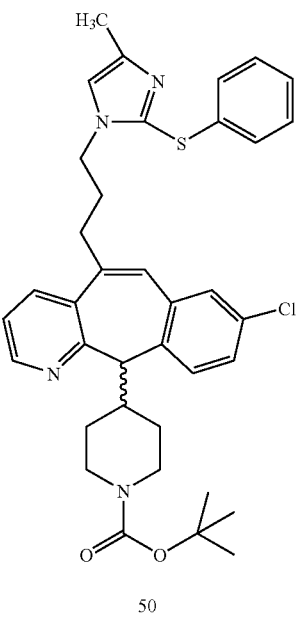

50

Compound (27) from PREPARATIVE EXAMPLE 4, STEP E was reacted in the same manner as EXAMPLE 8, substituting 4-methyl-2-phenylsulfanyl-1H-imidazole sodium (49), affording the title compound (50) as a light yellow solid. MS 643 ($MH^+$).

EXAMPLE 11

Step A

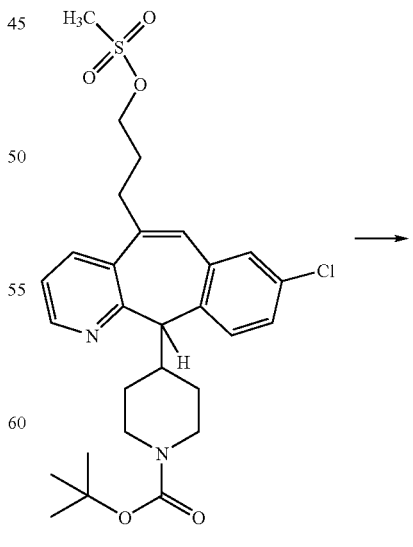

27

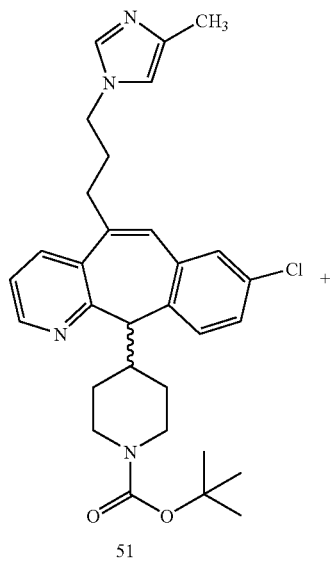
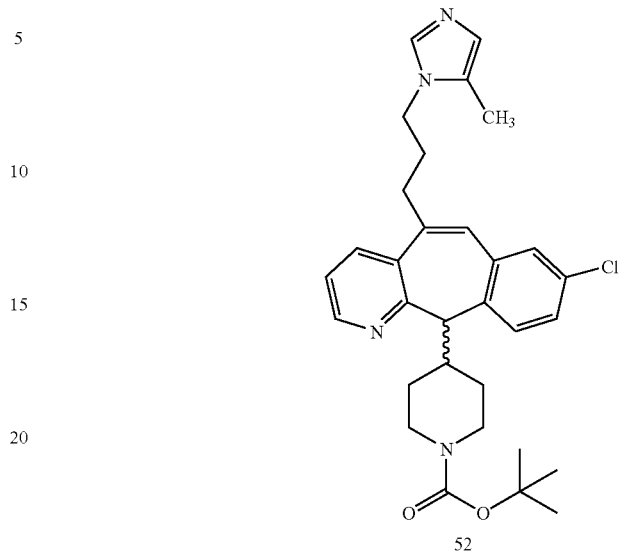
Compound (27) from PREPARATIVE EXAMPLE 4, STEP E, was treated in the same manner as in Example 9 above to afford a mixture of the 4 and 5-substituted imidazol title compounds (51) and (52).
Step B
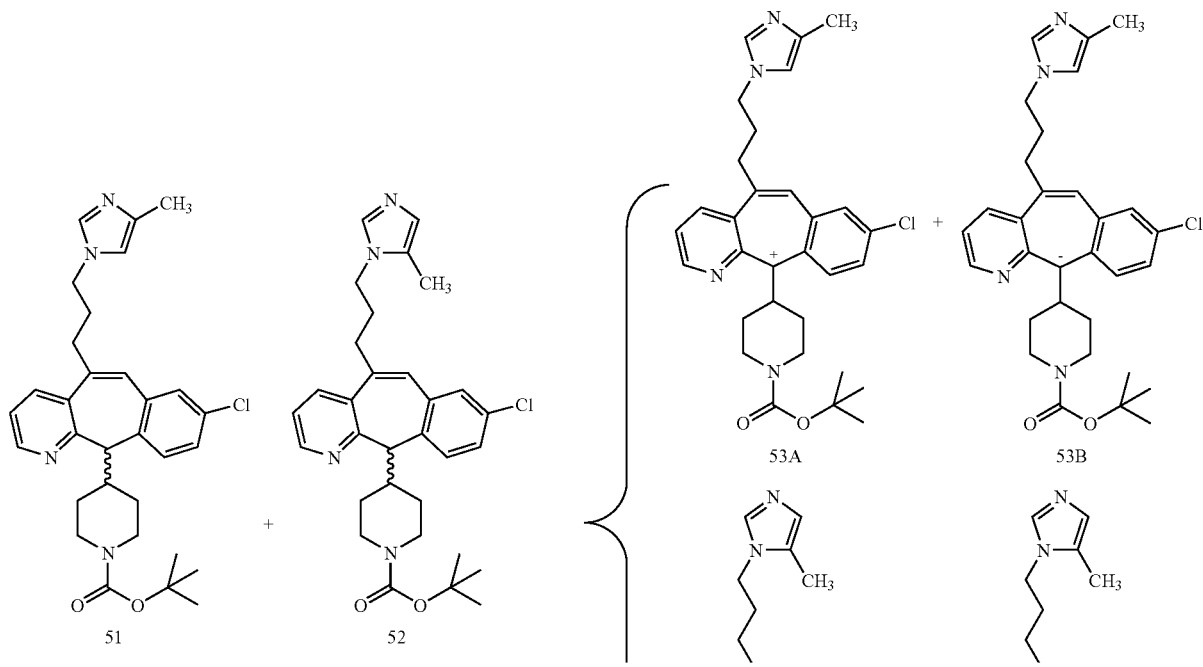

-continued

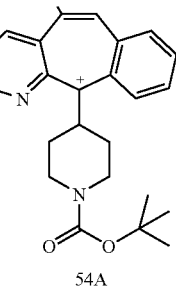
54A

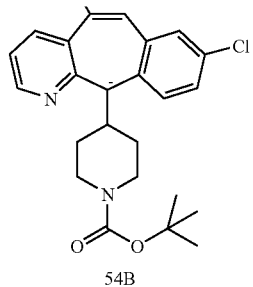
54B

The compounds from Step A above were further separated into a mixture of (4 and 5) (+) enantiomers and (4 and 5) (−) enantiomers using preparatory HPLC Chiral AD column, eluting with 20% Isopropanol-Hexane: 0.2% Diethyl amine. MS 532 (MH+). The pure (+) and (−) enantiomeric pairs were then reacted with triphenyl methyl chloride (Aldrich) in $CH_2Cl_2$ starting at 0° C. and warming to room temperature over 3 h. The crude product was purified by column chromatography eluting with 50% ethyl acetate-acetone, affording the pure (+) and (−) 4-methyl substituted enantiomers (53A) and (53B); MS 533 (MH+). The column was then flushed with 100% methanol, the fraction was concentrated and the residue was treated with methanol saturated with ammonia, overnight at reflux temperature. The product was purified by column chromatography eluting with 50% ethyl acetate-acetone, affording the pure (+) and (−) 5-methyl substituted enantiomers (54A) and (54B); MS 533 (MH+).

EXAMPLE 12

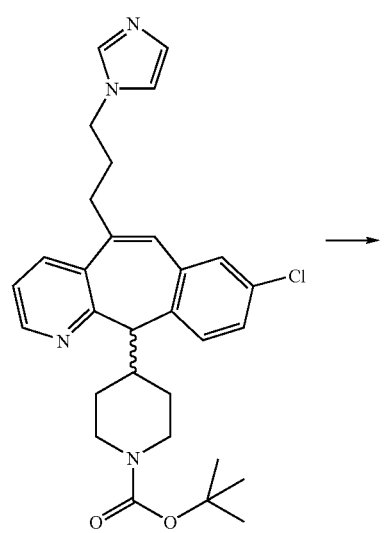
28

55

56

Compound (28) from PREPARATIVE EXAMPLE 4, STEP F, was separated into pure enatiomers by preparatory HPLC using a chiral AD column eluting with 20% Isopropanol:Hexane: 0.2% Diethyl amine to give pure title compounds (55) and (56). MS 519 (MH+).

EXAMPLE 13

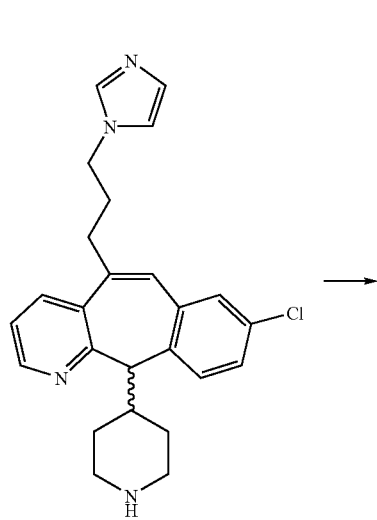

29

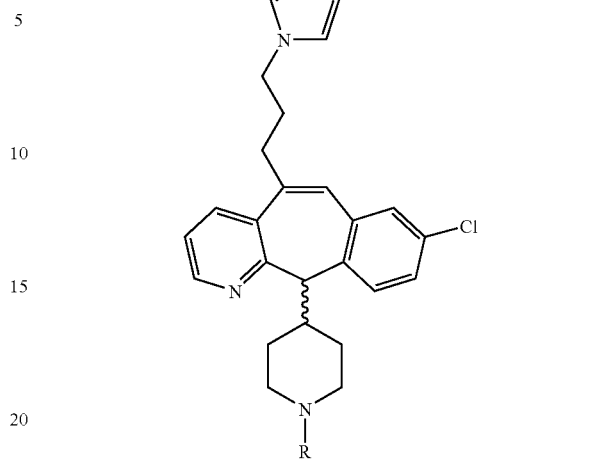

were prepared wherein R is defined in Table 2.

TABLE 2

| Ex | R = | Compound #: |
|---|---|---|
| 14 | ~~~C(O)NH-tBu | (58). MS 518 (MH+). |
| 15 | ~~~C(O)NH-cyclohexyl | (59). MS 544 (MH+). |

EXAMPLE 16

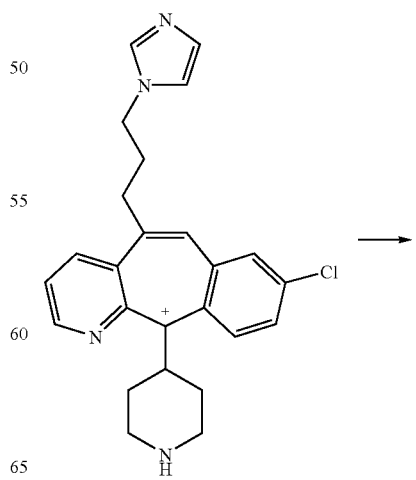

57

Compound (29) from PREPARATIVE EXAMPLE 4, STEP G (0.20 g, 0.48 mmole) was dissolved in CH$_2$Cl$_2$ (10 ml). Added triethyl amine (0.30 ml, 1.92 mmole) followed by trimethylsilyl isocyanate (Aldrich) (1.3 ml, 9.6 mmole) and stirred at room temperature over night. Quenched reaction with 1.0 N NaOH and extracted with CH$_2$Cl$_2$. Dried organic layer over MgSO$_4$, filtered and concentrated. Purified by column chromatography eluting with 3-5% Methanol saturated with Ammonia-CH$_2$Cl$_2$, affording the title compound (57) as a white solid. MS 464 (MH+).

EXAMPLES 14 AND 15

By substituting the appropriate isocyanates, and following the procedure described in EXAMPLE 13 above, compounds of the formula:

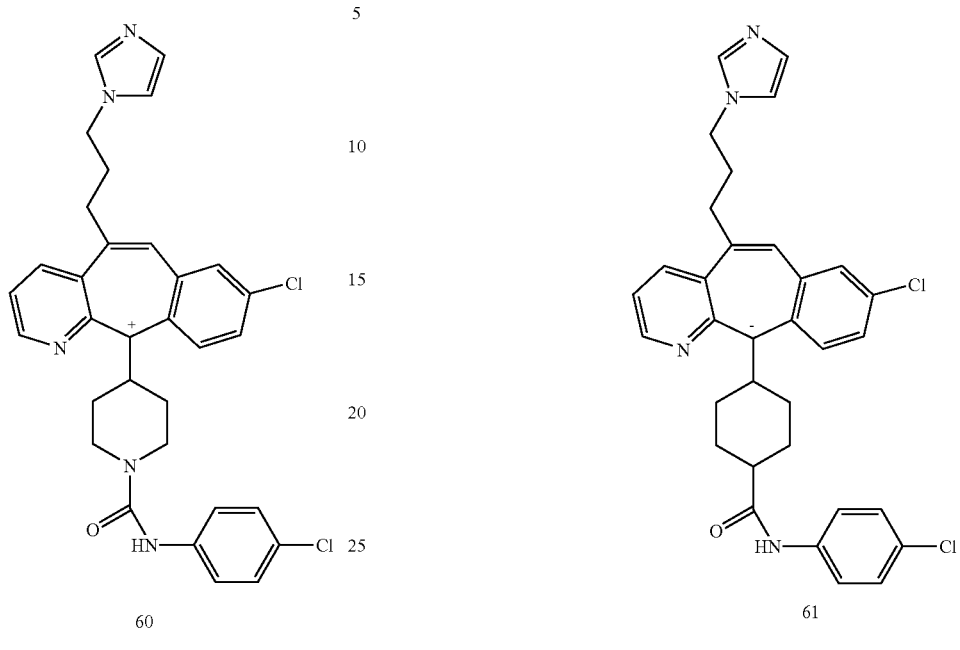

60

Compound (55) was deprotected following the procedure described in PREPARATIVE EXAMPLE 4, STEP G, to give the (+) enantiomer of the starting amine which was then reacted with 4-Chlorophenyl isocyanate (Aldrich) (0.05 g, 0.34 mmole) in the same manner as Example 13 above, affording the title compound (60) as a white solid. MS 572 (MH+).

EXAMPLE 17

61

Compound (56) was deprotected following the procedure described in PREPARATIVE EXAMPLE 4, STEP G to give the (−) enantiomer of the starting amine. Reacting in the same fashion as Example 16 above, afforded the title compound (61) as a white solid. MS 572 (MH+).

EXAMPLE 18

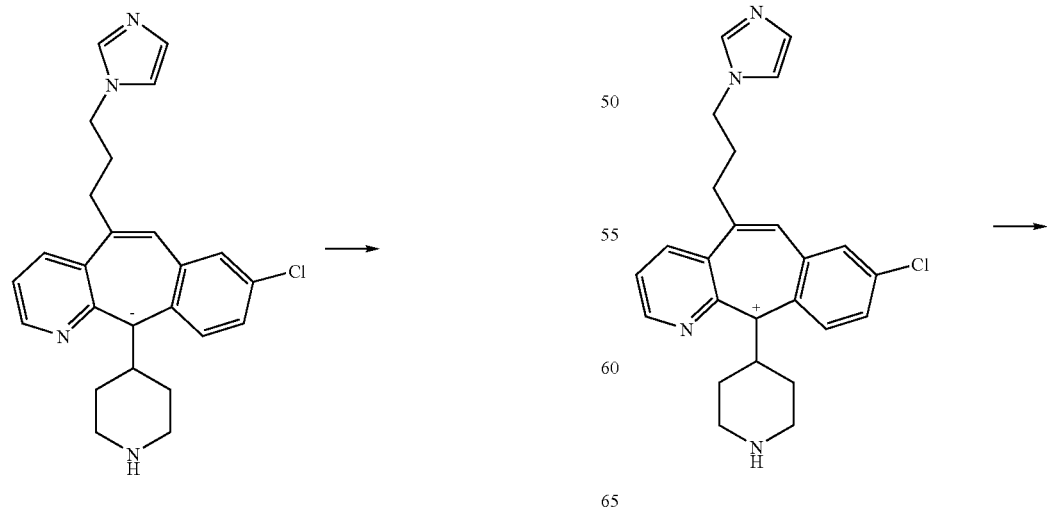

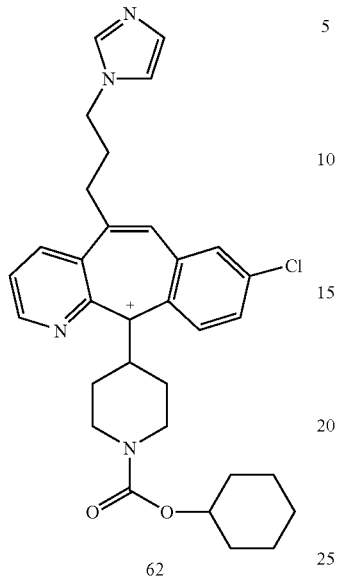

62

Following the procedure described in Example 16, substituting cyclohexyl chloroformate (BASF) in place of the isocyanate, afforded the title compound (62) as a white solid. MS 545 (MH⁺).

EXAMPLE 19

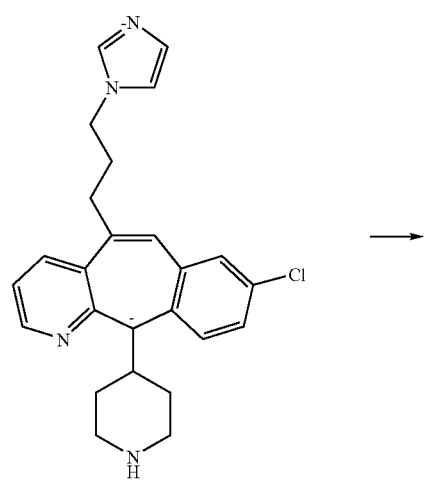

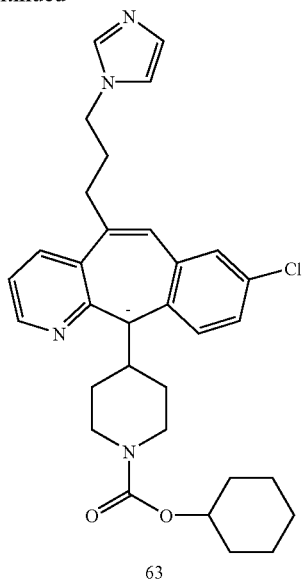

63

Following the same procedure as described in Example 18 above, substituting the (−) enantiomer of the starting amine from Example 17, afforded the title compound (63) as a white solid. MS 545 (MH⁺).

PREPARATIVE EXAMPLE 6

Step A

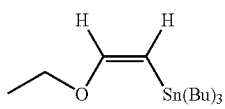

64

In a sealed tube, was added ethoxy ethyne (Fluka) followed by tributyltin hydride (Aldrich) and heated to 55° C. for two days. The reaction mixture was then concentrated to a brown red liquid. Purification via distillation afforded the title compound (64) as an off-white liquid. BP range 98°-115° C., (0.35 to 0.2 mmHg).

Step B

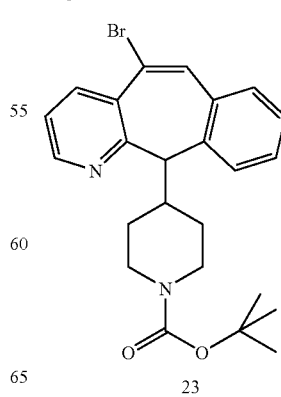

23

-continued

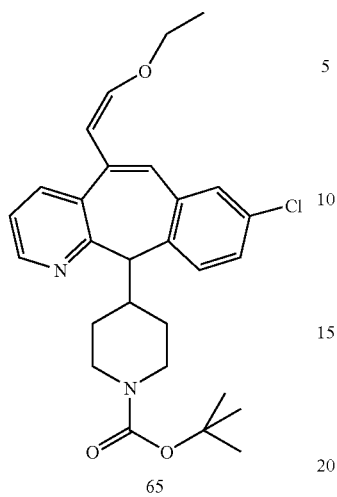

65

To a solution of compound (23) from Preparative Example 4, Step A (6.51 g, 13.29 mM), dichlorobis(triphenylphosphine) palladium(II) (Alrich) (0.373 g, 0.53 mM), and tetrabutylammonium chloride (Aldrich) (3.69 g, 13.29 mM) in DMF (50 ml) was added compound (64) from PREPARATIVE EXAMPLE 6, STEP A. The reaction stirred over night at 75-80° C. under nitrogen atmosphere. The reaction was cooled to room temperature, then a solution of KF (0.93 g, 15.94 mM) in H2O (70 ml) was added. A precipitate formed upon addition. The reaction mixture was stirred for fifteen minutes then added CH$_2$Cl$_2$ and stirred an additional fifteen minutes. The reaction mixture was extracted with CH$_2$Cl$_2$, the organic layer was dried over magnesium sulfate, filtered and concentrated. Purified by silica gel column chromatography eluting with 1:3%-1:1% ethyl acetate-hexanes affording the title compound (65) as a yellow solid, mp 86-90° C.

Step C

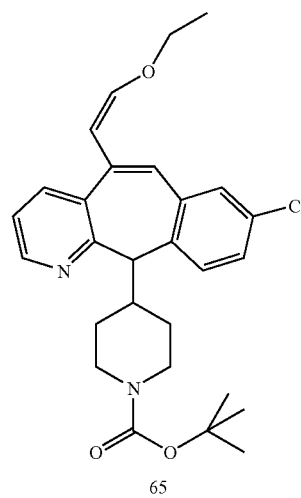

65

-continued

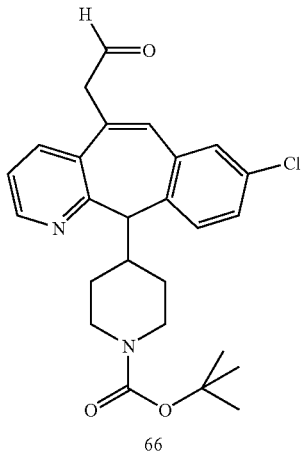

66

To a solution of compound (65) from Preparative Example 6, Step B (3.25 g, 6.76 mM) in THF/H2O (33.7 ml/7.3 ml), was added mercury (II) acetate. The reaction stirred at room temperature for fifteen minutes during which time a precipitate formed. To the mixture was then added saturated KI solution (70-80 ml) and was stirred for five minutes. Added CH$_2$Cl$_2$ and stirred for 1 h. The reaction was extracted with CH$_2$Cl$_2$ (2×100 ml). The organic layer was dried over magnesium sulfate, filtered and concentrated to afford the title compound (66) as a light brown solid. MS 453 (MH$^+$).

Step D

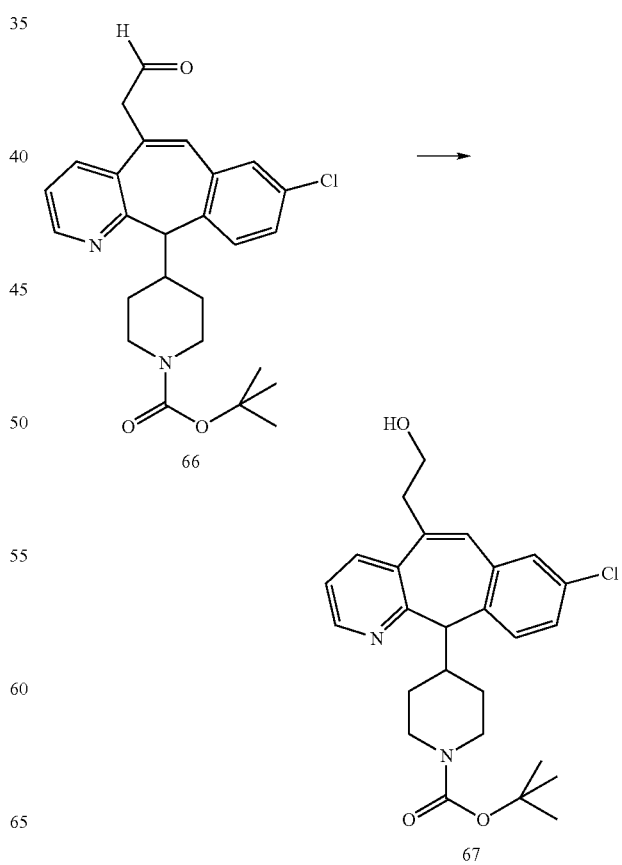

66

67

To a solution of compound (66) from Preparative Example 6, Step C (3.06 g, 6.8 mM) in ethanol (40 ml) was added sodium borohydride (0.31 g, 8.1 mM) in two portions over seven minutes. The reaction stirred for 45 minutes was then concentrated, taken up in ethyl acetate and washed with brine. Re-extracted brine layer with additional ethyl acetate and then combined organic layers, dried over magnesium sulfate, filtered and concentrated to a solid. Further purification by silica gel column chromatography eluting with 1:1-5:1 ethyl acetate-hexane afforded the title compound (67) as a white solid. MP range 120-130° C.; MS 455 (MH$^+$).

Step E

Step F

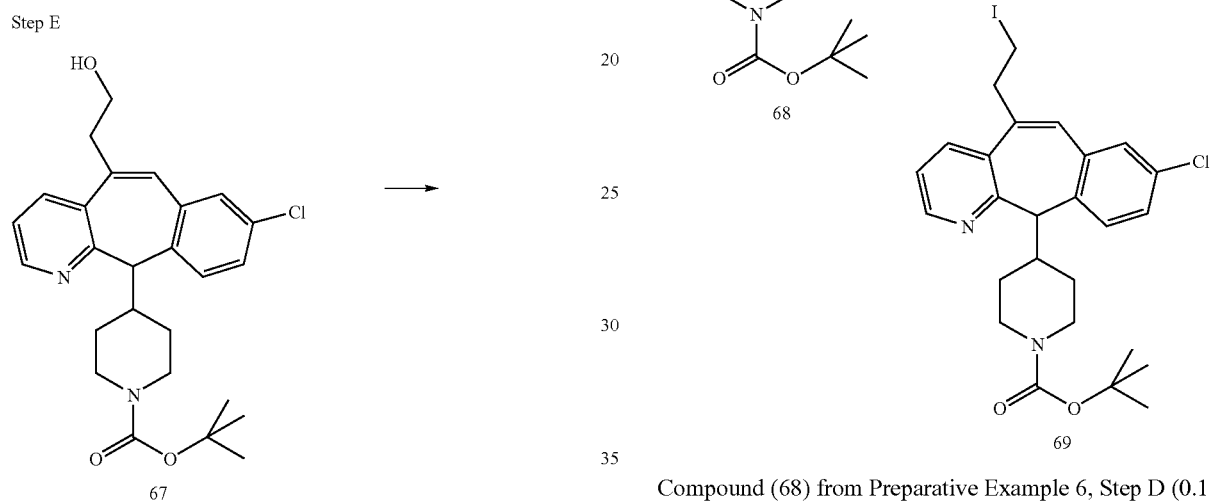

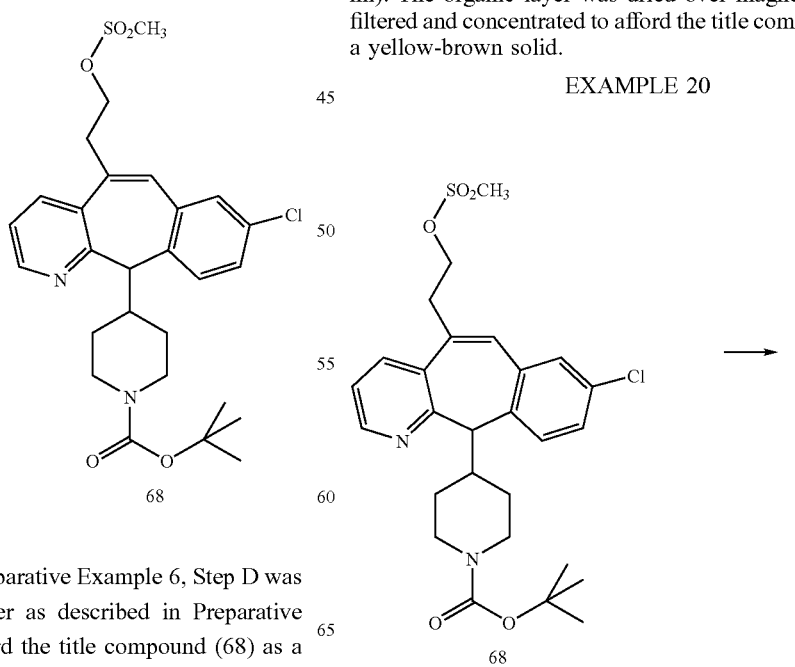

Compound (67) from Preparative Example 6, Step D was reacted in the same manner as described in Preparative Example 3, Step C, to afford the title compound (68) as a peach solid.

Compound (68) from Preparative Example 6, Step D (0.1 g, 0.19 mM) was dissolved in THF (2.5 ml). To the mixture was added LiI (Aldrich) (0.064 g, 0.48 mM) and stirred overnight at room temperature. The reaction mixture was concentrated, taken up in CH$_2$Cl$_2$ and washed with brine (25 ml). The organic layer was dried over magnesium sulfate, filtered and concentrated to afford the title compound (69) as a yellow-brown solid.

EXAMPLE 20

-continued

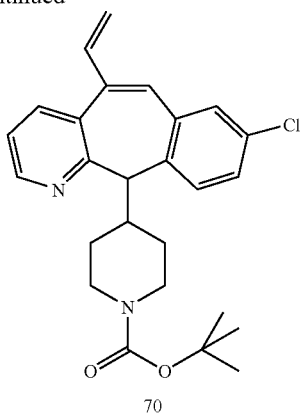

70

Compound (68) from Preparative Example 6, Step E, was reacted in the same manner as described in Example 8, Step B, resulting in the title compound (70) as a white solid, mp 94-101° C.

EXAMPLE 21

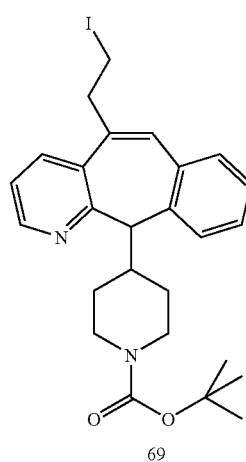

69

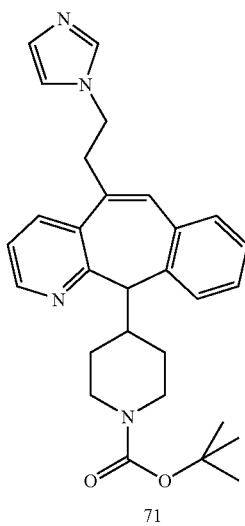

71

To compound (69) from Preparative Example 6, Step F (0.3 g, 0.05 mM) in CH$_3$CN (1 ml) was added imidazole (Aldrich) (0.014 g, 0.2 mM). The reaction was heated to 52° C. and stirred over night. The reaction was cooled, concentrated, then diluted with ethyl acetate and washed with brine. The organic layer was dried over magnesium sulfate, filtered and concentrated. The product was purified by silica gel column chromatography eluting with 0-5% methanol/saturated with ammonia:CH$_2$Cl$_2$ to afford the title compound (71) as a white solid. mp 95-104° C.; MS 505 (MH$^+$).

EXAMPLE 22

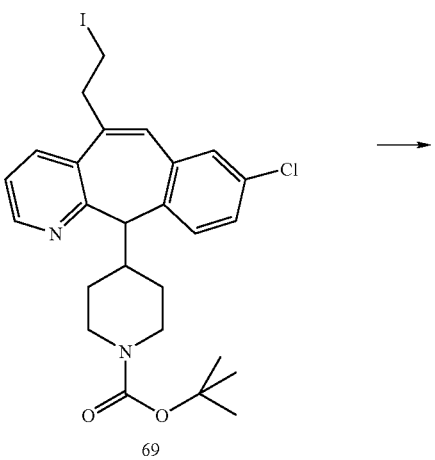

69

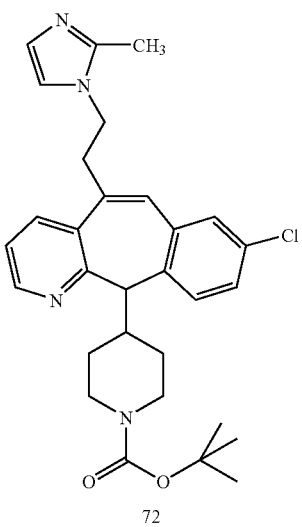

72

Substituting 2-methylimidazole for imidazole and reacting in essentially the same manner as Example 21, the title compound (72) was afforded as a light tan solid. mp 93-104° C.

EXAMPLE 23

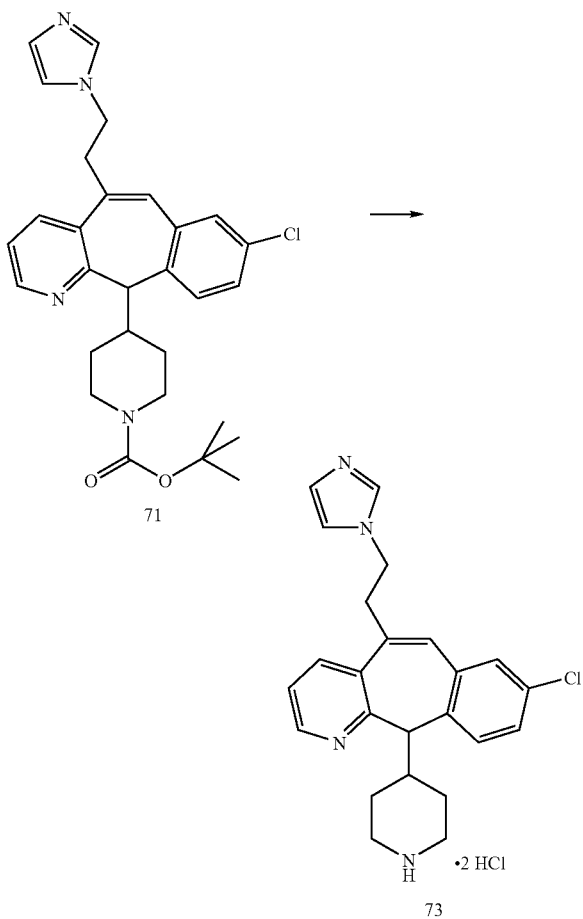

Compound (71) (0.31 g, 0.06 mM) from Example 21 was dissolved in 4M HCl/Dioxane (0.5 ml) and stirred for 1 h. Concentration of the reaction mixture afforded the title compound (73) as a light yellow solid. mp 195-205° C.

EXAMPLE 24

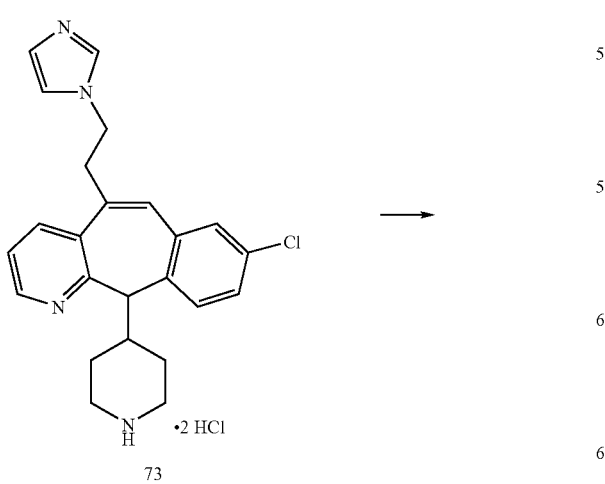

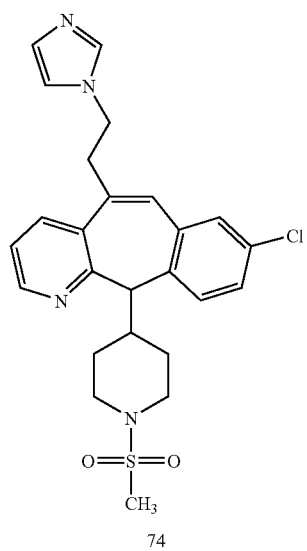

To a solution of compound (73) from Example 23 (0.026 g, 0.05 mM) in $CH_2Cl_2$, was added, triethyl amine (Aldrich) (0.046 ml, 0.33 mM) followed by methane sulfonyl chloride (Aldrich) (0.01 ml, 0.1 mM). The reaction stirred at room temperature for 36 h. The reaction was quenched with saturated sodium bicarbonate (50 ml) and extracted with ethyl acetate (2×75 ml). The organic layer was dried over magnesium sulfate, filtered and concentrated. The product was purified by preparatory thin layer chromatography eluting with 90:10 $CH_2Cl_2$: methanol saturated with ammonia to afford the title compound (74), mp 105-116° C.

EXAMPLE 25

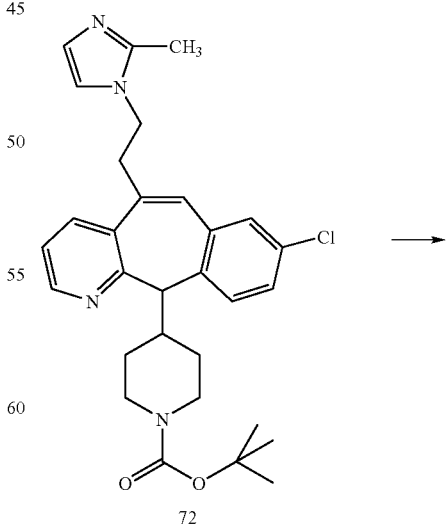

-continued

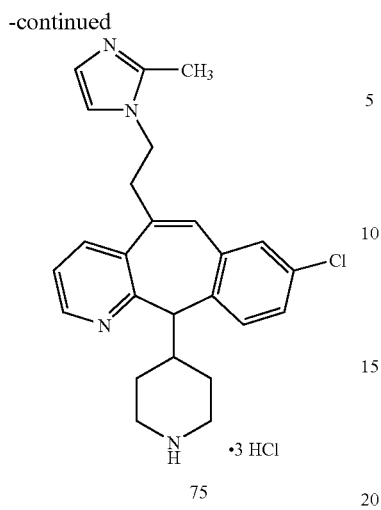

75

Compound (72) from Example 22 was stirred with 4M HCl/Dioxane over 2 h Concentration of reaction mixture afforded the title compound (75) as an off-white solid, mp 185-203° C.

EXAMPLE 26-29

Reacting compound (75) from Example 25, in the same manner as described in Example 13, and substituting the appropriate isocyanate, compounds of the formula:

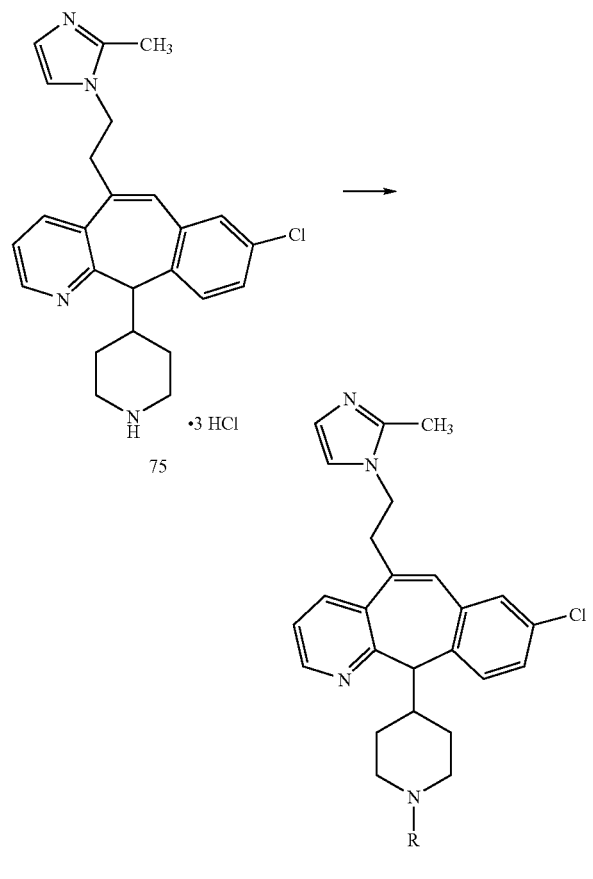

were prepared wherein R is defined in Table 3.

TABLE 3

| Ex | R = | Compound #: |
|---|---|---|
| 26 | ~~~~C(O)NH-C₆H₄-F (para) | (76). mp 133–144° C. |
| 27 | ~~~~C(O)NH-cyclohexyl | (77). mp 131–140° C. |
| 28 | ~~~~C(O)NH-t-Bu | (78). mp 125–132° C. |
| 29 | ~~~~C(O)NH-C₆H₄-CN (para) | (79). mp 160–172° C. |

EXAMPLE 30

Step A

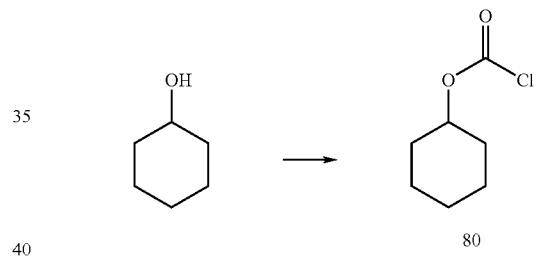

A solution of cyclohexanol (Aldrich) (25 ml, 0.2 mol) in CH₂Cl₂ (50 ml) was added dropwise over 1 h to a solution of phosgene in toluene (262 ml of a 1.93 M solution, 0.5 mol) at 0° C. The reaction was warmed to room temperature over 3 h. and stirred over night. The volatiles were removed to afford the title compound (80) as a colorless liquid.

Step B

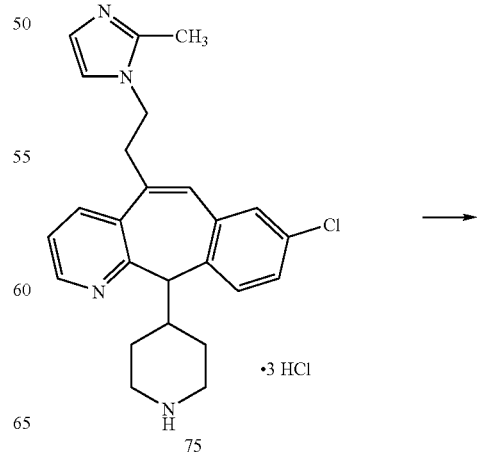

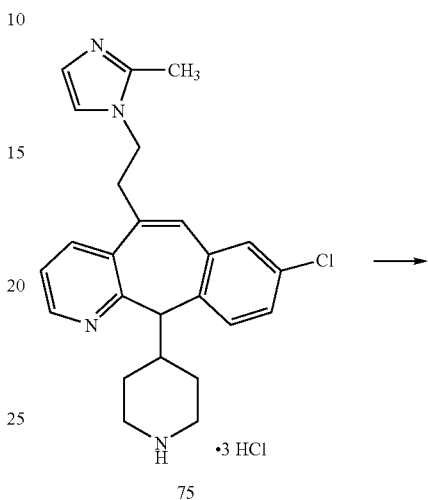

Reacting compound (75) from Example 25 in the same manner as described in Example 13, substituting the acid chloride (80) from Example 30, Step A in place of the isocyanate, afforded the title compound (81) as an off-white semi-solid. mp 89-98° C.

EXAMPLE 31

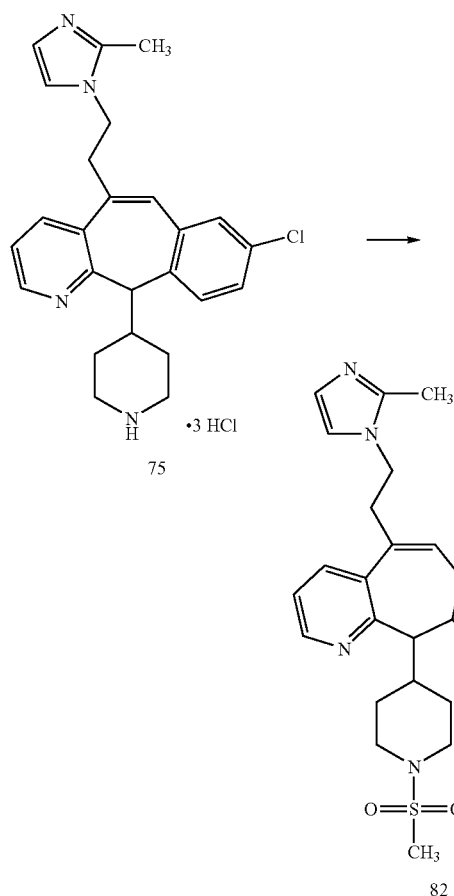

Reacting compound (75) from Example 25 in the same manner as described in Example 13 but substituting methanesulfonyl chloride in place of the isocyanate, afforded the title compound (82) as a tan semi-solid mp 120-129° C.

EXAMPLE 32

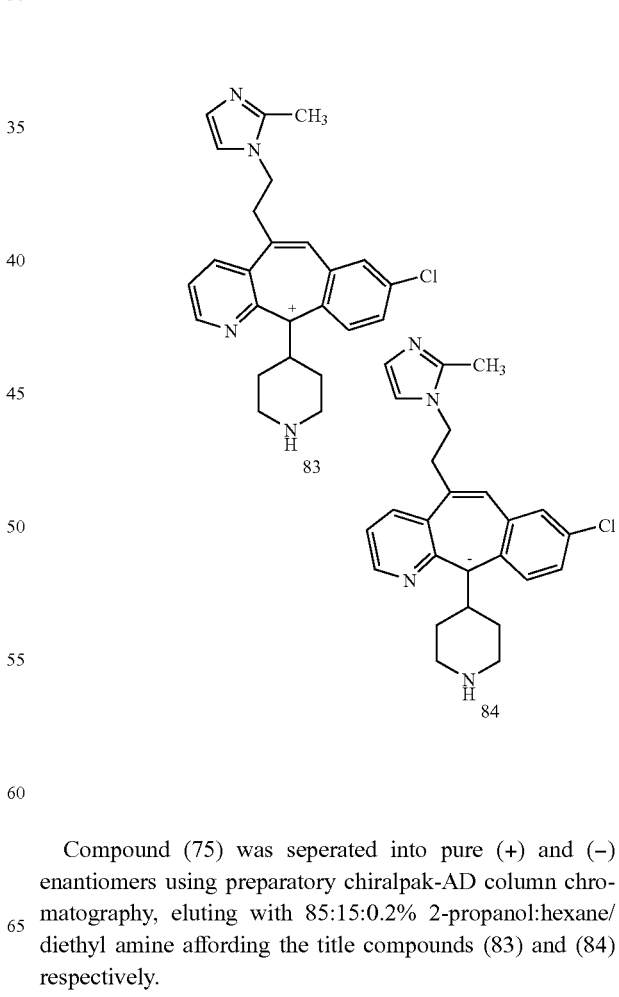

Compound (75) was seperated into pure (+) and (−) enantiomers using preparatory chiralpak-AD column chromatography, eluting with 85:15:0.2% 2-propanol:hexane/diethyl amine affording the title compounds (83) and (84) respectively.

EXAMPLE 33
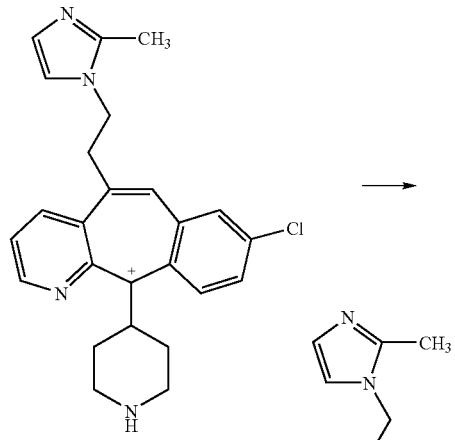
83
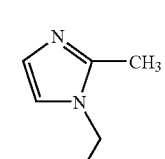
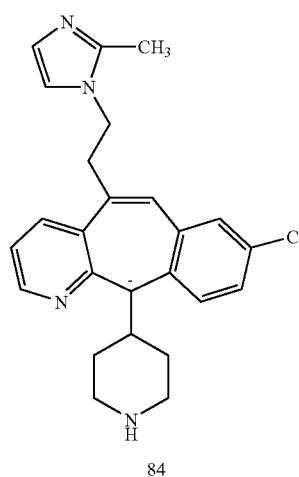
85
Compound (83) was reacted in the same manner as in Example 27 affording the title compound (85) as a white solid. mp 122-129° C.
EXAMPLE 34
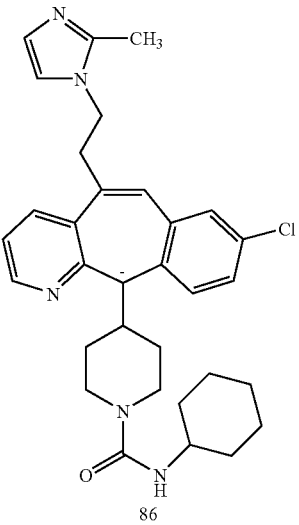
84
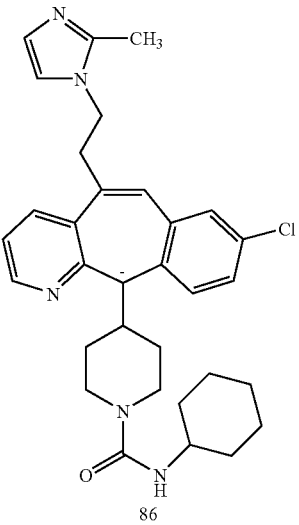
86
Compound (84) was reacted in the same manner as in Example 27 affording the title compound (86) as a white solid mp 118-133° C.
EXAMPLE 35
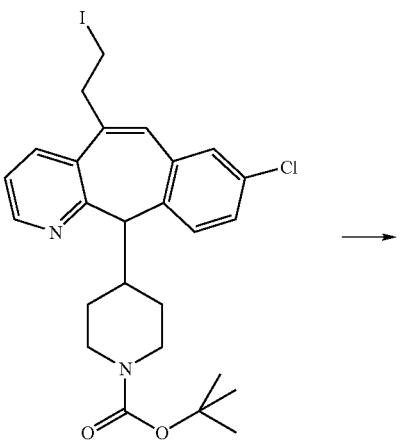
69
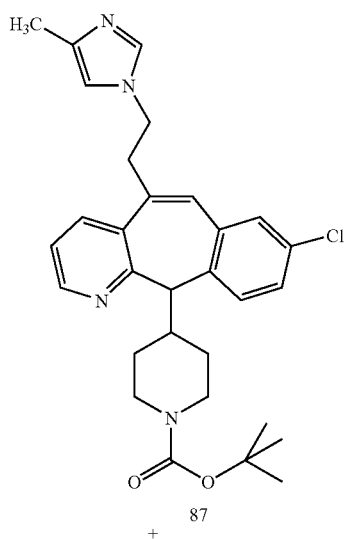
87

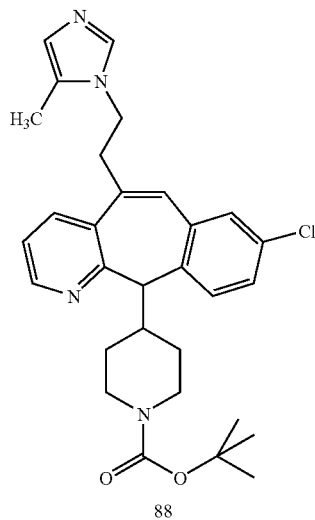

Compound (69) from Example 19 was reacted in the same manner as described in Example 21 substituting 4-methylimidazole for imidazole, to afford a mixture of the 4 and 5 substituted imidazole derivatives. The mixture (0.234 g, 0.45 mM) was subsequently treated with trityl chloride (Aldrich) (0.047 g, 0.17 mM) and separated by preparatory thin layer chromatography, eluting with 1:6% ethyl acetate-acetone affording the pure isomers (87) and (88) mp (87) 97-107° C. (white solid).

EXAMPLE 36

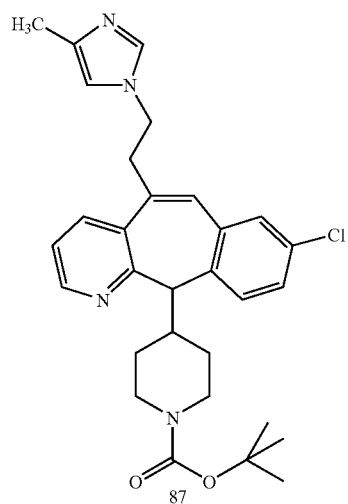

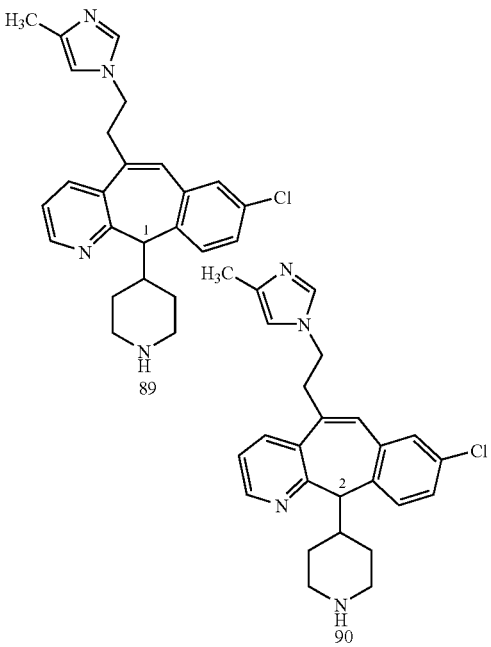

Compound (87) from Example 35 (0.085 g, 0.16 mM) was reacted in the same manner as described in Example 25. The resulting enantiomeric mixture was then separated by Preparatory Chiralpak-AD column chromatography eluting with 15-85% Isopropanol-Hexane, 0.2% diethylamine, affording enantiomers 1 and 2 as off-white solids.

EXAMPLE 37

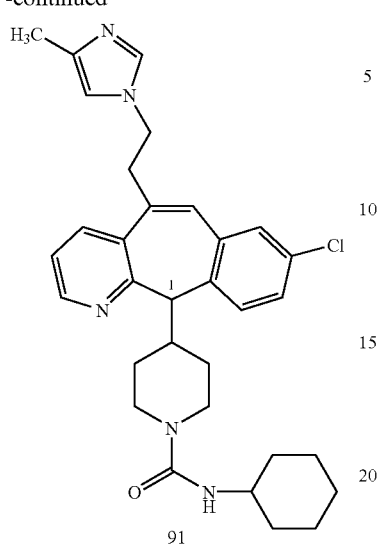

Enantiomerically pure compound (89) from Example 36 (0.02 g, 0.049 mM) was reacted in a similar manner as in Example 27 to afford the title compound (91) as a white solid. mp 130-142° C.

EXAMPLE 38

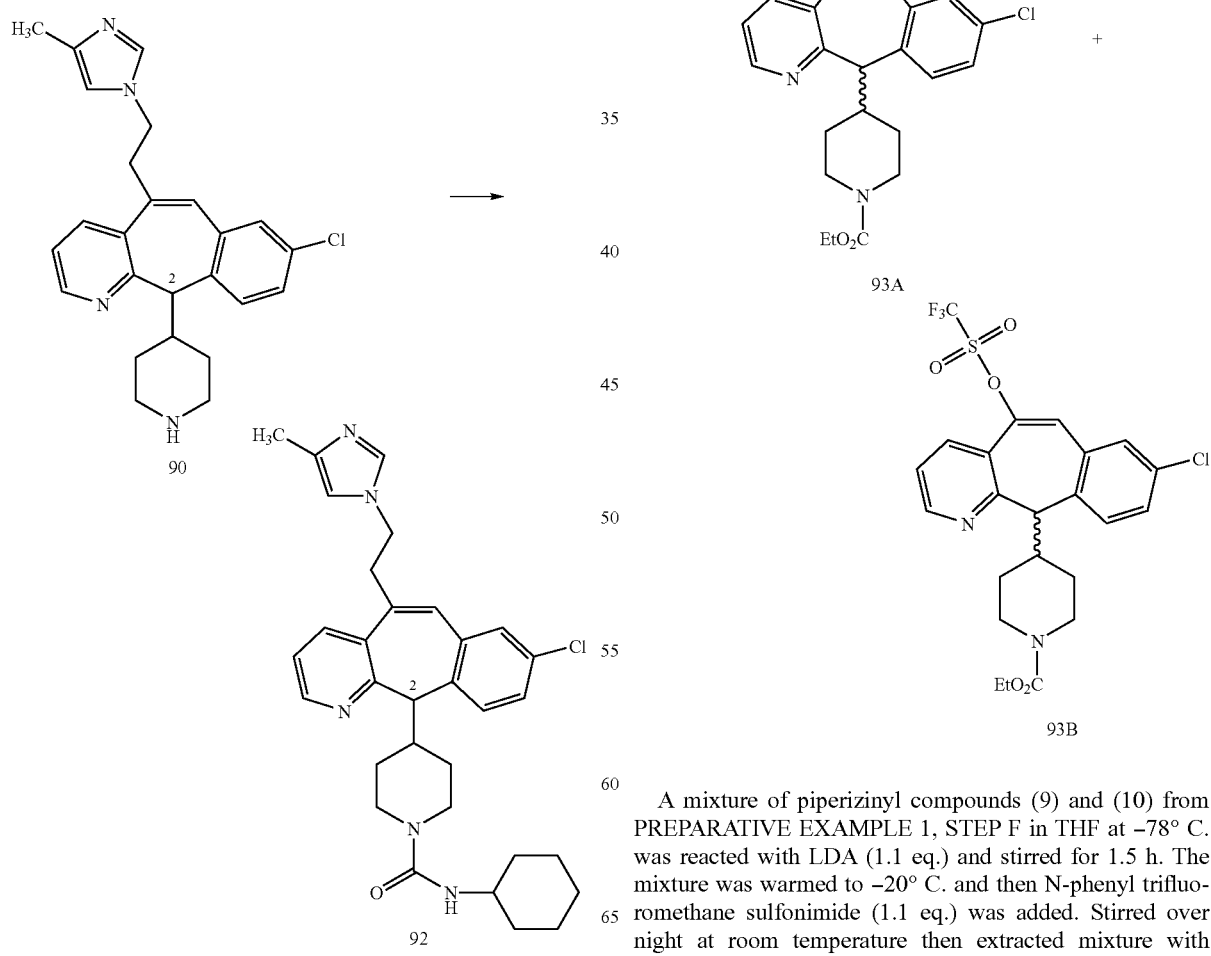

Enantiomerically pure compound (90) from Example 36 (0.023 g, 0.054 mM) was reacted in a similar manner as in Example 27 to afford the title compound (92). mp 125-135° C.

PREPARATIVE EXAMPLE 7

Step A

A mixture of piperizinyl compounds (9) and (10) from PREPARATIVE EXAMPLE 1, STEP F in THF at −78° C. was reacted with LDA (1.1 eq.) and stirred for 1.5 h. The mixture was warmed to −20° C. and then N-phenyl trifluoromethane sulfonimide (1.1 eq.) was added. Stirred over night at room temperature then extracted mixture with EtOAc and washed with $H_2O$. Dried over $Na_2SO_4$ and concentrated. Purification and separation by flash silica gel column chromatography afforded pure Compounds (93A & 93B).

Step B

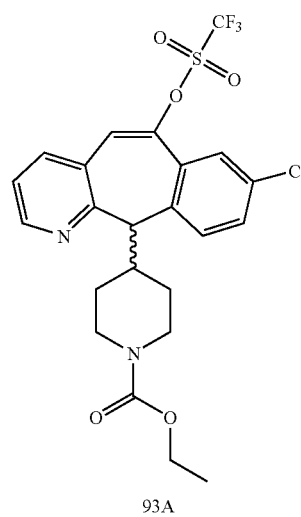

93A

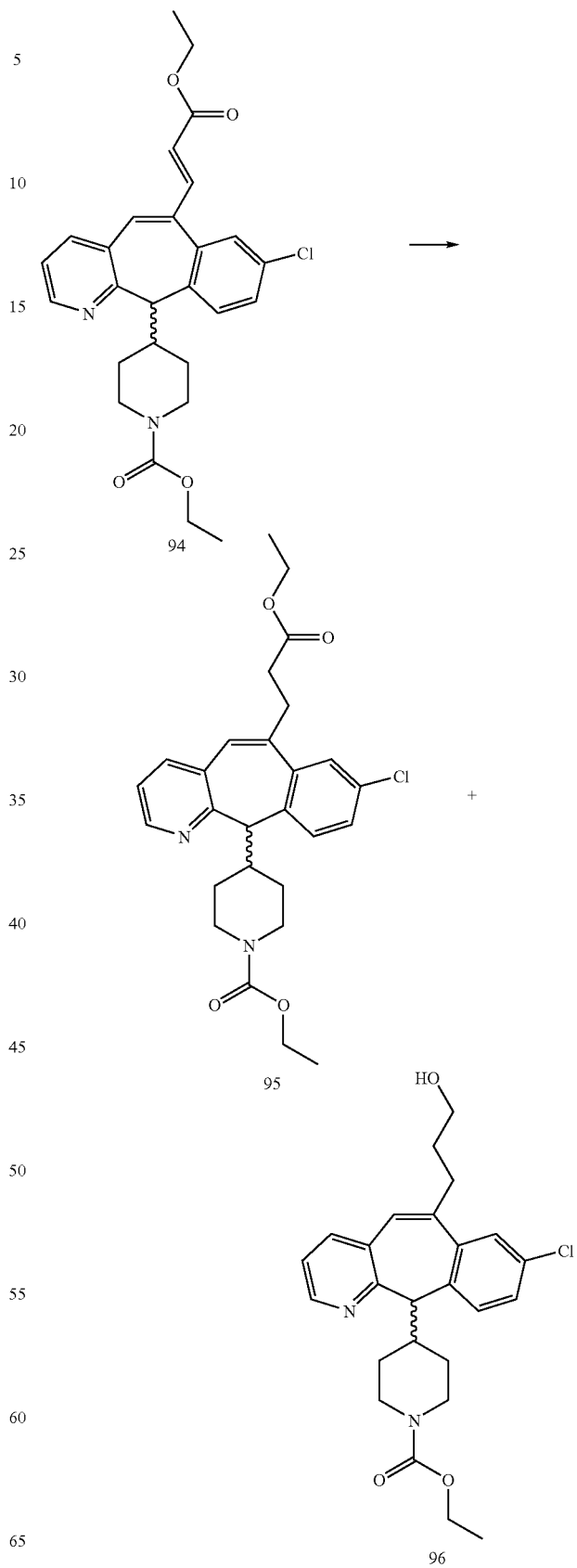

Compound (93A) from above was dissolved in DMF. Successively added, Et$_3$N (29 eq.), Ethyl acrylate (5.4 eq.), K$_2$CO$_3$ (5 eq.), Bu$_4$NBr (2 eq.) and Palladuim (II) acetate (0.13 eq.). The mixture stirred and heated to 100° C. for 4 h. After cooling, the mixture was concentrated and the residue was taken up in CH$_2$Cl$_2$ and extracted with CH$_2$Cl$_2$/H$_2$O. The organic layer was dried over Na$_2$SO$_4$ then concentrated and the residue purfied by flash silica column chromatography to afford the title compound (94).

Compound (94) was dissolved in EtOH cooled in an ice bath and reacted with NaBH₄ (15 eq.) for 3 min. Then added CuCl (2 eq) and stirred for 2 h. at room temperature. The mixture was filtered, concentrated and extracted with CH₂Cl₂. Washed with water then brine, dried over Na₂SO₄ and concentrated to a mixture of the title compound (95) and the hydroxy compound (96).

Step D

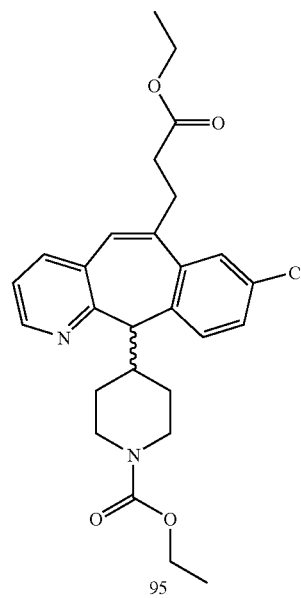

95

Compound (95), was then further reacted with LiBH₄(3 eq.) in THF at reflux temperature for 4 h. EtOAc was added and the mixture was washed with Na₂CO₃ then dried over Na₂SO₄ and concentrated to afford the title compound (96).

Step E

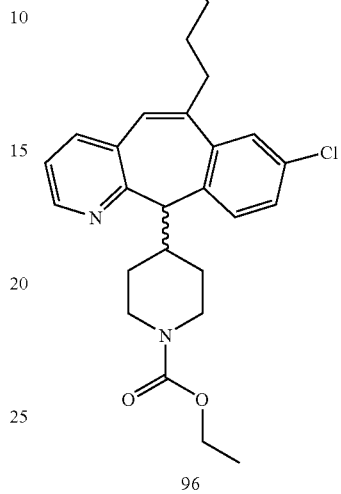

96

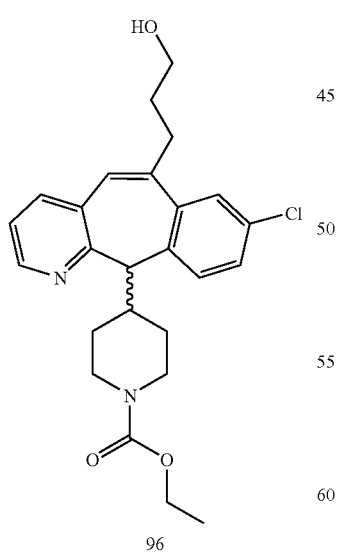

96

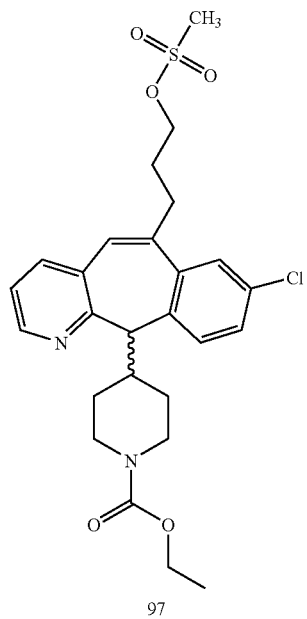

97

Dissolved compound (96) in CH₂Cl₂, added Et₃N (3 eq.) followed by methane sulfonylchloride (1.5 eq.). The mixture stirred at room temperature over night then diluted with CH₂Cl₂ and washed with Na₂CO₃. Dried over NaSO₄ and concentrated to afford the title compound (97).

Step F

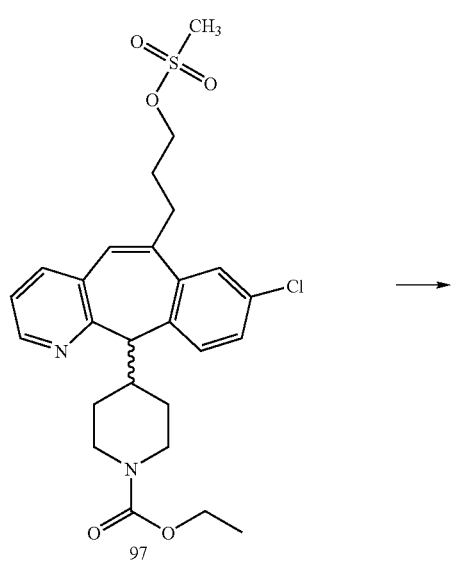

To a solution of sodium imidazole (Aldrich) in DMF was added, NaH (2 eq.). Stirred for 15 min. then added compound (97) (from above) (1 eq.) and stirred over night at room temperature. The reaction mixture was concentrated and then extracted with ethyl acetate. Washed with $Na_2CO_3$, dried over $NaSO_4$, filtered then concentrated. Crude product was purified by flash silica column chromatography. Further separation of pure (+) enantiomers and pure (−) enantiomers was accomplished on a chiracel AD column affording the title compounds (98) and (99).

Step G.

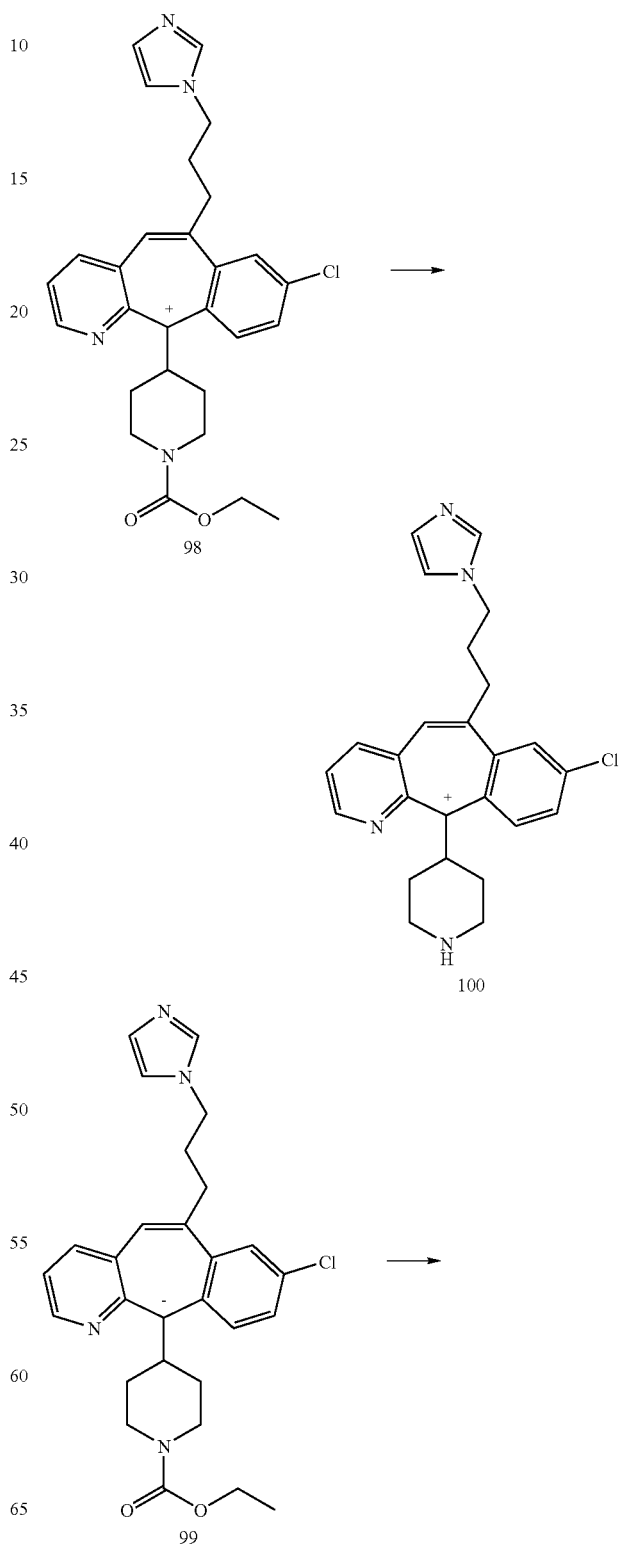

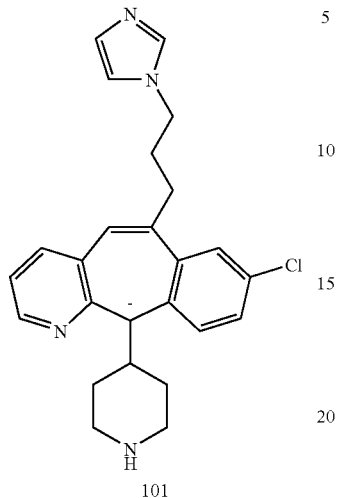

101

Compounds (98) and (99) were individually hydrolyzed to their free amines by refluxing in conc. HCl for 5 h. The reaction mixtures were separately poured into ice and basified with NH₄OH. The solutions were then extracted with CH₂Cl₂, dried over Na₂SO₄, filtered and concentrated to afford the title compounds (100) and (101).

PREPARATIVE EXAMPLE 8

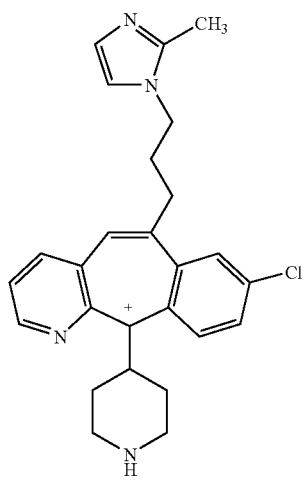

102

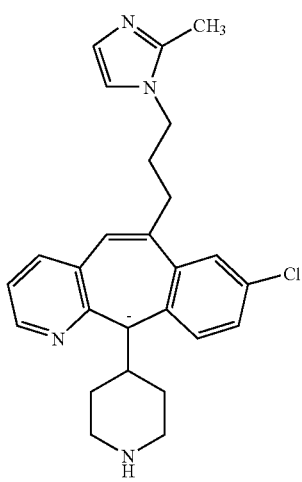

103

In a similar manner as described in Preparative Example 7, Steps A-G, substituting 2-methylimidazole for sodium imidazole, in Step F, the title compounds (102) and (103) were prepared.

PREPARATIVE EXAMPLE 9

Step A

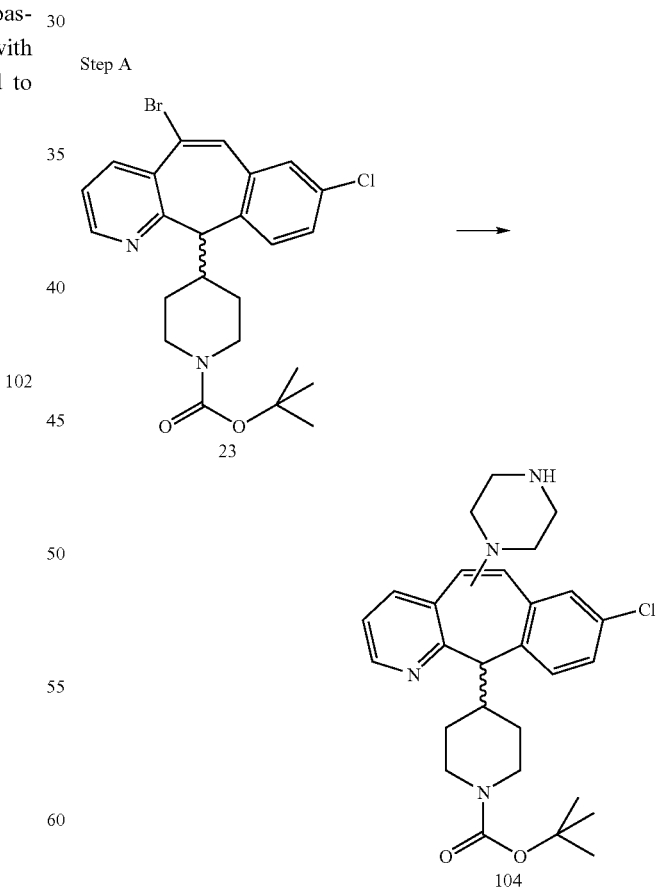

Compound (23) from Preparative Example 4 was reacted with piperazine in the same manner as described in Preparative Example 1, Step E, affording the title compound (104).

Step B

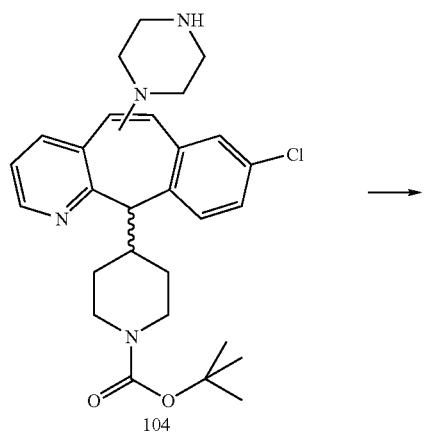
104

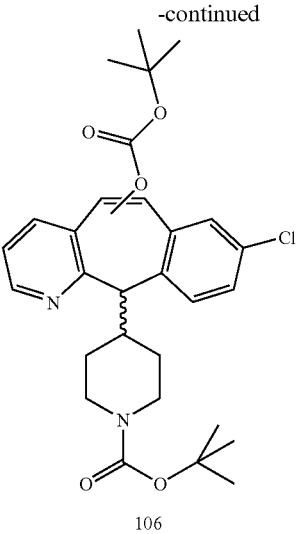
106

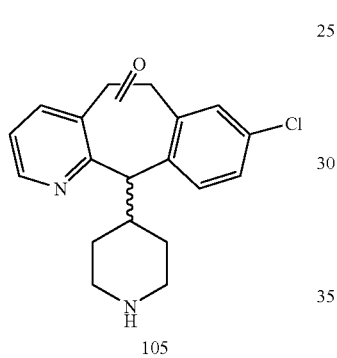
105

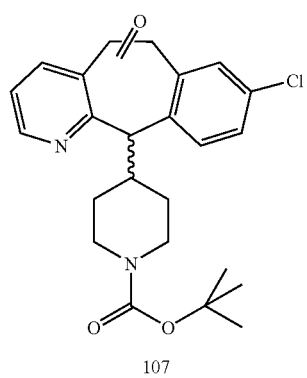
107

Compound (104) from above was hydrolyzed with 6N HCl over night at reflux temperature. The cooled reaction mixture was basified with 50% w/w NaOH and then extracted with 80% THF-EtOAc. The organic layer was dried over MgSO4, filtered and concentrated to dryness, affording the title compound (105).

Compound (105) was dissolved in 50:1 MeOH:H$_2$O then added di-tert-butyl dicarbonate (2 eq.). Adjusted pH to 9 and stirred for 4 h at room temperature. The reaction mixture was concentrated and extracted with CH$_2$Cl$_2$. The organic layer was washed with Na$_2$CO$_3$, dried, filtered and concentrated to dryness affording a mixture of title compounds (106) and (107).

Step C

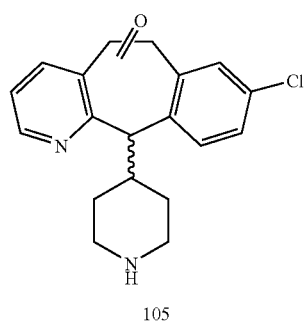
105

Step D

107

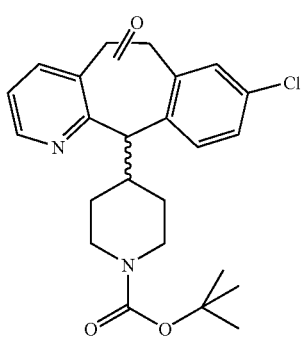

To the mixture of compounds (106) and (107) from Step C above, in 80% MeOH/H₂O at room temperature was added, cesium carbonate (2 eq.). The reaction stirred overnight. The mixture was then concentrated, extracted with CH₂Cl₂, washed with H₂O, dried over MgSO₄, filtered and concentrated to dryness affording the title compound (107).

Step E

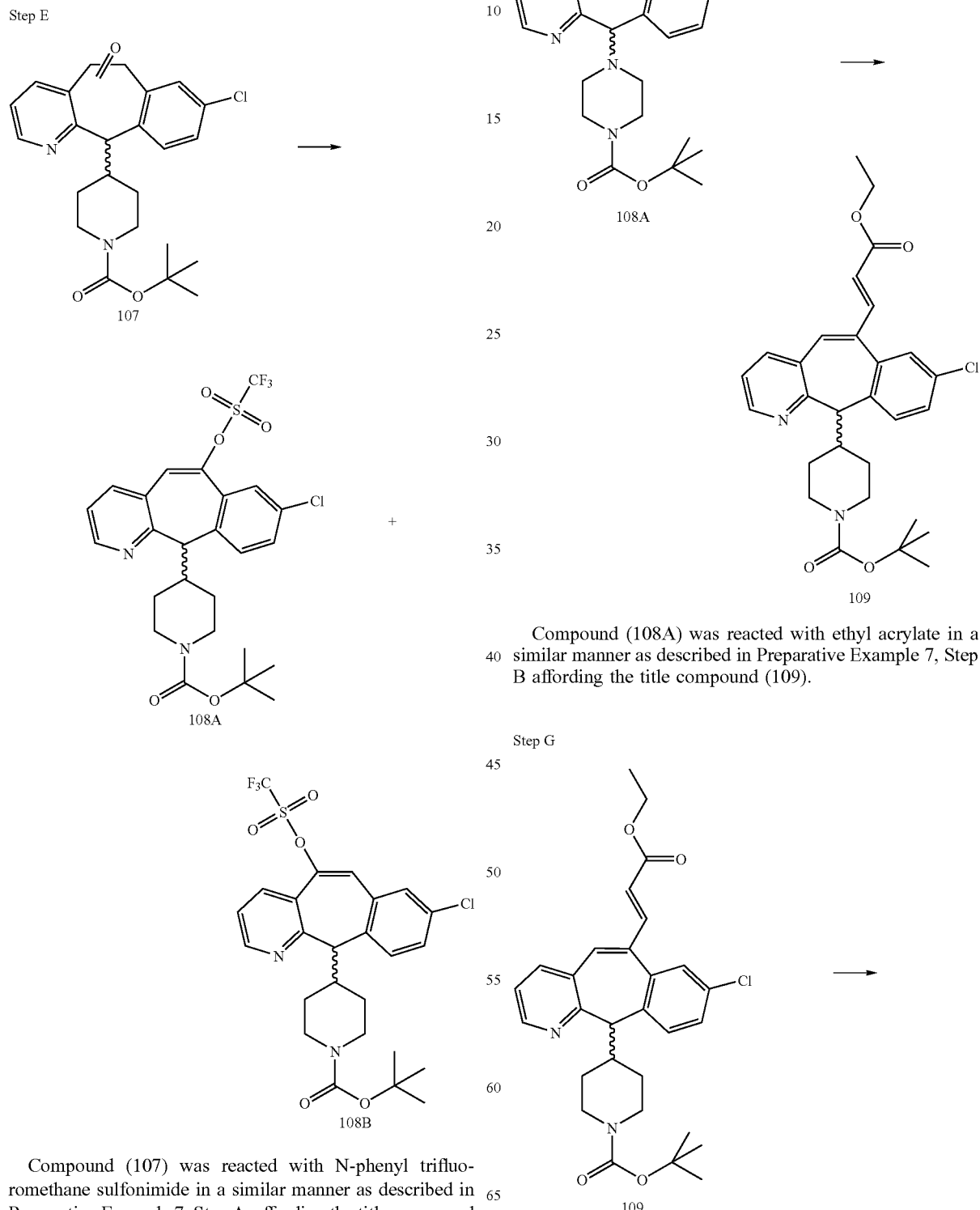

Compound (107) was reacted with N-phenyl trifluoromethane sulfonimide in a similar manner as described in Preparative Example 7, Step A, affording the title compound (108A & 108B).

Step F

Compound (108A) was reacted with ethyl acrylate in a similar manner as described in Preparative Example 7, Step B affording the title compound (109).

Step G

-continued

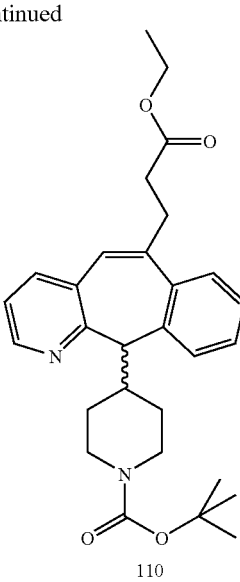
110

Compound (109) was reacted with NaBH₄ and CuCl in a similar manner as described in Preparative Example 7, Step C affording the title compound (110).

Step H

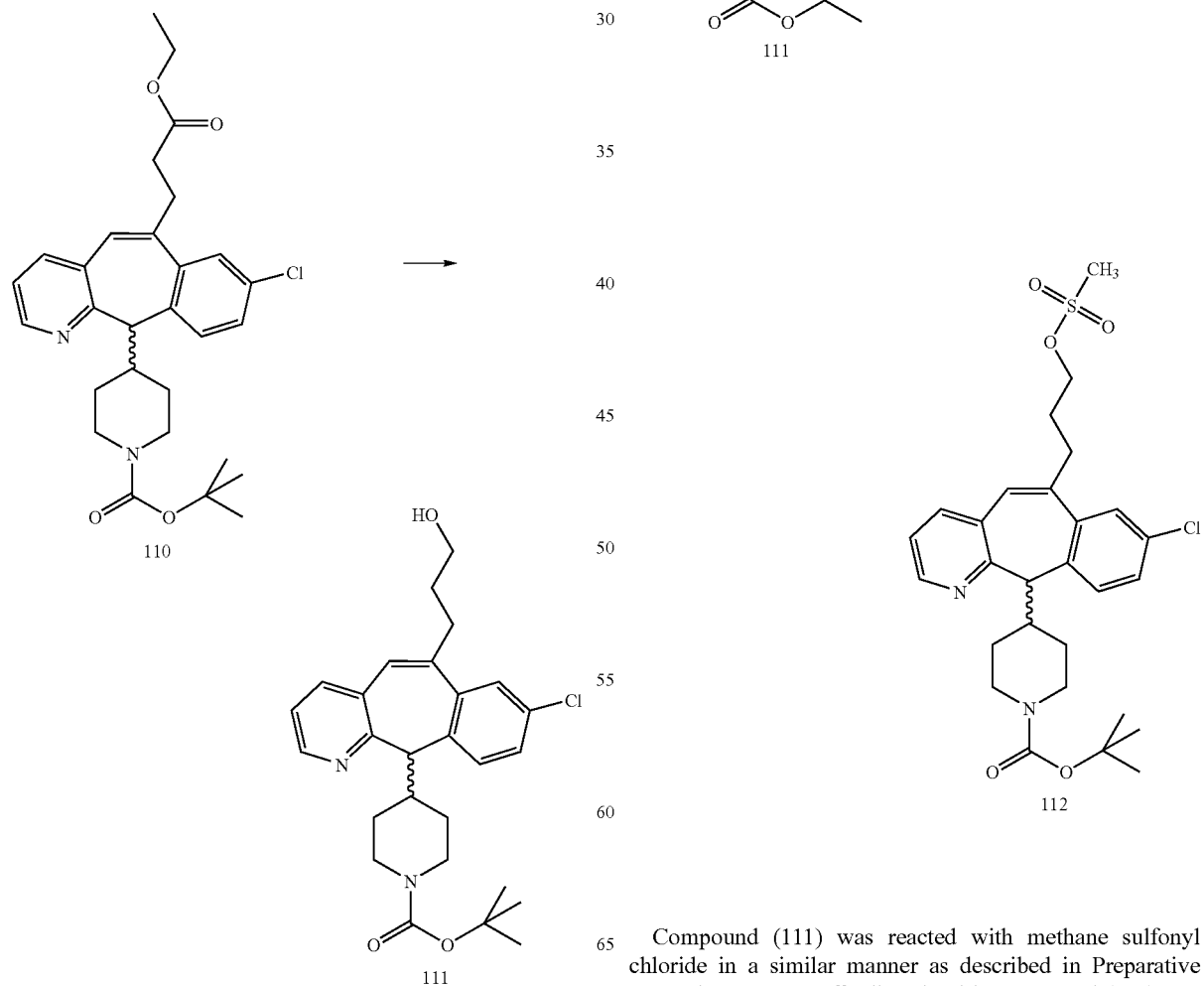

Dissolved compound (110) in THF and then added 1 M LiAlH₄/THF (1 eq.) and stirred for 1.5 h at room temperature. To the mixture was added H₂O and 15% NaOH then extracted with EtOAc. The reaction was washed with brine, dried over MgSO₄, filtered and concentrated. Purification by flash silica column chromatography eluting with 20% EtOAc/CH₂Cl₂ afforded the hydroxy title compound (111).

Step I

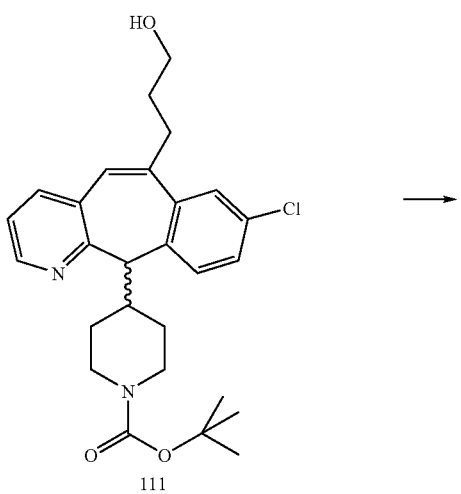

Compound (111) was reacted with methane sulfonyl chloride in a similar manner as described in Preparative Example 7, Step E affording the title compound (112).

Step J
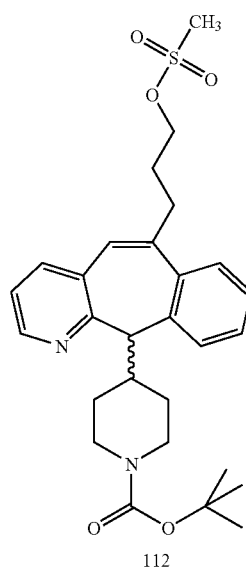
112
+
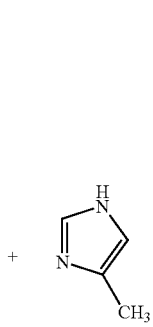
→
Compound (112) was reacted in a similar manner as Preparative Example 7, Step F substituting 4-methylimidazole for sodium imidazole. A mixture of (+,−)4 and (+,−)5-methylimidazoles resulted. The mixture was treated in the same manner as described in Example 11 affording pure stereoisomers (113), (114), (115) and (116).
Step K
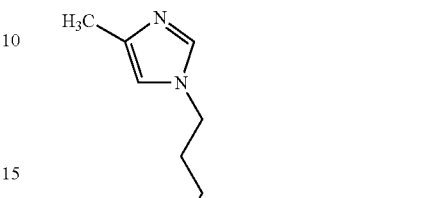
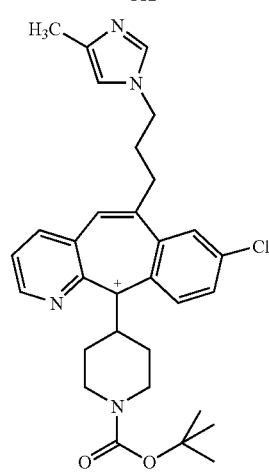
113
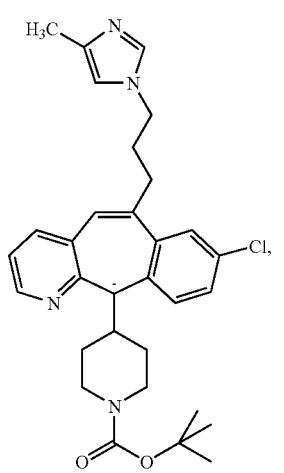
114
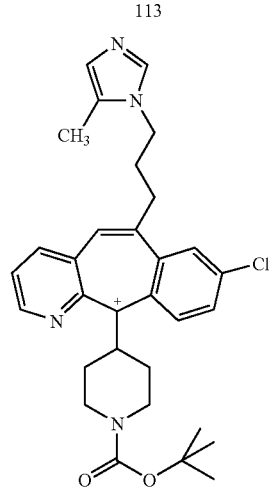
115
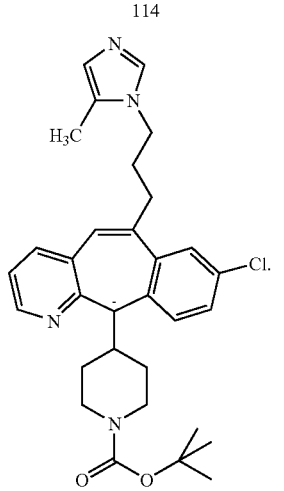
116
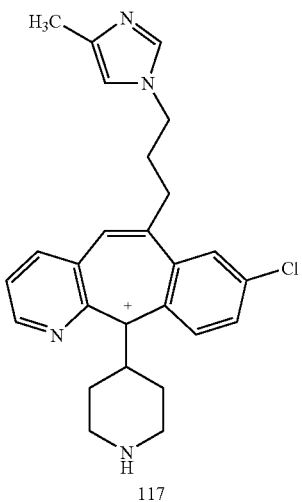
117
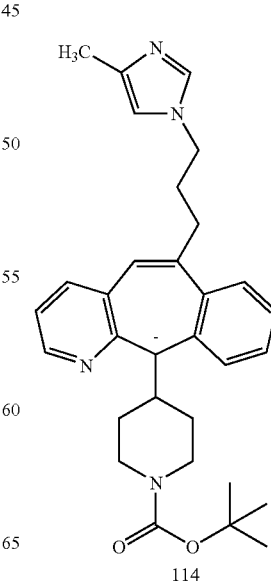
114

-continued

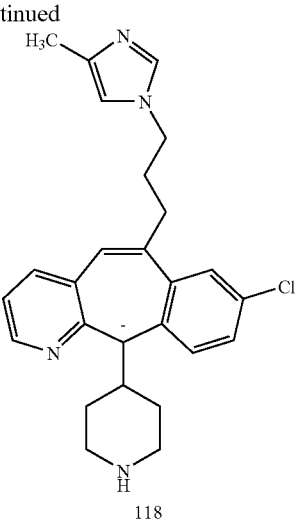
118

Compounds (113) and (114) were hydrolyzed to their free amines by stirring in HCl/Dioxane for 4 h. The mixtures were then concentrated to dryness affording the title compounds (117) and (118).

PREPARATIVE EXAMPLE 10

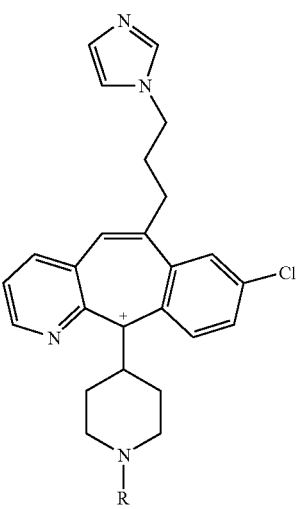
119

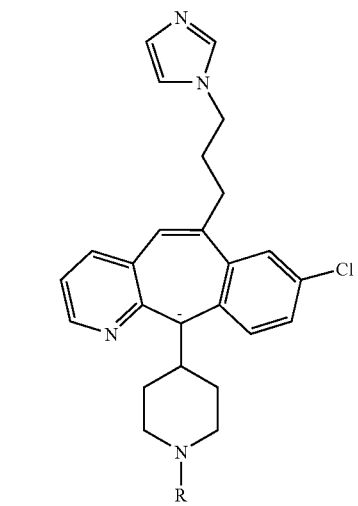
120

In a similar manner as described in Preparative Example 9, Steps A-K, substituting 4,5-dimethylimidazole in Step J, the title compounds (119) and (120) were prepared.

EXAMPLE 39-45

Reacting compounds (100) or (101) from Preparative Example 7, in the same manner as described in Example 13, substituting the appropriate isocyanate or chloroformate, compounds of the formula:

were prepared wherein R is defined in Table 4. In the column "Compound #" one compound # is the (+) isomer and the other compound # is the (−) isomer.

TABLE 4

| Ex | R = | Compound #: |
|---|---|---|
| 39 | ~~~~~NC(O)NH-C6H4-F (para) | (121) AND (122) |

TABLE 4-continued

| Ex | R = | Compound #: |
|---|---|---|
| 40 | cyclohexyl-NH-C(=O)- | (123) and (124) |
| 41 | tert-butyl-NH-C(=O)- | (125) AND (126). |
| 42 | 4-CN-phenyl-NH-C(=O)- | (127) AND (128). |
| 43 | ethyl-O-C(=O)- | (129) AND (130). |
| 44 | isopropyl-O-C(=O)- | (131) AND (132). |
| 45 | cyclohexyl-O-C(=O)- | (133) AND (134). |

EXAMPLE 46-51

Reacting compounds (102) or (103) from Preparative Example 8, in the same manner as described in Example 13, substituting the appropriate isocyanate or chloroformate, compounds of the formula:

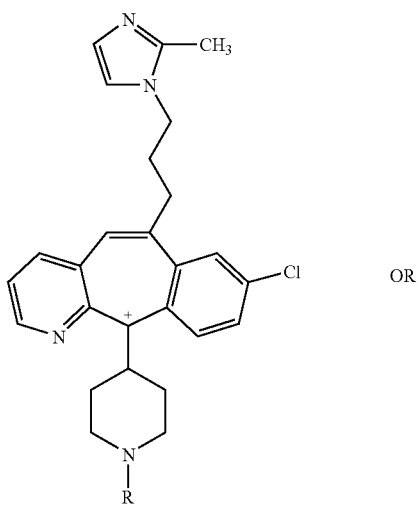

OR

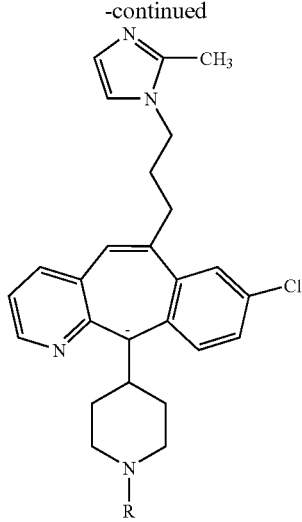

were prepared wherein R is as defined in Table 5. In the column "Compound #" one compound # is the (+) isomer and the other compound # is the (−) isomer.

TABLE 5

| Ex | R = | Compound #: |
|---|---|---|
| 46 | 4-F-phenyl-NH-C(=O)- | (135) AND (136). |
| 47 | cyclohexyl-NH-C(=O)- | (137) AND (138). |
| 48 | 4-CN-phenyl-NH-C(=O)- | (139) AND (140). |
| 49 | ethyl-O-C(=O)- | (141) AND (142) |
| 50 | isopropyl-O-C(=O)- | (143) AND (144). |
| 51 | cyclohexyl-O-C(=O)- | (145) AND (146). |

EXAMPLE 52-59

Reacting compounds (117) or (118) from Preparative Example 9, in the same manner as described in Example 13, substituting the appropriate isocyanate, chloroformate or sulfonyl chloride, compounds of the formula:

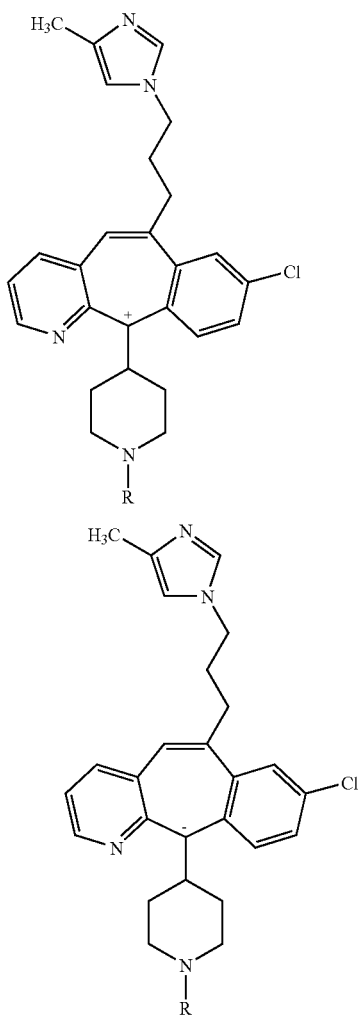

were prepared wherein R is defined in Table 6. In the column "Compound #" one compound # is the (+) isomer and the other compound # is the (−) isomer.

TABLE 6

| Ex | R = | Compound #: |
|---|---|---|
| 52 | ～C(O)NH-C6H4-F | (147) AND (148) |
| 53 | ～C(O)NH-cyclohexyl | (149) and (150) |
| 54 | ～C(O)NH-t-Bu | (151) AND (152). |

TABLE 6-continued

| Ex | R = | Compound #: |
|---|---|---|
| 55 | ～C(O)NH-C6H4-CN | (153) AND (154). |
| 56 | ～C(O)NH-C6H4-Cl | (155) AND (156) |
| 57 | ～S(O)2-CH3 | (157) AND (158). |
| 58 | ～C(O)O-iPr | (159) AND (160). |
| 59 | ～C(O)O-cyclohexyl | (161) AND (162). |

EXAMPLE 60-69

Reacting compounds (119) or (120) from Preparative Example 10, in the same manner as described in Example 13, substituting the appropriate isocyanate, chloroformate or sulfonyl chloride, compounds of the formula.

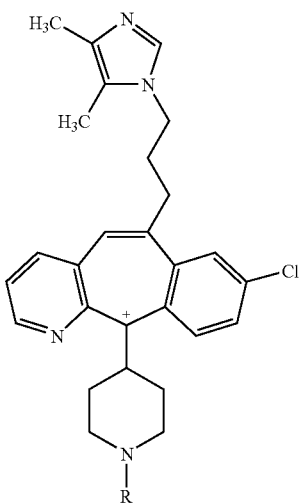

OR

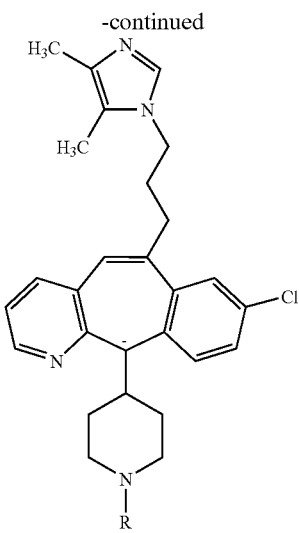

were prepared wherein R is defined in Table 7. In the column "Compound #" when there are two compounds listed for one example, one compound # is the (+) isomer and the other compound # is the (−) isomer.

TABLE 7

| Ex | R = | Compound #: |
|---|---|---|
| 60 | 4-F-phenyl-CH(–)-C(=O)NH– | (163) AND (164) |
| 61 | cyclohexyl-NH-C(=O)-CH(–)– | (165) and (166) |
| 62 | t-Bu-NH-C(=O)-CH(–)– | (167) AND (168) |
| 63 | 4-CN-phenyl-NH-C(=O)-CH(–)– | (169) AND (170) |
| 64 | CH₃-NH-C(=O)-CH(–)– | (171) (−)-isomer |
| 65 | 4-Cl-phenyl-NH-C(=O)-CH(–)– | (172) AND (173) |
| 66 | CH₃-S(=O)₂-CH(–)– | (174) AND (175) |

TABLE 7-continued

| Ex | R = | Compound #: |
|---|---|---|
| 67 | iPr-O-C(=O)-CH(–)– | (176) AND (177) |
| 68 | cyclohexyl-O-C(=O)-CH(–)– | (178) AND (179) |
| 69 | t-Bu-O-C(=O)-CH(–)– | (180) AND (181) |

PREPARATIVE EXAMPLE 11

Step A

182: imidazol-1-yl-C(Me)₂-CH₂-CO₂Et

Ethyl 2,2-dimethyl acrylate (50.0 g, 2.0 eq.) was stirred with imidazole (13.28 g, 200 mmol) at 90° for 48 hours. The resulting solution was cooled, diluted with 300 mL H₂O—CH₂Cl₂ (1:1) and separated. The aqueous layer was extracted with CH₂Cl₂ (2×75 mL) and the combined organic layer was dried over Na₂SO₄ and concentrated in vacuo. The crude mixture was purified by flash chromatography using a 10% MeOH in CH₂Cl₂ solution as eluent to give pure product as a clear oil. CIMS: MH$^+$=197.

Step B

182 → 183 (imidazol-1-yl-C(Me)₂-CH₂-CH₂-OH)

A solution of the title compound from Preparative Example 11, Step A, (10.0 g, 50.96 mmol) was treated with LiAlH₄ (51 mL, 1 M solution in ether, 1.0 eq.). The reaction mixture was stirred one hour before quenching by the dropwise additon of saturated Na₂SO₄ (~3.0 mL). The resulting slurry was dried with Na₂SO₄ (solid), diluted with EtOAc (100 mL) and filtered through a plug of Celite. The filtrate was concentrated to give crude product which was used without further purification. CIMS: MH$^+$=155.

Step C

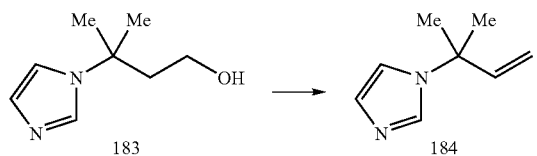

Iodine (3.83 g, 1.2 eq.) was added to a solution of Ph₃P (3.95 g, 1.2 eq.) and imidazole (1.02 g, 1.2 eq.) in CH₂Cl₂ (30 mL) portionwise over 15 minutes followed by a solution of the title compound from Preparative Example 11, Step B, (3.83 g, 12.56 mmol) in CH₂Cl₂ (10 mL). The resulting solution was stirred one hour before concentrating in vacuo. The residue was dissolved in THF (100 mL), treated with KOt-Bu (4.51 g, 3.2 eq.) and stirred at room temperature over night. The reaction mixture was diluted with water (100 mL) and CH₂Cl₂ (100 mL), separated, and the aqueous layer extracted with CH₂Cl₂ (2×50 mL). The combined organics were dried over Na₂SO₄, filtered, and concentrated under reduced pressure. The product was purified by flash chromatography using neat EtOAc then 5% MeOH in EtOAc as eluent to give a pale yellow oil (184).
CIMS: MH⁺=137.

Step D

Pd(OAc)₂ (0.023 g, 10 mol %) was added to a solution of the title compound (184) from Preparative Example 11, Step C, (0.30 g, 2.0 eq.), compound (23)(0.50 g, 1.02 mmol), Bu₄NBr (0.66 g, 2.0 eq.), TEA (2.84 mL, 20.eq.) and K₂CO₃ (0.70 g, 5.0 eq) in DMF (10 mL). The resulting solution was heated to 100° C. for 48 hours, cooled to room temperature, and concentrated under reduced pressure. The residue was diluted with water (50 mL) and CH₂Cl₂ (50 mL), separated, and the aqueous layer extracted with CH₂Cl₂ (2×25 mL). The combined organic layer was dried over Na₂SO₄, filtered, and concentrated in vacuo. The crude product was purified by flash column chromatography using an 8% MeOH in CH₂Cl₂ solution as eluent to yield a 4:1 mixture of the compound (184) and coupled product (185). This mixture (0.27 g) was stirred in CH₂Cl₂: TFA (7.0 mL, 5:2) for 1.5 hours. The crude product was concentrated under reduced pressure, neutralized with NaOH (1N), and extracted with CH₂Cl₂ (3×20 mL). The combined organics were dried over Na₂SO₄, filtered, and concentrated in vacuo. The crude residue was purified by flash chromatography using a 15% (10% NH₄OH in MeOH) solution in CH₂Cl₂ as eluent to give the title compound (185) as a tan solid. LCMS: MH⁺=445.

EXAMPLE 70

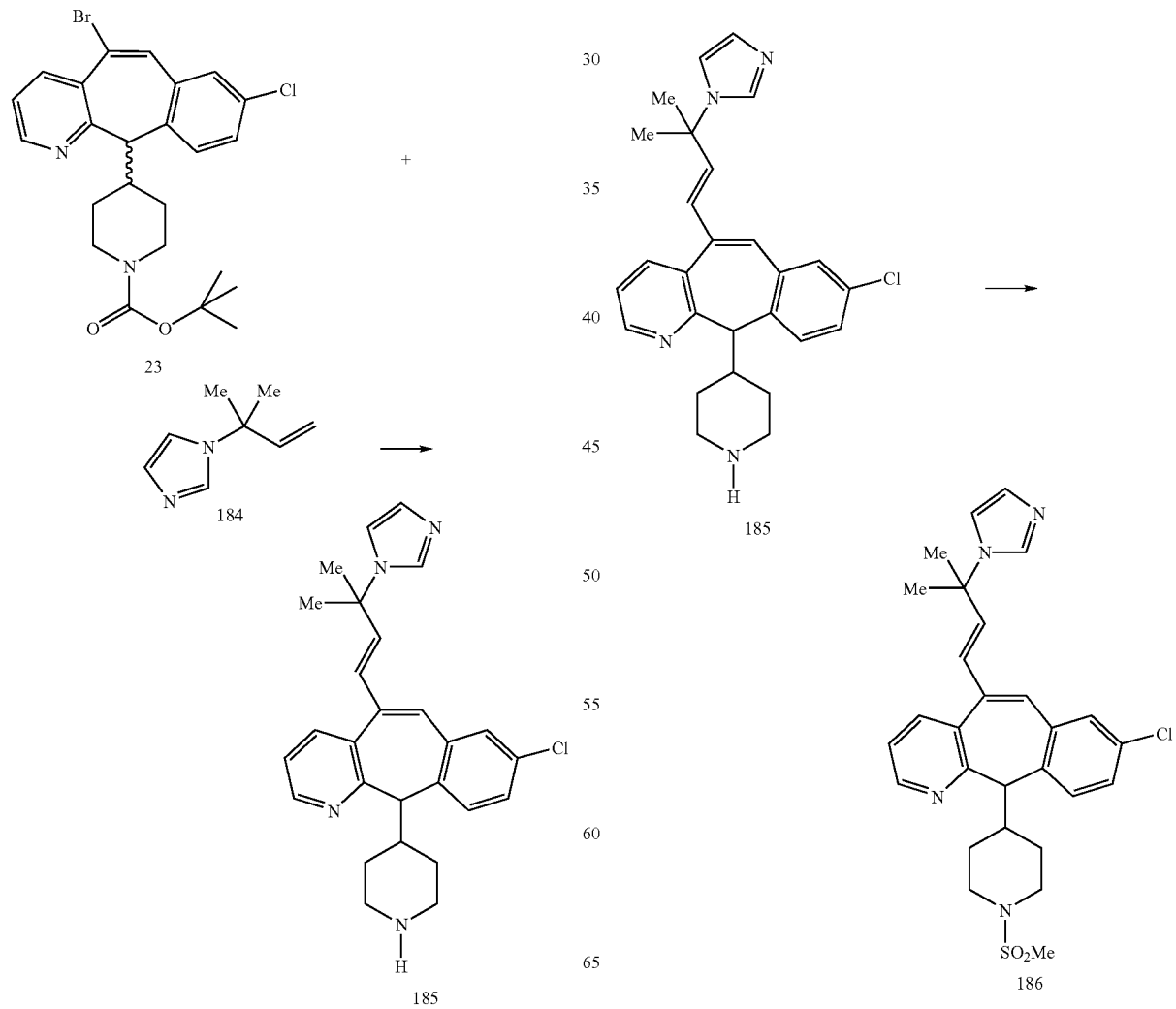

Methanesulfonyl chloride (0.005 mL, 1.3 eq) was added to a solution of Compound (185) from Preparative Example 11, Step D (0.02 g, 0.045 mmol) and TEA (0.010 mL, 1.5 eq.) in CH$_2$Cl$_2$ (1 mL). The resulting solution was stirred 12 hours at room temperature and diluted with saturated NaHCO$_3$ (5 mL), separated, and the aqueous layer extracted with CH$_2$Cl$_2$ (3×10 mL). The combined organic layer was dried over Na$_2$SO$_4$ and concentrated in vacuo. The crude product was purified by flash chromatography using an 8% (10% NH$_4$OH in MeOH) solution in CH$_2$Cl$_2$ as eluent to give the title compound (186) as a tan solid mp 124-129° C.; LCMS: MH$^+$=523.

EXAMPLE 71

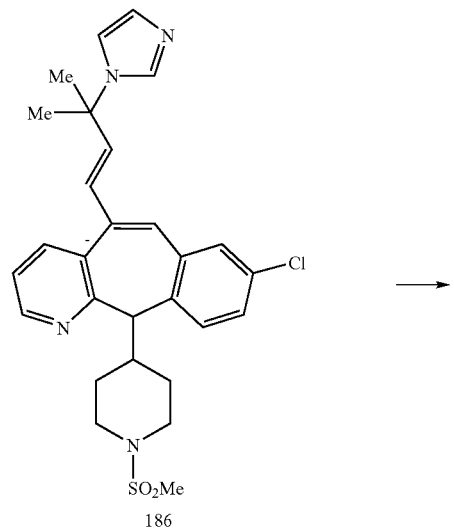

186 pTosNHNH$_2$ (0.085 g, 3 eq) was added to a solution of compound (186) from Example 70 (0.08 g, 0.0153 mmol) and DBU (0.11 mL, 5.0 eq.) in toluene (5 mL) and the resulting solution was heated to reflux. Subsequently, every 2 hours over 6 hours the solution was cooled and additional pTosNHNH$_2$ (3.0 eq) added and the solution heated to reflux. After heating at reflux 2 hours following the final addition the solution was cooled, diluted with CH$_2$Cl$_2$ (25 mL) and washed with saturated NaHCO$_3$ (3×20 mL). The organic layer was dried over Na$_2$SO$_4$, filtered, and concentrated under reduced pressure. The crude reaction mixture was purified by flash column chromatography using a 5% (10% NH$_4$OH in MeOH) solution in CH$_2$Cl$_2$ as eluent to give the title compound (187) as a tan solid. mp 112-116° C.; LCMS: MH$^+$=525.

PREPARATIVE EXAMPLE 12

Step A

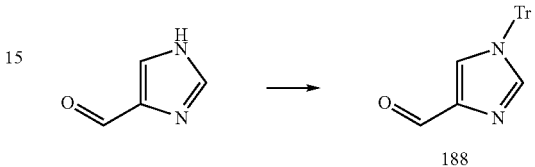

188

Literature compound 1H-imidazole-4-carbaldehyde was tritylated according to the literature procedure Kelley, et al.; J. Med. Chem 20(5), (1977), 721 affording the title compound (188).

Step B

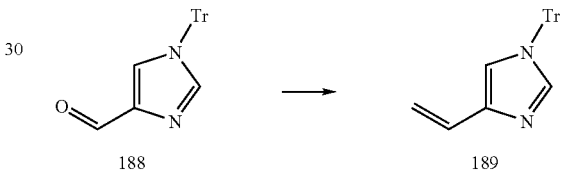

188                189 nBuLi (2.00 mL, 2.2 eq; 1.7M in hexanes) was added dropwise to Ph$_3$PCH$_3$Br (1.4 g, 2.3 eq) in THF (10 mL). The resulting orange solution was stirred 30 minutes at room temperature before cooling to −78° C. and adding the trityl protected 1(3)H-imidazole-4-carbaldehyde (0.50 g, 1.48 mmol) in THF (7.0 mL). The resulting solution was warmed slowly to room temperature and stirred overnight. The reaction was quenched by the addition of water (20 mL) and extracted with CH$_2$Cl$_2$ (3×20 mL). The combined organics were dried over Na$_2$SO$_4$ and concentrated in vacuo. The crude product was purified by flash chromatography using a 45% hexanes in EtOAc solution as eluent to yield the title compound (189) as a white solid.

Step C

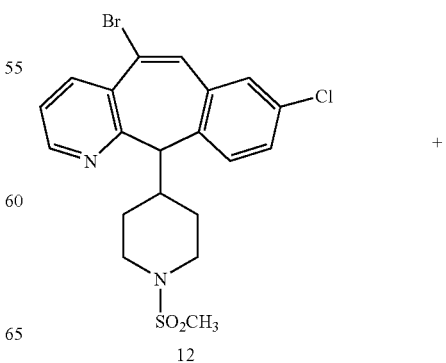

12

+

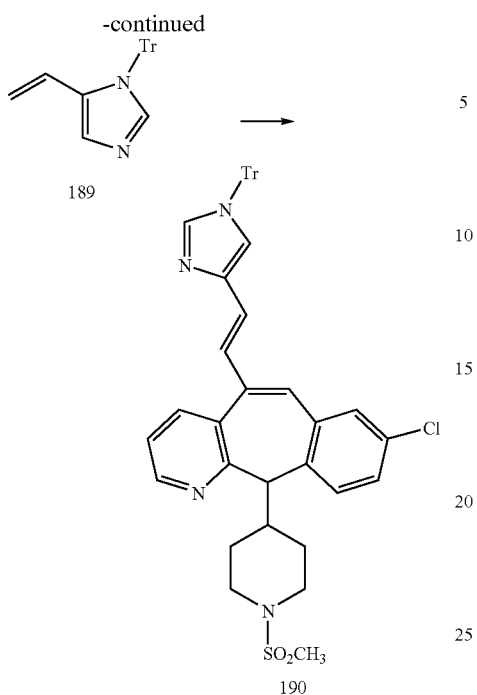

Pd(OAc)$_2$ (0.021 g, 0.10 eq.) was added to a solution of compound (12) from Preparative Example 2, Step B (0.44 g, 0.95 mmol), compound (189) from Preparative Example 12, Step B (0.32 g, 1.0 eq.), Bu$_4$NBr (0.61 g, 2.0 eq.), and K$_2$CO$_3$ (0.66 g, 5.0 eq.) in DMF (8.0 mL). The resulting solution was heated to 100° C. over night, cooled, and concentrated under reduced pressure. The residue was diluted with water (50 mL) and CH$_2$Cl$_2$ (50 mL), serparated, and the aqueous layer extracted with CH$_2$Cl$_2$ (2×50 mL). The combined organics were dried over Na$_2$SO$_4$ and concentrated in vacuo. The crude product was purified by flash chromatography using 100% EtOAc as eluent. LCMS: 723 (MH$^+$).

EXAMPLE 72

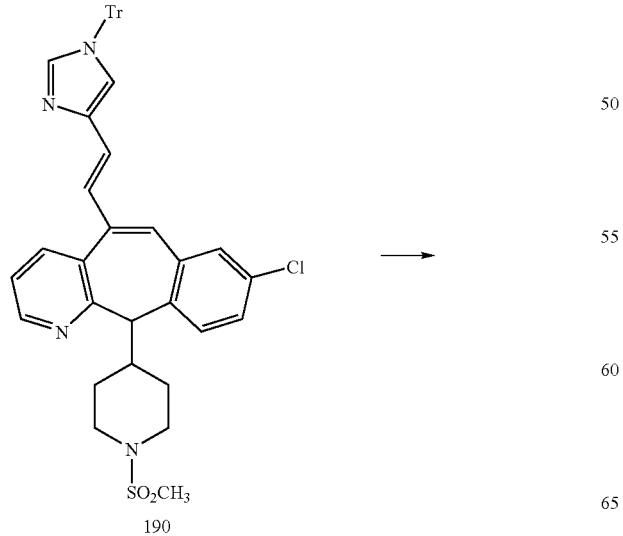

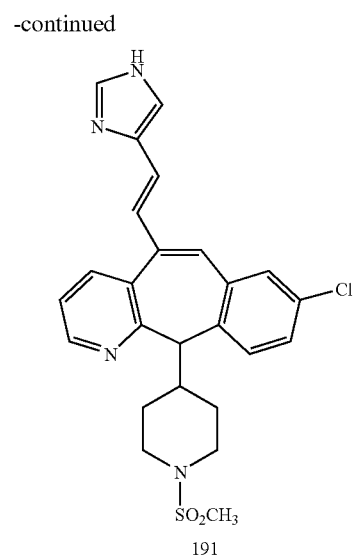

To a solution of the title compound from Preparative Example 12, Step C (1.43 g, 1.97 mmol) in water (70 mL) was added AcOH (70 mL). The resulting solution was heated at reflux two hours, cooled to room temperature and neutralized by the dropwise addition of 50% (w/w) NaOH. The solution was then extracted with CH$_2$Cl$_2$ (3×200 mL) and the combine organics were dried over Na$_2$SO$_4$ and concentrated under reduced pressure. The crude product was purified by flash chromatography using a 10% (10% NH$_4$OH in MeOH) solution in CH$_2$Cl$_2$ as eluent. mp=190° C. (dec.); LCMS: MH$^+$=483.

EXAMPLE 73

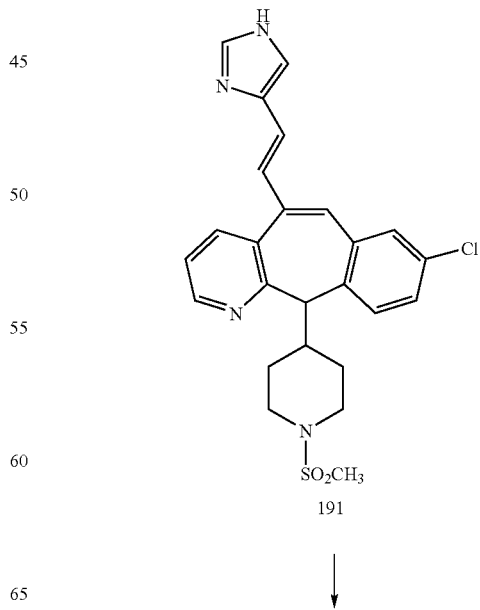

-continued

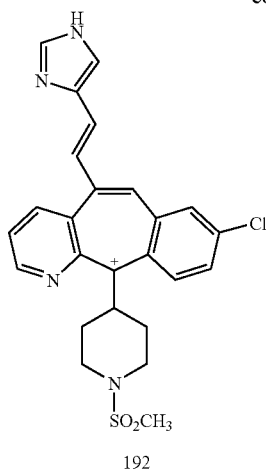

192

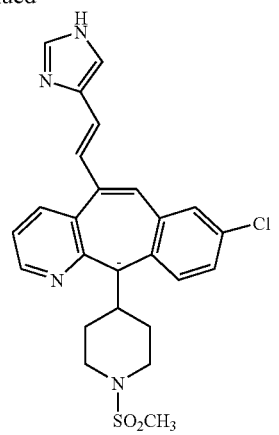

193

The title compound (191) from Example 72 was separated into individual (+)- and (−)-enantiomers by preparative HPLC using a ChiralPak AD column eluting with 70:30 hexanes: iPrOH containing 0.2% diethylamine as eluent.
Compound (192): FABMS: MH$^+$=481; mp=109-112° C.; $[\alpha]^{20}_D$=+398° (2.0 mg in 2.0 mL MeOH).
Compound (193): FABMS: MH$^+$=481; mp=126-129° C.; $[\alpha]^{20}_D$=−367° (2.0 mg in 2.0 mL MeOH).

EXAMPLE 74

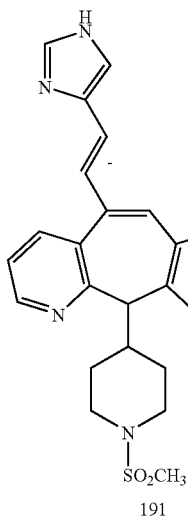

191

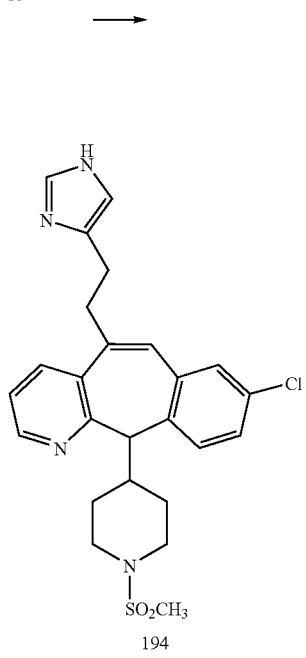

194

The title compound (191) from Example 72 was dissolved in toluene (50 mL) and DBU (0.26 mL, 5.0 eq.) and pTosNHNH$_2$ (0.33 g, 3.3 eq.) were added. The resulting solution was heated to reflux 2.5 hours before cooling to room temperature and adding additional pTosNHNH$_2$ (0.33 g, 3.3 eq.). The reaction mixture was heated at reflux for an additional 2 hours and cooling to room temperature. The resulting solution was diluted with saturated NaHCO$_3$ (100 mL) and extracted with CH$_2$Cl$_2$ (3×100 mL). The combined organics were washed with brine, dried over Na$_2$SO$_4$, filtered, and concentrated in vacuo. The crude product was purified by flash chromatography using a 5% (10% NH$_4$OH in MeOH) solution in CH$_2$Cl$_2$ as eluent to give pure product (194). mp=158-162; LCMS: MH$^+$=483.

EXAMPLE 75

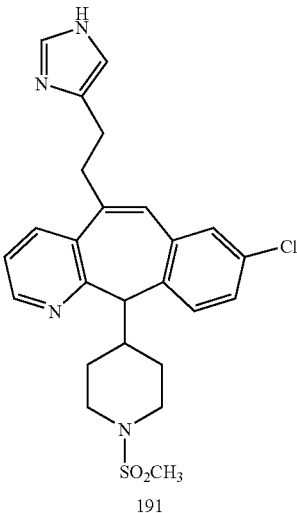

191

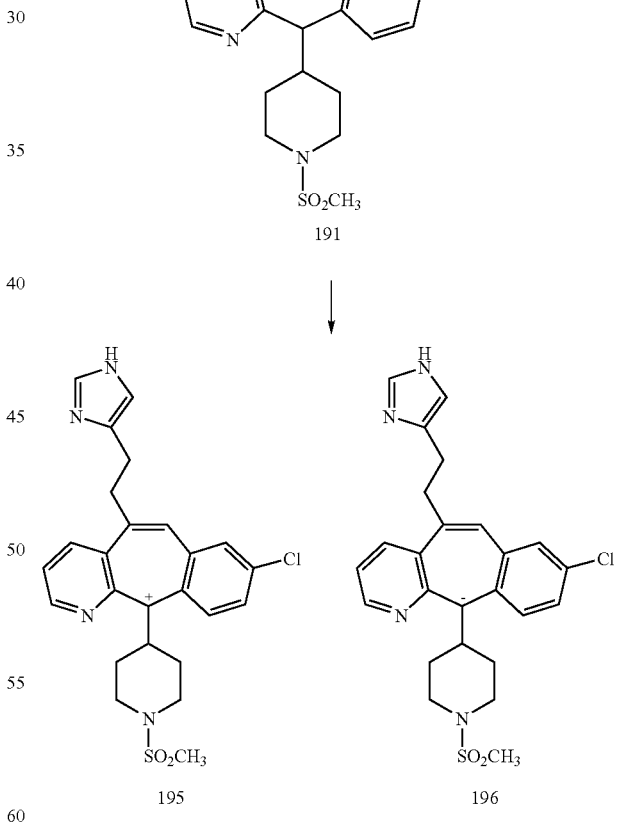

195          196

In a similar manner as described in Example 73 above, the following enantiomers were separated:
Compound (195): LCMS: MH$^+$=483; mp=129-131° C.; $[\alpha]^{20}_D$=+134° (2.0 mg in 2.0 mL MeOH).
Compound (196): LCMS: MH$^+$=483; mp=125-126° C.; $[\alpha]^{20}_D$=−105° (2.0 mg in 2.0 mL MeOH).

PREPARATIVE EXAMPLE 13

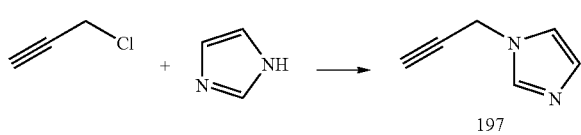

Imidazole (2.50 g, 36.72 mmol) and basic alumina (15 g) were combined and shaken 15 minutes before adding propargyl chloride (2.66 mL, 1.0 eq.). The resulting mixture was stirred 84 hours and suspended in EtOAc. The slurry was filtered and the filtrate was washed with H$_2$O and brine and dried over Na$_2$SO$_4$. The solution was filtered and concentrated under reduced pressure to give a clear oil.

EXAMPLE 76

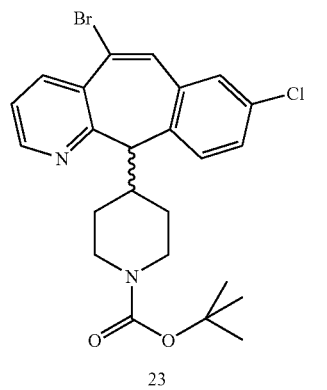

A solution of compound (23) (0.50 g, 1.02 mmol) and compound (197) from Preparative Example 13 (0.22 g, 2.0 eq.) in TEA (3.0 mL) and pyridine (0.5 mL) was deoxygenated 15 minutes before adding PdCl$_2$(PPh$_3$)$_2$ (0.018 g, 2.5 mol %) and CuI (0.002 g, 1.0 mol %). The resulting solution was heated for 48 hours. The reaction mixture was cooled to room temperature, diluted with H$_2$O, and extracted with CH$_2$Cl$_2$. The combined organic layer was dried over Na$_2$SO$_4$, filtered, and concentrated. The crude product was purified by flash chromatography using an 8% MeOH in CH$_2$Cl$_2$ solution as eluent. mp 109-112° C.; LCMS: 515 (MH$^+$).

PREPARATIVE EXAMPLE 14

Step A

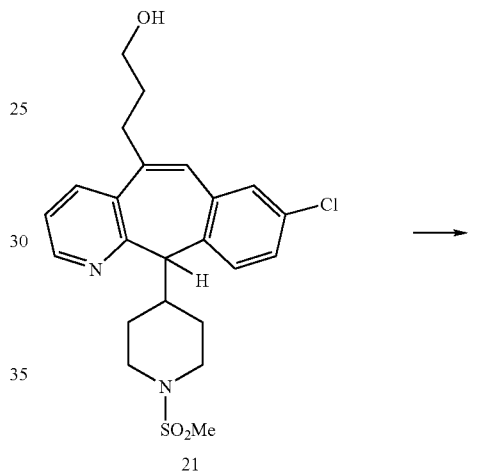

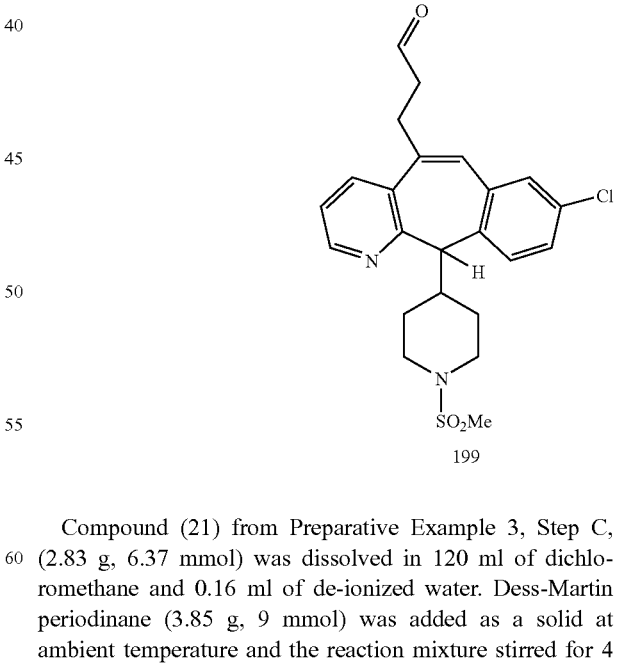

Compound (21) from Preparative Example 3, Step C, (2.83 g, 6.37 mmol) was dissolved in 120 ml of dichloromethane and 0.16 ml of de-ionized water. Dess-Martin periodinane (3.85 g, 9 mmol) was added as a solid at ambient temperature and the reaction mixture stirred for 4 hours. Then added a 20% Na$_2$S$_2$O$_3$ solution (50 ml) and stirred for 15 minutes. The layers were separated and the dichloromethane layer washed with saturated NaHCO$_3$, dried over magnesium sulfate, filtered and evaporated to obtain the title product (199). FABMS: 445 (MH+).

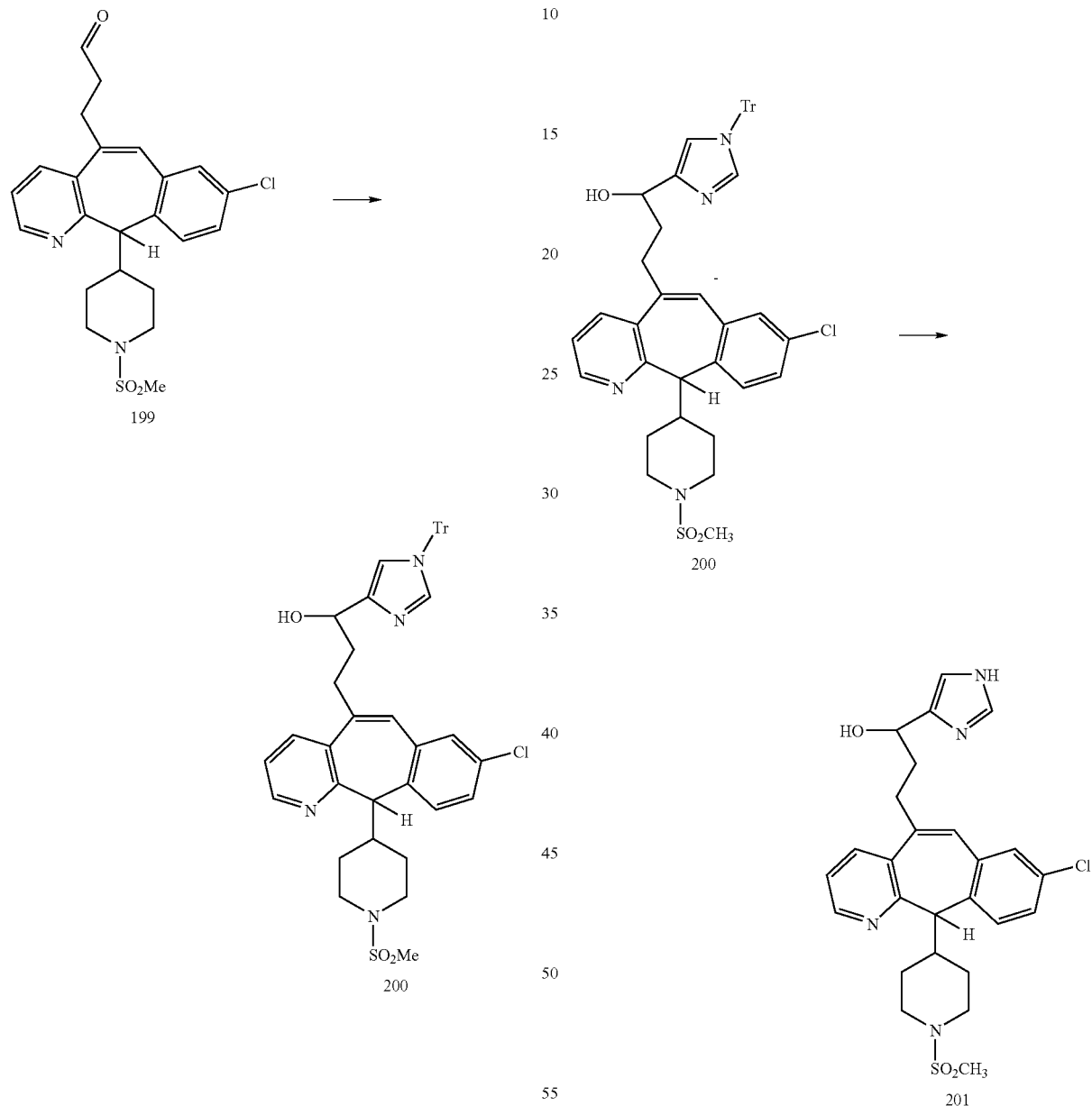

EXAMPLE 77

4-Iodo-1-trityl-imidazole (prepared according to the literature procedure Kirk, Kenneth L.; J. Heterocycl. Chem.; EN; 22; 1985; 57-59) (0.48 g, 1.1 mmol) was dissolved in 5 ml of dichloromethane under a dry nitrogen atmosphere. Ethylmagnesium bromide (0.36 ml). was added and the reaction mixture stirred. After 30 minutes compound (199) (0.44 g, 1 mmol) was dissolved in 5 ml of dichloromethane and added to the reaction mixture while stirring. After stirring 4 hours at ambient temperature, the mixture was washed with saturated ammonium chloride solution, dried over magnesium sulfate, filtered, and evaporated to give a solid residue. The product was chromatographed on a flash silica gel column using ethyl acetate as the eluent to obtain the title compound (200). FABMS: 756 (MH+).

Compound (200) (0.6 gm) was dissolved in 10 ml of trifluoroacetic acid and stirred at ambient temperature. After 7 hours the reaction mixture was evaporated to dryness under vacuum and chromatographed on silica gel using 5% 2N methanol:ammonia/dichloromethane to obtain title compound (201). FABMS: 514 (MH+).

PREPARATIVE EXAMPLE 15

Step A

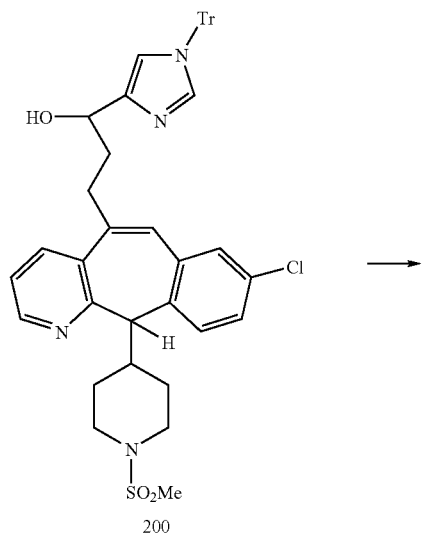

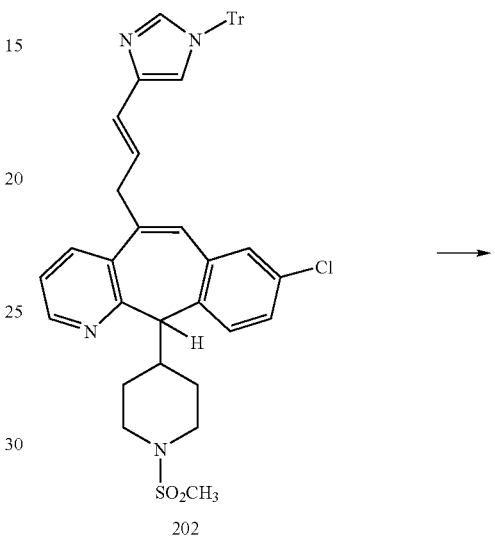

dichloromethane three times. Dried over magnesium sulfate, filtered and concentrated to dryness under vacuum to give a residue which was chromatographed on silica gel using ethyl acetate as the eluent to obtain the title compound (202). FABMS: 537 (MH$^+$).

Step B

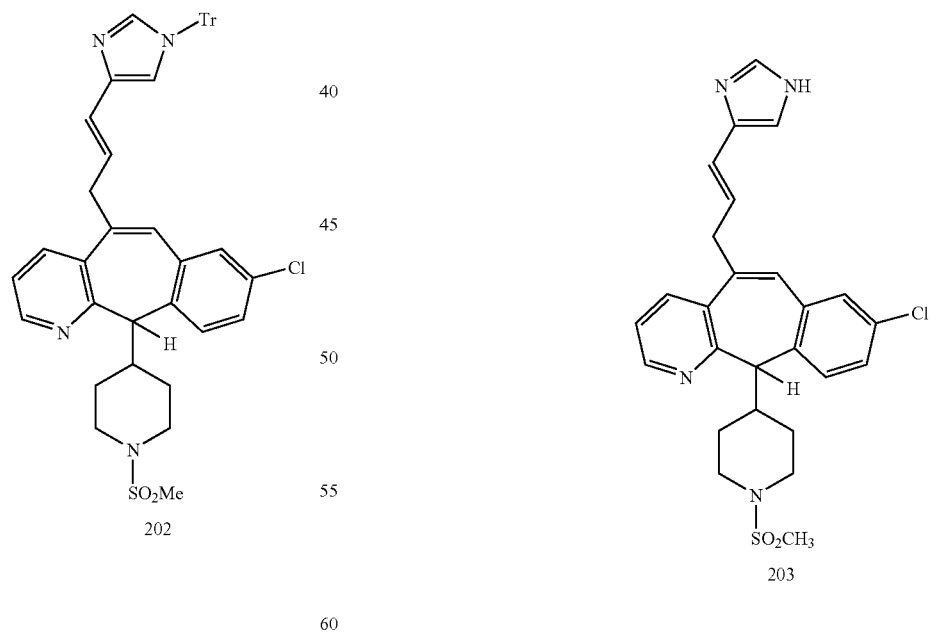

Compound (200) (0.5 g, 0.66 mmol) was dissolved in 5 ml of dichloromethane. Triethylamine (0.14 ml, 0.99 mmol) and methanesulfonyl chloride (0.062 ml, 0.79 mmol) were added and the reaction mixture stirred for 18 hours. The reaction mixture was added to brine and extracted with Compound (202) was detritylated in the same manner as EXAMPLE 77 affording the title compound (203). FABMS: 495 (MH$^+$).

EXAMPLE 78

PREPARATIVE EXAMPLE 16

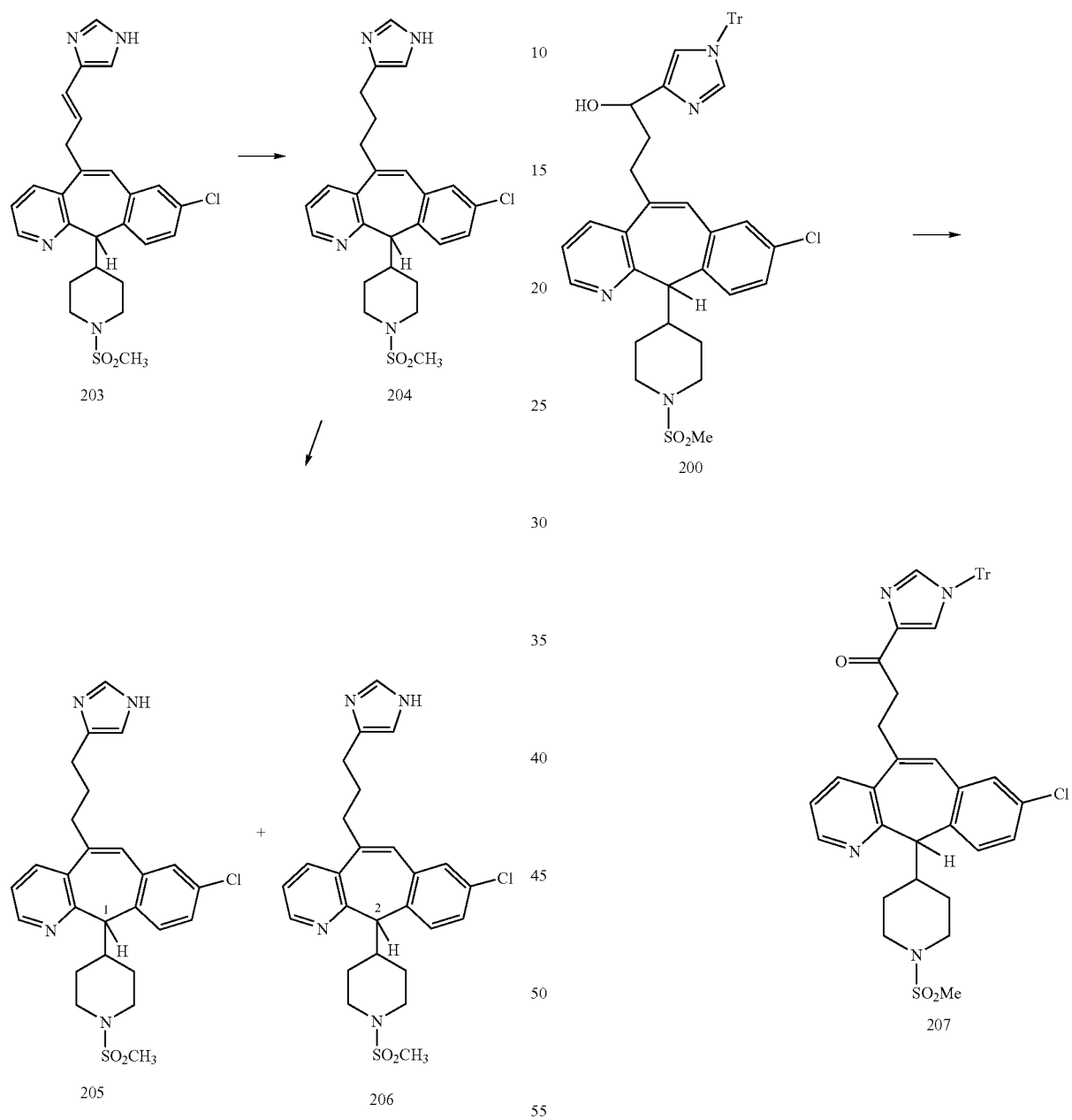

Compound (203) (77 mg) was hydrogenated over $PtO_2$ in ethanol at atmospheric hydrogen for 24 hours. After filtration of the catalyst followed by evaporation of the ethanol and chromatography on a Chiral Technologies® AD HPLC column the title product was obtained as two pure enantiomers (205) and (206). FABMS: 497 (MH$^+$).

Compound (200) (0.15 g, 0.198 mmol) was dissolved in 4 ml of dichloromethane and 5 uL of de-ionized water. Dess-Martin periodinane (0.12 g, 0.3 mmol) was added and the reaction mixture stirred for 4 h. 5 ml of a 20% $Na_2S_2O_3$ solution was added and the reaction mixture stirred for another 15 minutes. The layers were separated and the dichloromethane layer was washed with saturated $NaHCO_3$, dried over magnesium sulfate, filtered and evaporated to obtain the title compound (207). FABMS: 753 (MH$^+$).

EXAMPLE 79

PREPARATIVE EXAMPLE 17

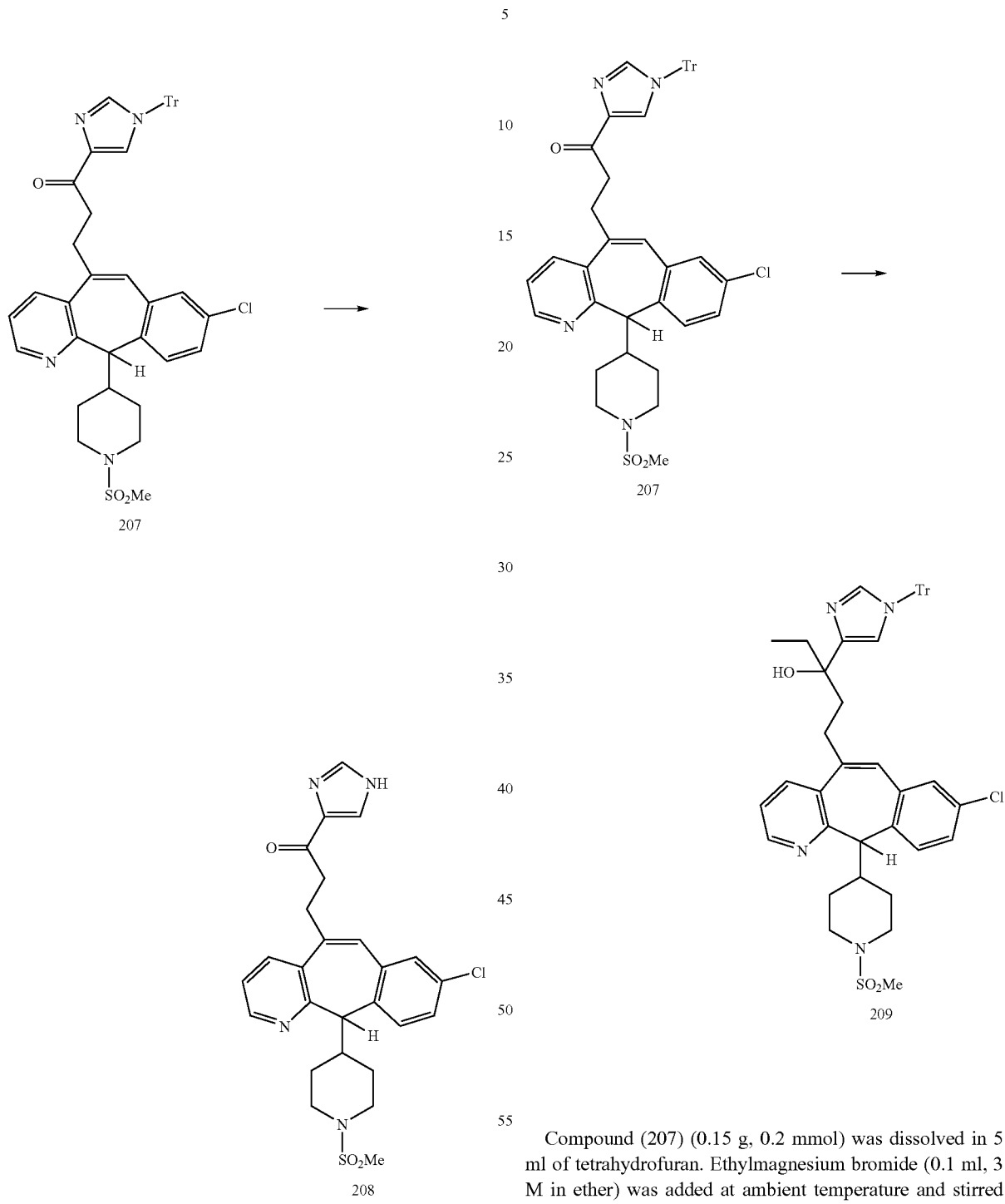

Compound (207) was detritylated in the same manner as Example 77 affording the title compound (208). FABMS: 511 (MH+).

Compound (207) (0.15 g, 0.2 mmol) was dissolved in 5 ml of tetrahydrofuran. Ethylmagnesium bromide (0.1 ml, 3 M in ether) was added at ambient temperature and stirred under a dry nitrogen atmosphere. After 2 hours, added another portion of ethylmagnesium bromide (0.1 ml, 3 M in ether). After 4 hours the reaction mixture was washed with saturated ammonium chloride, dried over magnesium sulfate, filtered and evaporated to obtain the title compound (209). The product was further purified by flash silica column chromatography eluting with 50% ethylacetate/hexanes. FABMS: 783 (MH+).

EXAMPLE 80

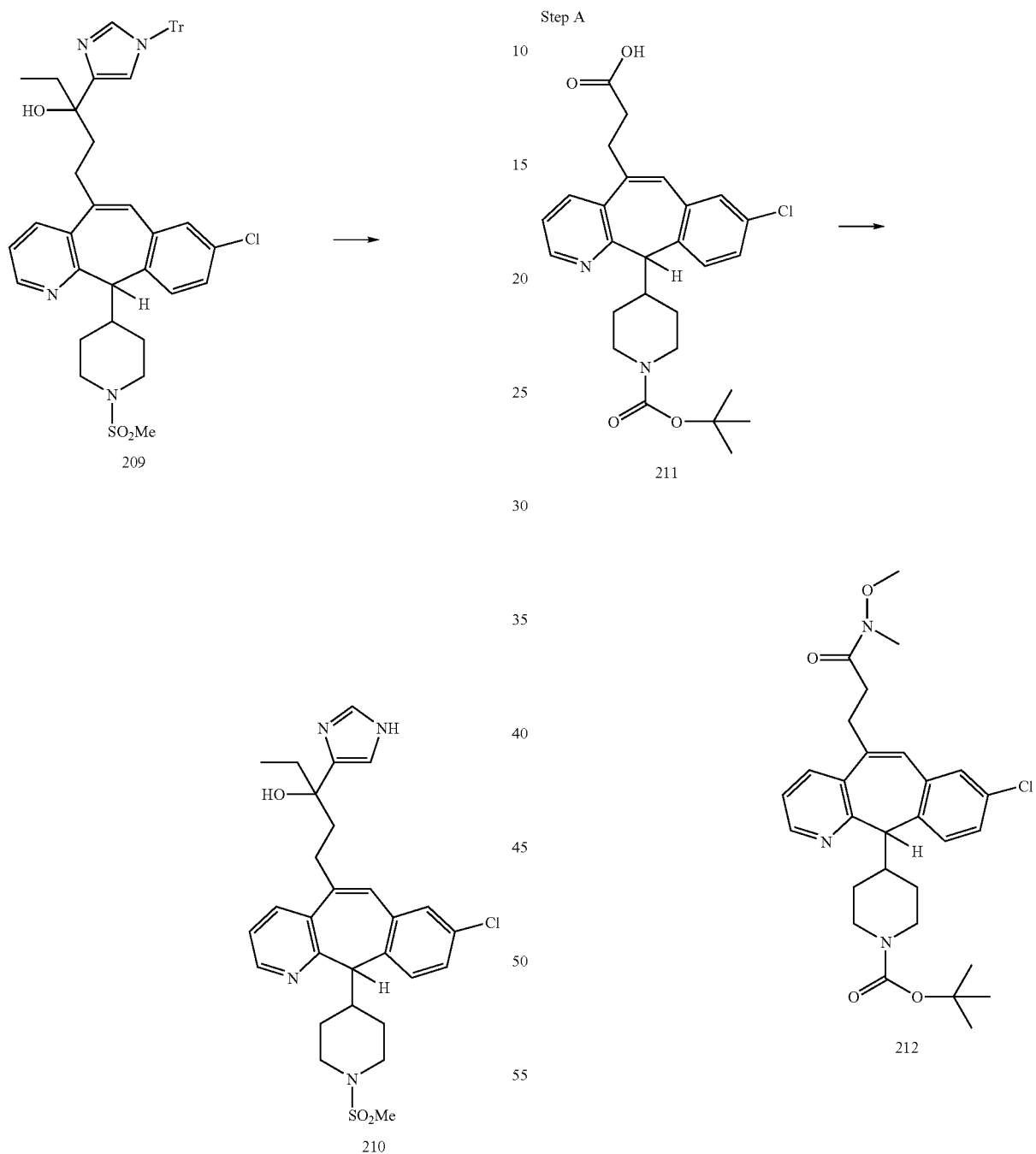

Compound (209) was detritylated in the same manner as Example 77 affording the title compound (210). FABMS: 541 (MH+).

PREPARATIVE EXAMPLE 18

Step A

Compound (211) (14 g, 29 mmol) prepared by NaOH hydrolysis of Compound (20) from Preparative Example 3, Step B, was dissolved in 400 ml of DMF. 1-(3-dimethylamino propyl)-3-ethylcarbodiimide hydrochloride (8.3 g, 43 mmol), 1-hydroxybenzotriazole (5.9 g, 43 mmol), triethylamine (40 ml), and N,O-dimethylhydroxylamine hydrochloride(3.8 g, 40 mmol) were added and the reaction

347 mixture stirred at room temperature under a dry nitrogen atmosphere. After 24 hours the reaction mixture was poured into brine and the product extracted with ethylacetate two times. After drying over magnesium sulfate, filtration, and chromatography on silica gel using 10% ethyl acetate/hexanes the title compound (212) was obtained.

Step B

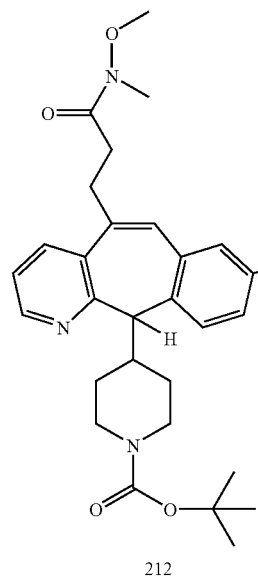

Compound (212) (0.53 g, 1.01 mmol) was treated as in PREPARATIVE Example 14, Step B to obtain the title compound (213) after silica gel chromatography.

348

EXAMPLE 81

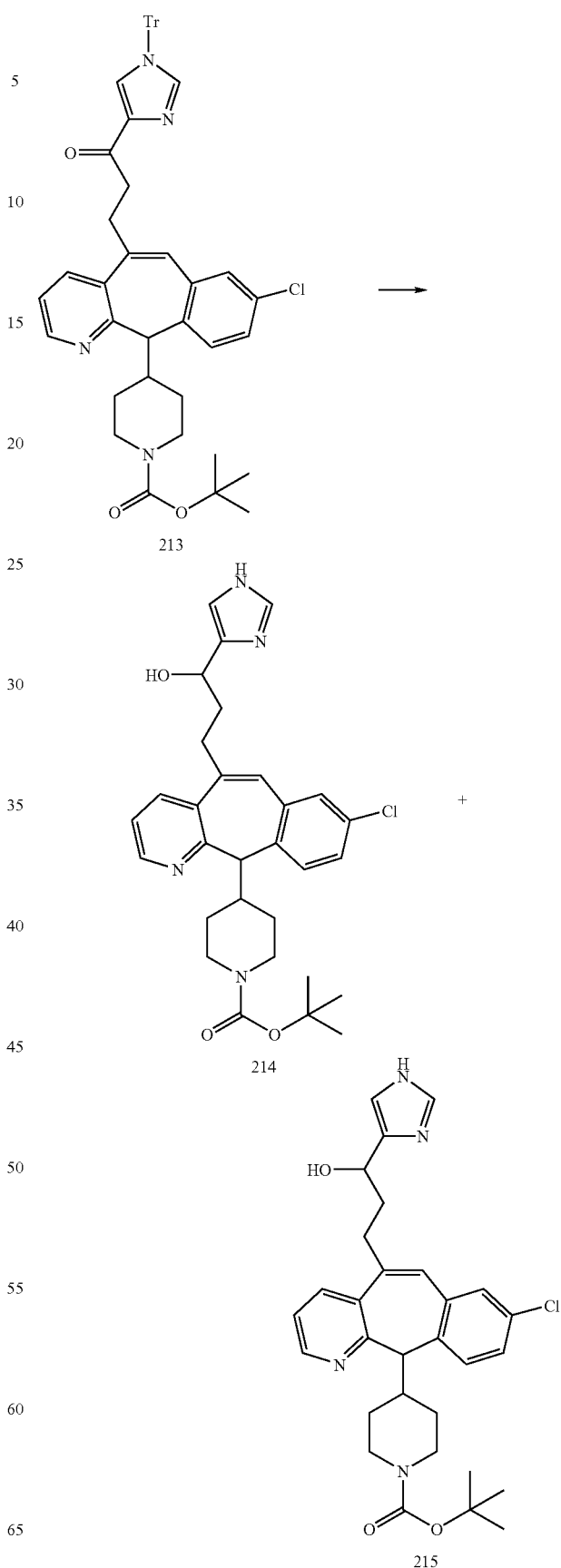

Compound (213) (300 mg, 0.387 mmol) was dissolved in methanol and sodium borohydride (50 mg) was added portionwise while stirring. After 1 hour the mixture was added to 1N HCl followed by the addition of 1N NaOH and extracted with ethylacetate to obtain a crude product which was treated with neat trifluoroacetic acid for 5 hrs, and evaporated to dryness. The mixture was dissolved in methanol and reacted with di-tert.butyldicarbonate (0.2 gm) while maintaining the pH at 10 with 1N NaOH for 1 hour. The mixture was then treated with 2N Methanolic ammonia for 15 minutes followed by evaporation of the solvents and chromatography on silica gel. Further separation of isomers was accomplished on a Chiral Technologies© AD HPLC column obtaining the pure isomers. (214) and (215). FABMS M+1=535

EXAMPLE 82

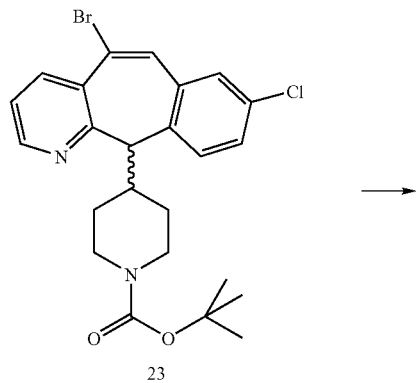
23

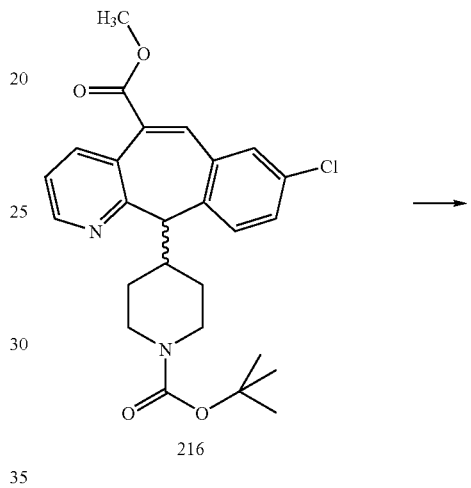
216

Compound (23) from Preparative Example 4, Step A (25.47 gm, 52 mmol) was dissolved in 300 ml of dry toluene and 39.5 ml of methanol. Palladium chloride (0.92 gm), triphenylphosphine (6.887 gm) and DBU (10.5 ml) were added and the reaction mixture transferred to a pressure reaction vessel. The reaction vessel was purged with carbon monoxide and then pressurized to 100 psi with carbon monoxide and the mixture stirred at 80° C. for 5 hours. The reaction was cooled in an ice bath and purged with nitrogen 34 times. The reaction mixture was transferred to a separatory funnel and 500 ml of ethylacetate was added. The mixture was washed with water three times, dried over magnesium sulfate, filtered and evaporated to dryness under vacuum to give a dark brown gum. The gum was purified by column chromatography on silica gel using 12.5%-25% ethylacetate/hexanes to obtain 12.58 gm of pure title product (216) FABMS: 469 (MH$^+$) and 9.16 gm of a mixture of two compounds.

PREPARATIVE EXAMPLE 19

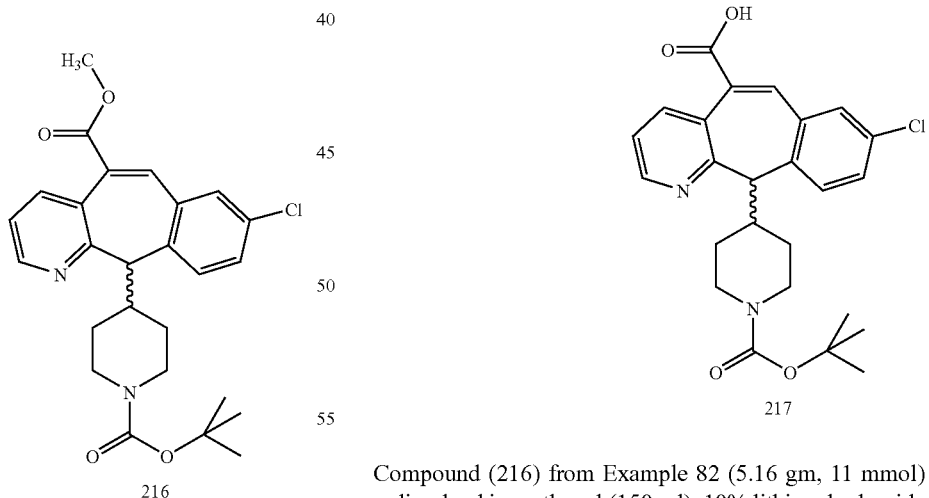
217

Compound (216) from Example 82 (5.16 gm, 11 mmol) was dissolved in methanol (150 ml). 10% lithium hydroxide (2.9 ml) was added along with dioxane (50 ml) and the reaction stirred for 4 hours. Added an additional portion of 10% lithium hydroxide (5.7 ml) and the reaction stirred for 18 hours. The reaction mixture was concentrated to s small volume and diluted with 50 ml of water The mixture was acidified to pH=3 with 10% citric acid and the product extracted with dichloromethane to obtain the title compound (217). FABMS: 455 (MH$^+$)

PREPARATIVE EXAMPLE 20

Step A

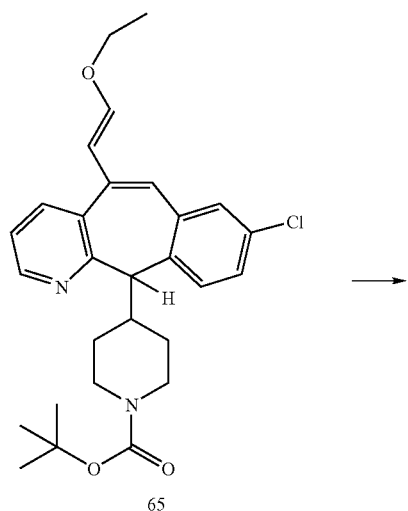

65

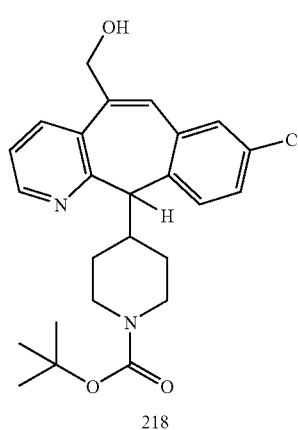

218

+

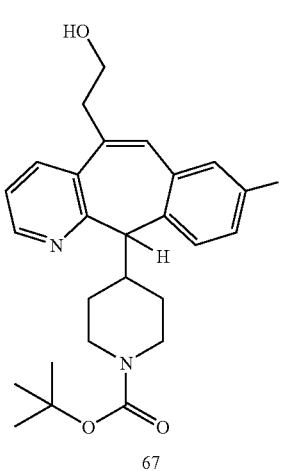

67

Compound (65) from Preparative Example (6), Step B, was let stand for approximately two weeks at room temperature, after which time the pressence of some aldehyde was observed by NMR of the crude material. This material was then treated as in Preparative Example 6, Steps C and D to afford a mixture of Compounds (218) and (67). The crude mixture was separated on flash silica column chromatography eluting with 1:1-3:1 ethyl acetate:hexanes to afford pure Compound (218).

Step B

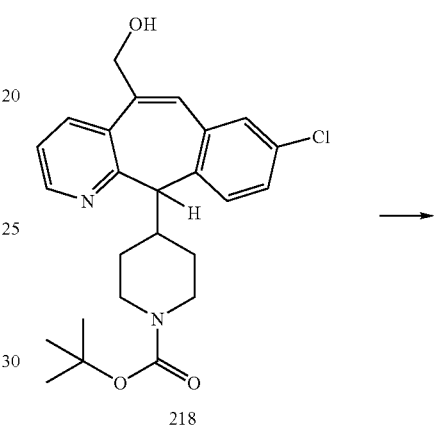

218

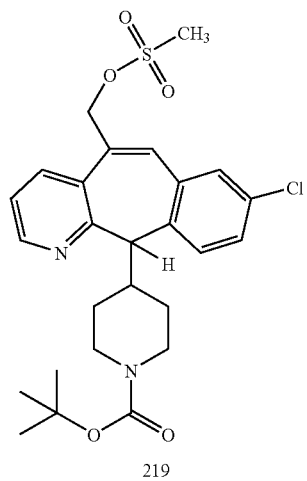

219

Compound (218) from Step A above, was combined with triethylamine (64.4 ml; 0.462 mmol) in $CH_2Cl_2$ (4 ml) treated with methyl sulfonyl chloride (17.93 ml; 0.231 mmol) and let stir over night at room temperature. The reaction mixture was diluted with $CH_2Cl_2$ (70 ml), quenched with brine (25 ml) and extracted. The organic layer was dried over $MgSO_4$, filtered and concentrated to give an off-white solid (219) (93 mg; 100%).

Step C

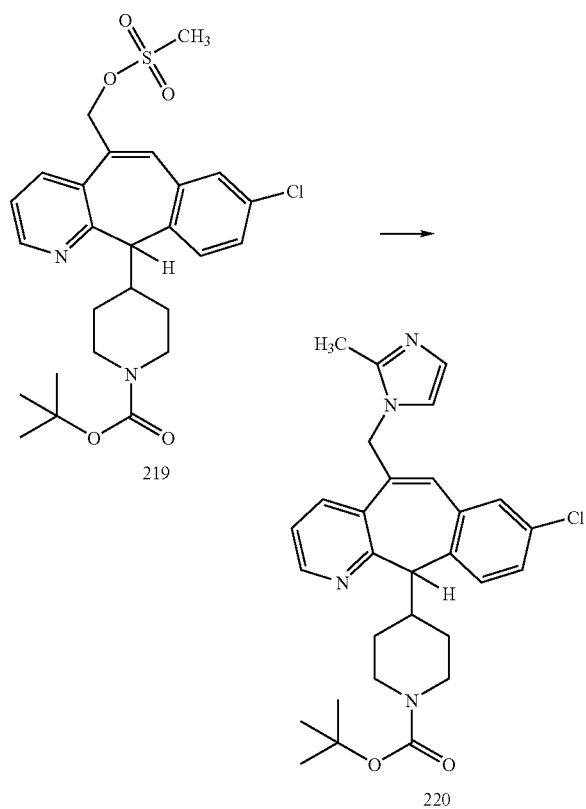

Compound (219) from Step B above, was taken up in DMF. To this solution was added a previously reacted solution of 2-methyl imidazole (145.27 mg; 1.734 mmol) and NaH (60%) (69.4 mg; 1.734 mmol) in DMF. The reaction mixture was allowed to stir at room temperature for two hours. The DMF was removed and the residue taken up in $CH_2Cl_2$ quenched with sat. aqueous $NaHCO_3$ and extracted with 2×100 ml $CH_2Cl_2$. The organic layers were combined and purified by preparative TLC plates to give an off-white solid. (220)

Step D

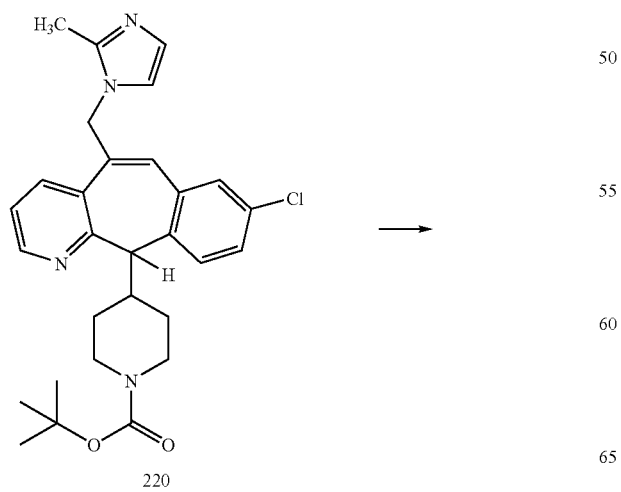

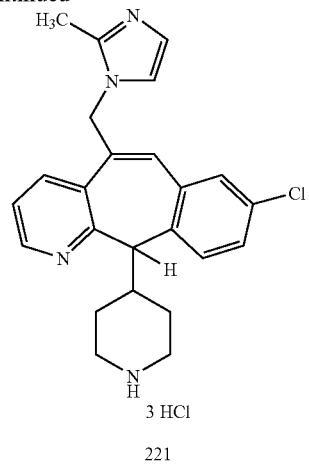

Compound (220) from Step C above, was dissolved in 1,4-Dioxane (3 ml). To this solution was then added 4M HCl in Dioxane (5 ml) and the reaction stirred for 3 hours at room temperature. The mixture was then concentrated and dried over night under high vacuum to afford the hydrochloride salt as an off-white solid. (221)

EXAMPLE 83

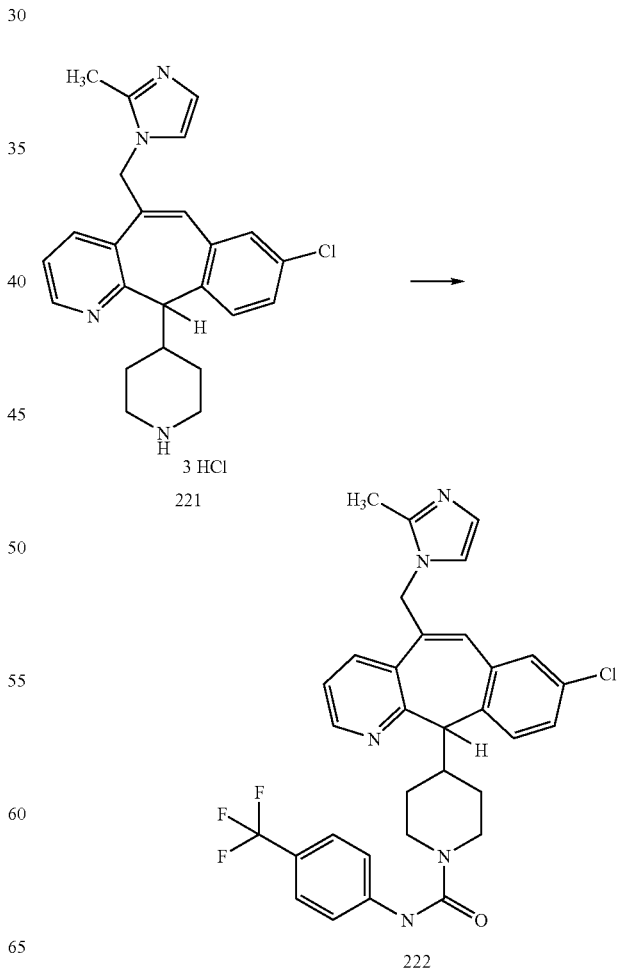

To a solution of compound (221) from Preparative Example 20, Step D (51 mg; 0.126 mmol) and triethylamine (61.47 ml; 0.441 mmol) in CH$_2$Cl$_2$ (2 ml) was added 4-trifluoromethylphenyl isocyanate (20.26 ml; 0.139 mmol) at 0° C. The reaction stirred for 2-3 hours under N$_2$ atmosphere. The CH$_2$Cl$_2$ and excess triethylamine were removed under vacuo and the resultant product was purified by preparatory thin layer chromatography eluting with 98:2 CH$_2$Cl$_2$/(sat.)MeOH/NH$_3$) affording the title compound as a white solid (222).

PREPARATIVE EXAMPLE 21

Step A

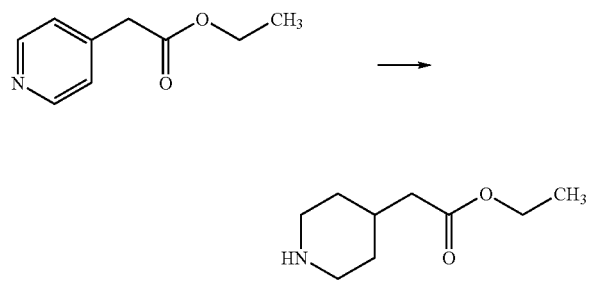

Commercially available Ethyl 4-Pyridyl Acetate (4.5 g; 27.2 mmol), EtOH (70 ml) and 10% Palladium on Charcoal (catalytic) was shaken under 55 psi hydrogen at room temperature for 94 hrs. The mixture was filtered through Celite and the cake was washed with (4×40 ml) of EtOH. The filtrate was concentrated and purified by flash silica column chromatography eluting with 3% (10% NH$_4$OH: MeOH)/CH$_2$Cl$_2$.

Step B

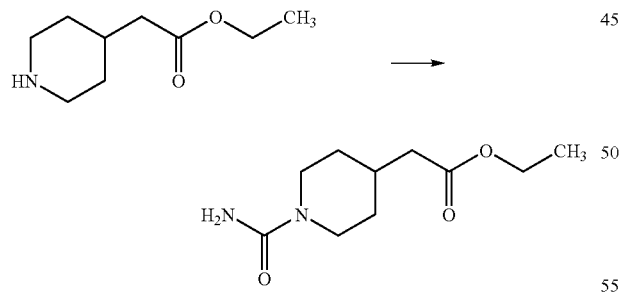

4-Pyridyl Acetic Acid (2.362 g) from Step A above, was taken up in CH$_2$Cl$_2$ (118 ml). To this was added trimethylsilyl isocyanate (27.87 ml). The reaction stirred for 67 hr then was diluted with CH$_2$Cl$_2$ (700 ml) and washed with saturated aqueous NaHCO$_3$ (150 ml). The aqueous layer was extracted with 2×200 ml CH$_2$Cl$_2$. The organic layers were combined, dried over MgSO$_4$, filtered and concentrated. The crude product was purified by flash silica column chromatography eluting with 2% (10% NH$_4$OH:MeOH)/CH$_2$Cl$_2$.

Step C

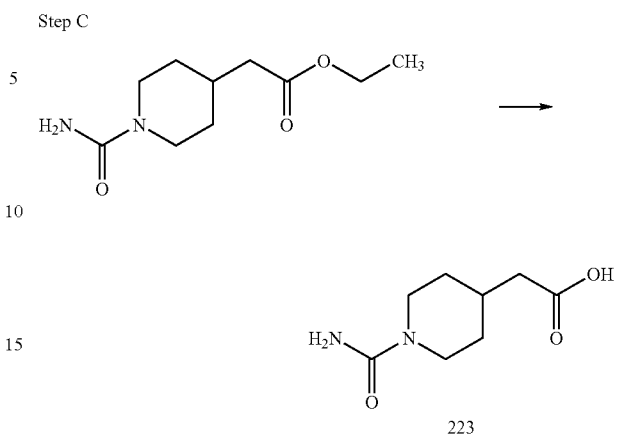

Product from Step B above (40.63 mg; 0.1896 mmol) was taken up in EtOH (2 ml) and CH$_2$Cl$_2$ (2 ml) and treated with 1 M LiOH (0.5 ml; 0.455 mmol). The reaction mixture was heated to 50° C. and stirred for 5 hr. The reaction was cooled to room temperature treated with 1N HCl (0.57 ml; 0.531 mmol) and stirred for 5 minutes. The resultant mixture was concentrated and dried under high vacuum for 4 days affording the title compound as a white solid. (223)

EXAMPLE 84

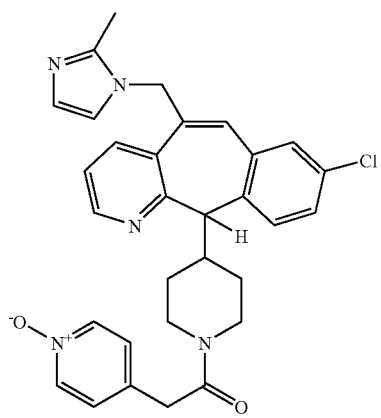

To a solution of Compound (221) from Preparative Example 20, Step D (51 mg; 126 mmol), 4-methylmorpholine (69.3 ml; 0.630 mmol), DEC (31.44 mg; 0.164 mmol), and HOBT (22.2 mg; 0.164 mmol) in DMF (2 ml) was added, 4-Pyridylacetic Acid 1-N-Oxide (disclosed in U.S. Pat. No. 5,719,148; Feb. 17, 1998). The reaction stirred for 3 hours at room temperature. The reaction was diluted with CH$_2$Cl$_2$ and washed two times with saturated aqueous NaHCO$_3$. The organic layers were combined, concentrated and purified by preparative thin layer chromatography eluting with 95:5 CH$_2$Cl$_2$:sat. MeOH/NH$_3$ affording the title compound as a white solid (224).

EXAMPLE 85

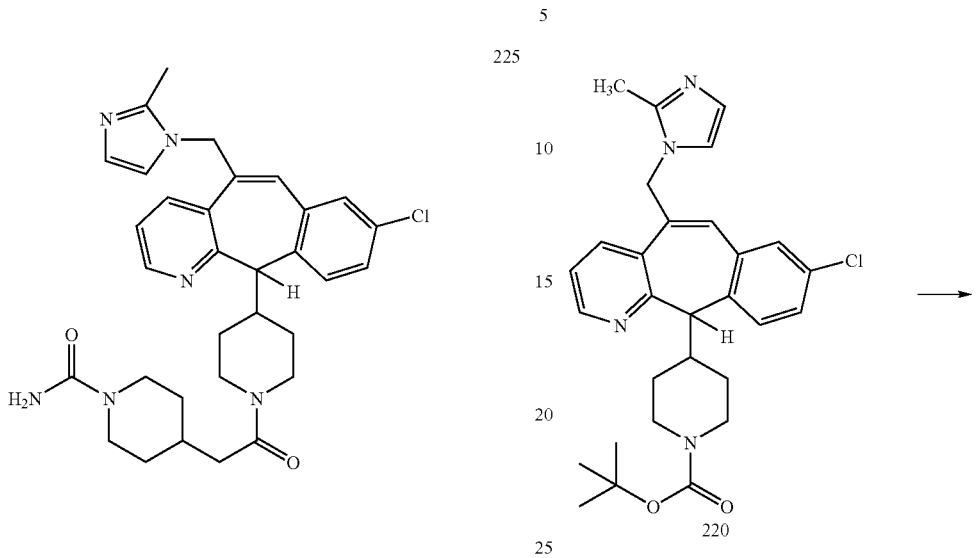

Compound (221) from Preparative Example 20, Step D (51 mg; 0.126 mmol) was combined with compound (223) from Preparative Example 21, Step C and reacted in the same manner as Example 84 to afford the title compound as a white solid. (145-155° C. dec.) MH+ 573.(225)

EXAMPLE 86

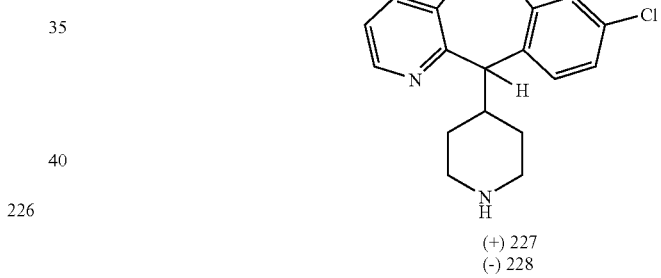

Compound (221) from Preparative Example 20, Step D (51 mg; 0.126 mmol) was combined with 4-Fluorophenylacetic acid (Acros) (29.29 mg; 0.190 mmol) and reacted in the same manner as Example 84 to afford the title compound as an off-white solid. (108-125° C. dec.) MH+ 541.(226)

PREPARATIVE EXAMPLE 22

Compound (220) from Preparative Example 20, Step C, (150 mg; 0.289 mmol) was treated with 4M HCl in Dioxane and allowed to stir for 2-3 hr at room temperature under a $N_2$ atmosphere. The crude mixture was separated into pure (+) isomer (227) and (−) isomer (228) by preparative chiral HPLC using an AD column, eluting with 85:15:2 Hexanes:IPA:DEA.

EXAMPLES 87-90

The appropriate (+) compound (227) or (−) compound (228) isomer from Preparative Example 22 above, was taken up in $CH_2Cl_2$ treated with the corresponding isocyanate and stirred at room temperature over night. Crude product was purified directly by preparative thin layer chromatography to afford compounds (229-232):

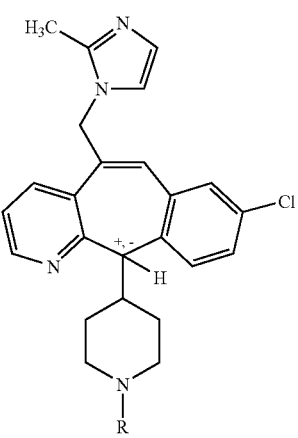

wherein R is as defined in Table 8.

TABLE 8

| Ex. | R | Compound # | |
|---|---|---|---|
| 87 | [4-F-phenyl amide] | (229) | (+)(148–156° C. dec.) MH+ 556. |
| 88 | [4-CN-phenyl amide] | (230) | (+)(155–166° C. dec.) MH+ 563. |
| 89 | [4-F-phenyl amide] | (231) | (−)(145–153° C. dec.) MH+ 556. |
| 90 | [4-CN-phenyl amide] | (232) | (−)(159–168° C. dec.) MH+ 563. |

PREPARATIVE EXAMPLE 23

Step A

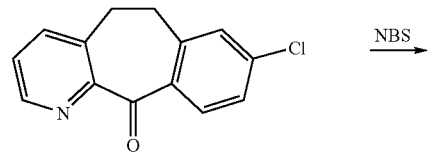

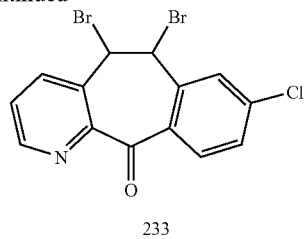

The tricyclic keto-compound (disclosed in U.S. Pat. No. 5,151,423) (30.0 g; 123.2 mmol) was combined with NBS (48.2 g; 271.0 mmol) and benzoyl peroxide (0.42 g) in CCl₄ (210 ml). The reaction was heated to 80° C. for 10 hr. The mixture was cooled and let stand for 8 hr. The resulting precipitate was filtered. Added MeOH (200 ml) and stirred the mixture over 2 days. The solid was filtered and dried under vacuum to a constant weight.

Step B

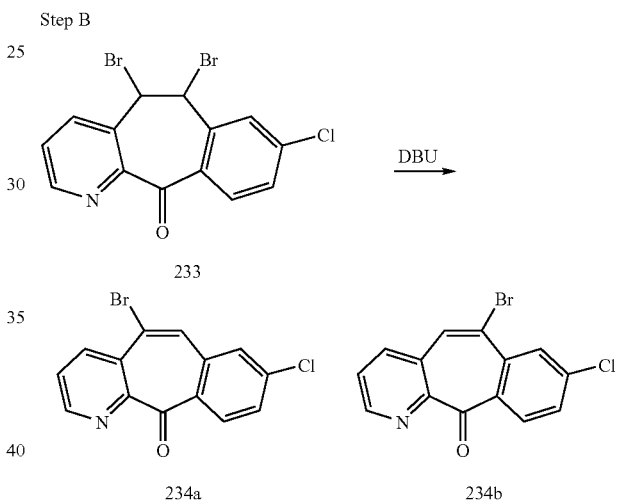

The dibromo compound (233) from Step A (35.72 g; 88.97 mmol) above was dissolved in CH₂Cl₂ (1.5 L) and cooled to 0° C. Dropwise, DBU (15.96 ml) was added and the suspension stirred for 3 hr. The reaction mixture was concentrated redissolved in CH₂Cl₂ (1.5 L) filtered through a bed of silica gel and rinsed with 5% EtOAc/CH₂Cl₂ (4 L). The combined rinses were concentrated and purified by flash silica gel column chromatography into pure 5 and 6 mono-bromo substituted compounds eluting with 10-30% EtOAc/Hex then 3%EtOAc/CH₂Cl₂.

Step C

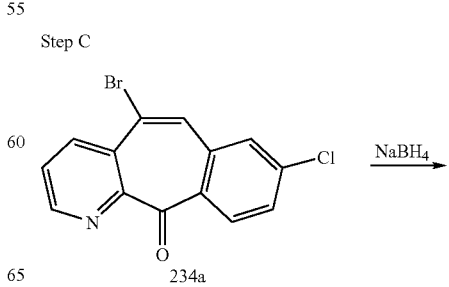

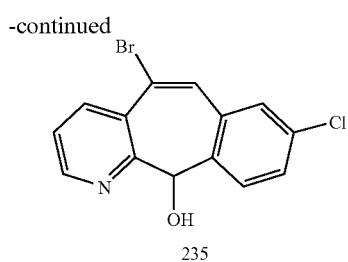

The 5-bromo substituted compound (234a) from Step B above (4.0 g; 12.45 mmol) was taken up in MeOH and cooled to 0° C. NaBH₄ (916.4 mg; 24.2 mmol) was added and the reaction mixture stirred for 5.5 hr. The solvent was removed and the resulting residue was used directly.

The alcohol compound (235) from Step C above (3.98 g; 12 mmol) was dissolved in CH₂Cl₂ cooled to 0° C. and treated with 2,6-Lutidine (5.73 ml; 49 mmol). SOCl₂ (1.8 ml; 24.6 mmol) was added and the reaction was allowed to stir and come to room temperature over 3 hr. The reaction mixture was poured into 0.5 N NaOH (80 ml) extracted and concentrated in vacuo. The crude product was taken up in CH₃CN and treated with 1,2,2,6,6-Pentamethylpiperidine (4.45 ml; 24.6 mmol) (Aldrich). The reaction was heated to 60-65° C. treated with tert-butyl 1-piperazinecarboxylate (2.32 g; 12 mmol) (Aldrich) and stirred over night under N₂ atmosphere. The reaction mixture was concentrated to dryness, redissolved in CH₂Cl₂ and washed with sat. aqueous NaCO₃. The organic layer was dried over Na₂SO₄, filtered and purified by flash silica gel column chromatography eluting with 1:4-1:2 EtOAc/Hexanes to afford the product as a white solid.

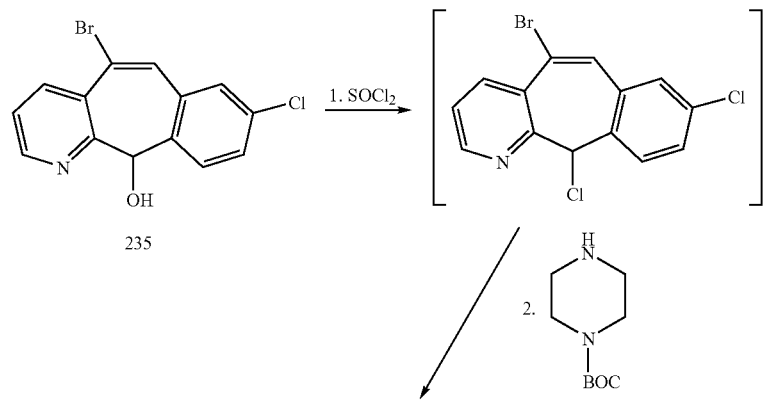

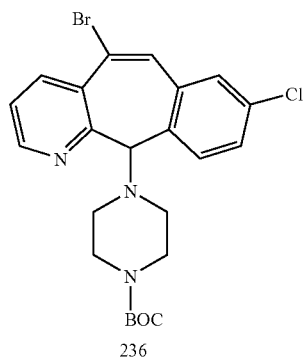

Step E

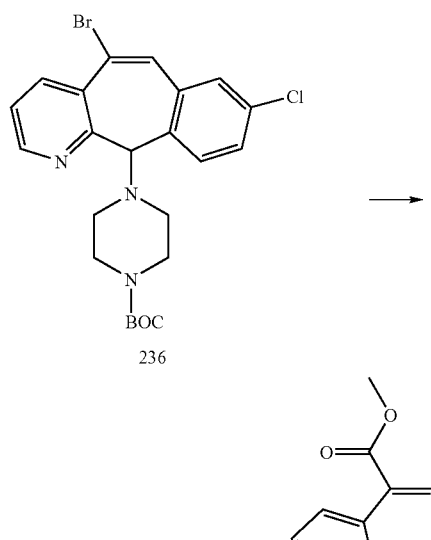
236

The BOC-protected bromo-compound (236) from Step D above (2 g; 4 mmol), triphenyl phosphine (0.54 g; 2 mmol), and palladium chloride (0.0723 g; 0.4 mmol) were combined in MeOH (10 ml) and toluene (30 ml). To this mixture was added DBU (0.835 ml; 5.5 mmol) and the mixture was sealed in a Parr bomb. The reaction mixture was stirred and subjected to 90 psi of CO at 80° C. for 5 hr. The reaction was diluted with EtOAc (200 ml) and washed with 2×80 ml H₂O. The organic layer was dried over MgSO₄, filtered and purified by flash silica column chromatography eluting with 1:3 EtOAc/Hexanes.

Step F

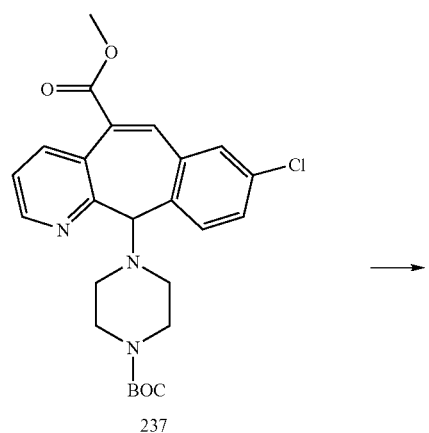
237

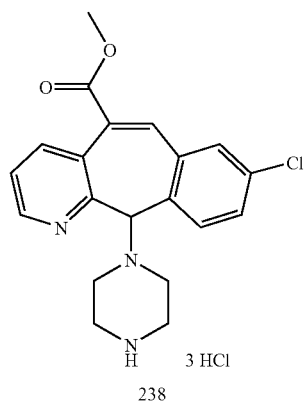
238

Compound (237) from Step E above (1.73 g; 3.681 mmol) was treated with 4 M HCl in Dioxane (35 ml) and allowed to stir at room temperature for 3 hr. The reaction mixture was concentrated in vacuo and the resulting tan solid was further dried under high vaccuum.

Step G

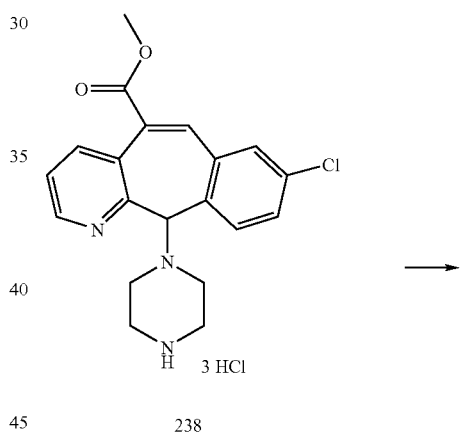
238

239

The HCl salt (238) from Step F above (1.36 g; 3.68 mmol) was dissolved in THF, cooled to 0° C., treated with 1 M DIBAL in cyclohexane (18.41 ml; 18 mmol) and stirred over night at room temperature. The mixture was concentrated to dryness and used directly in the next step.

Step H

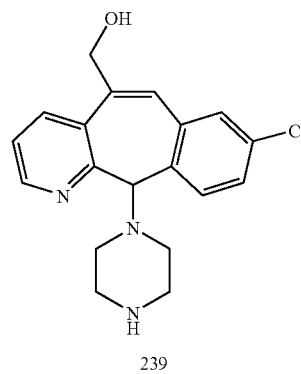
239

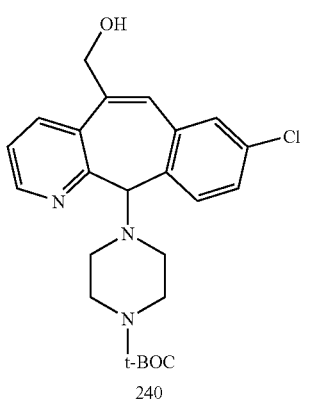
240

Step I

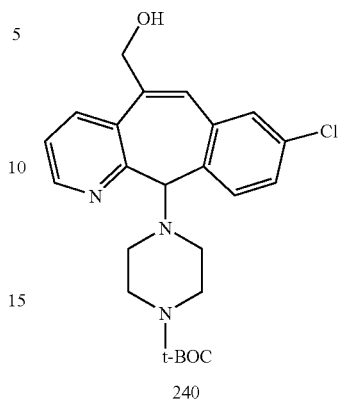
240

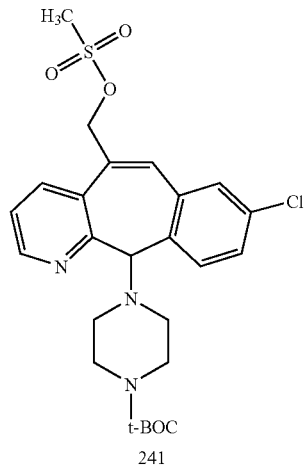
241

The alcohol (239) from Step G above was taken up in MeOH (50 ml) and H₂O (5 ml) and treated with Boc anhydride (1.56 g; 7.14 mmol). The pH was adjusted to approximately 10 with 1N NaOH. The reaction mixture was concentrated, taken up in CH₂Cl₂ and washed with H₂O (2×). The organic layer was dried over MgSO₄, filtered and concentrated to a tan solid containing both product and an impurity.

Alternatively, compound (237) was converted to compound (240) by first preparing the acylimidazole followed by NaBH₄ reduction using the following procedure:

Compound (237) from Step E above (7.0 mmol) was dissolved in a mixture of 15 mL methanol, 60 mL dioxane and 6 mL water containing 25 mL of 10% aqueous LiOH. The mixture was heated at 60° C. for 4 hr, then it was concentrated under vacuum and the pH adjusted to 5.2 with 10% aqueous citric acid. The residue was dissolved in CH₂Cl₂, washed with brine, dried over MgSO₄ and concentrated under vacuum to give the carboxylic acid. The acid was then dissolved in 20 mL THF containing 14 mmol of 1,1'-carbonyl diimidazole and heated at 38° C. for 18 hr. The mixture was then concentrated under vacuum to give the acylimidazole. The residue was dissolved in a mixture of 21.2 mL of THF and 5.3 mL water and cooled to 0° C. To the solution was added 35 mmol of NaBH₄ and it was stirred for 1.5 hr. 5 mL brine and 25 mL CH₂Cl₂ was then added. The organic layer was dried over MgSO₄ and concentrated under vacuum to give compound (240) in essentially a quantitative yield.

The crude product (240) from Step H above (200 mg; 0.45 mmol) was taken up in CH₂Cl₂ (2 ml) and treated with triethyl amine (126 ml; 0.91 mmol) followed by methanesulfonyl chloride (35 ml; 0.45 mmol). The reaction stirred over night at room temperature. The mixture was diluted with CH₂Cl₂ and quenched with sat. aqueous NaCl. The organic layer was dried over MgSO₄, filtered and concentrated to afford compound (241).

EXAMPLE 91

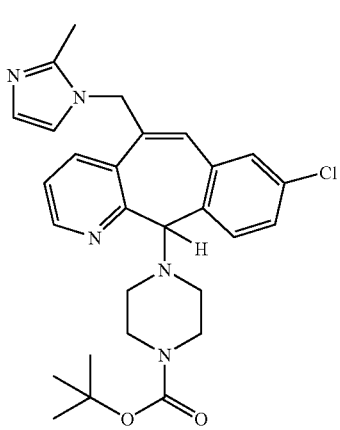
242

The mesylate compound (241) from Preparative Example 23, Step I above (230 mg; 0.442 mmol) was reacted in the same manner as Preparative Example 20, Step C. Purification of the crude product was accomplished by preparative TLC plates eluting with 95:5 CH$_2$Cl$_2$/MeOH(NH$_3$) followed by 1:1 EtOAc:Hexanes to afford the title compound as a light tan solid (242) 105-116° C. (dec) MH$^+$ 506.

PREPARATIVE EXAMPLE 24

Step A

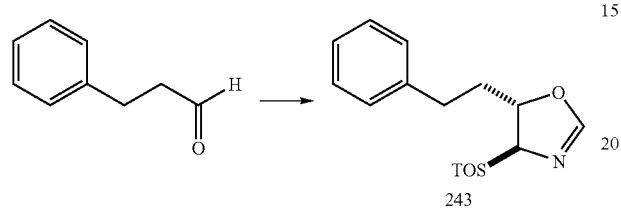
243

NaCN and 3-Phenylpropionaldehyde (ACROS) were dried overnight under vacuum. The aldehyde was then passed through activated Al$_2$O$_3$. Tosylmethyl isocyanide (5 g, 25.6 mmol) (ACROS) and dry 3-Phenylpropionaldehyde (3.36 g; 25.1 mmol) were combined in EtOH (42 ml) and stirred for 5 minutes. To the turbid mixture was added the dry NaCN (1.23 g; 25.1 mmol). An exothermic reaction was observed and after 5 minutes TLC showed consumption of starting material. The reaction was transferred to a sealed tube and used directly in the next experiment.

Step B

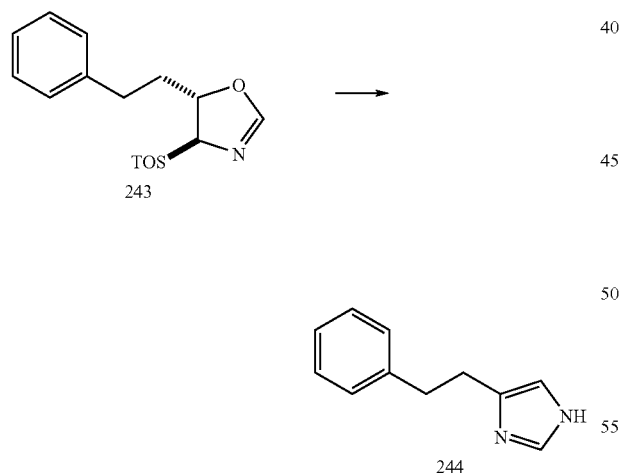
243

244

The crude product (243) from Step A above (25 mmol), was diluted up to 65 ml total volume with EtOH. To this mixture was added 7N NH$_3$ in MeOH (100 ml) and the reaction was heated to 90° C. over night (20 hr). The reaction was allowed to cool to room temperature and stirred for 2 hr then concentrated to dryness. The crude product was purified by flash silica column chromatoghraphy eluting with a gradient of 1-5% MeOH(sat. NH$_3$)/CH$_2$Cl$_2$ (244).

PREPARATIVE EXAMPLE 25

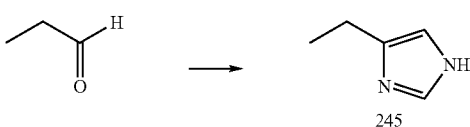
245

Propionaldehyde (1.5 g; 25.11 mmol) (ACROS) and tosylmethyl isocyanide (5 g; 25.6 mmol) were reacted in the same manner as Preparative Example 24 above to afford the title compound (245).

PREPARATIVE EXAMPLE 26

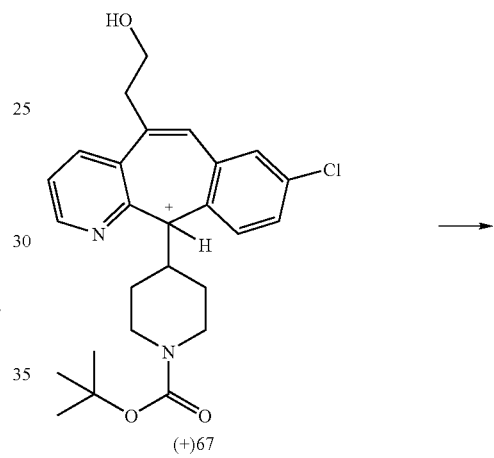

The (+) isomer of compound (67) from Preparative Example 6 isolated by chiral AD column chromatography was further reacted as in Preparative Example 6 to obtain compound (246).

EXAMPLE 92 AND 93

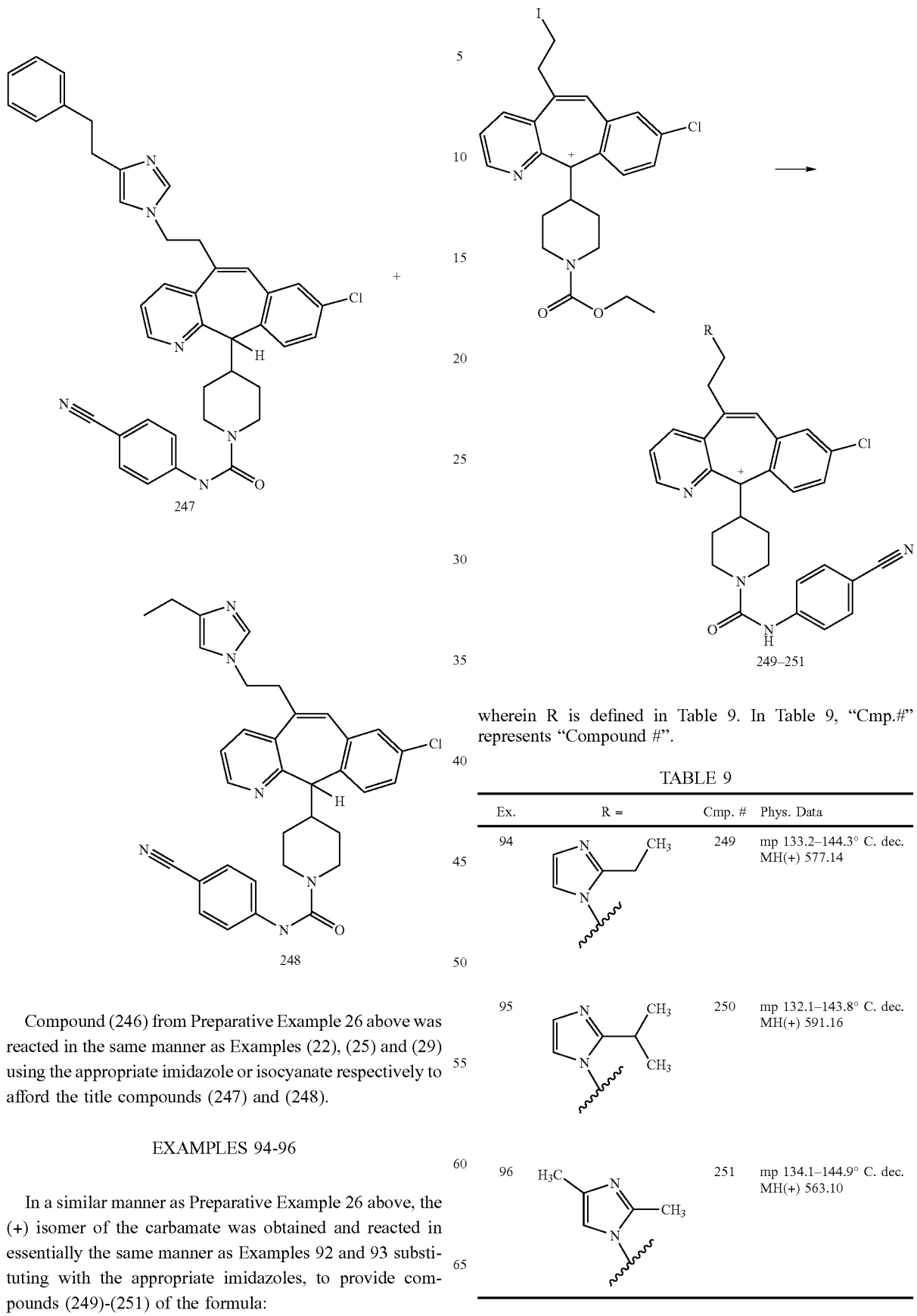

Compound (246) from Preparative Example 26 above was reacted in the same manner as Examples (22), (25) and (29) using the appropriate imidazole or isocyanate respectively to afford the title compounds (247) and (248).

EXAMPLES 94-96

In a similar manner as Preparative Example 26 above, the (+) isomer of the carbamate was obtained and reacted in essentially the same manner as Examples 92 and 93 substituting with the appropriate imidazoles, to provide compounds (249)-(251) of the formula:

wherein R is defined in Table 9. In Table 9, "Cmp.#" represents "Compound #".

TABLE 9

| Ex. | R = | Cmp. # | Phys. Data |
|---|---|---|---|
| 94 | (2-methylimidazol-1-yl)methyl | 249 | mp 133.2–144.3° C. dec. MH(+) 577.14 |
| 95 | (2-isopropylimidazol-1-yl)methyl | 250 | mp 132.1–143.8° C. dec. MH(+) 591.16 |
| 96 | (2,4-dimethylimidazol-1-yl)methyl | 251 | mp 134.1–144.9° C. dec. MH(+) 563.10 |

EXAMPLES 97-101

In essentially the same manner as in Preparative Example (20) and Example (29), compounds of the formula:

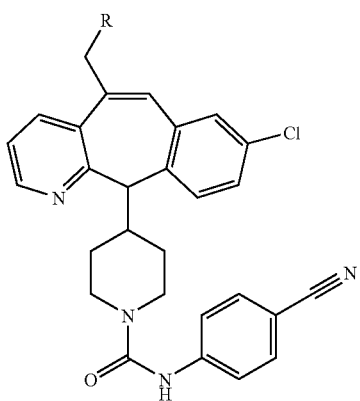

252–256 were prepared wherein R is as defined in Table 10. In Table 10, "Cmp.#" represents "Compound #".

TABLE 10

| EX. | R = | Cmp # | PHYS. DATA |
|---|---|---|---|
| 97 | (2-isopropyl imidazole) | 252 | mp 148–159° C. dec. MH(+) 577. |
| 98 | (4-methyl-2-methyl imidazole) | 253 | mp 134–142° C. dec. MH(+) 563. |
| 99 | (2-benzyl imidazole) | 254 | mp 90–102° C. dec. MH(+) 625. |
| 100 | (2-ethyl imidazole) | 255 | mp 126–139° C. dec. MH(+) 577. |

TABLE 10-continued

| EX. | R = | Cmp # | PHYS. DATA |
|---|---|---|---|
| 101 | (imidazol-1-yl) | 256 | mp 151–164° C. dec. MH(+) 535. |

EXAMPLE 102

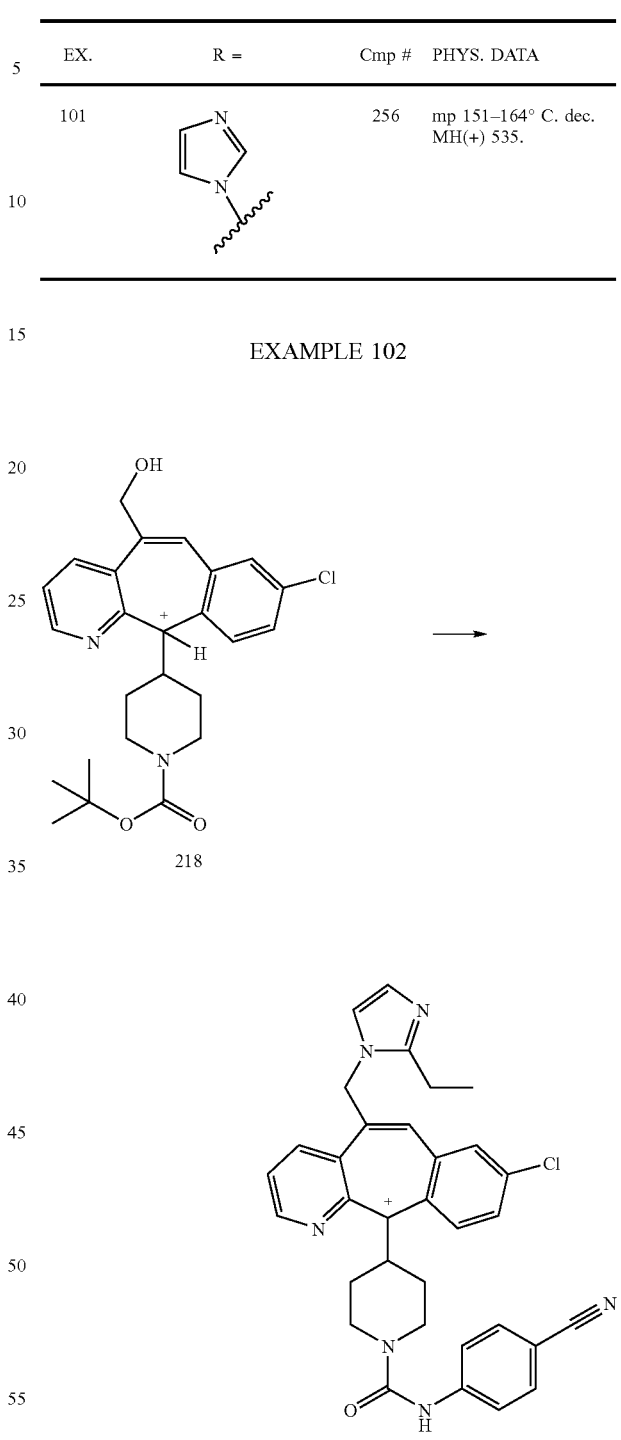

The (+) isomer of compound (218) obtained in essentially the same manner as Preparative Example (22), was further reacted in the same manner as in Preparative Example (6), Steps E and F, Examples (21), (23) and (29) sustituting with 2-Ethyl imidazole in Ex. (21) to afford the title compound (257). (146-157° C. dec.), MH$^+$ 564

PREPARATIVE EXAMPLE 27

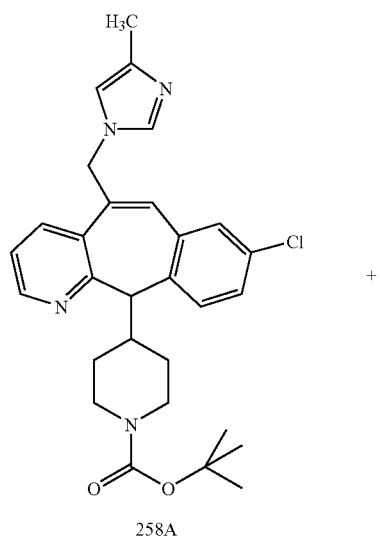

258A

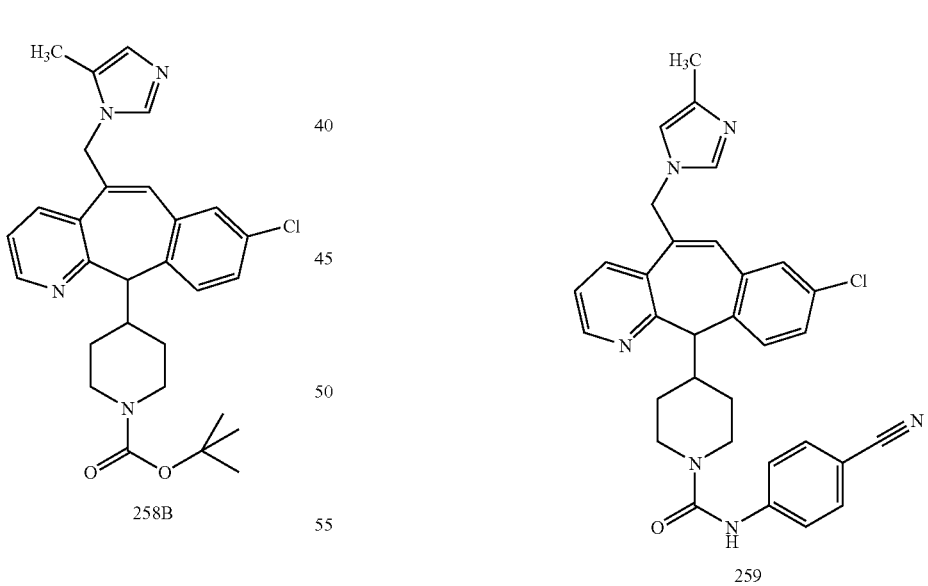

258B

EXAMPLE 103

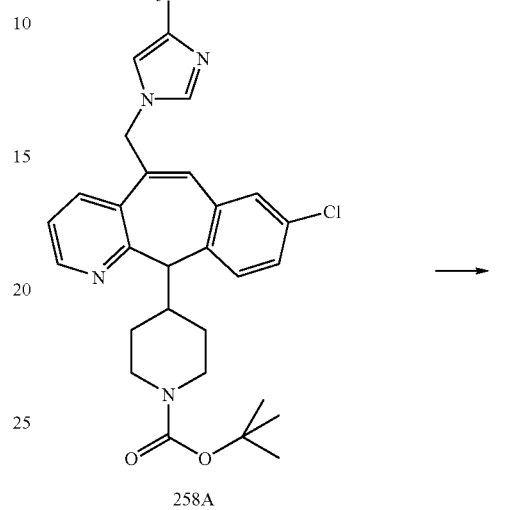

258A

259

In essentially the same manner as Preparative Example (20), substituting 4-methyl imidazole, compound (258) was prepared as a mixture of 4 and 5 substituted imidazole derivatives. This mixture was then reacted in a similar manner as Example 35 and the isomers separated (258A) and (258B).

The pure 4-methyl imidazole isomer (258A) was reacted as in Preparative Example 20, Step D, and Example (29) to afford the title compound as a white solid (259). (128-138° C. dec.) MH$^+$ 549

EXAMPLE 104

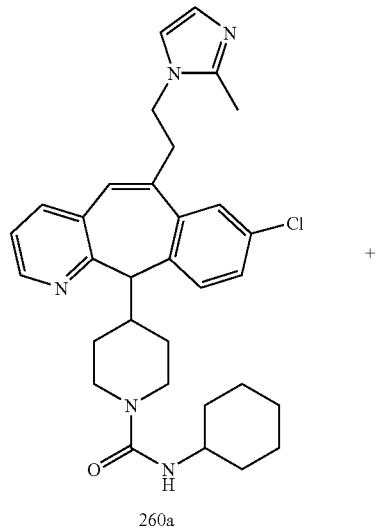

260a

260b

Step A

Compound (108) from Preparative Example 9, Step E, was reacted with compound (64) from Preparative Example 6, Step A in essentially the same manner as in Preparative Example 6, Steps B-F, to afford a mixture of one and two methylene spaced iodo intermediates.

Step B

The mixture of intermediates from Step A above was reacted in essentially the same manner as in Example 22 to afford a mixture of one and two methylene spaced imidazole derivatives.

Step C

The mixture from Step B above was reacted in the same manner as Preparative Example 20, Step D, followed by a reaction with phenyl isocyante in the same manner as Example 15 to afford the title compound as a 1:1 mixture (260a) and (260b) (133-145° C. dec.); MH$^+$ 544

PREPARATIVE EXAMPLE 28

Step A

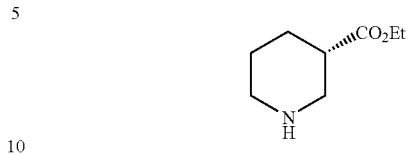

Ref: Gazz. Chim. Ital. (1972) 102, 189-195; J. Org. Chem. (1991) 56, 1166-1170.

Ethyl nipecotate (70.16 g, 0.446 mmol) and D-tartaric acid (67 g, 1.0 eq) were dissolved in hot 95% EtOH (350 mL). The resulting solution was cooled to room temperature and filtered and the crystals washed with ice-cold 95% EtOH. The crystals were then recrystallized from 95% EtOH (550 mL) to give the tartrate salt (38.5 g, 56% yield). The salt (38.5 g) was dissolved in water (300 mL) and cooled to 0° C. before neutralizing with 3M NaOH. The solution was extracted with CH$_2$Cl$_2$ (5×100 mL) and the combined organics dried over Na$_2$SO$_4$ and concentrated under reduced pressure to give a clear oil (19.0 g, 89% yield). CIMS: MH$^+$=158.

Step B

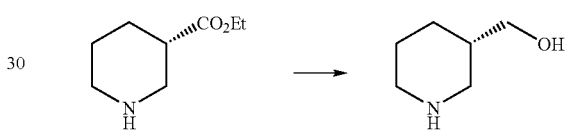

LAH (118 mL, 1.0 M in Et$_2$O, 1.0 eq.) was added to a solution of the product from Step A (18.5 g, 0.125 mmol) in THF (250 mL) at 0° C. over 20 minutes. The resulting solution was warmed slowly to room temperature and then heated at reflux 2 hours. The reaction was cooled to room temperature and quenched by the slow addition of saturated Na$_2$SO$_4$. The resulting slurry was dried by the addition of Na$_2$SO$_4$, filtered through Celite and concentrated to give a colorless oil (13.7 g, 98% crude yield). CIMS: MH$^+$=116; $[\alpha]^{20}_D = -8.4°$ (5.0 mg in 2 mL MeOH).

Step C

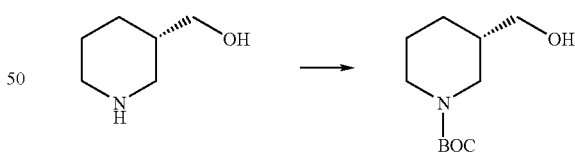

The product of Step B (13.6 g, 0.104 mmol) was dissolved in MeOH (100 mL) and H$_2$O (100 mL) di-tert-butyl dicarbonate (27.24,1.2 eq.) was then added portionwise keeping the pH>10.5 by the addition of 50% NaOH. The reaction mixture was stirred at room temperature an additional 2.5 hours and concentrated in vacuo. The residue was diluted with H$_2$O (350 mL) and extracted with CH$_2$Cl$_2$ (3×150 mL). The combined organics were dried over Na$_2$SO$_4$, filtered, and concentrated under reduced pressure. The crude product was purified by flash chromatography using a 50% EtOAc in hexanes solution as eluent to give a white solid (12.13 g, 48% yield). FABMS: MH$^+$=216; $[\alpha]^{20}_D = +15.2$ (5.0 mg in MeOH).

Step D

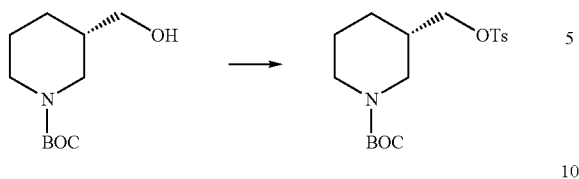

p-Toluenesulfonyl chloride (12.75 g, 1.2 eq.) was added portionwise to a solution of the product from Step C (12.00 g, 55.74 mmol) in nvridine (120 mL) at 0° C. The resulting solution was stirred at 0° C. overnight. The reaction mixture was diluted with EtOAc (300 mL) and washed with cold 1N HCl (5×300 mL), saturated NaHCO$_3$ (2×150 mL), H$_2$O (1×100 mL), and brine (1×100 mL), dried over Na$_2$SO$_4$ and concentrated in vacuo to give a pale yellow solid (21.0 g, 100% crude yield). FABMS: MH$^+$=370.

Step E

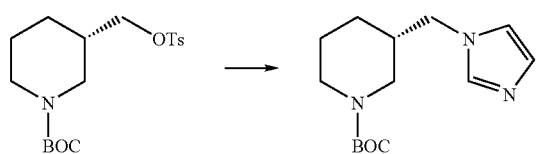

The product of Step D (21.0 g, 55.74 mmol) in DMF (300 mL) was treated with sodium imidazole (8.37 g, 1.5 eq.) and the resulting solution heated at 60° C. for 2 hours. The reaction mixture was cooled to room temperature and concentrated in vacuo. The residue was diluted with H$_2$O (300 mL) and extracted with CH$_2$Cl$_2$ (3×150 mL). The combined organic layer was dried over Na$_2$SO$_4$, filtered, and concentrated. The crude product was purified by flash chromatography using a 7% MeOH in CH$_2$Cl$_2$ solution as eluent to give a pale yellow solid (7.25 g, 49% yield). FABMS: MH$^+$=266; [α]$^{20}_D$=+8.0 (5.0 mg in MeOH).

Step F

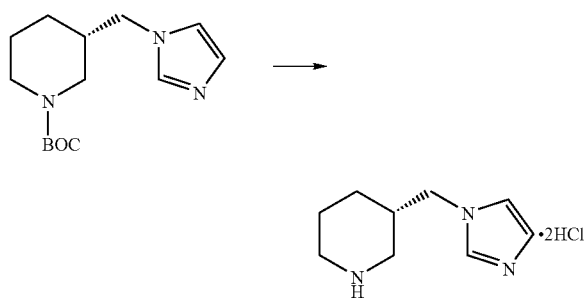

The product of Step E (5.50 g, 20.73 mmol) was stirred at room temperature in 4M HCl in dioxane (50 mL) overnight. The resulting solution was concentrated and the residue triturated with Et$_2$O to give Compound (261) as a yellow solid (4.90 g, 99% yield). CIMS: MH$^+$=166.

PREPARATIVE EXAMPLE 29

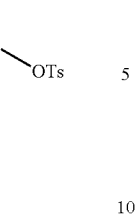 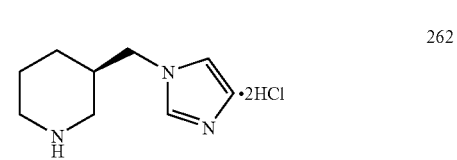

262

By essentially the same procedure set forth in Preparative Example 28 above, using L-tartaric acid instead of D-tartaric acid in Step A, Compound (262) was prepared.

PREPARATIVE EXAMPLE 30

Preparation of Compounds (263) and (264)

Step A

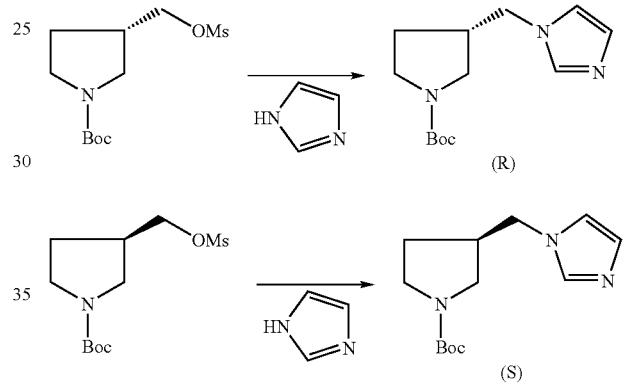

3(R)-(3-Methanesulfonyloxymethyl)pyrrolidine (J. Med. Chem. 1990, 33, 77-77) (0.993 g, 3.56 mmoles) was dissolved in anhydrous DMF (25 mL) and sodium imidazole (0.6 g, 10 mmoles) was added. The mixture was heated at 60° C. for 2 h and then evaporated to dryness. The product was extracted with CH$_2$C$_{l2}$ and washed with brine. The CH$_2$Cl$_2$ extract was evaporated to dryness to give the titled compound (263) (1.1409 g, 100%), ESMS: FABMS (M+1)= 252; $^1$HNMR (CDCl$_3$) 1.45 (s, 9H), 1.5-1.7 (m, 1H), 1.9-2.1 (m, 1H), 2.5-2.7 (m, 1H), 3.0-3.2 (m, 1H), 3.3-3.6 (m, 2H), 3.9 (dd, 2H), 6.9 (s, 1H), 7.1(s, 1H), 7.45 (s, 1H)

In a similar manner, the (S) isomer was prepared from 3(S)-(3-methanesulfonyloxymethyl)pyrrolidine (0.993 g, 3.56 mmol) to give the title compound (1.14 g, 100%).

Step B

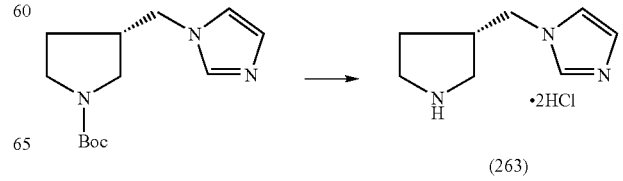

(263)

-continued

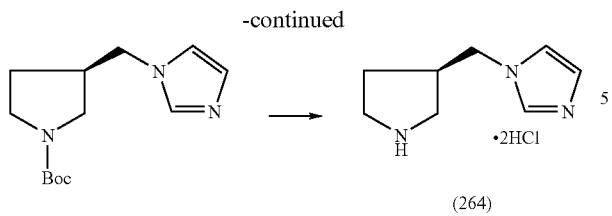

(264)

The (R) product (0.48 g, 1.91 mmoles) from Step A was stirred in 4N HCl in dioxane (10 mL) for 2 h and then evaporated to dryness to give the title compound (263) as the HCl salt.

In a similar manner the (S) isomer was prepared to give compound (264) as the HCl salt.

PREPARATIVE EXAMPLE 31

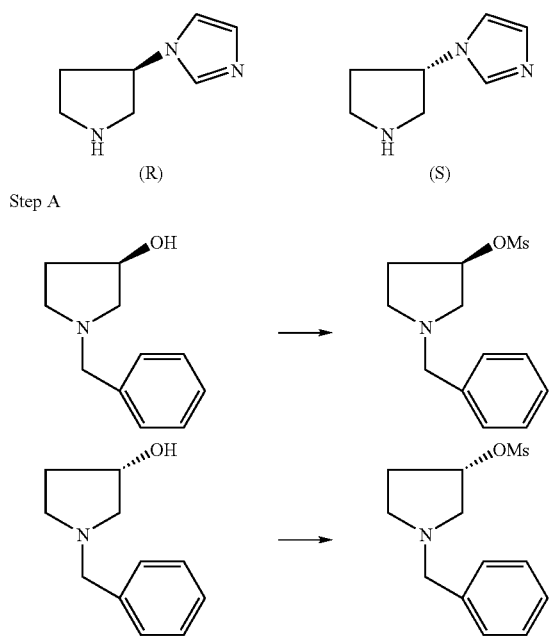

Step A

1N-Benzyl-3(R)-hydroxy-pyrrolidines (5 g, 28.21 mmol) and triethylamine (7.86 mL, 56.35 mmol) were dissolved in $CH_2Cl_2$ (50 mL) and the mixture was stirred under nitrogen at 0° C. Methanesulfonylchloride (2.62 mL, 33.87 mmol) was added and the solution was stirred at room temperature for 2 h. The solution was diluted with $CH_2Cl_2$ and washed with saturated aqueous sodium bicarbonate, water and dried ($MgSO_4$), filtered and evaporated to dryness to give the (R) title compound (7.2 g, 96.4%). FABMS (M+1)=256; $^1$HNMR ($CDCl_3$) 2.2 (m, 1H), 2.3 (m, 1H), 2.52 (m, 1H), 2.7-2.85 (m, 3H), 2.95 (s, 3H), 3.65 (q, 2H), 5.16 (m, 1H), 7.3 (s, 5H).

In a similar way the (S) isomer was prepared from 1N-Benzyl-3(S)-hydroxy-pyrrolidines (5 g, 28.21 mmoles) to give the (S) title compound (7.15 g, 98%).

Step B

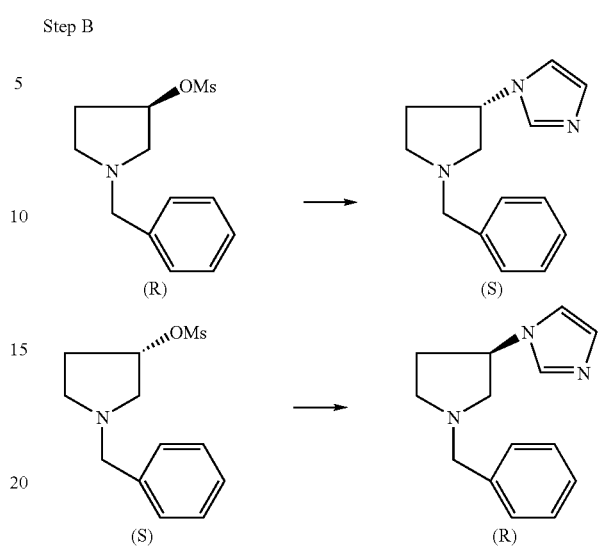

A solution of the (R) product from Step A (2.0 g, 7.84 mmoles) was added to a stirred solution of imidazole (1.1 g, 16.17 mmoles) in DMF (25 mL) under nitrogen atmosphere. The mixture was stirred at 60° C. for 16 h. DMF was evaporated in vacuo. The resulting crude product was extracted with $CH_2Cl_2$ and the extract was successively washed with water and brine, and the $CH_2Cl_2$ was evaporated to leave the title residue which was chromatographed on silica gel using 3% (10% conc $NH_4OH$ in methanol)—$CH_2Cl_2$ as eluant to give the title compound (0.95 g, 50.56%). FABMS (M+1)=228.

In a similar fashion the other isomer was prepared.

Step C

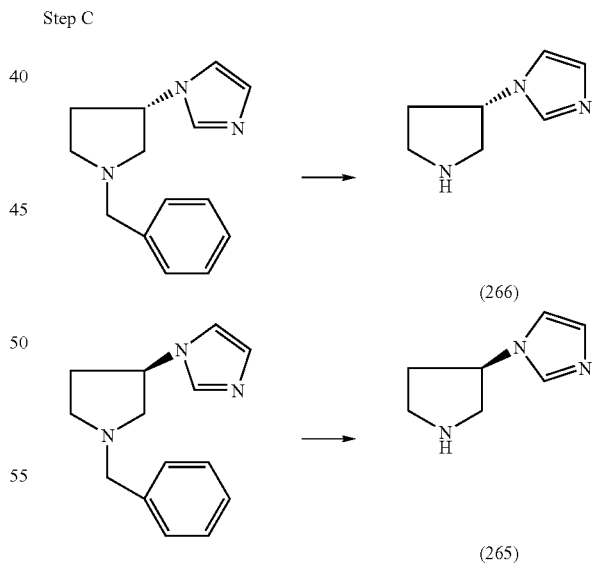

A mixture of the (S) product (0.95 g) from Step B and 10% Pd on carbon (0.5 g) in EtOH (20 mL) was shaken at 50 psi under an atmosphere of hydrogen for 24 h. The catalyst was filtered and the solvent removed to give the title compound (266) (0.522 g, 99.9%).

In a similar manner the (R) isomer was prepared from 1.0 g of the starting (R) product from Step B and 10% Pd on carbon (0.6 g) to give compound (265) in 99% yield.

PREPARATIVE EXAMPLE 32

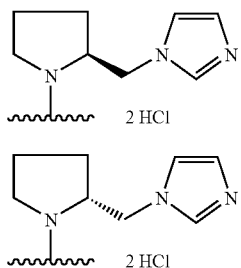

By essentially the same procedure set forth in Preparative Example 31 above, beginning with L or D-prolinol, the title compounds (267) and (268) were prepared.

EXAMPLE 105

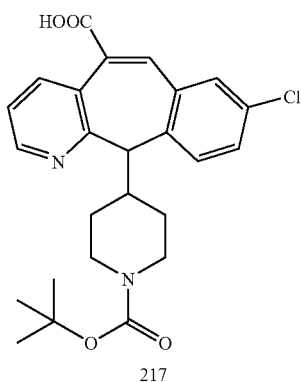

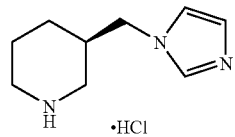

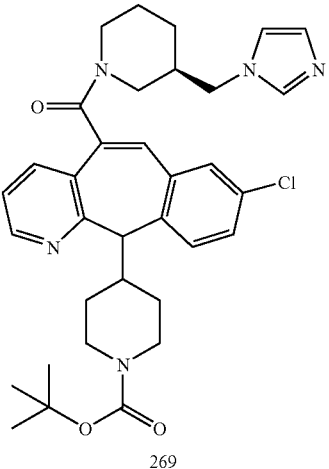

Compound (217) from Preparative Example 19 (0.227 g, 0.499 mmol) was added to a solution of Compound (262) from Preparative Example 29 (0.131 g, 0.649 mmol), DEC (0.249 g, 1.3 mmol), HOBT (0.175 g, 1.3 mmol) and NMM (0.5 mL) in DMF (25 mL). The resulting solution was stirred at room temperature for 24 hours. The reaction mixture was diluted with H$_2$O until precipitation ceased and slurry was filtered. The precipitate was diluted with CH$_2$Cl$_2$, washed with brine, dried over Na$_2$SO$_4$ and concentrated. The crude product was purified by chromatography using a 5% (10% NH$_4$OH in MeOH) solution in CH$_2$Cl$_2$ as eluent to give the title compound (269) (0.184 g, 62% yield).

EXAMPLES 106-111

Using the appropriate amine from the Preparative Examples 28-32, and following essentially the same procedure as in Example 105 above, compounds of the formula:

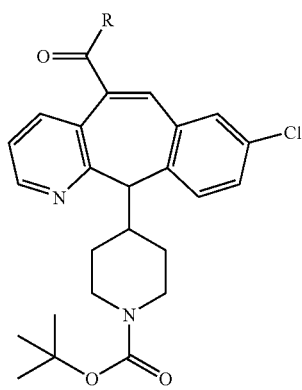

were prepared wherein R is defined in Table 11

TABLE 11

| EX. | R = | Compound # | PHYS. DATA |
|---|---|---|---|
| 106 | 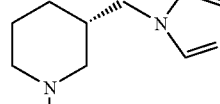 | 270 | MH$^+$ = 603 |
| 107 | 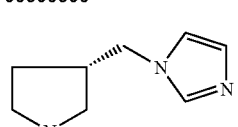 | 271 | MH$^+$ = 589 |
| 108 |  | 272 | MH$^+$ = 589 |
| 109 | 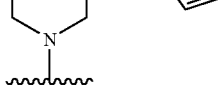 | 273 | MH$^+$ = 589 |

TABLE 11-continued

| EX. | R = | Compound # | PHYS. DATA |
|---|---|---|---|
| 110 | 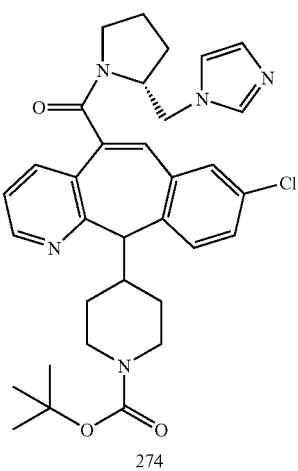 | 274 | MH$^+$ = 603 |
| 111 | | 275 | MH$^+$ = 603 |

EXAMPLE 112

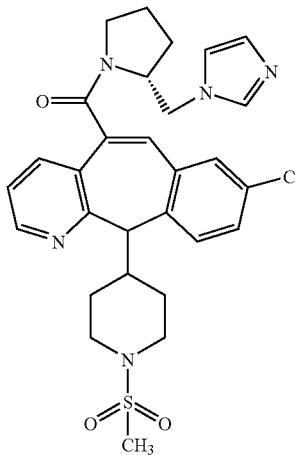

Compound (274) from Example 110 above (0.125 g, 0.213 mmoles) in CH$_2$Cl$_2$ (50 mL) was stirred with TFA (10 mL) at room temperature overnight. The reaction mixture was evaporated to give the TFA salt (0.28 g) which was redissolved in CH$_2$Cl$_2$ (50 mL) and cooled (ice water bath). Triethyl amine (0.1 mL) followed by methane sulfonyl chloride (0.038 g, 0.319 mmoles) were added and the reaction mixture was stirred at room temperature overnight. The reaction mixture was washed with sodium bicarbonate and water. The organic layer was dried over MgSO$_4$ and evaporated to dryness to give the title compound (276) (0.05 g, MH$^+$=567)

EXAMPLE 113

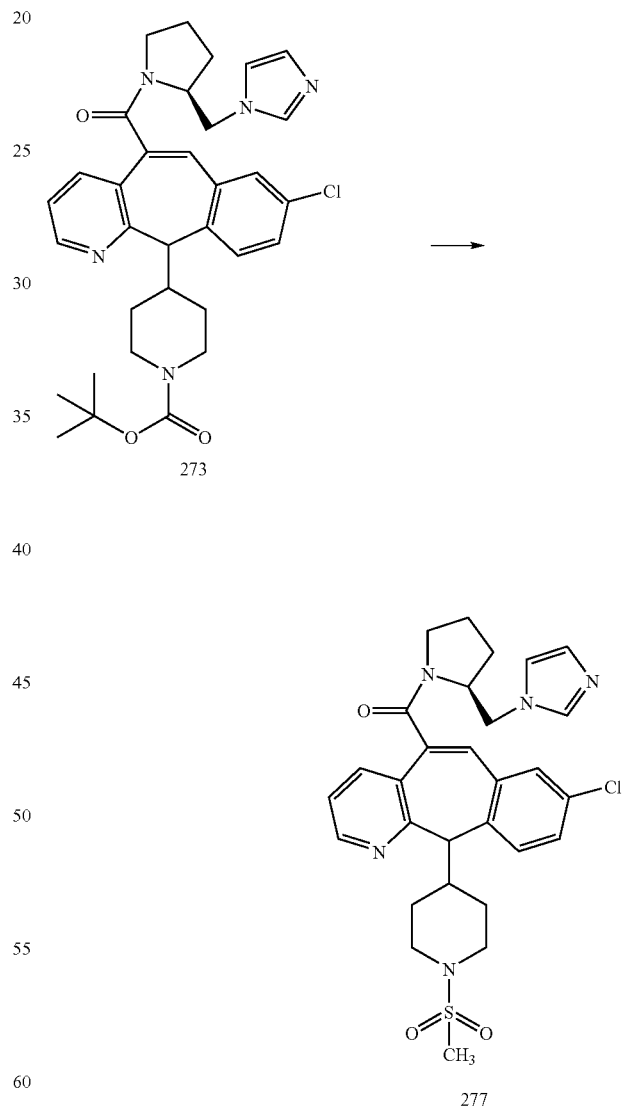

Starting with Compound (273) from Example 109 above and following essentially the same procedure as in Example 112 above, Compound (277) was prepared (MH$^+$=567).

PREPARATIVE EXAMPLE 33

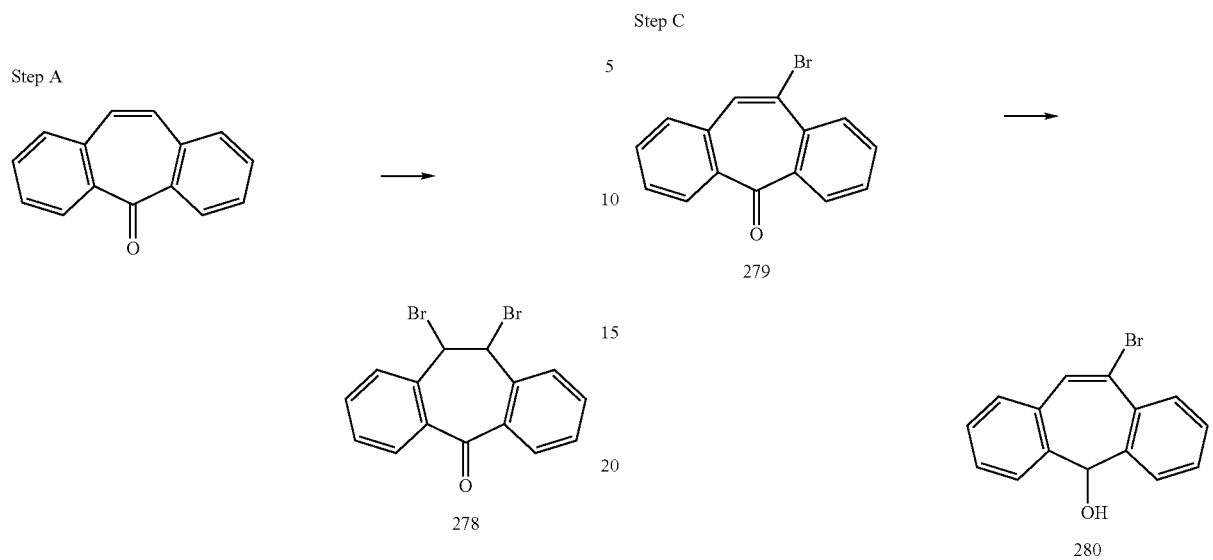

To a stirred solution of bromine (33.0 g, 210 mmol) in CCl$_4$ (100 ml) was added a solution of dibenzosuberenone (37.0 g, 179 mmol) in CCl$_4$ (200 ml) at room temperature. The resulting solution was stirred at room temperature for 1.5 hours. The white crystals were collected by filtration to give the product (278) (60.12 g, 92% yield, M+H=367).

Step B

A solution of the di-bromo compound (278) from step A (60.0 g, 163 mmol) and NaOH (20.0 g, 491 mmol) in MeOH (500 ml) was stirred and heated to reflux for 1.5 hours. The reaction mixture was then cooled to room temperature and stirred overnight. The mixture was evaporated to dryness then extracted with CH$_2$Cl$_2$—H$_2$O. The combined organic layer was dried over MgSO$_4$, filtered and evaporated to dryness to give a yellow solid (279) (46.34 g, 100% yield, M=285)

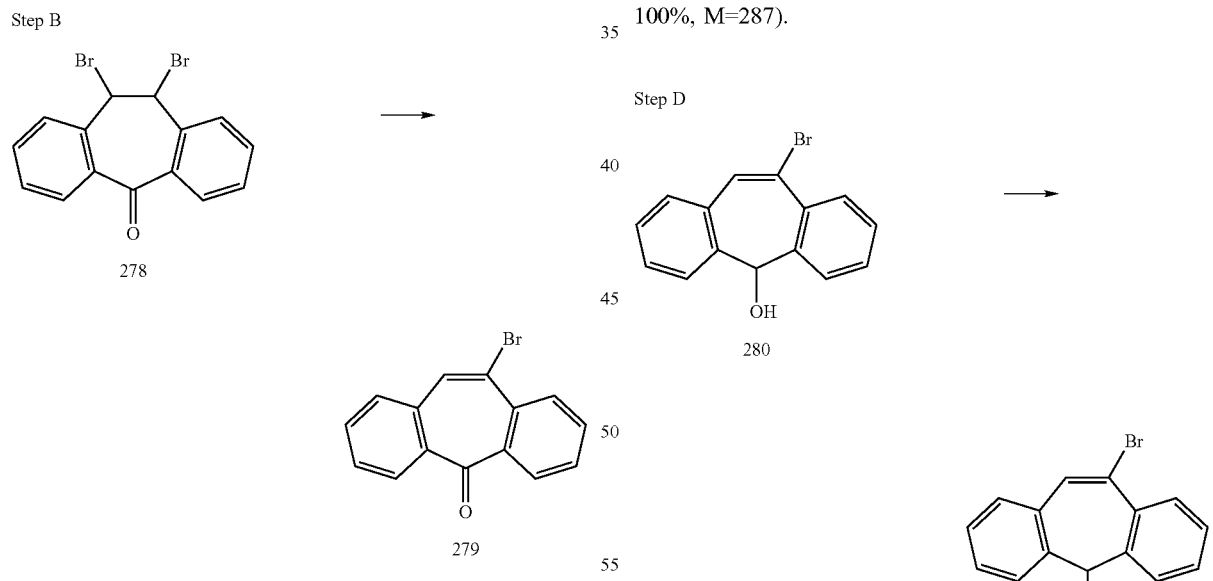

To a stirred solution of the mono-bromo compound (279) from step B (10.0 g, 35.07 mmol) in MeOH (200 ml) under nitrogen at 0° C. was added NaBH$_4$ (1.94 g, 51.2 mmol). The resulting solution was stirred at 0° C. for 1.5 hours, then evaporated, followed by extraction with CH$_2$Cl$_2$—H$_2$O. The combined organic layer was dried over MgSO$_4$, filtered, and evaporated to dryness to give a white solid (280) (10.3 g, 100%, M=287).

To a stirred solution of the alcohol (280) from Step C (10.0 g, 34.8 mmol) in CH$_2$Cl$_2$ (200 ml) at 0° C. was added 2,6-lutidine (14.9 g, 139.3 mmol) and thionyl chloride (8.28 g, 69.66 mmol). The resulting solution was warmed to room temperature and stirred overnight. The solution was then poured onto 0.5N NaOH solution, followed by extraction with $CH_2Cl_2$. The combined aqueous layer was dried over $Na_2SO_4$, filtered, and concentrated to dryness to give a crude brown oil (15.5 g). To a solution of this crude oil (15.5 g) in acetonitrile (200 ml) was added 2,6-Bis (dimethyl)-1-methyl piperidine (10.81 g, 69.66 mmol) and N-Boc piperidine (6.49 g, 34.83 mmol). The resulting mixture was warmed to 65° C. overnight. The mixture was evaporated to dryness, followed by extraction with $CH_2Cl_2$/saturated $NaHCO_3$. The combined organic layer was dried over $Na_2SO_4$, concentrated and purified by column chromatography on silica gel, eluting with 5% EtOAc/95% Hexane to give the protected N-Boc compound (281) (5.68 g, 36% yield, $MH^+$=455).

chloride (0.15 g, 0.88 mmol). The resulting mixture was purged with carbon oxide at 80 psi to 100 psi and heated to 78° C.-82° C. for 5 hours, followed by stirring at room temperature for overnight. The solution was then extracted with EtOAc. The combined organic layer was washed with water, brine, dried over $Na_2SO4$, filtered, evaporated and the crude product was purified by column chromatography on silica gel, eluting with 10% EtOAc/90% Hexane to give the ester compound (282) (2.1 g, 55% yield, $MH^+$=435).

Step F

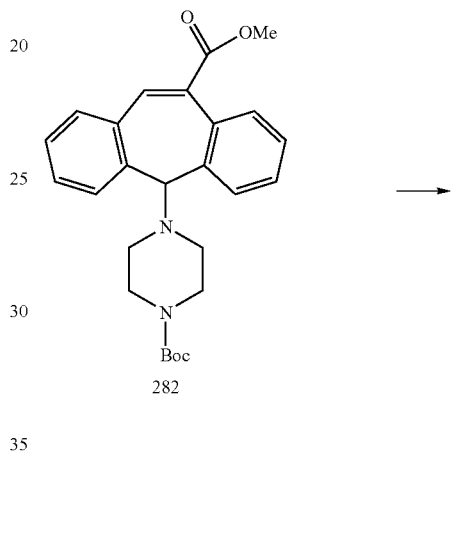

282

Step E

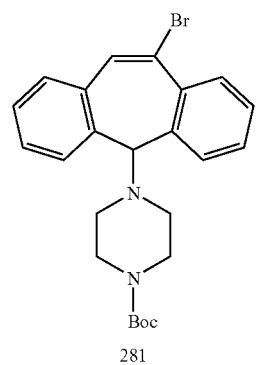

281

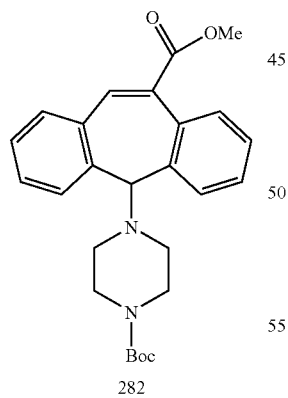

282

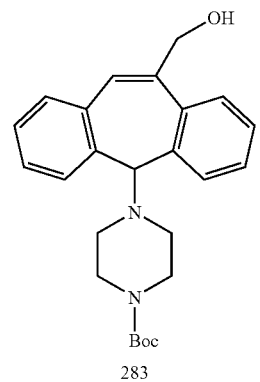

283

To a solution of the N-Boc compound (281) from Step D (4.0 g, 8.78 mmol) in anhydrous toluene (100 ml) and methanol (20 ml) was added triphenylphosphine (1.15 g, 4.39 mmol), DBU (1.81 g, 11.9 mmol) and palladium (II)

To a stirred solution of the ester compound (282) from Step E (1.2 g, 2.77 mmol) in THF (15 ml) at 0° C. was added a 1 M solution of DIBAL (16.62 ml, 16.62 mmol). The resulting solution was stirred at room temperature for 4 hours. To the solution was then added 10% potassium sodium tartarate, followed by extraction with EtOAc. The combined organic layer was dried over $Na_2SO4$, filtered, and evaporated to give a solid (283) (1.1 g, 100% yield, $MH^+$=406).

Step G

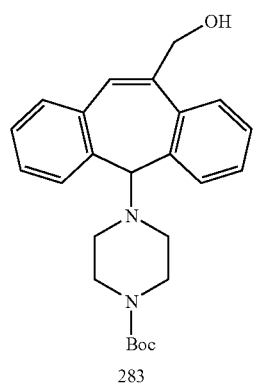

283

Step H

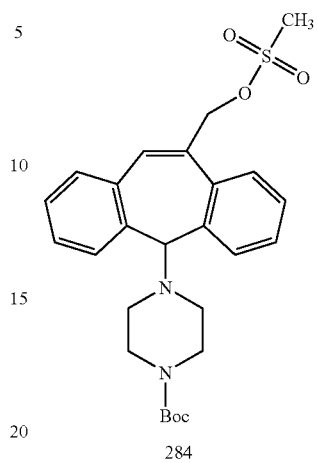

284

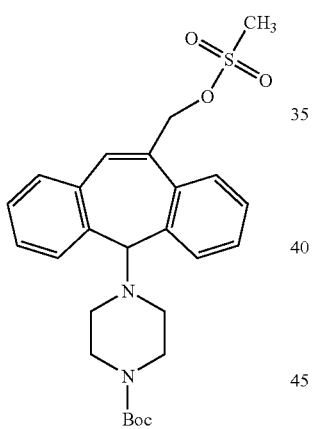

284

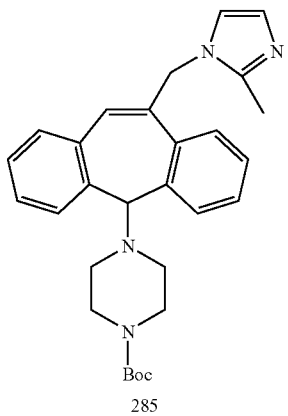

285

To a solution of the alcohol (283) from Step F (0.62 g, 1.52 mmol) in CH$_2$Cl$_2$ (15 ml) under nitrogen was added triethyl amine (0.64 ml, 4.56 mmol) and methane sulfonyl chloride (0.26 g, 2.29 mmol). The resulting solution was stirred at room temperature overnight. The mixture was washed with NaHCO$_3$ solution, dried over Na$_2$SO4, filtered and concentrated to dryness to give the mesylate compound (284) (0.53 g, 76% yield, M-CH$_3$SO$_3$H=389.1).

To a stirred solution of 1-methyl-imidazole (1.04 g, 12.7 mmol) in DMF (10 ml) under nitrogen, was added NaH (0.305 g, 12.7 mmol). The resulting solution was stirred at room temperature for 15 minutes, followed by the addition of the mesylate compound (284) from step G (2.05 g, 4.23 mmol). The reaction mixture was stirred at room temperature overnight, then evaporated to dryness, and extracted with an EtOAc-NaHCO$_3$ solution. The combined organic layer was dried over Na$_2$SO4, concentrated and the crude product purified by silica gel column chromatography eluting with 2% MeOH/98% NH$_3$—CH$_2$Cl$_2$ to give the product (285) (0.775 g, 39% yield, MH$^+$=471).

Step I

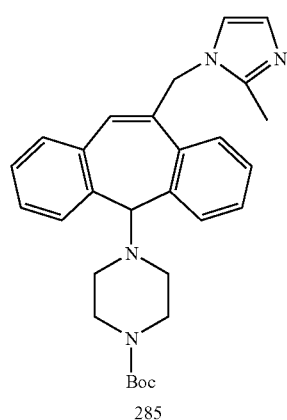
285

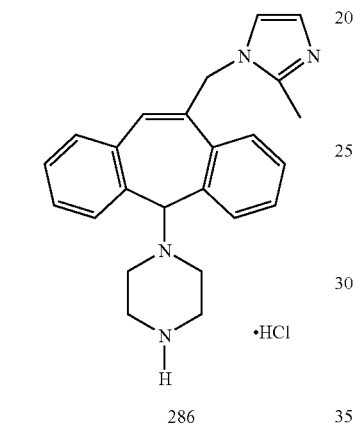
286

A solution of the product (285) from step H (0.3 g, 0.64 mmol) in 4M HCl in dioxane (40 ml) was stirred at room temperature for 3 hours and then concentrated to dryness to give the hydrochloride salt of the title product (286) (0.42 g, 100% yield, MH$^+$=371).

EXAMPLES 114 AND 115

The racemic mixture of Preparative Example 33, Step H above was seperated into its pure isomers by HPLC, using a Chiral AD column eluting with 15% IPA/75% Hexane/ 0.2% DEA to afford the compounds in Table 12.

TABLE 12

| EX. # | CMPD # | PHYS. DATA |
|---|---|---|
| 114 | 287 isomer 1 | MS M$^+$ = 471 |
| 115 | 288 isomer 2 | MS M$^+$ = 471 |

EXAMPLES 116-119

Starting with the piperazine compound (286) from Preparative Example 33 Step I, and reacting it with the appropriate isocyanate or sulfonyl chloride, following essentially the same procedure as indicated in Table 13, compounds of the formula:

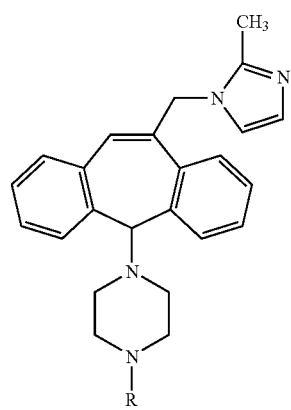
(286)

were prepared wherein R is defined in Table 13.

TABLE 13

| EX. # | PROCEDURE | R = | CMPD # | PHYS. DATA |
|---|---|---|---|---|
| 116 | Example 13 | ![structure with NH-C6H4-CN and C=O] | 289 isomer 1 | MS M$^+$ = 515 |
| 117 | Example 13 | ![structure with NH-C6H4-CN and C=O] | 290 isomer 2 | MS M$^+$ = 515 |
| 118 | Example 24 | O=S(=O)CH$_3$ | 291a isomer 1 | MS M$^+$ = 449 |
| 119 | Example 24 | O=S(=O)CH$_3$ | 291b isomer 2 | MS M$^+$ = 449 |

PREPARATIVE EXAMPLE 34

Step A

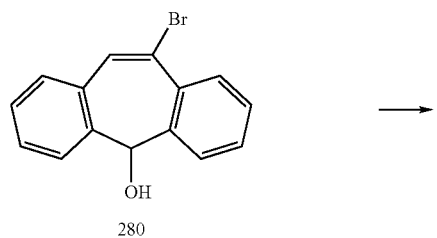

To a stirred solution of alcohol (280) from Preparative Example 33, Step C (30.0 g, 104.5 mmol) in CH$_2$Cl$_2$ (500 mL) under nitrogen at −20° C. was added thionyl chloride (106.7 mL, 1,46 mmol). The resulting solution was stirred at room temperature overnight and then evaporated to dryness. The crude mixtue was diluted with toluene (50 mL), followed by the addition of more SOCl$_2$ (106.7 mL) at room temperature. The resulting solution was heated to reflux for 2 hours until the reaction went to completion. The reaction mixture was then cooled to room temperature and concentrated to dryness to give a light brown solid (292) (35.67 g, 100% yield, M-BrCl=191).

Step B

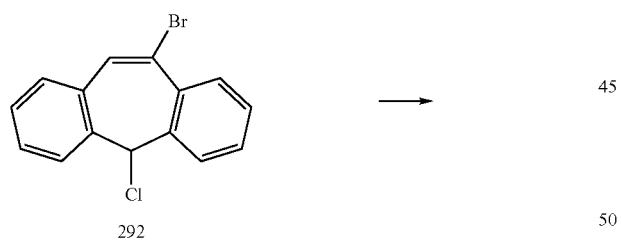

To a suspension of Mg (3.63 g) in anhydrous THF (95 mL) under nitrogen at room temperature was added 4-chloro-1-methyl piperidine (3 mL, 10% of the total amount) and one small crystal of iodine. The resulting solution was heated to reflux, followed by the addition of iodomethane (0.5 mL) and the remainder of the 4-chloro-1-methyl piperidine (27 mL). The reaction was stirred for one hour and then concentrated to dryness to give the crude Grignard reagent (0.8M).

To a stirred solution of the chloro compound (292) from Preparative Example 34, Step A (35.67 g, 116.7 mmol) in anhydrous THF (200 mL) under nitrogen at room temperature, was added dropwise the Grignard reagent (as obtained above) (0.8M, 146 mL, 116.7 mmol). The resulting solution was stirred at room temperature for 3 hours, followed by the extraction with EtOAc-H$_2$O. The combined organic layer was dried over MgSO$_4$, filtered and evaporated to dryness to give the product (293) (49.25 g, 100% yield, MH$^+$=368).

Step C

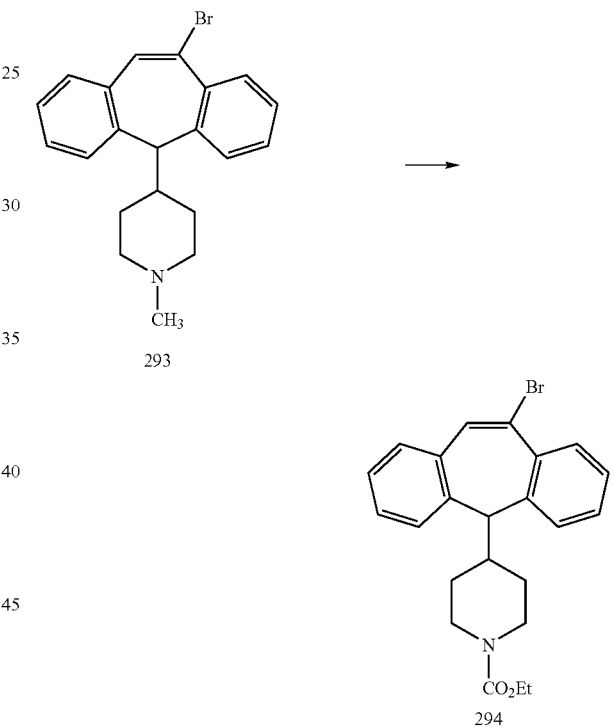

To a stirred solution of Compound (293) from Step B above (42.9 g, 116.5 Is mmol) in toluene (400 mL) under nitrogen was added triethylamine (49 mL, 349.5 mmol). The resulting solution was heated to refux, followed by the dropwise addition of ethyl chloroformate (126 g, 1165 mmol). Continued to heat the solution at the reflux temperature for 2 hours. The reaction was then stirred at room temperature overnight, followed by extraction with an EtOAc-1N NaOH solution. The combined organic layer was dried over MgSO$_4$, filtered, concentrated to dryness and the crude product purified by column chromatography on normal phase silica gel, eluting with 30% EtOAc/70% Hexane to give a light yellow solid (294) (2.99 g, 12% yield, MH$^+$=426.3).

Step D

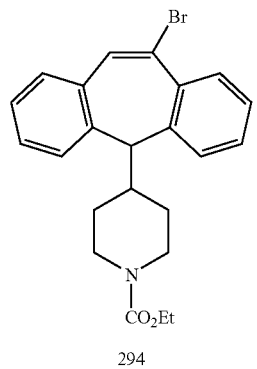

294

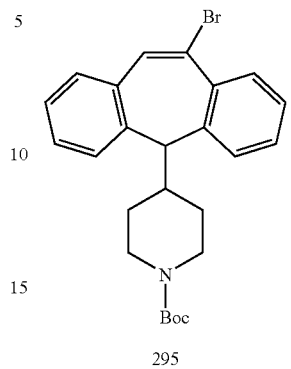

295

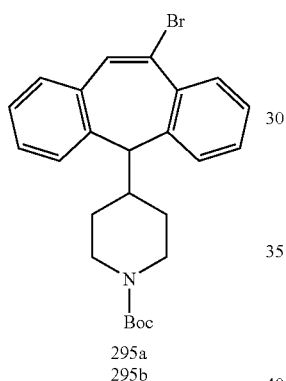

295a
295b

Step E

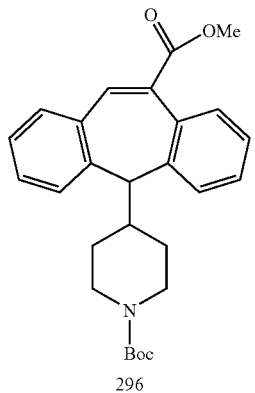

296

A solution of the ester (294) from step C above (3.34 g, 7.83 mmol) in 6N HCl (20 mL) was heated to reflux overnight. The reaction was cooled to room temperature and basified with NH$_4$OH solution, followed by extraction with CH$_2$Cl$_2$. The combined organic layer was dried over MgSO$_4$, filtered, and evaporated to dryness to give a crude free piperidine (2.80 g, 100% yield, MH$^+$=534)

To the crude material (as obtained above) (2.77 g, 7.82 mmol) in 50% MeOH/1% H$_2$O (200 mL) was added Di-tert-butyl dicarbonate (3.41 g, 15.64 mmol). The reaction mixture was adjusted to pH=9 and stirred at room temperature for 4 hours, evaporated to dryness then extracted with CH$_2$Cl$_2$—H$_2$O. The combined organic layer was dried over MgSO$_4$, filtered, concentrated to dryness and purified by HPLC, using chiral AD column, eluting with 15% IPA/75% Hexane/0.2% DEA to give the pure isomers of the N-Boc compounds (295a) and (295b) (3.42 g, 96% yield, MH$^+$=454).

To a stirred solution of the pure (+) or (−) isomer of the N-Boc compound from Step D above (4.0 g, 8.78 mmol) in anhydrous toluene (100 mL) and methanol (20 mL) was added triphenyl phosphine (1.15 g, 4.39 mmol), DBU (1.81 g, 11.9 mmol) and palladium (II) chloride (0.15 g, 0.88 mmol). The resulting mixture was purged with carbon monooxide at 80 psi to 100 psi and heated to 78° C.-82° C. for 5 hours, followed by stirring at room temperature overnight. The solution was then extracted with EtOAc. The combined organic layer was washed with water, brine, dried over Na$_2$SO4, filtered, evaporated and purified by column chromatography on silica gel, eluting with 10% EtOAc/90% Hexane to give the ester (296a) or (296b) (2.1 g, 55% yield, MH$^+$=435).

Step F

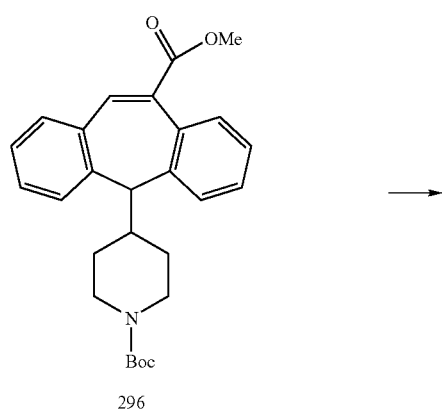
296

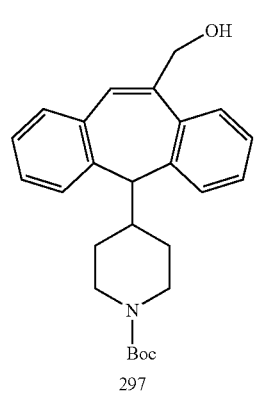
297

To a stirred solution of the (+) or (−) isomer of the ester from Step E above, (1.2 g, 2.77 mmol) in THF (15 mL) at 0° C. was added 1M solution of DIBAL (16.62 mL, 16.62 mmol). The resulting solution was stirred at room temperature for 4 hours. To the solution was then added 10% potential sodium tartarate, followed by extraction with EtOAc. The combined organic layer was dried over Na$_2$SO$_4$, filtered, and evaporated to give a solid (297a) or (297b) (1.1 g, 100% yield, MH$^+$=406).

Step G

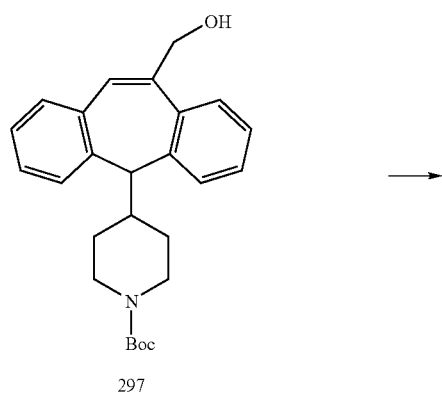
297

-continued

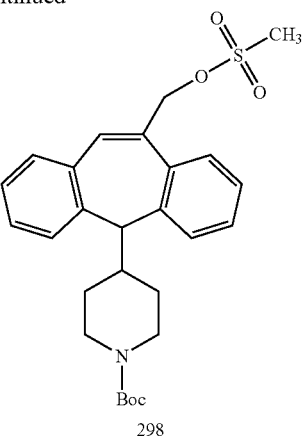
298

To a stirred solution of the (+) or (−) isomer of the alcohol from Step F, above (0.62 g, 1.52 mmol) in CH$_2$Cl$_2$ (15 mL) under nitrogen was added triethyl amine (0.64 mL, 4.56 mmol) and methane sulfonyl chloride (0.26 g; 2.29 mmol). The resulting solution was stirred at room temperature for overnight. The mixture was washed with NaHCO$_3$ solution, dried over Na$_2$SO4, filtered and concentrated to dryness to give the mesylate compound (298a) or (298b) (0.53 g, 76% yield, M-CH$_3$SO$_3$H=389.1).

Step H

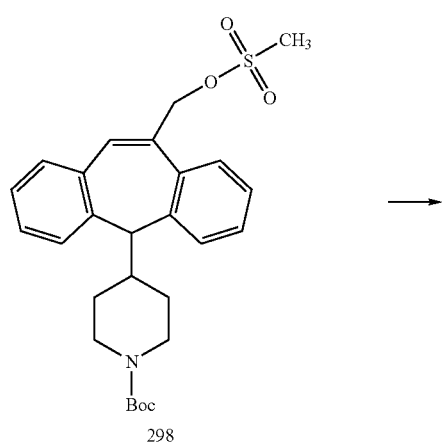
298

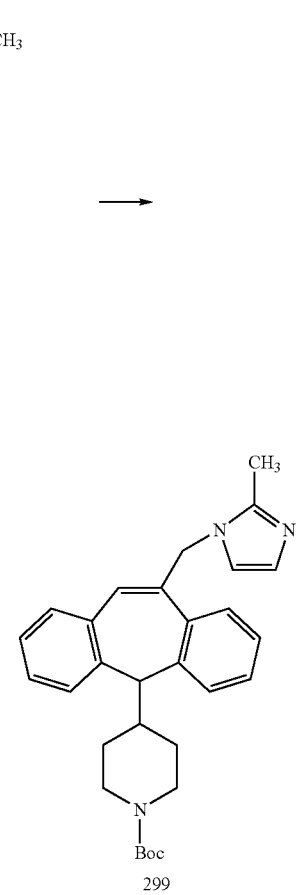
299

399

To a stirred solution of 1-methyl-imidazole (1.04 g, 12.7 mmol) in DMF (10 mL) under nitrogen, was added NaH (0.305 g, 12.7 mmol). The resulting solution was stirred at room temperature for 15 minutes, followed by the addition of the (+) or (−) isomer of the mesylate compound (299) from Step G above (2.05 g, 4.23 mmol). The reaction mixture was stirred at room temperature overnight then evaporated to dryness, followed by extraction with an EtOAc-NaHCO₃ solution. The combined organic layer was dried over Na₂SO4, concentrated and the crude product was purified by silica gel column chromatography, eluting with 2% MeOH/98% NH₃—CH₂Cl₂ to give the product (299a) or (299b) (0.775 g, 39% yield, MH⁺=471).

Step I

400

A solution of the (+) or (−) isomer of the product from Step I above (0.3 g, 0.64 mmol) in 4M HCl in dioxane (40 mL) was stirred at room temperature for 3 hours and then concentrated to dryness to give the HCl salt of the product (300a) or (300b) (0.42 g, 100% yield, MH⁺=371).

EXAMPLES 120 AND 121

Starting with the appropriate (+) or (−) isomer of Compound (300) and reacting in a similiar manner as in Example 13 using the appropriate isocyanate, compounds of the formula:

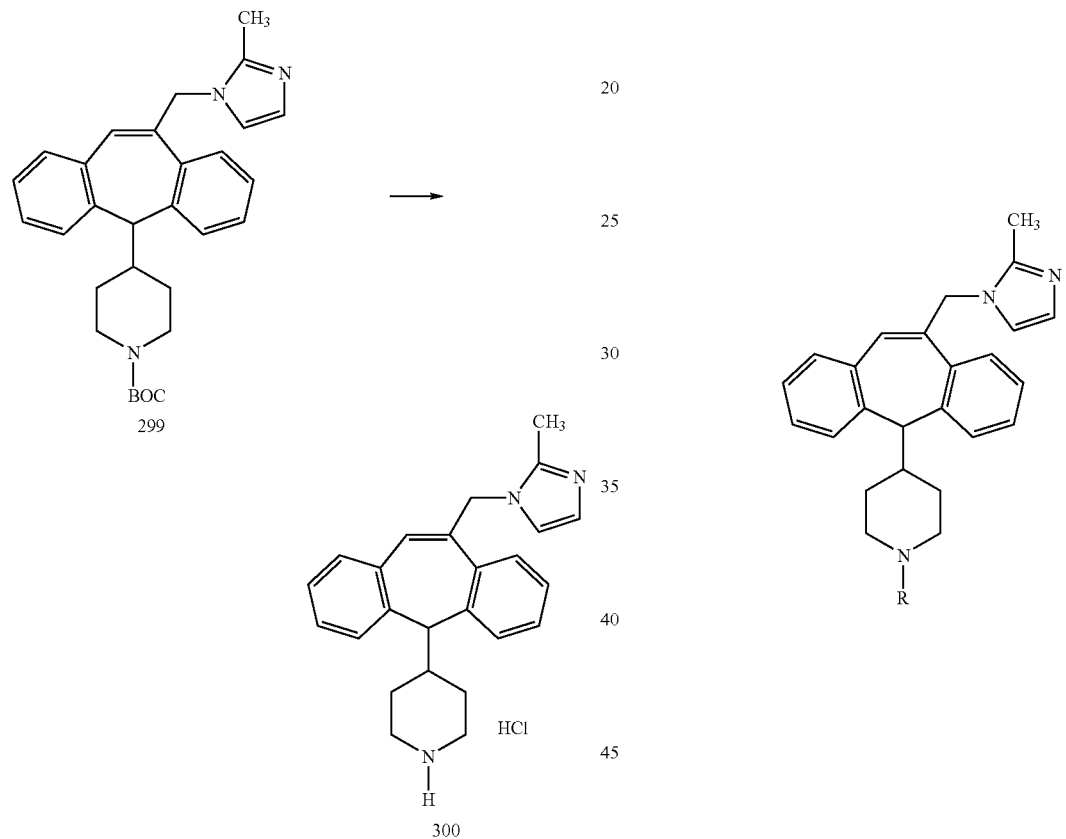

were prepared wherein R is defined in Table 14.

TABLE 14

| EX. # | PROCEDURE | R = | CMPD # | PHYS. DATA |
|---|---|---|---|---|
| 120 | Example 13 | (acetamido-phenyl-CN) | 301 isomer 1 | MS MH⁺ = 514 |
| 121 | Example 13 | (acetamido-phenyl-CN) | 302 isomer 2 | MS MH⁺ = 514 |

PREPARATIVE EXAMPLE 35

Step A

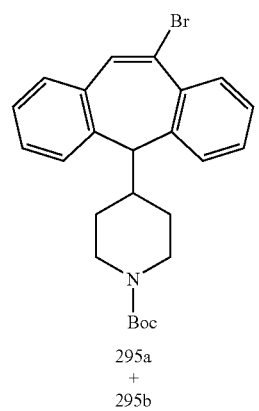

295a
+
295b

Step B

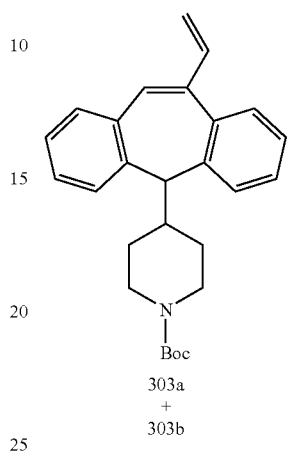

303a
+
303b

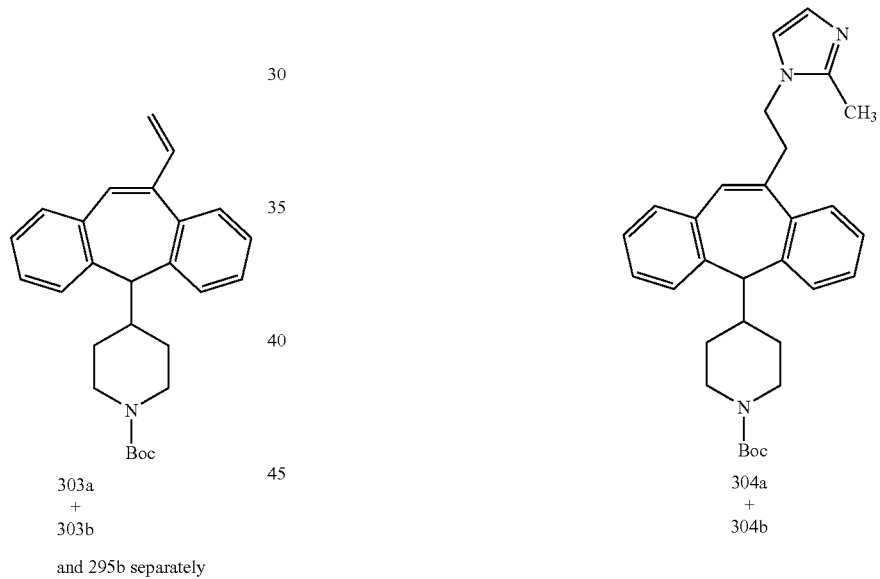

303a
+
303b and 295b separately

304a
+
304b

To a stirred solution of the bomo-compound (295a) from Preparative Example 34, Step D, (0.5 g, 1.10 mmol) in 1-methyl-2-pyrrolidinone (4.3 mL) under nitrogen, was added lithium chloride (0.14 g, 3.3 mmol), tri-2-furylphosphine (0.013 g, 0.04 mmol) and tris(dibenzylideneacetone)-dipalladium(0) (0.02 g, 0.02 mmol). The resulting solution was stirred at room temperature for 5 minutes, followed by the addition of tributyl (vinyl) tin (0.39 g, 1.24 mmol). The reaction was then heated to 85° C. for 2 hours, followed by extraction with EtOAc-H$_2$O. The combined organic layer was dried over MgSO$_4$, filtered, concentrated to dryness and purified by column chromatography on normal phase silica gel, eluted with 10% EtOAc/90% CH$_2$Cl$_2$ to give a light yellow liquid (303a) (0.06 g, 15% yield, MH$^+$=390).

To a stirred solution of 1-methyl imidazole (0.377 g, 4.6 mmol) in anhydrous THF (4 mL) under nitrogen at −78° C., was added 2.5M n-BuLi/Hexane (0.33 mL). The resulting solution was stirred at −78° C. for 30 minutes and then allowed to warm at room temperature. To this stirred solution was added the alkene compound (303a) from step A above,(0.78 g, 2.1 mmol) in THF. The resulting solution was then heated to 120° C. overnight then cooled to room temperature, and extracted with EtOAc—H$_2$O. The combined organic layer was dried over MgSO$_4$, filtered, evaporated and purified by column chromatography on normal phase silica gel, eluted with 3% MeOH/97% NH$_3$—CH$_2$Cl$_2$ to give a light yellow solid (304a) (0.09 g, 10% yield, MH$^+$=456.1).

Step C

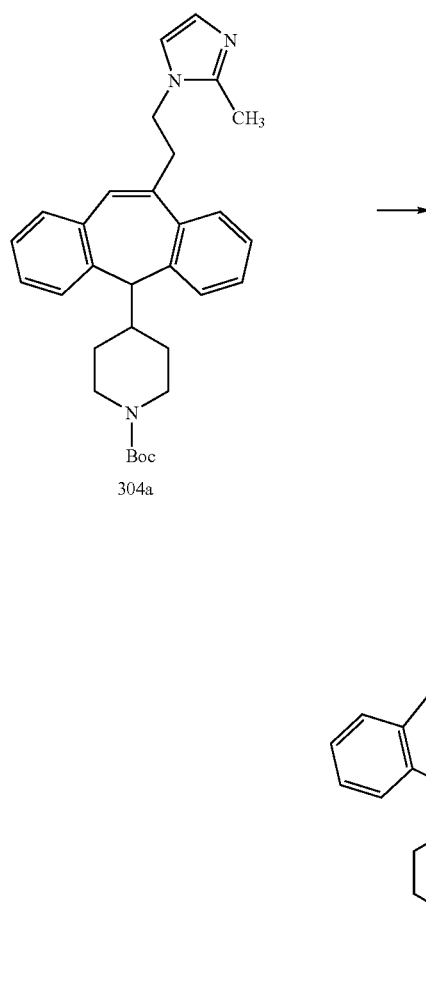

A solution of the product (304a) from Step B above (0.18 g, 3.72 mmol) in 4M HCl/dioxane (5 mL) was stirred at room temperature for 2 hours, then concentrated to dryness to give a crude off white solid (305a) (0.22 g, 100% yield. $MH^+=384.2$).

Using the same procedure as defined in Preparative Example 35 above starting with the Boc-protected Bromo compound (295b), compound (305b) was prepared ($MH^+= 384.2$).

EXAMPLES 122-125

Starting with the appropriate (+) or (−) isomer of Compound (305) (i.e., 305a and 305b) and reacting in a similiar manner as in Example 13 using the appropriate isocyanate, compounds of the formula:

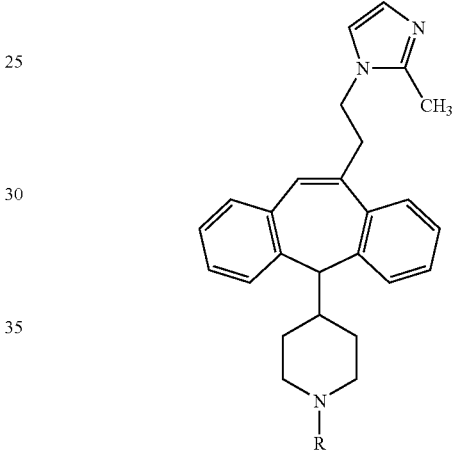

were prepared wherein R is defined in Table 15.

TABLE 15

| EX. # | PROCEDURE | R = | CMPD # | PHYS. DATA |
|---|---|---|---|---|
| 122 | Example 13 | -C(O)NH-C6H4-Cl | 306 isomer 1 | MS $MH^+$ = 537.1 m.p. = 118.1–119.0° C. |
| 123 | Example 13 | -C(O)NH-C6H4-Cl | 307 isomer 2 | MS $MH^+$ = 537.1 m.p. = 107.8–108.4° C. |
| 124 | Example 13 | -C(O)NH-C6H4-CN | 308 isomer 1 | MS $MH^+$ = 528.2 m.p. = 119.6–120.2° C. |

TABLE 15-continued

| EX. # | PROCEDURE | R = | CMPD # | PHYS. DATA |
|---|---|---|---|---|
| 125 | Example 13 |  | 309 isomer 2 | MS MH$^+$ = 528.2 m.p. = 120.5–121.3° C. |

PREPARATIVE EXAMPLE 36

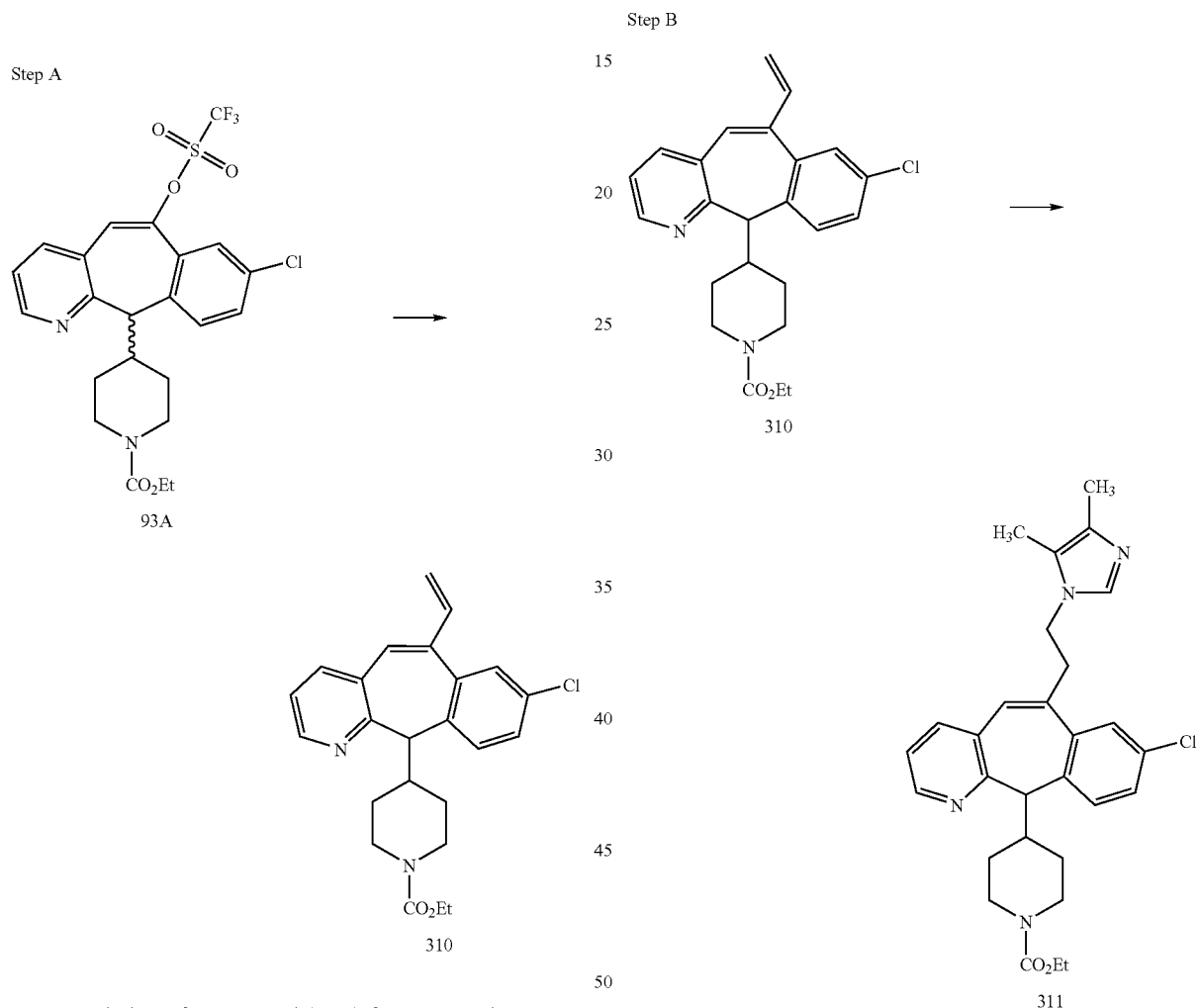

To a solution of Compound (93A) from Example 7, Step A (5.0 g, 10.02 mmol) in 1-methyl-2-pyrrolidinone (40 mL) under nitrogen at room temperature, was added LiCl (1.27 g, 30.06 mmol), Tri-2-furrylphosphine (0.093 g, 0.4 mmol) and tris(dibenzylidene acetone)dipalladium(0) (0.18 g, 0.2 mmol). The resulting solution was stirred at room temperature for 5 minutes, followed by the addition of tributyl(vinyl) tin (3.3 mL, 11.3 mmol) and stirred overnight at 80° C.-85° C. The solution was cooled to room temperature, followed by extraction with EtOAc-H$_2$O. The organic layer was dried over MgSO4, filtered, concentrated to dryness and purified by column chromatography on silica gel, eluted with 20% EtOAc/80% CH$_2$Cl$_2$ to give the product (310) (3.88 g, 95% yield, MH$^+$=409.1)

To a stirred solution of 4,5-dimethylimidazole (25.8 mg, 0.268 mmol) in anhydrous THF (0.2 mL) at −78° C. under Argon, was added 2.5M n-BuLi (0.032 mL, 0.08 mmol). The resulting solution was warmed to room temperature, followed by the addition of the alkene compound (310) from Step A above (0.1 g, 0.24 mmol) in anhydrous THF (0.2 mL). The solution was then heated in an oil bath to 120° C. for 25 hours, followed by extraction with CH$_2$Cl$_2$—H$_2$O. The combined organic layer was then washed with brine, dried over Na$_2$SO4, filtered and purified by column chromatography on silica gel, eluting with 5% MeOH/95% CH$_2$Cl$_2$ to give the product (311) (0.046 g, 100% yield, MH$^+$=505).

Step C

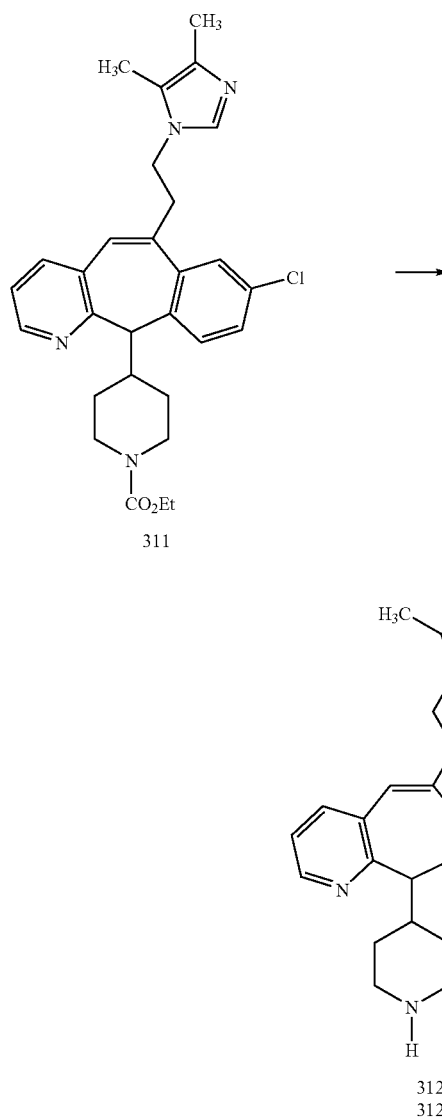

A solution of Compound (311) from Step B above (0.57 g, 1.28 mmol) in 6N HCl (20 mL) was heated to reflux for 24 hours then concentrated to dryness. To the residue was then added saturated NaHCO₃ and NaCl. The solution was extracted twice with CH$_2$Cl$_2$. The combined organic layer was dried over Na$_2$SO4 and concentrated to dryness to give the crude product (0.52 g, 93% yield). The crude material was then dissolved in 20% EtOH/80% Hexane/0.2% DEA and purified by HPLC on a preparative AD column, eluting with 20%-50% IPA/Hexane/0.2% DEA (UV=254 nm, Attn=1024, ABS=2) to give pure isomers of the product (312a) and (312b) (0.225 g, MH$^+$=433).

EXAMPLES 126-133

Starting with the appropriate (+) or (−) isomer of Compound (312) (i.e., 312a or 312b) and reacting in a similiar manner as in Example 13 using the appropriate isocyanate or sulfonyl chloride, compounds of the following formula:

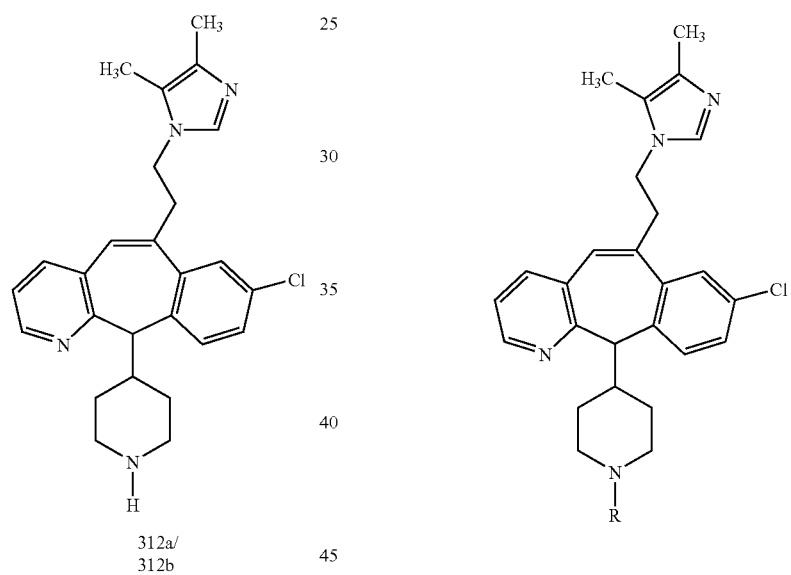

prepared wherein R is defined in Table 16.

TABLE 16

| EX. # | PROCEDURE | R = | CMPD # | PHYS. DATA Mass spec |
|---|---|---|---|---|
| 126 | Example 13 | ![acetamido-4-cyanophenyl] | 313 isomer 1 | M$^+$ = 577 |
| 127 | Example 13 | ![acetamido-4-cyanophenyl] | 314 isomer 2 | M$^+$ = 577 |

TABLE 16-continued
| EX. # | PROCEDURE | R = | CMPD # | PHYS. DATA Mass spec |
|---|---|---|---|---|
| 128 | Example 13 | acetanilide | 315 isomer 1 | M+ = 558 |
| 129 | Example 13 | acetanilide | 316 isomer 2 | M+ = 558 |
| 130 | Example 13 | 4-fluoroacetanilide | 317 isomer 1 | M+ = 570 |
| 131 | Example 13 | 4-fluoroacetanilide | 318 isomer 2 | M+ = 570 |
| 132 | Example 13 | methylsulfonyl | 319 isomer 1 | M+ = 511 |
| 133 | Example 13 | methylsulfonyl | 320 isomer 2 | M+ = 511 |
PREPARATIVE EXAMPLE 37
Step A
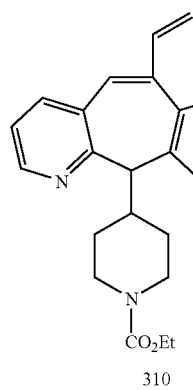
310
→
-continued
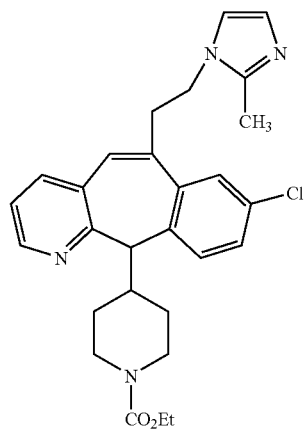
321

To a solution of Compound (310) from Preparative Example 36, Step A (0.66 g, 8.1 mmol) in THF (4.0 mL) under nitrogen at −78° C., was added dropwise 2.5M n-BuLi/Hexane (1.5 mL). The resulting solution was stirred at −78° C. for 30 minutes, then allowed to warm to room temperature, followed by the addition of 1-methyl imidazole (3.0 g, 7.3 mmol) in THF (3.0 mL). The solution was then heated to 120° C. over the weekend and then cooled down to room temperature and concentrated to dryness. The mixture was extracted with EtOAc-H₂O, dried over MgSO₄, filtered and purified by column chromatography on silica gel, eluting with 3% MeOH/97% NH₃—CH₂Cl₂ to give the product (321)(1.64 g, 46% yield, MH⁺=491.1).

Step B

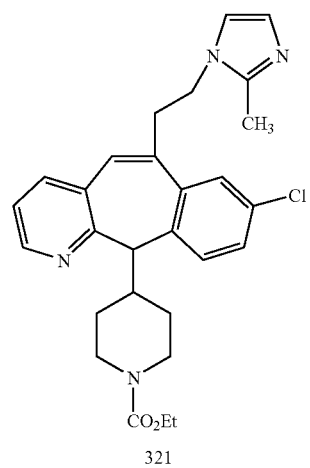
321

A solution of Compound (321) from Preparative Example 37, Step A above (0.6 g, 1.22 mmol) in 12N HCl (10 mL) was heated to reflux overnight then concentrated to dryness to give the residue as a gum. This residue was dissolved in saturated NaHCO₃, stirred for 10 minutes, saturated with NaCl and then stirred with CH₂Cl₂ for 10 minutes. The solid was filtered and the aqueous layer was extracted twice with CH₂Cl₂, and the organic layer was dried over Na₂SO₄, filtered and concentrated to dryness to give the Compound (322) as a light brown solid (566 ma, MH⁺=419.1).

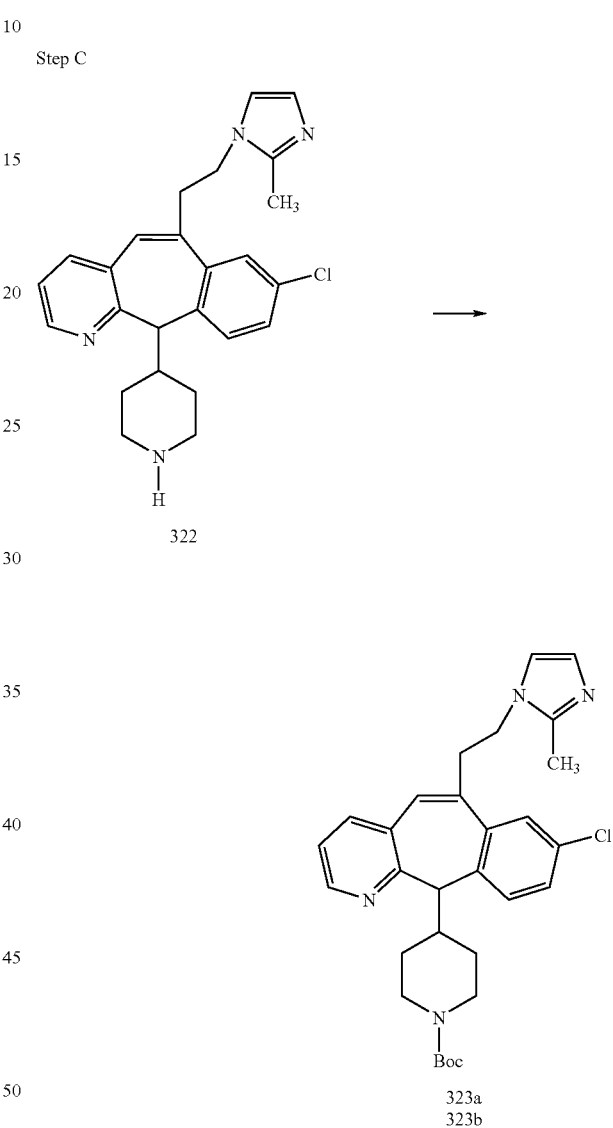

To a solution of Compound (322) from Step B above (0.566 g, 1.35 mmol) in IS MeOH (20 mL) and H₂O (1 mL) at 0° C., was added Boc anhydride (0.44 g, 2.02 mmol). The solution was basified with 1N NaOH solution to maintain pH=8.5-9.5 and concentrated to dryness, followed by extraction with CH₂Cl₂—H₂O. The combined organic layer was washed twice with H₂O then brine, dried over Na₂SO₄, filtered and concentrated to dryness to give a mixture of isomers 1 and 2 (0.63 g, 100% yield). The isomers were separated by HPLC on a prep AD column, eluting with 15%IPA/85%hexane/0.2%DEA (wave length=254 nm, Aftn=64, ABS=1) to give isomer 1 (323a) (0.28 g, MH⁺=519.2) and isomer 2 (323b) (0.28 g, MH⁺=519.2)

Step D

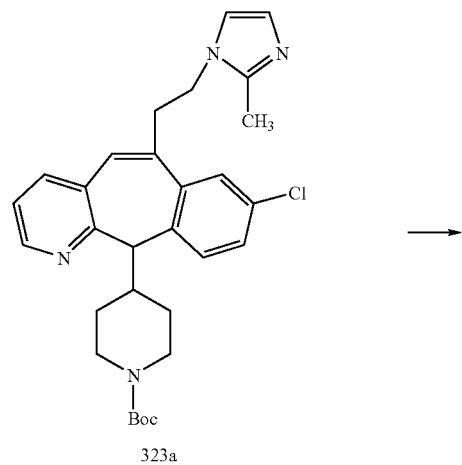

323a

→

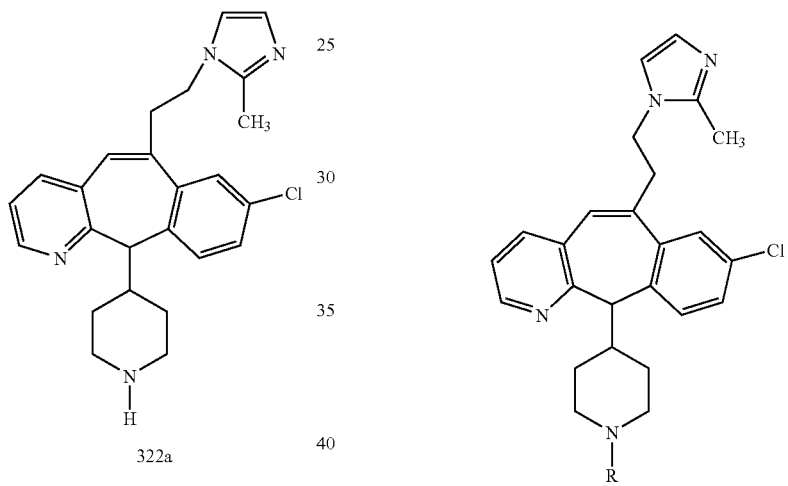

322a

A solution of Compound (323a) isomer 1 from Step C above (0.24 g, 0.46 mmol) in 4N HCl/Dioxane (20 mL) was stirred at room temperature for 1 hr. CH$_2$Cl$_2$ (7 mL) was added to the solution and the reaction continued to stir for 2 hrs before being concentrated to dryness. The solution was stirred for 5 minutes with saturated NaHCO$_3$, then saturated with NaCl and extracted three times with CH$_2$Cl$_2$. The combined organic layer was dried over Na$_2$SO$_4$, filtered and evaporated to dryness to give Compound (322a) isomer 1(0.163 g, 84% yield, MH⁺=419.2).

Compound (322b) was prepared in a similar manner as in Step D above, starting with Compound (323b) to give the other isomer (0.193 g, 84% yield, MH⁺=419.2)

EXAMPLES 134-147

Starting with compound 322a or 322b and reacting in a similar manner as in Example 13 using the appropriate chloroformate, isocyanate, or sulfonyl chloride (or in the case of carboxylic acid, using DEC mediated coupling), compounds of the formula:

were prepared wherein R is defined in Table 17.

TABLE 17

| EX. # | PROCEDURE | R = | CMPD # | PHYS. DATA |
|---|---|---|---|---|
| 134 | Example 13 | ‑C(=O)‑O‑cyclohexyl | 324 Isomer 1 | MS M⁺ = 545.2 |
| 135 | Example 13 | ‑C(=O)‑O‑cyclohexyl | 325 Isomer 2 | MS M⁺ = 545.2 |
| 136 | Example 13 | ‑C(=O)‑NH‑C$_6$H$_4$‑CN | 326 Isomer 1 | MS M⁺ = 563.2 |
| 137 | Example 13 | ‑C(=O)‑NH‑C$_6$H$_4$‑CN | 327 Isomer 2 | MS M⁺ = 563.2 |

TABLE 17-continued

| EX. # | PROCEDURE | R = | CMPD # | PHYS. DATA |
|---|---|---|---|---|
| 138 | Example 13 | acetamido-4-CF₃-phenyl | 328 Isomer 1 | MS M⁺ = 606.1 m.p. = 62.7–63.0° C. |
| 139 | Example 13 | acetamido-4-CF₃-phenyl | 329 Isomer 2 | MS M⁺ = 606.1 m.p. = 70.1–71.0° C. |
| 140 | Example 13 | acetamido-4-Cl-phenyl | 330 Isomer 1 | MS M⁺ = 572.1 m.p. = 120.1–121.4° C. |
| 141 | Example 13 | acetamido-4-Cl-phenyl | 331 Isomer 2 | MS M⁺ = 572.1 m.p. = 128.0–129.0° |
| 142 | Example 13 | acetamido-cyclohexyl | 332 Isomer 1 | MS M⁺ = 544.2 |
| 143 | Example 13 | acetamido-cyclohexyl | 333 Isomer 2 | MS M⁺ = 544.2 |
| 144 | Example 13 | (pyridyl-N-oxide)methylketone | 334 Isomer 1 | MS M⁺ = 554.1 m.p. = 111.9–112.0° C. |
| 145 | Example 13 | (pyridyl-N-oxide)methylketone | 335 Isomer 2 | MS M⁺ = 554.1 m.p. = 114.3–115° |
| 146 | Example 13 | methylsulfonyl | 336 Isomer 1 | MS M⁺ = 497.1 m.p. = 52.4–53.3° C. |
| 147 | Example 13 | methylsulfonyl | 337 Isomer 2 | MS M⁺ = 497.1 m.p. = 47.1–48.0° |

PREPARATIVE EXAMPLE 38

Step A

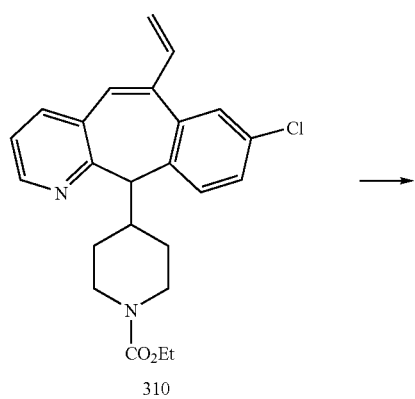
310

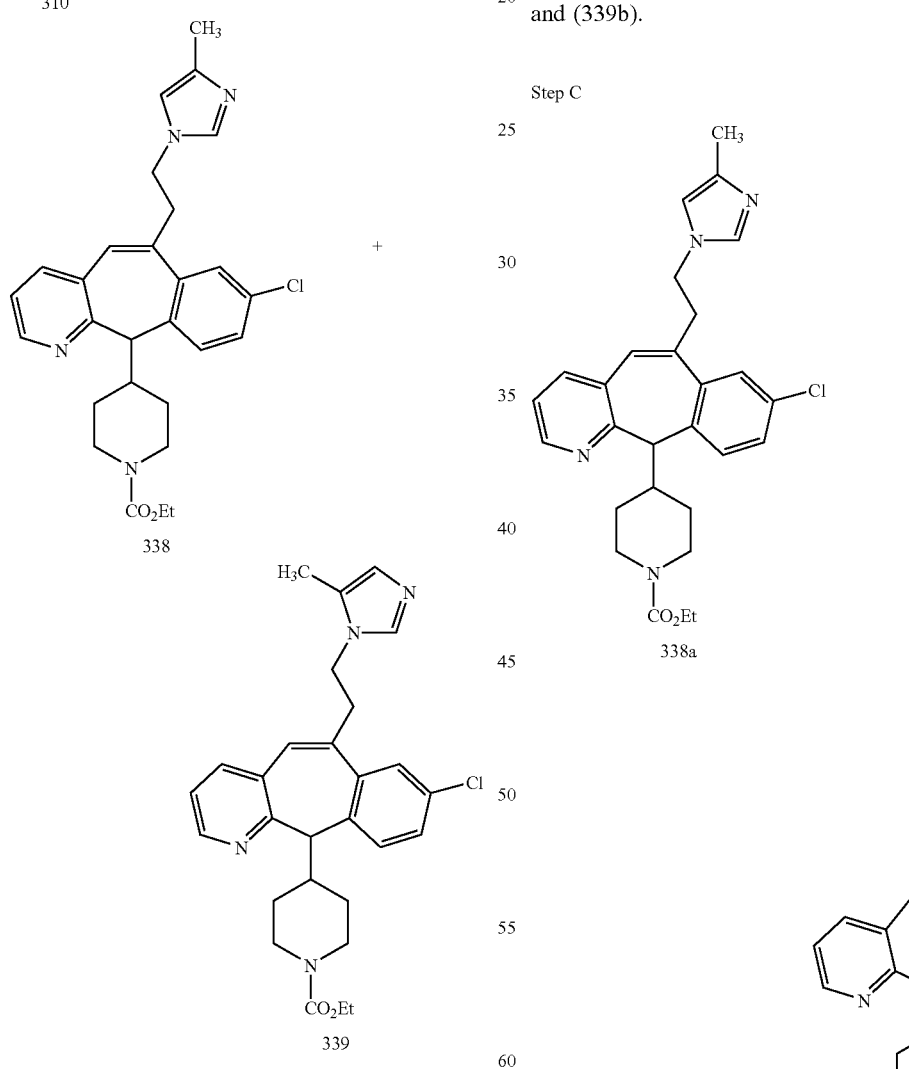

338

339

338a

Step C

Step B

In a similar manner as described in Example 11, the mixture of products from Step A, above were first seperated into a mixture of pure 4 and 5-substituted (+) enantiomers and pure 4 and 5-substituted (−) enantiomers using chiral HPLC column chromatography, then upon treatment with triphenyl methyl chloride following the procedure in Example 11, the compounds were further seperated into the pure isomers of the 4-substituted compound (338a) (MS M$^+$=491; mp=72.1-73.0° C.) and (338b) (MS M$^+$=491; mp=68.9-69.0° C.) and the 5-substituted compound (339a) and (339b).

dazole (0.66 g, 8.07 mmol) in THF. The solution was heated to 120° C. over night cooled down to room temperature and concentrated to dryness The reaction mixture was extracted with EtOAc-H$_2$O, and the organic layer was dried over MgSO$_4$, filtered and concentrated to give a mixture of 4-methyl substituted (338) and 5-methyl substituted (339) products (2.76 g, 76% yield, M$^+$=491.1).

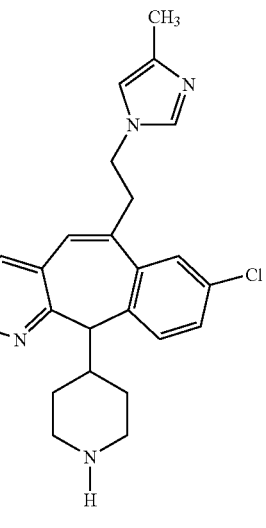
340a

To a solution of Compound (310) from Preparative Example 36 Step A (3.0 g, 7.34 mmol) in THF (8 mL) under nitrogen at −78° C., was added dropwise 2.5M n-BuLi/Hexane (0.65 mL, 8.07 mmol). The resulting solution was stirred at −78° C. for 30 minutes, then allowed to warm to room temperature, followed by the addition of 4-methylimi- A2q solution of Compound (338a) from step B above (0.035 g, 0.071 mmol) in 6N HCl (2.0 mL) was heated to reflux overnight. The solution was cooled to room temperature, basified with NH$_4$OH solution and extracted with CH$_2$Cl$_2$. The combined organic layer was dried over MgSO$_4$, filtered and concentrated to give pure isomer 1, Compound (340a) (0.0334 g, 100% yield, MH$^+$=419.1; mp=60.3-61.0° C.).

In a similar manner as above, starting with Compound (338b) (isomer 2), Compound (340b) (MH$^+$=419.1) was prepared.

EXAMPLES 148-156

Starting with the appropriate (+) or (−) isomer of Compound (340) (i.e., 340a or 340b) and reacting in a similar manner using the procedure shown in Table 18 with the appropriate chloroformate, isocyanate or sulfonyl chloide, compounds of the formula:

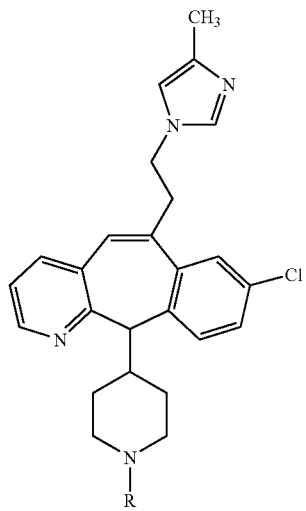

were prepared wherein R is defined in Table 18.

TABLE 18

| EX. # | PROCEDURE | R = | CMPD # | PHYS. DATA |
|---|---|---|---|---|
| 148 | Preparative Ex.4; Step A | BOC | 341 | MS MH$^+$ = 519<br>m.p. = 90.2–91.0° C. |
| 149 | Example 13 | ![cyclohexyl carbonate] | 342 isomer 1 | MS MH$^+$ = 545<br>m.p. = 58.8–59.6° C. |
| 150 | Example 13 | ![cyclohexyl carbonate] | 343 isomer 2 | MS MH$^+$ = 545<br>m.p. = 60.8–61.2° C. |
| 151 | Example 13 | ![4-cyanophenyl urea] | 344 isomer 1 | MS MH$^+$ = 545<br>m.p. = 98.7–99.5° C. |
| 152 | Example 13 | ![4-cyanophenyl urea] | 345 isomer 2 | MS MH$^+$ = 545<br>m.p. = 111.3–112.0° C. |
| 153 | Example 13 | ![cyclohexyl urea] | 346 isomer 1 | MS MH$^+$ = 544<br>m.p. = 77.1–77.8° C. |
| 154 | Example 13 | ![cyclohexyl urea] | 347 isomer 2 | MS MH$^+$ = 544<br>m.p. = 78.9–79.0° C. |
| 155 | Example 13 | ![methylsulfonyl] | 348 isomer 1 | MS MH$^+$ = 497<br>m.p. = 87.4–88.0° C. |

TABLE 18-continued

| EX. # | PROCEDURE | R = | CMPD # | PHYS. DATA |
|---|---|---|---|---|
| 156 | Example 13 | 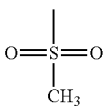 | 349 isomer 2 | MS MH+ = 497 m.p. = 88.8–89.0° C. |

PREPARATIVE EXAMPLE 39

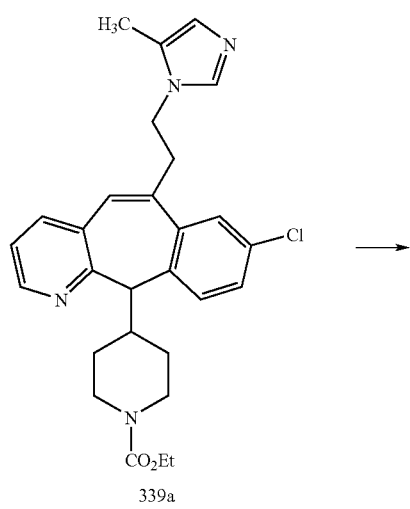

339a

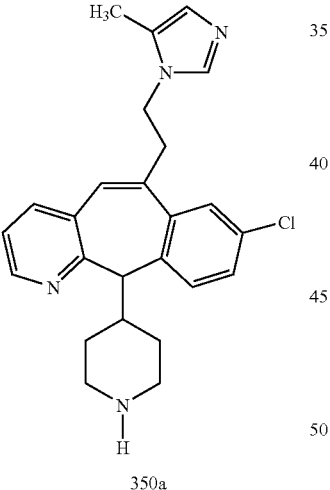

350a

Compound (339a) was reacted in a similar manner as in Preparative Example 38, Step C to give Compound (350a) (0.13 g, 76% yield, MH+=419.3).

Compound (350b) was prepared in the same manner as above.

EXAMPLES 157-160

Starting with the appropriate (+) or (−) isomer of Compound (350) (i.e., 350a or 350b) and reacting in a similar manner using the procedure indicated in the table below and the appropriate Boc or isocyanate reagent, compounds of the formula:

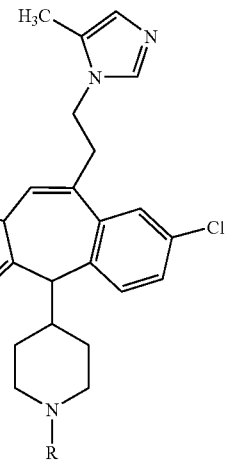

were prepared wherein R is defined in Table 19.

TABLE 19

| EX. # | PROCEDURE | R = | CMPD # | PHYS. DATA |
|---|---|---|---|---|
| 157 | Preparative Ex. 4; Step A | BOC | 351 isomer 1 | MS MH+ = 519 m.p. = 87.8–88.2° C. |
| 158 | Preparative Ex. 4; Step A | BOC | 352 isomer 2 | MS MH+ = 519 m.p. = |

TABLE 19-continued

| EX. # | PROCEDURE | R = | CMPD # | PHYS. DATA |
|---|---|---|---|---|
| | | | | 89.0–89.9° C. |
| 159 | Example 13 | (acetamido-phenyl-CN structure) | 353 isomer 1 | MS MH⁺ = 563 |
| 160 | Example 13 | (acetamido-phenyl-CN structure) | 354 isomer 2 | MS MH⁺ = 563 m.p. = 130.1–131.0° C. |

PREPARATIVE EXAMPLE 40

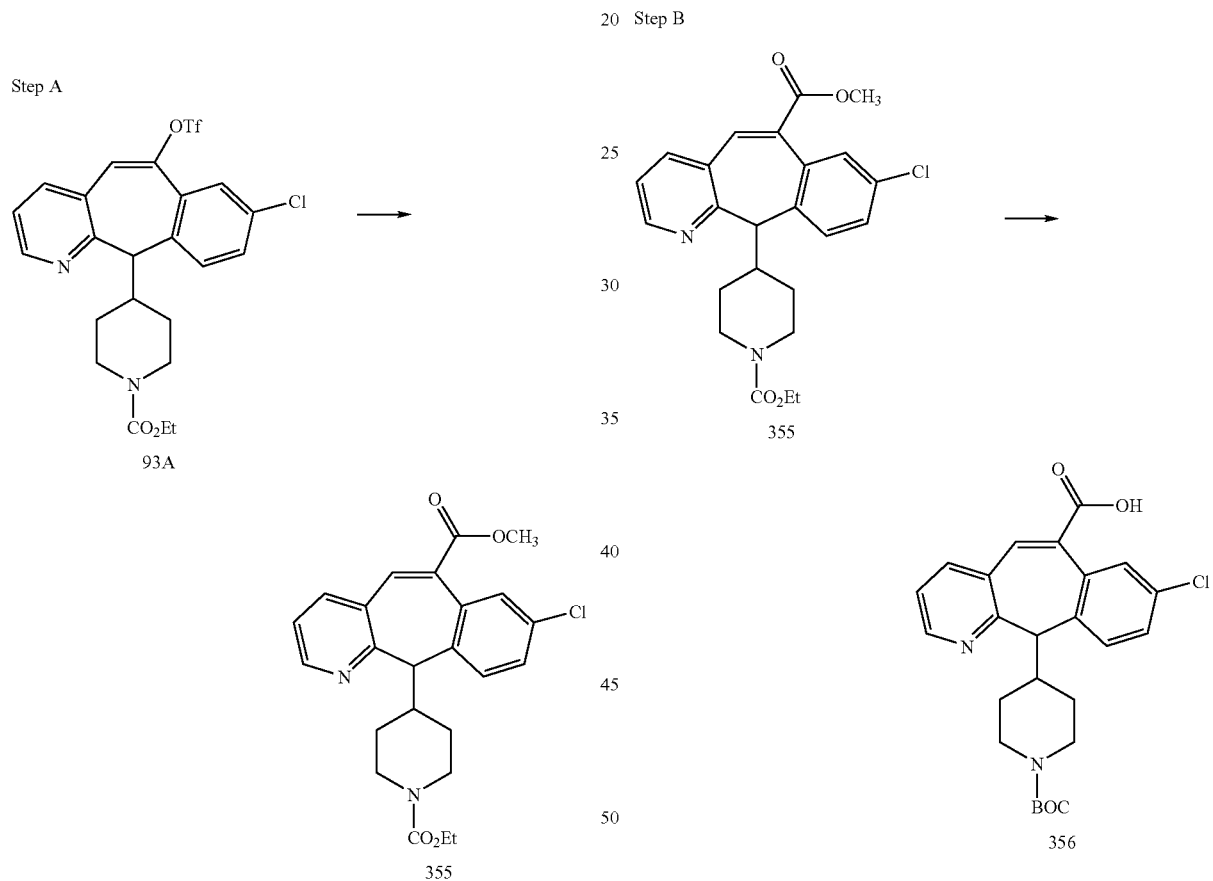

To a solution of Compound (93A) from Preparative Example 7, Step A (2.92 g, 5.5 mmol) in anhydrous toluene (70 mL) and MeOH (10 mL) was added triphenyl phosphine (0.72 g, 2.75 mmol), DBU (1.11 mL, 7.42 mmol) and PdCl$_2$ (0.097 g, 0.55 mmol). The resulting solution was purged with CO (100 psi), then heated to 80° C. for five hours. The solution was cooled to room temperature, purged with nitrogen and evaporated to dryness to give a brown oil. The product was purified by silica gel column chromatography eluting with 1% MeOH/99% CH$_2$Cl$_2$ to 4% MeOH/96% CH$_2$Cl$_2$ to give Compound (355) (2.22 g, 92.5% yield, MH⁺=441.1).

A solution of Compound (355) from Preparative Example 40, Step A (2.2 g, 4.99 mmol) in 6N HCl (50 mL) was heated to 100° C.-110° C. overnight. The solution was cooled to room temperature and evaporated to dryness to give the crude product. To a solution of the crude material in MeOH (50 mL) and H$_2$O (1 mL) at 0° C., was added Boc anhydride (1.63 g, 7.48 mmol). The resulting solution was basified with 1N NaOH to pH=8.5-9.5 and stirred for two hours at 0° C., then evaporated to dryness and extracted with EtOAc-5% Citric acid solution. The organic layer was washed with H$_2$O, then brine, dried over Na$_2$SO$_4$, filtered and concentrated to dryness to give Compound (356) as a yellow solid (2.29 g, 100% yield, MH⁺=455.1).

Step C

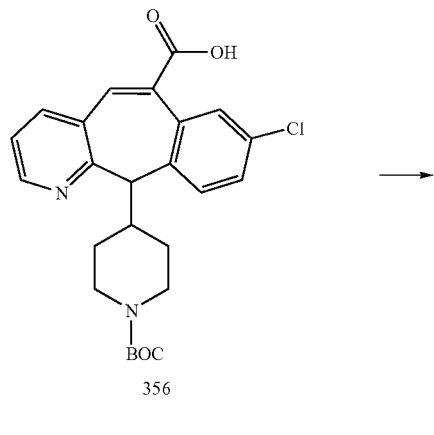

356

Step D

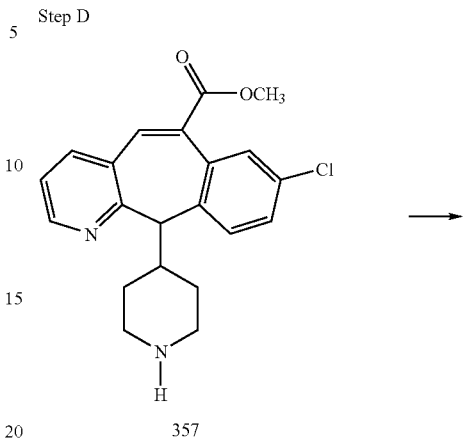

357

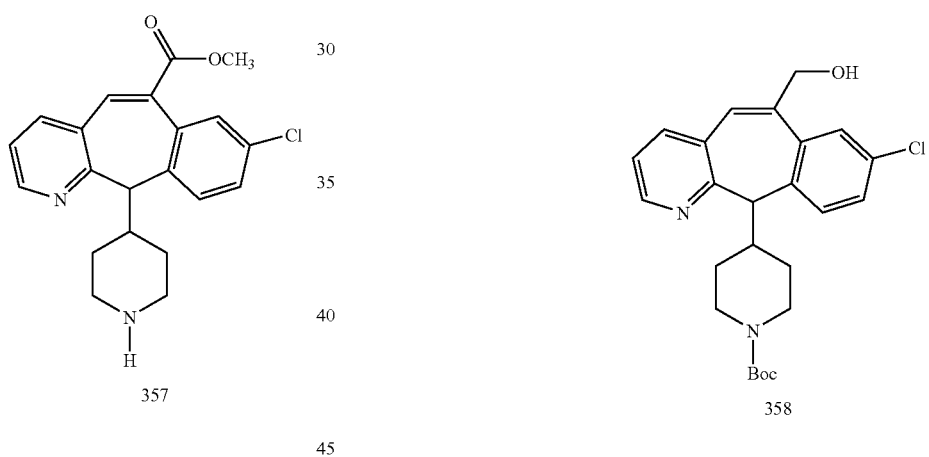

357                                                             358

To a solution of Compound (356) from Preparative Example 40, Step B above (2.26 g, 4.97 mmol) in anhydrous benzene (18.0 mL) and MeOH (2 mL), was added, over five minutes, (trimethylsilyl)diazomethane (3 mL, 5.99 mmol) in 2M 1N Hexane. The resulting solution was stirred at room temperature for one hour then evaporated to dryness to give 2.33 g of crude material (MH$^+$=369).

A solution of the crude material (obtained above) in 4N HCl in Dioxane (25 mL) was stirred at room temperature for one hour. The reaction was then evaporated to dryness and purified by flash silica gel column chromatography, eluting with 2% MeOH/98% CH$_2$Cl$_2$ to 6% MeOH/94% CH$_2$Cl$_2$ and then with 50% (10% NH$_4$OH/CH$_3$OH/50% CH$_2$Cl$_2$). The collected fractions were evaporated to dryness and diluted with CH$_2$Cl$_2$. The organic solution was then washed with saturated NaHCO$_3$ and brine, dried with Na$_2$SO$_4$, filtered and evaporated to dryness to afford Compound (357) (1.26 g, 68.3% yield, MH$^+$=369).

To a solution of Compound (357) from Preparative Example 40, Step C (0.6 g, 1.62 mmol) in anhydrous THF (6 mL) at 0° C. was added DIBAL (1 M solution in toluene) (9.78 mL, 9.78 mmol). The resulting solution was warmed to room temperature and stirred overnight. The solution was then quenched with MeOH and evaporated to dryness to give a crude product.

To the crude material (obtained above) in MeOH at 0° C. was added Boc anhydride (1.06 g, 4.9 mmol). The resulting solution was basified with 1N NaOH to pH=8.5-9.5, stirred for 1 hour and evaporated to dryness. The crude material was diluted with CH$_2$Cl$_2$ to give a slurry. The precipitate was then filtered through celite and the CH$_2$Cl$_2$ was washed with H$_2$O, brine, filtered over Na$_2$SO4 and concentrated to dryness. The crude alcohol product (358) (1.27 g, 100% yield) was used in the next step without further purification.

Step E

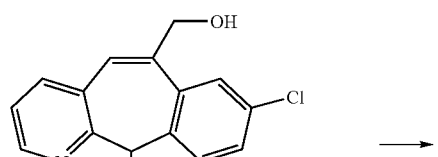

358

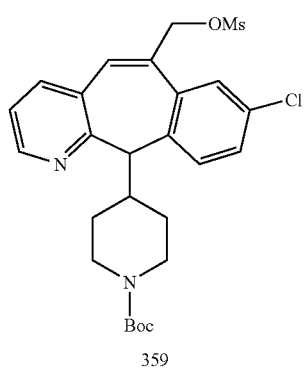

359

To a cooled solution of the alcohol (358) from Step D above (1.2 g, 2.73 mmol) in anhydrous CH$_2$Cl$_2$ (12 mL) at 0° C. was added triethyl amine (1.14 mL, 8.18 mmol) and methanesulfonyl chloride (0.3 mL, 4.1 mmol). The resulting solution was warmed to room temperature stirred overnight, then quenched with H$_2$O and stirred for 10 minutes. The reaction was washed with water, then brine, dried over Na$_2$SO$_4$, filtered and evaporated to dryness to give Compound (359) (1.22 g, 86% yield).

Step F

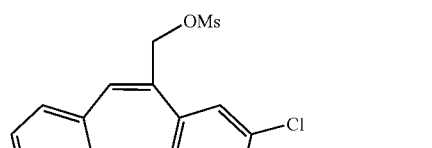

359

-continued

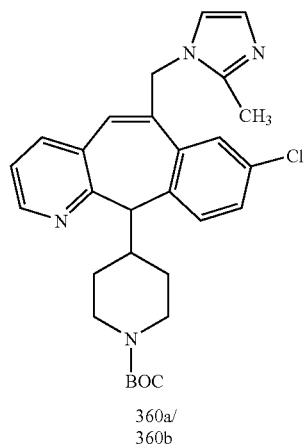

360a/
360b

To a solution of anhydrous DMF (5 mL) at 0° C. was added, NaH (0.19 g, 8.18 mmol) and 2-methylimidazole (0.67 g, 8.18 mmol). The resulting solution was warmed to room temperature and stirred for 20 minutes. To the reaction was added a solution of Compound (359) from Step E above (1.22 g, 2.3 mmol) in anhydrous DMF (5 mL). The resulting of solution was stirred at room temperature overnight, then diluted with EtOAc and washed with water then brine. The organic layer was dried over Na$_2$SO$_4$, concentrated to dryness and purified by silica gel column chromatography eluting with 1% MeOH/99% CH$_2$Cl$_2$ to 5% MeOH/CH$_2$Cl$_2$ to give the product as a mixture of isomers (1.18 g, 100% yield, MH$^+$=505.2). Separation of the product mixture by HPLC using a prep AD column, eluting with 25% IPA/75% hexane/0.2% DEA (isocratic 60 ml/min.) afforded pure isomer 1 (360a) (0.251 g, MH$^+$=505.1) and isomer 2 (360b) (0.251 g, MH$^+$=505.1) as light pink solids.

Step G

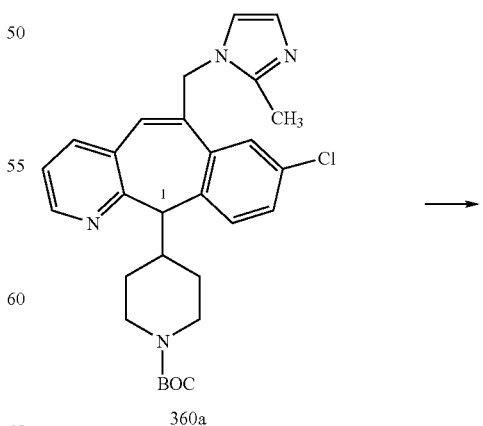

360a

-continued

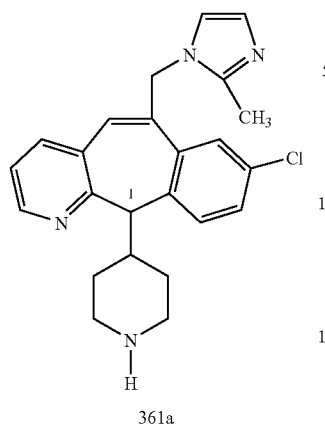

361a

A solution of Compound (360a) (isomer 1) from Step F above (0.2 g, 0.4 mmol) in 4N HCl in Dioxane (10 mL) was stirred at room temperature for 2 hours and then evaporated to dryness to afford Compound (361a) (0.292 g, 100% yield).

Compound (361b) (isomer 2) was prepared in a similar manner as above beginning with Compound (360b) from Preparative Example 40, Step F.

EXAMPLES 161-166

Starting with the appropriate (+) or (−) isomer of Compound (361) (i.e., 361a or 361b) and reacting in a similar manner as in Example 13 using the appropriate isocyanate shown in Table 20, compounds of the formula:

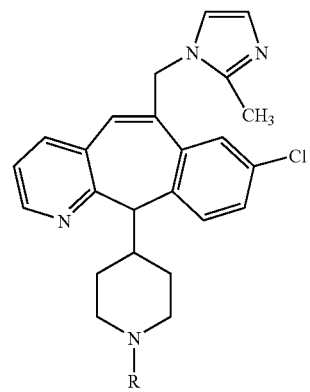

were prepared wherein R is defined in Table 20.

TABLE 20

| EX. # | PROCEDURE | R = | CMPD # | PHYS. DATA |
|---|---|---|---|---|
| 161 | Example 13 | ![structure]  acetamide-N-(4-cyanophenyl) | 362a isomer 1 | MS MH+ = 548 |
| 162 | Example 13 | acetamide-N-(4-cyanophenyl) | 362b isomer 2 | MS MH+ = 548 |
| 163 | Example 13 | acetamide-N-(4-fluorophenyl) | 363a isomer 1 | MS MH+ = 541 |
| 164 | Example 13 | acetamide-N-(4-fluorophenyl) | 363b isomer 2 | MS MH+ = 541 |
| 165 | Example 13 | acetamide-N-(4-chloropyridyl) | 364a isomer 1 | MS MH+ = 558 |
| 166 | Example 13 | acetamide-N-(4-chloropyridyl) | 364b isomer 2 | MS MH+ = 558 |

TABLE 20-continued

| EX. # | PROCEDURE | R = | CMPD # | PHYS. DATA |
|---|---|---|---|---|
| 166.1 | Example 13 | (structure: acetamido-phenol) | 364.1 | Mp 201.5–208.3° C. |

PREPARATIVE EXAMPLE 41

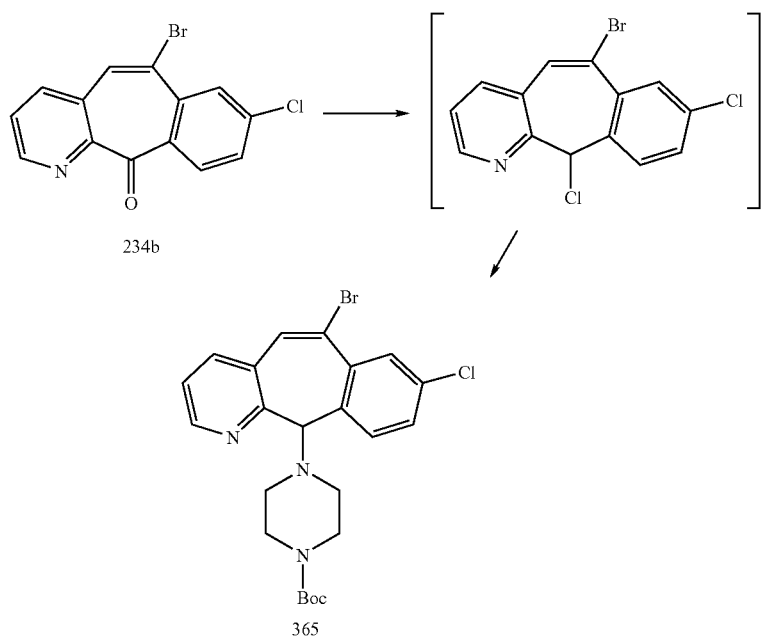

In essentially the same manner as in Preparative Example 23, Steps A-D, using the 6-Bromo substituted product from Step B, Compound (234b), the product Compound (365) was prepared (76.6 g, 100% yield).

PREPARATIVE EXAMPLE 42

Step A

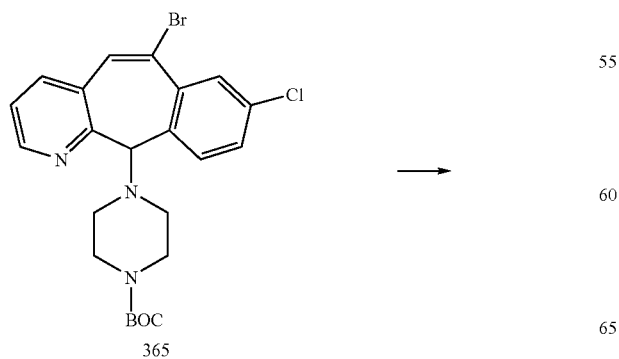

-continued

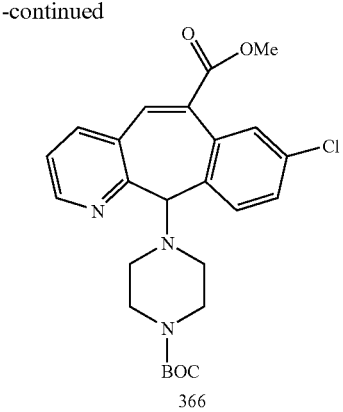

To a solution of Compound (365) from Preparative Example 41 (4.0 g, 8.16 mmol) in toluene (75 mL) and MeOH (20 mL), was added triphenyl phosphine (1.099 g, 4.08 mmol), DBU (1.7 g, 11.02 mmol) and palladium chloride (0.145 g, 0.82 mmol). The resulting solution was evacuated with CO at 100 psi and heated at 78° C.-82° C. for 5 hours, followed by the extraction with EtOAc-H$_2$O. The combined organic layer was then washed with brine, dried over Na₂SO4, concentrated to dryness and purified by column chromatography, eluting with 30% EtOAc/70% Hexane to give a Compound (366) (3.12 g, 100% yield, MH⁺=470.1).

Step B


366

A solution of Compound (366) from Step A above (3.1 g, 6.6 mmol) in 4M HCl/Dioxane (120 mL) was stirred for 3 hours and then concentrated to dryness to give the crude salt of Compound (367) (3.89 g, 100% yield, MH⁺=370.2)

Step C

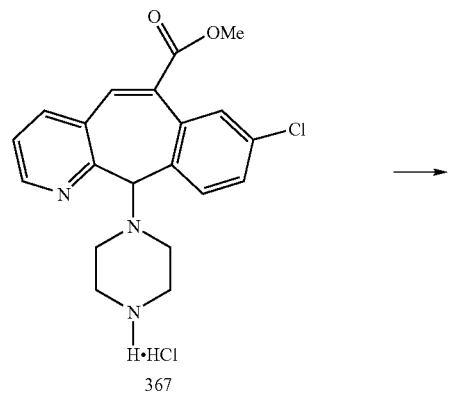

367

-continued

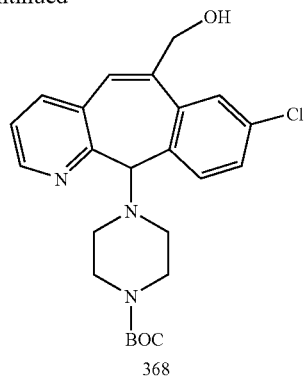

368

To a solution of Compound (367) from Step B above (3.43 g, 8.45 mmol) in THF (60 mL) at 0° C., was added DIBAL (7.21 g, 50.7 mmol). The resulting solution was warmed to room temperature, stirred overnight and then concentrated to dryness, followed by the addition of Boc anhydride (3.69 g, 16.9 mmol). The reaction was then extracted with CH₂Cl₂—H₂O, filtered over Na₂SO₄ and concentrated to dryness to afford Compound (368) (3.75 g, 100% yield, MH⁺=442.4).

Step C.1 Alternate Preparation of Compound (368)

A solution of compound 366 from step A above (23.46 g, 50.98 mmol) in CH₂Cl₂— MeOH—H₂O (120 mL, 600 mL, 60 mL respectively) combined with LiOH (12.0 g, 350.88 mmol) was refluxed at 40° C. overnight. Solvent was removed from the reaction mixture and the residue diluted with CH₂Cl₂ was acidified to pH 6 with 1N HCl. The organic layer was separated and washed with water, dried over Na₂SO₄ and concentrated. The product was dissolved in THF (285 mL) at 0° C. Triethyl amine (6 mL, 42.97 mmol) and ethyl chloroformate (4.1 mL, 42.97 mmol) were added and stirred at 0° C. for 1 h. The reaction mixture was filtered and the filtrate was cooled to −70° C. To this filtrate was added NaBH₄ (3.97 g, 104.94 mmol) and stirred for 1 heat −70° C. after which time 40 mL of MeOH was added dropwise. The solvents were removed and the residue taken up in methylene chloride, washed with sat. (aq) NaHCO₃, then brine, dried over Na₂SO₄ and concentrated to give Compound (368) as a solid.

Step D

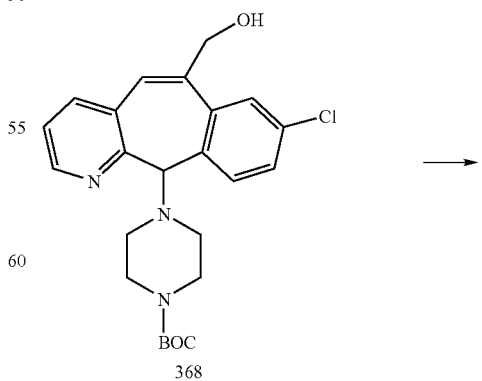

368

-continued

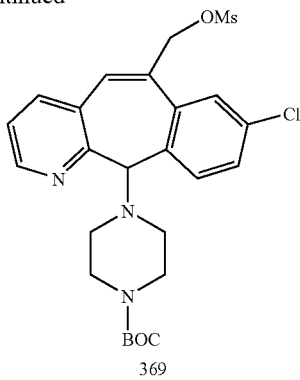

369

To a solution of Compound (368) from Step C above (3.74 g, 8.46 mmol) in CH$_2$Cl$_2$ (100 mL) was added triethyl amine (3.5 mL, 25.38 mmol) and methanesulfonyl chloride (1.45 g, 2.7 mmol). The resulting solution was stirred under nitrogen at room temperature for overnight and then washed with saturated NaHCO$_3$, then brine, and dried over Na$_2$SO$_4$ to give the mesylate compound (369) (3.86 g, 88% yield).

Step E

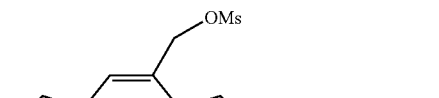

369

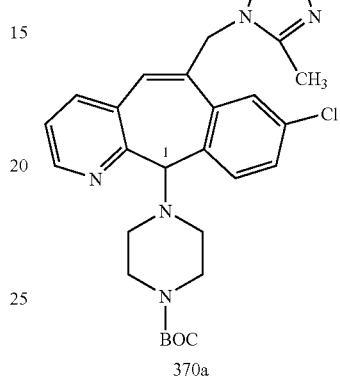

370a (isomer 1)
370b (isomer 2)

To a solution of 2-methylimidazole (2.43 g, 29.68 mmol) in DMF (30 mL) under N$_2$ was added NaH (0.53 g, 22.3 mmol) and stirred for 10 min, followed by the addition of Compound (369) from Step D above (3.86 g, 7.42 mmol). The solution was stirred over night. The solution was then concentrated to dryness and extracted with EtOAc-NaHCO$_3$, dried over Na$_2$SO$_4$, and concentrated. The crude product was purified by column chromatography, eluting with 2% MeOH—NH$_3$/98% CH$_2$Cl$_2$ to afford a mixture of isomers. Further separation was accomplished by Preparative HPLC Chiral AD Column chromatography, eluting with 25% IPA/75% hexane/0.2% DEA to give pure Compound (370a) (isomer 1) (0.160 g) and Compound (370b) (isomer 2) (0.140 g) (MH$^+$=506.1)

Step F

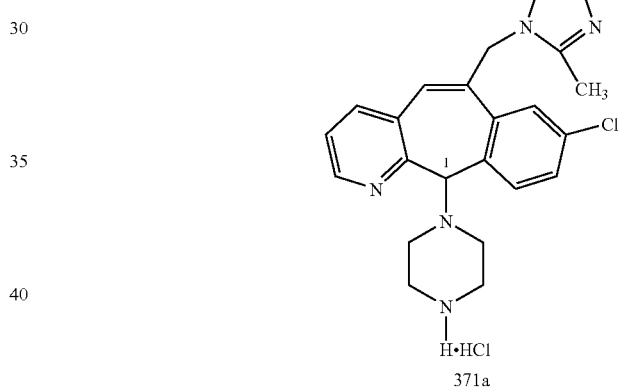

A solution of Compound (370a) (isomer 1) from Step E above (0.1059, 0.21 mmol) in 4M HCl/Dioxane (10 mL) was stirred at room temperature for 3 hours and concentrated to dryness to afford Compound (371a) (0.147 g, 100% yield)

Compound (370b) (isomer 2) from Step E was treated in the same manner as isomer 1 above, to afford Compound (371 b) (isomer 2).

EXAMPLE 167

To a solution of compound 371a (1.3 g, 2.94 mmol) in CH$_2$Cl$_2$ (60 mL) was added triethyl amine (1.3 mL, 9.4 mmol) and p-cyano phenyl isocyanate (0.466 g, 3.24 mmol). The resulting solution was stirred at room temperature overnight, followed by the extraction with CH$_2$Cl$_2$ and saturated NaHCO$_3$. The organic layer was dried over Na$_2$SO$_4$, evaporated and the residue purified by column chromatography, eluting with 1% -2% MeOH—NH$_3$/98% CH$_2$Cl$_2$ to afford compound (372) (0.870 g, 48% yield) see Table 21 below.

EXAMPLE 168

Compound 371b (isomer 2) was reacted in a similar manner as in Example 13 with p-cyano phenyl isocyanate to afford compound (373) see Table 21 below.

EXAMPLE 169

Compound 371a (isomer 1) was reacted in a similar manner as in Example 13 with p-chloro phenyl isocyanate to afford compound (374) see Table 21 below.

EXAMPLE 170

Compound 371b (isomer 2) was reacted in a similar manner as in Example 13 with p-chloro phenyl isocyanate to afford compound (375) see Table 21 below.

EXAMPLES 167-170.1

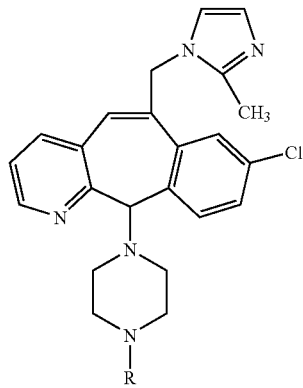

(R is defined in Table 21).

TABLE 21

| EX. # | PROCEDURE | R = | CMPD # | PHYS. DATA |
|---|---|---|---|---|
| 167 | Example 13 | acetamido-phenyl-CN | 372 isomer 1 S-isomer | MS MH+ = 550 |
| 168 | Example 13 | acetamido-phenyl-CN | 373 isomer 2 R-isomer | MS MH+ = 550 |
| 169 | Example 13 | acetamido-phenyl-Cl | 374 isomer 1 S-isomer | MS MH+ = 559 |
| 170 | Example 13 | acetamido-pyridyl-Cl | 375 isomer 2 R-isomer | MS MH+ = 559 |
| 170.1 | Example 13 | acetamido-phenyl | 375.1 isomer 1 | MS MH+ = 525 |

PREPARATIVE EXAMPLE 43

Step A

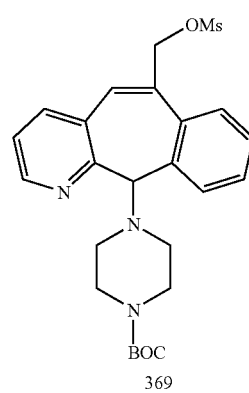
369

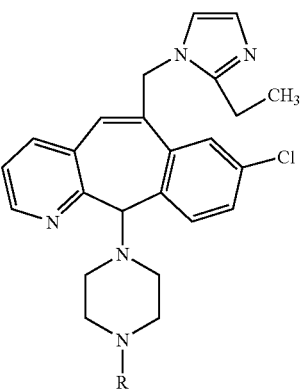
376a/
376b

Step B

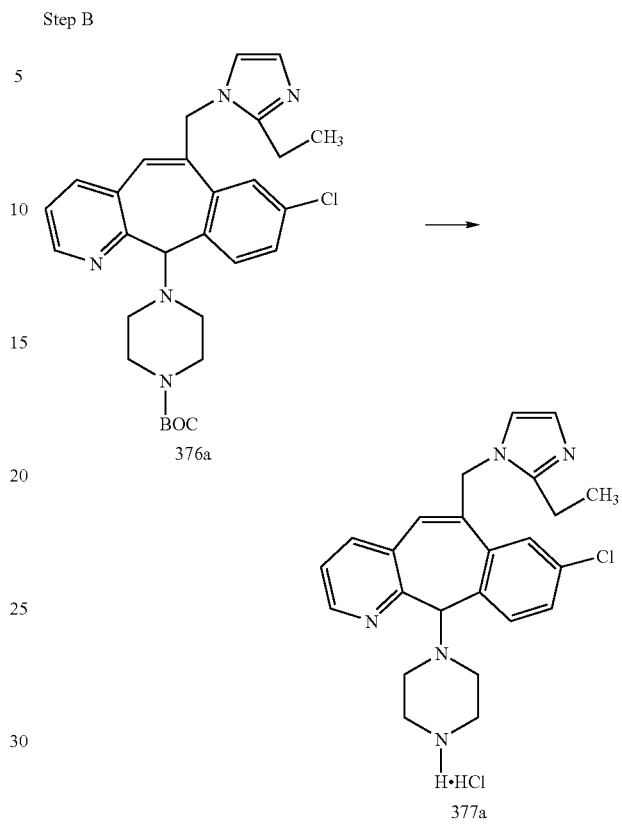

To a solution of 1-ethylimidazole (0.33 g, 3.46 mmol) in DMF (5 mL) under nitrogen was added NaH (0.083 g, 3.46 mmol) and stirred for 10 minutes, followed by the addition of Compound (369) from Preparative Example 42, Step D (0.6 g, 1.15 mmol) and stirred for over night. The solution was then evaporated to dryness, diluted with ethyl acetate, washed with sodium bicarbonate, dried over sodium sulfate and concentrated to dryness. The reaction mixture was purified by column chromatography on silica gel, eluted with 3% MeOH/97% CH$_2$Cl$_2$ to give a mixture of isomers. Further separation was accomplished using prep. HPLC with a chiral AD column to afford pure Compound (376a) (isomer 1) and Compound (376b) (isomer 2) (MH+=520.1).

A solution of Compound (376a) from Step A (0.107 g, 0.2 mmol) in 4M HCl in Dioxane (10 mL) was stirred for two hours at room temperature then concentrated to dryness to afford Compound (377a) (isomer 1) (0.13 g, 100% yield, MH$^+$=420.1).

Compound (376b) was reacted in a similar manner as above to afford Compound (377b) (isomer 2) (MH$^+$=420.1).

EXAMPLES 171-174

Starting with the appropriate (+) or (−) isomer of Compound (377) (i.e., 377a and 377b) and reacting in a similar manner as in Example 13 using the appropriate isocyanate as shown in Table 22 below, compounds of the formula:

were made wherein R is defined in Table 22.

TABLE 22

| EX. # | PROCEDURE | R = | CMPD # | PHYS. DATA |
|---|---|---|---|---|
| 171 | Example 13 | [acetamido-phenyl-CN] | 378 isomer 1 | MS MH+ = 504 |
| 172 | Example 13 | [acetamido-phenyl-CN] | 379 isomer 2 | MS MH+ = 504 |
| 173 | Example 13 | [acetamido-phenyl-Cl] | 380 isomer 1 | MS MH+ = 573 |
| 174 | Example 13 | [acetamido-phenyl-Cl] | 381 isomer 2 | MS MH+ = 573 |

PREPARATIVE EXAMPLE 44

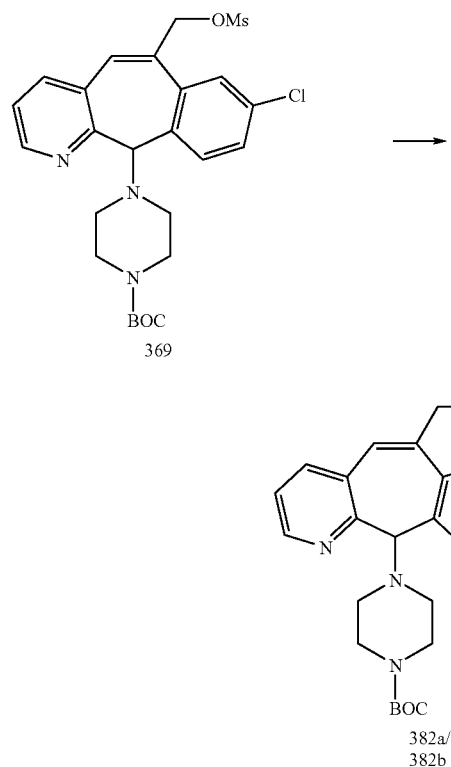

To a solution of Compound (369) from Preparative Example 42, Step D (0.5 g, 0.96 mmol) in CH$_3$CN (80 mL), was added piperazine (0.25 g, 2.88 mmol) and 2,6-bis(dimethyl)-1-methylpiperidine (0.597 g, 3.84 mmol). The resulting solution was stirred at room temperature for 4 hrs, concentrated to dryness and extracted with CH$_2$Cl$_2$—NaHCO$_3$. The combined organic layer was dried over Na$_2$SO$_4$ and purified by column chromatography on silica gel, eluting with 3% MeOH/97% CH$_2$Cl$_2$ to give the product of 2 isomers (0.28 g, 57% yield). These two isomers were seperated by HPLC on chiral AD column to give pure Compound (382a) (isomer 1) (0.136 g, MH$^+$=510.3) and Compound (382b) (isomer 2) (0.14 g, MH$^+$=510.3)

PREPARATIVE EXAMPLE 45

Step A

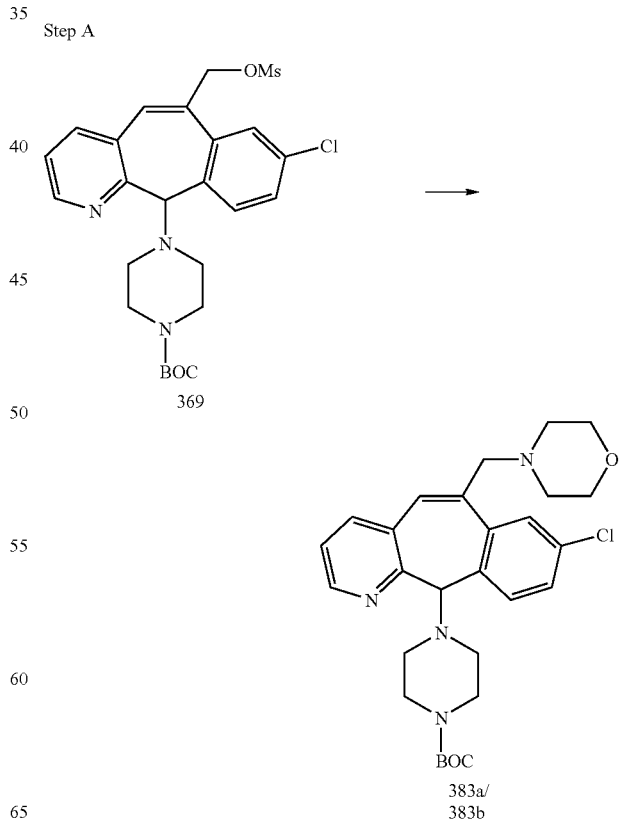

To a solution of Compound (369) from Preparative Example 42, Step D (1.2 g, 2.31 mmol) in CH₃CN (100 mL), was added morpholine (0.8 g, 9.23 mmol) and 2,6-bis (dimethyl)-1-methylpiperidine (1.9 g, 12.24 mmol). The resulting solution was stirred at room temperature overnight and concentrated to dryness, followed by extraction with CH₂Cl₂-NaHCO₃. The combined organic layer was dried over Na₂SO₄ and purified by column chromatography on silica gel, eluting with 1% NH₃-MeOH/99% CH₂Cl₂ to give the product of two isomers (1.1 g, 82% yield). These two isomers were separated by HPLC on chiral AD column to give pure Compound (383a) (isomer 1) (0.24 g, MH⁺=425.1) and Compound (383b) (isomer 2) (0.112 g, MH⁺=425.1).

Step B

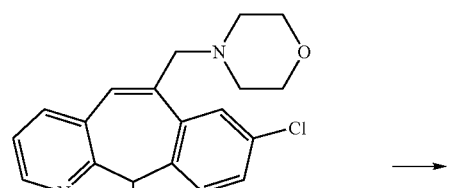

383a

A solution of Compound (383a) from Step A (0.19 g, 0.37 mmol) in 4M HCl/Dioxane (25 mL) was stirred at room temperature for 2.5 hrs and concentrated to dryness to give Compound (384a) (0.194 g, MH⁺=411.1).

Compound (384b) was prepared in a similar manner as above starting with Compound (383b) from Step A.

EXAMPLE 175

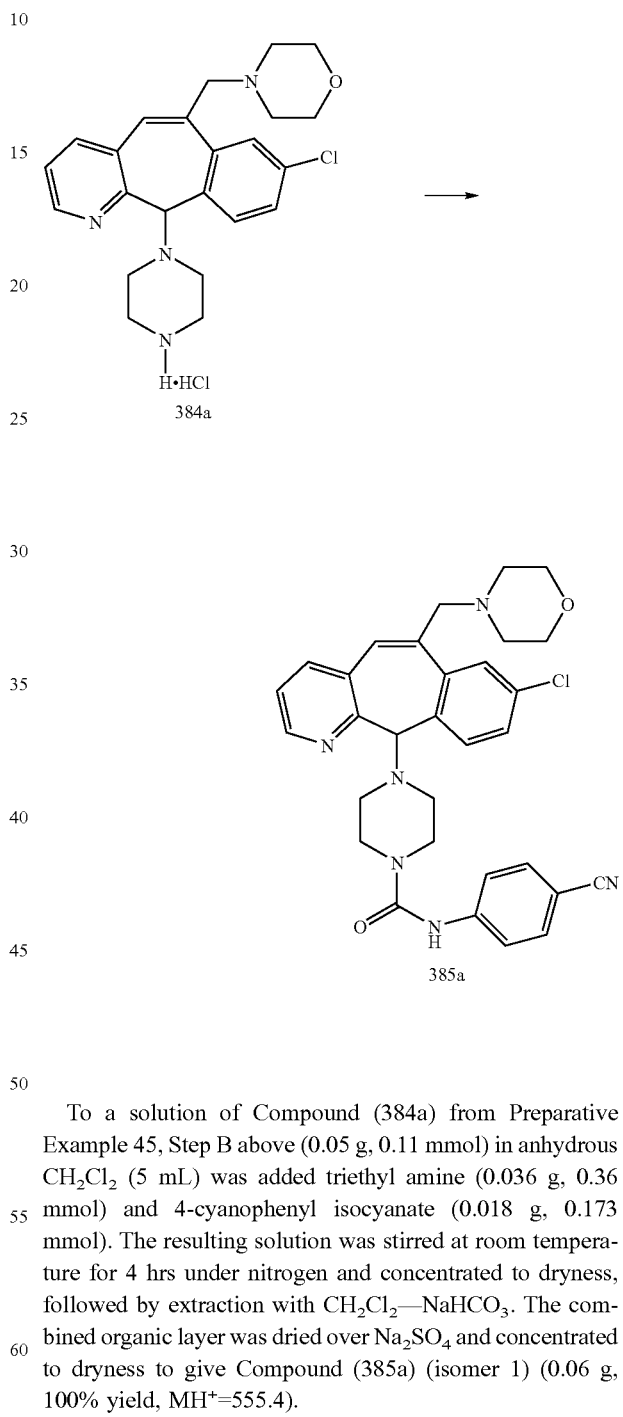

To a solution of Compound (384a) from Preparative Example 45, Step B above (0.05 g, 0.11 mmol) in anhydrous CH₂Cl₂ (5 mL) was added triethyl amine (0.036 g, 0.36 mmol) and 4-cyanophenyl isocyanate (0.018 g, 0.173 mmol). The resulting solution was stirred at room temperature for 4 hrs under nitrogen and concentrated to dryness, followed by extraction with CH₂Cl₂—NaHCO₃. The combined organic layer was dried over Na₂SO₄ and concentrated to dryness to give Compound (385a) (isomer 1) (0.06 g, 100% yield, MH⁺=555.4).

Starting with Compound (384b) from Preparative Example 45, Step B and reacting it in the same manner as above, Compound (385b) (isomer 2) was prepared (MH⁺=555.4).

PREPARATIVE EXAMPLE 46

Step A

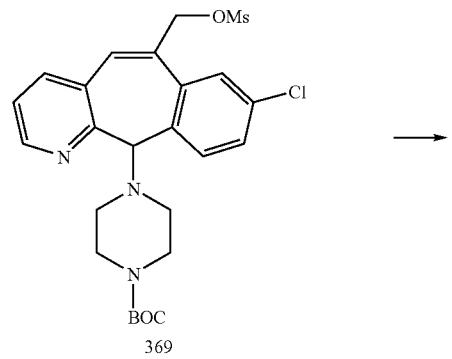
369

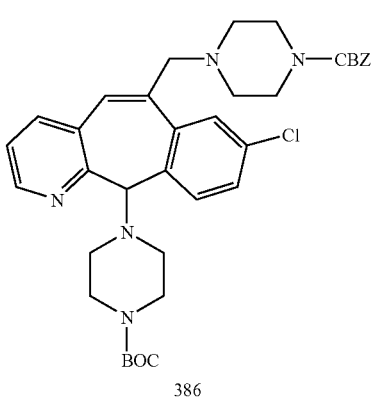
386

To a solution of Compound (369) from Preparative Example 42 Step D (3.0 g, 5.77 mmol) in CH₃CN (150 mL) was added 2,6-bis (dimethyl)-1 methyl piperidine (7.16 g, 16.16 mmol) and benzyl-1-piperazinecarboxylate (7.61 g, 34.62 mmol). The resulting solution was stirred overnight, concentrated to dryness, followed by extraction with CH$_2$Cl$_2$—NaHCO$_3$. The combined organic layer was dried over Na$_2$SO$_4$, concentrated to dryness and purified by column chromatography on silica gel, eluting with 1% NH$_3$-MeOH/99% CH$_2$Cl$_2$ and then 30% EtOAc/70% hexane to give the title product Compound (386) (1.24 g, 67% yield, MH$^+$=644.2)

Step B

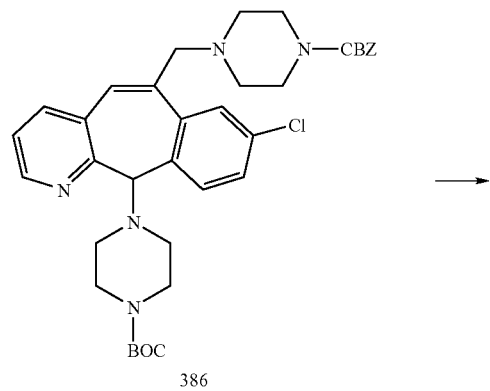
386

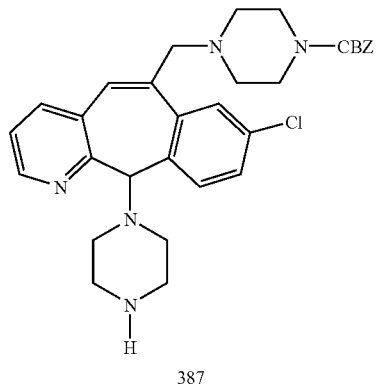
387

A solution of Compound (386) from Step A above (0.5 g, 0.77 mmol) in 4M HCl/Dioxane (50 mL) was stirred at room temperature for 2 hrs. The solution was then poured onto ice and basified with 1N NaOH solution, followed by extraction with CH$_2$Cl$_2$. The combined organic layer was dried over Na$_2$SO$_4$ and concentrated to dryness to give Compound (387) (0.43 g, 100% yield, MH$^+$=544.5).

Step C

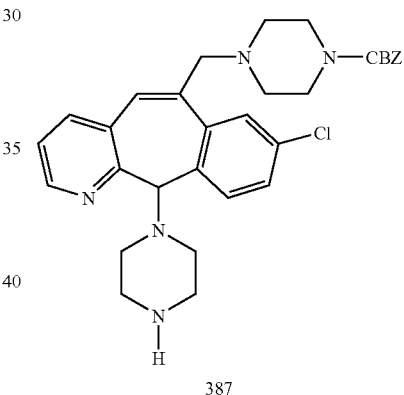
387

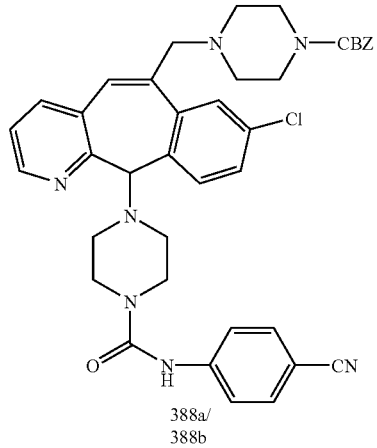
388a/388b

Compound (387) from Step B above was reacted in a similar manner to that described in Example 175 to give a mixture of 2 isomers (0.102 g, 55% yield). Further separation by HPLC, using a chiral AD column afforded pure Compound (388a) (isomer 1) (0.05 g, MH+=688.2) and Compound (388b) (isomer 2) (0.048 g, MH+=688.2).

EXAMPLES 176 AND 177

Reacting Compound (387) from Preparative Example 46, Step B in a similar manner as in Example 175 using the appropriate isocyanate as shown in Table 23 below, compounds of the formula:

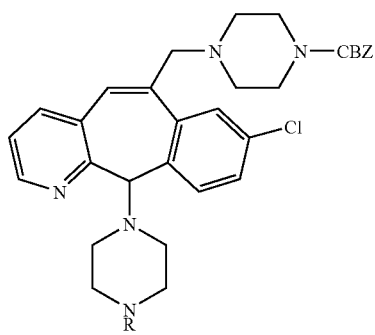

were prepared wherein R is defined in Table 23.

TABLE 23

| EX. # | PROCEDURE | R = | CMPD # | PHYS. DATA |
|---|---|---|---|---|
| 176 | Example 175 | NH-C6H4-CN) | 389 isomer 1 | MS MH+ = 688 |
| 177 | Example 175 | NH-C6H4-CN) | 390 isomer 1 | MS MH+ = 688 |

EXAMPLE 178

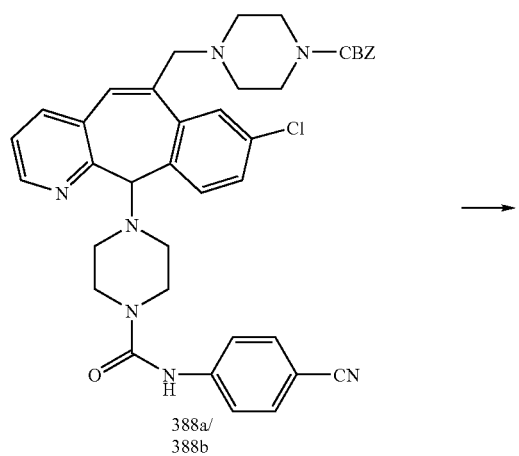

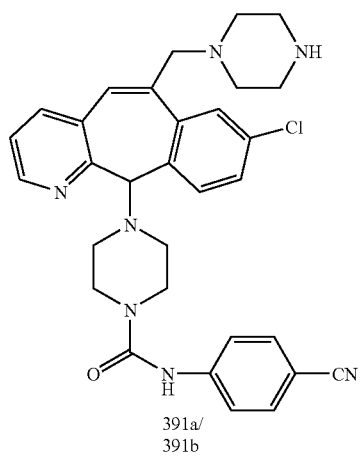

To a solution of Compound (388a) from Preparative Example 46, Step C (0.05 g, 0.086 mmol) in CH$_3$CN (1 mL) at 0° C. was added iodotrimethylsilane (0.05 mL, 0.343 mmol). The resulting solution was stirred at 0° C. for 1 hr and concentrated to dryness. The residue was then poured onto 1N HCl solution, followed by extraction with ether. The aqueous layer was then basified with 10% NH$_4$OH solution and then extracted with CH$_2$Cl$_2$. The combined organic layer was dried over Na$_2$SO$_4$ and concentrated to dryness affording Compound (391a) (isomer 1) (0.02 g, 42.5% yield, MH+=554.1).

Starting with Compound (388b) from Preparative Example 46, Step C, and reacting in the same manner as above, Compound (391b) (isomer 2) was prepared (MH+= 554.1).

PREPARATIVE EXAMPLE 47

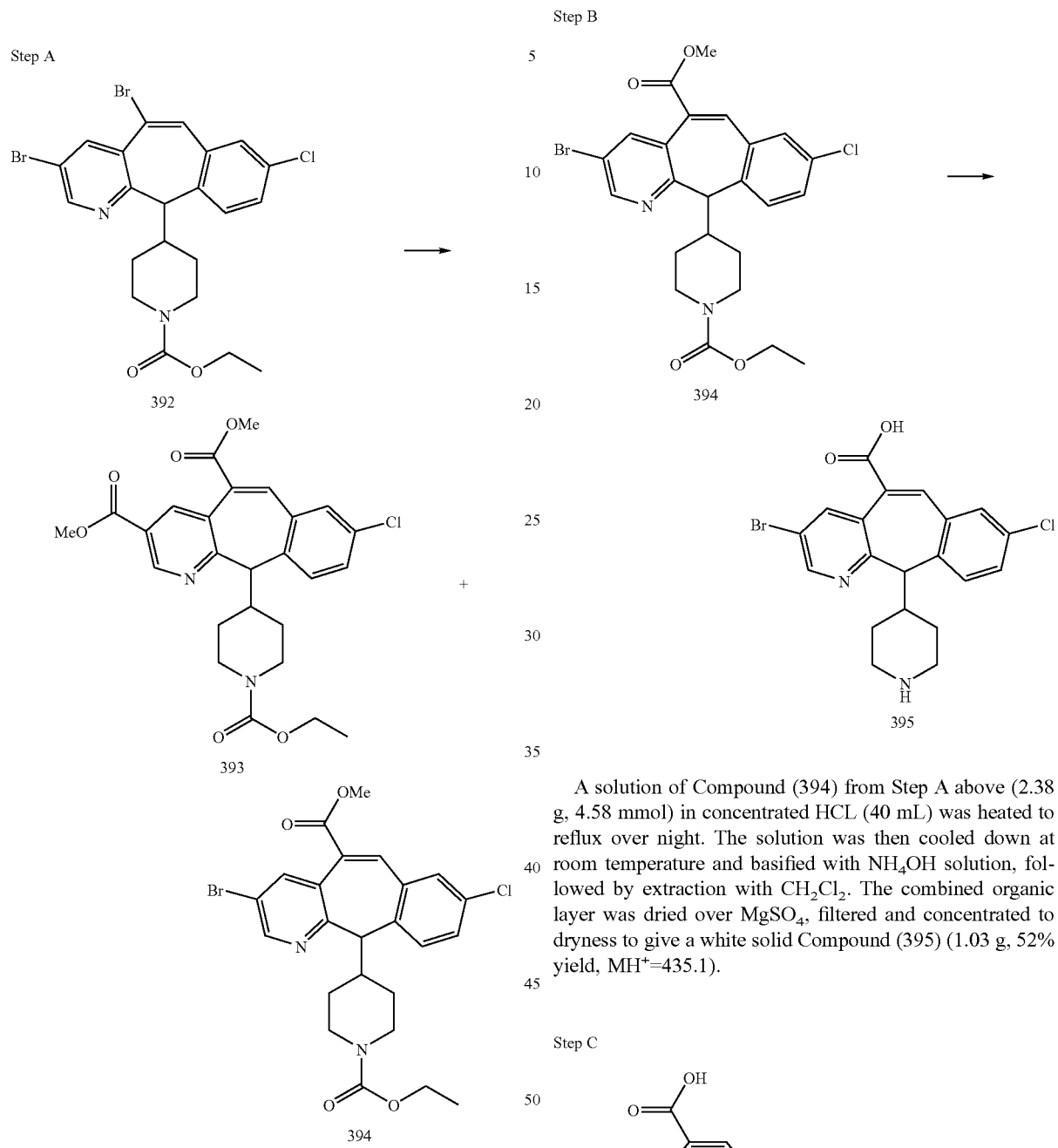

To a solution of Compound (392) prepared according to the procedure in, *The Journal of Medicinal Chemistry* (1998), 41(10), 1563 (5.0 g, 9.24 mmol) in MeOH (20 mL) and toluene (50 mL), at room temperature, was added triphenylphosphine (1.21 g, 4.62 mmol), DBU (1.90 g, 12.48 mmol) and palladium chloride (0.16 g, 0.92 mmol). The resulting solution was stirred at 80° C. for 6 hrs, then stirred at room temperature overnight. The solution was then concentrated to dryness to give two products. The desired product was purified by column chromatography on normal phase silica gel, eluting with 30% EtOAc/70% hexane to give a white solid compound (394) (2.24 g, 47% yield, $MH^+=521.1$)

A solution of Compound (394) from Step A above (2.38 g, 4.58 mmol) in concentrated HCL (40 mL) was heated to reflux over night. The solution was then cooled down at room temperature and basified with $NH_4OH$ solution, followed by extraction with $CH_2Cl_2$. The combined organic layer was dried over $MgSO_4$, filtered and concentrated to dryness to give a white solid Compound (395) (1.03 g, 52% yield, $MH^+=435.1$).

Step C

-continued

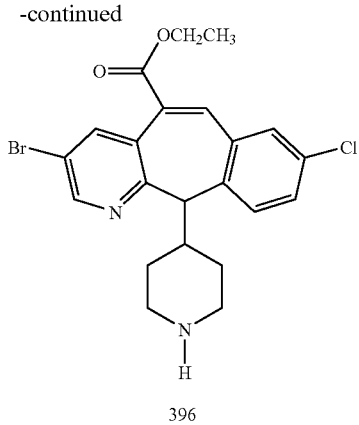
396

To a solution of Compound (395) from Step B (1.03 g, 2.37 mmol) in EtOH (50 mL, 200 proof) at room temperature, was bubbled in anhydrous CH$_2$Cl$_2$ gas for 5 minutes. The solution was then heated at 60° C. for 30 minutes, cooled down to room temperature and concentrated to dryness to afford Compound (396) (1.1 g, 100% yield, MH+=463.1)

Step D

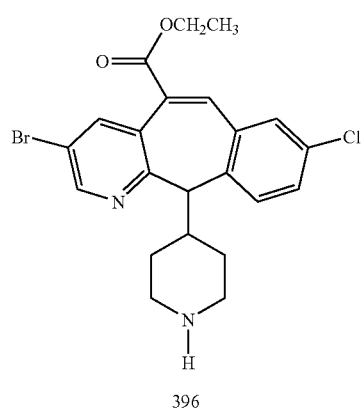
396

↓

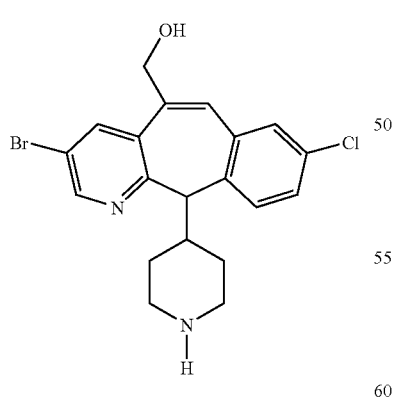
397

To a solution of Compound (396) from Step C (1.09 g, 2.19 mmol) in THF (10 mL) at 0° C. was added dropwise DIBAL/toluene (11.0 mL, 10.95 mmol). The resulting solution was stirred overnight at room temperature, then quenched with H$_2$O and concentrated to dryness to give a light brown solid Compound (397) (1.2 g, 100% yield, MH+=421.1).

Step E

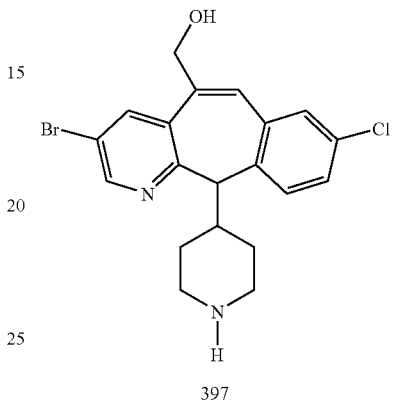
397

→

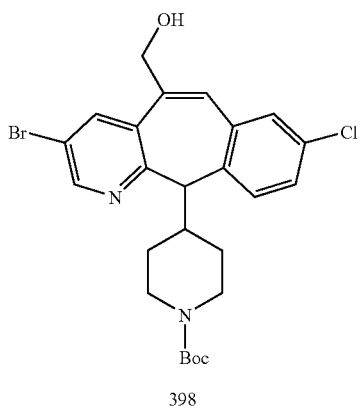
398

To a solution of Compound (397) from Step D (0.92 g, 2.19 mmol) in 50% MeOH/1% H$_2$O (50 mL) at room temperature, was added Boc anhydride (0.95 g, 4.38 mmol). The resulting solution was adjusted to pH=9 and stirred at room temperature for 4 hrs and concentrated to dryness, followed by extraction with CH$_2$Cl$_2$—H$_2$O. The combined organic layer was dried over MgSO$_4$, filtered and concentrated to dryness to give a light brown solid Compound (398) (0.91 g, 80% yield, MH$^+$=521.1).

Step F

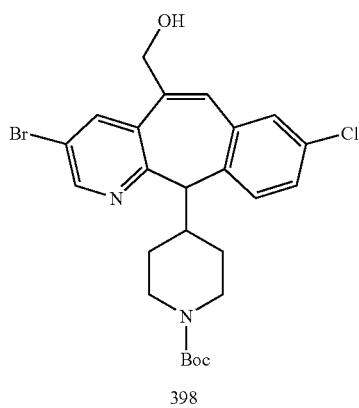

398

399

To a solution of Compound (398) from Step E (0.91 g, 1.75 mmol) in CH$_2$Cl$_2$ (10 mL) was added triethyl amine (0.73 mL, 5.25 mmol) and methanesulfonyl chloride (0.3 g, 2.62 mmol). The resulting solution was stirred at room temperature overnight and then washed with NaHCO$_3$ solution, dried over Na$_2$SO$_4$, filtered and concentrated to dryness to give the mesylate as a light yellow solid Compound (399) (0.94 g, 90% yield).

Step G

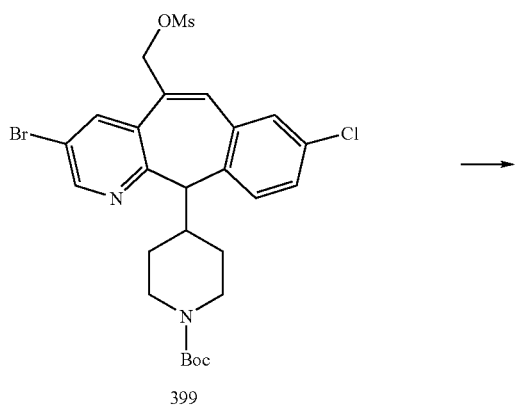

399

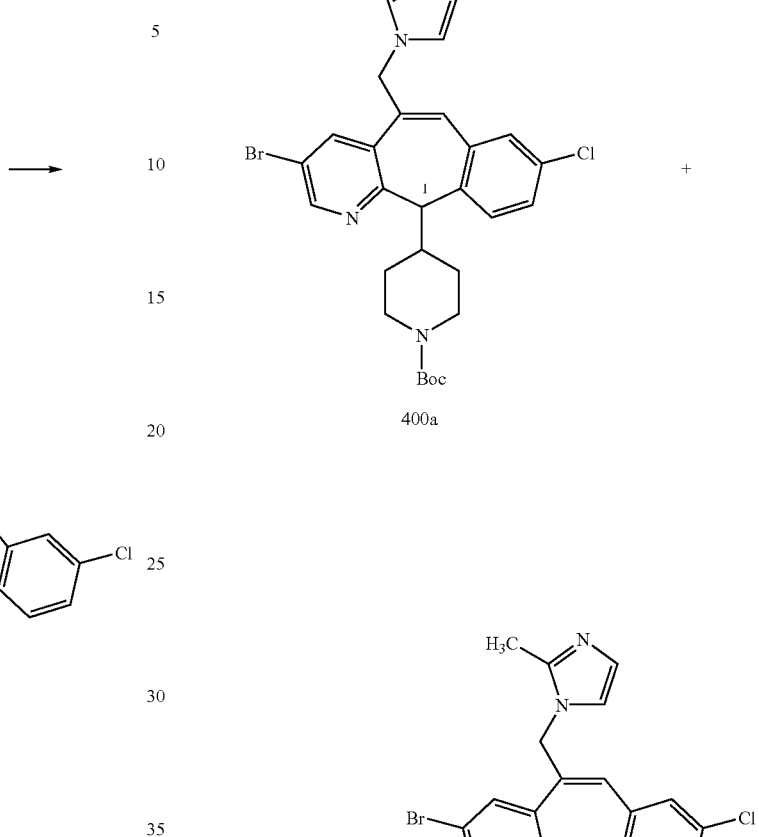

400a

400b

To a solution of Compound (399) from Step F (0.93 g, 1.60 mmol) in DMF (10 mL) under nitrogen, was added 2-methylimidazole (0.19 g, 2.3 mmol) and NaH (0.037 g). The resulting solution was stirred at room temperature for 15 minutes, then at 90° C. for 3 hrs. The solution was then cooled down to room temperature and concentrated to dryness, followed by extraction with CH$_2$Cl$_2$—NaHCO$_3$. The combined organic layer was dried over MgSO$_4$, filtered, concentrated and purified by column chromatography on normal phase silica gel, eluting with 5% MeOH—NH$_3$/95% CH$_2$Cl$_2$ to give mixture of two isomers as a light red solid (0.39 g, 42% yield, MH$^+$=585.1). The 2 isomers were separated by prep HPLC, using a chiral AD column, eluting with 15% IPA/85% hexane/0.2% DEA to give Compound (400a) (isomer 1) as a light brown solid (0.10 g, 11% yield) and Compound (400b) (isomer 2) as a white solid (0.10 g, 11% yield)

Step H

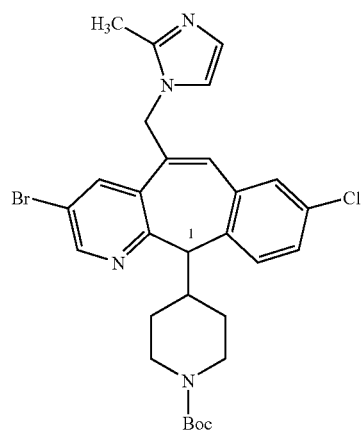

400a

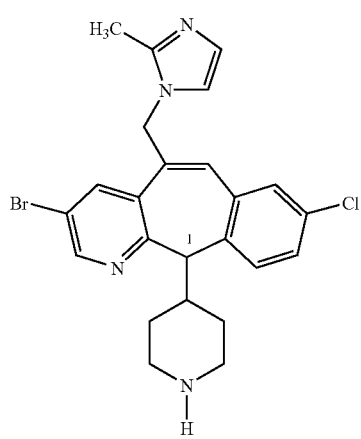

401

A solution of Compound (400a) (isomer 1) from Step G above (0.07 g, 0.12 mmol) in 4M HCl/Dioxane (3 mL) was stirred at room temperature for 3 hrs then concentrated to dryness to give a white solid Compound (401) (0.06 g, 100% yield)

Step I

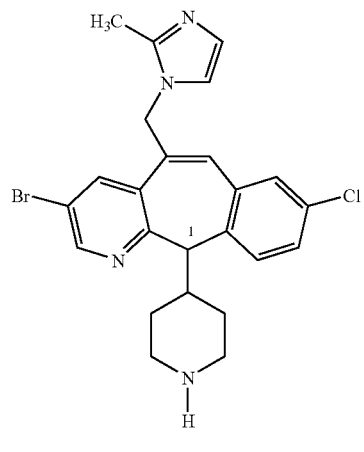

401

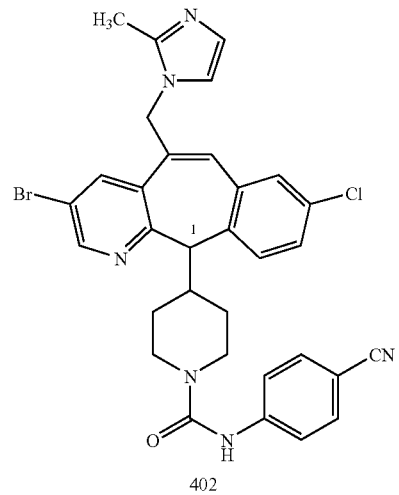

402

To a solution of Compound (401) from Step H above (0.057 g, 0.12 mmol) in CH$_2$Cl$_2$ (5 mL) under nitrogen, was added triethyl amine (0.026 g, 0.20 mmol) and 4-cyanophenyl isocyanate (0.019 g, 0.13 mmol). The resulting solution was stirred at room temperature overnight and then extracted with CH$_2$Cl$_2$—NaHCO$_3$. The combined organic layer was dried over Na$_2$SO$_4$, filtered, concentrated to dryness to afford Compound (402) (isomer 1) as a white solid (0.053 g, 70% yield, MH$^+$=629.3)

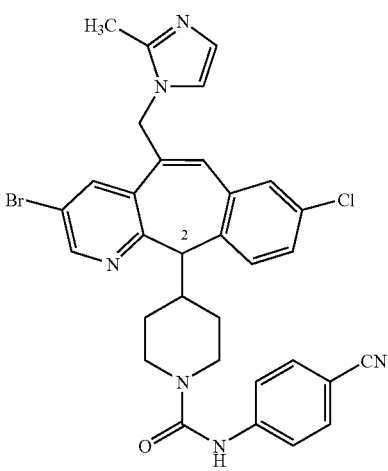

403

Compound (400b) was reacted in a similar manner as in Steps H and I above to afford Compound (403) (isomer 2) (0.059 g, 79% yield, MH+=629.3)

PREPARATIVE EXAMPLE 48

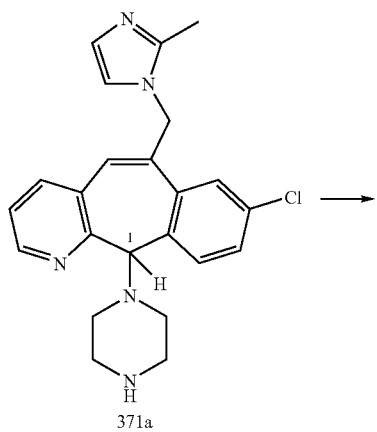

371a

404

Compound (371a) (isomer 1) from Preparative Example 42, Step F (70 mg, 0.17 mmol) was dissolved in 1 mL of ethanol and 50 uL of triethylamine. Dimethyl-N-cyanimidothiocarbonate (45 mg, 0.29 mmol) was added and the reaction mixture and stirred at 85° C. for 24 hours. The ethanol was evaporated under reduced pressure and the product chromatographed on silica gel using 5% methanolic-ammonia dichloromethane to obtain 47 mg of title product Compound (404) (FABMS M+1=504).

EXAMPLE 179

404

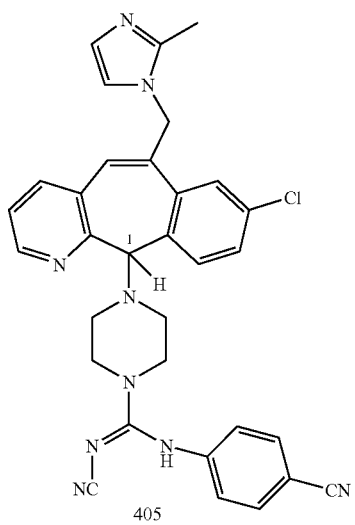

405

To a solution of para-cyanoanaline (53 mg, 0.45 mmol) in 1 ml N,N-dimethylformamide was added sodium hydride (18 mg, 0.45 mmol). After stirring under a dry nitrogen atmosphere for ½ hour, Compound (404) (isomer 1) from Preparative Example 48 above (40 mg, 0.08 mmol) was added and the reaction mixture stirred at 55° C. for 4 hours. The reaction mixture was cooled to ambient temperature and added to brine. The crude product was extracted with dichloromethane 3 times. The extracts were concentrated and the crude product chromatographed on silica gel using 5% methanolic-ammonia/dichloromethane to obtain 17.6 mg of title product.(405) FABMS M+1=574.1

EXAMPLES 180 AND 181
PREPARATIVE EXAMPLE 49
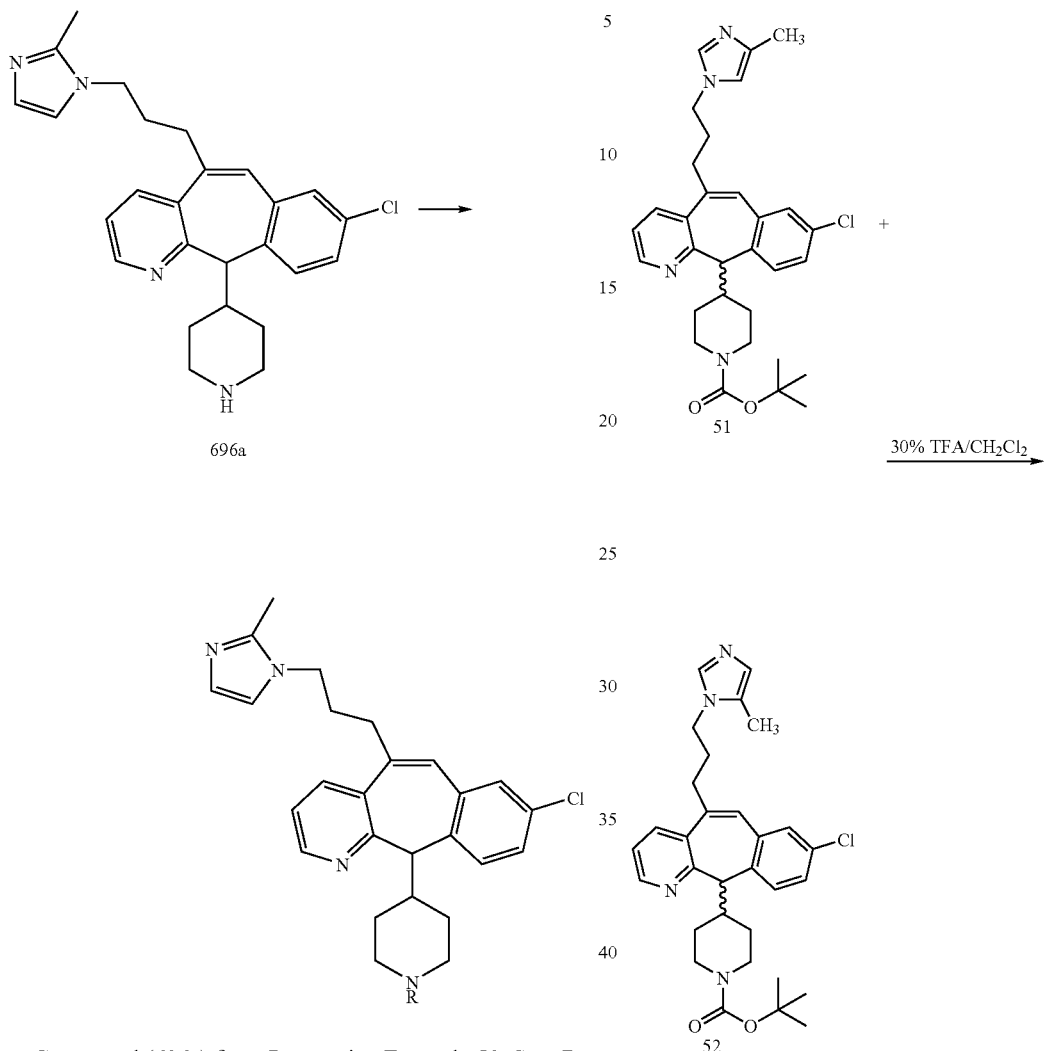
Compound (696a) from Preparative Example 59, Step B, was reacted in the same manner as in Preparative Example 48 and Example 179 substituting the appropriate R reagent to afford the compounds in Table 24.
TABLE 24
| EX. # | R = | CMPD # | PHYS. DATA |
|---|---|---|---|
| 180 | -C(=N-CN)-NH-C6H4-CN | 407 | FABMS MH+ = 601.1 |
| 181 | -C(=N-CN)-NH-cyclohexyl | 408 | FABMS MH+ = 531.1 |

-continued

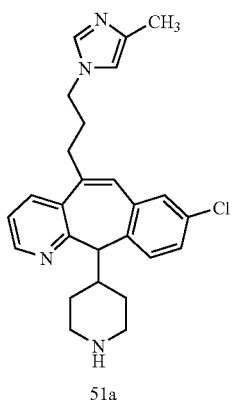

51a

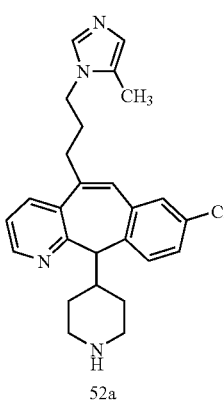

52a

Compounds (51) and (52) from Example 11, Step A, were reacted with TFA in CH$_2$Cl$_2$ to afford compounds (51 a) and (52a).

Library Preparation

Figure 1

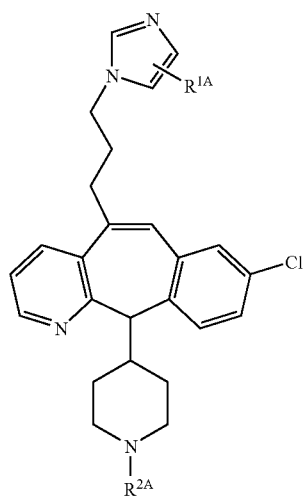

-continued

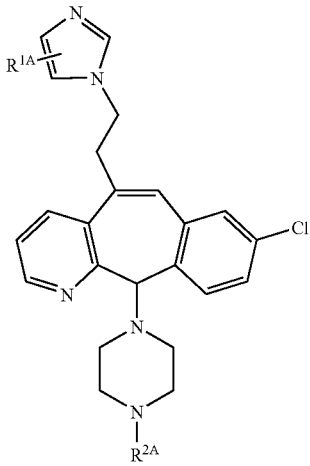

Figure 2

A library of compounds was prepared by solution phase parallel synthesis. A generic structure of these compounds is shown in FIG. 1 above. The R$^{1A}$ group on the imidazole ring can be H or CH$_3$, the R$^{2A}$ on N-1 of the piperidine is varied in the library.

Library compounds were prepared using compound (29) from Preparative Example 4 or Compounds (51 a) or (52a) from Preparative Example 49 above as templates as shown in Scheme A. Synthesis is initiated in test tubes by reacting compound (29), (51 a) or (52a) with multiple equivalents of a variety of isocyanates, amines, acids, acid chlorides, sulfonyl chlorides and chloroformates in dichloromethane or chloroform. When urea is the desired product, the reaction can be carried out using isocyanates directly, or alternatively, treating an amine with CDI for several hours, then subject the templates to this solution overnight. When acids are used, the reaction is carried out in the presence of a coupling reagent such as PyBrop and a base such as DIEA overnight. When acid chlorides, sulfonyl chlorides or chloroformates are used, the reaction is typically conducted in the presence of triethylamine. After reaction, an excess amount of polystyrene aminomethyl resin is added to the reaction test tubes, and the reaction allowed to stand overnight. At which time each test tube is filtered through a Bio-Rad Poly-Prep chromatography column into another test tube, and the resin is washed with dichloromethane and MeOH. The combined filtrate solution is concentrated by rotovap evaporation. The residue in each test tube is then dissolved in H$_2$O/CH$_3$CN (50/50, containing 1% TFA) and purified by Gilson 215 liquid Handling-HPLC system to give pure product. The product was identified by mass spectroscopy. Library compounds prepared in this fashion are shown in Table 25 and Table 26.

Scheme A

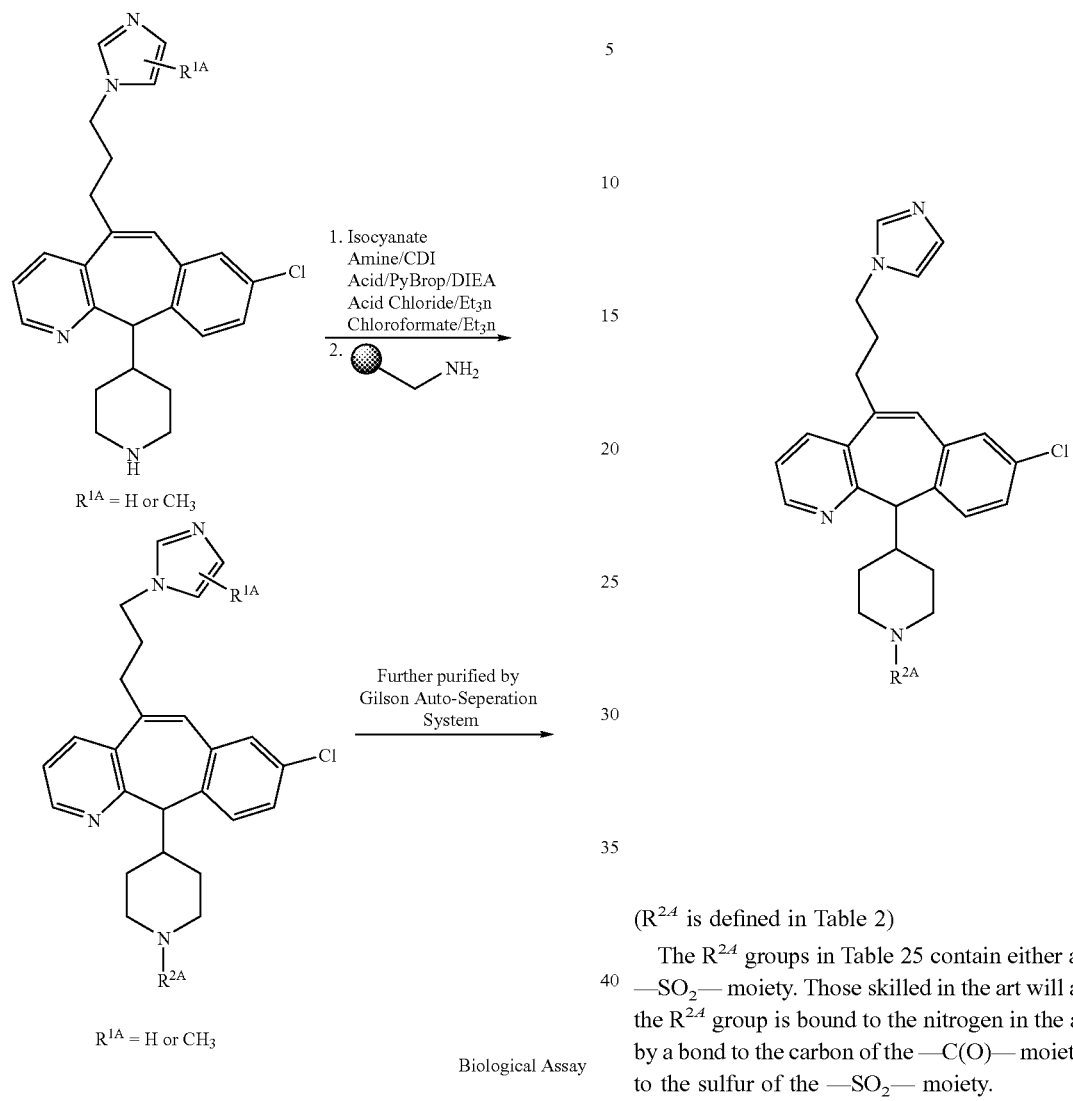

$R^{1A}$ = H or CH$_3$ $R^{1A}$ = H or CH$_3$

Biological Assay

EXAMPLES 182-283

($R^{2A}$ is defined in Table 2)

The $R^{2A}$ groups in Table 25 contain either a —C(O)— or —SO$_2$— moiety. Those skilled in the art will appreciate that the $R^{2A}$ group is bound to the nitrogen in the above formula by a bond to the carbon of the —C(O)— moiety or by a bond to the sulfur of the —SO$_2$— moiety.

TABLE 25

| EXAMPLE #. | R$^{2A}$ | COMPOUND # | PHYSICAL DATA |
|---|---|---|---|
| 182 | H$_3$C—C$_6$H$_4$—NH—C(O)—    2 TFA | 409 | Mass spec. MH$^+$ = 552 |
| 183 | F—C$_6$H$_4$—NH—C(O)—    2 TFA | 410 | Mass spec. MH$^+$ = 556 |

TABLE 25-continued
| EXAMPLE #. | R²ᴬ | COMPOUND # | PHYSICAL DATA |
|---|---|---|---|
| 184 | 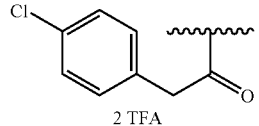<br>2 TFA | 411 | Mass spec.<br>MH⁺ = 571 |
| 185 | 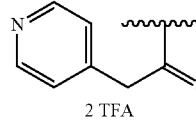<br>2 TFA | 412 | Mass spec.<br>MH⁺ = 538 |
| 186 | 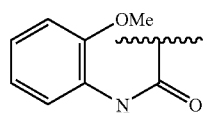<br>2 TFA | 413 | Mass spec.<br>MH⁺ = 568 |
| 187 | 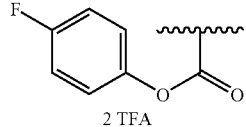<br>2 TFA | 414 | Mass spec.<br>MH⁺ = 557 |
| 188 | 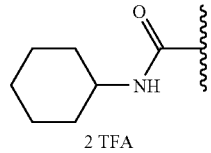<br>2 TFA | 415 | Mass spec.<br>MH⁺ = 544 |
| 189 | 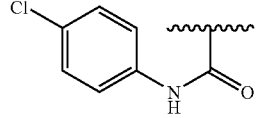<br>2 TFA | 416 | Mass spec.<br>MH⁺ = 572 |
| 190 | 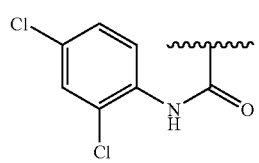<br>2 TFA | 417 | Mass spec.<br>MH⁺ = 606 |
| 191 | 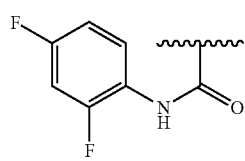<br>2 TFA | 418 | Mass spec.<br>MH⁺ = 574 |
| 192 | 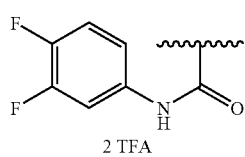<br>2 TFA | 419 | Mass spec.<br>MH⁺ = 574 |

TABLE 25-continued
| EXAMPLE #. | R²ᴬ | COMPOUND # | PHYSICAL DATA |
|---|---|---|---|
| 193 | 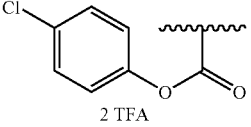<br>2 TFA | 420 | Mass spec.<br>MH⁺ = 573 |
| 194 | 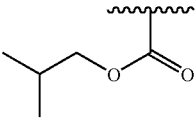 | 421 | Mass spec.<br>MH⁺ = 519 |
| 195 | 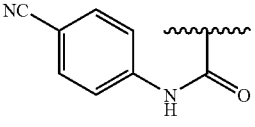<br>2 TFA | 422 | Mass spec.<br>MH⁺ = 563 |
| 196 | 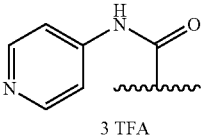<br>3 TFA | 423 | Mass spec.<br>MH⁺ = 539 |
| 197 | 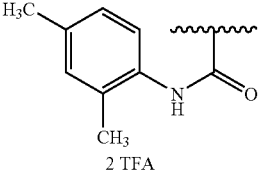<br>2 TFA | 424 | Mass spec.<br>MH⁺ = 566 |
| 198 | 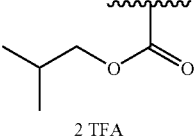<br>2 TFA | 425 | Mass spec.<br>MH⁺ = 505 |
| 199 | 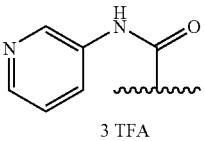<br>3 TFA | 426 | Mass spec.<br>MH⁺ = 539 |
| 200 | 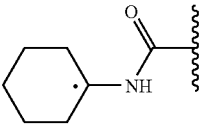 | 427 | Mass spec.<br>MH⁺ = 544 |
| 201 | 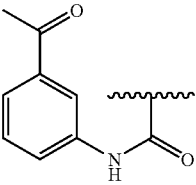 | 428 | Mass spec.<br>MH⁺ = 580 |

TABLE 25-continued
| EXAMPLE # | R²ᴬ | COMPOUND # | PHYSICAL DATA |
|---|---|---|---|
| 202 | 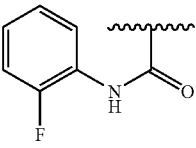<br>2 TFA | 429 | Mass spec.<br>MH⁺ = 556 |
| 203 | 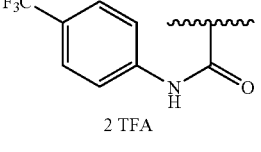<br>2 TFA | 430 | Mass spec.<br>MH⁺ = 606 |
| 204 | 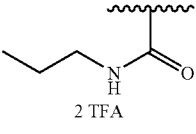<br>2 TFA | 431 | Mass spec.<br>MH⁺ = 518 |
| 205 | 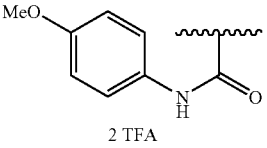<br>2 TFA | 432 | Mass spec.<br>MH⁺ = 568 |
| 206 | 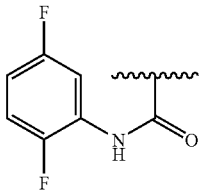<br>2 TFA | 433 | Mass spec.<br>MH⁺ = 574 |
| 207 | 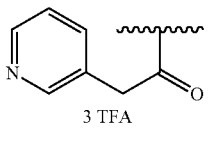<br>3 TFA | 434 | Mass spec.<br>MH⁺ = 538 |
| 208 | 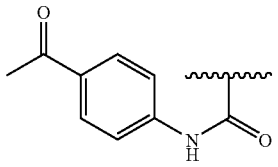 | 435 | Mass spec.<br>MH⁺ = 580 |
| 209 | 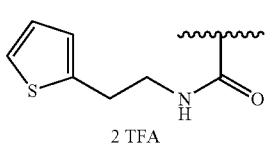<br>2 TFA | 436 | Mass spec.<br>MH⁺ = 572 |
| 210 | 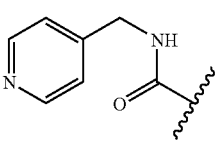<br>2 TFA | 437 | Mass spec.<br>MH⁺ = 553 |

TABLE 25-continued
| EXAMPLE #. | R2A | COMPOUND # | PHYSICAL DATA |
|---|---|---|---|
| 211 | 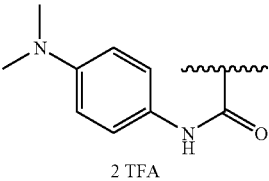 2 TFA | 438 | Mass spec. MH+ = 581 |
| 212 | 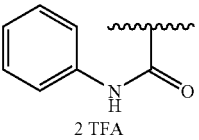 2 TFA | 439 | Mass spec. MH+ = 538 |
| 213 | 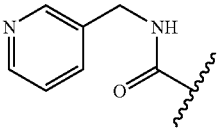 | 440 | Mass spec. MH+ = 553 |
| 214 | 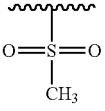 | 441 | Mass spec. MH+ = 497 |
| 215 | 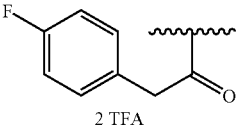 2 TFA | 442 | Mass spec. MH+ = 555 |
| 216 | 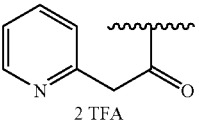 2 TFA | 443 | Mass spec. MH+ = 538 |
| 217 | 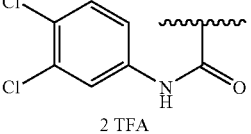 2 TFA | 444 | Mass spec. MH+ = 606 |
| 218 | 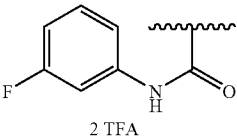 2 TFA | 445 | Mass spec. MH+ = 556 |
| 219 | 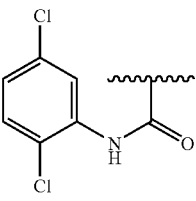 2 TFA | 446 | Mass spec. MH+ = 606 |
| 220 | 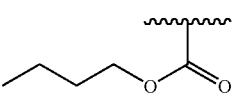 | 447 | Mass spec. MH+ = 519 |

TABLE 25-continued
| EXAMPLE #. | R2A | COMPOUND # | PHYSICAL DATA |
|---|---|---|---|
| 221 | 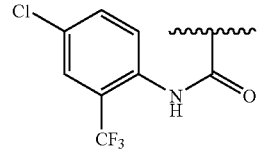 2 TFA | 448 | Mass spec. MH+ = 640 |
| 222 | 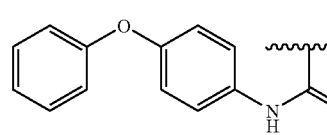 2 TFA | 449 | Mass spec. MH+ = 630 |
| 223 | 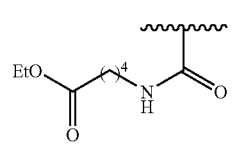 | 450 | Mass spec. MH+ = 604 |
| 224 | 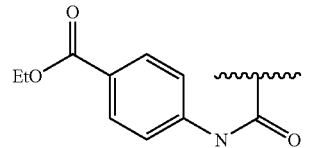 | 451 | Mass spec. MH+ = 610 |
| 225 | 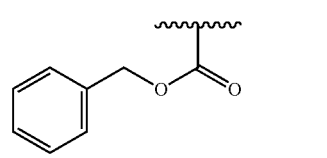 2 TFA | 452 | Mass spec. MH+ = 553 |
| 226 | 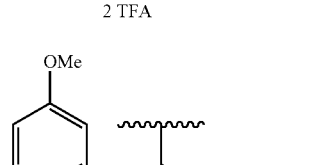 | 453 | Mass spec. MH+ = 568 |
| 227 | 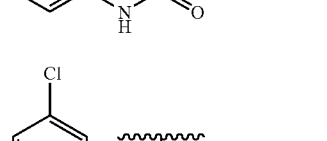 | 454 | Mass spec. M+ = 572 |
| 228 | 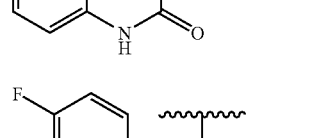 2 TFA | 455 | Mass spec. MH+ = 624 |
| 229 | 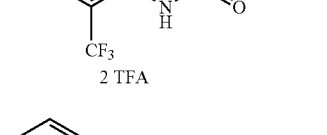 | 456 | Mass spec. MH+ = 572 |

TABLE 25-continued
| EXAMPLE #. | R²ᴬ | COMPOUND # | PHYSICAL DATA |
|---|---|---|---|
| 230 | 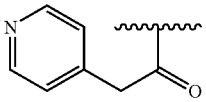 | 457 | Mass spec. MH⁺ = 554 |
| 231 | 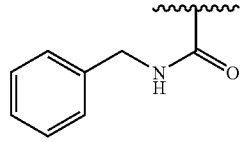<br>2 TFA | 458 | Mass spec. MH⁺ = 552 |
| 232 | 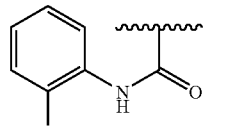<br>2 TFA | 459 | Mass spec. MH⁺ = 552 |
| 233 | 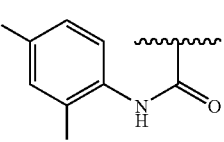<br>2 TFA | 460 | Mass spec. MH⁺ = 598 |
| 234 | 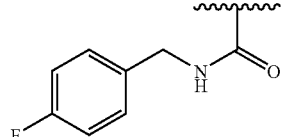<br>2 TFA | 461 | Mass spec. MH⁺ = 570 |
| 235 | 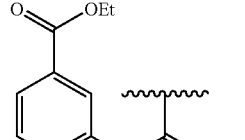 | 462 | Mass spec. MH⁺ = 610 |
| 236 | 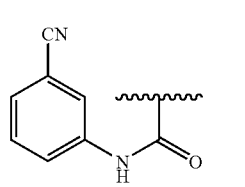 | 463 | Mass spec. MH⁺ = 563 |
| 237 | 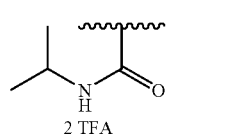<br>2 TFA | 464 | Mass spec. MH⁺ = 504 |
| 238 | 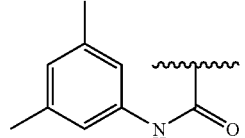<br>2 TFA | 465 | Mass spec. MH⁺ = 566 |

TABLE 25-continued
| EXAMPLE #. | R²ᴬ | COMPOUND # | PHYSICAL DATA |
|---|---|---|---|
| 239 | 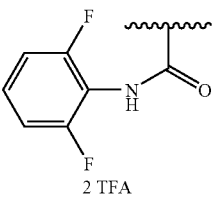 2 TFA | 466 | Mass spec. MH⁺ = 574 |
| 240 | 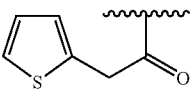 | 467 | Mass spec. MH⁺ = 543 |
| 241 | 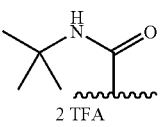 2 TFA | 468 | Mass spec. MH⁺ = 518 |
| 242 | 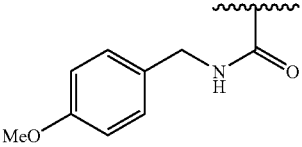 | 469 | Mass spec. MH⁺ = 582 |
| 243 | 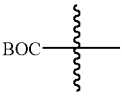 | 470 | Mass spec. MH⁺ = 519 |
| 244 | 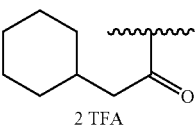 2 TFA | 471 | Mass spec. MH⁺ = 543 |
| 245 | 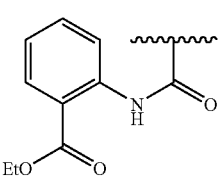 | 472 | Mass spec. MH⁺ = 610 |
| 246 | 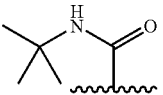 | 473 | Mass spec. MH⁺ = 518 |
| 247 | 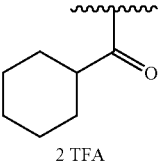 2 TFA | 474 | Mass spec. MH⁺ = 529 |
| 248 | 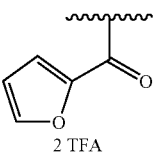 2 TFA | 475 | Mass spec. MH⁺ = 513 |

TABLE 25-continued

| EXAMPLE #. | R²ᴬ | COMPOUND # | PHYSICAL DATA |
|---|---|---|---|
| 249 | 2-CF₃-phenyl-NH-C(O)- | 476 | Mass spec. MH⁺ = 606 |
| 250 | ethyl ester -C(O)-O-Et, 2 TFA | 477 | Mass spec. MH⁺ = 491 |
| 251 | 3,5-dichlorophenyl-NH-C(O)-, 2 TFA | 478 | Mass spec. MH⁺ = 606 |
| 252 | EtO-C(O)-CH₂-NH-C(O)- | 479 | Mass spec. MH⁺ = 548 |
| 253 | cyclopropyl-C(O)-, 2 TFA | 480 | Mass spec. MH⁺ = 487 |
| 254 | butyl-S(O)₂- | 481 | Mass spec. MH⁺ = 539 |
| 255 | EtO-C(O)-CH₂-CH₂-NH-C(O)-O- | 482 | Mass spec. MH⁺ = 562 |
| 256 | F₃C-CH₂-S(O)₂- | 483 | Mass spec. MH⁺ = 565 |
| 257 | (CH₃)₂N-S(O)₂- | 484 | Mass spec. MH⁺ = 526 |
| 258 | 2,5-dimethoxyphenyl-NH-C(O)-, 2 TFA | 485 | Mass spec. MH⁺ = 598 |

TABLE 25-continued
| EXAMPLE #. | R²ᴬ | COMPOUND # | PHYSICAL DATA |
|---|---|---|---|
| 259 |  2 TFA | 486 | Mass spec. MH⁺ = 548 |
| 260 | 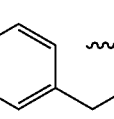 2 TFA | 487 | Mass spec. MH⁺ = 580 |
| 261 | 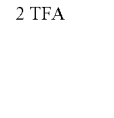 2 TFA | 488 | Mass spec. MH⁺ = 598 |
| 262 | 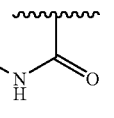 2 TFA | 489 | Mass spec. MH⁺ = 529 |
| 263 |  2 TFA | 490 | Mass spec. MH⁺ = 475 |
| 264 | 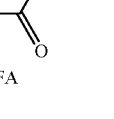 | 491 | Mass spec. MH⁺ = 573 |
| 265 | 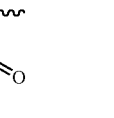 2 TFA | 492 | Mass spec. MH⁺ = 525 |
| 266 | 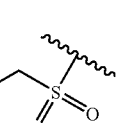 2 TFA | 493 | Mass spec. MH⁺ = 518 |
| 267 |  2 TFA | 494 | Mass spec. MH⁺ = 577 |

TABLE 25-continued
| EXAMPLE #. | R²ᴬ | COMPOUND # | PHYSICAL DATA |
|---|---|---|---|
| 268 | 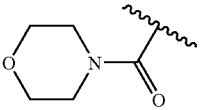 2 TFA | 495 | Mass spec. MH⁺ = 532 |
| 269 | 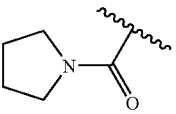 2 TFA | 496 | Mass spec. MH⁺ = 516 |
| 270 | 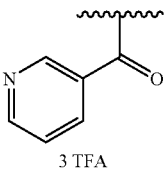 3 TFA | 497 | Mass spec. MH⁺ = 524 |
| 271 | 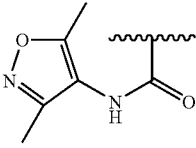 2 TFA | 498 | Mass spec. MH⁺ = 557 |
| 272 | 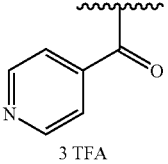 3 TFA | 499 | Mass spec. MH⁺ = 524 |
| 273 | 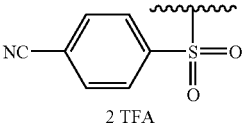 2 TFA | 500 | Mass spec. MH⁺ = 584 |
| 274 | 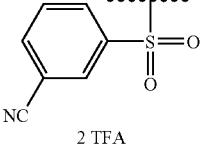 2 TFA | 501 | Mass spec. MH⁺ = 584 |
| 275 | 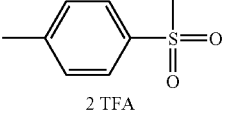 2 TFA | 502 | Mass spec. MH⁺ = 573 |
| 276 | 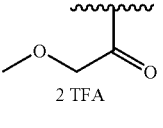 2 TFA | 503 | Mass spec. MH⁺ = 491 |

TABLE 25-continued
| EXAMPLE #. | R²ᴬ | COMPOUND # | PHYSICAL DATA |
|---|---|---|---|
| 277 | 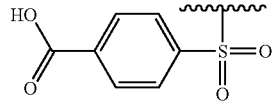 2 TFA | 504 | Mass spec. MH⁺ = 603 |
| 278 | 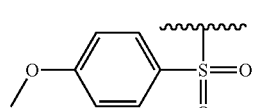 | 505 | Mass spec. MH⁺ = 589 |
| 279 | 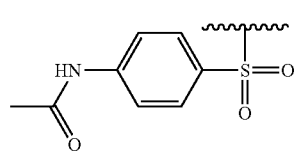 2 TFA | 506 | Mass spec. MH⁺ = 616 |
| 280 | 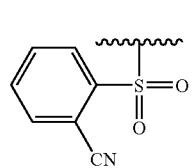 2 TFA | 507 | Mass spec. MH⁺ = 584 |
| 281 | 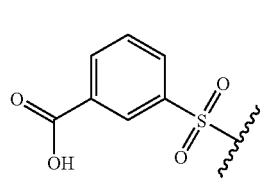 2 TFA | 508 | Mass spec. MH⁺ = 603 |
| 282 | 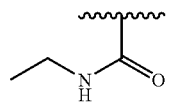 | 509 | Mass spec. MH⁺ = 490 |
| 283 | 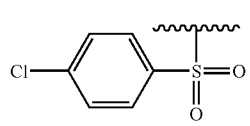 2 TFA | 510 | Mass spec. MH⁺ = 593 |

EXAMPLES 284-377
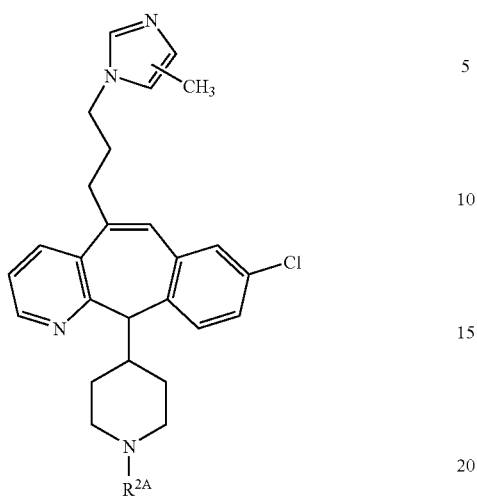
($R^{2A}$ is defined in Table 26).
TABLE 26
| EXAMPLE # | $R^{2A}$ | COMPOUND # | MH+ |
|---|---|---|---|
| 284 | 4-F-C6H4-O-C(=O)-C(CH3)2- , 2 TFA | 511 | 571 |
| 285 | 4-pyridyl-CH2-C(=O)-C(CH3)2- , 3 TFA | 512 | 552 |
| 286 | 4-Cl-C6H4-O-C(=O)-C(CH3)2- , 2 TFA | 513 | 587 |
| 287 | cyclohexyl-NH-C(=O)-C(CH3)2- | 514 | 558 |
| 288 | 4-NC-C6H4-NH-C(=O)-C(CH3)2- , 2 TFA | 515 | 577 |
| 289 | 4-F-C6H4-NH-C(=O)-CH2- , 2 TFA | 516 | 570 |

TABLE 26-continued
| EXAMPLE # | R²ᴬ | COMPOUND # | MH⁺ |
|---|---|---|---|
| 290 | 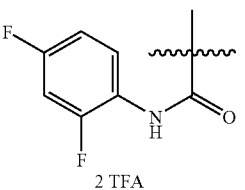 2 TFA | 517 | 588 |
| 291 | 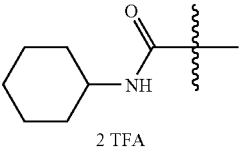 2 TFA | 518 | 558 |
| 292 | 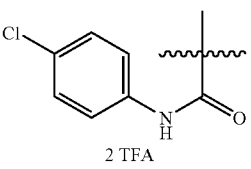 2 TFA | 519 | 586 |
| 293 | 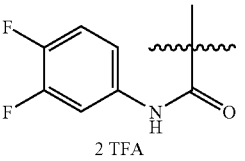 2 TFA | 520 | 588 |
| 294 | 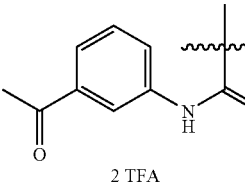 2 TFA | 521 | 594 |
| 295 | 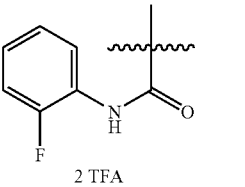 2 TFA | 522 | 570 |
| 296 | 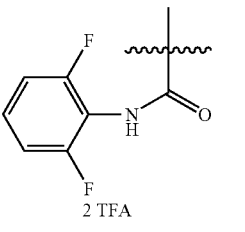 2 TFA | 523 | 588 |
| 297 | 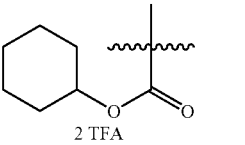 2 TFA | 524 | 559 |

TABLE 26-continued
| EXAMPLE # | R²ᴬ | COMPOUND # | MH⁺ |
|---|---|---|---|
| 298 | 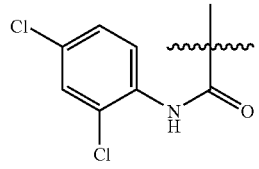 2 TFA | 525 | 620 |
| 299 | 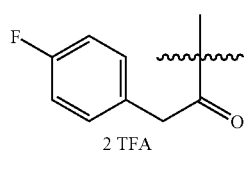 2 TFA | 526 | 569 |
| 300 | 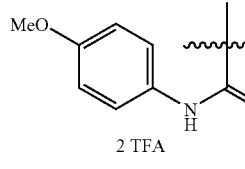 2 TFA | 527 | 582 |
| 301 | 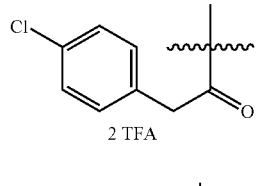 2 TFA | 528 | 585 |
| 302 | 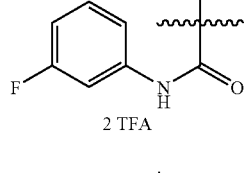 2 TFA | 529 | 570 |
| 303 | 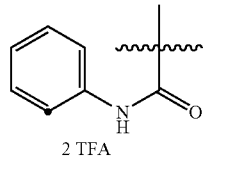 2 TFA | 530 | 552 |
| 304 | 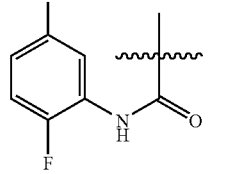 2 TFA | 531 | 588 |
| 305 | 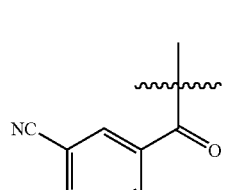 2 TFA | 532 | 562 |

TABLE 26-continued
| EXAMPLE # | R²ᴬ | COMPOUND # | MH⁺ |
|---|---|---|---|
| 306 | 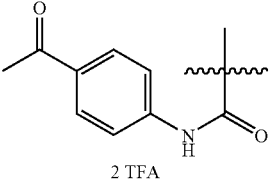 2 TFA | 533 | 594 |
| 307 | 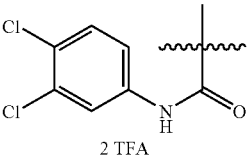 2 TFA | 534 | 620 |
| 308 | 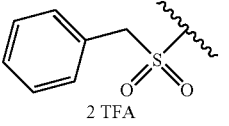 2 TFA | 535 | 587 |
| 309 | 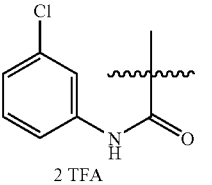 2 TFA | 536 | 586 |
| 310 | 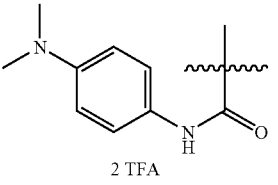 2 TFA | 537 | 595 |
| 311 | 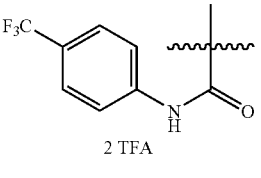 2 TFA | 538 | 620 |
| 312 | 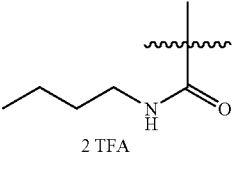 2 TFA | 539 | 532 |
| 313 | 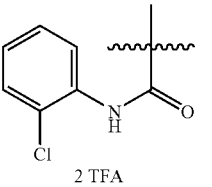 2 TFA | 540 | 586 |

TABLE 26-continued
| EXAMPLE # | R2A | COMPOUND # | MH+ |
|---|---|---|---|
| 314 | 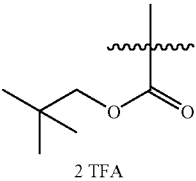 2 TFA | 541 | 547 |
| 315 | 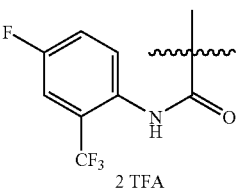 2 TFA | 542 | 638 |
| 316 | 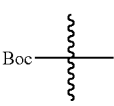 | 543 | 533 |
| 317 | 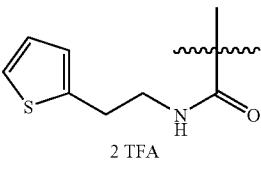 2 TFA | 544 | 586 |
| 318 | 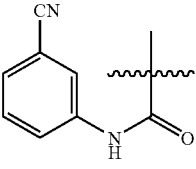 | 545 | 577 |
| 319 | 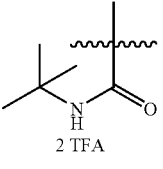 2 TFA | 546 | 532 |
| 320 | 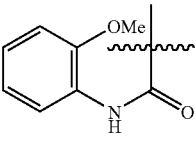 | 547 | 582 |
| 321 | 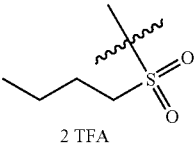 2 TFA | 548 | 553 |
| 322 | 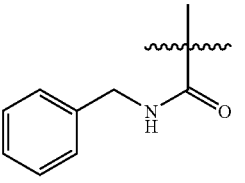 2 TFA | 549 | 566 |

TABLE 26-continued

| EXAMPLE # | R²ᴬ | COMPOUND # | MH⁺ |
|---|---|---|---|
| 323 | benzyl ester, 2 TFA | 550 | 567 |
| 324 | isopropyl ester, 2 TFA | 551 | 519 |
| 325 | cyclohexyl ketone, 2 TFA | 552 | 543 |
| 326 | thiophene-2-yl methyl ketone, 2 TFA | 553 | 557 |
| 327 | 4-fluorobenzyl amide, 2 TFA | 554 | 584 |
| 328 | 2,5-dichlorophenyl amide, 2 TFA | 555 | 620 |
| 329 | 3-(ethoxycarbonyl)phenyl amide, 2 TFA | 556 | 624 |

TABLE 26-continued
| EXAMPLE # | R2A | COMPOUND # | MH+ |
|---|---|---|---|
| 330 | 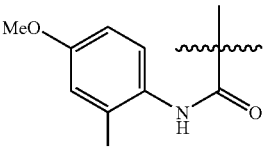 2 TFA | 557 | 612 |
| 331 | 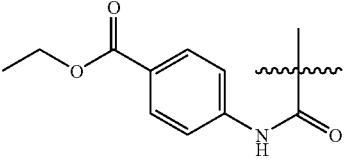 2 TFA | 558 | 624 |
| 332 | 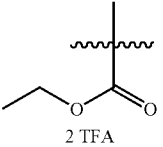 2 TFA | 559 | 505 |
| 333 | 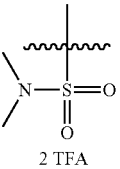 2 TFA | 560 | 540 |
| 334 | 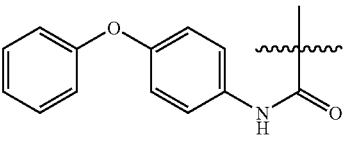 2 TFA | 561 | 644 |
| 335 | 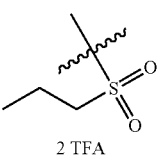 2 TFA | 562 | 539 |
| 336 | 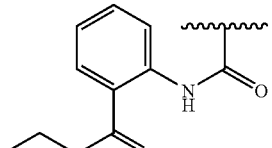 2 TFA | 563 | 624 |
| 337 | 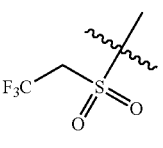 2 TFA | 564 | 579 |

TABLE 26-continued
| EXAMPLE # | R²ᴬ | COMPOUND # | MH⁺ |
|---|---|---|---|
| 338 | 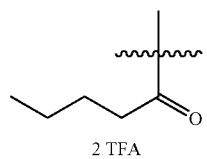 2 TFA | 565 | 517 |
| 339 | 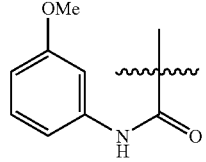 | 566 | 582 |
| 340 | 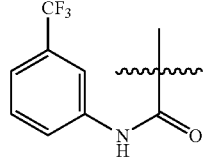 2 TFA | 567 | 620 |
| 341 | 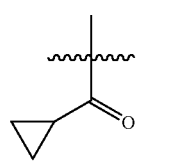 2 TFA | 568 | 501 |
| 342 | 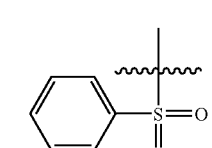 2 TFA | 569 | 598 |
| 343 | 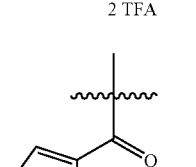 2 TFA | 570 | 543 |
| 344 | 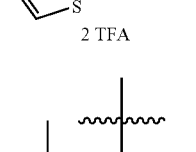 2 TFA | 571 | 518 |
| 345 | 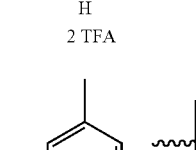 2 TFA | 572 | 580 |

TABLE 26-continued
| EXAMPLE # | R²ᴬ | COMPOUND # | MH⁺ |
|---|---|---|---|
| 346 | 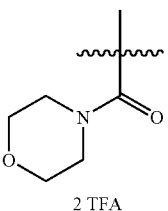<br>2 TFA | 573 | 546 |
| 347 | 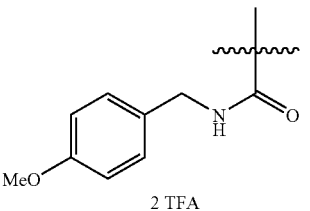<br>2 TFA | 574 | 596 |
| 348 | 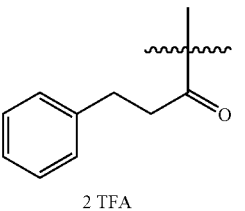<br>2 TFA | 575 | 565 |
| 349 | 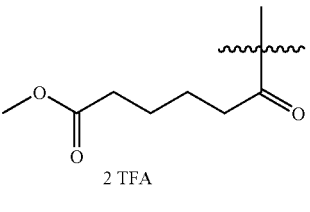<br>2 TFA | 576 | 575 |
| 350 | 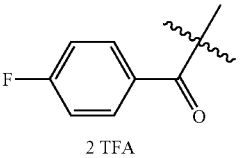<br>2 TFA | 577 | 555 |
| 351 | 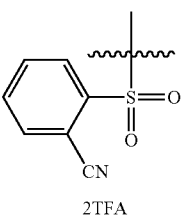<br>2TFA | 578 | 598 |
| 352 | 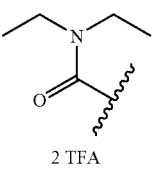<br>2 TFA | 579 | 532 |

TABLE 26-continued

| EXAMPLE # | R²ᴬ | COMPOUND # | MH⁺ |
|---|---|---|---|
| 353 | ethylamide group, 2 TFA | 580 | 504 |
| 354 | furan-2-yl ketone, 2 TFA | 581 | 527 |
| 355 | ethyl ketone, 2 TFA | 582 | 489 |
| 356 | neopentyl ketone, 2 TFA | 583 | 531 |
| 357 | EtO-glycine amide | 584 | 562 |
| 358 | 4-cyanophenyl ketone, 2 TFA | 585 | 562 |
| 359 | 4-acetamidophenyl sulfonyl, 2 TFA | 586 | 630 |

TABLE 26-continued
| EXAMPLE # | R²ᴬ | COMPOUND # | MH⁺ |
|---|---|---|---|
| 360 | 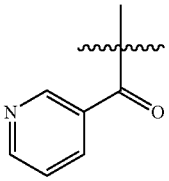<br>3 TFA | 587 | 538 |
| 361 | 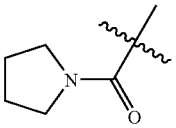<br>2 TFA | 588 | 530 |
| 362 | 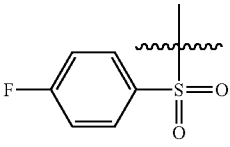<br>2 TFA | 589 | 591 |
| 363 | 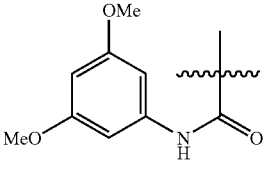<br>2 TFA | 590 | 612 |
| 364 | 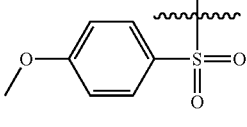<br>2 TFA | 591 | 603 |
| 365 | 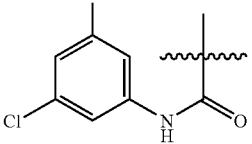<br>2 TFA | 592 | 620 |
| 366 | 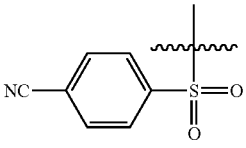<br>2 TFA | 593 | 598 |
| 367 | 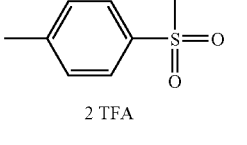<br>2 TFA | 594 | 587 |

TABLE 26-continued
| EXAMPLE # | R2A | COMPOUND # | MH+ |
|---|---|---|---|
| 368 | 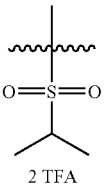<br>2 TFA | 595 | 539 |
| 369 | 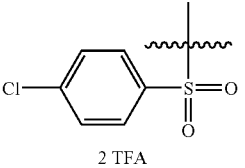<br>2 TFA | 596 | 607 |
| 370 | 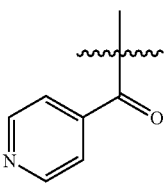<br>3 TFA | 597 | 538 |
| 371 | 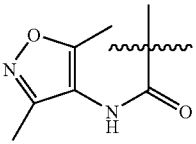<br>2 TFA | 598 | 571 |
| 372 | 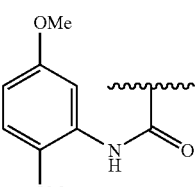<br>2 TFA | 599 | 612 |
| 373 | 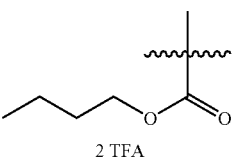<br>2 TFA | 600 | 533 |
| 374 | 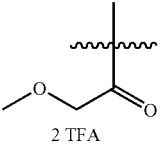<br>2 TFA | 601 | 505 |
| 375 | 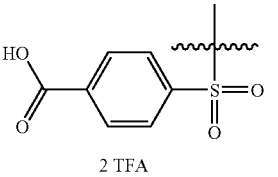<br>2 TFA | 602 | 617 |

TABLE 26-continued

| EXAMPLE # | R$^{2A}$ | COMPOUND # | MH$^+$ |
|---|---|---|---|
| 376 | 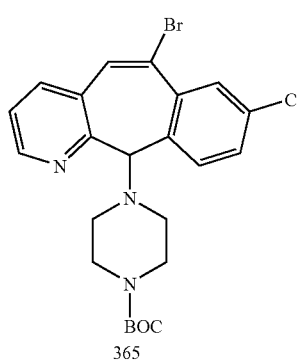 2 TFA | 603 | 617 |
| 377 | (3,4-dichlorobenzoyl group) 2 TFA | 604 | 605 |

PREPARATIVE EXAMPLE 50

Step A

Compound (605) wherein R$^1$=H or Compounds (606) and (607)/(608) wherein R$^1$=(2 or 4/5)CH$_3$.

Step B

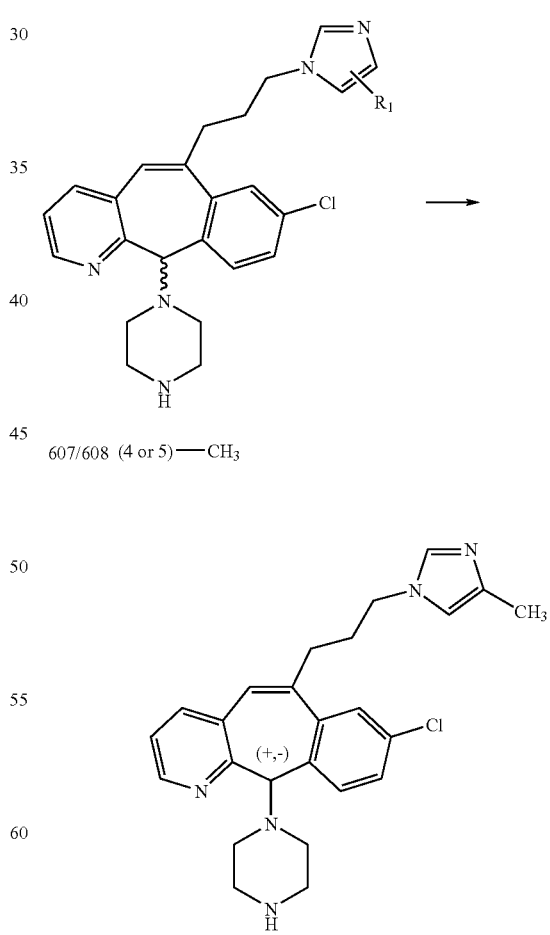

607/608 (4 or 5)—CH$_3$ 605 (R$^1$=H); (606) or
607/608 (R$^1$=(2 or 4/5)—CH$_3$)

Compound (365) from Preparative Example 41 was reacted in essentially the same manner as in Preparative Example 4, substituting the appropriate imidazole to obtain 607a & 607b -continued

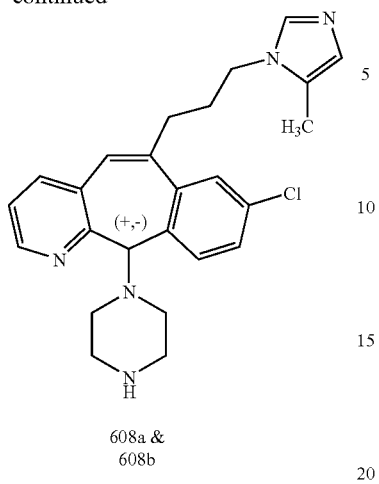

608a & 608b

Compounds (607) and (608) from Step A above were treated in the same manner as described in Example 11 to afford pure (+,−) 4-methylimidazole, and pure (+,−) 5-methylimidazole enantiomers; Compound (607a),(607b) and Compound (608a), (608b) respectively.

A library of compounds was prepared by the method described above starting with Compound (605), Compound (606), Compounds (607)/(608), (607a), (607b) or Compounds (608a) or (608b) used as the templates in Scheme A.

A generic structure of these compounds is shown in FIG. 2 above. The $R^{1A}$ group on the imidazole ring can be H or $CH_3$, the $R^{2A}$ on N-1 of the piperazine is varied in the library. Library compounds prepared in this fashion are shown in Table 27, Table 28 and Table 29.

EXAMPLES (378)-(396)

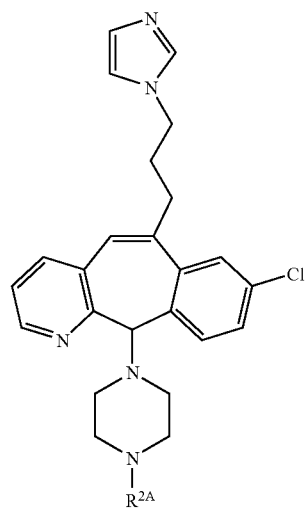

($R^{2A}$ is defined in Table 27).

TABLE 27

| EXAMPLE # | $R^{2A}$ | COMPOUND # | PHYSICAL DATA (MH+) |
|---|---|---|---|
| 378 | NC-C6H4-NH-C(O)- | 607 | 564 |
| 379 | NC-C6H4-NH-C(O)- | 608 1st Enantiomer | 564 |
| 380 | NC-C6H4-NH-C(O)- | 609 2nd Enantiomer | 564 |
| 381 | F,F-C6H3-NH-C(O)- | 610 | 575 |

TABLE 27-continued

| EXAMPLE # | R^{2A} | COMPOUND # | PHYSICAL DATA (MH+) |
|---|---|---|---|
| 382 | 4-methylphenyl-NH-C(O)- | 611 | 553 |
| 383 | 3-cyanophenyl-NH-C(O)- | 612 | 564 |
| 384 | 3-cyanophenyl-NH-C(O)- | 613 | 564 |
| 385 | Boc-C(CH3)2- | 614 | 520 |
| 386 | Boc-C(CH3)2- | 615 1st Isomer | 520 |
| 387 | Boc-C(CH3)2- | 616 2nd Isomer | 520 |
| 388 | 4-fluorophenyl-O-C(O)- ; 3 TFA | 617 | 558 |
| 389 | 4-fluorophenyl-NH-C(O)- ; 3 TFA | 618 | 557 |
| 390 | cyclohexyl-NH-C(O)- | 619 | 545 |
| 391 | cyclohexyl-NH-C(O)- | 620 1st Isomer | 545 |

TABLE 27-continued
| EXAMPLE # | R²ᴬ | COMPOUND # | PHYSICAL DATA (MH+) |
|---|---|---|---|
| 392 | (cyclohexyl-NH-C(O)-C(CH₃)₂-) | 621 2nd Isomer | 545 |
| 393 | (4-Cl-phenyl-NH-C(O)-C(CH₃)₂-) 3 TFA | 622 | 573 |
| 394 | (pyridine N-oxide-4-CH₂-C(O)-) | 623 | 555 |
| 395 | (phenyl-CH₂CH₂-NH-C(O)-C(CH₃)₂-) 3 TFA | 624 | 567 |
| 396 | H 4 TFA | 625 | 420 |
EXAMPLES 397-401
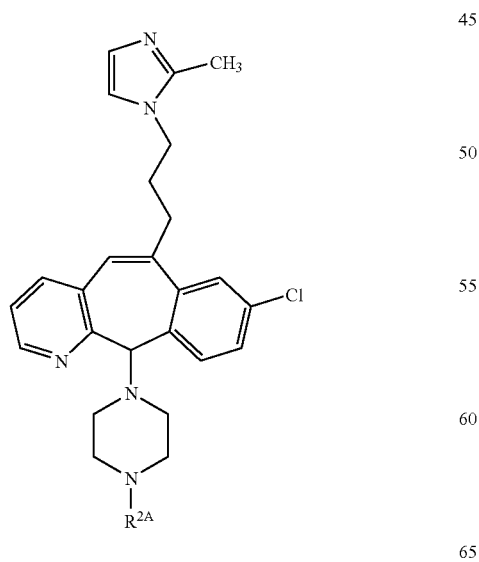
(R²ᴬ is defined in Table 28)

TABLE 28
| EXAMPLE # | R² | COMPOUND # | PHYSICAL DATA |
|---|---|---|---|
| 397 | NC—⟨C₆H₄⟩—NH—C(O)—C(CH₃)₂— | 626 2 Isomers | Mass spec. MH+ = 578 |
| 398 | NC—⟨C₆H₄⟩—NH—C(O)—C(CH₃)₂— 3 TFA | 627 2ⁿᵈ Enantiomer | Mass spec. MH+ = 578 |
| 399 | NC—⟨C₆H₄⟩—NH—C(O)—C(CH₃)₂— | 628 2ⁿᵈ Enantiomer | Mass spec. MH+ = 578 |
| 400 | NC—⟨C₆H₄⟩—NH—C(O)—C(CH₃)₂— | 629 1ˢᵗ Enantiomer | Mass spec. MH+ = 578 |
| 401 | Boc— | 630 2 Isomers | Mass spec. MH+ = 534 |
EXAMPLES 402-406
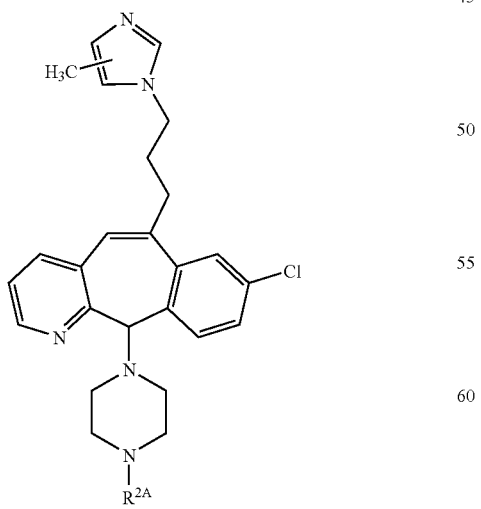
($R^{2A}$ is defined in Table 29).

TABLE 29

| EXAMPLE # | R² | COMPOUND # | PHYSICAL DATA |
|---|---|---|---|
| 402 | 4-NC-C6H4-NH-C(=O)-CH(Me)- (structure) | 631 Mixture of 4-Me and 5-Me | Mass spec. MH+ = 578 |
| 403 | 4-NC-C6H4-NH-C(=O)-CH(Me)- (structure) | 632 2nd enantiomer of 4-Me | Mass spec. MH+= 578 |
| 404 | 4-NC-C6H4-NH-C(=O)-CH(Me)- (structure) | 633 2nd enantiomer of 5-Me 1st enantiomer of 4-Me | Mass spec. MH+ = 578 |
| 405 | 4-NC-C6H4-NH-C(=O)-CH(Me)- (structure) | 634 1st enantiomer of 5-Me | Mass spec. MH+ = 578 |
| 406 | Boc- | 635 Mixture of 4-Me and 5-Me | Mass spec. MH+=534 |

PREPARATIVE EXAMPLE 51

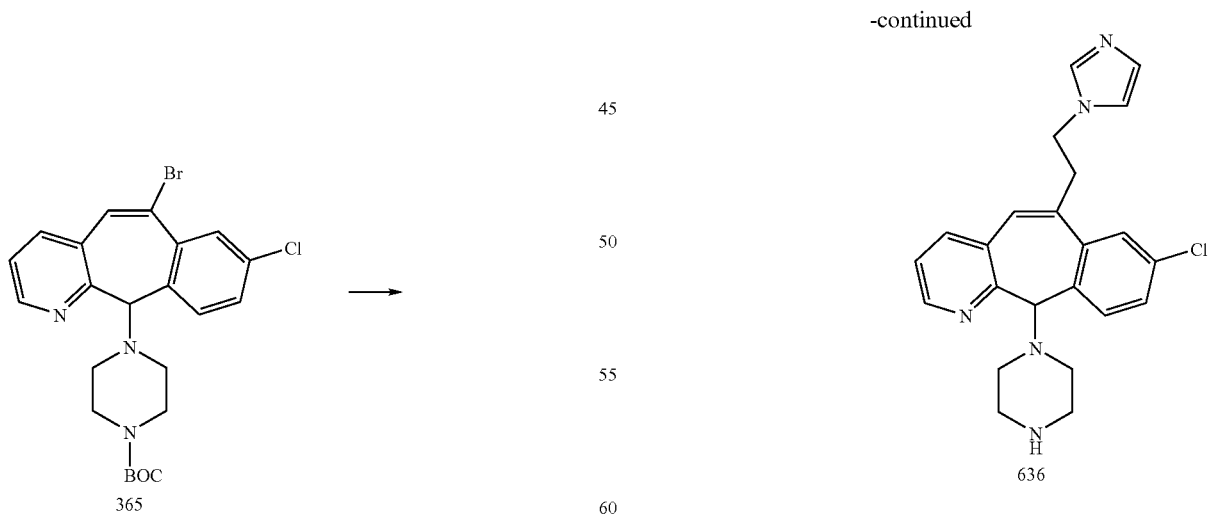

Compound (365) from Preparative Example 41, was reacted in essentially the same manner as Preparative Example 35 substituting Imidazole for 1-Methyl Imidazole in Step B to afford Compound (636) (MH⁺=406). Compound (636) was then reacted in the library fashion as described above following the procedure of Scheme A to afford the compounds in Table 30 below:

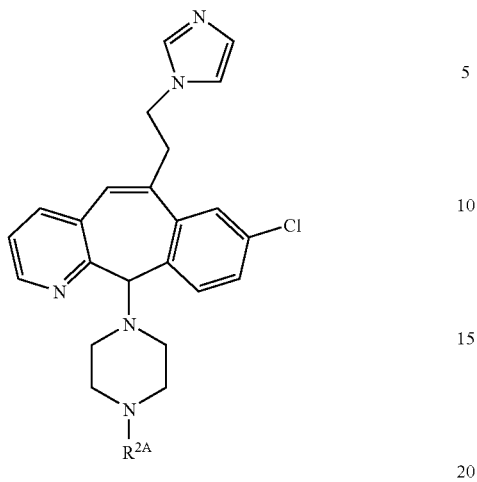
($R^{2A}$ is defined in Table 30).
TABLE 30
| EXAMPLE # | R² | COMPOUND # | PHYSICAL DATA |
|---|---|---|---|
| 407 | NC-C₆H₄-NH-C(O)- | 637 | Mass spec. MH+ = 550 |
| 408 | NC-C₆H₄-NH-C(O)- | 638 2ⁿᵈ Enantiomer | Mass spec. MH+ = 550 |
| 409 | NC-C₆H₄-NH-C(O)- | 639 1ˢᵗ Enantiomer | Mass spec. MH+ = 550 |
| 410 | Boc- | 640 | Mass spec. MH+ = 506 |
PREPARATIVE EXAMPLE 52
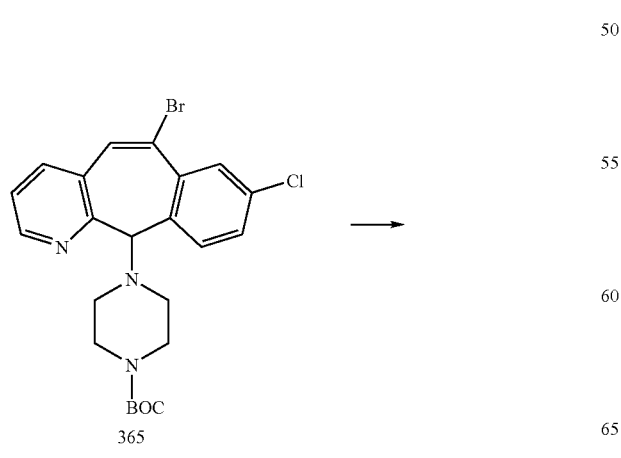
365
-continued
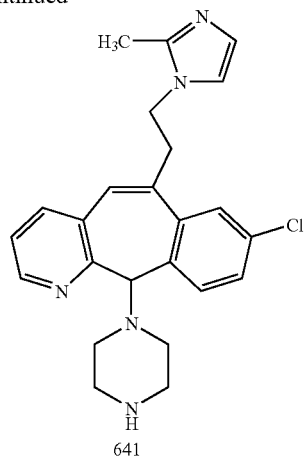
641

Compound (365) was reacted as above in Preparative Example 51, substituting 1-Methyl Imidazole for Imidazole to afford Compound (641) (MH+=420). Compound (641) was then further reacted in the Library fashion described above following the procedure in Scheme A to afford the compounds in Table 31 below.

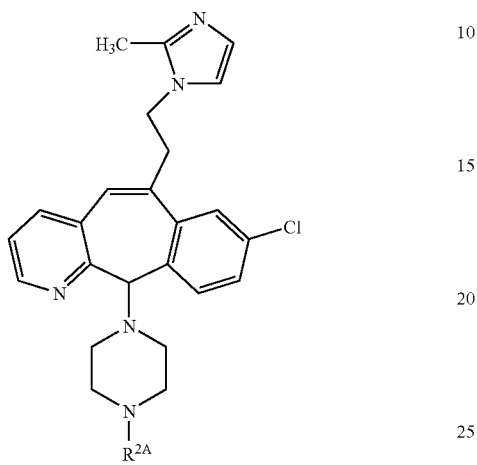

($R^{2A}$ is defined in Table 31).

TABLE 31

| EXAMPLE # | $R^2$ | COMPOUND # | PHYSICAL DATA |
|---|---|---|---|
| 411 | Boc— | 642 | Mass spec. MH$^+$ = 520 |
| 412 | NC—C$_6$H$_4$—NHC(O)— <br> 3 TFA | 643 | Mass spec. MH$^+$ = 564 |
| 413 | NC—C$_6$H$_4$—NHC(O)— | 644 <br> 1$^{st}$ Enantiomer | Mass spec. MH$^+$ = 564 |
| 414 | NC—C$_6$H$_4$—NHC(O)— | 645 <br> 2$^{nd}$ Enantiomer | Mass spec. MH$^+$ = 564 |

EXAMPLE 415

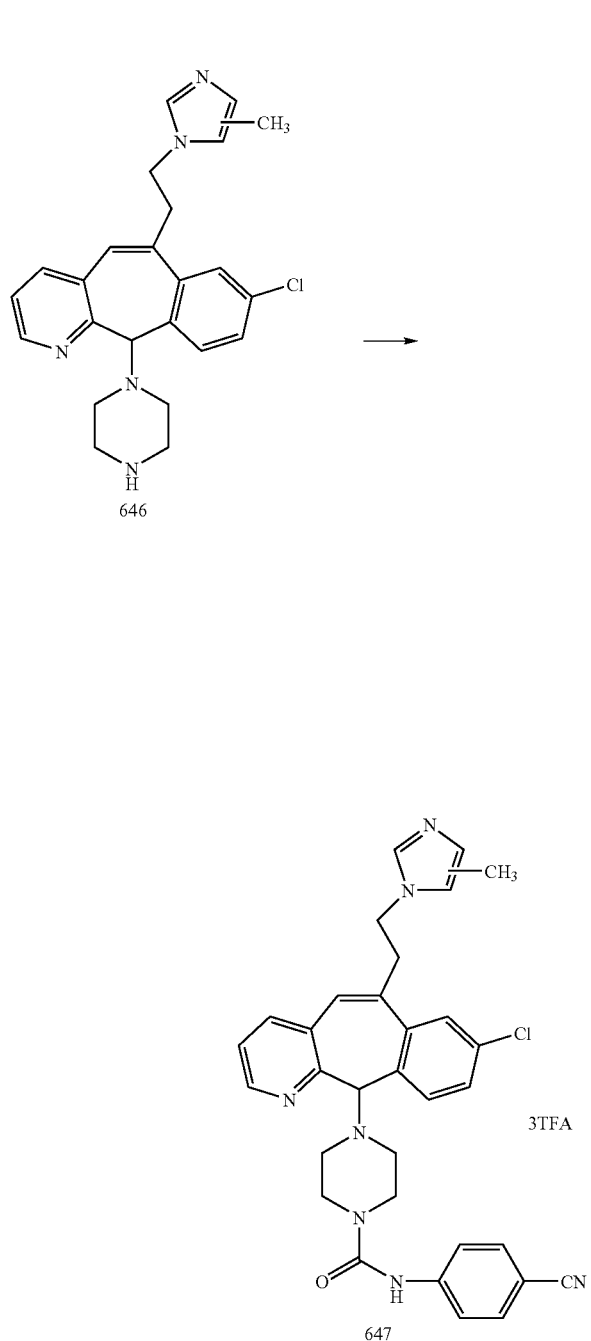

PREPARATIVE EXAMPLE 53

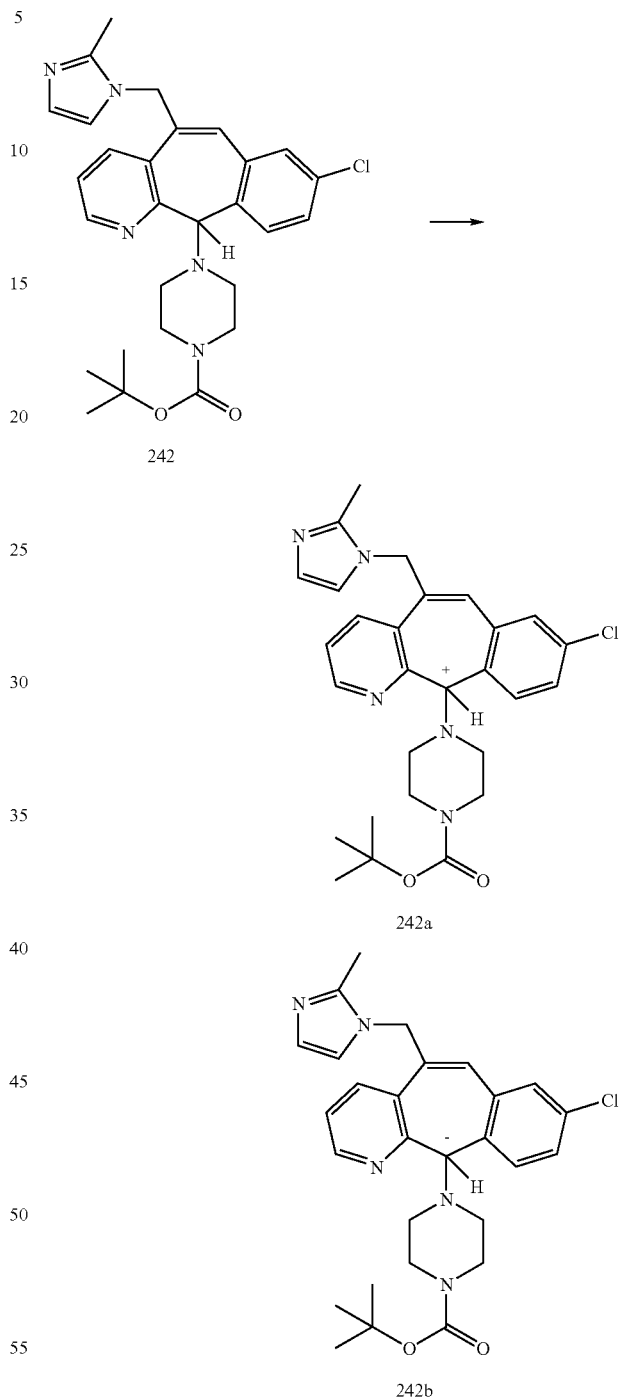

In the essentially the same manner as in Preparative Example 52 above, substituting 4-methylimidazole, the intermediate amine template was prepared Compound (646). This was then reacted in essentially the same manner as in Examples 411-414 above to afford the product Compound (647) as a mixture of 4 and 5-methylimidazole isomers (Mass spec. MH$^+$=564).

The racemic Compound (242) from Example 91 was separated by preparative chiral chromatography (Chiralpack AD, 5 cm×50 cm column, flow rate 100 mL/min., 20% 2-propanol/hexane+0.2% diethylamine) to afford the two enantiomers (242a) and (242b).

Compound (242a), $[\alpha]_D^{25}$=+144.8° (3.16 mg/2 mL MeOH)
Compound (242b), $[\alpha]_D^{25}$=−144.8° (2.93 mg/2 mL MeOH)

PREPARATIVE EXAMPLE 54

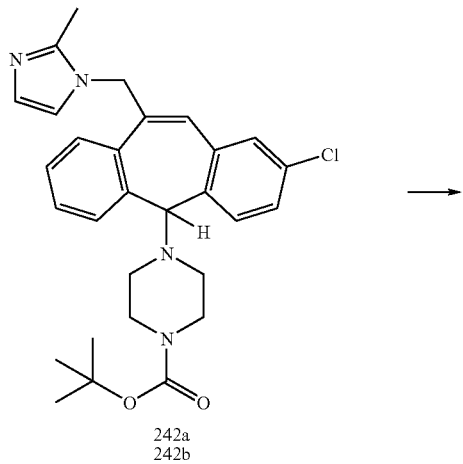

242a
242b

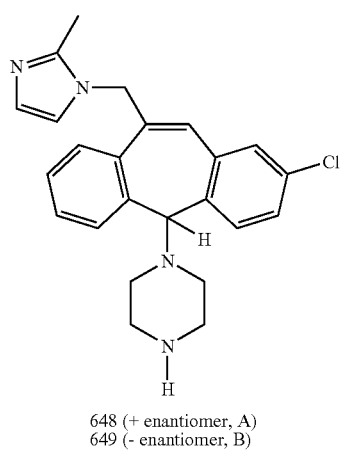

648 (+ enantiomer, A)
649 (− enantiomer, B)

Compounds (242a) and (242b) from Preparative Example 53 above were reacted separately in essentially the same manner as Preparative Example 19, Step D to obtain the hydrochloride salt of compounds Compound (648) and Compound (649).

(648) (+ enantiomer, isomer A), MH+=406.1793

(649) (− enantiomer, isomer B), MH+=406.1789

PREPARATIVE EXAMPLE 55

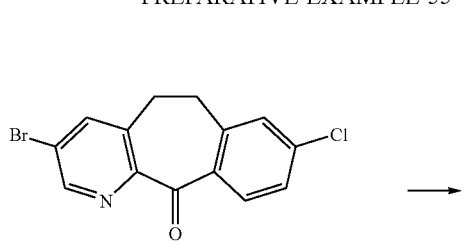

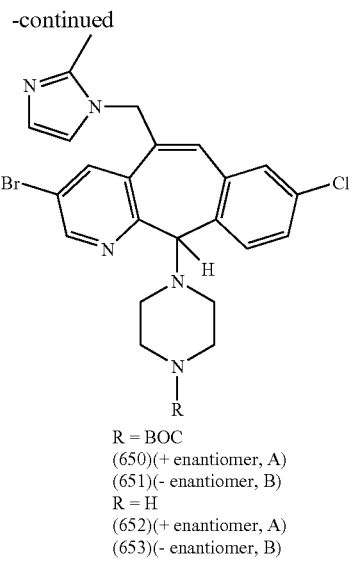

R = BOC
(650)(+ enantiomer, A)
(651)(− enantiomer, B)
R = H
(652)(+ enantiomer, A)
(653)(− enantiomer, B)

3-bromo-8-chloroazaketone (U.S. Pat. No. 5,977,128, Preparative Example 11, step A, (1999)) was reacted in essentially the same manner as in Preparative Example 23, and Example 91 to obtain the N-BOC derivatives (650) and (651). Compounds (650) and (651) were then reacted separately in essentially the same manner as in Preparative Example 19, Step D to obtain the enantiomers (652) (+ enantiomer, isomer A) and (653) (− enantiomer, isomer B).

Compound (650), BOC derivative, $[\alpha]_D^{25}=+69.6°$ (2.5 mg/2 mL MeOH)

Compound (651), BOC derivative, $[\alpha]_D^{25}=-90.0°$ (3.3 mg/2 mL MeOH)

Compound (652) (+ enantiomer, isomer A), MH+=485

Compound (653) (− enantiomer, isomer B), MH+=485

PREPARATIVE EXAMPLE 56

Step A

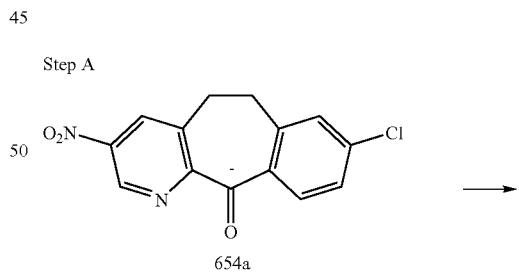

654a

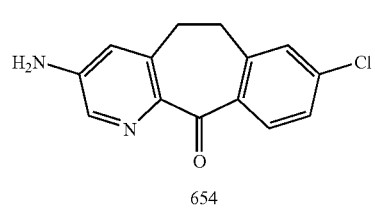

654

Compound (654a) (202 g; 0.7 mole) (J. Org. Chem. 1998, 63, 445) was dissolved in ethanol (5 L). To this mixture was added 12 N HCl (80 ml) and iron powder (180 g) and the reaction was refluxed over night. Additional HCl and iron was added to complete the reaction. The reaction mixture was filtered and the precipitate washed with hot methanol (1L). The filtrate was concentrated under vacuum to approximately 600 ml then partitioned between 4 L $CH_2CL_2$ and 1.3 L of 1.3 N NaOH. The organic layer was dried over $MgSO_4$ and filtered hot. The filtrate was concentrated under vacuum to give the aminoketone Compound (654) (184 g).

Step B

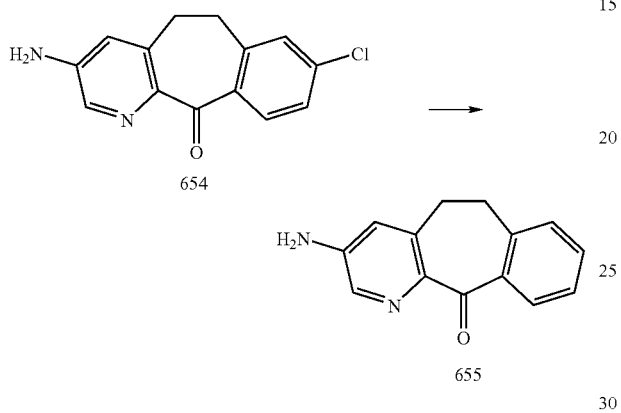

Compound (654) from Step A above (15 g; 57.98 mmol), was dissolved in 750 mL of ethanol containing 3.75 g of 5% Pd/C (50% in water) and 37.69 g (579.82 m mol) of ammonium formate. The mixture was brought to reflux for 2.5 hr then stirred at room temperature overnight. The reaction was filtered concentrated under vacuum and chromatographed on silica gel using 95:5 methylene chloride (saturated with ammonia) and methanol to give 6.15 g of the pure product Compound (655) as a yellow solid.

Step C

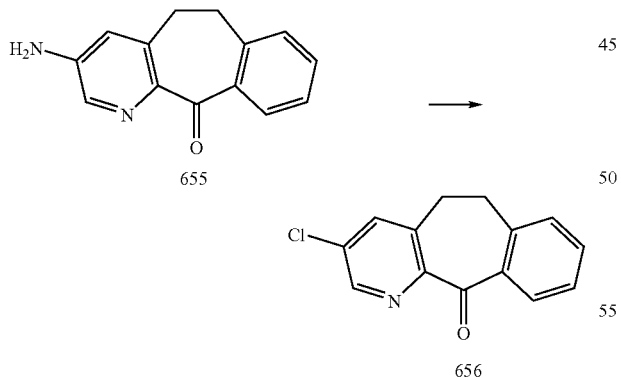

To a slurry of Compound (655) (4.79 g; 21.37 mmol) from Step A above, in 75 mL of acetonitrile cooled to 0° C. and under nitrogen, was added t-butylnitrite (10.31 g; 32.05 mmol) and $CuCl_2$ (3.45 g; 24.64 mmol). The mixture was warmed to room temp stirred over night and then concentrated under vacuum. The residue was slurried in 30 mL of 1N HCl, then neutralized with aqueous $NH_4OH$ and extracted with 3×100 mL of ethyl acetate. The organic layer was dried over $Na_2SO_4$, concentrated under vacuum, and chromatographed on silica gel using hexane:ethyl acetate (70:30) to obtain the pure product Compound (656).

Step D

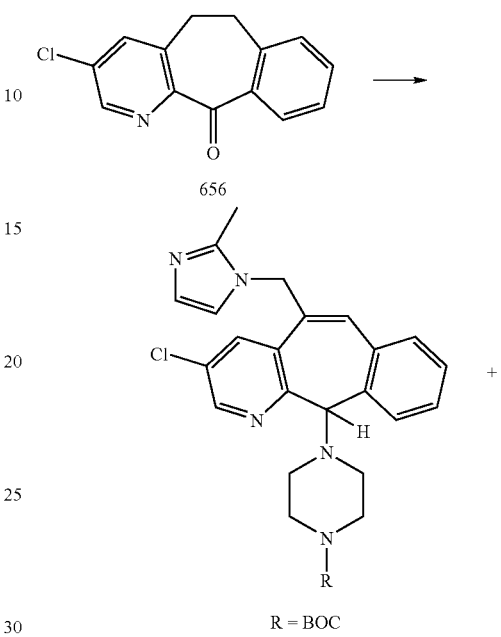

R = BOC
(657) (+ enantiomer, A)
(658) (- enantiomer, B)

R = H
(659) (+ enantiomer, A)
(660) (- enantiomer, B)

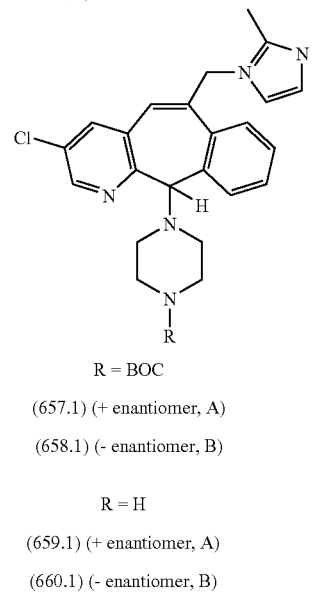

R = BOC
(657.1) (+ enantiomer, A)
(658.1) (- enantiomer, B)

R = H
(659.1) (+ enantiomer, A)
(660.1) (- enantiomer, B)

Compound (656) from Step B above was reacted in essentially the same manner as in Preparative Example 23, and then Example 91 to obtain the N-BOC derivatives (657), (658), (657.1) and (658.1). Compounds (657), (658), (657.1) and (658.1) were then reacted separately in essentially the same manner as in Preparative Example 19, Step D to obtain the enantiomers (659) (+ enantiomer, isomer A), (659.1) (+ enantiomer, isomer A), (660) (− enantiomer, isomer B) and (660.1) (− enantiomer, isomer B).
Compound (657), BOC derivative, $[\alpha]_D^{25}$=+59.9° (3.3 mg/2 mL MeOH)
Compound (658), BOC derivative, $[\alpha]_D^{25}$=−57.1° (3.3 mg/2 mL MeOH)
Compound (659), (+ enantiomer, isomer A), MH+=406
Compound (660), (− enantiomer, isomer B), MH+=406
Compound (659.1), (+ enantiomer, isomer A), MH+=406
Compound (660.1), (− enantiomer, isomer B), MH+=406

PREPARATIVE EXAMPLE 57

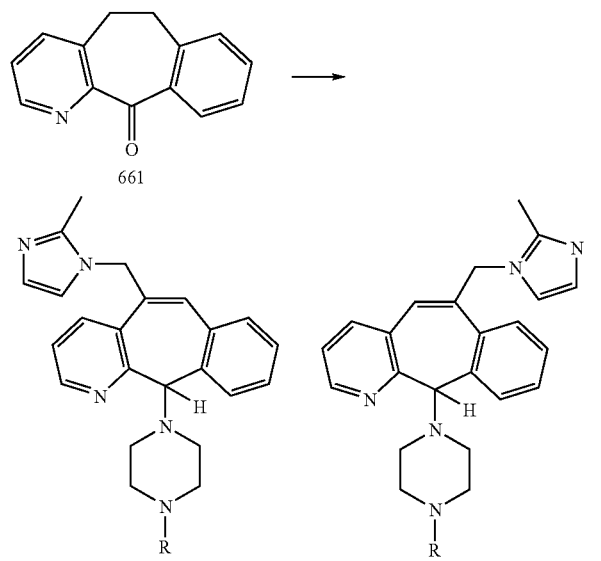

R = BOC
(662) (+ enantiomer, A)    (663) (+enantiomer, A)
(664) (− enantiomer, B)    (665) (− enantiomer, B)

R = H
(666) (+ enantiomer, A)    (667) (+enantiomer, A)
(668) (− enantiomer, B)    (669) (− enantiomer, B)

Compound (661) was reacted in essentially the same manner as in Preparative Example 23, and then Example 91 to obtain the N-BOC derivatives (662), (663), (664) and (665). Compounds (662), (663), (664) and (665) were then reacted separately in essentially the same manner as in Preparative Example 19, Step D to obtain the enantiomers (666) and (667) (+ enantiomer, isomer A) and (668) and (669) (− enantiomer, isomer B). The C5 and C-6 vinyl bromide intermediates were separated by silica gel chromatography using hexane:ethyl acetate (80:20) in essentially the same manner as was described in Preparative Example 23, Step B.
Compound (662), BOC derivative
Compound (663), BOC derivative
Compound (664), BOC derivative
Compound (665), BOC derivative
Compound (666) (+ enantiomer, isomer A), MH+=372

Compound (667) (+ enantiomer, isomer A), MH+=372
Compound (668) (− enantiomer, isomer B), MH+=372
Compound (669) (− enantiomer, isomer B), MH+=372

PREPARATIVE EXAMPLE 58

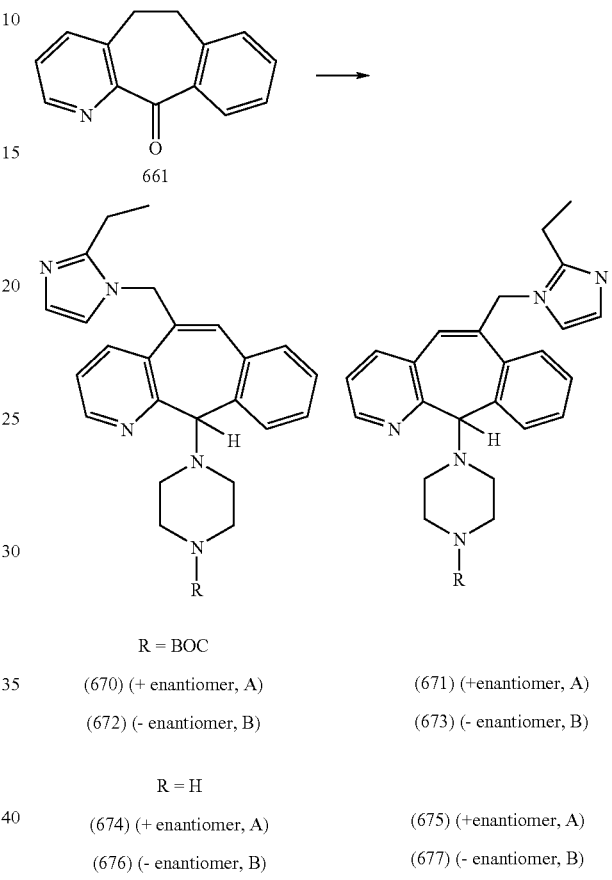

R = BOC
(670) (+ enantiomer, A)    (671) (+enantiomer, A)
(672) (− enantiomer, B)    (673) (− enantiomer, B)

R = H
(674) (+ enantiomer, A)    (675) (+enantiomer, A)
(676) (− enantiomer, B)    (677) (− enantiomer, B)

Compound (661) was reacted in essentially the same manner as in Preparative Example 23, and Example 91 substituting 2-ethylimidazole for 2-methylimidazole, to obtain the N-BOC derivatives (670), (671), (672) and (673). Compounds (670), (671), (672) and (673) were then reacted separately in essentially the same manner as in Preparative Example 19, Step D, to obtain the enantiomers (674) and (675) (+ enantiomer, isomer A) and (676) and (677) (− enantiomer, isomer B). The C5 and C-6 vinyl bromide intermediates were separated by silica gel chromatography using hexane:ethyl acetate (80:20) as described in Preparative Example 23, Step B.
Compound (670), BOC derivative, (+ enantiomer, A)
Compound (671), BOC derivative, (+ enantiomer, A)
Compound (672), BOC derivative, (− enantiomer, B)
Compound (673), BOC derivative, (− enantiomer, B)
Compound (674), (+ enantiomer, isomer A), MH+=386
Compound (675), (+ enantiomer, isomer A), MH+=386
Compound (676), (− enantiomer, isomer B), MH+=386
Compound (677), (− enantiomer, isomer B), MH+=386

EXAMPLES 416-419

Compound (648)
Compound (649) →

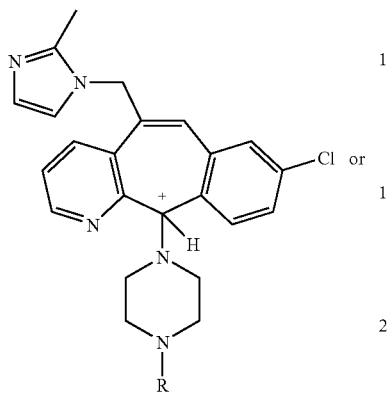

or

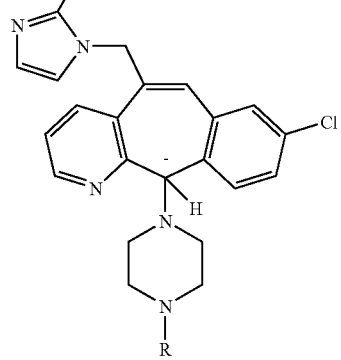

(R is defined in Table 32).

The appropriate (+) enantiomer (648) or (−) enantiomer (649) from Preparative Example 54 above, was taken up in CH$_2$Cl$_2$ treated with the corresponding isocyanate and stirred at room temperature over night. The crude product was purified directly by silica gel preparative thin layer chromatography or silica gel column chromatography to afford the following compounds in Table 32 below.

TABLE 32

| Example # | R | Enantiomer | Comp # | Phys. Data. |
|---|---|---|---|---|
| 416 | NC-C$_6$H$_4$-NHC(O)- | + | 678 | Mp = 162.2–165.6° C. [α]$_D^{25}$ = +98.2° (3 mg/ 2 mL MeOH) |
| 417 | NC-C$_6$H$_4$-NHC(O)- | − | 679 | Mp = 158.1-164.5° C. [α]$_D^{25}$ = −81.2° (2.6 mg/ 2 mL MeOH) |
| 418 | Cl-C$_6$H$_4$-NHC(O)- | + | 680 | Mp = 161.5–164.8° C. MH+ = 559.1787 |
| 419 | F-C$_6$H$_4$-NHC(O)- | + | 681 | Mp 157.7–161.7° C. MH+ = 543.2069 |

EXAMPLES 420 AND 421

Compound (652)
Compound (653) →

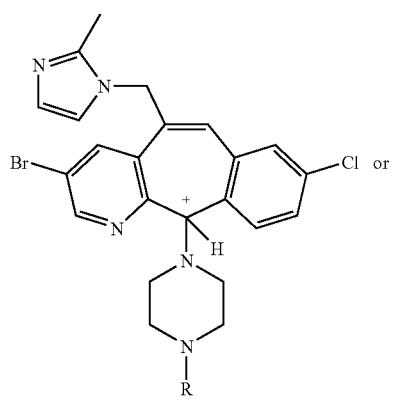

or

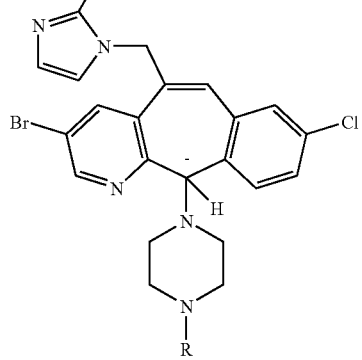

(R is defined in Table 33).

The appropriate (+) enantiomer (652) or (−) enantiomer (653) from Preparative Example 55 above, was taken up in $CH_2Cl_2$ treated with the corresponding isocyanate and stirred at room temperature over night. The crude product was purified directly by silica gel preparative thin layer chromatography or silica gel column chromatography to afford the following compounds in Table 33 below.

TABLE 33

| Example # | R | Enantiomer | Comp # | Phys. Data. |
|---|---|---|---|---|
| 420 | NC-C₆H₄-NH-C(=O)- | + | 682 | Mp = 168.8–172.3° C. |
| 421 | NC-C₆H₄-NH-C(=O)- | − | 683 | Mp = 172.5–177.7° C. |
| 421.1 | F₃CO-C₆H₄-NH-C(=O)- | + | 683.1 | Mp = 157.1–160.5° C. (dec) |
| 421.2 | HO-C₆H₄-NH-C(=O)- | + | 683.2 | Mp = 223.6–229.1° C. (dec) |

EXAMPLES 422 AND 423

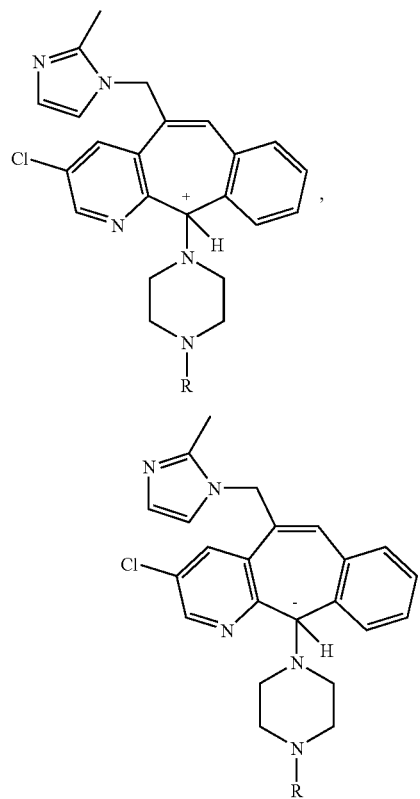

or

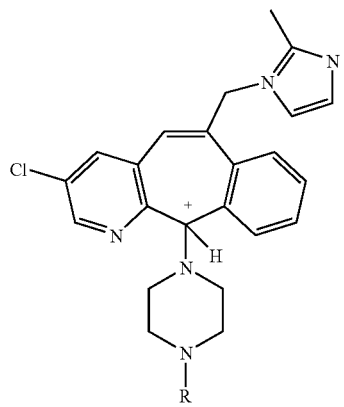

(R is defined in Table 34).

The appropriate compound (659) (+) enantiomer, (660) (−) enantiomer or (659A) (+) enantiomer from Preparative Example 56 above, was taken up in $CH_2Cl_2$ treated with the corresponding isocyanate and stirred at room temperature over night. The Crude product was purified directly by silica gel preparative thin layer chromatography or silica gel column chromatography to afford the following compounds in Table 34 below.

TABLE 34

| Example # | R | Enantiomer | Comp # | Phys. Data. |
|---|---|---|---|---|
| 422 | NC-C₆H₄-NHC(O)- | + | 684 | Mp = 155.9–165.1° C. |
| 423 | NC-C₆H₄-NHC(O)- | − | 685 | Mp = 154.2–164.8° C. |
| 492 | NC-C₆H₄-NHC(O)- | + | 806 | Mp = 157.1–160.5° C. $MH^+$= 689 |

EXAMPLES 424 AND 425

Compound (666) →
Compound (668)

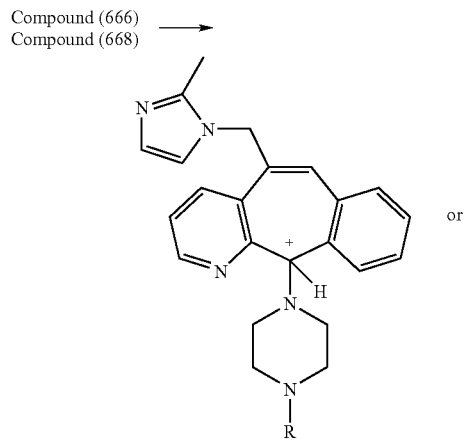

(R is defined in Table 35).

The appropriate (+) enantiomer (666) or (−) enantiomer (668) from Preparative Example 57 above, was taken up in CH$_2$Cl$_2$, treated with the corresponding isocyanate and stirred at room temperature over night. The crude product was purified directly by silica gel preparative thin layer chromatography or silica gel column chromatography to afford the following compounds in Table 35 below.

EXAMPLES 426 AND 427

Compound (674) →
Compound (676)

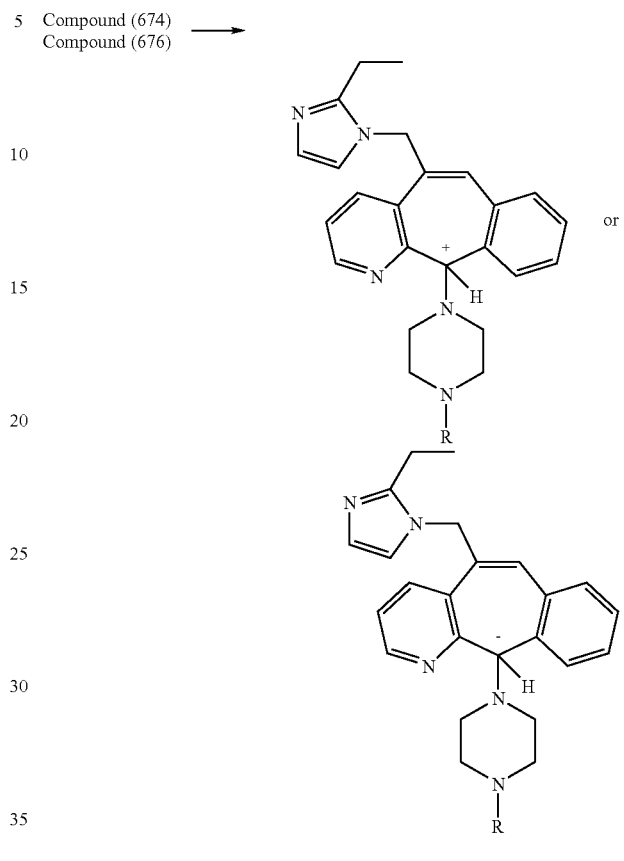

(R is defined in Table 36).

The appropriate (+) enantiomer (674) or (−) enantiomer (676) from Preparative Example 58 above, was taken up in CH$_2$Cl$_2$, treated with the corresponding isocyanate and stirred at room temperature over night. The crude product was purified directly by silica gel preparative thin layer chromatography or silica gel column chromatography to afford the following compounds in Table 36 below.

TABLE 35

| Example # | R | Enantiomer | Comp # | Phys. Data. |
|---|---|---|---|---|
| 424 | NC–C$_6$H$_4$–NH–C(O)– | + | 686 | Mp = 166–170° C. [α]$_D^{25}$ = +106.8° (1.45 mg/2 mL MeOH) |
| 425 | NC–C$_6$H$_4$–NH–C(O)– | − | 687 | Mp = 170-176° C. [α]$_D^{25}$ = −91° (2.78 mg/2 mL MeOH) |

TABLE 36

| Example # | R | Enantiomer | Comp # | Phys. Data. |
|---|---|---|---|---|
| 426 | 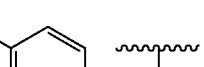 | + | 688 | Mp = 150–153° C. |
| 427 | 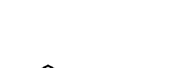 | − | 689 | Mp = 154–158° C. |

EXAMPLES 428 AND 429

Compound (667)
Compound (669) →

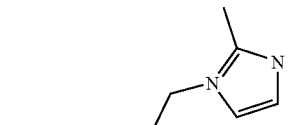

or

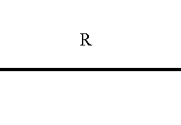

(R is defined in Table 37).

The appropriate (+) enantiomer (667) or (−) enantiomer (669) from Preparative Example 57 above, was taken up in CH$_2$Cl$_2$, treated with the corresponding isocyanate and stirred at room temperature over night. The crude product was purified directly by silica gel preparative thin layer chromatography or silica gel column chromatography to afford the following compounds in Table 37 below.

TABLE 37

| Example # | R | Enantiomer | Comp # | Phys. Data. |
|---|---|---|---|---|
| 428 |  | Isomer 1 | 690 | MH$^+$ = 516 |
| 429 |  | Isomer 2 | 691 | MH$^+$ = 516 |

EXAMPLES 430 AND 431

Compound (675)
Compound (677) →

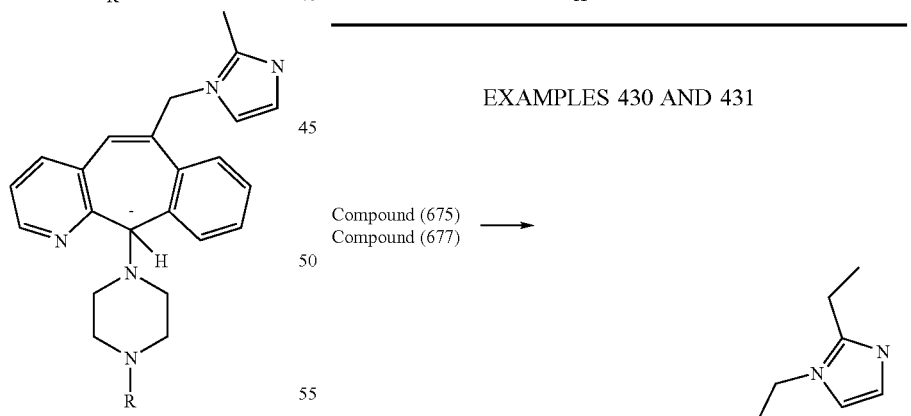

or

-continued

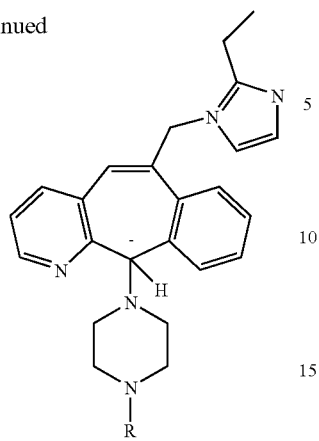

(R is defined in Table 38).

The appropriate (+) enantiomer (675) or (−) enantiomer (677) from Preparative Example 58 above, was taken up in CH$_2$Cl$_2$, treated with the corresponding isocyanate and stirred at room temperature over night. The crude product was purified directly by silica gel preparative thin layer chromatography or silica gel column chromatography to afford the following compounds in Table 38 below.

TABLE 38

| Example # | R | Enantiomer | Comp # | Phys. Data. |
|---|---|---|---|---|
| 430 | NC-C$_6$H$_4$-NHC(O)- | Isomer 1 | 692 | MH$^+$ = 530 |
| 431 | NC-C$_6$H$_4$-NHC(O)- | Isomer 2 | 693 | MH$^+$ = 530 |

PREPARATIVE EXAMPLE 59

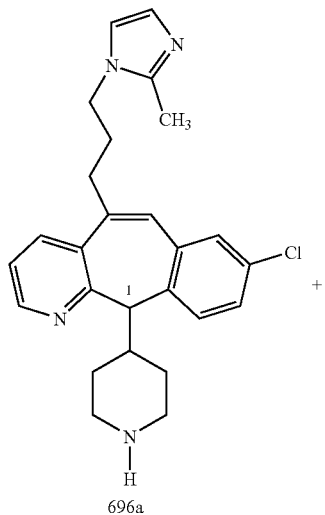
696a

+

-continued

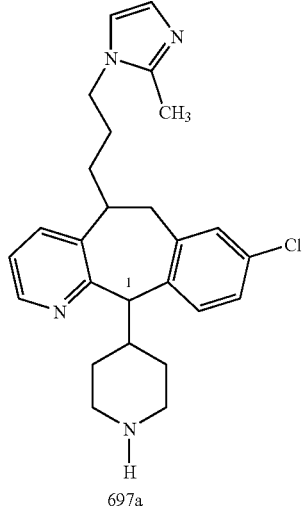
697a

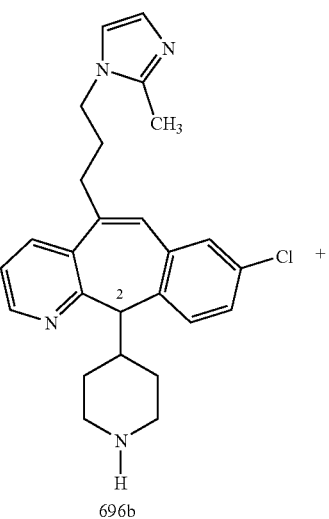
696b

+

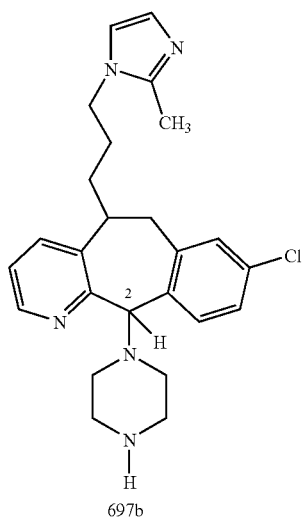
697b

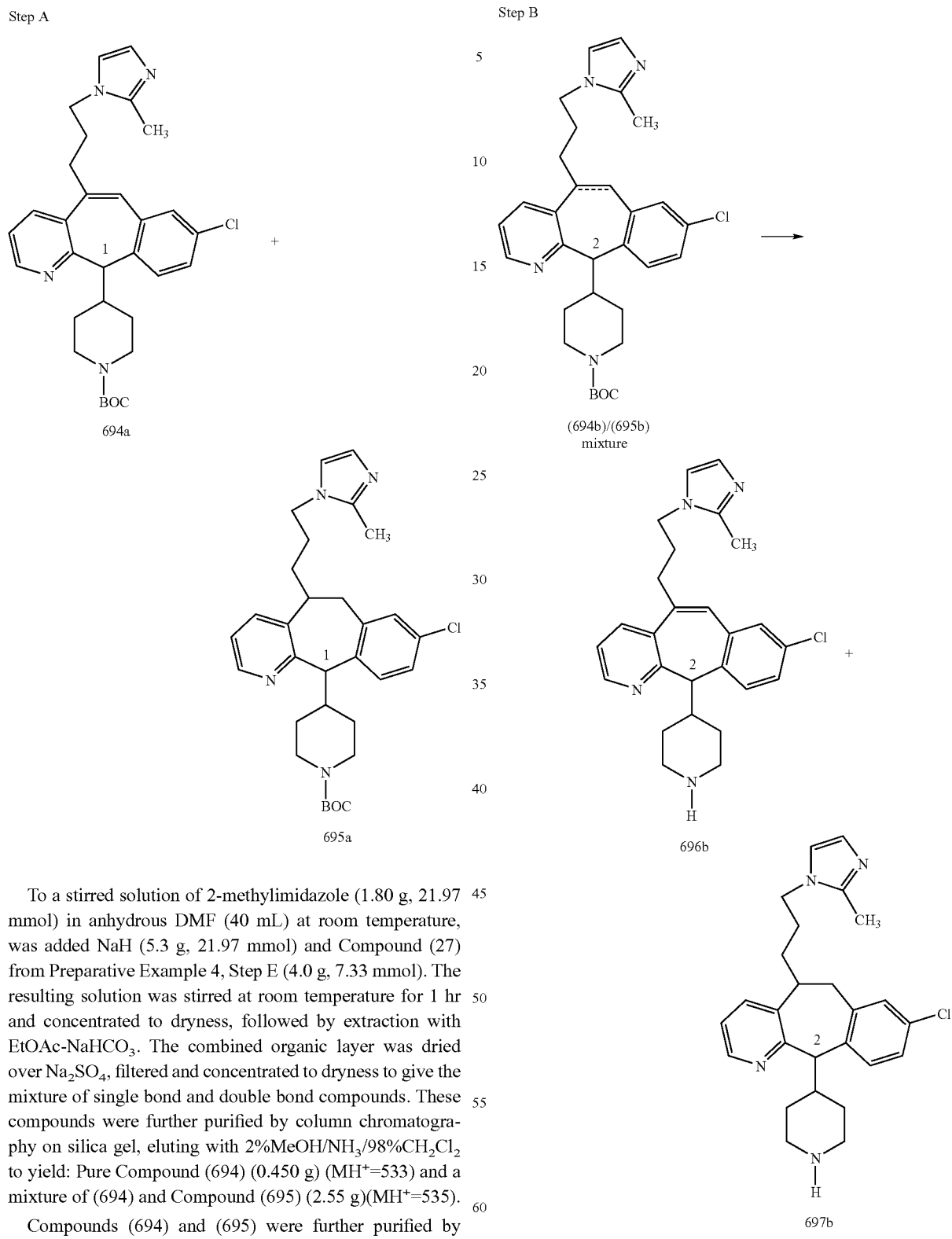

To a stirred solution of 2-methylimidazole (1.80 g, 21.97 mmol) in anhydrous DMF (40 mL) at room temperature, was added NaH (5.3 g, 21.97 mmol) and Compound (27) from Preparative Example 4, Step E (4.0 g, 7.33 mmol). The resulting solution was stirred at room temperature for 1 hr and concentrated to dryness, followed by extraction with EtOAc-NaHCO$_3$. The combined organic layer was dried over Na$_2$SO$_4$, filtered and concentrated to dryness to give the mixture of single bond and double bond compounds. These compounds were further purified by column chromatography on silica gel, eluting with 2%MeOH/NH$_3$/98%CH$_2$Cl$_2$ to yield: Pure Compound (694) (0.450 g) (MH$^+$=533) and a mixture of (694) and Compound (695) (2.55 g)(MH$^+$=535).

Compounds (694) and (695) were further purified by chiral prep HPLC, eluting with 15%IPA/85%Hexane/0.2%DEA to give: Compound (695a) (isomer 1; 0.58 g, MH$^+$=535.4) and Compound (694a) (isomer 1; 0.61 g, MH$^+$=533) and a mixture of compounds (694b) and (695b) (isomer 2 products; 0.84 g).

The mixture of compounds (694b/695b) from Step A above (0.8 g, 1.5 mmol) in 4N HCl/Dioxane (40 mL) was stirred at room temperature for 3 hrs and concentrated to dryness to give a mixture of deprotected compounds as product. The product was further purified by chiral HPLC, eluting with 15%1PA/85% hexane/0.2%DEA to give the pure compound (696b) (isomer 2; 0.29 g) and pure Compound (697b) (isomer 2, 0.19 g).

Step C

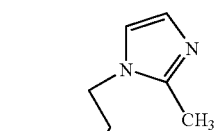

696a

+

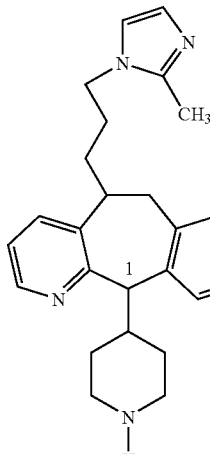

697a

Compounds (694a) and (695a) (pure isomer 1) were individually deprotected using 4N HCl/Dioxane in essentially the same method as that of the isomer 2 products described above, to give the corresponding N—H products (696a) (isomer 1) and (697a) (isomer 1).

EXAMPLES 432-437

Reacting Compound (696a) (isomer 1) in essentially the same manner as in Example 13 with the appropriate chloroformate or isocyanate, the following compounds listed in Table 39 below, were prepared.

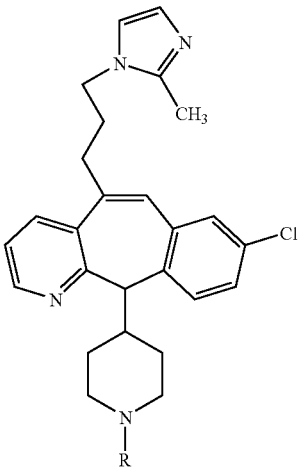

(R is defined in Table 39).

TABLE 39

| EXAMPLE # | R | COMPOUND # | PHYSICAL DATA |
|---|---|---|---|
| 432 | ![iPrOC(O)-] | 698 | MH+ = 519.1 |
| 433 | ![4-CN-C6H4-NHC(O)-] | 699 | MH+ = 577.1 |

TABLE 39-continued
| EXAMPLE # | R | COMPOUND # | PHYSICAL DATA |
|---|---|---|---|
| 434 | 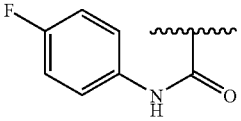 4-F-C6H4-NH-C(=O)-C(CH3)2- | 700 | MH+ = 570.1 |
| 435 | 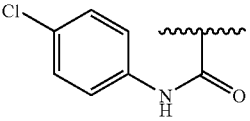 4-Cl-C6H4-NH-C(=O)-C(CH3)2- | 701 | MH+ = 585.1 |
| 436 | 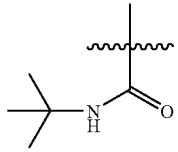 t-Bu-NH-C(=O)-C(CH3)2- | 702 | — |
| 437 | 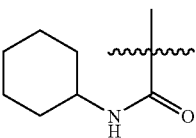 cyclohexyl-NH-C(=O)-C(CH3)2- | 703 | MH+ = 558.1 |
EXAMPLES 438-442
Reacting Compound (697a) (isomer 1) in essentially the same manner as in Example 13 with the appropriate chloroformate or isocyanate, the following compounds listed in Table 40 below were prepared.
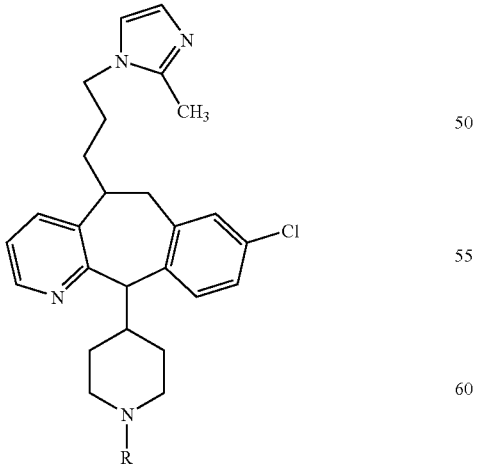
(R is defined in Table 40).

TABLE 40
| EXAMPLE # | R | COMPOUND # | PHYSICAL DATA |
|---|---|---|---|
| 438 | (isopropyl ester group) | 704 | MH+ = 521.1 |
| 439 | 4-cyanophenyl amide | 705 | MH+ = 579.1 |
| 440 | 4-fluorophenyl amide | 706 | MH+ = 572.1 |
| 441 | 4-chlorophenyl amide | 707 | MH+ = 587.1 |
| 442 | cyclohexyl amide | 708 | MH+ = 560.1 |
PREPARATIVE EXAMPLE 60
Step A
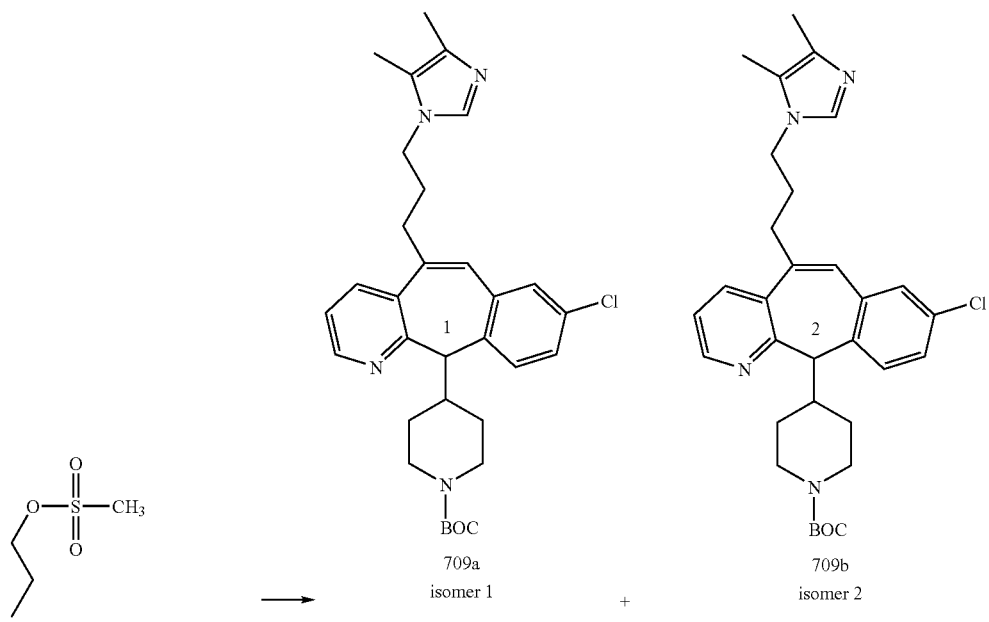
709a isomer 1 + 709b isomer 2

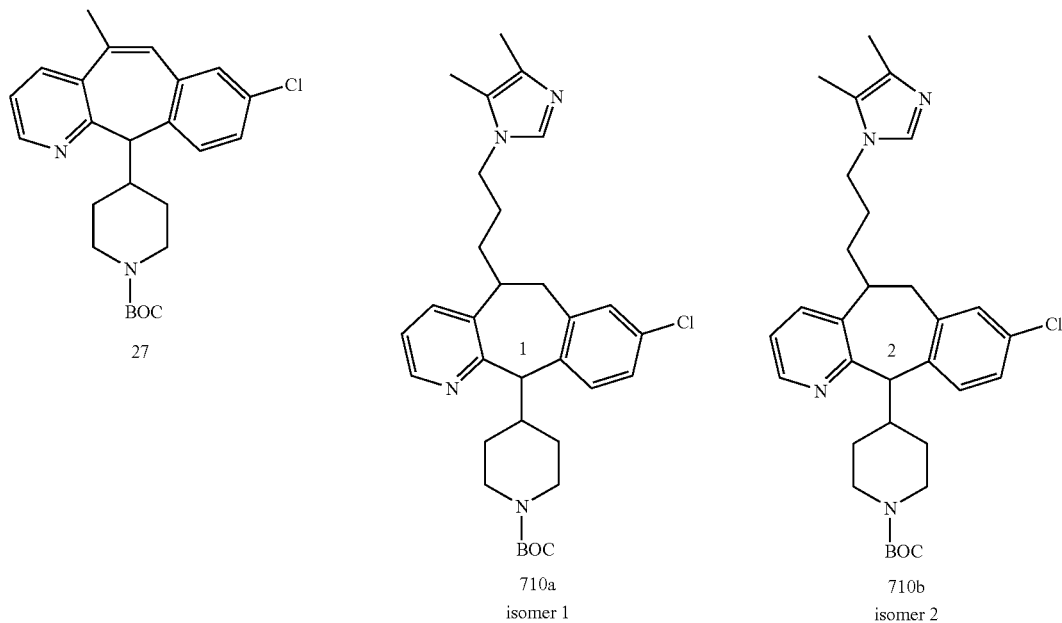

To a stirred solution of 4,5-Dimethylimidazole (1.08 g, 11.25 mmol) in anhydrous DMF (35 mL) at room temperature, was added NaH (0.27 g, 11.2 mmol) and stirred for 10 minutes, followed by the addition of Compound (27) from Preparative Example 4 Step E (4.0 g, 7.32 mmol). The resulting solution was stirred at room temperature overnight. To this solution was added the solution of 4,5-dimethylimidazole (0.35 g, 3.65 mmol) and NaH (0.088 g, 3.67 mmol) in DMF (5 mL). The resulting solution was heated at 80° C.-90° C. for 4 hrs, then cooled down to room temperature, followed by extraction with EtOAc-H$_2$O. The combined organic layer was washed with brine, dried over Na$_2$SO$_4$, filtered and concentrated to dryness and purified by column chromatography on silica gel, eluting with 50%EtOAc/50%hexane to 5%MeOH/CH$_2$Cl$_2$ to give the mixture of products Compound (709) and Compound (710) (1.2 g, MH+=547.3). The products were further purified by prep chiral HPLC, using a chiral AD column, eluting with 15%IPA/85%hexane/0.2%DEA to give 4 seperate compounds:

Compound (709a) isomer 1, (0.291 g, MH+=547.3), Compound (710a) isomer 1, (0.305 g, MH$^+$=549.3) and
Compound (709b) isomer 2, (0.280 g, MH+=547.3), Compound (710b) isomer 2, (0.2 g, MH+=549.3)

Step B

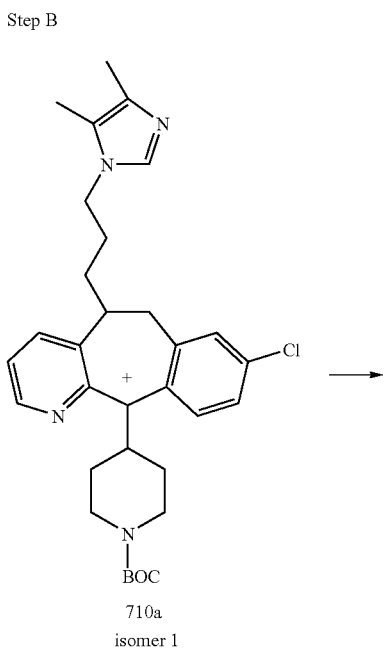

710a
isomer 1

-continued

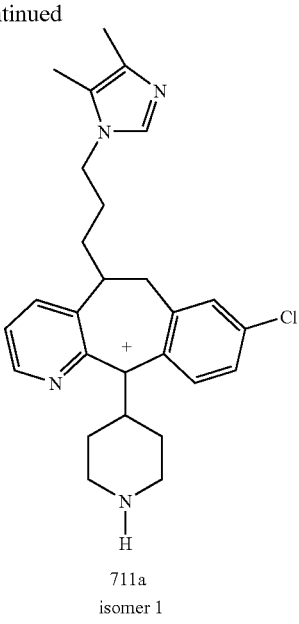

711a
isomer 1

A solution of Compound (710a), isomer 1 (0.245 g, 0.45 mmol) in 4N HCl/Dioxane (2 mL) was stirred at room temperature for 3 hrs then concentrated to dryness to give Compound (711a) isomer 1, product (0.184 g, 98% yield) (MH+=455.1).

Compounds (711b), (isomer 2); (712a) (isomer 1) and (712b) (isomer 2) were all prepared in a similar fashion to that of Compound (711a) isomer 1 in Step B above.

(711b) (0.085 g, 75% yield).

(712a) (0.141 g, 75% yield).
(712b) (0.106 g, 59% yield).

EXAMPLES 443-447

Reacting Compounds (711a) and (711b) seperately following the procedure described in Example 13 with the appropriate chloroformates or isocyanates, the following compounds listed in Table 41 below were prepared.

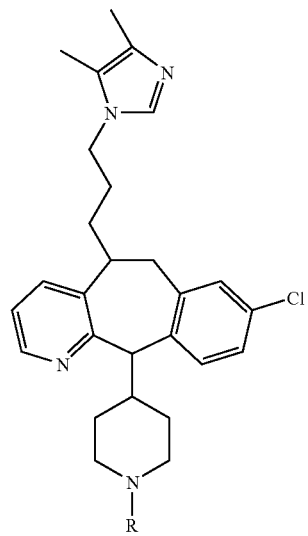

(R is defined in Table 41).

TABLE 41

| EXAMPLE # | R | COMPOUND # | PHYSICAL DATA |
|---|---|---|---|
| 443 | cyclohexyl-O-C(=O)- | 713 | MH+ = 575.1 |
| 444 | cyclohexyl-O-C(=O)- | 714 | MH+ = 575.1 |
| 445 | 4-NC-C6H4-NH-C(=O)- | 715 | MH+ = 593.2 |
| 446 | 4-NC-C6H4-NH-C(=O)- | 716 | MH+ = 593.2 |

TABLE 41-continued

| EXAMPLE # | R | COMPOUND # | PHYSICAL DATA |
|---|---|---|---|
| 447 | 4-F-C6H4-NH-C(O)-C(CH3)2- | 717 | MH+ = 586.1 |

EXAMPLES 448-454

Reacting Compounds (712a) and (712b) seperately following the procedure described in Example 13 with the appropriate chloroformates or isocyanates, the compounds listed in Table 42 below were prepared.

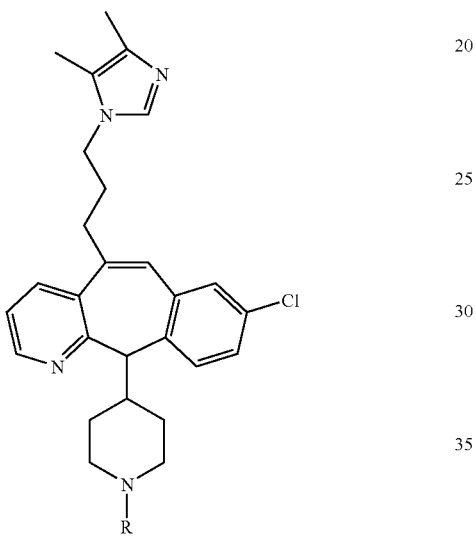

(R is defined in Table 42).

TABLE 42

| EXAMPLE # | R | COMPOUND # | PHYSICAL DATA |
|---|---|---|---|
| 448 | cyclohexyl-O-C(O)-C(CH3)2- | 718 | MH+ = 573.1 |
| 449 | cyclohexyl-O-C(O)-C(CH3)2- | 719 | MH+ = 573.1 |
| 450 | 4-NC-C6H4-NH-C(O)-C(CH3)2- | 720 | MH+ = 591.1 |

TABLE 42-continued
| EXAMPLE # | R | COMPOUND # | PHYSICAL DATA |
|---|---|---|---|
| 451 | 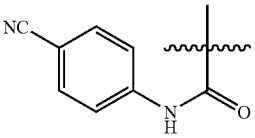 | 721 | MH+ = 591.1 |
| 452 | 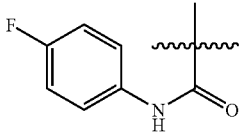 | 722 | MH+ = 584.1 |
| 453 | 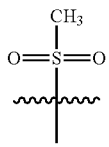 | 723 | MH+ = 525.1 |
| 454 | 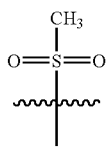 | 724 | MH+ = 525.1 |
PREPARATIVE EXAMPLE 61
Step A
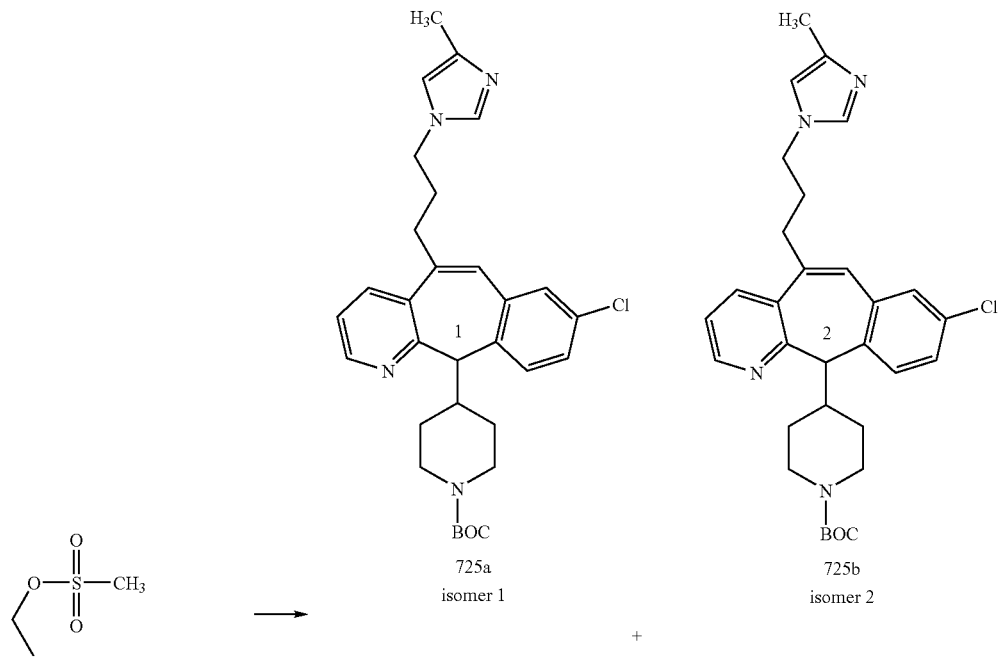

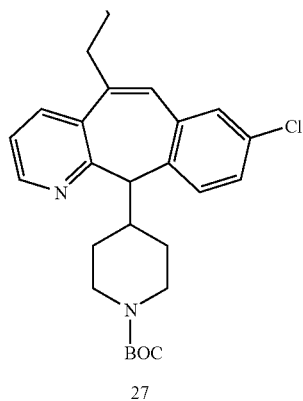

27

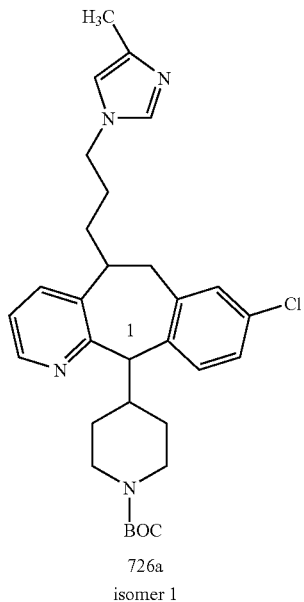

726a
isomer 1

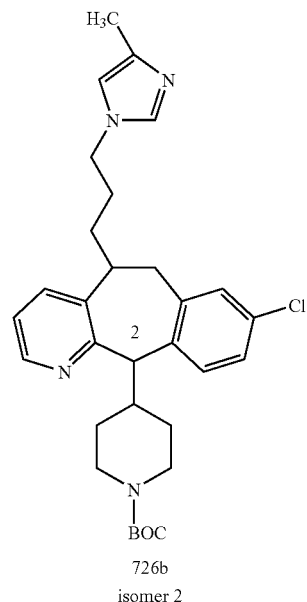

726b
isomer 2

Compound (27) from Preparative Example 4, Step E was reacted in essentially the same manner as described in Preparative Example 60, Step A above substituting 4-Methylimidazole for 4,5-Dimethylimidazole to obtain four seperate compounds as products (BOC derivatives).

Compound (725a) isomer 1, (0.69 g, MH$^+$=533.1).

Compound (725b) isomer 2, (0.10 g, MH$^+$=533.1).

Compound (726a) isomer 1, (0.35 g, MH$^+$=535.1).

Compound (726b) isomer 2, (0.22 g, MH$^+$=535.1).

Step B

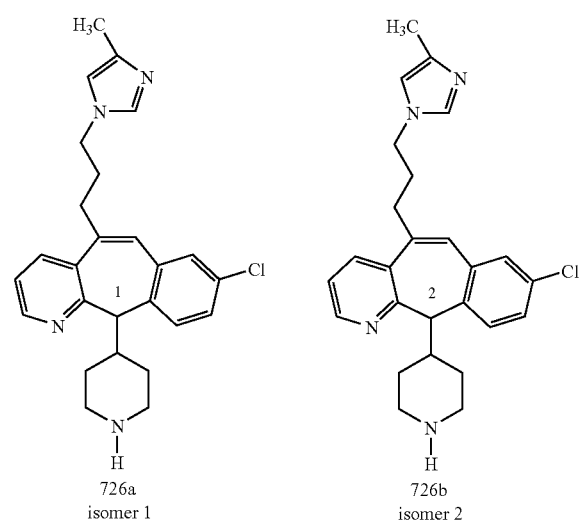

726a
isomer 1

726b
isomer 2

+

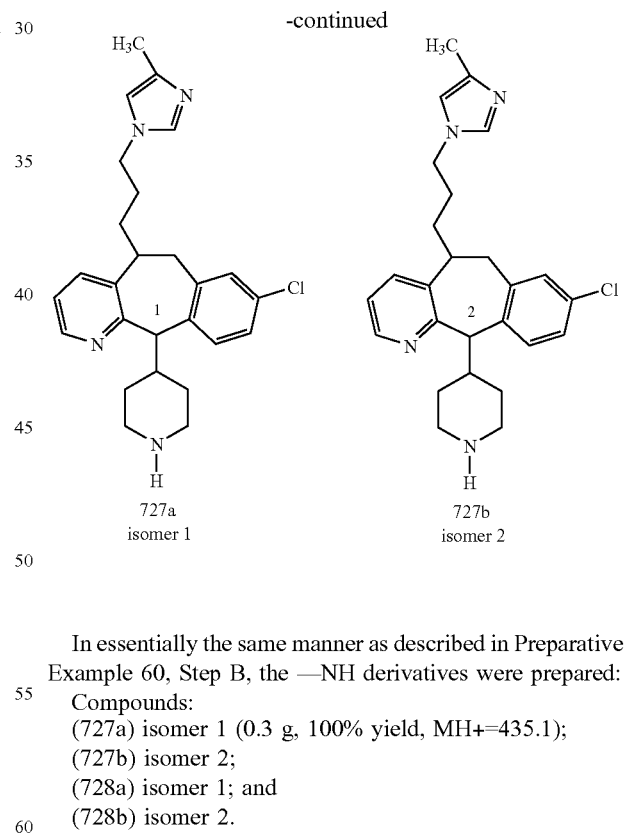

727a
isomer 1

727b
isomer 2

In essentially the same manner as described in Preparative Example 60, Step B, the —NH derivatives were prepared:

Compounds:
(727a) isomer 1 (0.3 g, 100% yield, MH+=435.1);
(727b) isomer 2;
(728a) isomer 1; and
(728b) isomer 2.

EXAMPLES 455-459

Reacting Compounds (727a) and (727b) seperately following the procedure described in Example 13 with the appropriate chloroformate or isocyanate, the following compounds listed in Table 43 below were prepared.

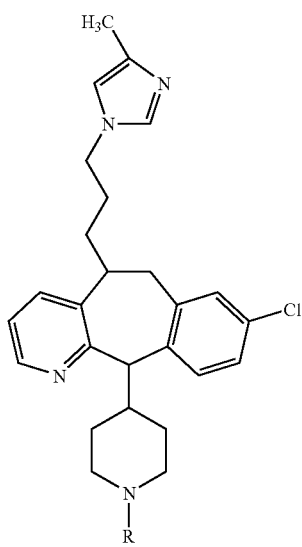

(R is defined in Table 43).

TABLE 43

| EXAMPLE # | R | COMPOUND # | PHYSICAL DATA |
|---|---|---|---|
| 455 | cyclohexyl-O-C(=O)-CH(CH₃)- | 729 | MH+ = 561.1 |
| 456 | 4-NC-C₆H₄-NH-C(=O)-CH(CH₃)- | 730 | MH+ = 581.1 |
| 457 | 4-F-C₆H₄-NH-C(=O)-CH(CH₃)- | 731 | MH+ = 572.1 |
| 458 | cyclohexyl-NH-C(=O)-CH(CH₃)- | 732 | MH+ = 560.1 |
| 459 | CH₃-S(=O)₂- | 733 | MH+ = 513.1 |

EXAMPLES 460-469

Reacting Compounds (728a) and (728b) seperately following the procedure described in Example 13 with the appropriate chloroformates and isocyanates, the following compounds listed in Table 44 below were prepared.

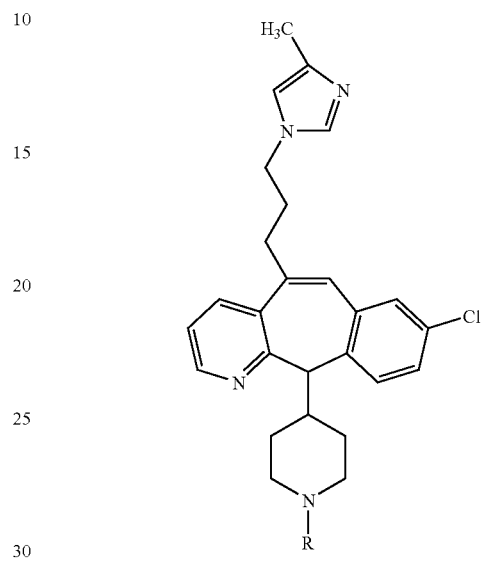

(R is defined in Table 44).

TABLE 44

| EXAMPLE # | R | COMPOUND # | PHYSICAL DATA |
|---|---|---|---|
| 460 | cyclohexyl-O-C(=O)-CH(CH₃)- | 734 | MH+ = 559.1 |
| 461 | cyclohexyl-O-C(=O)-CH(CH₃)- | 735 | MH+ = 559.1 |
| 462 | 4-NC-C₆H₄-NH-C(=O)-CH(CH₃)- | 736 | MH+ = 579.1 |

TABLE 44-continued

| EXAMPLE # | R | COMPOUND # | PHYSICAL DATA |
|---|---|---|---|
| 463 | NC-C6H4-NH-C(CH3)-C(=O)- | 737 | MH+ = 579.1 |
| 464 | 4-F-C6H4-NH-C(=O)-CH(CH3)- | 738 | MH+ = 570.1 |
| 465 | 4-F-C6H4-NH-C(=O)-CH(CH3)- | 739 | MH+ = 570.1 |
| 466 | cyclohexyl-NH-C(=O)-C(CH3)- | 740 | MH+ = 558.1 |
| 467 | cyclohexyl-NH-C(=O)-CH(CH3)- | 741 | MH+ = 558.1 |
| 468 | CH3-S(=O)2-C(CH3)- | 742 | MH+ = 511.1 |
| 469 | CH3-S(=O)2-CH(CH3)- | 743 | MH+ = 511.1 |

EXAMPLE 470

Step A

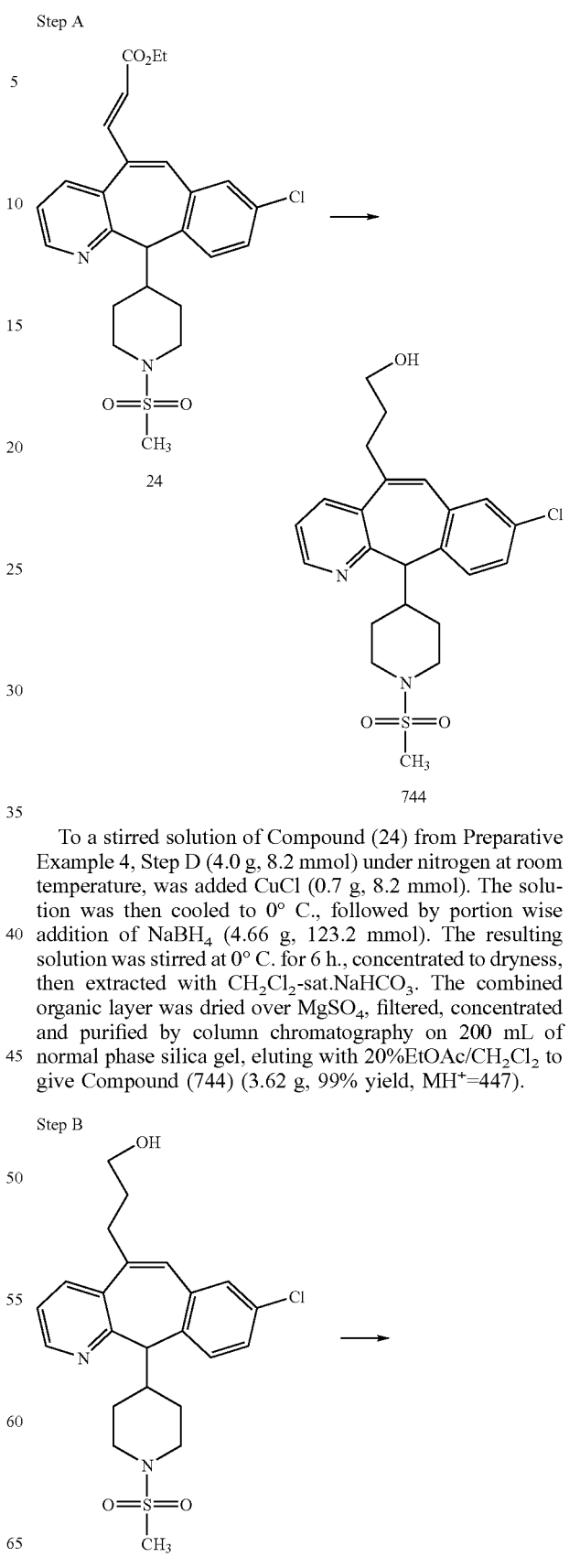

To a stirred solution of Compound (24) from Preparative Example 4, Step D (4.0 g, 8.2 mmol) under nitrogen at room temperature, was added CuCl (0.7 g, 8.2 mmol). The solution was then cooled to 0° C., followed by portion wise addition of $NaBH_4$ (4.66 g, 123.2 mmol). The resulting solution was stirred at 0° C. for 6 h., concentrated to dryness, then extracted with $CH_2Cl_2$-sat.$NaHCO_3$. The combined organic layer was dried over $MgSO_4$, filtered, concentrated and purified by column chromatography on 200 mL of normal phase silica gel, eluting with 20%EtOAc/$CH_2Cl_2$ to give Compound (744) (3.62 g, 99% yield, MH+=447).

Step B

Step C

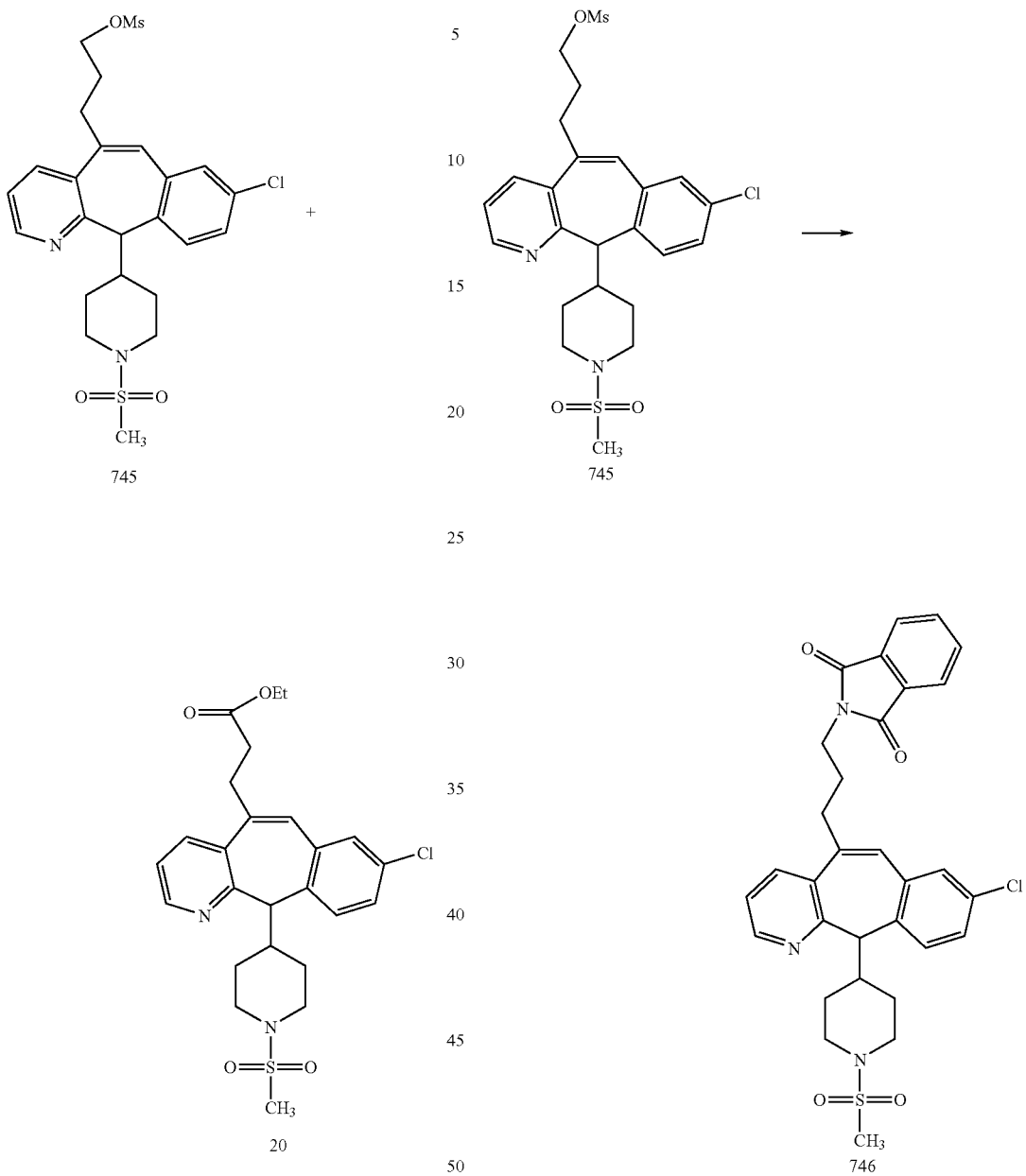

To a stirred solution of Compound (744) from Step A above (3.0 g, 5.7 mmol) in CH$_2$Cl$_2$ (100 mL) under nitrogen at room temperature, was added triethyl amine (2.4 mL, 17.1 mmol) and methanesulfonyl chloride (0.98 g, 8.7 mmol). The resulting solution was stirred at room temperature over night, then washed with saturated NaHCO$_3$. The combined organic layer was dried over Na$_2$SO$_4$, filtered, concentrated to dryness and purified by Biotage column chromatography, eluting with 30%EtOAc/70%CH$_2$Cl$_2$ to give Compound (745) as a white solid (1.19 g, MH$^+$=525.1) and Compound (20) (1.31 g, MH$^+$=489.1)

To a stirred solution of Compound (745) from Step B above (2.17 g, 4.3 mmol) in DMF (50 mL) under nitrogen at room temperature was added phthalimide potassium derivative (1.20 g, 0.5 mmol). The resulting solution was heated to 90° C. for 4 h., cooled down to room temperature, concentrated to dryness and extracted with CH$_2$Cl$_2$-sat-.NaHCO$_3$. The combined organic layer was dried over Na$_2$SO$_4$, filtered, concentrated to dryness and purified by column chromatography on silica gel, eluting with 50%-70%EtOAc/hexane to give Compound (746) as a white solid (1.76 g, 71% yield, MH$^+$=577.0).

Step D

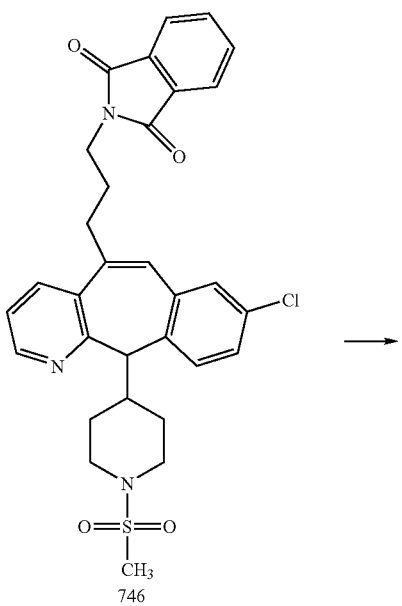

746

Step E

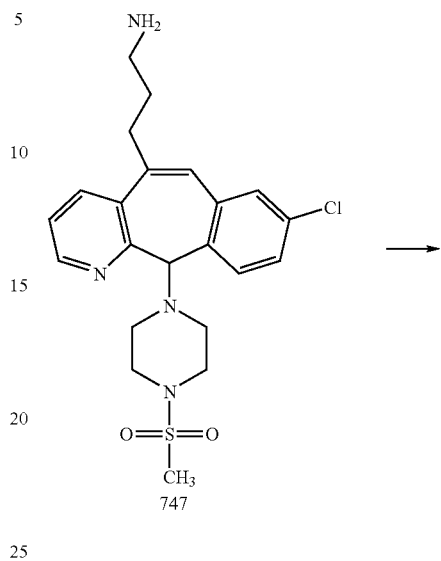

747

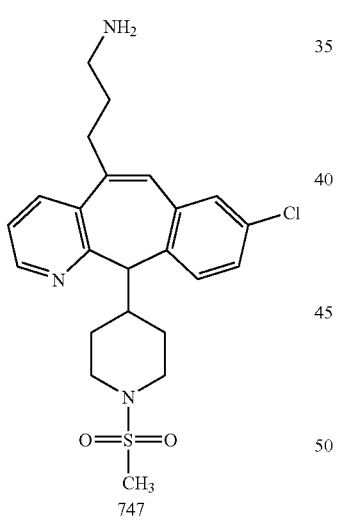

747

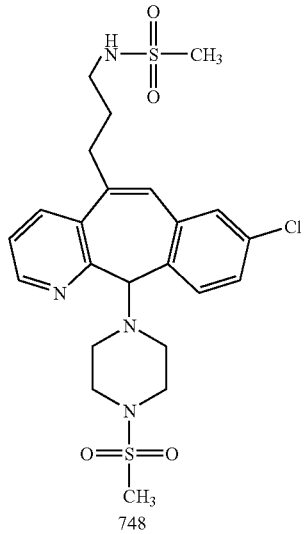

748

To a stirred solution of Compound (746) from Step C above (1.67 g, 2.9 mmol) in EtOH (50 mL) at room temperature, was added hydrazine monohydrate (0.29 g, 5.8 mmol). The resulting solution was heated to reflux for 4 h. cooled down to room temperature, concentrated to dryness and extracted with $CH_2Cl_2$—$H_2O$. The combined organic layer was dried over $MgSO_4$, filtered and concentrated to dryness to give Compound (747) as a white solid (1.23 g, 95% yield, $MH^+$=446.1)

To a stirred solution of Compound (747) from Step D (0.1 g, 0.22 mmol) in $CH_2Cl_2$ (5 mL) under nitrogen at room temperature, was added TEA (0.06 mL, 0.45 mmol) and methanesulfonyl chloride (0.038 g, 0.34 mmol). The resulting solution was stirred at room temperature over night, then washed with sat. $NaHCO_3$. The combined organic layer was dried over $Na_2SO_4$, filtered and purified by column chromatography on silica gel, eluting with 3% MeOH—$NH_3$/$CH_2Cl_2$ to give Compound (748) as a white solid (0.087 g, 76% yield, $MH^+$=524.0)

EXAMPLE 471

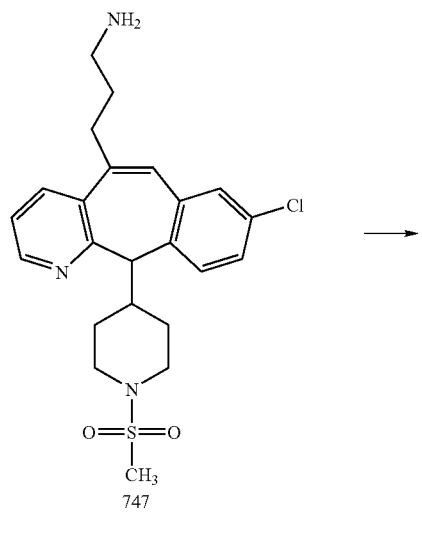

747

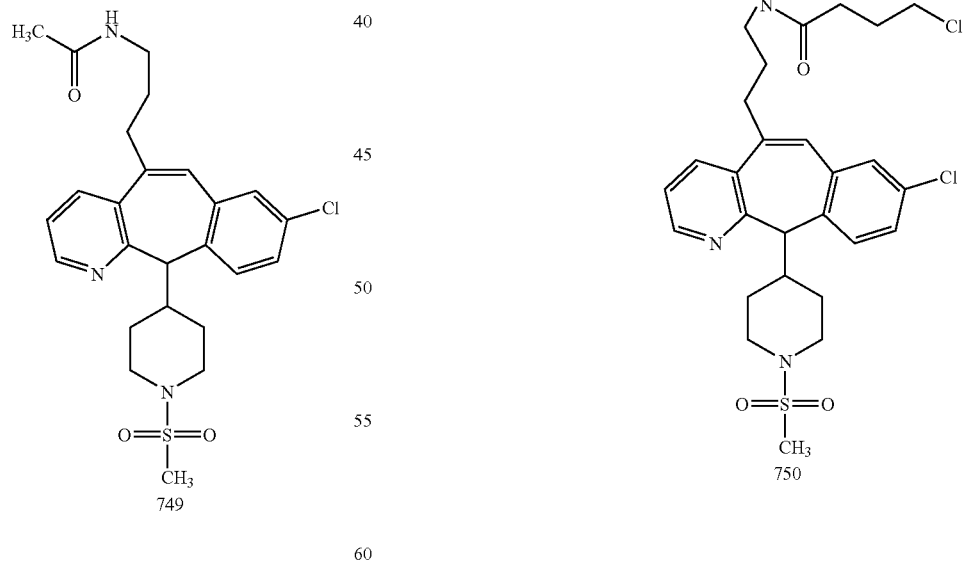

749

Reacting Compound (747) from Example 470 Step D above in essentially the same manner as in Step E of Example 470 substituting acetylchloride, Compound (749) was prepared.(0.048 g, 45% yield, MH+=488.2).

EXAMPLE 472

Step A

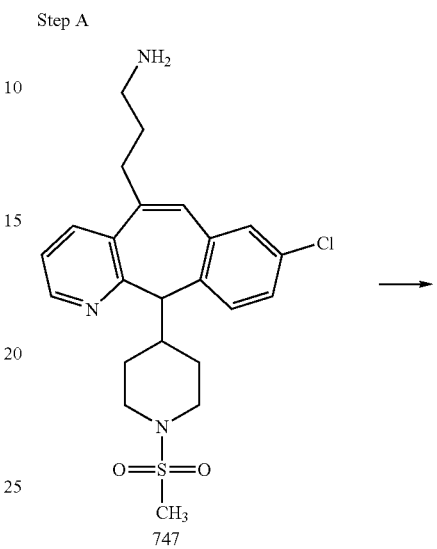

747

750

Reacting Compound (747) from Example 470 Step D above in essentially the same manner as in Step E of Example 470 substituting 4-Chlorobutyryl chloride (ACROS), Compound (750) was prepared (0.67 g, 100% yield, MH$^+$=514.1).

eluting with 1.5%MeOH—NH$_3$/98.5%CH$_2$Cl$_2$ to give Compound (751) as a white solid (0.15 g, 26% yield, MH$^+$=524.1)

EXAMPLE 473

Step B

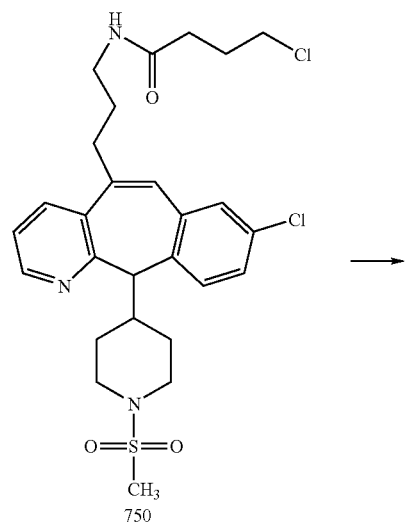

750

Step A

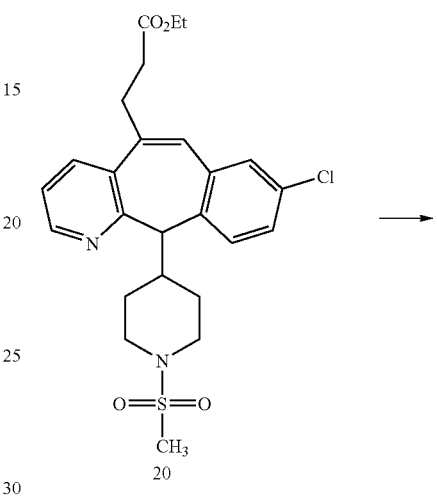

20

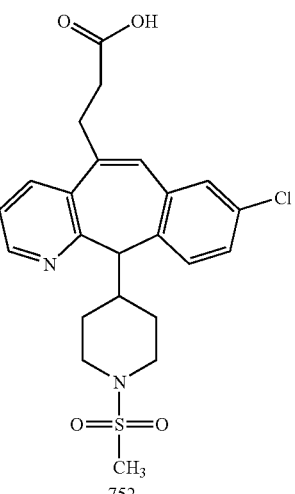

752

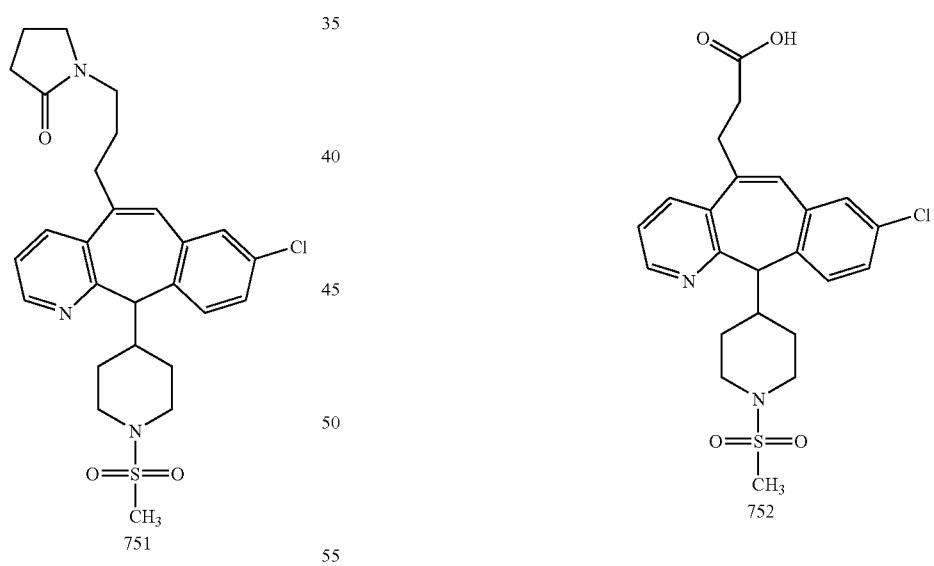

751

To a stirred solution of Compound (750) from Step A (0.575 g, 1.11 mmol) in toluene (15 mL) under nitrogen at room temperature, was added K$_2$CO$_3$ (0.55 g, 4.01 mmol). The resulting solution was stirred at room temperature over the weekend then heated to 55° C. for 7 h. The solution was then cooled down to room temperature, filtered, concentrated to dryness and purified by column chromatography, To a stirred solution of Compound (20) from Example 470, Step B (0.67 g, 1.37 mmol) in THF (5 mL), was added 1N NaOH solution (6.9 mL, 6.88 mmol). The resulting solution was stirred at room temperature overnight arid concentrated to dryness. The solution was then acidified with 10% citric acid and then extracted with CH$_2$Cl$_2$. The combined organic layer was dried over MgSO$_4$, filtered and concentrated to dryness to give Compound (752) as a light yellow product (0.33 g, 52% yield, MH$^+$=461.1)

EXAMPLE 474

Step B

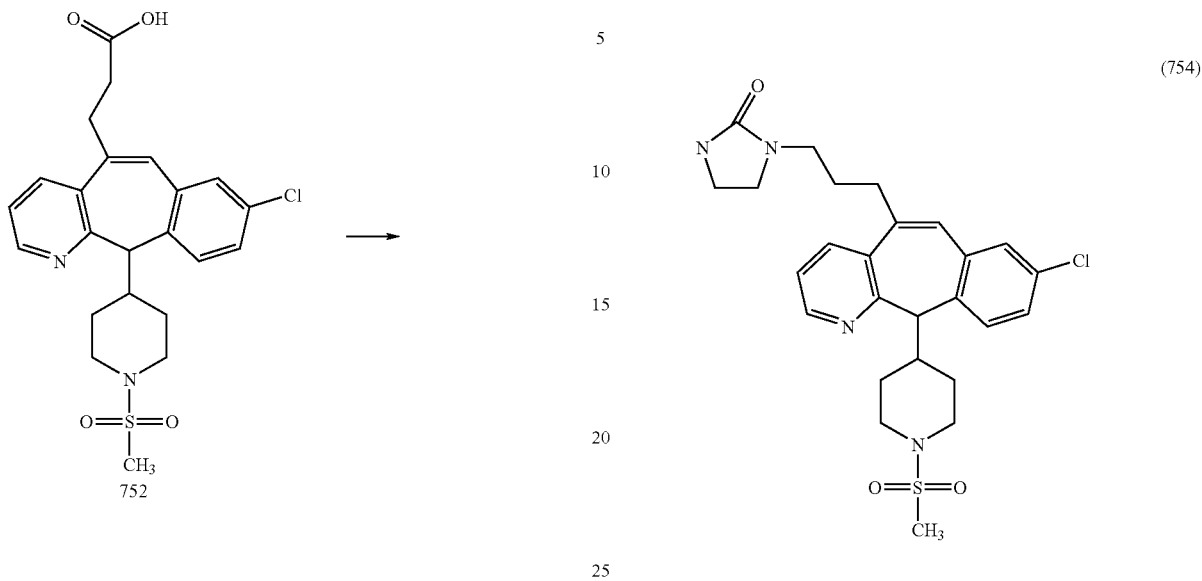

(754)

To a stirred solution of 2-imidazolidone (0.22 g, 2.0 mmol) in DMF (10 mL) was added NaH (0.28 g, 2.0 mmol). The resulting solution was stirred at room temperature for 1 hr. This solution was then added into a solution of Compound (22) from Preparative Example 3, Step C (0.67 g, 1.3 mmol) in DMF (20 mL) under nitrogen inlet at room temperature. The resulting solution was heated to 90° C. for 2 hrs, concentrated to dryness, then extracted with $CH_2Cl_2$-sat.$NaHCO_3$. The combined organic layer was then dried over $MgSO_4$, filtered, concentrated to dryness and purified by column chromatography on silica gel, eluting with 3% MeOH—$NH_3$/97% $CH_2Cl_2$ to give a light yellow solid (754) (0.17 g, 25% yield, $MH^+$=515.1).

EXAMPLE 475

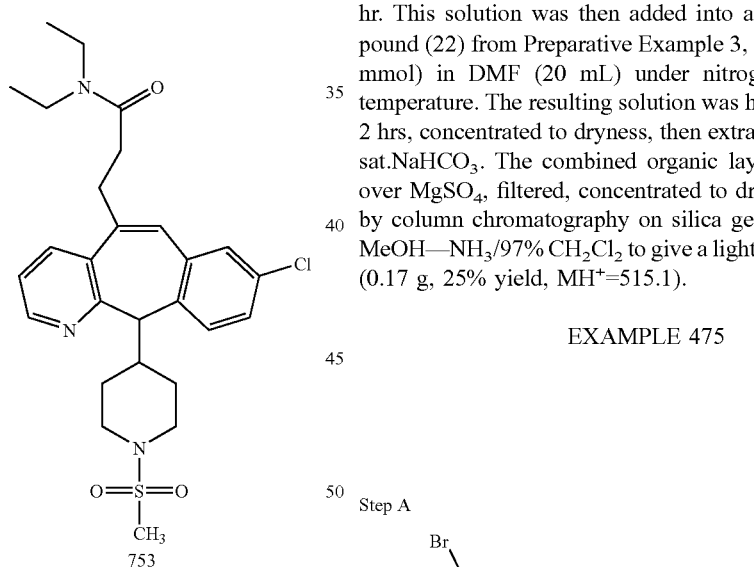

Step A

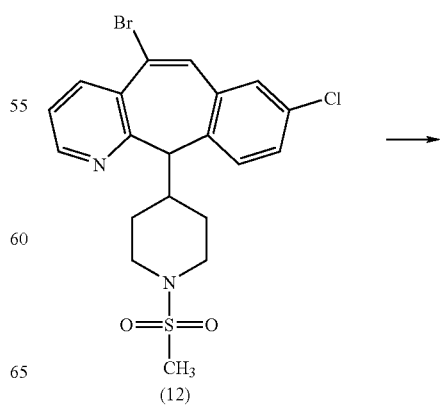

To a stirred solution of Compound (752) from Step A above (0.1 g, 0.23 mmol) in $CH_2Cl_2$ (5 mL) under nitrogen at room temperature, was added oxalyl chloride (0.97 g, 7.62 mmol) and diethyl amine (0.47 g, 6.43 mmol). The resulting solution was stirred at room temperature for 1 hr and concentrated to dryness. The crude product was then purified by column chromatography, eluting with 2%MeOH—$NH_3$/98%$CH_2Cl_2$ to give Compound (753) as a white solid (0.051 g, 49.5% yield, $MH^+$=516.1)

-continued

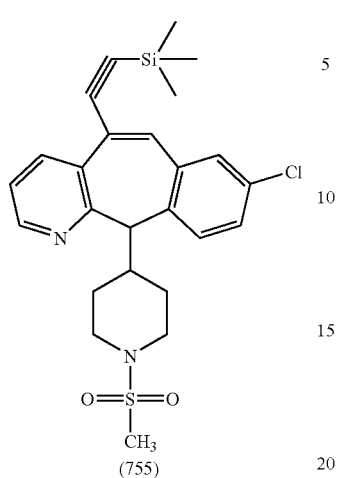

(755)

To a stirred solution of Compound (12) from Preparative Example 2, Step B (15.75 g, 0.336 mmol) in DMF (200 mL) under nitrogen inlet at room temperature, was added trimethylsilylacetalene (12.14 g, 124 mmol), bis(triphenylphosphine)palladium (II)dichloride (0.47 g, 0.67 mmol), Et$_3$N (13.1 mL, 94 mmol), CuI (0.89 g, 4.7 mmol) and NaI (1.53 g, 10 mmol). The resulting solution was stirred at room temperature overnight, concentrated to dryness, then extracted with CH$_2$Cl$_2$—H$_2$O. The combined organic layer was dried over MgSO$_4$, filtered, concentrated to dryness and purified by column chromatography on silica gel, eluting with 20% EtOAc/80% hexane to give the product (755) (12.35 g, M=485).

Step B

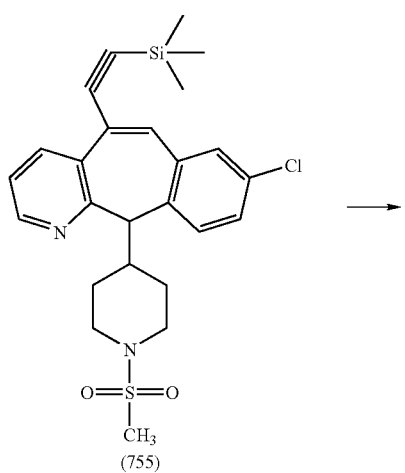

(755)

-continued

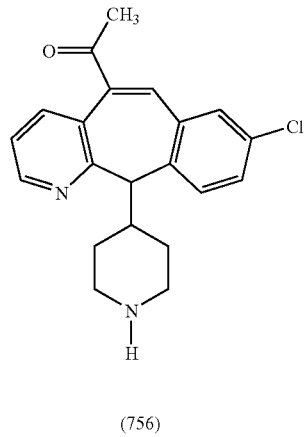

(756)

A solution of Compound (755) from Step A above (4.48 g, 9.24 mmol), in concentrated HCl (100 mL) was heated to reflux overnight. The solution was then cooled down to room temperature and basified with 50% NaOH solution (w/w) and then extracted with CH$_2$Cl$_2$. The combined organic layer was dried over MgSO$_4$, filtered and concentrated to dryness to give an off white solid (756) (4.40 g, 100% yield, MH$^+$=353.1).

Step C

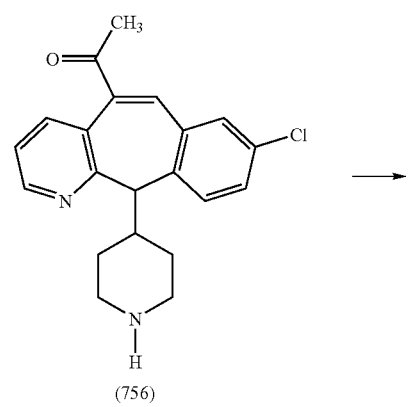

(756)

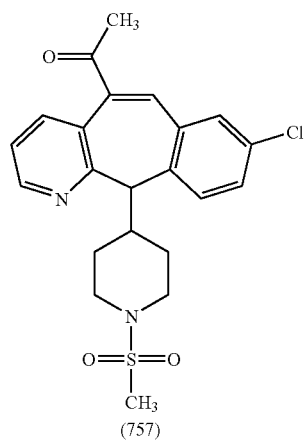

(757)

To a stirred solution of Compound (756) from step B (3.15 g, 8.93 mmol) in CH$_2$Cl$_2$ (100 mL) was added Et$_3$N (2.5 mL, 17.85 mmol) and methanesulfonyl chloride (0.51 g, 4.46 mmol). The resulting solution was stirred at room temperature overnight. The solution was then washed with saturated NaHCO$_3$ and the organic layer was dried over MgSO$_4$, filtered and concentrated to dryness to give a crude product (4.31 g, 100% yield, MH$^+$=431.1)

Step D

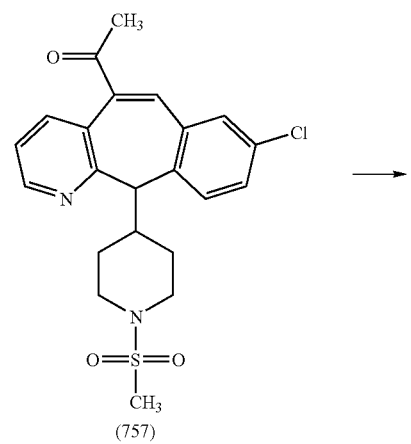
(757)

Step E

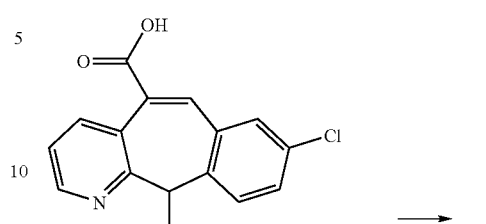
(758)

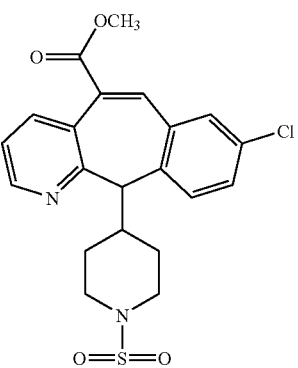
(759)

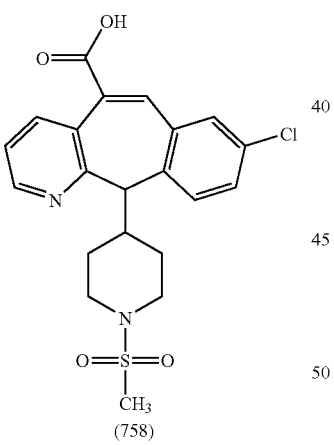
(758)

The solution of Compound (757) from Step C (3.84 g, 8.91 mmol) in 4% NaClO (150 mL) and 45% NaOH solution (15 mL) was heated to reflux for 2 hrs, then cooled down to room temperature, followed by addition of saturated sodium bisulfite solution (150 mL). The solution was then adjusted to pH=6.5 and extracted with CH$_2$Cl$_2$. The combined organic layer was dried over MgSO$_4$, filtered and concentrated to dryness to give a light yellow solid (3.31 g, 86% yield, MH$^+$=433.1).

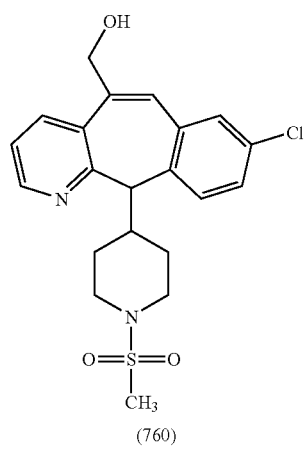
(760)

To a stirred solution of Compound (758) from step D (3.31 g, 7.65 mmol) in toluene (80 mL) and MeOH (50 mL) under nitrogen at room temperature, was added (trimethylsilyl)diazomethane (2.0M in hexane)(3.4 mL, 68.8 mmol) at 0° C., until the colorless solution turned to yellow solution. The resulting solution was stirred at 0° C. for half an hour and concentrated to dryness to give a crude product (759).

To a stirred cooling solution of the crude product (759) from above, in THF (30 mL) at 0° C. was added DIBAL (15.3 mL, 15.3 mmol). The resulting solution was stirred at 0° C. for 2 hrs, followed by extraction with 10% citric acid and 1N NaOH solution. The combined organic layer was dried over MgSO$_4$, filtered and concentrated to dryness to give a light yellow solid (760) (2.90 g, 90% yield, MH$^+$=419.1).

Step F

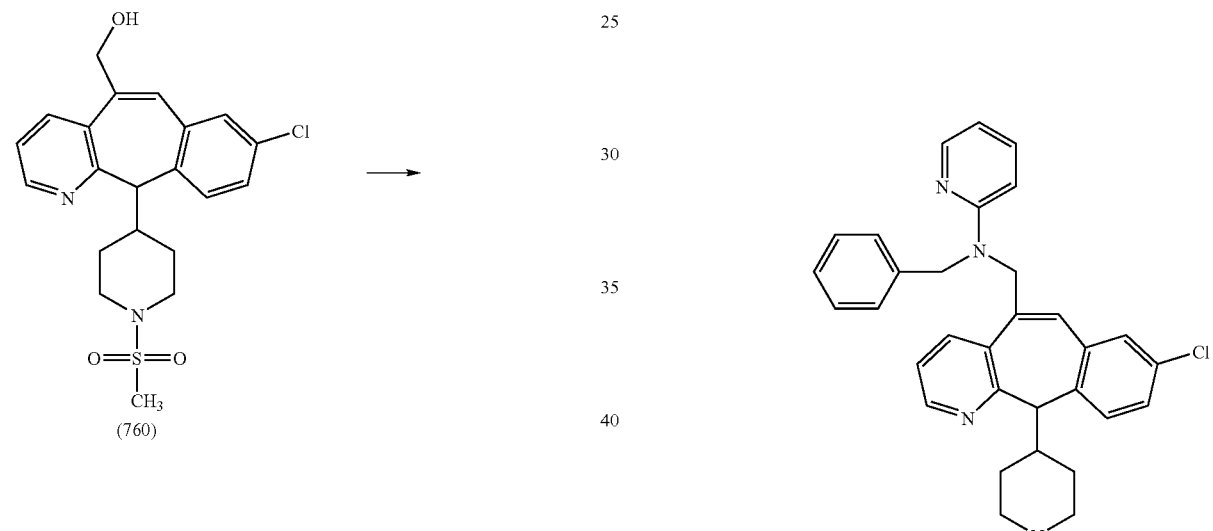

Reacting Compound (760) in essentially the same manner as Step C above, Compound (761) was prepared.

Step G

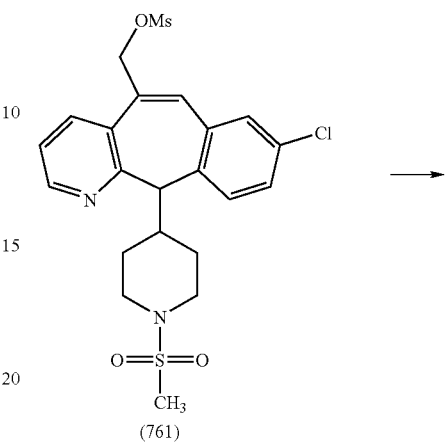

To a stirred solution of 2-benzylaminopyridine (0.115 g, 0.624 mmol) in DMF (10 mL) at room temperature, was added NaH (9.81 g, 0.41 mmol) and stirred for 0.5 hr. To a stirred solution of mesylate compound from step F (0.2 g, 0.41 mmol) in DMF (10 mL) under nitrogen inlet, was added the solution of 2-benzylaminopyridine in DMF above. The resulting solution was heated to 90° C. for 3 hrs, concentrated to dryness followed by extraction with CH$_2$Cl$_2$-sat.NaHCO$_3$, then dried over MgSO$_4$, filtered, concentrated to dryness and purified by column chromatography on silica gel, eluting with 5% MeOH—NH$_3$/CH$_2$Cl$_2$ to give a light yellow solid (762) (0.03 g, 13% yield, MH$^+$=585.1).

EXAMPLE 476

Step A

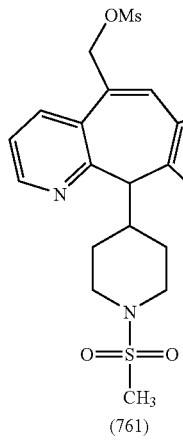

(761)

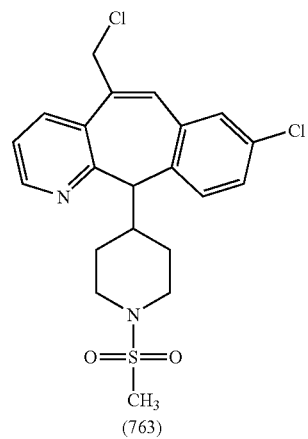

(763)

In essentially the same manner as Example 475, Step E, Compound (763) was prepared.

Step B

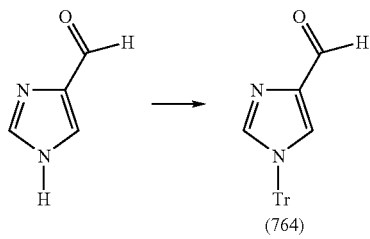

(764)

To a stirred solution of 4(5)-imidazolecarboxaldehyde (20.0 g, 0.208 mmol) in $CH_2Cl_2$ (200 mL), was added $Et_3N$ (29.0 mL, 0.208 mmol). The solution was then cooled down at 0° C., followed by addition of triphenylmethylchloride (52.8 g, 0.18 mmol) at 0° C. The resulting solution was stirred at room temperature overnight and then washed it with brine, water and concentrated to dryness to give a white solid (63.0 g, 98% yield, $MH^+$=339.1)

Step C

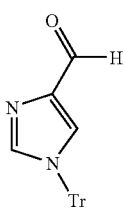 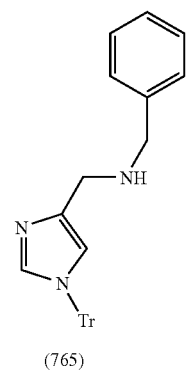

(765)

To a stirred solution of starting material benzyl amine (0.99 g, 8.87 mmol) in MeOH (50 mL) under nitrogen inlet at room temperature, was added sodium acetate (0.73 g, 8.87 mmol), 3°A molecular sieves (3.0 g) and aldehyde (3.0 g, 8.87 mmol). The resulting solution was stirred at room temperature overnight, followed by addition of $NaBH_4$ (0.67 g, 17.74 mmol), then stirred for 4 hrs and concentrated to dryness, followed by extraction with $CH_2Cl_2$-1N NaOH. The combined organic layer was dried over $MgSO_4$, filtered, concentrated to dryness and purified by column chromatography on silica gel, eluting with 2%MeOH—$NH_3$/98%$CH_2Cl_2$ to give light yellow oil (3.75 g, 98% yield, $MH^+$=430.2)

Step D

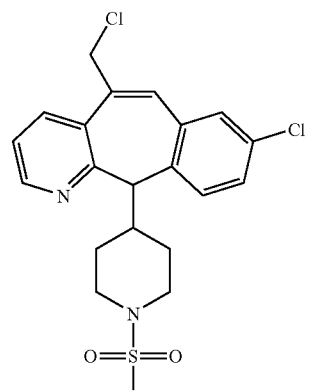

763

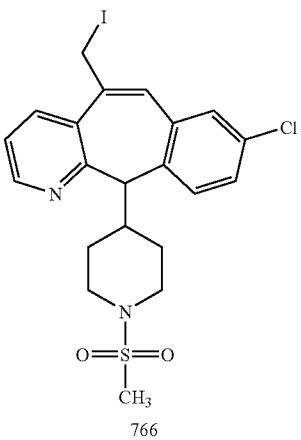

766

-continued

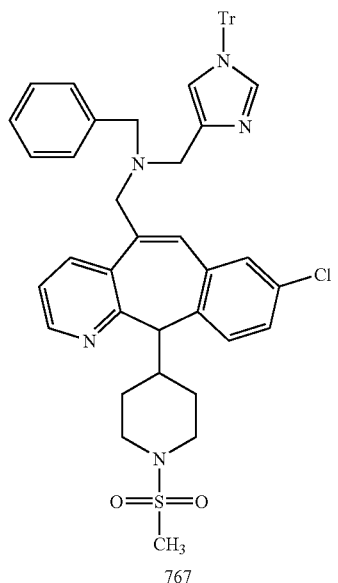

(767)

To a stirred solution of Compound (764) from step B (0.41 g, 1.14 mmol) in DMF (10 mL) under nitrogen at room temperature, was added NaH (0.02 g, 0.84 mmol). The resulting solution was stirred at room temperature for 1 hr.

To a stirred solution of Compound (763) from step A (0.4 g, 0.84 mmol) in acetone (30 mL) under nitrogen inlet at room temperature, was added NaI (0.12 g, 0.84 mmol). The resulting solution was heated to reflux for 1 hour and then concentrated to dryness to afford Compound (766). To crude Compound (766) was added, DMF (10 mL) and the solution of Compound (764) from above and NaH (0.02 g, 0.84 mmol). The resulting solution was heated to 90° C. for overnight, then concentrated to dryness and purified by column chromatography on silica gel, eluting with 2% MeOH—NH$_3$/98% CH$_2$Cl$_2$ to give Compound (767) as a yellow solid (0.23 g, 33% yield, MH$^+$=830.4)

Step E

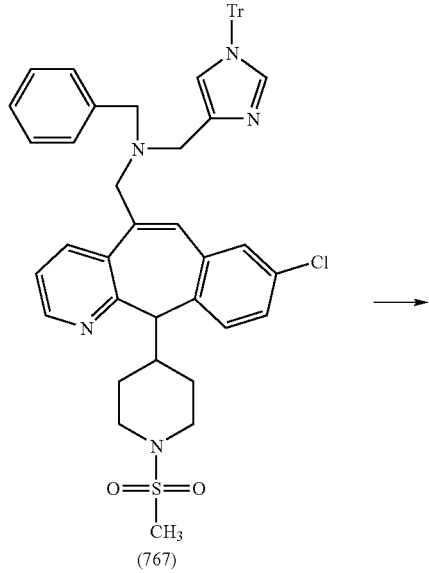

(767)

-continued

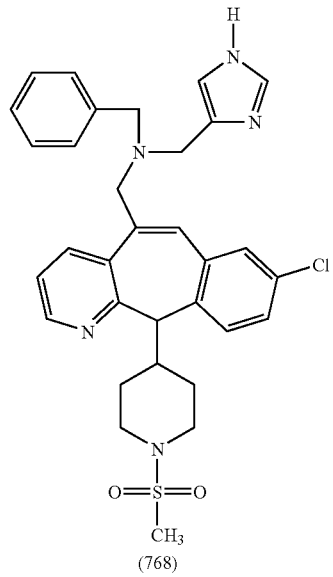

(768)

A solution of Compound (767) from step C (0.238 g, 0.29 mmol) in 80% acetic acid in H$_2$O was heated to reflux for 2 hrs and then concentrated to dryness, followed by extraction with CH$_2$Cl$_2$-1N NaOH. The combined organic layer was dried over MgSO$_4$, filtered, concentrated to dryness and purified by column chromatography on silica gel, eluting with 3% MeOH—NH$_3$/97%CH$_2$Cl$_2$ to give white solid (0.10 g, 62% yield, M=588.2).

PREPARATIVE EXAMPLE 62

Step A

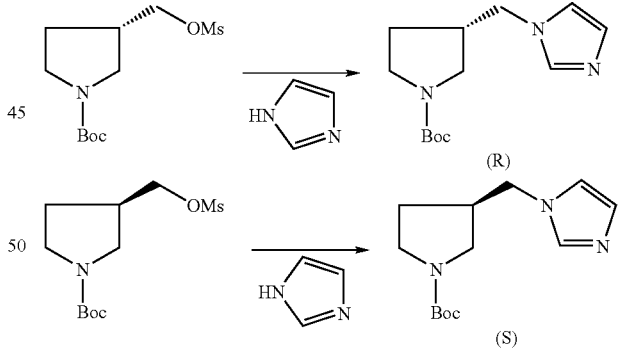

3(R)-(3-Methanesulfonyloxymethyl)pyrrolidine (J. Med. Chem. 1990, 33, 77-77) (0.993 g, 3.56 mmoles) was dissolved in anhydrous DMF (25 mL) and sodium imidazole (0.6 g, 10 mmoles) was added. The mixture was heated at 60° C. for 2 h and then evaporated to dryness. The product was extracted with CH$_2$Cl$_2$ and washed with brine. CH$_2$Cl$_2$ extract was evaporated to dryness to give the titled compound (1.1409 g, 100%), ESMS: FABMS (M+1)=252; $\delta_H$ (CDCl$_3$) 1.45 (s, 9H), 1.5-1.7 (m, 1H), 1.9-2.1 (m, 1H), 2.5-2.7 (m, 1H), 3.0-3.2 (m, 1H), 3.3-3.6 (m, 2H), 3.9 (dd, 2H), 6.9 (s, 1H), 7.1 (s, 1H), 7.45 (s, 1H)

In a similar manner, (S) isomer was prepared from 3(S)-(3-Methanesulfonyloxymethyl)pyrrolidine (0.993 g, 3.56 mmoles to give the title compound (1.1409 g, 100%).

Step B

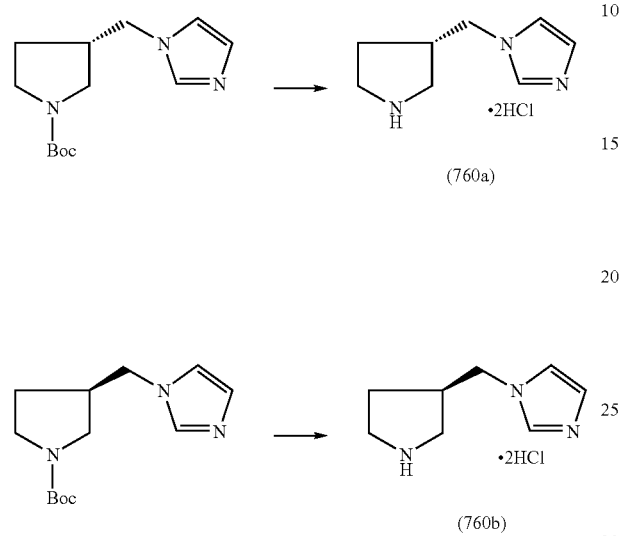

(760a)

(760b)

The title compound (0.48 g, 1.91 mmoles) from Step A was stirred in 4N HCl in dioxane (10 mL) for 2 h and then evaporated to dryness to give the title compound which was used to couple with the tricylic acid.

In a similar manner (S) isomer was prepared.

EXAMPLE 477

Step A

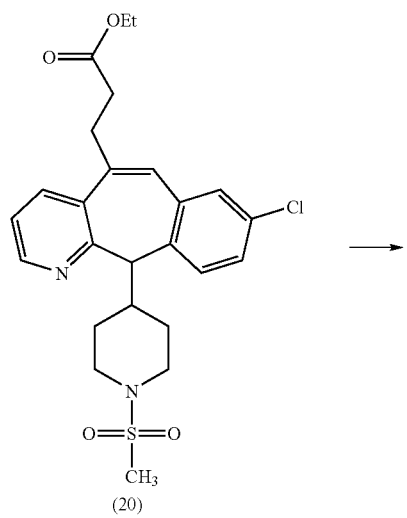

(20)

-continued

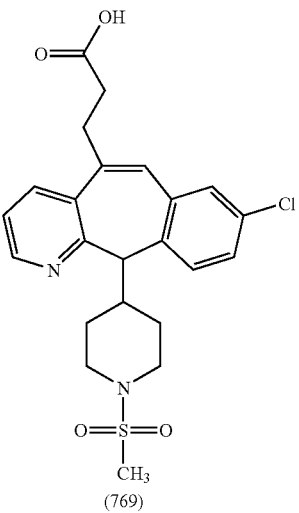

(769)

To a stirred solution of Compound (20) from preparative example 3 step B (4.86 g, 9.94 mmol) in EtOH (100 mL), was added 1N LiOH (80 mL). The resulting solution was then stirred at room temperature overnight and concentrated to dryness, followed by dissolving in $CH_2Cl_2$. The solution was then adjusted to pH=6.5-7.0 with 1N HCl. The aqueous layer was then separated and concentrated to dryness, then dissolved in THF to give the lithium salt (4.86 g, 100% yield, M+Li=467.1)

Step B (769)

-continued

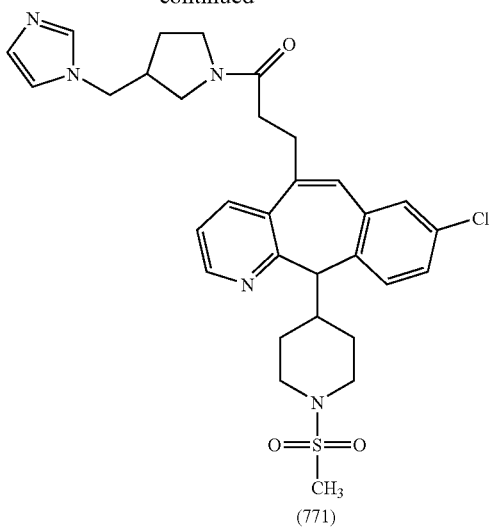
(771)

To a stirred solution of Compound (769) from step A above (0.38 g, 0.84 mmol) in DMF (10 mL) under nitrogen inlet at room temperature, was added Compound (770) from Preparative Example 62 (0.163 g, 1.09 mmol), benzotriazoyl-N-oxtris (dimethylamino)phosphoniumhexafluro phosphate (0.44 g, 1.01 mmol) and Et$_3$N (0.5 mL, 3.36 mmol). The resulting solution was stirred at room temperature overnight and concentrated to dryness, followed by extraction with CH$_2$Cl$_2$-10% Citric acid. The combined organic layer was then washed with saturated NaHCO3, brine, dried over MgSO$_4$, filtered, concentrated to dryness and purified by column chromatography on silica gel, eluting with 3% MeOH—NH$_3$/CH$_2$Cl$_2$ to give a light yellow solid (0.12 g, M=594.2).

PREPARATIVE EXAMPLE 63

Step A

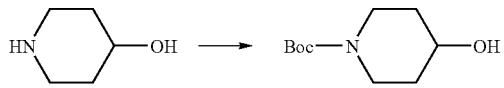

To a solution of 4-hydroxy-piperidine (2 g, 19.78 mmoles) and triethylamine (4.16 mL, 29.67 mmoles) in CH$_2$Cl$_2$ (20 mL), di-tert-butyldicarbonate (5.18 g, 23.72 mmoles) was added and stirred at room temperature for 16 h. The solution was diluted with CH$_2$Cl$_2$ and washed with water, dried (MgSO$_4$) filtered and evaporated to give the title compound (3.95 g, 99%). FABMS (M+1)=202.

Step B

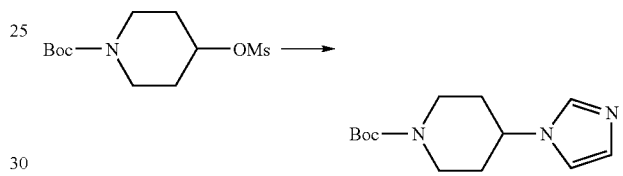

The title compound from Step A above (3.5 g, 17.39 mmoles) and triethylamine (4.85 mL, 34.79 mmoles) were dissolved in CH$_2$Cl$_2$ (30 mL) and the mixture was stirred under nitrogen at 0° C. Methanesulfonylchloride (1.62 mL, 20.88 mmoles) was added and the solution was stirred at room temperature for 2 h. The solution was diluted with CH$_2$Cl$_2$ and washed with saturated aqueous sodium bicarbonate, water and dried (MgSO$_4$), filtered and evaporated to dryness to give the title compound (4.68 g, 96.4%). ESMS: m/z=280 (MH$^+$)

Step C

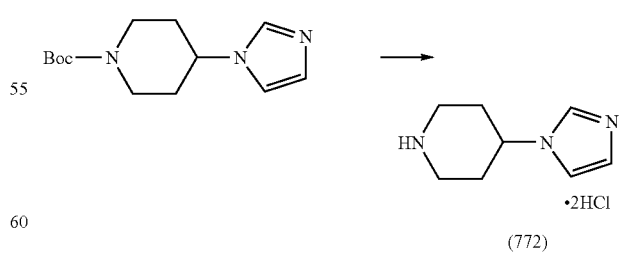

A solution of the title compound from Step B (4.0 g, 14.32 mmoles) in DMF (120 mL) was added to a stirred solution of NaH (0.52 g, 21.66 mmoles) and imidazole (1.46 g, 21.47 mmoles) in DMF (20 mL) under nitrogen atmosphere. The mixture was stirred at 60° C. for 16 h. DMF was evaporated in vacuo. The resulting crude product was extracted with CH$_2$Cl$_2$ and the extract was successively washed with water and brine, and the CH$_2$Cl$_2$ was evaporated to leave the title residue which was chromatographed on silica gel using 3% (10% conc NH$_4$OH in methanol)—CH$_2$Cl$_2$ as eluant to give the title compound (0.94 g, 26%). FABMS (M+1)=252; $\delta_H$ (CDCl$_3$) 1.4 (s, 9H), 1.6-1.8 (m, 2H), 2.0 (dd, 2H), 2.8 (dt, 2H), 4.05 (m, 1H), 4.2 m, 2H), 6.9 (s, 1H), 7.0 (s, 1H), 7.65 (s, 1H).

Step D (772)

The title compound (0.21 g, 0.836 mmoles) from Step C was stirred in 4N HCl in dioxane (5 mL) for 2 h and then evaporated to dryness to give the title compound (772) which was used to couple with the tricylic acid.

EXAMPLE 478

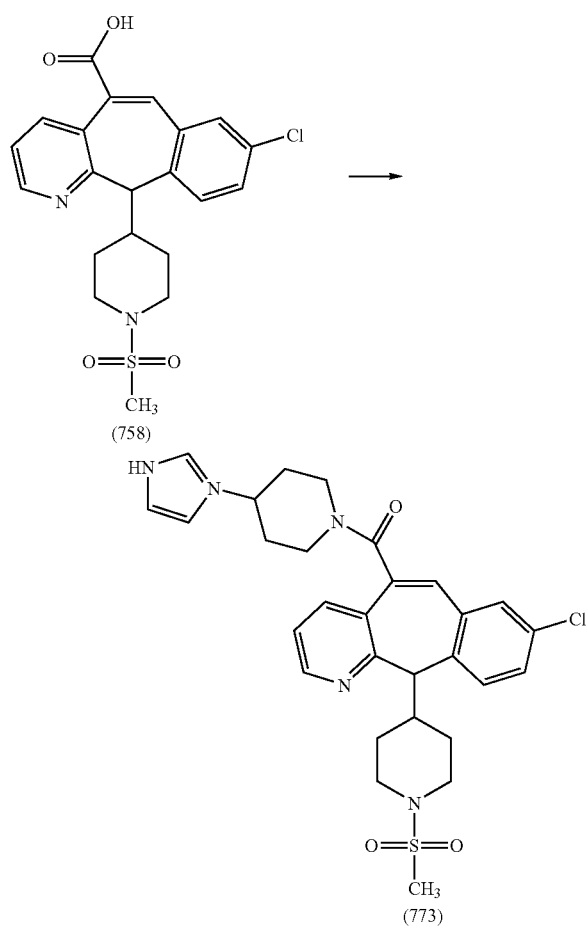

To a stirred solution of Compound (758) from Example 475 step D (0.2 g, 0.46 mmol) in CH₂Cl₂ (5 mL) under nitrogen at room temperature, was added Compound (772) from Preparative Example 63, Step D (0.19 g, 0.55 mmol), benzotriazoyl-N-oxy-tris-(dimethylamino)phosphonium-hexaflurophosphate (0.25 g, 0.55 mmol) and Et₃N (0.3 mL, 1.85 mmol). The resulting solution was stirred at room temperature overnight and concentrated to dryness, followed by extraction with CH₂Cl₂-10% citric acid. The combined organic layer was then washed with sat. NaHCO₃, brine, dried over MgSO₄, filtered, concentrated to dryness and purified by column chromatography on silica gel, eluting with 3%MeOH—NH₃/CH₂Cl₂ to give a white solid (773) (0.013 g, 5% yield, M=566.2)

EXAMPLE 479

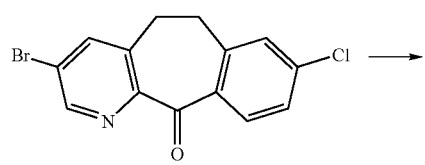

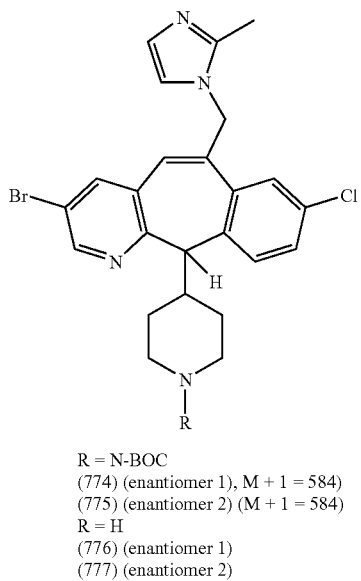

R = N-BOC
(774) (enantiomer 1), M + 1 = 584)
(775) (enantiomer 2) (M + 1 = 584)
R = H
(776) (enantiomer 1)
(777) (enantiomer 2)

3-bromo-8-chloroazaketone (U.S. Pat. No. 5,977,128, Preparative Example 11, step A, (1999)) was reacted in essentially the same manner as in Preparative Example 23, and Example 91 to obtain the N-BOC derivatives (774) and (775). Compounds (774) and (775) were then reacted separately in essentially the same manner as in Preparative Example 19, Step D to obtain the enantiomers (776) and (777).

EXAMPLE 480

In essentially the same manner as in Examples (420) and (421), Compounds (778) and (779) were prepared.

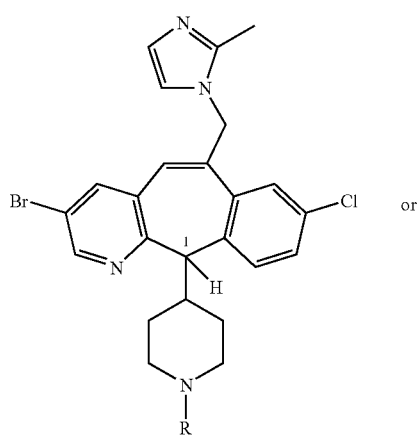

or

-continued

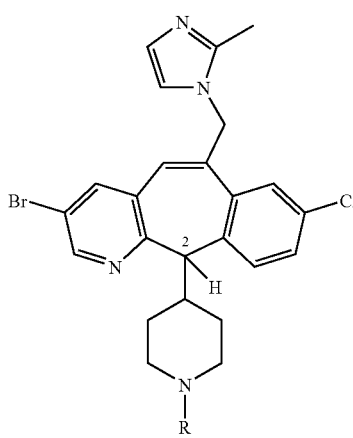

(R is defined in Table 45).

TABLE 45

| Compound # | R = | Enantiomer | FABMS (M + 1) |
|---|---|---|---|
| 778 | *-NH-C(=O)-C6H4-CN* | 1 | 628 |
| 779 | *-NH-C(=O)-C6H4-CN* | 2 | 628 |

Phys. Data (778): $^1$H-NMR (Varians 400 MHz, CDCl$_3$, ppm): δ=8.564 (1H, d, J=2 Hz), 7.784 (1H, d, J=2 Hz), 7.624 (1H, d, J=2 Hz), 7.51-7.37 (5H, m), 7.305 (1H, s), 7.267 (1H, s), 6.870 (1H, s), 6.867 (1H, s), 6.579 (1H, s), 5.282 (1H, d, J=16 Hz), 5.031 (1H, d, J=17 Hz), 4.576 (1H, s), 3.176 (4H, br ddd, J=6, 14 and 58 Hz), 2.485 (3H, s), 1.950 (4H, dd, J=6 and 9 Hz); MS (m/e) 630 (M+H), 340, 327, 293, 263, 249; HRMS (Jeol JMS-HX110A) calcd for $C_{31}H_{27}BrClN7O$ 628.1227 (M+1), found 628.1229.

EXAMPLE 481

In essentially the same manner as in Example 70, Compounds (780) and (781) were prepared.

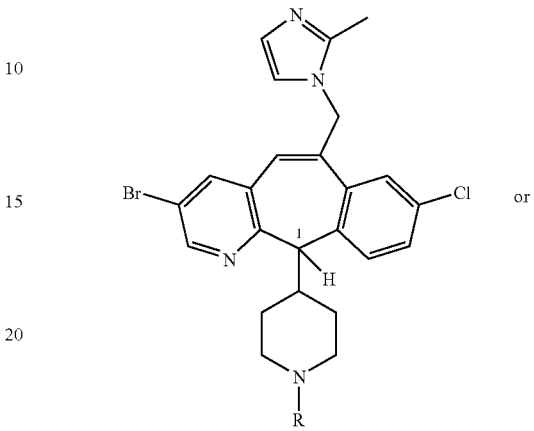

or (R is defined in Table 46).

TABLE 46

| Compound # | R = | Enantiomer | FABMS (M + 1) |
|---|---|---|---|
| 780 | -S(=O)$_2$-CH$_3$ | 1 | 562 |
| 781 | -S(=O)$_2$-CH$_3$ | 2 | 562 |

PREPARATIVE EXAMPLE 64

Step A

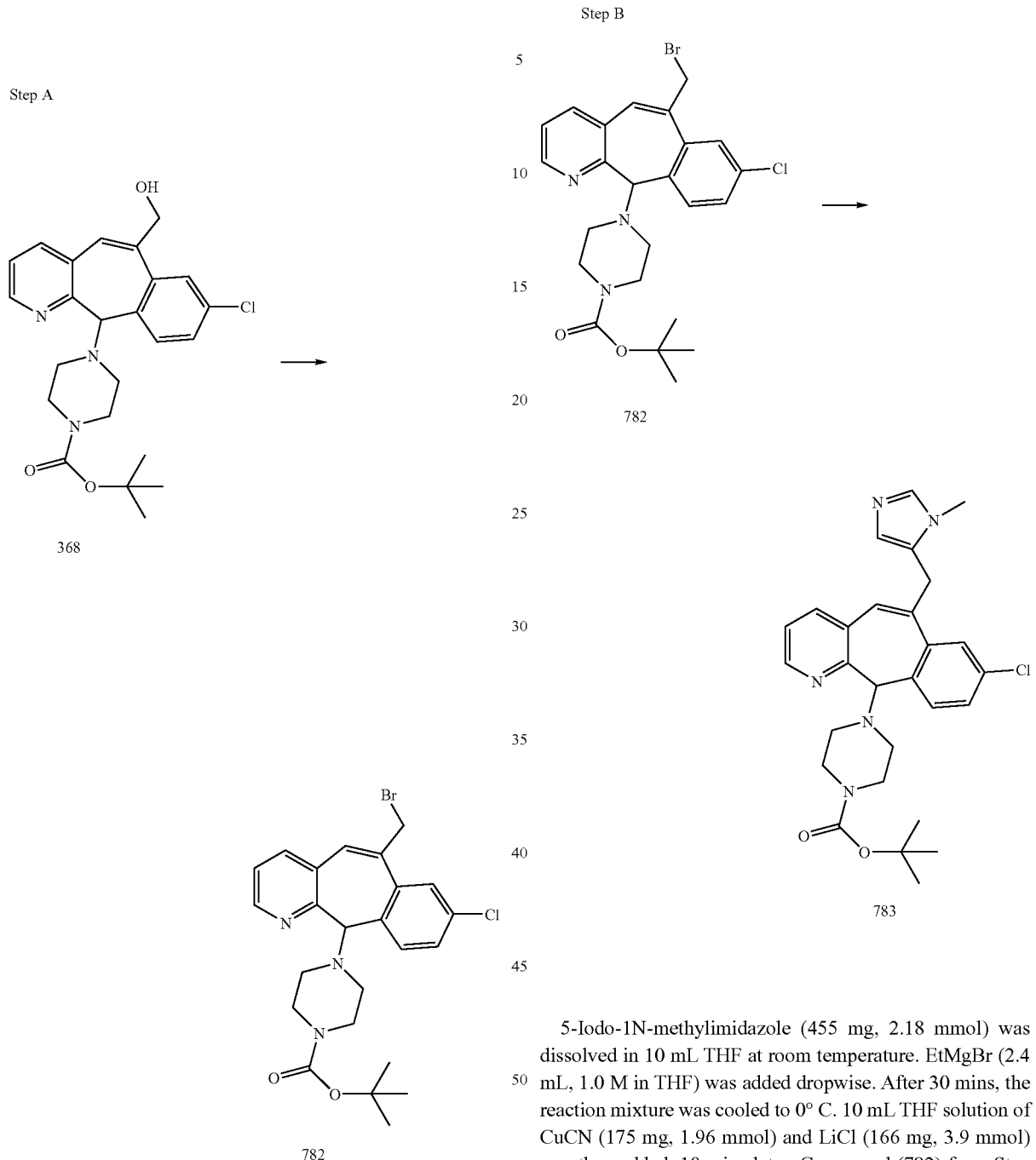

Step B

Compound (368) from Preparative Example 42, Step C (2.34 g, 5.29 mmol) was dissolved in 25 mL CH$_2$Cl$_2$ at 0° C. PPh$_3$ (1.66 g, 6.34 mmol) and NBS (1.03 g, 5.82 mmol) were added. After 90 mins, the reaction was diluted with CH$_2$Cl$_2$ (20 mL), washed with sat. NaHCO$_3$, brine and dried with MgSO$_4$. The crude product was purified on a silica gel column (4:1 hexanes/EtOAc to 2:1) to yield 1.8 g of Compound (782) as a light yellow solid. MS M+1504.

5-Iodo-1N-methylimidazole (455 mg, 2.18 mmol) was dissolved in 10 mL THF at room temperature. EtMgBr (2.4 mL, 1.0 M in THF) was added dropwise. After 30 mins, the reaction mixture was cooled to 0° C. 10 mL THF solution of CuCN (175 mg, 1.96 mmol) and LiCl (166 mg, 3.9 mmol) was then added. 10 mins later, Compound (782) from Step A above (989 mg, 1.96 mmol, in 10 mL THF) was added. The reaction was stirred overnight. Sat. NH$_4$Cl solution was added to quench the reaction. The resulting emulsion was filtered through a sintered funnel and the filtrate was extracted with EtOAc twice. The organic layer was washed with NaHCO$_3$ solution and brine, dried over magnesium sulfate, filtered and evaporated in vivo. The resulting crude material was chromatographed on a silica gel column (using 1:1 hexanes/EtOAc then 10:1 CH$_2$Cl$_2$/MeOH) to obtain 330 mg of the title product. MS M+1=506 The enantiomers were seperated on a chiral AD column.

EXAMPLE 482

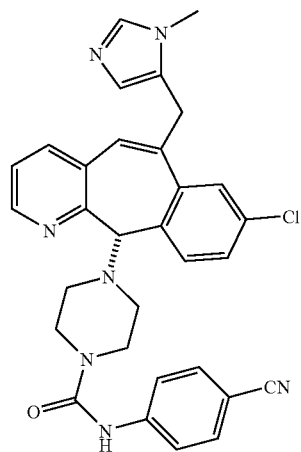

784

Compound (783) from Preparative Example 64, Step B above (40 mg) was dissolved in CH$_2$Cl$_2$ (5 mL) at room temperature followed by addition of TFA (0.5 mL). After 2 hrs, the solvent was evaporated in vivo and coevaporated with PhCH$_3$ twice. The crude mixture was then dissolved in CH$_2$Cl$_2$ (4 mL) and Et$_3$N was added dropwise till the solution became basic by PH paper. 4-Cyanophenyl isocyanate (14 mg) was added. After 5 minutes, the reaction mixture was evaporated in vivo to dryness. The crude material was then purified using prep TLC plate (10:1 CH$_2$Cl$_2$/MeOH) to get 23 mg of Compound (784) as a white solid. MS M+1550.

EXAMPLE (483)

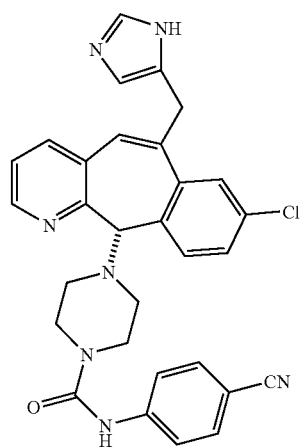

785

Compound (785) was prepared following essentially the same procedure as in Preparative Example 64 and Example 482, substituting 4-Iodo-1-tritylimidazole for 5-Iodo-1N-methyl imidazole.

EXAMPLE 484

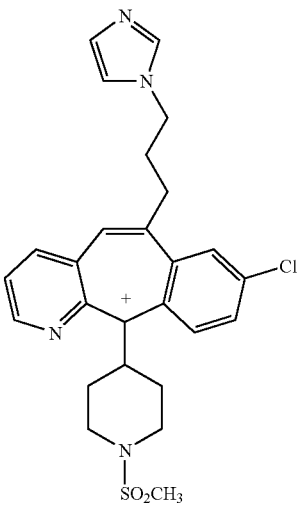

786

OR

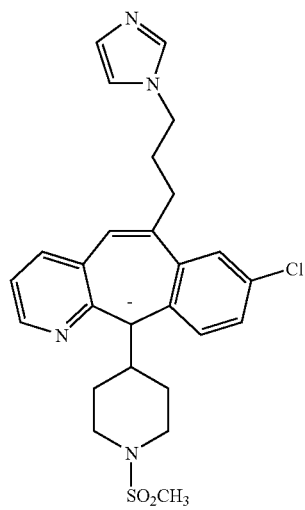

787

Compound (786) and (787) were prepared following essentially the same procedure as in Preparative Example 7, substituting ketones (15) and (16) from Preparative Example 2, Step D for ketones (9) and (10).

Compound (786) MH$^+$=497; $[\alpha]_D^{20}$=+15.3.

Compound (787) MH$^+$=497; $[\alpha]_D^{20}$=−13.4.

EXAMPLE 485

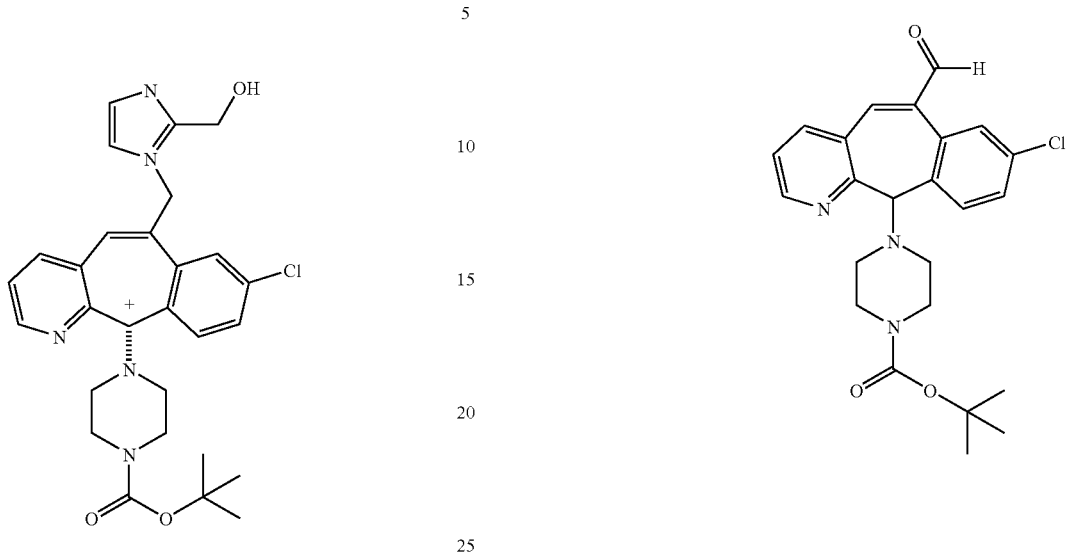

Following essentially the same procedure as in Preparative Example 33, Steps E-H, except substituting compound (365) for Compound (281) and 2-hydroxymethyl imidazole for 1-methylimidazole, compound (788) was prepared.

(788): $^1$H-NMR (Varians 400 MHz, CDCl$_3$, ppm): δ=8.5 (1H, dd), 7.34 (1H, s), 7.59 (1H, d), 7.4 (2H, m), 7.25 (2H, m), 7.04 (1H, s), 6.9 (1H, s), 6.6 (1H, s), 5.37 (2H, dd), 4.8 (2H, dd), 4.6 (1H, s), 3.2 (5H, br s), 2.0 (2H, br s), 1.9 (2H, br s), 1.4 (9H, s).

PREPARATIVE EXAMPLE 65

Step A

Step B

To a solution of the alcohol (3.8 g, 8.6 mmol) in CH$_2$Cl$_2$ (100 mL) under nirtogen was added MnO$_2$ (40 g). The resulting solution was stirred at room temperature for 4 days. The mixture was then filtered through a pad of Celite with ethyl acetate (500 mL) as the eluant. The filtrate was concentrated to yield a yellow liquid (4.0 g, MH+440.1). The crude material was separated into its pure isomers by HPLC, using a chiral AD column eluting with 20% IPA/80% Hexanes/0.2% DEA (isomer 1, 810 mg; isomer 2, 806 mg).

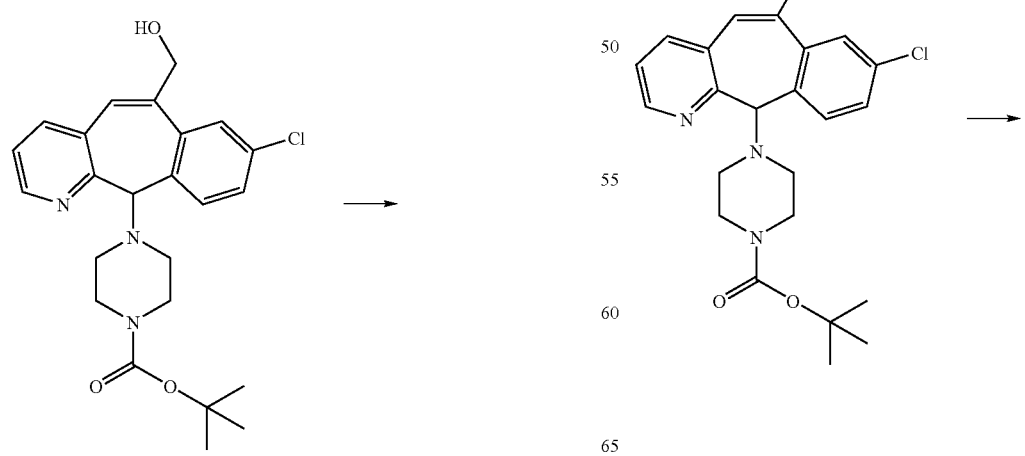

-continued

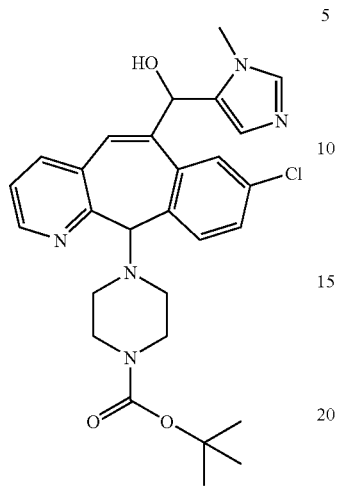

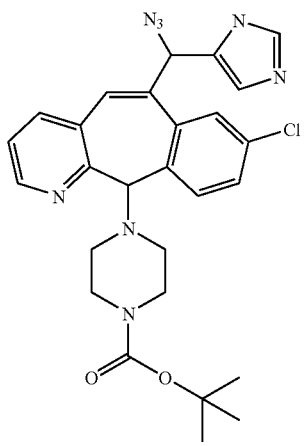

To a solution of imidazole Grignard prepared from 5-iodo-1N-methylimidazole (312 mg, 1.5 mmol, preparative example 64 step B) was added a solution of aldehyde (791) (380 mg, 0.86 mmol) in CH$_2$Cl$_2$ (10 mL). After stirring at room temperature overnight, the mixture was heated to 40° C. for one hour. After cooling to room temperature again, saturated NH$_4$Cl solution was added to quench the reaction. The organic layer was dried and the solvent was evaporated. The residue was then purified by silica gel column (from 2% to 10% MeOH in CH$_2$Cl$_2$) to give the product as a brown oil (207 mg, 46% yield, MH+=522.1). The diastereomers were then separated by HPLC, using a chiral AD column eluting with 20% IPA/80% Hexanes/0.2% DEA.

Step C

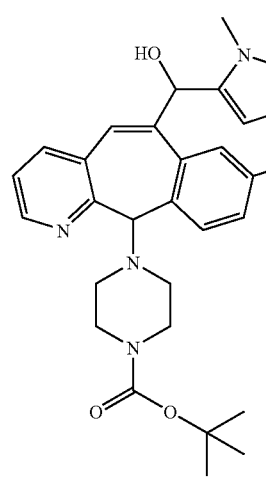

To a THF solution (5 mL) of (790) (200 mg, 0.38 mmol) at room temperature was added DPPA (210 mg, 0.76 mmol) followed by addition of DBU (120 mg, 0.76 mmol). The mixture was stirred overnight and then diluted with ethyl acetate (30 mL), washed with water twice and brine once. The organic layer was dried and the solvent was evaporated. The residue was purified by prep TLC (10% MeOH in CH$_2$Cl$_2$ with 0.2% NH$_3$) to give product (791) (102.8 mg, MH+547.1). Starting material (790) (58 mg) was also recovered. The diastereomers of (791) were separated on a chiral AD column.

EXAMPLE 486

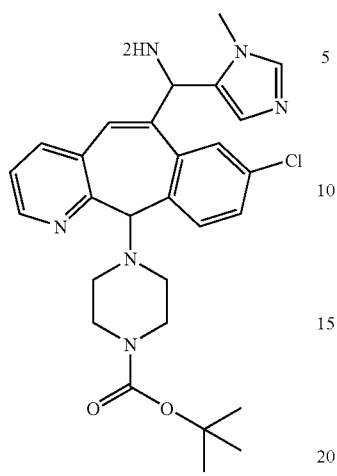

To a wet THF solution (3 mL) of (791) (48 mg, 0.09 mmol) was added PPh₃ (32 mg, 0.12 mmol) at room temperature. After stirring overnight, the reaction mixture was concentrated and the residue was purified with prep TLC (10% MeOH in CH₂Cl₂ with 0.2% NH₃) to give a white solid (24.3 mg). The white solid was then redissolved in THF/H₂O (5 mL/0.5 ml) and the mixture was heated to reflux overnight. The reaction mixture was then partitioned between ethyl acetate and water. The organic layer was dried and concentrated. The residue was purified with prep TLC (5% MeOH in CH₂Cl₂ with 0.2% NH₃) to yield a yellow solid (792) (8.3 mg, MH+521.1).

EXAMPLE 487

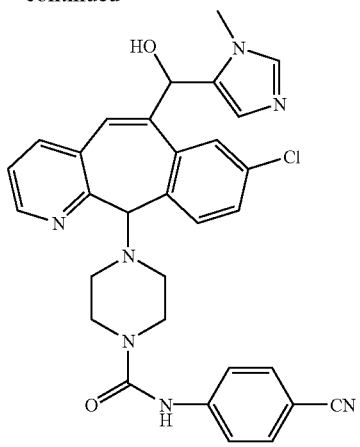

Compound (790) was converted to compound (793) following the essentially the same procedure as described in EXAMPLE 482. MS M$^{+1}$ 566.1.

EXAMPLE 488

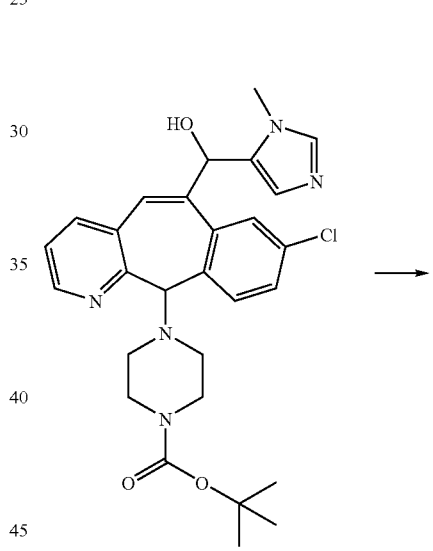

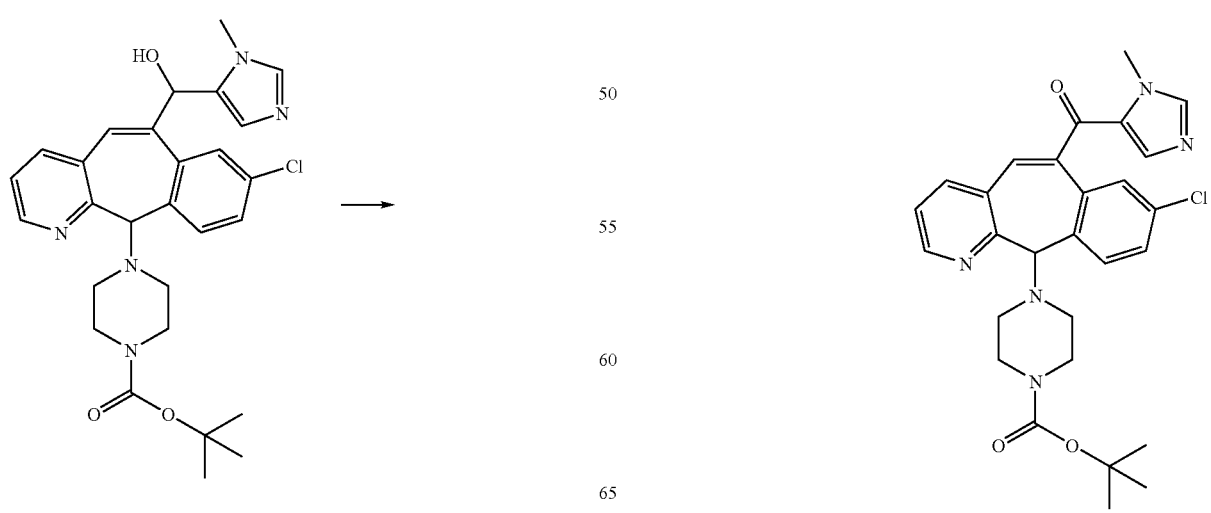

Compound (790) was converted to compound (794) following essentially the same procedure as described in PREPARATIVE EXAMPLE 65, Step A. MS M$^{+1}$ 520.1.

EXAMPLE 489

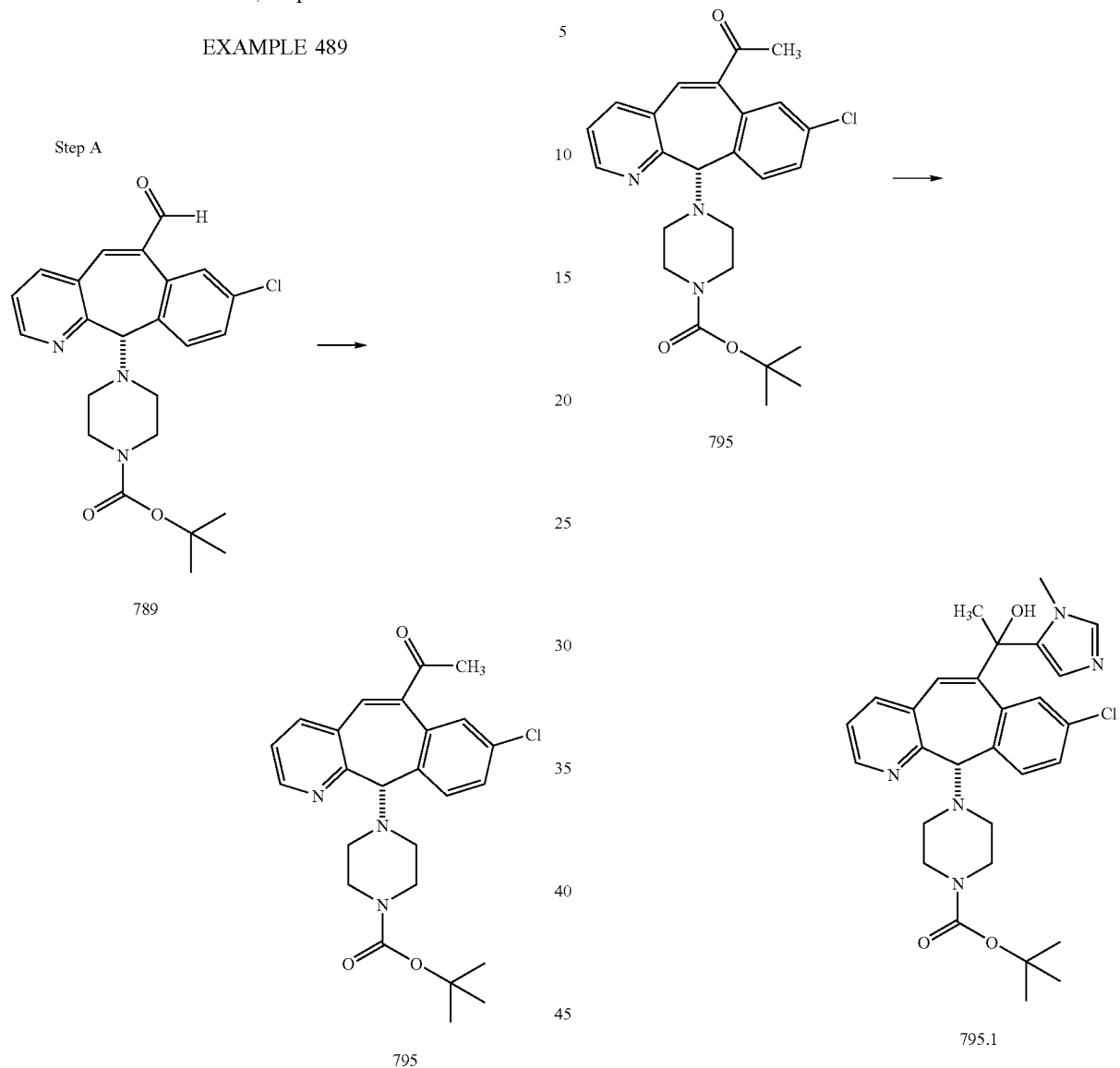

Aldehyde (789) from Preparative Example 65, Step A (150 mg, 0.34 mmol) was dissolved in THF (6 mL). To this solution was added MeMgBr (0.3 mL, 3.0 M in Et$_2$O) dropwise. After stirring at room temperature for 4 hrs, the reaction mixture was quenched with sat. NH$_4$Cl solution and extracted with ethyl acetate. The organic layer was washed with brine, dried and concentrated to give a yellow solid (150 mg). The crude product was then dissolved in CH$_2$Cl$_2$ (5 mL). To this solution was added Dess-Martin Periodinane (210 mg) and a drop of water. After 1 hr, aqueous Na$_2$S$_2$O$_3$ solution (4 mL, 10%) was added. The mixture was stirred for 10 min. and extracted with CH$_2$Cl$_2$. The organic layer was washed with NaHCO$_3$, dried and concentrated. The crude material was purified using prep TLC plates (5% methanol in CH$_2$Cl$_2$) to yield the methyl ketone product (795) as a yellow solid (70 mg).

To a solution of imidazole Grignard prepared from 5-iodo-1N-methylimidazole (624 mg, 3 mmol, see preparative example 64 step B using ClCH$_2$CH$_2$Cl as solvent instead of THF) was added a ClCH$_2$CH$_2$Cl (6 mL) solution of methyl ketone (795) (272 mg, 0.6 mmol). The mixture was heated to 60° C. for 1.5 hours. After cooling to room temperature, saturated NH$_4$Cl solution was added to quench the reaction. The organic layer was dried and then evaporated to dryness. The residue was then purified by silica gel column (from 2% to 10% MeOH in CH$_2$Cl$_2$) to give the product (795.1) as a brown solid (63 mg, 10:1 diastereomeric selectivity, MH+=536.1). Major diastereomer: (CDCl$_3$, 300 MHz) 8.47 (d, 1H), 7.66 (d, 1H), 7.57 (s, 1H), 7.54 (s, 1H), 7.34 (d, 1H), 7.25-7.22 (m, 1H), 7.05 (s, 1H), 6.89 (s, 1H), 6.82 (s, 1H), 4.61 (s, 1H), 3.84 (s, 3H), 3.24 (br s, 4H), 2.24 (m, 2H), 2.02-2.00 (m, 2H), 1.88 (s, 3H), 1.41 (s, 9H).

Step C

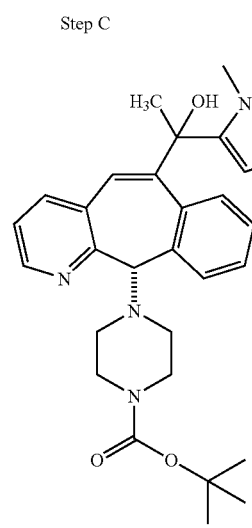

795.1

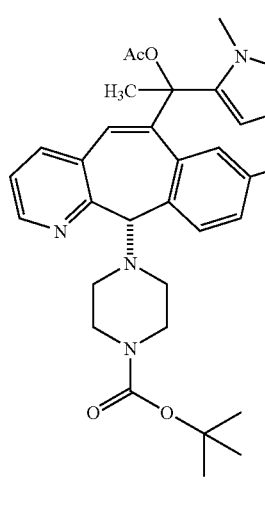

795.2

Compound (795.1) can be converted to acetate compound (795.2) by reacting it with 1 equivalent of acetic anhydride and 2 equivalents of pyridine.

Step D

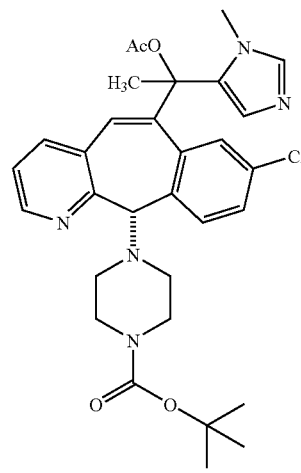

795.2

-continued

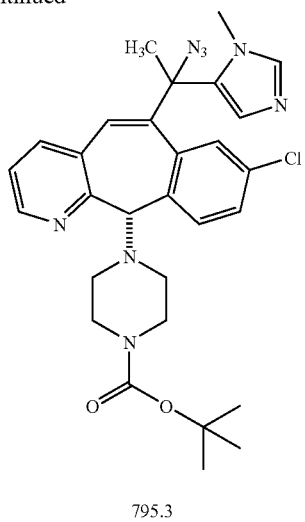

795.3

Compound (795.2) can be converted to compound (795.3) by reacting it with 1.5 equivalents of NaN$_3$, 15-crown-5, and a catalytic amount of Pd(dba)$_2$/PPh$_3$.

Alternatively, (795.3) can be synthesized by treating (795.1) with NaN$_3$, TFA followed by (Boc)$_2$O, and triethyl amine.

Step E

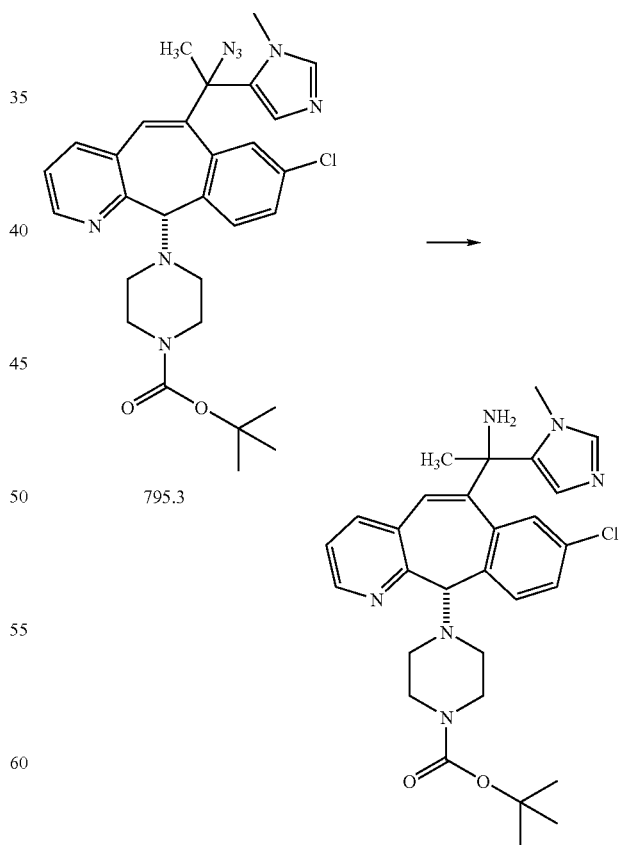

795.3

795.4

Compound (795.4) can be prepared by reacting (795.3) with P(CH$_3$)$_3$/H$_2$O.

PREPARATIVE EXAMPLE 66

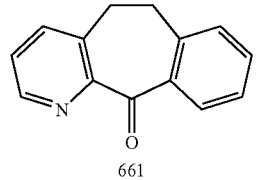

661

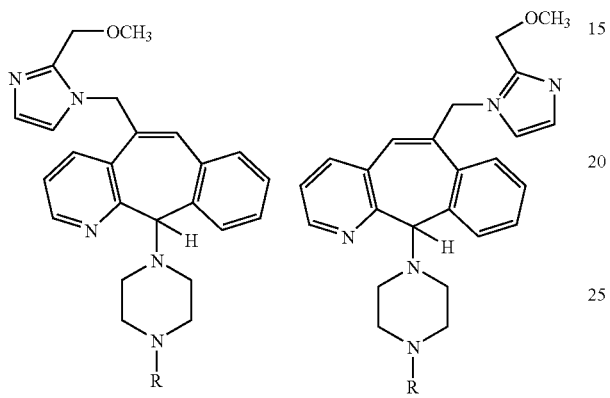

| R = BOC | R = BOC |
| --- | --- |
| (796) (+ enantiomer, A) | (797) (+enantiomer, A) |
| (798) (- enantiomer, B) | (799) (- enantiomer, B) |
| R = H | R = H |
| (800) (+ enantiomer, A) | (801) (+enantiomer, A) |
| (802) (- enantiomer, B) | (803) (- enantiomer, B) |

Compound 661 was reacted in essentially the same manner as in Preparative Example 23 and then Example 91 to obtain the N-BOC derivatives (796), (797), (798), and (799). Compounds (796), (797), (798), and (799) were then further reacted separately in essentially the same manner as in PREPARATIVE EXAMPLE 19, Step D to obtain the enantiomers (800), (801) (+enantiomers, isomer A) and (802), (803) (−enantiomers, isomer B). The C5 and C-6 vinyl bromide intermediates were separated by silica gel chromatography using hexane:ethyl acetate (80:20) as described in PREPARATIVE EXAMPLE 23, Step B.

EXAMPLE 490-491

The appropriate (+) enantiomer (800) or (−) enantiomer (802) from Preparative Example 66 above, was taken up in CH₂Cl₂ treated with the corresponding isocyanate and stirred at room temperature over night. The crude product was purified directly by silica gel preparative thin layer chromatography or silica gel column chromatography to afford compounds of the formula:

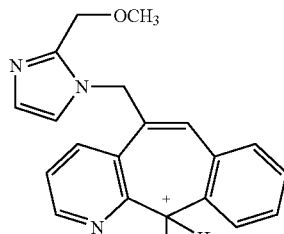 or

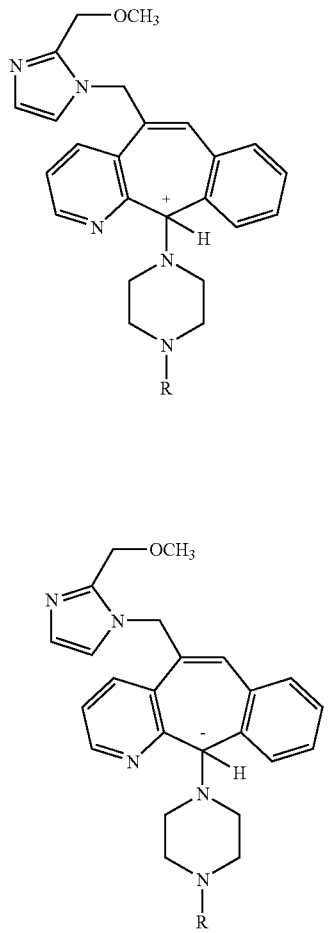

(wherein R is defined in Table 47).

TABLE 47

| Example # | R | Enantiomer | Comp # | Phys. Data. |
| --- | --- | --- | --- | --- |
| 490 | ![NC-C6H4-NHC(O)-] | + | (804) | Mp = 160–165 °C. [α]$_D^{25}$ = +84° (0.84 mg/1 mL MeOH) MH+ = 546 |
| 491 | ![NC-C6H4-NHC(O)-] | − | (805) | Mp = 158–163 °C. [α]$_D^{25}$ = −91.6° (0.84 mg/1 mL MeOH) MH+ = 546 |

PREPARATIVE EXAMPLE 67

Step A

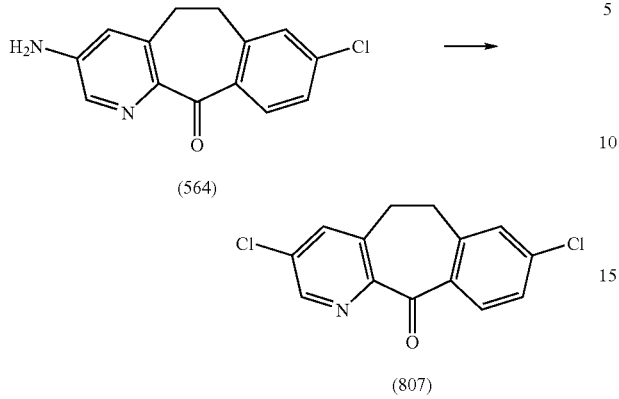

15.4 g (115 mmole) of CuCl$_2$ and 17 mL (144 mmol) of t-butyl nitrite was added to 400 mL of dry CH$_3$CN. The reaction mixture was cooled to 0° C. and 25 g of ketone (564) was added. The reaction was warmed to room temperature and stirred for two days. The mixture was concentrated under vacuum. Then 1N HCl was added to the residue until the pH was neutral, then NH$_4$OH was added until the pH was basic. After extraction with ethyl acetate, the organic layer was dried over MgSO$_4$ and concentrated under vacuum to give compound (807). Alternatively, the corresponding alcohol of 564 can be reacted as above followed by oxidation with MnO$_2$ in CH$_2$Cl$_2$ to give compound (807).

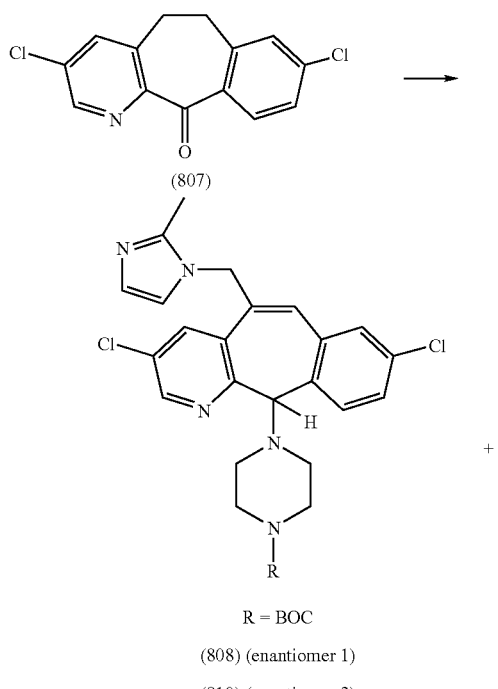

R = BOC
(808) (enantiomer 1)
(810) (enantiomer 2)

R = H
(812) (enantiomer 1)
(810) (enantiomer 2)

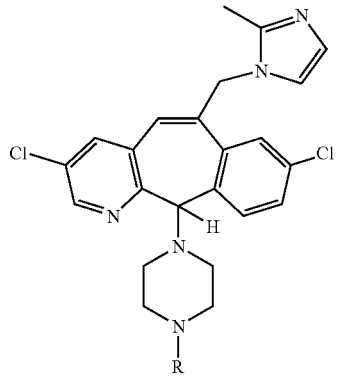

R = BOC
(809) (enantiomer 1)
(811) (enantiomer 2)

R = H
(813) (enantiomer 1)
(815) (enantiomer 2)

Compound (807) from step B above was reacted in essentially the same manner as in Preparative Example 23, and then Example 91 to obtain the N-BOC derivatives (808), (809), (810) and (811). These were then reacted separately in essentially the same manner as in Preparative Example 19, Step D to obtain the enantiomers (812) and (814), as well as enantiomers (813) and (815). The C5 and C-6 vinyl bromide intermediates were separated by silica gel chromatography using hexane:ethyl acetate as described in Preparative Example 23, Step B.

EXAMPLE 493

The appropriate enantiomer (812) (enantiomer 1) or (814) (enantiomer 2) from Preparative Example 67, Step B above, was taken up in CH$_2$Cl$_2$, treated with 4-cyanophenyl isocyanate and stirred at room temperature over night. The crude product was purified directly by silica gel preparative thin layer chromatography or silica gel column chromatography to afford compounds of the formula:

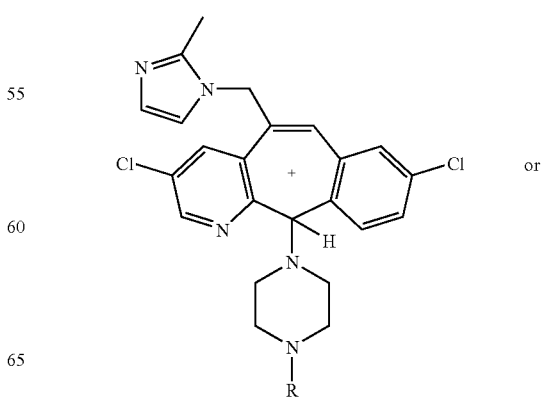 or

-continued

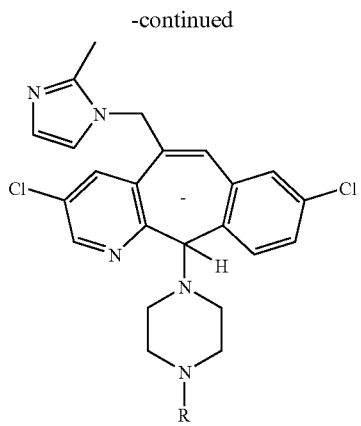

(wherein R is defined in Table 48).

TABLE 48

| Starting Cmp. # | R | Enantiomer | Comp # | Phys. Data. |
|---|---|---|---|---|
| (812) | NC-C6H4-NH-C(O)- | + | 816 | Mp = 175–181° C. $[\alpha]_D^{25}$ = +94.2° (1 mg/1 mL MeOH) |
| (814) | NC-C6H4-NH-C(O)- | − | (817) | Mp = 182–186° C. $[\alpha]_D^{25}$ = −120.3° (1 mg/1 mL MeOH) |

EXAMPLE 494

The appropriate enantiomer (813) (enantiomer 1) or (815) (enantiomer 2) from Preparative Example 67, Step B above, was taken up in CH$_2$Cl$_2$, treated with 4-cyanophenyl isocyanate and stirred at room temperature over night. The crude product was purified directly by silica gel preparative thin layer chromatography or silica gel column chromatography to afford compounds of the formula:

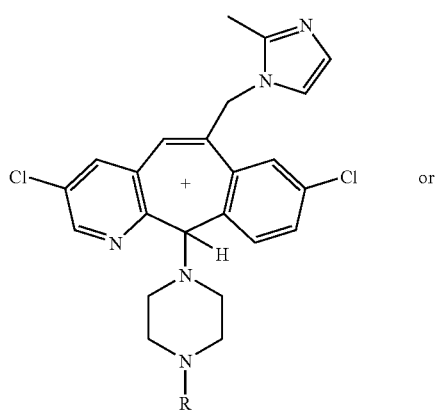

or

-continued

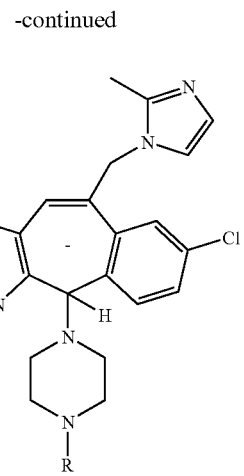

(wherein R is defined in Table 49).

TABLE 49

| Starting Cmp # | R | Enantiomer | Cmp # | Phys. Data. |
|---|---|---|---|---|
| (813) | NC-C6H4-NH-C(O)- | + | (818) | Mp = 176–181° C. $[\alpha]_D^{25}$ = +46.3° (0.79 mg/1 mL MeOH) MH+ = 584 |
| (815) | NC-C6H4-NH-C(O)- | − | (819) | Mp = 174–180° C. $[\alpha]_D^{25}$ = +43.3° (0.94 mg/1 mL MeOH) MH+ = 584 |

PREPARATIVE EXAMPLE 68

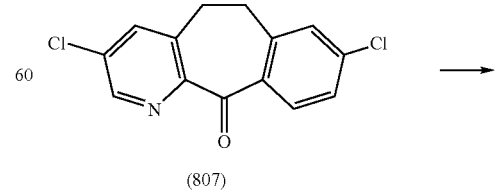

(807)

-continued

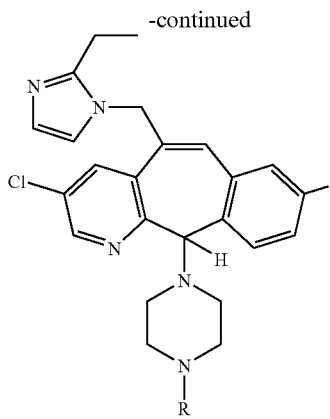

R = BOC
(820) (enantiomer 1)

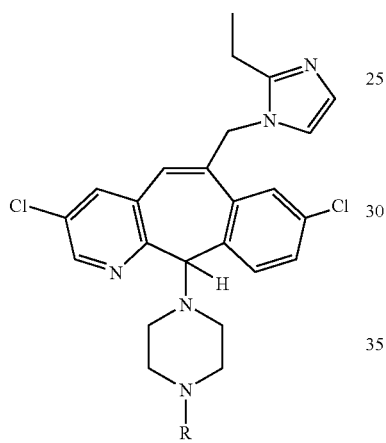

R = BOC
(821) (enantiomer 1)

Compound (807) from Preparative Example 67, Step A above was reacted in essentially the same manner as in Preparative Example 23, and then Example 91, substituting 2-ethylimidazole for 2-methylimidazole, to obtain the N-BOC derivatives (820), (821), (822) and (823). These were then reacted seperately in essentially the same manner as in Preparative Example 19, Step D to obtain the enantiomers (824) and (826), as well as enantiomers (825) and (827). The C5 and C-6 vinyl bromide intermediates were separated by silica gel chromatography using hexane:ethyl acetate as described in Preparative Example 23, Step B.

EXAMPLE 495

The appropriate enantiomer (824) (enantiomer 1) or (826) (enantiomer 2) from Preparative Example 68 above, was taken up in $CH_2Cl_2$, treated with 4-cyanophenyl isocyanate and stirred at room temperature over night. The crude product was purified directly by silica gel preparative thin layer chromatography or silica gel column chromatography to afford compounds of the formula:

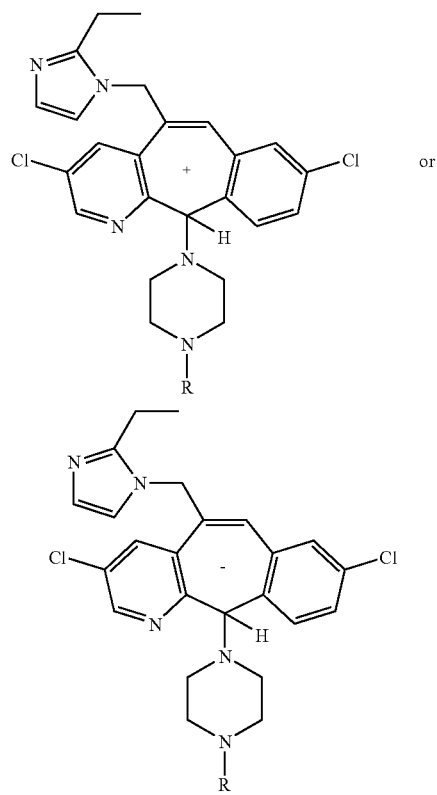

or (wherein R is defined in Table 50

TABLE 50

| Starting Cmp # | R | Enantiomer | Comp # | Phys. Data. |
|---|---|---|---|---|
| (824) | NC-C6H4-NH-C(=O)- | + | (828) | Mp = 176–182° C. $[\alpha]_D^{25}$ = +84.5° (1.3 mg/ 1 mL MeOH) MH+ = 598 |
| (826) | NC-C6H4-NH-C(=O)- | − | (829) | Mp = 175–182° C. $[\alpha]_D^{25}$ = −88.8° (1.14 mg/ 1 mL MeOH) MH+ = 598 |

EXAMPLE 496

The appropriate enantiomer (825) (enantiomer 1) or (827) (enantiomer 2) from Preparative Example 68 above, was taken up in $CH_2Cl_2$, treated with 4-cyanophenyl isocyanate and stirred at room temperature over night. The crude product was purified directly by silica gel preparative thin layer chromatography or silica gel column chromatography to afford compounds of the formula:

PREPARATIVE EXAMPLE 69

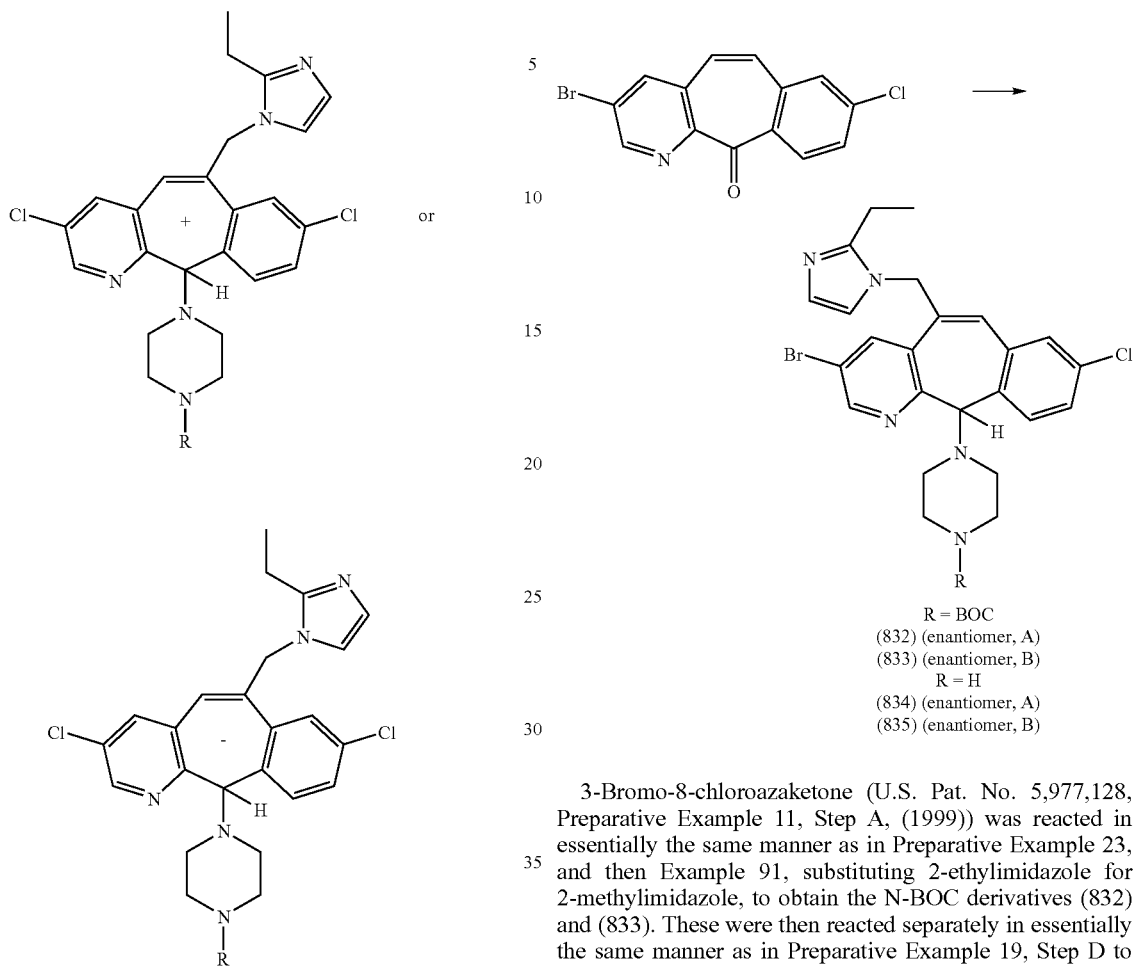

R = BOC
(832) (enantiomer, A)
(833) (enantiomer, B)
R = H
(834) (enantiomer, A)
(835) (enantiomer, B)

3-Bromo-8-chloroazaketone (U.S. Pat. No. 5,977,128, Preparative Example 11, Step A, (1999)) was reacted in essentially the same manner as in Preparative Example 23, and then Example 91, substituting 2-ethylimidazole for 2-methylimidazole, to obtain the N-BOC derivatives (832) and (833). These were then reacted separately in essentially the same manner as in Preparative Example 19, Step D to obtain the enantiomers (834) and (835).

EXAMPLE 497

The appropriate enantiomer (834) (enantiomer 1) or (835) (enantiomer 2) from Preparative Example 69 above, was taken up in $CH_2Cl_2$, treated with 4-cyanophenyl isocyanate and stirred at room temperature over night. The crude product was purified directly by silica gel preparative thin layer chromatography or silica gel column chromatography to afford compounds of the formula:

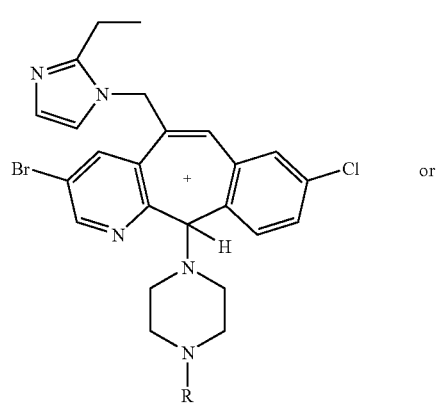

(wherein R is defined in Table 51).

TABLE 51

| Starting Cmp # | R | Enantiomer | Comp # | Phys. Data |
|---|---|---|---|---|
| (825) | NC-C₆H₄-NH-C(O)- | + | (830) | Mp = 170–174° C.<br>$[\alpha]_D^{25} = +39.1°$<br>(0.81 mg/1 mL MeOH)<br>MH+ = 598 |
| (827) | NC-C₆H₄-NH-C(O)- | – | (831) | Mp = 170–175° C.<br>$[\alpha]_D^{25} = -36.4°$<br>(0.96 mg/1 mL MeOH)<br>MH+ = 598 |

-continued

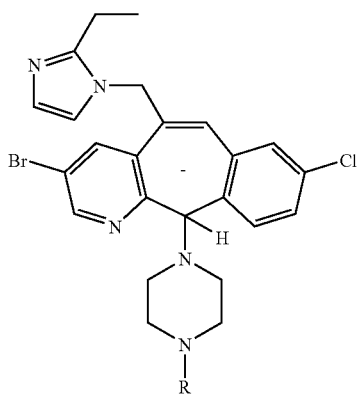

(wherein R is defined in Table 52).

TABLE 52

| Starting Cmp # | R | Enantiomer | Comp # | Phys. Data. |
|---|---|---|---|---|
| (834) | NC-C6H4-NH-C(=O)-CH(-)- | A | (836) | Mp = 172–179° C. (d) MH+ = 643 |
| (835) | NC-C6H4-NH-C(=O)-CH(-)- | B | (837) | Mp = 171.9–178.3° C. MH+ = 643 |

PREPARATIVE EXAMPLE 70

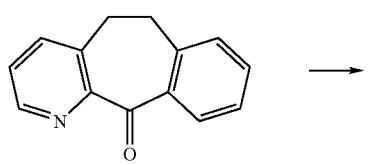 →

661

-continued

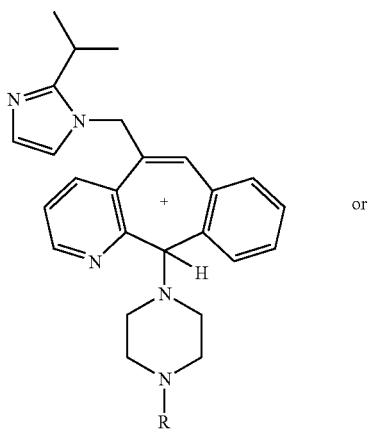

R = BOC
(838)
(839)

R = H
(840)
(841)

Compound 661 was reacted in essentially the same manner as in Preparative Example 23, and then Example 91, substituting 2-isopropylimidazole for 2-methylimidazole, to obtain the N-BOC derivatives (838) and (839). These were then reacted separately in essentially the same manner as in Preparative Example 19, Step D to obtain the enantiomers (840) and (841).

EXAMPLE 498

The appropriate enantiomer (840) (enantiomer 1) or (841) (enantiomer 2) from Preparative Example 70 above, was taken up in $CH_2Cl_2$, treated with 4-cyanophenyl isocyanate and stirred at room temperature over night. The crude product was purified directly by silica gel preparative thin layer chromatography or silica gel column chromatography to afford compounds of the formula:

or

-continued

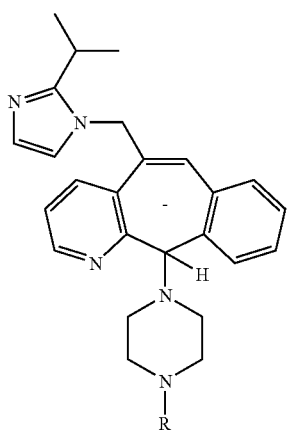

(wherein R is defined in Table 53).

TABLE 53

| Starting Cmp # | R | Enantiomer | Comp # | Phys. Data |
|---|---|---|---|---|
| (840) | NC-C6H4-NHC(O)- | A | (842) | Mp = 168–170° C. (d) $[\alpha]_D^{25}$ = +64.1° (0.66 mg/1 mL MeOH) |
| (841) | NC-C6H4-NHC(O)- | B | (843) | Mp = 166–171° C. $[\alpha]_D^{25}$ = −80.9° (0.85 mg/1 mL MeOH) |

PREPARATIVE EXAMPLE 71

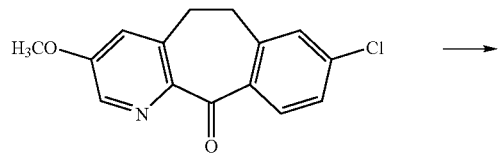 →

-continued

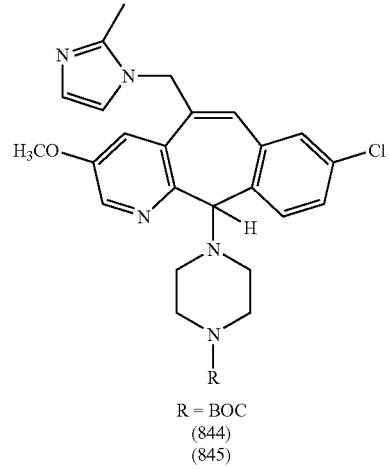

R = BOC
(844)
(845)

R = H
(846) (enantiomer, A)
(847) (enantiomer, B)

3-Methoxy-8-chloroazaketone (U.S. Pat. No. 5,977,128 (1999), Example 2, step D) was reacted in the same manner as in Preparative Example 23, and Example 91 to obtain the N-BOC derivatives (844) and (845). These compounds were then reacted seperately in essentially the same manner as in Preparative Example 19, Step D to obtain the enantiomers (846) (A) and (847) (B).

EXAMPLE 499

The appropriate enantiomer (846) (enantiomer A) or (847) (enantiomer B) from Preparative Example 71 above, was taken up in $CH_2Cl_2$, treated with 4-cyanophenyl isocyanate and stirred at room temperature over night. The crude product was purified directly by silica gel preparative thin layer chromatography or silica gel column chromatography to afford compounds of the formula:

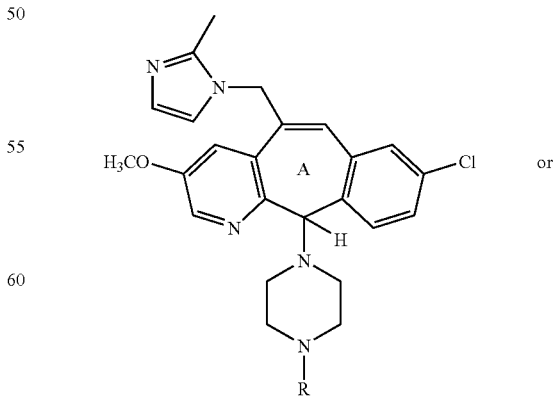 or

-continued
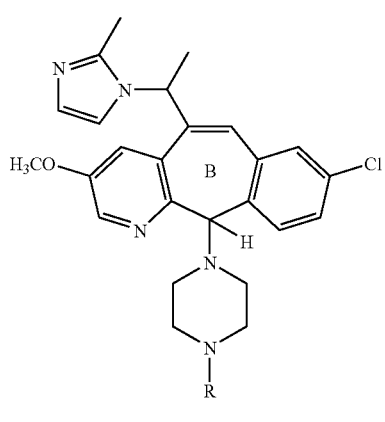
(wherein R is defined in Table 54).
TABLE 54
| Starting Cmp # | R | Enantiomer | Comp # | Phys. Data. |
|---|---|---|---|---|
| (846) | NC-C6H4-NH-C(O)- | A | (848) | Mp = 174.2–189.3° C. (d) MH+ = 580 |
| (847) | NC-C6H4-NH-C(O)- | B | (849) | Mp = 174.4–189.8° C. MH+ = 580 |
EXAMPLE 500
795.1
-continued
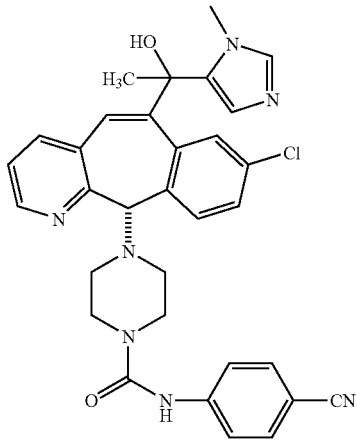
850
Compound (850) can be prepared by following essentially the same procedure as described in Example 482.
EXAMPLE 501
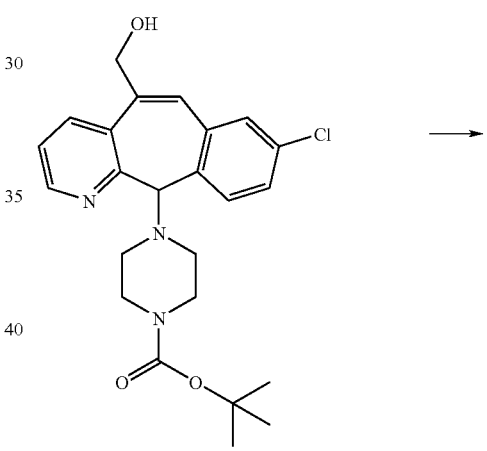
240
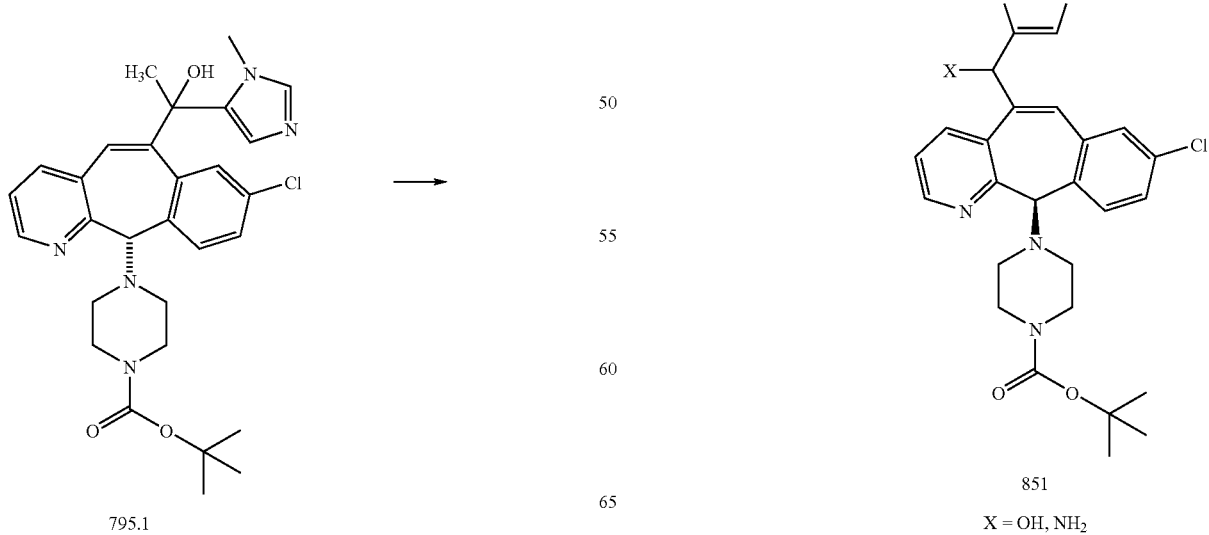
851
X = OH, NH₂

Starting with compound (240) from Preparative Example 23, Step H, compound (851) can be prepared following essentially the same procedure as described in Preparative Example 65, Steps A and B.

EXAMPLE 502

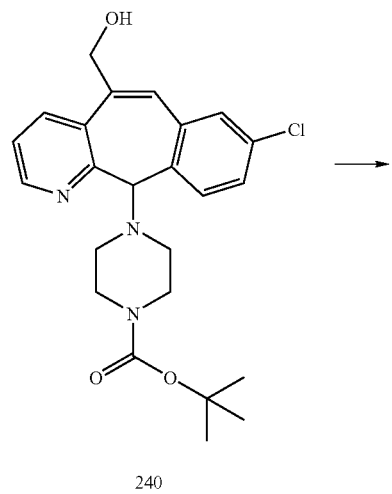

240

852

Starting with compound (240) from Preparative Example 23, Step H, compound (852) can be prepared following essentially the same procedures as described in Preparative Example 65, Step A and Example 489, Steps A-E.

PREPARATIVE EXAMPLE 72

Step A

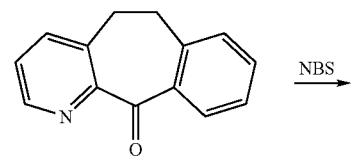

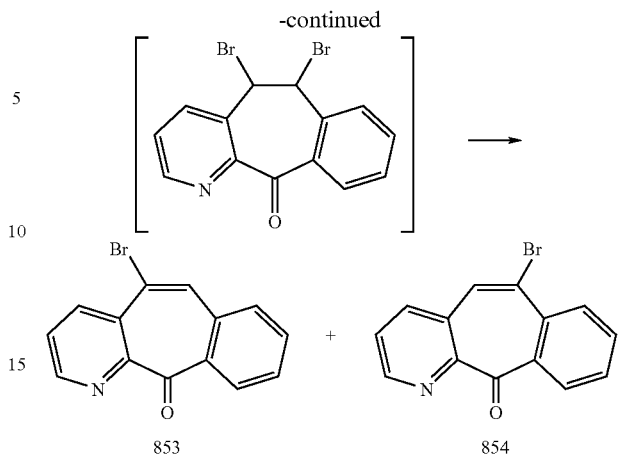

853    854

The starting tricyclic keto compound (disclosed in U.S. Pat. No. 5,151,423) (56.5 g; 270 mmol) was combined with NBS (105 g; 590 mmol) and benzoyl peroxide (0.92 g) in CCl$_4$. The reaction was heated at 80° C. for 5 hr. The mixture was cooled and the resulting precipitate was filtered and treated with DBU (25.59 ml) in THF (300 mL). The resulting solution was stirred at room temperature for 24 hrs, then evaporated, followed by extraction with CH$_2$Cl$_2$—H$_2$O. The organic layer was dried over MgSO$_4$, filtered and evaporated to dryness to give a mixture of two compounds which were separated on a flash silica gel column eluting with Hexane-50% EtOAc to give the title compound (853) $\delta_H$ (CDCl$_3$) 8.8 (dd, 1H), 8.45 (dd, 1H), 7.99 (m, 1H), 7.92 (s, 1H), 7.59-7.64 (m, 3H), 7.23 (dd, 1H) and (854) $\delta_H$ (CDCl$_3$) 8.19 (dd, 1H), 7.99 (dd, 1H), 7.82 (dd, 1H), 7.25-7.65 (m, 4H), 7.22 (s, 1H)

Step B

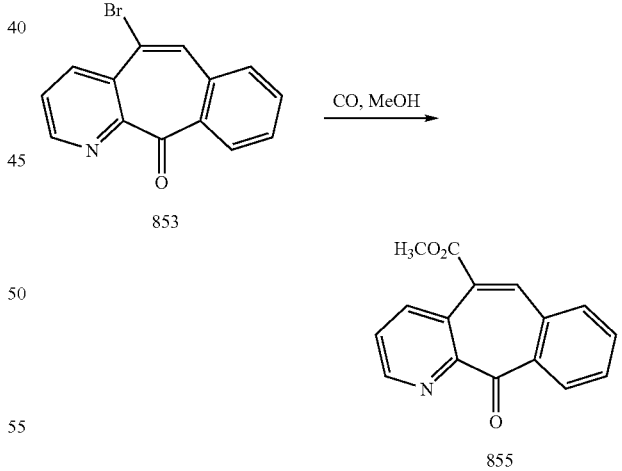

Compound (853) (25 g), triphenyl phosphine (13.75 g), and palladium chloride (1.5 g) were combine in MeOH (30 ml) and toluene (200 ml). To the mixture was added DBU (18 ml) and the mixture was sealed in a parr bomb. The mixture was stirred and subjected to 100 psi of CO at 80° C. for 5 hr. The reaction was diluted with EtOAc and washed with water. The organic layer was dried over MgSO$_4$, filtered and purified by flash chromatography eluting with CH$_2$Cl$_2$-10% EtOAc to give the title compound (855). $\delta_H$ (CDCl$_3$) 8.8 (dd, 1H), 8.40 (dd, 1H), 8.2 (s 1H), 8.04 (dd, 1H), 7.59-7.64 (m, 4H), 3.95 (s, 3H).

Step C

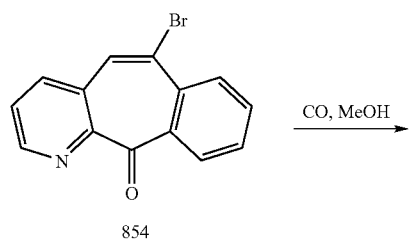

854

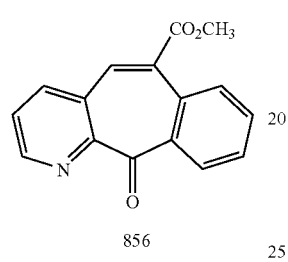

856

Reacting compound (854) in essentially the same manner as described in Step B above, gave the title compound (856). $\delta^H$ (CDCl$_3$) 8.85 (dd, 1H), 7.85-8.0 (m, 2H), 7.8 (s, 1H), 7.28-7.37 (m, 4).

Step D

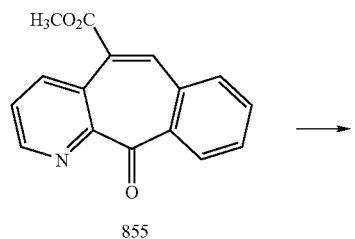

855

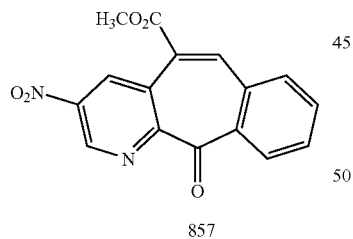

857

Compound (855) (19.5 g, 73.5 m mol) was dissolved in CH$_2$Cl$_2$ (100 mL) and cooled to 0° C. Tetrabutyl ammonium nitrate (31.36 g, 103 n mol) and trifluoro acetic anhydride (18.52 g, 88 m mol) were added and the mixture stirred at room temperature for 5 hrs. The reaction mixture was concentrated to dryness, followed by extraction with CH$_2$Cl$_2$—NaHCO$_3$. The combine organic layer was dried over MgSO$_4$ and concentration to dryness and the residue was chromatographed on silica gel using CH$_2$Cl$_2$ -EtOAc (25%) to give the title compound (857) (12.4 g), $\delta_H$ (CDCl$_3$) 9.45 (dd, 1H), 9.05 (dd, 1H), 8.28 (s, 1H), 8.0 (dd, 1H), 7.65 (m, 3H), 3.98 (s, 3H).

Step E

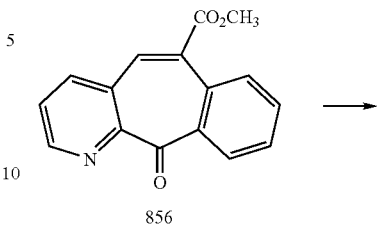

856

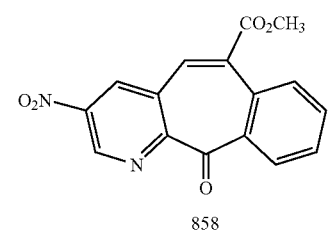

858

Reacting compound (856) in essentially the same manner as described in Step D above, gave the title compound (858). MH$^+$=311

Step F

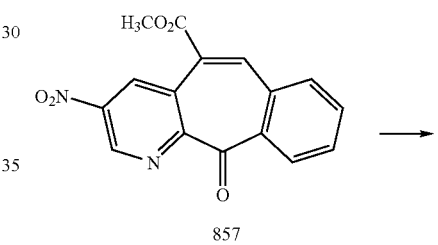

857

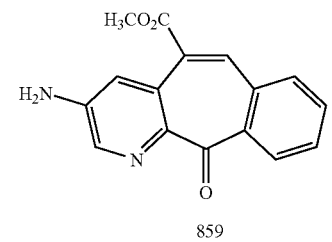

859

Compound (857) (6 g) was balloon hydrogenated in MeOH (100 mL) over Raney-Ni)4.2 g) at room temperature overnight. The catalyst was filtered off and the filtrate was evaporated to dryness to give the title compound (859) (4.66 g) MH$^+$=281

Step G

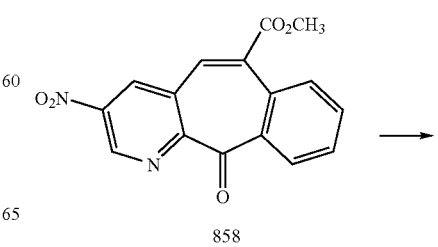

858

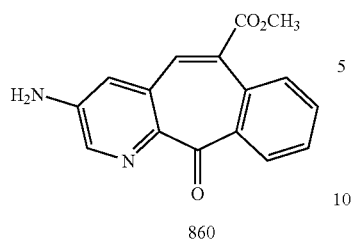
860

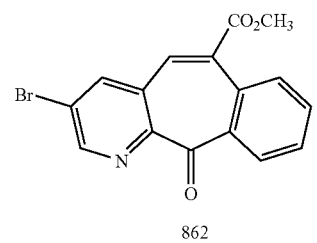
862

Reacting compound (858) in essentially the same manner as described in Step F above, gave the title compound (860) MH$^+$=281.

Reacting compound (861) in essentially the same manner as described in Step H above, gave the title compound (862) MH$^+$=345.

Step H

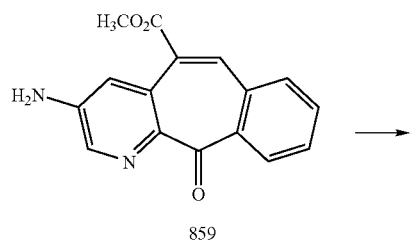
859

Step J

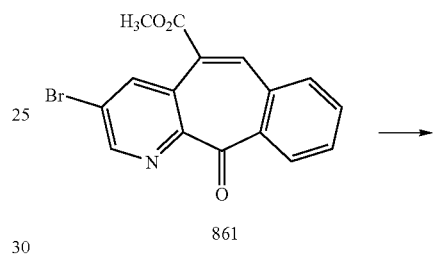
861

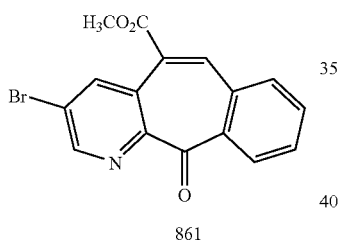
861

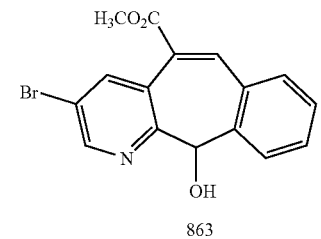
863

To a suspension of compound (859) (2.1 g) in 48% HBr, was added sodium nitrite (1.55 g) followed by bromine (2.11 mL) at 0° C. The mixture was stirred at room temperature overnight. Concentrated NH$_4$OH was then added dropwise until basic pH (to litmus paper). The reaction was extracted with CH$_2$Cl$_2$, washed with brine, dried over MgSO$_4$, filtered and the solvent evaporated to give the title compound (861) (1.75 g) MH$^+$=345.

To a stirred solution of compound (861) (1.6 g, 4.64 mmole) in MeOH (30 mL) under nitrogen at 0° C. was added NaBH$_4$ (0.3 g, 7.9 mmole). The resulting solution was stirred at room temperature for 24 hrs, then evaporated, followed by extraction with CH$_2$Cl$_2$—H$_2$O. The organic layer was dried over MgSO$_4$, filtered and evaporated to dryness to give the title compound (863) (1.58 g) MH$^+$=347.

Step I

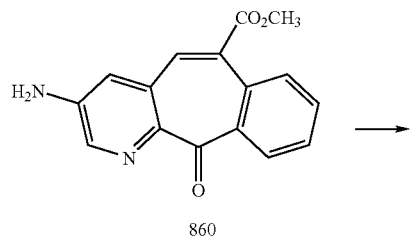
860

Step K

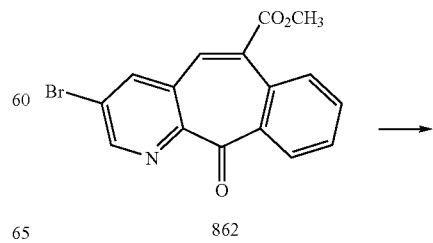
862

-continued

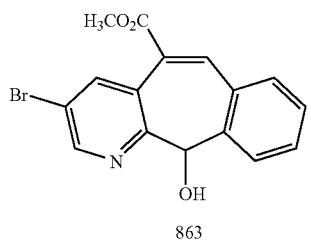
864

Reacting compound (862) in essentially the same manner as described in Step J above, gave the title compound (864). MH⁺=347

Step L

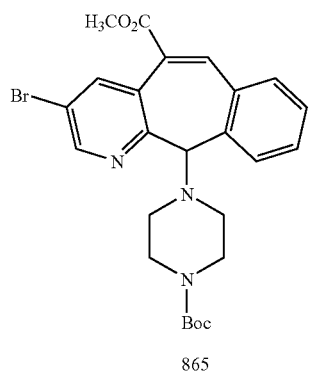
863

Compound 863 (1.57 g,) was stirred in thionyl chloride (10 mL) at room temperature for 4 hrs then evaporated to dryness. The resulting crude oil as taken up in acetonitrile (50 mL) and refluxed with N-Boc-piparazine (1.41 g) and triethyl amine (3.91 g) overnight. The mixture was evaporated to dryness, followed by extraction with CH₂Cl₂—NaHCO₃. The organic layer was dried over MgSO₄, filtered and evaporated to dryness to give a brown gum which was purified by column chromatography on silica gel, eluting with Hexane –20% EtOAc to give the title compound (865) (0.69 g). MH⁺=515.

Step M

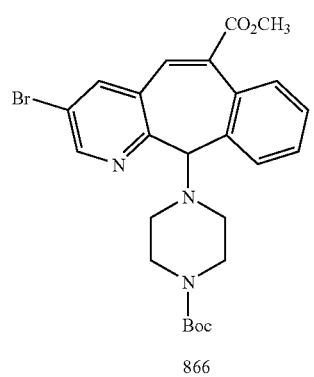
864

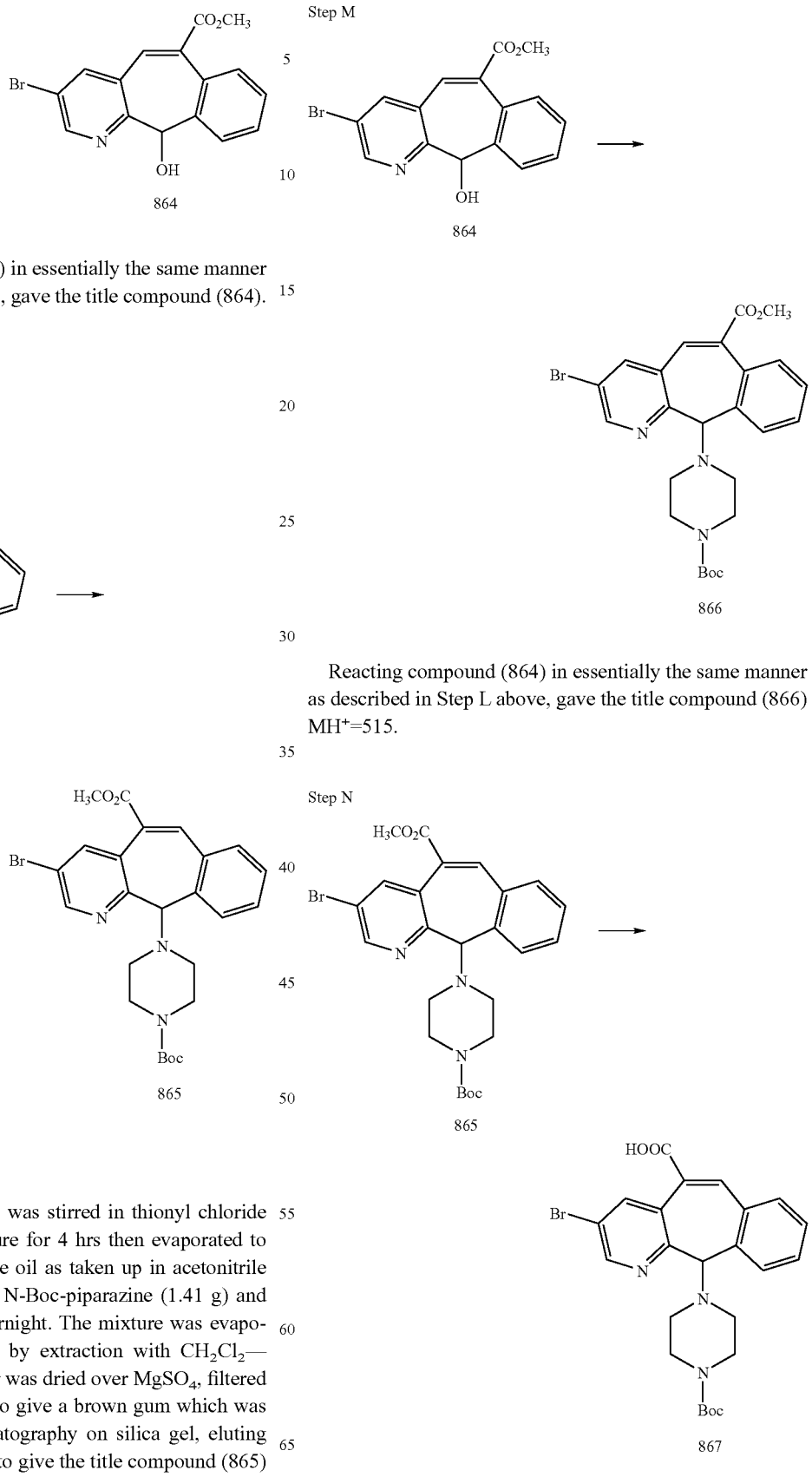
866

Reacting compound (864) in essentially the same manner as described in Step L above, gave the title compound (866) MH⁺=515.

Step N

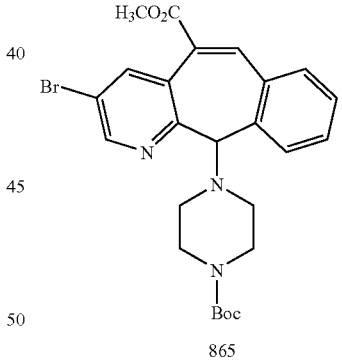
865

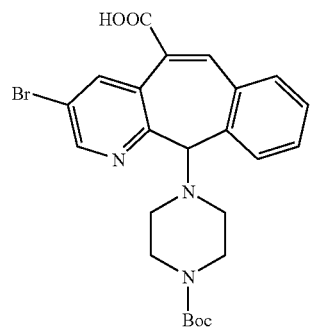
867

Compound (865) (0.65 g, 1.26 mmole) was refluxed with LiOH (0.45 g, 18.79 mmole) in MeOH (15 mL) and water (1 mL) for 2 hrs. 10% aq. Citric acid was added until pH=3.5, followed by extraction with $CH_2Cl_2$-brine. The organic layer was dried over $MgSO_4$ filtered and evaporated to dryness to give a white solid (867) (0.60 g) $MH^+$=501

Step O

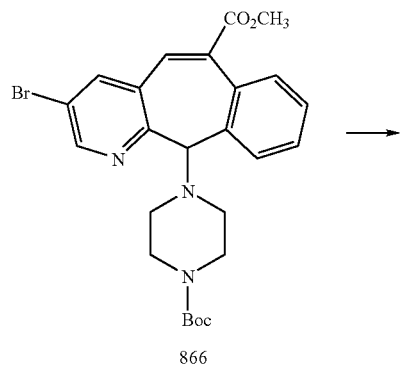
866

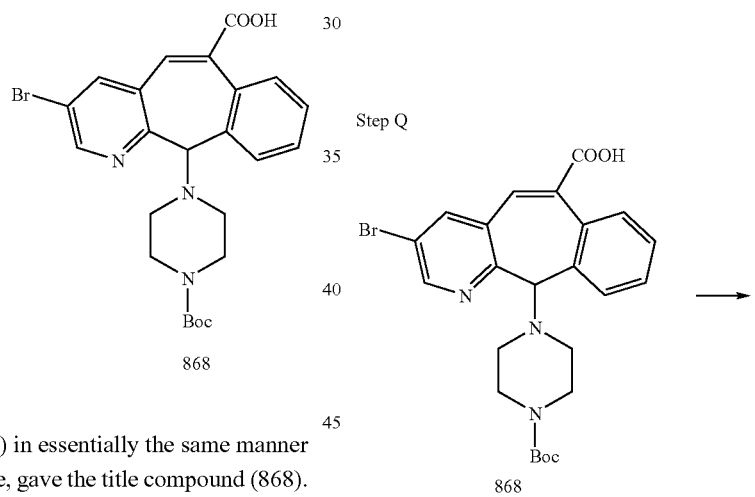
868

Reacting compound (866) in essentially the same manner as described in Step N above, gave the title compound (868). $MH^+$=501

Step P

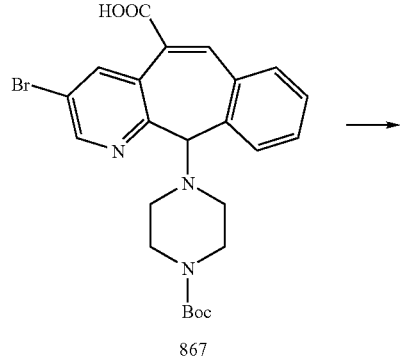
867

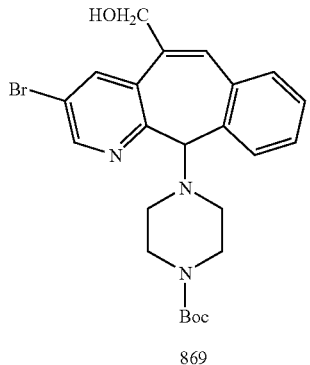
869

Compound (867) (0.60 g, 1.21 mmole) was stirred with carbonyl diimidazole (0.59 g, 3.63 mmole) in THF (15 mL) at 40° C. overnight. The reaction mixture was cooled in an ice-bath then added $NaBH_4$ (0.28 g, 7.31 mmole) and stirred at room temperature overnight. The mixture was evaporated to dryness, followed by extraction with $CH_2Cl_2$-water. The organic layer was dried over $MgSO_4$, filtered and evaporated to give a brown gum which was purified by column chromatography on silica gel, eluting with Hexane-50% EtOAc to give the title compound (869)(0.493 g) $MH^+$=487.

Step Q

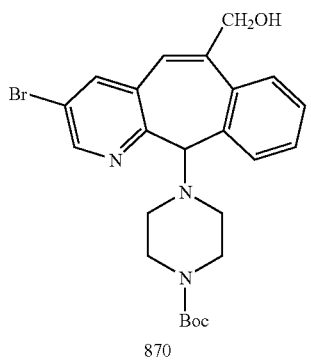
870

Reacting compound (868) in essentially the same manner as described in Step P above, gave the title compound (870). $MH^+$=487

Step R

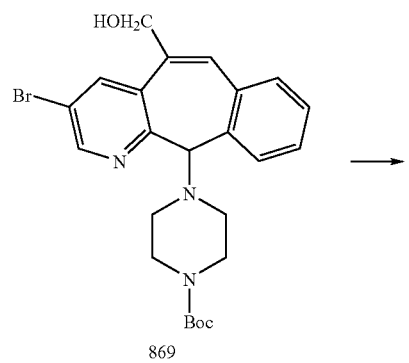
869

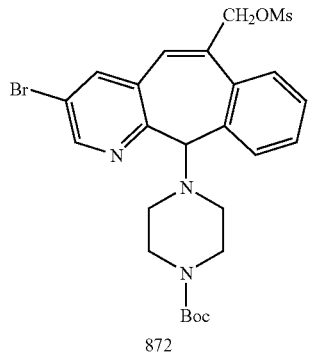
872

Reacting compound (870) in essentially the same manner as described in Step R above, gave the title compound (872). MH⁺=565

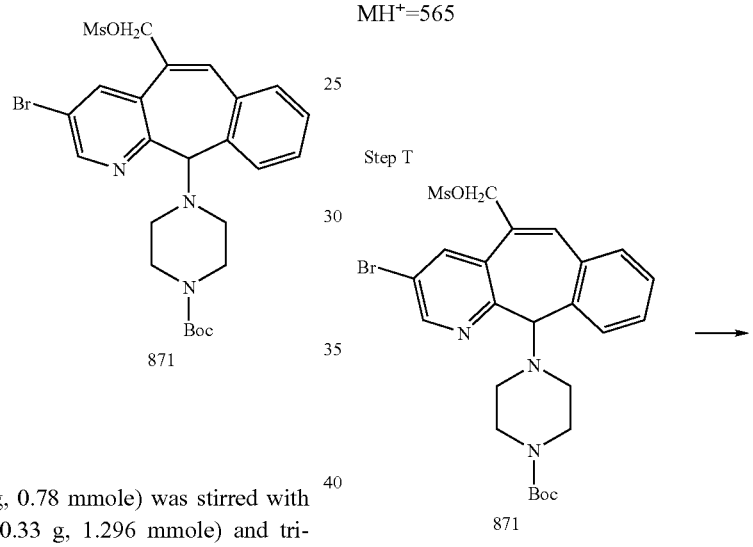
871

Compound (869) (0.38 g, 0.78 mmole) was stirred with methanesulfonyl-chloride (0.33 g, 1.296 mmole) and triethylamine (0.68 g, 6.72 mmole) in THF (10 mL) at room temperature overnight. The mixture was evaporated to dryness, followed by extraction with CH₂Cl₂-water. The organic layer was dried over MgSO₄, filtered and evaporated to dryness to give the title compound (871)(0.369 g). MH⁺=565

Step S

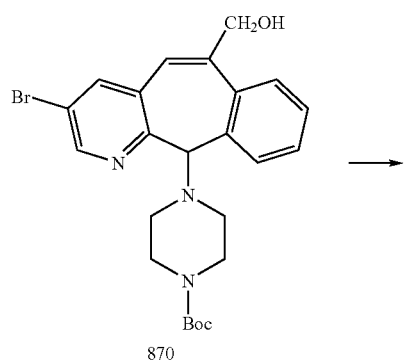
870

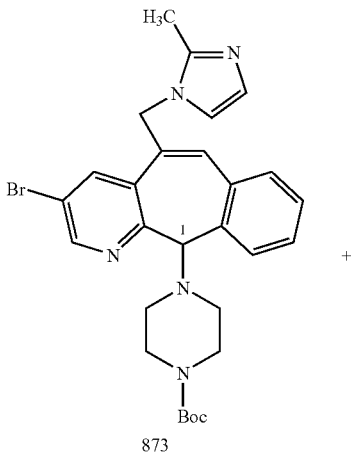
873

-continued

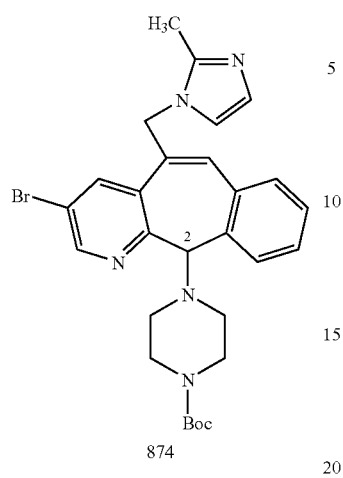
874

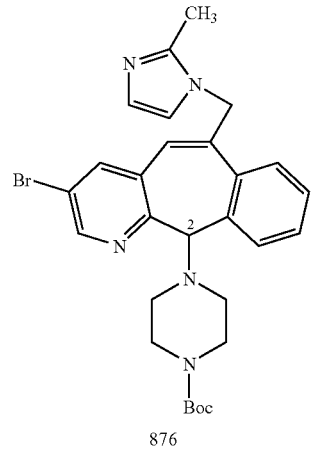
876

Compound (871) (0.0.369 g, 0.653 mmole) was stirred with 2-methylimidazole (0.188 g, 2.28 mmole) in DMF (5 mL) at room temperature overnight. The mixture was evaporated to dryness, followed by extraction with $CH_2Cl_2$-water. The organic layer was dried over $MgSO_4$, filtered, evaporated to dryness and then purified on silica-gel prep-plate chromatography, eluting with $CH_2Cl_2$-5% (MeOH-10% $NH_4OH$) to give the product as a mixture of isomers (1.126 g) $MH^+$=551. Separation of the product mixture by HPLC using a prep AD column, eluting with 20% IPA/80% hexane/ 0.2% DEA (isocratic 60 ml/min.) afforded pure isomer 1 (873) (0.06 g, $MH^+$=551 and isomer 2 (874) (0.0061 g) $MH^+$=551.

Step U

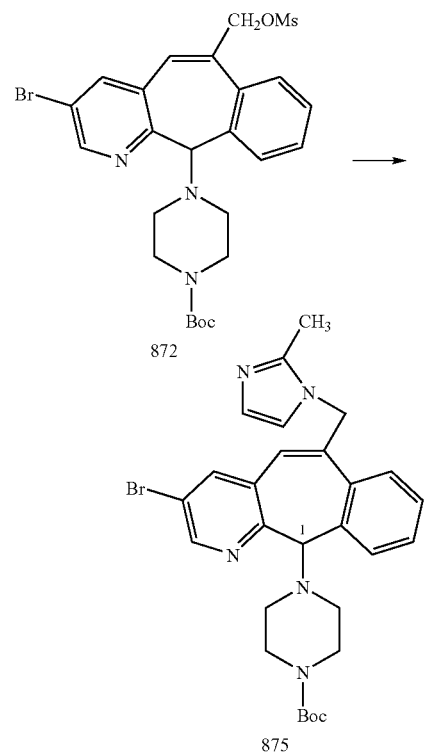

Reacting compound (872) in essentially the same manner as described in Step T above, gave the title compounds (875). $MH^+$=551, and (876) $MH^+$=551.

EXAMPLE 503

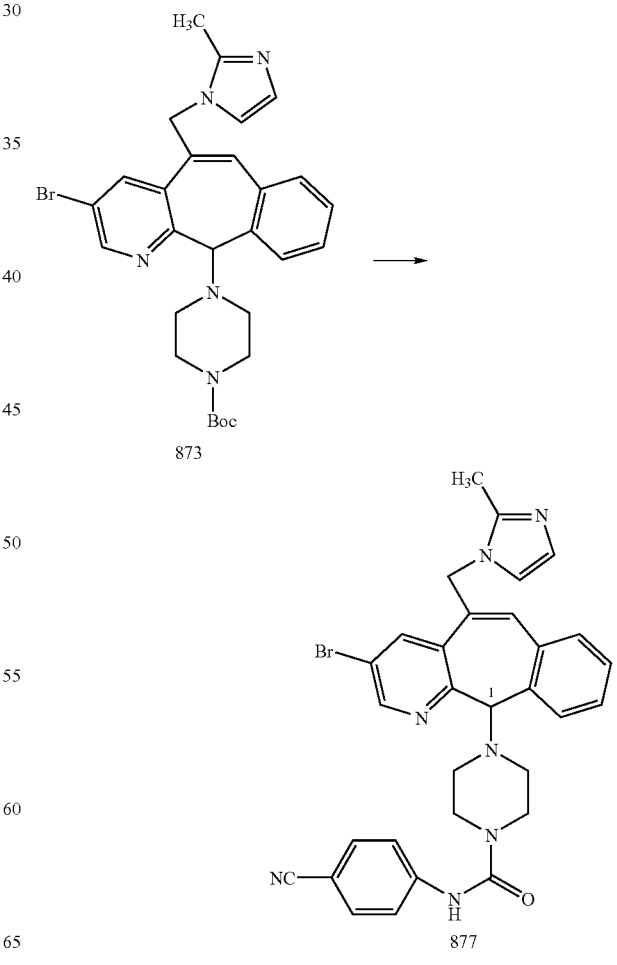

Compound (873) (0.043 g, 0.078 mmole) was stirred with TFA (5 mL) in CH$_2$Cl$_2$ (5 mL) for 4 hrs. at room temperature. The mixture was then evaporated to dryness. To the residue was added p-cyanophenylisocyanate (0.0123 g, 0.086 mmole) and triethylamine (0.5 mL) in CH$_2$Cl$_2$ (5 mL) and the mixture stirred at room temperature for 2 hrs. The mixture was evaporated to dryness, followed by extraction with CH$_2$Cl$_2$-brine. The organic layer was dried over MgSO$_4$, filtered and evaporated to dryness to give a brown gum which was purified by prep-plate chromatography on silica gel, eluting with CH$_2$Cl$_2$-5% (MeOH-10% NH$_4$OH) to give the title compound (877) (0.0394 g). MH$^+$=595, $\delta_H$ (CDCl$_3$) 8.6 (1H); 8.05 (1H); 7.22-7.5 (8H); 6.99 (1H); 6.95 (1H); 6.93 (1H); 4.99-5.25 (2H); 4.6 (1H); 3.1-3.25 (4H); 2.25 (3H), 1.8-2.05 (4H).

EXAMPLE 504

Reacting compound (874) in essentially the same manner as described in Example 503 above, gave the title compound. (873) MH$^+$=595, $\delta_H$ (CDCl$_3$) 8.6 (1H); 8.05 (1H); 7.22-7.5 (8H); 6.99 (1H); 6.95 (1H); 6.93 (1H); 4.99-5.25 (2H); 4.6 (1H); 3.1-3.25 (4H); 2.25 (3H), 1.8-2.05 (4H).

EXAMPLE 505

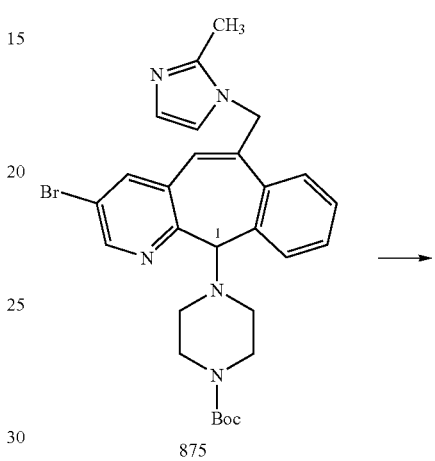

875

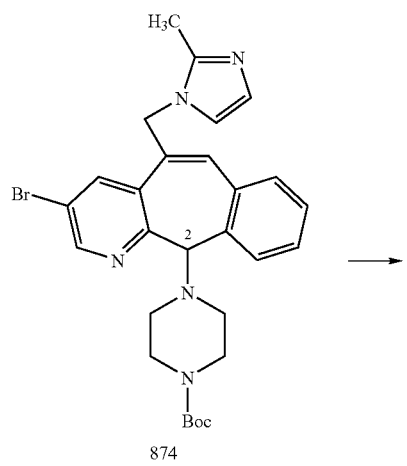

874

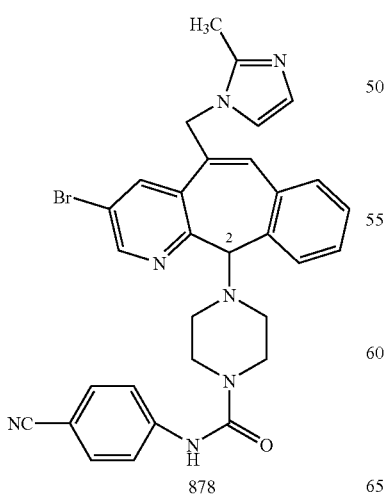

878

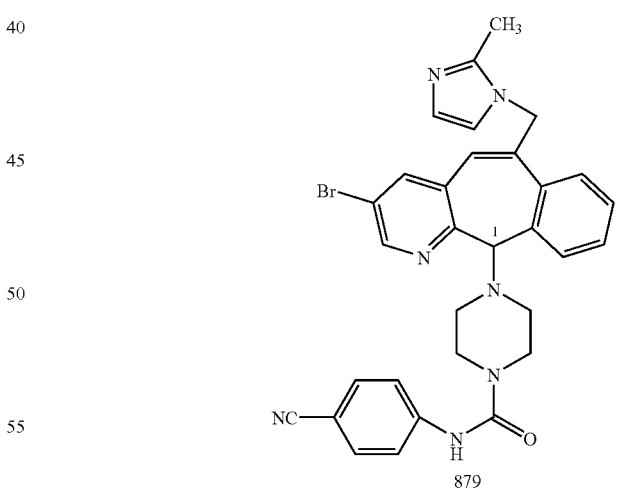

879

Reacting compound (875) in essentially the same manner as described in Example 503 above, gave the title compound (879). MH$^+$=595, $\delta_H$ (CDCl$_3$) 8.55 (1H); 7.78 (1H); 7.65 (1H); 7.4-7.51 (6H); 6.98 (1H); 6.9 (1H); 6.85 (1H); 5.05-5.3 (2H); 4.6 (1H); 3.1-3.25 (4H); 2.5 (3H), 1.8-2.00 (4H).

EXAMPLE 506

Diasteromeric separation of product (795.1):

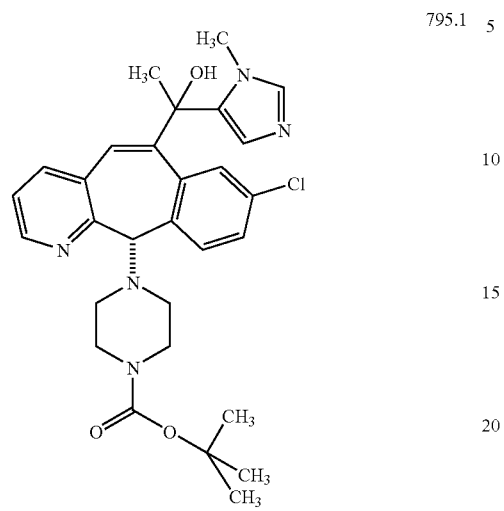

795.1 from Example 489, Step B, was done by PREP HPLC using the Prep Chiralcel OD Column and eluting with 20% IPA/HEXANES+0.2% DEA (initial mobile phase), then 25% IPA/HEXANES+0.2% DEA (final mobile phase) to give 795.1 isomer-1 (i.e., 795.1 a) and 795.1 isomer-2 (i.e., 795.1b).

Isomer-1—MH+=536.1 (CDCL3, 400 MHz) 8.437 (d, 1H), 8.22 (d, 1H), 7.54 (s, 1H), 7.49 (d, 1H), 7.37 (d, 1H), 7.31 (d, 1H), 7.19(m, 1H), 7.10 (s, 1H), 6.57 (s, 1H), 4.57 (s, 1H), 3.86 (s, 3H), 3.21 (br, s, 4H), 2.24 (m, 2H), 1.98 (m, 2H), 1.90 (s, 3H), 1.41 (s, 9H). m.p. 195-197° C.

Isomer-2—MH+=536.1 (CDCL3, 400 MHz) 8.47(d, 1H), 7.64 (d, 1H) 7.64 (d, 1H), 7.54 (s, 1H), 7.5(s, 1H), 7.35(d, 1H), 7.23(m, 1H), 7.21 (m, 1H), 7.22 (m, 1H), 7.14 (s, 1H), 6.8 (d, 1H), 4.59 (s, 1H), 3.76 (s, 3H), 3.23 (br.s.4H), 2.23 (m, 2H), 1.99 (m, 2H), 1.87 (s, 3H), 1.41 (s, 9H). m.p. 206-208° C.

EXAMPLE 507

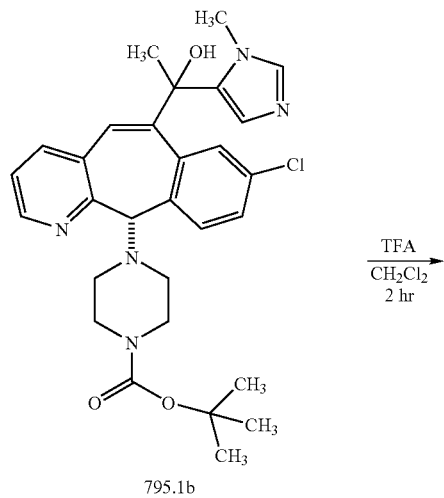

795.1b

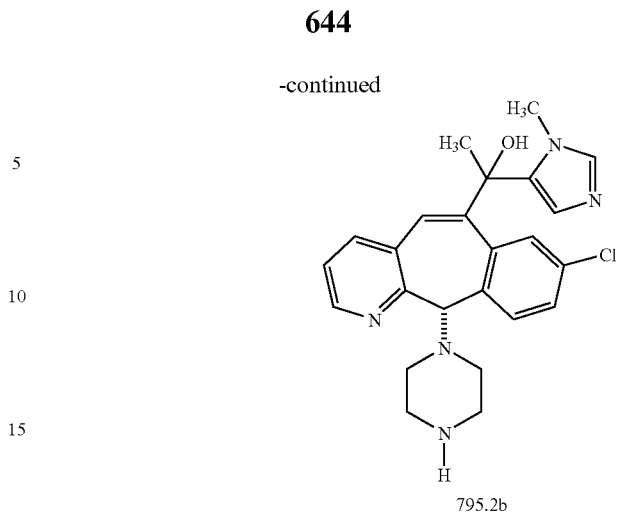

795.2b

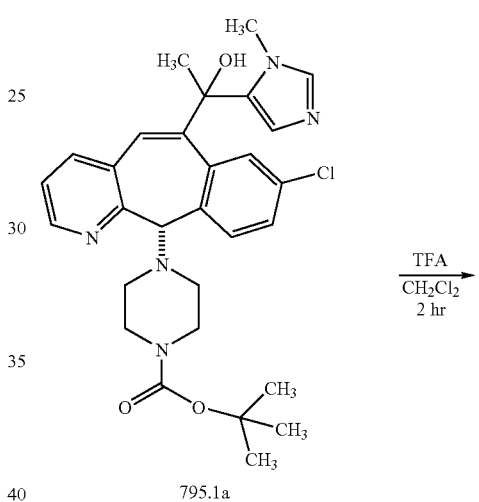

795.1a

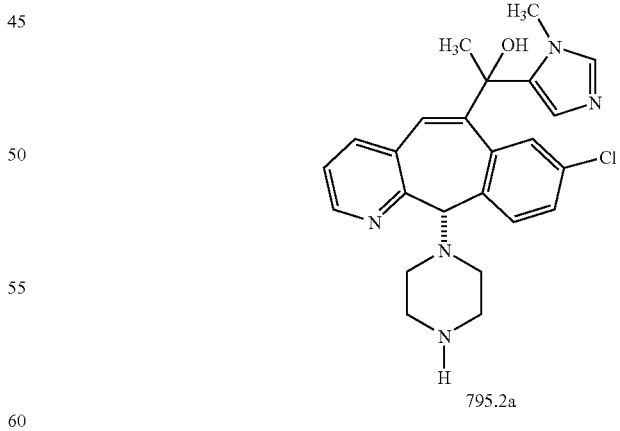

795.2a

Compound 795.1b (isomer 2, 0.093 g, 0.173 mmoles) was converted to 795.2b by reacting it with $CH_2Cl_2$(5.0 ml)/TFA (1.0 ml) at room temperature under $N_2$.

The same procedure was used to prepare 795.2a (isomer 1) from 795.1a.

EXAMPLE 508

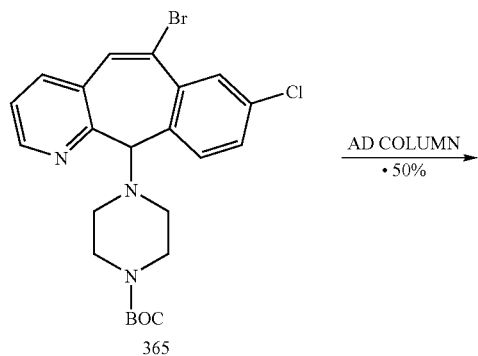

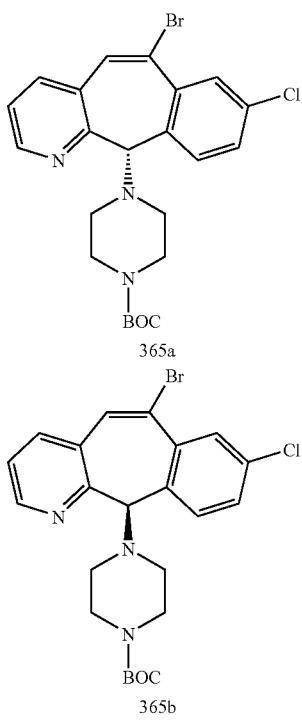

Separations of enantiomers 365a and 365b is accomplished by chiral HPLC using a Chiralpak AD column and eluting with IPA (20%) hexanes (80%)+0.2% DEA.

Isomer 365a: retention time=7.65 min; MH+=492.
Isomer 365b: retention time=12.16 min; MH+=492, m.p. 95-100° C.

PREPARATIVE EXAMPLE 73

Step A

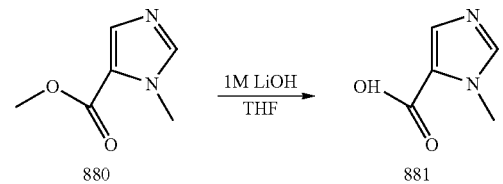

Dissolve (880) (2 eq. 14.2 mmol) in THF (20 ml), add 1 M LiOH(16 ml) and stir at room temperature for 1 hour or until reaction is complete. evaporate to dryness, then evaporate 3× with toluene, to obtain crude (881) as a solid.

Step B

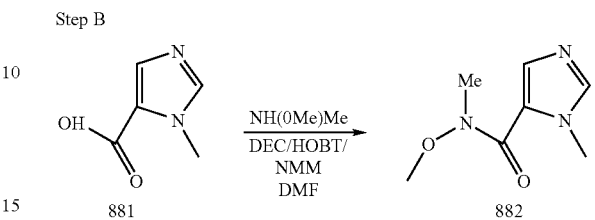

Take crude (881) from Step A, and dissolve in DMF (60 ml), and add NH(OMe)Me(3.14 g), DEC(6.14 g), HOBT (2.16 g), NMM(11 ml), and stir at room temperature over night. Add 1.0 N HCL until acetic (pH=2), wash with diethyl ether. Add, while stirring, K2CO₃ until basic ~pH=8, saturate with NaCl, and extract with (4×).CH₂Cl₂. Dry with MgSO₄, filter and evaporate to obtain product (882) (3.23 g).

Step C

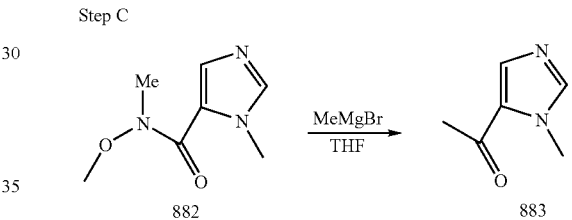

Took crude (882) (14.2 mmol), and dissolve in THF (100 ml). Cool in an iced bath and add MeMgBr (3 Molar in diethyl ether); (22.2 ml), dropwise over 10 minutes, under N₂. Let warm to 40° C. and stir for 4 hours or until reaction is complete. Cool in an iced bath and add saturated NH₄Cl. Extract with ethyl acetate and then 3× with CH₂Cl₂. Dry with MgSO₄, filter and evaporate. Store under vacuum to obtain crystals—(883)(1.78 g, 74%).

Step D

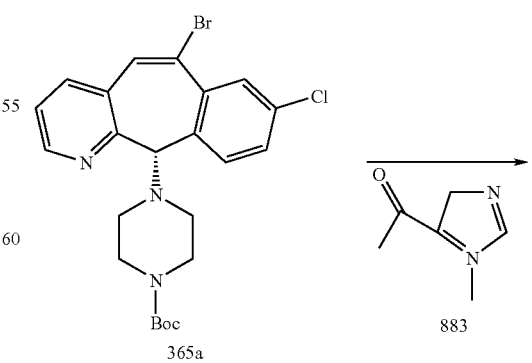

-continued

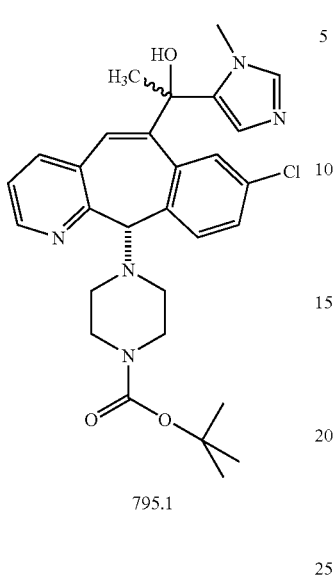

795.1

Dissolve 365 (0.24 g, 0.49 mmol) in THF (2.5 ml). Cool under $N_2$ to −78° C., add (1) (BuLi, 2.5M, 0.2 ml) and stir the resulting dark brown solution for 15 minutes. Dissolved 883 (0.116 g) from Step C in 0.5 mL of THF and add to reaction and stir at −78° C. for 3 hours. Add reaction mixture to brine and extract with ethyl acetate(2×). Dry with $MgSO_4$, filter and evaporate to obtain a yellow solid. Purified crude (0.29 g) by Prep Plate Chromatography to afford 0.0.15 g, 42% yield of the desired product (795.1).

EXAMPLE 509

-continued

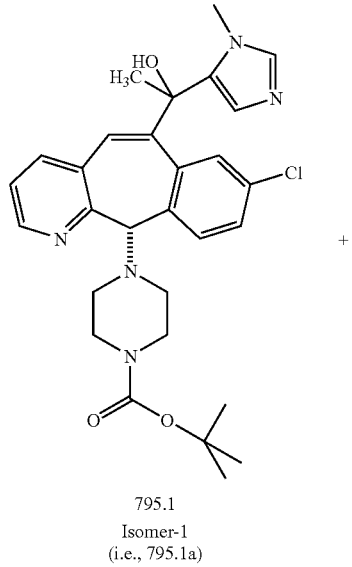

795.1
Isomer-1
(i.e., 795.1a)

+

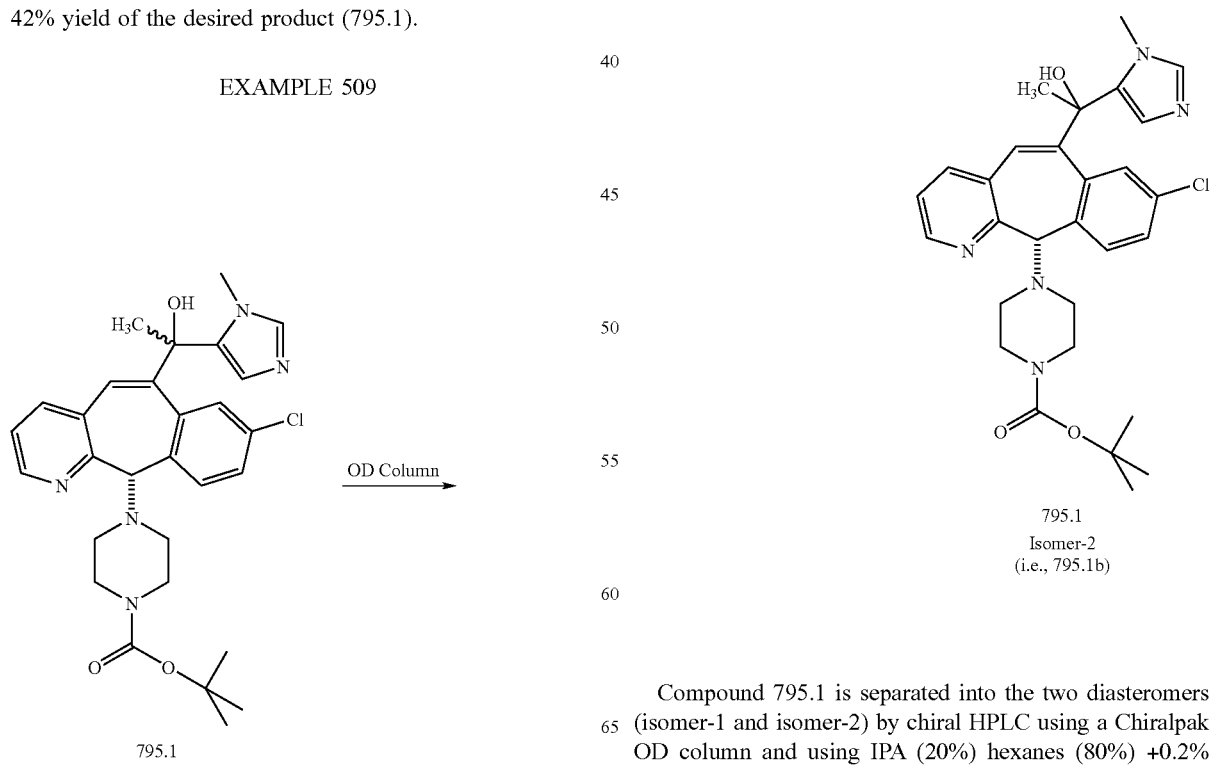

795.1
Isomer-2
(i.e., 795.1b)

Compound 795.1 is separated into the two diasteromers (isomer-1 and isomer-2) by chiral HPLC using a Chiralpak OD column and using IPA (20%) hexanes (80%) +0.2% DEA as described in EXAMPLE 506.

EXAMPLE 510

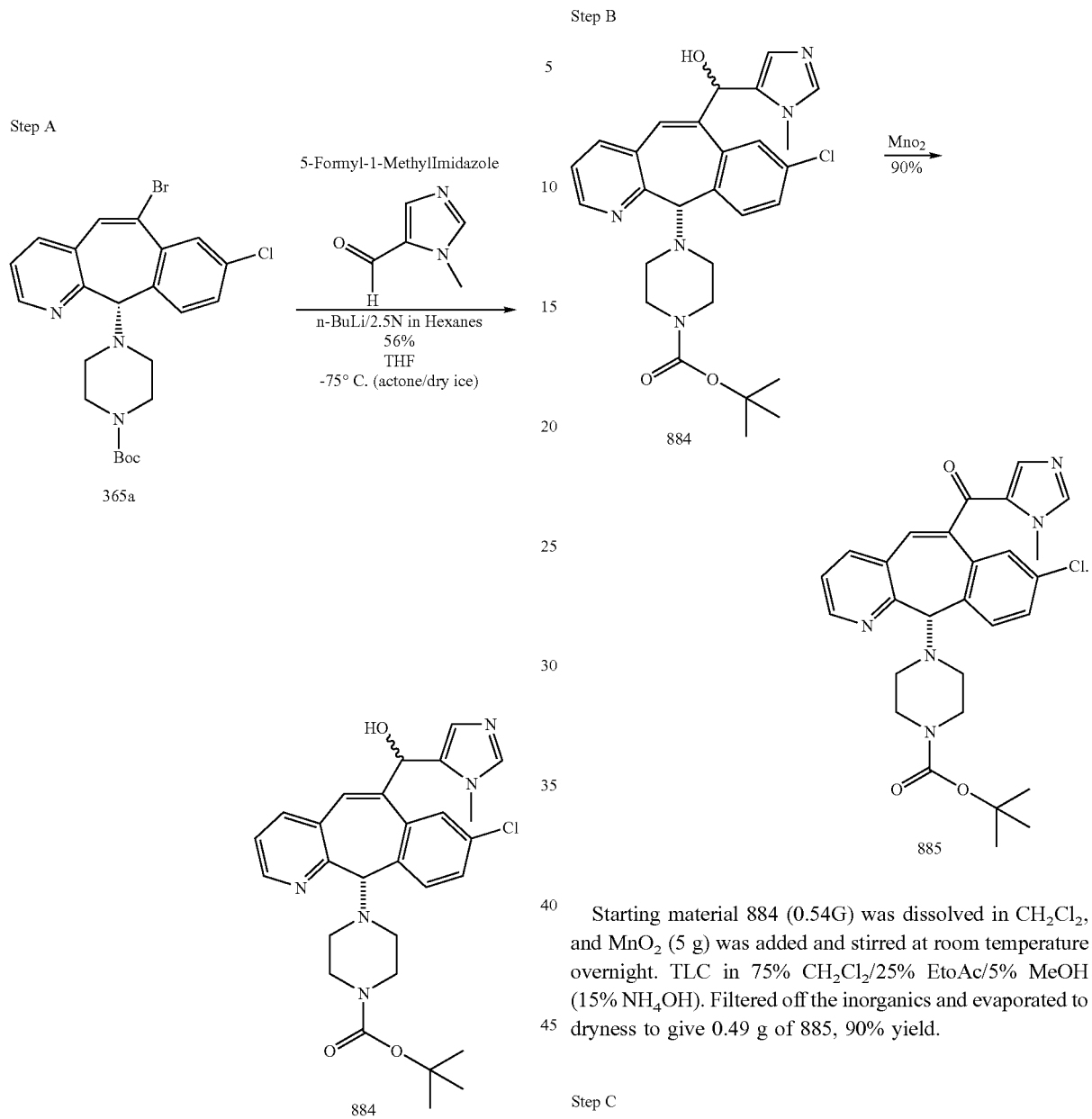

365a [0.9 g, 1.83 mmol] was dissolved in dry THF (15 ml) and cooled to −75° C. (dry ice/acetone bath). (N-BuLi) [(2.5N in Hexanes); 0.24 g, 1.5 ml, 3.74 mmol], was added dropwise at −75° C. and stirred for ~20 minutes. 5-Formyl-1-Methyl Imidazole (0.3 g, 2.75 mmol in 2 ml THF was added quickly and stirred at −75° C. for 3 hours. TLC with (H$_2$O-Ethyl Acetate). Reaction completed. Worked up by adding 10 ml of H$_2$O and extracted with Ethyl Acetate and washed with brine, dried over MgSO$_4$, filtered and evaporated to give crude product. Crude was purified by Flash Chromatography (silica gel column) using CH$_2$Cl$_2$/5% CH$_3$OH (15% NH$_4$OH) to give 0.54 g of compound 884, 56% yield.

Starting material 884 (0.54G) was dissolved in CH$_2$Cl$_2$, and MnO$_2$ (5 g) was added and stirred at room temperature overnight. TLC in 75% CH$_2$Cl$_2$/25% EtoAc/5% MeOH (15% NH$_4$OH). Filtered off the inorganics and evaporated to dryness to give 0.49 g of 885, 90% yield.

-continued

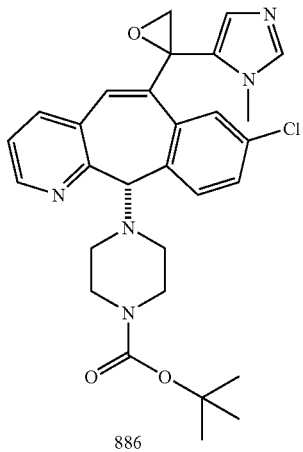

886

0.35 g, 1.71 mmol of $(CH_3)_3 S^+I^-$ was dissolved in dry DMSO (5 ml) and THF (5 ml). Sodium hydride (0.068 g, 1.71 mmol) was added, stirred for 10 minutes. The mixture was cooled to 0° C. Starting material 885 (0.3 g, 0.577 mmol) in (DMSO-THF 1:1, 5 ml) was added and stirred at 0° C. for 6 hours and then stored in the refrigerator for 18 hours. Quench with $H_2O$. Extracted with Ethyl Acetate and washed with brine, dried over MgSO4, filtered and evaporated to give 0.310 g of product, 886.

Step D

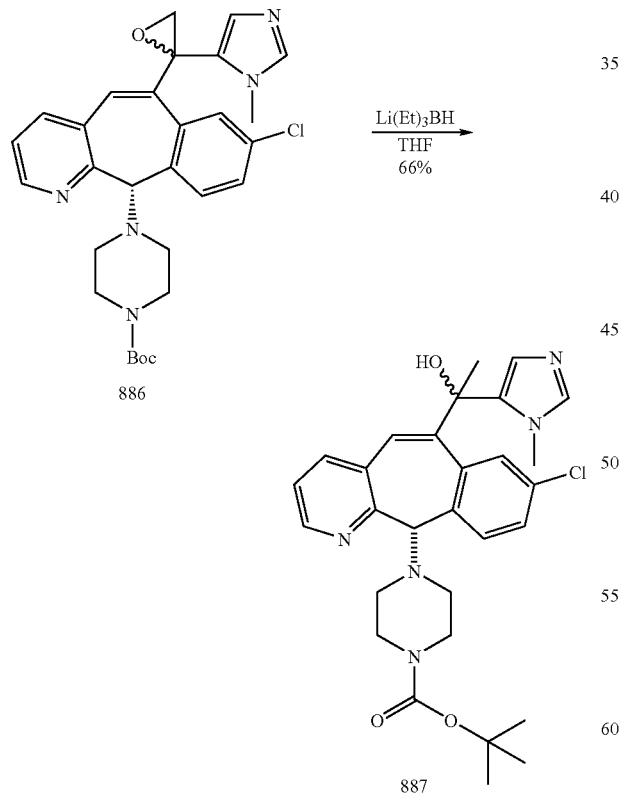

Dissolved 886 (0.28 g, 0.48 mmol) in THF(5 ml), added Li (Et)$_3$BH (0.8 ml, 0.8 mmol). After stirring for 1 hour, added to reaction ~10 ml of 1N HCL and stirred for 5 min. Added saturated sodium bicarbonate slowly until basic, and extracted with Ethyl Acetate (3×). Organic was dried over MgSO$_4$, filtered and evaporated to give crude product. Column chromatography on 12 g of silica and eluting with 2% to 4% MeOH.NH$_4$OH/CH$_2$Cl$_2$ to gave 170 mg, 66% yield of pure product, 887.

Step E

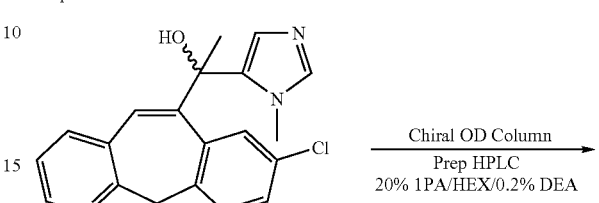

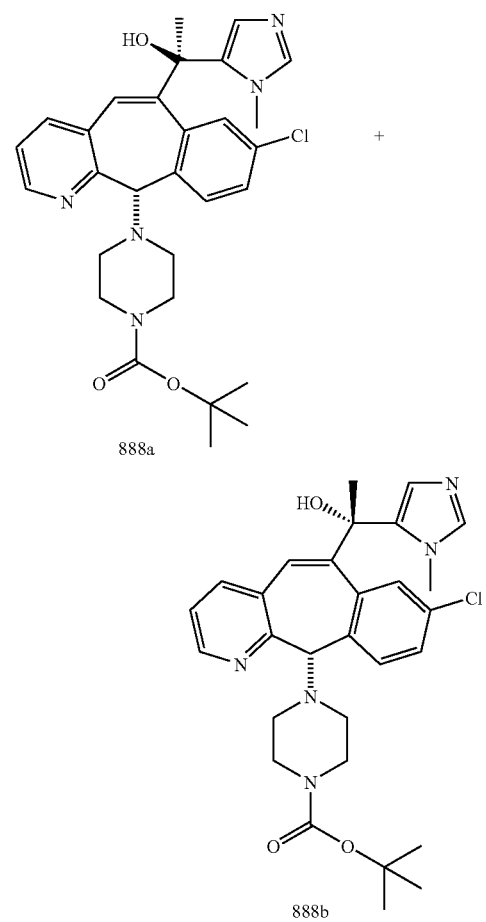

887 was separated by Chiral Prep HPLC using a Chiral Technologies OD column and eluting with 20% Isopropanol/Hexanes/0.2% DEA to give Compounds; 888a and 888b.

EXAMPLES 511-513

Each isomer, 795.2a and 795.2b from Example 507 was dissolved in CH$_2$Cl$_2$, treated with the corresponding isocyanates and stirred at room temperature overnight. The crude product was purified directly by silica gel preparative thin layer chromatography or silica gel chromatography to afford compounds of the formula:

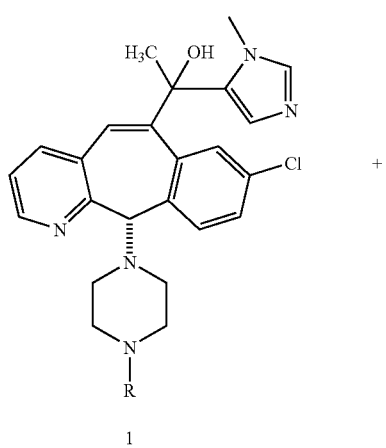

1

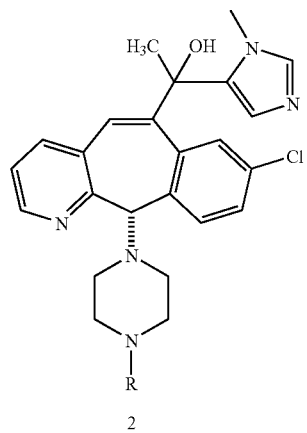

2 wherein R is defined in Table 55 and the numbers 1 and 2 in the formulas represent isomers 1 and 2, respectively.

TABLE 55

| Example | R | Isomer 1 Data | Isomer 2 Data |
|---|---|---|---|
| 511 | | m.p. 200–202° C. | m.p. 197–200° C. |
| 512 | | m.p. 185–190° C. | m.p. 200–205° C. |
| 513 | | m.p. 210–214° C. | m.p. 185–190° C. |

EXAMPLES 514-535

If one were to follow procedures similar to those of Examples 511-513 then one would obtain compounds of the formulas:

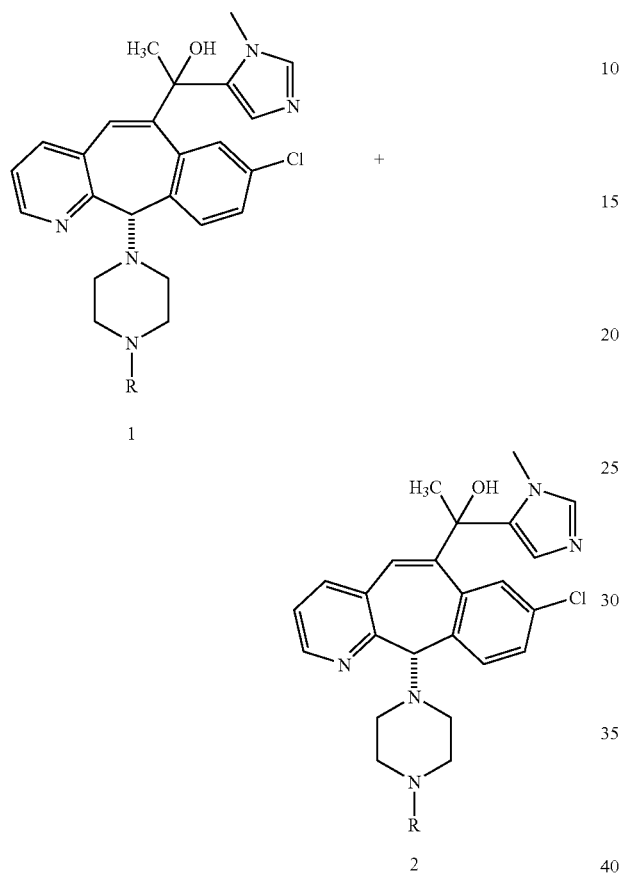

wherein R is defined in Table 56 and the numbers 1 and 2 in the formulas represent isomers 1 and 2, respectively.

TABLE 56

| Example | R Isomer 1 and Isomer 2 |
|---|---|
| 514 | —C(O)NH₂ |
| 515 | —C(O)NHCH₃ |
| 516 | —C(O)NH-isopropyl |

TABLE 56-continued

| Example | R Isomer 1 and Isomer 2 |
|---|---|
| 517 | —C(O)NH-ethyl |
| 518 | —C(O)NH-propyl |
| 519 | —C(O)NH-isobutyl |
| 520 | —C(O)NH-allyl |
| 521 | —C(O)NH-cyclopentyl |
| 522 | —C(O)NH-phenyl |
| 523 | —C(O)NH-(4-isopropylphenyl) |
| 524 | —C(O)NH-(4-bromophenyl) |
| 525 | —C(O)NH-(4-chlorophenyl) |
| 526 | —C(O)NH-(4-fluorophenyl) |

TABLE 56-continued

| Example | R<br>Isomer 1 and Isomer 2 |
|---|---|
| 527 | 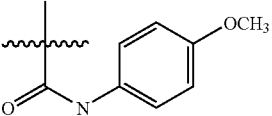 |
| 528 | 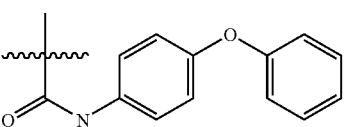 |
| 529 | 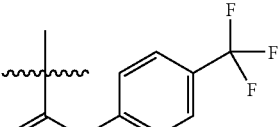 |
| 530 | 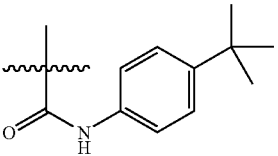 |
| 531 | 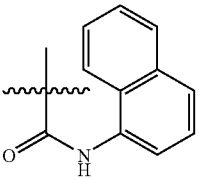 |
| 532 | 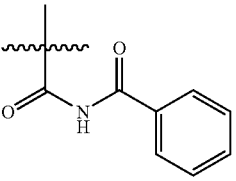 |
| 533 | 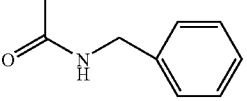 |
| 534 | 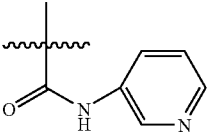 |
| 535 | 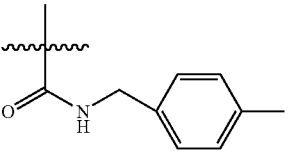 |

EXAMPLE 536

Each isomer, 795.2a and 795.2b from Example 507, was dissolved in anhydrous DMF at room temperature under nitrogen, followed by addition of the corresponding carboxylic acids, and the appropriate reagents: EDC, HOBT, and NMM. Reactions were then stirred at room temperature overnight. Solvents were removed via rotary evaporator yielding an oily residue. Residue was taken up in dichloromethane and washed with 1.0 N NaOH. Dry over $Na_2SO_4$, filtered and concentrated. Crudes were purified by Prep TLC using dichloromethane/methanol to give compounds of the formulas:

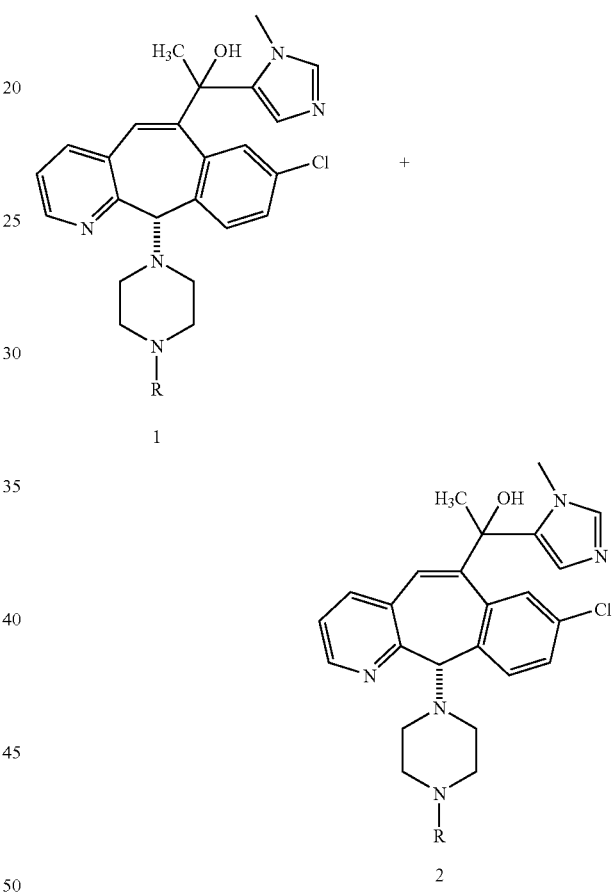

wherein R is defined in Table 57 and the numbers 1 and 2 in the formulas represent isomers 1 and 2, respectively.

TABLE 57

| Example | R | Data<br>Isomer 1 | Data<br>Isomer 2 |
|---|---|---|---|
| 536 | 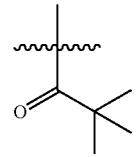 | m.p. 175–180° C. | — |

EXAMPLES 537-565
If one were to follow procedures similar to that of Example 536 then one would obtain compounds of the formulas:
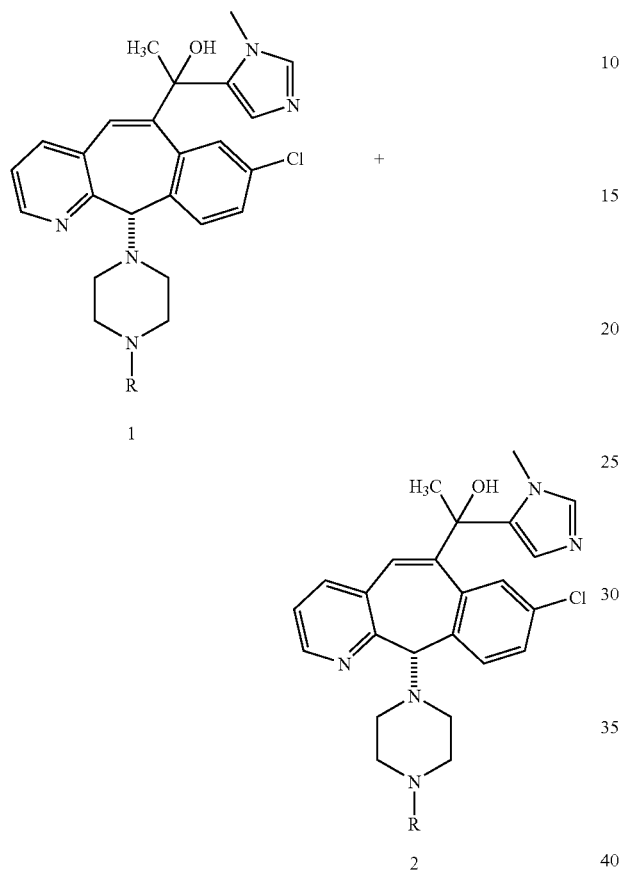
wherein R is defined in Table 58 and the numbers 1 and 2 in the formulas represent isomers 1 and 2, respectively.
TABLE 58
| Example | R Isomer 1 and Isomer 2 |
|---|---|
| 537 | |
| 538 | |
| 539 | |
TABLE 58-continued
| Example | R Isomer 1 and Isomer 2 |
|---|---|
| 540 | |
| 541 | |
| 542 | |
| 543 | |
| 544 | |
| 546 | |
| 547 | |
| 548 | |
| 549 | |

TABLE 58-continued

| Example | R Isomer 1 and Isomer 2 |
|---|---|
| 550 | 4-piperidinyl ketone |
| 551 | 1-methylcyclohexyl ketone |
| 552 | cyclohexylmethyl ketone |
| 553 | (piperidin-4-yl)methyl ketone |
| 554 | 2-methyl-1-(1-carbamoylpiperidin-4-yl)propan-2-yl ketone |
| 555 | pyridin-3-yl ketone |
| 556 | 4-chlorophenyl ketone |

TABLE 58-continued

| Example | R Isomer 1 and Isomer 2 |
|---|---|
| 557 | 4-bromophenyl ketone |
| 558 | 4-fluorophenyl ketone |
| 559 | 4-cyanophenyl ketone |
| 560 | 4-methylphenyl ketone |
| 561 | 4-methoxyphenyl ketone |
| 562 | pyridin-4-yl ketone |

TABLE 58-continued

| Example | R Isomer 1 and Isomer 2 |
|---|---|
| 563 | (structure: C(=O)-pyridine N-oxide (4-position)) |
| 564 | (structure: C(=O)-CH2-4-pyridyl) |
| 565 | (structure: C(=O)-CH2-pyridine N-oxide (4-position)) |

EXAMPLES 566-567

Each isomer, 795.2a and 795.2b from Example 507, was dissolved in anhydrous $CH_2Cl_2$ followed by $Et_3N$. Reactions were then treated with the corresponding sulfonyl chlorides and stirred at room temperature over night. Quench reaction with 1.0 N NaOH and extracted with $CH_2Cl_2$. Organic layer was dried over $MgSO_4$, filtered and concentrated. Purification by column chromatography eluting with methanol-$CH_2Cl_2$ afforded compounds of the formula:

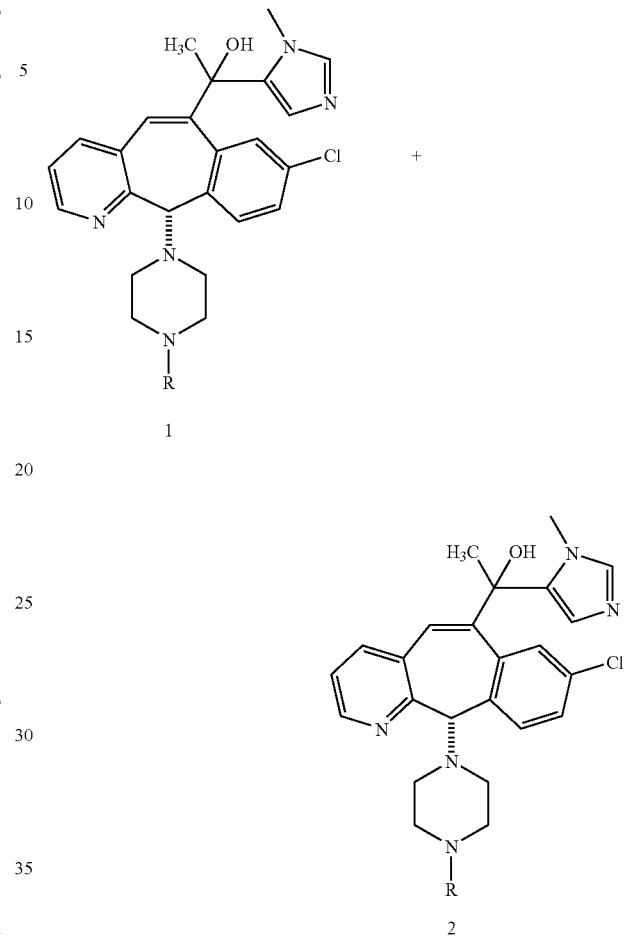

wherein R is defined in Table 59 and the numbers 1 and 2 in the formulas represent isomers 1 and 2, respectively.

TABLE 59

| Example | R | Data Isomer 1 | Data Isomer 2 |
|---|---|---|---|
| 566 | (methanesulfonyl) | mp = 215.4–217.5° C. | m.p. 185–188° C. |
| 567 | (4-chlorophenylsulfonyl) | * | mp = 182–186° C. |

* Isomer 1 for Example 567 would be obtained if one were to follow the described procedure.

EXAMPLES 568-589
If one were to follow procedures similar to those in Examples 566-567 thenone would obtain compounds of the formulas:
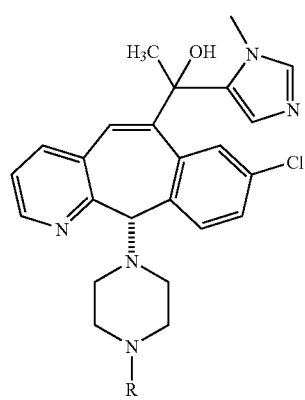
1
+
2
wherein R is defined in Table 60 and the numbers 1 and 2 in the formulas represent isomers 1 and 2, respectively.
TABLE 60
| Example | R<br>Isomer 1 and Isomer 2 |
|---|---|
| 568 | |
| 570 | |
| 571 | |
| 572 | |
| 573 | |
| 575 | |
| 576 | |
| 577 | |
| 578 | |
| 579 | |
| 580 | |
| 581 | |

TABLE 60-continued

| Example | R Isomer 1 and Isomer 2 |
|---|---|
| 582 | 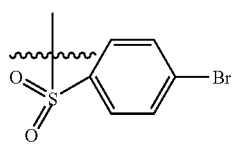 |
| 583 | 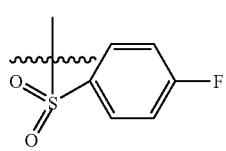 |
| 584 | 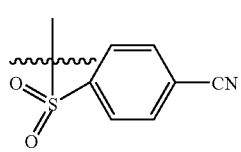 |
| 585 | 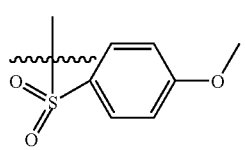 |
| 586 | 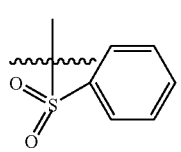 |
| 587 | 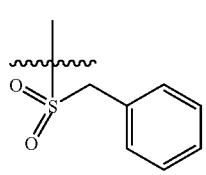 |
| 588 | 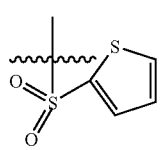 |

TABLE 60-continued

| Example | R Isomer 1 and Isomer 2 |
|---|---|
| 589 | 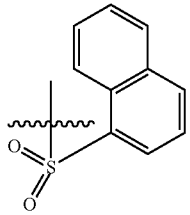 |

EXAMPLES 590-603

Each isomer, 795.2a and 795.2b from Example 507, was dissolved in anhydrous methylene chloride at room temperature. The reaction was cooled to 0° C. and TEA was added in. The respective chloroformates were then added dropwise, and reactions were stirred at 0° C. for until completed. Reactions were basified with 1.0 N NaOH to pH=8-10 followed by extraction with dichloromethane. Organic layer was combined, dried with $MgSO_4$, filtered and concentrated to yield crude products. Purification by Prep TLC using methylene chloride/acetone (95%/5%) afforded the compounds:

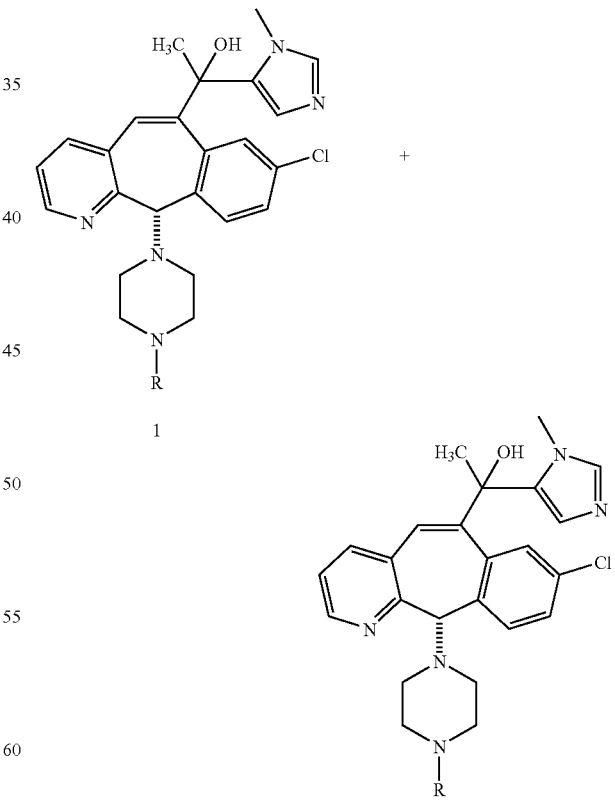

wherein R is defined in Table 61 and the numbers 1 and 2 in the formulas represent isomers 1 and 2, respectively.

TABLE 61

| Example | R | Data Isomer 1 | Data Isomer 2 |
|---------|---|---------------|---------------|
| 590 | tert-butyl ester | — | — |
| 591 | ethyl ester | * | 179.8–182.4° C. |
| 592 | isopropyl ester | 195–200° C. | 193.5–197.5° C. |
| 593 | isobutyl ester | * | 165.9–167.9° C. |
| 594 | neopentyl ester | 163.8–186.6° C. | mp = 173–175° C. |
| 595 | allyl ester | * | 173.9–176.2° C. |
| 596 | cyclopentyl ester | 180–182° C. | 172–174° C. |
| 597 | cyclohexyl ester | 165–170° C. | 185–188.5° C. |
| 598 | 2,2,2-trichloro-tert-butyl ester (CCl₃) | 184.3–186.6° C. | 191.2–192.9° C. |
| 599 | 2-cyano-2-propyl ester (CN) | * | 179.8–182.5° C. |
| 600 | 1-methylcyclopropyl ester | 175–180° C. | 175–178° C. |
| 601 | 1-methylcyclohexyl ester | 175–177° C. | 173–176° C. |

TABLE 61-continued

| Example | R | Data Isomer 1 | Data Isomer 2 |
|---|---|---|---|
| 602 | 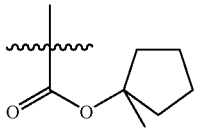 | 177–180° C. | 175–177° C. |
| 603 | 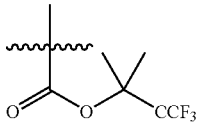 | 169.4–173.2° C. | 164.4–167.2° C. |

\* Isomer 1 for these examples would be obtained if one were to follow the described procedure.

PMR data for Example 592, isomer 1, (CD$_3$Cl) 8.44 (d, 1H), 8.23 (d, 1H), 7.54 (s, 1H), 7.48 (d, 1H), 7.37 (d, 1H), 7.32 (dd, 1H), 7.18 (dd, 1H), 7.10 (s, 1H), 6.58 (s, 1H), 4.87 (m, 1H), 4.58 (s, 1H), 3.86 (s, 3H), 3.25 (br s, 4H), 2.26 (br s, 2H), 1.99 (m, 2H), 1.90 (s, 3H), 1.21 (d, 6H).

EXAMPLES 604-614

If one were to follow procedures similar to those in Examples 590-603 then one would obtain compounds of the formulas:

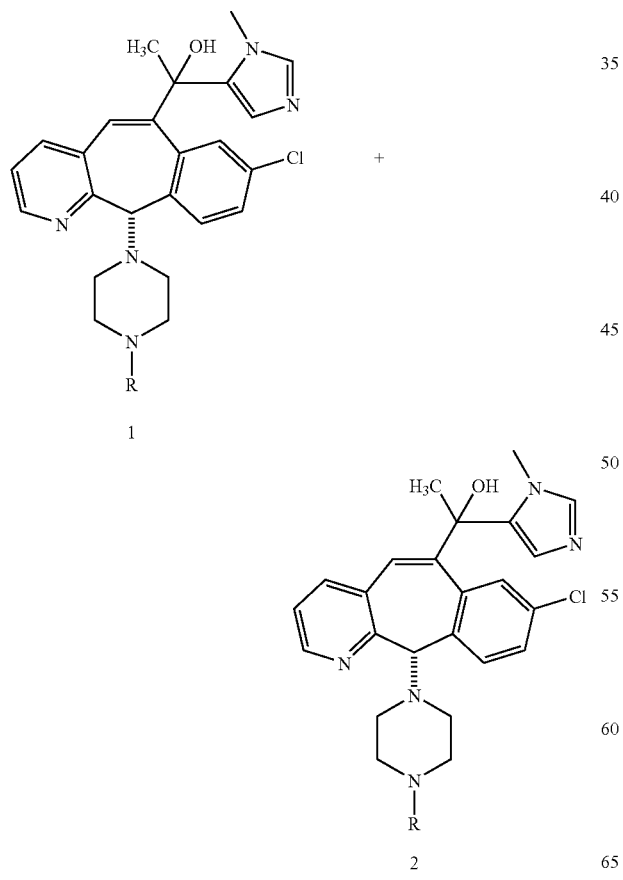

wherein R is defined in Table 62 and the numbers 1 and 2 in the formulas represent isomers 1 and 2, respectively.

TABLE 62

| Example | R Isomer 1 and Isomer 2 |
|---|---|
| 604 | 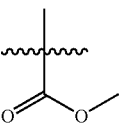 |
| 605 | 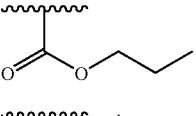 |
| 606 | 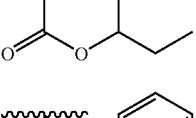 |
| 607 | 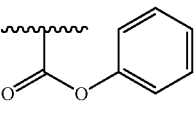 |
| 608 | 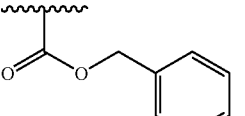 |
| 609 | 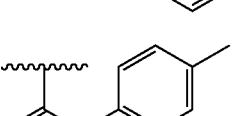 |
| 610 | 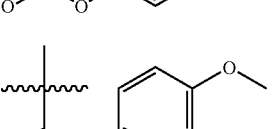 |
| 611 | 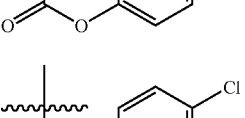 |

TABLE 62-continued

| Example | R Isomer 1 and Isomer 2 |
|---|---|
| 612 | ~~~-C(=O)-O-C6H4-Br (4-Br) |
| 613 | ~~~-C(=O)-O-C6H4-F (4-F) |
| 614 | ~~~-C(=O)-O-(1-naphthyl) |

PREPARATIVE EXAMPLE 74

R-O-H + Cl-C(=O)-Cl →[CH₂Cl₂, R.T./O.N.] Cl-C(=O)-O-R (wherein R is alkyl (e.g., ethyl) or cycloalkyl (e.g., cyclohexyl))

Dissolve Phosgene (3 mL, 1.93M in Toluene) in anhydrous ethyl ether and cooled to 0° C. A mixture of cyclohexyl alcohol (200 mg, 2 mmol) and pyridine (0.18 mL, 2.2 mmol) in ethyl ether (4 mL) was added in dropwise. After addition, reaction was allowed to warm to room temperature while stirring overnight. MgSO₄ was then added into reaction and the mixture was stirred for 5 min. After filtration, N₂ was bubbled into the solution for 30 min. It was then concentrated to 0.5 mL, diluted with CH₃Ph (10 mL) and stored as a stock solution at 4° C.

PREPARATIVE EXAMPLE 75

Step A

[Structure 889: H₂N-substituted tricyclic ketone with Cl] →

-continued

[Structure 890: Cl-substituted tricyclic ketone with Cl]

15.4 g (115 mmole) of CuCl₂ and 17 mL (144 mmol) of t-butyl nitrite was added to 400 mL of dry CH₃CN. The reaction mixture was cooled to 0° C. and 25 g of ketone (564)? was added. The reaction was warmed to room temperature and stirred for two days. The mixture was concentrated under vacuum. Then 1N HCl was added to the residue until the pH was neutral, then NH₄OH was added until the pH was basic. After extraction with ethyl acetate, the organic layer was dried over MgSO₄ and concentrated under vacuum to give compound 890. Alternatively, the corresponding alcohol of 889 can be reacted as above followed by oxidation with MnO₂ in CH₂Cl₂ to give compound 890.

Step B

[Structure 890] →

[Structure 891: Br, Cl, Cl tricyclic with piperazine-BOC]

+

[Structure 892: Br, Cl, Cl tricyclic isomer with piperazine-BOC]

Compound 890 from Step A above was reacted in essentially the same manner as in Preparative Example 23, Steps A-D, to get Compounds 891 and 892.

Step C
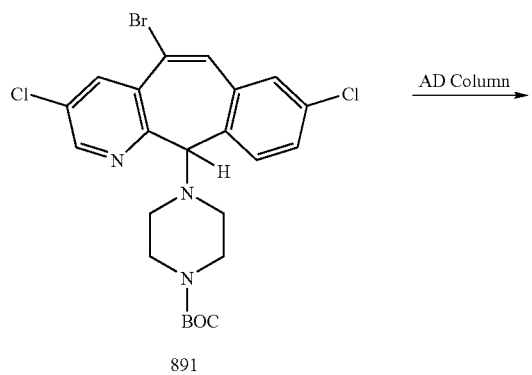
891
Step D
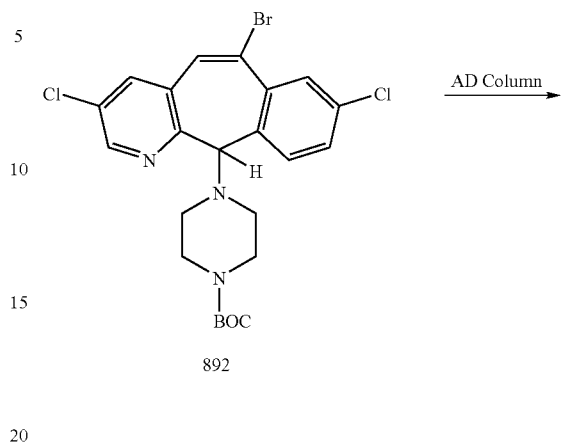
892
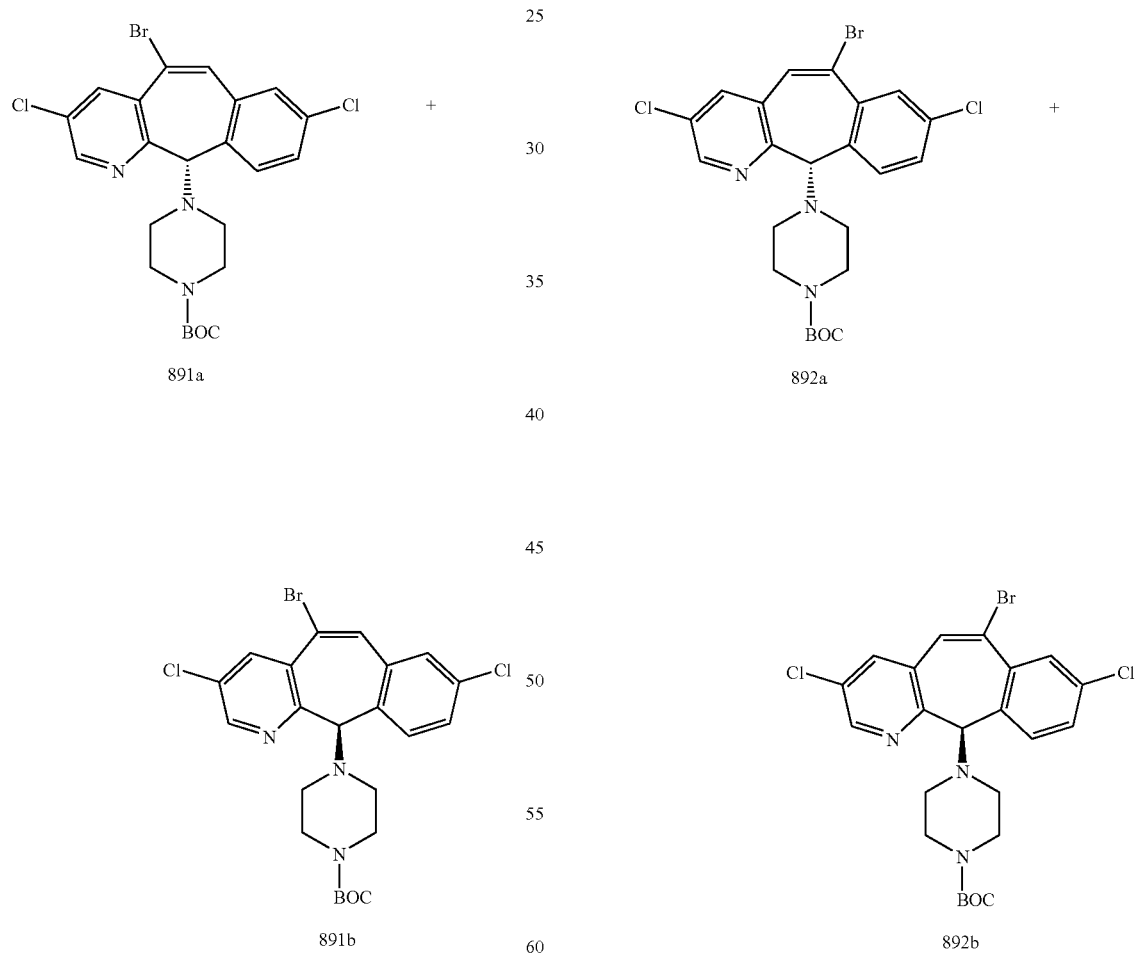
891 was separated into the respective enantiomers 891a and 891b, using a Chiral AD Prep HPLC Column as described in Example 508.
The 6-bromo substituted Compound 892 was separated into the enantiomers 892a and 892b using a Chiral AD Prep HPLC Column as described in Example 507.

PREPARATIVE EXAMPLE 76
Step A
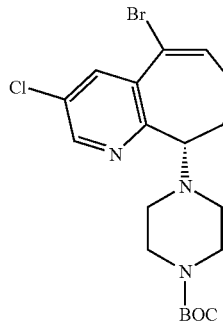
891a
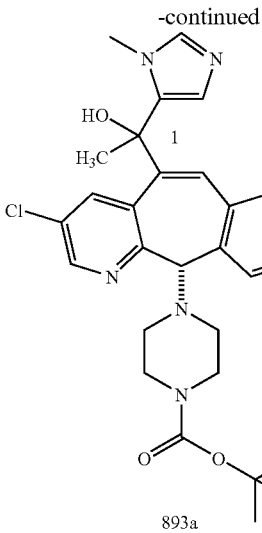
893a
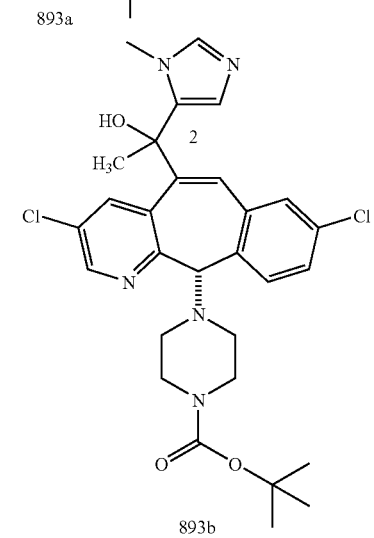
893b
Reacted 891a with the product of Preparative Example 73 using essentially the same procedure in Example 510 to obtain 893.
Step B
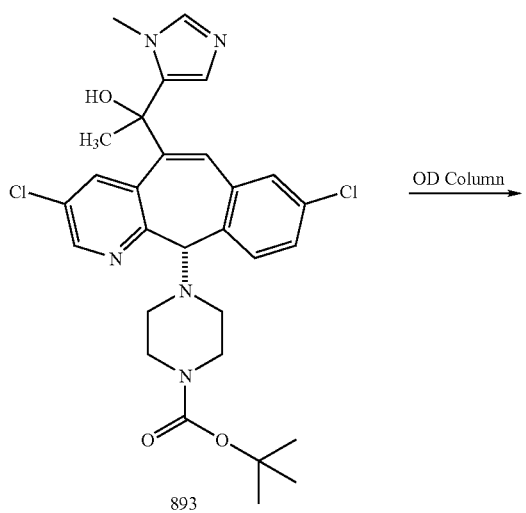
893
Chromatograph 893 by chiral HPLC using a Chiralcel OD column and eluting with IPA (20%) and hexanes (80%) with 0.2% DEA to obtain 893a (i.e., isomer 1), and 893b (i.e., isomer 2).
PREPARATIVE EXAMPLE 77
Step A
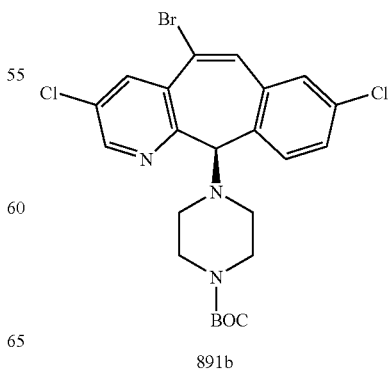
891b

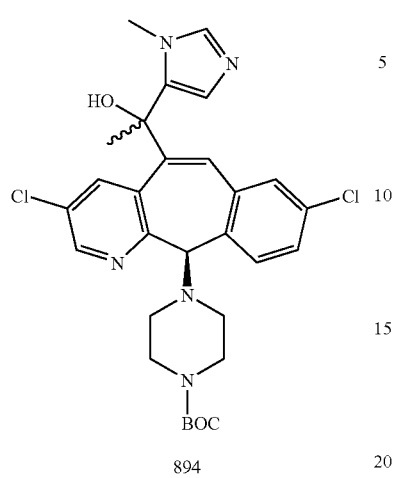

894

Reacted 891 b with the product of Preparative Example 73 using essentially the same procedure in Example 510 to obtain 893.

Step B

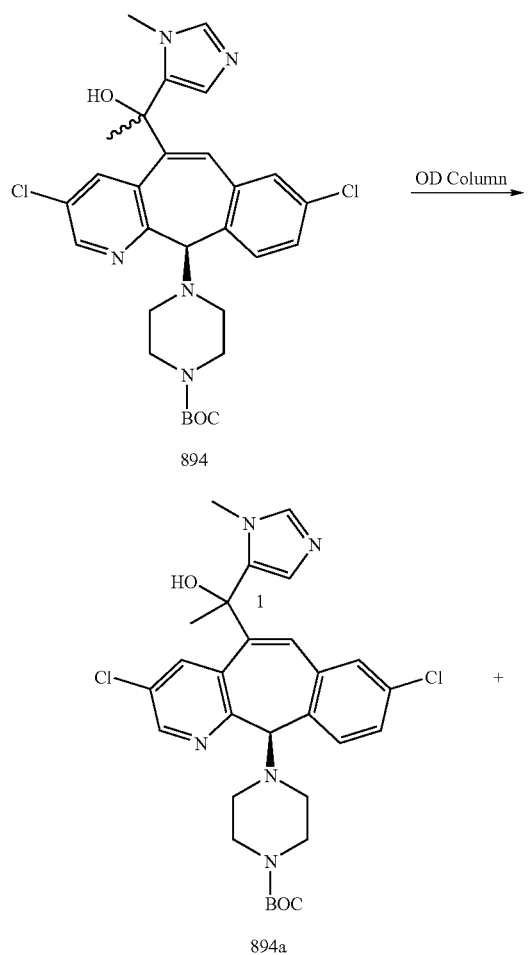

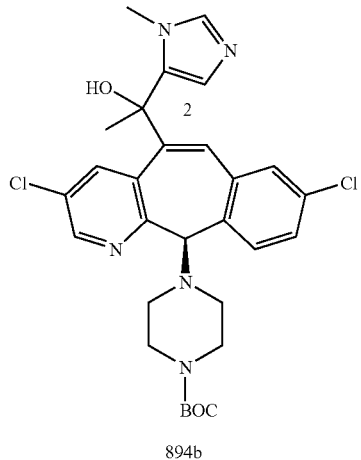

894b

Chromatograph 894 by chiral HPLC using a Chiralcel OD column and eluting with IPA (20%) and hexanes (80%) with 0.2% DEA to obtain 894a (i.e., isomer 1), and 894b (i.e., isomer 2).

PREPARATIVE EXAMPLE 78

Step A

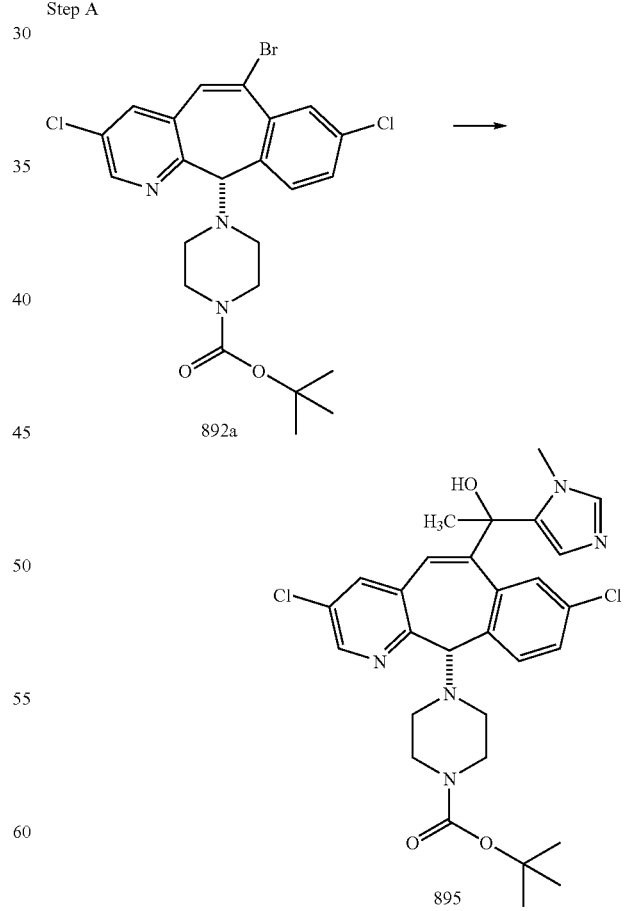

Reacted 892a with the product of Preparative Example 73 using essentially the same procedure in Example 510 to obtain 895.

PREPARATIVE EXAMPLE 79
Step A
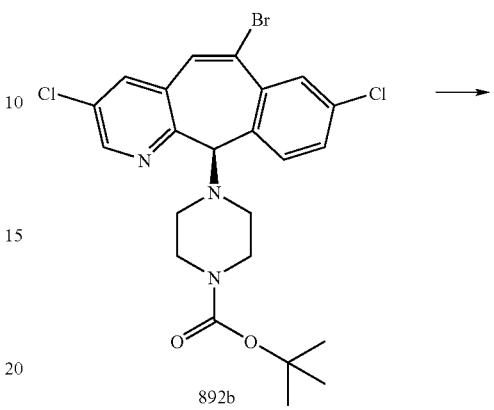
Reacted 892b with the product of Preparative Example 73 using essentially the same procedure in Example 510 to obtain 896.
Step B
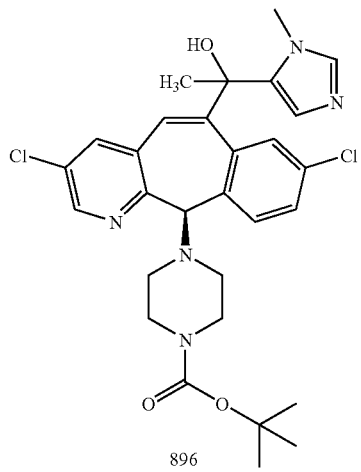
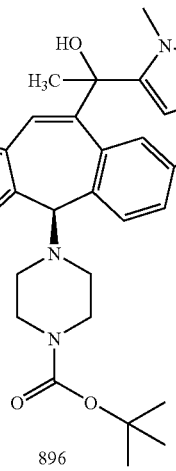
Step B
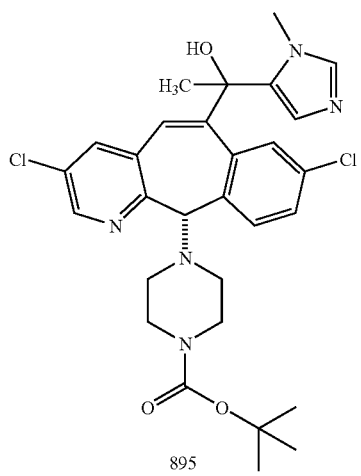
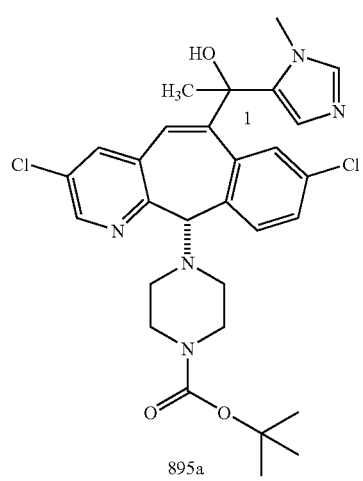
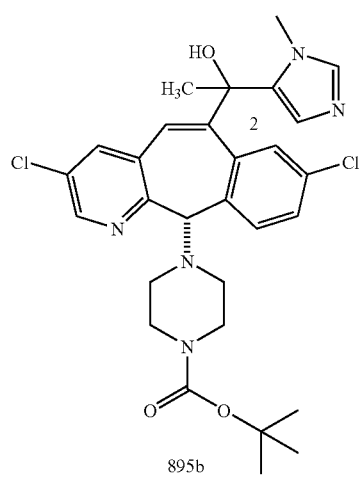
Chromatograph Compound 895 by chiral HPLC using a Chiralcel OD column and eluting with IPA (20%) and hexanes (80%) with 0.2% DEA to obtain 895a (i.e., isomer 1), and 895b (i.e., isomer 2).

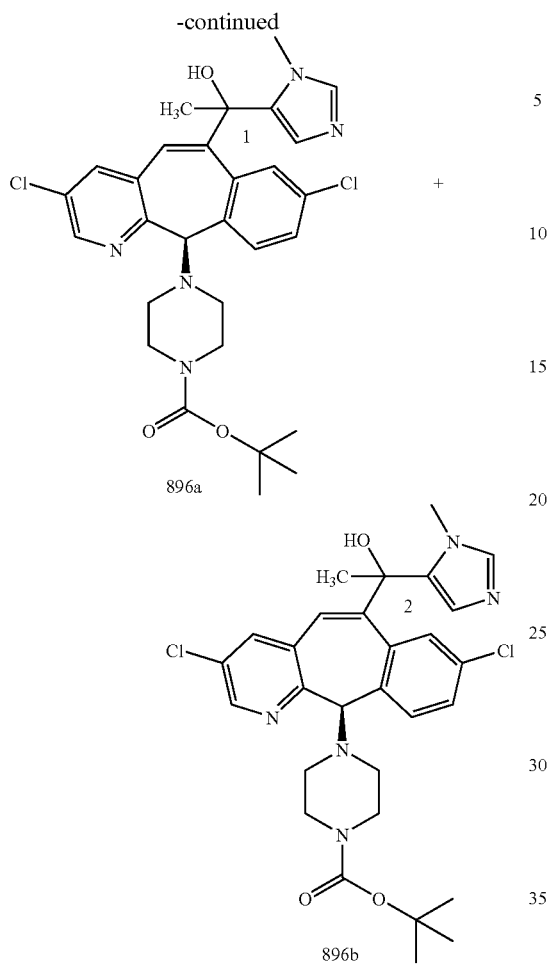

Chromatograph 896 by chiral HPLC using a Chiralcel OD column and eluting with IPA (20%) and hexanes (80%) with 0.2% DEA to obtain 896a (i.e., isomer 1), and 896b (i.e., isomer 2).

PREPARATIVE EXAMPLE 80

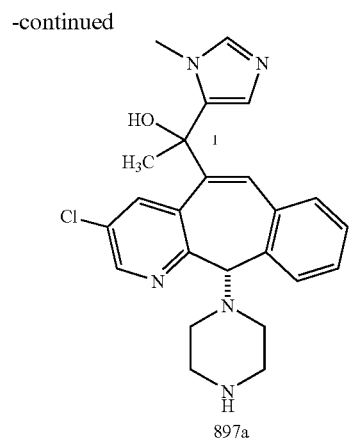

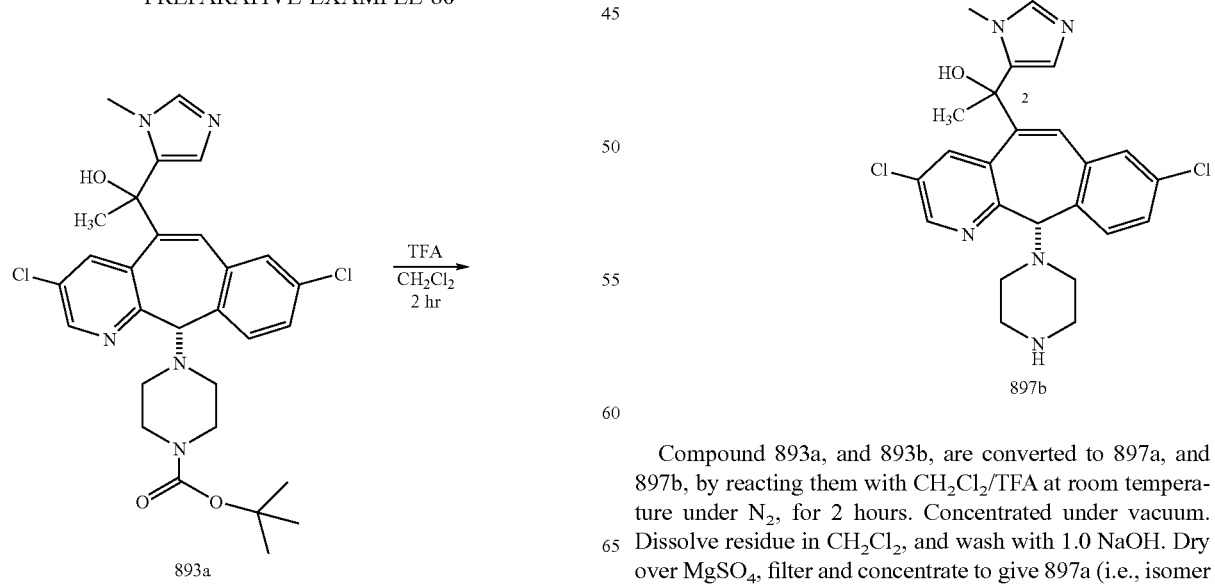

Compound 893a, and 893b, are converted to 897a, and 897b, by reacting them with CH$_2$Cl$_2$/TFA at room temperature under N$_2$, for 2 hours. Concentrated under vacuum. Dissolve residue in CH$_2$Cl$_2$, and wash with 1.0 NaOH. Dry over MgSO$_4$, filter and concentrate to give 897a (i.e., isomer 1) and 897b (i.e., isomer 2).

PREPARATIVE EXAMPLE 81
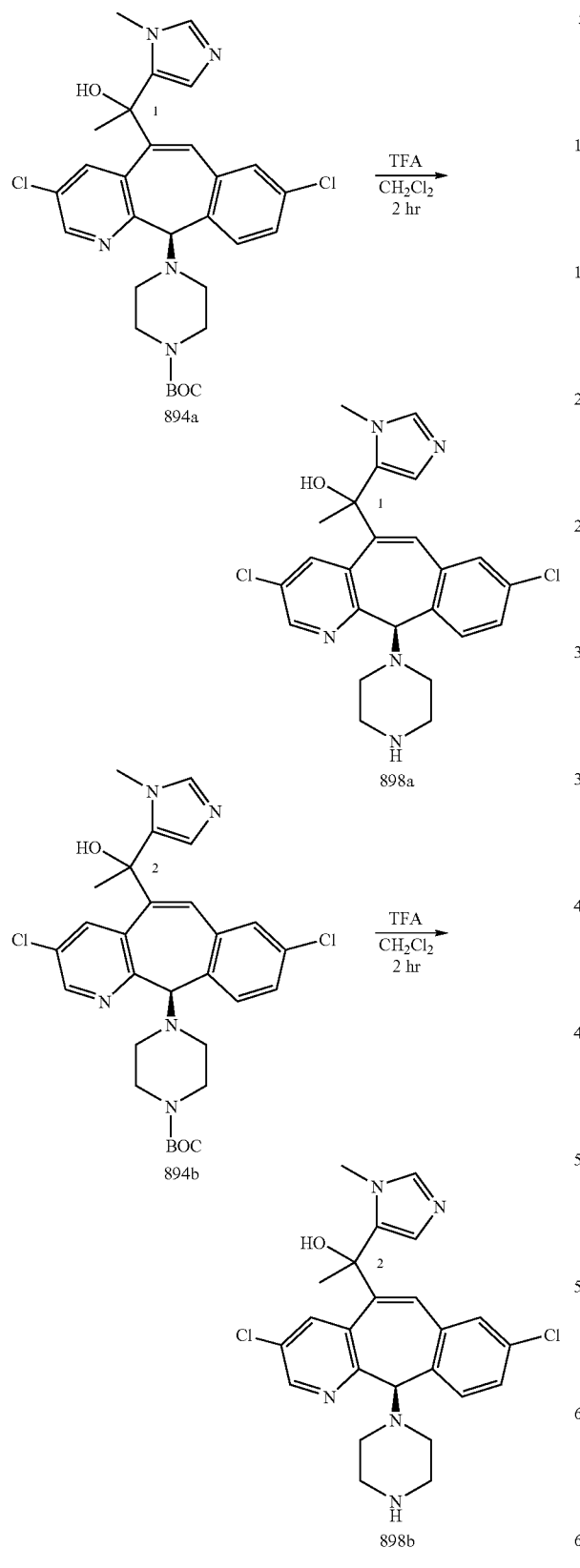
Following essentially the same procedure as in Preparative Example 80, Compounds 894a and 894b were individually reacted with TFA/CH₂CL₂ at room temperature under N₂, for 2 hours, to get compounds 898a (i.e., isomer 1) and 898b (i.e., isomer 2).
PREPARATIVE EXAMPLE 82
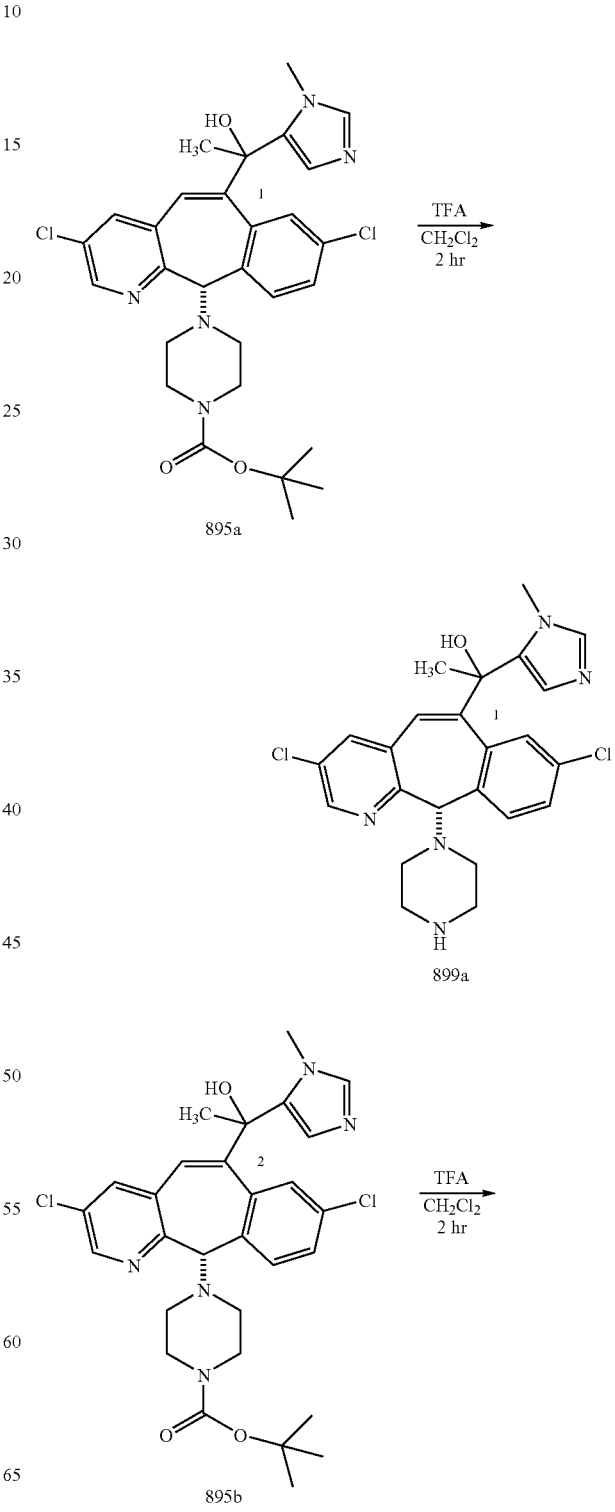

-continued

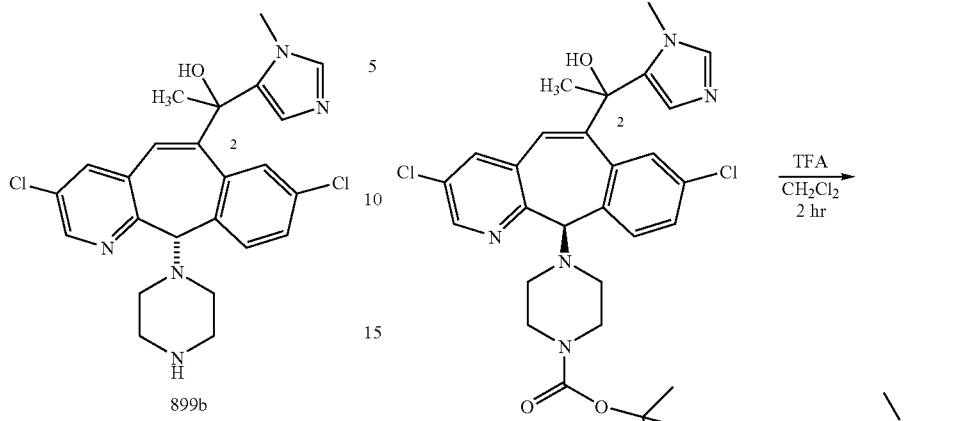

Using essentially the same procedure as in Preparative Example 80, 895a and 895b were individually reacted with TFA/CH₂CL₂ at room temperature under N₂, for 2 hours, to get compounds: 899a (i.e., isomer 1) and 899b (i.e., isomer 899b).

PREPARATIVE EXAMPLE 83

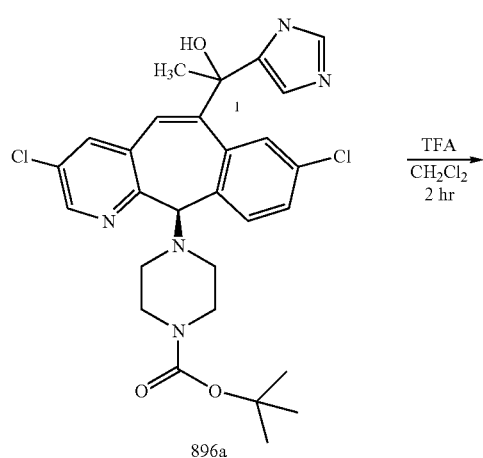

-continued

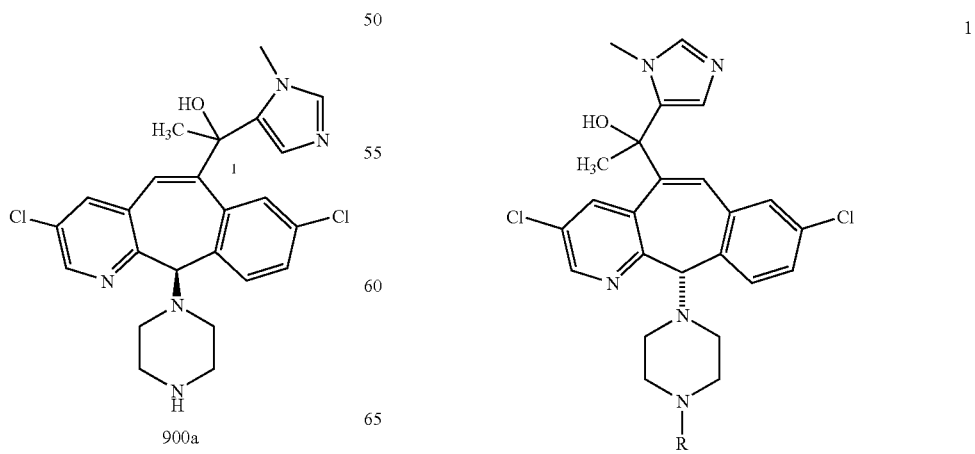

Using essentially the same procedure as in Preparative Example 80, 896a and 896b were individually reacted with TFA/CH₂CL₂ at room temperature under N₂, for 2 hours, to get compounds: 900a (i.e., isomer 1) and 900b (i.e., isomer 2).

EXAMPLES 615-639

If one were to dissolve each isomer, 897A and 897B, in CH₂Cl₂, treat with the corresponding isocyanates, stir at room temperature overnight, and purify the crude product directly by silica gel preparative thin layer chromatography or silica gel chromatography, then compounds of the formula:

-continued

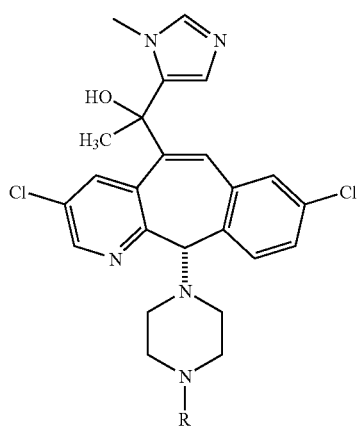

would be obtained wherein R is defined in Table 63, and the numbers 1 and 2 in the formulas represent isomers 1 and 2, respectively.

TABLE 63

| Example | R Isomer 1 and Isomer 2 |
|---|---|
| 615 | -C(=O)-NH$_2$ |
| 616 | -C(=O)-NH-CH$_3$ |
| 617 | -C(=O)-NH-isopropyl |
| 618 | -C(=O)-NH-ethyl |
| 619 | -C(=O)-NH-tert-butyl |
| 620 | -C(=O)-NH-propyl |

TABLE 63-continued

| Example | R Isomer 1 and Isomer 2 |
|---|---|
| 621 | -C(=O)-NH-isobutyl |
| 622 | -C(=O)-NH-CH$_2$-CH=CH$_2$ |
| 623 | -C(=O)-NH-cyclopentyl |
| 624 | -C(=O)-NH-cyclohexyl |
| 625 | -C(=O)-NH-phenyl |
| 626 | -C(=O)-NH-(4-CN-phenyl) |
| 627 | -C(=O)-NH-(4-isopropyl-phenyl) |
| 628 | -C(=O)-NH-(4-Br-phenyl) |
| 629 | -C(=O)-NH-(4-Cl-phenyl) |
| 630 | -C(=O)-NH-(4-F-phenyl) |

TABLE 63-continued

| Example | R Isomer 1 and Isomer 2 |
|---------|-------------------------|
| 631 | 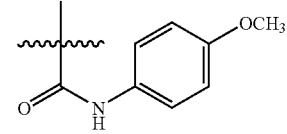 |
| 632 | 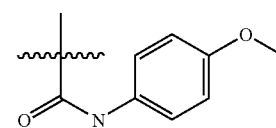 |
| 633 | 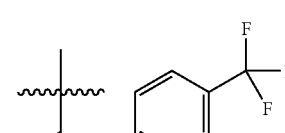 |
| 634 | 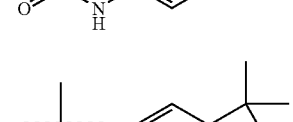 |
| 635 | 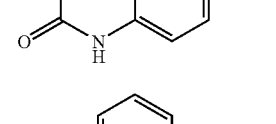 |
| 636 | 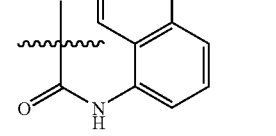 |
| 637 | 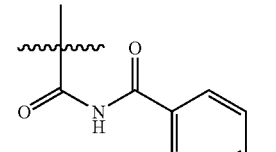 |
| 638 |  |
| 639 | 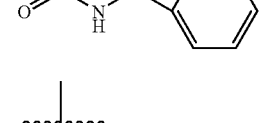 |

EXAMPLES 640-664

If one were to dissolve each isomer, 898a and 898b, in CH$_2$Cl$_2$, treat with the corresponding isocyanates, stir at room temperature overnight, and purify the crude product directly by silica gel preparative thin layer chromatography or silica gel chromatography obtain compounds of the formula:

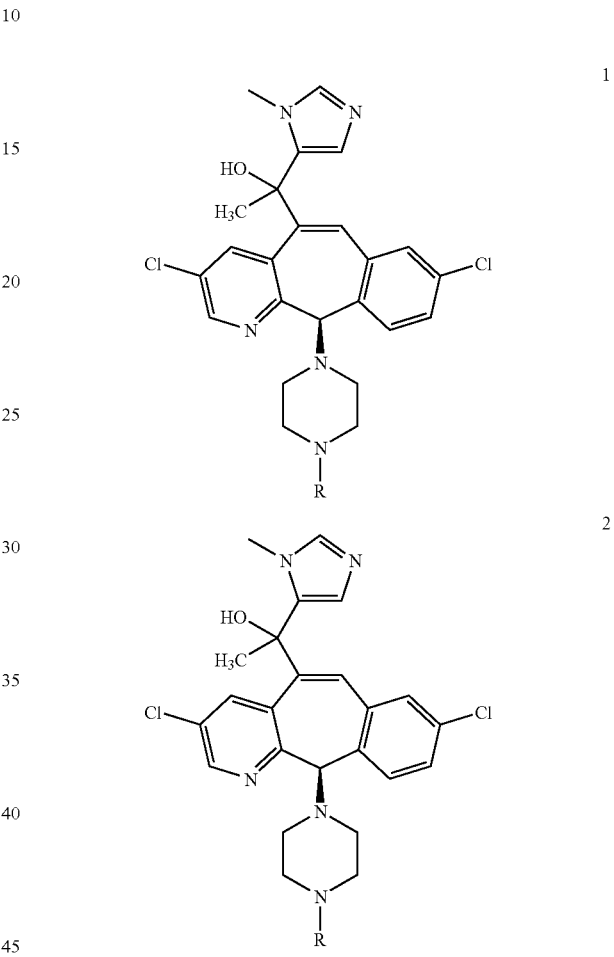

wherein R is defined in Table 64 and the numbers 1 and 2 in the formulas represent isomers 1 and 2, respectively.

TABLE 64

| Example | R Isomer 1 and Isomer 2 |
|---------|-------------------------|
| 640 |  |
| 641 |  |

TABLE 64-continued

| Example | R Isomer 1 and Isomer 2 |
|---|---|
| 642 | —C(O)NH-isopropyl |
| 643 | —C(O)NH-ethyl |
| 644 | —C(O)NH-tert-butyl |
| 645 | —C(O)NH-propyl |
| 646 | —C(O)NH-isobutyl |
| 647 | —C(O)NH-allyl |
| 648 | —C(O)NH-cyclopentyl |
| 649 | —C(O)NH-cyclohexyl |
| 650 | —C(O)NH-phenyl |
| 651 | —C(O)NH-(4-cyanophenyl) |
| 652 | —C(O)NH-(4-isopropylphenyl) |
| 653 | —C(O)NH-(4-bromophenyl) |
| 654 | —C(O)NH-(4-chlorophenyl) |
| 655 | —C(O)NH-(4-fluorophenyl) |
| 656 | —C(O)NH-(4-methoxyphenyl) |
| 657 | —C(O)NH-(4-phenoxyphenyl) |
| 658 | —C(O)NH-(4-trifluoromethylphenyl) |
| 659 | —C(O)NH-(4-tert-butylphenyl) |
| 660 | —C(O)NH-(1-naphthyl) |

TABLE 64-continued

| Example | R<br>Isomer 1 and Isomer 2 |
|---|---|
| 661 | 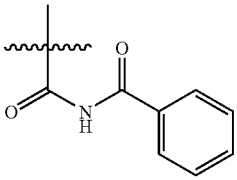 |
| 662 | 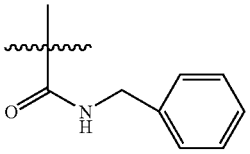 |
| 663 | 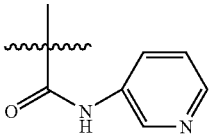 |
| 664 | 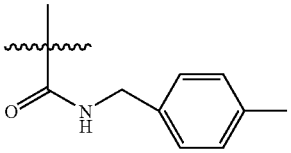 |

EXAMPLES 665-689

If one were to dissolve each isomer, 899a and 899b, in CH$_2$Cl$_2$, treat with the corresponding isocyanates, stir at room temperature overnight and purify the crude product directly by silica gel preparative thin layer chromatography or silica gel chromatography one would obtain compounds of the formula:

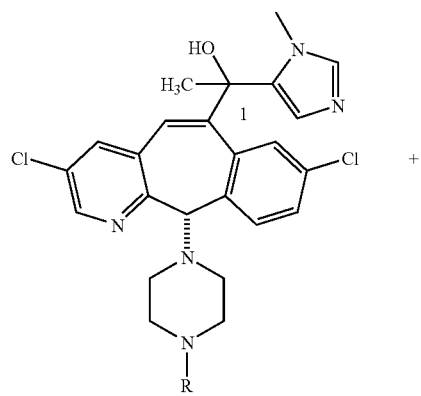

+

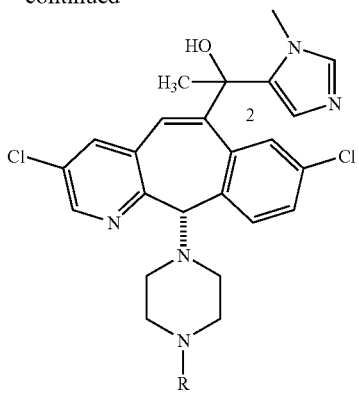

wherein R is defined in Table 65 and the numbers 1 and 2 in the formulas represent isomers 1 and 2, respectively.

TABLE 65

| Example | R |
|---|---|
| 665 | 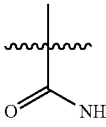 |
| 666 | 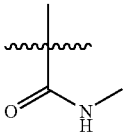 |
| 667 | 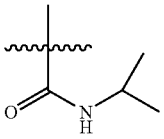 |
| 668 | 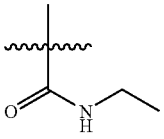 |
| 669 | 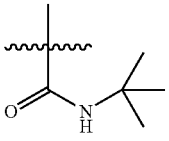 |
| 670 | 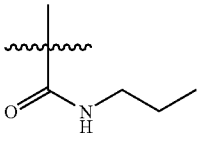 |
| 671 | 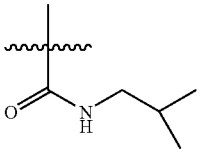 |

TABLE 65-continued

| Example | R |
|---------|---|
| 672 | *N-allyl amide* |
| 673 | *N-cyclopentyl amide* |
| 674 | *N-cyclohexyl amide* |
| 675 | *N-phenyl amide* |
| 676 | *N-(4-cyanophenyl) amide* |
| 677 | *N-(4-isopropylphenyl) amide* |
| 678 | *N-(4-bromophenyl) amide* |
| 679 | *N-(4-chlorophenyl) amide* |
| 680 | *N-(4-fluorophenyl) amide* |
| 681 | *N-(4-methoxyphenyl) amide* |
| 682 | *N-(4-phenoxyphenyl) amide* |
| 683 | *N-(4-trifluoromethylphenyl) amide* |
| 684 | *N-(4-tert-butylphenyl) amide* |
| 685 | *N-(1-naphthyl) amide* |
| 686 | *N-benzoyl amide* |
| 687 | *N-benzyl amide* |
| 688 | *N-(pyridin-3-yl) amide* |
| 689 | *N-(4-methylbenzyl) amide* |

EXAMPLES 690-714

If one were to dissolve each isomer, 900a and 900b, in CH$_2$Cl$_2$, treat with the corresponding isocyanates, stir at room temperature overnight, and purify the crude product directly by silica gel preparative thin layer chromatography or silica gel chromatography one would obtain compounds of the formula:

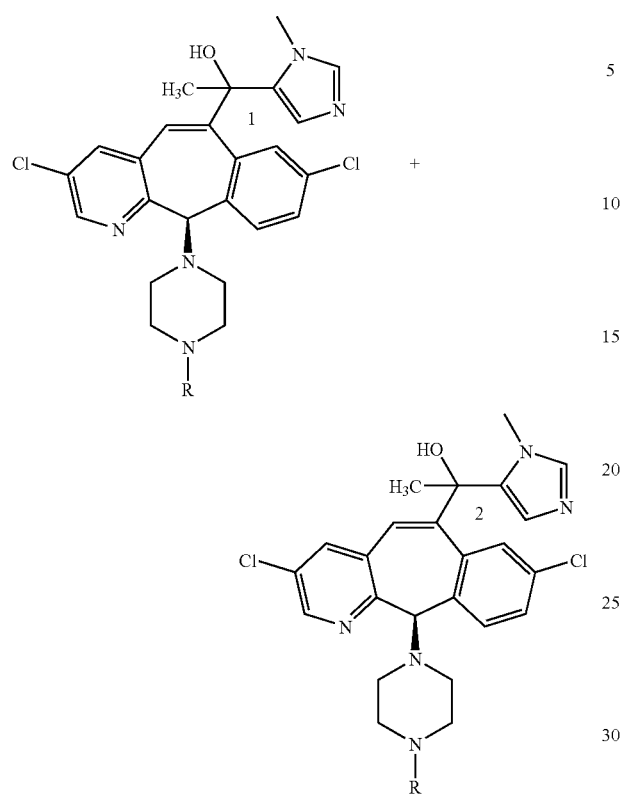
wherein R is defined in Table 66 and the numbers 1 and 2 in the formulas represent isomers 1 and 2, respectively.
TABLE 66
| Example | R Isomer 1 and isomer 2 |
|---|---|
| 690 | -C(O)NH₂ |
| 691 | -C(O)NHMe |
| 692 | -C(O)NH-iPr |
| 693 | -C(O)NHEt |
TABLE 66-continued
| Example | R Isomer 1 and isomer 2 |
|---|---|
| 694 | -C(O)NH-tBu |
| 695 | -C(O)NH-nPr |
| 696 | -C(O)NH-iBu |
| 697 | -C(O)NH-allyl |
| 698 | -C(O)NH-cyclopentyl |
| 699 | -C(O)NH-cyclohexyl |
| 700 | -C(O)NH-Ph |
| 701 | -C(O)NH-(4-CN-C₆H₄) |
| 702 | -C(O)NH-(4-iPr-C₆H₄) |
| 703 | -C(O)NH-(4-Br-C₆H₄) |

TABLE 66-continued
| Example | R Isomer 1 and isomer 2 |
|---|---|
| 704 | 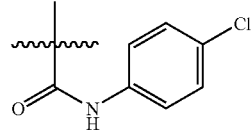 |
| 705 | 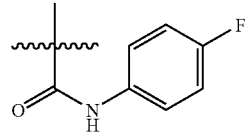 |
| 706 | 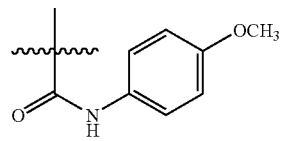 |
| 707 | 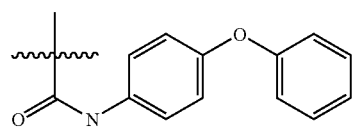 |
| 708 | 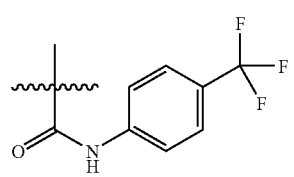 |
| 709 | 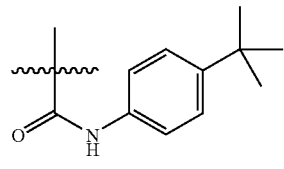 |
| 710 | 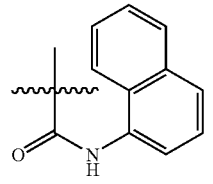 |
| 711 | 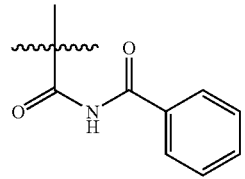 |
| 712 | 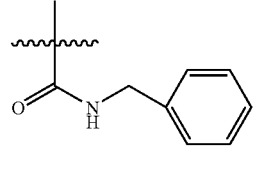 |
| 713 | 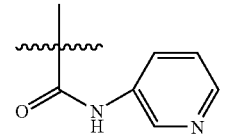 |
| 714 | 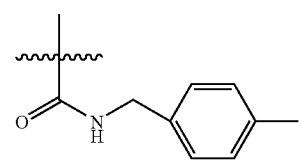 |
EXAMPLES 715-732
If one were to react each isomer, 897a and 897b following essentially the same procedure as in Examples 590-603 (see Preparative Example 74 for preparation of chloroformates), then one would obtain compounds of the formula:
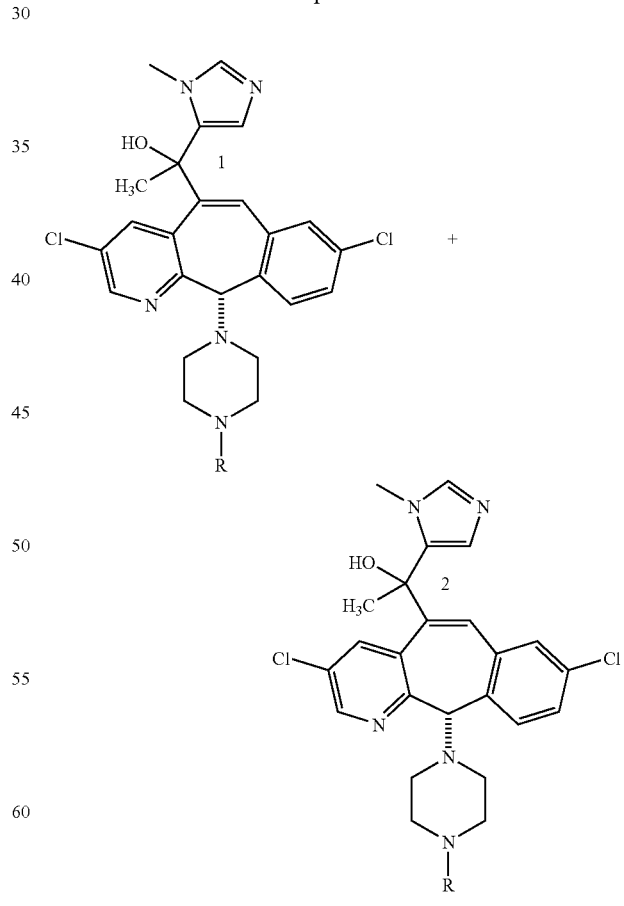
wherein R is defined in Table 67 and the numbers 1 and 2 in the formulas represent isomers 1 and 2, respectively.

TABLE 67

| Examples | R Isomer 1 and Isomer 2 |
|---|---|
| 715 | —O-C(=O)-O-CH₃ |
| 716 | —O-C(=O)-O-CH₂CH₃ |
| 717 | —O-C(=O)-O-propyl |
| 718 | —O-C(=O)-O-isopropyl |
| 719 | —O-C(=O)-O-isobutyl |
| 720 | —O-C(=O)-O-neopentyl |
| 721 | —O-C(=O)-O-allyl |
| 722 | —O-C(=O)-O-sec-butyl |
| 723 | —O-C(=O)-O-cyclopentyl |
| 724 | —O-C(=O)-O-cyclohexyl |
| 725 | —O-C(=O)-O-phenyl |
| 726 | —O-C(=O)-O-benzyl |
| 727 | —O-C(=O)-O-(4-methylphenyl) |

TABLE 67-continued

| Examples | R Isomer 1 and Isomer 2 |
|---|---|
| 728 | —O-C(=O)-O-(4-methoxyphenyl) |
| 729 | —O-C(=O)-O-(4-chlorophenyl) |
| 730 | —O-C(=O)-O-(4-bromophenyl) |
| 731 | —O-C(=O)-O-(4-fluorophenyl) |
| 732 | —O-C(=O)-O-(1-naphthyl) |

EXAMPLES 733-750

If one were to react each isomer, 898a and 898b following essentially the same procedure as in Examples 590-603 (see Preparative Example 74 for preparation of chloroformates), then one would obtain compounds of the formula:

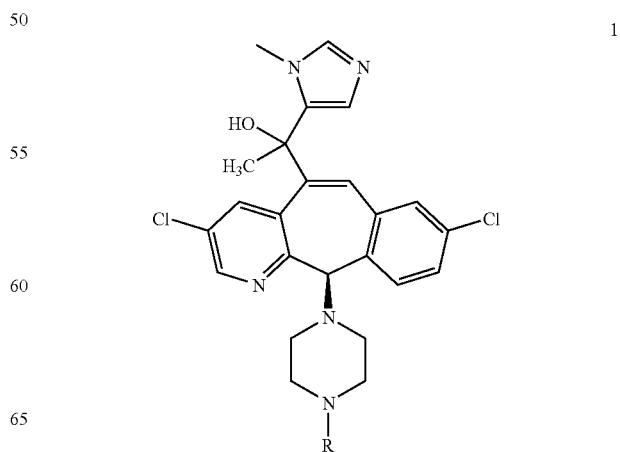

-continued

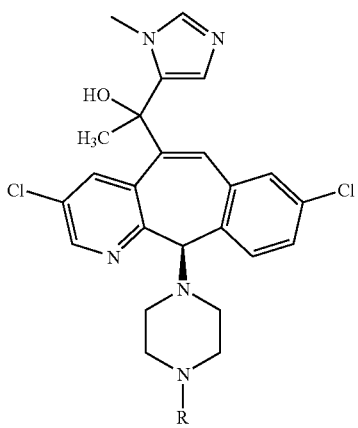

wherein R is defined in Table 68 and the numbers 1 and 2 in the formulas represent isomer 1 and isomer 2, respectively.

TABLE 68

| Example | R Isomer 1 and Isomer 2 |
|---|---|
| 733 | —C(O)O—CH₃ |
| 734 | —C(O)O—Et |
| 735 | —C(O)O—propyl |
| 736 | —C(O)O—iPr |
| 737 | —C(O)O—isobutyl |
| 738 | —C(O)O—neopentyl |
| 739 | —C(O)O—allyl |
| 740 | —C(O)O—sec-butyl |

TABLE 68-continued

| Example | R Isomer 1 and Isomer 2 |
|---|---|
| 741 | —C(O)O—cyclopentyl |
| 742 | —C(O)O—cyclohexyl |
| 743 | —C(O)O—phenyl |
| 744 | —C(O)O—benzyl |
| 745 | —C(O)O—(4-methylphenyl) |
| 746 | —C(O)O—(4-methoxyphenyl) |
| 747 | —C(O)O—(4-chlorophenyl) |
| 748 | —C(O)O—(4-fluorophenyl) |
| 749 | —C(O)O—(4-bromophenyl) |
| 750 | —C(O)O—(1-naphthyl) |

EXAMPLES 751-768

If one were to react each isomer, 899a and 899b following essentially the same procedure as in Examples 590-603 (see Preparative Example 74 for preparation of chloroformates), then one would obtain compounds of the formula:

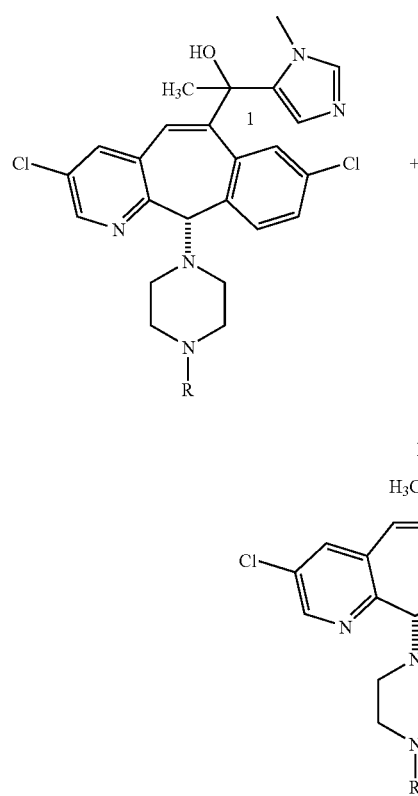

wherein R is defined in Table 69 and the numbers 1 and 2 in the formulas represent isomers 1 and 2, respectively.

TABLE 69

| Example | R Isomer 1 and Isomer 2 |
|---|---|
| 751 | —C(=O)OCH₃ |
| 752 | —C(=O)OCH₂CH₃ |
| 753 | —C(=O)O-n-propyl |
| 754 | —C(=O)O-isopropyl |
| 755 | —C(=O)O-isobutyl |

TABLE 69-continued

| Example | R Isomer 1 and Isomer 2 |
|---|---|
| 756 | —C(=O)OCH₂C(CH₃)₃ |
| 757 | —C(=O)OCH₂CH=CH₂ |
| 758 | —C(=O)O-sec-butyl |
| 759 | —C(=O)O-cyclopentyl |
| 760 | —C(=O)O-cyclohexyl |
| 761 | —C(=O)O-phenyl |
| 762 | —C(=O)OCH₂-phenyl |
| 763 | —C(=O)O-(4-methylphenyl) |
| 764 | —C(=O)O-(4-methoxyphenyl) |
| 765 | —C(=O)O-(4-bromophenyl) |
| 766 | —C(=O)O-(4-chlorophenyl) |
| 767 | —C(=O)O-(4-fluorophenyl) |

TABLE 69-continued

| Example | R<br>Isomer 1 and Isomer 2 |
|---|---|
| 768 | 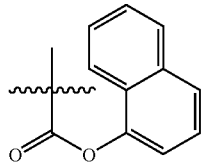 |

EXAMPLES 769-786

If one were to react each isomer, 900a and 900b following essentially the same procedure as in Examples 590-603 (see Preparative Example 74 for preparation of chloroformates), then one would obtain compounds of the formula:

1

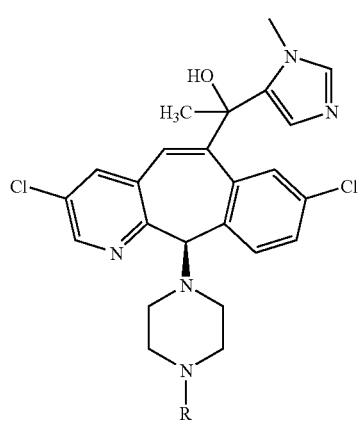

2

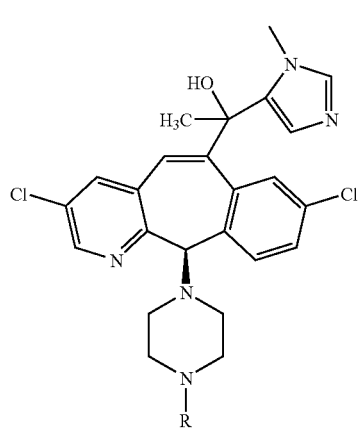

wherein R is defined in Table 70 and the numbers 1 and 2 in the formulas represent isomers 1 and 2, respectively.

TABLE 70

| Example | R<br>Isomer 1 and Isomer 2 |
|---|---|
| 769 | 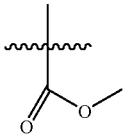 |
| 770 | 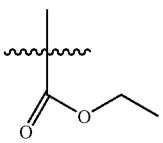 |
| 771 | 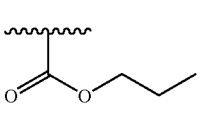 |
| 772 | 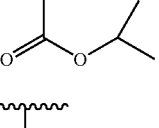 |
| 773 | 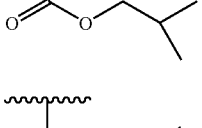 |
| 774 | 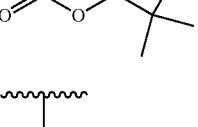 |
| 775 | 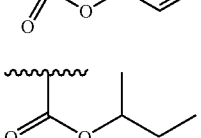 |
| 776 | 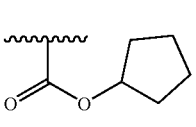 |
| 777 | 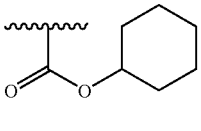 |
| 778 | 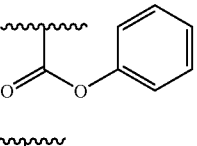 |
| 779 | 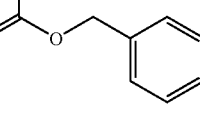 |
| 780 |  |

TABLE 70-continued
| Example | R Isomer 1 and Isomer 2 |
|---|---|
| 781 | 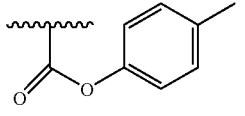 |
| 782 | 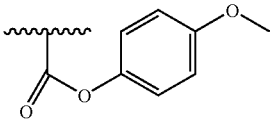 |
| 783 | 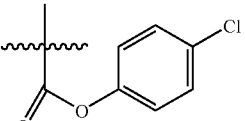 |
| 784 | 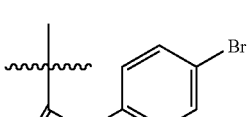 |
| 785 | 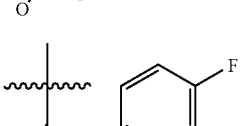 |
| 786 | 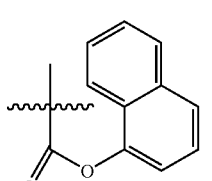 |
EXAMPLES 787-814
If one were to use 897a and 897b and follow essentially the same procedure as in Example 536 then one would obtain compounds of the formula:
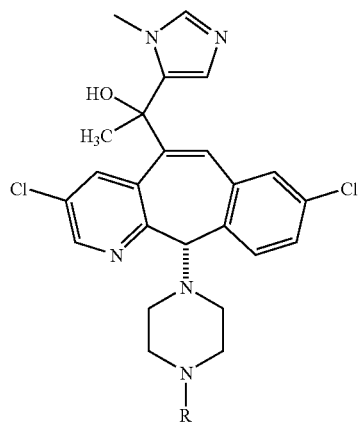
1
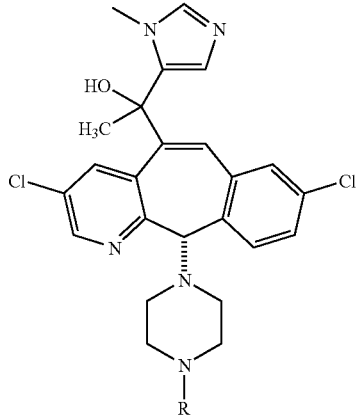
2
wherein R is defined in Table 71 and the numbers 1 and 2 in the formulas represent isomers 1 and 2, respectively.
TABLE 71
| Example | R Isomer 1 and Isomer 2 |
|---|---|
| 787 | 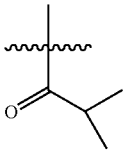 |
| 788 | 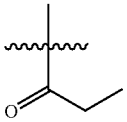 |
| 789 | 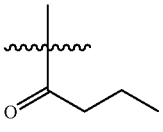 |
| 790 |  |
| 791 | 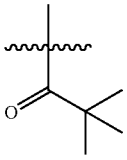 |
| 792 | 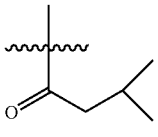 |

TABLE 71-continued

| Example | R Isomer 1 and Isomer 2 |
|---|---|
| 793 | 2-methylcyclopropyl ketone |
| 794 | 1-methylcyclopropyl ketone |
| 795 | cyclobutyl ketone |
| 796 | cyclopentyl ketone |
| 797 | cyclohexyl ketone |
| 798 | cyclohex-1-enyl ketone |
| 799 | piperidin-4-yl ketone |
| 800 | 1-methylcyclohexyl ketone |
| 801 | cyclohexylmethyl ketone (ketone with CH₂-cyclohexyl) |
| 802 | (piperidin-4-yl)methyl ketone |
| 803 | 1-(4-carbamoylpiperidin-4-yl)methyl ketone (with N-C(O)NH₂) |
| 804 | phenyl ketone |
| 805 | 4-chlorophenyl ketone |
| 806 | 4-bromophenyl ketone |
| 807 | 4-fluorophenyl ketone |
| 808 | 4-cyanophenyl ketone |
| 809 | 4-methylphenyl ketone |

TABLE 71-continued

| Example | R Isomer 1 and Isomer 2 |
|---|---|
| 810 | (4-methoxyphenyl)carbonyl |
| 811 | pyridin-4-ylcarbonyl |
| 812 | (1-oxidopyridin-4-yl)carbonyl |
| 813 | 2-(pyridin-4-yl)acetyl |
| 814 | 2-(1-oxidopyridin-4-yl)acetyl |

EXAMPLES 815–842

If one were to use 898a and 898b and follow essentially the same procedure as in Example 536 then one would obtain compounds of the formula:

wherein R is defined in Table 72 and the numbers 1 and 2 in the formulas represent isomers 1 and 2, respectively.

TABLE 72

| Example | R Isomer 1 and Isomer 2 |
|---|---|
| 815 | isobutyryl |
| 816 | propanoyl |
| 817 | butanoyl |

TABLE 72-continued
| Example | R Isomer 1 and Isomer 2 |
|---|---|
| 818 | 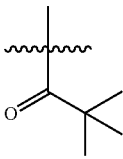 |
| 819 | 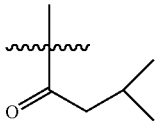 |
| 820 | 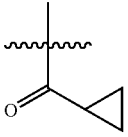 |
| 821 | 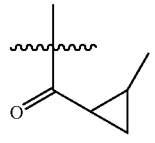 |
| 822 | 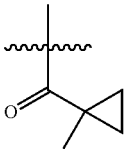 |
| 823 | 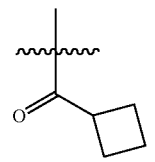 |
| 824 | 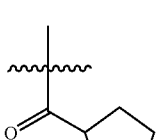 |
| 825 | 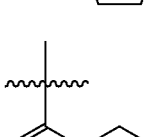 |
| 826 | 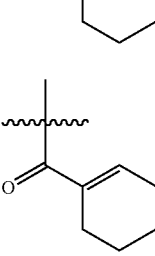 |
TABLE 72-continued
| Example | R Isomer 1 and Isomer 2 |
|---|---|
| 827 | 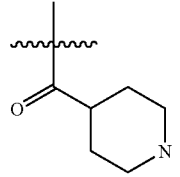 |
| 828 | 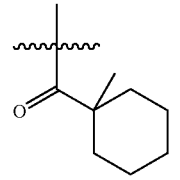 |
| 829 | 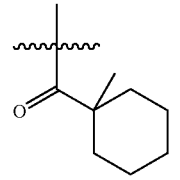 |
| 830 | 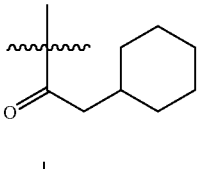 |
| 831 | 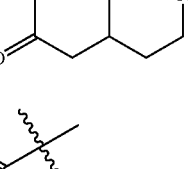 |
| 832 | 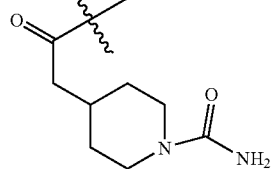 |
| 833 | 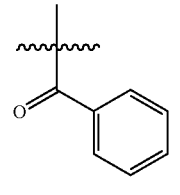 |
| 834 | 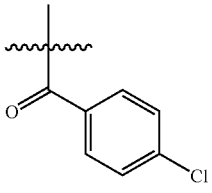 |

TABLE 72-continued
| Example | R Isomer 1 and Isomer 2 |
|---|---|
| 835 | 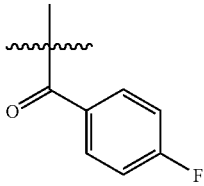 |
| 836 | 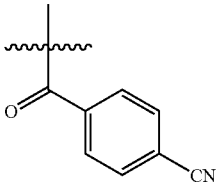 |
| 837 | 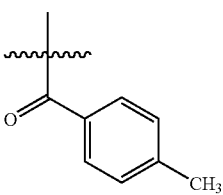 |
| 838 | 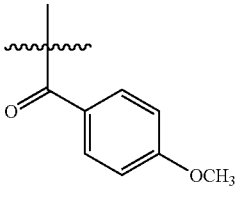 |
| 839 | 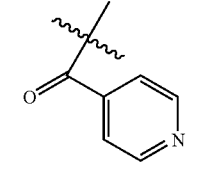 |
| 840 | 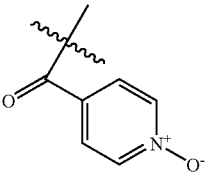 |
TABLE 72-continued
| Example | R Isomer 1 and Isomer 2 |
|---|---|
| 841 | 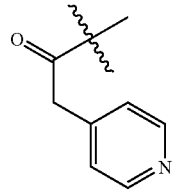 |
| 842 | 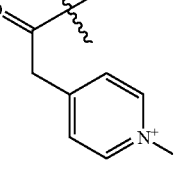 |
EXAMPLES 843-870
If one were to use 899a and 899b and follow essentially the same procedure as in Example 536 then one would obtain compounds of the formula:
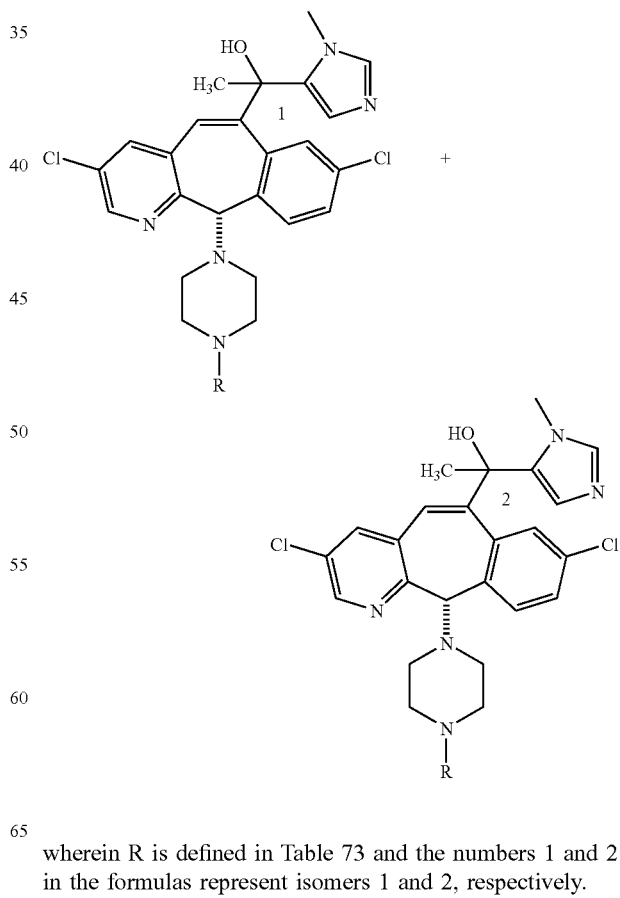
wherein R is defined in Table 73 and the numbers 1 and 2 in the formulas represent isomers 1 and 2, respectively.

TABLE 73
| Example | R Isomer 1 and Isomer 2 |
|---|---|
| 843 | 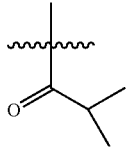 |
| 844 | 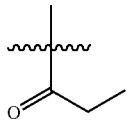 |
| 845 | 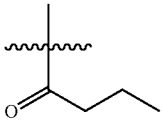 |
| 846 | 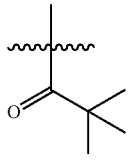 |
| 847 | 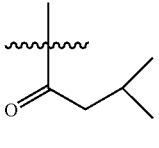 |
| 848 | 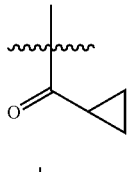 |
| 849 | 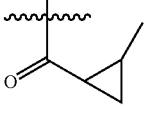 |
| 850 | 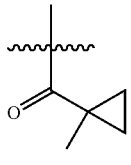 |
| 851 | 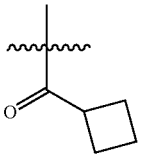 |
| 852 | 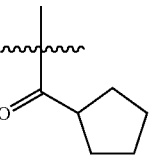 |
TABLE 73-continued
| Example | R Isomer 1 and Isomer 2 |
|---|---|
| 853 | 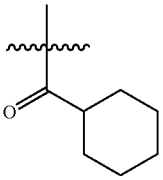 |
| 854 | 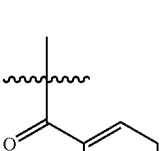 |
| 855 | 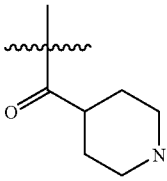 |
| 856 | 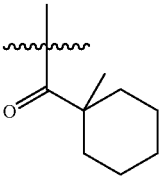 |
| 857 | 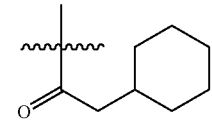 |
| 858 | 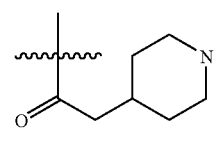 |
| 859 | 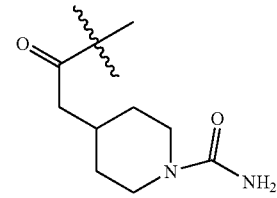 |
| 860 | 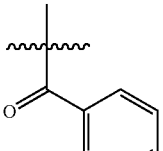 |

TABLE 73-continued
| Example | R Isomer 1 and Isomer 2 |
|---|---|
| 861 | 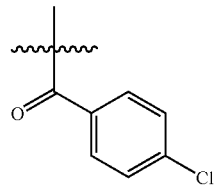 |
| 862 | 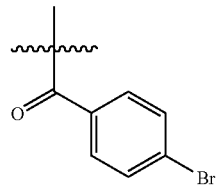 |
| 863 | 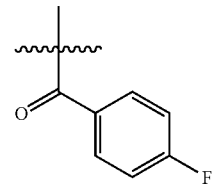 |
| 864 | 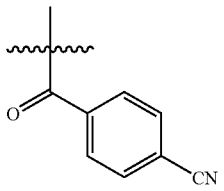 |
| 865 | 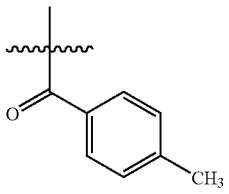 |
| 866 | 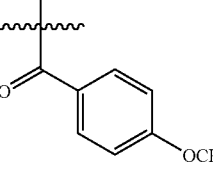 |
| 867 | 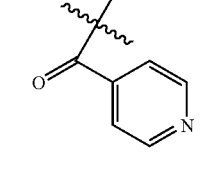 |
| 868 | 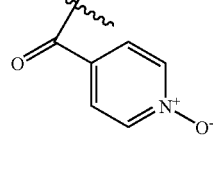 |
| 869 | 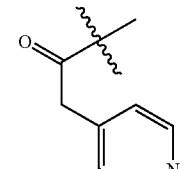 |
| 870 | 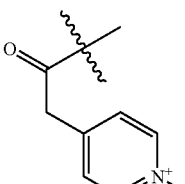 |
EXAMPLES 871-898
If one were to use 900a and 900b and follow essentially the same procedure as in Example 536 then one would obtain compounds of the formula:
1
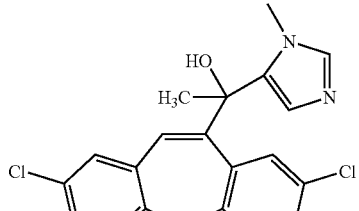
2
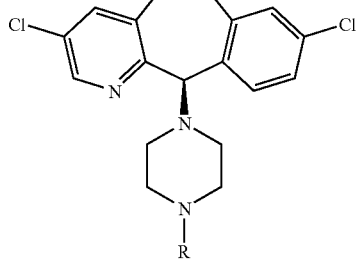
wherein R is defined in Table 74 and the numbers 1 and 2 in the formulas represent isomers 1 and 2, respectively.

TABLE 74
| Example | R Isomer 1 and Isomer 2 |
|---|---|
| 871 | 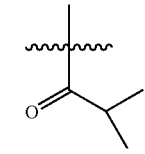 |
| 872 | 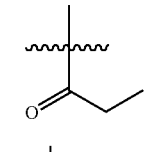 |
| 873 | 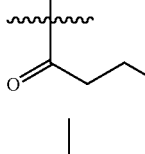 |
| 874 | 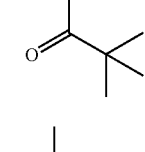 |
| 875 | 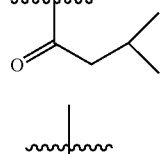 |
| 876 | 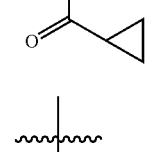 |
| 877 | 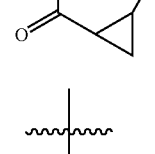 |
| 878 | 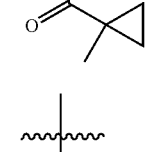 |
| 879 | 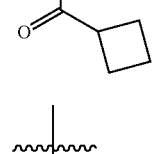 |
| 880 | 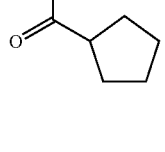 |
TABLE 74-continued
| Example | R Isomer 1 and Isomer 2 |
|---|---|
| 881 | 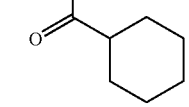 |
| 882 | 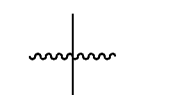 |
| 883 | 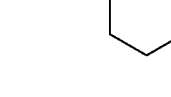 |
| 884 | 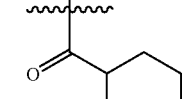 |
| 885 |  |
| 886 | 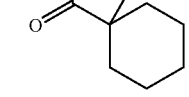 |
| 887 | 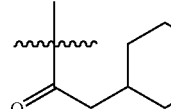 |
| 888 |  |

TABLE 74-continued
| Example | R Isomer 1 and Isomer 2 |
|---------|--------------------------|
| 889 | 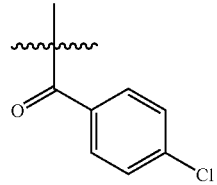 |
| 890 | 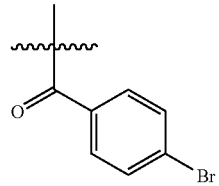 |
| 891 | 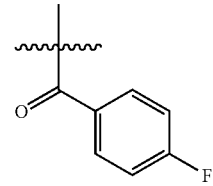 |
| 892 | 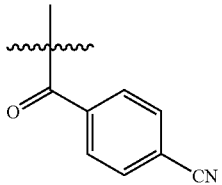 |
| 893 | 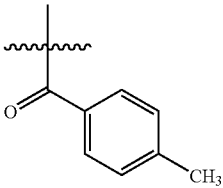 |
| 894 | 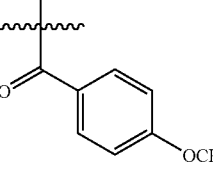 |
| 895 | 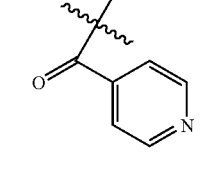 |
| 896 | 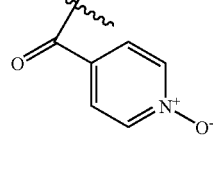 |
| 897 | 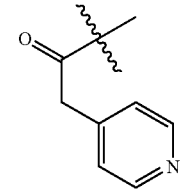 |
| 898 | 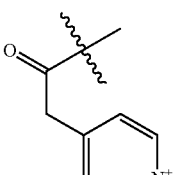 |
EXAMPLE 899-922
If one were to use 897a and 897b and follow essentially the same procedure as in Examples 566-567 then one would obtain compounds of the formula:
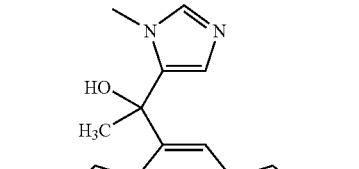
1
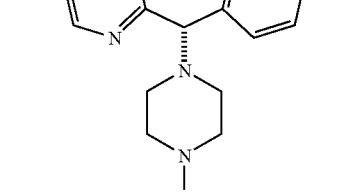
2 wherein R is defined in Table 75 and the numbers 1 and 2 in the formulas represent isomers 1 and 2, respectively.

TABLE 75

| Examples | R Isomer 1 and Isomer 2 |
|---|---|
| 899 | -S(O)₂-CH₃ |
| 900 | -S(O)₂-CH(CH₃)₂ |
| 902 | -S(O)₂-CH₂CH₂CH₃ |
| 903 | -S(O)₂-N(CH₃)₂ |
| 904 | -S(O)₂-C(CH₃)₃ |
| 905 | -S(O)₂-CF₃ |
| 907 | -S(O)₂-cyclopropyl |
| 908 | -S(O)₂-(4-methylphenyl) |
| 909 | -S(O)₂-(4-ethylphenyl) |

TABLE 75-continued

| Examples | R Isomer 1 and Isomer 2 |
|---|---|
| 910 | -S(O)₂-(4-isopropylphenyl) |
| 911 | -S(O)₂-(4-tert-butylphenyl) |
| 912 | -S(O)₂-(4-chlorophenyl) |
| 913 | -S(O)₂-(4-trifluoromethylphenyl) |
| 915 | -S(O)₂-(4-bromophenyl) |
| 916 | -S(O)₂-(4-fluorophenyl) |
| 917 | -S(O)₂-(4-cyanophenyl) |
| 918 | -S(O)₂-(4-methoxyphenyl) |
| 919 | -S(O)₂-phenyl |

TABLE 75-continued

| Examples | R<br>Isomer 1 and Isomer 2 |
|---|---|
| 920 | benzylsulfonyl group |
| 921 | 2-thienylsulfonyl group |
| 922 | 1-naphthylsulfonyl group |

EXAMPLES 923-946

If one were to use 898a and 898b and follow essentially the same procedure as in Examples 566-567 then one would obtain compounds of the formula:

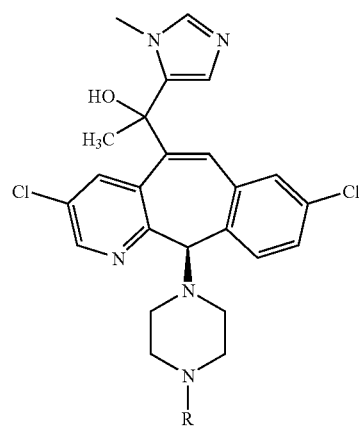

1

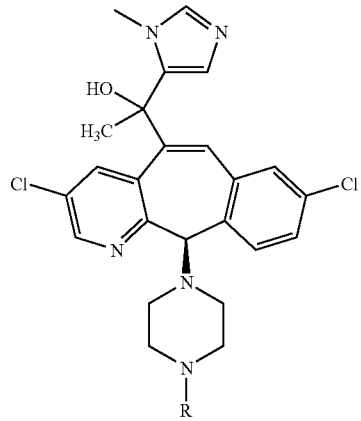

2 wherein R is defined in Table 76 and the numbers 1 and 2 in the formulas represent isomers 1 and 2, respectively.

TABLE 76

| Example | R<br>Isomer 1 and Isomer 2 |
|---|---|
| 923 | methylsulfonyl |
| 924 | isopropylsulfonyl |
| 926 | propylsulfonyl |
| 927 | dimethylaminosulfonyl |
| 928 | tert-butylsulfonyl |
| 929 | trifluoromethylsulfonyl |

TABLE 76-continued

| Example | R Isomer 1 and Isomer 2 |
|---|---|
| 931 | 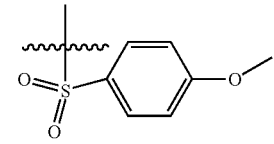 cyclopropyl sulfonyl |
| 932 | 4-methylphenyl sulfonyl |
| 933 | 4-ethylphenyl sulfonyl |
| 934 | 4-isopropylphenyl sulfonyl |
| 935 | 4-tert-butylphenyl sulfonyl |
| 936 | 4-chlorophenyl sulfonyl |
| 937 | 4-trifluoromethylphenyl sulfonyl |
| 939 | 4-bromophenyl sulfonyl |
| 940 | 4-fluorophenyl sulfonyl |
| 941 | 4-cyanophenyl sulfonyl |
| 942 | 4-methoxyphenyl sulfonyl |
| 943 | phenyl sulfonyl |
| 944 | benzyl sulfonyl |
| 945 | 2-thienyl sulfonyl |
| 946 | 1-naphthyl sulfonyl |

EXAMPLES 947-970

If one were to use 899a and 899b and follow essentially the same procedure as in Examples 566-567 then one would obtain compounds of the formula:

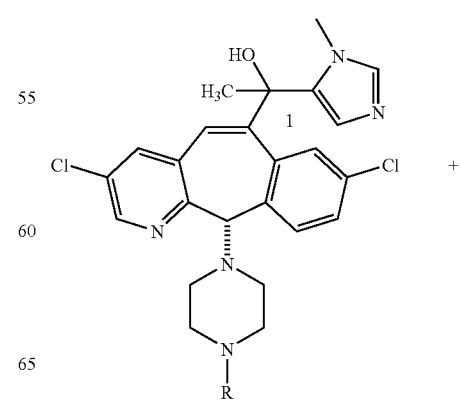 +

-continued
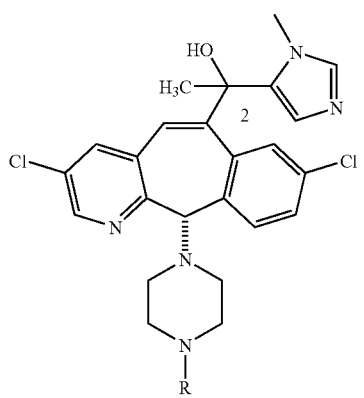
wherein R is defined in Table 77 and the numbers 1 and 2 in the formulas represent isomers 1 and 2, respectively.
TABLE 77
| Example | R Isomer 1 and Isomer 2 |
|---|---|
| 947 | 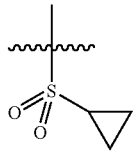 |
| 948 |  |
| 950 | 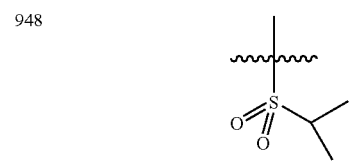 |
| 951 | 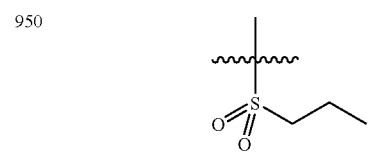 |
| 952 | 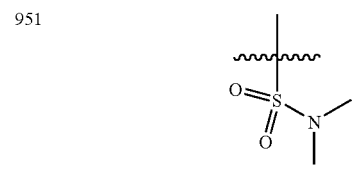 |
| 953 | 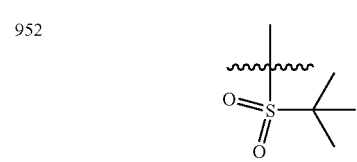 |
TABLE 77-continued
| Example | R Isomer 1 and Isomer 2 |
|---|---|
| 955 | 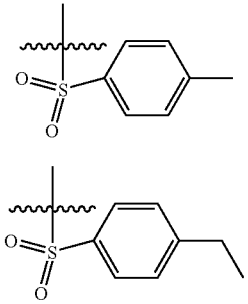 |
| 956 | |
| 957 | 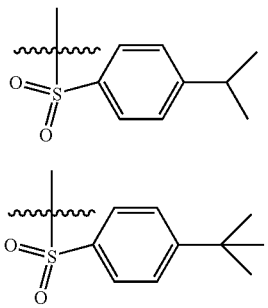 |
| 958 | |
| 959 |  |
| 960 | |
| 961 |  |
| 963 | |
| 964 | 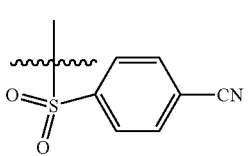 |
| 965 | 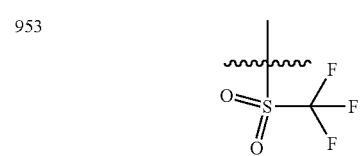 |

TABLE 77-continued

| Example | R Isomer 1 and Isomer 2 |
|---|---|
| 966 | *4-methoxyphenylsulfonyl* |
| 967 | *phenylsulfonyl* |
| 968 | *benzylsulfonyl* |
| 969 | *2-thienylsulfonyl* |
| 970 | *1-naphthylsulfonyl* |

EXAMPLES 971-995

If one were to use 900a and 900b and follow essentially the same procedure as in Examples 566-567 then one would obtain compounds of the formula:

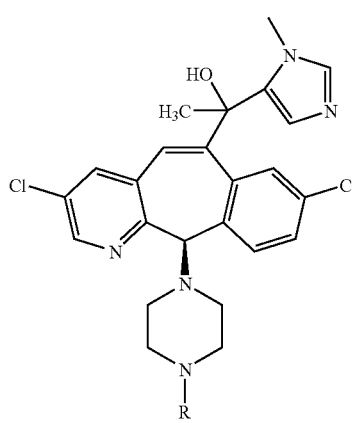

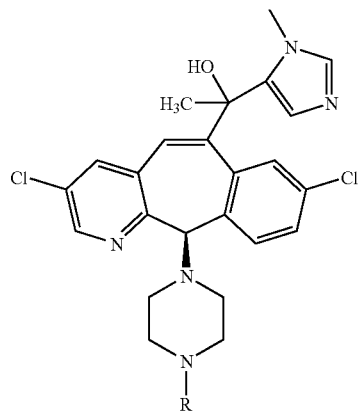

wherein R is defined in Table 78 and the numbers 1 and 2 in the formulas represent isomers 1 and 2, respectively.

TABLE 78

| Example | R Isomer 1 and Isomer 2 |
|---|---|
| 971 | *methylsulfonyl* |
| 973 | *isopropylsulfonyl* |
| 974 | *n-propylsulfonyl* |
| 975 | *dimethylaminosulfonyl* |
| 976 | *tert-butylsulfonyl* |
| 977 | *trifluoromethylsulfonyl* |

TABLE 78-continued

| Example | R Isomer 1 and Isomer 2 |
|---|---|
| 979 | (sulfonyl cyclopropyl) |
| 980 | (sulfonyl 4-methylphenyl) |
| 981 | (sulfonyl 4-ethylphenyl) |
| 982 | (sulfonyl 4-isopropylphenyl) |
| 983 | (sulfonyl 4-tert-butylphenyl) |
| 984 | (sulfonyl 4-chlorophenyl) |
| 985 | (sulfonyl 4-trifluoromethylphenyl) |
| 987 | (sulfonyl 4-bromophenyl) |
| 989 | (sulfonyl 4-fluorophenyl) |
| 990 | (sulfonyl 4-cyanophenyl) |

TABLE 78-continued

| Example | R Isomer 1 and Isomer 2 |
|---|---|
| 991 | (sulfonyl 4-methoxyphenyl) |
| 992 | (sulfonyl phenyl) |
| 993 | (sulfonyl benzyl) |
| 994 | (sulfonyl 2-thienyl) |
| 995 | (sulfonyl 1-naphthyl) |

PREPARATIVE EXAMPLE 84

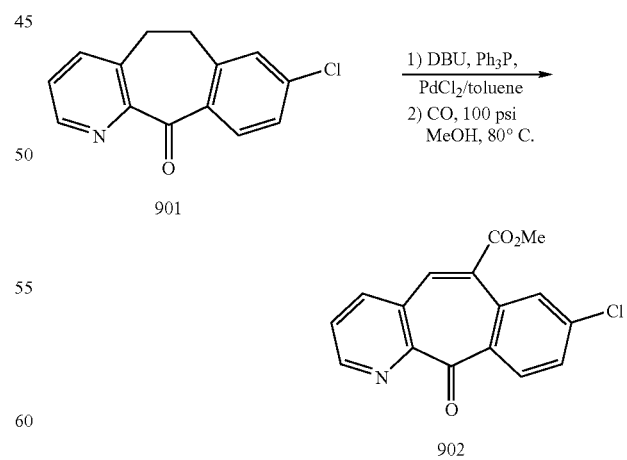

Starting material 901 (25 g, 78 mmol) was combined with DBU (15.7 ML, 105.3 mmol, 1.35 eq.); Ph₃P (9.44 g 0.39 mmol, 0.5 eq.); PdCl₂ (1.38 g, 7.8 mmol, 0.1 eq.); MeOH (50 ML)/Toluene (200 ML) in a flask and reacted in a Parr Shaker under CO, 100 psi at 80° C. When completed, the reaction was treated with H₂O and extracted with Ethyl Acetate. Dried over MgSO₄ and evaporated to get a black syrup. (71 g) Column chromatography (silica gel) and eluting with Hexanes, then 20% Ethyl Acetate/Hexanes to 40% E/H to give product 902, (39 g).

PREPARATIVE EXAMPLE 85

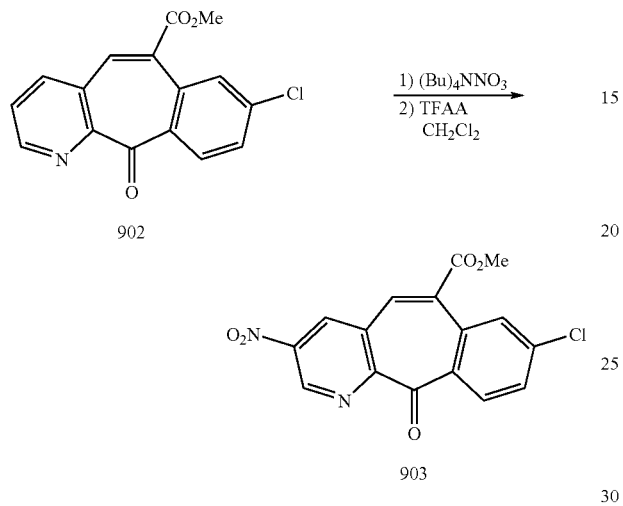

Dissolve (Bu)₄NNO₃ (21.15 g) in CH₂Cl₂ (220 ML) and cool in an ice bath under N₂ and dripped in TFAA (9.8 ML) and stir for 15 minutes. The resulting yellow solution is added slowly to a solution of starting material 902, (18.97 g) in CH₂Cl₂ (200 ML) while cooling in an ice bath (0° C.). Stir at 0° C. for 15-20 minutes, then allowed to war to room temperature for 3 hours. Reaction was treated with saturated NaHCO₃ and extracted with CH₂Cl₂. Isolated the organic layer and dried over MgSO₄, evaporated to dryness t give product as a syrup. Crude was chromatograph (twice) on SiO₂ using Hexanes, then eluting with 20% & 40% Ethyl Acetate/Hexanes). 30-40% yield of product 903 (7.89 g).

PREPARATIVE EXAMPLE 86

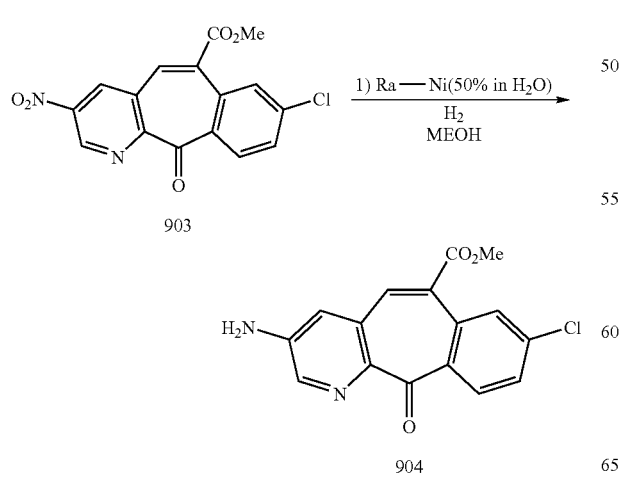

Ra-Ni ((50% in H₂O), 50 g), is washed with ETOH (5×, then decanted), the washed with MeOH (3×), then added to starting material 903 (7.89 g) in MeOH (80 ML), the resulting mixture is stirred under H₂ (balloom) overnight. Reaction is monitored by TLC. Added more RaNi (25 g, washed 5× with ETOH, then 3× w/MeOH). When completed reaction is filtered, the insoluble dark solid is washed with CH₂CL₂/MeOH until the color of the washings became light, combined filtration and evaporated to dryness to get a brown solid 904 (3.88 g of product).

PREPARATIVE EXAMPLE 87

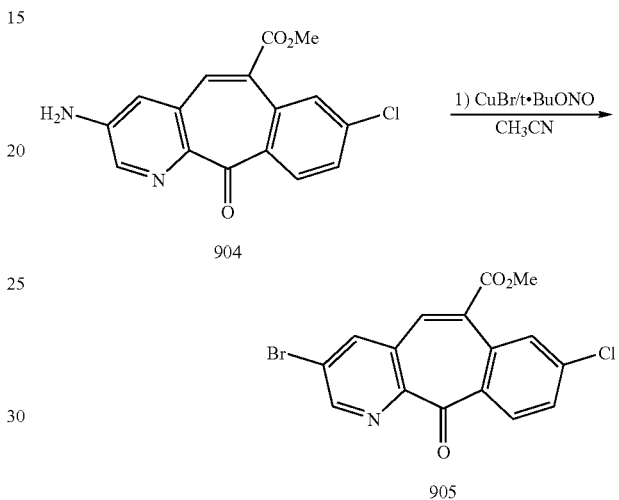

Suspend starting material 904 (0.5 g) in CH₃CN (20 ML), add CuBr (0.42 g) and cool in an ice bath under N₂. Add t-BuONO (0.28 g) and allow to stir and warm to room temperature. After 2 hours stir at 75° C., stir ~2 hours. After reaction is complete, add reaction to 1N HCL and stir. Then add Conc. NH₄OH until blue (basic). Extract with CH₂Cl₂, isolate the organic layer, dried over MgSO₄, filter and concentrated to give product 905.

PREPARATIVE EXAMPLE 88

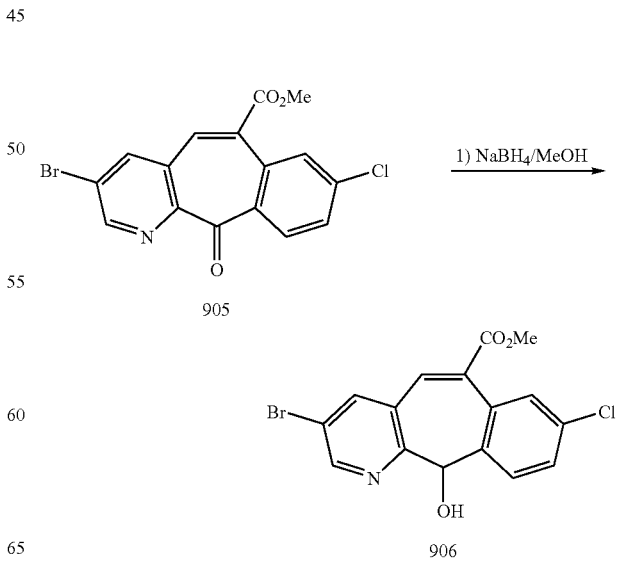

Starting material 905 (3 g, 7.92 mmol) is stirred in MeOH (100 ML) at 0° C. in an ice/H₂O bath, then NaBH4 is added to the cold solution in portions. Stir at 0° C. for 1 hour, then at room temperature for 1 hour. Add (20 ML) of 1.0 N HCL, stir for 10 minutes, basified with saturated NaHCO3, added to brine, extract with Ethyl Acetate, dried over MgSO₄, filtered and evaporated to dryness to give 3.6 g of compound 906.

PREPARATIVE EXAMPLE 89

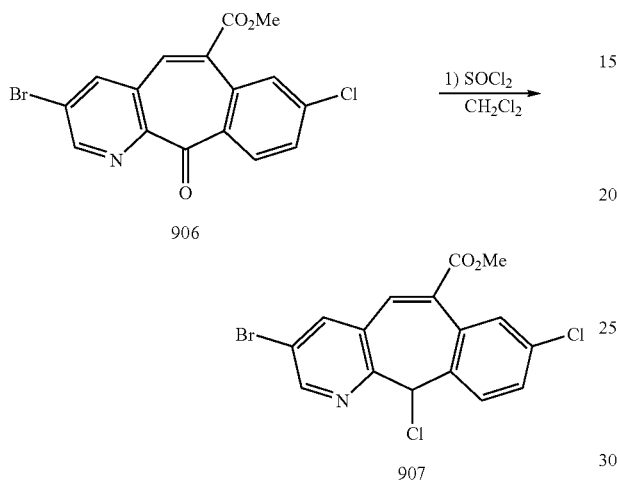

SOCl₂ (2.1 ML) was added to the solution of 906 (3.5 g) in CH₂Cl₂ (50 ML), stirred at room temperature for 5 hours. Additional (1.0 ML) of SOCl₂ was added, stirred for 2 hours, then overnight. Monitored reaction progress by TLC. Reaction mixture was evaporated to dryness and dried under vacuum to give 3.6 g of crude product 907.

PREPARATIVE EXAMPLE 90

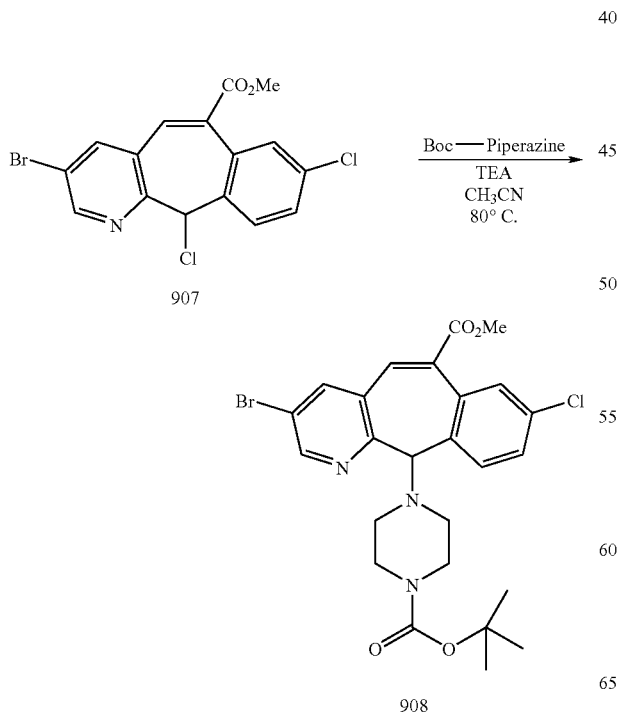

Boc-Piperazine (2.2 g, 2.5 eq.) was added to a mixture of starting material 907 (1.78 g, 4.68 mmol) and TEA (1.9 ML, 3 eq) was stirred in CH₃CN (100 ML), under N₂, heat to 80° C. for 5 hours. TLC then stirred at 80° C. over the weekend. Reaction is treated with 1.0N HCl and extracted with ethyl acetate, wash with brine followed by 1.0N NaOH, dried over MgSO₄. Filter and evaporated reaction to dryness to give crude 908 (62% yield).

PREPARATIVE EXAMPLE 91

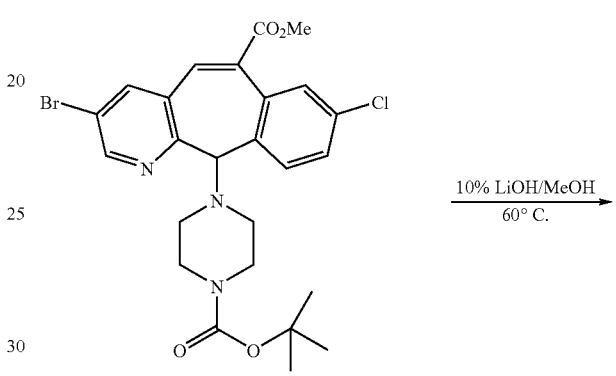

12 ML of a 10% LiOH solution (~4M) was added to a solution of starting material 908 (1.6 g) in MeOH (50 ML) and reaction was stirred at 60° C. A solid precipitated out. Mixture is stirred overnight. Reaction became a clear-yellow solution. Reaction was treated with 10% K₂HPO₄, and extracted with ethyl acetate, washed with brine, dried over MgSO₄, and evaporated to dryness to give 1.5 g of compound 909.

PREPARATIVE EXAMPLE 92

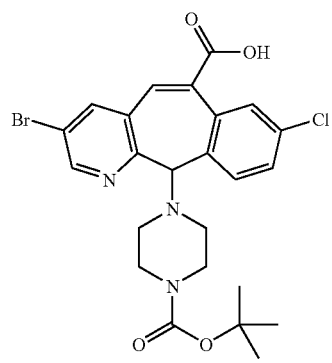

909

1) NHCH₃OCH₃•HCL, NMM, HOBT, DMAP/CH₂Cl₂
2) EDC
93%

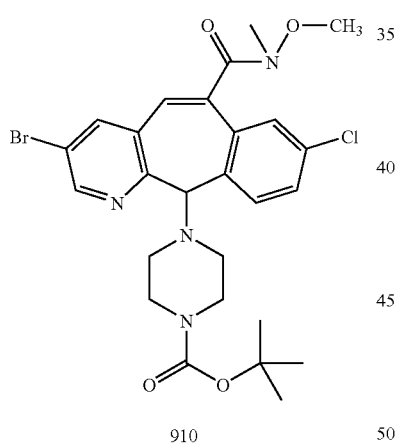

910

Combined starting materials 909 (1.5 g, ~7.8 mmol); NHCH₃OCH₃.HCl; NMM; HOBT; & DMAP in CH₂Cl₂ (20 ML) and stirred for 10 minutes, then EDC (0.64 g, 1.2 eq.) was added and stirred overnight at room temperature. Reaction was treated with 1N HCl, extracted with ethyl acetate, washed with brine followed by 1N NaOH. dried over MgSO₄, filtered and evaporated the filtrate to dryness to give 1.45 g) crude compound 910.

PREPARATIVE EXAMPLE 93

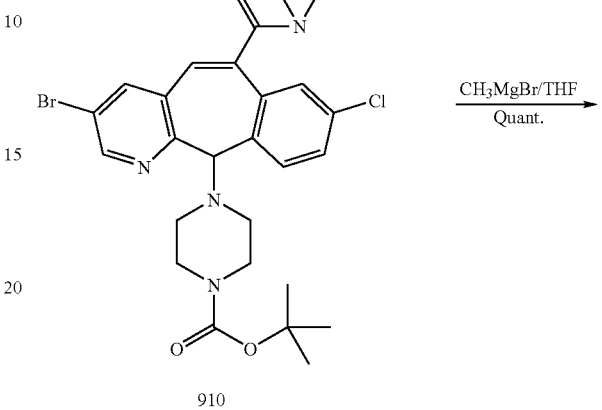

910

CH₃MgBr/THF
Quant.

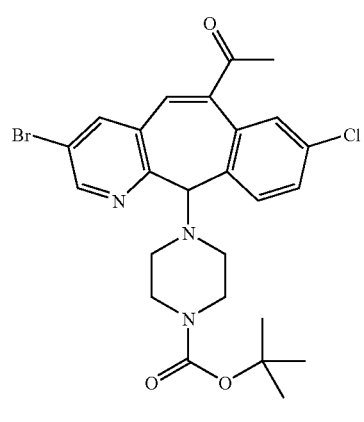

911

A 3M solution of CH₃MgBr/Ether (3.8 ML, 4.5 eq) was added dropwise to a solution of 910 (1.45 g, 2.5 mmol) in THF (50 ML), a dark brown solution resulted. Reaction was stirred under N₂ at room temperature for 2 hours. Reaction was then treated with a saturated NH₄Cl solution and extracted with ethyl acetate. Washed with brine and dried over MgSO₄, filtered and evaporated to dryness to get a yellow solid compound, which after column chromatography gave 1.33 g of compound 911 as a racemic mixture.

PREPARATIVE EXAMPLE 94

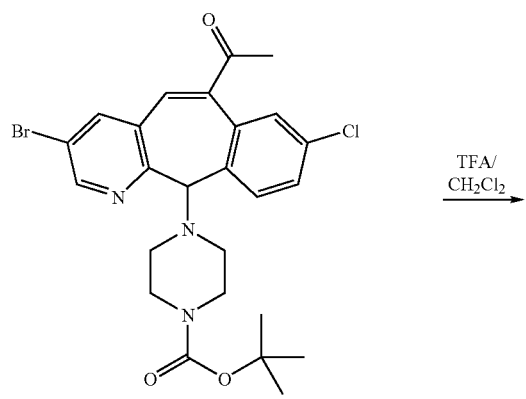

911

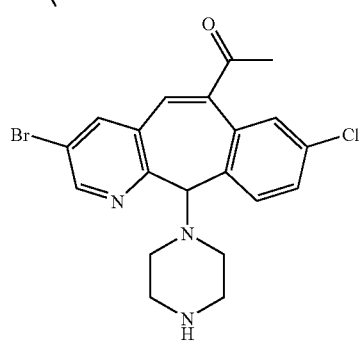

912

Starting material 911 (0.90 g) was dissolved in CH$_2$Cl$_2$ (35 ML) and TFA (35 ML) and stirred at room temperature overnight. Washed with 1.0 N NaOH, dried over MgSO$_4$, filtered and evaporated to dryness to give compound 912.

PREPARATIVE EXAMPLE 95

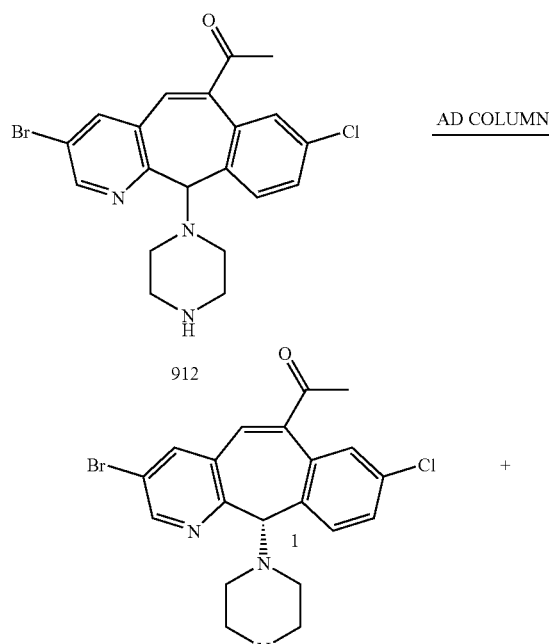

912 was separated into its enantiomers by Chiral Prep HPLC using a Chiral AD Column and eluting with 10% IPA/90% Hexanes+0.2% DEA to give compounds 912a and 912b.

PREPARATIVE EXAMPLE 96

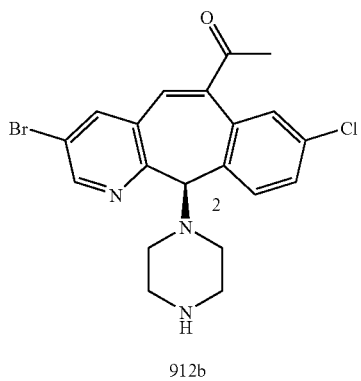

912a

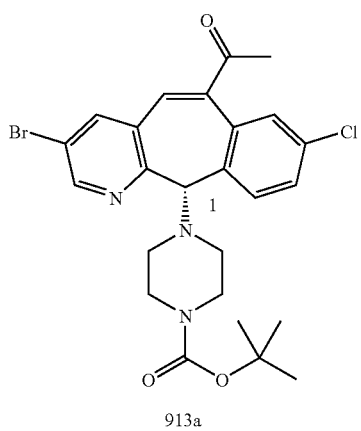

913a

Starting material 912a (0.284 g 0.656 mmol) was dissolved in CH$_2$Cl$_2$ (5 ML), TEA (1.83 ML, 2.0 eq.) and (BOC)$_2$O (0.215 g, 1.5 eq), and stirred at room temperature overnight. Reaction was evaporated and crude was purified by column chromatography using 10% & 25 Ethyl Acetate/Hexanes to give 0.3 g of compound 913a.

PREPARATIVE EXAMPLE 97

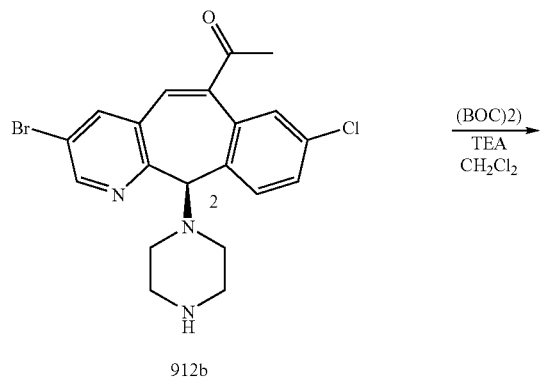

912b

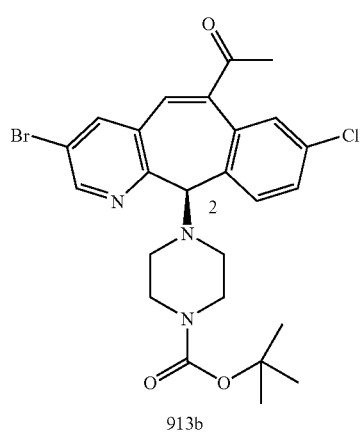

913b

Starting material 9121b (0.254 g 0.587 mmol) was dissolved in CH$_2$Cl$_2$ (5 ML), TEA (1.64 ML, 2.0 eq.) and (BOC)$_2$O (0.192 g, 1.5 eq), and stirred at room temperature overnight. Reaction was evaporated and crude was purified by column chromatography using 10% & 25 Ethyl Acetate/Hexanes to give 0.255 g of compound 913b.

PREPARATIVE EXAMPLE 98

Step A

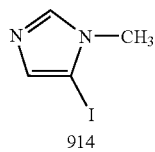

914

-continued

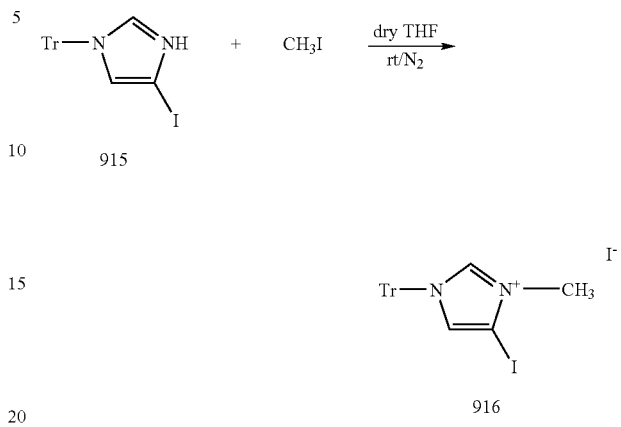

Suspended commercially available (from Acros) 915 (30 g, 68.8 mmol) in dry THF (600 ml) under dry N$_2$. Stirred at room temperature under N$_2$ until it formed a clear solution. Added CH$_3$I (50 ml, 114 g, 803.2 mmol) at room temperature, dropwise, under dry N$_2$. Stirred the suspension at room temperature under N$_2$ for 4 days, followed by TLC-(10% MeOH-2M NH$_3$/CH$_2$Cl$_2$). Filtered the suspension, washed solid with dry THF. Dried the solid under house Vacuum at 40° C. to give 31.11 g of a brown solid, compound 916.

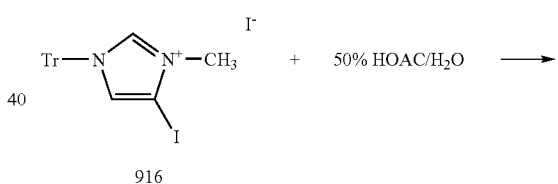

914

Suspended 916 (31.1 g, 53.79 mmol) in 200 ML of 50% HOAC/H$_2$O and heat under reflux overnight. Follow by TLC. When completed, allowed to cool to room temperature, filtered the resulting suspension. Washed with 50% HOAC/H$_2$O. Evaporated to dryness. Suspended the solid in CH$_2$Cl$_2$. Basified to pH 10-11 with 1N NaOH. Separated CH$_2$Cl$_2$ layer and extracted the aqueous phase 3× with CH$_2$CL$_2$. Combined organic layers and washed with Saturated NaCl solution. Dried over MgSO$_4$, evaporated to dryness to give 914 (8.68 g of an off-white solid).

PREPARATIVE EXAMPLE 99

Step A

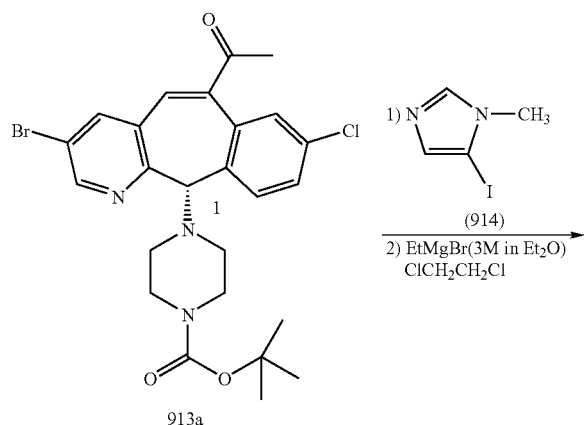

Step B

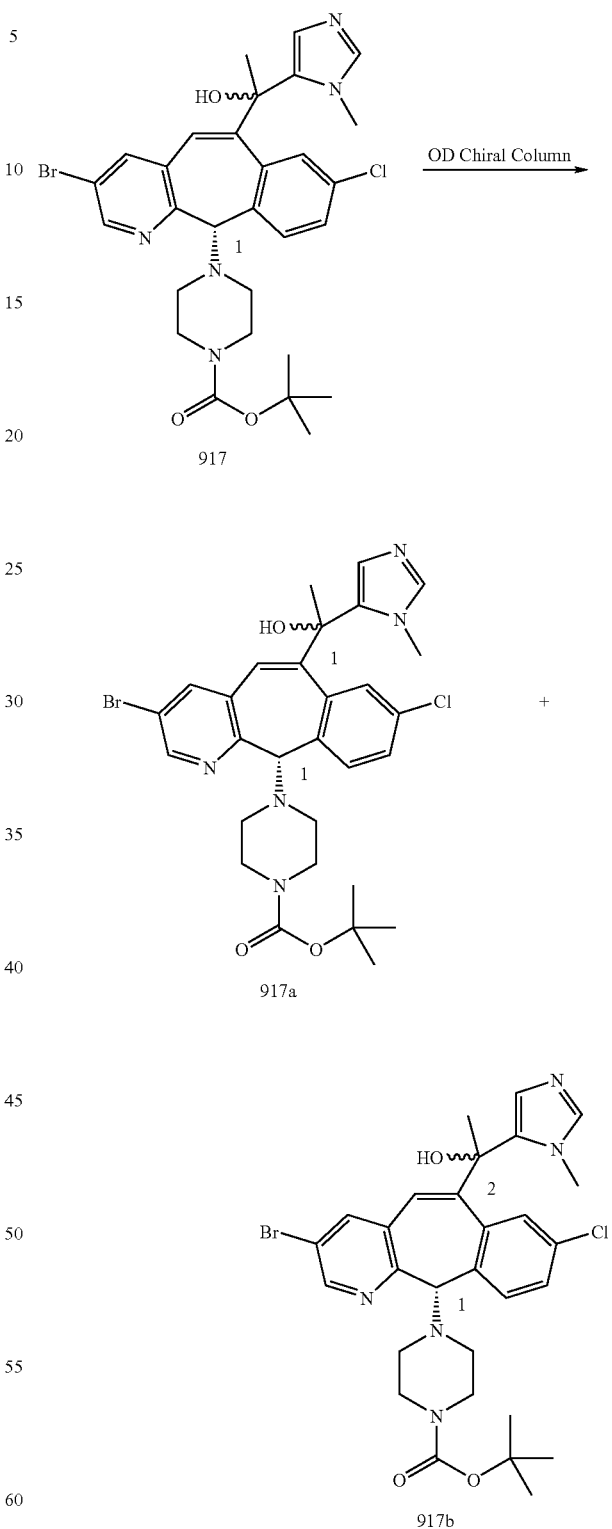

EtMgBr (3Molar in Et$_2$O) solution (2.89 mmol, 963 uL, 5.5 eq.) was dripped into a solution of 914 (0.656 g, 3.15 mmol, 6 eq.) in ClCH$_2$CH$_2$Cl (6 ML) for 30 minutes. To the white suspended mixture, 913a (0.280 g, 0.525 mmol) was then added and stirred at 60° C. for 3 hours. Reaction was treated with saturated NH$_4$Cl at 0° C. by pouring the reaction into the cold NH$_4$Cl. Extracted with Ethyl Acetate, dried over MgSO$_4$ and evaporated to dryness. Column Chromatography (SiO$_2$) eluted with 1%, 2% & 3% MeOH/CH$_2$Cl$_2$ gave 0.054 g of compound 917.

917 was separated by HPLC using a Chiral OD Column and eluting with 20% IPA/Hexanes to give 917a (isomer 1) and 917b (isomer 2).

PREPARATIVE EXAMPLE 100

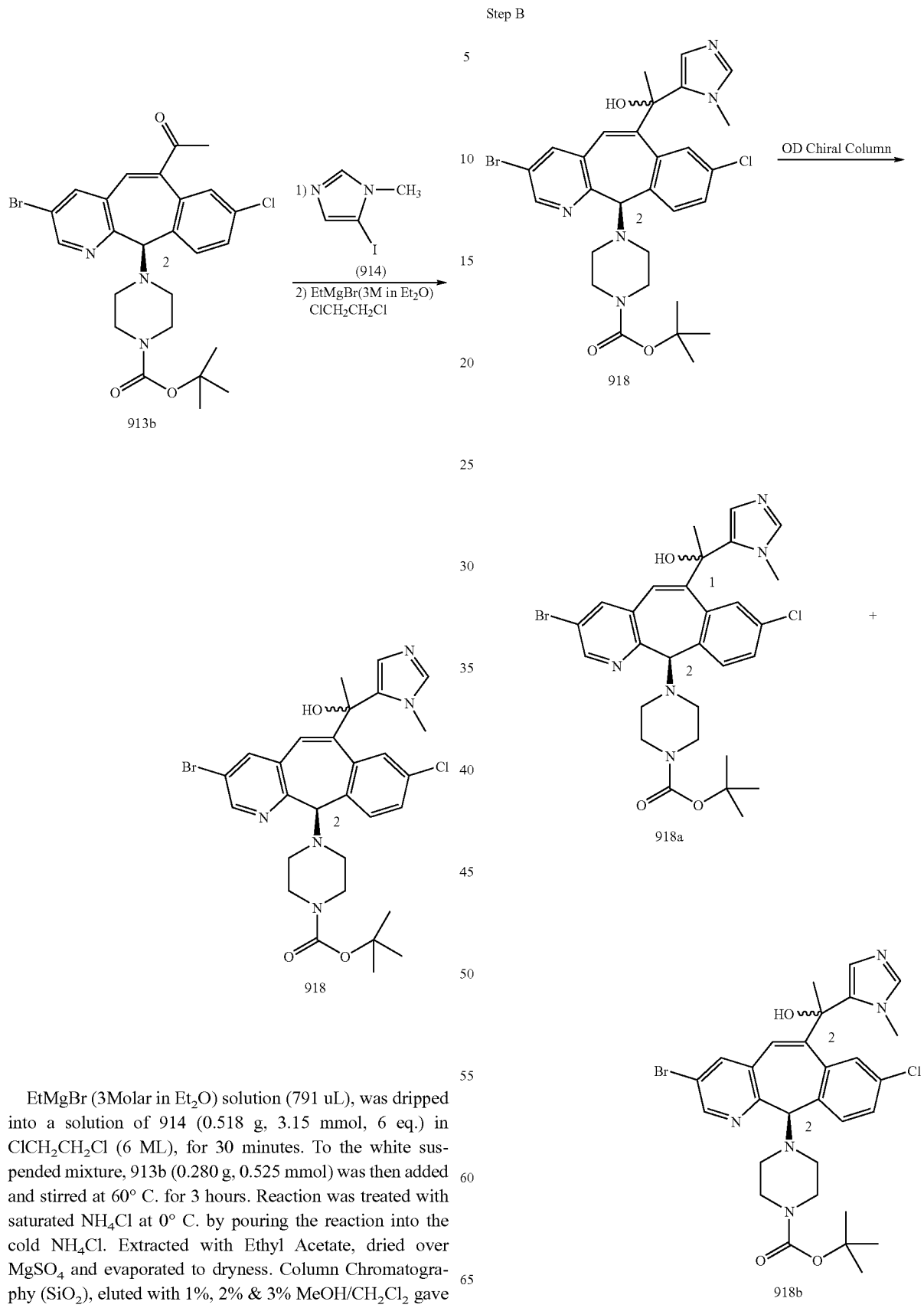

EtMgBr (3Molar in Et$_2$O) solution (791 uL), was dripped into a solution of 914 (0.518 g, 3.15 mmol, 6 eq.) in ClCH$_2$CH$_2$Cl (6 ML), for 30 minutes. To the white suspended mixture, 913b (0.280 g, 0.525 mmol) was then added and stirred at 60° C. for 3 hours. Reaction was treated with saturated NH$_4$Cl at 0° C. by pouring the reaction into the cold NH$_4$Cl. Extracted with Ethyl Acetate, dried over MgSO$_4$ and evaporated to dryness. Column Chromatography (SiO$_2$), eluted with 1%, 2% & 3% MeOH/CH$_2$Cl$_2$ gave 0.054 g of compound 918.

918 was separated by HPLC using a Chiral OD Column and eluting with 20% IPA/Hexanes to give Isomers 918a $^1$H NMR (400 MHz, CDCl$_3$, TMS) δ 1.419 (s, 9H), 1.457 (s, 1H), 1.894 (s, 3H), 2.05-1.87 (m, 2H), 2.30-2.15 (m, 2H), 3.214 (broad, 1H), 3.540 (s, 1H), 3.738 (s, 1H), 3.760 (s, 1H), 3.888 (s, 3H), 4.540 (s, 1H), 6.479 (s, 1H), 7.128 (s, 1H), 7.260 (d, 1H), 7.340 (s, 2H), 7.627 (d, J=2.4 Hz, 1H), 8.221 (s, 1H), 8.486 (d, J=2.8 Hz, 1H). (21) Mp=188-190° C., and 918b.

PREPARATIVE EXAMPLE 101

Reaction was then concentrated, and the residue taken up in CH$_2$Cl$_2$, and washed with 1.0 NaOH. Isolated organics are dried over MgSO$_4$, filtered and concentrated to give compound 919a.

PREPARATIVE EXAMPLE 102

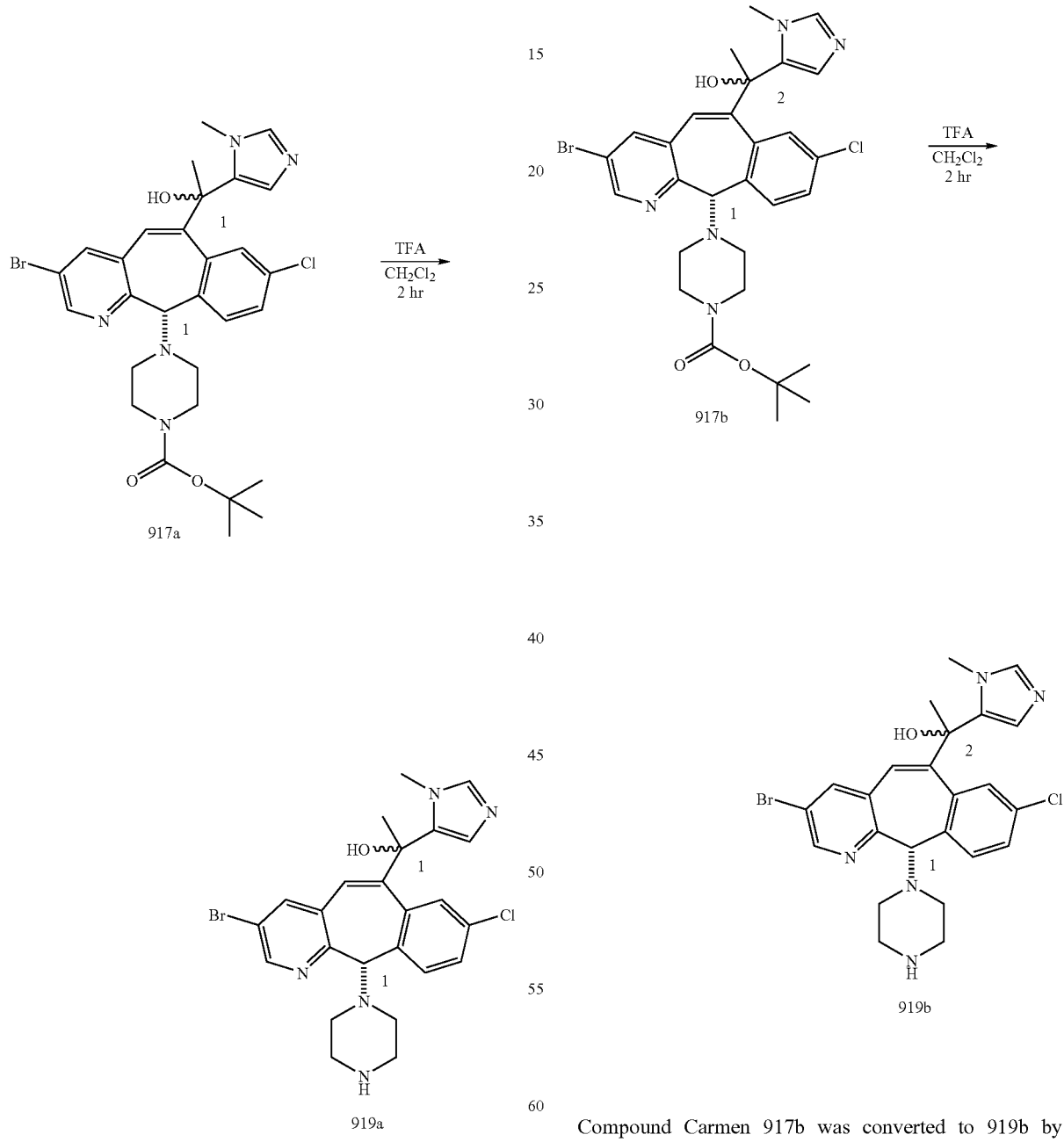

Compound 917a was converted to 919a by reacting with CH$_2$Cl$_2$/TFA at room temperature under N$_2$, for 2 hours.

Compound Carmen 917b was converted to 919b by reacting with CH$_2$Cl$_2$/TFA at room temperature under N$_2$, for 2 hours. Reaction was then concentrated, and the residue taken up in CH$_2$Cl$_2$, and washed with 1.0 NaOH. Isolated organics are dried over MgSO$_4$, filtered and concentrated to give compound 919b.

PREPARATIVE EXAMPLE 103

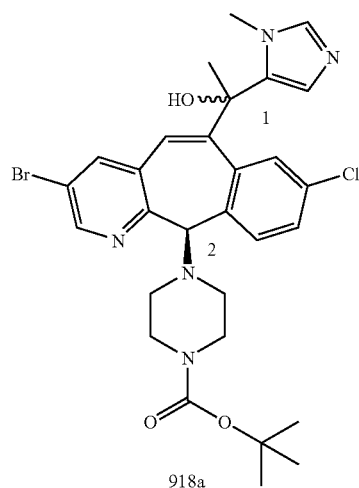

PREPARATIVE EXAMPLE 104

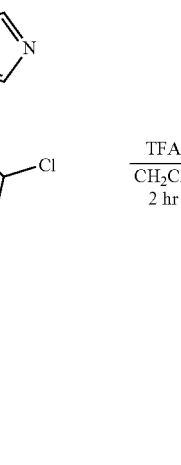

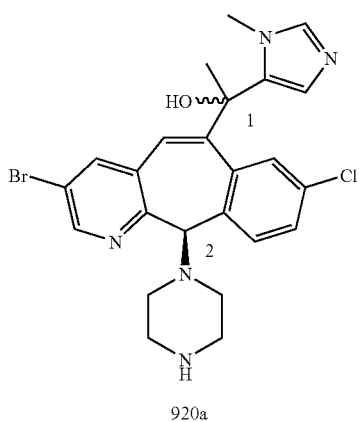

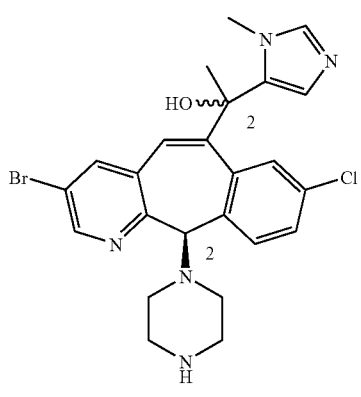

Compound 918a, was converted to 920a, by reacting with CH₂Cl₂/TFA at room temperature under N₂, for 2 hours. Reaction was then concentrated, and the residue taken up in CH₂Cl₂, and washed with 1.0 NaOH. Isolated organics are dried over MgSO₄, filtered and concentrated to give compounds 920a.

Compound 918b was converted to 920b by reacting with CH₂Cl₂/TFA at room temperature under N₂, for 2 hours. Reaction was then concentrated, and the residue taken up in CH₂Cl₂, and washed with 1.0 NaOH. Isolated organics are dried over MgSO₄, filtered and concentrated to give compound 920b.

EXAMPLES 996-1020

If one were to use isomers 919a and 919b in a procedure essentially the same as that in Examples 690-714 then one would obtain compounds of the formula:

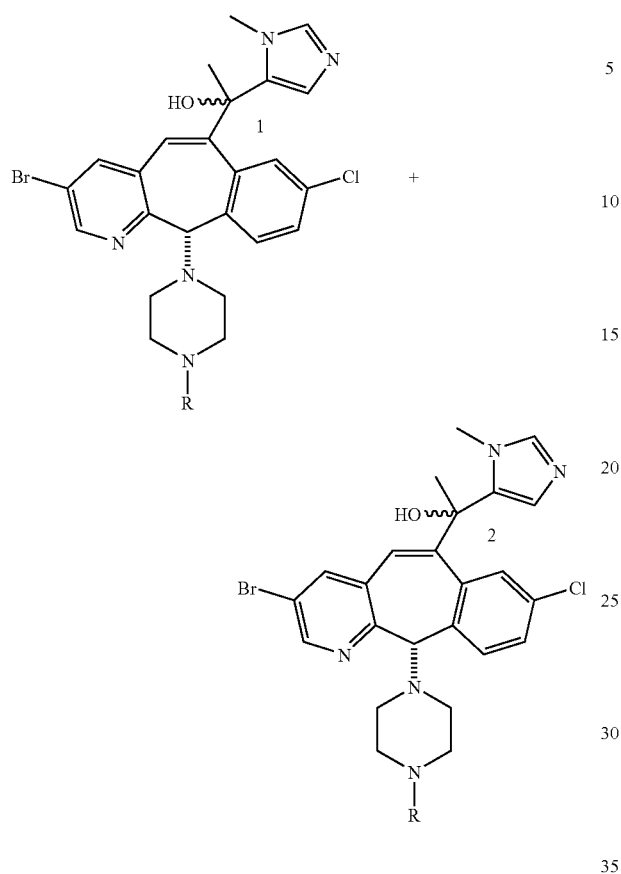
wherein R is defined in Table 79 and the numbers 1 and 2 in the formulas represent isomers 1 and 2, respectively.
TABLE 79
| Example | R Isomer 1 and Isomer 2 |
|---|---|
| 996 | 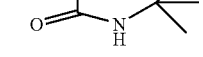 |
| 997 | 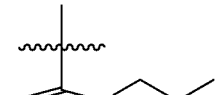 |
| 998 |  |
| 999 | 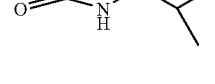 |
TABLE 79-continued
| Example | R Isomer 1 and Isomer 2 |
|---|---|
| 1000 | 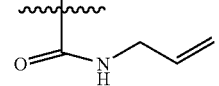 |
| 1001 |  |
| 1002 | 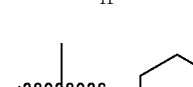 |
| 1003 | 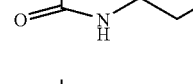 |
| 1004 | 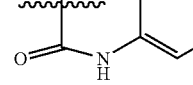 |
| 1005 | 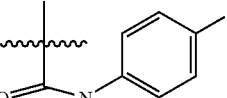 |
| 1006 | |
| 1007 | |
| 1008 | |
| 1009 | |

TABLE 79-continued

| Example | R Isomer 1 and Isomer 2 |
|---|---|
| 1010 | 4-chlorophenyl amide |
| 1011 | 4-fluorophenyl amide |
| 1012 | 4-methoxyphenyl amide |
| 1013 | 4-phenoxyphenyl amide |
| 1014 | 4-(trifluoromethyl)phenyl amide |
| 1015 | 4-tert-butylphenyl amide |
| 1016 | 1-naphthyl amide |
| 1017 | benzoyl-amino amide |
| 1018 | benzyl amide |
| 1019 | pyridin-3-yl amide |
| 1020 | (4-methylpyridin-4-yl)methyl amide |

EXAMPLES 1021-1045

If one were to use isomers 919a and 919b in a procedure essentially the same as that in Examples 690-714 then one would obtain compounds of the formula:

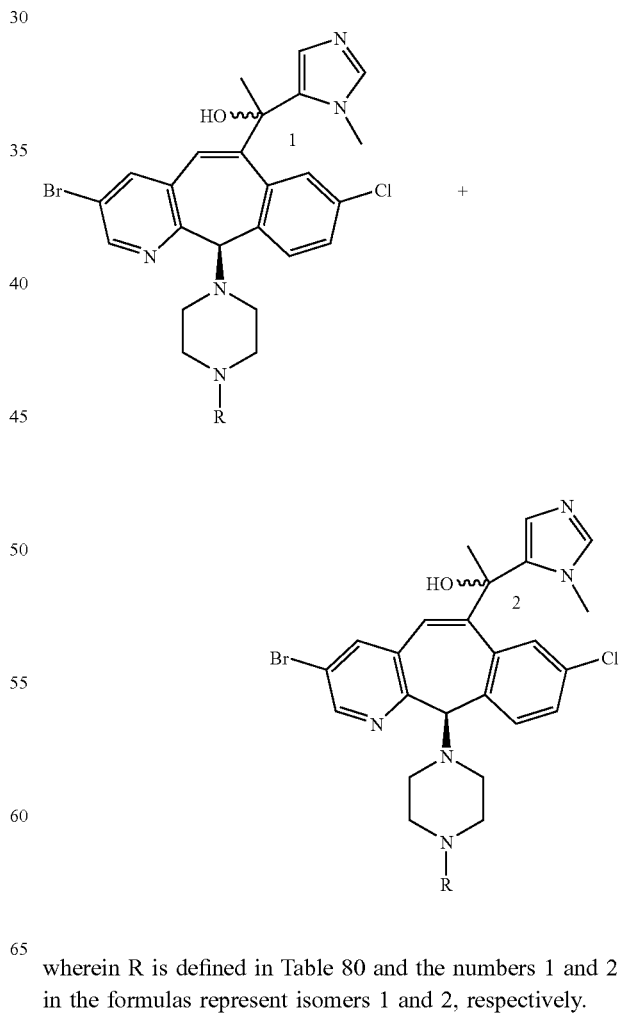

wherein R is defined in Table 80 and the numbers 1 and 2 in the formulas represent isomers 1 and 2, respectively.

TABLE 80

| Example | R Isomer 1 and Isomer 2 |
|---|---|
| 1021 | -C(=O)NH₂ |
| 1022 | -C(=O)NHCH₃ |
| 1023 | -C(=O)NH-iPr |
| 1024 | -C(=O)NHEt |
| 1025 | -C(=O)NH-tBu |
| 1026 | -C(=O)NH-nPr |
| 1027 | -C(=O)NH-iBu |
| 1028 | -C(=O)NH-allyl |
| 1029 | -C(=O)NH-cyclopentyl |
| 1030 | -C(=O)NH-cyclohexyl |
| 1031 | -C(=O)NH-phenyl |
| 1032 | -C(=O)NH-(4-CN-C₆H₄) |
| 1033 | -C(=O)NH-(4-iPr-C₆H₄) |
| 1034 | -C(=O)NH-(4-Br-C₆H₄) |
| 1035 | -C(=O)NH-(4-Cl-C₆H₄) |
| 1036 | -C(=O)NH-(4-F-C₆H₄) |
| 1037 | -C(=O)NH-(4-OCH₃-C₆H₄) |
| 1038 | -C(=O)NH-(4-OPh-C₆H₄) |
| 1039 | -C(=O)NH-(4-CF₃-C₆H₄) |
| 1040 | -C(=O)NH-(4-tBu-C₆H₄) |

TABLE 80-continued
| Example | R Isomer 1 and Isomer 2 |
|---|---|
| 1041 | 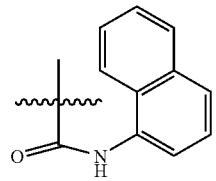 |
| 1042 | 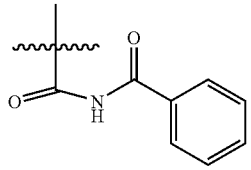 |
| 1043 | 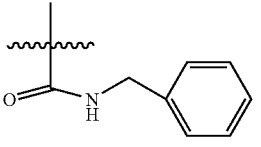 |
| 1044 | 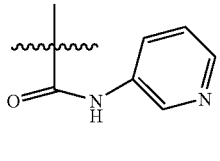 |
| 1045 | 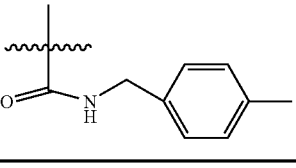 |
EXAMPLES 1046-1073
If one were to use isomers 919a and 919b in a procedure essentially the same as that in Example 536 the one would obtain compounds of the formula:
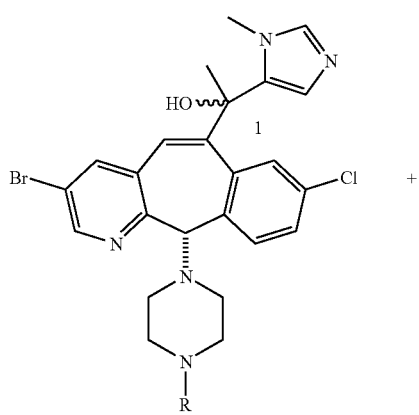
+
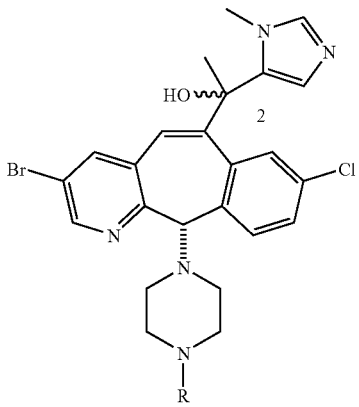
wherein R is defined in Table 81 and the numbers 1 and 2 in the formulas represent isomers 1 and 2, respectively.
TABLE 81
| Example | R Isomer 1 and Isomer 2 |
|---|---|
| 1046 | 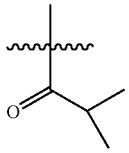 |
| 1047 | 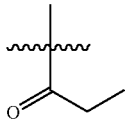 |
| 1048 | 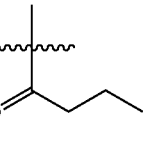 |
| 1049 | 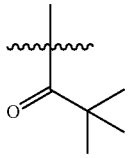 |
| 1050 | 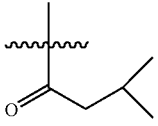 |
| 1051 | 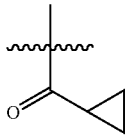 |

TABLE 81-continued

| Example | R Isomer 1 and Isomer 2 |
|---|---|
| 1052 | 1-methylcyclopropyl ketone |
| 1053 | 1-methylcyclopropyl ketone |
| 1054 | cyclobutyl ketone |
| 1055 | cyclopentyl ketone |
| 1056 | cyclohexyl ketone |
| 1057 | cyclohex-1-enyl ketone |
| 1058 | piperidin-4-yl ketone |
| 1059 | 1-methylcyclohexyl ketone |
| 1060 | cyclohexylmethyl ketone |
| 1061 | piperidin-4-ylmethyl ketone |
| 1062 | 1-(aminocarbonyl)piperidin-4-ylmethyl ketone |
| 1063 | phenyl ketone |
| 1064 | 4-chlorophenyl ketone |
| 1065 | 4-bromophenyl ketone |
| 1066 | 4-fluorophenyl ketone |
| 1067 | 4-cyanophenyl ketone |
| 1068 | 4-methylphenyl ketone |

TABLE 81-continued
| Example | R Isomer 1 and Isomer 2 |
|---|---|
| 1069 | 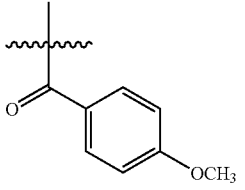 |
| 1070 | 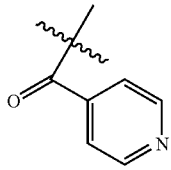 |
| 1071 | 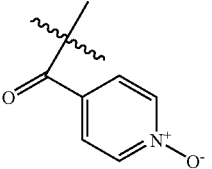 |
| 1072 | 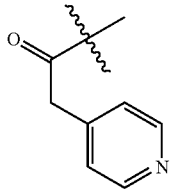 |
| 1073 | 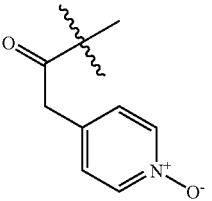 |
EXAMPLES 1074-1102
If one were to use isomers 920a and 920b in a procedure essentially the same as that in Example 536 then one would obtain compounds of the formula:
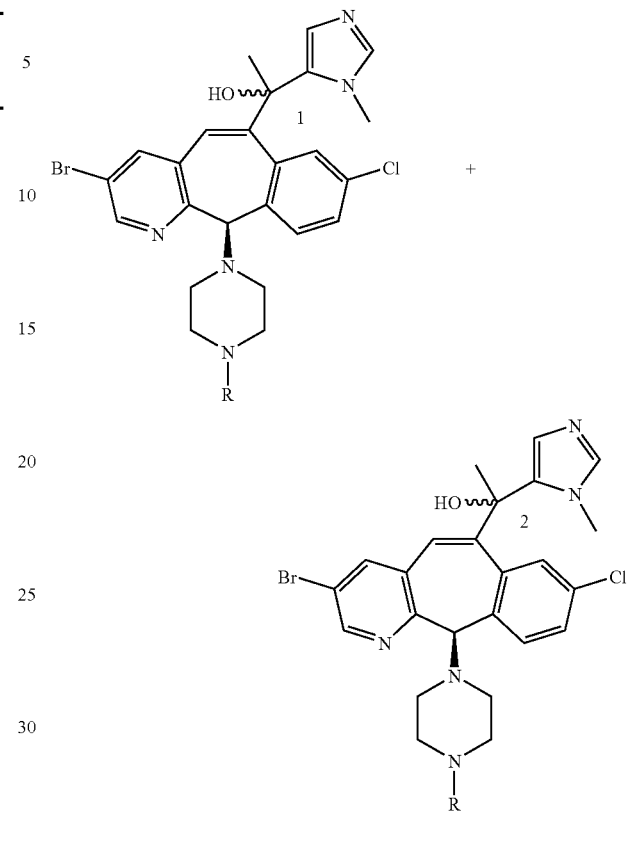
wherein R is defined in Table 82 and the numbers 1 and 2 in the formulas represent isomers 1 and 2, respectively.
TABLE 82
| Example | R Isomer 1 and Isomer 2 |
|---|---|
| 1075 | 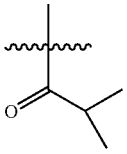 |
| 1076 | 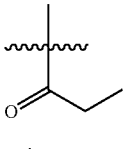 |
| 1077 | 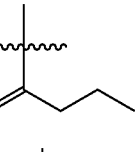 |
| 1078 | 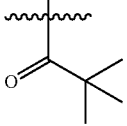 |

TABLE 82-continued
| Example | R Isomer 1 and Isomer 2 |
|---|---|
| 1079 | 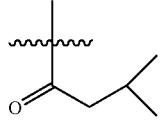 |
| 1080 | 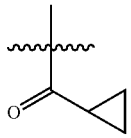 |
| 1081 | 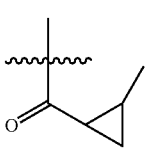 |
| 1082 | 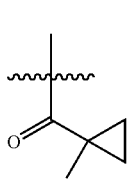 |
| 1083 | 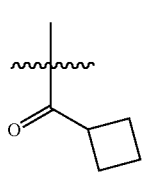 |
| 1084 | 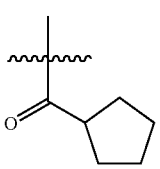 |
| 1085 | 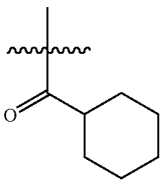 |
| 1086 | 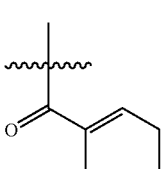 |
| 1087 | 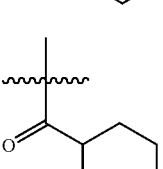 |
TABLE 82-continued
| Example | R Isomer 1 and Isomer 2 |
|---|---|
| 1088 | 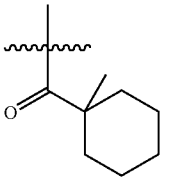 |
| 1089 | 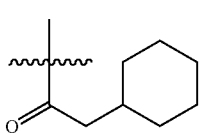 |
| 1090 | 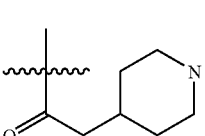 |
| 1091 | 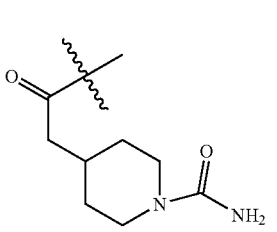 |
| 1092 | 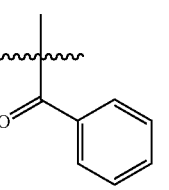 |
| 1093 | 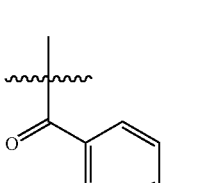 |
| 1094 | 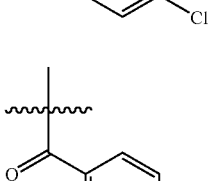 |
| 1095 | 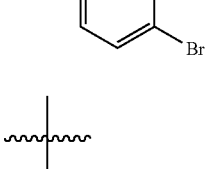 |

TABLE 82-continued

| Example | R Isomer 1 and Isomer 2 |
|---|---|
| 1096 | 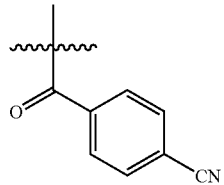 |
| 1097 | 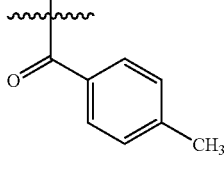 |
| 1098 | 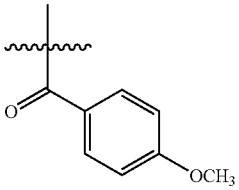 |
| 1099 | 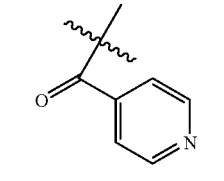 |
| 1100 | 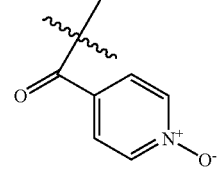 |
| 1101 | 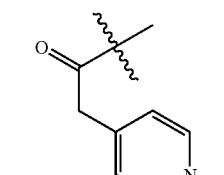 |
| 1102 | 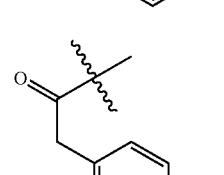 |

EXAMPLES 1103–1121

If one were to use isomers 919a and 919b in a procedure essentially the same as that in Examples 590-603 (wherein the chloroformates would be prepared according to Preparative Example 74) then one would obtain compounds of the formula:

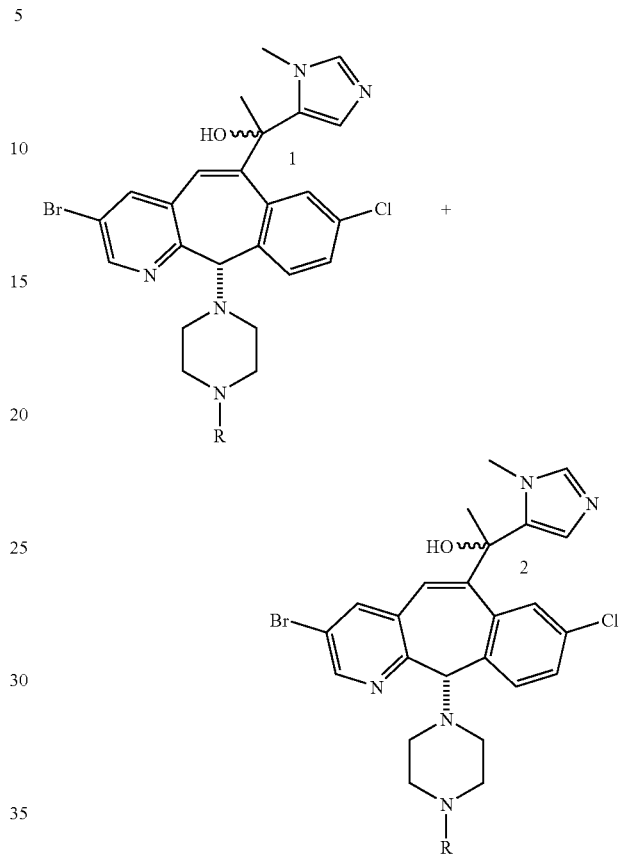

wherein R is defined in Table 83 and the numbers 1 and 2 in the formulas represent isomers 1 and 2, respectively.

TABLE 83

| Example | R Isomer 1 and Isomer 2 |
|---|---|
| 1103 | 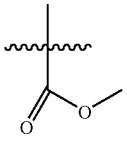 |
| 1104 | 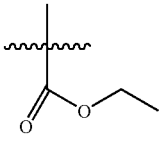 |
| 1105 | 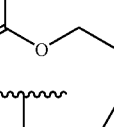 |
| 1106 | 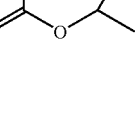 |

TABLE 83-continued

| Example | R Isomer 1 and Isomer 2 |
|---|---|
| 1107 | isobutyl ester |
| 1108 | neopentyl ester |
| 1109 | amide (C(O)NH2) |
| 1110 | sec-butyl ester |
| 1111 | allyl ester |
| 1112 | cyclopentyl ester |
| 1113 | cyclohexyl ester |
| 1114 | benzyl ester |
| 1115 | 4-methylphenyl ester |
| 1116 | 4-methoxyphenyl ester |
| 1117 | 4-chlorophenyl ester |
| 1118 | 4-fluorophenyl ester |
| 1119 | 4-bromophenyl ester |
| 1120 | phenyl ester |
| 1121 | naphthyl ester |

EXAMPLES 1122-1139

If one were to use isomer 920a and 920b in a procedure essentially the same as that in Example 590-603 (wherein the chloroformates would be prepared according to Preparative Example 74) then one would obtain compounds of the formula:

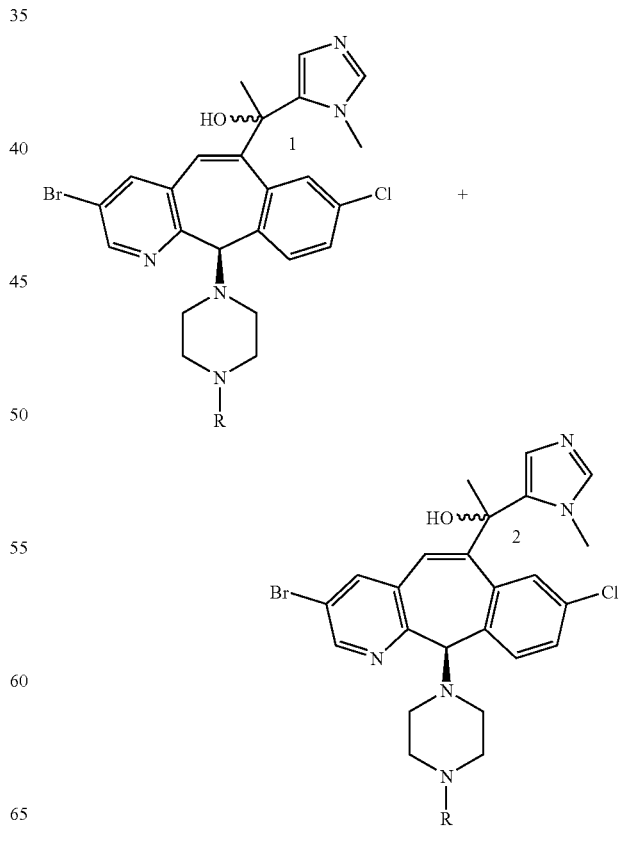

wherein R is defined in Table 84 and the numbers 1 and 2 in the formulas represent isomer 1 and isomer 2, respectively.
TABLE 84
| Example | R Isomer 1 and Isomer 2 |
|---|---|
| 1122 | |
| 1123 | |
| 1124 | |
| 1125 | |
| 1126 | |
| 1127 | |
| 1128 | |
| 1129 | |
| 1130 | |
| 1131 | |
| 1132 | |
| 1133 | |
TABLE 84-continued
| Example | R Isomer 1 and Isomer 2 |
|---|---|
| 1134 | |
| 1135 | |
| 1136 | |
| 1137 | |
| 1138 | |
| 1139 | |
EXAMPLES 1140-1163
If one were to use isomers 919a and 919b in a procedure essentially the same as that in Examples 566-567 then one would obtain compounds of the formula:
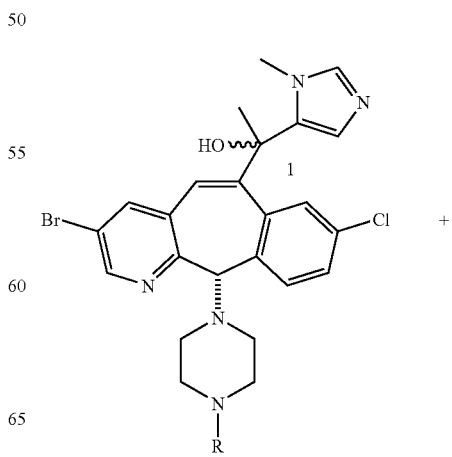
+

-continued

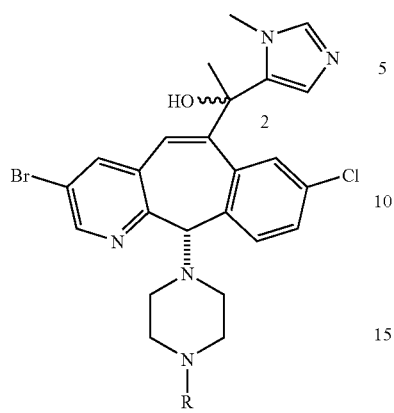

wherein R is defined in Table 85 and the numbers 1 and 2 in the formulas represent isomers 1 and 2, respectively.

TABLE 85

| Example | R Isomer 1 and Isomer 2 |
|---|---|
| 1140 | —S(O)₂CH₃ |
| 1141 | —S(O)₂CH(CH₃)₂ |
| 1143 | —S(O)₂CH₂CH₂CH₃ |
| 1144 | —S(O)₂N(CH₃)₂ |
| 1145 | —S(O)₂C(CH₃)₃ |
| 1146 | —S(O)₂CF₃ |

TABLE 85-continued

| Example | R Isomer 1 and Isomer 2 |
|---|---|
| 1148 | —S(O)₂-cyclopropyl |
| 1149 | —S(O)₂-(4-methylphenyl) |
| 1150 | —S(O)₂-(4-ethylphenyl) |
| 1151 | —S(O)₂-(4-isopropylphenyl) |
| 1152 | —S(O)₂-(4-tert-butylphenyl) |
| 1153 | —S(O)₂-(4-chlorophenyl) |
| 1154 | —S(O)₂-(4-trifluoromethylphenyl) |
| 1156 | —S(O)₂-(4-bromophenyl) |
| 1157 | —S(O)₂-(4-fluorophenyl) |

TABLE 85-continued

| Example | R Isomer 1 and Isomer 2 |
|---------|-------------------------|
| 1158 | 4-cyanophenyl sulfonyl |
| 1159 | 4-methoxyphenyl sulfonyl |
| 1160 | phenyl sulfonyl |
| 1161 | benzyl sulfonyl |
| 1162 | 2-thienyl sulfonyl |
| 1163 | 1-naphthyl sulfonyl |

EXAMPLES 1164-1187

If one were to use isomers 920a and 920b in a procedure essentially the same as that in Examples 566-567 then one would obtain compounds of the formula:

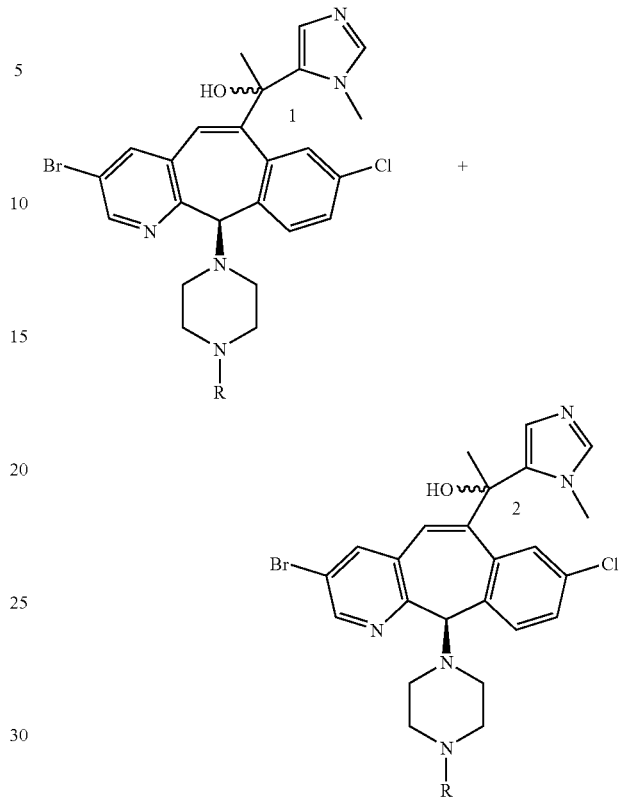

wherein R is defined in Table 86 and the numbers 1 and 2 in the formulas represent isomers 1 and 2, respectively.

TABLE 86

| Example | R Isomer 1 and Isomer 2 |
|---------|-------------------------|
| 1164 | methyl sulfonyl |
| 1165 | isopropyl sulfonyl |
| 1167 | propyl sulfonyl |
| 1168 | dimethylamino sulfonyl |

TABLE 86-continued
| Example | R Isomer 1 and Isomer 2 |
|---|---|
| 1169 | 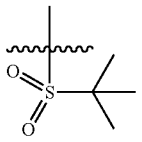 |
| 1170 | 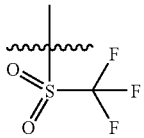 |
| 1172 | 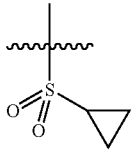 |
| 1173 | 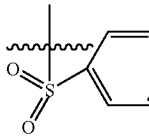 |
| 1174 | 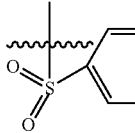 |
| 1175 | 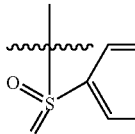 |
| 1176 | 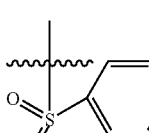 |
| 1177 | 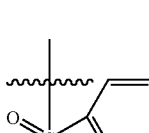 |
| 1178 | 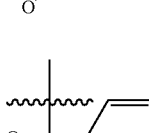 |
TABLE 86-continued
| Example | R Isomer 1 and Isomer 2 |
|---|---|
| 1180 | 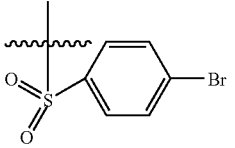 |
| 1181 | 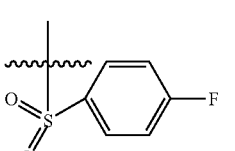 |
| 1182 | 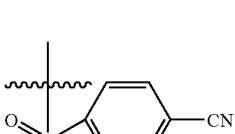 |
| 1183 | 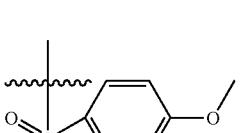 |
| 1184 | 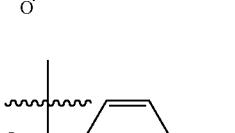 |
| 1185 |  |
| 1186 | 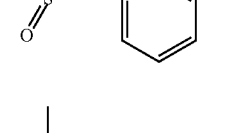 |
| 1187 | 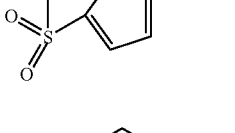 |

PREPARATIVE EXAMPLE 105

Step A

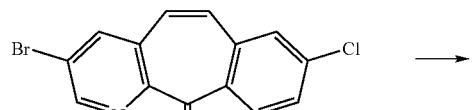

921

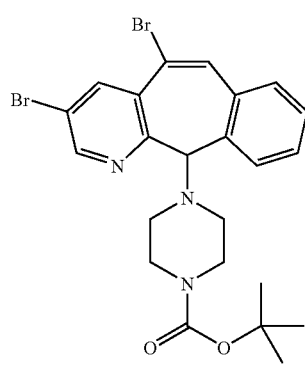

922

Compound 922 was reacted in essentially the same manner as in Preparative Example 23, Steps A-D to get compound 922.

Step B

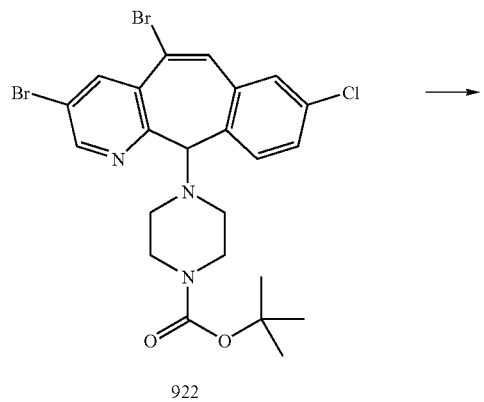

922

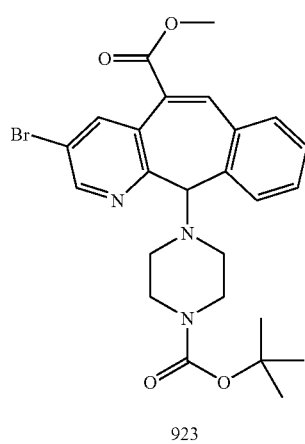

923

In essentially the same manner as in Preparative Example 42, Step A, using 922 as the starting material, compound 923 is prepared.

PREPARATIVE EXAMPLE 106

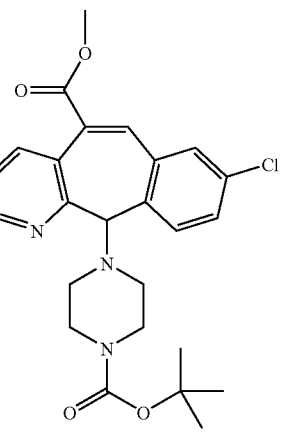

923

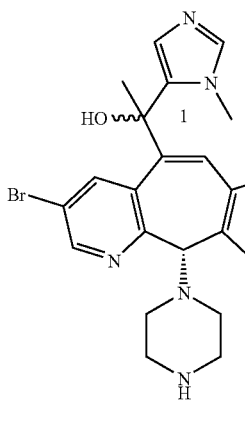

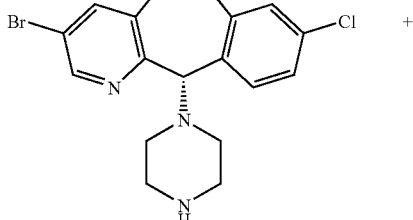

924a

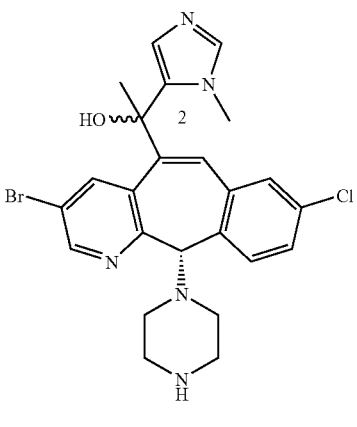

924b

Compound 923 from Preparative Example 105 Step B was reacted in essentially the same manner as in Preparative Examples 91-104 to get 924a (i.e., isomer 1) and 924b (i.e., isomer 2).

PREPARATIVE EXAMPLE 107

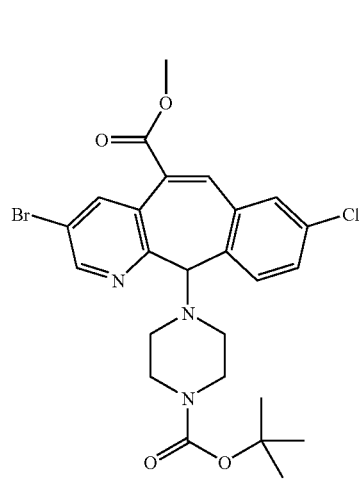

923

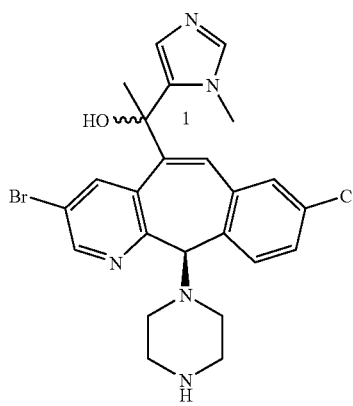

925a

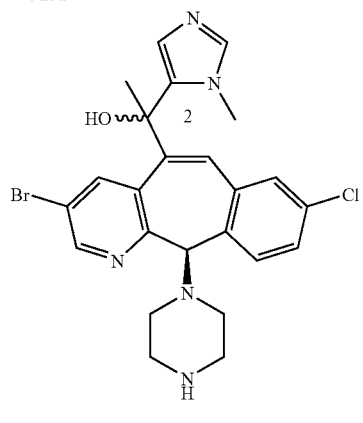

925b

Compound 923 from Preparative Example 105 Step B was reacted in essentially the same manner as in Preparative Examples 91-104 to get 925a (i.e., isomer 1) and 925b (i.e., isomer 2).

EXAMPLES 1188-1212

If one were to follow essential the same procedure as in Examples 690-714 using 924a and 924b then one would obtain compounds of the formula:

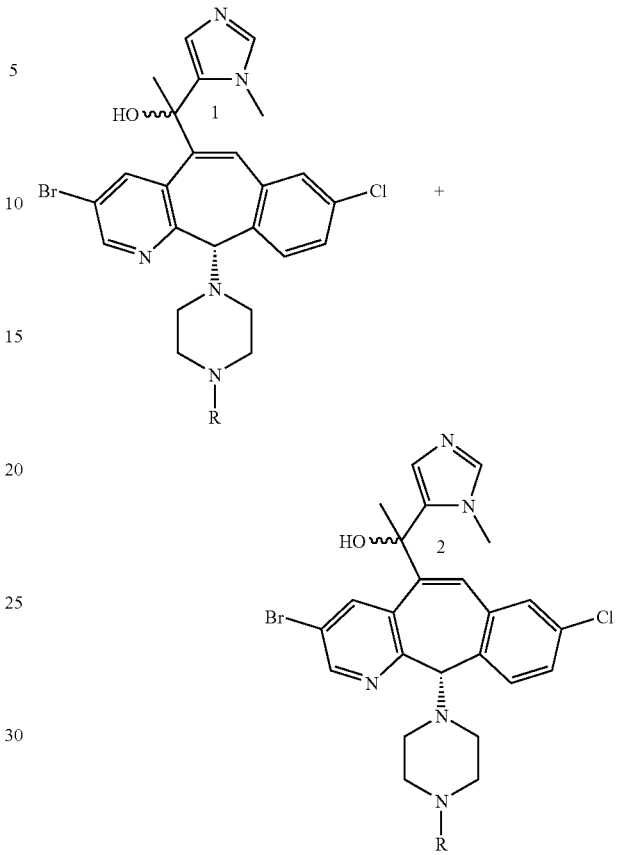

wherein R is defined in Table 87 and the numbers 1 and 2 in the formulas represent isomers 1 and 2, respectively.

TABLE 87

| Example | R<br>Isomer 1 and Isomer 2 |
|---|---|
| 1188 | ![structure with C(O)NH2] |
| 1189 | ![structure with C(O)NHCH3] |
| 1190 | ![structure with C(O)NH-iPr] |
| 1191 | ![structure with C(O)NHEt] |

TABLE 87-continued

| Example | R Isomer 1 and Isomer 2 |
|---|---|
| 1192 | -C(O)NH-tBu |
| 1193 | -C(O)NH-propyl |
| 1194 | -C(O)NH-isobutyl |
| 1195 | -C(O)NH-allyl |
| 1196 | -C(O)NH-cyclopentyl |
| 1197 | -C(O)NH-cyclohexyl |
| 1198 | -C(O)NH-phenyl |
| 1199 | -C(O)NH-(4-CN-phenyl) |
| 1200 | -C(O)NH-(4-isopropyl-phenyl) |
| 1201 | -C(O)NH-(4-Br-phenyl) |
| 1202 | -C(O)NH-(4-Cl-phenyl) |
| 1203 | -C(O)NH-(4-F-phenyl) |
| 1204 | -C(O)NH-(4-OCH$_3$-phenyl) |
| 1205 | -C(O)NH-(4-phenoxy-phenyl) |
| 1206 | -C(O)NH-(4-CF$_3$-phenyl) |
| 1207 | -C(O)NH-(4-tBu-phenyl) |
| 1208 | -C(O)NH-(1-naphthyl) |
| 1209 | -C(O)NH-C(O)-phenyl |
| 1210 | -C(O)NH-benzyl |

TABLE 87-continued

| Example | R Isomer 1 and Isomer 2 |
|---|---|
| 1211 | ![structure: C(=O)NH-pyridin-3-yl] |
| 1212 | ![structure: C(=O)NH-CH2-(4-methylphenyl)] |

EXAMPLES 1213-1238

If one were to follow essential the same procedure as in Examples 690-714 using 925a and 925b then one would obtain compounds of the formula:

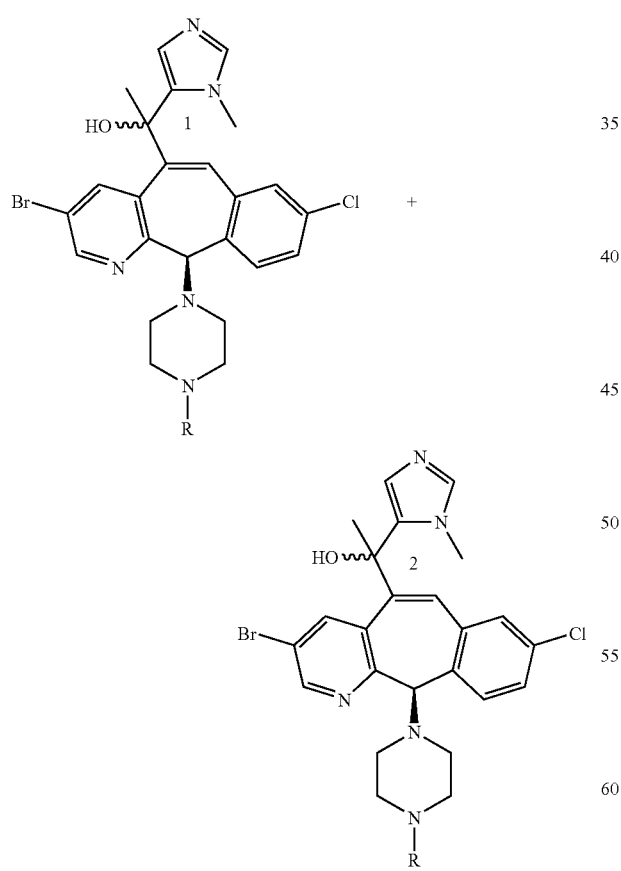

wherein R is defined in Table 88 and the numbers 1 and 2 in the formulas represent isomers 1 and 2, respectively.

TABLE 88

| Example | R Isomer 1 and Isomer 2 |
|---|---|
| 1213 | C(=O)NH₂ |
| 1214 | C(=O)NHCH₃ |
| 1215 | C(=O)NH-iPr |
| 1216 | C(=O)NHEt |
| 1217 | C(=O)NH-tBu |
| 1218 | C(=O)NH-nPr |
| 1219 | C(=O)NH-iBu |
| 1220 | C(=O)NH-allyl |
| 1221 | C(=O)NH-cyclopentyl |
| 1223 | C(=O)NH-cyclohexyl |

TABLE 88-continued
| Example | R Isomer 1 and Isomer 2 |
|---|---|
| 1224 | 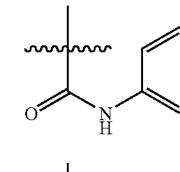 |
| 1225 | 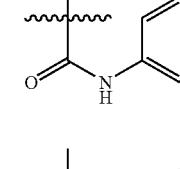 |
| 1226 | 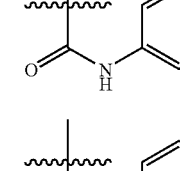 |
| 1227 | 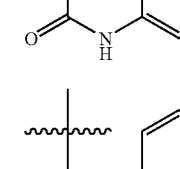 |
| 1228 | 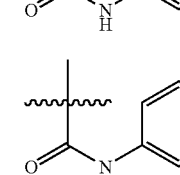 |
| 1229 | 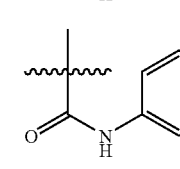 |
| 1230 | 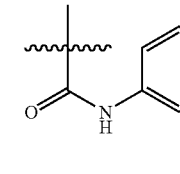 |
| 1231 | 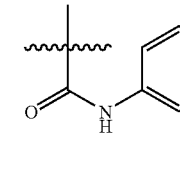 |
| 1232 | 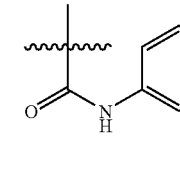 |
| 1233 |  |
TABLE 88-continued
| Example | R Isomer 1 and Isomer 2 |
|---|---|
| 1234 | 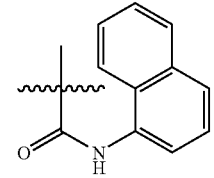 |
| 1235 | 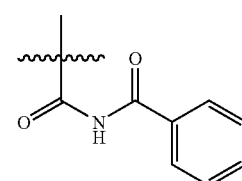 |
| 1236 | 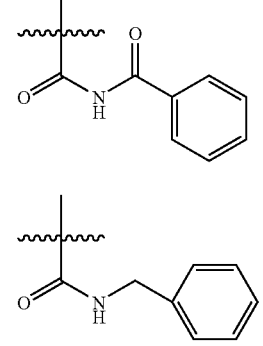 |
| 1237 | 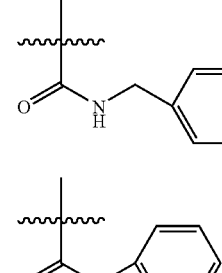 |
| 1238 | 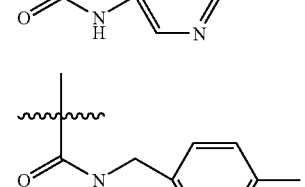 |
EXAMPLES 1239-1266
If one were to follow essentially the same procedure as in Example 536 using 924a and 924b then one would obtain compounds of the formula:
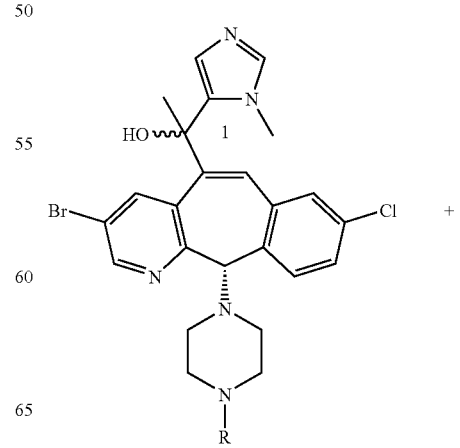

-continued
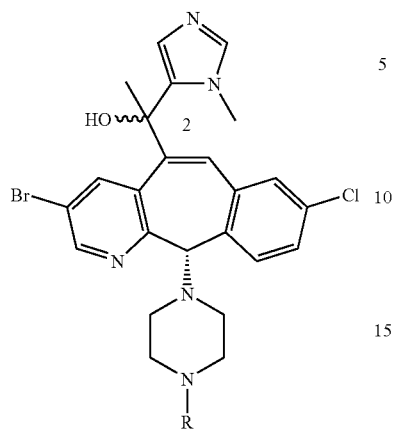
wherein R is defined in Table 89 and the numbers 1 and 2 in the formulas represent isomers 1 and 2, respectively.
TABLE 89
| Example | R Isomer 1 and Isomer 2 |
|---|---|
| 1239 | |
| 1240 | |
| 1241 | |
| 1242 | |
| 1243 | |
| 1244 | |
TABLE 89-continued
| Example | R Isomer 1 and Isomer 2 |
|---|---|
| 1245 | |
| 1246 | |
| 1247 | |
| 1248 | |
| 1249 | |
| 1250 | |
| 1251 | |
| 1252 | |
| 1253 | |

TABLE 89-continued
| Example | R Isomer 1 and Isomer 2 |
|---|---|
| 1254 | 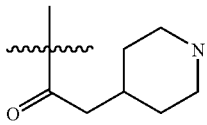 |
| 1255 | 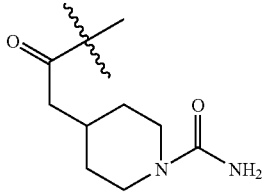 |
| 1256 | 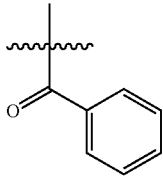 |
| 1257 | 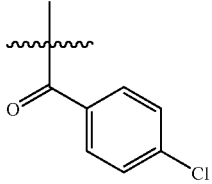 |
| 1258 | 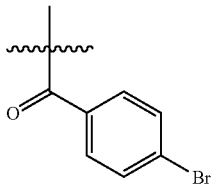 |
| 1259 | 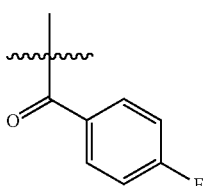 |
| 1260 | 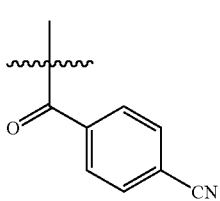 |
| 1261 | 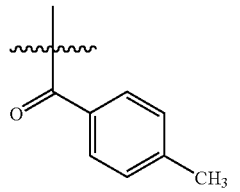 |
| 1262 | 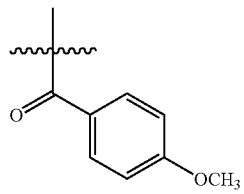 |
| 1263 | 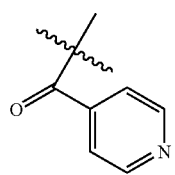 |
| 1264 | 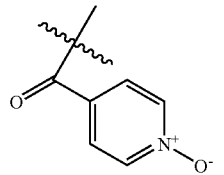 |
| 1265 | 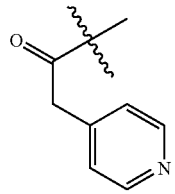 |
| 1266 | 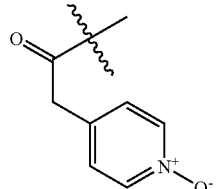 |

EXAMPLES 1267-1294

If one were to follow essentially the same procedure as in Example 536 using 925a and 925b then one would obtain compounds of the formula:

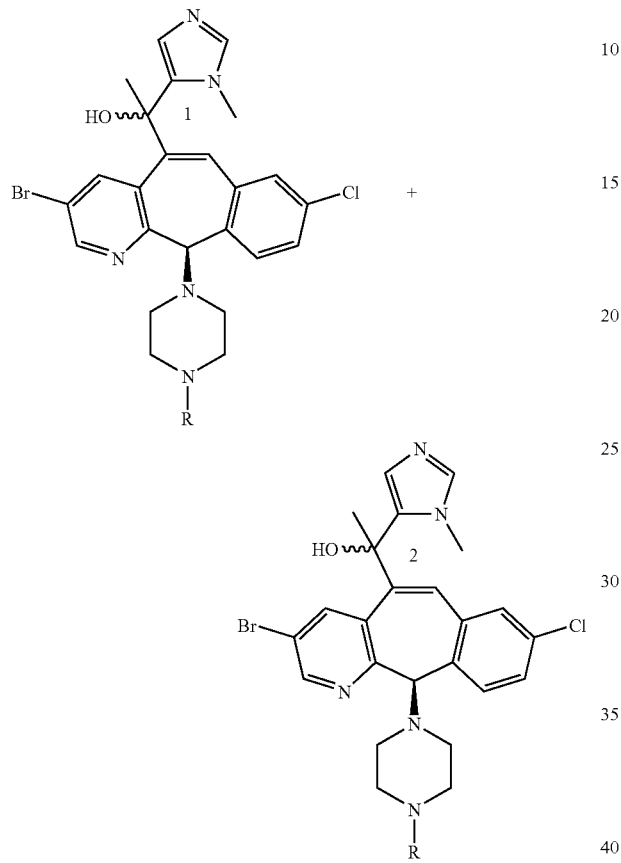

wherein R is defined in Table 90 and the numbers 1 and 2 in the formulas represent isomers 1 and 2, respectively.

TABLE 90

| Example | R Isomer 1 and Isomer 2 |
|---|---|
| 1267 | ![isobutyryl] |
| 1268 | ![propionyl-like] |
| 1269 | ![butyryl] |
| 1270 | ![pivaloyl] |
| 1271 | ![isovaleryl] |
| 1272 | ![cyclopropylcarbonyl] |
| 1273 | ![methylcyclopropylcarbonyl] |
| 1274 | ![1-methylcyclopropylcarbonyl] |
| 1275 | ![cyclobutylcarbonyl] |
| 1276 | ![cyclopentylcarbonyl] |
| 1277 | ![cyclohexylcarbonyl] |
| 1278 | ![cyclohexenylcarbonyl] |

TABLE 90-continued

| Example | R Isomer 1 and Isomer 2 |
|---|---|
| 1279 | 4-piperidinyl carbonyl |
| 1280 | 1-methylcyclohexyl carbonyl |
| 1281 | cyclohexylmethyl carbonyl |
| 1282 | (piperidin-4-yl)methyl carbonyl |
| 1283 | 2-methyl-2-[(1-carbamoylpiperidin-4-yl)methyl] carbonyl |
| 1284 | pyridin-3-yl carbonyl |
| 1285 | 4-chlorophenyl carbonyl |
| 1286 | 4-bromophenyl carbonyl |
| 1287 | 4-fluorophenyl carbonyl |
| 1288 | 4-cyanophenyl carbonyl |
| 1289 | 4-methylphenyl carbonyl |
| 1290 | 4-methoxyphenyl carbonyl |
| 1291 | pyridin-4-yl carbonyl |
| 1292 | pyridin-4-yl N-oxide carbonyl |

TABLE 90-continued

| Example | R Isomer 1 and Isomer 2 |
|---|---|
| 1293 | (structure: methyl ketone linked to 4-pyridyl) |
| 1294 | (structure: methyl ketone linked to 4-pyridyl N-oxide) |

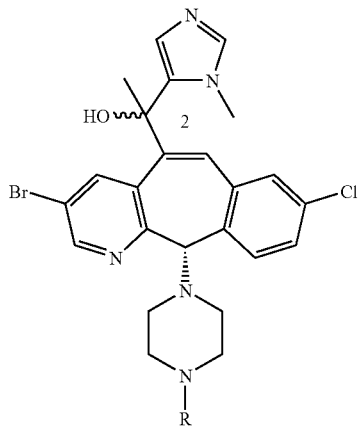

were prepared wherein R is defined in Table 91 and the numbers 1 and 2 in the formulas represent isomers 1 and 2, respectively.

TABLE 91

| Example | R | Isomer 1 | Isomer 2 |
|---|---|---|---|
| 1295 | (t-butyl carbamate group) | $^1$H NMR (400 MHz, CDCl$_3$, TMS)δ 1.417 (s, 9H), 1.454 (d, J=1.6 Hz, 1H), 1.857 (s, 3H), 2.20–2.05 (m, 4H), 3.205 (broad, 1 H), 3.432 (s, 1H), 3.612 (s, 1H), 3.731 (d, J=6.4 Hz, 1H), 3.853 (s, 3H), 4.575 (s, 1H), 6.538 (s, 1H), 7.086 (s, 1H), 7.114 (s, 1H), 7.262 (d, 2H), 7.540 (s, 1H), 8.530 (d, J=2.0 Hz, 1H), 8.876 (d, J=2.0 Hz, 1H). | mp = 184–185° C. |

EXAMPLE 1295

Following essentially the same procedure as Examples 590-603 (wherein the chloroformates are prepared following the procedure in Preparative Example 74) using 924a and 924b compounds of the formula:

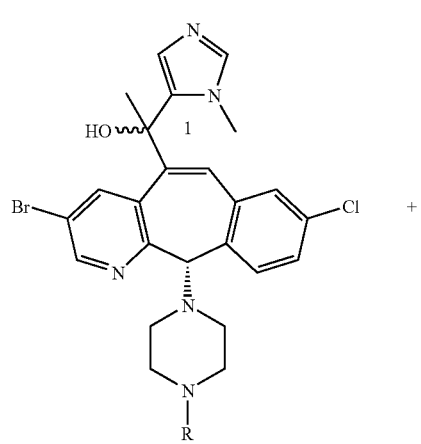

EXAMPLES 1296-1313

If one were to Follow essentially the same procedure as Examples 590-603 (wherein the chloroformates would be prepared following the procedure in Preparative Example 74) using 924a and 924b compounds of the formula:

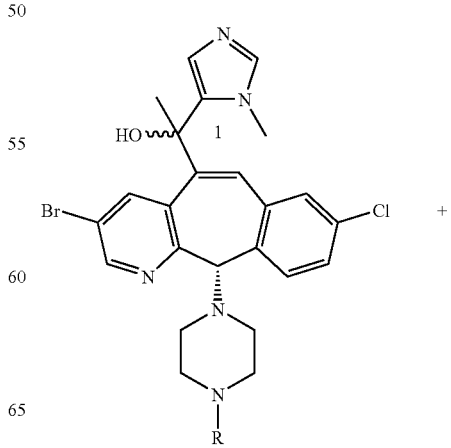

-continued

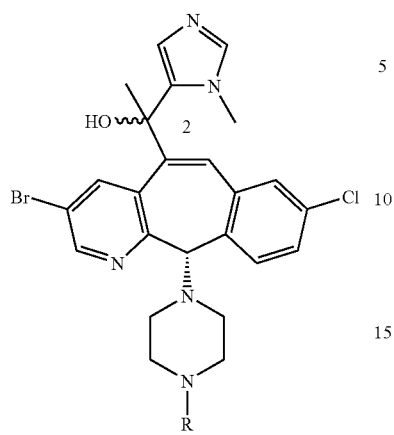

would be obtained wherein R is defined in Table 92 and the numbers 1 and 2 in the formulas represent isomers 1 and 2, respectively.

TABLE 92

| Example | R Isomer 1 and Isomer 2 |
|---|---|
| 1296 | —C(O)OCH₃ |
| 1297 | —C(O)OCH₂CH₃ |
| 1298 | —C(O)O-n-propyl |
| 1299 | —C(O)O-isopropyl |
| 1300 | —C(O)O-isobutyl |
| 1301 | —C(O)O-neopentyl |
| 1302 | —C(O)O-sec-butyl |

TABLE 92-continued

| Example | R Isomer 1 and Isomer 2 |
|---|---|
| 1303 | —C(O)O-allyl |
| 1304 | —C(O)O-cyclopentyl |
| 1305 | —C(O)O-cyclohexyl |
| 1306 | —C(O)O-phenyl |
| 1307 | —C(O)O-benzyl |
| 1308 | —C(O)O-(4-methylphenyl) |
| 1309 | —C(O)O-(4-methoxyphenyl) |
| 1310 | —C(O)O-(4-chlorophenyl) |
| 1311 | —C(O)O-(4-bromophenyl) |
| 1312 | —C(O)O-(4-fluorophenyl) |
| 1313 | —C(O)O-(1-naphthyl) |

EXAMPLE 1314

Following essentially the same procedure as Examples 590-603 (wherein the chloroformates are prepared following the procedure in Preparative Example 74) using 924a and 924b compounds of the formula:

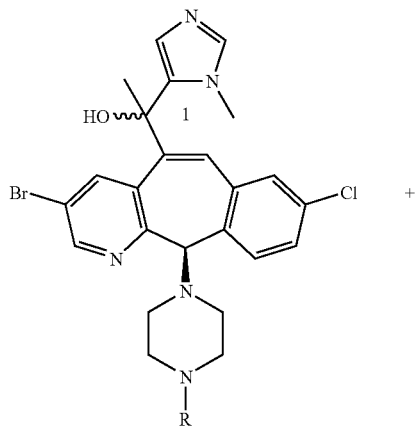

were prepared wherein R is defined in Table 93 and the numbers 1 and 2 in the formulas represent isomers 1 and 2, respectively.

EXAMPLES 1315-1332

If one were to follow essentially the same procedure as Examples 590-603 (wherein the chloroformates would be prepared following the procedure in Preparative Example 74) using 924a and 924b compounds of the formula:

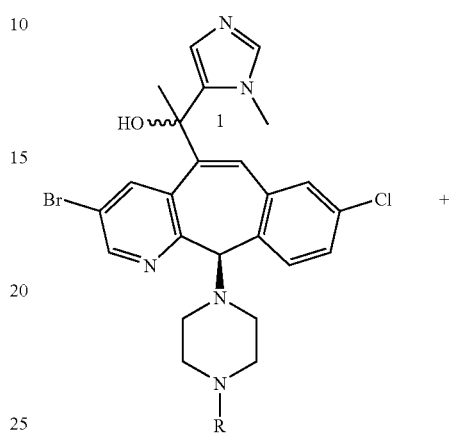

would be obtained wherein R is defined in Table 94 and the numbers 1 and 2 in the formulas represent isomers 1 and 2, respectively.

TABLE 93

| Example | R | Isomer 1 | Isomer 2 |
|---|---|---|---|
| 1314 | 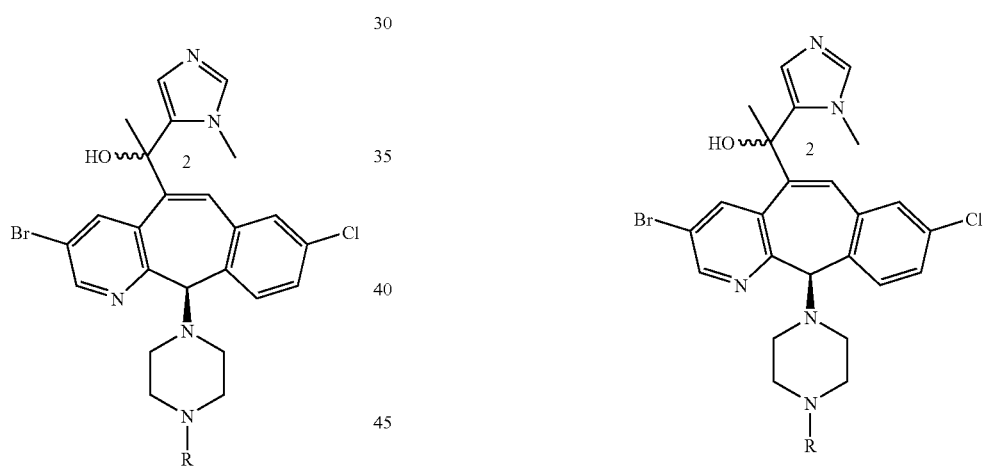 | $^1$H NMR (400 MHz, CDCl$_3$, TMS) δ 1.418 (s, 9H), 1.456 (s, 1H), 1.859 (s, 3H), 2.20–2.05 (m, 4H), 3.205 (broad, 1H), 3.612 (s, 1H), 3.692 (s, 1H), 3.740 (s, 1H), 3.854 (s, 3H), 4.576 (s, 1H), 6.541 (s, 1H), 7.090 (s, 1H), 7.116 (s, 1H), 7.262 (d, 2H), 7.548 (s, 1H), 8.530 (d, J=2.0 Hz, 1H), 8.864 (d, J=2.0 Hz, 1H) | mp = 183–184° C. |

TABLE 94
| Example | R Isomer 1 and Isomer 2 |
|---|---|
| 1315 | 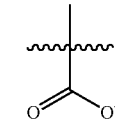 |
| 1316 | 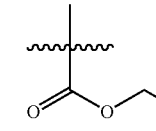 |
| 1317 | 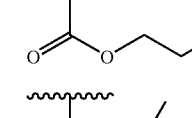 |
| 1318 | 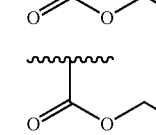 |
| 1319 | 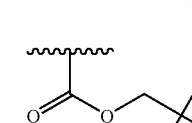 |
| 1320 | 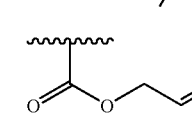 |
| 1321 | 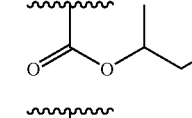 |
| 1322 | 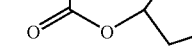 |
| 1323 | 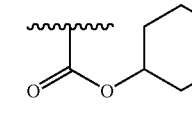 |
| 1324 | 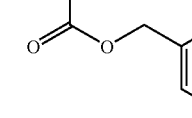 |
| 1325 | 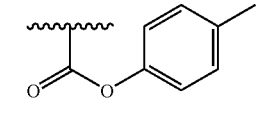 |
| 1326 | 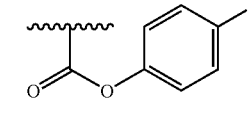 |
| 1327 |  |
TABLE 94-continued
| Example | R Isomer 1 and Isomer 2 |
|---|---|
| 1328 | 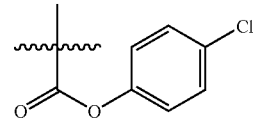 |
| 1329 | 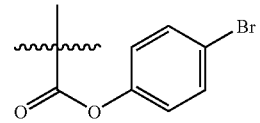 |
| 1330 | 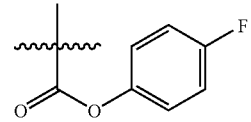 |
| 1331 | 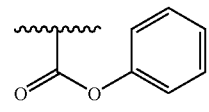 |
| 1332 | 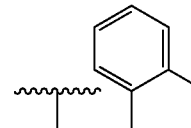 |
EXAMPLES 1333-1356
If one were to follow essentially the same procedure as Examples 566-567 using the 924a and 924b compounds of the formula:
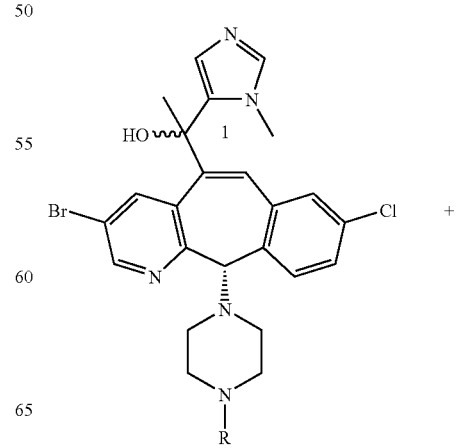
+

-continued

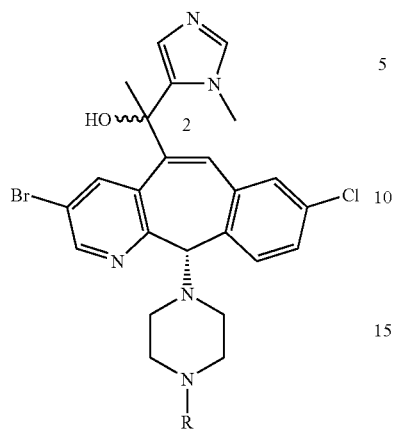

would be obtained wherein R is defined in Table 95 and the numbers 1 and 2 in the formulas represent isomers 1 and 2, respectively.

TABLE 95

| Example | R Isomer 1 and Isomer 2 |
|---|---|
| 1333 | methanesulfonyl |
| 1334 | isopropylsulfonyl |
| 1336 | propylsulfonyl |
| 1337 | N,N-dimethylsulfamoyl |
| 1338 | tert-butylsulfonyl |
| 1339 | trifluoromethylsulfonyl |

TABLE 95-continued

| Example | R Isomer 1 and Isomer 2 |
|---|---|
| 1341 | cyclopropylsulfonyl |
| 1342 | 4-methylphenylsulfonyl |
| 1343 | 4-ethylphenylsulfonyl |
| 1344 | 4-isopropylphenylsulfonyl |
| 1345 | 4-tert-butylphenylsulfonyl |
| 1346 | 4-chlorophenylsulfonyl |
| 1347 | 4-trifluoromethylphenylsulfonyl |
| 1349 | 4-bromophenylsulfonyl |
| 1350 | 4-fluorophenylsulfonyl |

TABLE 95-continued

| Example | R Isomer 1 and Isomer 2 |
|---------|------------------------|
| 1351    | 4-cyanophenylsulfonyl  |
| 1352    | 4-methoxyphenylsulfonyl |
| 1353    | phenylsulfonyl         |
| 1354    | benzylsulfonyl         |
| 1355    | 2-thienylsulfonyl      |
| 1356    | 1-naphthylsulfonyl     |

EXAMPLES 1357–1380

If one were to follow essentially the same procedure as Examples 566–567 using 925a and 925b compounds of the formula:

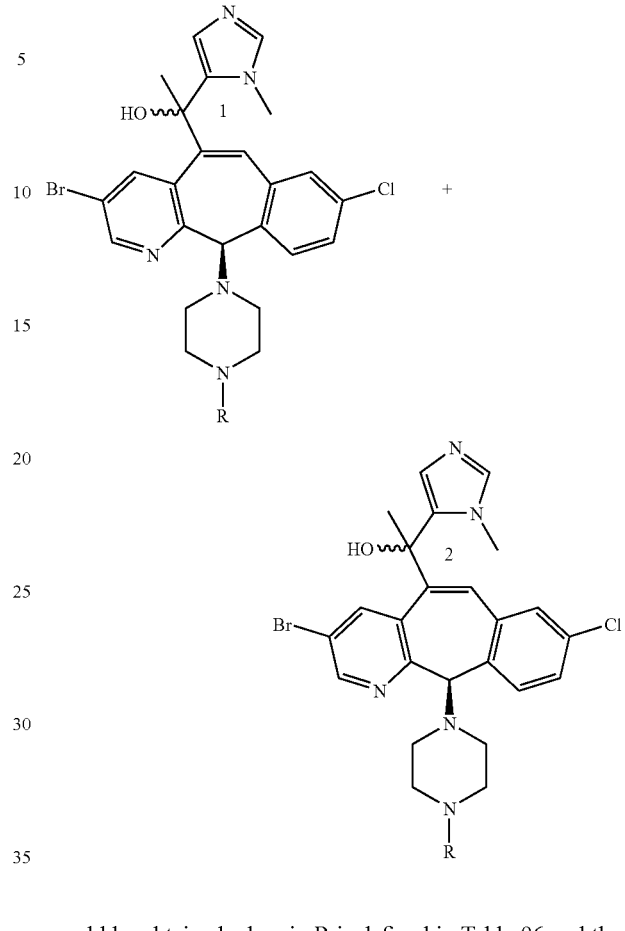

would be obtained wherein R is defined in Table 96 and the numbers 1 and 2 in the formulas represent isomers 1 and 2, respectively.

TABLE 96

| Example | R Isomer 1 and Isomer 2 |
|---------|-------------------------|
| 1357    | methylsulfonyl          |
| 1358    | isopropylsulfonyl       |
| 1360    | n-propylsulfonyl        |

TABLE 96-continued

| Example | R Isomer 1 and Isomer 2 |
|---|---|
| 1361 | -S(O)₂N(CH₃)₂ |
| 1362 | -S(O)₂-tBu |
| 1363 | -S(O)₂CF₃ |
| 1365 | -S(O)₂-cyclopropyl |
| 1366 | -S(O)₂-(4-methylphenyl) |
| 1367 | -S(O)₂-(4-ethylphenyl) |
| 1368 | -S(O)₂-(4-isopropylphenyl) |
| 1369 | -S(O)₂-(4-tert-butylphenyl) |
| 1370 | -S(O)₂-(4-chlorophenyl) |
| 1371 | -S(O)₂-(4-trifluoromethylphenyl) |
| 1373 | -S(O)₂-(4-bromophenyl) |
| 1374 | -S(O)₂-(4-fluorophenyl) |
| 1375 | -S(O)₂-(4-cyanophenyl) |
| 1376 | -S(O)₂-(4-methoxyphenyl) |
| 1377 | -S(O)₂-phenyl |
| 1378 | -S(O)₂-CH₂-phenyl |
| 1379 | -S(O)₂-(2-thienyl) |

TABLE 96-continued
| | R |
|Example | Isomer 1 and Isomer 2 |
1380
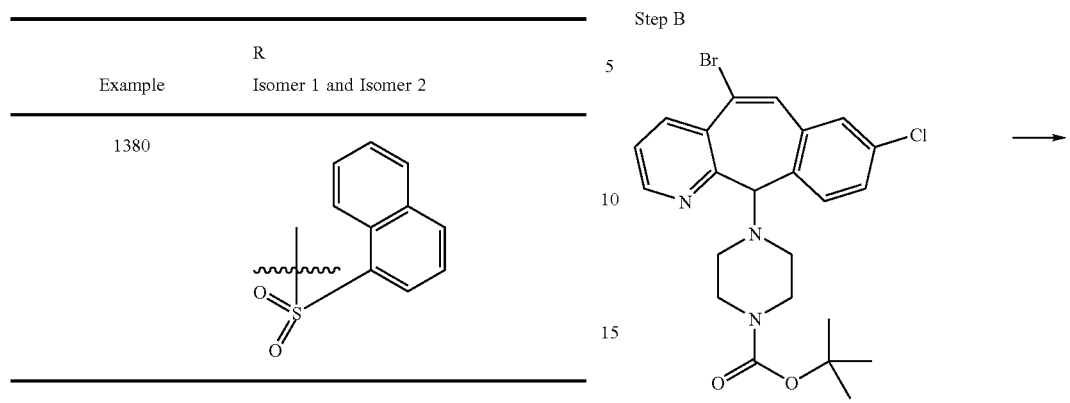
PREPARATIVE EXAMPLE 108
Step A
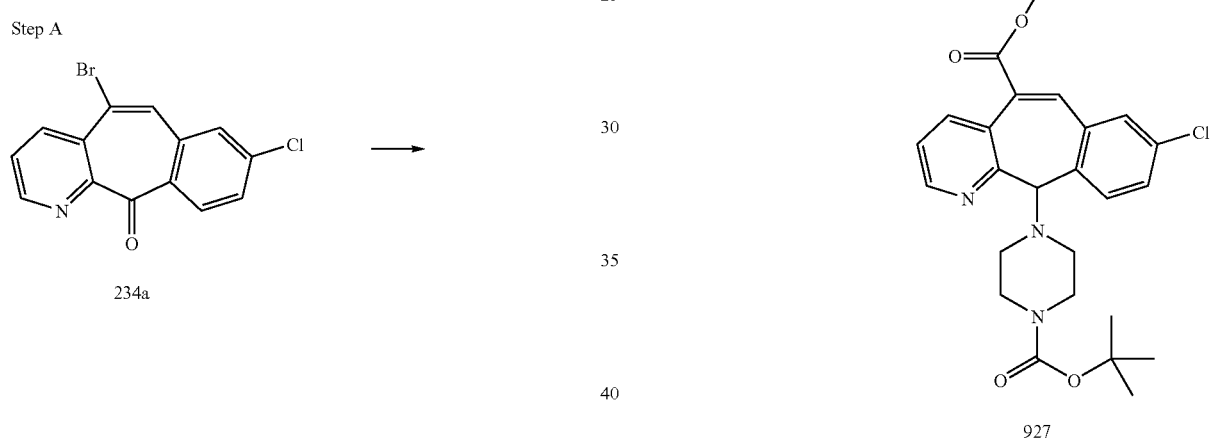
234a
926
In essentially the same manner as in Preparative Example 23, Steps A-D, use compound 234a (from Step B) to prepare 926.
Step B
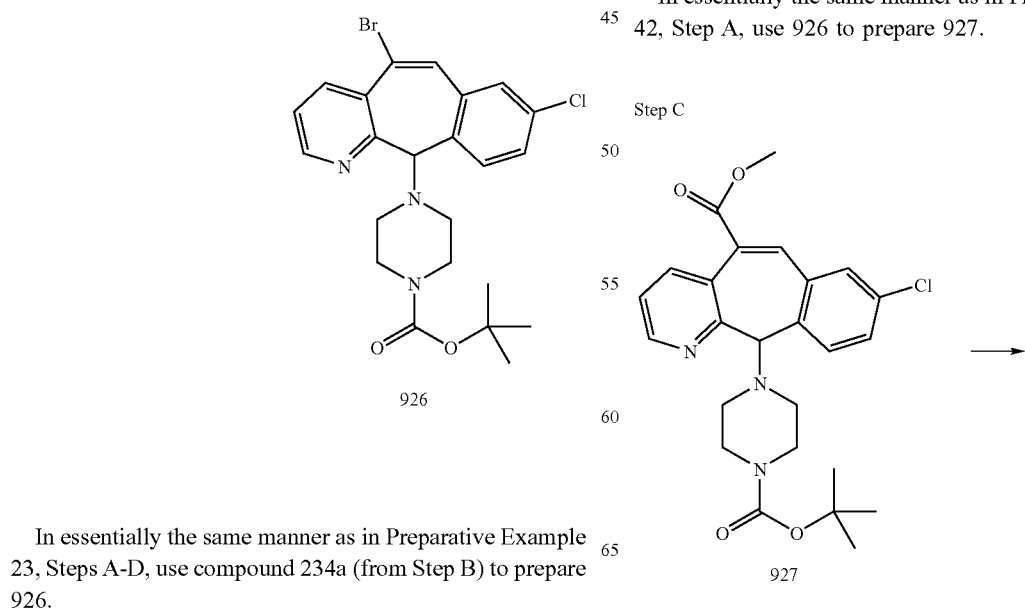
926
927
In essentially the same manner as in Preparative Example 42, Step A, use 926 to prepare 927.
Step C
927

-continued

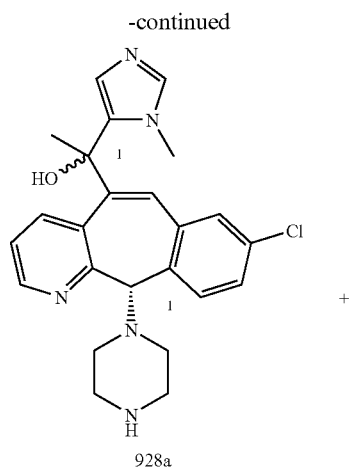
928a

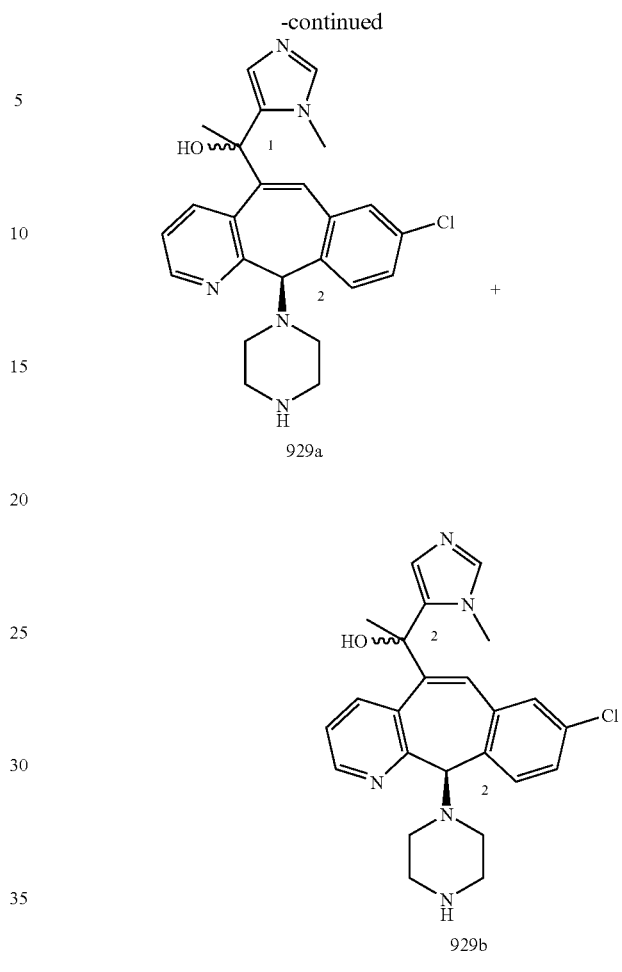
929a

928b

929b

Compound 927 from Step B was reacted in essentially the same manner as in Preparative Examples 91-104 to get compounds 928a and 928b.

Compound 927 from Step B was reacted in essentially the same manner as in Preparative Examples 91-104 to get compounds 929a and 929b.

EXAMPLES 1381-1405

If one were to follow essentially the same procedure as in Examples 690-714 using 928a and 928b compounds of the formulas:

Step D

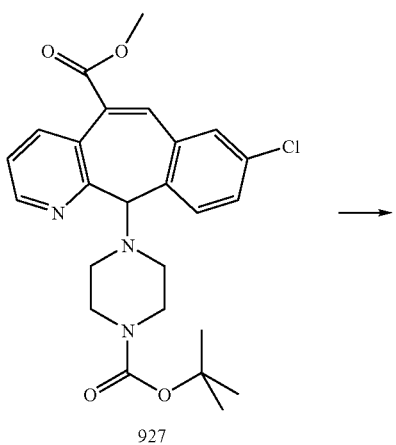
927

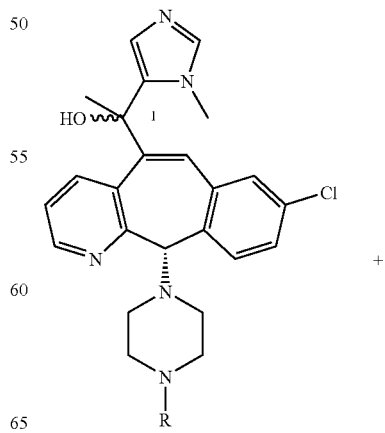

-continued

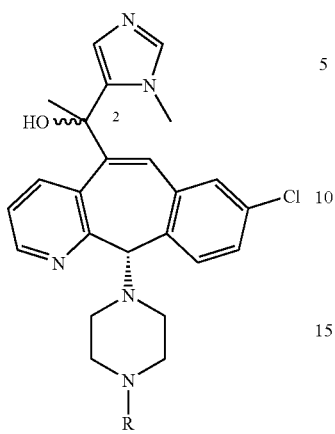

would be obtained wherein R is defined in Table 97 and the numbers 1 and 2 in the formulas represent isomers 1 and 2, respectively.

TABLE 97

| Example | R Isomer 1 and isomer 2 |
|---|---|
| 1381 | —C(=O)NH₂ |
| 1382 | —C(=O)NHCH₃ |
| 1383 | —C(=O)NH-iPr |
| 1384 | —C(=O)NHEt |
| 1385 | —C(=O)NH-tBu |
| 1386 | —C(=O)NH-nPr |

TABLE 97-continued

| Example | R Isomer 1 and isomer 2 |
|---|---|
| 1387 | —C(=O)NH-iBu |
| 1388 | —C(=O)NH-allyl |
| 1389 | —C(=O)NH-cyclopentyl |
| 1390 | —C(=O)NH-cyclohexyl |
| 1391 | —C(=O)NH-phenyl |
| 1392 | —C(=O)NH-(4-CN-phenyl) |
| 1393 | —C(=O)NH-(4-iPr-phenyl) |
| 1394 | —C(=O)NH-(4-Br-phenyl) |
| 1395 | —C(=O)NH-(4-Cl-phenyl) |
| 1396 | —C(=O)NH-(4-F-phenyl) |

TABLE 97-continued
| Example | R Isomer 1 and isomer 2 |
|---------|-------------------------|
| 1397    | 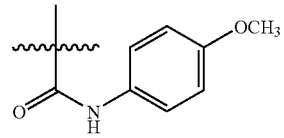    |
| 1398    | 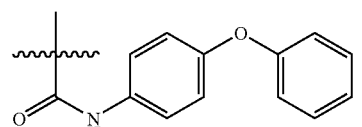    |
| 1399    | 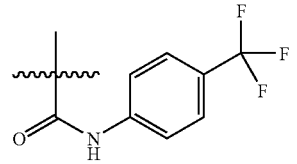    |
| 1400    | 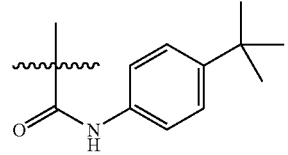    |
| 1401    | 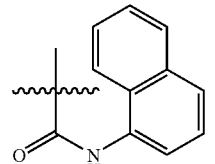    |
| 1402    | 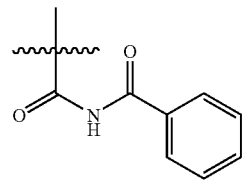    |
| 1403    | 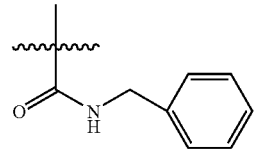    |
| 1404    | 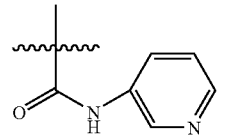    |
| 1405    | 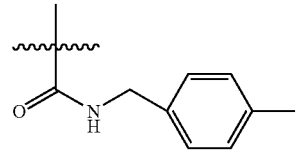    |
EXAMPLES 1406-1431
If one were to follow essentially the same procedure as in Examples 690-714 using 929a and 929b compounds of the formulas:
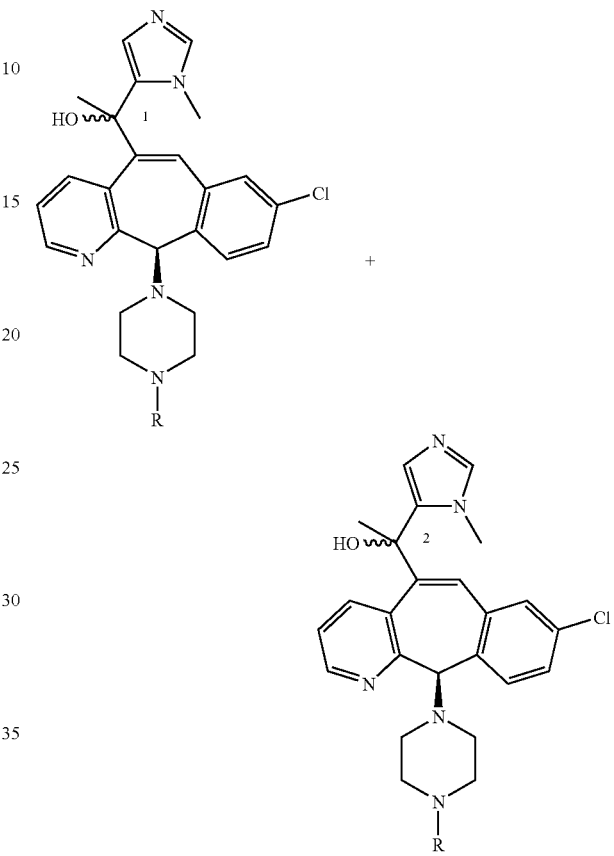
would be obtained wherein R is defined in Table 98 and the numbers 1 and 2 in the formulas represent isomers 1 and 2, respectively.
TABLE 98
| Example | R Isomer 1 and Isomer 2 |
|---------|-------------------------|
| 1406    | 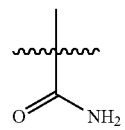   |
| 1407    | 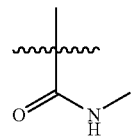   |
| 1408    | 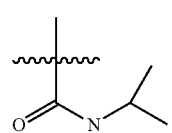   |

TABLE 98-continued

| Example | R Isomer 1 and Isomer 2 |
|---|---|
| 1409 | -C(O)NH-ethyl |
| 1411 | -C(O)NH-tert-butyl |
| 1412 | -C(O)NH-propyl |
| 1413 | -C(O)NH-isobutyl |
| 1414 | -C(O)NH-allyl |
| 1415 | -C(O)NH-cyclopentyl |
| 1416 | -C(O)NH-cyclohexyl |
| 1417 | -C(O)NH-phenyl |
| 1418 | -C(O)NH-(4-cyanophenyl) |
| 1419 | -C(O)NH-(4-isopropylphenyl) |
| 1420 | -C(O)NH-(4-bromophenyl) |
| 1421 | -C(O)NH-(4-chlorophenyl) |
| 1422 | -C(O)NH-(4-fluorophenyl) |
| 1423 | -C(O)NH-(4-methoxyphenyl) |
| 1424 | -C(O)NH-(4-phenoxyphenyl) |
| 1425 | -C(O)NH-(4-trifluoromethylphenyl) |
| 1426 | -C(O)NH-(4-tert-butylphenyl) |
| 1427 | -C(O)NH-(1-naphthyl) |
| 1428 | -C(O)NH-C(O)-phenyl |

TABLE 98-continued
| Example | R Isomer 1 and Isomer 2 |
|---|---|
| 1429 | 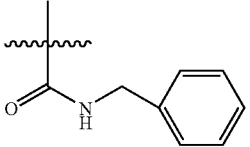 |
| 1430 | 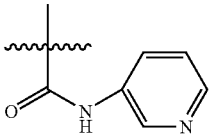 |
| 1431 | 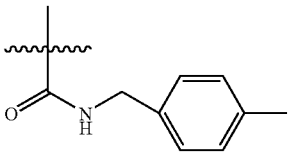 |
EXAMPLES 1432-1459
If one were to follow essentially the same procedure as in Example 536 using 928a and 928b compounds of the formulas:
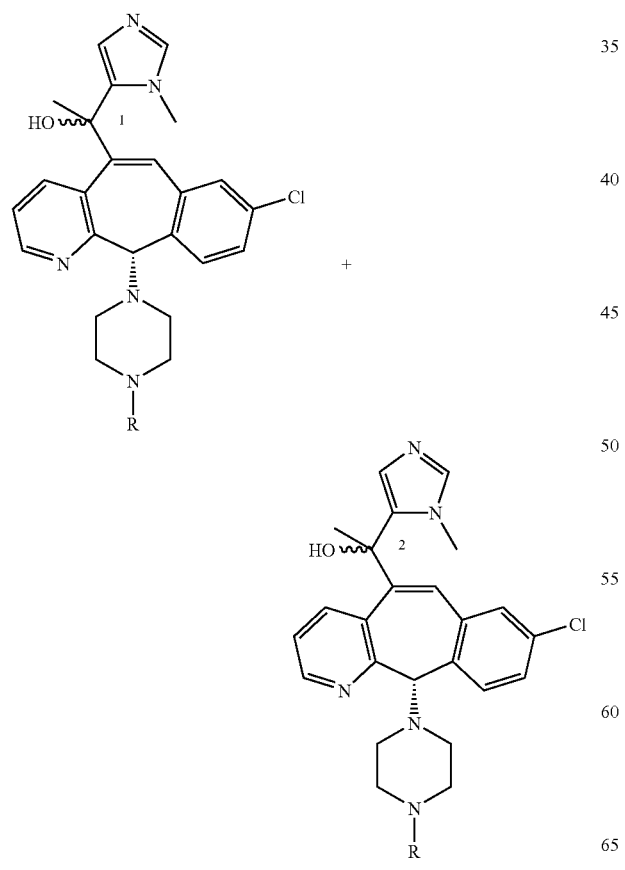
would be obtained wherein R is defined in Table 99 and the numbers 1 and 2 in the formulas represent isomers 1 and 2, respectively.
TABLE 99
| Example | R Isomer 1 and Isomer 2 |
|---|---|
| 1432 | 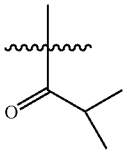 |
| 1433 | 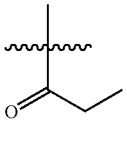 |
| 1434 | 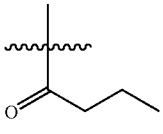 |
| 1435 | 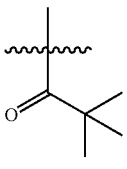 |
| 1436 | 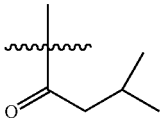 |
| 1437 | 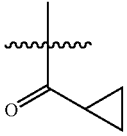 |
| 1438 | 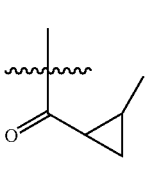 |
| 1439 | 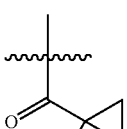 |
| 1440 | 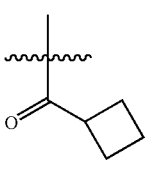 |

TABLE 99-continued

| Example | R Isomer 1 and Isomer 2 |
|---|---|
| 1441 | acyl cyclopentane |
| 1442 | acyl cyclohexane |
| 1443 | acyl cyclohexenyl |
| 1444 | acyl piperidin-4-yl |
| 1445 | acyl 1-methylcyclohexyl |
| 1446 | acyl-CH2-cyclohexyl |
| 1447 | acyl-CH2-piperidin-4-yl |
| 1448 | gem-dimethyl acyl-CH2-(1-carbamoylpiperidin-4-yl) |

TABLE 99-continued

| Example | R Isomer 1 and Isomer 2 |
|---|---|
| 1449 | benzoyl |
| 1450 | 4-chlorobenzoyl |
| 1451 | 4-bromobenzoyl |
| 1452 | 4-fluorobenzoyl |
| 1453 | 4-cyanobenzoyl |
| 1454 | 4-methylbenzoyl |
| 1455 | 4-methoxybenzoyl |
| 1456 | isonicotinoyl (gem-dimethyl) |

TABLE 99-continued
| Example | R Isomer 1 and Isomer 2 |
|---|---|
| 1457 | 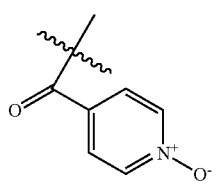 |
| 1458 | 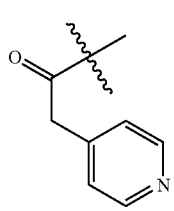 |
| 1459 | 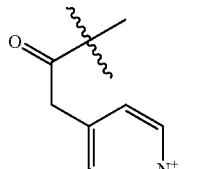 |
EXAMPLES 1460-1487
If one were to follow essentially the same procedure as in Example 536 using 929a and 929b compounds of the formulas:
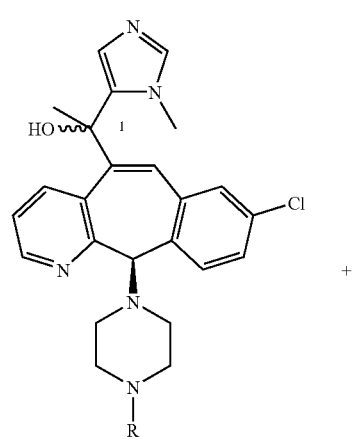
+
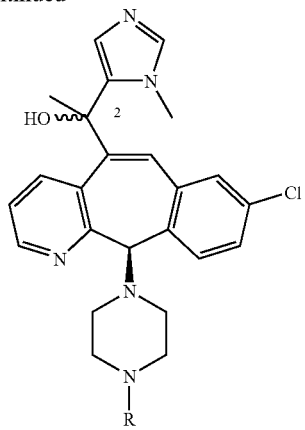
would be obtained wherein R is defined in Table 100 and the numbers 1 and 2 in the formulas represent isomers 1 and 2, respectively.
TABLE 100
| Example | R Isomer 1 and Isomer 2 |
|---|---|
| 1460 | 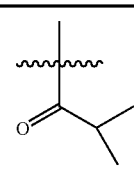 |
| 1461 | 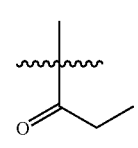 |
| 1462 | 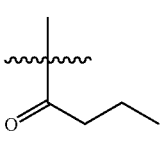 |
| 1463 | 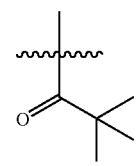 |
| 1464 | 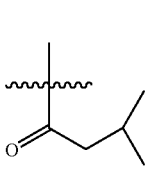 |
| 1465 | 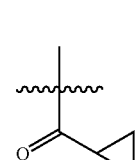 |

TABLE 100-continued

| Example | R Isomer 1 and Isomer 2 |
|---|---|
| 1466 | 1-methylcyclopropyl ketone |
| 1467 | 1-methylcyclopropyl ketone |
| 1468 | cyclobutyl ketone |
| 1469 | cyclopentyl ketone |
| 1470 | cyclohexyl ketone |
| 1471 | cyclohexenyl ketone |
| 1472 | piperidin-4-yl ketone |
| 1473 | 1-methylcyclohexyl ketone |
| 1474 | cyclohexylmethyl ketone (via CH₂) |
| 1475 | piperidin-4-ylmethyl ketone |
| 1476 | 4-(aminocarbonyl)piperidin-1-yl methyl ketone |
| 1477 | phenyl ketone |
| 1478 | 4-chlorophenyl ketone |
| 1479 | 4-bromophenyl ketone |
| 1480 | 4-fluorophenyl ketone |
| 1481 | 4-cyanophenyl ketone |
| 1482 | 4-methylphenyl ketone |

TABLE 100-continued

| Example | R Isomer 1 and Isomer 2 |
|---|---|
| 1483 | 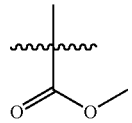 |
| 1484 | |
| 1485 | |
| 1486 | |
| 1487 | |

EXAMPLES 1488-1505

If one were to follow essentially the same procedure as in Examples 590-603 using 928a and 928b (wherein the chloroformates could be prepared following essentially the same procedure as in Preparative Example 74) compounds of the formulas:

would be obtained wherein R is defined in Table 101 and the numbers 1 and 2 in the formulas represent isomers 1 and 2, respectively.

TABLE 101

| Example | R Isomer 1 and Isomer 2 |
|---|---|
| 1488 | 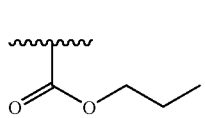 |
| 1489 | |
| 1490 | |
| 1491 | |

TABLE 101-continued

| Example | R Isomer 1 and Isomer 2 |
|---|---|
| 1492 | ![structure] |
| 1493 | ![structure] |
| 1494 | ![structure] |
| 1495 | ![structure] |
| 1496 | ![structure] |
| 1497 | ![structure] |
| 1498 | ![structure] |
| 1499 | ![structure] |
| 1500 | ![structure] |
| 1501 | ![structure] |
| 1502 | ![structure] |
| 1503 | ![structure] |
| 1504 | ![structure] |
| 1505 | ![structure] |

EXAMPLES 1506-1524

If one were to follow essentially the same procedure as in Examples 590-603 using 929a and 929b (wherein the chloroformates could be prepared following essentially the same procedure as in Preparative Example 74) compounds of the formulas:

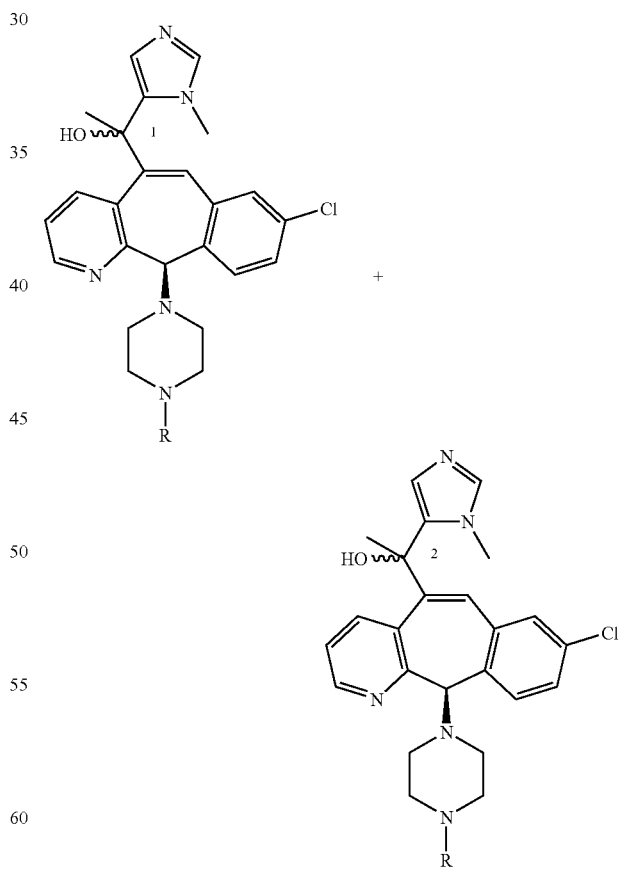

would be obtained wherein R is defined in Table 102 and the numbers 1 and 2 in the formulas represent isomers 1 and 2, respectively.

TABLE 102

| Example | R Isomer 1 and Isomer 2 |
|---|---|
| 1506 | methyl ester |
| 1507 | ethyl ester |
| 1508 | propyl ester |
| 1509 | isopropyl ester |
| 1510 | tert-butyl ester |
| 1511 | isobutyl ester |
| 1512 | neopentyl ester |
| 1513 | allyl ester |
| 1514 | sec-butyl ester |
| 1515 | cyclopentyl ester |
| 1516 | cyclohexyl ester |
| 1517 | phenyl ester |
| 1518 | benzyl ester |

TABLE 102-continued

| Example | R Isomer 1 and Isomer 2 |
|---|---|
| 1519 | 4-methylphenyl ester |
| 1520 | 4-methoxyphenyl ester |
| 1521 | 4-chlorophenyl ester |
| 1522 | 4-bromophenyl ester |
| 1523 | 4-fluorophenyl ester |
| 1524 | naphthyl ester |

EXAMPLES 1525-1548

If one were to follow essentially the same procedure as in Examples 566-567 using 928a and 928b compounds of the formulas:

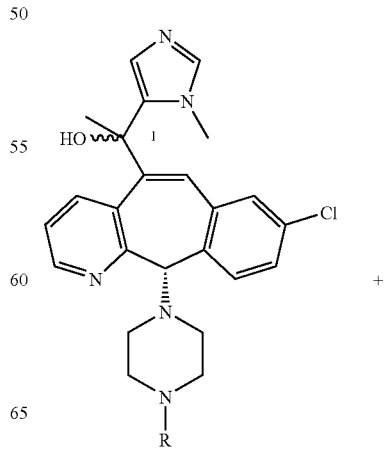

+

-continued
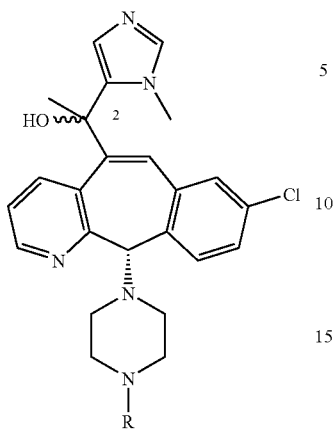
would be obtained wherein R is defined in Table 103 and the numbers 1 and 2 in the formulas represent isomers 1 and 2, respectively.
TABLE 103
| Example | R Isomer 1 and Isomer 2 |
|---|---|
| 1525 | 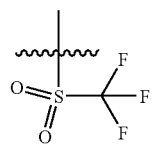 |
| 1526 | |
| 1527 | |
| 1528 | |
| 1529 | 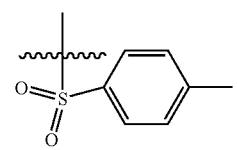 |
| 1530 | |
TABLE 103-continued
| Example | R Isomer 1 and Isomer 2 |
|---|---|
| 1531 | 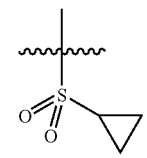 |
| 1533 | |
| 1534 | 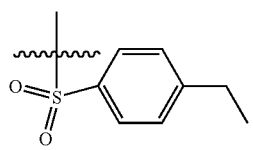 |
| 1535 | 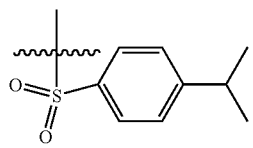 |
| 1536 | 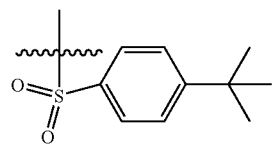 |
| 1537 | 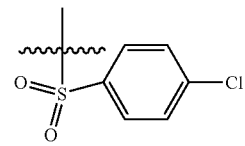 |
| 1538 | 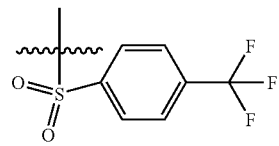 |
| 1539 | |
| 1541 | 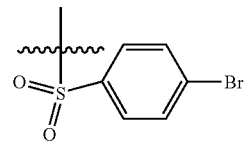 |

TABLE 103-continued

| Example | R Isomer 1 and Isomer 2 |
|---|---|
| 1542 | 4-fluorophenylsulfonyl |
| 1543 | 4-cyanophenylsulfonyl |
| 1544 | 4-methoxyphenylsulfonyl |
| 1545 | phenylsulfonyl |
| 1546 | benzylsulfonyl |
| 1547 | 2-thienylsulfonyl |
| 1548 | 1-naphthylsulfonyl |

EXAMPLES 1549-1572

If one were to follow essentially the same procedure as in Examples 566-567 using 929a and 929b compounds of the formulas:

would be obtained wherein R is defined in Table 104 and the numbers 1 and 2 in the formulas represent isomers 1 and 2, respectively.

TABLE 104

| Example | R Isomer 1 and Isomer 2 |
|---|---|
| 1549 | methylsulfonyl |
| 1550 | isopropylsulfonyl |
| 1552 | propylsulfonyl |

TABLE 104-continued

| Example | R Isomer 1 and Isomer 2 |
|---|---|
| 1553 | -S(O)₂N(CH₃)₂ |
| 1554 | -S(O)₂-tBu |
| 1555 | -S(O)₂CF₃ |
| 1557 | -S(O)₂-cyclopropyl |
| 1558 | -S(O)₂-(4-methylphenyl) |
| 1559 | -S(O)₂-(4-ethylphenyl) |
| 1560 | -S(O)₂-(4-isopropylphenyl) |
| 1561 | -S(O)₂-(4-tert-butylphenyl) |
| 1562 | -S(O)₂-(4-chlorophenyl) |
| 1563 | -S(O)₂-(4-trifluoromethylphenyl) |
| 1565 | -S(O)₂-(4-bromophenyl) |
| 1566 | -S(O)₂-(4-fluorophenyl) |
| 1567 | -S(O)₂-(4-cyanophenyl) |
| 1568 | -S(O)₂-(4-methoxyphenyl) |
| 1569 | -S(O)₂-phenyl |
| 1570 | -S(O)₂-CH₂-phenyl |
| 1571 | -S(O)₂-(2-thienyl) |
| 1572 | -S(O)₂-(1-naphthyl) |

EXAMPLE 1573
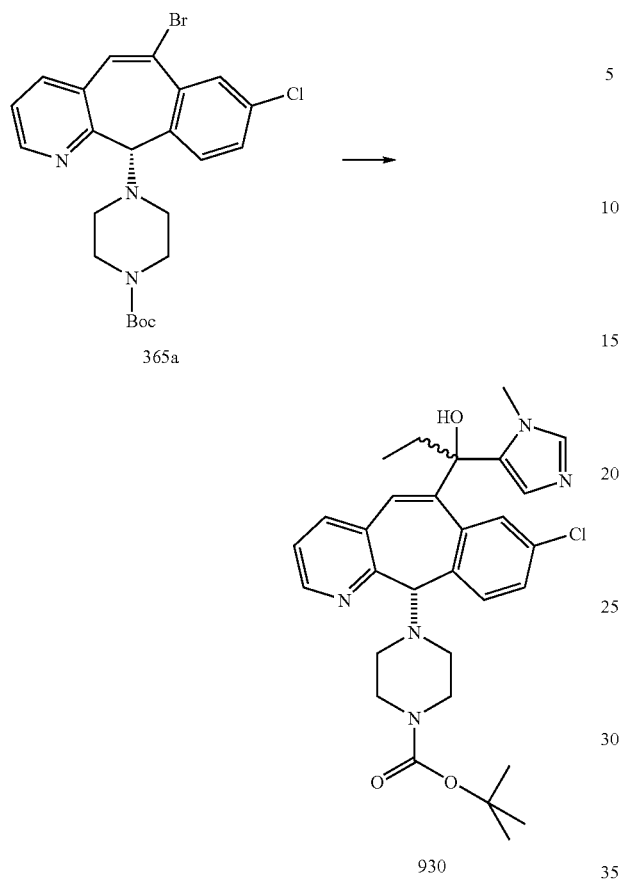
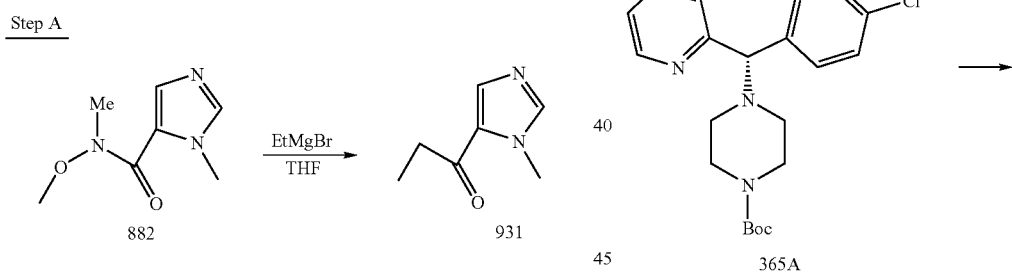
React 882, from Preparative Example 73 Step B, with ethylmagnesium bromide following the procedure described in Preparative Example 73 Step C.
Step B
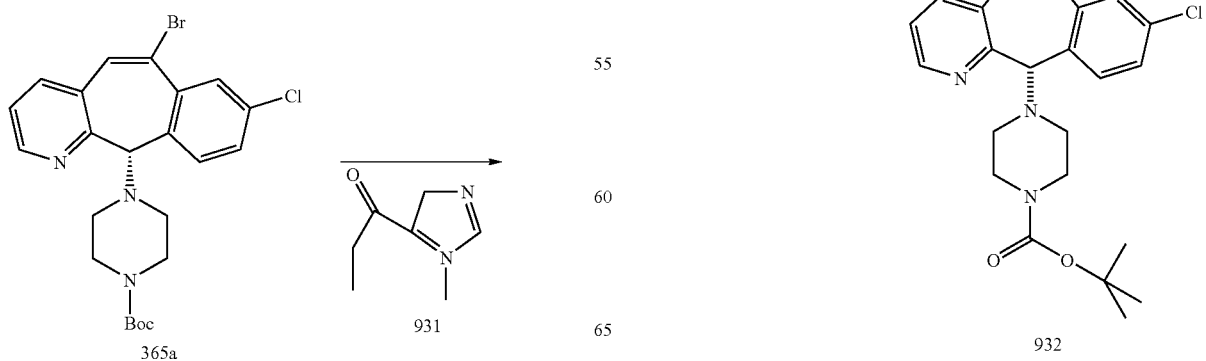
-continued
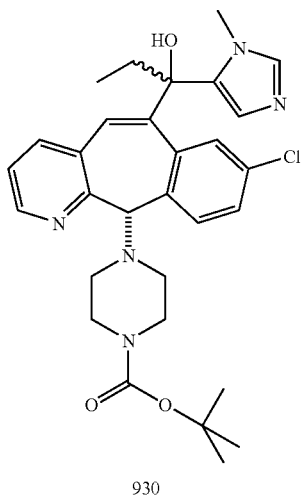
React 365a with 931 (from Step A) following essentially the same procedure as in Preparative Example 73, Step D, to give the 930 as a white solid, mp=163-165° C.
EXAMPLE 1574

Step A

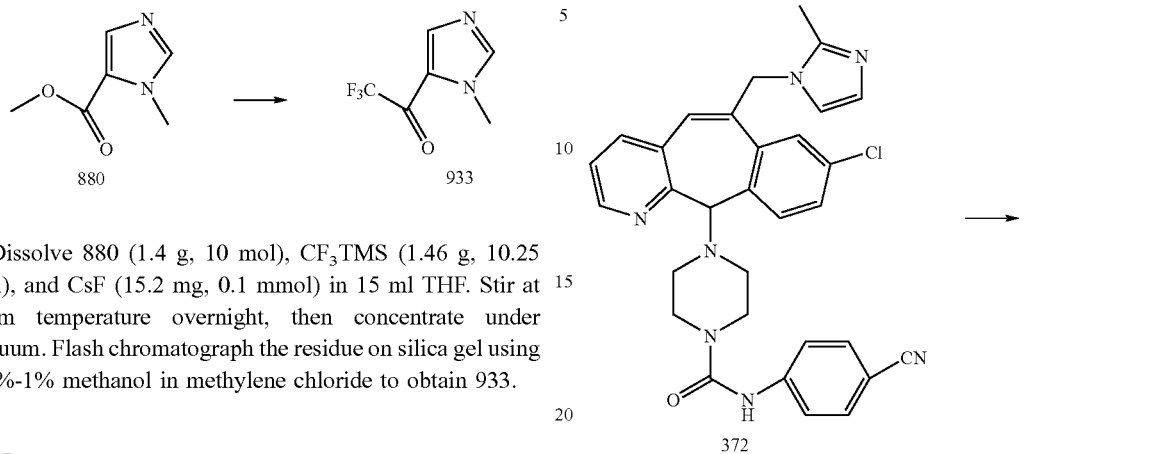

Dissolve 880 (1.4 g, 10 mol), CF$_3$TMS (1.46 g, 10.25 mol), and CsF (15.2 mg, 0.1 mmol) in 15 ml THF. Stir at room temperature overnight, then concentrate under vacuum. Flash chromatograph the residue on silica gel using 0.5%-1% methanol in methylene chloride to obtain 933.

Step B

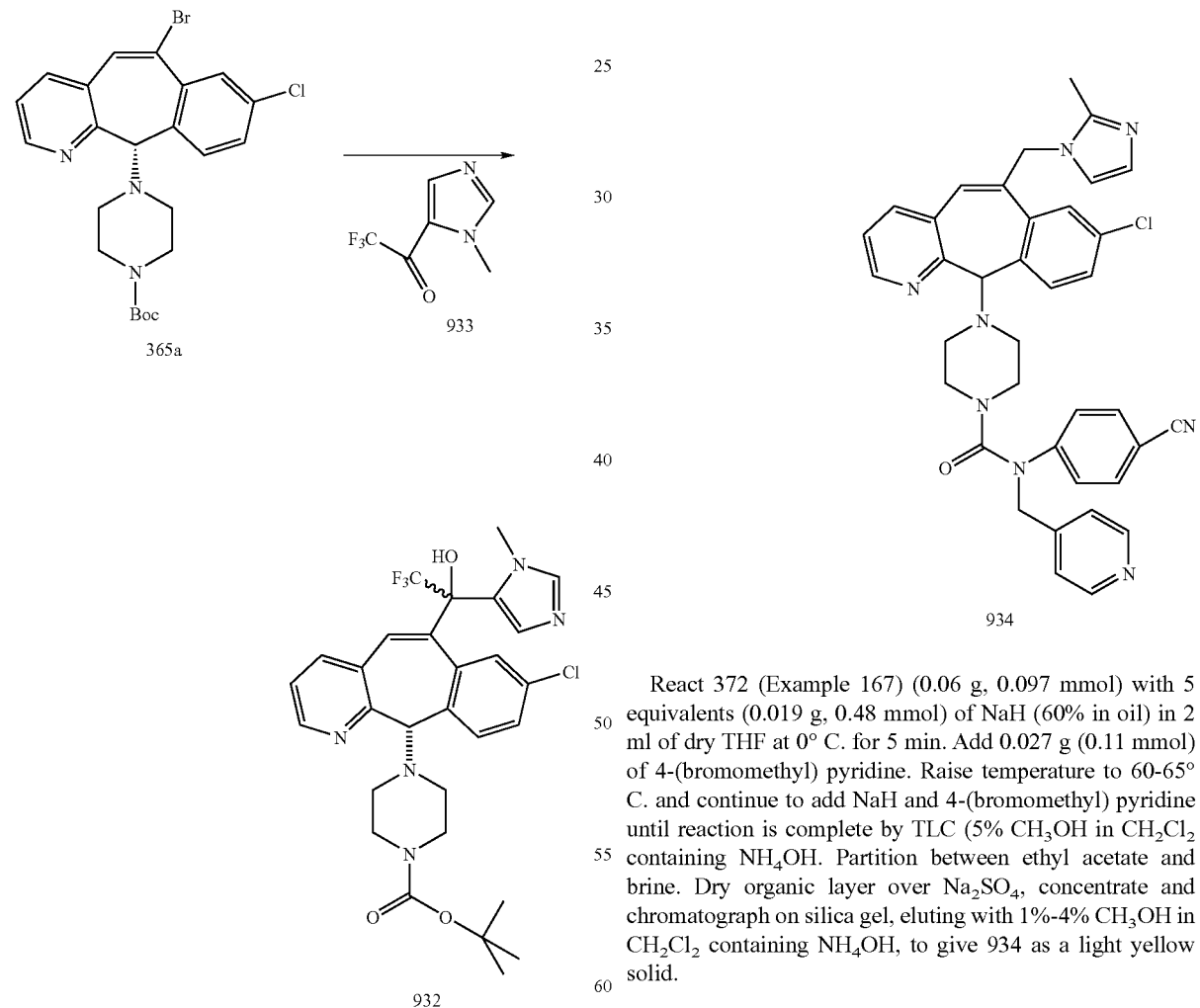

React 365a with the 933 (from Step A) following essentially the same procedure as in Preparative Example 73, Step D, to give 932, mp=189.9-190.1° C.

EXAMPLE 1575

React 372 (Example 167) (0.06 g, 0.097 mmol) with 5 equivalents (0.019 g, 0.48 mmol) of NaH (60% in oil) in 2 ml of dry THF at 0° C. for 5 min. Add 0.027 g (0.11 mmol) of 4-(bromomethyl) pyridine. Raise temperature to 60-65° C. and continue to add NaH and 4-(bromomethyl) pyridine until reaction is complete by TLC (5% CH$_3$OH in CH$_2$Cl$_2$ containing NH$_4$OH. Partition between ethyl acetate and brine. Dry organic layer over Na$_2$SO$_4$, concentrate and chromatograph on silica gel, eluting with 1%-4% CH$_3$OH in CH$_2$Cl$_2$ containing NH$_4$OH, to give 934 as a light yellow solid.

EXAMPLE 1576

Following essentially the same procedure as in Example 1575, compound 372 was reacted with 2-(bromomethyl) pyridine.HBr to afford compound 935 identified in Table 105 below.

EXAMPLE 1577

Following essentially the same procedure as in Example 1575, compound 372 was reacted with 3-(bromomethyl)pyridine.HBr to afford compound 936 identified in Table 105 below.

EXAMPLE 1578

Following essentially the same procedure as in Example 1575, compound 372 was reacted with benzyl bromide to afford compound 937 identified in Table 105 below.

EXAMPLE 1579

Following essentially the same procedure as in Example 1575, compound 372 was reacted with $CH_{3I}$ to afford compound 938 identified in Table 105 below.

TABLE 105

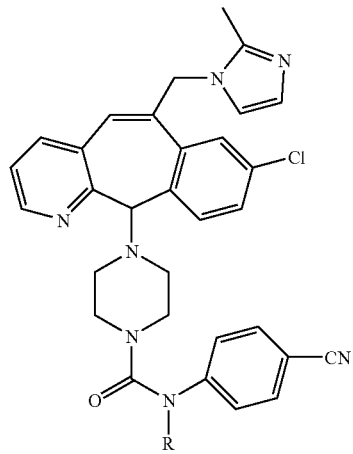

| Example | R = | Compound | PHYS. DATA |
|---|---|---|---|
| 1575 | 4-pyridylmethyl | 934 | $MH^+ = 641$ |
| 1576 | 2-pyridylmethyl | 935 | $MH^+ = 641$ |
| 1577 | 3-pyridylmethyl | 936 | $MH^+ = 641$ |

TABLE 105-continued

| Example | R = | Compound | PHYS. DATA |
|---|---|---|---|
| 1578 | benzyl | 937 | $MH^+ = 640$ |
| 1579 | $CH_3$ | 938 | $MH^+ = 564$ |

EXAMPLE 1580

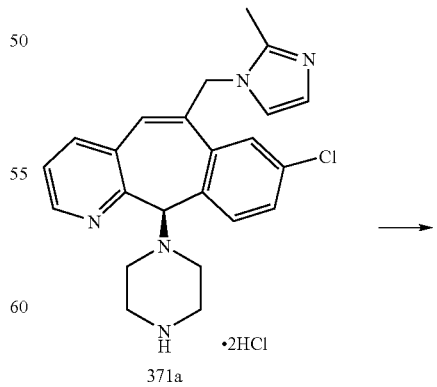

371a ·2HCl

-continued

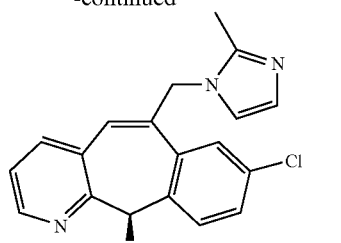
939

Step A

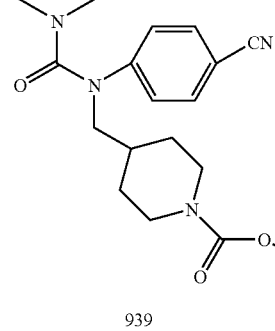

To a 125 ml flask, was added 4-hydroxymethyl piperidine (940) (1 g, 8.68 mmol) and 20 ml of MeOH, cool to 0° C., then added Boc-anhydride (2.84 g, 13.02 mmol, 1.5 eq.), and adjust to pH 8.5-9.5 over 1 hour with 13 ml, 13.0 mmol, 1.5 eq. of 1.0 N NaOH. Reaction was allowed to warm to room temperature and stirred for 1 hour. TLC with 20% EtoAc/CH₂Cl₂. Removed most MeOH via evaporation. Added CH₂Cl₂ and washed with H₂O, brine and filtered through Na₂SO₄. The solvent was evaporated to give 1.82 g of a clear oil. Oily product crystallized upon standing to give a white solid product 941.

Step B

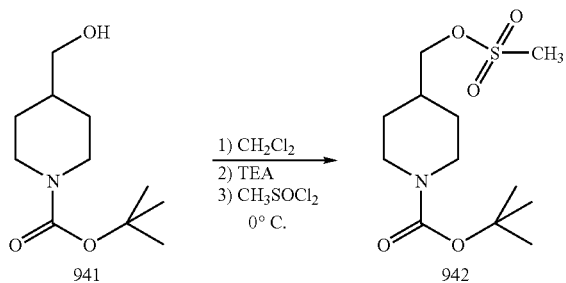

941 (0.3 g, 1.395 mmol) was transferred into a flask and dissolved in anhydrous CH₂Cl₂. Cool to 0° C. Added 129 ul, 1.67 mmol, 1.2 eq., of methanesulfonyl chloride and triethylamine (129 ul, 2.09 mmol, 1.5 eq.). Allowed to warm to room temperature while stirring for 1 hour. TLC with 20% EtoAc/CH₂Cl₂. Added saturated NaHCO₃, and stir 3-4 minutes, separated the CH₂Cl₂ layer, washed with H₂O, brine and filtered through Na₂SO₄. Solvent was evaporated to give 0.423 g of a clear oil, compound 942.

Step C

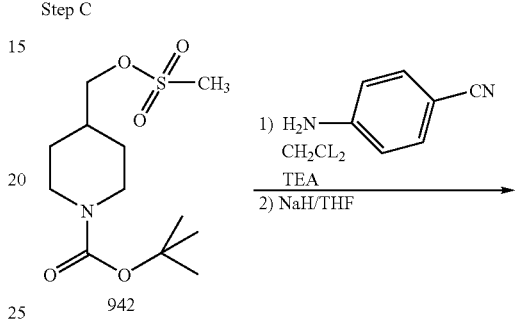

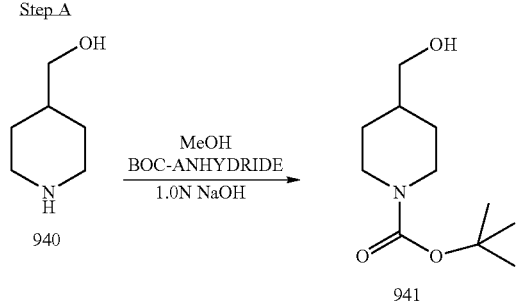
943

942 (0.1 g, 3.413 mmol) was transferred into a reaction flask and added anhydrous CH₂Cl₂ (1 ml), followed by addition of (1) 4-aminobenzonitrile (0.040 g, 3.4 mmol) and triethylamine (61 ul, 4.4 mmol, 1.3 eq.) and stir at room temperature for 10 minutes. TLC with 10% EtoAc/CH₂Cl₂, reaction still did not complete. Stir for 1½ hour, TLC again, reaction stopped. Removed solvent to dryness. Added to residue, (1 ml) of anhydrous THF at room temperature, then added 0.0136 g, 3.4 mmol of NaH (60% in oil Disp.). Let stir for ½ hour, followed reaction progress by TLC. Added to reaction mixture additional NaH (0.136 g, 3.4 mmol), stirred for ½ hour, monitored reaction by TLC, then heated reaction mixture to 60° C. in an oil bath for 45 minutes then overnight. Removed solvent in rotary evaporator under vacuum. Residue was dissolved in CH₂Cl₂ and washed with H₂O, then brine. Filtered through Na₂SO₄, removed solvent to dryness to give 0.125 g of crude product. Crude was purified by flash chromatography using (silica gel) and eluting with CH₂Cl₂ then with 1-5% EtoAc/CH₂Cl₂. Isolated 0.035 g of product, 943.

Step D

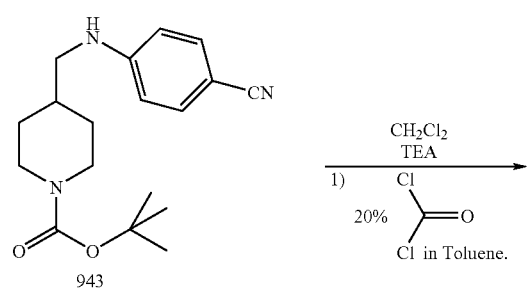

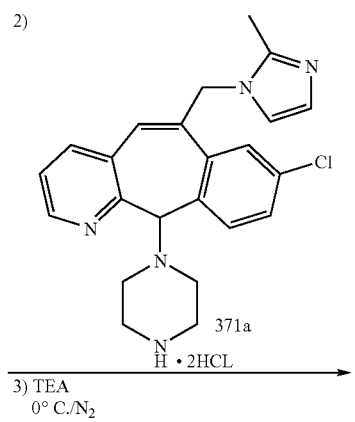

943 (0.034 g, 0.11 mmol) was transferred into a reaction flask and dissolved in CH₂Cl₂ (3 ml) and cooled to 0° C. TEA (60 ul, 0.43 mmol, 4 eq.) was added, followed by (213 ul, 0.0427 g, 0.43 mmol, 4 eq.) of a 20% phosgene/toluene solution. Reaction was allowed to stir at 0° C. for 1½ hours. After 1½ hours, N₂ was bubbled into the reaction for ~10 minutes, then added 0.056 g, 0.12 mmol, 1.1 eq., of starting material (2)-compound 371a (Preparative Example 42, Step F) followed by triethylamine (33 ul, 0.24 mmol, 2.2 eq.) in 1 ml of CH₂Cl₂. Allowed to stir at 0° C. for 1½ hours. Reaction mixture was washed with NaHCO₃, then H₂O, then brine and organic layer was filtered through Na₂SO₄. Removed solvent to dryness to give 0.083 g of crude product. Purified on flash silica gel column eluting with 2, 4, 6, 8% (10% NH₄OH/CH₃OH)/CH₂Cl₂). Isolated product gave 0.039 g of 939, MH$^+$=747.

EXAMPLE 1581

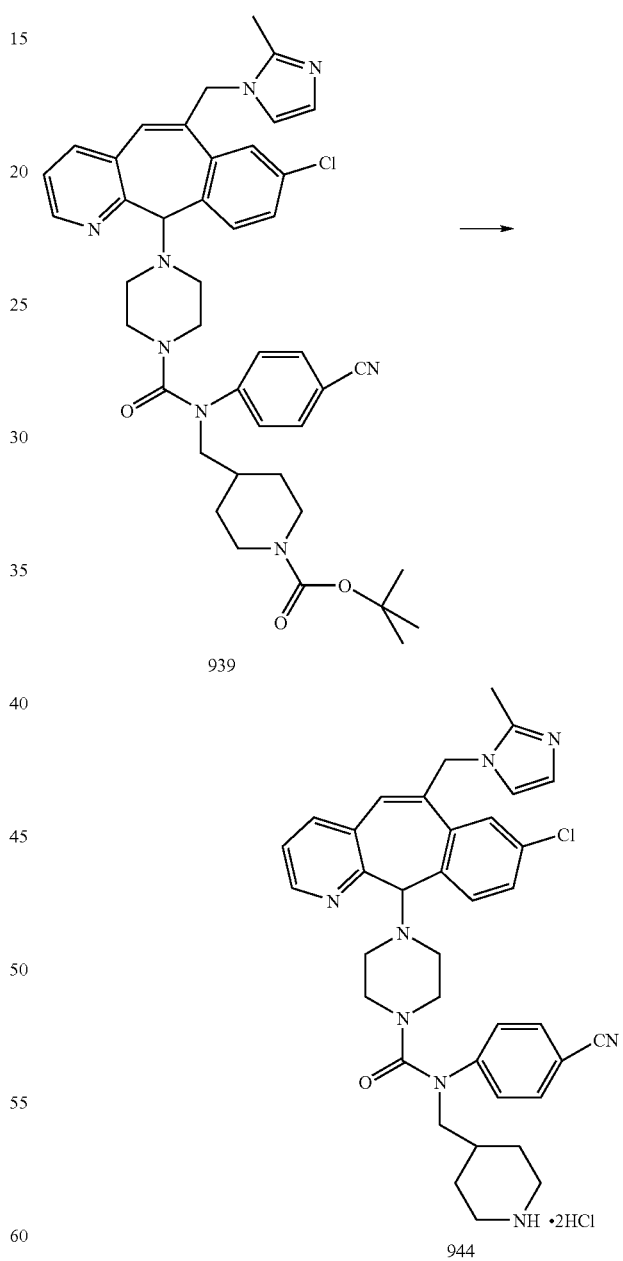

939 was reacted in the same manner as Compound 360a (Preparative Example 40, STEP G), using (0.118 g, 0.25 mmol) of 939 and (5 ml) of 4N HCL in dioxane to give 0.252 g of 944, MH$^+$=647.

EXAMPLE 1582

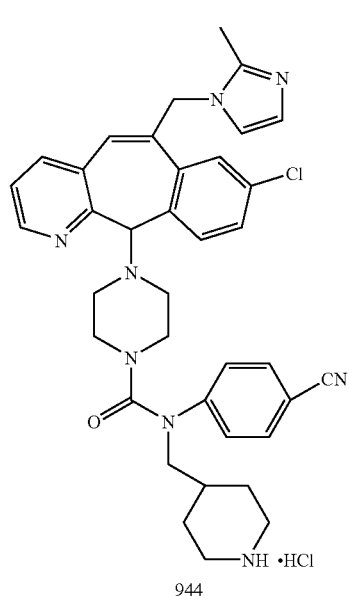

In a 100 ml flask was added 944 (0.073 g, 0.067024 mmol) and 5 ml of anhydrous CH₂Cl₂ and stirred followed by addition of TEA (37 ul, 4 eq.) and trimethylsilyl isocyanate (90 ul, 0.07 mmol, 10 eq.). Reaction was allowed to stir at room temperature for 1 hour. TLC with 7% (10% NH₄OH/CH₃OH)/CH₂Cl₂. Stir 1½ hours, then added saturated NaHCO₃ and stirred for 10 minutes, separated CH₂Cl₂ layer, and washed with H₂O, brine and dried over Na2SO4, filtered and concentrated filtrate to dryness to give 0.056 g of crude product. Purified on Flash silica gel column eluting with CH₂Cl₂, then with 1-7% (10% NH₄OH/CH₃OH)/CH₂Cl₂. Isolated 0.038 g of the desired product, 945, MH⁺=690.

EXAMPLE 1583

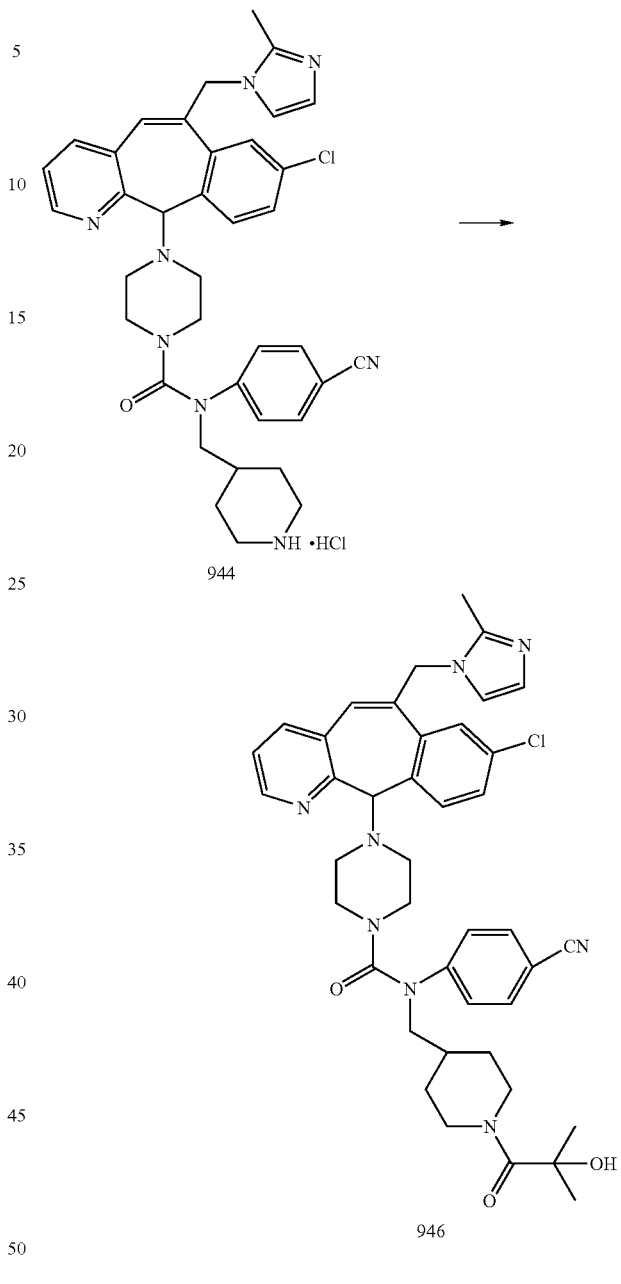

In a 50 ml reaction flask was added (0.0092 g, 0.0882 mmol, 1.05 eq.) of 2-hydroxy isobutyric acid [CAS 594-61-6] in 1 ml of anhydrous DMF and 1 ml of anhydrous CH₂Cl₂ followed by addition of NMM (46 ul, 0.42 mmol, 5 eq.); HOBT (0.0178 g, 0.11 mmol, 1.3 eq.), DEC (0.024 g, 0.13 mmol, 1.5 eq.). Reaction mixture was allowed to stir at room temperature for ~10 minutes, then added 944 (0.084 g, 0.08 mmol, 1 eq.) in 1 ml of DMF and 1 ml of CH₂Cl₂. Reaction was allowed to stir at room temperature overnight. Removed solvent in rotary evaporator, added EtoAc and washed with saturated NaHCO₃, then 3(X) with H₂O, then with Brine. Organic layer was filtered through Na₂SO4, evaporated filtrate to dryness to give 0.087 g of crude product. Purified crude on a Flash silica gel column eluting with CH₂Cl₂— 1-5% (10% NH₄OH/CH₃OH)/CH₂Cl₂, to give 0.048 g of a white solid Compound 946, MH⁺=733.

EXAMPLE 1584

EXAMPLE 1585

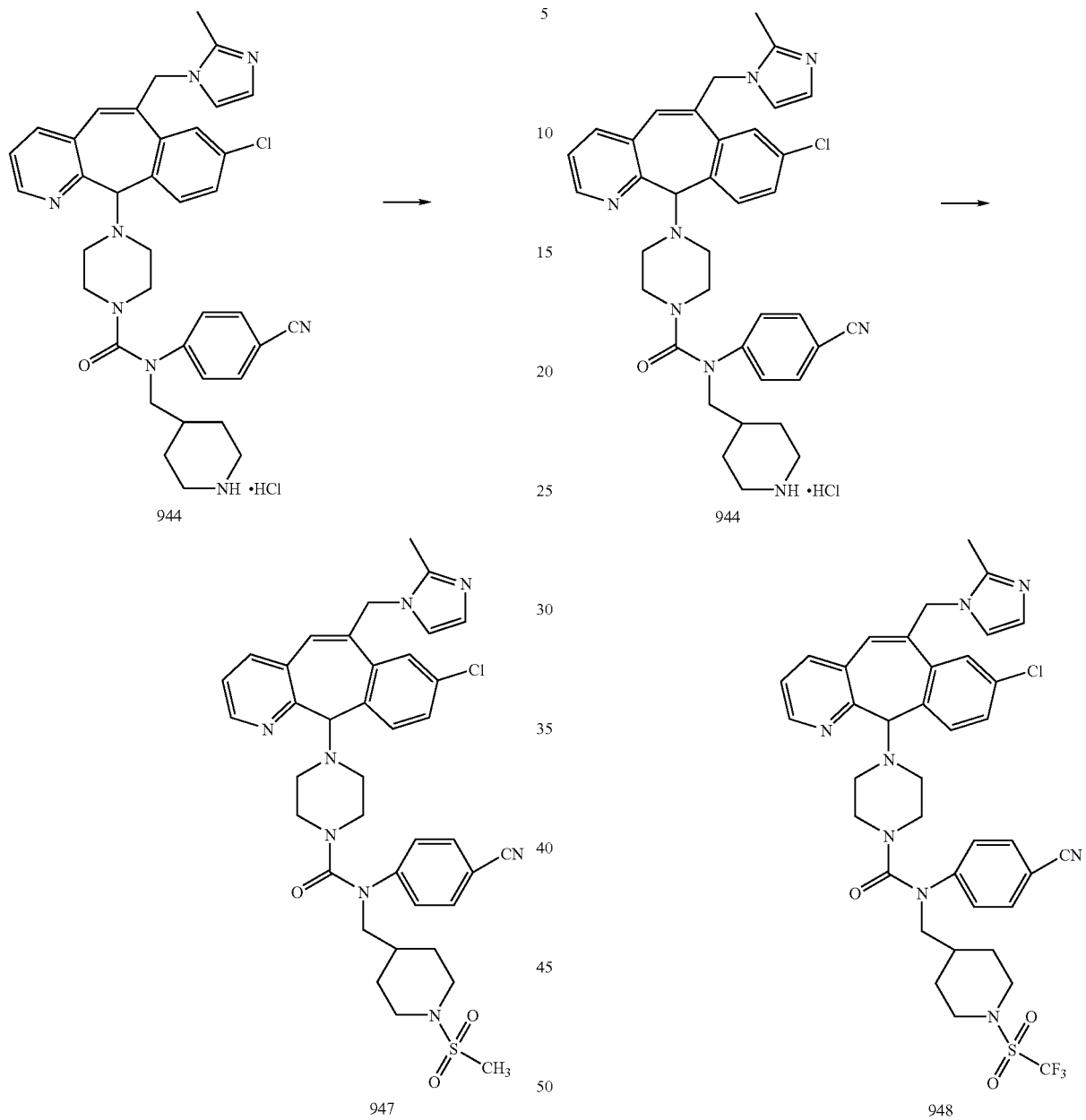

In a 50 ml flask was transferred (0.084 g, 0.084 mmol) of 944 and 2 ml of anhydrous $CH_2Cl_2$ followed by addition of triethylamine (50 ul, 4.2 mmol, 5 eq.) and methanesulfonylchloride (7.8 ul, 0.10 mmol, 1.2 eq.). Reaction was allowed to stir at room temperature overnight. Tlc with 5% (10% $NH_4OH/CH_3OH$)/$CH_2Cl_2$. Added saturated $NaHCO_3$ and stirred vigorously 5-10 minutes. Separated $CH_2Cl_2$ layer and washed with $H_2O$, Brine and filtered through $Na_2SO_4$. Filtrate was evaporated to dryness to give 0.080 g of crude product. Purified crude on a Flash silica gel column eluting with $CH_2Cl_2$-1-4% (10% $NH_4OH/CH_3OH$)/$CH_2Cl_2$, to give 0.041 g—compound 947, $MH^+$=725.

In a 50 ml flask was transferred (0.084 g, 0.084 mmol) of 944 and 2 ml of anhydrous $CH_2Cl_2$ followed by addition of triethylamine (58 ul, 4.2 mmol, 5 eq.) and triflic anhydride (16.9 ul, 0.1008 mmol, 1.2 eq.). Reaction was allowed to stir at room temperature overnight. TLC with 5% (10% $NH_4OH/CH_3OH$)/$CH_2Cl_2$. Added saturated NaHCO3 and stirred vigorously 5-10 minutes. Separated $CH_2Cl_2$ layer and washed with $H_2O$, brine and filtered through Na2SO4. Filtrate was evaporated to dryness to give 0.065 g of crude product. Purified crude on a Flash silica gel column eluting with $CH_2Cl_2$-1-4% (10% $NH_4OH/CH_3OH$)/$CH_2Cl_2$, to give 0.028 g—compound 948, $MH^+$=779.

EXAMPLE 1586

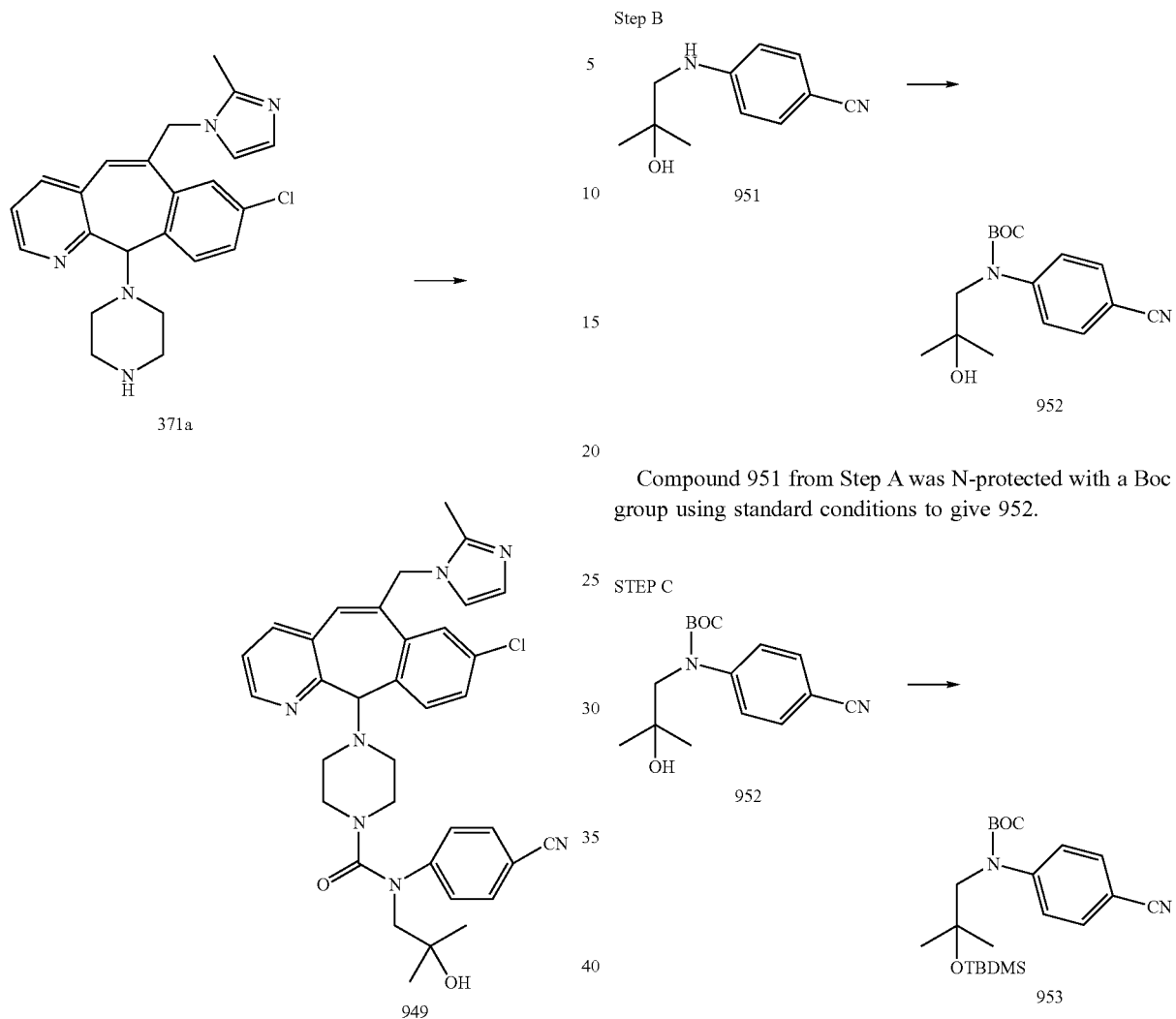

Step A

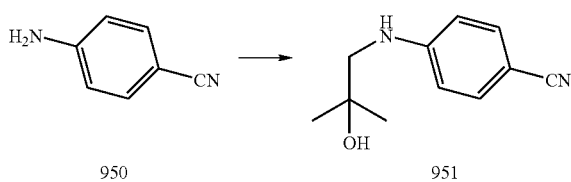

4-aminobenzonitrile (0.1 g, 0.85 mmol) was dissolved in (5 ml)of CH$_2$Cl$_2$. To this solution was added isobutylene oxide (61 mg, 0.85 mmol) and 1 g of silica gel. Reaction mixture was stirred at room temperature for 16 hours. Isobutylene oxide (0.75 µl, 8 mmol) was added and reaction was heated to 60° C. for 16 hours. 4-aminobenzonitrile (200 mg, 1.6 mmol) and isobutylene oxide(0.75 µl, 8 mmol) was added and reaction refluxed for another 7 hours. Volatile solvents evaporated and material chromatographed on silica gel column, eluting with 1-9% ethyl acetate/CH$_2$Cl$_2$, to give 295 mg of the desired product-951.

Step B

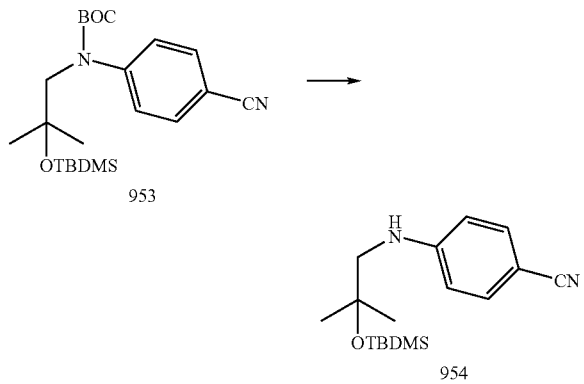

Compound 951 from Step A was N-protected with a Boc group using standard conditions to give 952.

STEP C

Compound 952 from Step B was O-protected using tetrabutyldimethylsilyl(TBDMS) to give 953.

Step D

The Boc group of 953 Step C was deprotected using HCl-Dioxane to give 954.

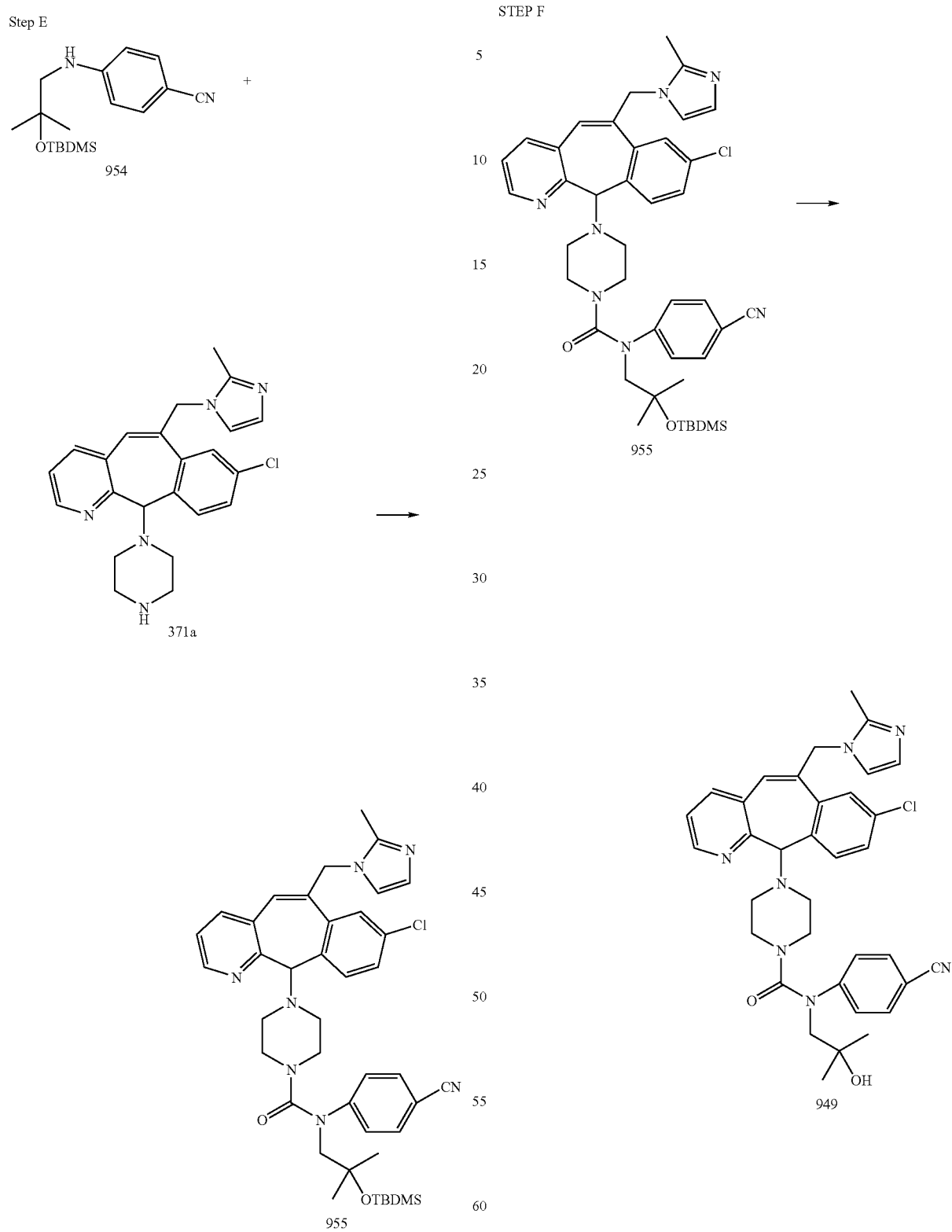
Compound 954 from Step D was treated in a similar way to compound of Example 1580, Step D, to give 955.
Compound 955 from Step E, was deprotected by treatment with tetrabutylammoniumfluoride(TBAF) to give the title compound 949.

EXAMPLE 1587

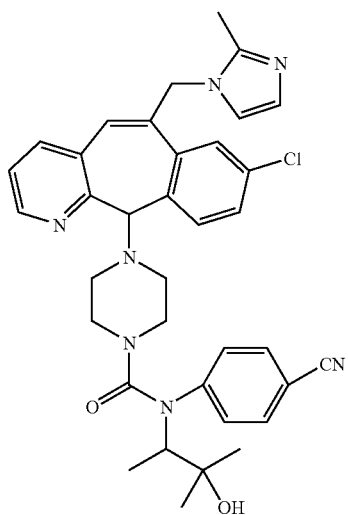

956

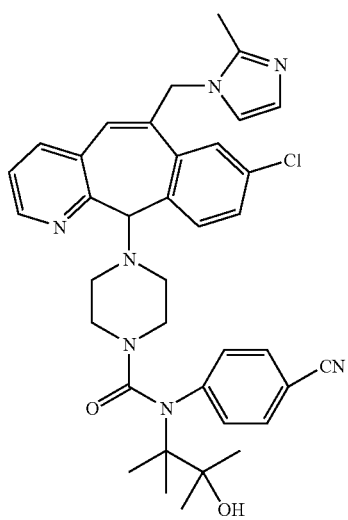

957

956 and 957 were prepared in a similar manner to 949 using the appropriate substituted starting epoxide.

PREPARATIVE EXAMPLE 109

Step A

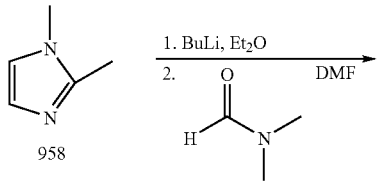

958

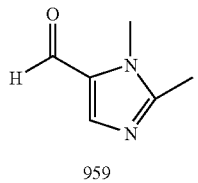

959

To a stirred solution of 1,2-dimethylimidazole, compound 958 (1.92 g, 1 eq. 20 mmol) in 50 ml of Et$_2$O, was added BuLi (2.5 M in Hexanes, 1 eq. 20 mmol, 8 ml) and stirred at room temperature, a yellow suspension results. Stirred for 1.5 hr, more precipitate forms. Reaction mixture was treated with 3.5 ml of DMF, stirred for 2-5 hours or until reaction was complete. Quench reaction with NH$_4$Cl solution and extract with CH$_2$Cl$_2$, wash organic 3× with brine. Isolate organic and evaporate to dryness to obtain product as a crude. Purification from Prep Plate Chromatography 10:1 CH$_2$Cl$_2$:MeOH:2N NH$_3$ afforded 0.52 g of compound 959, ~21%.

Step B

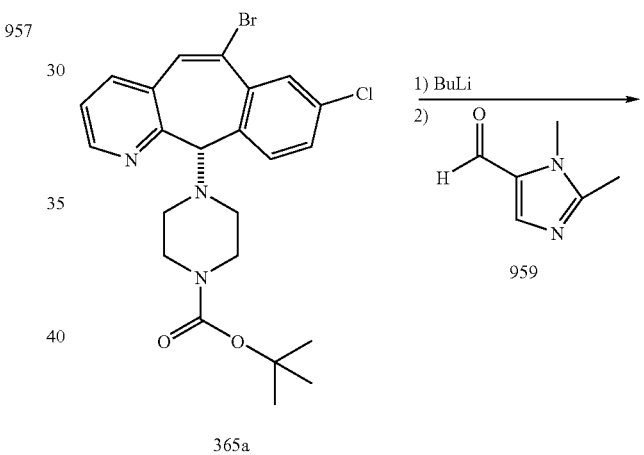

365a

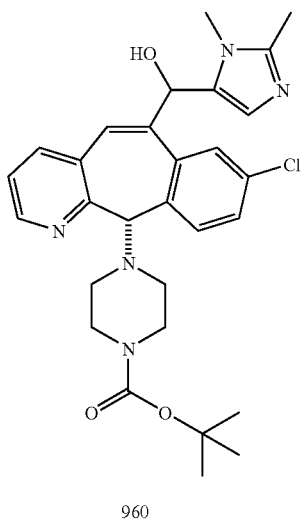

960

Following essentially the same procedures as in Example 510 (Step A), but using compound 959 (0.25 g, 2 mmol) as the intermediate, compound 960 was prepared. Yellow solid (0.54 g), 50% yield.

Step C

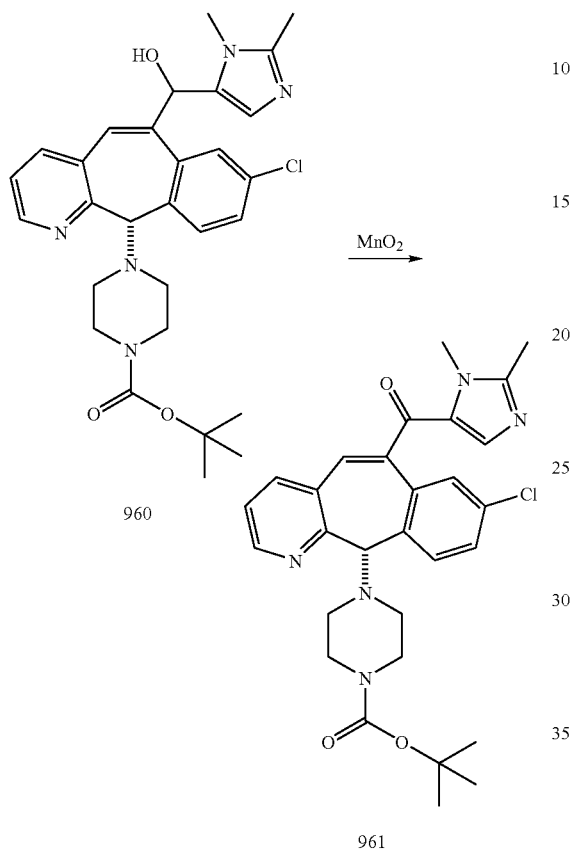

960

961

Following essentially the same procedures as in Example 510 (Step B) but using Compound 960 (0.45 g, 0.84 mmol) as the starting material, compound 961 was prepared. Light yellow solid (0.372).

Step D

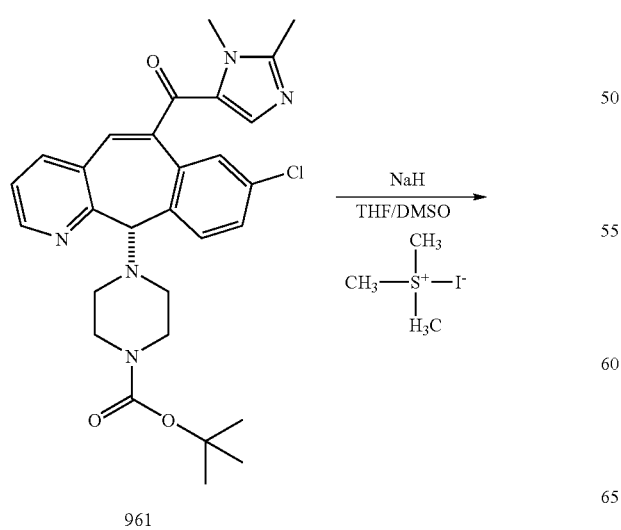

961

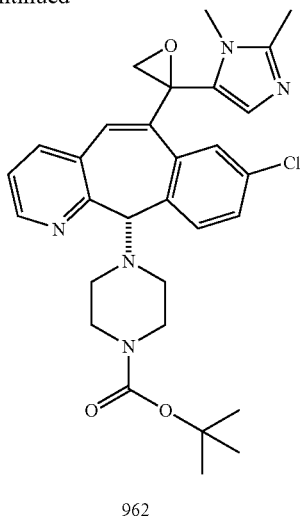

962

Following essentially the same procedures as in Example 510 (Step C) but using Compound 961 (0.267 g, 0.5 mmol) as the starting material, compound 962 was prepared.

Step E

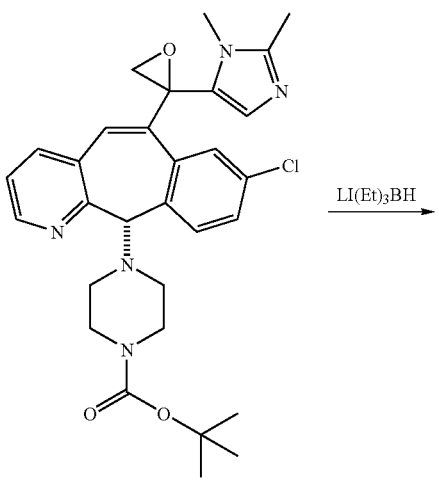

962

963

Following essentially the same procedures as in Example 510 (Step D) but using Compound 962 (0.5 mmol) as the starting material, compound 963 was prepared. (0.18 g).

Step F

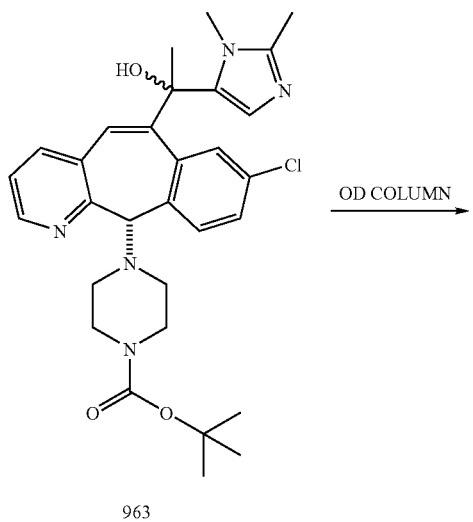

Following essentially the same procedures as in Example 510 (Step E), Compound 963 was separated by Chiral HPLC to give compounds 963a and 963b. Chiral OD Prep HPLC Column, eluting with IPA (10%) hexanes (80%)+0.2% DEA Isomer 1, compound 963a: retention time=7.61 min
Isomer 2, compound 963b: retention time=10.56 min

PREPARATIVE EXAMPLE 110

Step A

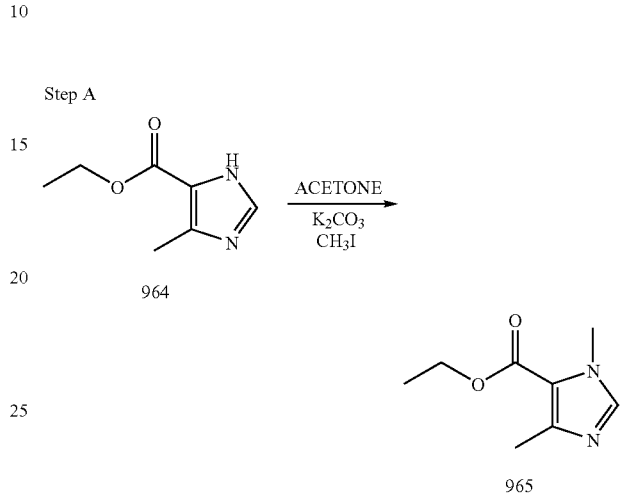

To a stirred solution of 964 (Ethyl 4-methyl-5-imidazole carboxylate, 7.7 g, 50 mmol) in 100 ml of acetone at room temperature, was added $K_2CO_3$ (6.9 g, 50 mmol) portion-wise. Stirred at room temperature for 25 minutes, added in MeI (5 ml, 80 mmol) stirred for 2½ h, (monitored reaction by TLC). Additional $K_2CO_3$ (3.09 g, 22 mmol) and MeI (3 ml) were added. Stirred reaction for 16 h, then filtered reaction mixture and rinsed with acetone (80 ml). A clear filtrate obtained. Filtrate was evaporated and the residue was chromatographed (eluent methylene chloride/methanol (60:1) to afford 1.8 g of solid. This solid was purified by Prep Plate chromatography ((20:1) $CH_2Cl_2$:MeOH $NH_3$), compound still impure. Another column chromatography ((50:1) $CH_2Cl_2$:MeOH.$NH_3$) was done to afford 383 mg of the desired product, compound 965.

Step B

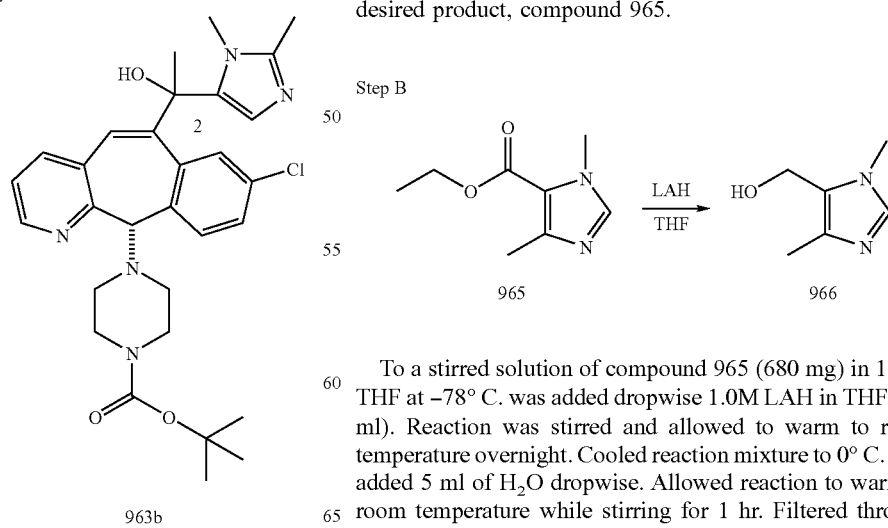

To a stirred solution of compound 965 (680 mg) in 10 ml THF at −78° C. was added dropwise 1.0M LAH in THF (5.0 ml). Reaction was stirred and allowed to warm to room temperature overnight. Cooled reaction mixture to 0° C. then added 5 ml of $H_2O$ dropwise. Allowed reaction to warm to room temperature while stirring for 1 hr. Filtered through celite and rinsed with 20 ml THF/40 ml $H_2O$. A clear filtrate obtained. Filtrate afforded compound 966.

Step C

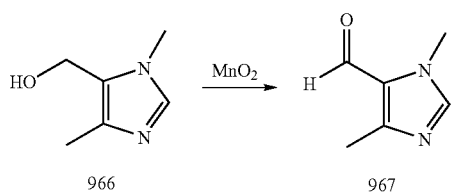

To a stirred solution of compound 966 (~4 mmol) at room temperature was added (3.0 g) of MnO₂, a suspension resulted. Heated reaction mixture to a gentle reflux for 18 hr. Additional MnO₂/THF was added (6.0 g/20 ml). Stirred at reflux for 24 hr. Cooled to room temperature, filtered through celite and rinsed with 50 ml MeOH Solvent was evaporated and azeotroped residue with toluene to afford crude product. Crude was purified by column chromatography (20:1 CH₂Cl₂/MeOH), then (8:1 CH₂Cl₂:MeOH) to elute out desired product as a white solid, compound 967.

Step D

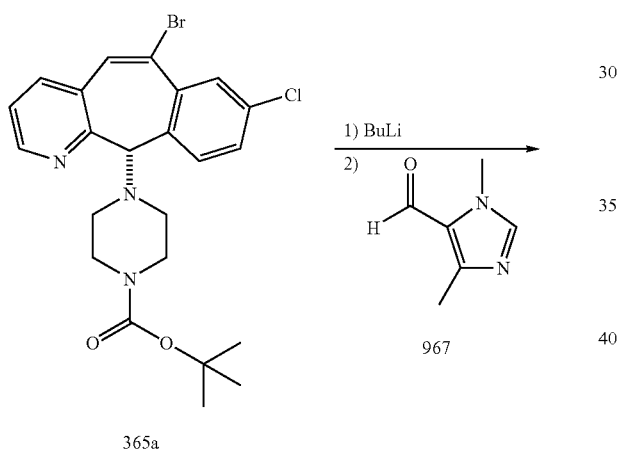

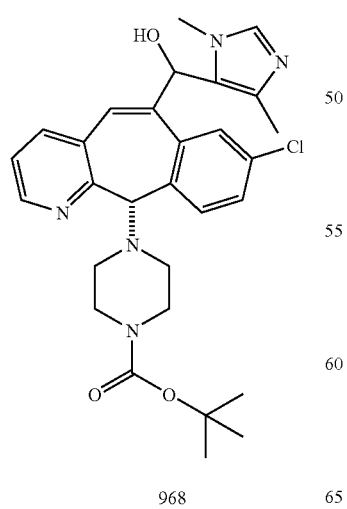

If one were to follow essentially the same procedures as in Example 510 (Step A), but using compound 967 as the intermediate, then one could prepare compound 968 could be prepared.

Step E

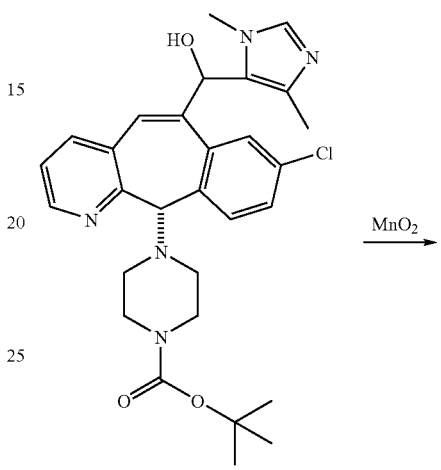

If one were to follow essentially the same procedures as in Example 510 (Step B), but using compound 968 as the starting materithen al, then one could prepare compound 969.

Step F
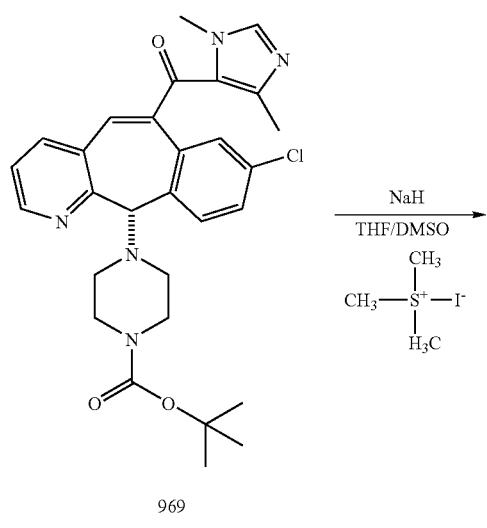
969
Step G
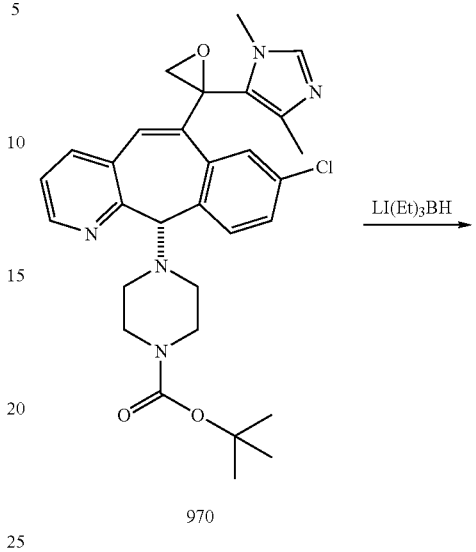
970
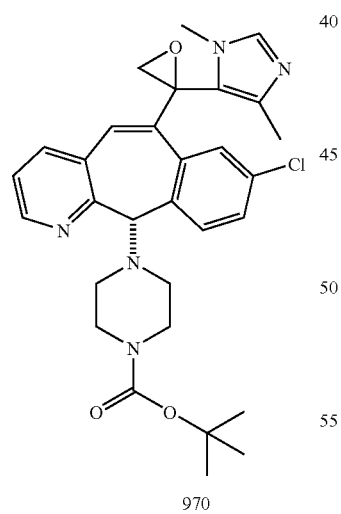
970
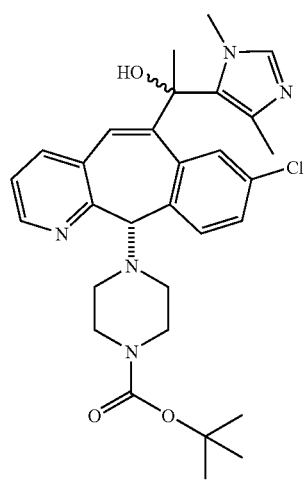
971
If one were to follow essentially the same procedures as in Example 510 (Step C), but using compound 969 as the starting material, then one could prepare compound 970.
If one were to follow essentially the same procedures as in Example 510 (Step D), but using Compound 970 as the starting material, then one could prepare compound 971.

Step H

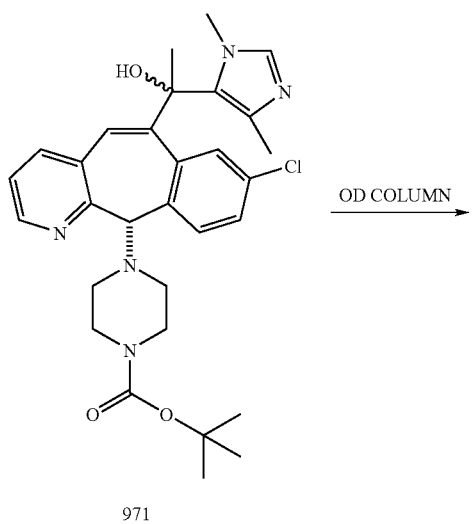

971

OD COLUMN →

971a

+

971b

If one were to follow essentially the same procedures as in Example 510 (Step E), then compound 971 could be separated by Chiral HPLC to give compounds 971a and 971b.

PREPARATIVE EXAMPLE 111

Step A

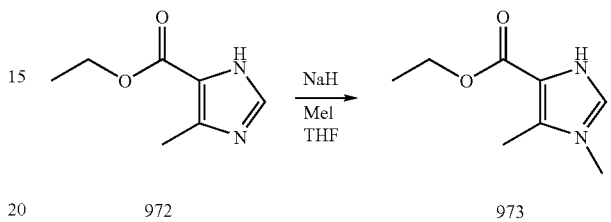

972    973

To a stirred solution of 972 (ethyl 4-methyl-5-imidazole carboxylate, 3.08 g, 20 mmol) in 30 ml of THF, at room temperature, was added NaH (0.8 g, 20 mmol) portionwise. Stirred at room temperature for 10 minutes, then cooled to 0° C. Added in MeI (1.5 ml, 24 mmol) stirred for 2 h, quenched with saturated NH$_4$Cl, extracted with ethyl acetate (2×), and washed with brine. Purified crude by column chromatography using a 20:1 CH$_2$Cl$_2$:MeOH, to afford product, compound 973.

Step B

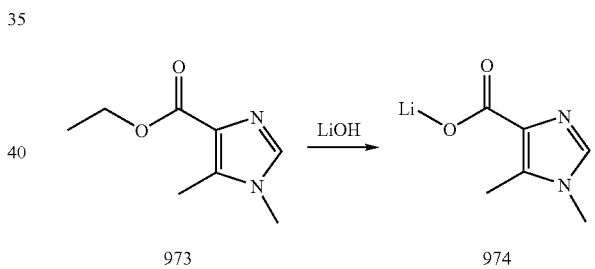

973    974

To a stirred solution of compound 973 (0.9 g) in 15 ml THF, was added 3 ml of a 10% LiOH solution and stirred reaction for 2 days. Evaporated solvent, azeotroped once with toluene, evaporated solvent to afford product, compound 974.

Step C

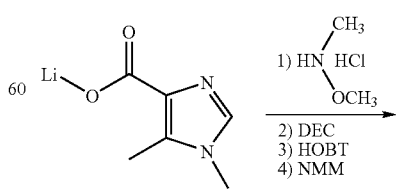

974

-continued

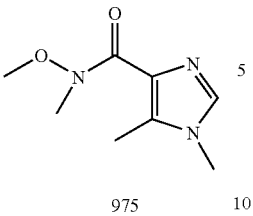

975

To a stirred solution of compound 974 (~5.4 mmol) in 40 ml of anhydrous DMF at room temperature under N₂, was added, 1.05 g, 10.8 mmol of (1); 2.07 g, 10.8 mmol of (2); 0.729 g, 5.4 mmol of (3); and 5.5 ml, 50 mmol of (4). Reaction mixture was stirred at room temperature for 5 hours. Reaction progress was monitored by TLC. Added 1N HCl until pH<5, extracted with diethyl ether (2×), cooled to 0° C. then basified with saturated NaHCO₃, extracted with CH₂Cl₂, dry with MgSO₄, evaporated the solvent to afford 0.6 g of compound 975, brown oil.

Step D

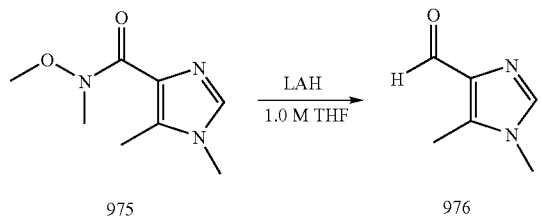

975    976

To compound 975 (0.590 g, 3.2 mmol) in 5 ml of toluene at −70° C., was added (3.6 ml, 3.6 mmol of LAH (1M in THF)) dropwise. Reaction mixture was stirred at temperatures ranging from −70° C. to −50° C. for 30 minutes. Quenched reaction with 4 ml brine, and stirred at room temperature for 20 minutes. Reaction was eluted through a cake of celite with ethyl acetate/CH₂Cl₂. Dried filtrate, evaporated solvent to afford 0.162 g of product (yellow oil), compound 976.

Step E

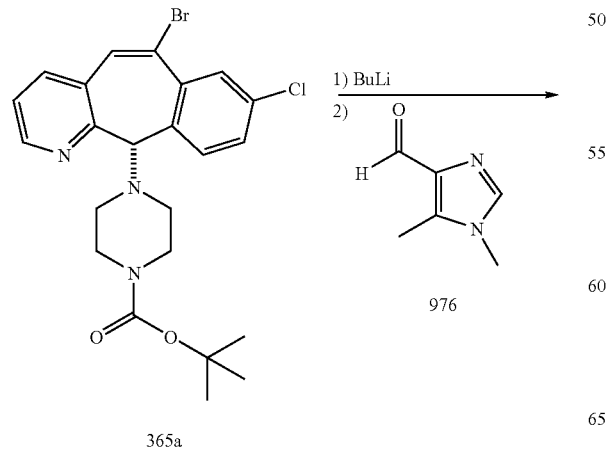

365a    976

-continued

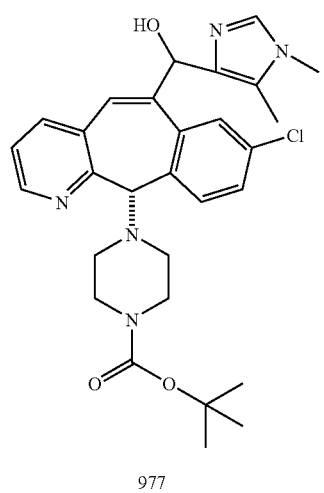

977

Following essentially the same procedures as in Example 510 (Step A), reacting compound 365a (0.612 g, 1.25 mmol) but using compound 976 (0.152 g) as the intermediate, compound 977 was prepared.(Yellow solid, 0.408 g).

Step F

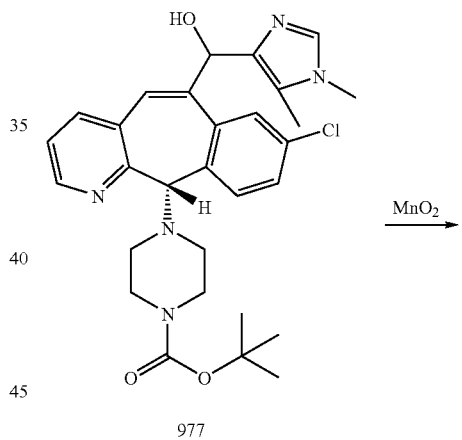

977

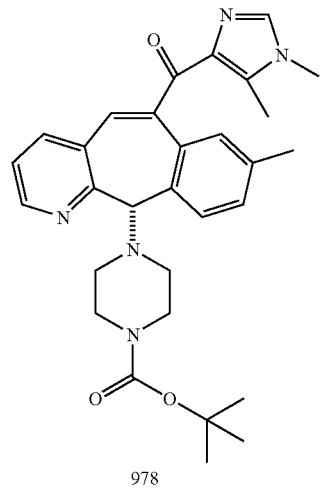

978

If one were to follow essentially the same procedures as in Example 510 (Step B), but using Compound 977 as the starting material, then one could prepare compound 978.

Step G

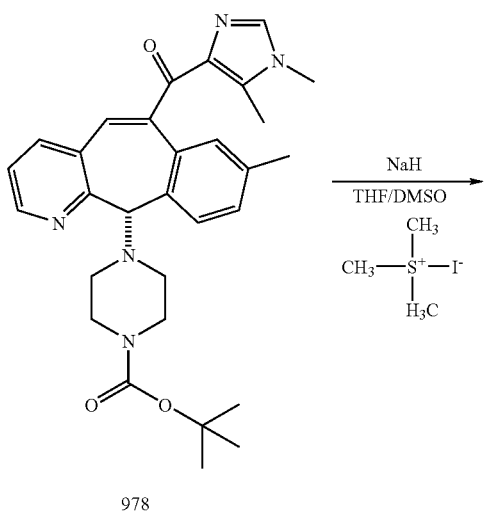

978

Step H

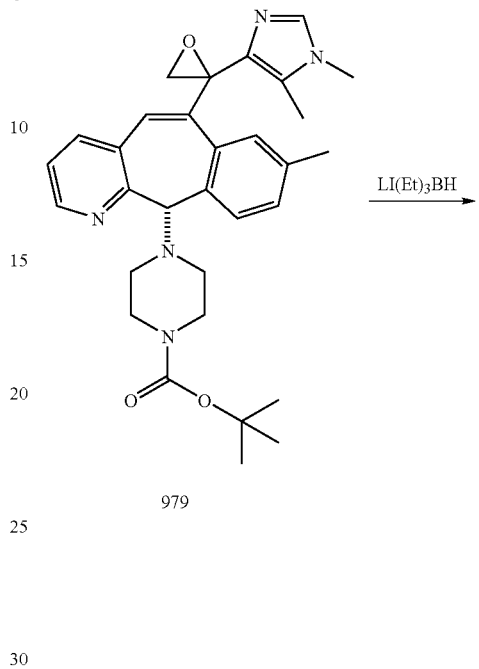

979

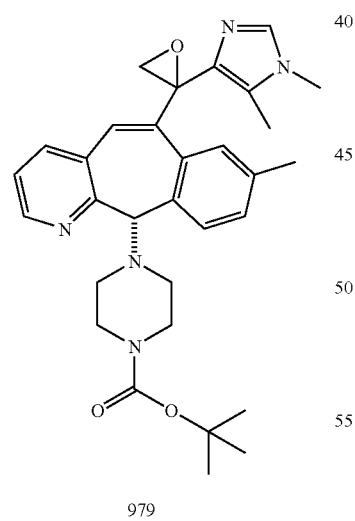

979

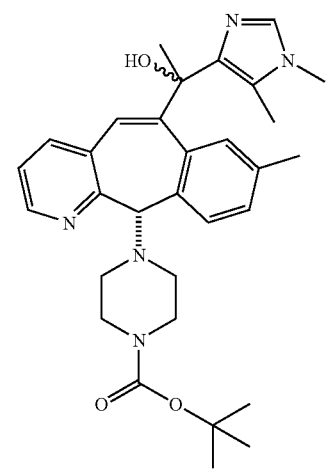

980

If one were to follow essentially the same procedures as in Example 510 (Step C), but using compound 978 as the starting material, then compound 979 could be prepared.

If one were to follow essentially the same procedures as in Example 510 (Step D), but using Compound 979 as the starting material, then one could prepare compound 980.

Step I

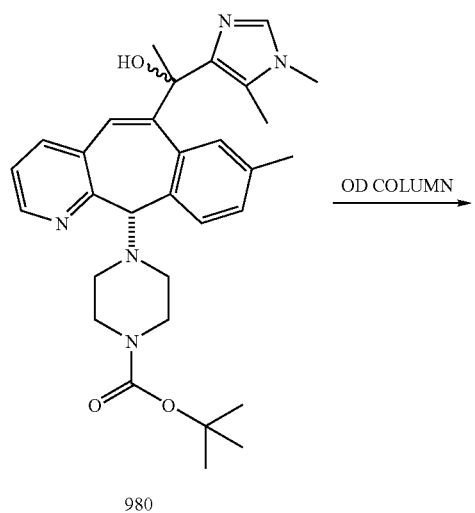

980

OD COLUMN

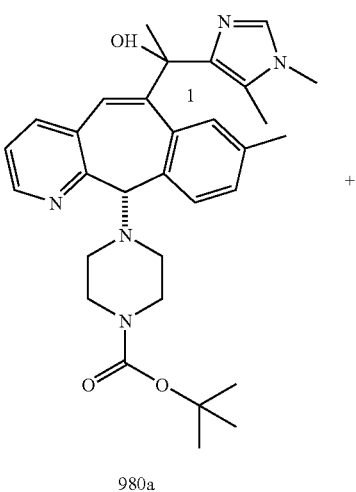

980a

+

980b

If one were to follow essentially the same procedures as in Example 510 (Step E), compound 980 could be separated by Chiral HPLC using a Chiral OD Prep HPLC column to give compounds 980a and 980b.

PREPARATIVE EXAMPLE 112

Step A

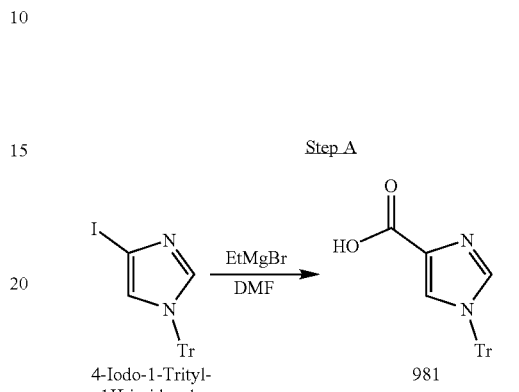

4-Iodo-1-Trityl-1H-imidazole

981

Rep. Org. Prep. Proceed. Int. (1996) 28(6), 709-710.

To a stirred solution of 4-iodo-1-trityl-1H-imidazole (4.36 g, 10 mmol) in THF (100 ml) was added EtMgBr (4 ml, 12 mmol) and let stir for 30 minutes. DMF (0.93 ml, 12 mmol) was added and let stir for 1 hour. The reaction was poured into saturated ammonium chloride and extracted with EtOAc. The organic layer was dried with MgSO$_4$, filtered, and concentrated under vacuo to yield 3.5 g of light yellow solid.

Step B

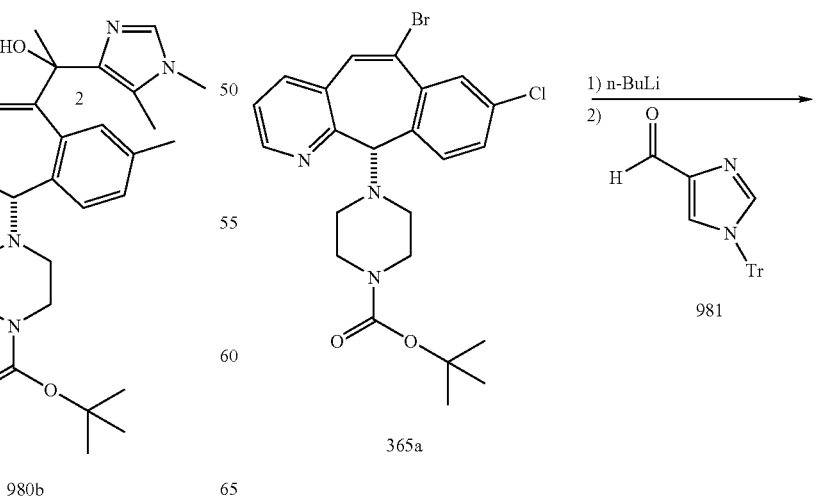

365a

-continued

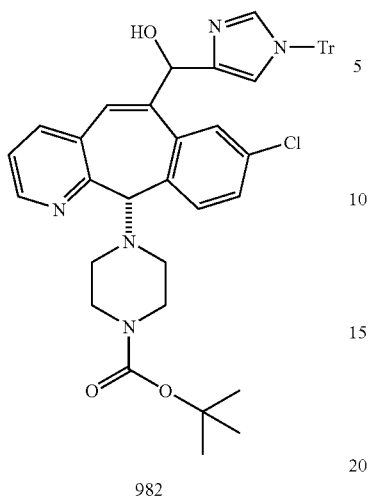
982

-continued

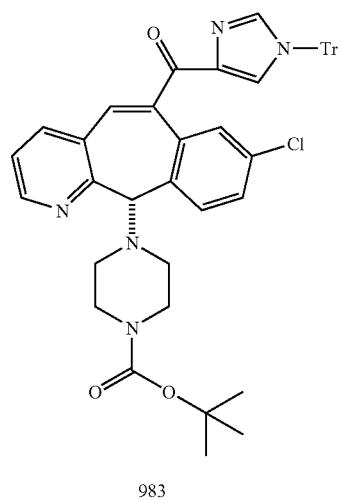
983

Following essentially the same procedures as in Example 510 (Step A), but using compound 981 (0.72 g) as the intermediate and MgBr.Et₂O (2.58 g in 50 ml THF, 7.5 ml), crude compound 982 was obtained. The crude material was purified via preparative plate chromatography (1-3% MeOH with NH₃/CH₂Cl₂) to obtain pure product, compound 982 (0.29, 39%).

Following essentially the same procedures as in Example 510 (Step B), but using compound 982 (0.29 g) as the starting material, compound 983 was prepared (0.29 g). The crude material was purified via preparative plate chromatography (2% MeOH with NH₃/CH₂Cl₂) to yield 0.237 g of pure product, compound 983.

Step C

Step D

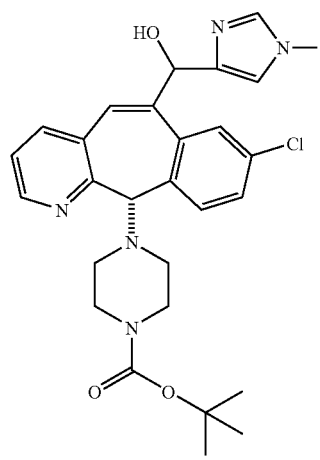
982

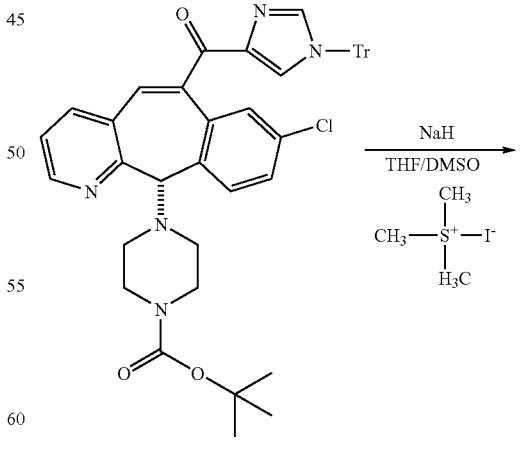
983

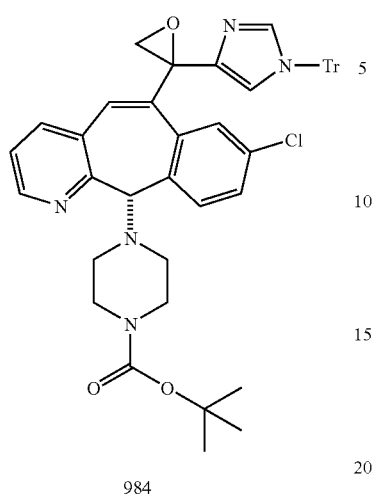

984

Following essentially the same procedures as in Example 510 (Step C), but using compound 983 (230 mg) as the starting material, compound 984 was prepared (222 mg).

Step E

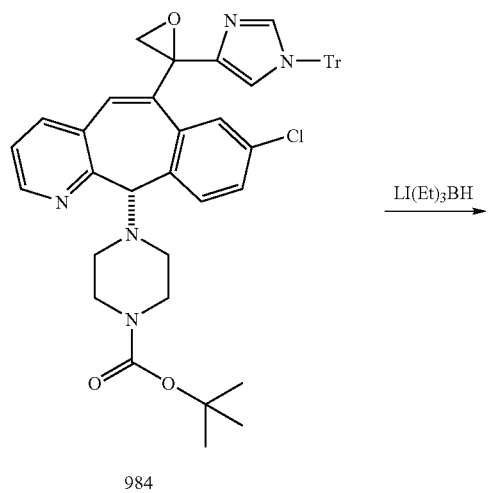

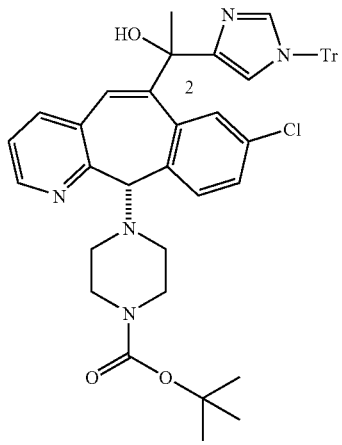

985b

Following essentially the same procedures as in Example 510 (Step D), but using compound 984 (0.2 g) as the starting material, crude isomers 985a and 985b were prepared. The isomers were purified and separated via preparative plate chromatography (5% MeOH with NH$_3$/CH$_2$Cl$_2$) to obtain 0.16 g of pure 985a and 0.06 g of pure 985b.

PREPARATIVE EXAMPLE 113

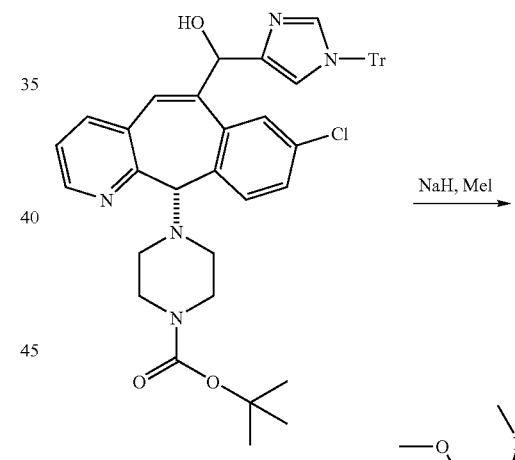

982

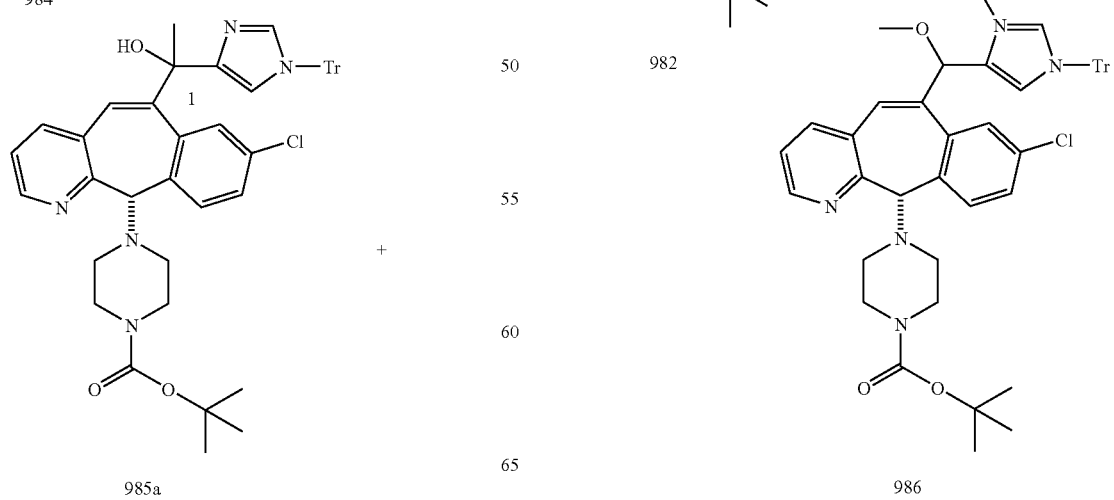

887

To compound 982 (390 mg) dissolved in THF (3 ml) was added NaH (60% in mineral oil, 28 mg). After 5 minutes, iodomethane was added and let stir for several hours. The reaction was concentrated under vacuo and carried on crude to the next reaction.

PREPARATIVE EXAMPLE 114

Step A

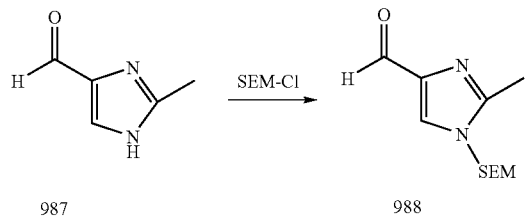

To a stirred solution of 987 (2-methyl-1H-imidazole-4-carboxaldehyde, 1 g, 9.09 mmol) in 10 ml of DMF at 0° C. was added NaH (60% in mineral oil (0.36 g)) portionwise. Stirred mixture for ½ hr, then added SEM-Cl (2.02 ml, 9.9 mmol). Stirred reaction until completed. Added reaction mixture to brine and extracted with CH$_2$Cl$_2$ (3×). Evaporated solvent to get an oil. Column chromatography (CH$_2$Cl$_2$ (100%-2% MeOH.NH$_3$/CH$_2$Cl$_2$) afforded 1.68 g of product, compound 988 (77%).

Step B

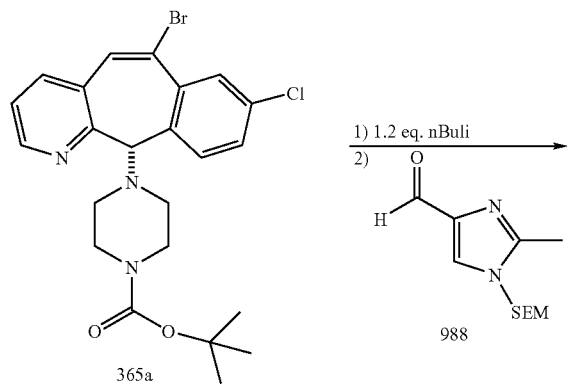

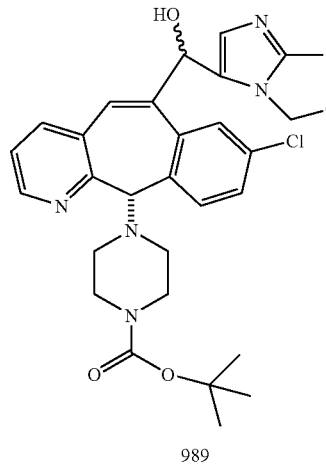

888

Following essentially the same procedures as in Example 510 (Step A), reacting compound 365a (0.12 g, 0.25 mmol) but using compound 988 (0.1 g) as the intermediate, compound 989 was prepared (96 mg, 56%).

Step C

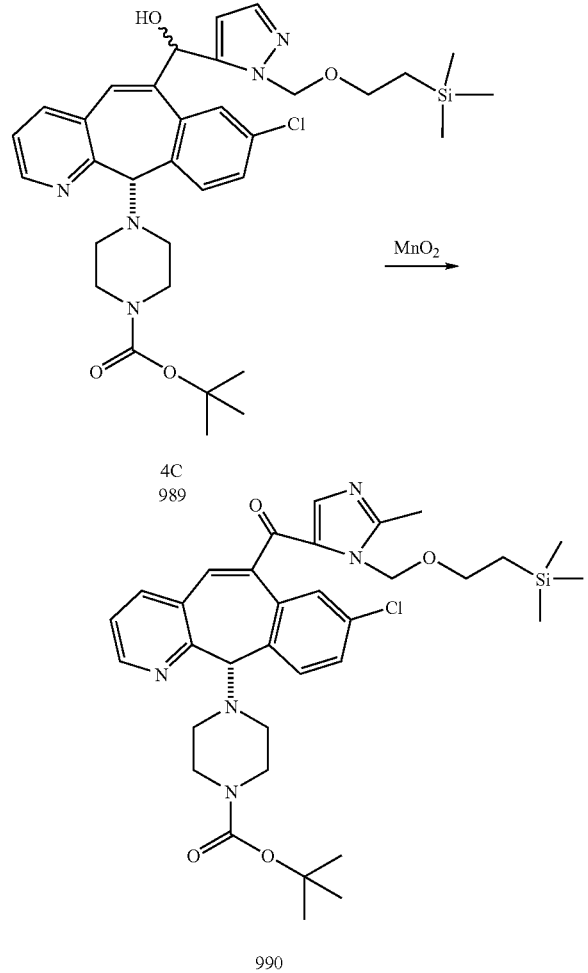

Following essentially the same procedures as in Example 510 (Step B), but using Compound 989 (0.52 g, 0.79 mmol) as the starting material, compound 990 was prepared.

Step D

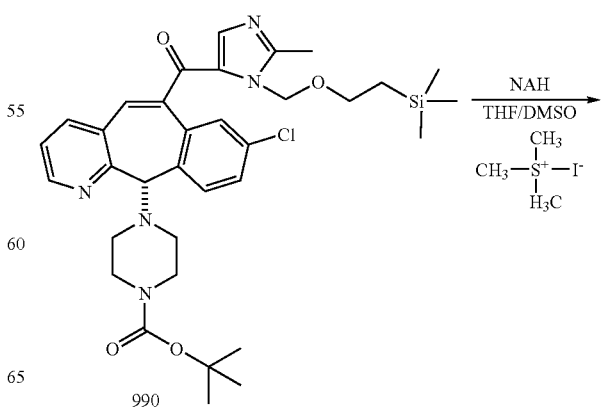

-continued

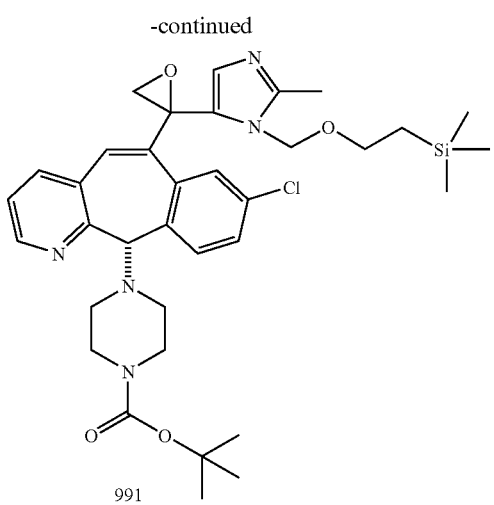

991

Following essentially the same procedures as in Example 510 (Step C), but using compound 990 (0.51 g, 0.79 mmol) as the starting material, compound 991 was prepared.

Step E

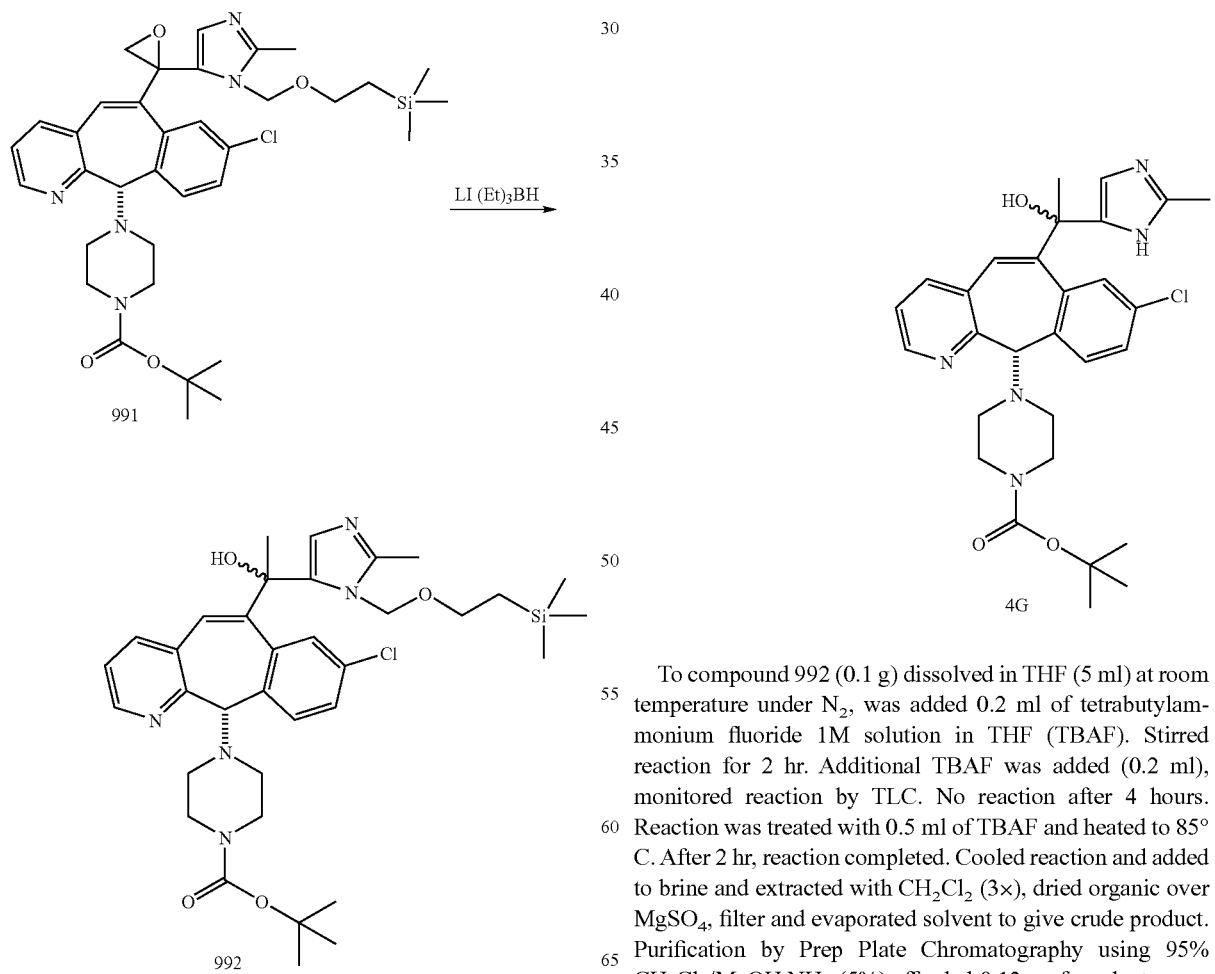

Following essentially the same procedures as in Example 510 (Step D), but using Compound 991 (0.79 mmol) as the starting material, compound 992 was prepared.

Step F

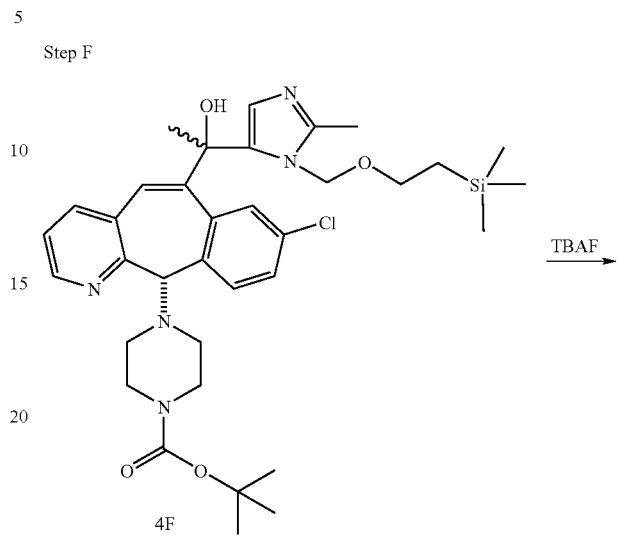

To compound 992 (0.1 g) dissolved in THF (5 ml) at room temperature under $N_2$, was added 0.2 ml of tetrabutylammonium fluoride 1M solution in THF (TBAF). Stirred reaction for 2 hr. Additional TBAF was added (0.2 ml), monitored reaction by TLC. No reaction after 4 hours. Reaction was treated with 0.5 ml of TBAF and heated to 85° C. After 2 hr, reaction completed. Cooled reaction and added to brine and extracted with $CH_2Cl_2$ (3×), dried organic over $MgSO_4$, filter and evaporated solvent to give crude product. Purification by Prep Plate Chromatography using 95% $CH_2Cl_2$/MeOH.$NH_3$ (5%) afforded 0.12 g of product, compound 993.

PREPARATIVE EXAMPLE 115

Step G

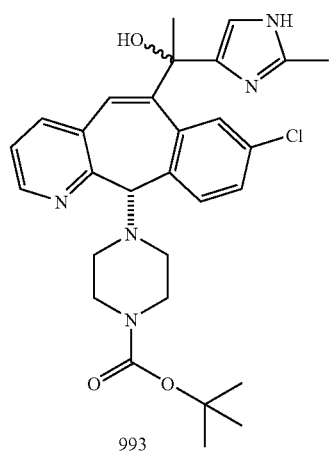
993

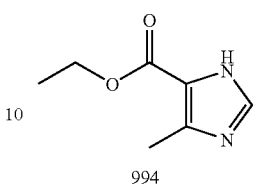
OD COLUMN

Step A

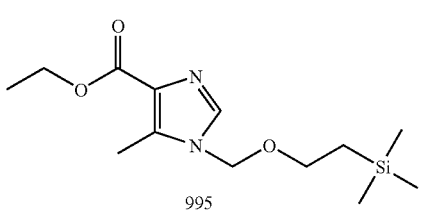
994

SEM—Cl

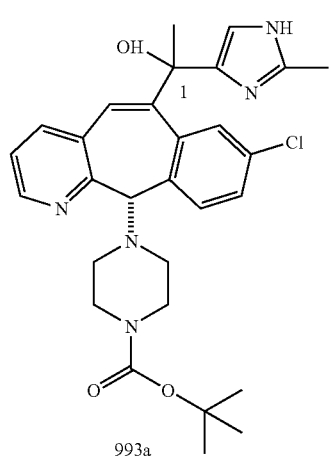
993a

+

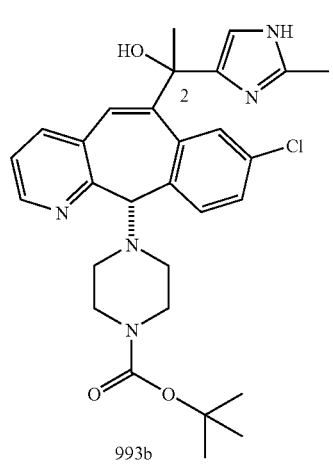
993b

To a stirred solution of 994 (3.08 g, 20 mmol) in 15 ml of DMF at 0° C. was added NaH (60% in mineral oil, 0.80 g) portionwise. After stirring for several minutes, SEM-Cl (3.54 ml, 20 mmol) was added and let the reaction stir overnight. Brine was added to the reaction and extracted with EtOAc. The organic layer was washed with water and brine, dried with MgSO$_4$, filtered and concentrated under vacuum. Purified by flash elute column chromatography (CH2Cl2/MeOH, 50:1 to 20:1) to afford 4.54 g of yellow oil, compound 995.

Step B

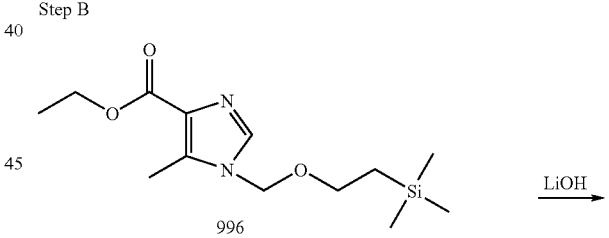
996

LiOH

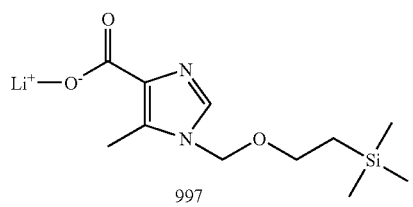
997

If one were to follow essentially the same procedures as in Example 510 (Step E), then compound 993 could be separated by Chiral HPLC to give compounds 993a and 993b, using a Chiral OD Prep HPLC Column.

To a stirred solution of compound 995 (3.5 g) in THF (50 ml) was added a LiOH solution (1 M, 24 ml) and stirred for 2 days. The reaction was not complete; therefore, 25 ml of MeOH and another 10 ml of the LiOH solution was added and the reaction was heated to 40° C. for 2 hours. The reaction was concentrated under vacuo, azeotroped once with toluene, and evaporated to dryness to afford compound 996, which was carried on directly without further purification.

Step C

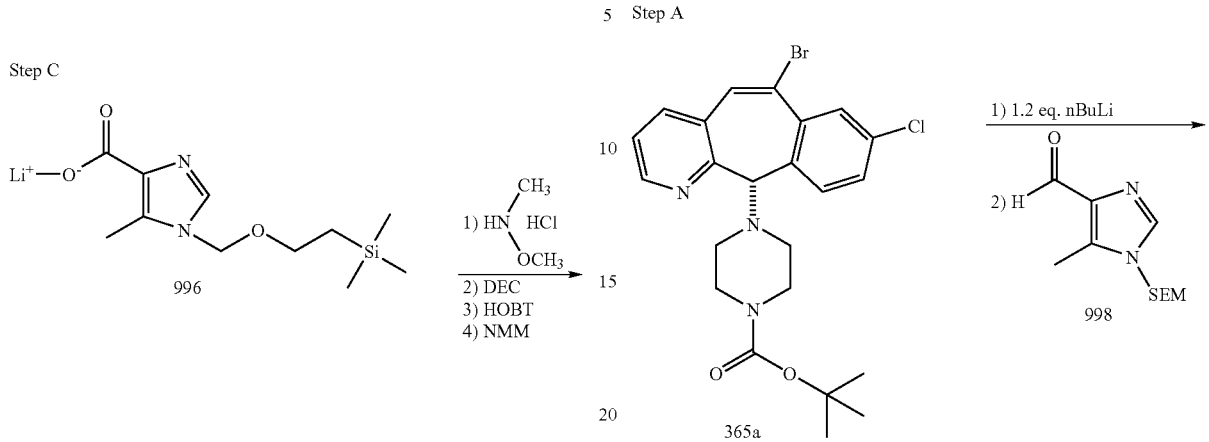

Following a similar procedure to that described in Preparative Example 111 Step C, but using compound 996, compound 997 was prepared (5.37 g crude).

Step D

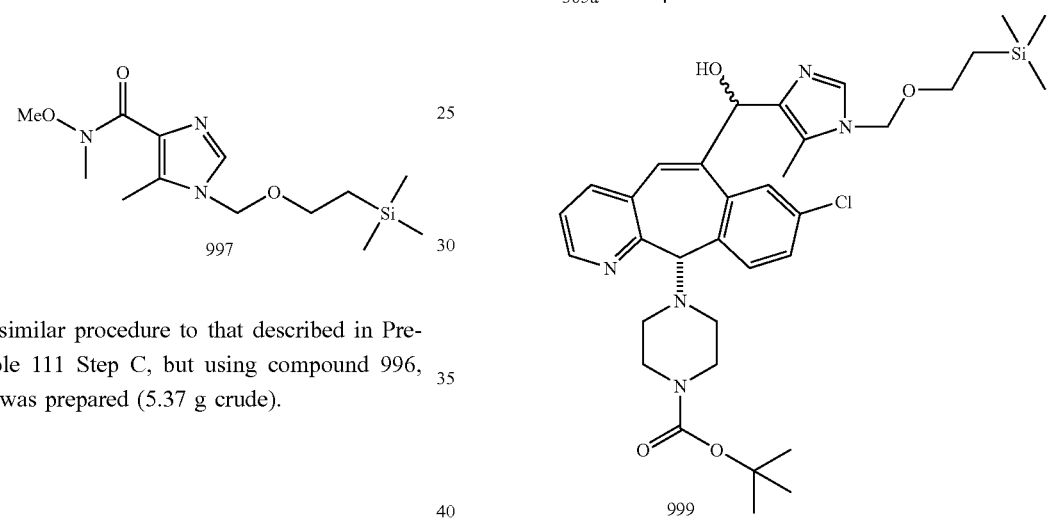

Following a similar procedure to that described in Preparative Example 111 Step D, but using compound 997 (4.2 g), compound 998 was prepared.

PREPARATIVE EXAMPLE 116

Step A

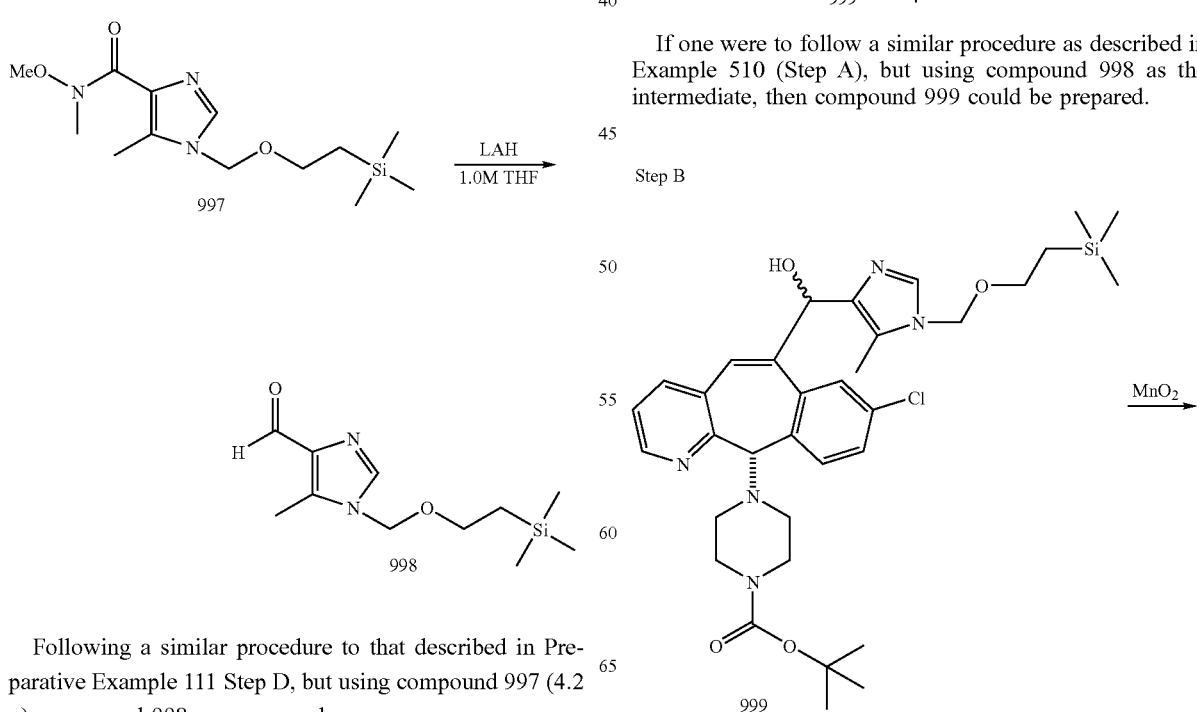

If one were to follow a similar procedure as described in Example 510 (Step A), but using compound 998 as the intermediate, then compound 999 could be prepared.

Step B

-continued

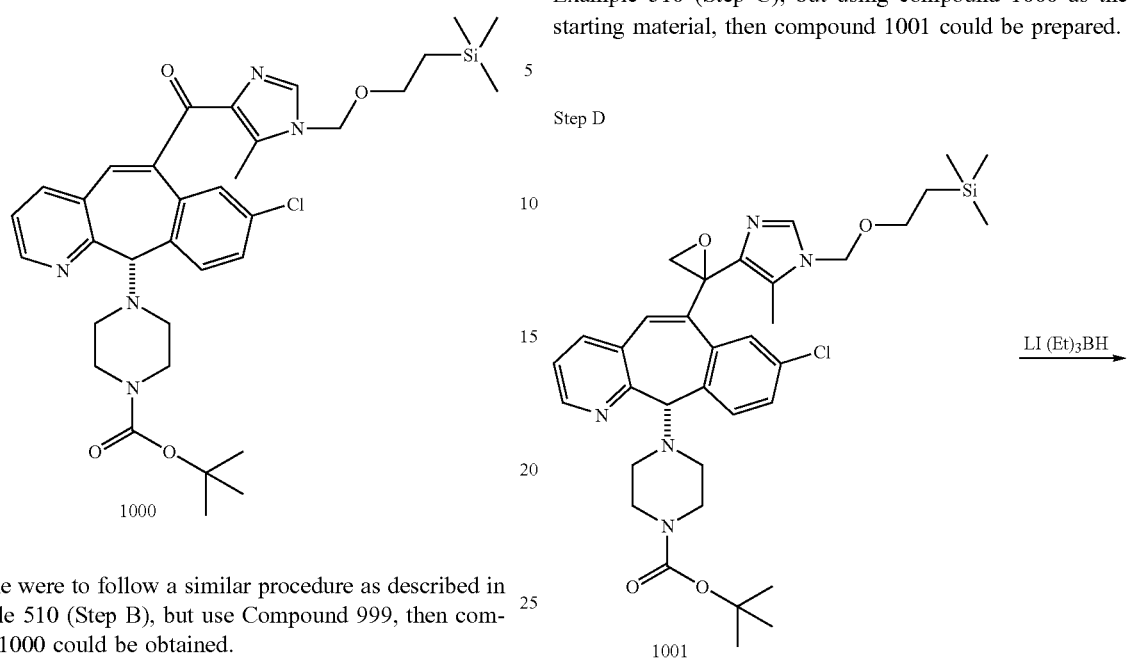

1000

If one were to follow a similar procedure as described in Example 510 (Step B), but use Compound 999, then compound 1000 could be obtained.

Step C

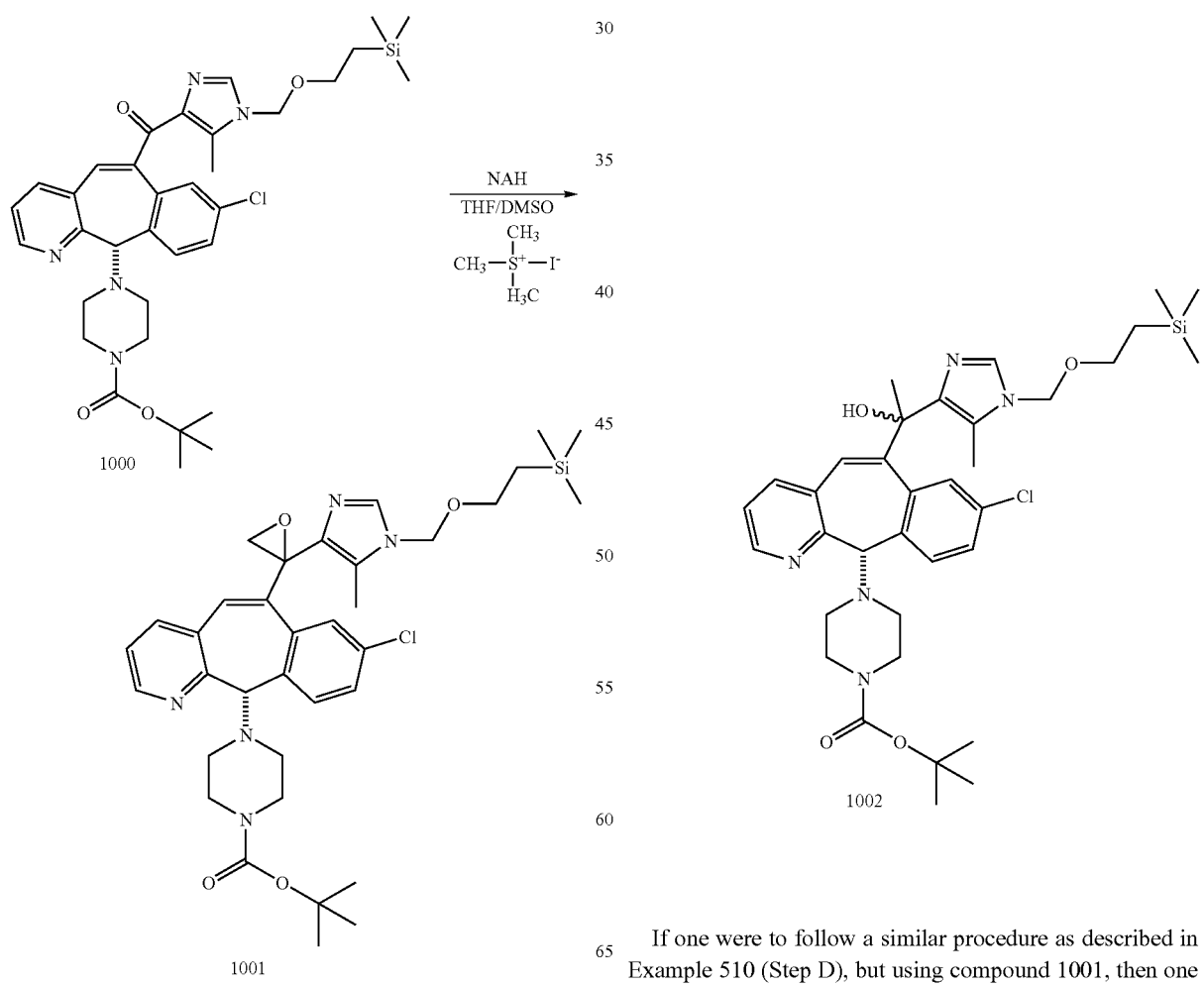

If one were to follow a similar procedure as described in Example 510 (Step C), but using compound 1000 as the starting material, then compound 1001 could be prepared.

Step D

If one were to follow a similar procedure as described in Example 510 (Step D), but using compound 1001, then one could obtain compound 1002.

Step E
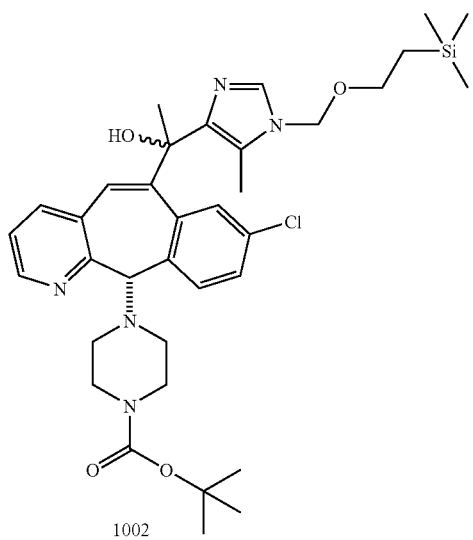
Step F
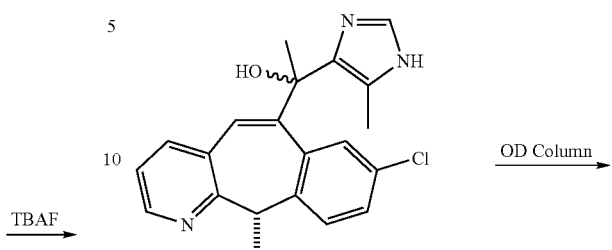
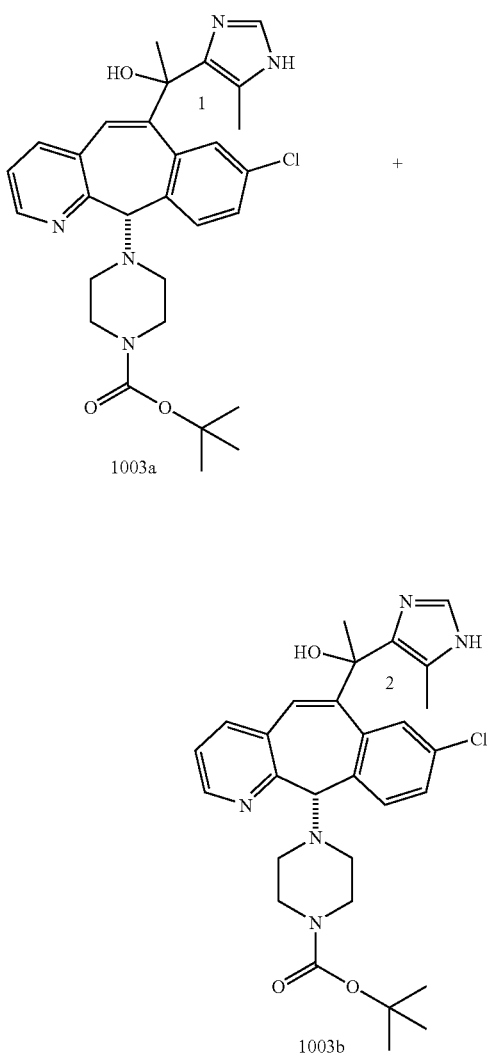
If one were to follow a similar procedure as described in Preparative Example 114 (Step F), but using compound 1002, then one could obtain compound 1003.

899

If one were to follow a similar procedure as described in Example 510 (Step E), then compound 1003 could be separated by Chiral HPLC to give compounds 1003a and 1003b.

EXAMPLE 1588

Compound 963a (Isomer 1) and compound 963b (Isomer 2) were converted to compound 1004a and compound 1004b by following a similar procedure as described in Example 507.

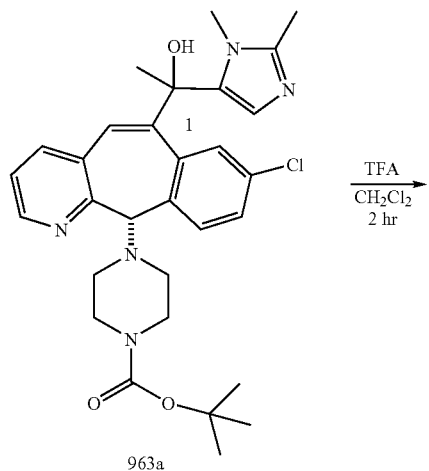

900

-continued

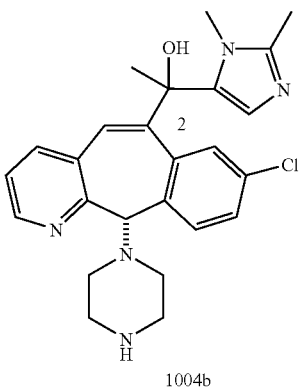

EXAMPLE 1589

Compound 971a (Isomer 1) and compound 971b (Isomer 2) were converted to compound 1005a and compound 1005b by following a similar procedure as described in Example 507.

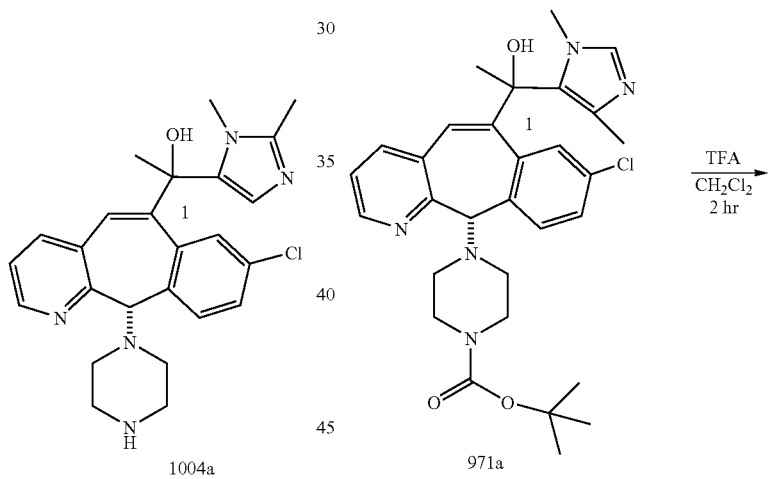

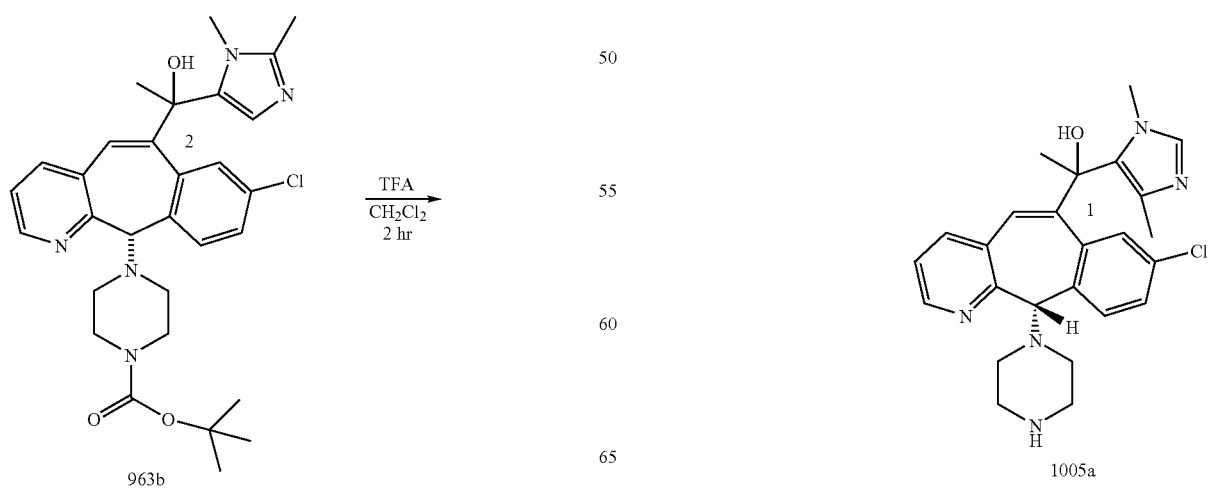

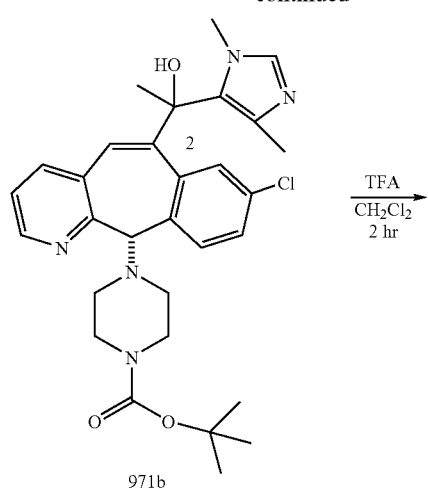
971b
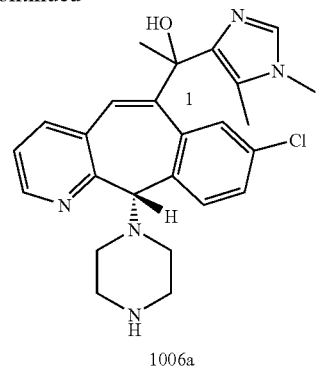
1006a
EXAMPLE 1590
Compound 980a (Isomer 1) and compound 980b (Isomer 2) were converted to compound 1006a and compound 1006b by following a similar procedure as described in Example 507.
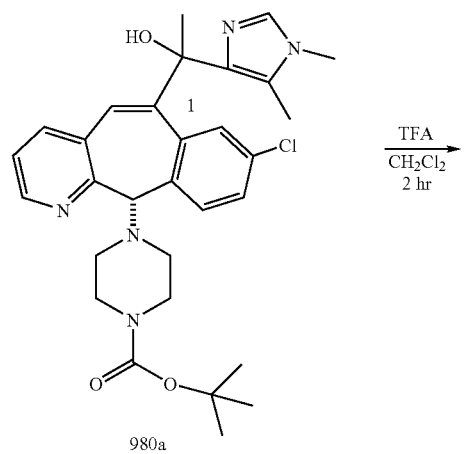
980a
EXAMPLE 1591
Isomers 985a and 985b were converted to compound 1007a and compound 1007b by following a similar procedure as described in Example 507.

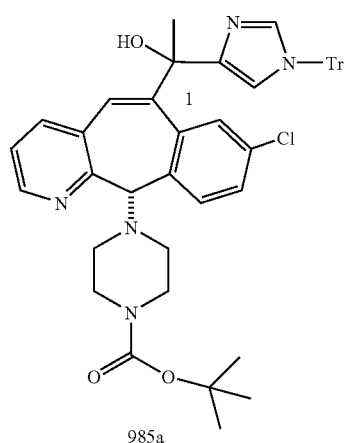

985a

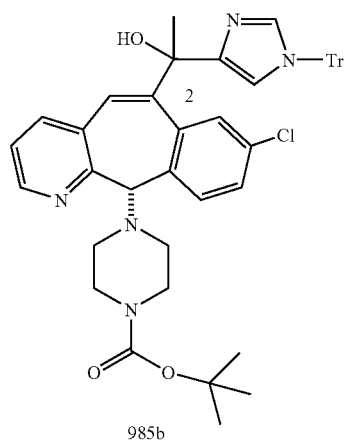

985b

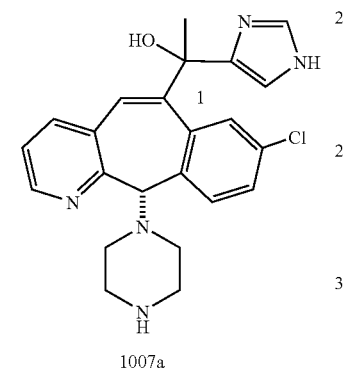

1007a

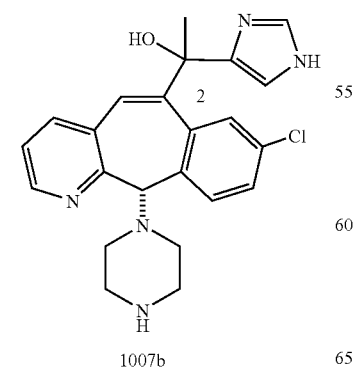

1007b

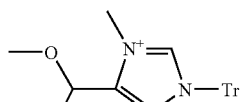

TFA →

TFA →

EXAMPLE 1592

To the product from Preparative Example 113 dissolved in CH$_2$Cl$_2$ (5 ml) was added trifluoroacetic acid (1 ml) and let stir for 1 hour. The reaction was concentrated under vacuo and carried on crude to the next reaction.

986

$\xrightarrow{\text{THF}}{\text{TFA}}$

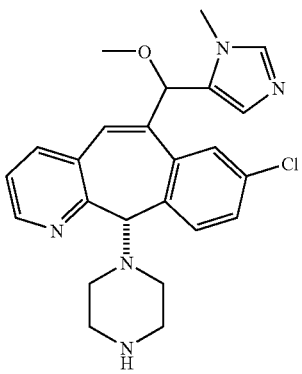

1008

EXAMPLE 1593

Compound 993a (Isomer 1) and compound 993b (Isomer 2) were converted to compound 1009a and compound 1009b by following a similar procedure as in Example 507.

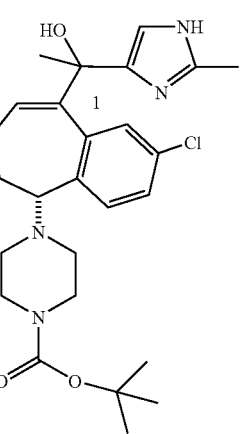

993a $\xrightarrow[\text{CH}_2\text{Cl}_2]{\text{TFA}}{2 \text{ hr}}$

-continued
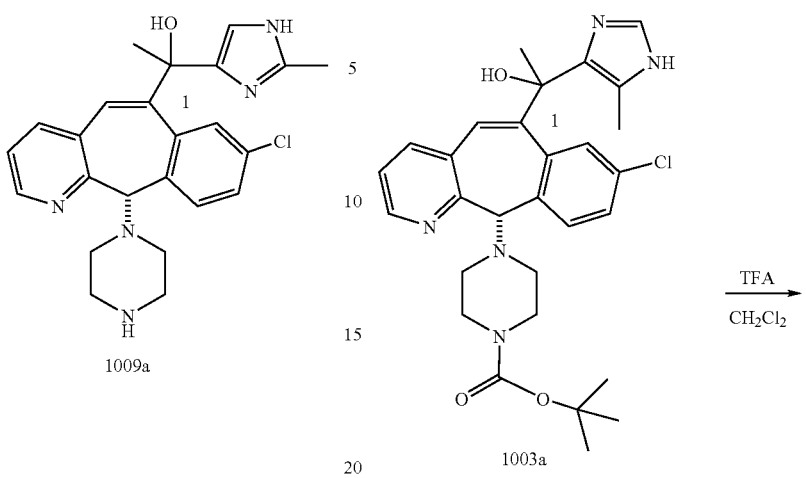
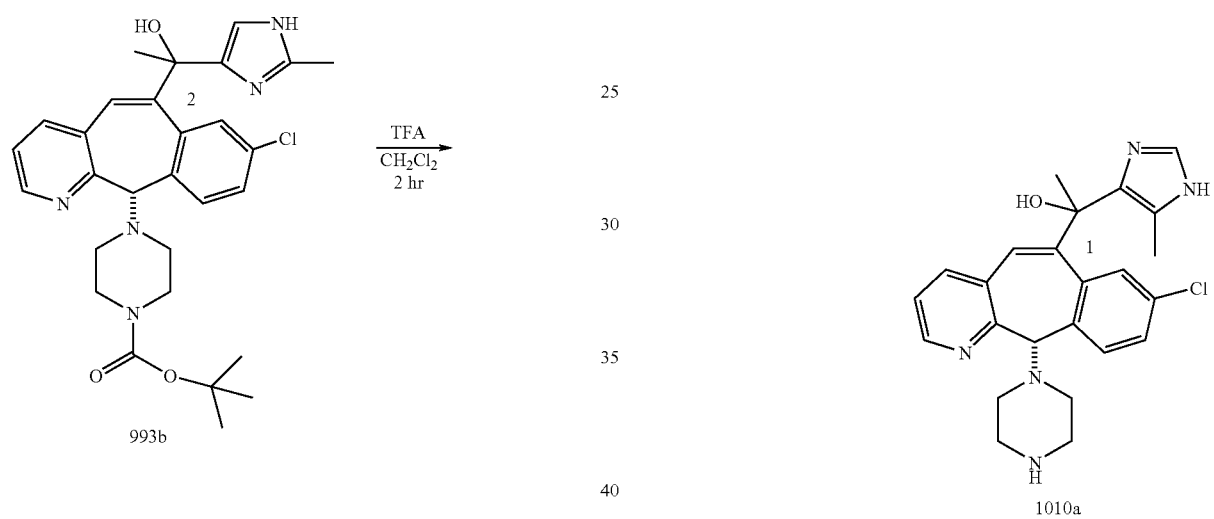
EXAMPLE 1594
If one were to follow a similar procedure as described in Example 507, then compound 1003a (isomer 1) and compound 1003b (Isomer 2) can be converted to compound 1010a and compound 1010b.
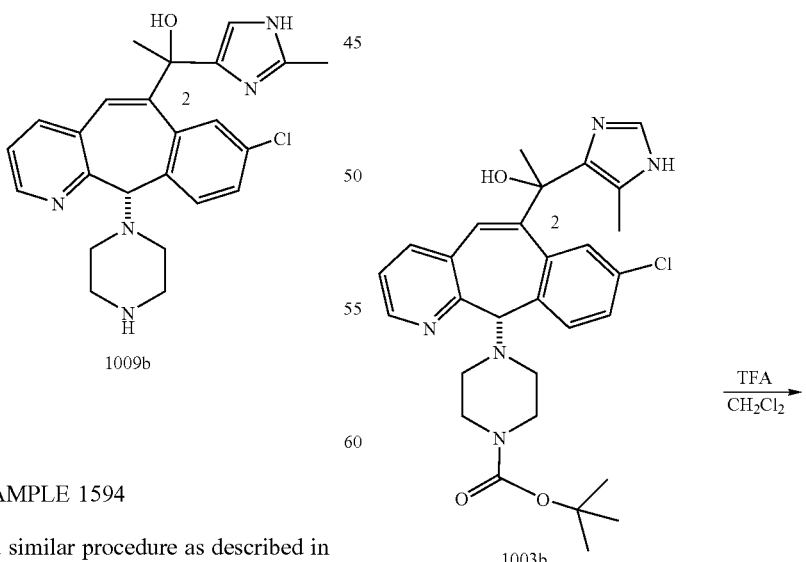

-continued

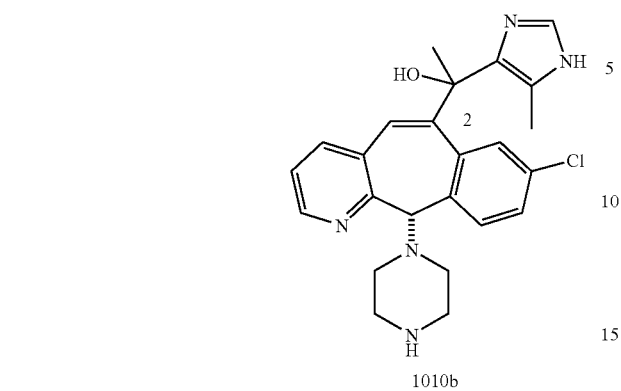

1010b

EXAMPLE 1595-1619

If one were to react each isomer, 1004a and 1004b, from Example 1588 in essentially the same manner as in Example 511-513, then one would obtain compounds of the formulas:

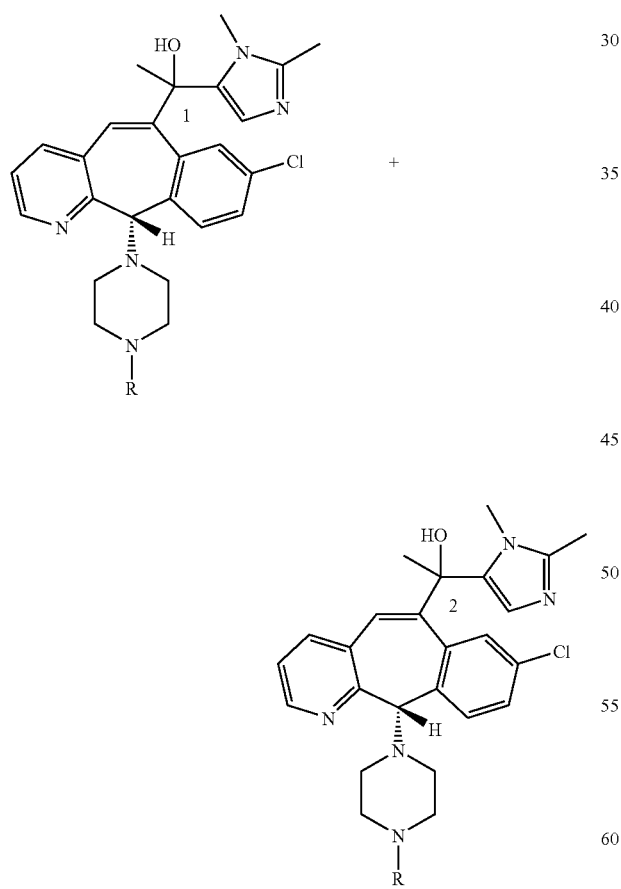

wherein R is defined in Table 106 and the numbers 1 and 2 in the formulas represent isomers 1 and 2, respectively.

TABLE 106

| Example | R Isomer 1 and Isomer 2 |
|---|---|
| 1595 | —C(O)NH₂ |
| 1596 | —C(O)NHCH₃ |
| 1597 | —C(O)NH-iPr |
| 1598 | —C(O)NHEt |
| 1599 | —C(O)NH-tBu |
| 1600 | —C(O)NH-nPr |
| 1601 | —C(O)NH-iBu |
| 1602 | —C(O)NH-allyl |
| 1603 | —C(O)NH-cyclopentyl |
| 1604 | —C(O)NH-cyclohexyl |

TABLE 106-continued
| Example | R Isomer 1 and Isomer 2 |
|---|---|
| 1605 | 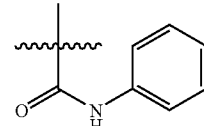 |
| 1606 | 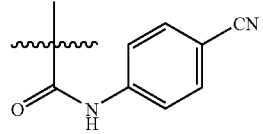 |
| 1607 | 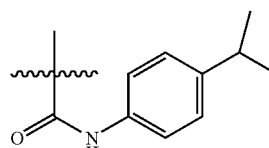 |
| 1608 | 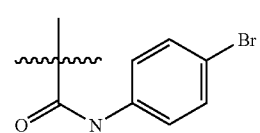 |
| 1609 | 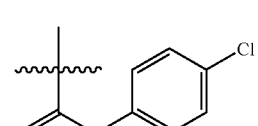 |
| 1610 | 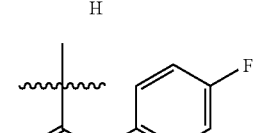 |
| 1611 | 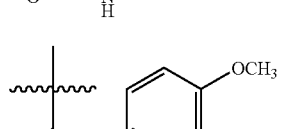 |
| 1612 | 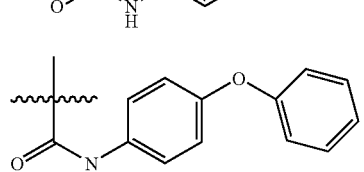 |
| 1613 | 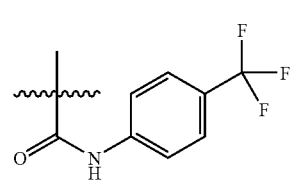 |
| 1614 | 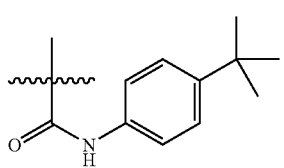 |
| 1615 | 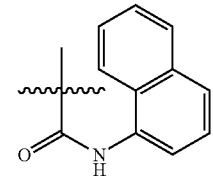 |
| 1616 | 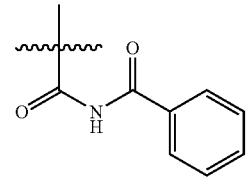 |
| 1617 | 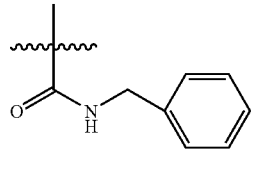 |
| 1618 | 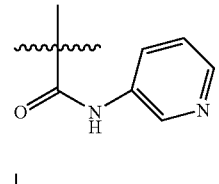 |
| 1619 | 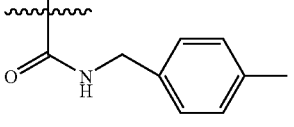 |
EXAMPLE 1620-1647
If one were to react each isomer, 1004a 1004b, from Example 1588 in essentially the same manner as in Example 536, then one would obtain compounds of the formulas:
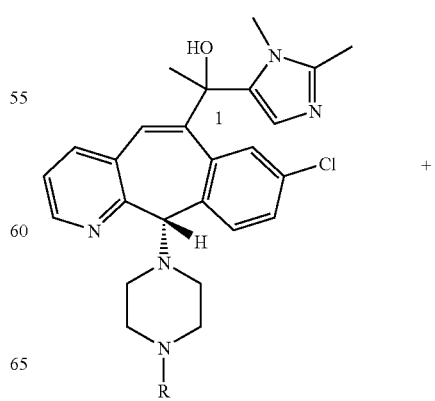

-continued
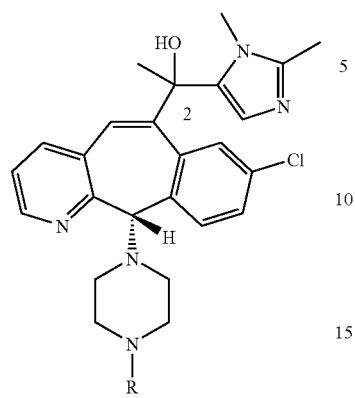
wherein R is defined in Table 107 and the numbers 1 and 2 in the formulas represent isomers 1 and 2, respectively.
TABLE 107
| Example | R Isomer 1 and Isomer 2 |
|---|---|
| 1620 | |
| 1621 | |
| 1622 | |
| 1623 | |
| 1624 | |
| 1625 | |
TABLE 107-continued
| Example | R Isomer 1 and Isomer 2 |
|---|---|
| 1626 | |
| 1627 | |
| 1628 | |
| 1629 | |
| 1630 | |
| 1631 | |
| 1632 | |
| 1633 | |
| 1634 | |

TABLE 107-continued
| Example | R Isomer 1 and Isomer 2 |
|---|---|
| 1635 | 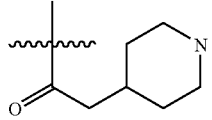 |
| 1636 | 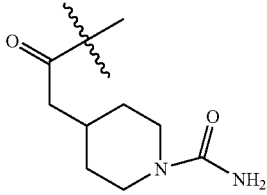 |
| 1637 | 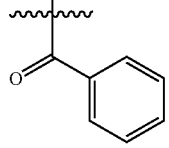 |
| 1638 | 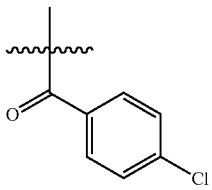 |
| 1639 | 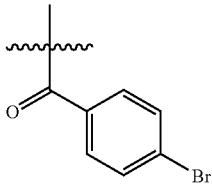 |
| 1640 | 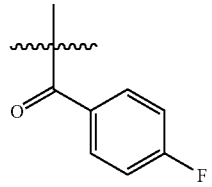 |
| 1641 | 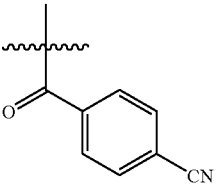 |
| 1642 | 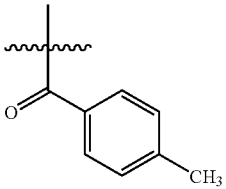 |
TABLE 107-continued
| Example | R Isomer 1 and Isomer 2 |
|---|---|
| 1643 | 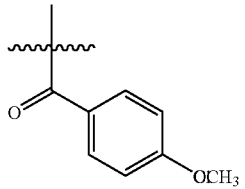 |
| 1644 | 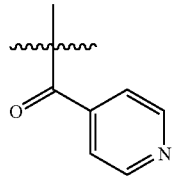 |
| 1645 | 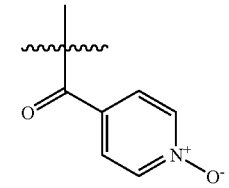 |
| 1646 | 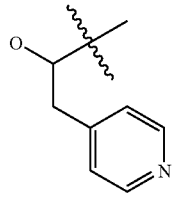 |
| 1647 | 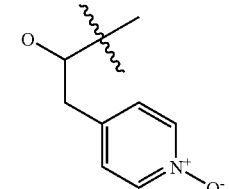 |
EXAMPLE 1648-1671
If one were to react each isomer, 1004a and 1004b, from Example 1588 in essentially the same manner as in Examples 566 then one would obtain compounds of the formulas:

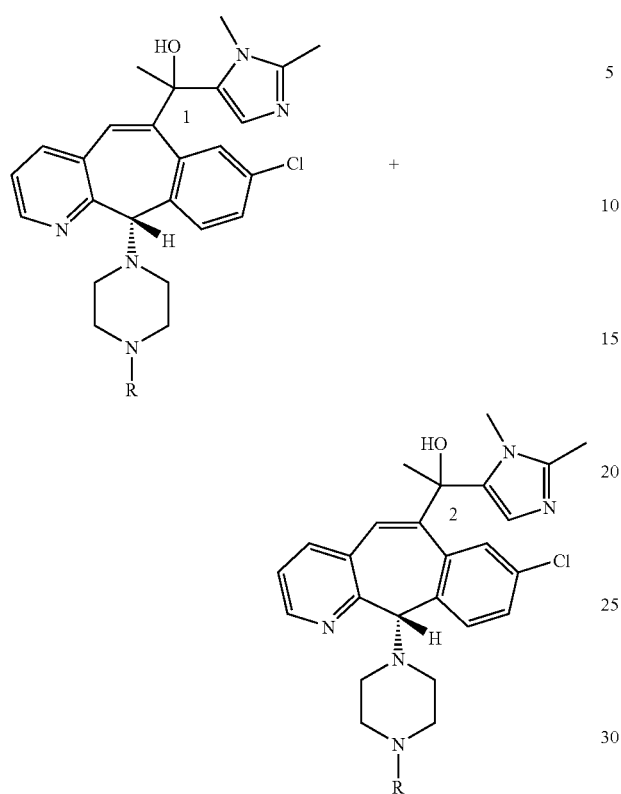
wherein R is defined in Table 108 and the numbers 1 and 2 in the formulas represent isomers 1 and 2, respectively.

TABLE 108-continued

| Example | R Isomer 1 and Isomer 2 |
|---|---|
| 1665 | 4-F-phenyl-SO₂- |
| 1666 | 4-CN-phenyl-SO₂- |
| 1667 | 4-OMe-phenyl-SO₂- |
| 1668 | phenyl-SO₂- |
| 1669 | benzyl-SO₂- |
| 1670 | 2-thienyl-SO₂- |
| 1671 | 1-naphthyl-SO₂- |

EXAMPLE 1672-1690

If one were to react each isomer, 1004a and 1004b, from Example 1588 in essentially the same manner as in Examples 590-603 (wherein the chloroformates could be prepared according to Preparative Example 74), then one would obtain compounds of the formulas:

[Structure 1: isomer 1 — tricyclic compound with HO, dimethylimidazole, Cl, piperazine-N-R substituents]

+

[Structure 2: isomer 2 — tricyclic compound with HO, dimethylimidazole, Cl, piperazine-N-R substituents]

wherein R is defined in Table 109 and the numbers 1 and 2 in the formulas represent isomer 1 and isomer 2, respectively.

TABLE 109

| Example | R Isomer 1 and Isomer 2 |
|---|---|
| 1672 | -C(O)-O-t-Bu |
| 1673 | -C(O)-O-Me |
| 1674 | -C(O)-O-Et |
| 1675 | -C(O)-O-propyl |
| 1676 | -C(O)-O-iPr |

TABLE 109-continued

| Example | R Isomer 1 and Isomer 2 |
|---|---|
| 1677 | isobutyl ester |
| 1678 | neopentyl ester |
| 1679 | allyl ester |
| 1680 | sec-butyl ester |
| 1681 | cyclopentyl ester |
| 1682 | cyclohexyl ester |
| 1683 | phenyl ester |
| 1684 | benzyl ester |
| 1685 | 4-methylphenyl ester |
| 1686 | 4-methoxyphenyl ester |
| 1687 | 4-chlorophenyl ester |
| 1688 | 4-bromophenyl ester |
| 1689 | 4-fluorophenyl ester |
| 1690 | naphthalenyl ester |

EXAMPLES 1691–1715

If one were to react each isomer, 1005a and 1005b, from Example 1589 in essentially the same manner as in Examples 511–513 then one would obtain compounds of the formulas:

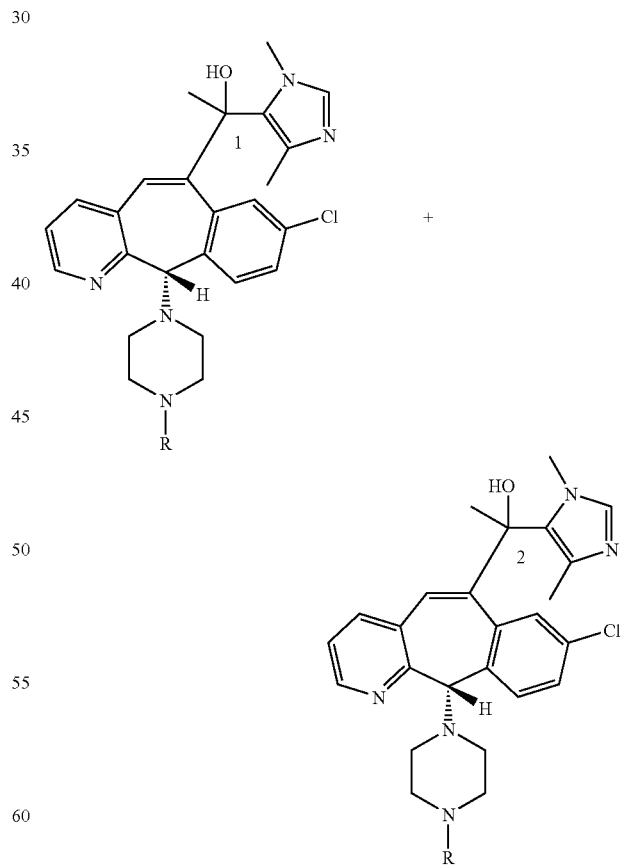

wherein R is defined in Table 110 and the numbers 1 and 2 in the formulas represent isomer 1 and isomer 2, respectively.

TABLE 110

| Example | R Isomer 1 and Isomer 2 |
|---|---|
| 1691 | -C(=O)NH₂ |
| 1692 | -C(=O)NHCH₃ |
| 1693 | -C(=O)NH-iPr |
| 1694 | -C(=O)NHEt |
| 1695 | -C(=O)NH-tBu |
| 1696 | -C(=O)NH-nPr |
| 1697 | -C(=O)NH-iBu |
| 1698 | -C(=O)NH-allyl |
| 1699 | -C(=O)NH-cyclopentyl |
| 1700 | -C(=O)NH-cyclohexyl |

TABLE 110-continued

| Example | R Isomer 1 and Isomer 2 |
|---|---|
| 1701 | -C(=O)NH-phenyl |
| 1702 | -C(=O)NH-(4-CN-phenyl) |
| 1703 | -C(=O)NH-(4-iPr-phenyl) |
| 1704 | -C(=O)NH-(4-Br-phenyl) |
| 1705 | -C(=O)NH-(4-Cl-phenyl) |
| 1706 | -C(=O)NH-(4-F-phenyl) |
| 1707 | -C(=O)NH-(4-OCH₃-phenyl) |
| 1708 | -C(=O)NH-(4-phenoxy-phenyl) |
| 1709 | -C(=O)NH-(4-CF₃-phenyl) |
| 1710 | -C(=O)NH-(4-tBu-phenyl) |

TABLE 110-continued
| Example | R Isomer 1 and Isomer 2 |
|---|---|
| 1711 | 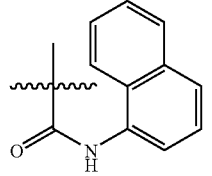 |
| 1712 | 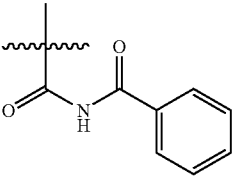 |
| 1713 | 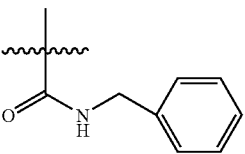 |
| 1714 | 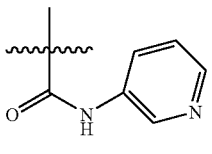 |
| 1715 | 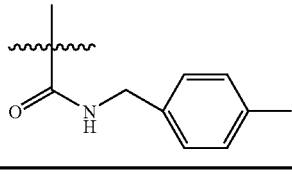 |
EXAMPLES 1716-1743
If one were to react each isomer, 1005a and 1005b, from Example 1589 in essentially the same manner as in Example 536, then one would obtain compounds of the formulas:
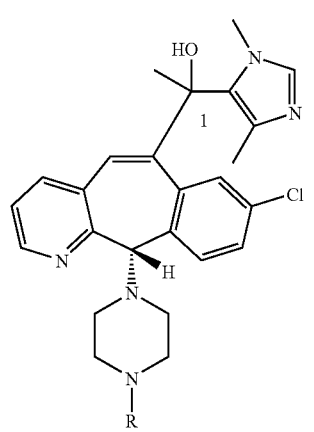
+
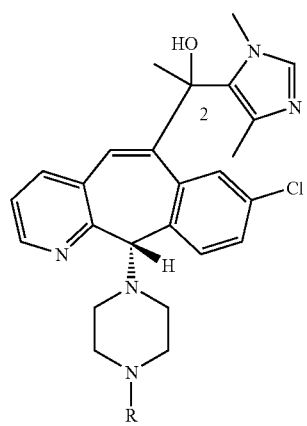
wherein R is defined in Table 111 and the numbers 1 and 2 in the formulas represent isomers 1 and 2, respectively.
TABLE 111
| Example | R Isomer 1 and Isomer 2 |
|---|---|
| 1716 | 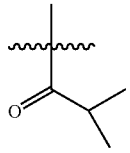 |
| 1717 | 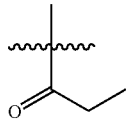 |
| 1718 | 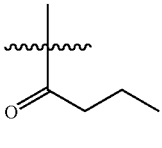 |
| 1719 | 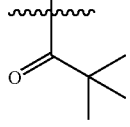 |
| 1720 | 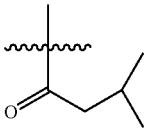 |
| 1721 | 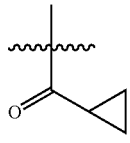 |

TABLE 111-continued

| Example | R Isomer 1 and Isomer 2 |
|---------|-------------------------|
| 1722 | 1-methylcyclopropyl ketone |
| 1723 | 1-methylcyclopropyl ketone (quaternary) |
| 1724 | cyclobutyl ketone |
| 1725 | cyclopentyl ketone |
| 1726 | cyclohexyl ketone |
| 1727 | cyclohexenyl ketone |
| 1728 | piperidin-4-yl ketone |
| 1729 | 1-methylcyclohexyl ketone |
| 1730 | cyclohexylmethyl ketone (β-keto) |

TABLE 111-continued

| Example | R Isomer 1 and Isomer 2 |
|---------|-------------------------|
| 1731 | piperidin-4-ylmethyl ketone |
| 1732 | 1-(piperidin-4-yl)-carboxamide β-keto |
| 1733 | phenyl ketone |
| 1734 | 4-chlorophenyl ketone |
| 1735 | 4-bromophenyl ketone |
| 1736 | 4-fluorophenyl ketone |
| 1737 | 4-cyanophenyl ketone |
| 1738 | 4-methylphenyl ketone |

TABLE 111-continued
| Example | R Isomer 1 and Isomer 2 |
|---|---|
| 1739 | 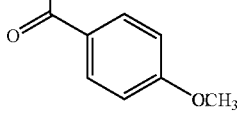 |
| 1740 | 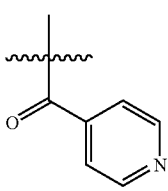 |
| 1741 | 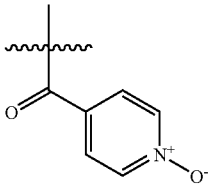 |
| 1742 | 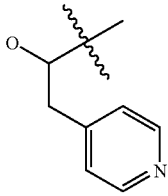 |
| 1743 | 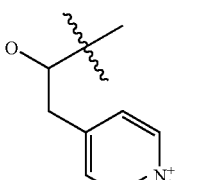 |
EXAMPLES 1744-1767
If one were to react each isomer, 1005a and 1005b, from Example 1589 in essentially the same manner as in Examples 566-567, then one would obtain compounds of the formulas:
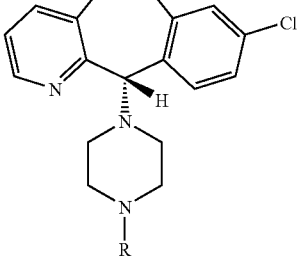
+
wherein R is defined in Table 112 and the numbers 1 and 2 in the formulas represent isomers 1 and 2, respectively.
TABLE 112
| Example | R Isomer 1 and Isomer 2 |
|---|---|
| 1744 | 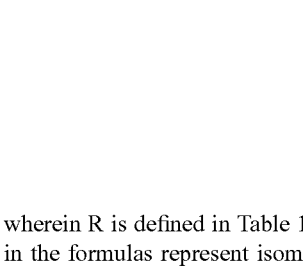 |
| 1745 | 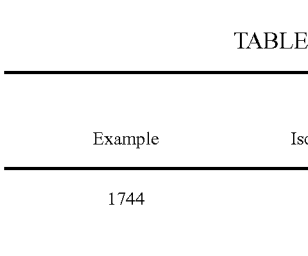 |
| 1747 | 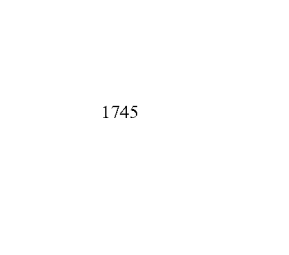 |

TABLE 112-continued

| Example | R Isomer 1 and Isomer 2 |
|---|---|
| 1748 | -S(O)₂-N(CH₃)₂ |
| 1749 | -S(O)₂-C(CH₃)₃ |
| 1750 | -S(O)₂-CF₃ |
| 1752 | -S(O)₂-cyclopropyl |
| 1753 | -S(O)₂-(4-methylphenyl) |
| 1754 | -S(O)₂-(4-ethylphenyl) |
| 1755 | -S(O)₂-(4-isopropylphenyl) |
| 1756 | -S(O)₂-(4-tert-butylphenyl) |
| 1757 | -S(O)₂-(4-chlorophenyl) |
| 1758 | -S(O)₂-(4-trifluoromethylphenyl) |
| 1760 | -S(O)₂-(4-bromophenyl) |
| 1761 | -S(O)₂-(4-fluorophenyl) |
| 1762 | -S(O)₂-(4-cyanophenyl) |
| 1763 | -S(O)₂-(4-methoxyphenyl) |
| 1764 | -S(O)₂-phenyl |
| 1765 | -S(O)₂-CH₂-phenyl |
| 1766 | -S(O)₂-(2-thienyl) |
| 1767 | -S(O)₂-(1-naphthyl) |

EXAMPLES 1768-1786

If one were to react each isomer, 1005a and 1005a, from Example 1589 in essentially the same manner as in Examples 590-603 (wherein the chloroformates would be prepared according to Preparative Example 74) then one would obtain compounds of the formulas:

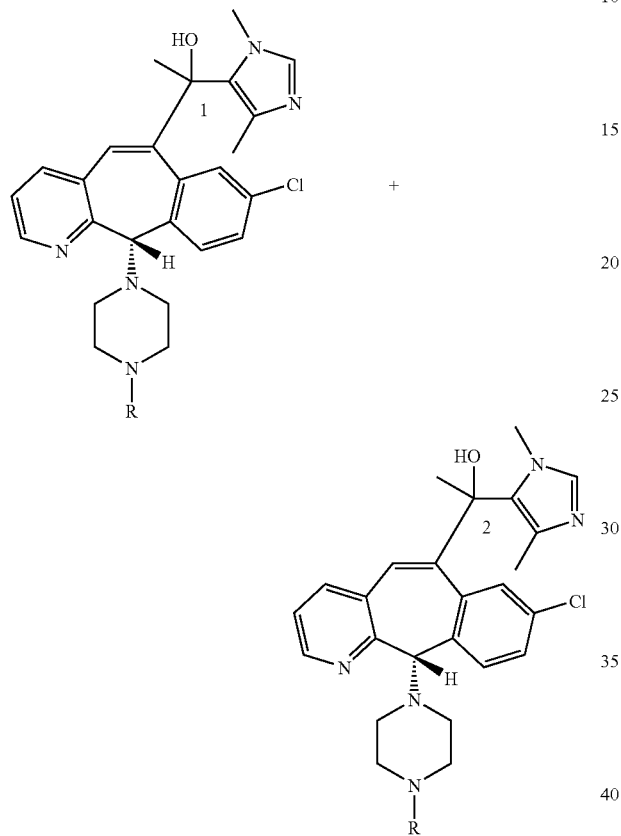

wherein R is defined in Table 113 and the numbers 1 and 2 in the formulas represent isomers 1 and 2, respectively.

TABLE 113

| Example | R Isomer 1 and Isomer 2 |
|---|---|
| 1768 | |
| 1769 | |
| 1770 | |
| 1771 | |
| 1772 | |
| 1773 | |
| 1774 | |
| 1775 | |
| 1776 | |
| 1777 | |
| 1778 | |
| 1779 | |
| 1780 | |
| 1781 | |
| 1782 | |
| 1783 | |

TABLE 113-continued

| Example | R Isomer 1 and Isomer 2 |
|---|---|
| 1784 | 4-bromophenyl ester |
| 1785 | 4-fluorophenyl ester |
| 1786 | 1-naphthyl ester |

EXAMPLES 1787-1811

If one were to react each isomer, 1006a and 1006b, from Example 1590 in essentially the same manner as in Examples 511-513 then one would obtain compounds of the formulas:

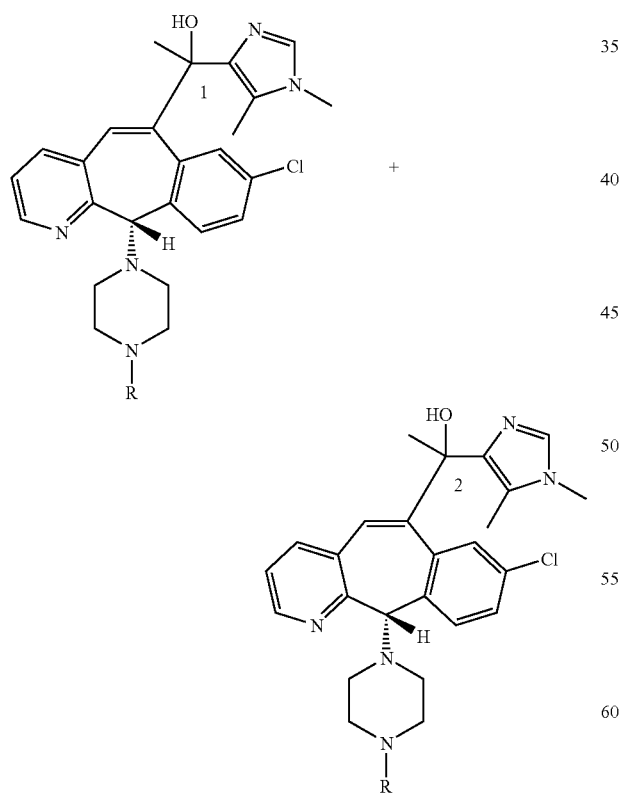

wherein R is defined in Table 114 and the numbers 1 and 2 in the formulas represent isomers 1 and 2, respectively.

TABLE 114

| Example | R Isomer 1 and Isomer 2 |
|---|---|
| 1787 | C(O)NH$_2$ |
| 1788 | C(O)NHMe |
| 1789 | C(O)NHiPr |
| 1790 | C(O)NHEt |
| 1791 | C(O)NHtBu |
| 1792 | C(O)NHnPr |
| 1793 | C(O)NHiBu |
| 1794 | C(O)NH-allyl |
| 1795 | C(O)NH-cyclopentyl |
| 1796 | C(O)NH-cyclohexyl |

TABLE 114-continued
| Example | R Isomer 1 and Isomer 2 |
|---|---|
| 1797 | 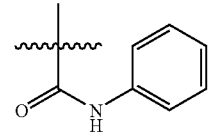 |
| 1798 | 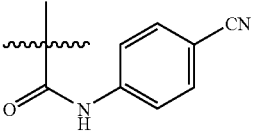 |
| 1799 | 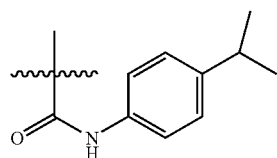 |
| 1800 | 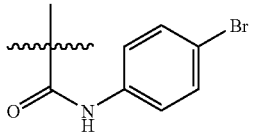 |
| 1801 | 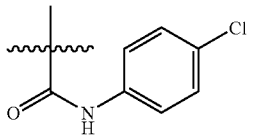 |
| 1802 | 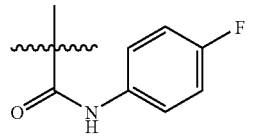 |
| 1803 | 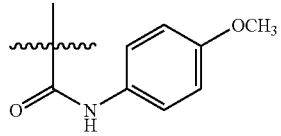 |
| 1804 | 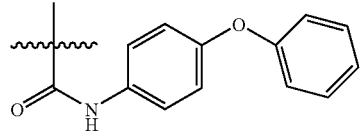 |
| 1805 | 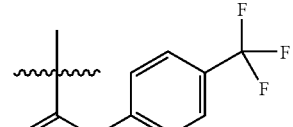 |
| 1806 | 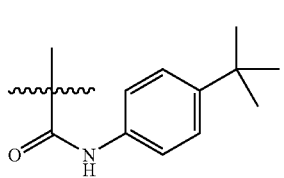 |
TABLE 114-continued
| Example | R Isomer 1 and Isomer 2 |
|---|---|
| 1807 | 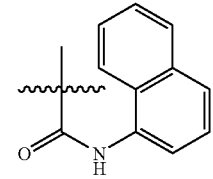 |
| 1808 | 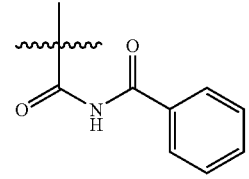 |
| 1809 | 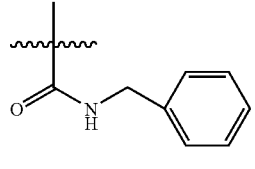 |
| 1810 | 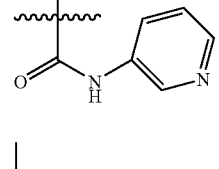 |
| 1811 | 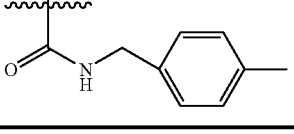 |
EXAMPLES 1812-1839
If one were to react each isomer, 1006a and 1006b, from Example 1590 in essentially the same manner as in Example 536, then one would obtain compounds of the formulas:
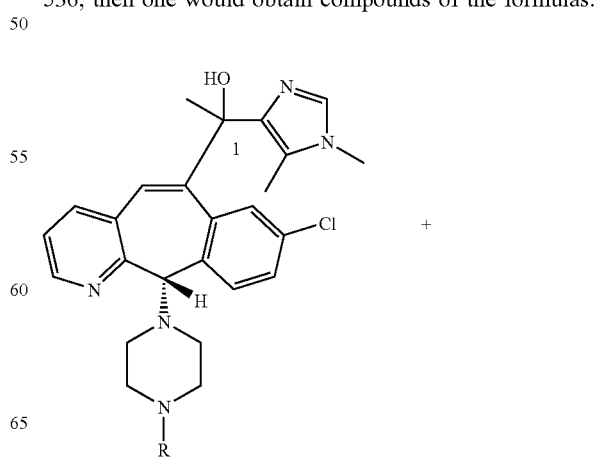

-continued
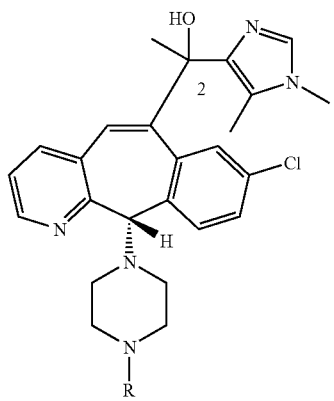
wherein R is defined in Table 115 and the numbers 1 and 2 in the formulas represent isomers 1 and 2, respectively.
TABLE 115
| Example | R Isomer 1 and Isomer 2 |
|---|---|
| 1812 | |
| 1813 | |
| 1814 | |
| 1815 | |
| 1816 | |
| 1817 | |
TABLE 115-continued
| Example | R Isomer 1 and Isomer 2 |
|---|---|
| 1818 | 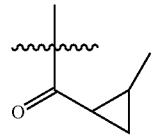 |
| 1819 | 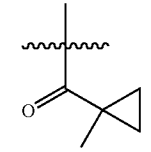 |
| 1820 | 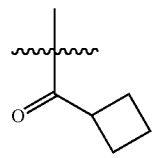 |
| 1821 | 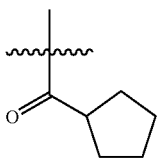 |
| 1822 | 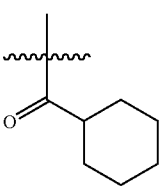 |
| 1823 | 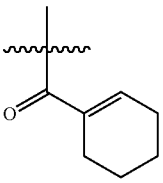 |
| 1824 | 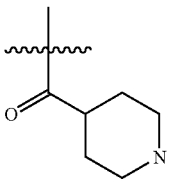 |
| 1825 | 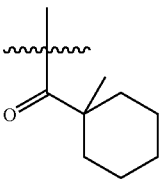 |
| 1826 | 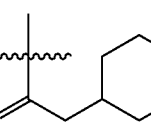 |

TABLE 115-continued
| Example | R Isomer 1 and Isomer 2 |
|---|---|
| 1827 | 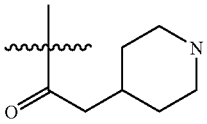 |
| 1828 | 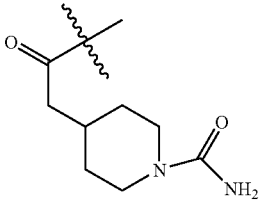 |
| 1829 | 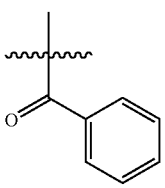 |
| 1830 | 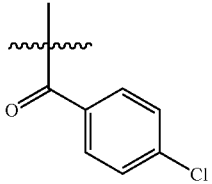 |
| 1831 | 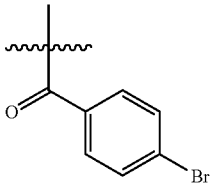 |
| 1832 | 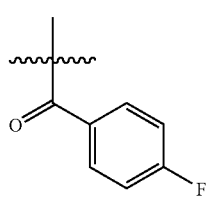 |
| 1833 | 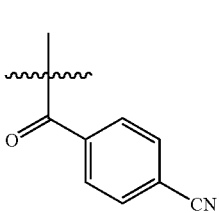 |
TABLE 115-continued
| Example | R Isomer 1 and Isomer 2 |
|---|---|
| 1834 | 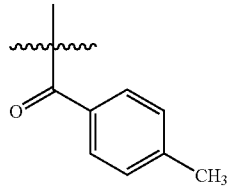 |
| 1835 | 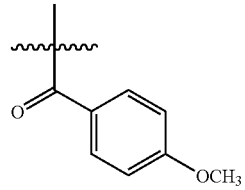 |
| 1836 | 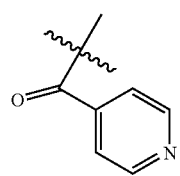 |
| 1837 | 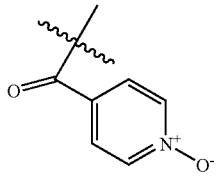 |
| 1838 | 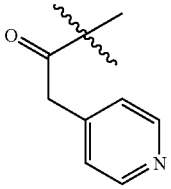 |
| 1839 | 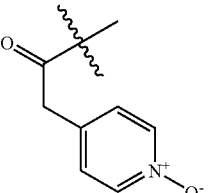 |
EXAMPLES 1840-1861
If one were to react each isomer, 1006a and 1006b, from Example 1590 in essentially the same manner as in Examples 566-567, then one would obtain compounds of the formulas:

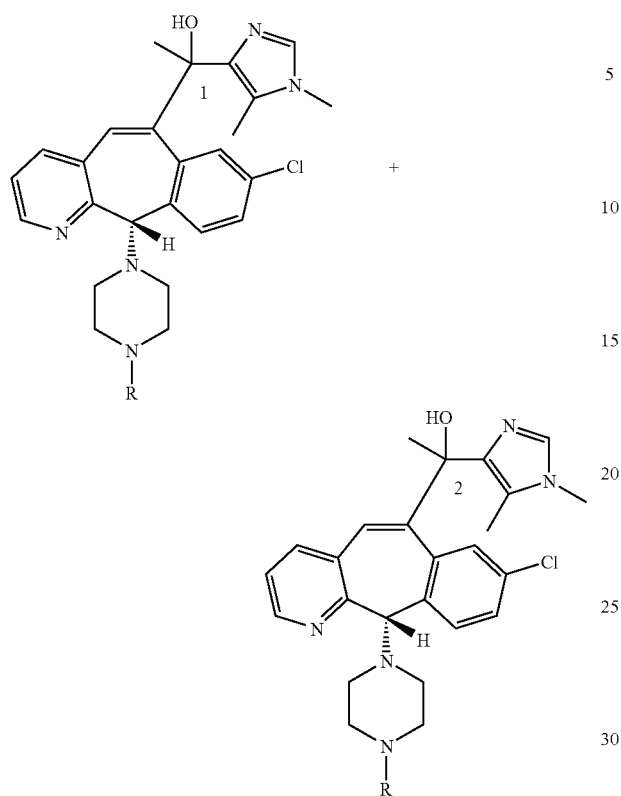
wherein R is defined in Table 116 and the numbers 1 and 2 in the formulas represent isomers 1 and 2, respectively.
TABLE 116
| Example | R Isomer 1 and Isomer 2 |
|---|---|
| 1840 | —S(O)₂—CH₃ |
| 1841 | —S(O)₂—CH(CH₃)₂ |
| 1842 | —S(O)₂—CH₂CH₂CH₃ |
| 1843 | —S(O)₂—N(CH₃)₂ |
TABLE 116-continued
| Example | R Isomer 1 and Isomer 2 |
|---|---|
| 1844 | —S(O)₂—C(CH₃)₃ |
| 1845 | —S(O)₂—CF₃ |
| 1847 | —S(O)₂-cyclopropyl |
| 1848 | —S(O)₂—C₆H₄—CH₃ (p) |
| 1849 | —S(O)₂—C₆H₄—CH₂CH₃ (p) |
| 1850 | —S(O)₂—C₆H₄—CH(CH₃)₂ (p) |
| 1851 | —S(O)₂—C₆H₄—C(CH₃)₃ (p) |
| 1852 | —S(O)₂—C₆H₄—CF₃ (p) |
| 1853 | —S(O)₂—C₆H₄—Cl (p) |
| 1854 | —S(O)₂—C₆H₄—Br (p) |

TABLE 116-continued

| Example | R Isomer 1 and Isomer 2 |
|---|---|
| 1855 | 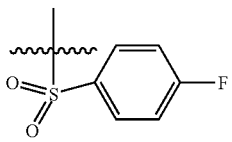 |
| 1856 | 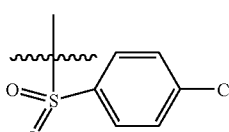 |
| 1857 | 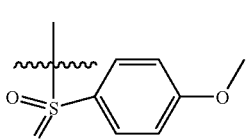 |
| 1858 | 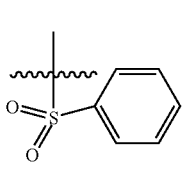 |
| 1859 | 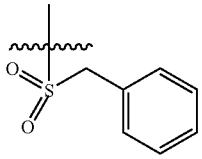 |
| 1860 | 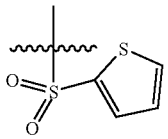 |
| 1861 | 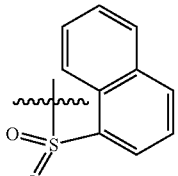 |

EXAMPLES 1862-1880

If one were to react each isomer, 1006a and 1006b, from Example 1590 in essentially the same manner as in Examples 590-603 (wherein the chloroformates could be prepared according to Preparative Example 74), then one would obtain compounds of the formulas:

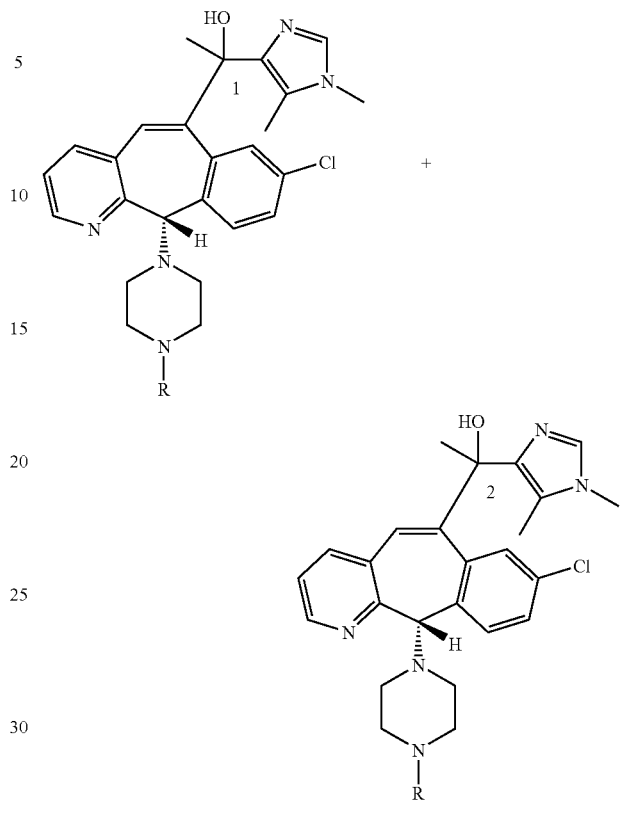

wherein R is defined in Table 117 and the numbers 1 and 2 in the formulas represent isomers 1 and 2, respectively.

TABLE 117

| Example | R Isomer 1 and Isomer 2 |
|---|---|
| 1862 | 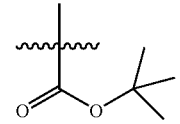 |
| 1863 | 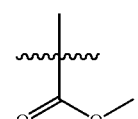 |
| 1864 |  |
| 1865 |  |

TABLE 117-continued
| Example | R Isomer 1 and Isomer 2 |
|---|---|
| 1866 | 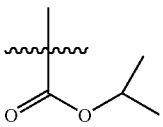 |
| 1867 | 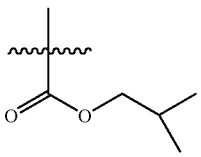 |
| 1868 | 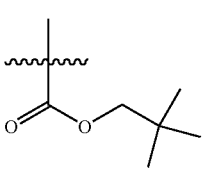 |
| 1869 | 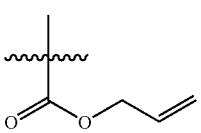 |
| 1870 | 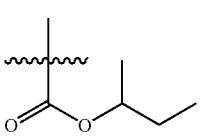 |
| 1871 | 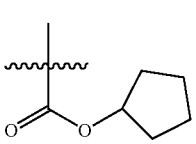 |
| 1872 | 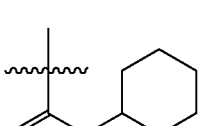 |
| 1873 | 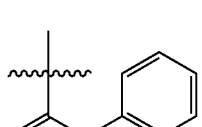 |
| 1874 | 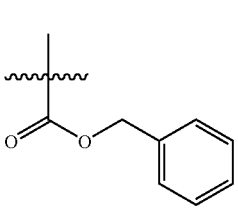 |
| 1875 | 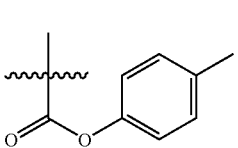 |
TABLE 117-continued
| Example | R Isomer 1 and Isomer 2 |
|---|---|
| 1876 | 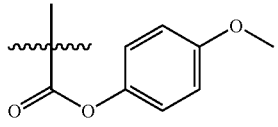 |
| 1877 | 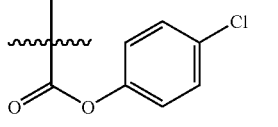 |
| 1878 | 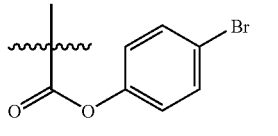 |
| 1879 | |
| 1880 | |
EXAMPLES 1881-1905
If one were to react each isomer, 1007a and 1007b, from Example 1591 in essentially the same manner as in Examples 511-513 then one would obtain compounds of the formulas:
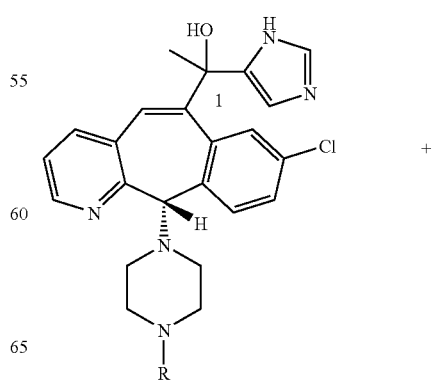
+

-continued

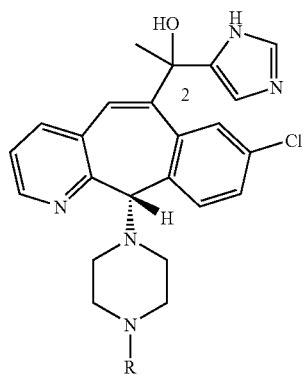

wherein R is defined in Table 118 and the numbers 1 and 2 in the formulas represent isomers 1 and 2, respectively.

TABLE 118

| Example | R Isomer 1 and Isomer 2 |
|---|---|
| 1881 | -C(O)NH₂ |
| 1882 | -C(O)NHCH₃ |
| 1883 | -C(O)NH-iPr |
| 1884 | -C(O)NHEt |
| 1885 | -C(O)NH-tBu |
| 1886 | -C(O)NH-nPr |

TABLE 118-continued

| Example | R Isomer 1 and Isomer 2 |
|---|---|
| 1887 | -C(O)NH-isobutyl |
| 1888 | -C(O)NH-allyl |
| 1889 | -C(O)NH-cyclopentyl |
| 1890 | -C(O)NH-cyclohexyl |
| 1891 | -C(O)NH-phenyl |
| 1892 | -C(O)NH-(4-CN-phenyl) |
| 1893 | -C(O)NH-(4-iPr-phenyl) |
| 1894 | -C(O)NH-(4-Br-phenyl) |
| 1895 | -C(O)NH-(4-Cl-phenyl) |
| 1896 | -C(O)NH-(4-F-phenyl) |

TABLE 118-continued

| Example | R Isomer 1 and Isomer 2 |
|---------|-------------------------|
| 1897 | 4-methoxyphenyl amide |
| 1898 | 4-phenoxyphenyl amide |
| 1899 | 4-(trifluoromethyl)phenyl amide |
| 1900 | 4-tert-butylphenyl amide |
| 1901 | 1-naphthyl amide |
| 1902 | benzoylaminomethyl ketone |
| 1903 | benzylamide |
| 1904 | pyridin-3-yl amide |
| 1905 | 4-methylbenzyl amide |

EXAMPLES 1906-1933

If one were to react each isomer, 1007a and 1007b, from Example 1591 in essentially the same manner as in Example 536, then one would obtain compounds of the formulas:

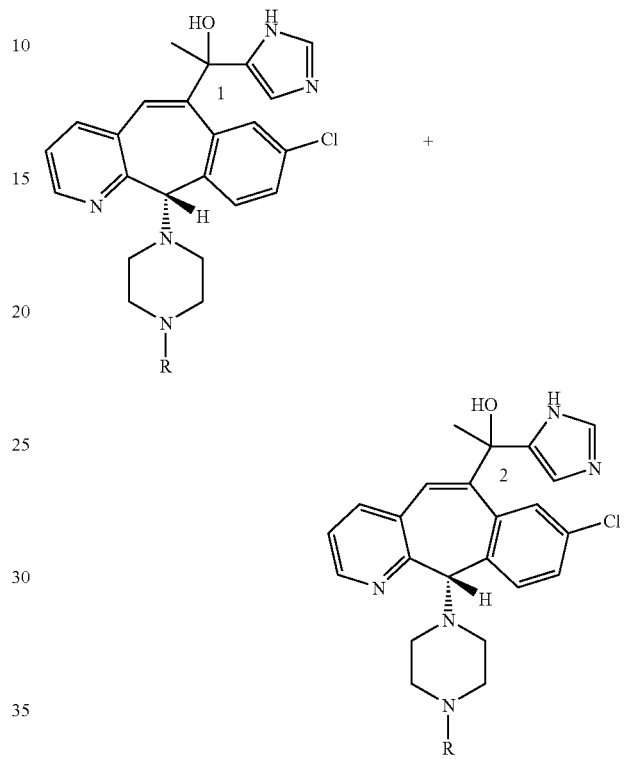

wherein R is defined in Table 119 and the numbers 1 and 2 in the formulas represent isomers 1 and 2, respectively.

TABLE 119

| Example | R Isomer 1 and Isomer 2 |
|---------|-------------------------|
| 1906 | isobutyryl |
| 1907 | propanoyl |
| 1908 | butanoyl |

TABLE 119-continued
| Example | R Isomer 1 and Isomer 2 |
|---|---|
| 1909 | 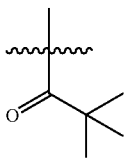 |
| 1910 | 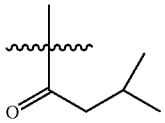 |
| 1911 | 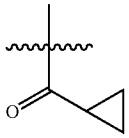 |
| 1912 | 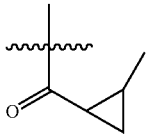 |
| 1913 | 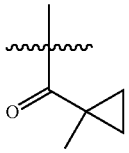 |
| 1914 | 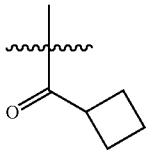 |
| 1915 | 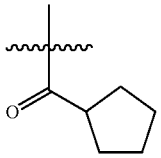 |
| 1916 | 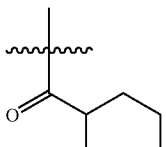 |
| 1917 | 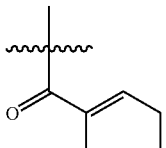 |
| 1918 | 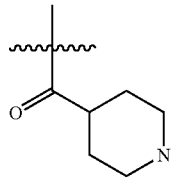 |
| 1919 | 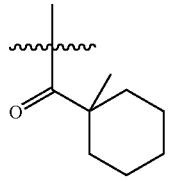 |
| 1920 | 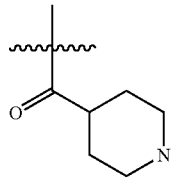 |
| 1921 | 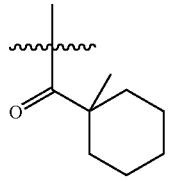 |
| 1922 | 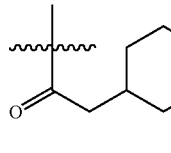 |
| 1923 | 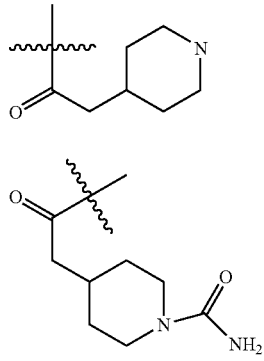 |
| 1924 | 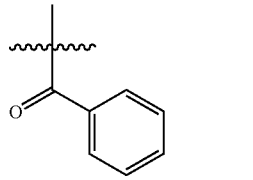 |
| 1925 | 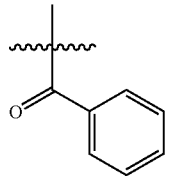 |

TABLE 119-continued

| Example | R Isomer 1 and Isomer 2 |
|---|---|
| 1926 | 4-fluorobenzoyl |
| 1927 | 4-cyanobenzoyl |
| 1928 | 4-methylbenzoyl |
| 1929 | 4-methoxybenzoyl |
| 1930 | pyridine-4-carbonyl |
| 1931 | (1-oxidopyridin-4-yl)carbonyl |
| 1932 | 2-(pyridin-4-yl)acetyl |
| 1933 | 2-(1-oxidopyridin-4-yl)acetyl |

EXAMPLES 1934-1956

If one were to react each isomer, 1007a and 1007b, from Example 1591 in essentially the same manner as in Examples 566-567, then one would obtain compounds of the formulas:

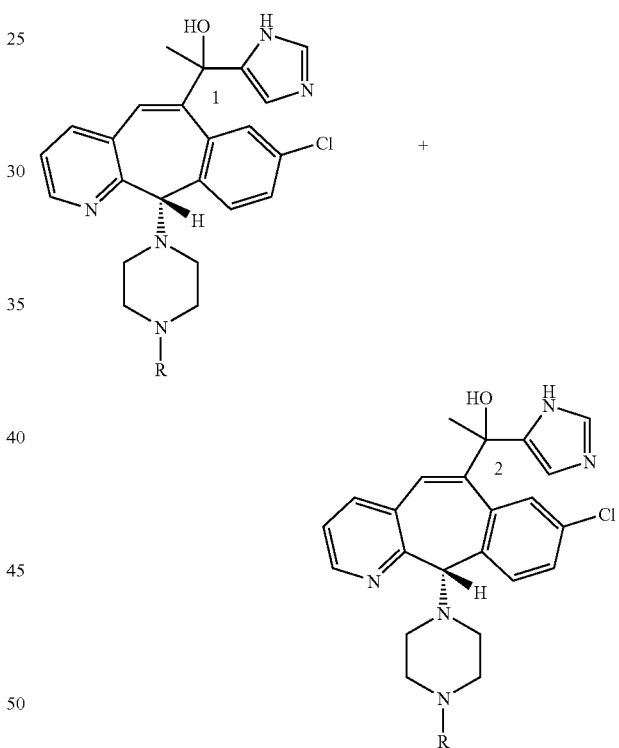

wherein R is defined in Table 120 and the numbers 1 and 2 in the formulas represent isomers 1 and 2, respectively.

TABLE 120

| Example | R Isomer 1 and Isomer 2 |
|---|---|
| 1935 | methanesulfonyl |

TABLE 120-continued

| Example | R Isomer 1 and Isomer 2 |
|---|---|
| 1936 | isopropylsulfonyl |
| 1937 | propylsulfonyl |
| 1938 | N,N-dimethylsulfamoyl |
| 1939 | tert-butylsulfonyl |
| 1940 | trifluoromethylsulfonyl |
| 1942 | cyclopropylsulfonyl |
| 1943 | 4-methylphenylsulfonyl |
| 1944 | 4-ethylphenylsulfonyl |
| 1945 | 4-isopropylphenylsulfonyl |
| 1946 | 4-tert-butylphenylsulfonyl |
| 1947 | 4-trifluoromethylphenylsulfonyl |
| 1948 | 4-chlorophenylsulfonyl |
| 1949 | 4-bromophenylsulfonyl |
| 1950 | 4-fluorophenylsulfonyl |
| 1951 | 4-cyanophenylsulfonyl |
| 1952 | 4-methoxyphenylsulfonyl |
| 1953 | phenylsulfonyl |
| 1954 | benzylsulfonyl |
| 1955 | thiophen-2-ylsulfonyl |

TABLE 120-continued

| Example | R Isomer 1 and Isomer 2 |
|---|---|
| 1956 | 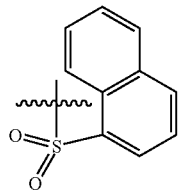 |

EXAMPLES 1957-1975

If one were to react each isomer, 1007a and 1007b, from Example 1591 in essentially the same manner as in Examples 590-603 (wherein the chloroformates could be prepared according to Preparative Example 74), then one would obtain compounds of the formulas:

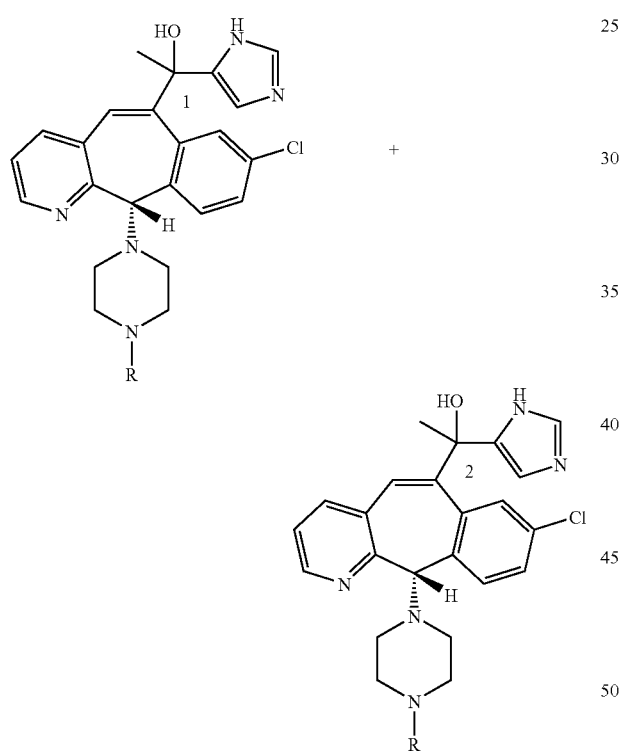

wherein R is defined in Table 121 and the numbers 1 and 2 in the formulas represent isomers 1 and 2, respectively.

TABLE 121

| Example | R Isomer 1 and Isomer 2 |
|---|---|
| 1957 | 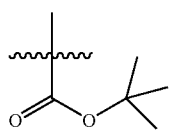 |
| 1958 | 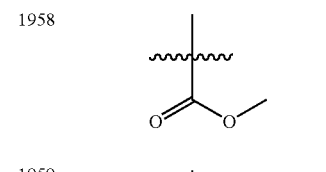 |
| 1959 | 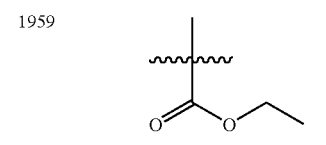 |
| 1960 | 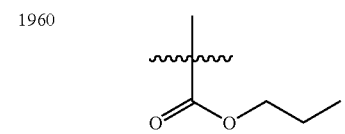 |
| 1961 | 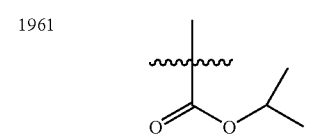 |
| 1962 | 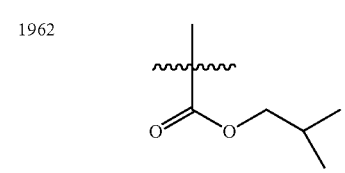 |
| 1963 | 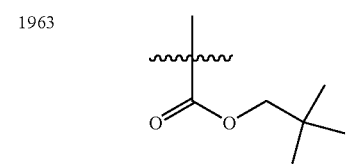 |
| 1964 | 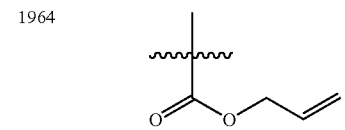 |
| 1965 | 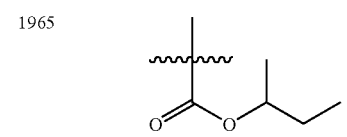 |
| 1966 | 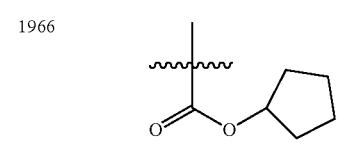 |
| 1967 | 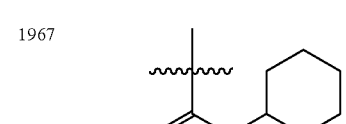 |

TABLE 121-continued

| Example | R Isomer 1 and Isomer 2 |
|---|---|
| 1968 | phenyl ester |
| 1969 | benzyl ester |
| 1970 | 4-methylphenyl ester |
| 1971 | 4-methoxyphenyl ester |
| 1972 | 4-chlorophenyl ester |
| 1973 | 4-bromophenyl ester |
| 1974 | 4-fluorophenyl ester |
| 1975 | 1-naphthyl ester |

EXAMPLES 1976-2000

If one were to react each isomer, 1009a and 1009b, from Example 1593 in essentially the same manner as in Examples 511-513 then one would obtain compounds of the formulas:

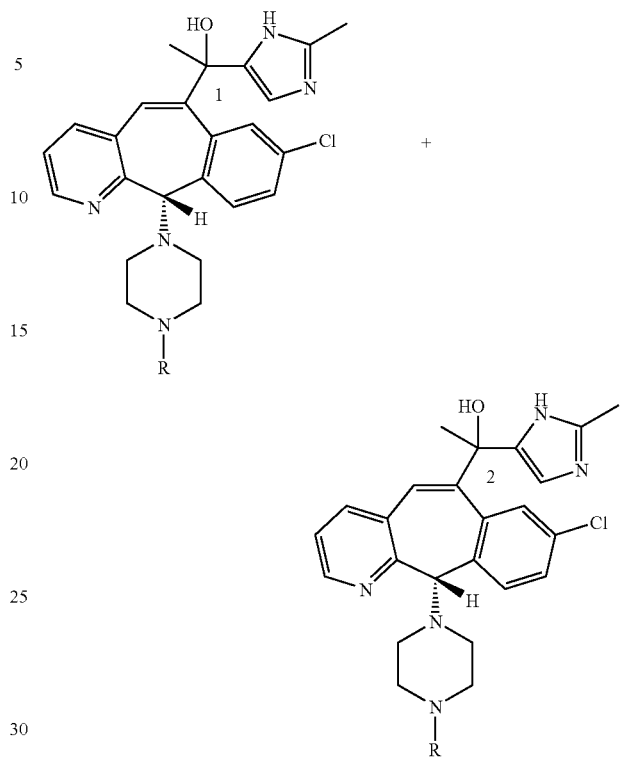

wherein R is defined in Table 122 and the numbers 1 and 2 in the formulas represent isomers 1 and 2, respectively.

TABLE 122

| Example | R Isomer 1 and Isomer 2 |
|---|---|
| 1976 | C(O)NH₂ |
| 1977 | C(O)NHMe |
| 1978 | C(O)NHiPr |
| 1979 | C(O)NHEt |

TABLE 122-continued

| Example | R Isomer 1 and Isomer 2 |
|---|---|
| 1980 | -C(O)NH-tBu |
| 1981 | -C(O)NH-propyl |
| 1982 | -C(O)NH-isobutyl |
| 1983 | -C(O)NH-allyl |
| 1984 | -C(O)NH-cyclopentyl |
| 1985 | -C(O)NH-cyclohexyl |
| 1986 | -C(O)NH-phenyl |
| 1987 | -C(O)NH-(4-CN-phenyl) |
| 1988 | -C(O)NH-(4-isopropyl-phenyl) |
| 1989 | -C(O)NH-(4-Br-phenyl) |
| 1990 | -C(O)NH-(4-Cl-phenyl) |
| 1991 | -C(O)NH-(4-F-phenyl) |
| 1992 | -C(O)NH-(4-OCH$_3$-phenyl) |
| 1993 | -C(O)NH-(4-phenoxy-phenyl) |
| 1994 | -C(O)NH-(4-CF$_3$-phenyl) |
| 1995 | -C(O)NH-(4-tBu-phenyl) |
| 1996 | -C(O)NH-(1-naphthyl) |
| 1997 | -C(O)NH-C(O)-phenyl |
| 1998 | -C(O)NH-CH$_2$-phenyl |

TABLE 122-continued
| Example | R Isomer 1 and Isomer 2 |
|---|---|
| 1999 | |
| 2000 | |
EXAMPLES 2001-2028
If one were to react each isomer, 1009a and 1009b, from Example 1593 in essentially the same manner as in Example 536, then one would obtain compounds of the formulas:
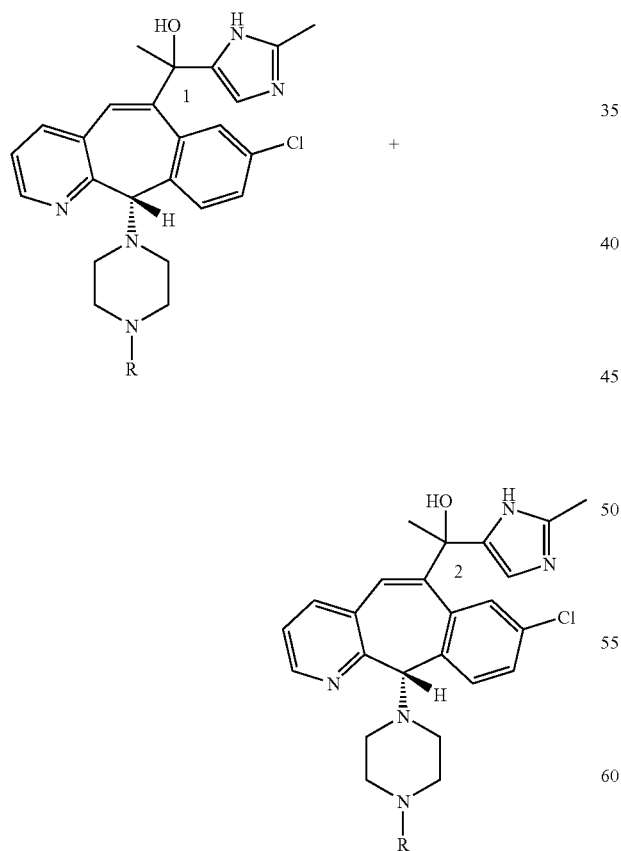
wherein R is defined in Table 123 and the numbers 1 and 2 in the formulas represent isomers 1 and 2, respectively.
TABLE 123
| Example | R Isomer 1 and Isomer 2 |
|---|---|
| 2001 | |
| 2002 | |
| 2003 | |
| 2004 | |
| 2005 | |
| 2006 | |
| 2007 | |
| 2008 | |
| 2009 | |
| 2010 | |

TABLE 123-continued
| Example | R Isomer 1 and Isomer 2 |
|---|---|
| 2011 | 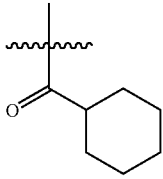 |
| 2012 | 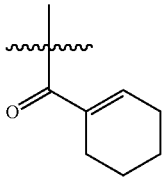 |
| 2013 | 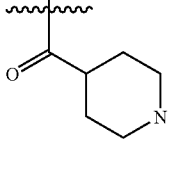 |
| 2014 | 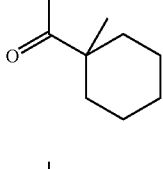 |
| 2015 | 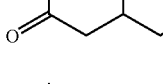 |
| 2016 | 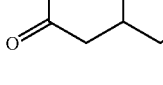 |
| 2017 | 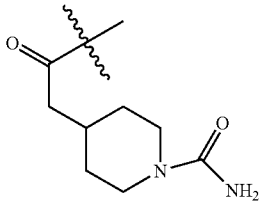 |
| 2018 | 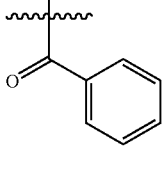 |
| 2019 | 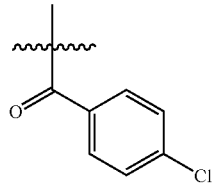 |
| 2020 | 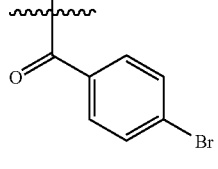 |
| 2021 | 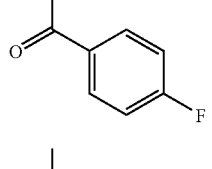 |
| 2022 | 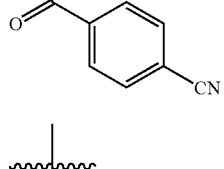 |
| 2023 | 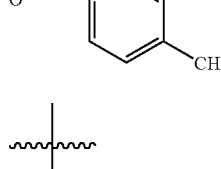 |
| 2024 | 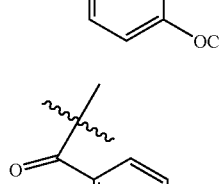 |
| 2025 |  |
| 2026 | 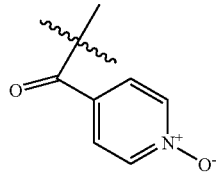 |

TABLE 123-continued

| Example | R Isomer 1 and Isomer 2 |
|---|---|
| 2027 | (4-pyridyl-CH2-C(O)-C(CH3)—) |
| 2028 | (4-pyridyl N-oxide-CH2-C(O)-C(CH3)—) |

EXAMPLES 2028–2049

If one were to react each isomer, 1009a and 1009b, from Example 1593 in essentially the same manner as in Examples 566–567, then one would obtain compounds of the formulas:

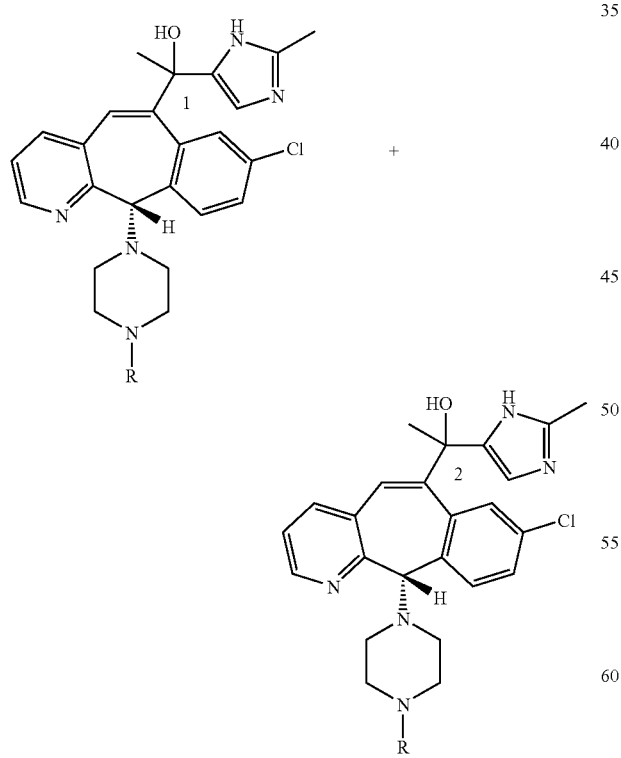

wherein R is defined in Table 124 and the numbers 1 and 2 in the formulas represent isomers 1 and 2, respectively.

TABLE 124

| Example | R Isomer 1 and Isomer 2 |
|---|---|
| 2028 | —S(O)2CH3 |
| 2029 | —S(O)2CH(CH3)2 |
| 2030 | —S(O)2CH2CH2CH3 |
| 2031 | —S(O)2N(CH3)2 |
| 2032 | —S(O)2C(CH3)3 |
| 2033 | —S(O)2CF3 |
| 2035 | —S(O)2-cyclopropyl |
| 2036 | —S(O)2-(4-methylphenyl) |
| 2037 | —S(O)2-(4-ethylphenyl) |
| 2038 | —S(O)2-(4-isopropylphenyl) |

TABLE 124-continued

| Example | R Isomer 1 and Isomer 2 |
|---|---|
| 2039 | 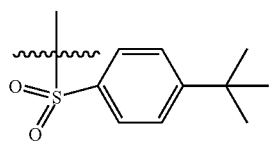 |
| 2040 | 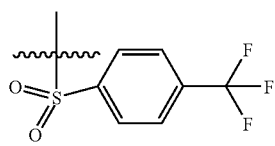 |
| 2041 | 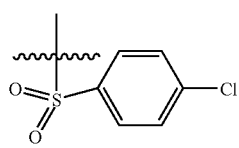 |
| 2042 | 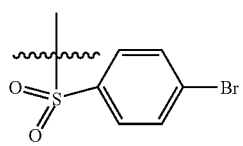 |
| 2043 | 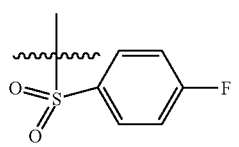 |
| 2044 | 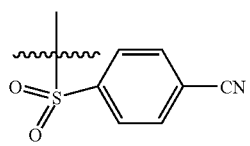 |
| 2045 | 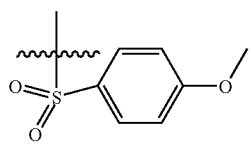 |
| 2046 | 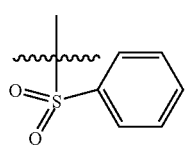 |
| 2047 | 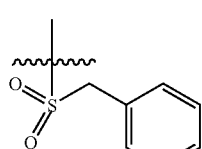 |
| 2048 | 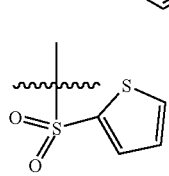 |

TABLE 124-continued

| Example | R Isomer 1 and Isomer 2 |
|---|---|
| 2049 | 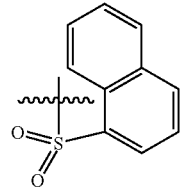 |

EXAMPLES 2050-2068

If one were to react each isomer, 1009a and 1009b, from Example 1593 in essentially the same manner as in Examples 590-603 (wherein the chloroformates could be prepared according to Preparative Example 74), then one would obtain compounds of the formulas:

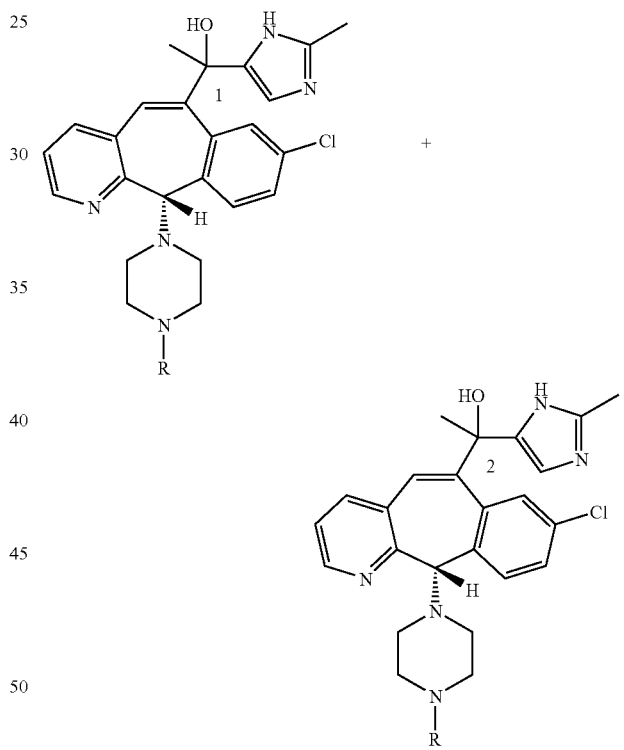

wherein R is defined in Table 125 and the numbers 1 and 2 in the formulas represent isomers 1 and 2, respectively.

TABLE 125

| Example | R Isomer 1 and Isomer 2 |
|---|---|
| 2050 | 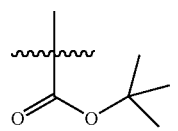 |

TABLE 125-continued

| Example | R Isomer 1 and Isomer 2 |
|---|---|
| 2051 | methyl ester |
| 2052 | ethyl ester |
| 2053 | propyl ester |
| 2054 | isopropyl ester |
| 2055 | isobutyl ester |
| 2056 | neopentyl ester |
| 2057 | allyl ester |
| 2058 | sec-butyl ester |
| 2059 | cyclopentyl ester |
| 2060 | cyclohexyl ester |
| 2061 | phenyl ester |
| 2062 | benzyl ester |
| 2063 | 4-methylphenyl ester |
| 2064 | 4-methoxyphenyl ester |
| 2065 | 4-chlorophenyl ester |
| 2066 | 4-bromophenyl ester |
| 2067 | 4-fluorophenyl ester |
| 2068 | 1-naphthyl ester |

EXAMPLES 2069-2093

If one were to react isomer, 1010a and 1010b, from Example 1594 in essentially the same manner as in Examples 511-513 then one would obtain compounds of the formulas:

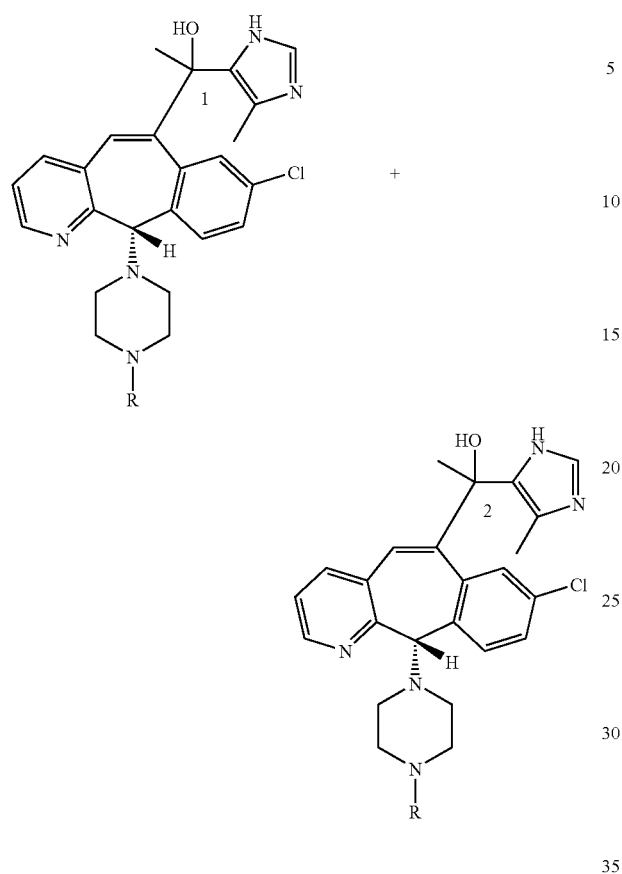
wherein R is defined in Table 126 and the numbers 1 and 2 in the formulas represent isomers 1 and 2, respectively.
TABLE 126
| Example | R Isomer 1 and Isomer 2 |
|---|---|
| 2069 | —C(O)NH₂ |
| 2070 | —C(O)NHCH₃ |
| 2071 | —C(O)NH-iPr |
| 2072 | —C(O)NHEt |
TABLE 126-continued
| Example | R Isomer 1 and Isomer 2 |
|---|---|
| 2073 | —C(O)NH-tBu |
| 2074 | —C(O)NH-nPr |
| 2075 | —C(O)NH-iBu |
| 2076 | —C(O)NH-allyl |
| 2077 | —C(O)NH-cyclopentyl |
| 2078 | —C(O)NH-cyclohexyl |
| 2079 | —C(O)NH-phenyl |
| 2080 | —C(O)NH-(4-CN-phenyl) |
| 2081 | —C(O)NH-(4-iPr-phenyl) |
| 2082 | —C(O)NH-(4-Br-phenyl) |

TABLE 126-continued

| Example | R Isomer 1 and Isomer 2 |
|---|---|
| 2083 | 4-chlorophenyl amide |
| 2084 | 4-fluorophenyl amide |
| 2085 | 4-methoxyphenyl amide |
| 2086 | 4-phenoxyphenyl amide |
| 2087 | 4-(trifluoromethyl)phenyl amide |
| 2088 | 4-tert-butylphenyl amide |
| 2089 | 1-naphthyl amide |
| 2090 | benzoyl-amide |
| 2091 | benzyl amide |
| 2092 | pyridin-3-yl amide |
| 2093 | 4-methylbenzyl amide |

EXAMPLES 2094-3021

If one were to react each isomer, 1010a and 1010b, from Example 1594 in essentially the same manner as in Example 536, then one would obtain compounds of the formulas:

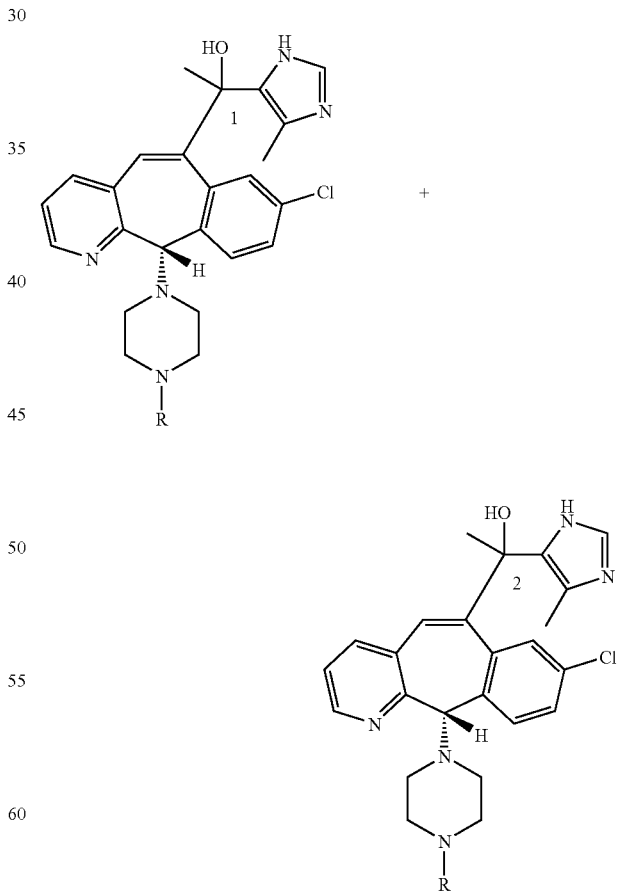

wherein R is defined in Table 127 and the numbers 1 and 2 in the formulas represent isomers 1 and 2, respectively.

TABLE 127
| Example | R Isomer 1 and Isomer 2 |
|---|---|
| 2094 | 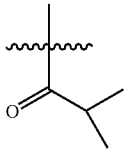 |
| 2095 | 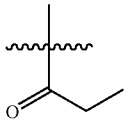 |
| 2096 | 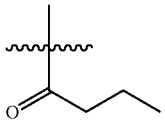 |
| 2097 | 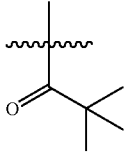 |
| 2098 | 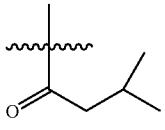 |
| 2099 | 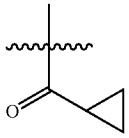 |
| 3000 | 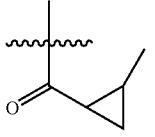 |
| 3001 | 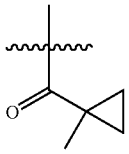 |
| 3002 | 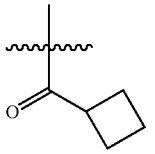 |
| 3003 | 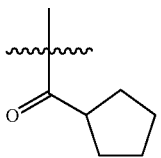 |
TABLE 127-continued
| Example | R Isomer 1 and Isomer 2 |
|---|---|
| 3004 | 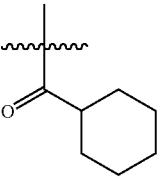 |
| 3005 | 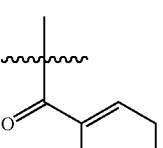 |
| 3006 |  |
| 3007 | 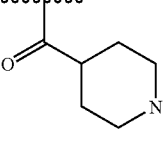 |
| 3008 | 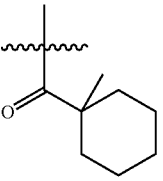 |
| 3009 | 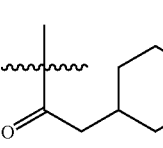 |
| 3010 | 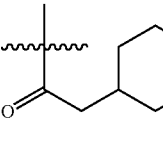 |
| 3011 | 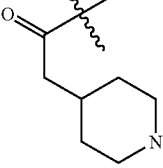 |

TABLE 127-continued

| Example | R Isomer 1 and Isomer 2 |
|---|---|
| 3012 | 4-chlorobenzoyl |
| 3013 | 4-bromobenzoyl |
| 3014 | 4-fluorobenzoyl |
| 3015 | 4-cyanobenzoyl |
| 3016 | 4-methylbenzoyl |
| 3017 | 4-methoxybenzoyl |
| 3018 | isonicotinoyl |
| 3019 | isonicotinoyl N-oxide |
| 3020 | 2-(pyridin-4-yl)acetyl |
| 3021 | 2-(pyridin-4-yl N-oxide)acetyl |

EXAMPLES 3022-3043

If one were to react each isomer, 1010a and 1010b, from Example 1594 in essentially the same manner as in Examples 566-567, then one would obtain compounds of the formulas:

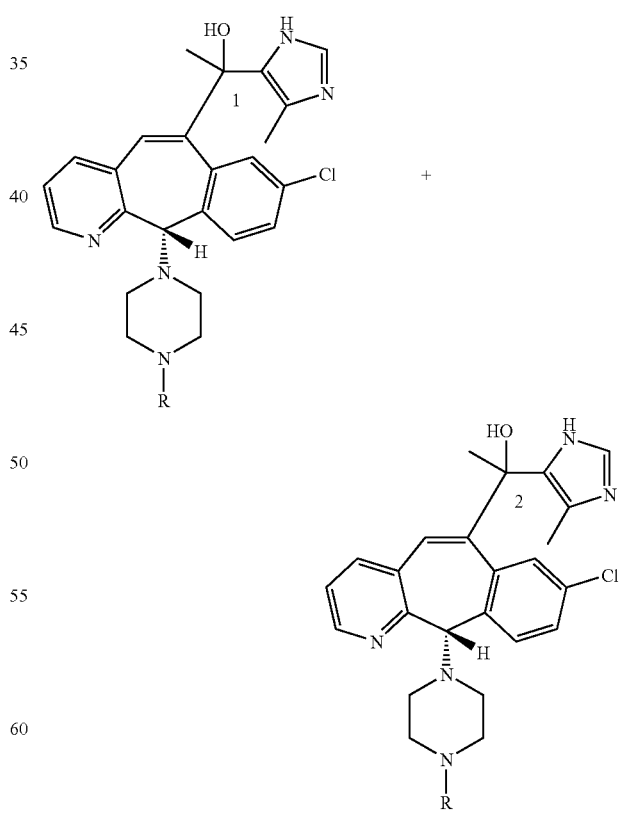

wherein R is defined in Table 128 and the numbers 1 and 2 in the formulas represent isomers 1 and 2, respectively.

TABLE 128

| Example | R Isomer 1 and Isomer 2 |
|---|---|
| 3022 | -S(=O)₂-CH₃ |
| 3023 | -S(=O)₂-CH(CH₃)₂ |
| 3024 | -S(=O)₂-CH₂CH₂CH₃ |
| 3025 | -S(=O)₂-N(CH₃)₂ |
| 3026 | -S(=O)₂-C(CH₃)₃ |
| 3027 | -S(=O)₂-CF₃ |
| 3029 | -S(=O)₂-cyclopropyl |
| 3030 | -S(=O)₂-(4-methylphenyl) |
| 3031 | -S(=O)₂-(4-ethylphenyl) |
| 3032 | -S(=O)₂-(4-isopropylphenyl) |
| 3033 | -S(=O)₂-(4-tert-butylphenyl) |
| 3034 | -S(=O)₂-(4-trifluoromethylphenyl) |
| 3035 | -S(=O)₂-(4-chlorophenyl) |
| 3036 | -S(=O)₂-(4-bromophenyl) |
| 3037 | -S(=O)₂-(4-fluorophenyl) |
| 3038 | -S(=O)₂-(4-cyanophenyl) |
| 3039 | -S(=O)₂-(4-methoxyphenyl) |
| 3040 | -S(=O)₂-phenyl |
| 3041 | -S(=O)₂-CH₂-phenyl |
| 3042 | -S(=O)₂-(2-thienyl) |

TABLE 128-continued

| Example | R Isomer 1 and Isomer 2 |
|---|---|
| 3043 | 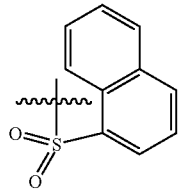 |

EXAMPLES 3044-3062

If one were to react each isomer, 1010a and 1010b, from Example 1594 in essentially the same manner as in Examples 590-603 (wherein the chloroformates could be prepared according to Preparative Example 74), then one would obtain compounds of the formulas:

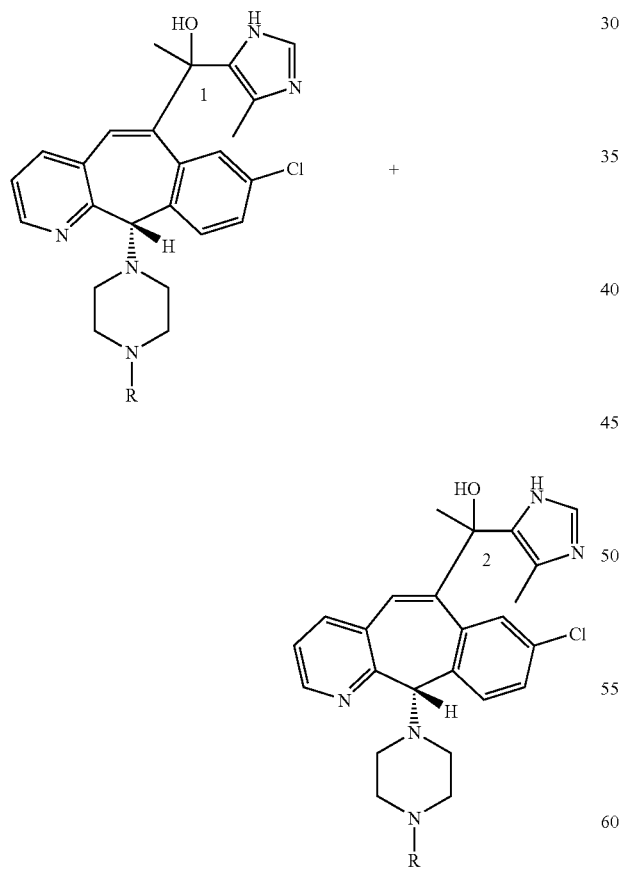

wherein R is defined in Table 129 and the numbers 1 and 2 in the formulas represent isomers 1 and 2, respectively.

TABLE 129

| Example | R Isomer 1 and Isomer 2 |
|---|---|
| 3044 | 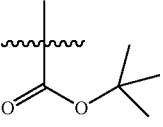 |
| 3045 | 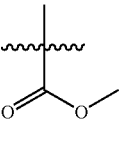 |
| 3046 | 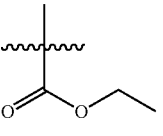 |
| 3047 | 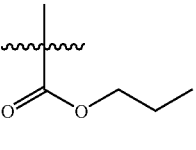 |
| 3048 | 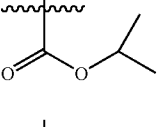 |
| 3049 | 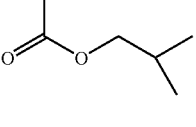 |
| 3050 | 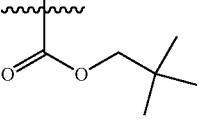 |
| 3051 | 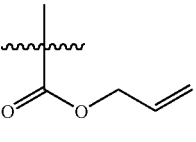 |
| 3052 | 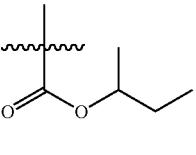 |
| 3053 | 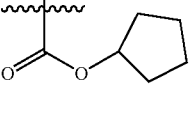 |

TABLE 129-continued

| Example | R Isomer 1 and Isomer 2 |
|---|---|
| 3054 | cyclohexyl ester |
| 3055 | phenyl ester |
| 3056 | benzyl ester |
| 3057 | 4-methylphenyl ester |
| 3058 | 4-methoxyphenyl ester |
| 3059 | 4-chlorophenyl ester |
| 3060 | 4-bromophenyl ester |
| 3061 | 4-fluorophenyl ester |
| 3062 | 1-naphthyl ester |

EXAMPLES 3063-3087

If one were to follow procedures similar to those in Examples 511-513, but using compound 1008 from Example 1592, then one would obtain compounds of the formula:

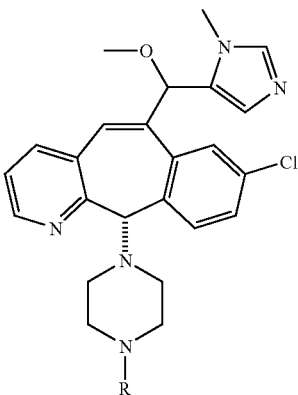

wherein R is defined in Table 130.

TABLE 130

| Example | R |
|---|---|
| 3063 | C(O)NH₂ |
| 3064 | C(O)NHMe |
| 3065 | C(O)NHiPr |
| 3066 | C(O)NHEt |
| 3067 | C(O)NHtBu |
| 3068 | C(O)NHnPr |
| 3069 | C(O)NHiBu |

TABLE 130-continued

| Example | R |
|---|---|
| 3070 | -C(O)NH-allyl |
| 3071 | -C(O)NH-cyclopentyl |
| 3072 | -C(O)NH-cyclohexyl |
| 3073 | -C(O)NH-phenyl |
| 3074 | -C(O)NH-(4-cyanophenyl) |
| 3075 | -C(O)NH-(4-isopropylphenyl) |
| 3076 | -C(O)NH-(4-bromophenyl) |
| 3077 | -C(O)NH-(4-chlorophenyl) |
| 3078 | -C(O)NH-(4-fluorophenyl) |
| 3079 | -C(O)NH-(4-methoxyphenyl) |
| 3080 | -C(O)NH-(4-phenoxyphenyl) |
| 3081 | -C(O)NH-(4-trifluoromethylphenyl) |
| 3082 | -C(O)NH-(4-tert-butylphenyl) |
| 3083 | -C(O)NH-(1-naphthyl) |
| 3084 | -C(O)NH-C(O)-phenyl |
| 3985 | -C(O)NH-benzyl |
| 3086 | -C(O)NH-(3-pyridyl) |
| 3087 | -C(O)NH-(4-methylbenzyl) |

EXAMPLES 3088–3115

If one were to follow a procedure similar to that in Example 536, but using compound 1008 from Example 1592, then one would obtain compounds of the formula:

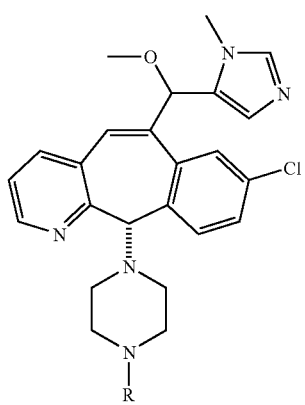
wherein R is defined in Table 131.
TABLE 131
| Example | R |
|---|---|
| 3088 | |
| 3089 | |
| 3090 | |
| 3091 | |
| 3092 | |
| 3093 | |
| 3094 | |
TABLE 131-continued
| Example | R |
|---|---|
| 3095 | |
| 3096 | |
| 3097 | |
| 3098 | |
| 3099 | |
| 3100 | |
| 3101 | |
| 3102 | |
| 3103 | |

TABLE 131-continued

| Example | R |
|---|---|
| 3104 | piperidine-4-yl-CH2-C(=O)- with N-C(=O)NH2 |
| 3105 | C6H5-C(=O)- |
| 3106 | 4-Cl-C6H4-C(=O)- |
| 3107 | 4-Br-C6H4-C(=O)- |
| 3108 | 4-F-C6H4-C(=O)- |
| 3109 | 4-CN-C6H4-C(=O)- |
| 3110 | 4-CH3-C6H4-C(=O)- |
| 3111 | 4-OCH3-C6H4-C(=O)- |
| 3112 | pyridin-4-yl-C(=O)- |
| 3113 | (1-oxidopyridin-4-yl)-C(=O)- |
| 3114 | pyridin-4-yl-CH2-C(=O)- |
| 3115 | (1-oxidopyridin-4-yl)-CH2-C(=O)- |

EXAMPLES 3116-3137

If one were to follow procedures similar to those in Examples 566-567, but using compound 1008 from Example 1592, then one would obtain compounds of the formula:

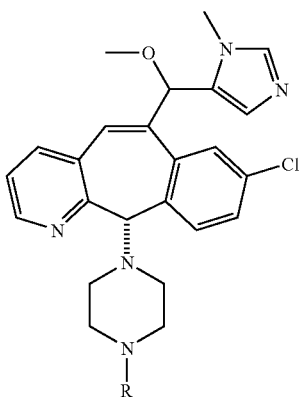
wherein R is defined in Table 132.
TABLE 132
| Example | R |
|---|---|
| 3116 | -S(O)₂CH₃ |
| 3117 | -S(O)₂CH(CH₃)₂ |
| 3118 | -S(O)₂CH₂CH₂CH₃ |
| 3119 | -S(O)₂N(CH₃)₂ |
| 3120 | -S(O)₂C(CH₃)₃ |
| 3121 | -S(O)₂CF₃ |
TABLE 132-continued
| Example | R |
|---|---|
| 3123 | -S(O)₂-cyclopropyl |
| 3124 | -S(O)₂-(4-methylphenyl) |
| 3125 | -S(O)₂-(4-ethylphenyl) |
| 3126 | -S(O)₂-(4-isopropylphenyl) |
| 3127 | -S(O)₂-(4-tert-butylphenyl) |
| 3128 | -S(O)₂-(4-trifluoromethylphenyl) |
| 3129 | -S(O)₂-(4-chlorophenyl) |
| 3130 | -S(O)₂-(4-bromophenyl) |
| 3131 | -S(O)₂-(4-fluorophenyl) |

TABLE 132-continued

| Example | R |
|---|---|
| 3132 | [4-cyanophenyl sulfonyl] |
| 3133 | [4-methoxyphenyl sulfonyl] |
| 3134 | [phenyl sulfonyl] |
| 3135 | [benzyl sulfonyl] |
| 3136 | [2-thienyl sulfonyl] |
| 3137 | [1-naphthyl sulfonyl] |

EXAMPLES 3138-3156

If one were to follow procedures similar to those in Examples 590-603 (wherein the chloroformates would be prepared according to Preparative Example 74), but using compound 1008 from Example 1592), then one would obtain compounds of the formula:

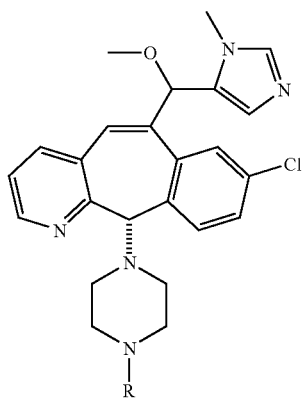

wherein R is defined in Table 133.

TABLE 133

| Example | R |
|---|---|
| 3138 | [C(O)O-tert-butyl] |
| 3139 | [C(O)O-methyl] |
| 3140 | [C(O)O-ethyl] |
| 3141 | [C(O)O-n-propyl] |
| 3142 | [C(O)O-isopropyl] |
| 3143 | [C(O)O-isobutyl] |
| 3144 | [C(O)O-neopentyl] |

TABLE 133-continued

| Example | R |
|---|---|
| 3145 | allyl ester |
| 3146 | sec-butyl ester |
| 3147 | cyclopentyl ester |
| 3148 | cyclohexyl ester |
| 3149 | phenyl ester |
| 3150 | benzyl ester |
| 3151 | 4-methylphenyl ester |
| 3152 | 4-methoxyphenyl ester |
| 3153 | 4-chlorophenyl ester |
| 3154 | 4-bromophenyl ester |
| 3155 | 4-fluorophenyl ester |
| 3156 | 1-naphthyl ester |

PREPARATIVE EXAMPLE 117

Step A

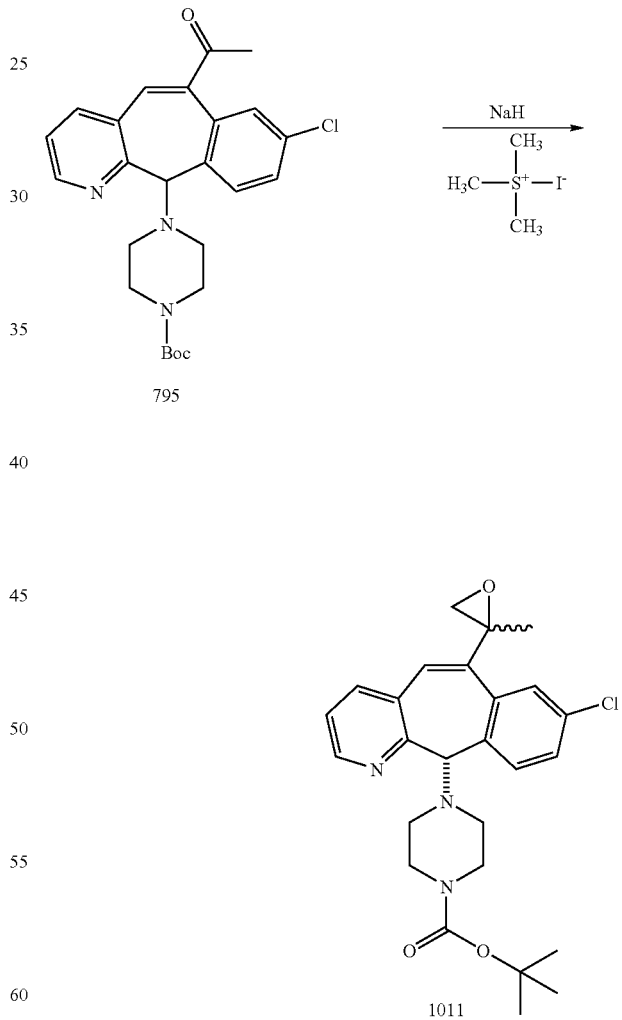

Following the same procedure as described in Example 510 Step C, but using compound 795 (3 g) from Example 489, the desired crude product was obtained (3.3 g).

Step B

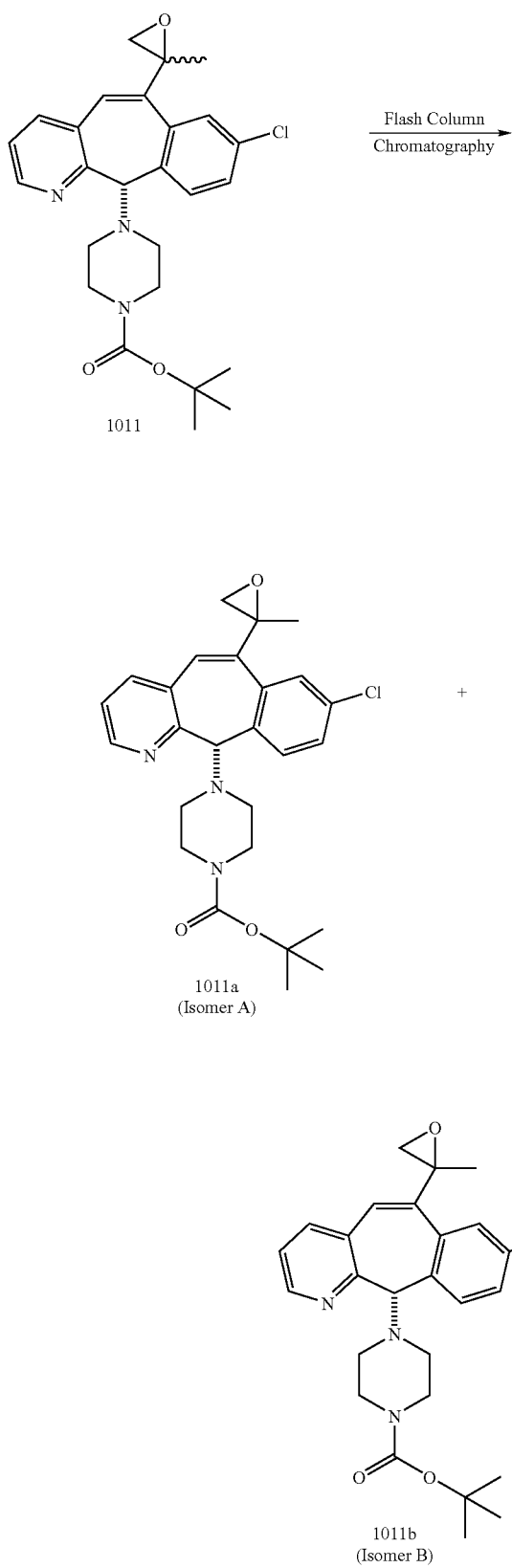

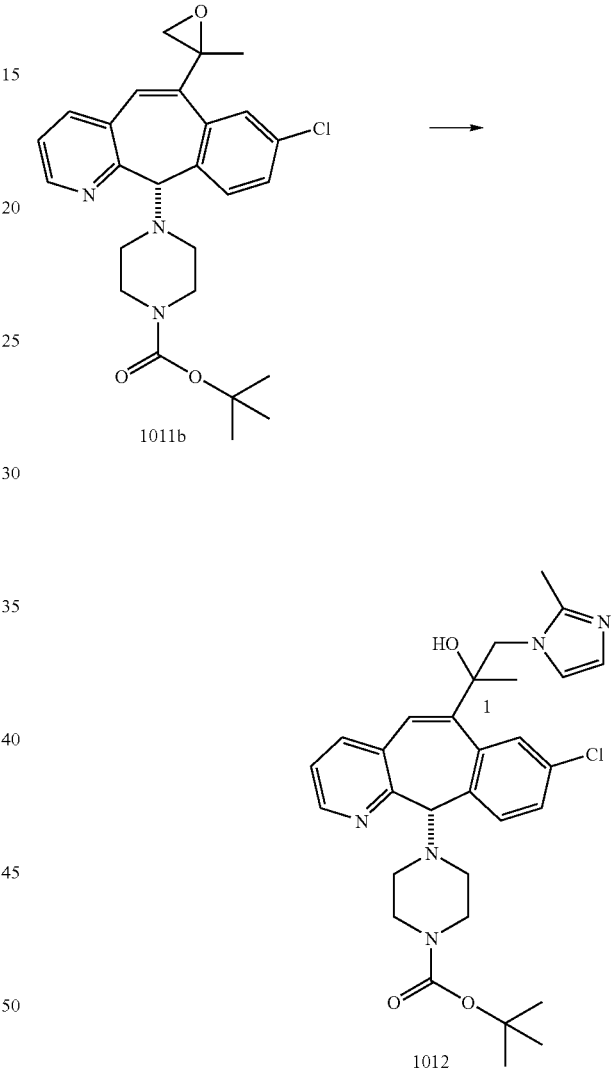

The crude material above (1011) was separated by flash column chromatography (40% EtOAc/Hex) to yield pure isomer A (1011a) (1.23 g) and an impure isomer B (1011b) (1.64 g). Impure isomer B was triterated in $CH_2Cl_2$/MeOH and filtered to give pure isomer 1011b (0.7 g).

Step C

2-Methylimidazole (1.1 g) was dissolved in dry DMF (15 ml) followed by the addition of NaH (60% in mineral oil, 300 mg). After stirring for 20 minutes, compound 1011b (1.2 g) was added and the solution was heated to 90° C. for 4 hours. The reaction was concentrated under vacuo, dissolved in $CH_2Cl_2$ and washed with brine. The organic layer was dried, concentrated under vacuo and purified via flash column chromatography (6% MeOH/$CH_2Cl_2$+$NH_4OH$) to give the desired product (1.47 g).

Step D
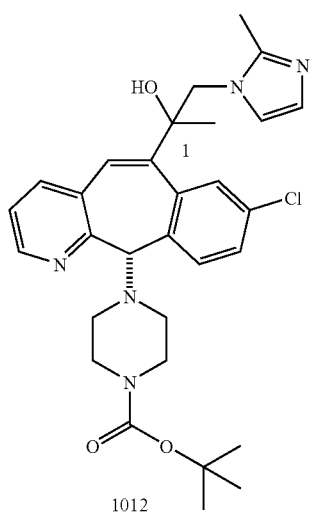
1012
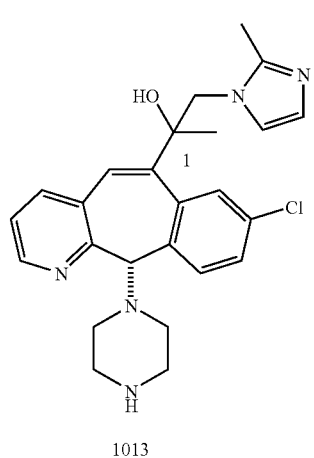
1013
Compound 1012 (1.4 g) was converted to compound 1013 (1.09 g) by following the procedure set forth in Example 507.
PREPARATIVE EXAMPLE 118
Step A
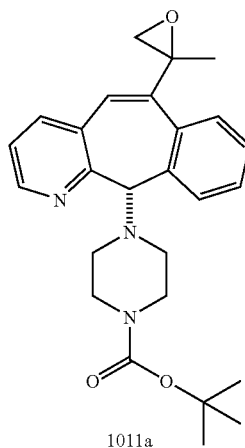
1011a
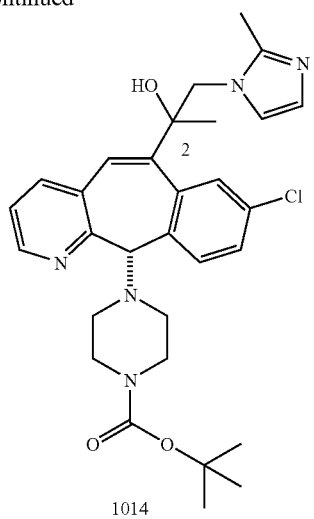
1014
Following the same procedure as described in Preparative Example 117 Step C, but using compound 1011a (696 mg), the desired compound was obtained (903 mg).
Step B
1014
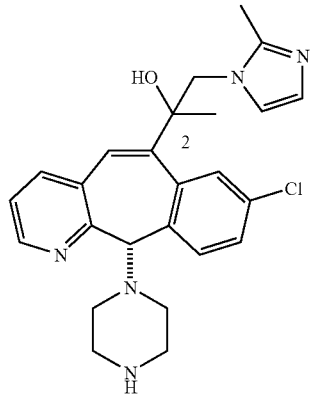
1015
Compound 1014 (0.9 g) was converted to compound 1015 (0.58 g) by following the procedure set forth in Example 507.

EXAMPLES 3157-3162

Compound 1015 from Preparative Example 118 Step B was reacted in essentially the same manner as in Example 511-513 to afford the compounds in Table 134.

TABLE 134

| Example | Compound |
|---------|----------|
| 3157    |          |

TABLE 134-continued

| Example | Compound |
|---------|----------|
| 3158    |          |
| 3159    |          |
| 3160    |          |

TABLE 134-continued

| Example | Compound |
|---|---|
| 3161 | (structure) |
| 3162 | (structure) |

EXAMPLES 3163–3168

Compound 1013 from Preparative Example 117 Step D was reacted in essentially the same manner as in Examples 511-513 to afford the compounds in Table 135.

TABLE 135

| Example | Compound |
|---|---|
| 3163 | (structure) |
| 3164 | (structure) |
| 3165 | (structure) |

TABLE 135-continued
| Example | Compound |
|---|---|
| 3166 | 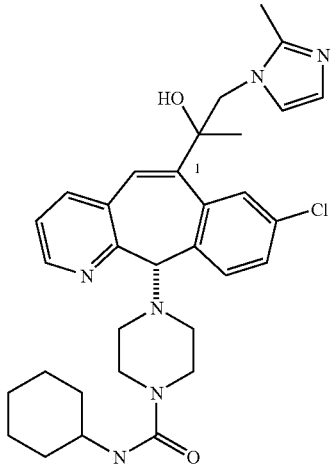 |
| 3167 | 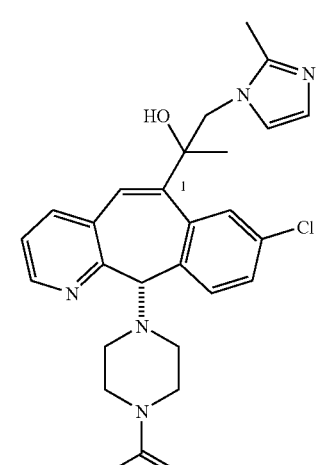 |
| 3168 | 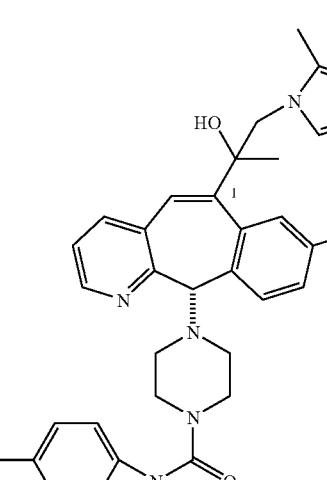 |
EXAMPLES 3169-3187
If one were to follow procedures similar to those in Examples 511-513, but using compounds 1013 (Preparative Example 117) and 1015 (Preparative Example 118), then one would obtain compounds of the formulas:
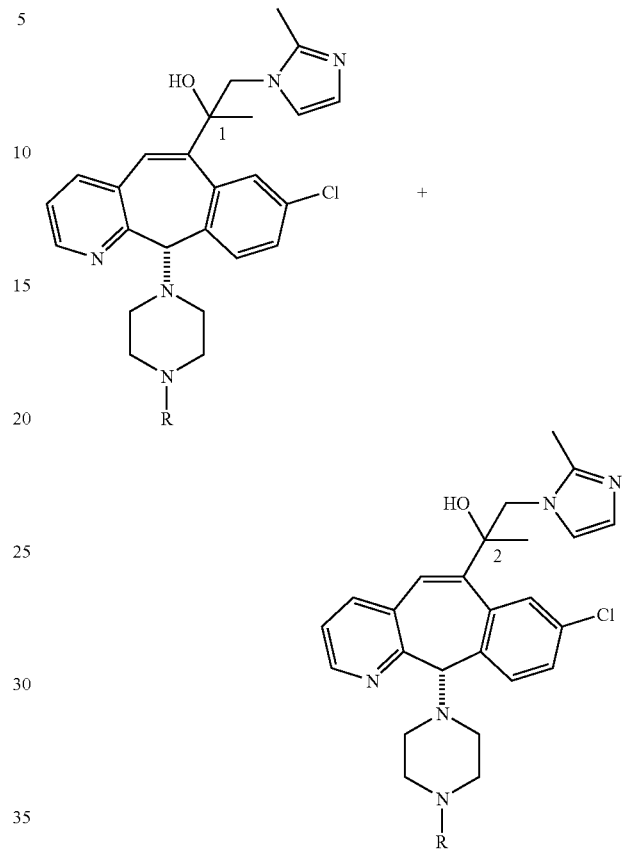
respectively, wherein R is defined in Table 136.
TABLE 136
| Example | R Isomer 1 and Isomer 2 |
|---|---|
| 3169 | 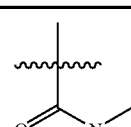 |
| 3170 | 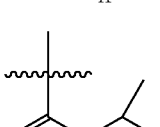 |
| 3171 | 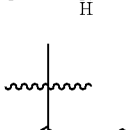 |
| 3172 | 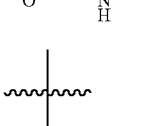 |

TABLE 136-continued

| Example | R Isomer 1 and Isomer 2 |
|---------|-------------------------|
| 3173 | isobutyl amide |
| 3174 | allyl amide |
| 3175 | cyclopentyl amide |
| 3176 | phenyl amide |
| 3177 | 4-bromophenyl amide |
| 3178 | 4-chlorophenyl amide |
| 3179 | 4-fluorophenyl amide |
| 3180 | 4-methoxyphenyl amide |
| 3181 | 4-phenoxyphenyl amide |
| 3182 | 4-tert-butylphenyl amide |
| 3183 | 1-naphthyl amide |
| 3184 | benzoyl amide |
| 3185 | benzyl amide |
| 3186 | 3-pyridyl amide |
| 3187 | 4-methylbenzyl amide |

EXAMPLES 3188–3215

If one were to follow a procedure similar to that in Example 536, but using compounds 1013 (Preparative Example 117) and 1015 (Preparative Example 118), then one would obtain compounds of the formulas:

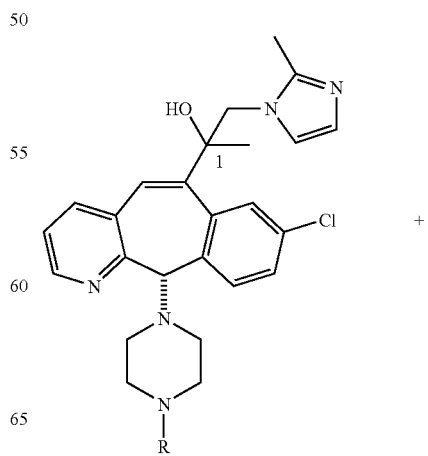

-continued
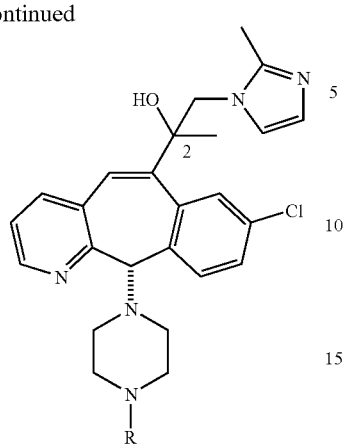
respectively, wherein R is defined in Table 137.
TABLE 137
| Example | R Isomer 1 and Isomer 2 |
|---|---|
| 3188 | 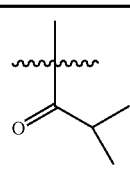 |
| 3189 | 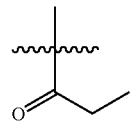 |
| 3190 | 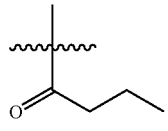 |
| 3191 | 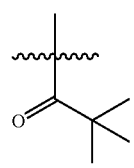 |
| 3192 | 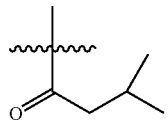 |
| 3193 | 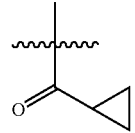 |
| 3194 | 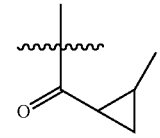 |
TABLE 137-continued
| Example | R Isomer 1 and Isomer 2 |
|---|---|
| 3195 | 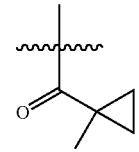 |
| 3196 | 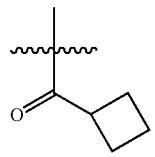 |
| 3197 | 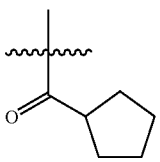 |
| 3198 | 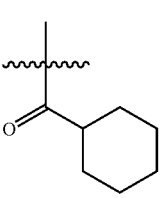 |
| 3199 | 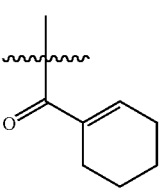 |
| 3200 | 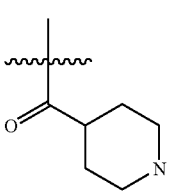 |
| 3201 | 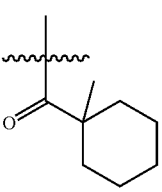 |
| 3202 | 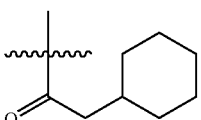 |
| 3203 | 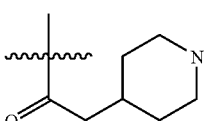 |

TABLE 137-continued
| Example | R Isomer 1 and Isomer 2 |
|---|---|
| 3204 | 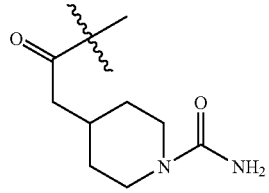 |
| 3205 | 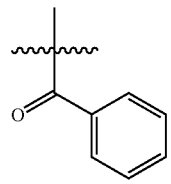 |
| 3206 | 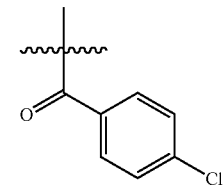 |
| 3207 | 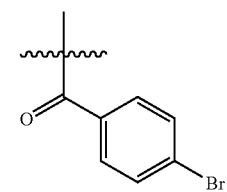 |
| 3208 | 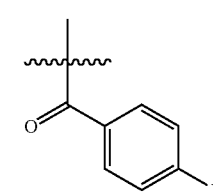 |
| 3209 | 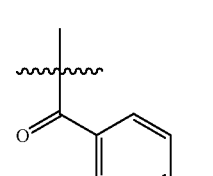 |
| 3210 | 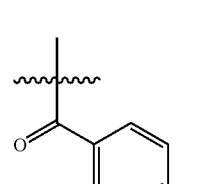 |
TABLE 137-continued
| Example | R Isomer 1 and Isomer 2 |
|---|---|
| 3211 | |
| 3212 | |
| 3213 | |
| 3214 | |
| 3215 | |
EXAMPLES 3216-3237
If one were to follow procedures similar to those in Examples 566-567 but using compounds 1013 (Preparative Example 117) and 1015 (Preparative Example 118), then one would obtain compounds of the formulas:

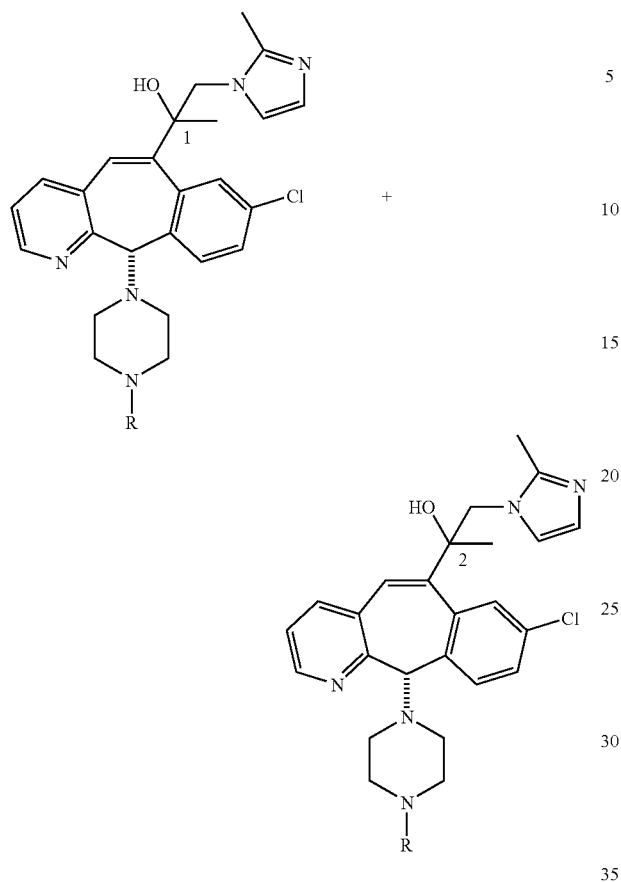

respectively, wherein R is defined in Table 138.

TABLE 138

| Example | R Isomer 1 and Isomer 2 |
|---|---|
| 3216 | methanesulfonyl |
| 3217 | isopropylsulfonyl |
| 3218 | propylsulfonyl |
| 3219 | N,N-dimethylsulfamoyl |

TABLE 138-continued

| Example | R Isomer 1 and Isomer 2 |
|---|---|
| 3220 | tert-butylsulfonyl |
| 3221 | trifluoromethylsulfonyl |
| 3223 | cyclopropylsulfonyl |
| 3224 | 4-methylphenylsulfonyl |
| 3225 | 4-ethylphenylsulfonyl |
| 3226 | 4-isopropylphenylsulfonyl |
| 3227 | 4-tert-butylphenylsulfonyl |
| 3228 | 4-trifluoromethylphenylsulfonyl |
| 3229 | 4-chlorophenylsulfonyl |

TABLE 138-continued

| Example | R Isomer 1 and Isomer 2 |
|---|---|
| 3230 | 4-bromophenylsulfonyl |
| 3231 | 4-fluorophenylsulfonyl |
| 3232 | 4-cyanophenylsulfonyl |
| 3233 | 4-methoxyphenylsulfonyl |
| 3234 | phenylsulfonyl |
| 3235 | benzylsulfonyl |
| 3236 | 2-thienylsulfonyl |
| 3237 | 1-naphthylsulfonyl |

EXAMPLES 3237-3255

If one were to follow procedures similar to those in Examples 590-603 (wherein the chloroformates could be prepared according to Preparative Example 74, but using compounds 1013 (Preparative Example 117) and 1015 (Preparative Example 118), then one would obtain compounds of the formulas:

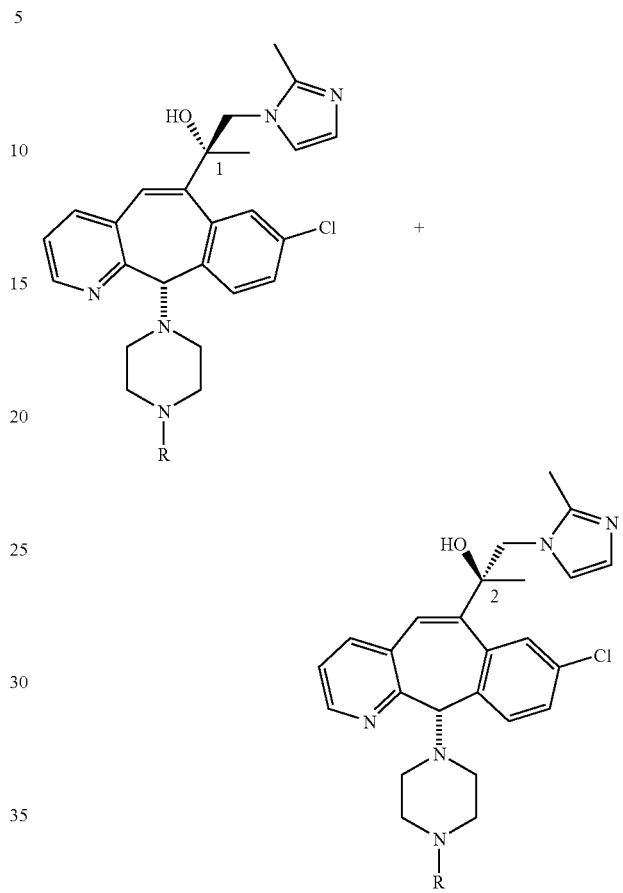

respectively, wherein R is defined in Table 139.

TABLE 139

| Example | R |
|---|---|
| 3237 | —C(O)O-t-Bu |
| 3238 | —C(O)OMe |
| 3239 | —C(O)OEt |
| 3240 | —C(O)O-n-Pr |

TABLE 139-continued
| Example | R |
|---|---|
| 3241 | 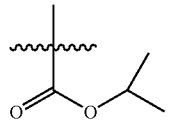 |
| 3242 | 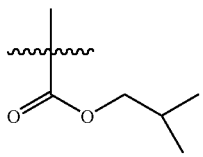 |
| 3243 | 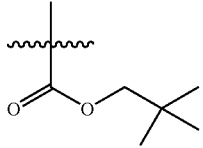 |
| 3244 | 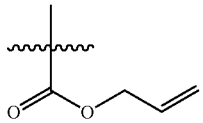 |
| 3245 | 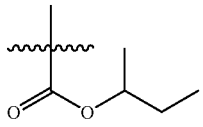 |
| 3246 | 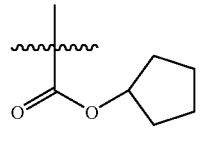 |
| 3247 | 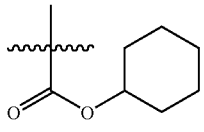 |
| 3248 | 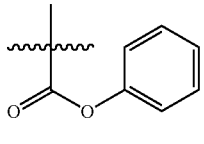 |
| 3249 | 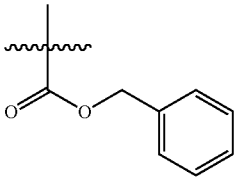 |
TABLE 139-continued
| Example | R |
|---|---|
| 3250 | 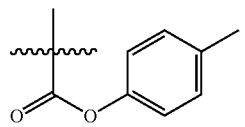 |
| 3251 | 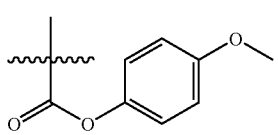 |
| 3252 | 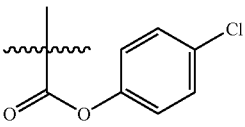 |
| 3253 | 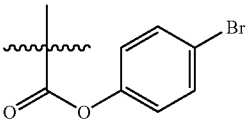 |
| 3254 | 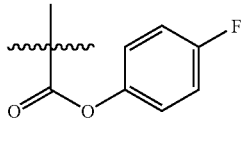 |
| 3255 | 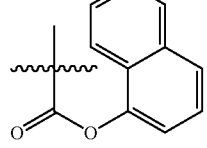 |
EXAMPLE 3256
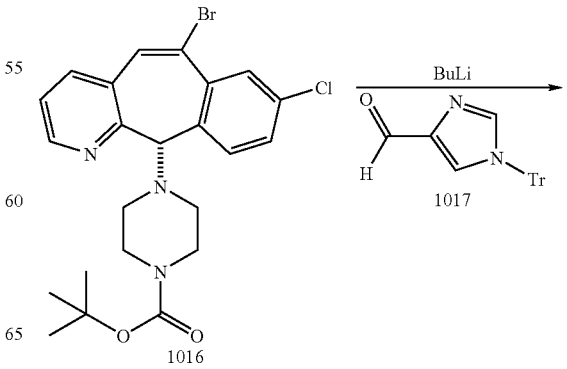

-continued

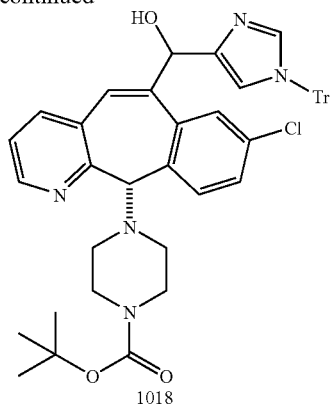
1018

1. NaH, MeI
2. TFA
3. (Boc)₂O, TEA
1018 →

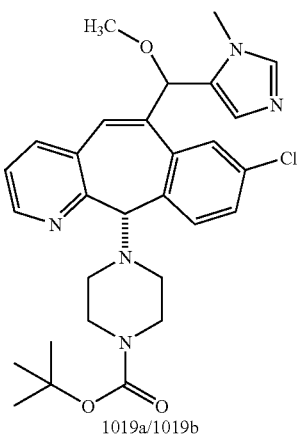
1019a/1019b

To a THF (freshly distilled, 10 mL) solution of 1016 (980 mg, 2 mmol) kept at −78° C., BuLi (1.6 mL, 2.5 M hexanes solution, 4 mmol) was added in dropwise. After 15 min, THF (6 mL) solution of 1017 (676 mg, 2 mmol) was added in. After stirring at −78° C. for 1.5 hrs, the reaction mixture was participated between ethyl acetate and brine at room temperature. The aqueous layer was extracted with ethyl acetate once. The combined ethyl acetate layers was dried and concentrated in vacuo. The resulting crude was purified with silica gel column eluting with methanol/methylene chloride (2%-5%). Compound 1018 (834 mg) was obtained as a light yellow solid.

Compound 1018 (390 mg, 0.52 mmol) was dissolved in THF (3 mL) at room temperature. NaH (28 mg, 60% in mineral oil, 0.7 mmol) was added in followed by MeI (1.0 mL) 5 min later. After stirring for 20 hrs, the mixture was evaporated to dryness in vacuo. The resulting crude was taken up in CH₂Cl₂ (5 mL) and TFA (1 mL) was added. One hour later, the mixture was evaporated to dryness. The crude was retaken up in CH₂Cl₂ and made to PH>8 by addition of triethyl amine (ca. 0.6 mL). (Boc)₂O (320 mg, 1.5 mmol) was then added. After stirring for 30 mins, the solvents were removed in vacuo and the residue was participated between CH₂Cl₂ and H₂O. The organic layer was dried and concentrated. The crude was purified with prep TLC plates using 10% methanol (2M NH₃)/CH₂Cl₂ to yield a light yellow solid (121 mg). The product was separated by a semi-prep OD HPLC column eluting with 30% IPA/Hexane/0.2% DEA to give pure isomers 1019a (44.8 mg, isomer 1, MH⁺=536) and 1019b (53.6 mg, isomer 2, MH⁺=536).

EXAMPLE 3257

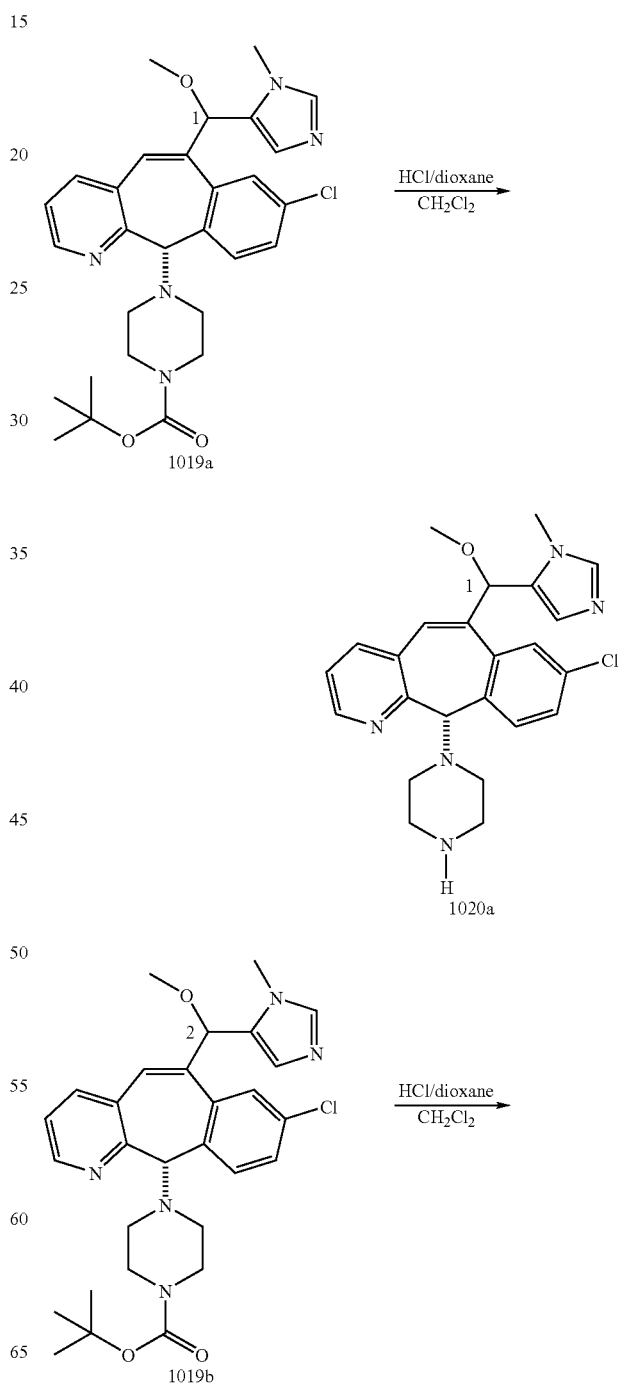

-continued

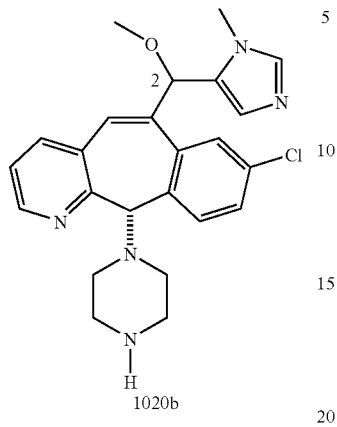
1020b

Compound 1019b (isomer 2) was converted to 1020b by reacting it with 20% 4M HCl(dioxane)/CH$_2$Cl$_2$ at room temperature under N$_2$ overnight.

The same procedure was used to prepare 1020a (isomer 1) from 1019a.

EXAMPLES 3258-3260

Each isomer, 1020a and 1020b from Example 3257 was dissolved in CH$_2$Cl$_2$, TEA was added in till PH>8 and followed by the corresponding isocyanates. Once TLC indicated the complete consumption of starting material, the solvent was concentrated in vacuo. The residue was purified by silica gel preparative thin layer chromatography or silica gel chromatography to afford compounds of the formulas:

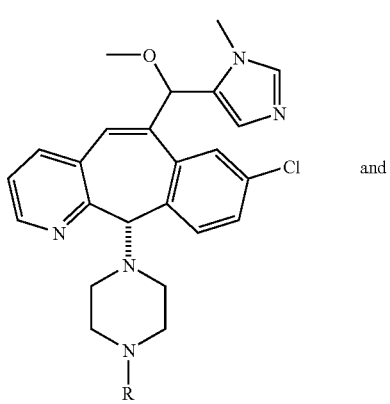

and

-continued

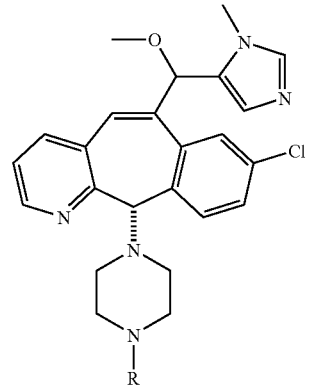

wherein R is defined in Table 140 and the numbers 1 and 2 in the formulas represent isomers 1 and 2, respectively.

TABLE 140

| EXAMPLE | R | Isomer 1 Data | Isomer 2 Data |
|---|---|---|---|
| 3258 | | MH$^+$ 535 | MH$^+$ 535 |
| 3259 | | MH$^+$ 561 | MH$^+$ 561 |
| 3260 | | MH$^+$ 580 | MH$^+$ 580 |

EXAMPLES 3261-3263

Isomer 1020a from Example 3257 was dissolved in CH$_2$Cl$_2$ at room temperature under nitrogen, followed by addition of the corresponding carboxylic acid, and the appropriate reagents: EDC, HOBt and NMM. Reaction was then stirred overnight and added in 1N HCl till pH=2. After stirring for 5 min, it was then basicified with sat. NaHCO$_3$ followed by extraction of CH$_2$Cl$_2$. The organic solvent was concentrated in vacuo and the residue was then purified by silica gel column to give compounds of the formula:

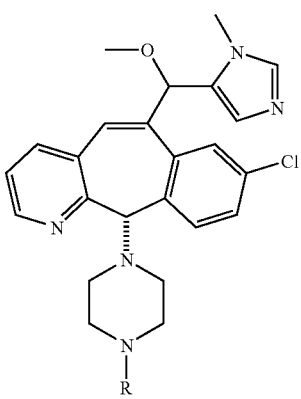

wherein R is defined in Table 141 and the number 1 in the formula represents isomer 1.

TABLE 141

| EXAMPLE | R | Isomer 1 Data |
|---|---|---|
| 3261 | 2-OH) | MH+ 522 |
| 3262 | (OH)-CH3) | MH+ 584 |
| 3263 | (OH)-CH3 opposite) | MH+ 584 |

EXAMPLE 3264

Isomer 1020b from Example 3257 was dissolved in CH$_2$Cl$_2$ at room temperature under nitrogen, followed by addition of diisopropylethyl amine to pH>8. Reaction was then treated with the corresponding sulfonyl chloride and stirred at room temperature till TLC indicated the completion of reaction. Quench reaction with brine and extract with CH$_2$Cl$_2$. Organic layer was dried and concentrated. The residue was purified by silica gel column to give a compound of the formula:

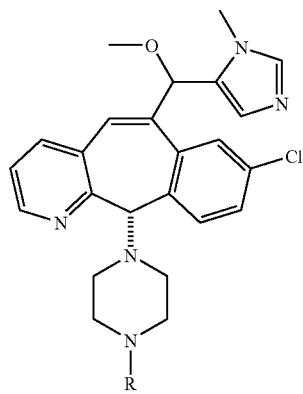

wherein R is defined in Table 142 and the number 2 in the formula represents isomer 2.

TABLE 142

| EXAMPLE | R | Isomer 2 Data |
|---|---|---|
| 3264 | (=O)) | MH+ 514 |

EXAMPLES 3265-3267

Isomer 1020b from Example 3257 was dissolved in CH$_2$Cl$_2$ at room temperature under nitrogen, followed by addition of TEA. Reactions were then treated with the respective chloroformates (made from the corresponding alcohols according to Preparative Example 74) and stirred at room temperature till TLC indicated the completion of reactions. Quench reactions with brine and extract with CH$_2$Cl$_2$. Organic layer was dried and concentrated. The residue was purified by silica gel column to give compounds of the formula:

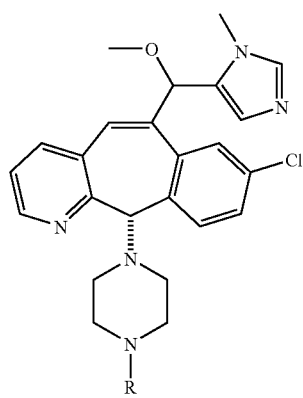

wherein R is defined in Table 142 and the number 2 in the formula represents isomer 2.

TABLE 142
| EXAMPLE | R | Isomer 2 Data |
|---|---|---|
| 3265 | isopropyl ester | MH+ 522 |
| 3266 | cyclohexyl ester | MH+ 562 |
| 3267 | tetrahydropyran-4-yl ester | MH+ 564 |
EXAMPLE 3268
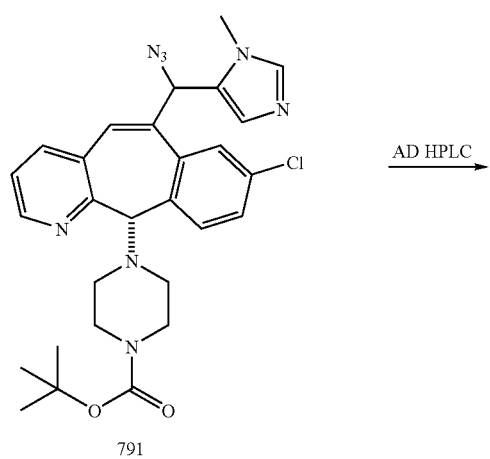
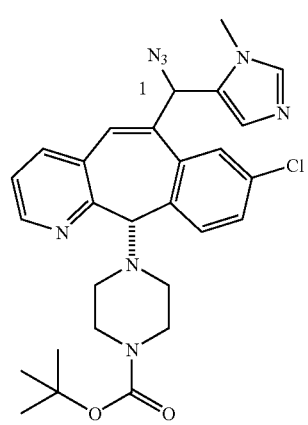
PREPARATIVE EXAMPLE 65
Compound 791 was separated by AD HPLC column eluting with 15%-30% IPA/Hexanes/0.2% DEA to give pure isomers 791a (isomer 1, MH+=547.1) and 791b (isomer 2, MH+=547.1).
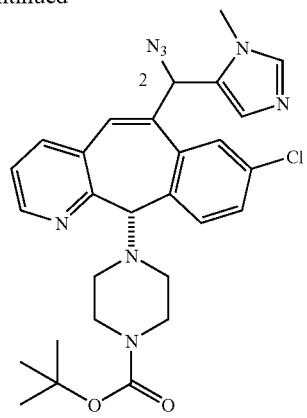
EXAMPLE 3269
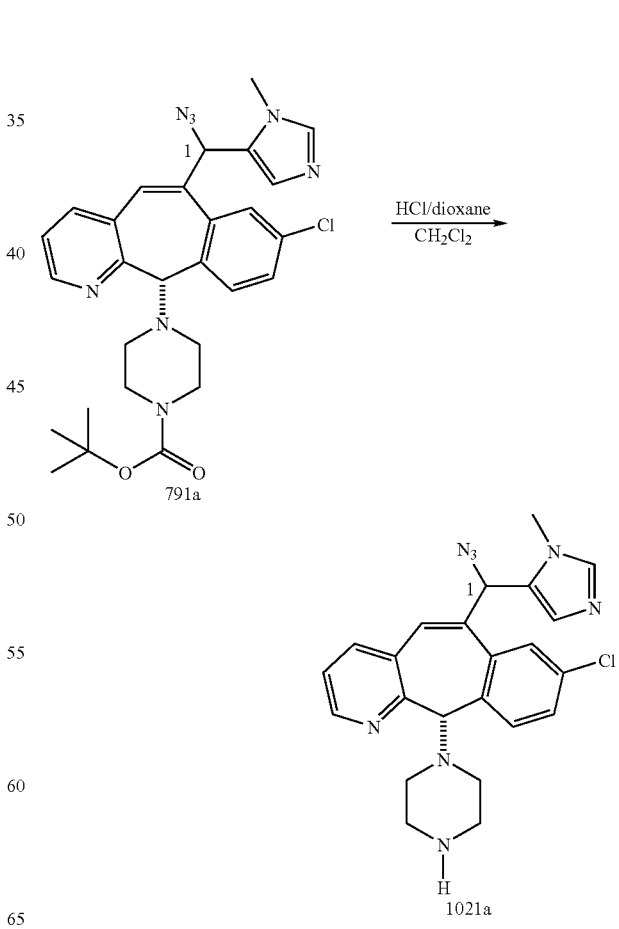

-continued

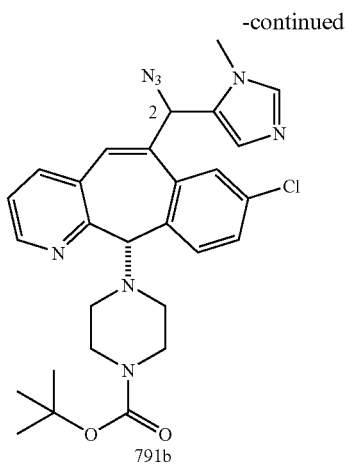

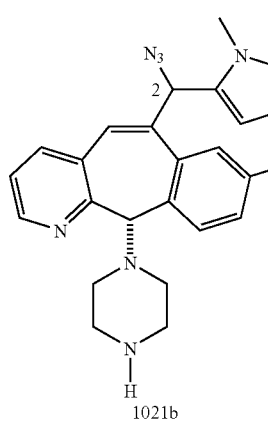

Compound 791b (isomer 2) was converted to 1021b by reacting it with 20% 4M HCl(dioxane)/CH$_2$Cl$_2$ at room temperature under N$_2$ overnight.

The same procedure was used to prepare 1021 a (isomer 1) from 791a.

EXAMPLE 3270

Each isomer, 1021a and 1021b from Example 3269 was dissolved in CH$_2$Cl$_2$, TEA was added in till PH>8 and followed by the corresponding isocyanate. Once TLC indicated the complete consumption of starting material, the solvent was concentrated in vacuo. The residue was purified by silica gel preparative thin layer chromatography or silica gel chromatography to afford compounds of the formulas

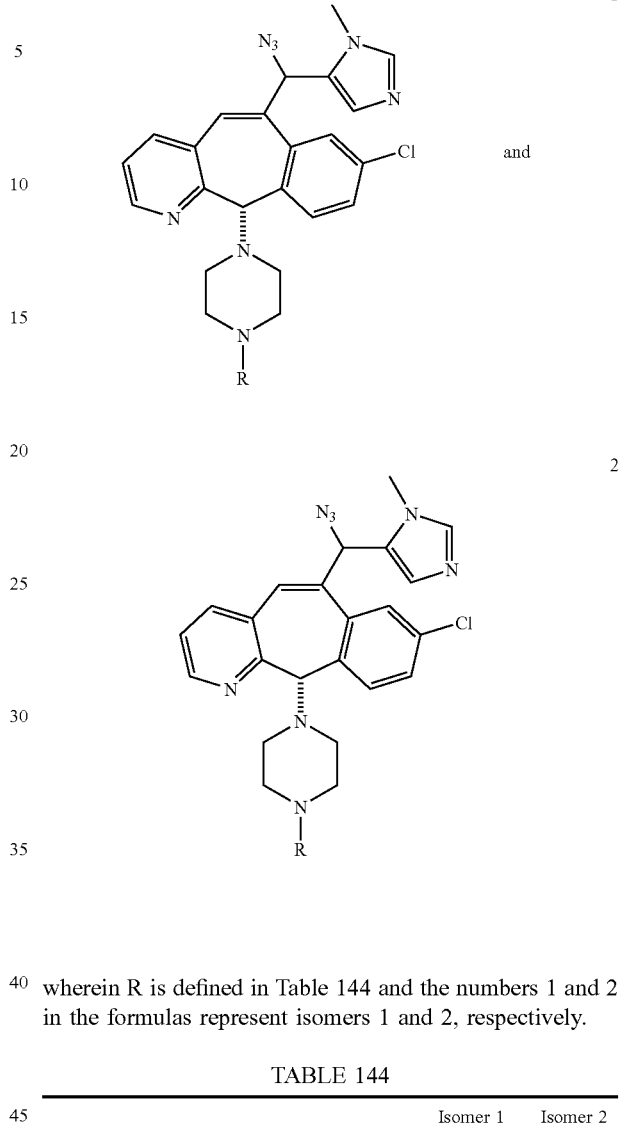

wherein R is defined in Table 144 and the numbers 1 and 2 in the formulas represent isomers 1 and 2, respectively.

TABLE 144

| EXAMPLE | R | Isomer 1 Data | Isomer 2 Data |
|---|---|---|---|
| 3270 | (structure with CN group) | MH$^+$ 591 | MH$^+$ 591 |

EXAMPLE 3271

Each isomer, 1021a and 1021b from Example 3269 was dissolved in CH$_2$Cl$_2$ at room temperature under nitrogen, followed by addition of the corresponding carboxylic acid, and the appropriate reagents: EDC, HOBt and NMM. Reaction was then stirred overnight and added in 1N HCl till pH=2. After stirring for 5 min, it was then basicified with sat. NaHCO$_3$ followed by extraction of CH$_2$Cl$_2$. The organic solvent was concentrated in vacuo and the residue was then purified by silica gel column to give compounds of the formulas:

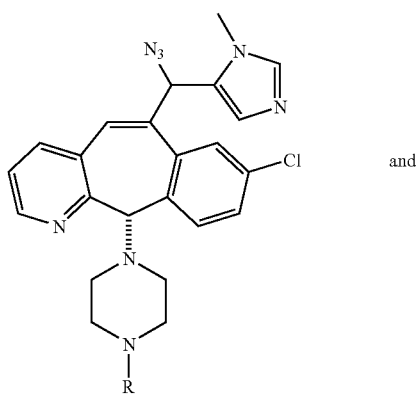

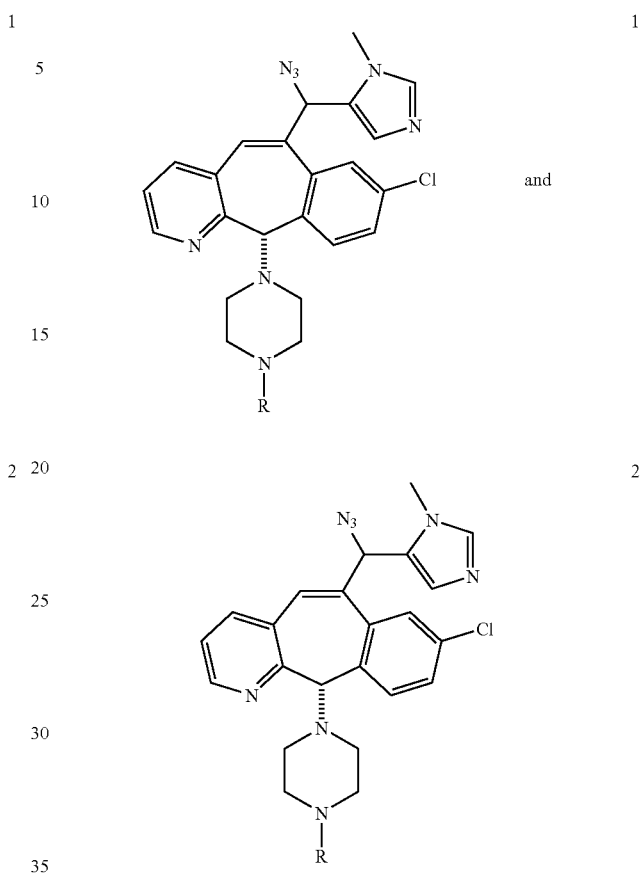

wherein R is defined in Table 145 and the numbers 1 and 2 in the formulas represent isomers 1 and 2, respectively.

wherein R is defined in Table 146 and the numbers 1 and 2 in the formulas represent isomers 1 and 2, respectively.

TABLE 145

| EXAMPLE | R | Isomer 1 Data | Isomer 2 Data |
|---|---|---|---|
| 3271 | ![structure with O, OH and methyl] | MH+ 533 | MH+ 533 |

TABLE 146

| EXAMPLE | R | Isomer 1 Data | Isomer 2 Data |
|---|---|---|---|
| 3272 | ![O=S=O structure] | MH+ 525 | MH+ 525 |

EXAMPLE 3272

Each isomer, 1021a and 1021b from Example 3269 was dissolved in $CH_2Cl_2$ at room temperature under nitrogen, followed by addition of diisopropylethyl amine to PH>8. Reactions were then treated with the corresponding sulfonyl chloride and stirred at room temperature till TLC indicated the completion of reactions. Quench reactions with brine and extract with $CH_2Cl_2$. Organic layer was dried and concentrated. The residue was purified by silica gel column to give compounds of the formulas:

EXAMPLE 3273

Each isomer, 1021a and 1021b from Example 3269 was dissolved in $CH_2Cl_2$ at room temperature under nitrogen, followed by addition of TEA. Reactions were then treated with the respective chloroformate (made from the corresponding alcohols according to Preparative Example 74) and stirred at room temperature till TLC indicated the completion of reactions. Quench reactions with brine and extract with $CH_2Cl_2$. Organic layer was dried and concentrated. The residue was purified by silica gel column to give compounds of the formulas:

EXAMPLES 3274-3278
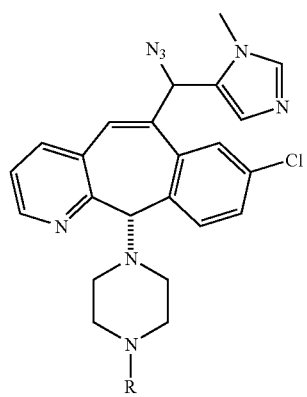
and
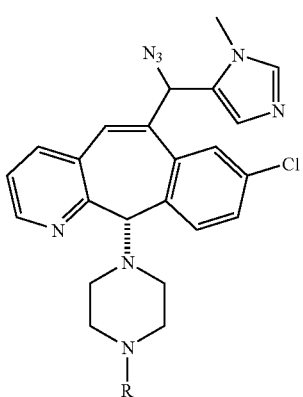
wherein R is defined in Table 147 and the number 1 and 2 in the formulas represent isomers 1 and 2, respectively.
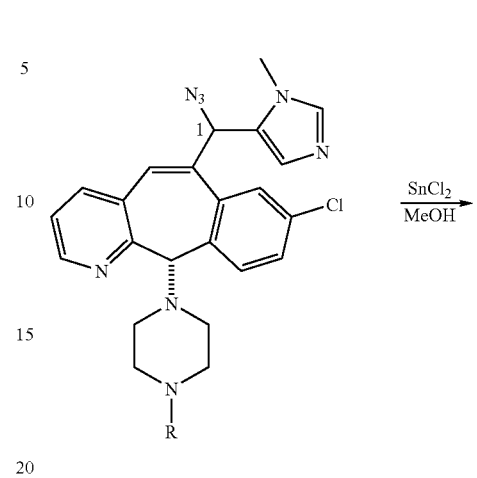
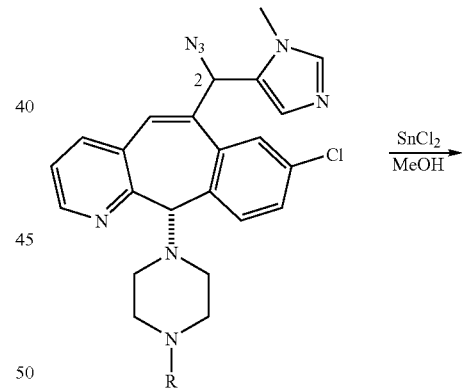
TABLE 147
| EXAMPLE | R | Isomer 1 Data | Isomer 2 Data |
|---------|---|---------------|---------------|
| 3273 | ![isopropyl carbamate] | MH+ 533 | MH+ 533 |

Each isomer from Examples 3268 and 3270-3273 was dissolved in MeOH at room temperature under nitrogen, followed by addition of excess SnCl$_2$. Reactions were stirred at room temperature overnight and then concentrated in vacuo. The residue was stirred in a mixture of 1N NaOH and ethyl acetate for 30 mins. Extract with ethyl acetate several times and wash the organic layer with brine. Organic layer was dried and evaporated to dryness. The crude was purified by silica gel column to give compounds of the formulas:

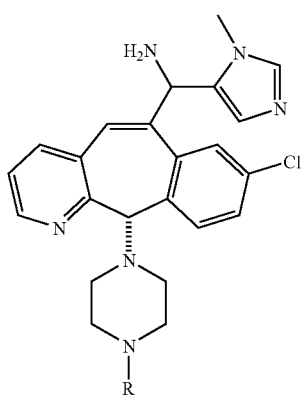

and

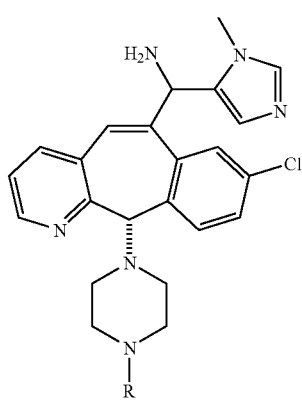

wherein R is defined in Table 148 and the numbers 1 and 2 in the formulas represent isomers 1 and 2, respectively.

TABLE 148

| EXAMPLE | R | Isomer 1 Data | Isomer 2 Data |
|---------|---|---------------|---------------|
| 3274 | 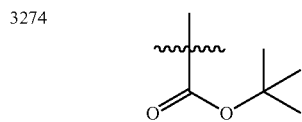 | MH$^+$ 521 | MH$^+$ 521 |
| 3275 | 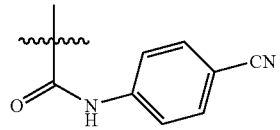 | MH$^+$ 565 | MH$^+$ 565 |

TABLE 148-continued

| EXAMPLE | R | Isomer 1 Data | Isomer 2 Data |
|---------|---|---------------|---------------|
| 3276 | | MH$^+$ 499 | MH$^+$ 499 |
| 3277 | | —* | MH$^+$ 507 |

*Isomer 1 of Example 3277 was not made.

EXAMPLES 3278-3279

Following a procedure similar to that of Example 3270 the azide compound

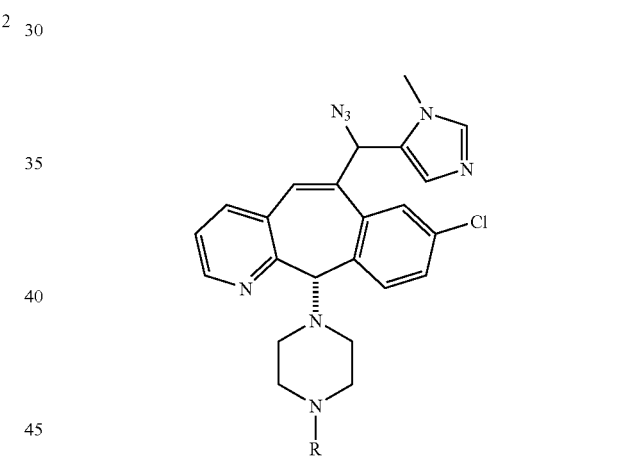

is prepared wherein R is

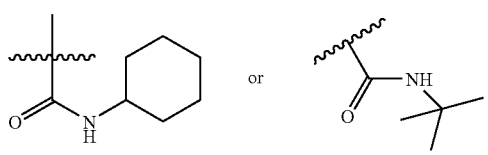

and the number 2 in the formula represents isomer 2.

Then, following a procedure similar to that of Examples 3274 to 3278 the amino compound of formula:

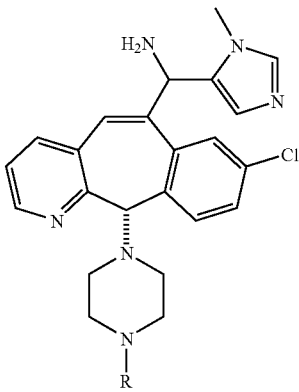

is prepared from the azide compound wherein R is defined in Table 149 and the number 2 in the formula represents isomer 2.

TABLE 149

| EXAMPLE | R | Isomer 2 Data |
|---------|---|---------------|
| 3278 | (cyclohexyl amide) | MH+ 547 |
| 3279 | (t-butyl amide) | MH+ 521 |

EXAMPLE 3280

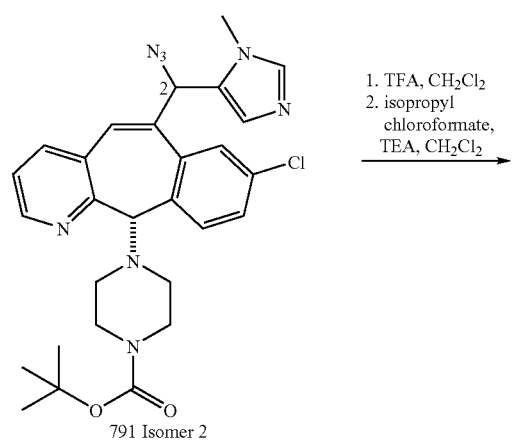

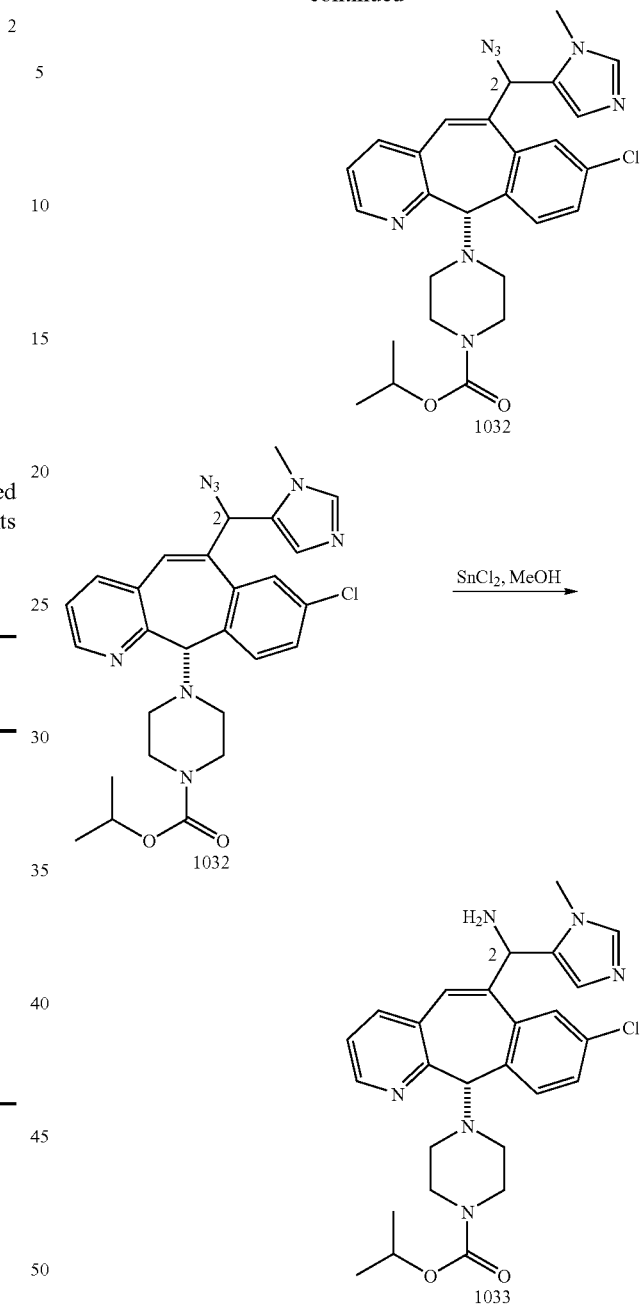

Isomer 2 of Compound 791 (70 mg, 0.13 mmol) was dissolved in CH$_2$Cl$_2$ (5 mL) at room temperature. TFA (1 mL) was added in. After the reaction mixture was stirred under N$_2$ for 1 hour, it was evaporated to dryness with CH$_3$Ph. The residue was retaken up in CH$_2$Cl$_2$ (5 mL) and the solution was made to pH>8 by addition of triethyl amine (ca. 0.2 mL). Isopropyl chloroformate (0.13 mL, 1.0 M in CH$_3$Ph) was then added in dropwise. After stirring for 1 hr, the reaction was quenched with water and the mixture was extracted with CH$_2$Cl$_2$ twice. The organic layer was dried and concentrated. The crude was purified with prep TLC plates using 10% methanol (2M NH$_3$)/CH$_2$Cl$_2$ to give Compound 1032 as a light yellow solid (50 mg). MS M+1 533.

Compound 1032 (160 mg, 0.3 mmol) was dissolved in MeOH (5 mL) at room temperature and SnCl$_2$ (150 mg, 0.79 mmol) was added in. After 3 hrs, majority of solvent was removed in vacuo. To the residue was added 30 mL 1N NaOH and 20 mL ethyl acetate. The turbid solution became clear after stirring for 20 min. Extract the aqueous layer once with ethyl acetate. The combined organic layer was dried and concentrated. The crude was purified by prep TLC plates using 10% methanol (2M NH$_3$)/CH$_2$Cl$_2$ to give compound 1033 as a light yellow solid (90.0 mg). M.P. 132-135° C. MS M+1 507.

EXAMPLE 3281

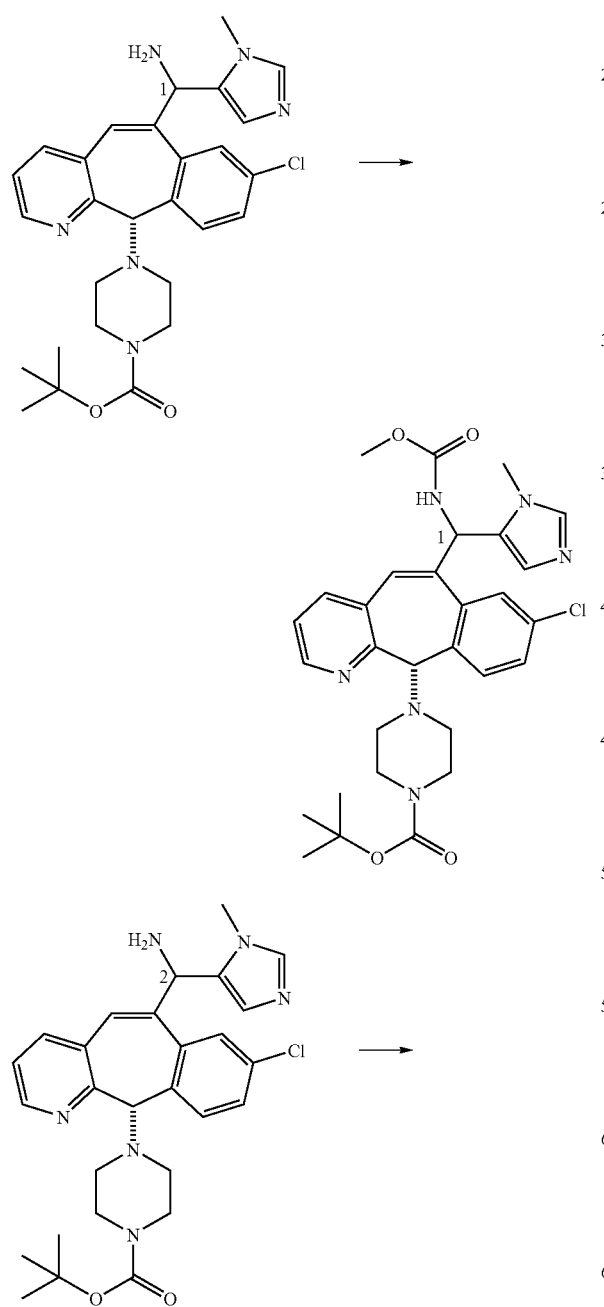

-continued

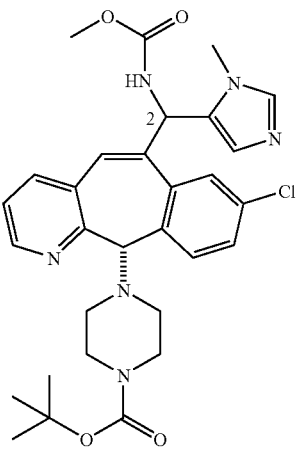

To a solution of compound 792 (Example 486) (0.052 gm, 0.1 mmole) in 5 ml of dry dichloromethane was added 0.02 gm of triethylamine and 0.01 g of methyl-chloroformate. After stirring for two hours under dry nitrogen the reaction mixture was washed with brine and the organic phase separated, dried over Magnesium sulfate, filtered and evaporated to obtain a crude mixture. The crude mixture was chromatographed on silica gel using 10% methanol/dichloromethane as the eluent to obtain 0.019 gm of final product. MH+ 579 (Isomer 1) and MH+ 579 (Isomer 2).

EXAMPLES 3282-3287f

Following a procedure similar to that in Example 3281, but using the corresponding sulfonyl chloride, isocyanate, chloroformate or acid chloride of the R$^{9b}$ substituent, compounds of the formulas:

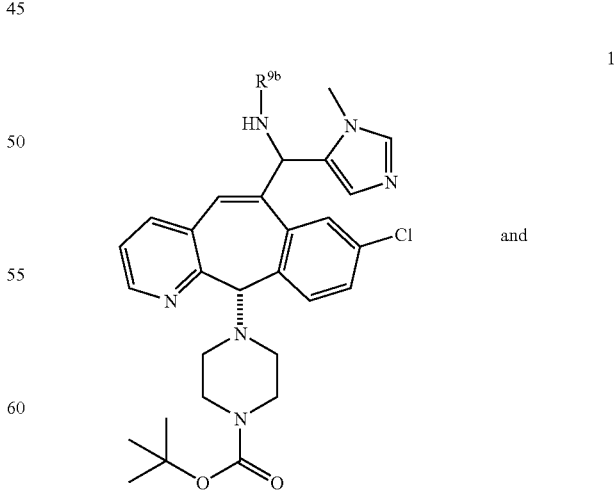

and

-continued
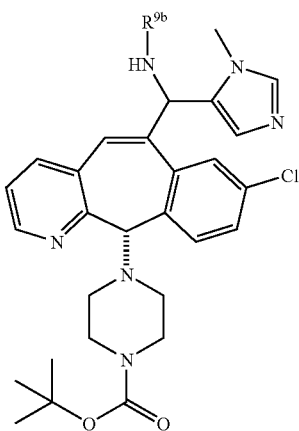
were prepared wherein $R^{9b}$ is defined in Table 150 and the numbers 1 and 2 in the formulas represent Isomers 1 and 2, respectively.
TABLE 150
| Example | $R^{9b}$ | Isomer 1 Data | Isomer 2 Data |
|---|---|---|---|
| 3282 | | MH+ 563 | MH+ 563 |
| 3283 | | MH+ 564 | MH+ 564 |
| 3284 | | MH+ 592 | MH+ 592 |
| 3285 | | MH+ 599 | MH+ 599 |
| 3286 | | MH+ 607 | MH+ 607 |
| 3287 | | MH+ 620 | MH+ 620 |
| 3287a | | — | MH+ 593.1 |
| 3287b | | | MH+ 606.1 |
| 3287c | | | MH+ 589.1 |
| 3287d | | | MH+ 591.3 |
| 3287e | | | MH+ 605.1 |
| 3287f | | | MH+ 593.3 |
EXAMPLE 3288
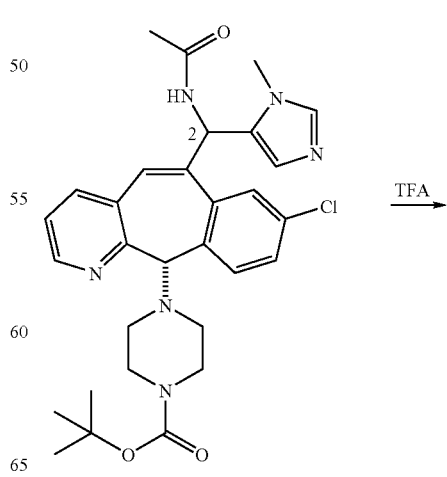
TFA →

1043
-continued
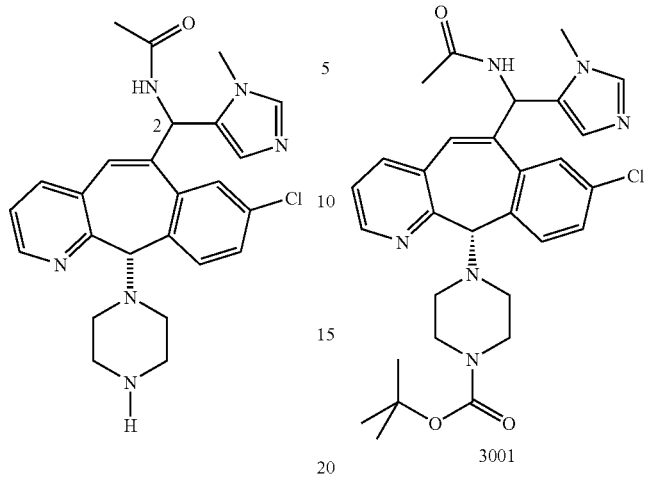
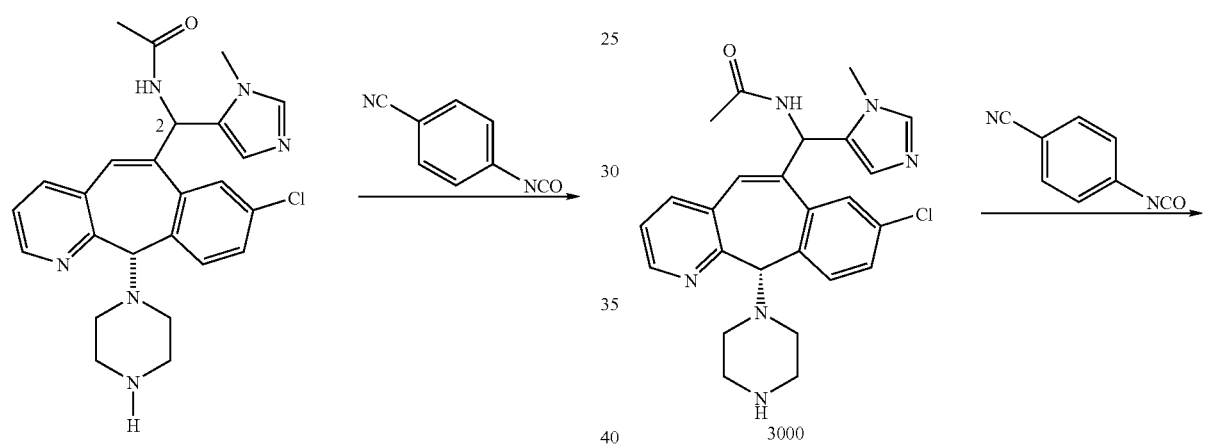
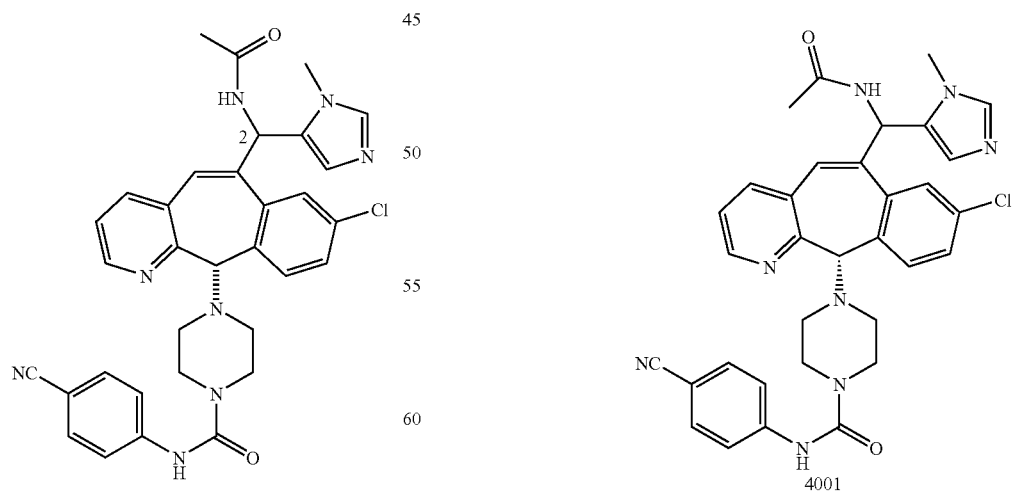
1044
-continued
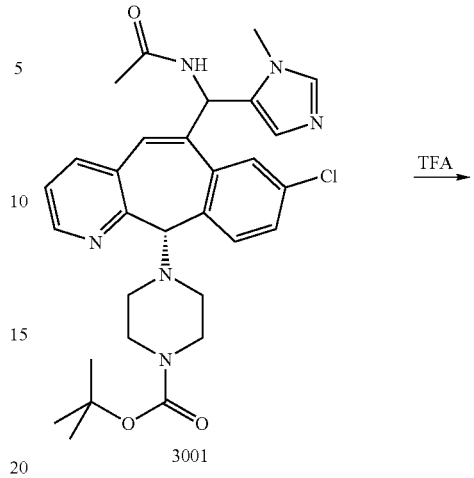

To a solution of the compound of Example 3282 (Isomer 2) (150 mg) was added 10 ml of dichloromethane and 2 ml of trifluoroacetic acid. The mixture was stirred for 1.5 hrs and then evaporated to dryness. The mixture was azeotroped with dichloromethane two times and re-dissolved in 15 ml of dichloromethane and 0.5 ml of triethyl amine. To 0.08 mmol of the resulting compound was added 15 mg of 4-cyanophenylisocyanate. The reaction was stirred for 1 hr and then concentrated. The residue was chromatographed on silica gel using 10% methanol/dichloromethane to obtain 0.033 gm of product. MH+607 (Isomer 2).

EXAMPLES 3289-3291

Following a procedure similar to that in Example 3288 compounds of the formula:

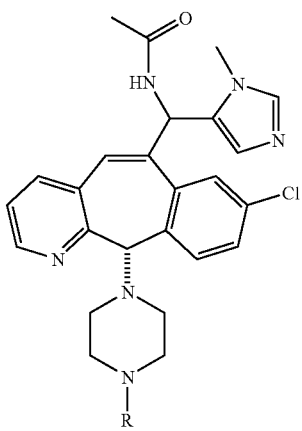

were prepared using the corresponding chloroformate or isocyanate for substituent R, wherein R is defined in Table 151, and the number 2 in the formula represents Isomer 2.

TABLE 151

| Example | R | Isomer 2 Data |
|---|---|---|
| 3289 | ![](isopropyl carbamate) | MH+ 549 |
| 3290 | ![](t-butyl urea) | MH+ 562 |
| 3291 | ![](tetrahydropyranyl carbamate) | MH+ 591 |

EXAMPLES 3291-3297

Using the compound of Example 3287 (Isomer 2) and following a procedure similar to that in Example 3288 compounds of the formula:

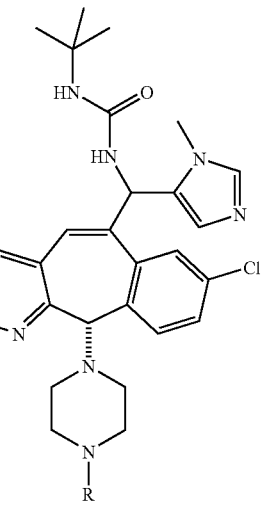

were prepared using the corresponding isocyanate, sulfonyl chloride, or chloroformate for substituent R, wherein R is defined in Table 152, and the number 2 in the formula represents Isomer 2.

TABLE 152

| Example | R | Isomer 2 Data |
|---|---|---|
| 3292 | ![](4-cyanophenyl urea) | MH+ 664 |
| 3293 | | MH+ 598 |
| 3294 | ![](tetrahydropyranyl carbamate) | MH+ 648 |
| 3295 | ![](t-butyl urea) | MH+ 619 |
| 3296 | ![](cyclohexyl urea) | MH+ 645 |
| 3297 | ![](isopropyl carbamate) | MH+ 606 |

EXAMPLES 3298-3302

Using the compound of Example 3285 (Isomer 2) and following a procedure similar to that in Example 3288 compounds of the formula:

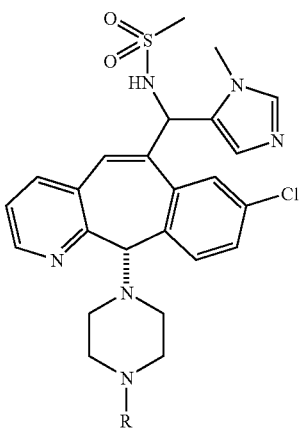

were prepared using the corresponding isocyanate, sulfonyl chloride, or chloroformate for substituent R, wherein R is defined in Table 153, and the number 2 in the formula represents Isomer 2.

TABLE 153

| Example | R | Isomer 2 Data |
|---|---|---|
| 3298 | *tert*-butyl-NH-C(O)- | MH+ 598 |
| 3299 | H₂N-C(O)- | MH+ 542 |
| 3300 | iPr-O-C(O)- | MH+ 585 |
| 3301 | tetrahydropyran-4-yl-O-C(O)- | MH+ 627 |
| 3302 | CH₃-S(O)₂- | MH+ 577 |

EXAMPLES 3303-4618

If one were to follow the procedures of Examples 3258-3267, 3270-3302, using the corresponding isocyanates, acid chlorides, sulfonyl chlorides or chloroformates of substituent R defined in Table 154, then one would obtain compounds of the formulas:

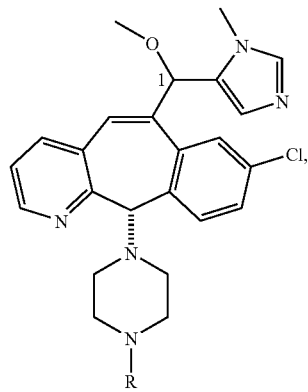

1022a

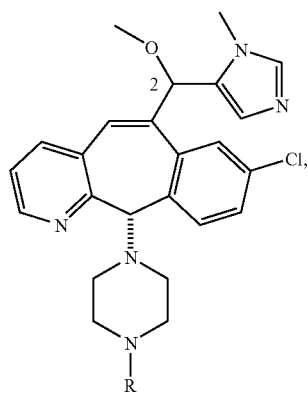

1022b

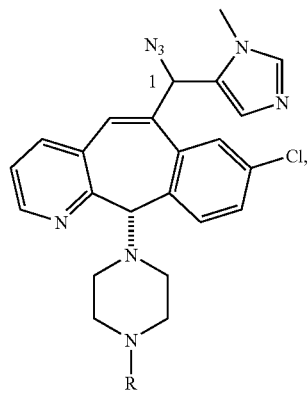

1023a

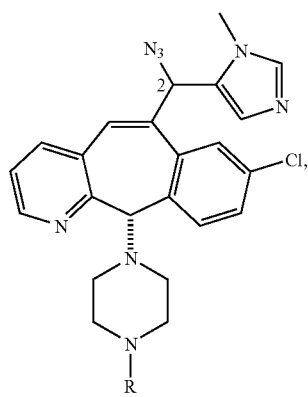

1023b

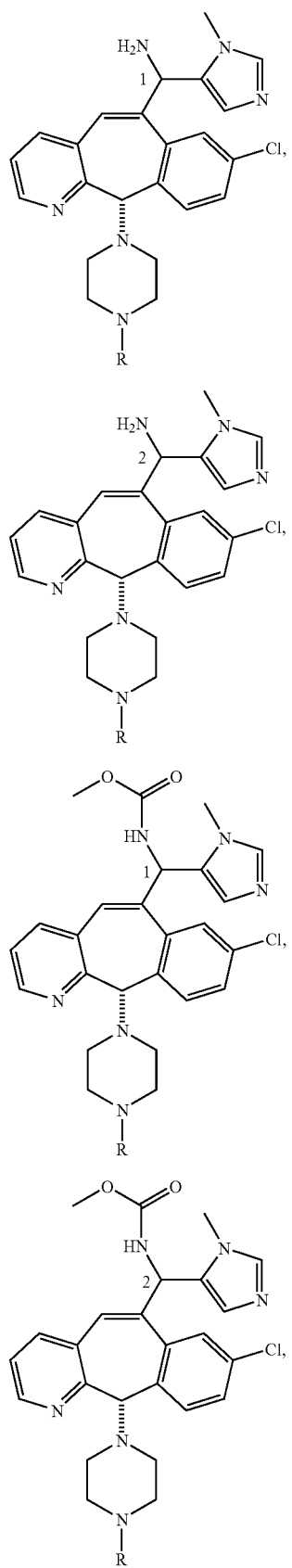
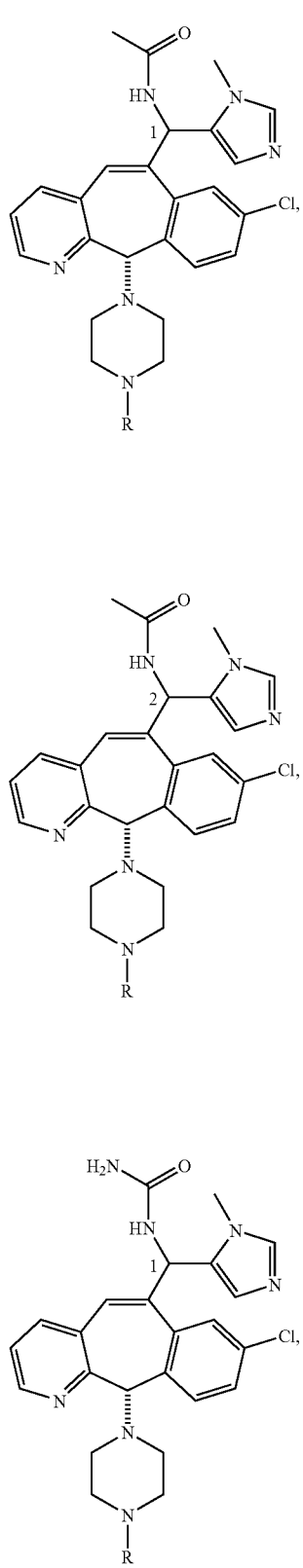

| 1051 | 1052 |
|---|---|
| -continued | -continued |
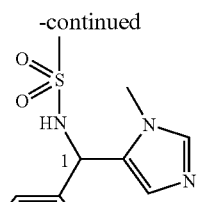
1027b
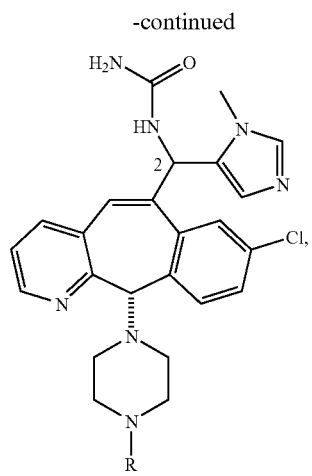
1028a
1028b
1029a
1029b
1030a
1030b -continued
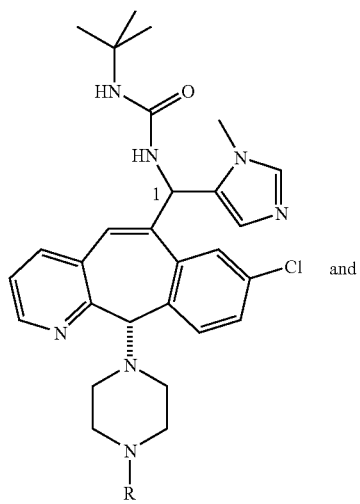
and
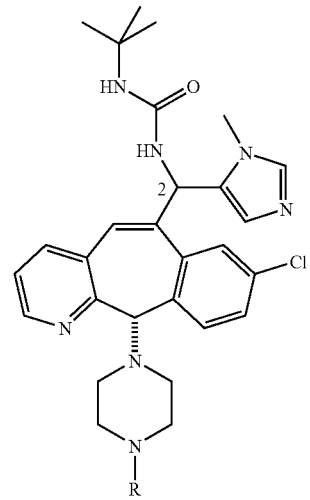
wherein R is defined in Table 154 and the numbers 1 and 2 in the formulas represent Isomers 1 and 2, respectively. "Ex." represents "Example" and "Compd." represents "Compound" in the table.
TABLE 154
| Ex. | Compd. | Ex. | Compd. | Ex. | Compd | R |
|---|---|---|---|---|---|---|
| 3303 | 1022a | 3309 | 1025a | 3316 | 1028b | |
| 3304 | 1022b | 3310 | 1025b | 3317 | 1029a | |
| 3305 | 1023a | 3311 | 1026a | 3318 | 1030a | |
| 3306 | 1023b | 3312 | 1026b | 3319 | 1030b | |
| 3307 | 1024a | 3313 | 1027a | 3320 | 1031a | |
| 3308 | 1024b | 3314 | 1027b | 3321 | 1031b | |
| | | 3315 | 1028a | | | |
| 3322 | 1022a | 3328 | 1025a | 3335 | 1028b | |
| 3323 | 1022b | 3329 | 1025b | 3336 | 1029a | |
| 3324 | 1023a | 3330 | 1026a | 3337 | 1029b | |
| 3325 | 1023b | 3331 | 1026b | 3338 | 1030a | |
| 3326 | 1024a | 3332 | 1027a | 3339 | 1030b | |
| 3327 | 1024b | 3333 | 1027b | 3340 | 1031a | |
| | | 3334 | 1028a | 3341 | 1031b | |
| 3342 | 1022a | 3348 | 1025a | 3355 | 1028b | |
| 3343 | 1022b | 3349 | 1025b | 3356 | 1029a | |
| 3344 | 1023a | 3350 | 1026a | 3357 | 1029b | |
| 3345 | 1023b | 3351 | 1026b | 3358 | 1030a | |
| 3346 | 1024a | 3352 | 1027a | 3359 | 1030b | |
| 3347 | 1024b | 3353 | 1027b | 3360 | 1031a | |
| | | 3354 | 1028a | 3361 | 1031b | |
| 3362 | 1022a | 3368 | 1025a | 3375 | 1028b | |
| 3363 | 1022b | 3369 | 1025b | 3376 | 1029a | |
| 3364 | 1023a | 3370 | 1026a | 3377 | 1029b | |
| 3365 | 1023b | 3371 | 1026b | 3378 | 1030a | |
| 3366 | 1024a | 3372 | 1027a | 3379 | 1030b | |
| 3367 | 1024b | 3373 | 1027b | 3380 | 1031a | |
| | | 3374 | 1028a | 3381 | 1031b | |
| 3382 | 1023a | 3386 | 1026a | 3391 | 1028b | |
| 3383 | 1023b | 3387 | 1027a | 3392 | 1029a | |
| 3384 | 1025a | 3388 | 1027b | 3393 | 1030a | |
| 3385 | 1025b | 3389 | 1028a | 3394 | 1030b | |
| | | 3390 | 1028b | 3395 | 1031a | |

TABLE 154-continued

| Ex. | Compd. | Ex. | Compd. | Ex. | Compd | R |
|---|---|---|---|---|---|---|
| 3396 | 1022a | 3402 | 1025a | 3409 | 1028b | N-propyl amide |
| 3397 | 1022b | 3403 | 1025b | 3410 | 1029a | |
| 3398 | 1023a | 3404 | 1026a | 3411 | 1029b | |
| 3399 | 1023b | 3405 | 1026b | 3412 | 1030a | |
| 3400 | 1024a | 3406 | 1027a | 3413 | 1030b | |
| 3401 | 1024b | 3407 | 1027b | 3414 | 1031a | |
| | | 3408 | 1028a | 3415 | 1031b | |
| 3416 | 1022a | 3422 | 1025a | 3429 | 1028b | N-isobutyl amide |
| 3417 | 1022b | 3423 | 1025b | 3430 | 1029a | |
| 3418 | 1023a | 3424 | 1026a | 3431 | 1029b | |
| 3419 | 1023b | 3425 | 1026b | 3432 | 1030a | |
| 3420 | 1024a | 3426 | 1027a | 3433 | 1030b | |
| 3421 | 1024b | 3427 | 1027b | 3434 | 1031a | |
| | | 3428 | 1028a | 3435 | 1031b | |
| 3436 | 1022a | 3442 | 1025a | 3449 | 1028b | N-allyl amide |
| 3437 | 1022b | 3443 | 1025b | 3450 | 1029a | |
| 3438 | 1023a | 3444 | 1026a | 3451 | 1029b | |
| 3439 | 1023b | 3445 | 1026b | 3452 | 1030a | |
| 3440 | 1024a | 3446 | 1027a | 3453 | 1030b | |
| 3441 | 1024b | 3447 | 1027b | 3454 | 1031a | |
| | | 3448 | 1028a | 3455 | 1031b | |
| 3456 | 1022a | 3462 | 1025a | 3469 | 1028b | N-cyclopentyl amide |
| 3457 | 1022b | 3463 | 1025b | 3470 | 1029a | |
| 3458 | 1023a | 3464 | 1026a | 3471 | 1029b | |
| 3459 | 1023b | 3465 | 1026b | 3472 | 1030a | |
| 3460 | 1024a | 3466 | 1027a | 3473 | 1030b | |
| 3461 | 1024b | 3467 | 1027b | 3474 | 1031a | |
| | | 3468 | 1028a | 3475 | 1031b | |
| 3476 | 1022a | 3482 | 1025a | 3489 | 1028b | N-cyclohexyl amide |
| 3477 | 1022b | 3483 | 1025b | 3490 | 1029a | |
| 3478 | 1023a | 3484 | 1026a | 3491 | 1029b | |
| 3479 | 1023b | 3485 | 1026b | 3492 | 1030a | |
| 3480 | 1024a | 3486 | 1027a | 3493 | 1030b | |
| 3481 | 1024b | 3487 | 1027b | 3494 | 1031a | |
| | | 3488 | 1028a | | | |
| 3495 | 1022a | 3501 | 1025a | 3508 | 1028b | N-phenyl amide |
| 3496 | 1022b | 3502 | 1025b | 3509 | 1029a | |
| 3497 | 1023a | 3503 | 1026a | 3510 | 1029b | |
| 3498 | 1023b | 3504 | 1026b | 3511 | 1030a | |
| 3499 | 1024a | 3505 | 1027a | 3512 | 1030b | |
| 3500 | 1024b | 3506 | 1027b | 3513 | 1031a | |
| | | 3507 | 1028a | 3514 | 1031b | |
| 3515 | 1022a | 3521 | 1025a | 3527 | 1028b | N-(4-cyanophenyl) amide |
| 3516 | 1022b | 3522 | 1025b | 3528 | 1029a | |
| 3517 | 1023a | 3523 | 1026a | 3529 | 1029b | |
| 3518 | 1023b | 3524 | 1027a | 3530 | 1030a | |
| 3519 | 1024a | 3525 | 1027b | 3531 | 1030b | |
| 3520 | 1024b | 3526 | 1028a | 3532 | 1031a | |
| 3533 | 1022a | 3539 | 1025a | 3546 | 1028b | N-(4-isopropylphenyl) amide |
| 3534 | 1022b | 3540 | 1025b | 3547 | 1029a | |
| 3535 | 1023a | 3541 | 1026a | 3547 | 1029b | |
| 3536 | 1023b | 3542 | 1026b | 3548 | 1030a | |
| 3537 | 1024a | 3543 | 1027a | 3549 | 1030b | |
| 3538 | 1024b | 3544 | 1027b | 3550 | 1031a | |
| | | 3545 | 1028a | 3551 | 1031b | |
| 3552 | 1022a | 3558 | 1025a | 3565 | 1028b | N-(4-bromophenyl) amide |
| 3553 | 1022b | 3559 | 1025b | 3566 | 1029a | |
| 3554 | 1023a | 3560 | 1026a | 3567 | 1029b | |
| 3555 | 1023b | 3561 | 1026b | 3568 | 1030a | |
| 3556 | 1024a | 3562 | 1027a | 3569 | 1030b | |
| 3557 | 1024b | 3563 | 1027b | 3570 | 1031a | |
| | | 3664 | 1028a | 3571 | 1031b | |

TABLE 154-continued
| Ex. | Compd. | Ex. | Compd. | Ex. | Compd | R |
|---|---|---|---|---|---|---|
| 3572 | 1022a | 3578 | 1025a | 3585 | 1028b | 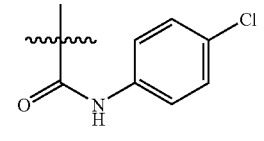 |
| 3573 | 1022b | 3579 | 1025b | 3586 | 1029a | |
| 3574 | 1023a | 3580 | 1026a | 3587 | 1029b | |
| 3575 | 1023b | 3581 | 1026b | 3588 | 1030a | |
| 3576 | 1024a | 3582 | 1027a | 3589 | 1030b | |
| 3577 | 1024b | 3583 | 1027b | 3580 | 1031a | |
| | | 3584 | 1028a | 3591 | 1031b | |
| 3592 | 1022a | 3598 | 1025a | 3605 | 1028b | 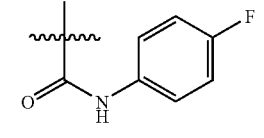 |
| 3593 | 1022b | 3599 | 1025b | 3606 | 1029a | |
| 3594 | 1023a | 3600 | 1026a | 3607 | 1029b | |
| 3595 | 1023b | 3601 | 1026b | 3608 | 1030a | |
| 3596 | 1024a | 3602 | 1027a | 3609 | 1030b | |
| 3597 | 1024b | 3603 | 1027b | 3610 | 1031a | |
| | | 3604 | 1028a | 3611 | 1031b | |
| 3612 | 1022a | 3618 | 1025a | 3625 | 1028b | 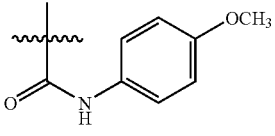 |
| 3613 | 1022b | 3619 | 1025b | 3626 | 1029a | |
| 3614 | 1023a | 3620 | 1026a | 3627 | 1029b | |
| 3615 | 1023b | 3621 | 1026b | 3628 | 1030a | |
| 3616 | 1024a | 3622 | 1027a | 3629 | 1030b | |
| 3617 | 1024b | 3623 | 1027b | 3630 | 1031a | |
| | | 3624 | 1028a | 3631 | 1031b | |
| 3632 | 1022a | 3638 | 1025a | 3645 | 1028b | 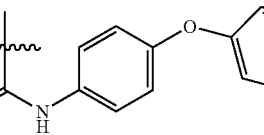 |
| 3633 | 1022b | 3639 | 1025b | 3646 | 1029a | |
| 3634 | 1023a | 3640 | 1026a | 3647 | 1029b | |
| 3635 | 1023b | 3641 | 1026b | 3648 | 1030a | |
| 3636 | 1024a | 3642 | 1027a | 3649 | 1030b | |
| 3637 | 1024b | 3643 | 1027b | 3650 | 1031a | |
| | | 3644 | 1028a | 3651 | 1031b | |
| 3652 | 1022a | 3658 | 1025a | 3665 | 1028b | 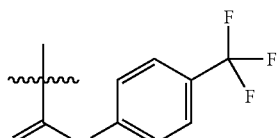 |
| 3653 | 1022b | 3659 | 1025b | 3666 | 1029a | |
| 3654 | 1023a | 3660 | 1026a | 3667 | 1029b | |
| 3655 | 1023b | 3661 | 1026b | 3668 | 1030a | |
| 3656 | 1024a | 3662 | 1027a | 3669 | 1030b | |
| 3657 | 1024b | 3663 | 1027b | 3670 | 1031a | |
| | | 3664 | 1028a | 3671 | 1031b | |
| 3672 | 1022a | 3678 | 1025a | 3685 | 1028b | 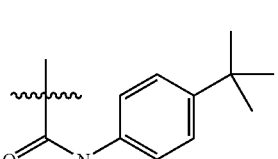 |
| 3673 | 1022b | 3679 | 1025b | 3686 | 1029a | |
| 3674 | 1023a | 3680 | 1026a | 3687 | 1029b | |
| 3675 | 1023b | 3681 | 1026b | 3688 | 1030a | |
| 3676 | 1024a | 3682 | 1027a | 3689 | 1030b | |
| 3677 | 1024b | 3683 | 1027b | 3690 | 1031a | |
| | | 3684 | 1028a | 3691 | 1031b | |
| 3692 | 1022a | 3698 | 1025a | 3705 | 1028b | 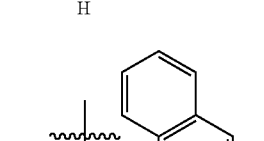 |
| 3693 | 1022b | 3699 | 1025b | 3706 | 1029a | |
| 3694 | 1023a | 3700 | 1026a | 3707 | 1029b | |
| 3695 | 1023b | 3701 | 1026b | 3708 | 1030a | |
| 3696 | 1024a | 3702 | 1027a | 3709 | 1030b | |
| 3697 | 1024b | 3703 | 1027b | 3710 | 1031a | |
| | | 3704 | 1028a | 3711 | 1031b | |
| 3712 | 1022a | 3718 | 1025a | 3725 | 1028b | 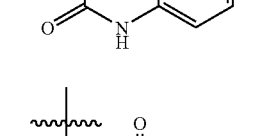 |
| 3713 | 1022b | 3719 | 1025b | 3726 | 1029a | |
| 3714 | 1023a | 3720 | 1026a | 3727 | 1029b | |
| 3715 | 1023b | 3721 | 1026b | 3728 | 1030a | |
| 3716 | 1024a | 3722 | 1027a | 3729 | 1030b | |
| 3717 | 1024b | 3723 | 1027b | 3730 | 1031a | |
| | | 3724 | 1028a | 3731 | 1031b | |
| 3732 | 1022a | 3738 | 1025a | 3745 | 1028b | 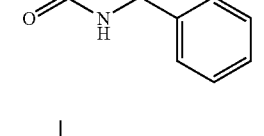 |
| 3733 | 1022b | 3739 | 1025b | 3746 | 1029a | |
| 3734 | 1023a | 3740 | 1026a | 3747 | 1029b | |
| 3735 | 1023b | 3741 | 1026b | 3748 | 1030a | |
| 3736 | 1024a | 3742 | 1027a | 3749 | 1030b | |
| 3737 | 1024b | 3743 | 1027b | 3750 | 1031a | |
| | | 3744 | 1028a | 3751 | 1031b | |

TABLE 154-continued
| Ex. | Compd. | Ex. | Compd. | Ex. | Compd | R |
|---|---|---|---|---|---|---|
| 3752 | 1022a | 3758 | 1025a | 3765 | 1028b | 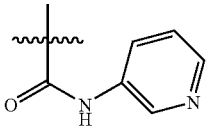 |
| 3753 | 1022b | 3759 | 1025b | 3766 | 1029a | |
| 3754 | 1023a | 3760 | 1026a | 3767 | 1029b | |
| 3755 | 1023b | 3761 | 1026b | 3768 | 1030a | |
| 3756 | 1024a | 3762 | 1027a | 3769 | 1030b | |
| 3757 | 1024b | 3763 | 1027b | 3770 | 1031a | |
| | | 3764 | 1028a | 3771 | 1031b | |
| 3772 | 1022a | 3778 | 1025a | 3785 | 1028b | 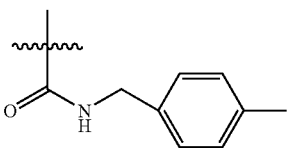 |
| 3773 | 1022b | 3779 | 1025b | 3786 | 1029a | |
| 3774 | 1023a | 3780 | 1026a | 3787 | 1029b | |
| 3775 | 1023b | 3781 | 1026b | 3788 | 1030a | |
| 3776 | 1024a | 3782 | 1027a | 3789 | 1030b | |
| 3777 | 1024b | 3783 | 1027b | 3790 | 1031a | |
| | | 3784 | 1028a | 3791 | 1031b | |
| 3792 | 1022a | 3798 | 1025a | 3805 | 1028b | 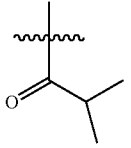 |
| 3793 | 1022b | 3799 | 1025b | 3806 | 1029a | |
| 3794 | 1023a | 3800 | 1026a | 3807 | 1029b | |
| 3795 | 1023b | 3801 | 1026b | 3808 | 1030a | |
| 3796 | 1024a | 3802 | 1027a | 3809 | 1030b | |
| 3797 | 1024b | 3803 | 1027b | 3810 | 1031a | |
| | | 3804 | 1028a | 3811 | 1031b | |
| 3812 | 1022a | 3818 | 1025a | 3825 | 1028b | 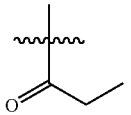 |
| 3813 | 1022b | 3819 | 1025b | 3826 | 1029a | |
| 3814 | 1023a | 3820 | 1026a | 3827 | 1029b | |
| 3815 | 1023b | 3821 | 1026b | 3828 | 1030a | |
| 3816 | 1024a | 3822 | 1027a | 3829 | 1030b | |
| 3817 | 1024b | 3823 | 1027b | 3830 | 1031a | |
| | | 3824 | 1028a | 3831 | 1031b | |
| 3832 | 1022a | 3838 | 1025a | 3845 | 1028b | 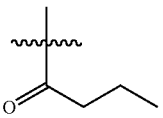 |
| 3833 | 1022b | 3839 | 1025b | 3846 | 1029a | |
| 3834 | 1023a | 3840 | 1026a | 3847 | 1029b | |
| 3835 | 1023b | 3841 | 1026b | 3848 | 1030a | |
| 3836 | 1024a | 3842 | 1027a | 3849 | 1030b | |
| 3837 | 1024b | 3843 | 1027b | 3850 | 1031a | |
| | | 3844 | 1028a | 3851 | 1031b | |
| 3852 | 1022a | 3858 | 1025a | 3865 | 1028b | 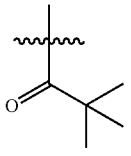 |
| 3853 | 1022b | 3859 | 1025b | 3866 | 1029a | |
| 3854 | 1023a | 3860 | 1026a | 3867 | 1029b | |
| 3855 | 1023b | 3861 | 1026b | 3868 | 1030a | |
| 3856 | 1024a | 3862 | 1027a | 3869 | 1030b | |
| 3857 | 1024b | 3863 | 1027b | 3870 | 1031a | |
| | | 3864 | 1028a | 3871 | 1031b | |
| 3872 | 1022a | 3878 | 1025a | 3885 | 1028b | 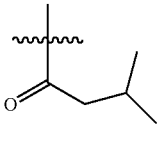 |
| 3873 | 1022b | 3879 | 1025b | 3886 | 1029a | |
| 3874 | 1023a | 3880 | 1026a | 3887 | 1029b | |
| 3875 | 1023b | 3881 | 1026b | 3888 | 1030a | |
| 3876 | 1024a | 3882 | 1027a | 3889 | 1030b | |
| 3877 | 1024b | 3883 | 1027b | 3890 | 1031a | |
| | | 3884 | 1028a | 3891 | 1031b | |
| 3892 | 1022b | 3897 | 1025a | 3904 | 1028b | 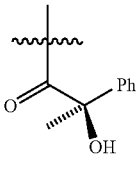 |
| 3893 | 1023a | 3898 | 1025b | 3905 | 1029a | |
| 3894 | 1023b | 3899 | 1026a | 3906 | 1029b | |
| 3895 | 1024a | 3900 | 1026b | 3907 | 1030a | |
| 3896 | 1024b | 3901 | 1027a | 3908 | 1030b | |
| | | 3902 | 1027b | 3909 | 1031a | |
| | | 3903 | 1028a | 3910 | 1031b | |
| 3911 | 1022b | 3916 | 1025a | 3923 | 1028b | 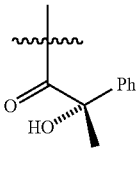 |
| 3912 | 1023a | 3917 | 1025b | 3924 | 1029a | |
| 3913 | 1023b | 3918 | 1026a | 3925 | 1029b | |
| 3914 | 1024a | 3919 | 1026b | 3926 | 1030a | |
| 3915 | 1024b | 3920 | 1027a | 3927 | 1030b | |
| | | 3921 | 1027b | 3928 | 1031a | |
| | | 3922 | 1028a | 3929 | 1031b | |

TABLE 154-continued

| Ex. | Compd. | Ex. | Compd. | Ex. | Compd | R |
|---|---|---|---|---|---|---|
| 3930 | 1022b | 3935 | 1026b | 3941 | 1029a | 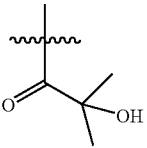 |
| 3931 | 1024a | 3936 | 1027a | 3942 | 1029b | |
| 3932 | 1025a | 3937 | 1027b | 3943 | 1030a | |
| 3933 | 1025b | 3938 | 1028a | 3944 | 1030b | |
| 3934 | 1026a | 3940 | 1028b | 3945 | 1031a | |
| | | | | | 1031b | |
| 3946 | 1022a | 3952 | 1025a | 3959 | 1028b | 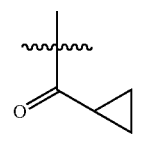 |
| 3947 | 1022b | 3953 | 1025b | 3960 | 1029a | |
| 3948 | 1023a | 3954 | 1026a | 3961 | 1029b | |
| 3949 | 1023b | 3955 | 1026b | 3962 | 1030a | |
| 3950 | 1024a | 3956 | 1027a | 3963 | 1030b | |
| 3951 | 1024b | 3957 | 1027b | 3964 | 1031a | |
| | | 3958 | 1028a | 3965 | 1031b | |
| 3966 | 1022a | 3972 | 1025a | 3979 | 1028b | 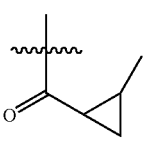 |
| 3967 | 1022b | 3973 | 1025b | 3980 | 1029a | |
| 3968 | 1023a | 3974 | 1026a | 3981 | 1029b | |
| 3969 | 1023b | 3975 | 1026b | 3982 | 1030a | |
| 3970 | 1024a | 3976 | 1027a | 3983 | 1030b | |
| 3971 | 1024b | 3977 | 1027b | 3984 | 1031a | |
| | | 3978 | 1028a | 3985 | 1031b | |
| 3986 | 1022a | 3992 | 1025a | 3999 | 1028b | 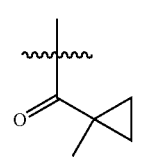 |
| 3987 | 1022b | 3993 | 1025b | 3400A | 1029a | |
| 3988 | 1023a | 3994 | 1026a | 3401A | 1029b | |
| 3989 | 1023b | 3995 | 1026b | 3402A | 1030a | |
| 3990 | 1024a | 3996 | 1027a | 3403A | 1030b | |
| 3991 | 1024b | 3997 | 1027b | 3404A | 1031a | |
| | | 3998 | 1028a | 3405A | 1031b | |
| 3406A | 1022a | 3412A | 1025a | 3419A | 1028b | 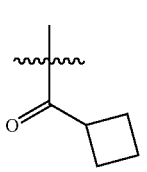 |
| 3407A | 1022b | 3413A | 1025b | 3420A | 1029a | |
| 3408A | 1023a | 3414A | 1026a | 3421A | 1029b | |
| 3409A | 1023b | 3415A | 1026b | 3422A | 1030a | |
| 3410A | 1024a | 3416A | 1027a | 3423A | 1030b | |
| 3411A | 1024b | 3417A | 1027b | 3424A | 1031a | |
| | | 3418A | 1028a | 3425A | 1031b | |
| 3426A | 1022a | 3432A | 1025a | 3439 | 1028b | 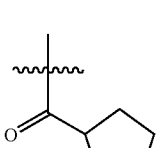 |
| 3427A | 1022b | 3433A | 1025b | 3440A | 1029a | |
| 3428A | 1023a | 3434A | 1026a | 3441A | 1029b | |
| 3429A | 1023b | 3435A | 1026b | 3442A | 1030a | |
| 3430A | 1024a | 3436A | 1027a | 3443A | 1030b | |
| 3431A | 1024b | 3437A | 1027b | 3444A | 1031a | |
| | | 3438A | 1028a | 3445A | 1031b | |
| 3446A | 1022a | 3452A | 1025a | 3459A | 1028b | 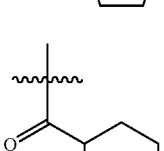 |
| 3447A | 1022b | 3453A | 1025b | 3460A | 1029a | |
| 3448A | 1023a | 3454A | 1026a | 3461A | 1029b | |
| 3449A | 1023b | 3455A | 1026b | 3462A | 1030a | |
| 3450A | 1024a | 3456A | 1027a | 3463A | 1030b | |
| 3451A | 1024b | 3457A | 1027b | 3464A | 1031a | |
| | | 3458A | 1028a | 3465A | 1031b | |
| 3466A | 1022a | 3472A | 1025a | 3479A | 1028b | 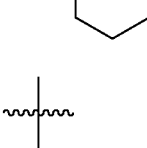 |
| 3467A | 1022b | 3473A | 1025b | 3480A | 1029a | |
| 3468A | 1023a | 3474A | 1026a | 3481A | 1029b | |
| 3469A | 1023b | 3475A | 1026b | 3482A | 1030a | |
| 3470A | 1024a | 3476A | 1027a | 3483A | 1030b | |
| 3471A | 1024b | 3477A | 1027b | 3484A | 1031a | |
| | | 3478A | 1028a | 3485A | 1031b | |
| 3486A | 1022a | 3492A | 1025a | 3499A | 1028b | 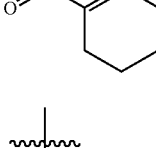 |
| 3487A | 1022b | 3493A | 1025b | 3500A | 1029a | |
| 3488A | 1023a | 3494A | 1026a | 3501A | 1029b | |
| 3489A | 1023b | 3495A | 1026b | 3502A | 1030a | |
| 3490A | 1024a | 3496A | 1027a | 3503A | 1030b | |
| 3491A | 1024b | 3497A | 1027b | 3504A | 1031a | |
| | | 3498A | 1028a | 3505A | 1031b | |

TABLE 154-continued

| Ex. | Compd. | Ex. | Compd. | Ex. | Compd | R |
|---|---|---|---|---|---|---|
| 3506A | 1022a | 3512A | 1025a | 3519A | 1028b | 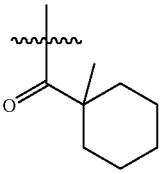 |
| 3507A | 1022b | 3513A | 1025b | 3520A | 1029a | |
| 3508A | 1023a | 3514A | 1026a | 3521A | 1029b | |
| 3509A | 1023b | 3515A | 1026b | 3522A | 1030a | |
| 3510A | 1024a | 3516A | 1027a | 3523A | 1030b | |
| 3511A | 1024b | 3517A | 1027b | 3524A | 1031a | |
| | | 3518A | 1028a | 3525A | 1031b | |
| 3526A | 1022a | 3532A | 1025a | 3539A | 1028b | 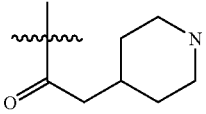 |
| 3527A | 1022b | 3533A | 1025b | 3540A | 1029a | |
| 3528A | 1023a | 3534A | 1026a | 3541A | 1029b | |
| 3529A | 1023b | 3535A | 1026b | 3542A | 1030a | |
| 3530A | 1024a | 3536A | 1027a | 3543A | 1030b | |
| 3531A | 1024b | 3537A | 1027b | 3544A | 1031a | |
| | | 3538A | 1028a | 3545A | 1031b | |
| 3546A | 1022a | 3552A | 1025a | 3559A | 1028b | 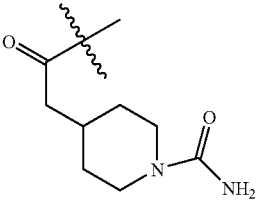 |
| 3547A | 1022b | 3553A | 1025b | 3560A | 1029a | |
| 3548A | 1023a | 3554A | 1026a | 3561A | 1029b | |
| 3549A | 1023b | 3555A | 1026b | 3562A | 1030a | |
| 3550A | 1024a | 3556A | 1027a | 3563A | 1030b | |
| 3551A | 1024b | 3557A | 1027b | 3564A | 1031a | |
| | | 3558A | 1028a | 3565A | 1031b | |
| 3566A | 1022a | 3572A | 1025a | 3579A | 1028b | 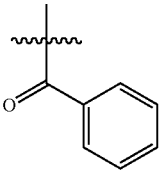 |
| 3567A | 1022b | 3573A | 1025b | 3580A | 1029a | |
| 3568A | 1023a | 3574A | 1026a | 3581A | 1029b | |
| 3569A | 1023b | 3575A | 1026b | 3582A | 1030a | |
| 3570A | 1024a | 3576A | 1027a | 3583A | 1030b | |
| 3571A | 1024b | 3577A | 1027b | 3584A | 1031a | |
| | | 3578A | 1028a | 3585A | 1031b | |
| 3586A | 1022a | 3592A | 1025a | 3599A | 1028b | 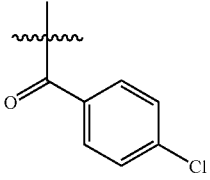 |
| 3587A | 1022b | 3593A | 1025b | 3600A | 1029a | |
| 3588A | 1023a | 3594A | 1026a | 3601A | 1029b | |
| 3589A | 1023b | 3595A | 1026b | 3602A | 1030a | |
| 3590A | 1024a | 3596A | 1027a | 3603A | 1030b | |
| 3591A | 1024b | 3597A | 1027b | 3604A | 1031a | |
| | | 3598A | 1028a | 3605A | 1031b | |
| 3606A | 1022a | 3612A | 1025a | 3619A | 1028b | 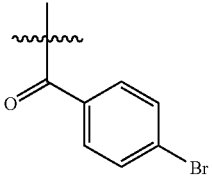 |
| 3607A | 1022b | 3613A | 1025b | 3620A | 1029a | |
| 3608A | 1023a | 3614A | 1026a | 3621A | 1029b | |
| 3609A | 1023b | 3615A | 1026b | 3622A | 1030a | |
| 3610A | 1024a | 3616A | 1027a | 3623A | 1030b | |
| 3611A | 1024b | 3617A | 1027b | 3624A | 1031a | |
| | | 3618A | 1028a | 3625A | 1031b | |
| 3626A | 1022a | 3632A | 1025a | 3639A | 1028b | 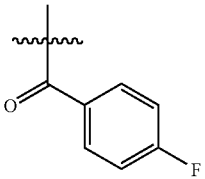 |
| 3627A | 1022b | 3633A | 1025b | 3640A | 1029a | |
| 3628A | 1023a | 3634A | 1026a | 3641A | 1029b | |
| 3629A | 1023b | 3635A | 1026b | 3642A | 1030a | |
| 3630A | 1024a | 3636A | 1027a | 3643A | 1030b | |
| 3631A | 1024b | 3637A | 1027b | 3644A | 1031a | |
| | | 3638A | 1028a | 3645A | 1031b | |
| 3646A | 1022a | 3652A | 1025a | 3659A | 1028b | |
| 3647A | 1022b | 3653A | 1025b | 3660A | 1029a | |
| 3648A | 1023a | 3654A | 1026a | 3661A | 1029b | |
| 3649A | 1023b | 3655A | 1026b | 3662A | 1030a | |
| 3650A | 1024a | 3656A | 1027a | 3663A | 1030b | |
| 3651A | 1024b | 3657A | 1027b | 3664A | 1031a | |
| | | 3658A | 1028a | 3665A | 1031b | |

TABLE 154-continued

| Ex. | Compd. | Ex. | Compd. | Ex. | Compd | R |
|---|---|---|---|---|---|---|
| 3666A | 1022a | 3672A | 1025a | 3679A | 1028b | |
| 3667A | 1022b | 3673A | 1025b | 3680A | 1029a | |
| 3668A | 1023a | 3674A | 1026a | 3681A | 1029b | 4-cyanobenzoyl |
| 3669A | 1023b | 3675A | 1026b | 3682A | 1030a | |
| 3670A | 1024a | 3676A | 1027a | 3683A | 1030b | |
| 3671A | 1024b | 3677A | 1027b | 3684A | 1031a | |
| | | 3678A | 1028a | 3685A | 1031b | |
| 3686A | 1022a | 3692A | 1025a | 3699A | 1028b | |
| 3687A | 1022b | 3693A | 1025b | 3700A | 1029a | |
| 3688A | 1023a | 3694A | 1026a | 3701A | 1029b | 4-methylbenzoyl |
| 3689A | 1023b | 3695A | 1026b | 3702A | 1030a | |
| 3690A | 1024a | 3696A | 1027a | 3703A | 1030b | |
| 3691A | 1024b | 3697A | 1027b | 3704A | 1031a | |
| | | 3698A | 1028a | 3705A | 1031b | |
| 3706A | 1022a | 3712A | 1025a | 3719A | 1028b | |
| 3707A | 1022b | 3713A | 1025b | 3720A | 1029a | |
| 3708A | 1023a | 3714A | 1026a | 3721A | 1029b | 4-methoxybenzoyl |
| 3709A | 1023b | 3715A | 1026b | 3722A | 1030a | |
| 3710A | 1024a | 3716A | 1027a | 3723A | 1030b | |
| 3711A | 1024b | 3717A | 1027b | 3724A | 1031a | |
| | | 3718A | 1028a | 3725A | 1031b | |
| 3726A | 1022a | 3732A | 1025a | 3739A | 1028b | |
| 3727A | 1022b | 3733A | 1025b | 3740A | 1029a | |
| 3728A | 1023a | 3734A | 1026a | 3741A | 1029b | isonicotinoyl |
| 3729A | 1023b | 3735A | 1026b | 3742A | 1030a | |
| 3730A | 1024a | 3736A | 1027a | 3743A | 1030b | |
| 3731A | 1024b | 3737A | 1027b | 3744A | 1031a | |
| | | 3738A | 1028a | 3745A | 1031b | |
| 3746A | 1022a | 3752A | 1025a | 3759A | 1028b | |
| 3747A | 1022b | 3753A | 1025b | 3760A | 1029a | |
| 3748A | 1023a | 3754A | 1026a | 3761A | 1029b | isonicotinoyl N-oxide |
| 3749A | 1023b | 3755A | 1026b | 3762A | 1030a | |
| 3750A | 1024a | 3756A | 1027a | 3763A | 1030b | |
| 3751A | 1024b | 3757A | 1027b | 3764A | 1031a | |
| | | 3758A | 1028a | 3765a | 1031b | |
| 3766A | 1022a | 3772A | 1025a | 3779A | 1028b | |
| 3767A | 1022b | 3773A | 1025b | 3780A | 1029a | |
| 3768A | 1023a | 3774A | 1026a | 3781A | 1029b | (4-pyridyl)acetyl |
| 3769A | 1023b | 3775A | 1026b | 3782A | 1030a | |
| 3770A | 1024a | 3776A | 1027a | 3783A | 1030b | |
| 3771A | 1024b | 3777A | 1027b | 3784A | 1031a | |
| | | 3778A | 1028a | 3785A | 1031b | |
| 3786A | 1022a | 3792A | 1025a | 3799A | 1028b | |
| 3787A | 1022b | 3793A | 1025b | 3800A | 1029a | |
| 3788A | 1023a | 3794A | 1026a | 3801A | 1029b | (4-pyridyl N-oxide)acetyl |
| 3789A | 1023b | 3795A | 1026b | 3802A | 1030a | |
| 3790A | 1024a | 3796A | 1027a | 3803A | 1030b | |
| 3791A | 1024b | 3797A | 1027b | 3804A | 1031a | |
| | | 3798A | 1028a | 3805A | 1031b | |
| 3806A | 1022a | 3812A | 1025a | 3818A | 1028a | |
| 3807A | 1022b | 3813A | 1025b | 3819A | 1028b | |
| 3808A | 1023a | 3814A | 1026a | 3820A | 1029a | methylsulfonyl |
| 3809A | 1023b | 3815A | 1026b | 3821A | 1030a | |
| 3810A | 1024a | 3816A | 1027a | 3822A | 1030b | |
| 3811A | 1024b | 3817A | 1027b | 3823A | 1031a | |

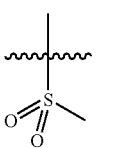

TABLE 154-continued

| Ex. | Compd. | Ex. | Compd. | Ex. | Compd | R |
|---|---|---|---|---|---|---|
| 3824A | 1022a | 3830A | 1025a | 3837A | 1028b | isopropylsulfonyl |
| 3825A | 1022b | 3831A | 1025b | 3838A | 1029a | |
| 3826A | 1023a | 3832A | 1026a | 3839A | 1029b | |
| 3827A | 1023b | 3833A | 1026b | 3840A | 1030a | |
| 3828A | 1024a | 3834A | 1027a | 3841A | 1030b | |
| 3829A | 1024b | 3835A | 1027b | 3842A | 1031a | |
| | | 3836A | 1028a | 3843A | 1031b | |
| 3844A | 1022a | 3850A | 1025a | 3857A | 1028b | n-propylsulfonyl |
| 3845A | 1022b | 3851A | 1025b | 3858A | 1029a | |
| 3846A | 1023a | 3852A | 1026a | 3859A | 1029b | |
| 3847A | 1023b | 3853A | 1026b | 3860A | 1030a | |
| 3848A | 1024a | 3854A | 1027a | 3861A | 1030b | |
| 3849A | 1024b | 3855A | 1027b | 3862A | 1031a | |
| | | 3856A | 1028a | 3863A | 1031b | |
| 3864A | 1022a | 3870A | 1025a | 3877A | 1028b | N,N-dimethylsulfamoyl |
| 3865A | 1022b | 3871A | 1025b | 3878A | 1029a | |
| 3866A | 1023a | 3872A | 1026a | 3879A | 1029b | |
| 3867A | 1023b | 3873A | 1026b | 3880A | 1030a | |
| 3868A | 1024a | 3874A | 1027a | 3881A | 1030b | |
| 3869A | 1024b | 3875A | 1027b | 3882A | 1031a | |
| | | 3876A | 1028a | 3883A | 1031b | |
| 3884A | 1022a | 3890A | 1025a | 3897A | 1028b | tert-butylsulfonyl |
| 3885A | 1022b | 3891A | 1025b | 3898A | 1029a | |
| 3886A | 1023a | 3892A | 1026a | 3899A | 1029b | |
| 3887A | 1023b | 3893A | 1026b | 3900A | 1030a | |
| 3888A | 1024a | 3894A | 1027a | 3901A | 1030b | |
| 3889A | 1024b | 3895A | 1027b | 3902A | 1031a | |
| | | 3896A | 1028a | 3903A | 1031b | |
| 3904A | 1022a | 3910A | 1025a | 3917A | 1028b | trifluoromethylsulfonyl |
| 3905A | 1022b | 3911A | 1025b | 3918A | 1029a | |
| 3906A | 1023a | 3912A | 1026a | 3919A | 1029b | |
| 3907A | 1023b | 3913A | 1026b | 3920A | 1030a | |
| 3908A | 1024a | 3914A | 1027a | 3921A | 1030b | |
| 3909A | 1024b | 3915A | 1027b | 3922A | 1031a | |
| | | 3916A | 1028a | 3923A | 1031b | |
| 3944A | 1022a | 3950A | 1025a | 3957A | 1028b | cyclopropylsulfonyl |
| 3945A | 1022b | 3951A | 1025b | 3958A | 1029a | |
| 3946A | 1023a | 3952A | 1026a | 3959A | 1029b | |
| 3947A | 1023b | 3953A | 1026b | 3960A | 1030a | |
| 3948A | 1024a | 3954A | 1027a | 3961A | 1030b | |
| 3949A | 1024b | 3955A | 1027b | 3962A | 1031a | |
| | | 3956A | 1028a | 3963A | 1031b | |
| 3964A | 1022a | 3970A | 1025a | 3977A | 1028b | p-tolylsulfonyl |
| 3965A | 1022b | 3971A | 1025b | 3978A | 1029a | |
| 3966A | 1023a | 3972A | 1026a | 3979A | 1029b | |
| 3967A | 1023b | 3973A | 1026b | 3980A | 1030a | |
| 3968A | 1024a | 3974A | 1027a | 3981A | 1030b | |
| 3969A | 1024b | 3975A | 1027b | 3982A | 1031a | |
| | | 3976A | 1028a | 3983A | 1031b | |
| 3984A | 1022a | 3990A | 1025a | 3997A | 1028b | 4-ethylphenylsulfonyl |
| 3985A | 1022b | 3991A | 1025b | 3998A | 1029a | |
| 3986A | 1023a | 3992A | 1026a | 3999A | 1029b | |
| 3987A | 1023b | 3993A | 1026b | 4000A | 1030a | |
| 3988A | 1024a | 3994A | 1027a | 4001A | 1030b | |
| 3989A | 1024b | 3995A | 1027b | 4002A | 1031a | |
| | | 3996A | 1028a | 4003A | 1031b | |
| 4004 | 1022a | 4010 | 1025a | 4017 | 1028b | 4-isopropylphenylsulfonyl |
| 4005 | 1022b | 4011 | 1025b | 4018 | 1029a | |
| 4006 | 1023a | 4012 | 1026a | 4019 | 1029b | |
| 4007 | 1023b | 4013 | 1026b | 4020 | 1030a | |
| 4008 | 1024a | 4014 | 1027a | 4021 | 1030b | |
| 4009 | 1024b | 4015 | 1027b | 4022 | 1031a | |
| | | 4016 | 1028a | 4023 | 1031b | |

TABLE 154-continued
| Ex. | Compd. | Ex. | Compd. | Ex. | Compd | R |
|---|---|---|---|---|---|---|
| 4024 | 1022a | 4030 | 1025a | 4037 | 1028b | 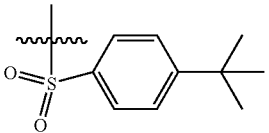 |
| 4025 | 1022b | 4031 | 1025b | 4038 | 1029a | |
| 4026 | 1023a | 4032 | 1026a | 4039 | 1029b | |
| 4027 | 1023b | 4033 | 1026b | 4040 | 1030a | |
| 4028 | 1024a | 4034 | 1027a | 4041 | 1030b | |
| 4029 | 1024b | 4035 | 1027b | 4042 | 1031a | |
|  |  | 4036 | 1028a | 4043 | 1031b | |
| 4044 | 1022a | 4050 | 1025a | 4057 | 1028b | 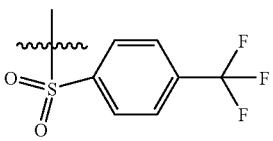 |
| 4045 | 1022b | 4051 | 1025b | 4058 | 1029a | |
| 4046 | 1023a | 4052 | 1026a | 4059 | 1029b | |
| 4047 | 1023b | 4053 | 1026b | 4060 | 1030a | |
| 4048 | 1024a | 4054 | 1027a | 4061 | 1030b | |
| 4049 | 1024b | 4055 | 1027b | 4062 | 1031a | |
|  |  | 4056 | 1028a | 4063 | 1031b | |
| 4064 | 1022a | 4070 | 1025a | 4077 | 1028b | 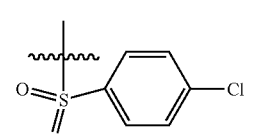 |
| 4065 | 1022b | 4071 | 1025b | 4078 | 1029a | |
| 4066 | 1023a | 4072 | 1026a | 4079 | 1029b | |
| 4067 | 1023b | 4073 | 1026b | 4080 | 1030a | |
| 4068 | 1024a | 4074 | 1027a | 4081 | 1030b | |
| 4069 | 1024b | 4075 | 1027b | 4082 | 1031a | |
|  |  | 4076 | 1028a | 4083 | 1031b | |
| 4084 | 1022a | 4090 | 1025a | 4097 | 1028b | 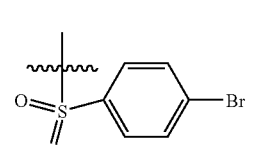 |
| 4085 | 1022b | 4091 | 1025b | 4098 | 1029a | |
| 4086 | 1023a | 4092 | 1026a | 4099 | 1029b | |
| 4087 | 1023b | 4093 | 1026b | 4100 | 1030a | |
| 4088 | 1024a | 4094 | 1027a | 4101 | 1030b | |
| 4089 | 1024b | 4095 | 1027b | 4102 | 1031a | |
|  |  | 4096 | 1028a | 4103 | 1031b | |
| 4104 | 1022a | 4110 | 1025a | 4117 | 1028b | 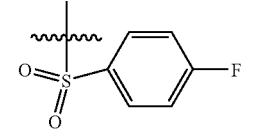 |
| 4105 | 1022b | 4111 | 1025b | 4118 | 1029a | |
| 4106 | 1023a | 4112 | 1026a | 4119 | 1029b | |
| 4107 | 1023b | 4113 | 1026b | 4120 | 1030a | |
| 4108 | 1024a | 4114 | 1027a | 4121 | 1030b | |
| 4109 | 1024b | 4115 | 1027b | 4122 | 1031a | |
|  |  | 4116 | 1028a | 4123 | 1031b | |
| 4124 | 1022a | 4130 | 1025a | 4137 | 1028b | 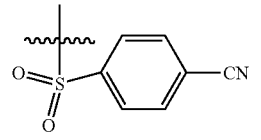 |
| 4125 | 1022b | 4131 | 1025b | 4138 | 1029a | |
| 4126 | 1023a | 4132 | 1026a | 4139 | 1029b | |
| 4127 | 1023b | 4133 | 1026b | 4140 | 1030a | |
| 4128 | 1024a | 4134 | 1027a | 4141 | 1030b | |
| 4129 | 1024b | 4135 | 1027b | 4142 | 1031a | |
|  |  | 4136 | 1028a | 4143 | 1031b | |
| 4144 | 1022a | 4150 | 1025a | 4157 | 1028b | 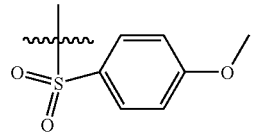 |
| 4145 | 1022b | 4151 | 1025b | 4158 | 1029a | |
| 4146 | 1023a | 4152 | 1026a | 4159 | 1029b | |
| 4147 | 1023b | 4153 | 1026b | 4160 | 1030a | |
| 4148 | 1024a | 4154 | 1027a | 4161 | 1030b | |
| 4149 | 1024b | 4155 | 1027b | 4162 | 1031a | |
|  |  | 4156 | 1028a | 4163 | 1031b | |
| 4164 | 1022a | 4170 | 1025a | 4177 | 1028b | 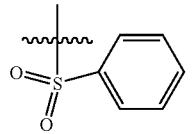 |
| 4165 | 1022b | 4171 | 1025b | 4178 | 1029a | |
| 4166 | 1023a | 4172 | 1026a | 4179 | 1029b | |
| 4167 | 1023b | 4173 | 1026b | 4180 | 1030a | |
| 4168 | 1024a | 4174 | 1027a | 4181 | 1030b | |
| 4169 | 1024b | 4175 | 1027b | 4182 | 1031a | |
|  |  | 4176 | 1028a | 4183 | 1031b | |
| 4184 | 1022a | 4190 | 1025a | 4197 | 1028b | 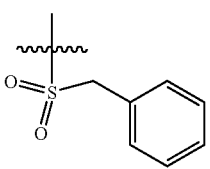 |
| 4185 | 1022b | 4191 | 1025b | 4198 | 1029a | |
| 4186 | 1023a | 4192 | 1026a | 4199 | 1029b | |
| 4187 | 1023b | 4193 | 1026b | 4200 | 1030a | |
| 4188 | 1024a | 4194 | 1027a | 4201 | 1030b | |
| 4189 | 1024b | 4195 | 1027b | 4202 | 1031a | |
|  |  | 4196 | 1028a | 4203 | 1031b | |

TABLE 154-continued

| Ex. | Compd. | Ex. | Compd. | Ex. | Compd | R |
|---|---|---|---|---|---|---|
| 4204 | 1022a | 4210 | 1025a | 4217 | 1028b | thiophene-2-sulfonyl |
| 4205 | 1022b | 4211 | 1025b | 4218 | 1029a | |
| 4206 | 1023a | 4212 | 1026a | 4219 | 1029b | |
| 4207 | 1023b | 4213 | 1026b | 4220 | 1030a | |
| 4208 | 1024a | 4214 | 1027a | 4221 | 1030b | |
| 4209 | 1024b | 4215 | 1027b | 4222 | 1031a | |
| | | 4216 | 1028a | 4223 | 1031b | |
| 4224 | 1022a | 4230 | 1025a | 4237 | 1028b | naphthalene-1-sulfonyl |
| 4225 | 1022b | 4231 | 1025b | 4238 | 1029a | |
| 4226 | 1023a | 4232 | 1026a | 4239 | 1029b | |
| 4227 | 1023b | 4233 | 1026b | 4240 | 1030a | |
| 4228 | 1024a | 4234 | 1027a | 4241 | 1030b | |
| 4229 | 1024b | 4235 | 1027b | 4242 | 1031a | |
| | | 4236 | 1028a | 4243 | 1031b | |
| 4244 | 1022a | 4250 | 1025a | 4257 | 1028b | methoxycarbonyl |
| 4245 | 1022b | 4251 | 1025b | 4258 | 1029a | |
| 4246 | 1023a | 4252 | 1026a | 4259 | 1029b | |
| 4247 | 1023b | 4253 | 1026b | 4260 | 1030a | |
| 4248 | 1024a | 4254 | 1027a | 4261 | 1030b | |
| 4249 | 1024b | 4255 | 1027b | 4262 | 1031a | |
| | | 4256 | 1028a | 4263 | 1031b | |
| 4264 | 1022a | 4270 | 1025a | 4277 | 1028b | ethoxycarbonyl |
| 4265 | 1022b | 4271 | 1025b | 4278 | 1029a | |
| 4266 | 1023a | 4272 | 1026a | 4279 | 1029b | |
| 4267 | 1023b | 4273 | 1026b | 4280 | 1030a | |
| 4268 | 1024a | 4274 | 1027a | 4281 | 1030b | |
| 4269 | 1024b | 4275 | 1027b | 4282 | 1031a | |
| | | 4276 | 1028a | 4283 | 1031b | |
| 4284 | 1022a | 4290 | 1025a | 4297 | 1028b | propoxycarbonyl |
| 4285 | 1022b | 4291 | 1025b | 4298 | 1029a | |
| 4286 | 1023a | 4292 | 1026a | 4299 | 1029b | |
| 4287 | 1023b | 4293 | 1026b | 4300 | 1030a | |
| 4288 | 1024a | 4294 | 1027a | 4301 | 1030b | |
| 4289 | 1024b | 4295 | 1027b | 4302 | 1031a | |
| | | 4296 | 1028a | 4303 | 1031b | |
| 4304 | 1022a | 4310 | 1025a | 4316 | 1028b | isopropoxycarbonyl |
| 4305 | 1022b | 4311 | 1025b | 4317 | 1029a | |
| 4306 | 1023a | 4312 | 1026a | 4317 | 1030a | |
| 4307 | 1023b | 4313 | 1027a | 4320 | 1031a | |
| 4308 | 1024a | 4314 | 1027b | | | |
| 4309 | 1024b | 4315 | 1028a | | | |
| 4321 | 1022a | 4327 | 1025a | 4334 | 1028b | isobutoxycarbonyl |
| 4322 | 1022b | 4328 | 1025b | 4335 | 1029a | |
| 4323 | 1023a | 4329 | 1026a | 4336 | 1029b | |
| 4324 | 1023b | 4330 | 1026b | 4337 | 1030a | |
| 4325 | 1024a | 4331 | 1027a | 4338 | 1030b | |
| 4326 | 1024b | 4332 | 1027b | 4339 | 1031a | |
| | | 4333 | 1028a | 4340 | 1031b | |
| 4341 | 1022a | 4347 | 1025a | 4354 | 1028b | neopentyloxycarbonyl |
| 4342 | 1022b | 4348 | 1025b | 4355 | 1029a | |
| 4343 | 1023a | 4349 | 1026a | 4356 | 1029b | |
| 4344 | 1023b | 4350 | 1026b | 4357 | 1030a | |
| 4345 | 1024a | 4351 | 1027a | 4358 | 1030b | |
| 4346 | 1024b | 4352 | 1027b | 4359 | 1031a | |
| | | 4353 | 1028a | 4360 | 1031b | |
| 4361 | 1022a | 4367 | 1025a | 4374 | 1028b | allyloxycarbonyl |
| 4362 | 1022b | 4368 | 1025b | 4375 | 1029a | |
| 4363 | 1023a | 4369 | 1026a | 4376 | 1029b | |
| 4364 | 1023b | 4370 | 1026b | 4377 | 1030a | |
| 4365 | 1024a | 4371 | 1027a | 4378 | 1030b | |
| 4366 | 1024b | 4372 | 1027b | 4379 | 1031a | |
| | | 4373 | 1028a | 4380 | 1031b | |

TABLE 154-continued

| Ex. | Compd. | Ex. | Compd. | Ex. | Compd | R |
|---|---|---|---|---|---|---|
| 4381 | 1022a | 4387 | 1025a | 4394 | 1028b | sec-butyl ester |
| 4382 | 1022b | 4388 | 1025b | 4395 | 1029a | |
| 4383 | 1023a | 4389 | 1026a | 4396 | 1029b | |
| 4384 | 1023b | 4390 | 1026b | 4397 | 1030a | |
| 4385 | 1024a | 4391 | 1027a | 4398 | 1030b | |
| 4386 | 1024b | 4392 | 1027b | 4399 | 1031a | |
| | | 4393 | 1028a | 4400 | 1031b | |
| 4401 | 1022a | 4407 | 1025a | 4414 | 1028b | cyclopentyl ester |
| 4402 | 1022b | 4408 | 1025b | 4415 | 1029a | |
| 4403 | 1023a | 4409 | 1026a | 4416 | 1029b | |
| 4404 | 1023b | 4410 | 1026b | 4417 | 1030a | |
| 4405 | 1024a | 4411 | 1027a | 4418 | 1030b | |
| 4406 | 1024b | 4412 | 1027b | 4419 | 1031a | |
| | | 4413 | 1028a | 4420 | 1031b | |
| 4421 | 1022a | 4427 | 1025a | 4434 | 1028b | cyclohexyl ester |
| 4422 | 1022b | 4428 | 1025b | 4435 | 1029a | |
| 4423 | 1023a | 4429 | 1026a | 4436 | 1029b | |
| 4424 | 1023b | 4430 | 1026b | 4437 | 1030a | |
| 4425 | 1024a | 4431 | 1027a | 4438 | 1030b | |
| 4426 | 1024b | 4432 | 1027b | 4439 | 1031a | |
| | | 4433 | 1028a | 4440 | 1031b | |
| 4441 | 1022a | 4447 | 1025a | 4454 | 1028b | phenyl ester |
| 4442 | 1022b | 4448 | 1025b | 4455 | 1029a | |
| 4443 | 1023a | 4449 | 1026a | 4456 | 1029b | |
| 4444 | 1023b | 4450 | 1026b | 4457 | 1030a | |
| 4445 | 1024a | 4451 | 1027a | 4458 | 1030b | |
| 4446 | 1024b | 4452 | 1027b | 4459 | 1031a | |
| | | 4453 | 1028a | 4460 | 1031b | |
| 4461 | 1022a | 4467 | 1025a | 4474 | 1028b | benzyl ester |
| 4462 | 1022b | 4468 | 1025b | 4475 | 1029a | |
| 4463 | 1023a | 4469 | 1026a | 4476 | 1029b | |
| 4464 | 1023b | 4470 | 1026b | 4477 | 1030a | |
| 4465 | 1024a | 4471 | 1027a | 4478 | 1030b | |
| 4466 | 1024b | 4472 | 1027b | 4479 | 1031a | |
| | | 4473 | 1028a | 4480 | 1031b | |
| 4481 | 1022a | 4487 | 1025a | 4494 | 1028b | 4-methylphenyl ester |
| 4482 | 1022b | 4488 | 1025b | 4495 | 1029a | |
| 4483 | 1023a | 4489 | 1026a | 4496 | 1029b | |
| 4484 | 1023b | 4490 | 1026b | 4497 | 1030a | |
| 4485 | 1024a | 4491 | 1027a | 4498 | 1030b | |
| 4486 | 1024b | 4492 | 1027b | 4499 | 1031a | |
| | | 4493 | 1028a | 4500 | 1031b | |
| 4501 | 1022a | 4507 | 1025a | 4514 | 1028b | 4-methoxyphenyl ester |
| 4502 | 1022b | 4508 | 1025b | 4515 | 1029a | |
| 4503 | 1023a | 4509 | 1026a | 4516 | 1029b | |
| 4504 | 1023b | 4510 | 1026b | 4517 | 1030a | |
| 4505 | 1024a | 4511 | 1027a | 4518 | 1030b | |
| 4506 | 1024b | 4512 | 1027b | 4519 | 1031a | |
| | | 4513 | 1028a | 4520 | 1031b | |
| 4521 | 1022a | 4527 | 1025a | 4534 | 1028b | 4-chlorophenyl ester |
| 4522 | 1022b | 4528 | 1025b | 4535 | 1029a | |
| 4523 | 1023a | 4529 | 1026a | 4536 | 1029b | |
| 4524 | 1023b | 4530 | 1026b | 4537 | 1030a | |
| 4525 | 1024a | 4531 | 1027a | 4538 | 1030b | |
| 4526 | 1024b | 4532 | 1027b | 4539 | 1031a | |
| | | 4533 | 1028a | 4540 | 1031b | |
| 4541 | 1022a | 4547 | 1025a | 4554 | 1028b | 4-bromophenyl ester |
| 4542 | 1022b | 4548 | 1025b | 4555 | 1029a | |
| 4543 | 1023a | 4549 | 1026a | 4556 | 1029b | |
| 4544 | 1023b | 4550 | 1026b | 4557 | 1030a | |
| 4545 | 1024a | 4551 | 1027a | 4558 | 1030b | |
| 4546 | 1024b | 4552 | 1027b | 4559 | 1031a | |
| | | 4553 | 1028a | 4560 | 1031b | |

TABLE 154-continued

| Ex. | Compd. | Ex. | Compd. | Ex. | Compd | R |
|---|---|---|---|---|---|---|
| 4561 | 1022a | 4567 | 1025a | 4574 | 1028b | |
| 4562 | 1022b | 4568 | 1025b | 4575 | 1029a | |
| 4563 | 1023a | 4569 | 1026a | 4576 | 1029b | 4-fluorophenyl carbonate |
| 4564 | 1023b | 4570 | 1026b | 4577 | 1030a | |
| 4565 | 1024a | 4571 | 1027a | 4578 | 1030b | |
| 4566 | 1024b | 4572 | 1027b | 4579 | 1031a | |
| | | 4573 | 1028a | 4580 | 1031b | |
| 4581 | 1022a | 4587 | 1025a | 4594 | 1028b | |
| 4582 | 1022b | 4588 | 1025b | 4595 | 1029a | |
| 4583 | 1023a | 4589 | 1026a | 4596 | 1029b | 1-naphthyl carbonate |
| 4584 | 1023b | 4590 | 1026b | 4597 | 1030a | |
| 4585 | 1024a | 4591 | 1027a | 4598 | 1030b | |
| 4586 | 1024b | 4592 | 1027b | 4599 | 1031a | |
| | | 4593 | 1028a | 4600 | 1031b | |
| 4601 | 1022a | 4607 | 1025a | 4613 | 1028b | |
| 4602 | 1022b | 4608 | 1025b | 4614 | 1029a | |
| 4603 | 1023a | 4609 | 1026a | 4615 | 1030a | tetrahydropyran-4-yl carbonate |
| 4604 | 1023b | 4600 | 1027a | 4616 | 1030b | |
| 4605 | 1024a | 4611 | 1027b | 4617 | 1031a | |
| 4606 | 1024b | 4612 | 1028a | 4618 | 1031b | |

EXAMPLE 4619

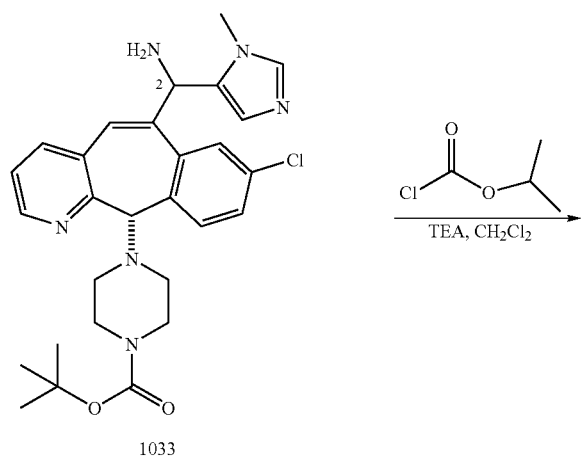

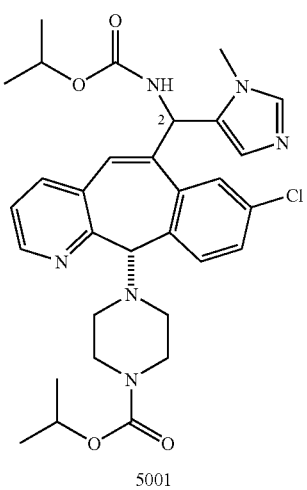

To a $CH_2Cl_2$ (5 mL) solution of compound 1033 (Example 3280) (35 mg, 0.07 mmol) was added 0.03 mL of triethyl amine followed by isopropyl chloroformate (0.084 mL, 1.0 M in $CH_3Ph$, 0.084 mmol). The reaction was stirred at room temperature under $N_2$ for 1 hr. It was then quenched with saturated $NaHCO_3$ solution and extracted with $CH_2Cl_2$ several times. The combined organic solution was dried ($MgSO_4$) and evaporated to dryness. The residue was purified by prep TLC plates using 10% methanol (2M $NH_3$)/$CH_2Cl_2$ to give compound 5001 as an off white solid (15.0 mg). M.P. 152-155° C. (dec). MS M+1 593.

Assays

FPT activity was determined by measuring the transfer of [$^3$H] farnesyl from [$^3$H] farnesyl pyrophosphate to a biotinylated peptide derived from the C-terminus of H-ras (biotin-CVLS). The reaction mixture contains: 50 mM Tris pH7.7, 5 MM $MgCl_2$, 5 μM $Zn^{++}$, 5 mM DTT, 0.1% Triton-X, 0.05 μM peptide, 0.03 nM purified human farnesyl protein transferase, 0.180 μM [$^3$H] farnesyl pyrophosphate, plus the indicated concentration of tricyclic compound or vehicle control in a total volume of 100 μl. The reaction was incubated in a Vortemp shaking incubator at 37° C., 45 RPM for 60 minutes and stopped with 150 μl of 0.25 M EDTA containing 0.5% BSA and 1.3 mg/ml Streptavidin SPA beads. Radioactivity was measured in a Wallach 1450 Microbeta liquid scintillation counter. Percent inhibition was calculated relative to the vehicle control.

COS Cell $IC_{50}$ (Cell-Based Assay) were determined following the assay aprocedures described in WO 95/10516, published Apr. 20, 1995. GGPT $IC_{50}$ (inhibition of geranylgeranyl protein transferase, in vitro enzyme assay), Cell Mat Biochemical assay and anti-tumor activity (in vivo anti-tumor studies) could be determined by the assay procedures described in WO 95/10516. The disclosure of WO 95/10516 is incorporated herein by reference thereto.

Various tumor cells ($5 \times 10^5$ to $8 \times 10^6$) were innoculated subcutaneously into the flank of 5-6 week old athymic nu/nu female mice. Three tumor cell models were used: mouse fibroblasts transformed with H-Ras; HTB-177 human non small cell lung cancer cells or LOX human melanoma cells.

Animals were treated with beta cyclodextran vehicle only or compounds in vehicle twice a day (BID) or once a day (QD) for 7 days per week for 1 (×1), 2 (×2) or 3 (×3) weeks. The percent inhibition of tumor growth relative to vehicle controls were determined by tumor measurements. The results are reported in Table 155.

TABLE 155

| Compound No. | Tumor | Dose (MPK) | Route and Schedule | Average % Tumor Inhibition |
|---|---|---|---|---|
| (372) | H-Ras fibroblasts | 40 | po, BID, x2 | 92 |
| " | H-Ras fibroblasts | 10 | po, BID, x2 | 70 |
| " | H-Ras fibroblasts | 80 | po, QD, x2 | 91 |
| " | H-Ras fibroblasts | 20 | po, QD, x2 | 55 |
| " | H-Ras fibroblasts | 60 | po, BID, x2 | 98 |
| " | H-Ras fibroblasts | 20 | po, BID, x2 | 59 |
| " | H-Ras fibroblasts | 6.6 | po, BID, x2 | 19 |
| " | HTB-177 | 60 | po, BID, x3 | 87 |
| " | HTB-177 | 20 | po, BID, x3 | 43 |
| " | HTB-177 | 120 | po, QD, x3 | 54 |
| " | HTB-177 | 40 | po, QD, x3 | 11 |
| " | HTB-177 | 80 | po, BID, x3 | 96 |
| " | HTB-177 | 40 | po, BID, x3 | 79 |
| " | HTB-177 | 20 | po, BID, x3 | 47 |
| " | LOX | 15 | po, BID, x1 | 20.9 |
| " | LOX | 30 | po, BID, x1 | 54.8 |
| " | LOX | 60 | po, BID, x1 | 90.3 |

(The schedule "po, BID, x3", for example, means orally, twice a day for 7 days (14 times per week) for 3 weeks).

Soft Agar Assay

Anchorage-independent growth is a characteristic of tumorigenic cell lines. Human tumor cells can be suspended in growth medium containing 0.3% agarose and an indicated concentration of a farnesyl transferase inhibitor. The solution can be overlayed onto growth medium solidified with 0.6% agarose containing the same concentration of farnesyl transferase inhibitor as the top layer. After the top layer is solidified, plates can be incubated for 10-16 days at 37° C. under 5% $CO_2$ to allow colony outgrowth. After incubation, the colonies can be stained by overlaying the agar with a solution of MTT (3-[4,5-dimethyl-thiazol-2-yl]-2,5-diphenyltetrazolium bromide, Thiazolyl blue) (1 mg/mL in PBS). Colonies can be counted and the $IC_{50}$'s can be determined.

There are compounds of this invention have an FPT $IC_{50}$ in the range of 0.05 nM to 100 nM and a Soft Agar $IC_{50}$ in the range of <0.5 nM to 50 nM.

The compound of Example 4916 had an FPT $IC_{50}$ of 1.2 nM, and a Soft Agar $IC_{50}$ of <0.5 nM.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington: The Science and Practice of Pharmacy, 20$^{th}$ Edition, (2000), Lippincott Williams & Wilkins, Baltimore, Md.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparations subdivided into suitably sized unit doses containing appropriate quantities of the active component, e.g., an effective amount to achieve the desired purpose.

The quantity of active compound in a unit dose of preparation may be varied or adjusted from about 0.01 mg to about 1000 mg, preferably from about 0.01 mg to about 750 mg, more preferably from about 0.01 mg to about 500 mg, and most preferably from about 0.01 mg to about 250 mg according to the particular application.

The actual dosage employed may be varied depending upon the requirements of the patient and the severity of the condition being treated. Determination of the proper dosage regimen for a particular situation is within the skill in the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.04 mg/day to about 4000 mg/day, in two to four divided doses.

The chemotherapeutic agent and/or radiation therapy can be administered in association with the compounds of the present invention according to the dosage and administration schedule listed in the product information sheet of the approved agents, in the Physicians Desk Reference (PDR) as well as therapeutic protocols well known in the art. Dosages and dosage regimens are exemplified in the embodiments of this invention. Additional examples of dosages and dosage regimens of chemotherapeutic agents useful in this invention are given in Table 156.

TABLE 156

Examplary Chemotherapeutic Agents Dosage and Dosage Regimens

| | |
|---|---|
| Cisplatin: | 50–100 mg/m$^2$ every 4 weeks (IV)* |
| Carboplatin: | 300–360 mg/m$^2$ every 4 weeks (IV) |
| Taxotere: | 60–100 mg/m$^2$ every 3 weeks (IV) |

*(IV)-intravenously

It will be apparent to those skilled in the art that the administration of the chemotherapeutic agent and/or radiation therapy can be varied depending on the disease being treated and the known effects of the chemotherapeutic agent and/or radiation therapy on that disease. Also, in accordance with the knowledge of the skilled clinician, the therapeutic protocols (e.g., dosage amounts and times of administration) can be varied in view of the observed effects of the administered chemotherapeutic agents (i.e., antineoplastic agent or radiation) on the patient, and in view of the observed responses of the disease to the administered therapeutic agents.

In an example of combination therapy in the treatment of pancreatic cancer, the compound of Formula (1.0) is administered orally in a range of from 50 to 400 mg/day, in two divided doses, in association with the antineoplastic agent, gemcitabine, which is administered at a dosage of from 750 to 1350 mg/m$^2$ weekly for three out of four weeks during the course of treatment.

In an example of combination therapy in the treatment of lung cancer, the compound of Formula (1.0) is administered orally in a range of from 50 to 400 mg/day, in two divided doses, in association with the antineoplastic agent, paclitaxel, which is administered at a dosage of from 65 to 175 mg/m$^2$ once every three weeks.

In an example of combination therapy in the treatment of gliomas, the compound of Formula (1.0) is administered orally in a range of from 50 to 400 mg/day, in two divided doses; in association with the antineoplastic agent, temozolomide, which is administered at a dosage of from 100 to 250 mg/m$^2$.

In another example of combination therapy in the treatment of cancer, the compound of Formula (1.0) is administered orally in a range of from 50 to 400 mg/day, in two divided doses, in association with the antineoplastic agent, cisplatin, which is administered intravenously in a range of from 50 to 100 mg/m2 once every four weeks.

In another example of combination therapy in the treatment of cancer, the compound of Formula (1.0) is administered orally in a range of from 50 to 400 mg/day, in two divided doses, in association with the antineoplastic agent, carboplatin, which is administered intravenously in a range of from 300-360 mg/m2 once every four weeks.

In another example of combination therapy in the treatment of cancer, the compound of Formula (1.0) is administered orally in a range of from 50 to 400 mg/day, in two divided doses, in association with the chemotherapeutic agent, carboplatin, which is administered intravenously in a range of from 300 to 360 mg/m2 once every four weeks and the chemotherapeutic agent, paclitaxel, which is administered at a dosage of from 65 to 175 mg/m$^2$ once every three weeks.

In another example of combination therapy in the treatment of cancer, the compound of Formula (1.0) is administered orally in a range of from 50 to 400 mg/day, in two divided doses, in association with the chemotherapeutic agent, Cisplatin, which is administered intravenously in a range of from 50 to1 00 mg/m2 once every four weeks and the chemotherapeutic agent, Gemcitabine, which is administered at a dosage of from 65 to 175 mg/m$^2$ once every three weeks.

The signal transduction inhibition therapy can be administered according to the dosage and administration schedule listed in the product information sheet of the approved agents, in the Physicians Desk Reference (PDR) as well as therapeutic protocols well known in the art. Examples of ranges of dosage and dosage regimens of some signal transduction inhibitors are given Table 157.

TABLE 157

Examplary Signal Transduction Inhibitors Dosage and Dosage Regimens

| | |
|---|---|
| Iressa (ZD1839) - EGF receptor kinase inhibitor: | 150–700 mg/day (oral) |
| OSI-774 - EGF receptor kinase inhibitor: | 100–1000 mg/day (oral) |
| Herceptin - HER-2/neu antibody: | 100–250 mg/m$^2$/week (IV)* |
| C225 - EGF receptor antibody: | 200–500 mg/m$^2$/week (IV) |
| ABX-EGF - EGF receptor antibody: | 0.2–2 mg/kg every 2 weeks (IV) |
| Gleevec (STI-571) - bcr/abl kinase inhibitor: | 300–1000 mg/day (oral) |

*(IV)-intravenously

It will be apparent to those skilled in the art that the administration of the signal tranduction inhibitor can be varied depending on the disease being treated and the known effects of the signal transduction inhibitor therapy on that disease. Also, in accordance with the knowledge of the skilled clinician, the therapeutic protocols (e.g., dosage amounts and times of administration) can be varied in view of the observed effects of the administered signal transduction inhibitors on the patient, and in view of the observed responses of the disease to the administered therapeutic agents.

In another example of combination therapy in the treatment of cancer, the compound of Formula (1.0) is administered orally in a range of from 50 to 400 mg/day, in two divided doses in association with the signal tranduction inhibitor, EGF receptor kinase inhibitor, Iressa (ZD1839), which is administered orally in the range of 150-700 mg/day.

The FPT inhibitor compound of formula (1.0), the chemotherapeutic agent, signal transduction inhibitor and/or radiation can be administered by different routes. For example, the FPT inhibitor compound of formula (1.0) can be administered orally, while the chemotherapeutic agent may be administered intravenously. The initial administration can be made according to established protocols known in the art, and then, based upon the observed effects, the dosage, modes of administration and times of administration can be modified by the skilled clinician.

The particular choice of the chemotherapeutic agent, signal transduction inhibitor and/or radiation to use with the FPT inhibitor of this invention will depend upon the diagnosis of the attending physicians and their judgement of the condition of the patient and the appropriate treatment protocol.

The FPT inhibitor compound of formula (1.0), chemotherapeutic agent, signal transduction inhibitor and/or radiation may be administered concurrently (e.g., simultaneously, just prior to or after, or within the same treatment protocol) or sequentially. Determination of the sequence of administration can be determined by the skilled clinician. Some factors that the skilled clinician can use to determine the treatment protocol are the nature of the proliferative disease, the condition of the patient, and the actual choice of chemotherapeutic agent, signal transduction inhibitor and/or radiation to be administered in conjunction (i.e., within a single treatment protocol) with the FPT inhibitor compound of formula (1.0).

If the FPT inhibitor compound of formula (1.0), chemotherapeutic agent, signal transduction inhibitor and/or radiation are not administered simultaneously then the FPT inhibitor compound of formula (1.0) may be administered first followed by the administration of the chemotherapeutic agent, signal transduction inhibitor and/or radiation, or the chemotherapeutic agent, signal transduction inhibitor and/or radiation can be administered first followed by the administration of the FPT inhibitor compound of formula (1.0). This alternate administration may be repeated during a single treatment protocol until the treatment protocol is completed. The determination of the order of administration, and the number of repititions of administration of each therapeutic agent during a treatment protocol, is well within the knowledge of the skilled physician after evaluation of the disease being treated and the condition of the patient.

Thus, in accordance with experience and knowledge, the practicing physician can modify each protocol for the administration of a component (therapeutic agent—i.e., FPT inhibitor compound of formula (1.0), chemotherapeutic agent, signal transduction inhibitor or radiation) of the treatment according to the individual patient's needs, as the treatment proceeds.

The attending clinician, in judging whether treatment is effective at the dosage administered, will consider the general well-being of the patient as well as more definite signs such as relief of disease-related symptoms, inhibition of tumor growth, actual shrinkage of the tumor, or inhibition of metastasis. Size of the tumor can be measured by standard methods such as radio-logical studies, e.g., CAT or MRI scan, and successive measure-ments can be used to judge whether or not growth of the tumor has been retarded or even reversed. Relief of disease-related symptoms such as pain, and improvement in overall condition can also be used to help judge effectiveness of treatment.

Additional pharmaceutical and method of treating embodiments of this invention are set forth below.

An embodiment of this invention is directed to a pharmaceutical composition comprising an effective amount of compound of formula 1.0 in combination with a pharmaceutically acceptable carrier.

An embodiment of this invention is directed to a pharmaceutical composition comprising an effective amount of compound of formula 1.4 in combination with a pharmaceutically acceptable carrier.

An embodiment of this invention is directed to a method for treating the abnormal growth of cells in a patient in need of such treatment comprising administering to said patient an effective amount of a compound of formula 1.0.

An embodiment of this invention is directed to a method of treating tumors in a patient in need of such treatment comprising administering to said patient an effective amount of a compound of formula 1.0.

An embodiment of this invention is directed to a method of treating tumors expressing an activated ras oncogene in a patient in need of such treatment comprising administering to said patient an effective amount of a compound of formula 1.0.

An embodiment of this invention is directed to a method of treating tumors in a patient in need of such treatment wherein said tumors are selected from the group consisting of: pancreatictumors, lung tumors, myeloid leukemias, thyroid follicular tumors, myelodysplastic syndrome, head and neck tumors, melanomas, breast tumor, prostate tumors, ovarian tumors, bladder tumors, glioma tumors, epidermal tumors and colon tumors, comprising administering to said patient an effective amount of a compound of formula 1.0

An embodiment of this invention is directed to a method of inhibiting ras farnesyl protein transferase in a patient in need of such treatment comprising administering to said patient an effective amount of a compound of formula 1.0.

An embodiment of this invention is directed to a method of treating tumors, wherein the Ras protein is activated as a result of oncogenic mutation in genes other than the Ras gene, in a patient in need of such treatment comprising administering to said patient an effective amount of a compound of formula 1.0.

An embodiment of this invention is directed to a method of treating tumors in a patient in need of such treatment comprising administering concurrently or sequentially to said patient, an effective amount of a compound of formula 1.0 in combination with an effective amount of at least one chemotherapeutic agent and/or radiation.

An embodiment of this invention is directed to a method of treating tumors in a patient in need of such treatment comprising administering concurrently or sequentially to said patient, an effective amount of a compound of formula 1.0 in combination with an effective amount of at least one chemotherapeutic agent and/or radiation, wherein said tumors are selected from the group consisting of: pancreatic tumors, lung tumors, myeloid leukemias, thyroid follicular tumors, myelodysplastic syndrome, head and neck tumors, melanomas, breast tumor, prostate tumors, ovarian tumors, bladder tumors, glioma tumors, epidermal tumors and colon tumors.

An embodiment of this invention is directed to a method of treating tumors in a patient in need of such treatment comprising administering concurrently or sequentially to said patient, an effective amount of a compound of formula 1.0 in combination with an effective amount of at least one chemotherapeutic agent and/or radiation, wherein said tumors are selected from the group consisting of lung cancer, head and neck cancer, bladder cancer, breast cancer, prostate cancer and myeloid leukemias.

An embodiment of this invention is directed to a method of treating tumors in a patient in need of such treatment comprising administering concurrently or sequentially to said patient, an effective amount of a compound of formula 1.0 in combination with an effective amount of at least one chemotherapeutic agent and/or radiation, wherein said chemotherapeutic agent is an antineoplastic agent selected from: Uracil mustard, Chlormethine, Cyclophosphamide, Ifosfamide, Melphalan, Chlorambucil, Pipobroman, Triethylenemelamine, Triethylenethiophosphoramine, Busulfan, Carmustine, Lomustine, Streptozocin, Dacarbazine, Temozolomide, Methotrexate, 5-Fluorouracil, Floxuridine, Cytarabine, 6-Mercaptopurine, 6-Thioguanine, Fludarabine phosphate, Pentostatine, Gemcitabine, Vinblastine, Vincristine, Vindesine, Bleomycin, Dactinomycin, Daunorubicin, Doxorubicin, Epirubicin, Idarubicin, Taxol, Taxotere, Mithramycin. Deoxycoformycin, Mitomycin-C, L-Asparaginase, Interferons, Etoposide, Teniposide 17α-Ethinylestradiol, Diethylstilbestrol, Testosterone, Prednisone, Fluoxymesterone, Dromostanolone propionate, Testolactone, Megestrolacetate, Tamoxifen, Methylprednisolone, Methyltestosterone, Prednisolone, Triamcinolone, Chlorotrianisene, Hydroxyprogesterone, Aminoglutethimide, Estramustine, Medroxyprogesteroneacetate, Leuprolide, Flutamide, Toremifene, goserelin, Cisplatin, Carboplatin, Hydroxyurea, Amsacrine, Procarbazine, Mitotane, Mitoxantrone, Levamisole, Navelbene, CPT-11, Anastrazole, Letrazole, Capecitabine, Reloxafine, Droloxafine, and Hexamethylmelamine.

An embodiment of this invention is directed to a method of treating tumors in a patient in need of such treatment comprising administering concurrently or sequentially to said patient, an effective amount of a compound of formula 1.0 in combination with an effective amount of at least one chemotherapeutic agent and/or radiation, wherein said chemotherapeutic agent is a microtubule affecting agent selected from allocolchicine, Halichondrin B, colchicine, colchicine derivatives, dolastatin 10, maytansine, rhizoxin, paclitaxel, paclitaxel derivatives, Taxotere, thiocolchicine, trityl cysteine, vinblastine sulfate, vincristine sulfate, epothilone A, epothilone, discodermolide, estramustine, nocodazole and MAP4.

An embodiment of this invention is directed to a method of treating tumors in a patient in need of such treatment comprising administering concurrently or sequentially to said patient, an effective amount of a compound of formula 1.0 in combination with an effective amount of at least one chemotherapeutic agent and/or radiation, wherein said chemotherapeutic agent is selected from Gemcitabine, Cisplatin, Carboplatin, paclitaxel, paclitaxel derivatives, and Taxotere.

An embodiment of this invention is directed to a method of treating tumors in a patient in need of such treatment comprising administering concurrently or sequentially to said patient, an effective amount of a compound of formula 1.0 in combination with an effective amount of at least one chemotherapeutic agent and/or radiation, wherein the compound of formula 1.0 is selected from the group consisting of:

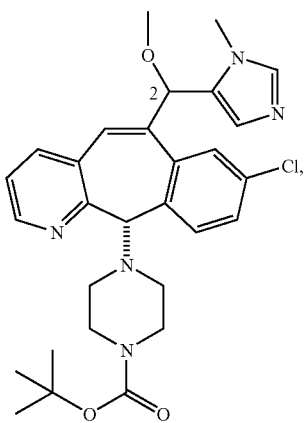

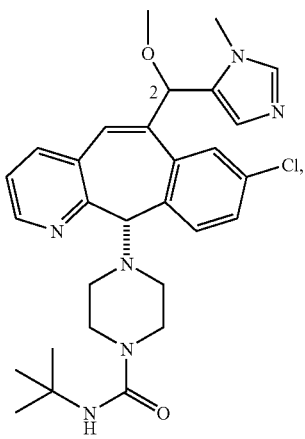

-continued

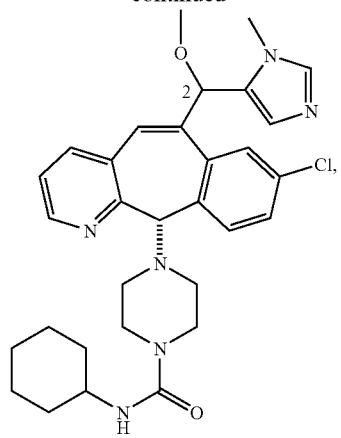

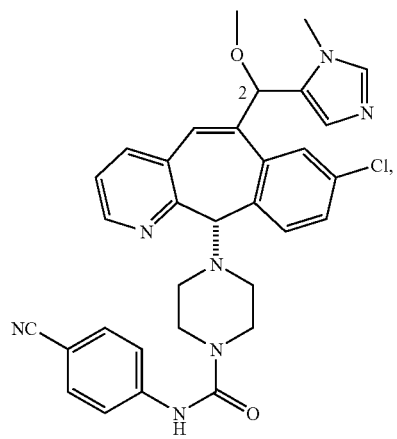

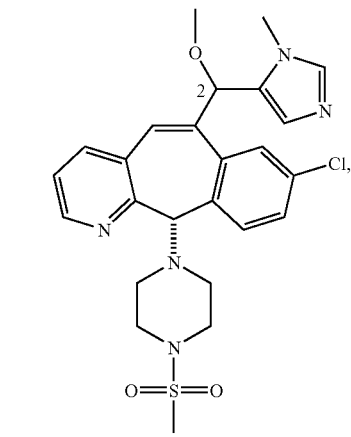

1085 -continued
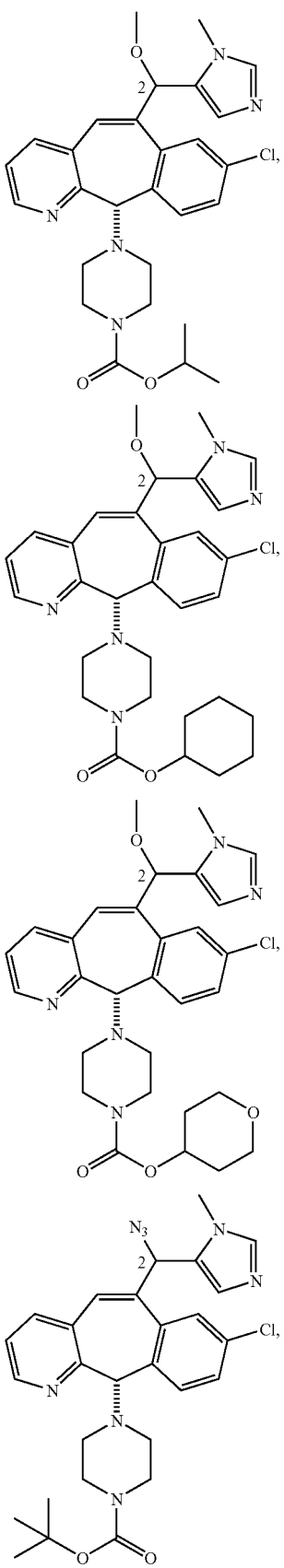
1086 -continued
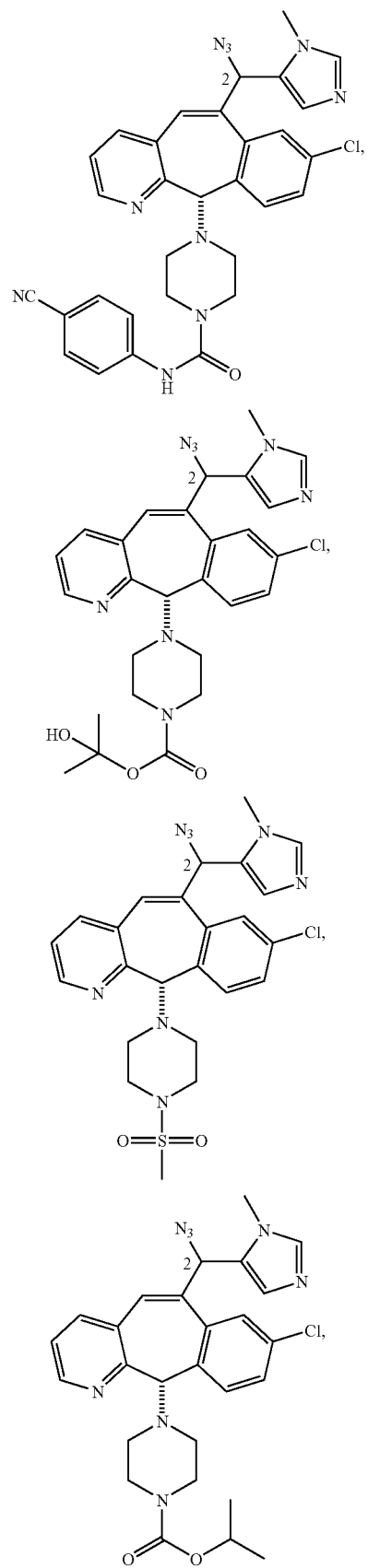

| 1087 | 1088 |
|---|---|
| -continued | -continued |
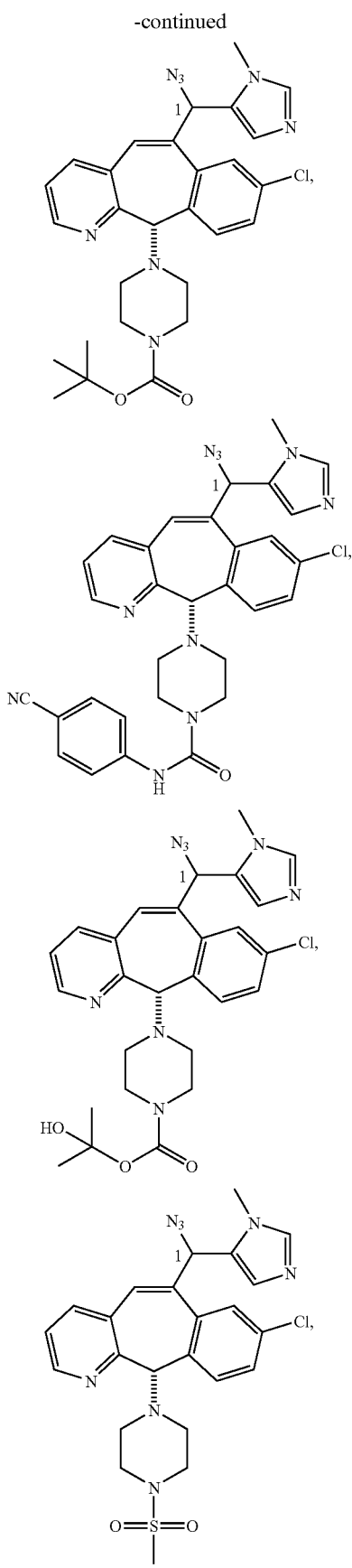
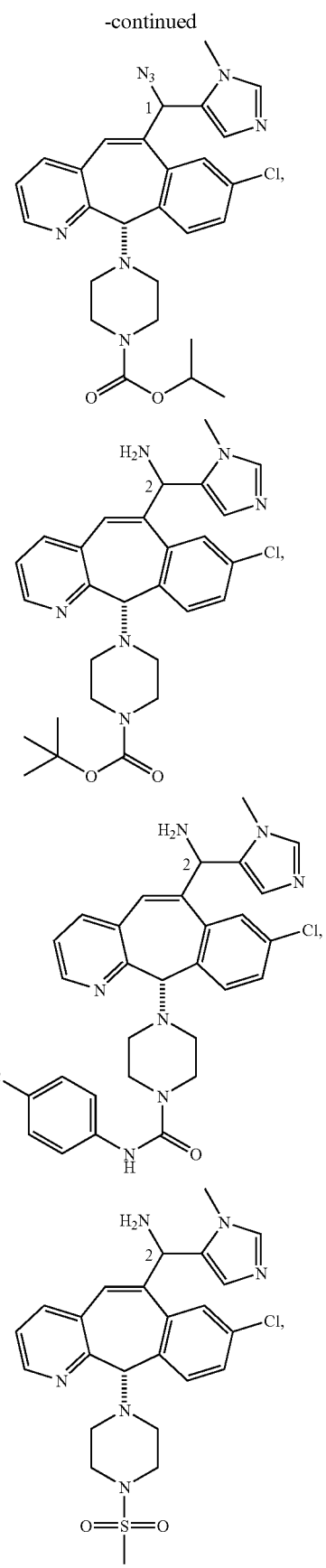

1089 1090
-continued -continued
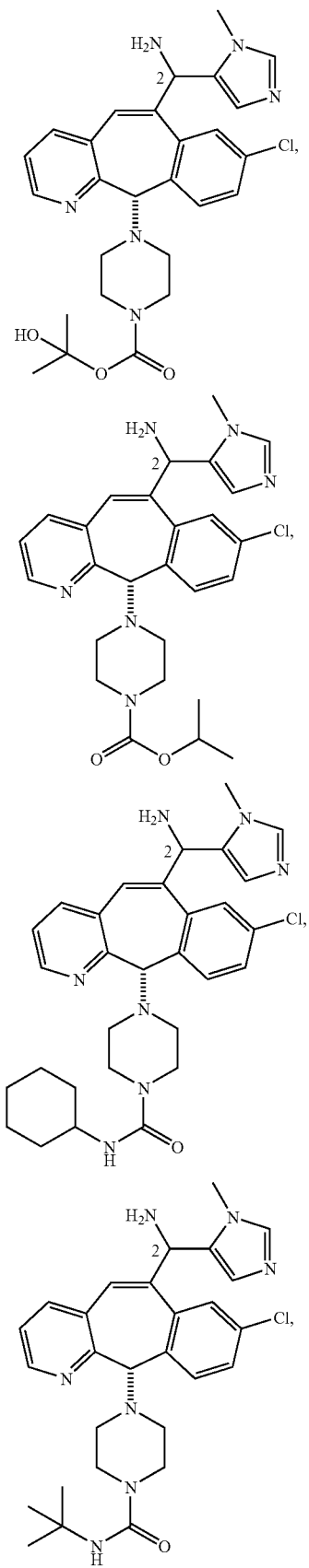
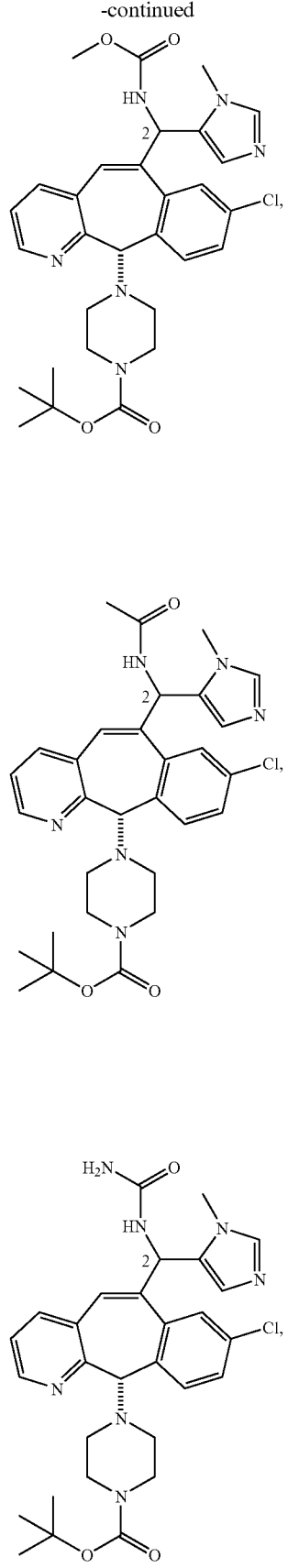

1091
-continued
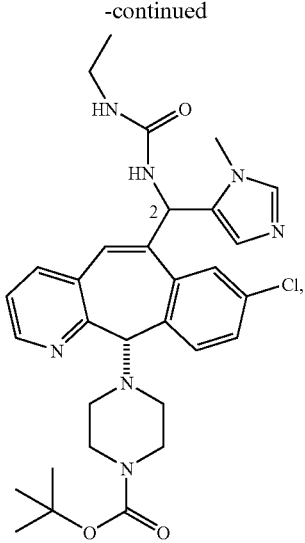
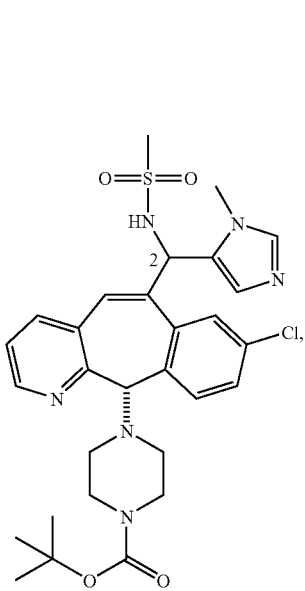
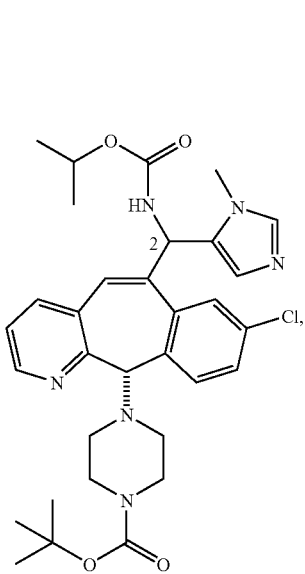
1092
-continued
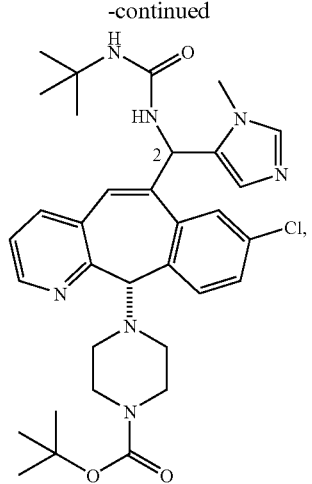
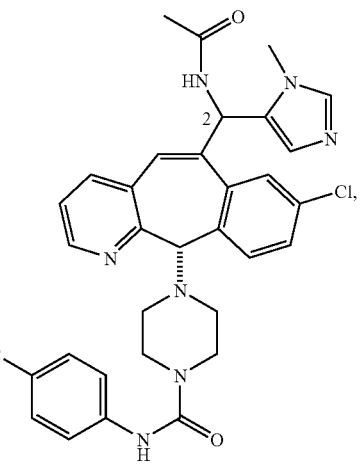
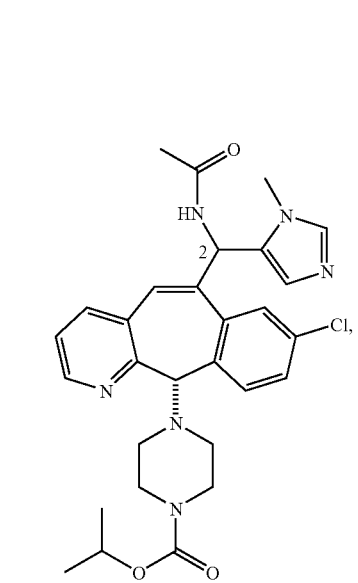

1093
-continued
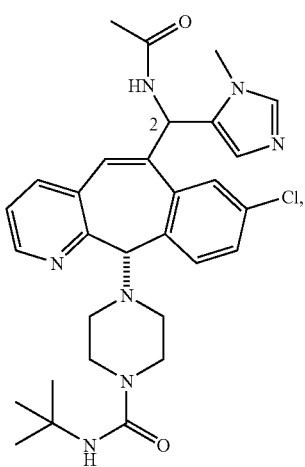
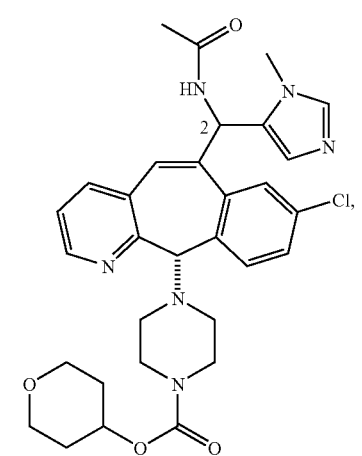
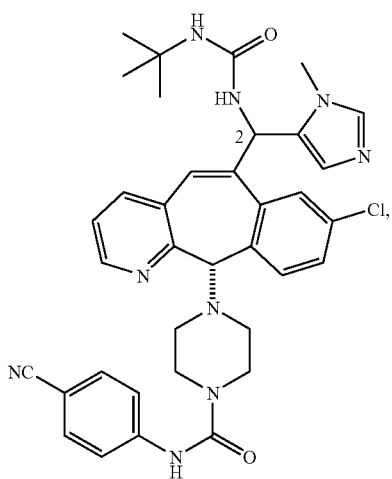
1094
-continued
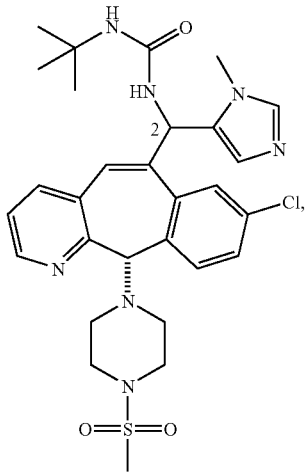
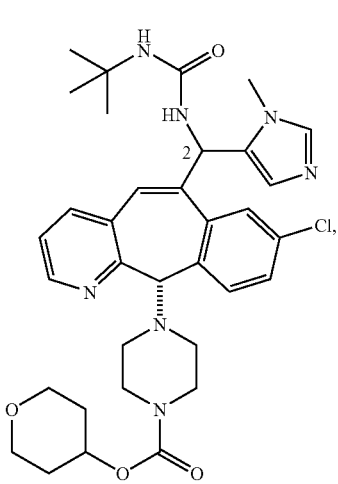
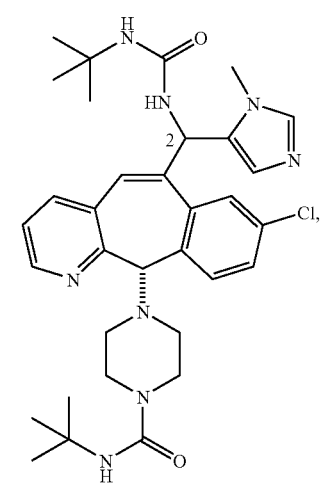

1095
-continued
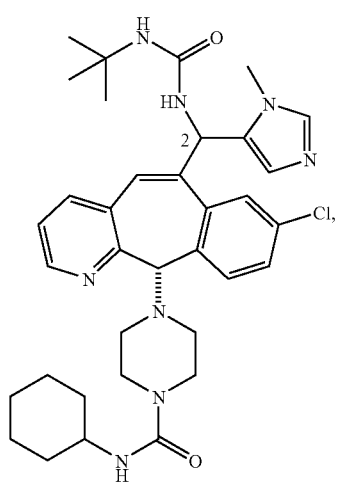
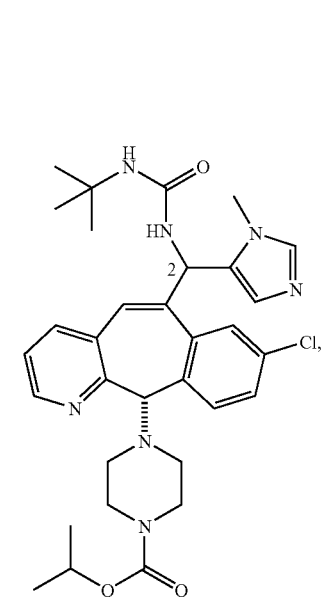
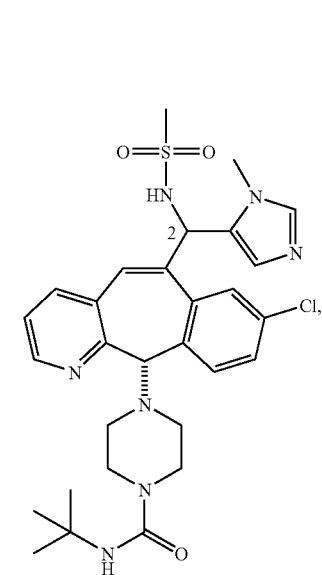
1096
-continued
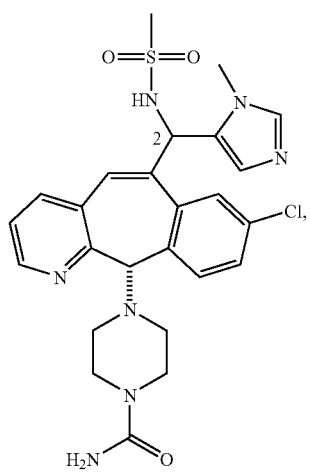
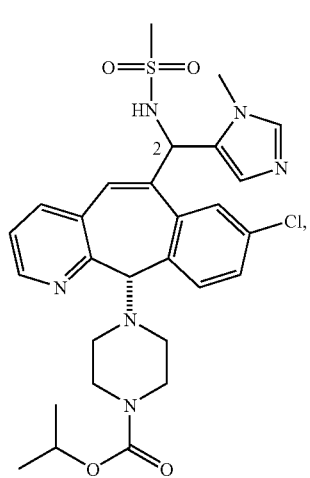
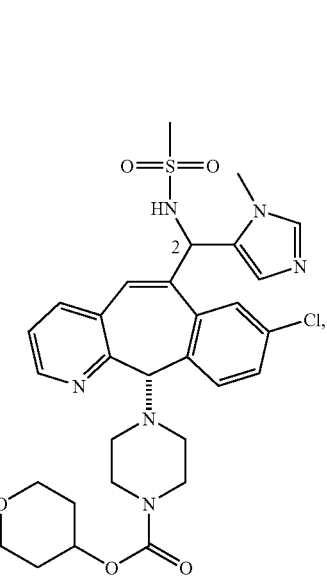

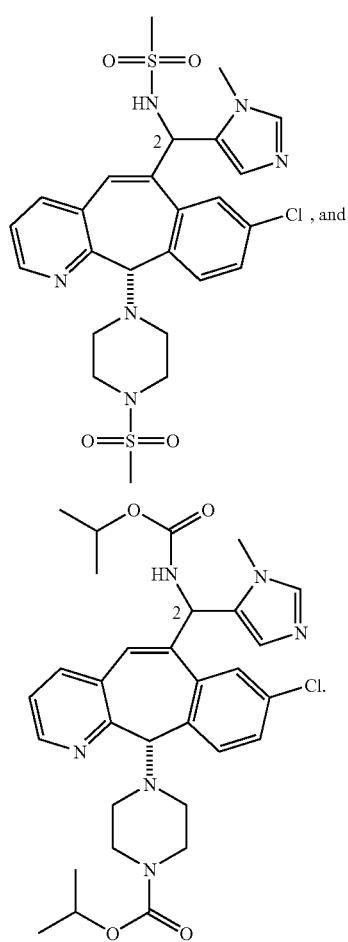

An embodiment of this invention is directed to a method of treating tumors in a patient in need of such treatment comprising administering concurrently or sequentially to said patient, an effective amount of a compound of formula 1.0 in combination with an effective amount of at least one chemotherapeutic agent and/or radiation, wherein the compound of formula 1.0 is selected from the group consisting of:

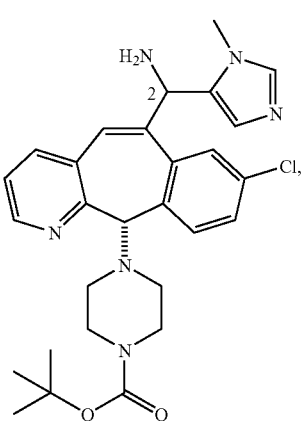

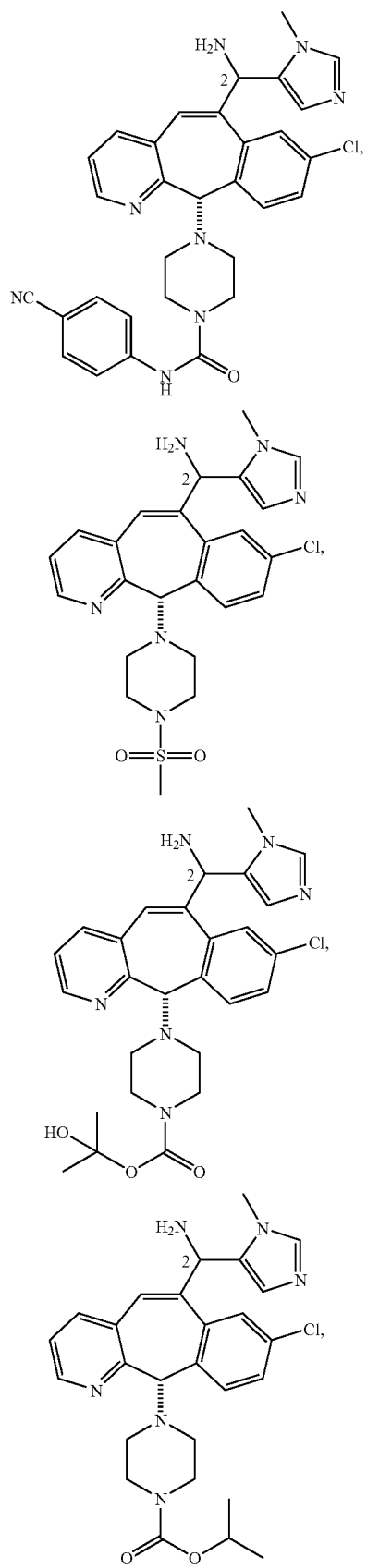

-continued
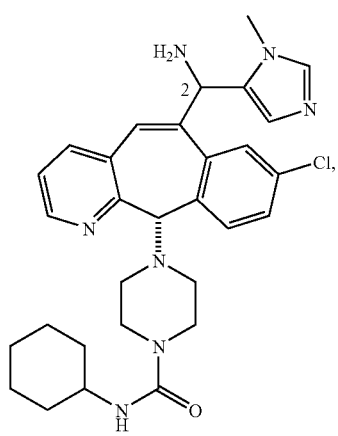
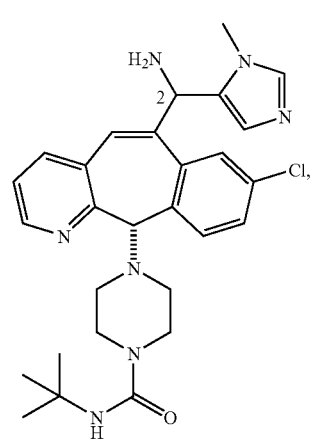
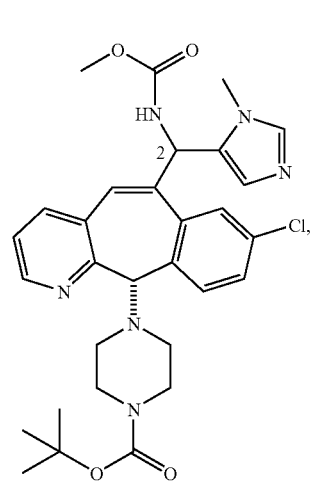
-continued
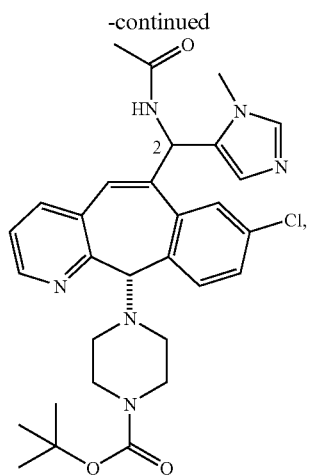
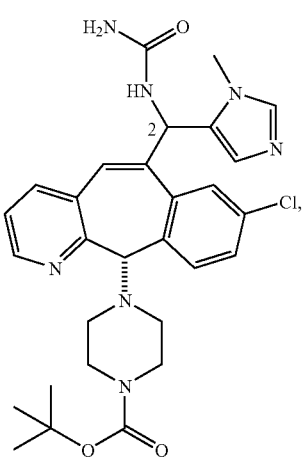
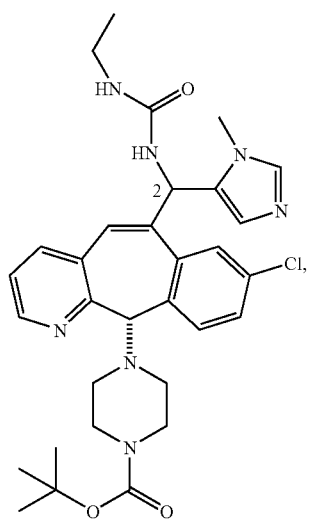

-continued
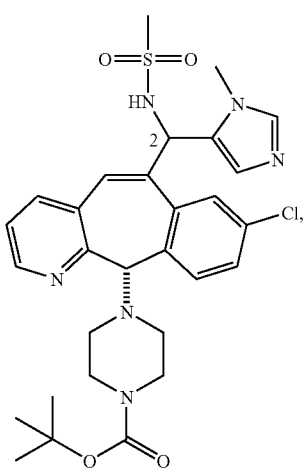
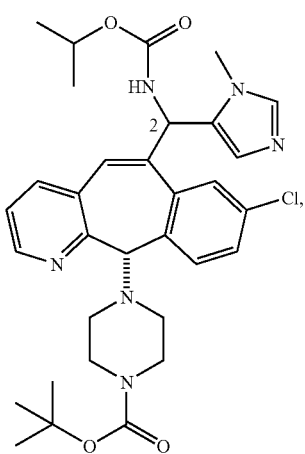
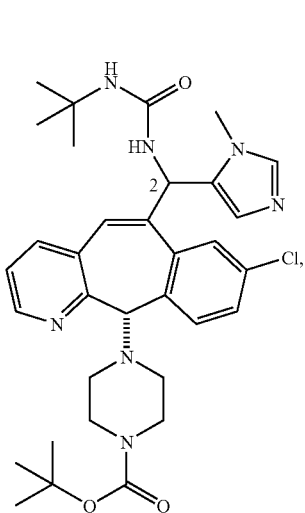
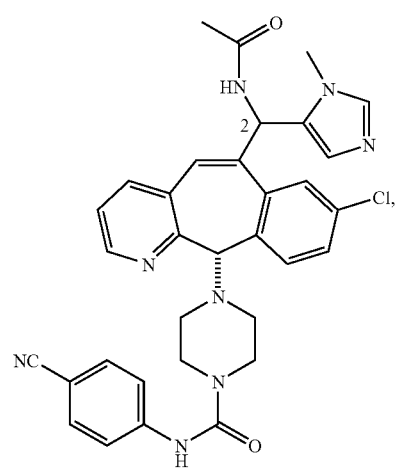
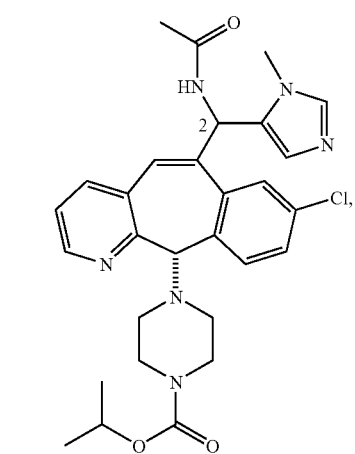
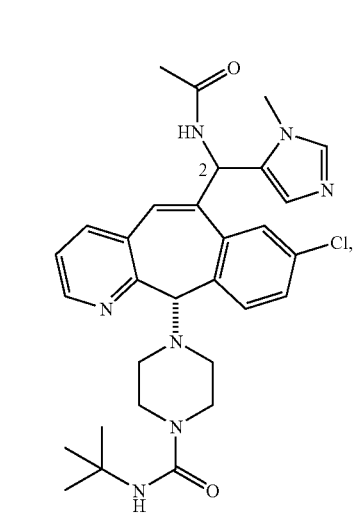

1103
-continued
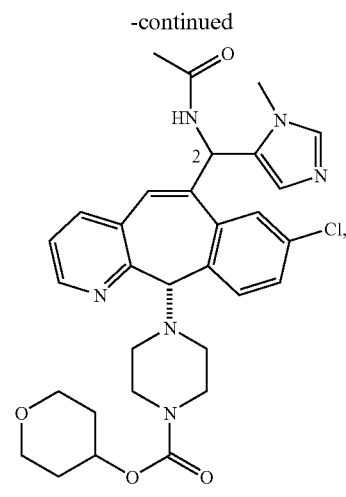
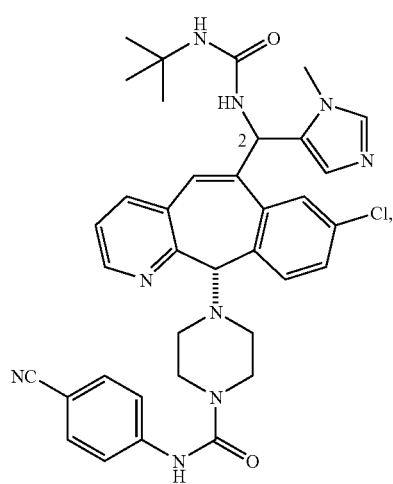
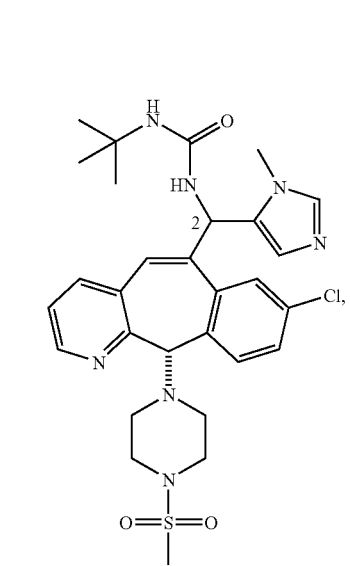
1104
-continued
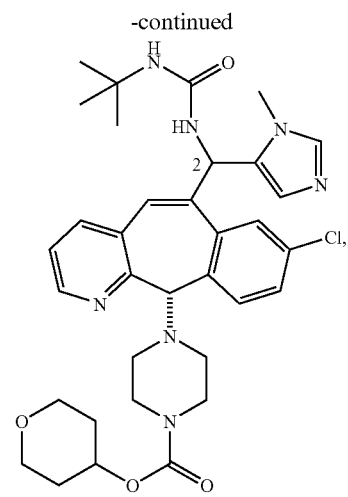
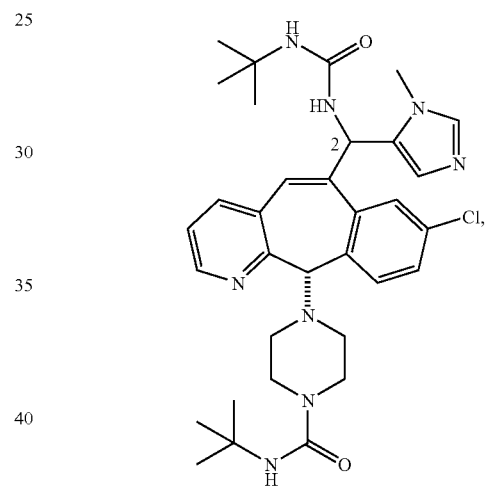
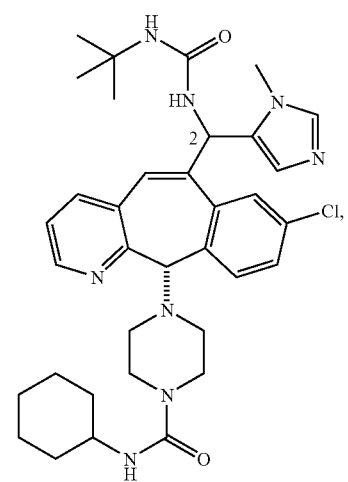

1105
-continued
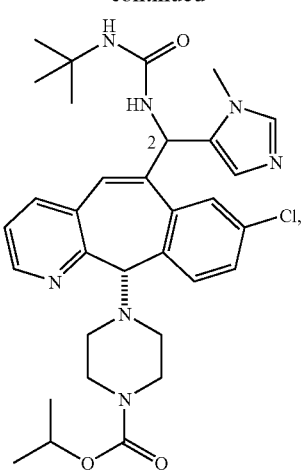
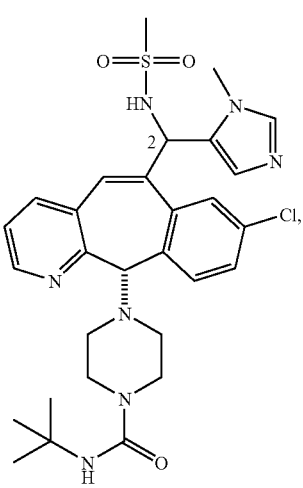
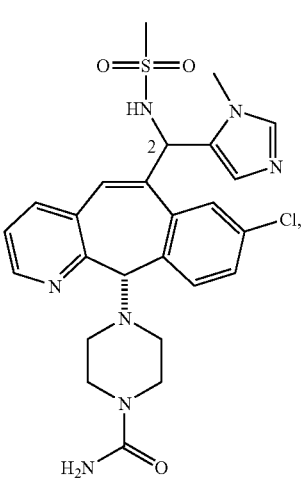
1106
-continued
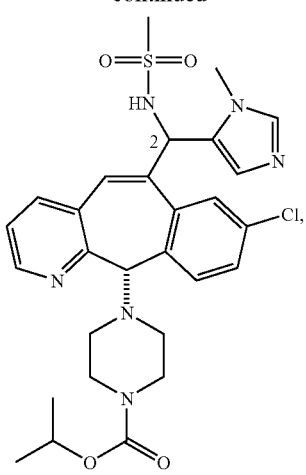
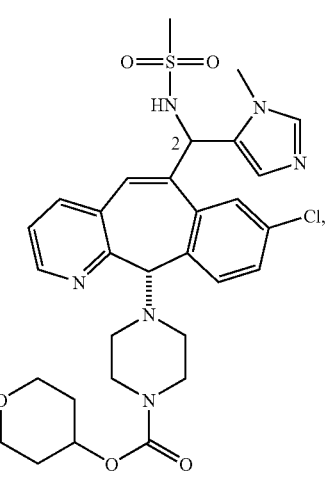
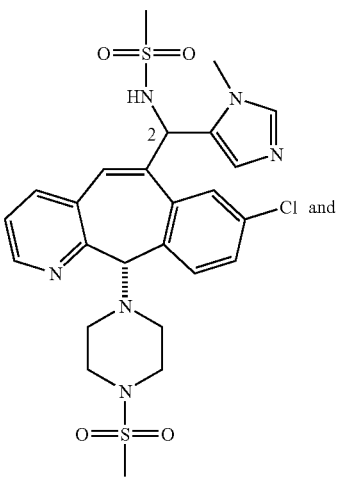

-continued

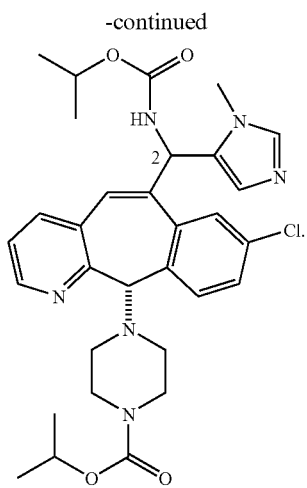

An embodiment of this invention is directed to a method of treating tumors in a patient in need of such treatment comprising administering concurrently or sequentially to said patient, an effective amount of a compound of formula 1.0 in combination with an effective amount of at least one chemotherapeutic agent and/or radiation, wherein the compound of formula 1.0 is selected from the group consisting of:

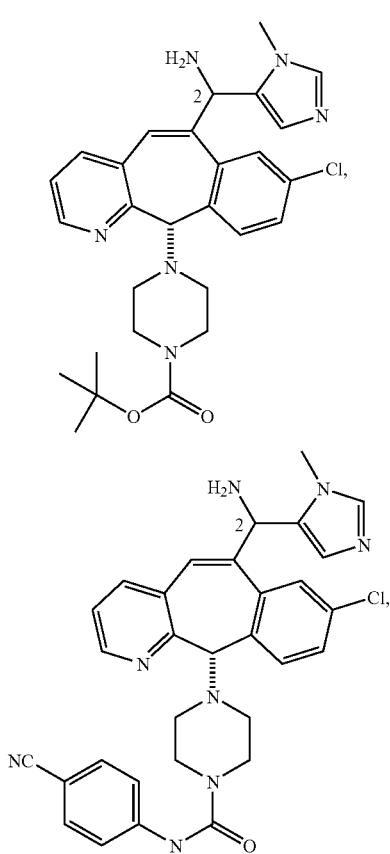

-continued

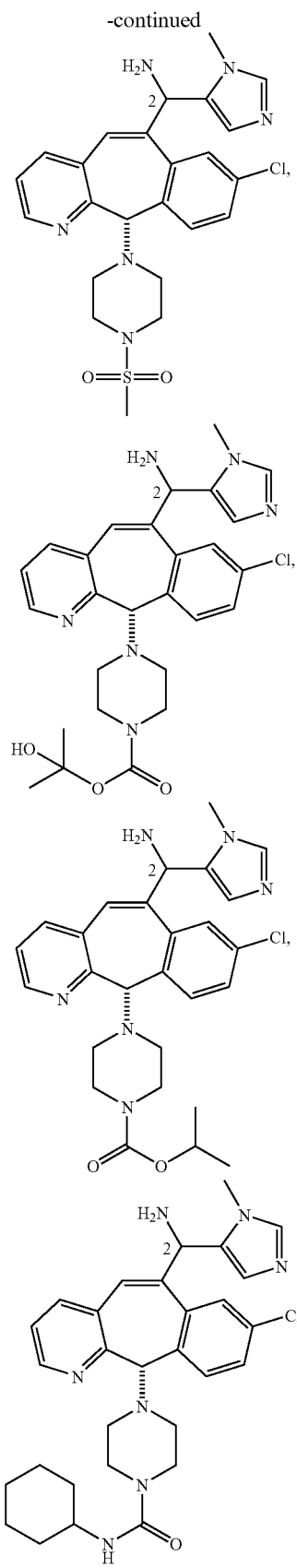

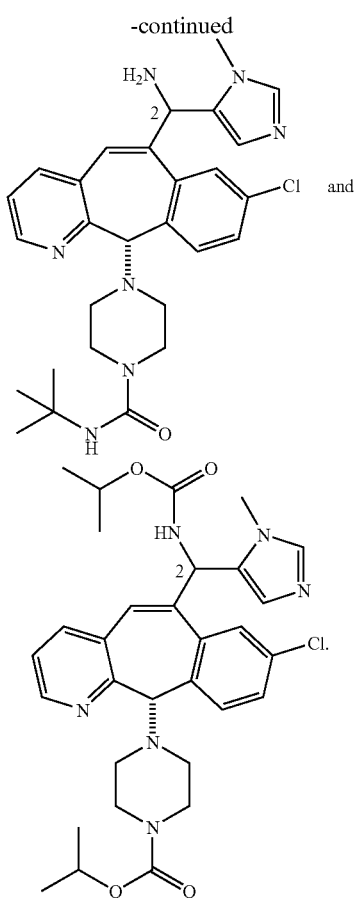

An embodiment of this invention is directed to a method of treating tumors in a patient in need of such treatment comprising administering concurrently or sequentially to said patient, an effective amount of a compound of formula 1.0 in combination with an effective amount of at least one chemotherapeutic agent and/or radiation, wherein the tumors treated are selected from the group consisting of: lung cancer, head and neck cancer, bladder cancer, breast cancer, prostate cancer and myeloid leukemias; wherein the chemotherapeutic agent is selected from the group consisting of: paclitaxel, a paclitaxel derivative, taxotere, cyclophosphamide, 5-fluorouracil, temozolomide, vincristine, cisplatin, carboplatin, and gemcitabine.

An embodiment of this invention is directed to a method of lung cancer in a patient in need of such treatment comprising administering concurrently or sequentially to said patient, an effective amount of a compound of formula 1.0 in combination with an effective amount of at least one chemotherapeutic agent and/or radiation, wherein the chemotherapeutic agent is selected from the group consisting of: carboplatin, taxol and taxotere.

An embodiment of this invention is directed to a method of lung cancer in a patient in need of such treatment comprising administering concurrently or sequentially to said patient, an effective amount of a compound of formula 1.0 in combination with an effective amount of at least one chemotherapeutic agent and/or radiation, wherein the chemotherapeutic agent is selected from the group consisting of: gemcitabine and cisplatin.

An embodiment of this invention is directed to a method of treating tumors in a patient in need of such treatment comprising administering concurrently or sequentially to said patient, an effective amount of a compound of formula 1.0 in combination with an effective amount taxol and/or radiation, wherein the tumors treated are selected from the group consisting of: lung cancer, head and neck cancer, bladder cancer, breast cancer, prostate cancer and myeloid leukemias.

An embodiment of this invention is directed to a method of treating tumors in a patient in need of such treatment comprising administering, concurrently or sequentially, to said patient an effective amount of a compound of formula 1.0 in combination with an effective amount of at least one signal transduction inhibitor.

An embodiment of this invention is directed to a method of treating tumors in a patient in need of such treatment comprising administering, concurrently or sequentially, to said patient an effective amount of a compound of formula 1.0 in combination with an effective amount of at least one signal transduction inhibitor, wherein the tumors are selected from the group consisting of: pancreatic tumors, lung tumors, myeloid leukemias, thyroid follicular tumors, myelodysplastic syndrome, head and neck tumors, melanomas, breast tumors, prostate tumors, ovarian tumors, bladder tumors, gliomas and colon tumors.

An embodiment of this invention is directed to a method of treating tumors in a patient in need of such treatment comprising administering, concurrently or sequentially, to said patient an effective amount of a compound of formula 1.0 in combination with an effective amount of at least one signal transduction inhibitor, wherein the signal tranduction inhibitor is selected from the group consisting of: a bcr/abl kinase inhibitor, an epidermal growth factor receptor inhibitor, and a HER-2/neu receptor inhibitor.

An embodiment of this invention is directed to a method of treating tumors in a patient in need of such treatment comprising administering, concurrently or sequentially, to said patient an effective amount of a compound of formula 1.0 in combination with an effective amount of at least one signal transduction inhibitor, wherein the signal tranduction inhibitor is selected from the group consisting of: Gleevec, Iressa, OSI-774, Imclone C225, Abgenix ABX-EGF, and Herceptin.

An embodiment of this invention is directed to a method of treating tumors in a patient in need of such treatment comprising administering, concurrently or sequentially, to said patient an effective amount of a compound of formula 1.0 in combination with an effective amount of at least one signal transduction inhibitor, wherein the tumors treated are selected from the group consisting of: lung tumors, head and neck tumors, bladder tumors, breast tumors, prostate tumors and myeloid leukemias; and the signal transduction inhibitor is selected from the group consisting of: Gleevec, Iressa, OSI-774, Imclone C225, Abgenix ABX-EGF; and Herceptin.

An embodiment of this invention is directed to a method of treating cancer in a patient in need of such treatment comprising administering to said patient an effective amount of an FPT inhibitor compound of formula 1.4F (e.g., 1.4F wherein X is N) and at least two different antineoplastic agents selected from the group consisting of:

(1) taxanes;
(2) platinum coordinator compounds;
(3) EGF inhibitors that are antibodies;
(4) EGF inhibitors that are small molecules;
(5) VEGF inhibitors that are antibodies;
(6) VEGF kinase inhibitors that are small molecules;

(7) estrogen receptor antagonists or selective estrogen receptor modulators;
(8) anti-tumor nucleoside derivatives;
(9) epothilones;
(10) topoisomerase inhibitors;
(11) vinca alkaloids;
(12) antibodies that are inhibitors of αVβ3 integrins; or
(13) small molecule inhibitors of αVβ3 integrins
(14) folate antagonists;
(15) ribonucleotide reductase inhibitors;
(16) anthracyclines;
(17) biologics;
(18) Thalidomide (or related Imid); and
(19) Gleevec.

An embodiment of this invention is directed to a method of treating cancer in a patient in need of such treatment comprising administering to said patient an effective amount of an FPT inhibitor compound of formula 1.4F (e.g., 1.4F wherein X is N) and at least two different antineoplastic agents selected from the group consisting of:
(1) taxanes;
(2) platinum coordinator compounds;
(3) EGF inhibitors that are antibodies;
(4) EGF inhibitors that are small molecules;
(5) VEGF inhibitors that are antibodies;
(6) VEGF kinase inhibitors that are small molecules;
(7) estrogen receptor antagonists or selective estrogen receptor modulators;
(8) anti-tumor nucleoside derivatives;
(9) epothilones;
(10) topoisomerase inhibitors;
(11) vinca alkaloids;
(12) antibodies that are inhibitors of αVβ3 integrins; or
(13) small molecule inhibitors of αVβ3 integrins
(14) folate antagonists;
(15) ribonucleotide reductase inhibitors;
(16) anthracyclines;
(17) biologics; and
(18) Thalidomide (or related Imid).

An embodiment of this invention is directed to a method of treating cancer in a patient in need of such treatment comprising administering to said patient an effective amount of an FPT inhibitor compound of formula 1.4F (e.g., 1.4F wherein X is N) and at least two different antineoplastic agents selected from the group consisting of:
(1) taxanes;
(2) platinum coordinator compounds;
(3) EGF inhibitors that are antibodies;
(4) EGF inhibitors that are small molecules;
(5) VEGF inhibitors that are antibodies;
(6) VEGF kinase inhibitors that are small molecules;
(7) estrogen receptor antagonists or selective estrogen receptor modulators;
(8) anti-tumor nucleoside derivatives;
(9) epothilones;
(10) topoisomerase inhibitors;
(11) vinca alkaloids;
(12) antibodies that are inhibitors of αVβ3 integrins; or
(13) small molecule inhibitors of αVβ3 integrins
(14) folate antagonists;
(15) ribonucleotide reductase inhibitors;
(16) anthracyclines; and
(17) biologics.

An embodiment of this invention is directed to a method of treating cancer in a patient in need of such treatment comprising administering to said patient an effective amount of an FPT inhibitor compound of formula 1.4F (e.g., 1.4F wherein X is N) and at least two different antineoplastic agents selected from the group consisting of:
(1) taxanes;
(2) platinum coordinator compounds;
(3) EGF inhibitors that are antibodies;
(4) EGF inhibitors that are small molecules;
(5) VEGF inhibitors that are antibodies;
(6) VEGF kinase inhibitors that are small molecules;
(7) estrogen receptor antagonists or selective estrogen receptor modulators;
(8) anti-tumor nucleoside derivatives;
(9) epothilones;
(10) topoisomerase inhibitors;
(11) vinca alkaloids;
(12) antibodies that are inhibitors of αVβ3 integrins; and
(13) small molecule inhibitors of αVβ3 integrins.

An embodiment of this invention is directed to a method of treating cancer in a patient in need of such treatment comprising administering to said patient an effective amount of an FPT inhibitor compound of formula 1.4F (e.g., 1.4F wherein X is N) and two antineoplastic agents, wherein one antineoplastic agent is a taxane, and the other antineoplastic agent is a platinum coordinator compound.

An embodiment of this invention is directed to a method of treating cancer in a patient in need of such treatment comprising administering to said patient an effective amount of an FPT inhibitor compound of formula 1.4F (e.g., 1.4F wherein X is N) and two antineoplastic agents, wherein one antineoplastic agent is a taxane, and the other antineoplastic agent is a platinum coordinator compound, wherein said taxane is selected from paclitaxel or docetaxel, and said platinum coordinator compound is selected from carboplatin or cisplatin.

An embodiment of this invention is directed to a method of treating cancer in a patient in need of such treatment comprising administering to said patient an effective amount of an FPT inhibitor compound of formula 1.4F (e.g., 1.4F wherein X is N) and two antineoplastic agents, wherein one antineoplastic agent is a taxane, and the other antineoplastic agent is a platinum coordinator compound, wherein said taxane is paclitaxel and said platinum coordinator compound is carboplatin.

An embodiment of this invention is directed to a method of treating cancer in a patient in need of such treatment comprising administering to said patient an effective amount of an FPT inhibitor compound of formula 1.4F (e.g., 1.4F wherein X is N) and two antineoplastic agents, wherein one antineoplastic agent is a taxane, and the other antineoplastic agent is a platinum coordinator compound, wherein said taxane is paclitaxel and said platinum coordinator compound is cisplatin.

An embodiment of this invention is directed to a method of treating cancer in a patient in need of such treatment comprising administering to said patient an effective amount of an FPT inhibitor compound of formula 1.4F (e.g., 1.4F wherein X is N) and two antineoplastic agents, wherein one antineoplastic agent is a taxane, and the other antineoplastic agent is a platinum coordinator compound, wherein said taxane is docetaxel and said platinum coordinator compound is cisplatin.

An embodiment of this invention is directed to a method of treating cancer in a patient in need of such treatment comprising administering to said patient an effective amount of an FPT inhibitor compound of formula 1.4F (e.g., 1.4F wherein X is N) and two antineoplastic agents, wherein one antineoplastic agent is a taxane, and the other antineoplastic agent is a platinum coordinator compound, wherein said taxane is docetaxel and said platinum coordinator compound is carboplatin.

An embodiment of this invention is directed to a method of treating cancer in a patient in need of such treatment comprising administering to said patient an effective amount of an FPT inhibitor compound of formula 1.4F (e.g., 1.4F wherein X is N) and two antineoplastic agents, wherein one antineoplastic agent is a taxane, and the other antineoplastic agent is a platinum coordinator compound, wherein said taxane is paclitaxel administered in an amount of about 150 mg to about 250 mg/m$^2$ once every three weeks per cycle, and said platinum coordinator compound is carboplatin administered once every three weeks per cycle in amount of to provide an AUC of about 5 to about 8.

An embodiment of this invention is directed to a method of treating cancer in a patient in need of such treatment comprising administering to said patient an effective amount of an FPT inhibitor compound of formula 1.4F (e.g., 1.4F wherein X is N) and two antineoplastic agents, wherein one antineoplastic agent is a taxane, and the other antineoplastic agent is a platinum coordinator compound, wherein said taxane is docetaxel administered in an amount of about 50 mg to about 100 mg/m$^2$ once every three weeks per cycle, and said platinum coordinator compound is cisplatin administered in amount of about 60 mg to about 100 mg/m$^2$ once every three weeks per cycle.

An embodiment of this invention is directed to a method of treating cancer in a patient in need of such treatment comprising administering to said patient an effective amount of an FPT inhibitor compound of formula 1.4F (e.g., 1.4F wherein X is N) and two antineoplastic agents, wherein one antineoplastic agent is a taxane, and the other antineoplastic agent is a platinum coordinator compound, wherein said FPT inhibitor is administered in an amount of about 50 mg to about 200 mg twice a day.

An embodiment of this invention is directed to a method of treating cancer in a patient in need of such treatment comprising administering to said patient an effective amount of an FPT inhibitor compound of formula 1.4F (e.g., 1.4F wherein X is N) and two antineoplastic agents, wherein one antineoplastic agent is a taxane, and the other antineoplastic agent is a platinum coordinator compound, wherein said FPT inhibitor is administered in an amount of about 75 mg to about 125 mg twice a day.

An embodiment of this invention is directed to a method of treating cancer in a patient in need of such treatment comprising administering to said patient an effective amount of an FPT inhibitor compound of formula 1.4F (e.g., 1.4F wherein X is N) and two antineoplastic agents, wherein one antineoplastic agent is a taxane, and the other antineoplastic agent is a platinum coordinator compound, wherein said FPT inhibitor is selected from the group consisting of:

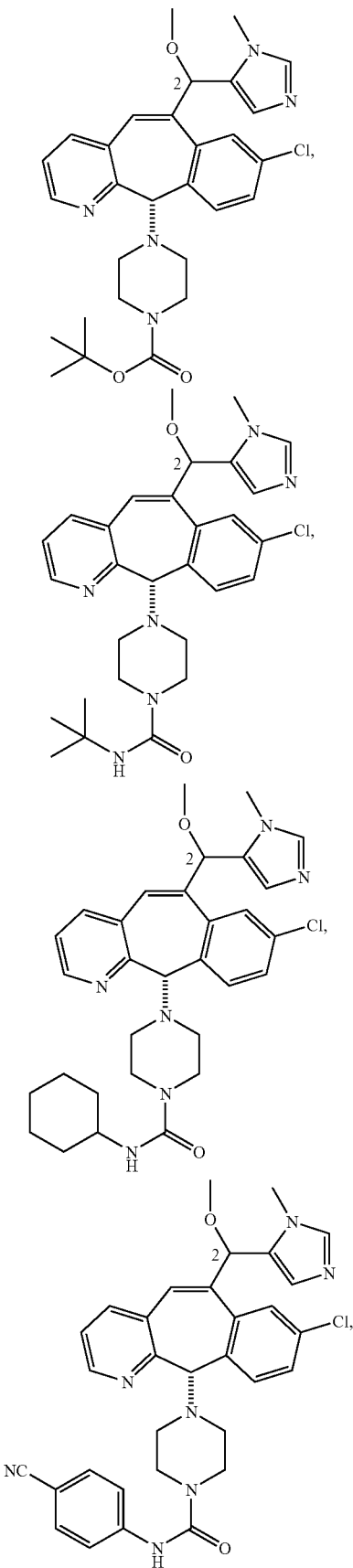

1115
-continued
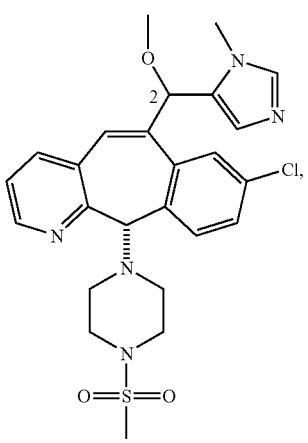
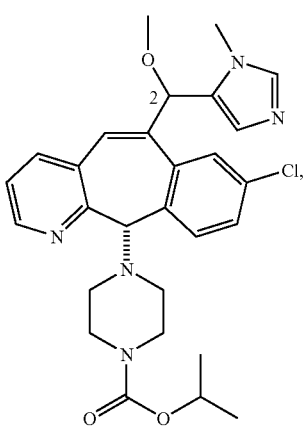
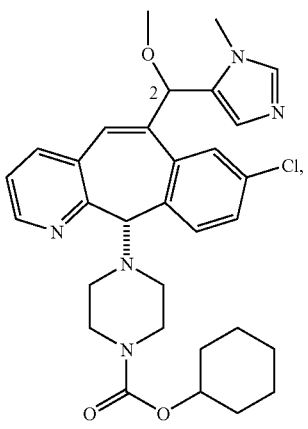
1116
-continued
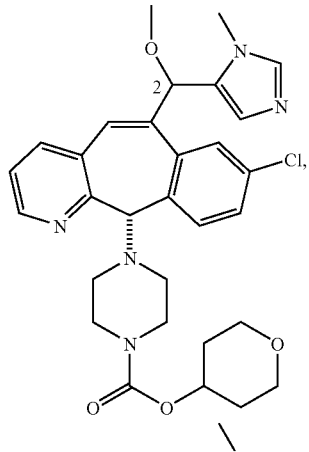
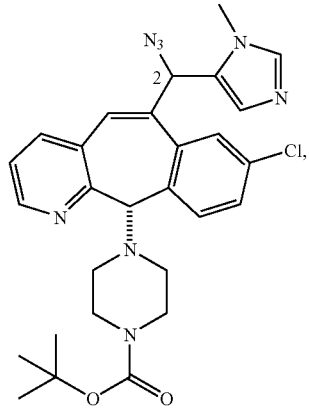
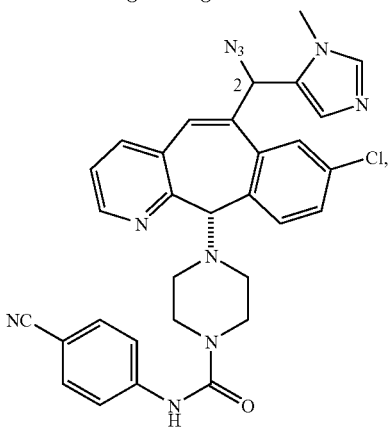
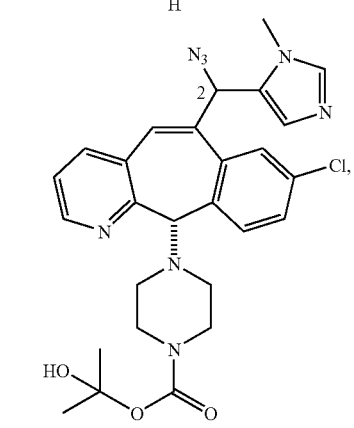

1117
-continued
1118
-continued
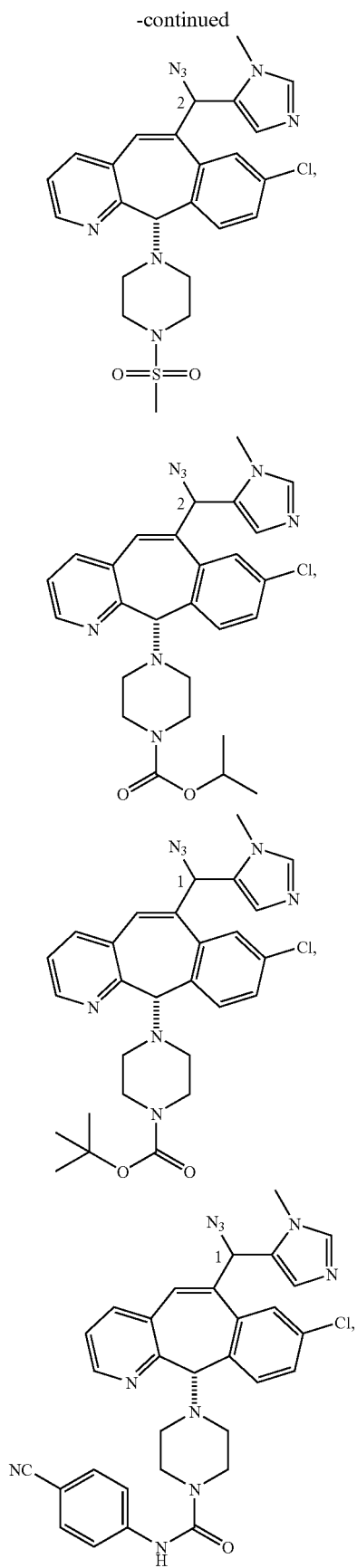
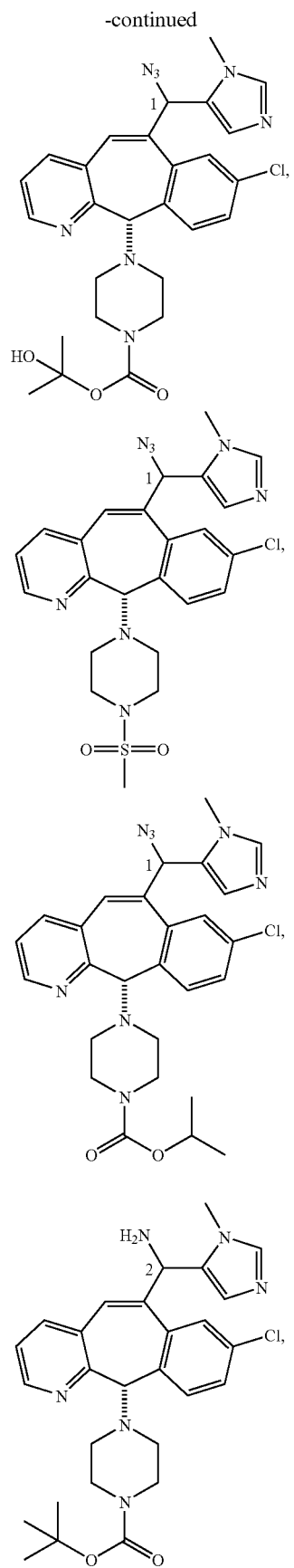

1119
-continued
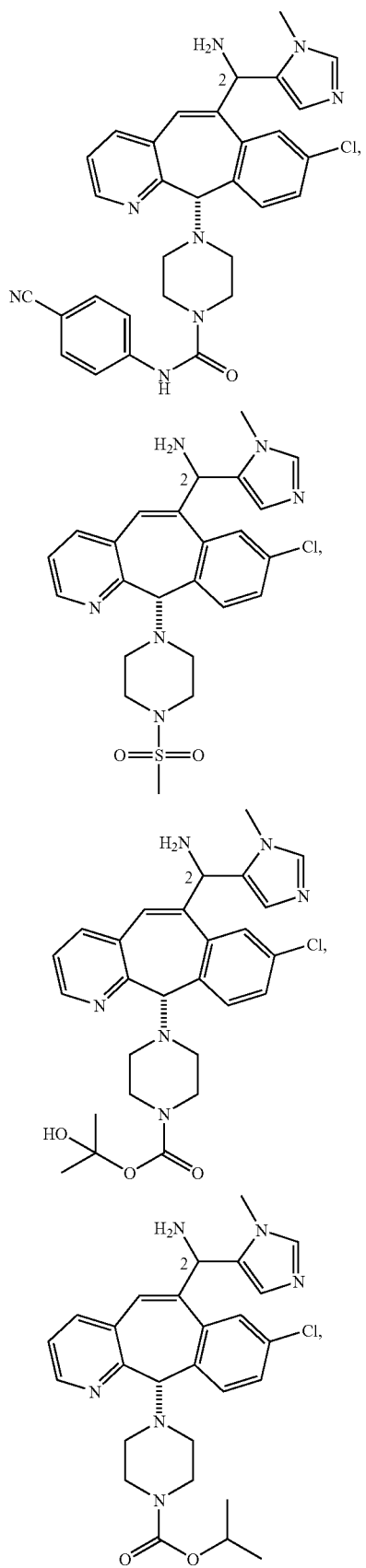
1120
-continued
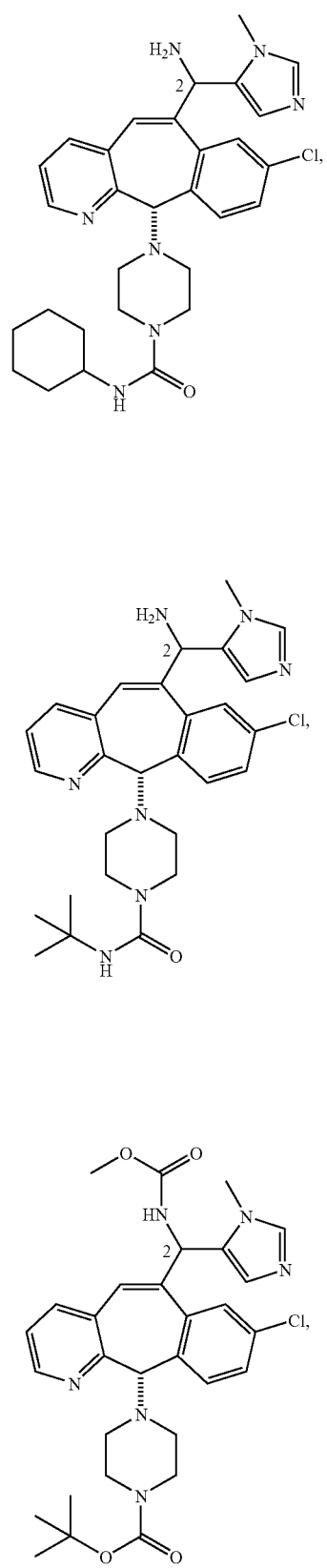

1121
-continued
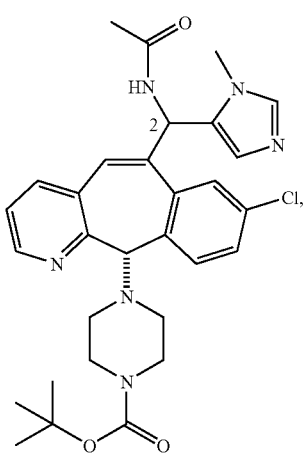
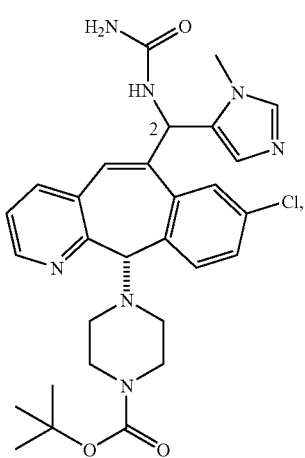
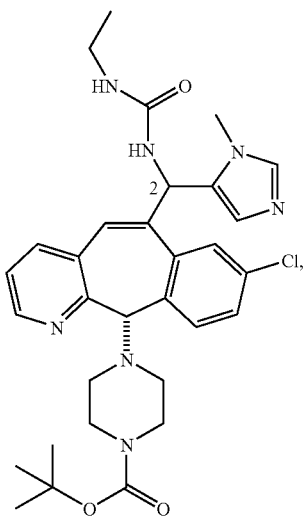
1122
-continued
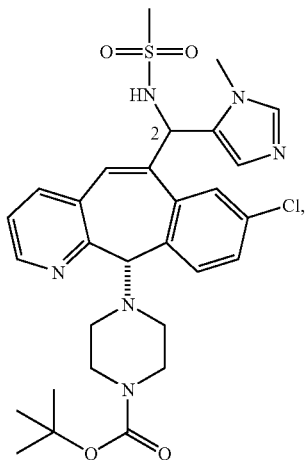
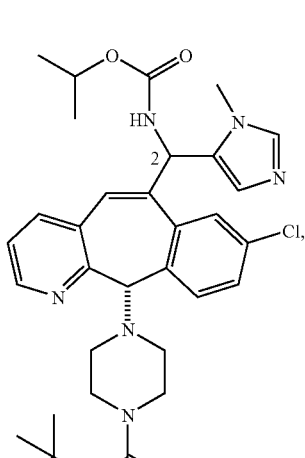
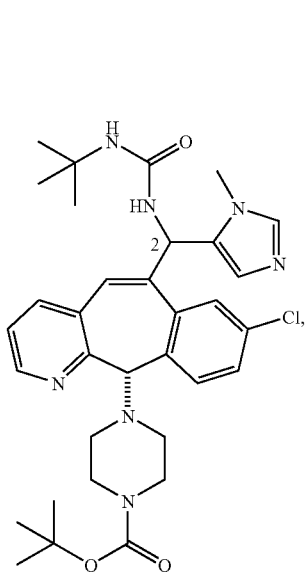

1123
-continued
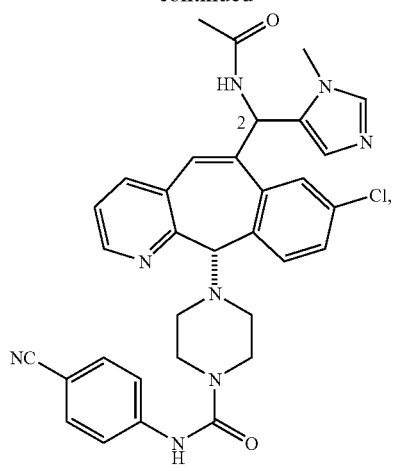
1124
-continued
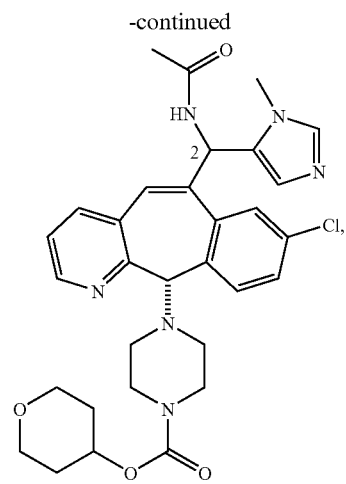
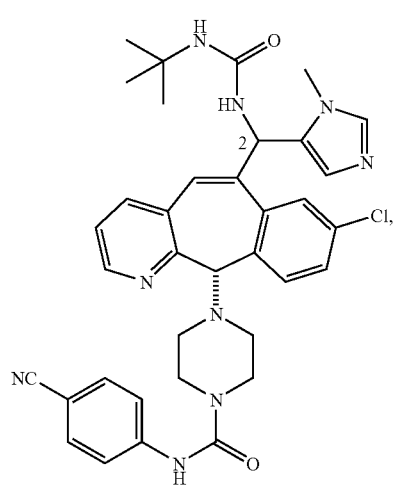
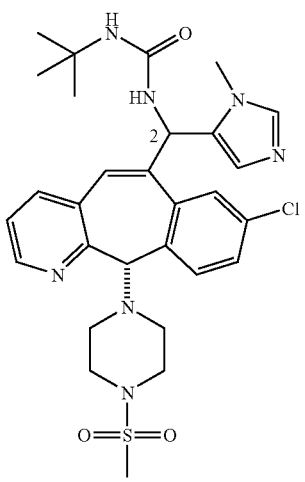

1125

-continued

1126

-continued

-continued

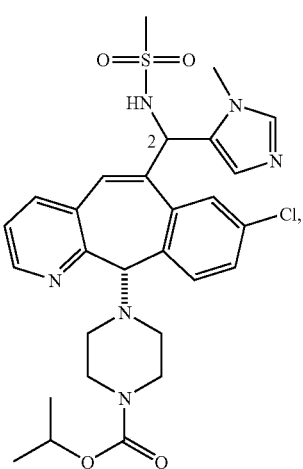

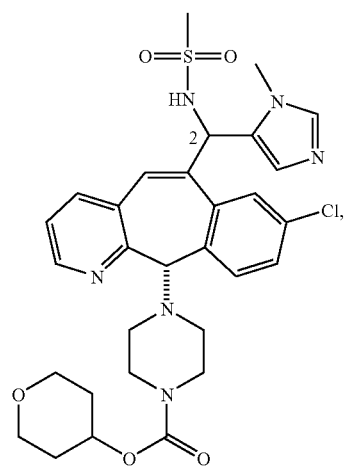

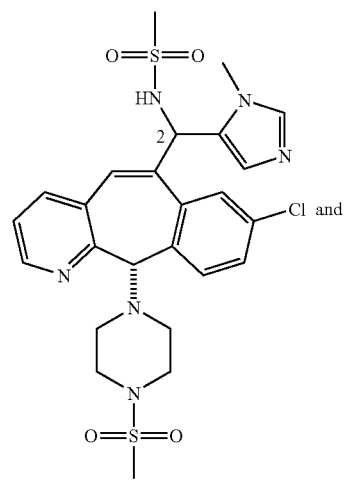

-continued

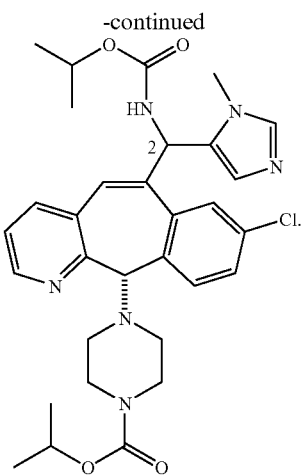

An embodiment of this invention is directed to a method of treating cancer in a patient in need of such treatment comprising administering to said patient an effective amount of an FPT inhibitor compound of formula 1.4F (e.g., 1.4F wherein X is N) and two antineoplastic agents, wherein one antineoplastic agent is a taxane, and the other antineoplastic agent is a platinum coordinator compound, wherein said FPT inhibitor is selected from the group consisting of:

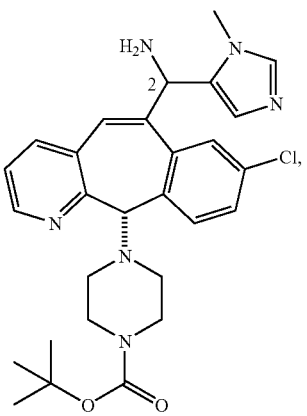

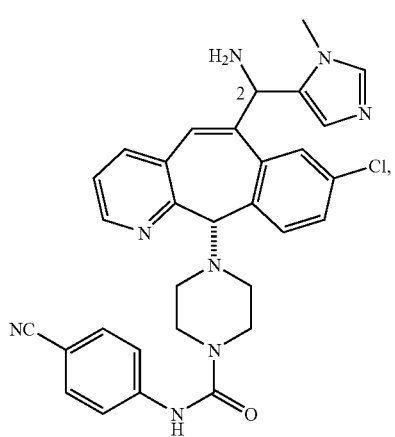

1129
-continued
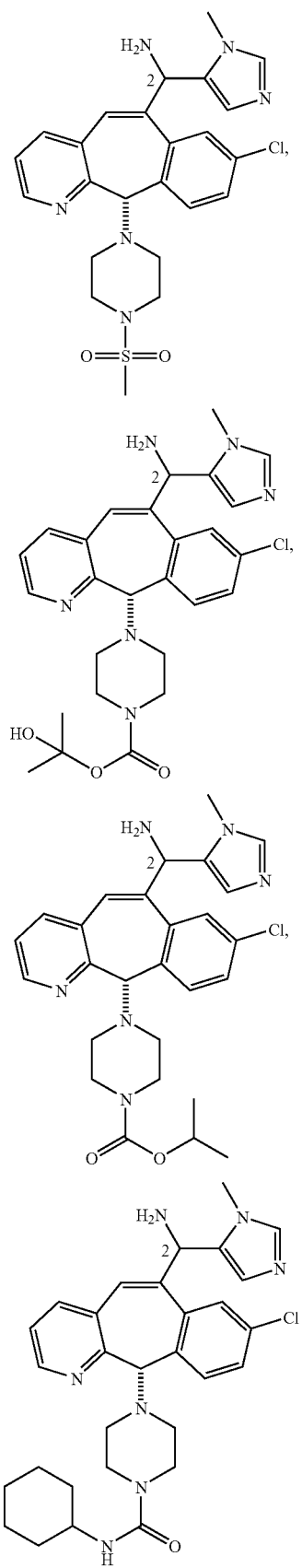
1130
-continued
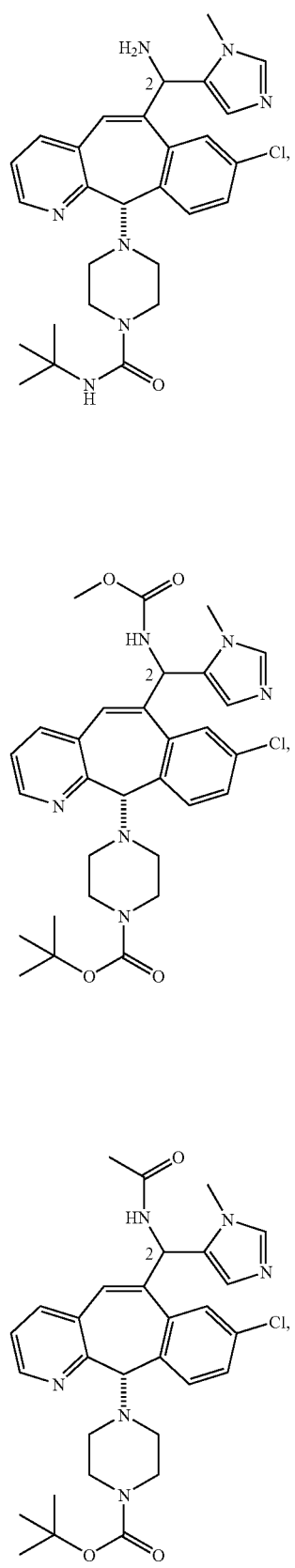

1131
-continued
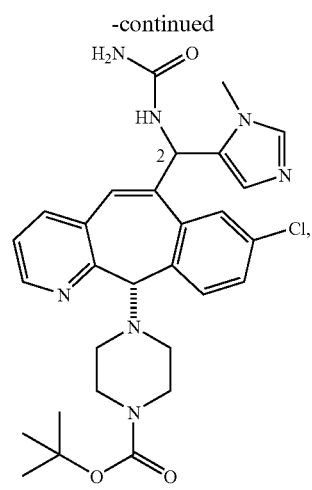
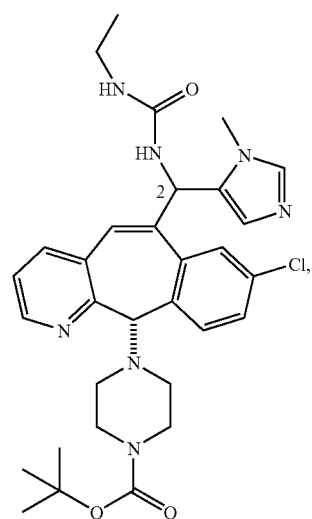
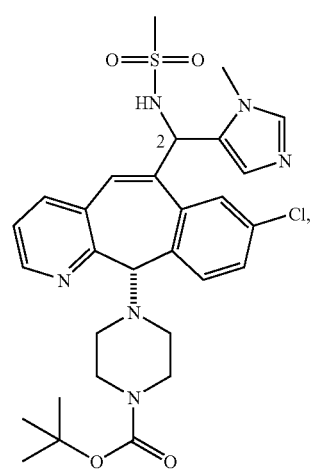
1132
-continued
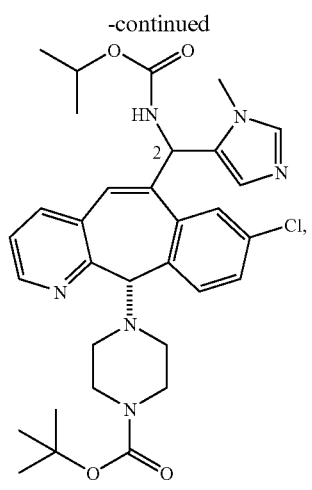
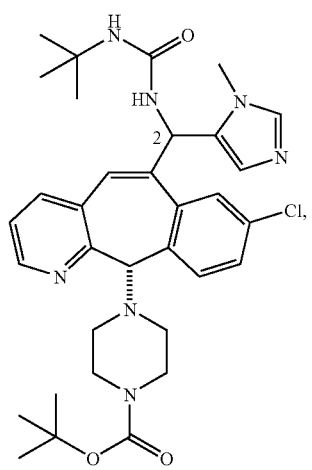
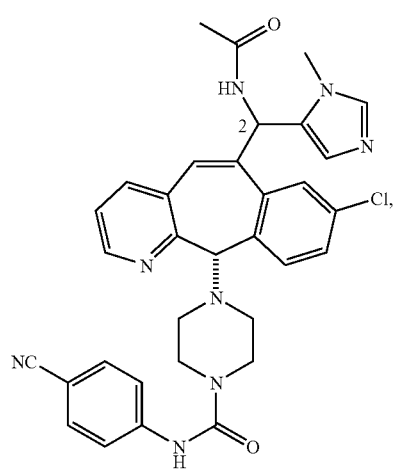

1133
-continued
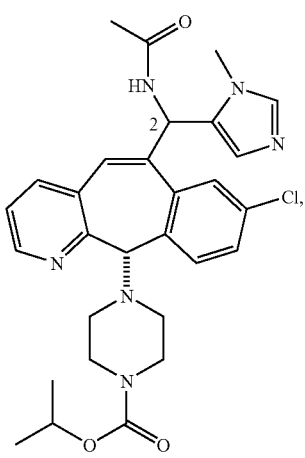
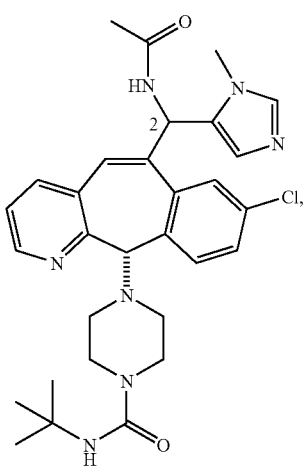
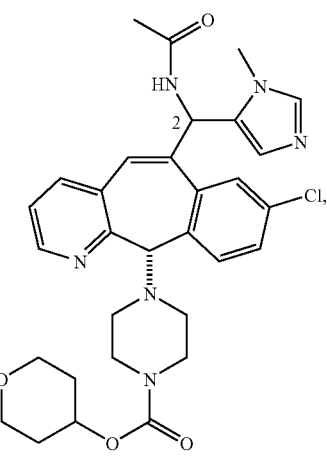
1134
-continued
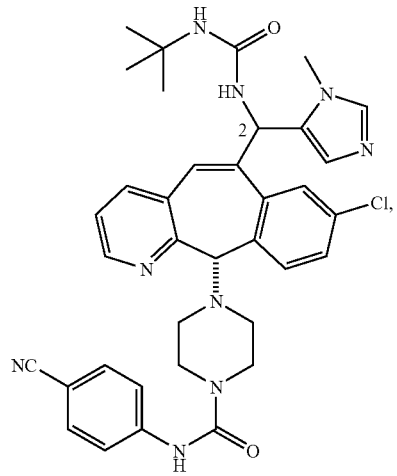
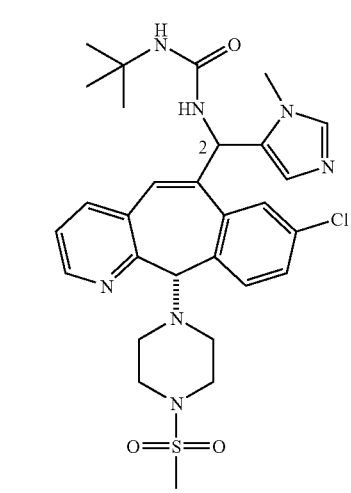
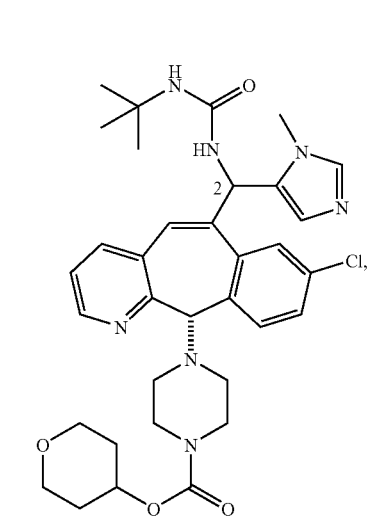

1135
-continued
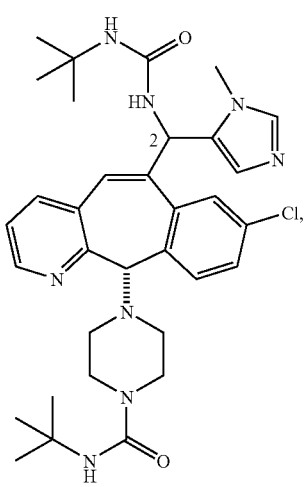
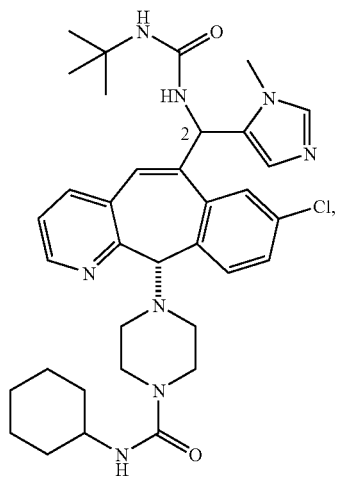
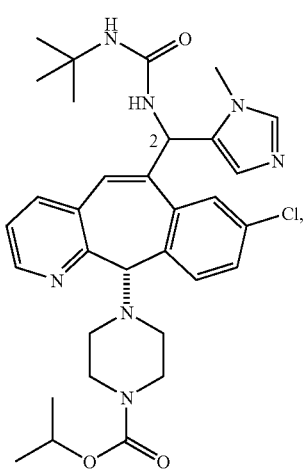
1136
-continued
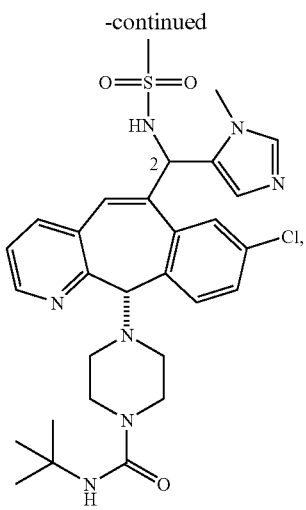
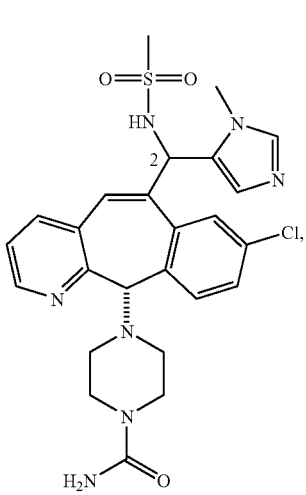
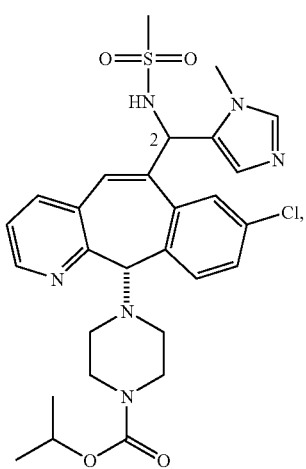

1137

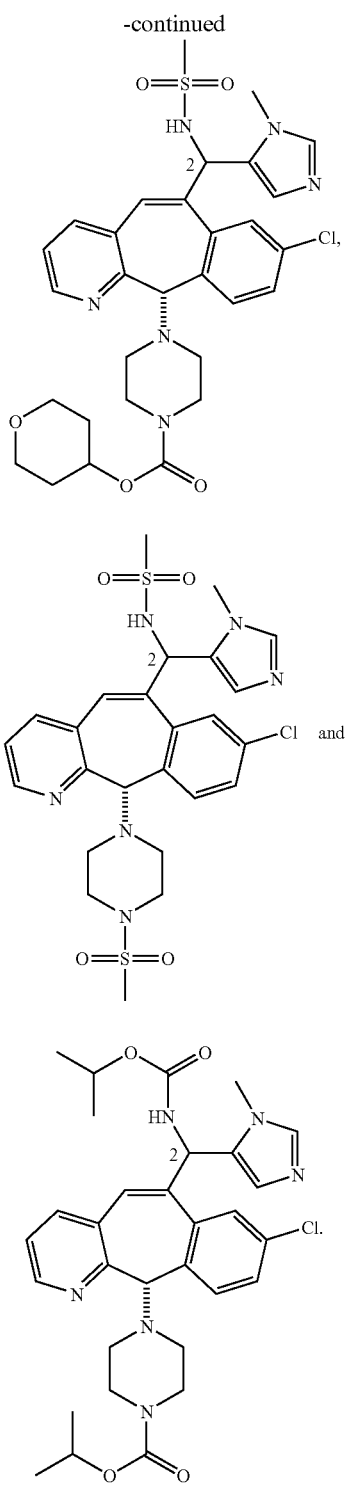

1138

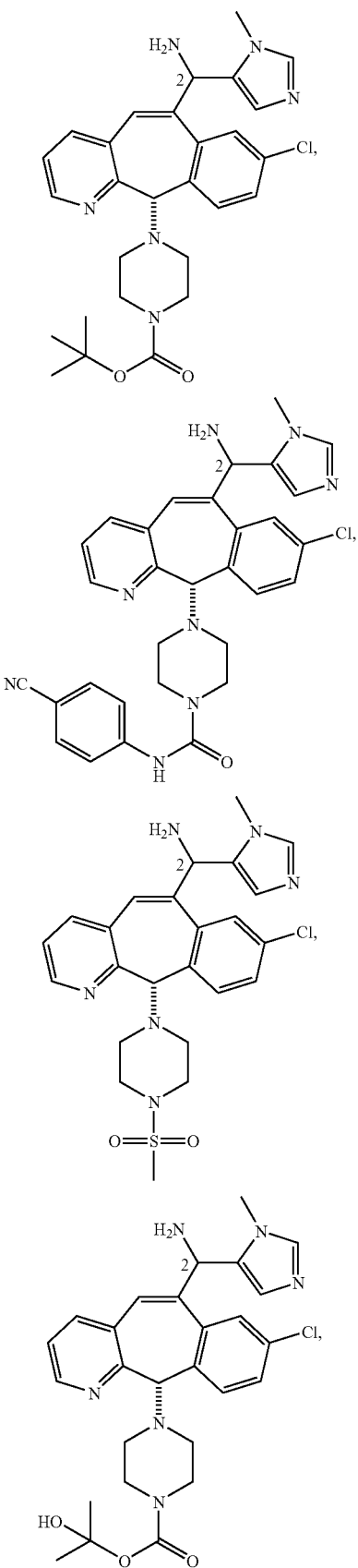

An embodiment of this invention is directed to a method of treating cancer in a patient in need of such treatment comprising administering to said patient an effective amount of an FPT inhibitor compound of formula 1.4F (e.g., 1.4F wherein X is N) and two antineoplastic agents, wherein one antineoplastic agent is a taxane, and the other antineoplastic agent is a platinum coordinator compound, wherein said FPT inhibitor is selected from the group consisting of:

-continued

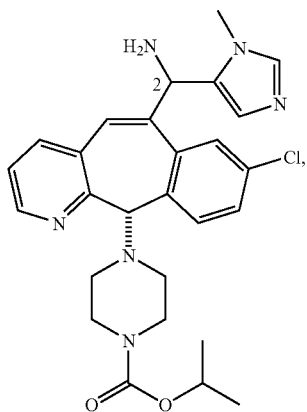

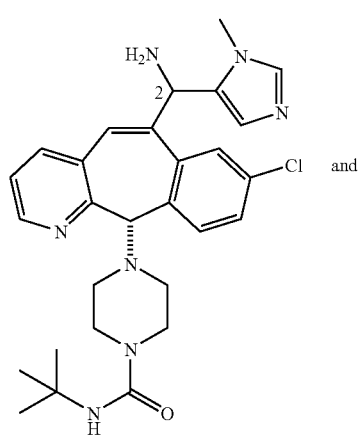

-continued

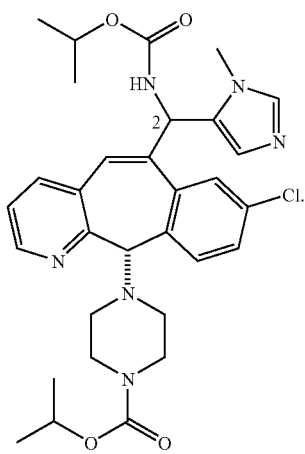

An embodiment of this invention is directed to a method of treating cancer in a patient in need of such treatment comprising administering to said patient an effective amount of an FPT inhibitor compound of formula 1.4F (e.g., 1.4F wherein X is N) and two antineoplastic agents, wherein one antineoplastic agent is a taxane, and the other antineoplastic agent is a platinum coordinator compound, wherein said FPT inhibitor is:

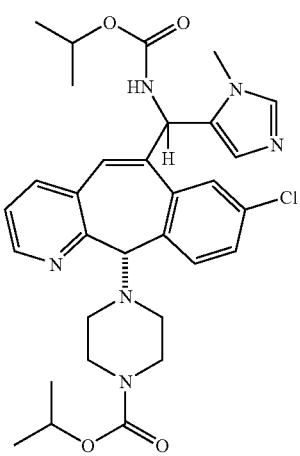

An embodiment of this invention is directed to a method of treating cancer in a patient in need of such treatment comprising administering to said patient an effective amount of an FPT inhibitor compound of formula 1.4F (e.g., 1.4F wherein X is N) and two antineoplastic agents, wherein one antineoplastic agent is a taxane, and the other antineoplastic agent is a platinum coordinator compound, wherein said FPT inhibitor is:

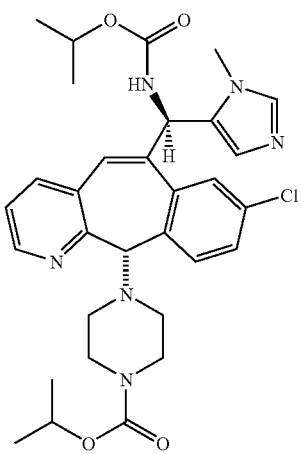

An embodiment of this invention is directed to a method of treating cancer in a patient in need of such treatment comprising administering to said patient an effective amount of an FPT inhibitor compound of formula 1.4F (e.g., 1.4F wherein X is N) and two antineoplastic agents, wherein one antineoplastic agent is a taxane, and the other antineoplastic agent is a platinum coordinator compound, wherein said FPT inhibitor is:

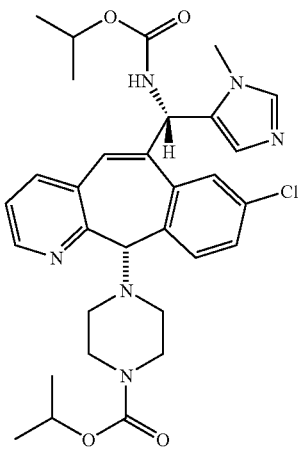

An embodiment of this invention is directed to a method of treating cancer in a patient in need of such treatment comprising administering to said patient an effective amount of an FPT inhibitor compound of formula 1.4F (e.g., 1.4F wherein X is N) and two antineoplastic agents, wherein one antineoplastic agent is a taxane, and the other antineoplastic agent is a platinum coordinator compound, wherein the treatment is given for one to four weeks per cycle.

An embodiment of this invention is directed to a method of treating cancer in a patient in need of such treatment comprising administering to said patient an effective amount of an FPT inhibitor compound of formula 1.4F (e.g., 1.4F wherein X is N) and two antineoplastic agents, wherein one antineoplastic agent is a taxane, and the other antineoplastic agent is a platinum coordinator compound, wherein non small cell lung cancer is treated.

An embodiment of this invention is directed to a method of treating cancer in a patient in need of such treatment comprising administering to said patient an effective amount of an FPT inhibitor compound of formula 1.4F (e.g., 1.4F wherein X is N) and two antineoplastic agents, wherein one antineoplastic agent is a taxane, and the other antineoplastic agent is an EGF inhibitor that is an antibody.

An embodiment of this invention is directed to a method of treating cancer in a patient in need of such treatment comprising administering to said patient an effective amount of an FPT inhibitor compound of formula 1.4F (e.g., 1.4F wherein X is N) and two antineoplastic agents, wherein one antineoplastic agent is a taxane, and the other antineoplastic agent is an EGF inhibitor that is an antibody, wherein said taxane is paclitaxel and said EGF inhibitor is Herceptin.

An embodiment of this invention is directed to a method of treating cancer in a patient in need of such treatment comprising administering to said patient an effective amount of an FPT inhibitor compound of formula 1.4F (e.g., 1.4F wherein X is N) and two antineoplastic agents, wherein one antineoplastic agent is an antinucleoside derivative, and the other antineoplastic agent is a platinum coordinator compound.

An embodiment of this invention is directed to a method of treating cancer in a patient in need of such treatment comprising administering to said patient an effective amount of an FPT inhibitor compound of formula 1.4F (e.g., 1.4F wherein X is N) and two antineoplastic agents, wherein one antineoplastic agent is an antinucleoside derivative, and the other antineoplastic agent is a platinum coordinator compound, wherein said antinucleoside derivative is gemcitabine and said platinum coordinator compound is cisplatin.

An embodiment of this invention is directed to a method of treating cancer in a patient in need of such treatment comprising administering to said patient an effective amount of an FPT inhibitor compound of formula 1.4F (e.g., 1.4F wherein X is N) and two antineoplastic agents, wherein one antineoplastic agent is an antinucleoside derivative, and the other antineoplastic agent is a platinum coordinator compound, wherein said antinucleoside derivative is gemcitabine and said platinum coordinator compound is carboplatin.

An embodiment of this invention is directed to a method of treating non small cell lung cancer in a patient in need of such treatment comprising administering to said patient therapeutically effective amounts of:
(a) an FPT inhibitor of formula 1.4F (e.g., 1.4F wherein X is N); and
(b) carboplatin; and
(c) paclitaxel.

An embodiment of this invention is directed to a method of treating non small cell lung cancer in a patient in need of such treatment comprising administering to said patient therapeutically effective amounts of:
(a) an FPT inhibitor of formula 1.4F (e.g., 1.4F wherein X is N); and
(b) carboplatin; and
(c) paclitaxel,
wherein said FPT inhibitor is administered twice a day, said carboplatin is administered once every three weeks per cycle, and said paclitaxel is administered once every three weeks per cycle, said treatment being given for one to four weeks per cycle.

An embodiment of this invention is directed to a method of treating non small cell lung cancer in a patient in need of such treatment comprising administering to said patient therapeutically effective amounts of:

(a) an FPT inhibitor of formula 1.4F (e.g., 1.4F wherein X is N); and
(b) carboplatin; and
(c) paclitaxel, wherein said FPT inhibitor is administered in an amount of about 50 mg to about 200 mg twice a day, said carboplatin is administered once every three weeks per cycle in an amount to provide an AUC of about 5 to about 8, said paclitaxel is administered once every three weeks per cycle in an amount of about 150 to about 250 mg/m$^2$, wherein said carboplatin and said paclitaxel are administered on the same day, and said treatment being. given for one to four weeks per cycle.

An embodiment of this invention is directed to a method of treating non small cell lung cancer in a patient in need of such treatment comprising administering to said patient therapeutically effective amounts of:
(a) an FPT inhibitor of formula 1.4F (e.g., 1.4F wherein X is N); and
(b) carboplatin; and
(c) paclitaxel, wherein said FPT inhibitor is administered in an amount of about 75 mg to about 125 mg twice a day, said carboplatin is administered once every three weeks per cycle in an amount to provide an AUC of about 5 to about 8, said paclitaxel is administered once every three weeks per cycle in an amount of about 150 to about 250 mg/m$^2$, said carboplatin and said paclitaxel are administered on the same day, and said treatment being given for one to four weeks per cycle An embodiment of this invention is directed to a method of treating non small cell lung cancer in a patient in need of such treatment comprising administering to said patient therapeutically effective amounts of:
(a) an FPT inhibitor of formula 1.4F (e.g., 1.4F wherein X is N); and
(b) carboplatin; and
(c) paclitaxel, wherein said FPT inhibitor is administered in an amount of about 100 mg twice a day, said carboplatin is administered once every three weeks per cycle in an amount to provide an AUC of about 5 to about 8, said paclitaxel is administered once every three weeks per cycle in an amount of about 150 to about 250 mg/m$^2$, wherein said carboplatin and said paclitaxel are administered on the same day, and said treatment being given for one to four weeks per cycle.

An embodiment of this invention is directed to a method of treating non small cell lung cancer in a patient in need of such treatment comprising administering to said patient therapeutically effective amounts of:
(a) an FPT inhibitor of formula 1.4F (e.g., 1.4F wherein X is N); and
(b) carboplatin; and
(c) paclitaxel, wherein said FPT inhibitor is administered in an amount of about 100 mg twice a day, said carboplatin is administered once every three weeks per cycle in an amount to provide an AUC of about 5 to about 8, said paclitaxel is administered once every three weeks per cycle in an amount of about 175 to about 225 mg/m$^2$, wherein said carboplatin and said paclitaxel are administered on the same day, and said treatment being given for one to four weeks per cycle.

An embodiment of this invention is directed to a method of treating non small cell lung cancer in a patient in need of such treatment comprising administering to said patient therapeutically effective amounts of:
(a) an FPT inhibitor of formula 1.4F (e.g., 1.4F wherein X is N); and
(b) carboplatin; and
(c) paclitaxel, wherein said FPT inhibitor is administered in an amount of about 100 mg twice a day, said carboplatin is administered once every three weeks per cycle in an amount to provide an AUC of about 6, said paclitaxel is administered once every three weeks per cycle in an amount of about 175 mg/m$^2$, wherein said carboplatin and said paclitaxel are administered on the same day, and said treatment being given for one to four weeks per cycle.

An embodiment of this invention is directed to a method of treating non small cell lung cancer in a patient in need of such treatment comprising administering to said patient therapeutically effective amounts of:
(a) an FPT inhibitor of formula 1.4F (e.g., 1.4F wherein X is N); and:
(b) cisplatin; and
(c) gemcitabine.

An embodiment of this invention is directed to a method of treating non small cell lung cancer in a patient in need of such treatment comprising administering to said patient therapeutically effective amounts of:
(a) an FPT inhibitor of formula 1.4F (e.g., 1.4F wherein X is N); and:
(b) cisplatin; and
(c) gemcitabine wherein said FPT inhibitor is administered twice a day, said cisplatin is administered once every three or four weeks per cycle, and said gemcitabine is administered once a week per cycle, said treatment being given for one to seven weeks per cycle.

An embodiment of this invention is directed to a method of treating non small cell lung cancer in a patient in need of such treatment comprising administering to said patient therapeutically effective amounts of:
(a) an FPT inhibitor of formula 1.4F (e.g., 1.4F wherein X is N); and:
(b) cisplatin; and
(c) gemcitabine wherein said FPT inhibitor is administered in an amount of about 50 mg to about 200 mg twice a day, said cisplatin is administered once every three or four weeks per cycle in an amount of about 60 to about 100 mg/m$^2$, said gemcitabine is administered once a week per cycle in an amount of about 750 to about 1250 mg/m$^2$, and said treatment being given for one to seven weeks per cycle.

An embodiment of this invention is directed to a method of treating non small cell lung cancer in a patient in need of such treatment comprising administering to said patient therapeutically effective amounts of:
(a) an FPT inhibitor of formula 1.4F (e.g., 1.4F wherein X is N); and:
(b) cisplatin; and
(c) gemcitabine wherein said FPT inhibitor is administered in an amount of about 75 mg to about 125 mg twice a day, said cisplatin is administered once every three or four weeks per cycle in an amount of about 60 to about 100 mg/m$^2$, said gemcitabine is administered once a week per cycle in an amount of about 750 to about 1250 mg/m$^2$, and said treatment being given for one to seven weeks per cycle.

An embodiment of this invention is directed to a method of treating non small cell lung cancer in a patient in need of such treatment comprising administering to said patient therapeutically effective amounts of:
(a) an-FPT inhibitor of formula 1.4F (e.g., 1.4F wherein X is N); and:
(b) cisplatin; and
(c) gemcitabine wherein said FPT inhibitor is administered in an amount of about 100 mg twice a day, said cisplatin is administered once every three or four weeks per cycle in an amount of about 60 to about 100 mg/m$^2$, and said gemcitabine is administered once a week per cycle in an amount of about 750 to about 1250 mg/m$^2$, and said treatment being given for one to seven weeks per cycle.

An embodiment of this invention is directed to a method of treating non small cell lung cancer in a patient in need of such treatment comprising administering to said patient therapeutically effective amounts of:
(a) an FPT inhibitor of formula 1.4F (e.g., 1.4F wherein X is N); and
(b) carboplatin; and
(c) gemcitabine.

An embodiment of this invention is directed to a method of treating non small cell lung cancer in a patient in need of such treatment comprising administering to said patient therapeutically effective amounts of:
(a) an FPT inhibitor of formula 1.4F (e.g., 1.4F wherein X is N); and
(b) carboplatin; and
(c) gemcitabine, wherein said FPT inhibitor is administered twice a day, said carboplatin is administered once every three weeks per cycle, and said gemcitabine is administered once a week per cycle, said treatment being given for one to seven weeks per cycle.

An embodiment of this invention is directed to a method of treating non small cell lung cancer in a patient in need of such treatment comprising administering to said patient therapeutically effective amounts of:
(a) an FPT inhibitor of formula 1.4F (e.g., 1.4F wherein X is N); and
(b) carboplatin; and
(c) gemcitabine, wherein said FPT inhibitor is administered in an amount of about 50 mg to about 200 mg twice a day, said carboplatin is administered once every three weeks per cycle in an amount to provide an AUC of about 5 to about 8, said gemcitabine is administered once a week per cycle in an amount of about 750 to about 1250 mg/m$^2$, and said treatment being given for one to seven weeks per cycle.

An embodiment of this invention is directed to a method of treating non small cell lung cancer in a patient in need of such treatment comprising administering to said patient therapeutically effective amounts of:
(a) an FPT inhibitor of formula 1.4F (e.g., 1.4F wherein X is N); and
(b) carboplatin; and
(c) gemcitabine, said treatment being given for one to seven weeks per cycle, wherein said FPT inhibitor is administered in an amount of about 75 mg to about 125 mg twice a day, said carboplatin is administered once every three weeks per cycle in an amount to provide an AUC of about 5 to about 8, and said gemcitabine is administered once a week per cycle in an amount of about 750 to about 1250 mg!m$^2$, and said treatment being given for one to seven weeks per cycle.

An embodiment of this invention is directed to a method of treating of non small cell lung cancer in a patient in need of such treatment comprising administering to said patient therapeutically effective amounts of:
(a) an FPT inhibitor of formula 1.4F (e.g., 1.4F wherein X is N); and
(b) carboplatin; and
(c) gemcitabine, wherein said FPT inhibitor is administered in an amount of about 100 mg twice a day, said carboplatin is administered once every three weeks per cycle in an amount to provide an AUC of about 5 to about 8, said gemcitabine is administered once a week per cycle in an amount of about 750 to about 1250 mg/m$^2$, and said treatment being given for one to seven weeks per cycle.

An embodiment of this invention is directed to a method of treating cancer in a patient in need of such treatment comprising administering to said patient therapeutically effective amounts of an FPT inhibitor compound of formula 1.4F (e.g., 1.4F wherein X is N) and an antineoplastic agent selected from the group consisting of:
(1) EGF inhibitors that are antibodies;
(2) EGF inhibitors that are small molecules;
(3) VEGF inhibitors that are antibodies; or
(4) VEGF kinase inhibitors that are small molecules.

An embodiment of this invention is directed to a method of treating cancer in a patient in need of such treatment comprising administering to said patient therapeutically effective amounts of an FPT inhibitor compound of formula 1.4F (e.g., 1.4F wherein X is N) and an antineoplastic agent selected from the group consisting of: Herceptin, Cetuximab, Tarceva, Iressa, bevacizumab, IMC-1C11, SU5416, and SU6688.

An embodiment of this invention is directed to a method of treating cancer in a patient in need of such treatment comprising administering to said patient therapeutically effective amounts of an FPT inhibitor compound of formula 1.4F (e.g., 1.4F wherein X is N) and an antineoplastic agent selected from the group consisting of:
(1) EGF inhibitors that are antibodies;
(2) EGF inhibitors that are small molecules;
(3) VEGF inhibitors that are antibodies; or
(4) VEGF kinase inhibitors that are small molecules, wherein the FPT inhibitor is administered twice a day, said antineoplastic agent that is an antibody is administered once a week per cycle and said antineoplastic agent that is a small molecule is administered daily, said treatment being given for one to four weeks per cycle.

An embodiment of this invention is directed to a method of treating cancer in a patient in need of such treatment comprising administering to said patient therapeutically effective amounts of an FPT inhibitor compound of formula 1.4F (e.g., 1.4F wherein X is N) and an antineoplastic agent selected from the group consisting of:
(1) EGF inhibitors that are antibodies;
(2) EGF inhibitors that are small molecules;
(3) VEGF inhibitors that are antibodies; or
(4) VEGF kinase inhibitors that are small molecules, wherein said FPT inhibitor is administered in an amount of about 50 mg to about 200 mg twice a day, and said antineoplastic agent that is an antibody is administered once a week per cycle in an amount of about 2 to about 10 mg/m$^2$, and said antineoplastic agent that is a small molecule is administered daily in an amount of about 50 to about 2400 mg/m², and said treatment being given for one to four weeks per cycle.

An embodiment of this invention is directed to a method of treating cancer in a patient in need of such treatment comprising administering to said patient therapeutically effective amounts of an FPT inhibitor compound of formula 1.4F (e.g., 1.4F wherein X is N) and an antineoplastic agent selected from the group consisting of:
(1) EGF inhibitors that are antibodies;
(2) EGF inhibitors that are small molecules;
(3) VEGF inhibitors that are antibodies; or
(4) VEGF kinase inhibitors that are small molecules,
wherein said FPT inhibitor is administered in an amount of about 75 mg to about 125 mg twice a day, and said antineoplastic agent that is an antibody is administered once a week per cycle in an amount of about 2 to about 10 mg/m², and said antineoplastic agent that is a small molecule is administered daily in an amount of about 50 to about 2400 mg/m², and said treatment being given for one to four weeks per cycle.

An embodiment of this invention is directed to a method of treating cancer in a patient in need of such treatment comprising administering to said patient therapeutically effective amounts of an FPT inhibitor compound of formula 1.4F (e.g., 1.4F wherein X is N) and an antineoplastic agent selected from the group consisting of:
(1) EGF inhibitors that are antibodies;
(2) EGF inhibitors that are small molecules;
(3) VEGF inhibitors that are antibodies; or
(4) VEGF kinase inhibitors that are small molecules,
said treatment being given for one to four weeks per cycle, wherein said FPT inhibitor is administered in an amount of about 100 mg twice a day, and said antineoplastic agent that is an antibody is administered once a week per cycle in an amount of about 2 to about 10 mg/m², and said antineoplastic agent that is a small molecule is administered daily in an amount of about 50 to about 2400 mg/M2, and said treatment being given for one to four weeks per cycle.

An embodiment of this invention is directed to a method of treating cancer in a patient in need of such treatment comprising administering to said patient an effective amount of an FPT inhibitor compound of formula 1.4F (e.g., 1.4F wherein X is N) and two antineoplastic agents, wherein one antineoplastic agent is a taxane, and the other antineoplastic agent is a platinum coordinator compound, wherein said taxane is paclitaxel administered in an amount of about 150 mg to about 250 mg/m² once a week per cycle, and said platinum coordinator compound is carboplatin administered once a week per cycle in an amount to provide an AUC of about 5 to about 8.

An embodiment of this invention is directed to a method of treating cancer in a patient in need of such treatment comprising administering to said patient an effective amount of an FPT inhibitor compound of formula 1.4F (e.g., 1.4F wherein X is N) and two antineoplastic agents, wherein one antineoplastic agent is a taxane, and the other antineoplastic agent is a platinum coordinator compound, wherein said taxane is docetaxel administered in an amount of about 50 mg to about 100 mg/m² once a week per cycle, and said platinum coordinator compound is cisplatin administered in amount of about 60 mg to about 100 mg/m² once a week per cycle.

An embodiment of this invention is directed to a method of treating of non small cell lung cancer in a patient in need of such treatment comprising administering to said patient therapeutically effective amounts of:
(a) an FPT inhibitor of formula 1.4F (e.g., 1.4F wherein X is N); and
(b) carboplatin; and
(c) docetaxel.

An embodiment of this invention is directed to a method of treating squamous cell cancer of the head and neck, in a patient in need of such treatment comprising administering therapeutically effective amounts of:
(a) an FPT inhibitor of formula 1.4F (e.g., 1.4F wherein X is N); and
(b) one or more antineoplastic agents selected from the group consisting of:
(1) taxanes; and
(2) platinum coordinator compounds.

An embodiment of this invention is directed to a method of treating squamous cell cancer of the head and neck, in a patient in need of such treatment comprising administering therapeutically effective amounts of:
(a) an FPT inhibitor of formula 1.4F (e.g., 1.4F wherein X is N);
(b) at least two different antineoplastic agents selected from the group consisting of:
(1) taxanes;
(2) platinum coordinator compounds; and
(3) anti-tumor nucleoside derivatives (e.g., 5-Fluorouracil).

An embodiment of this invention is directed to a method of treating CML in a patient in need of such treatment comprising administering therapeutically effective amounts of:
(a) an FPT inhibitor of formula 1.4F (e.g., 1.4F wherein X is N);
(b) Gleevec; and
(c) interferon (e.g., Intron-A).

An embodiment of this invention is directed to a method of treating CML in a patient in need of such treatment comprising administering therapeutically effective amounts of:
(a) an FPT inhibitor of formula 1.4F (e.g., 1.4F wherein X is N);
(b) Gleevec; and
(c) pegylated interferon (e.g., Peg-Intron, and Pegasys).

An embodiment of this invention is directed to a method of treating AML in a patient in need of such treatment comprising administering therapeutically effective amounts of:
(a) an FPT inhibitor of formula 1.4F (e.g., 1.4F wherein X is N);
(b) an anti-tumor nucleoside derivative (e.g., Cytarabine (i.e., Ara-C)).

An embodiment of this invention is directed to a method of treating AML in a patient in need of such treatment comprising administering therapeutically effective amounts of:
(a) an FPT inhibitor of formula 1.4F (e.g., 1.4F wherein X is N);
(b) an anti-tumor nucleoside derivative (e.g., Cytarabine (i.e., Ara-C)); and
(c) an anthracycline.

An embodiment of this invention is directed to a method of treating non-Hodgkin's lymphoma in a patient in need of such treatment comprising administering therapeutically effective amounts of:

(a) an FPT inhibitor of formula 1.4F (e.g., 1.4F wherein X is N);

(b) Rituximab (Rituxan).

An embodiment of this invention is directed to a method of treating non-Hodgkin's lymphoma in a patient in need of such treatment comprising administering therapeutically effective amounts of:

(a) an FPT inhibitor of formula 1.4F (e.g., 1.4F wherein X is N);

(b) Rituximab (Rituxan); and (c) an anti-tumor nucleoside derivative (e.g., Fludarabine (i.e., F-ara-A).

An embodiment of this invention is directed to a method of treating non-Hodgkin's lymphoma in a patient in need of such treatment comprising administering therapeutically effective amounts of:

(a) an FPT inhibitor of formula 1.4F (e.g., 1.4F wherein X is N);

(b) Genasense (antisense to BCL-2).

An embodiment of this invention is directed to a method of treating multiple myeloma in a patient in need of such treatment comprising administering therapeutically effective amounts of:

(a) an FPT inhibitor of formula 1.4F (e.g., 1.4F wherein X is N);

(b) a proteosome inhibitor (e.g., PS-341 (Millenium)).

An embodiment of this invention is directed to a method of treating multiple myeloma in a patient in need of such treatment comprising administering therapeutically effective amounts of:

(a) an FPT inhibitor of formula 1.4F (e.g., 1.4F wherein X is N);

(b) Thalidomide or related imid.

An embodiment of this invention is directed to a method of treating multiple myeloma in a patient in need of such treatment comprising administering therapeutically effective amounts of:

(a) an FPT inhibitor of formula 1.4F (e.g., 1.4F wherein X is N);

(b) Thalidomide.

Other embodiments of this invention are directed to the embodiments described above using an FPT inhibitor of formula 1.4F (e.g., 1.4F wherein X is N) wherein in addition to the administration of the FPT inhibitor and antineoplastic agents radiation therapy is also administered prior to, during, or after the treatment cycle.

For the embodiments of this invention using compounds of formula 1.4F (e.g., 1.4F wherein X is N), the compounds of formula 1.4F are preferably selected from the group consisting of:

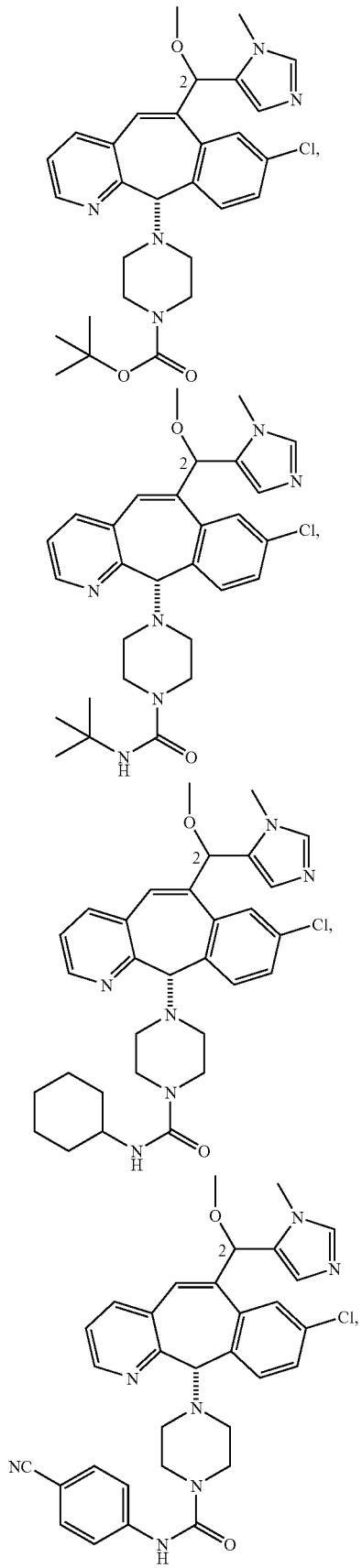

-continued
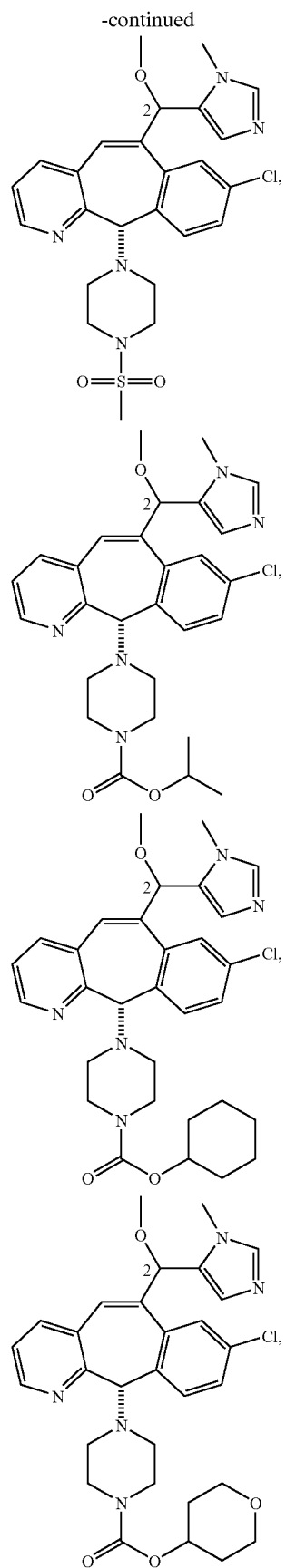
-continued
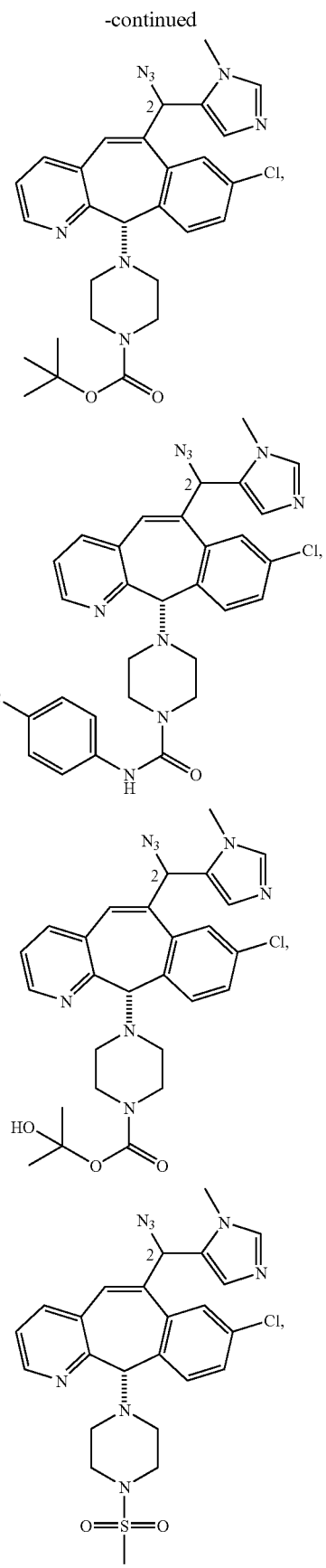

1153
-continued
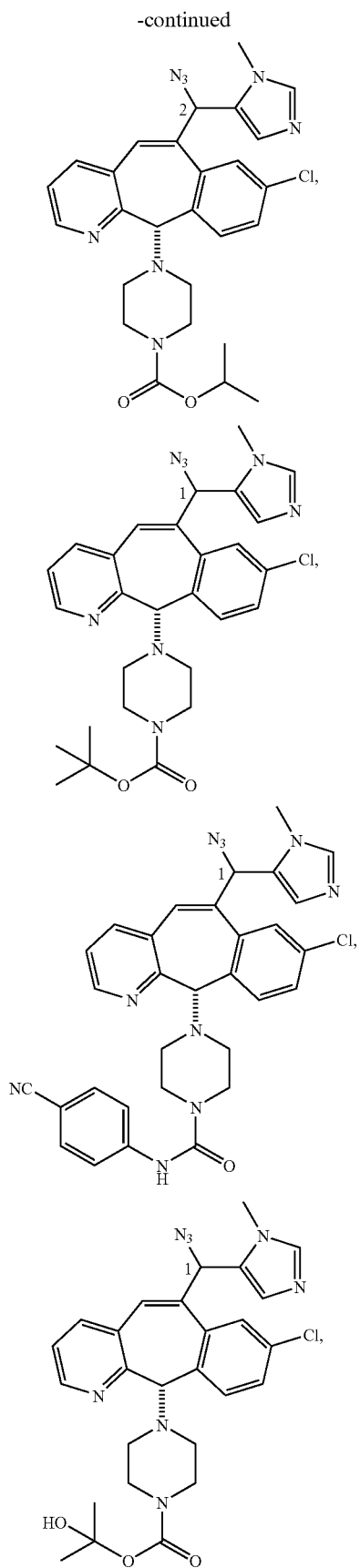
1154
-continued
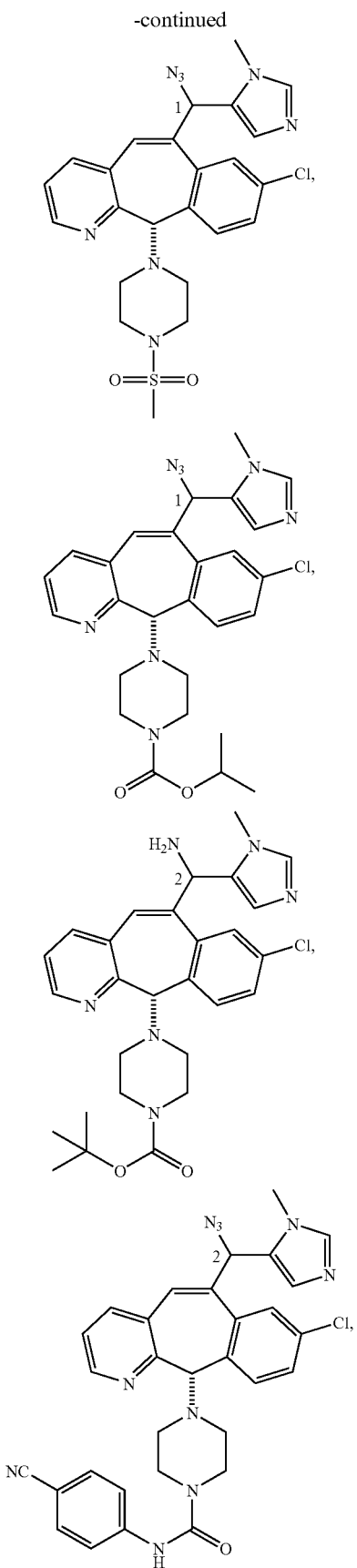

1155 -continued
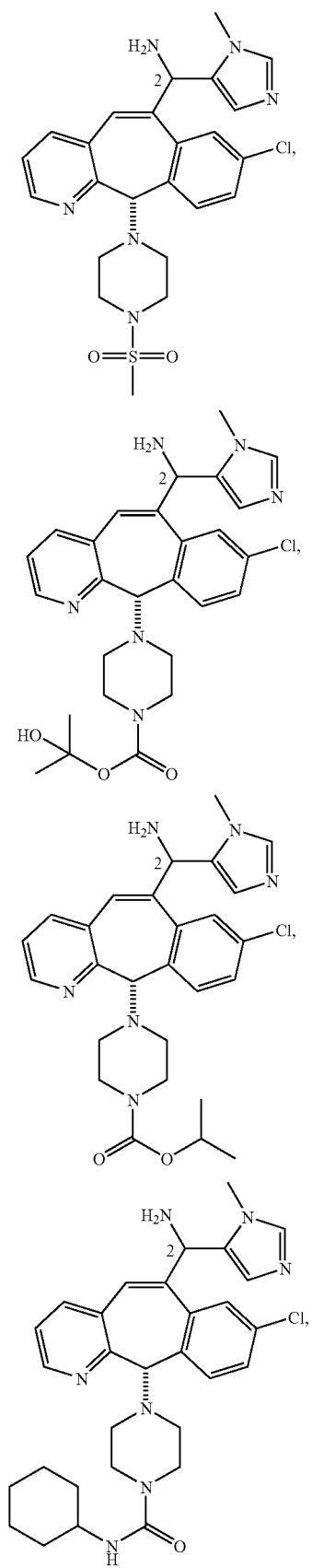
1156 -continued
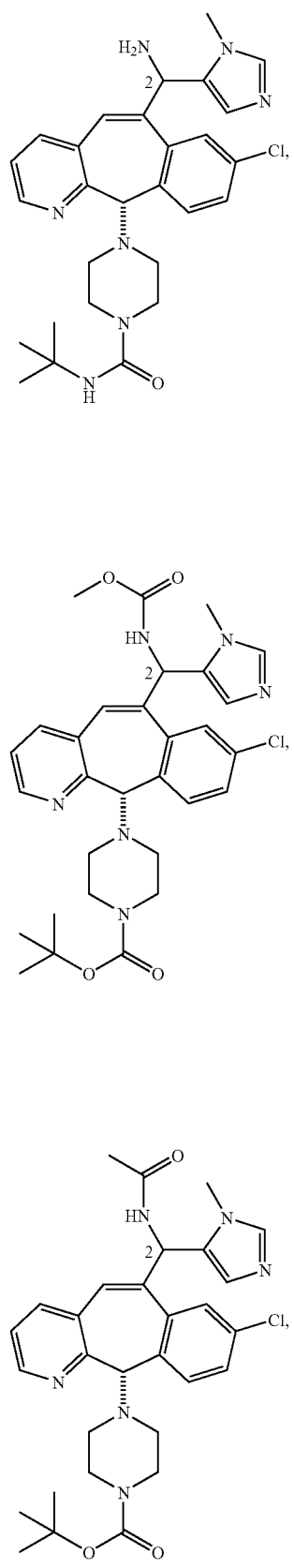

-continued
1157
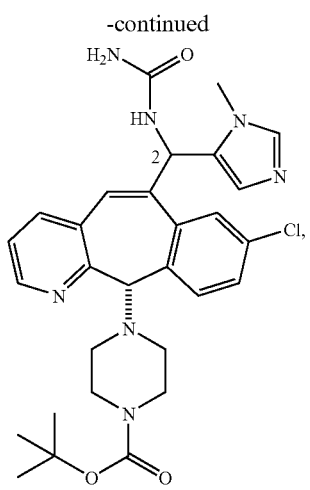
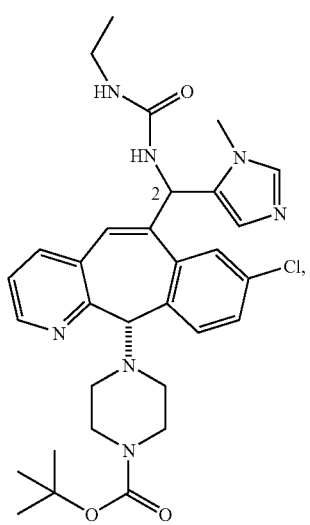
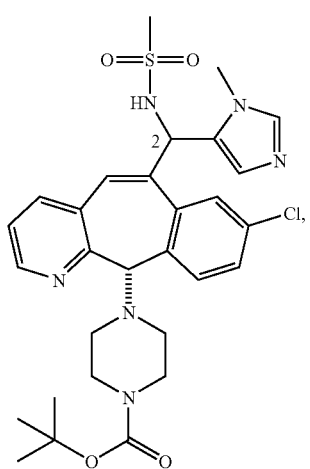
1158
-continued
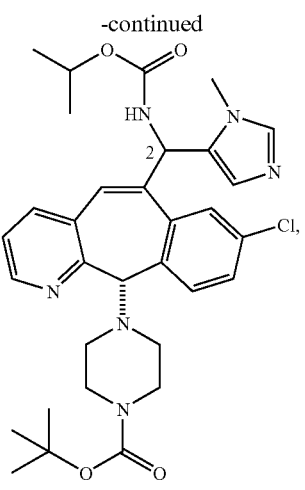
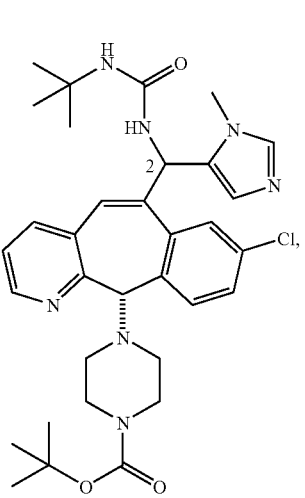
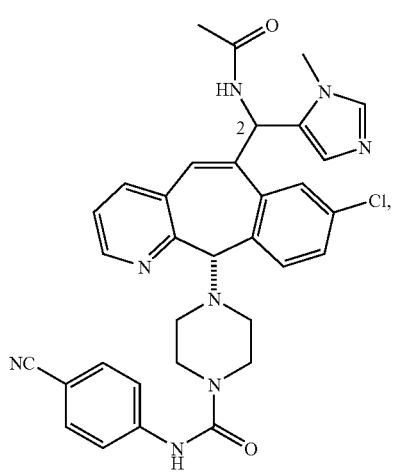

-continued
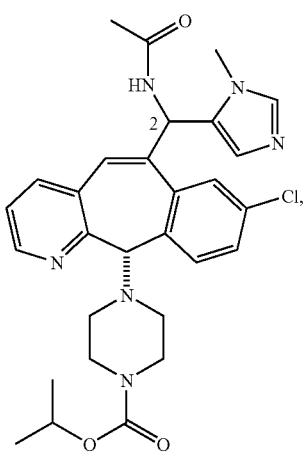
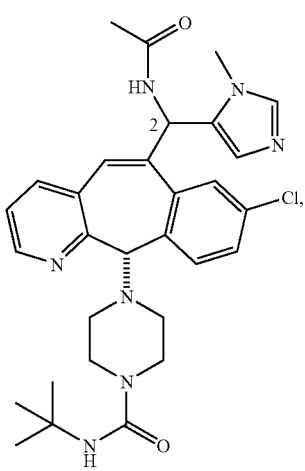
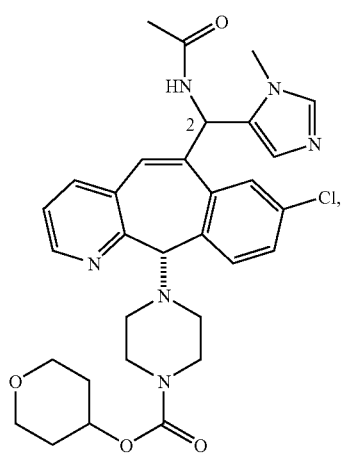
-continued
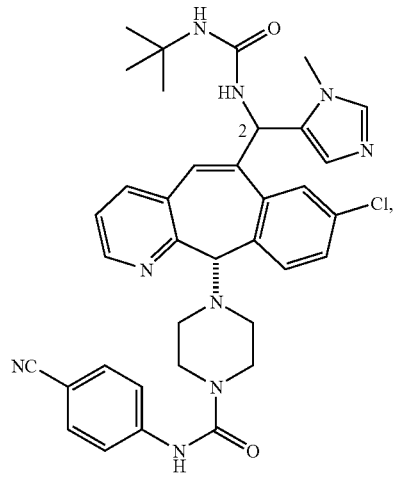
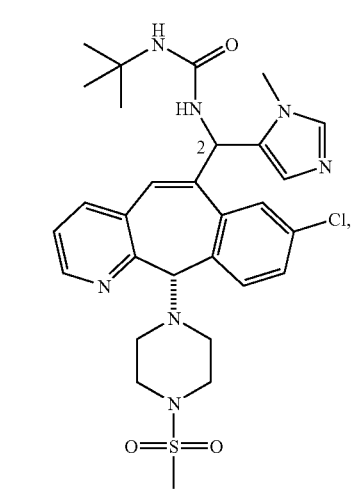
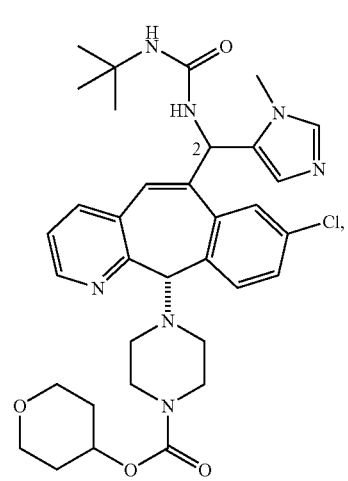

1161
-continued
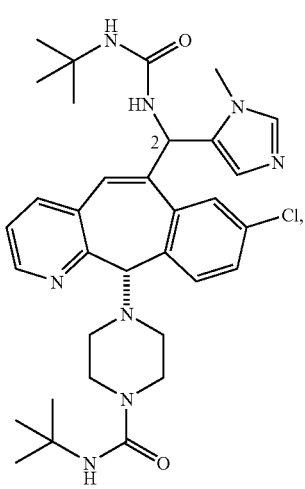
1162
-continued
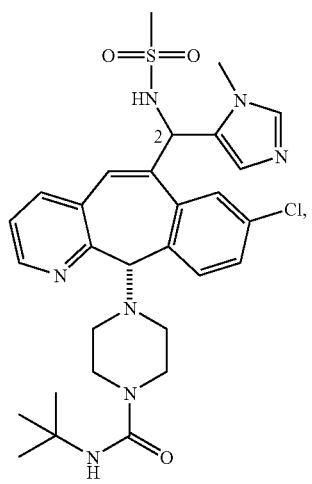
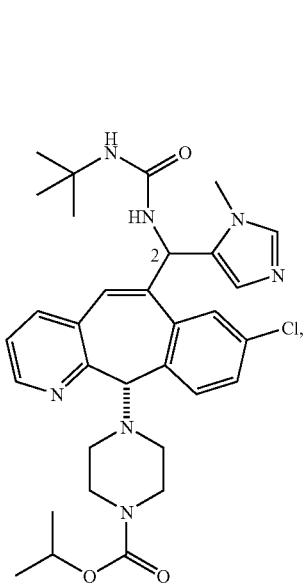
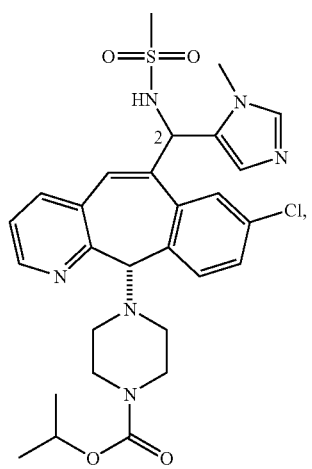

1163
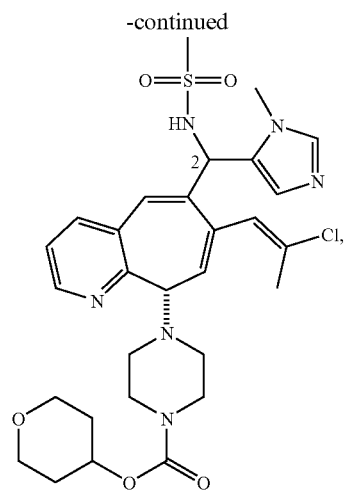
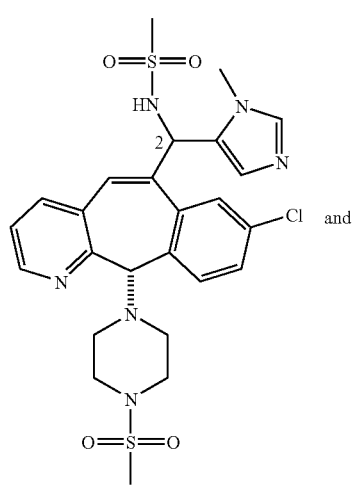
and
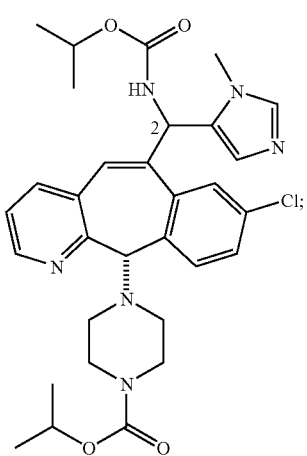
more preferably selected from the group consisting of:
1164
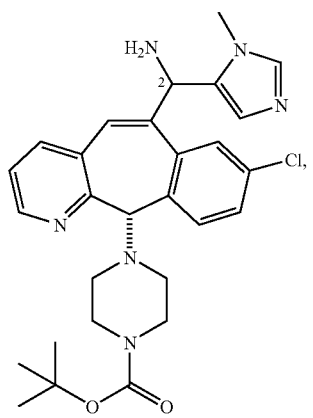
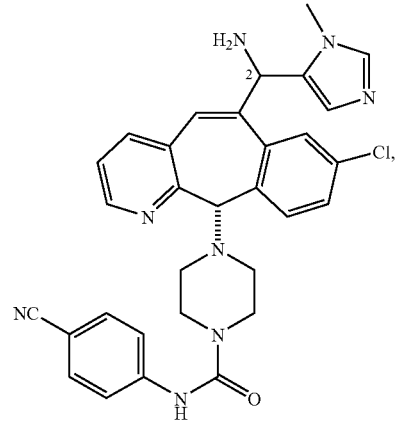
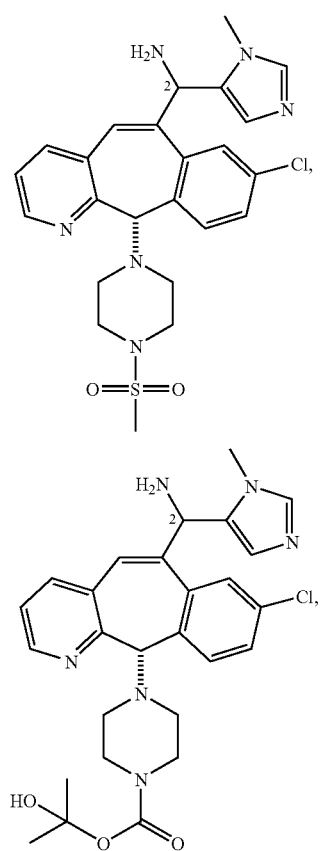

1165
-continued
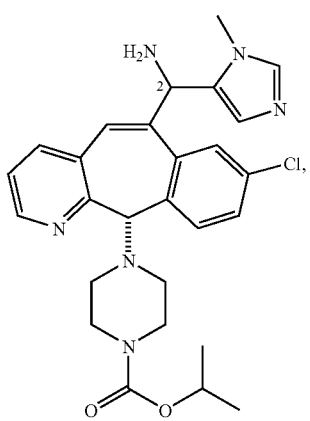
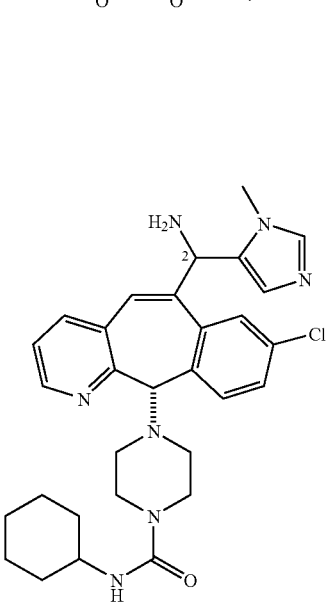
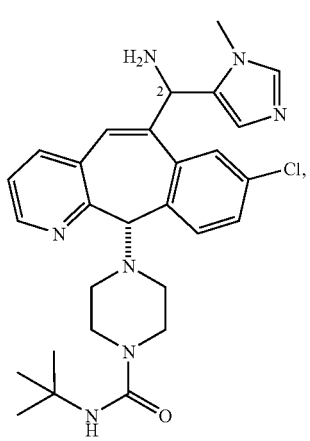
1166
-continued
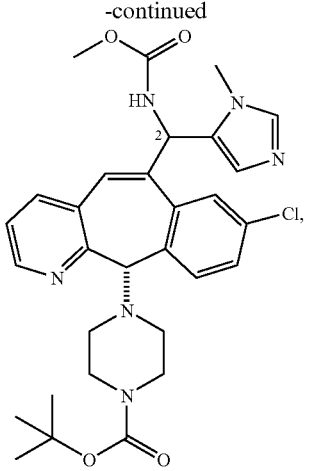
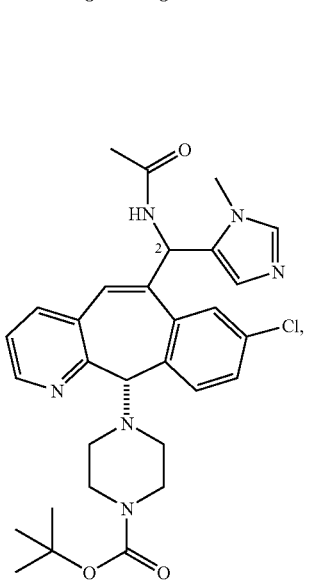
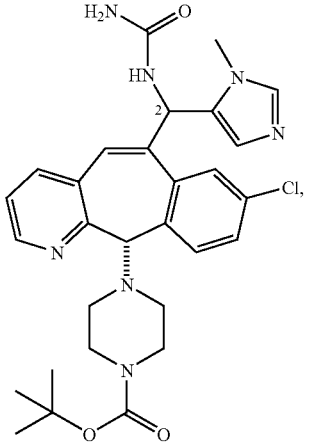

1167
-continued
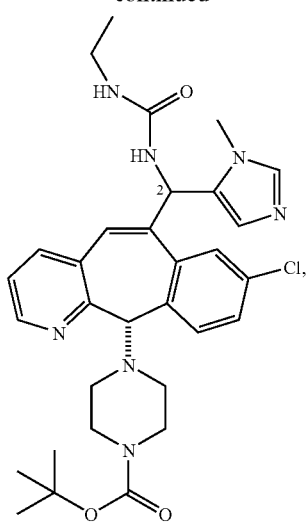
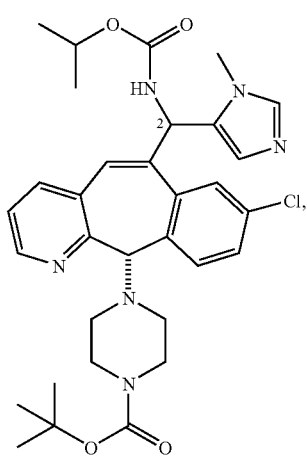
1168
-continued
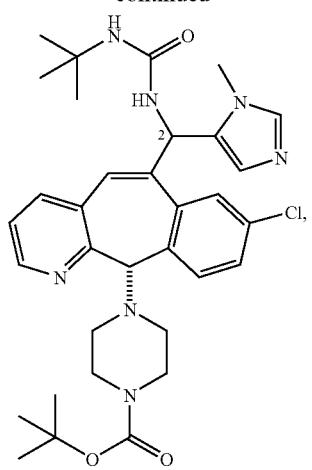
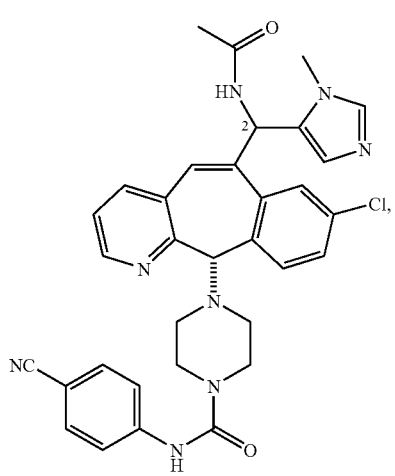

1169
-continued
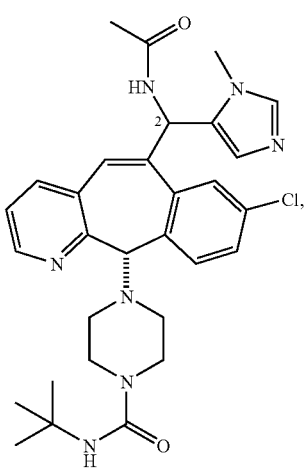
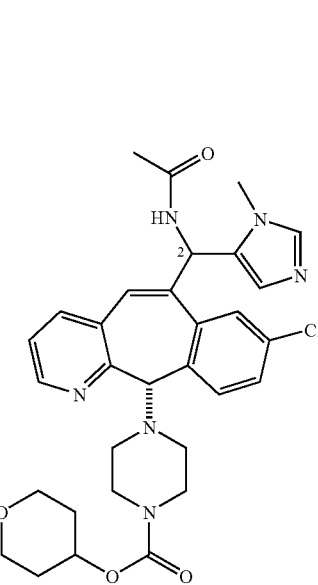
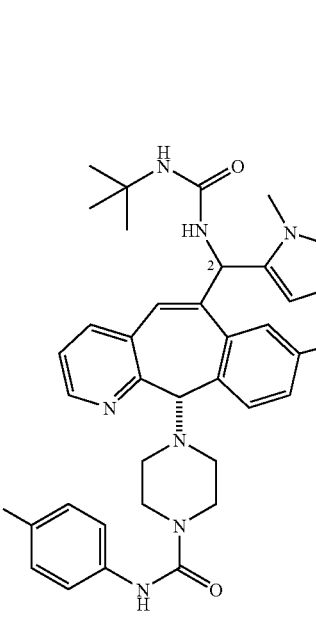
1170
-continued
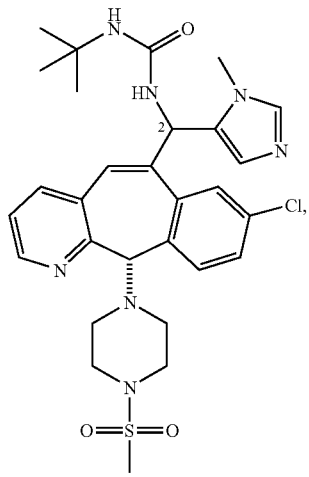
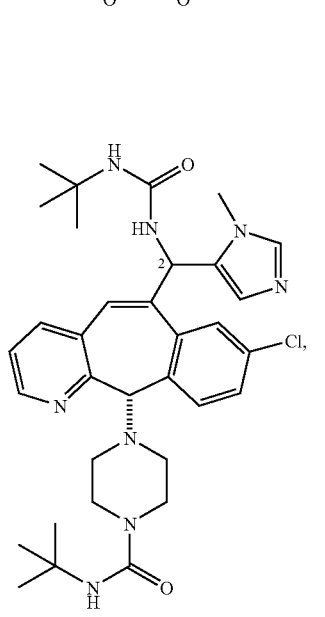

1171
-continued
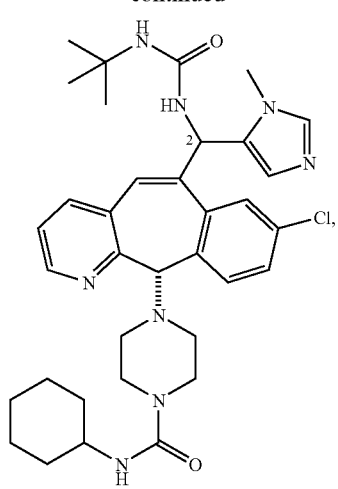
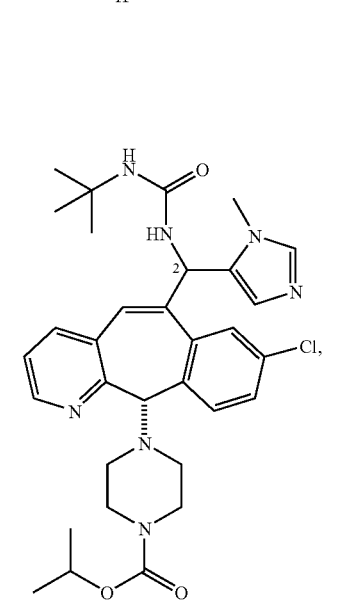
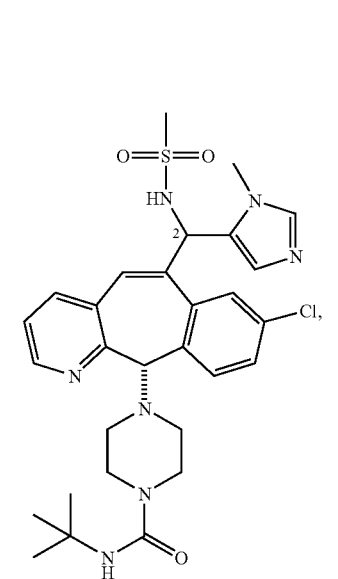
1172
-continued
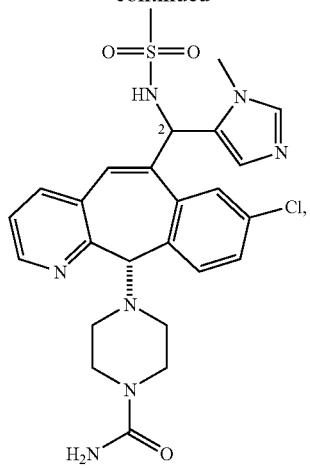
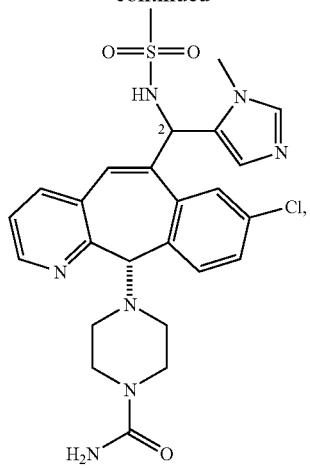
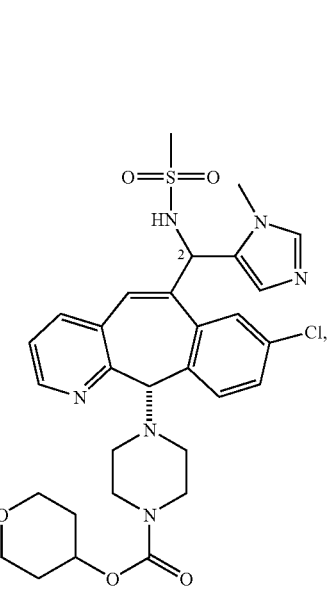

1173
-continued
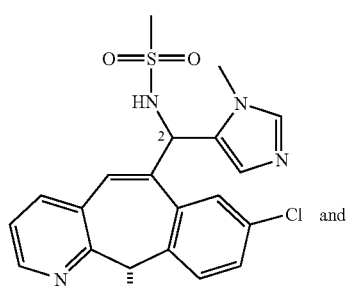
and
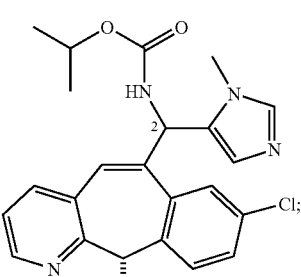
most preferably selected from the group consisting of:
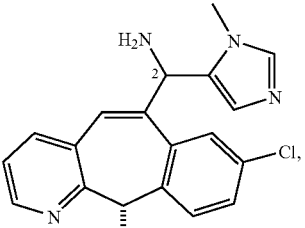
1174
-continued
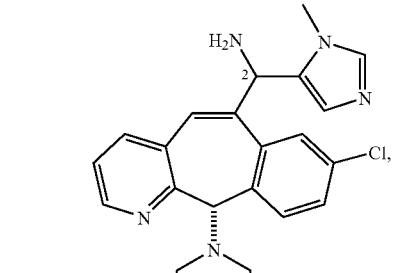
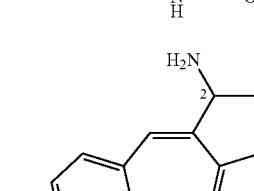
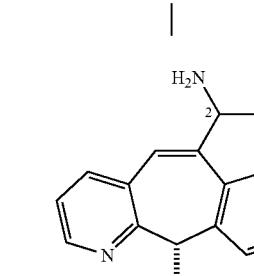
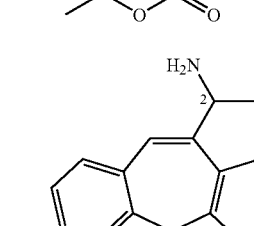

-continued

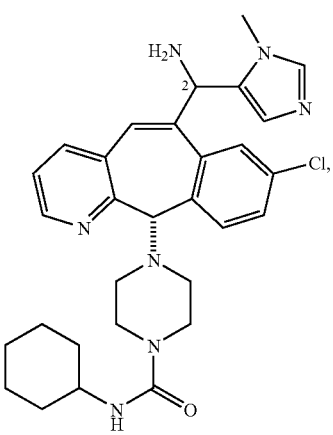

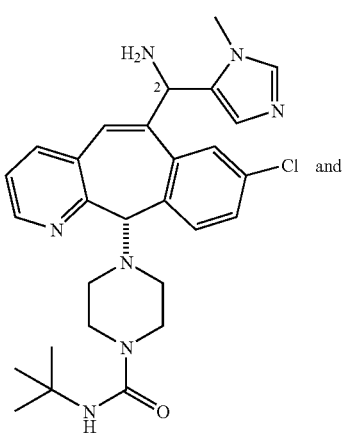

and

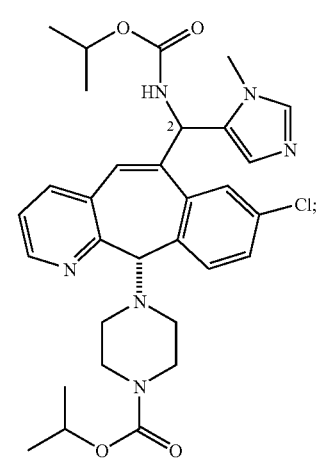

even more preferably

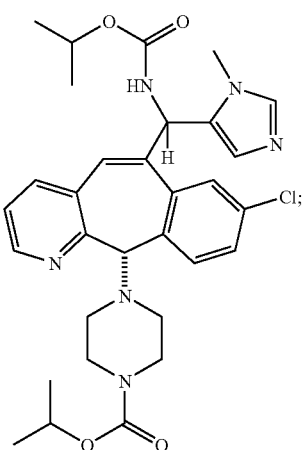

and still more preferably

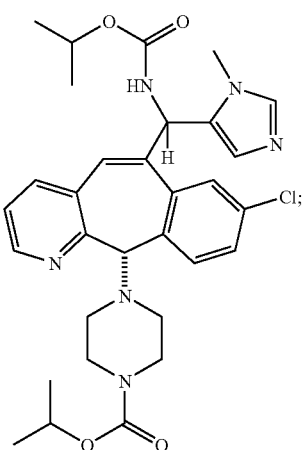

or

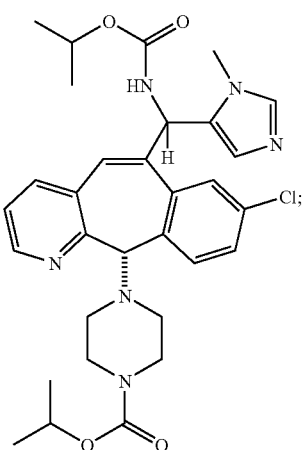

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:
1. A compound of the formula:

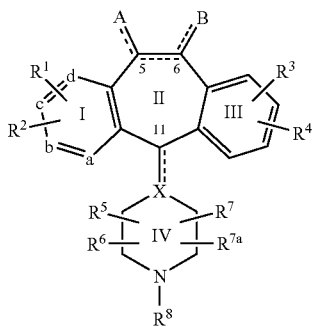

(1.0)

or a pharmaceutically acceptable salt or solvate thereof, wherein:
- a represents N or $N^+O^-$, and the remaining b, c, and d groups represent carbon, wherein each carbon has an $R^1$ or $R^2$ group bound to said carbon; or
- the dotted line (---) represents optional bonds;
- X represents N and the optional bond is absent;
- the C-5 to C-6 double bond is present;
- A is H;
- B is the group:

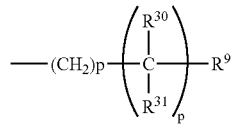

wherein p of the $-(CH_2)_p-$ moiety of said B group is 0, and wherein p of the

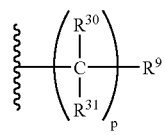

moiety of said B group is 1, one of $R^{30}$ or $R^{31}$ is $-NHR^{9b}$ and the remaining $R^{30}$ or $R^{31}$ is selected from the group consisting of: H, alkyl, aryl, and arylalkyl;
each $R^1$ and $R^2$ is independently selected from the group consisting of:
(1) H;
(2) Halo;
(3) $-CF_3$,
(4) $-OR^{10}$;
(5) $-COR^{10}$,
(6) $-SR^{10}$;
(7) $-S(O)_tR^{15}$ wherein t is 0, 1 or 2;
(8) $-N(R^{10})_2$;
(9) $-NO_2$;
(10) $-OC(O)R^{10}$;
(11) $-CO_2R^{10}$;
(12) $-OCO_2R^{15}$;
(13) $-CN$;
(14) $-NR^{10}COOR^{15}$;
(15) $-SR^{15}C(O)OR^{15}$;
(16) $-SR^{15}N(R^{13})_2$ provided that $R^{15}$ in $-SR^{15}N(R^{13})_2$ is not $-CH_2$ and
wherein each $R^{13}$ is independently selected from the group consisting of: H and $-C(O)OR^{15}$;
(17) benzotriazol-1-yloxy;
(18) tetrazol-5-ylthio;
(19) substituted tetrazol-5-ylthio;
(20) alkynyl;
(21) alkenyl; and
(22) alkyl,
said alkyl or alkenyl group optionally being substituted with halogen, $-OR^{10}$ or $-CO_2R^{10}$;
$R^3$ and $R^4$ are the same or different and each independently represent H, and any of the substituents of $R^1$ and $R^2$;
$R^5$, $R^6$, $R^7$ and $R^{7a}$ each independently represent: H, $-CF_3$, $-COR^{10}$, alkyl or aryl, said alkyl or aryl optionally being substituted with $-S(O)_tR^{15}$, $-NR^{10}COOR^{15}$, $-C(O)R^{10}$, or $-CO_2R^{10}$, or $R^6$ is combined with R to represent =O or =S;
$R^8$ is selected from the group consisting of:

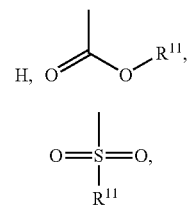

(2.0)

(3.0)

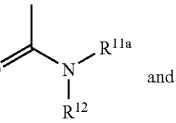

(4.0)

and

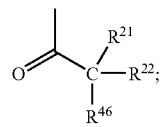

(5.0)

$R^9$ is substituted imidazolyl substituted with one or more substituents selected from the group consisting of:
(1) $-OH$, provided that when there is more than one $-OH$ group then each $-OH$ group is bound to a different carbon atom;
(2) $-CO_2R^{14}$;
(3) $-CH_2OR^{14}$,
(4) halogen;
(5) alkyl;
(6) amino;
(7) trityl;
(8) heterocycloalkyl;
(9) cycloalkyl;
(10) arylalkyl;
(11) heteroaryl;
(12) heteroarylalkyl and

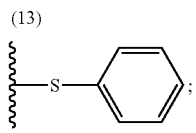
(13)

wherein $R^{14}$ is independently selected from: H; alkyl; aryl, arylalkyl, heteroaryl and heteroarylalkyl;
$R^{9a}$ is selected from the group consisting of: alky and arylalkyl;
$R^{9b}$ is selected from the group consisting of:
(1) —C(O)$R^{9a}$;
(2) —SO$_2$$R^{9a}$;
(3) —C(O)NH$R^{9a}$;
(4) —C(O)O$R^{9a}$; and
(5) —C(O)N($R^{9c}$)$_2$;
Each $R^{9c}$ is independently selected from the group consisting of: H, alkyl and arylalkyl;
$R^{10}$ is selected from the group consisting of: H; alkyl; aryl and arylalkyl;
$R^{11}$ is selected from the group consisting of:
(1) alkyl;
(2) substituted alkyl;
(3) unsubstituted aryl;
(4) substituted aryl;
(5) unsubstituted cycloalkyl;
(6) substituted cycloalkyl;
(7) unsubstituted heteroaryl;
(8) substituted heteroaryl;
(9) heterocycloalkyl; and
(10) substituted heterocycloalkyl;
wherein said substituted alkyl, substituted cycloalkyl, and substituted heterocycloalkyl $R^{11}$ groups are substituted with one or more substituents selected from the group consisting of:
(1) —OH, provided that when there is more than one —OH group then each —OH group is bound to a different carbon atom;
(2) fluoro; and
(3) alkyl; and
wherein said substituted aryl and substituted heteroaryl $R^{11}$ groups are substituted with one or more substituents independently selected from the group consisting of:
(1) —OH, provided that when there is more than one —OH group then each —OH group is bound to a different carbon atom;
(2) halogen; and
(3) alkyl;
$R^{11a}$ is selected from the group consisting of:
(1) H;
(2) OH;
(3) alkyl;
(4) substituted alkyl;
(5) aryl;
(6) substituted aryl;
(7) unsubstituted cycloalkyl;
(8) substituted cycloalkyl;
(9) unsubstituted heteroaryl;
(10) substituted heteroaryl;
(11) heterocycloalkyl;
(12) substituted heterocycloalkyl; and
(13) —O$R^{9a}$;

wherein said substituted alkyl, substituted cycloalkyl, and substituted heterocycloalkyl $R^{11a}$ groups are substituted with one or more substituents independently selected from the group consisting of:
(1) —OH provided that when there is more than one —OH group then each —OH group is bound to a different carbon atom;
(2) —CN;
(3) —CF$_3$;
(4) fluoro;
(5) alkyl;
(6) cycloalkyl;
(7) heterocycloalkyl;
(8) arylalkyl;
(9) heteroarylalkyl;
(10) alkenyl and
(11) heteroalkenyl; and
wherein said substituted aryl and substituted heteroaryl $R^{11a}$ groups have one or more substituents independently selected from the group consisting of:
(1) —OH provided that when there is more than one —OH group then each —OH group is bound to a different carbon atom;
(2) —CN;
(3) —CF$_3$;
(4) halogen;
(5) alkyl;
(6) cycloalkyl;
(7) heterocycloalkyl;
(8) arylalkyl;
(9) heteroarylalkyl;
(10) alkenyl; and
(11) heteroalkenyl;
$R^{12}$ is selected from the group consisting of: H, alkyl, piperidine Ring V, cycloalkyl, and -alkyl-(piperidine Ring V);
$R^{15}$ is selected from the group consisting of: alkyl and aryl;
$R^{21}$, $R^{22}$ and $R^{46}$ are independently selected from the group consisting of:
(1) —H;
(2) alkyl;
(3) unsubstituted aryl;
(4) substituted aryl substituted with one or more substituents independently selected from the group consisting of: alkyl, halogen, CF$_3$ and OH;
(5) unsubstituted cycloalkyl;
(6) substituted cycloalkyl substituted with one or more substituents independently selected from the group consisting of: alkyl, halogen, CF$_3$ and OH;
(7) heteroaryl of the formula,

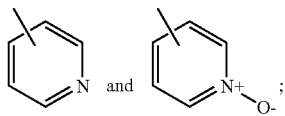

(8) heterocycloalkyl of the formula:

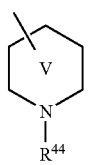

wherein $R^{44}$ is selected from the group consisting of:
(a) —H,
(b) alkyl;
(c) alkylcarbonyl;
(d) alkyloxy carbonyl;
(e) haloalkyl; and
(f) —C(O)NH($R^{51}$);
(9) —$NH_2$ provided that only one of $R^{21}$, $R^{22}$, and $R^{46}$ group can be —$NH_2$, and provided that when one of $R^{21}$, $R^{22}$, and $R^{46}$ is —$NH_2$ then the remaining groups are not —OH;
(10) —OH provided that only one of $R^{21}$, $R^{22}$, and $R^{46}$ group can be —OH, and provided that when one of $R^{21}$, $R^{22}$, and $R^{46}$ is —OH then the remaining groups are not —$NH_2$; and
(11) alkyl substituted with one or more substituents selected from the group consisting of: —OH and —$NH_2$, and provided that there is only one —OH or one —$NH_2$ group on a substituted carbon; or
(12) $R^{21}$ and $R^{22}$ taken together with the carbon to which they are bound form a cyclic ring selected from the group consisting of:
(a) unsubstituted cycloalkyl;
(b) cycloalkyl substituted with one or more substituents independently selected from the group consisting of: alkyl, halogen, $CF_3$ and OH;
(c) unsubstituted cycloalkenyl;
(d) cycloalkenyl substituted with one or more substituents independently selected from the group consisting of: alkyl, halogen, $CF_3$ and OH;
(e) heterocycloalkyl;
(f) unsubstituted aryl;
(g) aryl substituted with one or more substituents independently selected from the group consisting of: alkyl, halogen, —CN, —$CF_3$, —OH and alkoxy; and
(i) heteroaryl selected from the group consisting of:

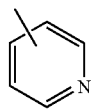 and 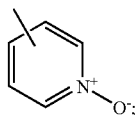

$R^{51}$ is selected from the group consisting of: H, and alkyl; and
provided that a ring carbon atom adjacent to a ring heteroatom in a substituted heterocycloalkyl moiety is not substituted with a heteroatom or a halo atom; and
provided that a ring carbon atom, that is not adjacent to a ring heteroatom, in a substituted heterocycloalkyl moiety, is not substituted with more than one heteroatom; and
provided that a ring carbon atom, that is not adjacent to a ring heteroatom, in a substituted heterocycloalkyl moiety, is not substituted with a heteroatom and a halo atom; and
provided that a ring carbon in a substituted cycloalkyl moiety is not substituted with more than one heteroatom; and
provided that a carbon atom in a substituted alkyl moiety is not substituted with more than one heteroatom; and
provided that the same carbon atom in a substituted alkyl moiety is not substituted with both heteroatoms and halo atoms.

2. A compound of claim 1 having the structure:

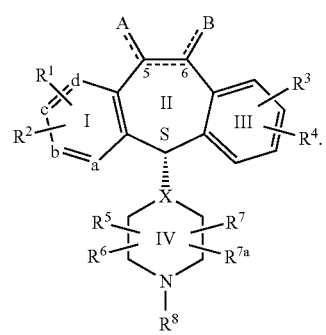

(1.0B)

3. The compound of claim 1 wherein $R^1$ to $R^4$ are each independently selected from H or halo.
4. The compound of claim 1 wherein $R^5$ to $R^7$ are H.
5. The compound of claim 1 wherein $R^8$ is group 2.0, or 4.0.
6. The compound of claim 1 wherein:
(1) $R^{11}$ is selected from the group consisting of: alkyl, cycloalkyl and substituted cycloalkyl wherein the substituents are selected from the group consisting of: halo, alkyl and amino;
(2) $R^{11a}$ is selected from: alkyl, unsubstituted aryl, substituted aryl, cycloalkyl or substituted cycloalkyl, wherein the substituents on said substituted groups are selected from the group consisting of: halo, —ON or $CF_3$;
(3) $R^{12}$, $R^{21}$, and $R^{22}$ are H; and
(4) $R^{46}$ is selected from the group consisting of: unsubstituted aryl,

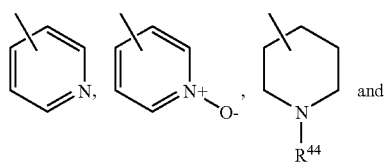

substituted aryl wherein the substituents are selected from the group consisting of: alkyl, alkylcarbonyl and haloalkyl, and wherein $R^{44}$ is selected from the group consisting of: H or —C(O)$NH_2$.

7. The compound of claim 1 wherein:
(1) $R^1$ to $R^4$ are each independently selected from the group consisting of: H and halo;
(2) $R^5$, $R^6$, $R^7$, and $R^{7a}$ are H;
(3) a is N;
(4) $R^8$ is group 2.0 or 4.0;

(5) $R^{11}$ is selected from the group consisting of: alkyl, cycloalkyl and substituted cycloalkyl wherein the substituents are selected from the group consisting of: halo, alkyl and amino;

(6) $R^{11a}$ is selected from the group consisting of: alkyl, unsubstituted aryl, substituted aryl, cycloalkyl or substituted cycloalkyl, wherein the substituents on said substituted groups are selected from the group consisting of: halo, —CN and $CF_3$;

(7) $R^{12}$ is H; and (8) the substituents for said substituted $R^9$ imidazolyl are each independently selected from the group consisting of:
  (1) —OH;
  (2) —$CO_2R^{14}$;
  (3) —$CH_2OR^{14}$;
  (4) halo,
  (5) alkyl;
  (6) amino;
  (7) trityl;
  (8) heterocycloalkyl;
  (9) arylalkyl;
  (10) heteroaryl and
  (11) heteroarylalkyl;

wherein $R^{14}$ is independently selected from the group consisting of: H and alkyl.

8. The compound of claim 1 wherein said substituted imidazolyl is:

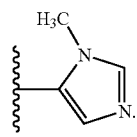

9. The compound of claim 1 wherein B is selected from the group consisting of:

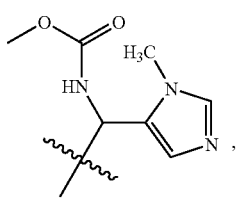 , 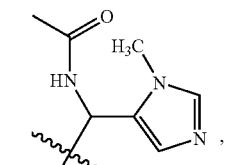 ,

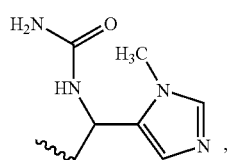 , 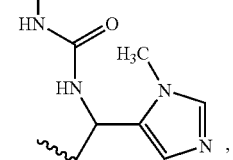 ,

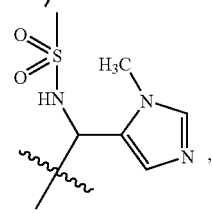 , 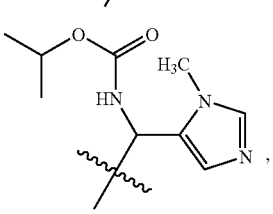 ,

-continued

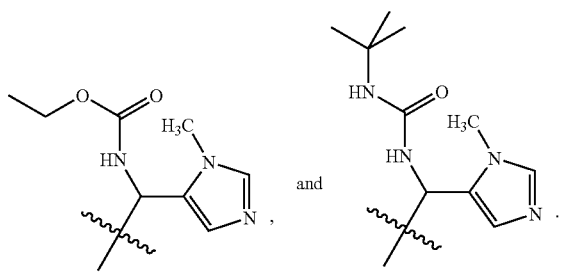 and

10. The compound of claim 1 wherein $R^8$ is selected from the group consisting of:

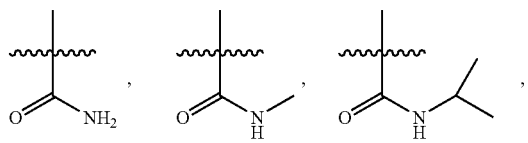

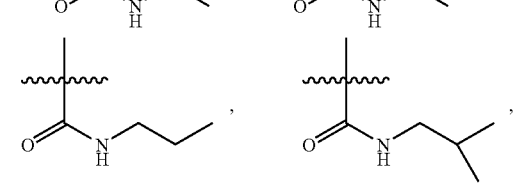

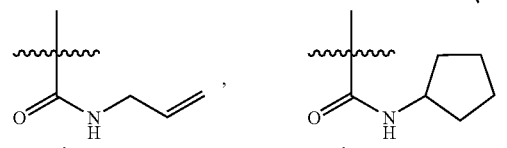

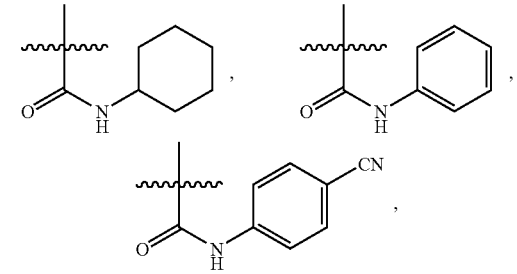

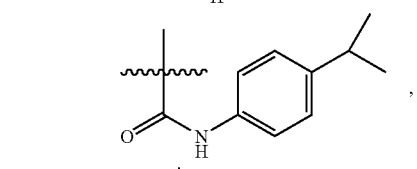

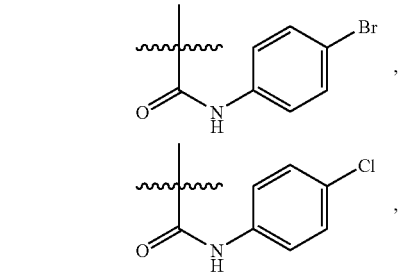

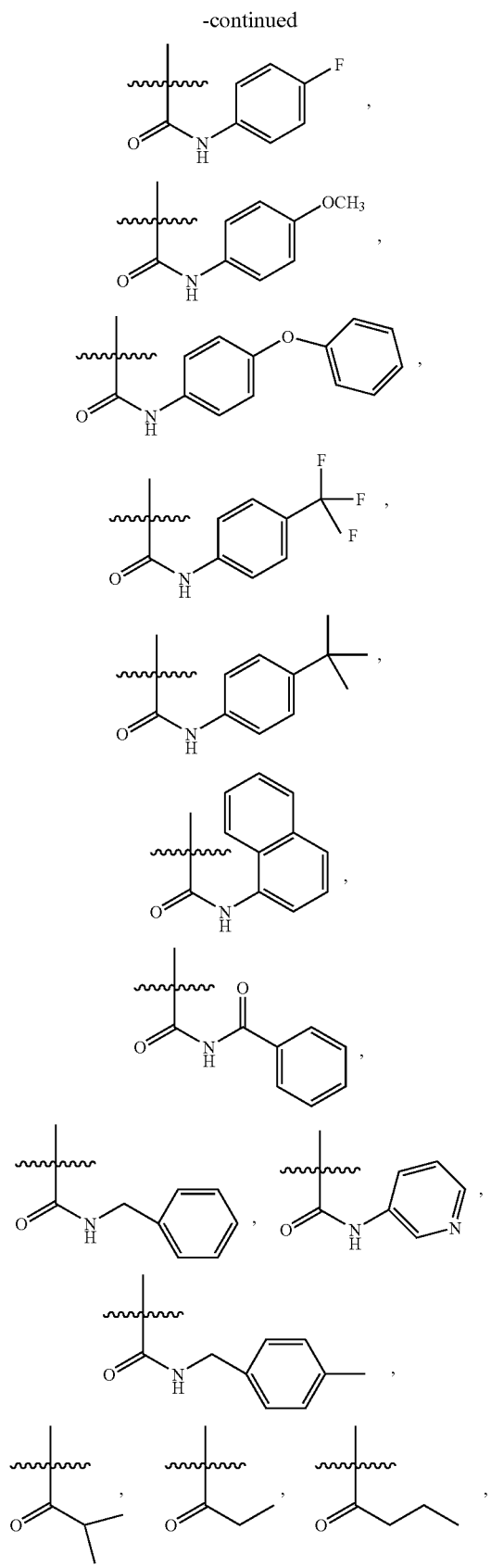
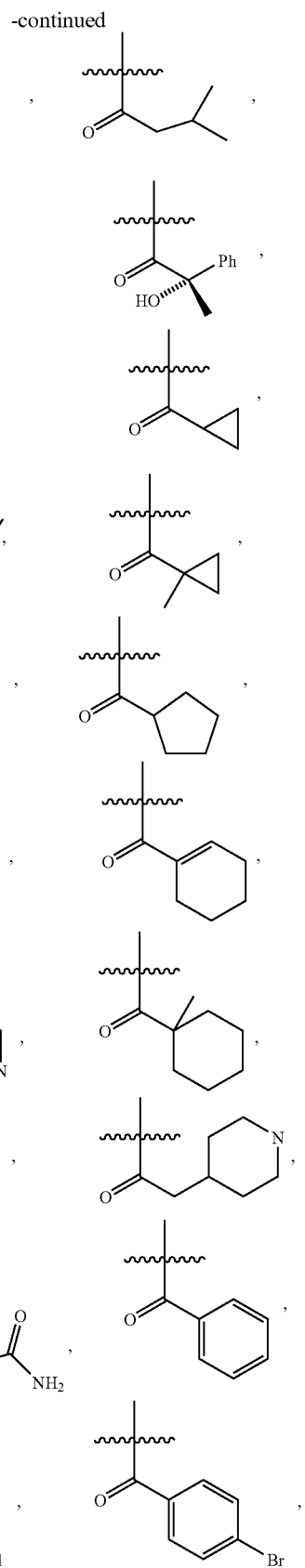

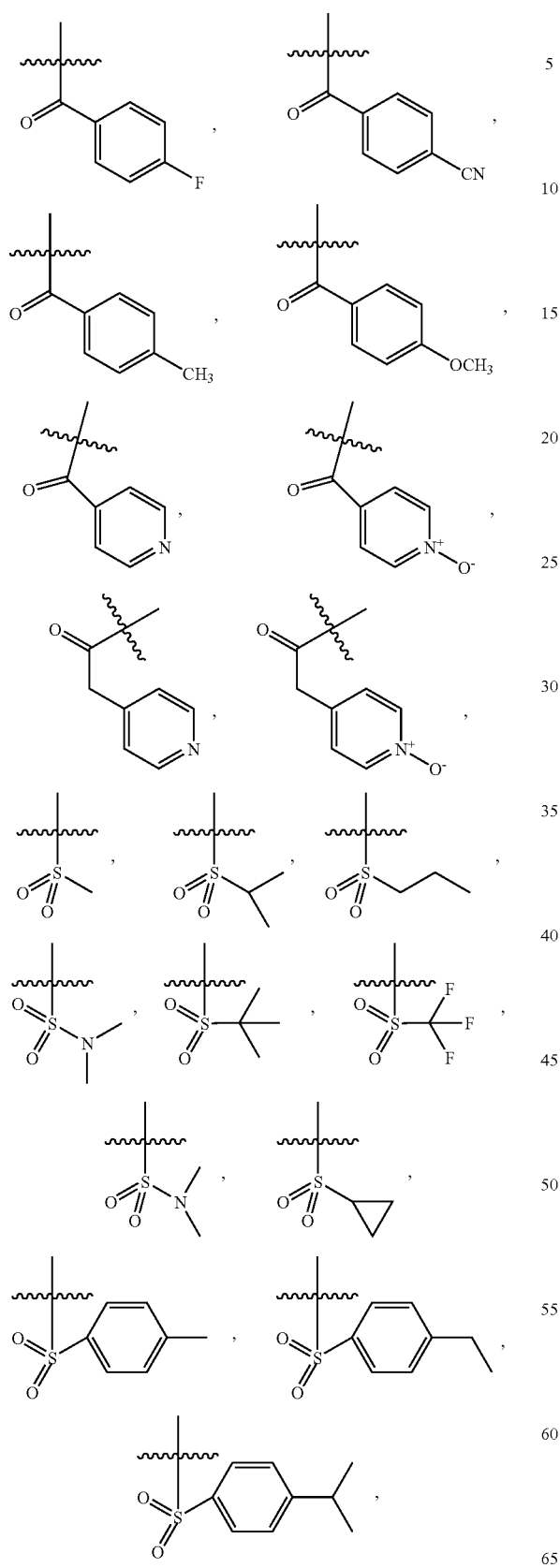
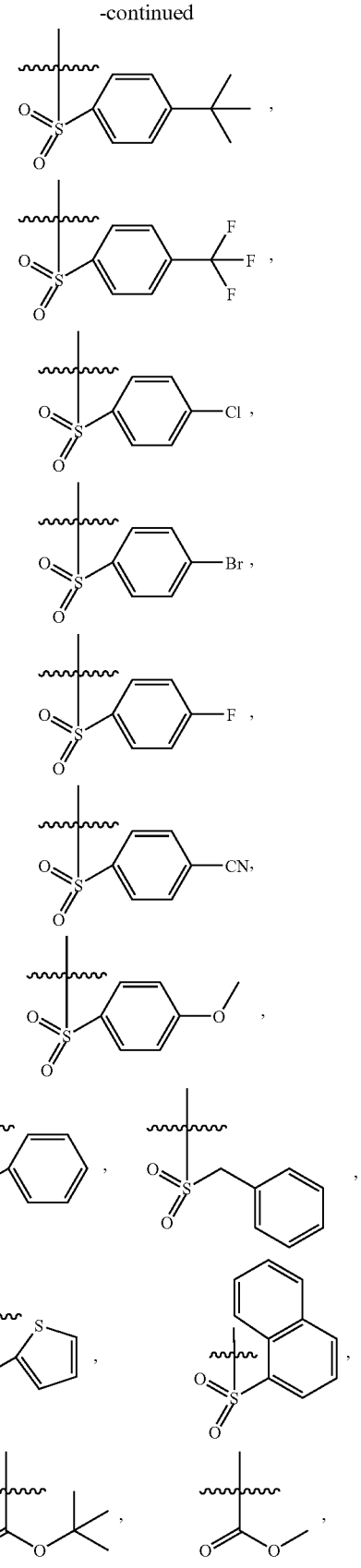

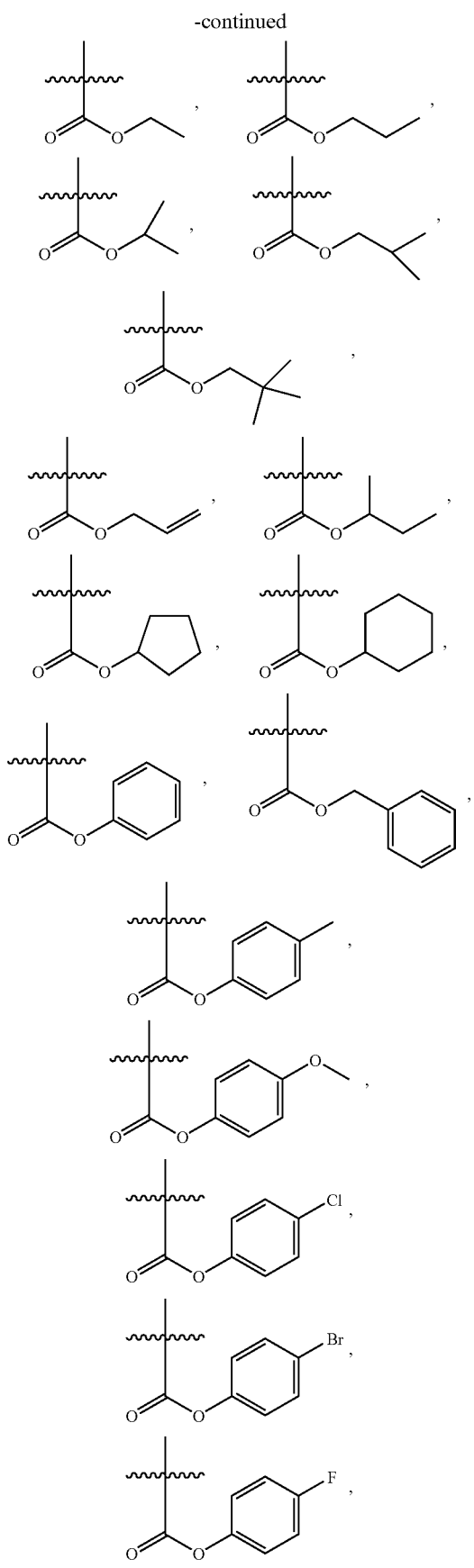

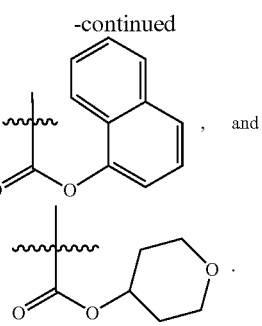, and

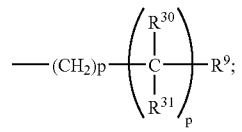.

11. A compound of the formula:

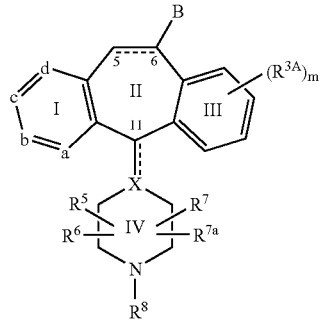

(1.4A)

or a pharmaceutically acceptable salt or solvate thereof, wherein:
- (A) a represents N or $N^{30}O^{31}$, and the remaining b, c, and d groups represent $CR^1$ wherein each $R^1$ group on each carbon is the same or different; or
- (B) the dotted lines (---) represent optional bonds;
- (C) X represents N and the optional bond (to C11) is absent;
- (D) B is the group:

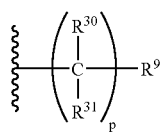

and in said B group:
- (1) p of the $—(CH_2)_p—$ moiety is 0;
- (2) p of the $$\begin{Bmatrix} R^{30} \\ | \\ -C- \\ | \\ R^{31} \end{Bmatrix}_p -R^9$$

moiety is 1;
- (3) $R^{30}$ is $—NHR^{9b}$ and $R^{31}$ is selected from the group consisting of: H and alkyl; and
- (4) $R^9$ is substituted imidazolyl substituted with one or more substituents selected from the group consisting of: alkyl;

(E) $R^1$ is selected from the group consisting of:
  (1) H;
  (2) halo;
  (3) —CE3;
  (4) —OR$^{10}$;
  (5) COR$^{10}$;
  (6) —SR$^{10}$;
  (7) —S(O)$_t$R$^{15}$;
  (8) —N(R$^{10}$)$_2$;
  (9) —NO$_2$;
  (10) —OC(O)R$^{10}$;
  (11) CO$_2$R$^{10}$;
  (12) —OCO$_2$R$^{15}$;
  (13) —CN;
  (14) —NR$^{10}$COOR$^{15}$;
  (15) —SR$^{15}$C(O)OR$^{15}$;
  (16) —SR$^{15}$N(R$^{13}$)$_2$ wherein each R$^{13}$ is independently selected from the group consisting of: H and —C(O)OR$^{15}$, and provided that R$^{15}$ in —SR$^{15}$N(R$^{13}$)$_2$ is not —CH$_2$;
  (17) benzotriazol-1-yloxy;
  (18) tetrazol-5-ylthio;
  (19) substituted tetrazol-5-ylthio;
  (20) alkynyl;
  (21) alkenyl;
  (22) alkyl;
  (23) alkyl substituted with one or more substitutents independently selected from the group consisting of: halogen, —OR$^{10}$ and —CO$_2$R$^{10}$;
  (24) alkenyl substituted with one or more substitutents independently selected from the group consisting of: halogen, —OR$^{10}$ and —CO$_2$R$^{10}$;
(F) Each $R^{3A}$ is independently selected from the group consisting of:
  (1) halo;
  (2) —CF$_3$;
  (3) —OR$^{10}$;
  (4) COR$^{10}$;
  (5) —SR$^{10}$;
  (6) —S(O)$_t$R$^{15}$;
  (7) —N(R$^{10}$)$_2$;
  (8) —NO$_2$;
  (9) —OC(O)R$^{10}$;
  (10) CO$_2$R$^{10}$;
  (11) —OCO$_2$R$^{15}$;
  (12) —CN;
  (13) —NR$^{10}$COOR$^{15}$;
  (14) —SR$^{15}$C(O)OR$^{15}$;
  (15) —SR$^{15}$N(R$^{13}$)$_2$ wherein each R$^{13}$ is independently selected from the group consisting of: H and —C(O)OR$^{15}$, and provided that R$^{15}$ in —SR$^{15}$N(R$^{13}$)$_2$ is not —CH$_2$;
  (16) benzotriazol-1-yloxy;
  (17) tetrazol-5-ylthio;
  (18) substituted tetrazol-5-ylthio;
  (19) alkynyl;
  (20) alkenyl;
  (21) alkyl;
  (22) alkyl substituted with one or more substitutents independently selected from the group consisting of: halogen, —OR$^{10}$ and —CO$_2$R$^{10}$; and
  (23) alkenyl substituted with one or more (e.g., 1, 2 or 3) substitutents independently selected from the group consisting of: halogen, —OR$^{10}$ and —CO$_2$R$^{10}$;
(G) m is 0, 1 or 2;
(H) t is 0, 1 or 2

(I) $R^5$, $R^6$, $R^7$ and $R^{7a}$ are each independently selected from the group consisting of:
  (1) H;
  (2) —CF$_3$;
  (3) —COR$^{13}$;
  (4) alkyl;
  (5) unsubstituted aryl;
  (6) alkyl substituted with one or more groups selected from the group consisting of: —S(O)$_t$R$^{15}$, —NR$^{10}$COOR$^{15}$, —C(O)R$^{10}$, and —CO$_2$R$^{10}$; and
  (7) aryl substituted with one or more groups selected from the group consisting of: —S(O)$_t$R$^{15}$, —NR$^{10}$COOR$^{15}$, —C(O)R$^{10}$, and —CO$_2$R$^{10}$; or
(J) $R^5$ together with $R^6$ represents =O or =S;
(K) $R^8$ is selected from the group consisting of:

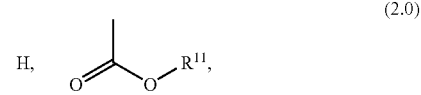
(2.0)

(3.0)

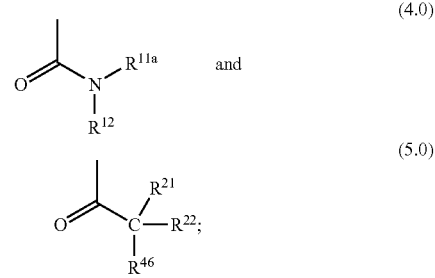
and
(4.0)

(5.0)

(L) $R^{9a}$ is selected from the group consisting of: alky and arylalkyl;
(M) $R^{9b}$ is selected from the group consisting of:
  (1) —C(O)R$^{9a}$;
  (2) —SO$_2$R$^{9a}$;
  (3) —C(O)NHR$^{9a}$;
  (4) —C(O)OR$^{9a}$; and
  (5) —C(O)N(R$^{9c}$)$_2$;
(N) Each $R^{9c}$ is independently selected from the group consisting of: H, alkyl and arylalkyl;
(O) $R^{10}$ is selected from the group consisting of: H; alkyl; aryl and arylalkyl;
(P) $R^{11}$ is selected from the group consisting of:
  (1) alkyl;
  (2) substituted alkyl;
  (3) unsubstituted aryl;
  (4) substituted aryl;
  (5) unsubstituted cycloalkyl;
  (6) substituted cycloalkyl;
  (7) unsubstituted heteroaryl;
  (8) substituted heteroaryl;
  (9) heterocycloalkyl; and
  (10) substituted heterocycloalkyl;
wherein said substituted alkyl, substituted cycloalkyl, and substituted heterocycloalkyl $R^{11}$ groups are substituted with one or more substituents selected from the group consisting of:

(1) —OH;
(2) fluoro; and
(3) alkyl; and wherein said substituted aryl and substituted heteroaryl $R^{11}$ groups are substituted with one or more substituents selected from the group consisting of:
(1) —OH;
(2) halogen; and
(3) alkyl;

(Q) $R^{11a}$ is selected from the group consisting of:
(1) H;
(2) OH;
(3) alkyl;
(4) substituted alkyl;
(5) unsubstituted aryl;
(6) substituted aryl;
(7) unsubstituted cycloalkyl;
(8) substituted cycloalkyl;
(9) unsubstituted heteroaryl;
(10) substituted heteroaryl;
(11) heterocycloalkyl; and
(12) substituted heterocycloalkyl;

wherein said substituted alkyl, substituted cycloalkyl, and substituted heterocycloalkyl $R^{11a}$ groups are substituted with one or more substituents selected from the group consisting of:
(1) —OH;
(2) —CN;
(3) —CF$_3$;
(4) fluoro;
(5) alkyl;
(6) cycloalkyl;
(7) heterocycloalkyl;
(8) arylalkyl;
(9) heteroarylalkyl;
(10) alkenyland
(11) heteroalkenyl; and wherein said substituted aryl and substituted heteroaryl $R^{11a}$ groups are substituted with one or more substituents selected from the group consisting of:
(1) —OH;
(2) —CN;
(3) —CF$_3$;
(4) halogen;
(5) alkyl;
(6) cycloalkyl;
(7) heterocycloalkyl;
(8) arylalkyl;
(9) heteroarylalkyl;
(10) alkenyl and
(11) heteroalkenyl;

(R) R is selected from the group consisting of: H, alkyl, piperidine Ring V, cycloalkyl, and -alkyl-(piperidine ring V);
(S) $R^{15}$ is selected from the group consisting of: alkyl and aryl;
(T) $R^{21}$, $R^{22}$ and $R^{46}$ are independently selected from the group consisting of:
(1) H;
(2) alkyl;
(3) unsubstituted aryl;
(4) substituted aryl substituted with one or more substituents independently selected from the group consisting of: alkyl, halogen, CF$_3$ and OH;
(5) unsubstituted cycloalkyl;
(6) substituted cycloalkyl substituted with one or more substituents independently selected from: alkyl, halogen, CF$_3$ or OH;
(7) heteroaryl of the formula,

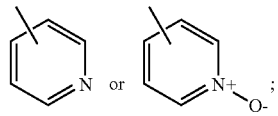

(8) piperidine Ring V:

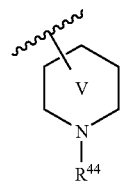

wherein $R^{44}$ is selected from the group consisting of:
(a) H,
(b) alkyl;
(c) alkylcarbonyl;
(d) alkyloxy carbonyl;
(e) haloalkyl; and
(f) —C(O)NH($R^{51}$);

(9) —NH$_2$ provided that only one of $R^{21}$, $R^{22}$, and $R^{46}$ group can be —NH$_2$, and provided that when one of $R^{21}$, $R^{22}$, and $R^{46}$ is —NH$_2$ then the remaining groups are not —OH;
(10) —OH provided that only one of $R^{21}$, $R^{22}$, and $R^{46}$ group can be —OH, and provided that when one of $R^{21}$, $R^{22}$, and $R^{46}$ is —OH then the remaining groups are not NH$_2$; and
(11) alkyl substituted with one or more substituents selected from the group consisting of: —OH and —NH$_2$, and provided that there is only one —OH or one —NH$_2$ group on a substituted carbon; or
(12) $R^{21}$ and $R^{22}$ taken together with the carbon to which they are bound form a cyclic ring selected from the group consisting of:
(a) unsubstituted cycloalkyl;
(b) cycloalkyl substituted with one or more substituents independently selected from the group consisting of: alkyl, halogen, CF$_3$ and OH;
(c) unsubstituted cycloalkenyl;
(d) cycloalkenyl substituted with one or more substituents independently selected from the group consisting of: alkyl, halogen, CF$_3$ and OH; (e) heterocycloalkyl of the formula:

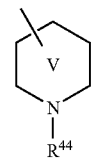

wherein R$^{44}$ is selected from the group consisting of:
(1) —H,
(2) alkyl;
(3) alkylcarbonyl;
(4) alkyloxy carbonyl;
(5) haloalkyl; and
(6) —C(O)NH(R$^{51}$);
(f) unsubstituted aryl;
(g) aryl substituted with one or more substituents independently selected from the group consisting of: alkyl, halogen, —CN, —CF$_3$, OH and alkoxy; and
(i) heteroaryl selected from the group consisting of:

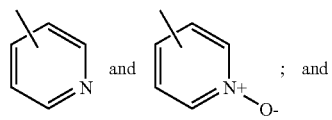

(U) R$^{51}$ is selected from the group consisting of: —H and alkyl; and
(V) provided that a ring carbon atom adjacent to a ring heteroatom in a substituted heterocycloalkyl moiety is not substituted with a heteroatom or a halo atom; and
(W) provided that a ring carbon atom, that is not adjacent to a ring heteroatom, in a substituted heterocycloalkyl moiety, is not substituted with more than one heteroatom; and
(X) provided that a ring carbon atom, that is not adjacent to a ring heteroatom, in a substituted heterocycloalkyl moiety, is not substituted with a heteroatom and a halo atom; and
(Y) provided that a ring carbon in a substituted cycloalkyl moiety is not substituted with more than one heteroatom; and
(Z) provided that a carbon atom in a substituted alkyl moiety is not substituted with more than one heteroatom; and
(AA) provided that the same carbon atom in a substituted alkyl moiety is not substituted with both heteroatoms and halo atoms.

12. The compound of claim 11 wherein:
(1) b, c and d are CR$^1$ groups wherein all of said R$^1$ substituents are H, or one R$^1$ substituent is halo and the remaining two R$^1$ substituents are hydrogen; and
(2) m is 1, and R$^{3A}$ is halo, or m is 2 and each R$^{3A}$ is the same or different halo.

13. The compound of claim 12 wherein said substituted imidazolyl is:

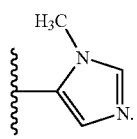

14. The compound of claim 13 wherein m is 1 and R$^{3A}$ is halo.

15. The compound of claim 14 wherein said halo is Cl.

16. The compound of claim 15 wherein said Cl is bound to C-8.

17. The compound of claim 16 wherein b, c and d are CR$^1$ groups wherein all of said R$^1$ substituents are H.

18. The compound of claim 17 wherein R$^8$ is 2.0.

19. The compound of claim 18 wherein R$^{11}$ is alkyl.

20. The compound of claim 19 wherein said alkyl is selected from the group consisting of: isopropyl and t-butyl.

21. The compound of claim 20 wherein said alkyl is isopropyl.

22. A compound of the formula:

(1.4F)

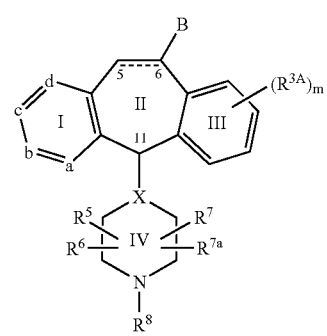

or a pharmaceutically acceptable salt or solvate thereof, wherein the dotted line (---) represents an optional bond, and wherein:
(A) B is the group:

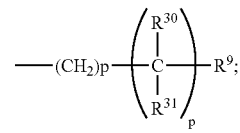

wherein in said B group:
(1) p of the —(CH$_2$)$_p$— moiety is 0;
(2) p of the

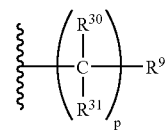

moiety is 1;
(3) R$^{30}$ is —NHR$^{9b}$ and R$^{31}$ is selected from the group consisting of: H
(4) R$^9$ is substituted imidazolyl substituted with one or more substituents selected from the group consisting of: alkyl;
(B) a is N;
(C) b, c and d are CR$^1$ groups wherein all of said R$^1$ substituents are H, or one R$^1$ substituent is halo and the remaining two R$^1$ substituents are hydrogen;
(D) m is 1, and R$^{3A}$ is halo, or m is 2 and each R$^{3A}$ is the same or different halo;
(E) X is N;
(F) R$^5$, R$^6$, R$^7$, and R$^{7a}$ are H;

(G) $R^8$ is selected from the group consisting of:

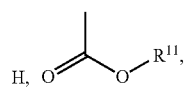 (2.0)

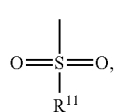 (3.0)

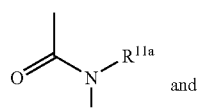 and (4.0)

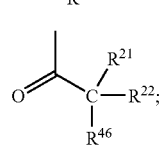 (5.0)

(H) $R^{9a}$ is selected from the group consisting of: alky and arylalkyl;
(I) $R^{9b}$ is selected from the group consisting of:
  (1) —C(O)$R^{9a}$;
  (2) —SO$_2$$R^{9a}$;
  (3) —C(O)NH$R^{9a}$;
  (4) —C(O)O$R^{9a}$; and
  (5) —C(O)N($R^{9c}$)$_2$;
(J) Each $R^{9c}$ is independently selected from the group consisting of: H, alkyl and arylalkyl;
(K) $R^{11}$ is selected from the group consisting of:
  (1) alkyl;
  (2) substituted alkyl;
  (3) unsubstituted aryl;
  (4) substituted aryl;
  (5) unsubstituted cycloalkyl;
  (6) substituted cycloalkyl;
  (7) unsubstituted heteroaryl;
  (8) substituted heteroaryl;
  (9) heterocycloalkyl; and
  (10) substituted heterocycloalkyl;
wherein said substituted alkyl, substituted cycloalkyl, and substituted heterocycloalkyl $R^{11}$ groups are substituted with one or more substituents selected from the group consisting of:
  (1) —OH;
  (2) fluoro; and
  (3) alkyl; and
wherein said substituted aryl and substituted heteroaryl $R^{11}$ groups are substituted with one or more substituents selected from the group consisting of:
  (1) —OH;
  (2) halogen; and
  (3) alkyl;
(L) $R^{11a}$ is selected from the group consisting of:
  (1) H;
  (2) OH;
  (3) alkyl;
  (4) substituted alkyl;
  (5) unsubstituted aryl;
  (6) substituted aryl;
  (7) unsubstituted cycloalkyl;
  (8) substituted cycloalkyl;
  (9) unsubstituted heteroaryl;
  (10) substituted heteroaryl;
  (11) heterocycloalkyl; and
  (12) substituted heterocycloalkyl;
wherein said substituted alkyl, substituted cycloalkyl, and substituted heterocycloatkyl $R^{11a}$ groups are substituted with one or more substituents selected from the group consisting of:
  (1) —OH;
  (2) —CN;
  (3) —CF$_3$;
  (4) fluoro;
  (5) alkyl;
  (6) cycloalkyl;
  (7) heterocycloalkyl;
  (8) arylalkyl;
  (9) heteroarylalkyl;
  (10) alkenyl and
  (11) heteroalkenyl; and
wherein said substituted aryl and substituted heteroaryl $R^{11a}$ groups are substituted with one or more substituents selected from the group consisting of:
  (1) —OH;
  (2) —CN;
  (3) —CF$_3$;
  (4) halogen (e.g Br, Cl or F);
  (5) alkyl;
  (6) cycloalkyl;
  (7) heterocycloalkyl;
  (8) arylalkyl;
  (9) heteroarylalkyl;
  (10) alkenyl and
  (11) heteroalkenyl;
(M) $R^{12}$ is selected from the group consisting of: H, alkyl, piperidine ring V, cycloalkyl, and -alkyl-(piperidine ring V);
(N) $R^{21}$, $R^{22}$ and $R^{46}$ are independently selected from the group consisting of:
  (1) H;
  (2) alkyl;
  (3) unsubstituted aryl;
  (4) substituted aryl substituted with one or more substituents independently selected from the group consisting of: alkyl, halogen, CF$_3$ and OH;
  (5) unsubstituted cycloalkyl;
  (6) substituted cycloalkyl substituted with one or more substituents independently selected from: alkyl, halogen, CF$_3$ or OH;
  (7) heteroaryl of the formula,

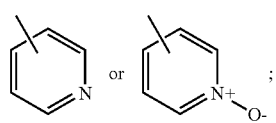

(8) piperidine ring V:

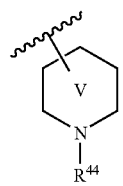

wherein $R^{44}$ is selected from the group consisting of:
(a) H,
(b) alkyl;
(c) alkylcarbonyl;
(d) alkyloxy carbonyl;
(e) haloalkyl; and
(f) —C(O)NH($R^{51}$);
(9) —$NH_2$ provided that only one of $R^{21}$, $R^{22}$, and $R^{46}$ group can be —$NH_2$, and provided that when one of $R^{21}$, $R^{22}$, and $R^{46}$ is —$NH_2$ then the remaining groups are not —OH;
(10) —OH provided that only one of $R^{21}$, $R^{22}$, and $R^{46}$ group can be —OH, and provided that when one of $R^{21}$, $R^{22}$, and $R^{46}$ is —OH then the remaining groups are not —$NH_2$; and
(11) alkyl substituted with one or more substituents selected from the group consisting of: —OH and —$NH_2$, and provided that there is only one —OH or one —$NH_2$ group on a substituted carbon; or
(12) $R^{21}$ and $R^{22}$ taken together with the carbon to which they are bound form a cyclic ring selected from the group consisting of:
(a) unsubstituted cycloalkyl;
(b) cycloalkyl substituted with one or more substituents independently selected from the group consisting of: alkyl, halogen, $CF_3$ and OH;
(c) unsubstituted cycloalkenyl;
(d) cycloalkenyl substituted with one or more substituents independently selected from the group consisting of: alkyl, halogen, $CF_3$ and OH;
(e) heterocycloalkyl of the formula:

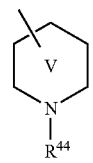

wherein $R^{44}$ is selected from the group consisting of:
(1) —H,
(2) alkyl;
(3) alkylcarbonyl;
(4) alkyloxy carbonyl;
(5) haloalkyl; and
(6) —C(O)NH($R^{51}$);
(f) unsubstituted aryl;

(g) aryl substituted with one or more substituents independently selected from the group consisting of: alkyl, halogen, —CN, —$CF_3$, OH and alkoxy; and
(i) heteroaryl selected from the group consisting of:

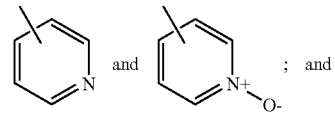

(V) $R^{51}$ is selected from the group consisting of: —H and alkyl; and
(W) rovided that a ring carbon atom adjacent to a ring heteroatom in a substituted heterocycloalkyl moiety is not substituted with a heteroatom or a halo atom; and
(X) provided that a ring carbon atom, that is not adjacent to a ring heteroatom, in a substituted heterocycloalkyl moiety, is not substituted with more than one heteroatom; and
(Y) provided that a ring carbon atom, that is not adjacent to a ring heteroatom, in a substituted heterocycloalkyl moiety, is not substituted with a heteroatom and a halo atom; and
(Z) provided that a ring carbon in a substituted cycloalkyl moiety is not substituted with more than one heteroatom; and
(AA) provided that a carbon atom in a substituted alkyl moiety is not substituted with more than one heteroatom; and
(AB) provided that the same carbon atom in a substituted alkyl moiety is not substituted with both heteroatoms and halo atoms.

23. The compound of claim 22 wherein said substituted imidazolyl is:

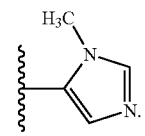

24. The compound of claim 23 wherein m is 1 and $R^{3.4}$ is halo.
25. The compound of claim 24 wherein said halo is Cl.
26. The compound of claim 25 wherein said Cl is bound to C-8.
27. The compound of claim 25 wherein b, c and d are $CR^1$ groups wherein all of said $R^1$ substituents are H.
28. The compound of claim 27 wherein $R^8$ is 2.0.
29. The compound of claim 28 wherein $R^{11}$ is alkyl.
30. The compound of claim 29 wherein said alkyl is selected from the group consisting of: isopropyl and t-butyl.
31. The compound of claim 30 wherein said alkyl is isopropyl.

32. The compound of claim 22 having the structure:
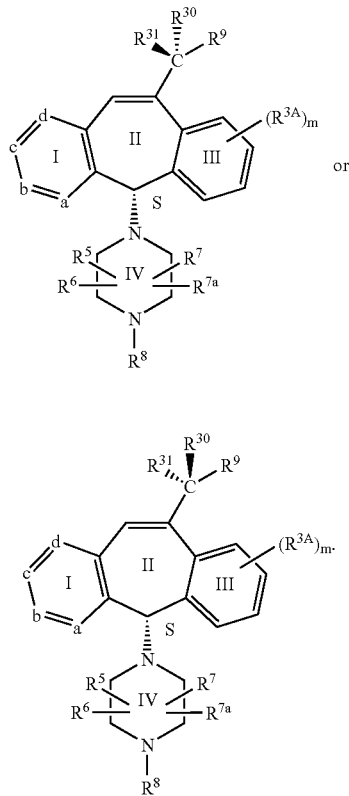
(1.6A)
or
(1.7A)
33. The compound of claim 22 wherein B is selected from the group consisting of:
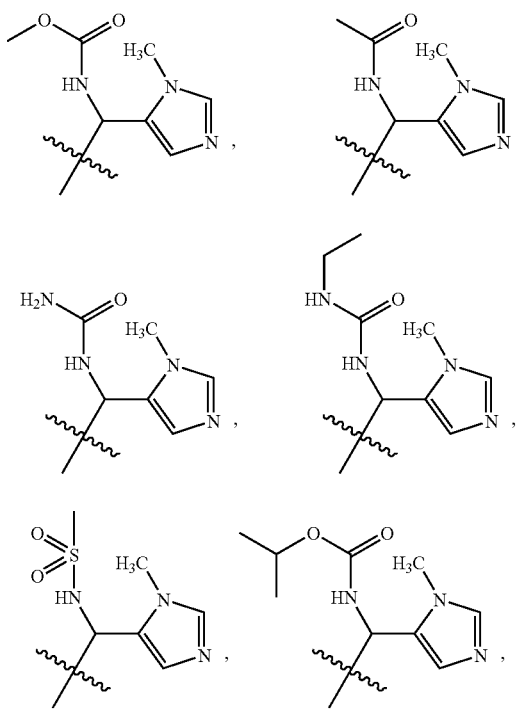
34. The compound of claim 22 wherein B is selected from the group consisting of:
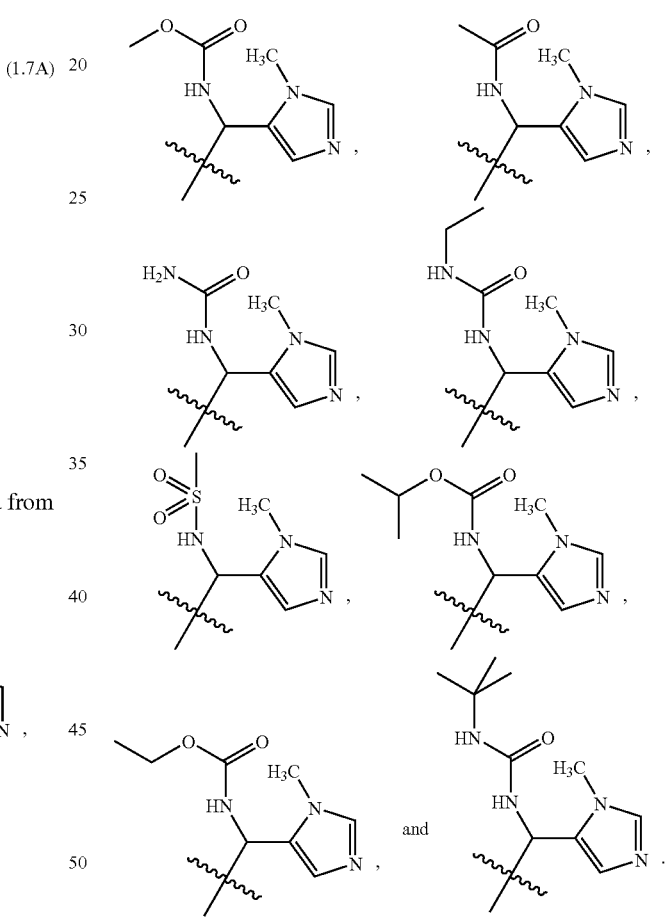
35. The compound of claim 22 wherein B is:
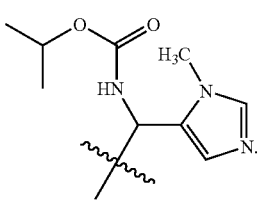
36. The compound of claim 22 wherein $R^8$ is selected from the group consisting of:

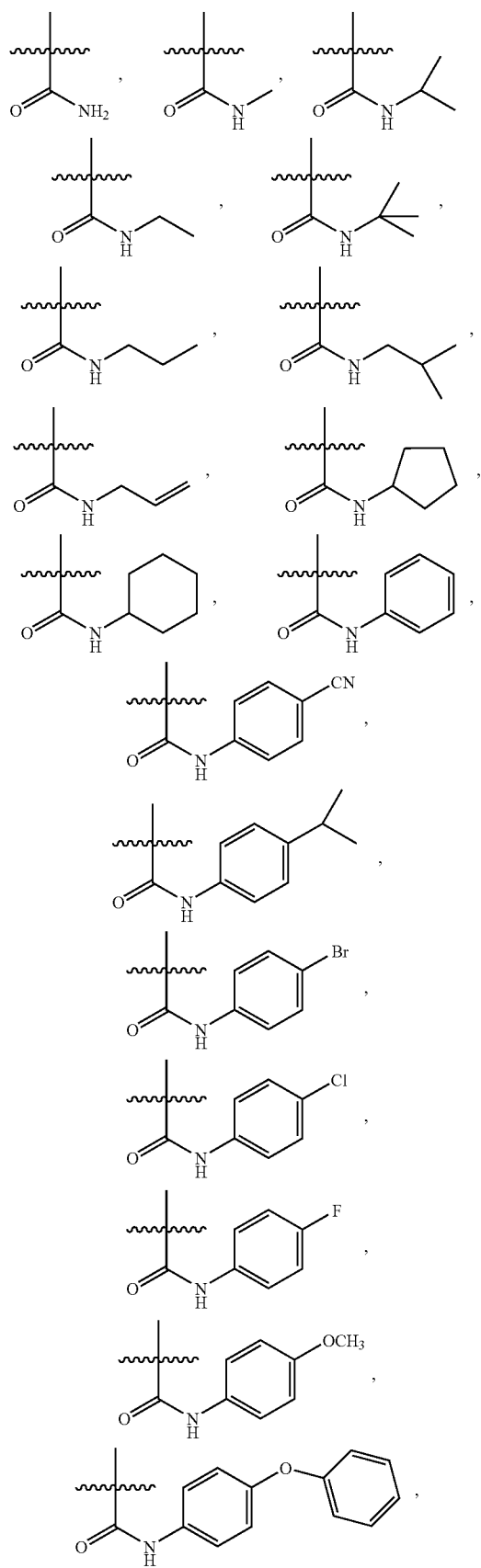
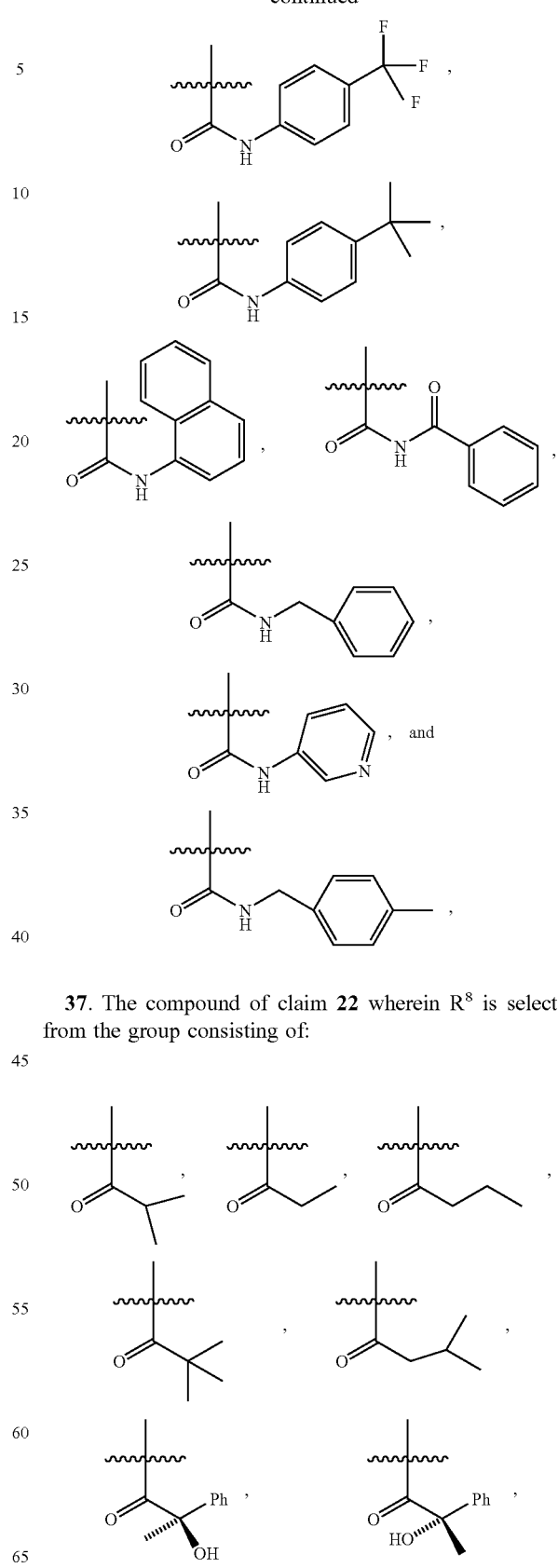
37. The compound of claim 22 wherein $R^8$ is selected from the group consisting of:
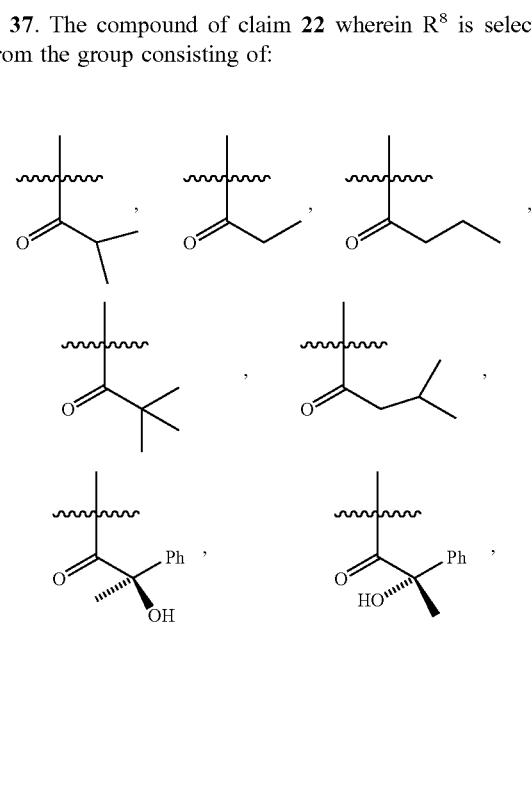

-continued
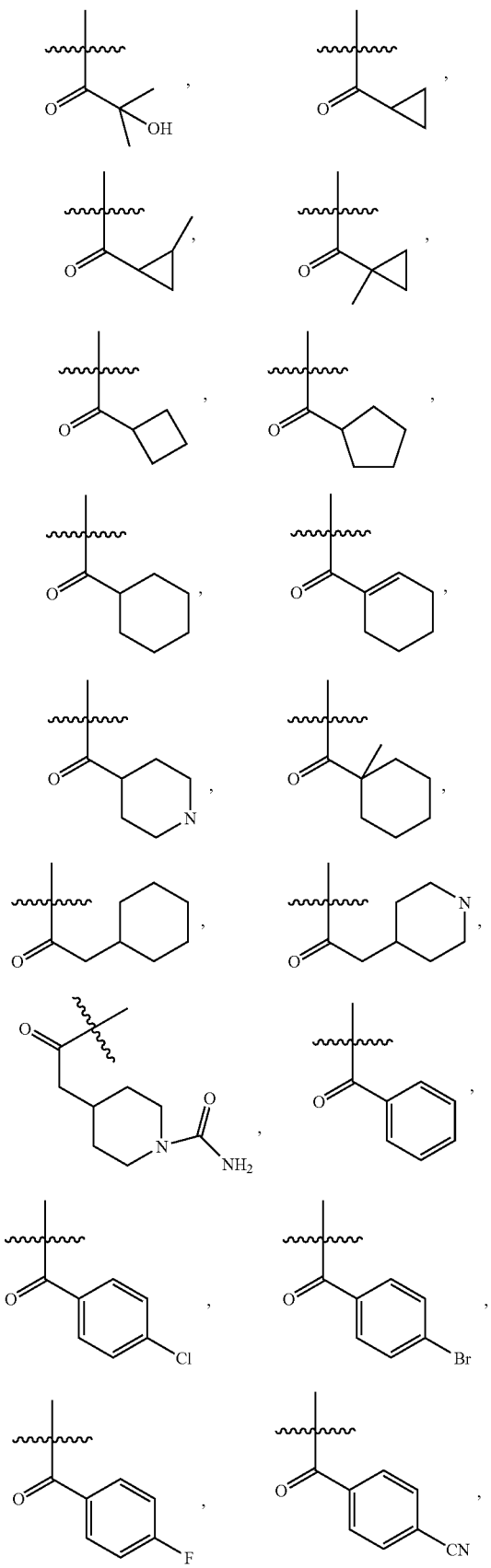
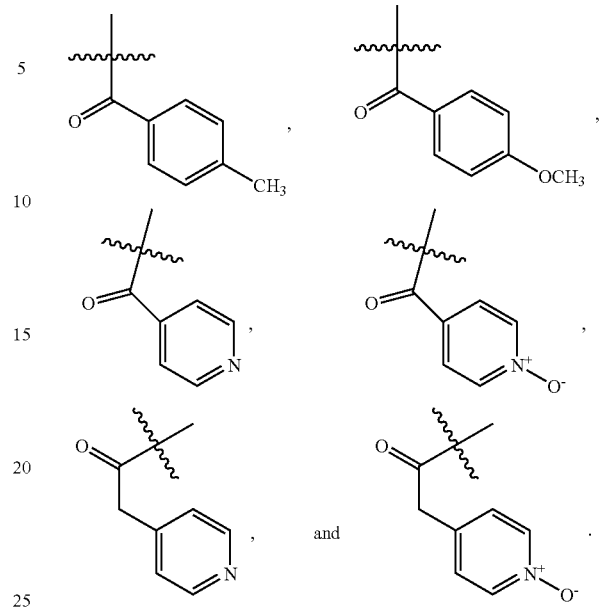
and
38. The compound of claim 22 wherein $R^8$ is selected from the group consisting of:
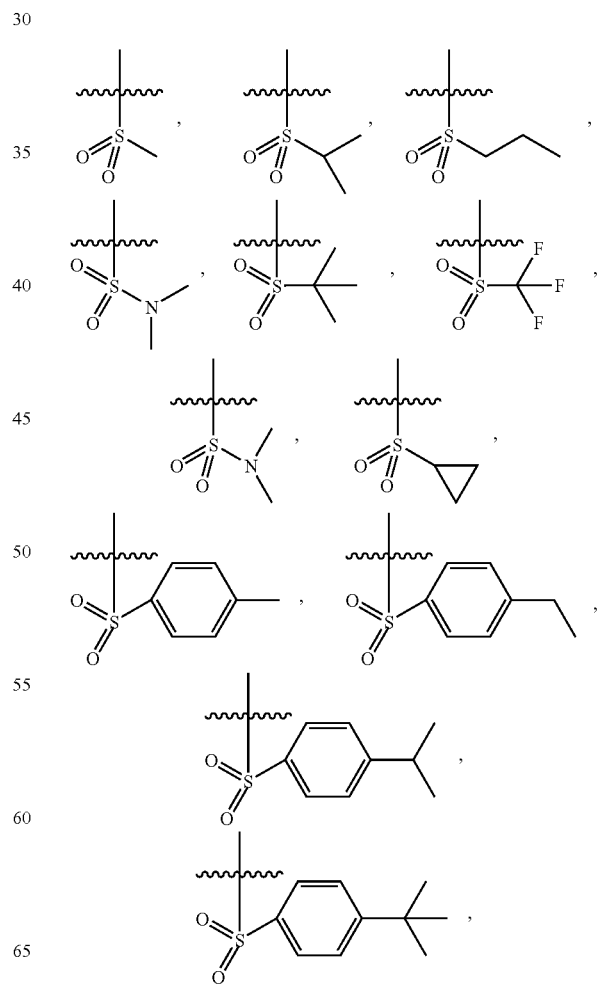

-continued
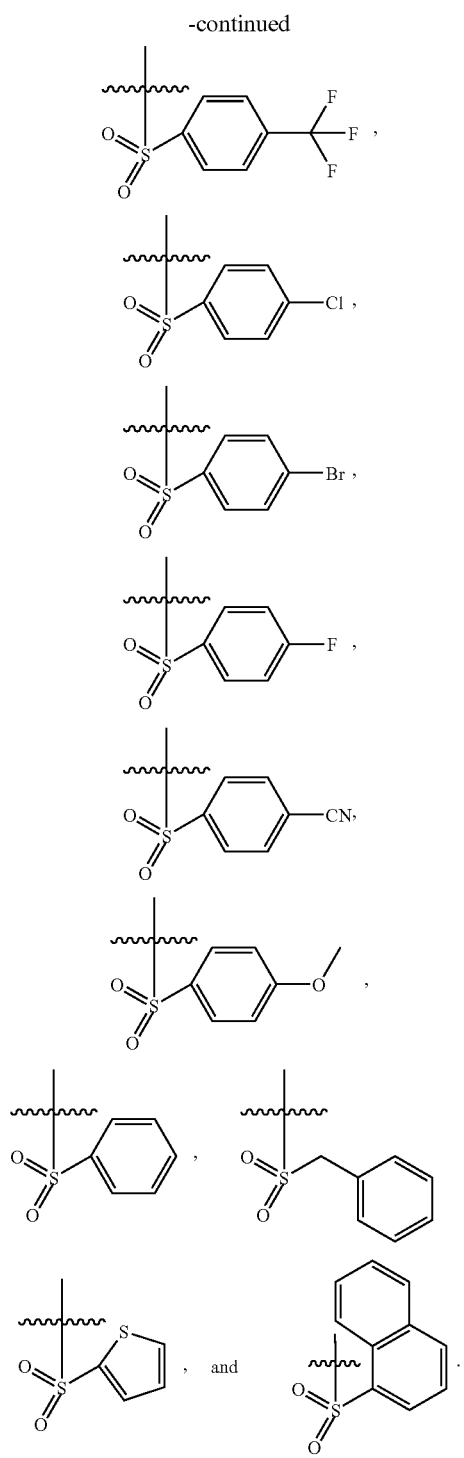
39. The compound of claim 22 wherein $R^8$ is selected from the group consisting of:
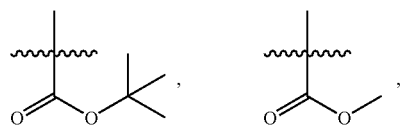
-continued
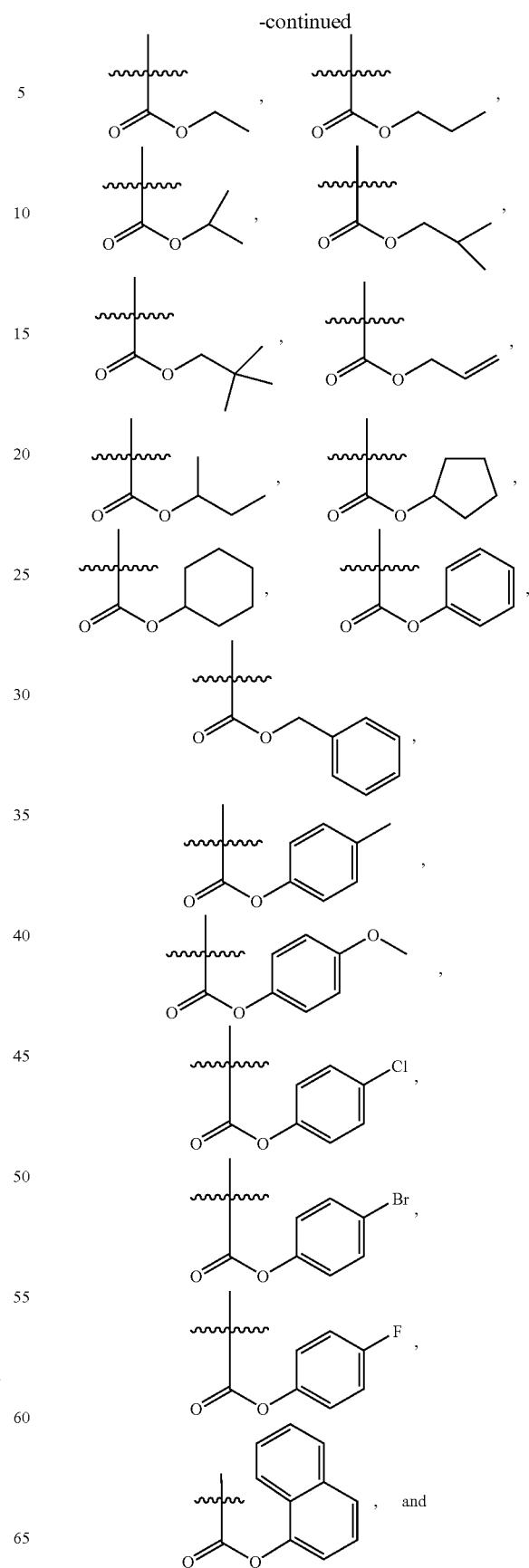

-continued
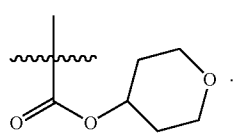
40. The compound of claim 1 selected from the group consisting of:
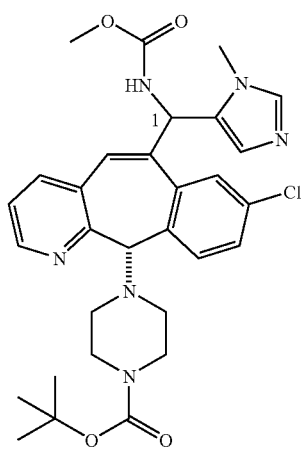
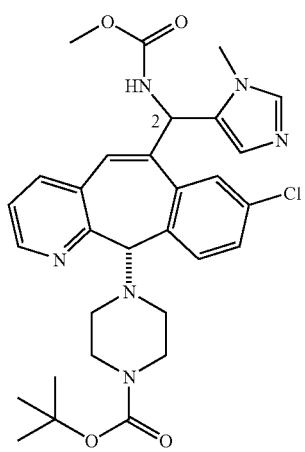
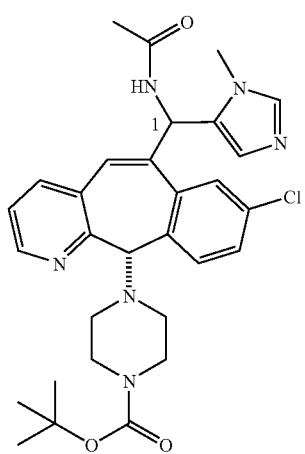
-continued
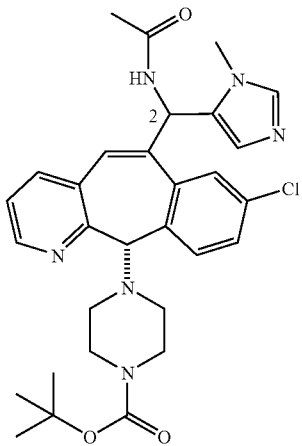
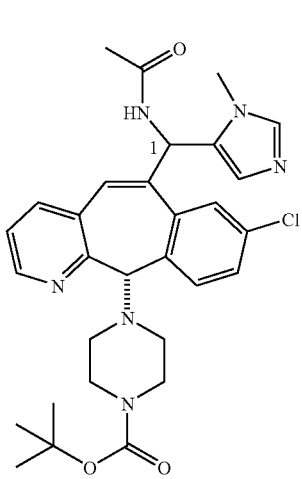
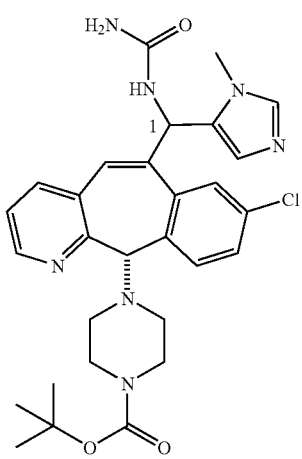

1211
-continued
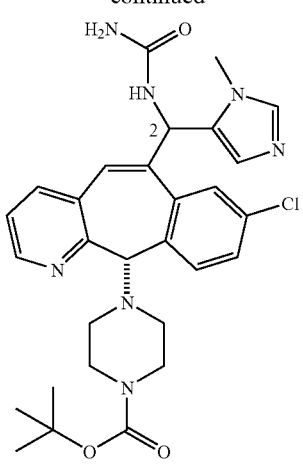
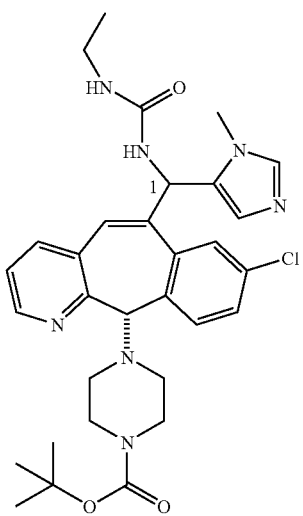
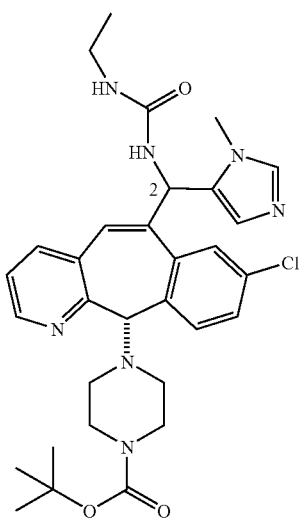
1212
-continued
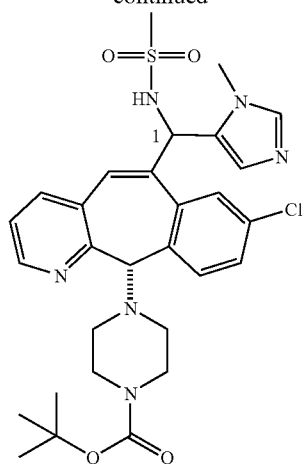
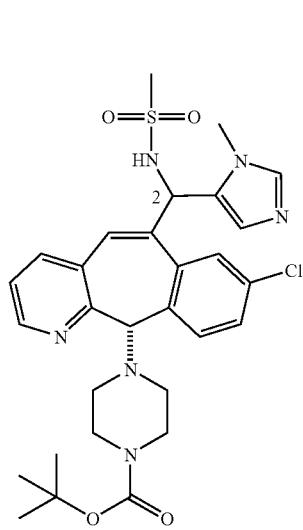
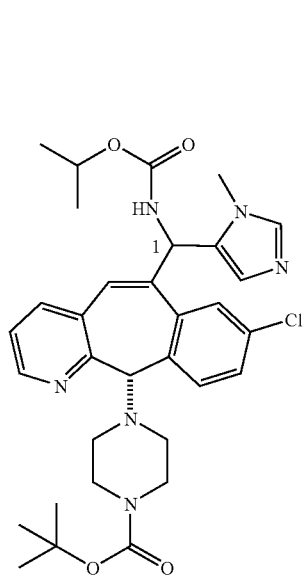

1213
-continued

1214
-continued

1215

-continued

1216

-continued

1217
-continued
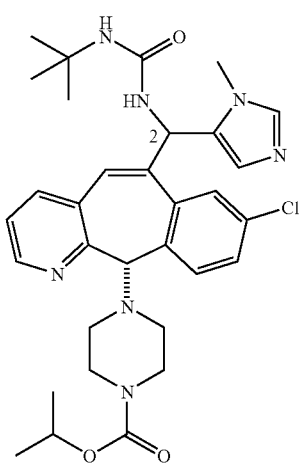
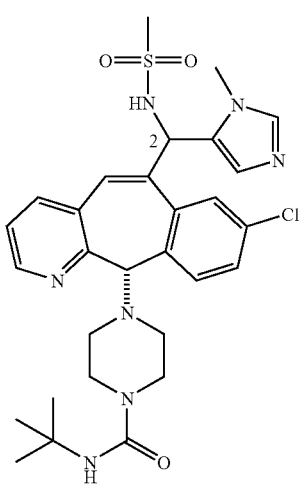
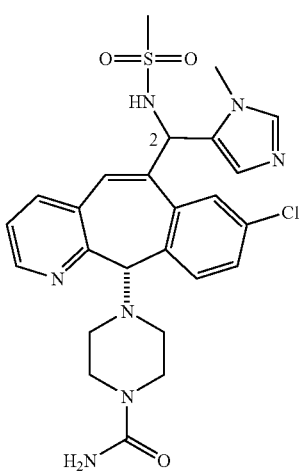
1218
-continued
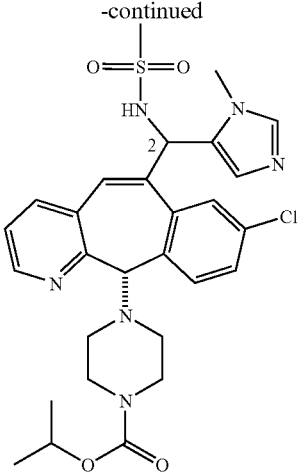
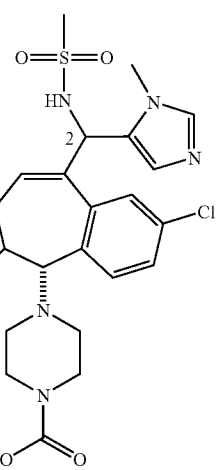
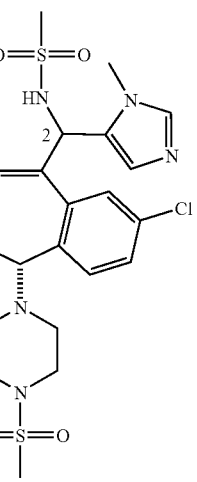

1219
-continued
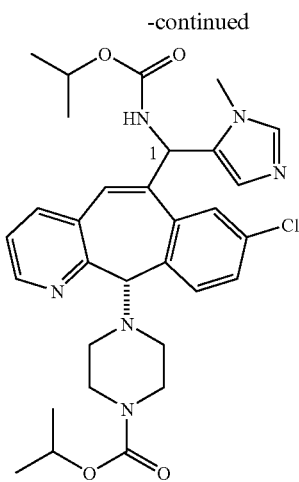
and
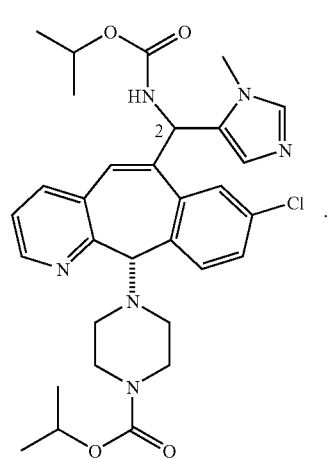
41. The compound of claim 1 selected from the group consisting of:
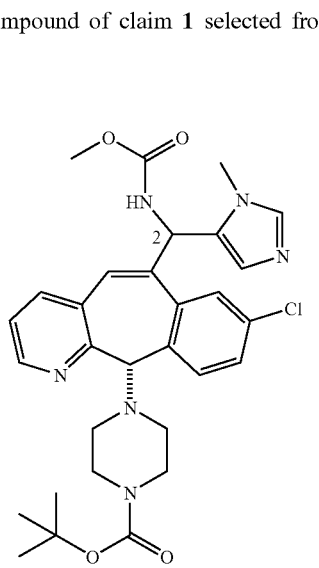
1220
-continued
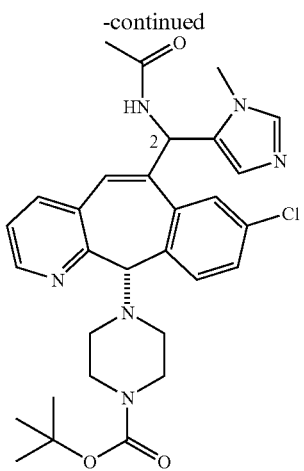
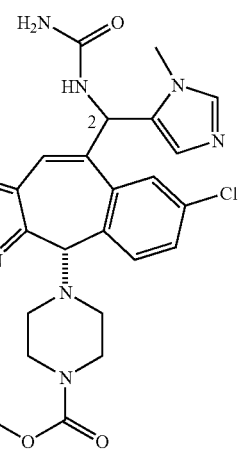
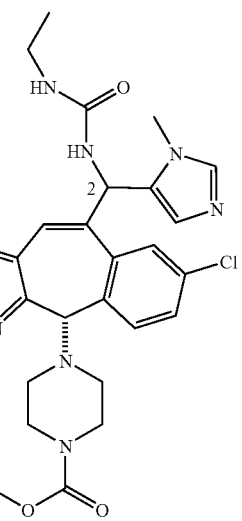

1221
-continued
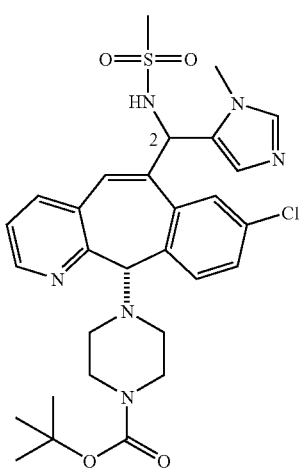
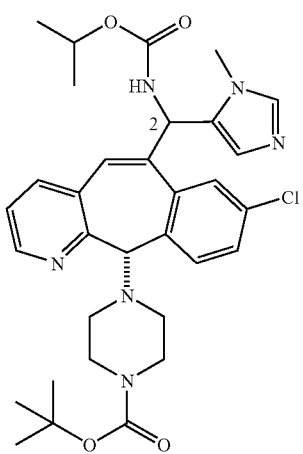
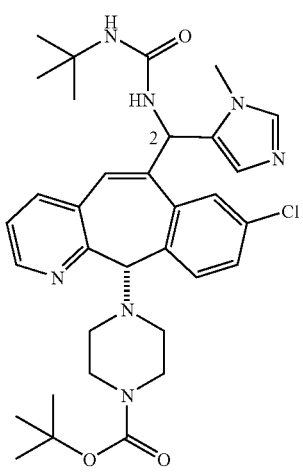
1222
-continued
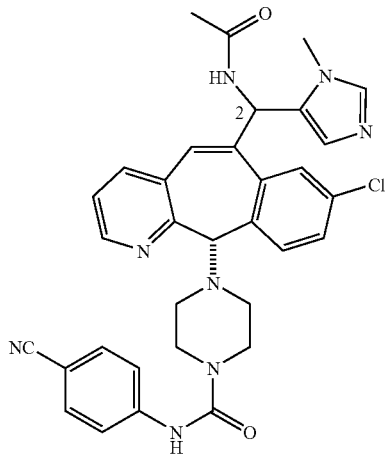
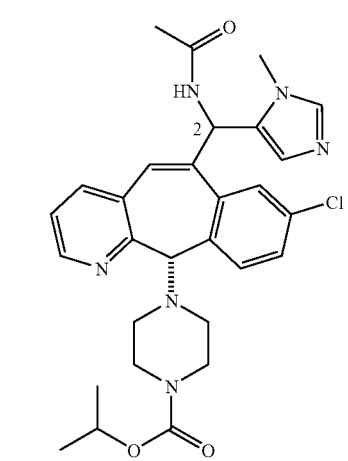
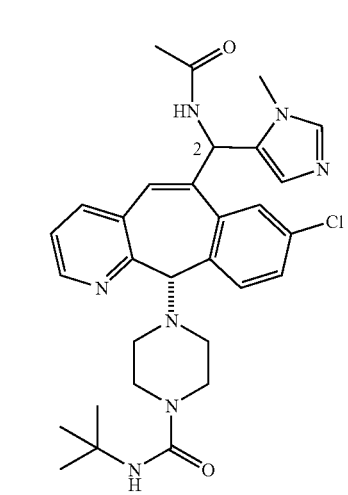

1223
-continued
1224
-continued
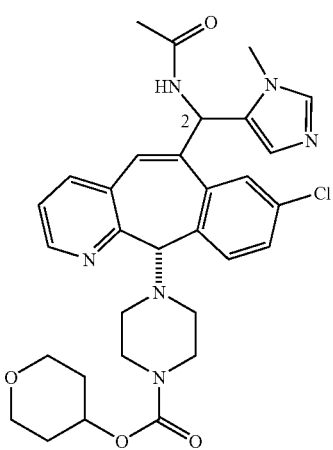
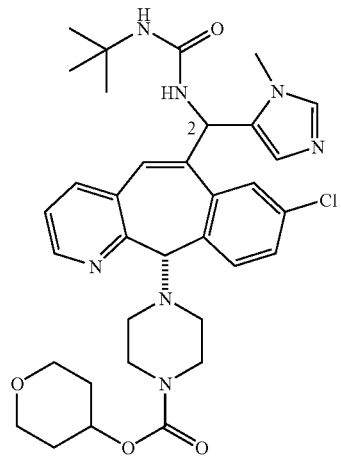

1225
-continued
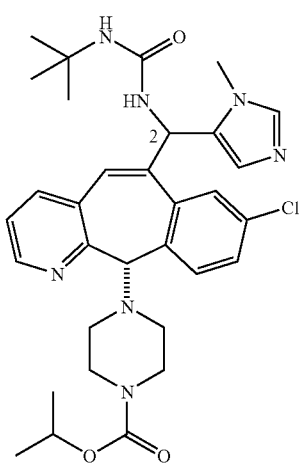
1226
-continued
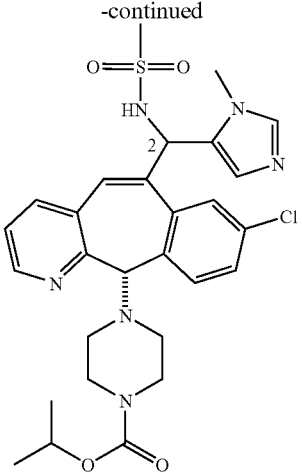
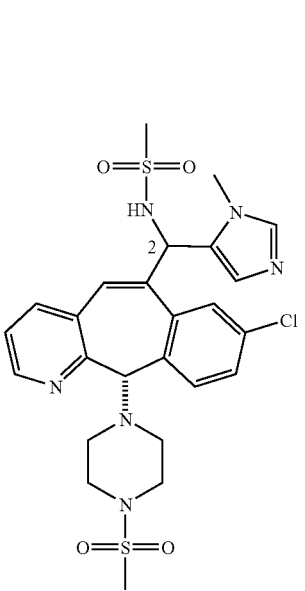
and 1227
-continued
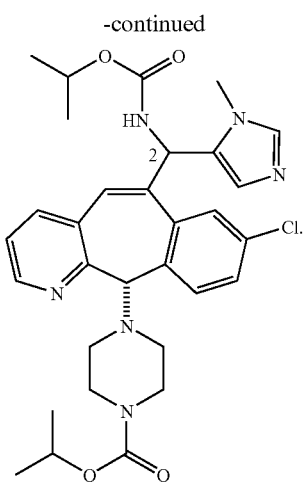
42. The compound of claim 1 selected from the group consisting of:
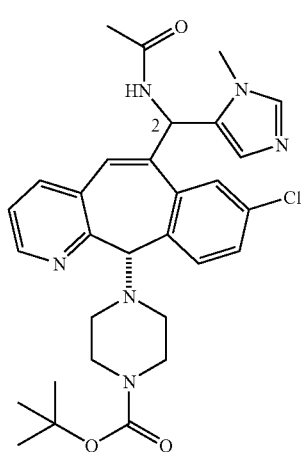
1228
-continued
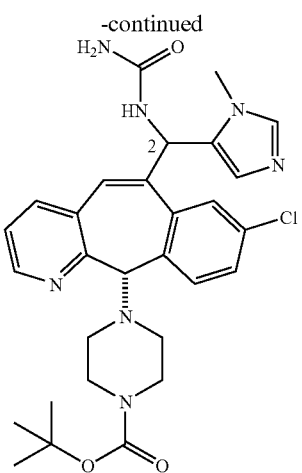
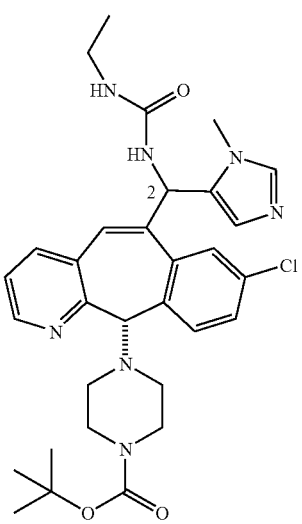
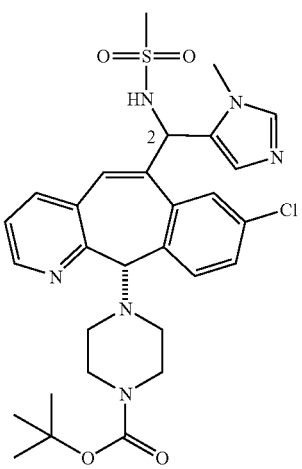

1229
-continued
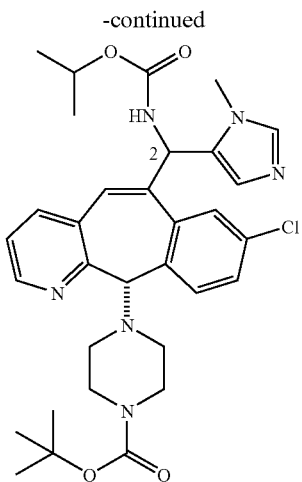
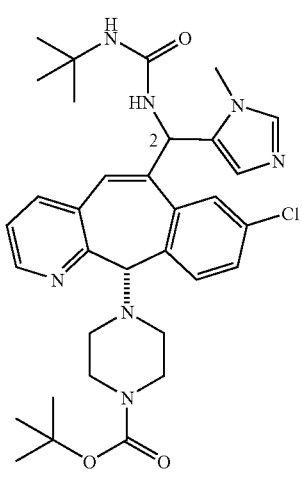
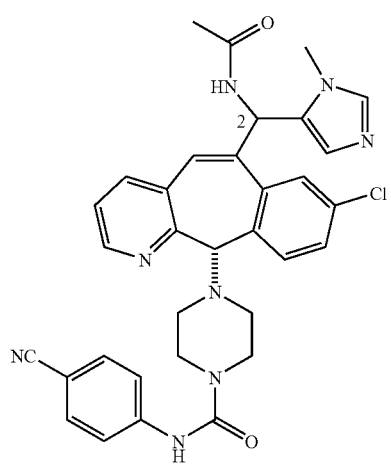
1230
-continued
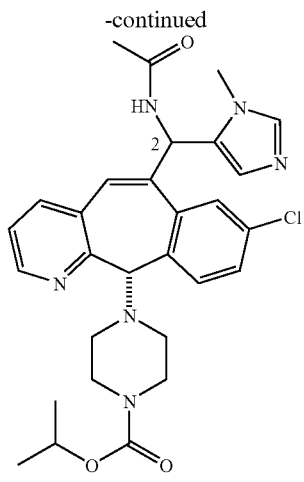
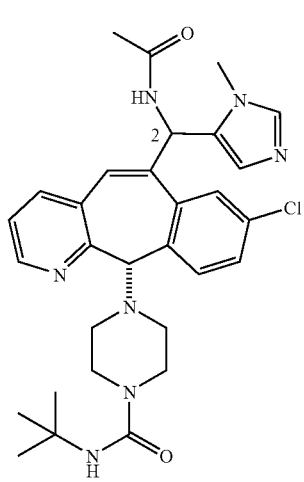
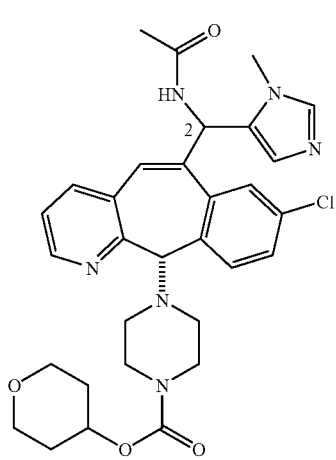

1231
-continued
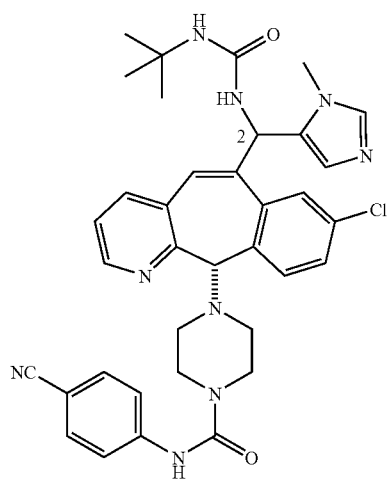
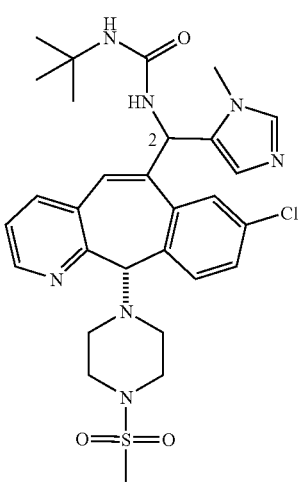
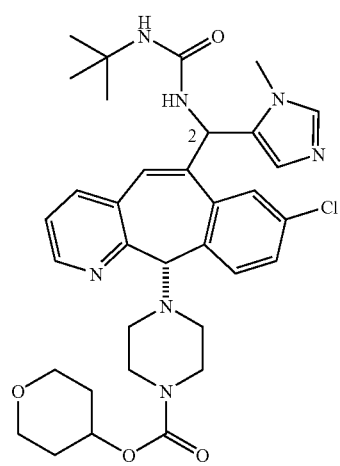
1232
-continued
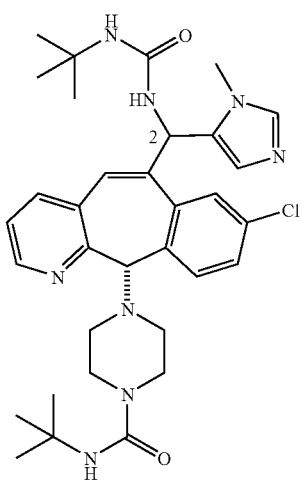
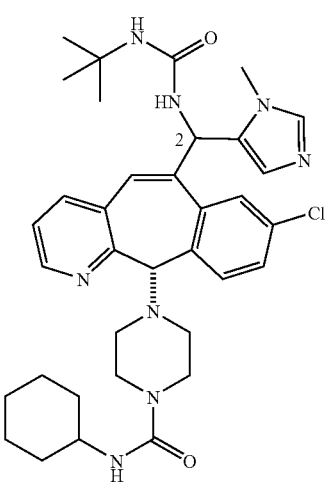
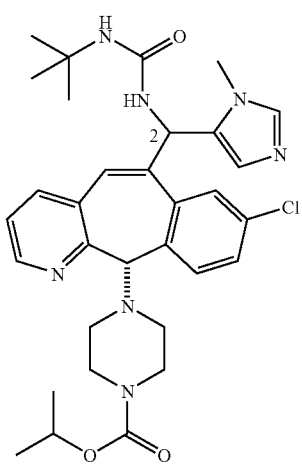

1233
-continued
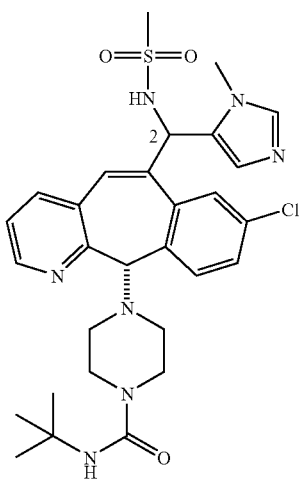
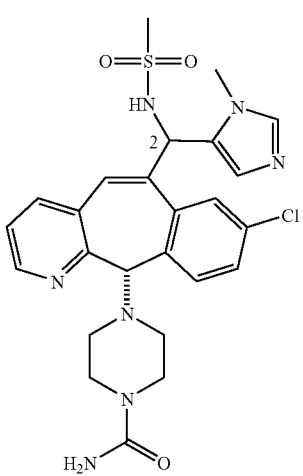
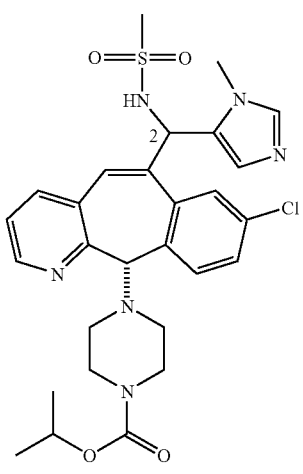
1234
-continued
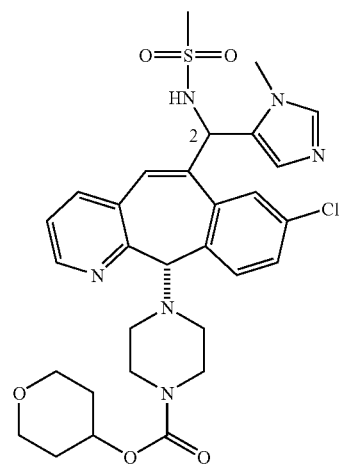
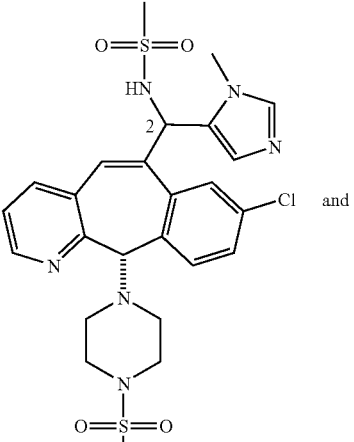
and
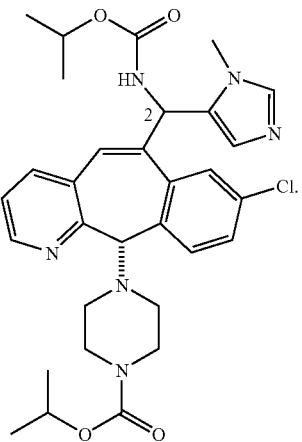

43. The compound of claim 1 having the formula:
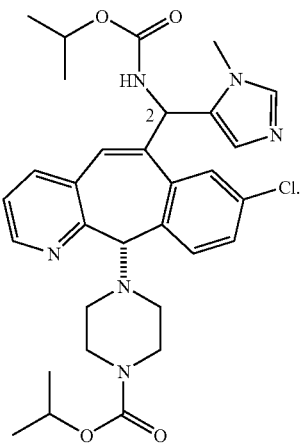
44. The compound of claim 1 selected from the group consisting of:
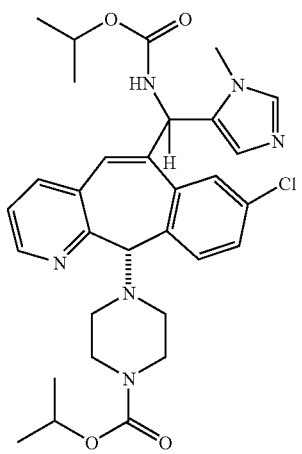
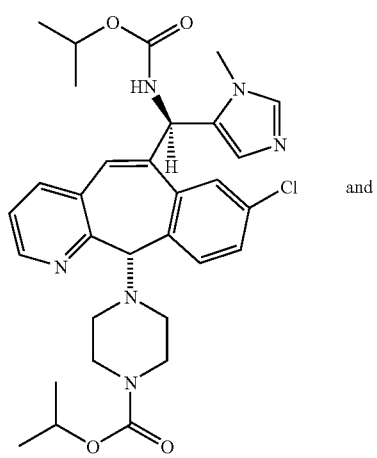
and
45. The compound of claim 1 having the formula:
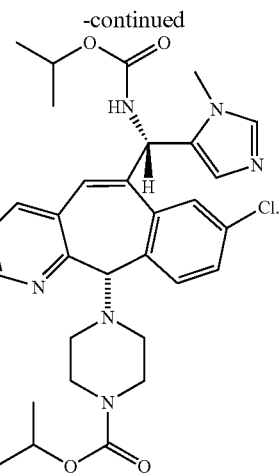
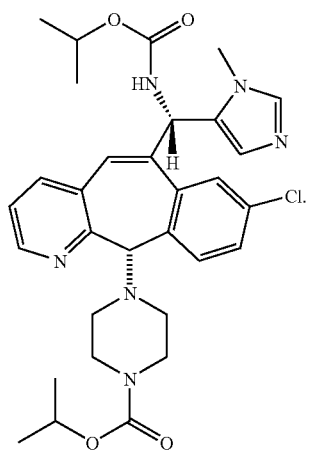
46. The compound of claim 1 having the formula:
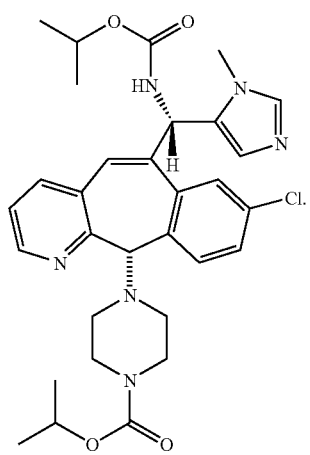

47. A pharmaceutical composition comprising an effective amount of compound of claim 1 in combination with a pharmaceutically acceptable carrier.

48. A pharmaceutical composition comprising an effective amount of compound of claim 22 in combination with a pharmaceutically acceptable carrier.

49. The compound of claim 1 selected from the group consisting of:

(1)
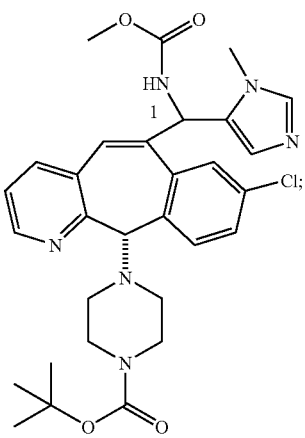
(Example 3281)

(2)
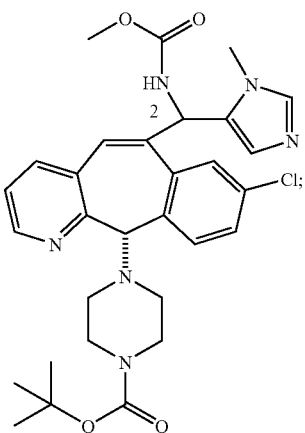
(Example 3281)

(3)
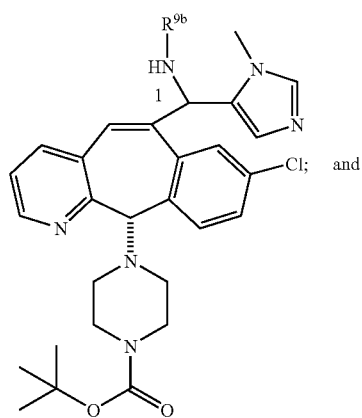
and

-continued

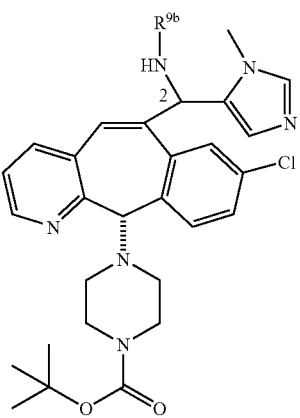

wherein:

| Example | $R^{9b}$ is selected from the group consisting of: |
|---|---|
| 3282 | 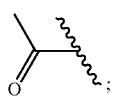 |
| 3283 | 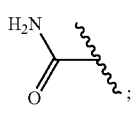 |
| 3284 | 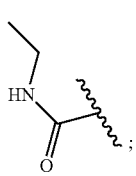 |
| 3285 | 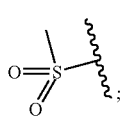 |
| 3286 | 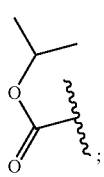 |
| 3287 | 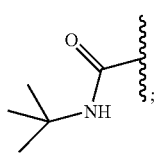 |
| 3287a | 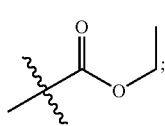 |

-continued
| Example | R⁹ᵇ is selected from the group consisting of: |
|---|---|
| 3287b | 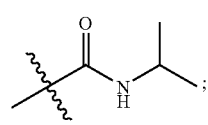 |
| 3287c | 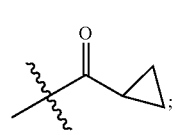 |
| 3287d | 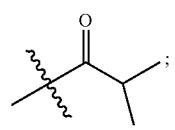 |
| 3287e | 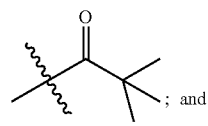; and |
| 3287f | 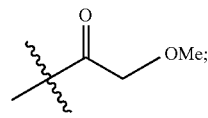 |
(4)
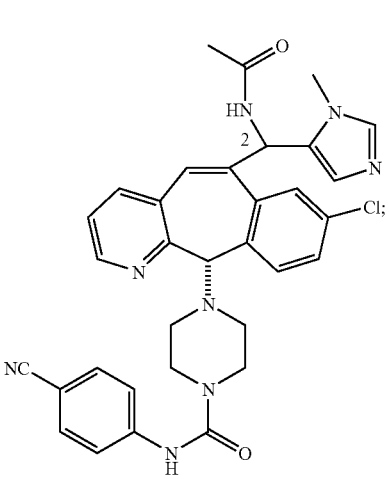
(Example 3288)
(5)
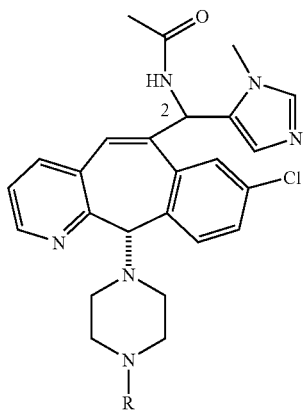
wherein:
| Example | R is selected from the group consisting of: |
|---|---|
| 3289 | 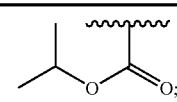 |
| 3290 | 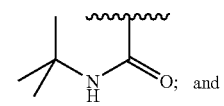; and |
| 3291 | 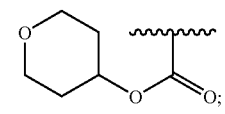 |
(6)
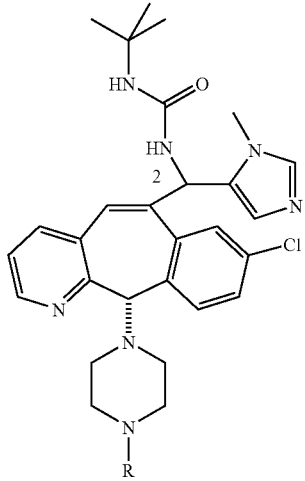

1241
wherein R is:
| Example | R is selected from the group consisting of: |
|---|---|
| 3292 | 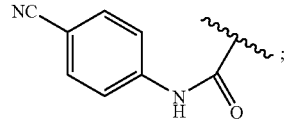 ; |
| 3293 | 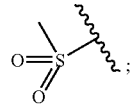 ; |
| 3294 | 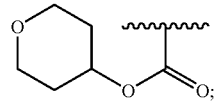 ; |
| 3295 | 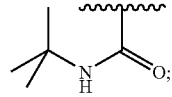 ; |
| 3296 | 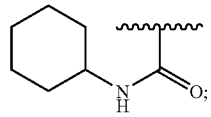 ; and |
| 3297 | 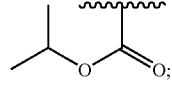 ; |
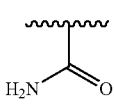
(7)
wherein:
| Example | R is selected from the group consisting of: |
|---|---|
| 3298 | 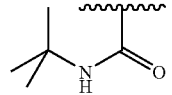 |
1242
-continued
| Example | R is selected from the group consisting of: |
|---|---|
| 3299 | 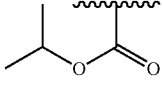 |
| 3300 | 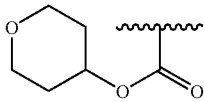 |
| 3301 | 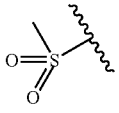 |
| 3302 | 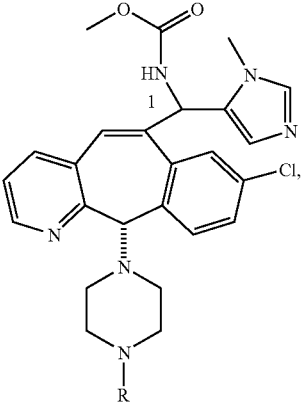 |
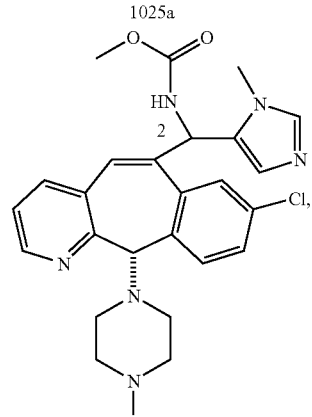
(8)
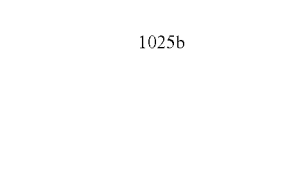
1025a
1025b -continued
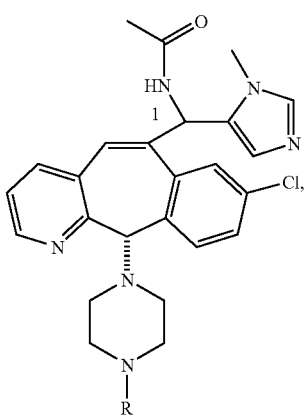
1026a
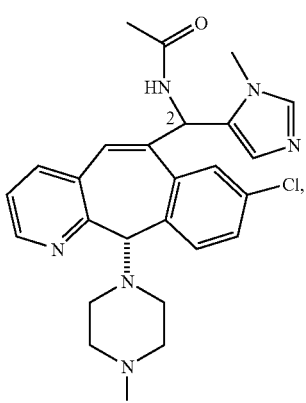
1026b
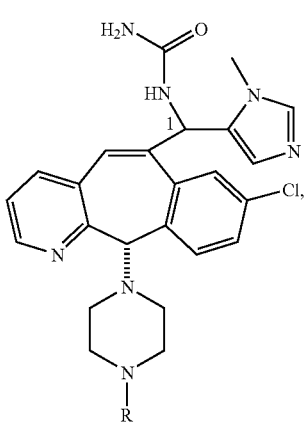
1027a
-continued
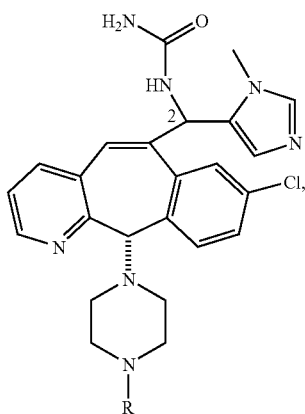
1027b
wherein:
| Ex. | Compd. | Ex. | Compd | R is selected from the group consisting of: |
|---|---|---|---|---|
| 3309 | 1025a | 3316 | 1028b | |
| 3310 | 1025b | 3317 | 1029a | |
| 3311 | 1026a | 3318 | 1030a | ⸺C(O)NH$_2$ |
| 3312 | 1026b | 3319 | 1030b | |
| 3313 | 1027a | 3320 | 1031a | |
| 3314 | 1027b | 3321 | 1031b | |
| 3315 | 1028a | | | |
| 3328 | 1025a | 3335 | 1028b | |
| 3329 | 1025b | 3336 | 1029a | |
| 3330 | 1026a | 3337 | 1029b | |
| 3331 | 1026b | 3338 | 1030a | ⸺C(O)NHMe |
| 3332 | 1027a | 3339 | 1030b | |
| 3333 | 1027b | 3340 | 1031a | |
| 3334 | 1028a | 3341 | 1031b | |
| 3348 | 1025a | 3355 | 1028b | |
| 3349 | 1025b | 3356 | 1029a | |
| 3350 | 1026a | 3357 | 1029b | |
| 3351 | 1026b | 3358 | 1030a | ⸺C(O)NHiPr |
| 3352 | 1027a | 3359 | 1030b | |
| 3353 | 1027b | 3360 | 1031a | |
| 3354 | 1028a | 3361 | 1031b | |
| 3368 | 1025a | 3375 | 1028b | |
| 3369 | 1025b | 3376 | 1029a | |
| 3370 | 1026a | 3377 | 1029b | |
| 3371 | 1026b | 3378 | 1030a | ⸺C(O)NHEt |
| 3372 | 1027a | 3379 | 1030b | |
| 3373 | 1027b | 3380 | 1031a | |
| 3374 | 1028a | 3381 | 1031b | |
| 3384 | 1025a | 3391 | 1028b | |
| 3385 | 1025b | 3392 | 1029a | |
| 3386 | 1026a | 3393 | 1030a | |
| 3387 | 1027a | 3394 | 1030b | ⸺C(O)NHtBu |
| 3388 | 1027b | 3395 | 1031a | |
| 3389 | 1028a | | | |
| 3390 | 1028b | | | |
| 3402 | 1025a | 3409 | 1028b | |
| 3403 | 1025b | 3410 | 1029a | |
| 3404 | 1026a | 3411 | 1029b | |
| 3405 | 1026b | 3412 | 1030a | ⸺C(O)NHnPr |
| 3406 | 1027a | 3413 | 1030b | |
| 3407 | 1027b | 3414 | 1031a | |
| 3408 | 1028a | 3415 | 1031b | |

-continued

| Ex. | Compd. | Ex. | Compd | R is selected from the group consisting of: |
|---|---|---|---|---|
| 3422 | 1025a | 3429 | 1028b | |
| 3423 | 1025b | 3430 | 1029a | |
| 3424 | 1026a | 3431 | 1029b | isobutylamide (–C(O)NH–CH₂CH(CH₃)₂) |
| 3425 | 1026b | 3432 | 1030a | |
| 3426 | 1027a | 3433 | 1030b | |
| 3427 | 1027b | 3434 | 1031a | |
| 3428 | 1028a | 3435 | 1031b | |
| 3442 | 1025a | 3449 | 1028b | |
| 3443 | 1025b | 3450 | 1029a | |
| 3444 | 1026a | 3451 | 1029b | allylamide (–C(O)NH–CH₂CH=CH₂) |
| 3445 | 1026b | 3452 | 1030a | |
| 3446 | 1027a | 3453 | 1030b | |
| 3447 | 1027b | 3454 | 1031a | |
| 3448 | 1028a | 3455 | 1031b | |
| 3462 | 1025a | 3469 | 1028b | |
| 3463 | 1025b | 3470 | 1029a | |
| 3464 | 1026a | 3471 | 1029b | cyclopentylamide |
| 3465 | 1026b | 3472 | 1030a | |
| 3466 | 1027a | 3473 | 1030b | |
| 3467 | 1027b | 3474 | 1031a | |
| 3468 | 1028a | 3475 | 1031b | |
| 3482 | 1025a | 3489 | 1028b | |
| 3483 | 1025b | 3490 | 1029a | |
| 3484 | 1026a | 3491 | 1029b | cyclohexylamide |
| 3485 | 1026b | 3492 | 1030a | |
| 3486 | 1027a | 3493 | 1030b | |
| 3487 | 1027b | 3494 | 1031a | |
| 3488 | 1028a | | | |
| 3501 | 1025a | 3508 | 1028b | |
| 3502 | 1025b | 3509 | 1029a | |
| 3503 | 1026a | 3510 | 1029b | phenylamide |
| 3504 | 1026b | 3511 | 1030a | |
| 3505 | 1027a | 3512 | 1030b | |
| 3506 | 1027b | 3513 | 1031a | |
| 3507 | 1028a | 3514 | 1031b | |
| 3521 | 1025a | 3527 | 1028b | |
| 3522 | 1025b | 3528 | 1029a | |
| 3523 | 1026a | 3529 | 1029b | 4-cyanophenylamide |
| 3524 | 1027a | 3530 | 1030a | |
| 3525 | 1027b | 3531 | 1030b | |
| 3526 | 1028a | 3532 | 1031a | |
| 3539 | 1025a | 3546 | 1028b | |
| 3540 | 1025b | 3547 | 1029a | |
| 3541 | 1026a | 3548 | 1029b | 4-isopropylphenylamide |
| 3542 | 1026b | 3549 | 1030a | |
| 3543 | 1027a | 3550 | 1030b | |
| 3544 | 1027b | 3551 | 1031a | |
| 3545 | 1028a | | 1031b | |
| 3558 | 1025a | 3565 | 1028b | |
| 3559 | 1025b | 3566 | 1029a | |
| 3560 | 1026a | 3567 | 1029b | 4-bromophenylamide |
| 3561 | 1026b | 3568 | 1030a | |
| 3562 | 1027a | 3569 | 1030b | |
| 3563 | 1027b | 3570 | 1031a | |
| 3664 | 1028a | 3571 | 1031b | |
| 3578 | 1025a | 3585 | 1028b | |
| 3579 | 1025b | 3586 | 1029a | |
| 3580 | 1026a | 3587 | 1029b | 4-chlorophenylamide |
| 3581 | 1026b | 3588 | 1030a | |
| 3582 | 1027a | 3589 | 1030b | |
| 3583 | 1027b | 3590 | 1031a | |
| 3684 | 1028a | 3591 | 1031b | |

| Ex. | Compd. | Ex. | Compd | R is selected from the group consisting of: |
|---|---|---|---|---|
| 3598 | 1025a | 3605 | 1028b | |
| 3599 | 1025b | 3606 | 1029a | |
| 3600 | 1026a | 3607 | 1029b | 4-fluorophenylamide |
| 3601 | 1026b | 3608 | 1030a | |
| 3602 | 1027a | 3609 | 1030b | |
| 3603 | 1027b | 3610 | 1031a | |
| 3604 | 1028a | 3611 | 1031b | |
| 3618 | 1025a | 3625 | 1028b | |
| 3619 | 1025b | 3626 | 1029a | |
| 3620 | 1026a | 3627 | 1029b | 4-methoxyphenylamide |
| 3621 | 1026b | 3628 | 1030a | |
| 3622 | 1027a | 3629 | 1030b | |
| 3623 | 1027b | 3630 | 1031a | |
| 3624 | 1028a | 3631 | 1031b | |
| 3638 | 1025a | 3645 | 1028b | |
| 3639 | 1025b | 3646 | 1029a | |
| 3640 | 1026a | 3647 | 1029b | 4-phenoxyphenylamide |
| 3641 | 1026b | 3648 | 1030a | |
| 3642 | 1027a | 3649 | 1030b | |
| 3643 | 1027b | 3650 | 1031a | |
| 3644 | 1028a | 3651 | 1031b | |
| 3658 | 1025a | 3665 | 1028b | |
| 3659 | 1025b | 3666 | 1029a | |
| 3660 | 1026a | 3667 | 1029b | 4-trifluoromethylphenylamide |
| 3661 | 1026b | 3668 | 1030a | |
| 3662 | 1027a | 3669 | 1030b | |
| 3663 | 1027b | 3670 | 1031a | |
| 3664 | 1028a | 3671 | 1031b | |
| 3678 | 1025a | 3685 | 1028b | |
| 3679 | 1025b | 3686 | 1029a | |
| 3680 | 1026a | 3687 | 1029b | 4-tert-butylphenylamide |
| 3681 | 1026b | 3628 | 1030a | |
| 3682 | 1027a | 3689 | 1030b | |
| 3683 | 1027b | 3690 | 1031a | |
| 3684 | 1028a | 3691 | 1031b | |
| 3698 | 1025a | 3705 | 1028b | |
| 3699 | 1025b | 3706 | 1029a | |
| 3700 | 1026a | 3707 | 1029b | naphthalen-1-ylamide |
| 3701 | 1026b | 3708 | 1030a | |
| 3702 | 1027a | 3709 | 1030b | |
| 3703 | 1027b | 3710 | 1031a | |
| 3704 | 1028a | 3711 | 1031b | |
| 3718 | 1025a | 3725 | 1028b | |
| 3719 | 1025b | 3726 | 1029a | |
| 3720 | 1026a | 3727 | 1029b | benzoylamide |
| 3721 | 1026b | 3728 | 1030a | |
| 3722 | 1027a | 3729 | 1030b | |
| 3723 | 1027b | 3730 | 1031a | |
| 3724 | 1028a | 3731 | 1031b | |
| 3738 | 1025a | 3745 | 1028b | |
| 3739 | 1025b | 3746 | 1029a | |
| 3740 | 1026a | 3747 | 1029b | benzylamide |
| 3741 | 1026b | 3748 | 1030a | |
| 3742 | 1027a | 3749 | 1030b | |
| 3743 | 1027b | 3750 | 1031a | |
| 3744 | 1028a | 3751 | 1031b | |
| 3758 | 1025a | 3765 | 1028b | |
| 3759 | 1025b | 3766 | 1029a | |
| 3760 | 1026a | 3767 | 1029b | pyridin-3-ylamide |
| 3761 | 1026b | 3768 | 1030a | |
| 3762 | 1027a | 3769 | 1030b | |
| 3763 | 1027b | 3770 | 1031a | |
| 3764 | 1028a | 3771 | 1031b | |

-continued

| Ex. | Compd. | Ex. | Compd | R is selected from the group consisting of: |
|---|---|---|---|---|
| 3778 | 1025a | 3785 | 1028b | |
| 3779 | 1025b | 3786 | 1029a | |
| 3780 | 1026a | 3787 | 1029b | |
| 3781 | 1026b | 3728 | 1030a | -C(O)-NH-CH₂-(4-phenyl) |
| 3782 | 1027a | 3789 | 1030b | |
| 3783 | 1027b | 3790 | 1031a | |
| 3784 | 1028a | 3791 | 1031b | |
| 3798 | 1025a | 3805 | 1028b | |
| 3799 | 1025b | 3806 | 1029a | |
| 3800 | 1026a | 3807 | 1029b | |
| 3801 | 1026b | 3808 | 1030a | -CH=C(H)-CH(CH₃)₂ (vinyl isopropyl) |
| 3802 | 1027a | 3809 | 1030b | |
| 3803 | 1027b | 3810 | 1031a | |
| 3804 | 1028a | 3811 | 1031b | |
| 3818 | 1025a | 3825 | 1028b | |
| 3819 | 1025b | 3826 | 1029a | |
| 3820 | 1026a | 3827 | 1029b | |
| 3821 | 1026b | 3828 | 1030a | -C(O)-CH₂-CH₃ |
| 3822 | 1027a | 3829 | 1030b | |
| 3823 | 1027b | 3830 | 1031a | |
| 3824 | 1028a | 3831 | 1031b | |
| 3838 | 1025a | 3845 | 1028b | |
| 3839 | 1025b | 3846 | 1029a | |
| 3840 | 1026a | 3847 | 1029b | |
| 3841 | 1026b | 3848 | 1030a | -C(O)-CH₂-CH₂-CH₃ |
| 3842 | 1027a | 3849 | 1030b | |
| 3843 | 1027b | 3850 | 1031a | |
| 3844 | 1028a | 3851 | 1031b | |
| 3858 | 1025a | 3865 | 1028b | |
| 3859 | 1025b | 3866 | 1029a | |
| 3860 | 1026a | 3867 | 1029b | |
| 3861 | 1026b | 3868 | 1030a | -CH=C(H)-C(CH₃)₃ (vinyl t-butyl) |
| 3862 | 1027a | 3869 | 1030b | |
| 3863 | 1027b | 3870 | 1031a | |
| 3864 | 1028a | 3871 | 1031b | |
| 3878 | 1025a | 3885 | 1028b | |
| 3879 | 1025b | 3886 | 1029a | |
| 3880 | 1026a | 3887 | 1029b | |
| 3881 | 1026b | 3828 | 1030a | -C(O)-CH₂-CH(CH₃)₂ |
| 3882 | 1027a | 3889 | 1030b | |
| 3883 | 1027b | 3890 | 1031a | |
| 3884 | 1028a | 3891 | 1031b | |
| 3897 | 1025a | 3904 | 1028b | |
| 3898 | 1025b | 3905 | 1029a | |
| 3899 | 1026a | 3906 | 1029b | |
| 3900 | 1026b | 3907 | 1030a | -C(O)-C(Ph)(CH₃)(OH) |
| 3901 | 1027a | 3908 | 1030b | |
| 3902 | 1027b | 3909 | 1031a | |
| 3903 | 1028a | 3910 | 1031b | |
| 3916 | 1025a | 3923 | 1028b | |
| 3917 | 1025b | 3924 | 1029a | |
| 3918 | 1026a | 3925 | 1029b | |
| 3919 | 1026b | 3926 | 1030a | -C(O)-C(Ph)(CH₃)(OH) (enantiomer) |
| 3920 | 1027a | 3927 | 1030b | |
| 3921 | 1027b | 3928 | 1031a | |
| 3922 | 1028a | 3929 | 1031b | |
| 3932 | 1025a | 3941 | 1029a | |
| 3933 | 1025b | 3942 | 1029b | |
| 3934 | 1026a | 3943 | 1030a | |
| 3935 | 1026b | 3944 | 1030b | -C(O)-C(CH₃)₂-OH |
| 3936 | 1027a | 3945 | 1031a | |
| 3937 | 1027b | | 1031b | |
| 3938 | 1028a | | | |
| 3040 | 1028b | | | |

| Ex. | Compd. | Ex. | Compd | R is selected from the group consisting of: |
|---|---|---|---|---|
| 3952 | 1025a | 3959 | 1028b | |
| 3953 | 1025b | 3960 | 1029a | |
| 3954 | 1026a | 3961 | 1029b | |
| 3955 | 1026b | 3962 | 1030a | -C(O)-cyclopropyl |
| 3956 | 1027a | 3963 | 1030b | |
| 3957 | 1027b | 3964 | 1031a | |
| 3958 | 1028a | 3965 | 1031b | |
| 3972 | 1025a | 3979 | 1028b | |
| 3973 | 1025b | 3980 | 1029a | |
| 3974 | 1026a | 3981 | 1029b | |
| 3975 | 1026b | 3982 | 1030a | -C(O)-(2-methylcyclopropyl) |
| 3976 | 1027a | 3983 | 1030b | |
| 3977 | 1027b | 3984 | 1031a | |
| 3978 | 1028a | 3985 | 1031b | |
| 3992 | 1025a | 3999 | 1028b | |
| 3993 | 1025b | 3400A | 1029a | |
| 3994 | 1026a | 3401A | 1029b | |
| 3995 | 1026b | 3402A | 1030a | -C(O)-(1-methylcyclopropyl) |
| 3996 | 1027a | 3403A | 1030b | |
| 3997 | 1027b | 3404A | 1031a | |
| 3998 | 1028a | 3405A | 1031b | |
| 3412A | 1025a | 3419A | 1028b | |
| 3413A | 1025b | 3420A | 1029a | |
| 3414A | 1026a | 3421A | 1029b | |
| 3415A | 1026b | 3422A | 1030a | -C(O)-cyclobutyl |
| 3416A | 1027a | 3423A | 1030b | |
| 3417A | 1027b | 3424A | 1031a | |
| 3418A | 1028a | 3425A | 1031b | |
| 3432A | 1025a | 3439A | 1028b | |
| 3433A | 1025b | 3440A | 1029a | |
| 3434A | 1026a | 3441A | 1029b | |
| 3435A | 1026b | 3442A | 1030a | -C(O)-cyclopentyl |
| 3436A | 1027a | 3443A | 1030b | |
| 3437A | 1027b | 3444A | 1031a | |
| 3438A | 1028a | 3445A | 1031b | |
| 3452A | 1025a | 3459A | 1028b | |
| 3453A | 1025b | 3460A | 1029a | |
| 3454A | 1026a | 3461A | 1029b | |
| 3455A | 1026b | 3462A | 1030a | -C(O)-cyclohexyl |
| 3456A | 1027a | 3463A | 1030b | |
| 3457A | 1027b | 3464A | 1031a | |
| 3458A | 1028a | 3465A | 1031b | |
| 3472A | 1025a | 3479A | 1028b | |
| 3473A | 1025b | 3480A | 1029a | |
| 3474A | 1026a | 3481A | 1029b | |
| 3475A | 1026b | 3482A | 1030a | -C(O)-(cyclohex-1-enyl) |
| 3476A | 1027a | 3483A | 1030b | |
| 3477A | 1027b | 3484A | 1031a | |
| 3478A | 1028a | 3485A | 1031b | |
| 3492A | 1025a | 3499A | 1028b | |
| 3493A | 1025b | 3500A | 1029a | |
| 3494A | 1026a | 3501A | 1029b | |
| 3495A | 1026b | 3502A | 1030a | -C(O)-(piperidin-4-yl) |
| 3496A | 1027a | 3503A | 1030b | |
| 3497A | 1027b | 3504A | 1031a | |
| 3498A | 1028a | 3505A | 1031b | |

-continued

| Ex. | Compd. | Ex. | Compd | R is selected from the group consisting of: |
|---|---|---|---|---|
| 3512A | 1025a | 3519A | 1028b | 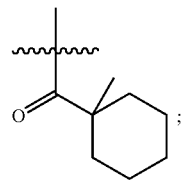 |
| 3513A | 1025b | 3520A | 1029a | |
| 3514A | 1026a | 3521A | 1029b | |
| 3515A | 1026b | 3522A | 1030a | |
| 3516A | 1027a | 3523A | 1030b | |
| 3517A | 1027b | 3524A | 1031a | |
| 3518A | 1028a | 3525A | 1031b | |
| 3532A | 1025a | 3539A | 1028b | 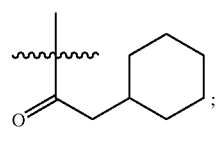 |
| 3533A | 1025b | 3540A | 1029a | |
| 3534A | 1026a | 3541A | 1029b | |
| 3535A | 1026b | 3542A | 1030a | |
| 3536A | 1027a | 3543A | 1030b | |
| 3537A | 1027b | 3544A | 1031a | |
| 3538A | 1028a | 3545A | 1031b | |
| 3552A | 1025a | 3559A | 1028b | 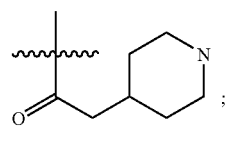 |
| 3553A | 1025b | 3560A | 1029a | |
| 3554A | 1026a | 3561A | 1029b | |
| 3555A | 1026b | 3562A | 1030a | |
| 3556A | 1027a | 3563A | 1030b | |
| 3557A | 1027b | 3564A | 1031a | |
| 3558A | 1028a | 3565A | 1031b | |
| 3572A | 1025a | 3579A | 1028b | 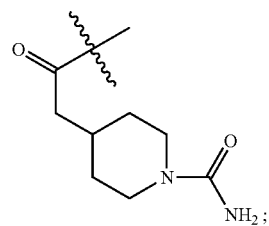 |
| 3573A | 1025b | 3580A | 1029a | |
| 3574A | 1026a | 3581A | 1029b | |
| 3575A | 1026b | 3582A | 1030a | |
| 3576A | 1027a | 3583A | 1030b | |
| 3577A | 1027b | 3584A | 1031a | |
| 3578A | 1028a | 3585A | 1031b | |
| 3592A | 1025a | 3599A | 1028b | 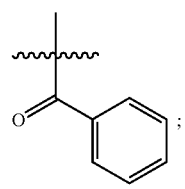 |
| 3593A | 1025b | 3600A | 1029a | |
| 3594A | 1026a | 3601A | 1029b | |
| 3595A | 1026b | 3602A | 1030a | |
| 3596A | 1027a | 3603A | 1030b | |
| 3597A | 1027b | 3604A | 1031a | |
| 3598A | 1028a | 3605A | 1031b | |
| 3612A | 1025a | 3619A | 1028b | 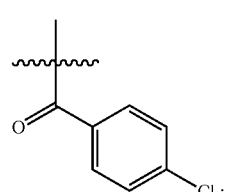 |
| 3613A | 1025b | 3620A | 1029a | |
| 3614A | 1026a | 3621A | 1029b | |
| 3615A | 1026b | 3622A | 1030a | |
| 3616A | 1027a | 3623A | 1030b | |
| 3617A | 1027b | 3624A | 1031a | |
| 3618A | 1028a | 3625A | 1031b | |
| 3632A | 1025a | 3639A | 1028b | 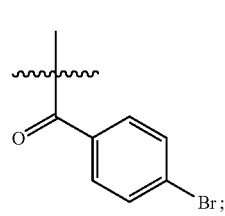 |
| 3633A | 1025b | 3640A | 1029a | |
| 3634A | 1026a | 3641A | 1029b | |
| 3635A | 1026b | 3642A | 1030a | |
| 3636A | 1027a | 3643A | 1030b | |
| 3637A | 1027b | 3644A | 1031a | |
| 3638A | 1028a | 3645A | 1031b | |
| 3652A | 1025a | 3659A | 1028b | 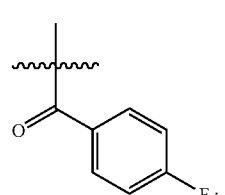 |
| 3653A | 1025b | 3660A | 1029a | |
| 3654A | 1026a | 3661A | 1029b | |
| 3655A | 1026b | 3662A | 1030a | |
| 3656A | 1027a | 3663A | 1030b | |
| 3657A | 1027b | 3664A | 1031a | |
| 3658A | 1028a | 3665A | 1031b | |

-continued

| Ex. | Compd. | Ex. | Compd | R is selected from the group consisting of: |
|---|---|---|---|---|
| 3672A | 1025a | 3679A | 1028b | 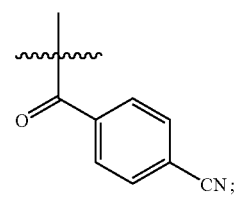 |
| 3673A | 1025b | 3680A | 1029a | |
| 3674A | 1026a | 3681A | 1029b | |
| 3675A | 1026b | 3682A | 1030a | |
| 3676A | 1027a | 3683A | 1030b | |
| 3677A | 1027b | 3684A | 1031a | |
| 3678A | 1028a | 3685A | 1031b | |
| 3692A | 1025a | 3699A | 1028b | 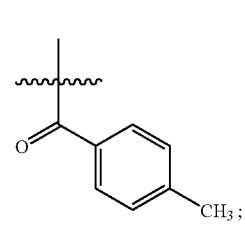 |
| 3693A | 1025b | 3700A | 1029a | |
| 3694A | 1026a | 3701A | 1029b | |
| 3695A | 1026b | 3702A | 1030a | |
| 3696A | 1027a | 3703A | 1030b | |
| 3697A | 1027b | 3704A | 1031a | |
| 3698A | 1028a | 3705A | 1031b | |
| 3712A | 1025a | 3719A | 1028b | 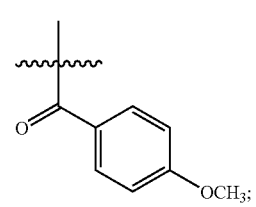 |
| 3713A | 1025b | 3720A | 1029a | |
| 3714A | 1026a | 3721A | 1029b | |
| 3715A | 1026b | 3722A | 1030a | |
| 3716A | 1027a | 3723A | 1030b | |
| 3717A | 1027b | 3724A | 1031a | |
| 3718A | 1028a | 3725A | 1031b | |
| 3732A | 1025a | 3739A | 1028b | 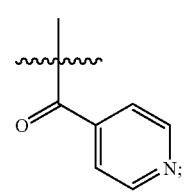 |
| 3733A | 1025b | 3740A | 1029a | |
| 3734A | 1026a | 3741A | 1029b | |
| 3735A | 1026b | 3742A | 1030a | |
| 3736A | 1027a | 3743A | 1030b | |
| 3737A | 1027b | 3744A | 1031a | |
| 3738A | 1028a | 3745A | 1031b | |
| 3752A | 1025a | 3759A | 1028b | 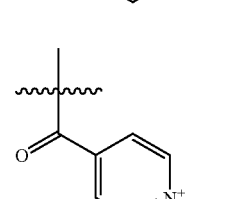 |
| 3753A | 1025b | 3760A | 1029a | |
| 3754A | 1026a | 3761A | 1029b | |
| 3755A | 1026b | 3762A | 1030a | |
| 3756A | 1027a | 3763A | 1030b | |
| 3757A | 1027b | 3764A | 1031a | |
| 3758A | 1028a | 3765A | 1031b | |
| 3772A | 1025a | 3779A | 1028b | 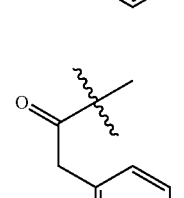 |
| 3773A | 1025b | 3780A | 1029a | |
| 3774A | 1026a | 3781A | 1029b | |
| 3775A | 1026b | 3782A | 1030a | |
| 3776A | 1027a | 3783A | 1030b | |
| 3777A | 1027b | 3784A | 1031a | |
| 3778A | 1028a | 3785A | 1031b | |
| 3792A | 1025a | 3799A | 1028b | 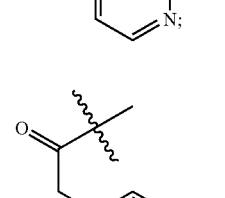 |
| 3793A | 1025b | 3800A | 1029a | |
| 3794A | 1026a | 3801A | 1029b | |
| 3795A | 1026b | 3802A | 1030a | |
| 3796A | 1027a | 3803A | 1030b | |
| 3797A | 1027b | 3804A | 1031a | |
| 3798A | 1028a | 3805A | 1031b | |

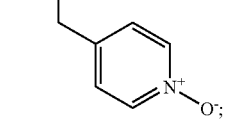

-continued

| Ex. | Compd. | Ex. | Compd | R is selected from the group consisting of: |
|---|---|---|---|---|
| 3812A | 1025a | 3818A | 1028a | |
| 3813A | 1025b | 3819A | 1028b | |
| 3814A | 1026a | 3820A | 1029a | |
| 3815A | 1026b | 3821A | 1029b | 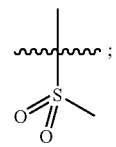 |
| 3816A | 1027a | 3822A | 1030a | |
| 3817A | 1027b | 3823A | 1030b | |
| | | 3823A | 1031a | |
| 3830A | 1025a | 3837A | 1028b | |
| 3831A | 1025b | 3838A | 1029a | |
| 3832A | 1026a | 3839A | 1029b | |
| 3833A | 1026b | 3840A | 1030a | 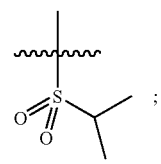 |
| 3834A | 1027a | 3841A | 1030b | |
| 3835A | 1027b | 3842A | 1031a | |
| 3836A | 1028a | 3843A | 1031b | |
| 3850A | 1025a | 3857A | 1028b | |
| 3851A | 1025b | 3858A | 1029a | |
| 3852A | 1026a | 3859A | 1029b | |
| 3853A | 1026b | 3860A | 1030a | 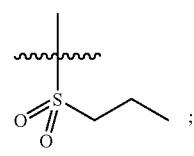 |
| 3854A | 1027a | 3861A | 1030b | |
| 3855A | 1027b | 3862A | 1031a | |
| 3856A | 1028a | 3863A | 1031b | |
| 3870A | 1025a | 3877A | 1028b | |
| 3871A | 1025b | 3878A | 1029a | |
| 3872A | 1026a | 3879A | 1029b | |
| 3873A | 1026b | 3880A | 1030a | 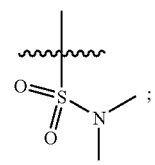 |
| 3874A | 1027a | 3881A | 1030b | |
| 3875A | 1027b | 3882A | 1031a | |
| 3876A | 1028a | 3883A | 1031b | |
| 3890A | 1025a | 3897A | 1028b | |
| 3891A | 1025b | 3898A | 1029a | |
| 3892A | 1026a | 3899A | 1029b | |
| 3893A | 1026b | 3900A | 1030a | 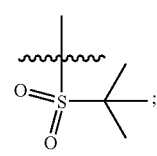 |
| 3894A | 1027a | 3901A | 1030b | |
| 3895A | 1027b | 3902A | 1031a | |
| 3896A | 1028a | 3903A | 1031b | |
| 3910A | 1025a | 3917A | 1028b | |
| 3911A | 1025b | 3918A | 1029a | |
| 3912A | 1026a | 3919A | 1029b | |
| 3913A | 1026b | 3920A | 1030a | 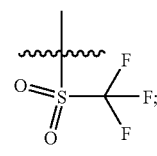 |
| 3914A | 1027a | 3921A | 1030b | |
| 3915A | 1027b | 3922A | 1031a | |
| 3916A | 1028a | 3923A | 1031b | |
| 3950A | 1025a | 3957A | 1028b | |
| 3951A | 1025b | 3958A | 1029a | |
| 3952A | 1026a | 3959A | 1029b | |
| 3953A | 1026b | 3960A | 1030a | 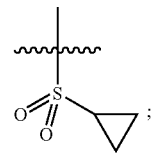 |
| 3954A | 1027a | 3961A | 1030b | |
| 3955A | 1027b | 3862A | 1031a | |
| 3956A | 1028a | 3863A | 1031b | |
| 3970A | 1025a | 3977A | 1028b | |
| 3971A | 1025b | 3978A | 1029a | |
| 3972A | 1026a | 3979A | 1029b | |
| 3973A | 1026b | 3980A | 1030a | 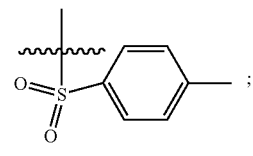 |
| 3974A | 1027a | 3981A | 1030b | |
| 3975A | 1027b | 3882A | 1031a | |
| 3976A | 1028a | 3883A | 1031b | |
| 3990A | 1025a | 3997A | 1028b | |
| 3991A | 1025b | 3998A | 1029a | |
| 3992A | 1026a | 3999A | 1029b | |
| 3993A | 1026b | 4000 | 1030a | 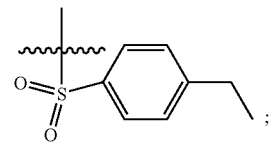 |
| 3994A | 1027a | 4001 | 1030b | |
| 3995A | 1027b | 4002 | 1031a | |
| 3996A | 1028a | 4003 | 1031b | |

-continued

| Ex. | Compd. | Ex. | Compd | R is selected from the group consisting of: |
|---|---|---|---|---|
| 4010 | 1025a | 4017 | 1028b | |
| 4011 | 1025b | 4018 | 1029a | |
| 4012 | 1026a | 4019 | 1029b | |
| 4013 | 1026b | 4020 | 1030a | 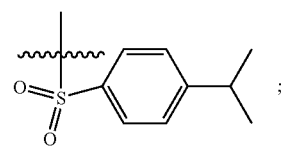 |
| 4014 | 1027a | 4021 | 1030b | |
| 4015 | 1027b | 4022 | 1031a | |
| 4016 | 1028a | 4023 | 1031b | |
| 4030 | 1025a | 4037 | 1028b | |
| 4031 | 1025b | 4038 | 1029a | |
| 4032 | 1026a | 4039 | 1029b | |
| 4033 | 1026b | 4040 | 1030a | 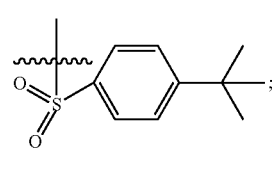 |
| 4034 | 1027a | 4041 | 1030b | |
| 4035 | 1027b | 4042 | 1031a | |
| 4036 | 1028a | 4043 | 1031b | |
| 4050 | 1025a | 4057 | 1028b | |
| 4051 | 1025b | 4058 | 1029a | |
| 4052 | 1026a | 4059 | 1029b | |
| 4053 | 1026b | 4060 | 1030a | 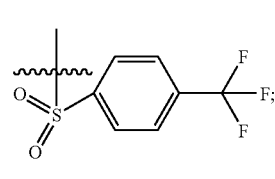 |
| 4054 | 1027a | 4061 | 1030b | |
| 4055 | 1027b | 4062 | 1031a | |
| 4056 | 1028a | 4063 | 1031b | |
| 4070 | 1025a | 4077 | 1028b | |
| 4071 | 1025b | 4078 | 1029a | |
| 4072 | 1026a | 4079 | 1029b | |
| 4073 | 1026b | 4080 | 1030a | 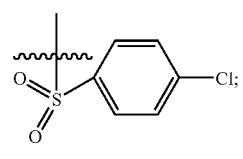 |
| 4074 | 1027a | 4081 | 1030b | |
| 4075 | 1027b | 4082 | 1031a | |
| 4076 | 1028a | 4083 | 1031b | |
| 4090 | 1025a | 4097 | 1028b | |
| 4091 | 1025b | 4098 | 1029a | |
| 4092 | 1026a | 4099 | 1029b | |
| 4093 | 1026b | 4100 | 1030a | 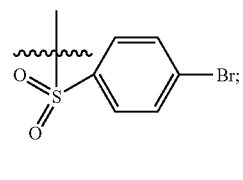 |
| 4094 | 1027a | 4101 | 1030b | |
| 4095 | 1027b | 4102 | 1031a | |
| 4096 | 1028a | 4103 | 1031b | |
| 4110 | 1025a | 4117 | 1028b | |
| 4111 | 1025b | 4118 | 1029a | |
| 4112 | 1026a | 4119 | 1029b | |
| 4113 | 1026b | 4120 | 1030a | 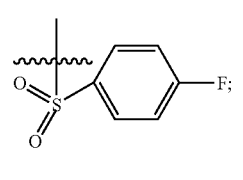 |
| 4114 | 1027a | 4121 | 1030b | |
| 4115 | 1027b | 4122 | 1031a | |
| 4116 | 1028a | 4123 | 1031b | |
| 4130 | 1025a | 4137 | 1028b | |
| 4131 | 1025b | 4138 | 1029a | |
| 4132 | 1026a | 4139 | 1029b | |
| 4133 | 1026b | 4140 | 1030a | 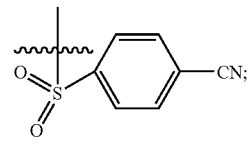 |
| 4134 | 1027a | 4041 | 1030b | |
| 4135 | 1027b | 4142 | 1031a | |
| 4136 | 1028a | 4043 | 1031b | |
| 4150 | 1025a | 4157 | 1028b | |
| 4151 | 1025b | 4158 | 1029a | |
| 4152 | 1026a | 4159 | 1029b | |
| 4153 | 1026b | 4160 | 1030a | 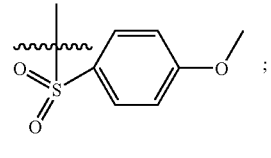 |
| 4154 | 1027a | 4061 | 1030b | |
| 4155 | 1027b | 4162 | 1031a | |
| 4156 | 1028a | 4063 | 1031b | |
| 4170 | 1025a | 4177 | 1028b | |
| 4171 | 1025b | 4178 | 1029a | |
| 4172 | 1026a | 4179 | 1029b | |
| 4173 | 1026b | 4180 | 1030a | 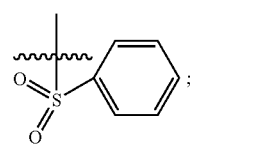 |
| 4174 | 1027a | 4081 | 1030b | |
| 4175 | 1027b | 4182 | 1031a | |
| 4176 | 1028a | 4083 | 1031b | |

-continued

| Ex. | Compd. | Ex. | Compd | R is selected from the group consisting of: |
|---|---|---|---|---|
| 4190 | 1025a | 4197 | 1028b | |
| 4191 | 1025b | 4198 | 1029a | |
| 4192 | 1026a | 4199 | 1029b | benzylsulfonyl |
| 4193 | 1026b | 4200 | 1030a | |
| 4194 | 1027a | 4101 | 1030b | |
| 4195 | 1027b | 4202 | 1031a | |
| 4196 | 1028a | 4203 | 1031b | |
| 4210 | 1025a | 4217 | 1028b | |
| 4211 | 1025b | 4218 | 1029a | |
| 4212 | 1026a | 4219 | 1029b | thiophene-2-sulfonyl |
| 4213 | 1026b | 4220 | 1030a | |
| 4214 | 1027a | 4101 | 1030b | |
| 4215 | 1027b | 4222 | 1031a | |
| 4216 | 1028a | 4213 | 1031b | |
| 4230 | 1025a | 4237 | 1028b | |
| 4231 | 1025b | 4238 | 1029a | |
| 4232 | 1026a | 4239 | 1029b | naphthalene-1-sulfonyl |
| 4233 | 1026b | 4240 | 1030a | |
| 4234 | 1027a | 4241 | 1030b | |
| 4235 | 1027b | 4142 | 1031a | |
| 4236 | 1028a | 4243 | 1031b | |
| 4250 | 1025a | 4257 | 1028b | |
| 4251 | 1025b | 4258 | 1029a | |
| 4252 | 1026a | 4259 | 1029b | methoxycarbonyl |
| 4253 | 1026b | 4260 | 1030a | |
| 4254 | 1027a | 4261 | 1030b | |
| 4255 | 1027b | 4162 | 1031a | |
| 4256 | 1028a | 4263 | 1031b | |
| 4270 | 1025a | 4277 | 1028b | |
| 4271 | 1025b | 4278 | 1029a | |
| 4272 | 1026a | 4279 | 1029b | ethoxycarbonyl |
| 4273 | 1026b | 4280 | 1030a | |
| 4274 | 1027a | 4281 | 1030b | |
| 4275 | 1027b | 4182 | 1031a | |
| 4276 | 1028a | 4283 | 1031b | |
| 4290 | 1025a | 4297 | 1028b | |
| 4291 | 1025b | 4298 | 1029a | |
| 4292 | 1026a | 4299 | 1029b | n-propoxycarbonyl |
| 4293 | 1026b | 4300 | 1030a | |
| 4294 | 1027a | 4301 | 1030b | |
| 4295 | 1027b | 4202 | 1031a | |
| 4296 | 1028a | 4303 | 1031b | |
| 4310 | 1025a | 4316 | 1028b | |
| 4311 | 1025b | 4317 | 1029a | |
| 4312 | 1026a | 4317 | 1030a | isopropoxycarbonyl |
| 4313 | 1026b | 4320 | 1031a | |
| 4314 | 1027a | | | |
| 4315 | 1027b | | | |
| 4316 | 1028a | | | |
| 4327 | 1025a | 4334 | 1028b | |
| 4328 | 1025b | 4335 | 1029a | |
| 4329 | 1026a | 4336 | 1029b | isobutoxycarbonyl |
| 4330 | 1026b | 4337 | 1030a | |
| 4331 | 1027a | 4338 | 1030b | |
| 4332 | 1027b | 4339 | 1031a | |
| 4333 | 1028a | 4340 | 1031b | |
| 4347 | 1025a | 4354 | 1028b | |
| 4348 | 1025b | 4355 | 1029a | |
| 4349 | 1026a | 4356 | 1029b | neopentyloxycarbonyl |
| 4350 | 1026b | 4357 | 1030a | |
| 4351 | 1027a | 4358 | 1030b | |
| 4352 | 1027b | 4359 | 1031a | |
| 4353 | 1028a | 4360 | 1031b | |

| Ex. | Compd. | Ex. | Compd | R is selected from the group consisting of: |
|---|---|---|---|---|
| 4367 | 1025a | 4374 | 1028b | |
| 4368 | 1025b | 4375 | 1029a | |
| 4369 | 1026a | 4376 | 1029b | allyloxycarbonyl |
| 4370 | 1026b | 4377 | 1030a | |
| 4371 | 1027a | 4378 | 1030b | |
| 4372 | 1027b | 4379 | 1031a | |
| 4373 | 1028a | 4380 | 1031b | |
| 4387 | 1025a | 4394 | 1028b | |
| 4388 | 1025b | 4395 | 1029a | |
| 4389 | 1026a | 4396 | 1029b | sec-butoxycarbonyl |
| 4390 | 1026b | 4397 | 1030a | |
| 4391 | 1027a | 4398 | 1030b | |
| 4392 | 1027b | 4399 | 1031a | |
| 4393 | 1028a | 4400 | 1031b | |
| 4407 | 1025a | 4414 | 1028b | |
| 4408 | 1025b | 4415 | 1029a | |
| 4409 | 1026a | 4416 | 1029b | cyclopentyloxycarbonyl |
| 4410 | 1026b | 4417 | 1030a | |
| 4411 | 1027a | 4418 | 1030b | |
| 4412 | 1027b | 4419 | 1031a | |
| 4413 | 1028a | 4420 | 1031b | |
| 4427 | 1025a | 4434 | 1028b | |
| 4428 | 1025b | 4435 | 1029a | |
| 4429 | 1026a | 4436 | 1029b | cyclohexyloxycarbonyl |
| 4430 | 1026b | 4337 | 1030a | |
| 4431 | 1027a | 4438 | 1030b | |
| 4432 | 1027b | 4439 | 1031a | |
| 4433 | 1028a | 4440 | 1031b | |
| 4447 | 1025a | 4454 | 1028b | |
| 4448 | 1025b | 4455 | 1029a | |
| 4449 | 1026a | 4456 | 1029b | phenoxycarbonyl |
| 4450 | 1026b | 4357 | 1030a | |
| 4451 | 1027a | 4458 | 1030b | |
| 4452 | 1027b | 4459 | 1031a | |
| 4453 | 1028a | 4460 | 1031b | |
| 4467 | 1025a | 4474 | 1028b | |
| 4468 | 1025b | 4475 | 1029a | |
| 4469 | 1026a | 4476 | 1029b | benzyloxycarbonyl |
| 4470 | 1026b | 4377 | 1030a | |
| 4471 | 1027a | 4478 | 1030b | |
| 4472 | 1027b | 4479 | 1031a | |
| 4473 | 1028a | 4480 | 1031b | |
| 4487 | 1025a | 4494 | 1028b | |
| 4488 | 1025b | 4495 | 1029a | |
| 4489 | 1026a | 4496 | 1029b | p-tolyloxycarbonyl |
| 4490 | 1026b | 4397 | 1030a | |
| 4491 | 1027a | 4498 | 1030b | |
| 4492 | 1027b | 4499 | 1031a | |
| 4493 | 1028a | 4500 | 1031b | |
| 4507 | 1025a | 4514 | 1028b | |
| 4508 | 1025b | 4515 | 1029a | |
| 4509 | 1026a | 4516 | 1029b | 4-methoxyphenoxycarbonyl |
| 4510 | 1026b | 4417 | 1030a | |
| 4511 | 1027a | 4518 | 1030b | |
| 4512 | 1027b | 4519 | 1031a | |
| 4513 | 1028a | 4520 | 1031b | |
| 4527 | 1025a | 4534 | 1028b | |
| 4528 | 1025b | 4535 | 1029a | |
| 4529 | 1026a | 4536 | 1029b | 4-chlorophenoxycarbonyl |
| 4530 | 1026b | 4337 | 1030a | |
| 4531 | 1027a | 4438 | 1030b | |
| 4532 | 1027b | 4539 | 1031a | |
| 4533 | 1028a | 4540 | 1031b | |

-continued
| Ex. | Compd. | Ex. | Compd | R is selected from the group consisting of: |
|---|---|---|---|---|
| 4547 | 1025a | 4554 | 1028b | |
| 4548 | 1025b | 4555 | 1029a | |
| 4549 | 1026a | 4556 | 1029b | ⟶—C(=O)O—C₆H₄—Br (para); |
| 4550 | 1026b | 4357 | 1030a | |
| 4551 | 1027a | 4458 | 1030b | |
| 4552 | 1027b | 4559 | 1031a | |
| 4553 | 1028a | 4560 | 1031b | |
| 4567 | 1025a | 4574 | 1028b | |
| 4568 | 1025b | 4575 | 1029a | |
| 4569 | 1026a | 4576 | 1029b | ⟶—C(=O)O—C₆H₄—F (para); |
| 4570 | 1026b | 4377 | 1030a | |
| 4571 | 1027a | 4478 | 1030b | |
| 4572 | 1027b | 4579 | 1031a | |
| 4573 | 1028a | 4580 | 1031b | |
| 4587 | 1025a | 4594 | 1028b | |
| 4588 | 1025b | 4595 | 1029a | |
| 4589 | 1026a | 4596 | 1029b | ⟶—C(=O)O-naphthyl; and |
| 4590 | 1026b | 4397 | 1030a | |
| 4591 | 1027a | 4498 | 1030b | |
| 4592 | 1027b | 4599 | 1031a | |
| 4593 | 1028a | 4600 | 1031b | |
| 4607 | 1025a | 4614 | 1028b | |
| 4608 | 1025b | 4615 | 1029a | |
| 4609 | 1026a | 4616 | 1029b | ⟶—C(=O)O-(tetrahydropyran-4-yl) |
| 4610 | 1026b | 4417 | 1030a | |
| 4611 | 1027a | 4518 | 1030b | |
| 4612 | 1027b | 4619 | 1031a | |
| 4613 | 1028a | 4620 | 1031b | |
wherein "compd" represents "compound"; and
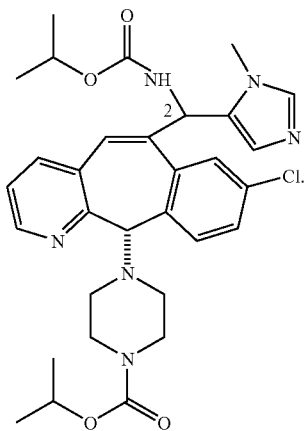
(196)
(Example 4619)
* * * * *